US012465648B2

(12) United States Patent
Jin et al.

(10) Patent No.: US 12,465,648 B2
(45) Date of Patent: Nov. 11, 2025

(54) HETEROBIFUNCTIONAL COMPOUNDS AS DEGRADERS OF HPK1

(71) Applicant: ICAHN SCHOOL OF MEDICINE AT MOUNT SINAI, New York, NY (US)

(72) Inventors: Jian Jin, New York, NY (US); Steven Burakoff, New York, NY (US); H. Umit Kaniskan, New York, NY (US); Sansana Sawasdikosol, New York, NY (US); He Chen, New York, NY (US); Joshua Brody, New York, NY (US); Nina Bhardwaj, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 752 days.

(21) Appl. No.: 17/604,636

(22) PCT Filed: May 5, 2020

(86) PCT No.: PCT/US2020/031527
§ 371 (c)(1),
(2) Date: Oct. 18, 2021

(87) PCT Pub. No.: WO2020/227325
PCT Pub. Date: Nov. 12, 2020

(65) Prior Publication Data

US 2023/0022524 A1 Jan. 26, 2023

Related U.S. Application Data

(60) Provisional application No. 62/843,816, filed on May 6, 2019.

(51) Int. Cl.
*A61K 47/55* (2017.01)
*A61K 39/395* (2006.01)
(Continued)

(52) U.S. Cl.
CPC .......... *A61K 47/55* (2017.08); *A61K 39/3955* (2013.01); *A61K 47/545* (2017.08);
(Continued)

(58) Field of Classification Search
CPC .. C07D 487/04; C07D 417/14; C07D 401/14; C07D 403/14; A61K 47/55; A61K 39/3955; A61K 47/545; A61P 35/00
See application file for complete search history.

(56) References Cited

U.S. PATENT DOCUMENTS

| | | | |
|---|---|---|---|
| 5,691,147 | A | 11/1997 | Draetta et al. |
| 8,377,937 | B2 | 2/2013 | Bencsik et al. |

(Continued)

FOREIGN PATENT DOCUMENTS

| | | |
|---|---|---|
| CN | 102822165 | 12/2012 |
| CN | 103189067 | 7/2013 |

(Continued)

OTHER PUBLICATIONS

Ye et al. ACS Med Chem Lett 2023 14 1 5-10 DOI: 10.1021/acsmedchemlett.2c00238 (Year: 2023).*

(Continued)

*Primary Examiner* — Kortney L. Klinkel
*Assistant Examiner* — Sophia Reilly
(74) *Attorney, Agent, or Firm* — Fish & Richardson P.C.

(57) ABSTRACT

Disclosed are Hematopoietic Progenitor Kinase 1 (HPK1) degradation/disruption compounds including a HPK1 ligand, a degradation/disruption tag and a linker, and methods for use of such compounds in the treatment of HPK1-mediated diseases.

3 Claims, 13 Drawing Sheets

(51) Int. Cl.

| | |
|---|---|
| ***A61K 47/54*** | (2017.01) |
| ***A61P 35/00*** | (2006.01) |
| ***C07D 401/14*** | (2006.01) |
| ***C07D 403/14*** | (2006.01) |
| ***C07D 417/14*** | (2006.01) |
| ***C07D 487/04*** | (2006.01) |

(52) U.S. Cl.

CPC ............ *A61P 35/00* (2018.01); *C07D 401/14* (2013.01); *C07D 403/14* (2013.01); *C07D 417/14* (2013.01); *C07D 487/04* (2013.01)

(56) References Cited

U.S. PATENT DOCUMENTS

| | | | |
|---|---|---|---|
| 8,648,096 | B2 | 2/2014 | Muller et al. |
| 9,809,603 | B1 | 11/2017 | Jacques |
| 9,822,094 | B2 | 11/2017 | Man et al. |
| 2002/0098161 | A1 | 7/2002 | Uhrich |
| 2004/0063773 | A1 | 4/2004 | Tang et al. |
| 2011/0172107 | A1 | 7/2011 | Katz et al. |
| 2011/0196150 | A1 | 8/2011 | Man et al. |
| 2014/0031325 | A1 | 1/2014 | Bartlett et al. |
| 2014/0356322 | A1 | 12/2014 | Crews et al. |
| 2015/0119435 | A1 | 4/2015 | Crews et al. |
| 2015/0274738 | A1 | 10/2015 | Gray et al. |
| 2015/0291562 | A1 | 10/2015 | Crew et al. |
| 2016/0045504 | A1 | 2/2016 | Grembecka et al. |
| 2017/0008904 | A1 | 1/2017 | Crew et al. |
| 2017/0114098 | A1 | 4/2017 | Aivado et al. |
| 2017/0121321 | A1 | 5/2017 | Crews et al. |
| 2017/0224685 | A1 | 8/2017 | Duncan et al. |
| 2017/0283807 | A1 | 10/2017 | Mounir et al. |
| 2018/0072741 | A1 | 3/2018 | Vechorkin et al. |
| 2018/0086767 | A1 | 3/2018 | Fesik et al. |
| 2018/0134684 | A1 | 5/2018 | Bradner et al. |
| 2018/0186800 | A1 | 7/2018 | Yamamoto et al. |
| 2019/0092768 | A1 | 3/2019 | Gray et al. |
| 2019/0255041 | A1 | 8/2019 | Jin et al. |
| 2019/0336503 | A1 | 11/2019 | Jin et al. |
| 2019/0367525 | A1 | 12/2019 | Ioannidis et al. |
| 2020/0338070 | A1 | 10/2020 | Jin et al. |
| 2020/0399266 | A1 | 12/2020 | Jin et al. |
| 2021/0261538 | A1 | 8/2021 | Jin et al. |
| 2021/0283261 | A1 | 9/2021 | Jin et al. |
| 2021/0355140 | A1 | 11/2021 | Shunatona et al. |
| 2021/0395244 | A1 | 12/2021 | Jin et al. |
| 2022/0054488 | A1 | 2/2022 | Jin et al. |
| 2023/0022524 | A1 | 1/2023 | Jin et al. |
| 2023/0070613 | A1 | 3/2023 | Jin et al. |
| 2023/0167106 | A1 | 6/2023 | Jin et al. |
| 2023/0391765 | A1 | 12/2023 | Jin et al. |
| 2025/0136589 | A1 | 5/2025 | Jin et al. |

FOREIGN PATENT DOCUMENTS

| | | | | |
|---|---|---|---|---|
| CN | 104736569 | | 6/2015 | |
| CN | 105085620 | | 11/2015 | |
| CN | 105175284 | | 12/2015 | |
| CN | 108137507 | | 6/2018 | |
| CN | 109071552 | | 12/2018 | |
| CN | 109790143 | | 5/2019 | |
| CN | 112778303 | | 5/2021 | |
| JP | 2007-512364 | | 5/2007 | |
| JP | 2008-525526 | | 7/2008 | |
| JP | 2009-542721 | | 12/2009 | |
| JP | 2009-542723 | | 12/2009 | |
| JP | 2010-532386 | | 10/2010 | |
| JP | 2010-532387 | | 10/2010 | |
| JP | 2015-508414 | | 3/2015 | |
| JP | 2016-540811 | A | 12/2016 | |
| JP | 2017-513862 | | 6/2017 | |
| JP | 2018-502097 | | 1/2018 | |
| JP | 2018-526430 | | 9/2018 | |
| JP | 2019-514883 | | 5/2020 | |
| JP | 2021-511342 | | 5/2021 | |
| MX | 2018000471 | | 4/2018 | |
| MX | 2018000360 | | 6/2018 | |
| WO | WO 2008/109104 | | 9/2008 | |
| WO | WO 2012/142504 | A1 | 10/2012 | |
| WO | WO 2014/100719 | | 6/2014 | |
| WO | WO 2015/101293 | | 7/2015 | |
| WO | WO 2015/104677 | | 7/2015 | |
| WO | WO 2015/192123 | | 12/2015 | |
| WO | WO 2016/073956 | | 5/2016 | |
| WO | WO 2016/105518 | | 6/2016 | |
| WO | WO 2016/106518 | | 7/2016 | |
| WO | WO 2016/115480 | | 7/2016 | |
| WO | WO 2016/149668 | | 9/2016 | |
| WO | WO 2016/168992 | | 10/2016 | |
| WO | WO 2016/174130 | | 11/2016 | |
| WO | WO 2016/197032 | | 12/2016 | |
| WO | WO 2016/208595 | | 12/2016 | |
| WO | WO 2017/011371 | | 1/2017 | |
| WO | WO 2017/011590 | | 1/2017 | |
| WO | WO 2017/024317 | | 2/2017 | |
| WO | WO 2017/024319 | | 2/2017 | |
| WO | WO 2017/046036 | A1 | 3/2017 | |
| WO | WO 2017/079267 | | 5/2017 | |
| WO | WO 2017/147700 | | 9/2017 | |
| WO | WO 2017/147701 | | 9/2017 | |
| WO | WO 2017/185031 | | 10/2017 | |
| WO | WO 2017/197051 | | 11/2017 | |
| WO | WO 2017/197055 | | 11/2017 | |
| WO | WO 2018/049200 | | 3/2018 | |
| WO | WO-2018049152 | A1 * | 3/2018 | .............. A61P 35/00 |
| WO | WO 2018/098280 | | 5/2018 | |
| WO | WO 2018/106870 | | 6/2018 | |
| WO | WO 2018/117177 | | 6/2018 | |
| WO | WO 2018/119441 | | 6/2018 | |
| WO | WO 2018/144649 | | 8/2018 | |
| WO | WO 2019/084030 | | 5/2019 | |
| WO | WO 2019/222380 | | 11/2019 | |
| WO | WO 2019/246570 | | 12/2019 | |
| WO | WO 2020/252043 | | 12/2020 | |
| WO | WO 2021/021904 | | 2/2021 | |
| WO | WO 2021/057872 | | 4/2021 | |
| WO | WO 2023/006063 | | 2/2023 | |

OTHER PUBLICATIONS

Zeng et al. Bioorganic Chemistry 2024 143 107016 1-9 DOI: 10.1016/j.bioorg.2023.107016 (Year: 2024).*

Ishoey et al., "Translation Termination Factor GSPT1 Is a Phenotypically Relevant Off-Target of Heterobifunctional Phthalimide Degraders," ACS Chemical Biology, Jan. 22, 2018, 13(3):553-560.

Office Action in Chinese Appln. No. 202080049386.9, mailed on Feb. 2, 2024, 23 pages (with Machine translation).

Karaman et al., "A quantitative analysis of kinase inhibitor selectivity," Nature biotechnology, Jan. 2008, 26(1):127-132.

Office Action in Japanese Appln. No. 2021-565854, mailed on May 7, 2024, 6 pages (with English translation).

Herrera-Montavez et al., "MEK1/2-Targeting PROTACs Promote the Collateral Degradation of CRAF in KRAS Mutant Cells," bioRxiv, Jun. 2023, retrieved from URL<https://doi.org/10.1101/2023.06.15.545136]>, 28 pages.

AU Office Action in Australian Appln. No. 2022201488, dated Feb. 14, 2023, 6 pages.

CN Office Action in Chinese Appln. No. 201980030599.4, dated Jan. 5, 2023, 13 pages (with English Translation).

EP Extended European Search Report in European Appln. No. 20802303.6, dated Dec. 23, 2022, 6 pages.

EP Office Action in European Appln. No. 17863645.2, dated Nov. 11, 2022, 6 pages.

Fioravanti et al., "Six years (2012-2018) of researches on catalytic EZH2 inhibitors: The boom of the 2-pyridone compounds," Manuscript, The Chemical Record, 2018, 18(12):1818-1832.

Kumar et al., "EZH2 Inhibitor GSK126 for Cancer Treatment: Metabolism, drug transporter and rat pharmacokinetic studies," Medical Research Archives, 2015, Issue 3, 31 pages.

(56) References Cited

OTHER PUBLICATIONS

PCT Invitation to Pay Additional Fees in International Appln. No. PCT/US2022/050929, dated Feb. 6, 2023, 3 pages.
Stazi et al., "EZH2 inhibitors: a patent review (2014-2016)," Expert Opinion on Therapeutic Patents, 2017, 27(7):797-813.
Office Action in Chinese Appln. No. 201980054694.8, mailed on Sep. 1, 2023, 21 pages (with Machine translation).
EP Extended European Search Report in European Appln. No. 19821826.5, dated May 3, 2022, 10 pages.
Fisher et al., "Targeted protein degradation and the enzymology of degraders," Current Opinion in Chemical Biology, 2018, 44:47-55.
CN Office Action in Chinese Appln. No. 201780081246.8, dated Mar. 4, 2023, 16 pages (with English Translation).
EP Office Action in European Appln. No. 17877800.7, Apr. 13, 2023, 7 pages.
EP Office Action in European Appln. No. 19763958.6, dated May 10, 2023, 4 pages.
EP Office Action in European Appln. No. 19821826.5, dated Apr. 12, 2023, 4 pages.
JP Office Action in Japanese Appln. No. 2020-546159, dated May 9, 2023, 14 pages (with English Translation).
JP Office Action in Japanese Appln. No. 2020-570728, dated Jun. 27, 2023, 11 pages (with English Translation).
JP Office Action in Japanese Appln. No. 2021-500187, dated Jul. 4, 2023, 12 pages (with English Translation).
PCT International Preliminary Report on Patentability in International Appln. No. PCT/US2021/055574, dated May 4, 2023, 8 pages.
PCT International Search Report and Written Opinion in International Appln. No. PCT/US2022/050929, dated Apr. 7, 2023, 13 pages.
Popow et al., "Highly selective PTK2 proteolysis targeting chimeras to probe focal adhesion kinase scaffolding functions," Journal of Medicinal Chemistry, 2019, 62(5):2508-2520.
Wang et al., "Discovery of potent 2-Aryl-6,7-dihydro-5H-pyrrolo[1,2-α] imidazoles as WDR5-WIN-site inhibitors using fragment-based methods and structure-based design," Journal of Medicinal Chemistry, 2018, 61(13):5623-5642.
Wei et al., "Discovery of a first-in-class mitogen-activated protein kinase kinase 1/2 degrader," Journal of Medicinal Chemistry, 2019, 62(23):10897-10911.
Xue et al., "Protein degradation through covalent inhibitor-based PROTACs," Chemical Communications, 2020, 56(10):1521-1524.
PCT International Search Report and Written Opinion in International Appln. No. PCT/US2022/013225, dated Jun. 6, 2022, 24 pages.
U.S. Appl. No. 16/926,418, filed Jul. 10, 2020, Jian Jin.
U.S. Appl. No. 16/467,888, filed Jun. 7, 2019, Jian Jin.
U.S. Appl. No. 16/977,654, filed Sep. 2, 2020, Jian Jin.
U.S. Appl. No. 17/938,502, filed Oct. 6, 2022, Jian Jin.
U.S. Appl. No. 17/254,345, filed Dec. 21, 2020, Jian Jin.
U.S. Appl. No. 17/336,059, filed Jun. 1, 2021, Jian Jin.
Abramovich et al., "Hox regulation of normal and leukemic hematopoietic stem cells," Curr. Opin. Hematol., May 2005, 12(3):210-216.
Addie et al., "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases," J. Med. Chem., Mar. 2013, 56(5):2059-2073.
Aguilar et al., "Discovery of 4-((3'R,4'S,5'R)-6"-Chloro-4'-(3-chloro-2-fluorophenyl)l'-ethyl-2"-oxodispiro[cyclohexane-1,2'-pyrrolidine-3',3 "-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," Journal of Medicinal Chemistry, Mar. 2017, 60(7):2819-2839.
Alinari et al., "Selective inhibition of protein arginine methyltransferase 5 blocks initiation and maintenance of B-cell transformation," Blood, Apr. 2015, 125(16):2530-2543.
Alzabin et al., "Hematopoietic progenitor kinase 1 is a critical component of prostaglandin E2-mediated suppression of the anti-tumor immune response," Cancer Immunol. Immunother., 2010, 59:419-429.
Alzabin et al., "Hematopoietic Progenitor Kinase 1 Is a Negative Regulator of Dendritic Cell Activation," J Immunol, 2009, 182:6187-6194.
Anders et al., "Differential expression analysis for sequence count data," Genome Biol., 2010 11:R106.
Armstrong et al., "MLL translocations specify a distinct gene expression profile that distinguishes a unique leukemia," Nat Genet., Jan. 2002, 30:41-47.
Artinger et al., "An MLL-dependent network sustains hematopoiesis," Proc. Natl. Acad. Sci. USA, Jul. 2013, 110(29):12000-12005.
Asiaban et al., "Cell-Based Ligand Discovery for the ENL YEATS Domain," ACS Chem. Biol., Apr. 2020, 15(4):895-903.
AU Notice of Allowance in Australian Appln. No. 2017348322, dated Dec. 14, 2021, 3 pages.
AU Office Action in Australian Appln. No. 2017348322, dated Dec. 10, 2020, 7 pages.
AU Office Action in Australian Appln. No. 2017348322, dated Sep. 27, 2021, 2 pages.
Ayton et al., "Molecular mechanisms of leukemogenesis mediated by MLL fusion proteins," Oncogene, Oct. 2001, 20:5695-5707.
Bachman et al., "EZH2 Expression Is Associated With High Proliferation Rate and Aggressive Tumor Subgroups in Cutaneous Melanoma and Cancers of the Endometrium, Prostate, and Breast," J. Clin. Oncol., 2006, 24(2):268-273.
Bai et al., "Targeted degradation of BET proteins in triple-negative breast cancer," Cancer Res., May 1, 2017, 77(9):2476-2487.
Basiorka et al. "Lenalidomide Stabilizes the Erythropoietin Receptor by Inhibiting the E3 Ubiquitin Ligase RNF41," Cancer Res., Apr. 2016, 76:3531-3540.
Bennett et al., "The Role of Nuclear Receptor-Binding SET Domain Family Histone Lysine Methyltransferases in Cancer," Cold Spring Harb. Perspect. Med., Jun. 2017, 7(6):a026708.
Berge et al., "Pharmaceutical Salts," Journal of Pharmaceutical Science, 1997, 66:1-19.
Bilsland et al., "Behavioral and neurochemical alterations in mice deficient in anaplastic lymphoma kinase suggest therapeutic potential for psychiatric indications," Neuropsychopharmacology, 2008, 33:685-700.
Biondi et al., "Biological and therapeutic aspects of infant leukemia. ," Blood, Jul. 2000, 96:24-33.
Biswas et al., "Function of leukemogenic mixed lineage leukemia 1 (MLL) fusion proteins through distinct partner protein complexes," Proc. Natl. Acad. Sci. USA, Sep. 2011, 108(38):15751-15756.
Bitoun et al., "The mixed-lineage leukemia fusion partner 10 AF4 stimulates RNA polymerase II transcriptional elongation and mediates coordinated chromatin remodeling," Human Molecular Genetics, Jan. 2007, 16:92-106.
Blake et al., "Discovery and preclinical pharmacology of a selective ATP-competitive Akt inhibitor (GDC-0068) for the treatment of human tumors," J. Med. Chem., Sep. 2012, 55(18):8110-8127.
Bolshan et al., "Synthesis, optimization, and evaluation of novel small molecules as antagonists of WDR5-MLL interaction," ACS Medicinal Chemistry Letters, Mar. 2013, 4(3):353-357.
Bondeson et al., "Catalytic in vivo protein knockdown by small-molecule PROTACs," Nature Chemical Biology, 2015, 11(8):611-617.
Bondeson et al., "Lessons in PROTAC design from selective degradation with a promiscuous warhead," Cell Chem. Biol., Jan. 2018, 25:78-87e5.
Bottcher et al., "Fragment-based discovery of a chemical probe for the PWWP1 domain of NSD3," Nat. Chem. Biol., Aug. 2019, 15:822-829.
Bourdi et al., "Safety Assessment of Metarrestin in Dogs: A Clinical Candidate Targeting a Subnuclear Structure Unique to Metastatic Cancer Cell," Regul. Toxicol. Pharmacol., Aug. 2020, 116:104716.
Bracken et al., "EZH2 is downstream of the pRB-E2F pathway, essential for proliferation and amplified in cancer," EMBO J., 2003, 22(20)5323-5335.

(56) References Cited

OTHER PUBLICATIONS

Bradley et al., "EZH2 Inhibitor Efficacy in Non-Hodgkin's Lymphoma Does Not Require Suppression of H3K27 Monomethylation," Chem. Biol., 2014, 21(11):1463-1475.
Brand et al., "Homolog-selective degradation as a strategy to probe the function of CDK6 in AML," Cell Chem. Biol., Feb. 2019, 26(2):300-306e9.
Brauer et al., "Building a better understanding of the intracellular tyrosine kinase PTK6—BRK by BRK," Biochim. Biophys. Acta., Aug. 2010, 1806:66-73.
Braun et al., "Coordinated Splicing of Regulatory Detained Introns within Oncogenic Transcripts Creates an Exploitable Vulnerability in Malignant Glioma," Cancer Cell, Oct. 2017, 32(4):411-426.
Brooun et al., "Polycomb repressive complex 2 structure with inhibitor reveals a mechanism of activation and drug resistance," Nat. Commun., Apr. 28, 2016, 7:11384, 12 pages.
Browne et al., "Regulation of peptide-chain elongation in mammalian cells," Eur. J. Biochem., Nov. 2002, 269:5360-5368.
Buckley et al., "HaloPROTACS: use of small molecule PROTACs to induce degradation of HaloTag fusion proteins," ACS Chemical Biology, Aug. 2015, 10(8):1831-1837.
Buckley et al., "Small-molecule control of intracellular protein levels through modulation of the ubiquitin proteasome system," Angew Chem. Int. Ed. Engl., 2014, 53(9):2312-2330.
Buckley et al., "Small-molecule inhibitors of the interaction between the E3 ligase VHL and HIF1α," Angew Chem Int. Ed. Engl., 2012, 51(46):11463-11467.
Buckley et al., "Targeting the von Hippel-Lindau E3 ubiquitin ligase using small molecules to disrupt the VHL/HIF-1α interaction," Journal of the American Chemical Society, 2012, 134(10):4465-4468.
Burkhart et al., "Cellular mechanisms of tumour suppression by the retinoblastoma gene," Nature Reviews Cancer, 2008, 8(9):671-682.
Burnet, "The concept of immunological surveillance," Progress Exp. Tumor Res., 1970, 13:1-27.
Burslem et al., "Small-molecule modulation of protein homeostasis," Chem. Rev., Aug. 2017, 117(17):11269-11301.
Burslem et al., "The advantages of targeted protein degradation over inhibition: An RTK case study," Cell Chem. Biol., Jan. 2018, 25:67-77e3.
Cai et al., "Subunit composition and substrate specificity of a MOF-containing histone acetyltransferase distinct from the male-specific lethal (MSL) complex," The Journal of Biological Chemistry, Feb. 2010, 285(7):4268-4272.
Cai et al., "ZFX Mediates Non-canonical Oncogenic Functions of the Androgen Receptor Splice Variant 7 in Castrate-Resistant Prostate Cancer," 2018, Mol. Cell 72, 341-354 e346.
Campbell et al., "EPZ011989, A Potent, Orally-Available EZH2 Inhibitor with Robust in Vivo Activity," ACS Med. Chem. Lett., 2015, 6(5):491-495.
Cao et al., "Regulation and functional role of eEF1A2 in pancreatic carcinoma," Biochem. Biophys. Res. Commun., 2009, 380(1):11-16.
Cao et al., "Role of Histone H3 Lysine 27 Methylation in Polycomb-Group Silencing," Science, 2002, 298(5595):1039-1043.
Cao et al., "Targeting MLL1 H3K4 methyltransferase activity in mixed-lineage leukemia," Molecular Cell, Jan. 2014, 53(2):247-261.
Cappuzzo et al., "Erlotinib as maintenance treatment in advanced non-small-cell lung cancer: a multicentre, randomised, placebo-controlled phase 3 study," Lancet Oncol., Jun. 2010, 11:521-529.
Cardenas et al., "Enantioselective Synthesis of Pyrrolopyrirnidine Scaffolds through Cation-Directed Nucleophilic Aromatic Substitution," Org. Lett., Mar. 2018, 20:2037-2041.
Carugo et al., "In vivo functional platform targeting patient-derived xenografts identifies WDR5-Myc association as a critical determinant of pancreatic cancer," Cell Reports, Jun. 2016, 16(1):133-147.
Castro et al., "Breast tumor kinase and extracellular signal-regulated kinase 5 mediate Met receptor signaling to cell migration in breast cancer cells," Breast Cancer Research, 2010, 12:R60, 15 pages.
Chamberlain et al., "Structure of the human Cereblon-DDB1-lenalidomide complex reveals basis for responsiveness to thalidomide analogs," Nat. Struct. Mol. Biol., 2014, 21(9):803-809.
Chang et al., "EZH2 promotes expansion of breast tumor initiating cells through activation of RAF1-β-catenin signaling, " Cancer Cell, 2011, 19(1):86-100.
Chan-Penebre et al., "A selective inhibitor of PRMT5 with in vivo and in vitro potency in MCL models," Nature Chemical Biology, Apr. 2015, 11:432-437.
Chau et al., "An Anatomical Site and Genetic-Base Prognostic Model for Patients With Nuclear Protein in Testis (NUT) Midline Carcinoma: Analysis of 124 Patients," JNCI Cancer Spectr 4, 2020, pkz094 2020.
Chawade et al., "Normalyzer: a tool for rapid evaluation of normalization methods for omics data sets," J. Proteome. Res., 2014, 13:3114-31202014.
Chen et al., "Design, synthesis, and initial evaluation of affinity-based small molecular probe for detection of WDR5," Bioorganic Chemistry, Feb. 2018, 76:380-385.
Chen et al., "Gene expression profiling of WDR5 regulated genes in bladder cancer," Genomics Data, Sep. 2015, 5:27-29.
Chen et al., "PTK6 promotes hepatocellular carcinoma cell proliferation and invasion," Am. J. Transl. Res., Oct. 2016, (10):4354-4361.
Chen et al., "Upregulated WDR5 promotes proliferation, self-renewal and chemoresistance in bladder cancer via mediating H3K4 trimethylation," Scientific Reports, Feb. 2015, 5: 12 pages.
Chi et al., "Covalent histone modifications—miswritten, misinterpreted and mis-erased in human cancers," Nat. Rev. Cancer, 2010, 10:457-469.
Choi et al., "EML4-ALK mutations in lung cancer that confer resistance to ALK inhibitors," N. Engl. J. Med., Oct. 2010, 363(18):1734-1739.
Choi et al., "Identification of novel isoforms of the EML4-ALK transforming gene in non-small cell lung cancer," Cancer Res., Jul. 2008, 68(13):4971-4976.
Christott et al., "Discovery of a Selective Inhibitor for the YEATS Domains of ENL/AF9.," SLAS Discov., 2019, 24:133-141.
Chung et al., "Cbx8 acts non-canonically with Wdr5 to promote mammary tumorigenesis," Cell Reports, Jul. 2016, 16(2):472-486.
Clinicaltrials.gov [online], "Metarrestin (ML-246) in Subjects with Metastatic Solid Tumors," Jan. 10, 2020, retrieved on Mar. 16, 2022, retrieved from URL<https://clinicaltrials.gov/ct2/show/NCT04222413>, 12 pages.
CN Office Action in Chinese Appln. No. 201780081246.8, dated Dec. 2, 2021, 18 pages (with English Translation).
CN Office Action in Chinese Appln. No. 201780081246.8, dated Jun. 4, 2021, 19 pages (with English Translation).
CN Office Action in Chinese Appln. No. 201780085879.6, dated Jan. 5, 2022, 18 pages (with English Translation).
Corthay, "Does the immune system naturally protect against cancer? Front. Immunol.," May 2014, 5(197):1-8.
Cromm et al., "Addressing kinase-independent functions of Fak via PROTAC-mediated degradation," J. Am. Chem. Soc., Nov. 2018, 140(49):17019-17026.
Cromm et al., "Targeted protein degradation: from chemical biology to drug discovery," Cell Chem. Biol., Sep. 2017, 24(9):1181-1190.
Czermin et al., "*Drosophila* enhancer of Zeste/ESC complexes have a histone H3 methyltransferase activity that marks chromosomal Polycomb sites," Cell, 2002, 111(2):185-196.
Dai et al., "WDR5 expression is prognostic of breast cancer outcome," PLoS One, Sep. 2015, 10: 15 pages.
Davies et al., "Monoacidic Inhibitors of the Kelch-like ECH-Associated Protein 1: Nuclear Factor Erythroid 2-Related Factor 2 (KEAP1 :NRF2) Protein-Protein Interaction with High Cell Potency Identified by Fragment-Based Discovery," Journal of Medicinal Chemistry, Apr. 2016, 59(8):3991-4006.
Dawson et al., "Inhibition of BET recruitment to chromatin as an effective treatment for MLL-fusion leukaemia," Nature, 2011, 478:529-15 533.
Deng et al., "Protein arginine methyltransferase 5 functions as an epigenetic activator of the androgen receptor to promote prostate cancer cell growth," Oncogene, 2017, 36:1223-1231.

(56) References Cited

OTHER PUBLICATIONS

Derry et al., "Altered localization and activity of the intracellular tyrosine kinase BRK/Sik in prostate tumor cells," Oncogene, Jul. 2003, 22:4212-4220.
Deshpande et al., "Chromatin modifications as therapeutic targets in MLL-rearranged leukemia," Trends Immunol., Nov. 2012, 33(11):563-570.
Dias et al., "Structural analysis of the KANSL1/WDR5/KANSL2 complex reveals that WDR5 is required for efficient assembly and chromatin targeting of the NSL complex," Genes & Development, May 2014, 28(9):929-942.
Douglass, Jr. et al., "A comprehensive mathematical model for three-body binding equilibria," J. Am. Chem. Soc., Apr. 2013, 135(16):6092-6099.
Du et al., "FOXC1, a target of polycomb, inhibits metastasis of breast cancer cells," Breast Cancer Res. Treat., 2012, 131(1):65-73.
Duanmin et al., "eEF1A2 protein expression correlates with lymph node metastasis and decreased survival in pancreatic ductal adenocarcinoma," Hepatogastroenterology, Jun. 2013, 60(124):870-875.
Dumble et al., "Discovery of novel AKT inhibitors with enhanced anti-tumor effects in combination with the MEK inhibitor," PloS One, Jun. 2014, 9(6), 11 pages.
EA Office Action in Eurasian Appln. No. 201991071, dated Jun. 10, 2020, 4 pages (with English translation).
Ee et al., "An embryonic stem cell-specific NuRD complex functions through interaction with WDR5," Stem Cell Reports, Jun. 2017, 8(6): 9 pages.
EP Extended European Search Report in European Appln. No. 17863645.2, dated Aug. 6, 2020, 10 pages.
EP Extended European Search Report in European Appln. No. 17877800.7, dated Feb. 19, 2021, 9 pages.
EP Extended European Search Report in European Appln. No. 19757825.5, dated Jan. 26, 2022, 14 pages.
EP Extended European Search Report in European Appln. No. 19763958.6, dated Dec. 8, 2021, 12 pages.
EP Extended European Search Report in European Appln. No. 19830269.7, dated Mar. 7, 2022, 6 pages.
EP Office Action in European Appln. No. 17863645.2, dated Apr. 6, 2021, 7 pages.
EP Office Action in European Appln. No. 17863645.2, dated Mar. 11, 2022, 5 pages.
EP Office Action in European Appln. No. 19821826.5, dated Jan. 13, 2022, 4 pages.
EP Partial Supplementary Search Report in European Appln. No. 19757825.5, dated Oct. 18, 2021, 16 pages.
Erb et al. (2017). Transcription control by the ENL YEATS domain in acute leukaemia. Nature 543, 270-274.
Fabian et al., "A small molecule-kinase interaction map for clinical kinase inhibitors," Nat. Biotechnol., Mar. 2005, 23(3):329-336.
Fan et al., "A Kinase Inhibitor Targeted to mTORC1 Drives Regression in Glioblastoma," Cancer Cell, Mar. 2017, 31(3):424-435.
Fan et al., "BAHCC1 binds H3K27me3 via a conserved BAH module to mediate gene silencing and oncogenesis," Nature genetics, 2020, 52:1384-1396.
fda.gov [online], "Data Standards Manual (Monographs)," Feb. 27, 2018, retrieved on Feb. 7, 2022, retrieved from URL <https://www.fda.gov/drugs/electronic-regulatory-submission-and-review/data-standards-manual-monographs>, 1 page.
fda.gov [online], "Development & Approval Process | Drugs," Oct. 28, 2019, retrieved on Feb. 4, 2022, retrieved from URL <https://www.fda.gov/drugs/development-approval-process-drugs>, 4 pages.
Fei et al., "PROTAC and its Application in the Treatment of Cancer," Chemistry of Life, Aug. 2014, 34(4):549-554 (with English abstract).
Ferguson et al., "Kinase inhibitors: the road ahead," Nat. Rev. Drug Discov., May 2018, 17:353-377.
Ferrando et al., "Gene expression signatures in MLL-rearranged T-lineage and B-precursor acute leukemias: dominance of HOX dysregulation," Blood, Jul. 2003, 102(1):262-268.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," The Lancet Oncology, 2015, 16(1):25-35.
Fischer et al., "Structure of the DDB1-CRBN E3 ubiquitin ligase in complex with thalidomide," Nature, Aug. 2014, 512(7512):49-53.
Frankowski et al., "Metarrestin, a perinucleolar compartment inhibitor, effectively suppresses metastasis," Science Translational Medicine, May 2018, 10(441), 13 pages.
Frost et al., "Potent and selective chemical probe of hypoxic signalling downstream of HIF-α hydroxylation via VHL inhibition," Nat. Commun., Nov. 2016, 7:13312, 12 pages.
Fujii et al., "Enhancer of Zeste Homologue 2 (EZH2) Down-regulates RUNX3 by Increasing Histone H3 Methylation," J. Biol. Chem., 2008, 283(25):17324-17332.
Fujii et al., "MEKERK pathway regulates EZH2 overexpression in association with aggressive breast cancer subtypes," Oncogene, 2011, 30(39):4118-4128.
Gadd et al., "A Children's Oncology Group and TARGET initiative exploring the genetic landscape of Wilms tumor," Nat. Genet., Oct. 2017, 49:1487-1494.
Galdeano et al., "Structure-guided design and optimization of small molecules targeting the protein-protein interaction between the von Hippel-Lindau (Vhl) E3 ubiquitin ligase and the hypoxia inducible factor (HIF) alpha subunit with in vitro nanomolar affinities," J. Med. Chem., 2014, 57(20):8657-8663.
Gao et al., "ZLD1122, a novel EZH2 and EZH1 small molecular inhibitor, blocks H3K27 methylation and diffuse large B cell lymphoma cell growth," RSC Adv., 2016, 6:28512-28521.
Garapaty-Rao et al., "Identification of EZH2 and EZH1 small molecule inhibitors with selective impact on diffuse large B cell lymphoma cell growth," Chem. Biol., 2013, 20(11):1329-1339.
Garnar-Wortzel et al., "Chemical Inhibition of ENL/AF9 YEATS Domains in Acute Leukemia," ACS Central Science, Apr. 2021, 7(5):815-830.
Ge et al., "WDR5 high expression and its effect on tumorigenesis in leukemia," Oncotarget, Jun. 2016, 7(25):37740-37754.
Gehling et al., "Discovery, design, and synthesis of indole-based EZH2 inhibitors," Bioorg. Med. Chem. Lett., 2015, 25(17):3644-3649.
Genscript.com [online], "Gen Script Make Research Easy," available on or before Mar. 3, 2015, retrieved on Mar. 17, 2022, retrieved from URL<https://www.genscript.com/gRNAdatabase.html>.
Gillis et al., "Biochemical and biological characterization of lymphocyte regulatory molecules; V. Identification of an interleukin 2-producing human leukemia T cell line," The Journal of experimental medicine, Dec. 1980,152:1709-1719.
Github.com [online], "ProteiNorm," Jul. 27, 2020, retrieved on Mar. 17, 2022, retrieved from URL <https://github.com/ByrumLab/proteiNorm>, 3 page.
Gluz et al., "Triplenegative breast cancer—current status and future directions," Ann. Oncol., 2009, 20(12):1913-1927.
Godin-Heymann et al., "The T790M 'gatekeeper' mutation in EGFR mediates resistance to low concentrations of an irreversible EGFR inhibitor," Mol. Cancer Ther., Apr. 2008, 7(4):874-879.
Gonzalez et al., "Downregulation of EZH2 decreases growth of estrogen receptor-negative invasive breast carcinoma and requires BRCA1," Oncogene, 2009, 28(6):843-853.
Gonzalez et al., "EZH2 expands breast stem cells through activation of NOTCH1 signaling," Proc. Natl. Acad. Sci. USA, 2014, 111(8):3098-3103.
Grabe et al., "C797S Resistance: The undruggable EGFR mutation in non-small cell lung cancer?" ACS Med. Chem. Lett., 2018, 9:779-782.
Grebien et al., "Pharmacological targeting of the Wdr5-MLL interaction in C/EBPα N-terminal leukemia," Nature Chemical Biology, Aug. 2015, 11(8): 11 pages.
Guarnaccia et al., "Moonlighting with WDR5: A cellular multitasker," Journal of Clinical Medicine, Feb. 2018, 7(2): 17 pages.

(56) References Cited

OTHER PUBLICATIONS

Gullà et al., "Protein arginine methyltransferase 5 has prognostic relevance and is a druggable target in multiple myeloma," Leukemia, 2018, 32:996-1002.
Haegebarth et al., "Protein tyrosine kinase 6 negatively regulates growth and promotes enterocyte differentiation in the small intestine," Mol. Cell Biol., Jul. 2006, 26:4949-4957.
Hallberg et al., "Mechanistic insight into ALK receptor tyrosine kinase in human cancer biology," Nature Reviews Cancer, Oct. 2013, 13:685-700.
Hamilton et al., "Targeting CDK4/6 in patients with cancer," Cancer Treatment Reviews, 2016, 45:129-138.
Han et al., "Discovery of ARD-69 as a Highly Potent Proteolysis Targeting Chimera (PROTAC) Degrader of Androgen Receptor (AR) for the Treatment of Prostate Cancer," Journal of Medicinal Chemistry, Jan. 2019, 62:941-964.
Harvey et al., "Brk protects breast cancer cells from autophagic cell death induced by loss of anchorage," The American Journal of Pathology, Sep. 2009, 175:1226-1234.
Harvey et al., "Use of RNA interference to validate Brk as a novel therapeutic target in breast cancer: Brk promotes breast carcinoma cell proliferation," Oncogene, Aug. 2003, 22:5006-5010.
He et al., "HIV-1 Tat and Host AFF4 Recruit Two Transcription Elongation Factors into a Bifunctional Complex for Coordinated Activation of HIV-I Transcription," Mol. Cell., May 2010, 38(3):428-438.
He et al., "Human Polymerase-Associated Factor complex (PAFc) connects the Super Elongation Complex (SEC) to RNA polymerase II on chromatin," Proc. Natl. Acad. Sci. USA, Sep. 2011, 108(36):E636-E645.
Heerding et al., "Identification of 4-(2-(4-amino-1,2,5-oxadiazol-3-yl)-1-ethyl-7-{[(3S)-3-piperidinylmethyl]oxy }-1H-imidazo[4,5-c]pyridin-4-yl)-2-methyl-3-butyn-2-ol (GSK690693), a novel inhibitor of AKT kinase," Journal of Medicinal Chemistry, Sep. 2008, 51(18):5663-5679.
Heidenreich et al., "Structure-Based Approach toward Identification of Inhibitory Fragments for Eleven-Nineteen-Leukemia Protein (ENL)," J. Med. Chem., Nov. 2018, 61(23):10929-10934.
Henning et al., "Degradation of Akt using protein-catalyzed capture agent," Journal of Peptide Science, 2016, 22:196-200.
Herbst et al., "Gefitinib—a novel targeted approach to treating cancer," Nat. Rev. Cancer, Dec. 2004, 4:956-965.
Hernandez et al., "The Kinase Activity of Hematopoietic Progenitor Kinase 1 Is Essential for the Regulation of T Cell Function," Cell reports, Oct. 2018, 25:80-94.
Herrera-Abreu et al., "Early adaptation and acquired resistance to CDK4/6 inhibition in estrogen receptor-positive breast cancer," Cancer Research, 2016, 76(8):2301-2313.
Hess, "MLL: a histone methyltransferase disrupted in leukemia," Trends Mol. Med., Oct. 2004, 10(10):500-507.
Higa et al., "CUL4-DDB 1 ubiquitin ligase interacts with multiple WD40-repeat proteins and regulates histone methylation," Nature Cell Biology, Nov. 2006, 8(11):1277-1283.
Hirai et al., "MK-2206, an allosteric Akt inhibitor, enhances antitumor efficacy by standard chemotherapeutic agents or molecular targeted drugs in vitro and in vivo," Molecular Cancer Therapeutics, Jul. 2010, 9(7):1956-1967.
Hiroyuki et al., "The structure of bestatin," The Journal of Antibiotics, Jan. 1976, 29(1):100-101.
Hirsch et al., "Lung cancer: current therapies and new targeted treatments," Lancet, Jan. 2017, 389:299-311.
Holm et al., "Global H3K27 trimethylation and EZH2 abundance in breast tumor subtypes," Mol. Oncol., 2012, 6(5):494-506.
Hsu et al., "Recognition of histone acetylation by the GAS41 YEATS domain promotes H2A.Z deposition in non-small cell lung cancer," Genes Dev., 2018, 32:58-69.
Hu et al., "Human HPK1, a novel human hematopoietic progenitor kinase that activates the JNK/SAPK kinase cascade," Genes Dev., Sep. 1996, 10:2251-2264.
Hu et al., "Small Molecule Inhibitors of Protein Arginine Methyltransferases," Expert Opinion Investigational Drugs, 2016, 25:335-358.
Huang et al., "A Chemoproteomic Approach to Query the Degradable Kinome Using a Multi-kinase Degrader," Cell Chemical Biology, Jan. 2018, 25(1):88-99.
Huang et al., "Covalent inhibition of NSD1 histone methyltransferase," Nat. Chem. Biol, 2020, 16:1403-1410.
Huber et al., "Variance stabilization applied to microarray data calibration and to the quantification of differential expression," Bioinformatics, 2002, 18 Suppl 1:S96-104.
IN Office Action in Indian Appln. No. 201917020814, dated Jun. 23, 2021, 6 pages (with English Translation).
Irie et al., "PTK6 regulates IGF-1-induced anchorage-independent survival," PLoS One, Jul. 2010, 5(7):el1729.
Ito et al., "Identification of a primary target of thalidomide teratogenicity," Science, Mar. 2010, 327(5971):1345-1350.
Ito et al., "PTK6 Inhibition Suppresses Metastases of Triple-Negative Breast Cancer via SNAIL-Dependent E-Cadherin regulation," Cancer Res., Aug. 2016, 76:4406-4417.
Ito et al., "PTK6 regulates growth and survival of endocrine therapy-resistant ER+ breast cancer cells," NPJ Breast Cancer, Nov. 2017, 3:45.
Iwahara et al., "Molecular characterization of ALK, a receptor tyrosine kinase expressed specifically in the nervous system," Oncogene, Jan. 30, 1997, 14:439-449.
Jakobsson et al., "The dual methyltransferase METTL13 targets N terminus and Lys55 of eEF1A and modulates codon-specific translation rates," Nature Communications, Aug. 2018, 15 pages.
Jiang et al., "Development of dual and selective degraders of cyclin-dependent kinases 4 and 6," Angew. Chem. Int. Ed. Engl., May 2019, 58(19):6321-6326.
Jiang et al., "Targeting BRK-Positive Breast Cancers with Small-Molecule Kinase Inhibitors," Cancer Res., Jan. 2017, 77:175-186.
Jiao et al., "Structural basis of histone H3K27 trimethylation by an active polycomb repressive complex 2," Science, 2015, 350(6258):aac4383.
Jin et al., "Targeting methyltransferase PRMT5 eliminates leukemia stem cells in chronic myelogenous leukemia," The Journal of Clinical Investigation, Oct. 2016, 126:3961-3980.
JP Office Action in Japanese Appln. No. 2019-522841, dated Oct. 5, 2021, 14 pages (with English Translation).
JP Office Action in Japanese Appln. No. 2019-530811, dated Dec. 14, 2021, 4 pages (with English Translation).
Jude et al., "Unique and independent roles for MLL in adult hematopoietic stem cells and progenitors," Cell Stem Cell, Sep. 2007, 1(3):324-337.
Justin et al., "Structural basis of oncogenic histone H3K27M inhibition of human polycomb repressive complex 2," Nat. Commun., 2016, 7:11316.
Kanda et al., "Protein arginine methyltransferase 5 is associated with malignant phenotype and peritoneal metastasis in gastric cancer," International Journal of Oncology, Jun. 2016, 49:1195-1202.
Kanis et al., "A small molecule inhibitor of the perinucleolar compartment, ML246, attenuates growth and spread of ovarian cancer," Gynecol. Oncol. Res. Pract., 2018, 5:7.
Kanis et al., "Metarrestin: A novel compound active against ovarian cancer," Gynecol Oncol., Oct. 2015, 139(1):190.
Kaniskan et al., "Selective inhibitors of protein methyltransferases," Journal of Medicinal Chemistry, 2015, 58:1596-1629.
Karatas et al., "Discovery of a highly potent, cell-permeable macrocyclic peptidomimetic (MM-589) targeting the WD repeat domain 5 protein (WDR5)-mixed lineage leukemia (MLL) protein-protein interaction," Journal of Medicinal Chemistry, Jun. 2017, 60(12):4818-4839.
Khalyfa et al., "Characterization of elongation factor-1A (eEF1A-1) and eEF1A-2/S1 protein expression in normal and wasted mice," Journal of Biological Chemistry, 2001, 276:22915-22922.
Kiefer et al., "HPK1, a hematopoietic protein kinase activating the SAPK/JNK pathway," EMBO J., Dec. 1996, 15(24):7013-7025.

(56) References Cited

OTHER PUBLICATIONS

Kim et al., "Targeted disruption of the EZH2-EED complex inhibits EZH2-dependent cancer" Nature Chemical Biology, 2013, 9:643-650.
Kim et al., "Targeting EZH2 in cancer," Nat. Med., 2016, 22(2):128-134.
Kleer et al., "EZH2 is a marker of aggressive breast cancer and promotes neoplastic transformation of breast epithelial cells," PNAS, 2003, 100(20):11606-11611.
Klein et al., "Yaf9 subunit of the NuA4 and SWR1 complexes targets histone H3K27ac through its YEATS domain," Nucleic Acids Res., Jan. 2018, 46:421-430.
Knutson et al., "A selective inhibitor of EZH2 blocks H3K27 methylation and kills mutant lymphoma cells," Nat. Chem. Biol., 8(11):890-896.
Knutson et al., "Durable tumor regression in genetically altered malignant rhabdoid tumors by inhibition of methyltransferase EZH2," Proc. Natl. Acad. Sci. USA., 2013, 110(19):7922-7927.
Kobayashi et al., "EGFR mutation and resistance of non-small-cell lung cancer to gefitinib," N. Engl. J. Med., Feb. 2005, 352(8):786-792.
Koivunen et al., "EML4-ALK fusion gene and efficacy of an ALK kinase inhibitor in lung cancer," Clinical Cancer Research, Jul. 1, 2008, 14(13):4275-4283.
Konze et al., "An Orally Bioavailable Chemical Probe of the Lysine Methyltransferases EZH2 and EZHI," ACS Chem. Biol., 2013, 8(6):1324-1334.
Krause et al., "Tyrosine kinases as targets for cancer therapy," N. Engl. J. Med., Jul. 2005, 353(2):172-187.
Krivtsov et al., "MLL translocations, histone modifications and leukaemia stem-cell development," Nat. Rev. Cancer, Nov. 2007, 7:823-833.
Kryukov et al., "MTAP deletion confers enhanced dependency on the PRMT5 arginine methyltransferase in cancer cells," Science, 2016, 351(6278):1214-1218.
Kuenzi et al., "Polypharmacology-based ceritinib repurposing using integrated functional proteomics," Nat. Chem. Biol., Dec. 2017, 13(12):1222-1231.
Kung et al., "Design and Synthesis of Pyridone-Containing 3,4-Dihydroisoquinoline-1(2H)-ones as a Novel Class of Enhancer of Zeste Homolog 2 (EZH2) Inhibitors," J. Med. Chem., 2016, 59(18):8306-8325.
Kuzmichev et al., "Histone methyltransferase activity associated with a human multiprotein complex containing the Enhancer of Zeste protein," Genes Dev., 2002, 16(22):2893-2905.
Kwak et al., "Anaplastic lymphoma kinase inhibition in non-small-cell lung cancer," New England Journal of Medicine, Oct. 28, 2010, 363(18):1693-1703.
Lai et al., "Induced protein degradation: an emerging drug discovery paradigm," Nat. Rev. Drug Discov., Feb. 2017, 16(2):101-114.
Lai et al., "Modular PROTAC design for the degradation of oncogenic BCR-ABL," Angewandte Chemie International Edition English, Jan. 2016, 55(2):807-810.
Lapierre et al., "Discovery of 3-(3-(4-(1-Aminocyclobutyl)phenyl)-5-phenyl-3H-imidazo[4,5-b]pyridin-2-yl)pyridin-2-amine (ARQ 092): An orally bioavailable, selective, and potent allosteric AKT inhibitor," Journal of Medicinal Chemistry, 2016, 59:6455-6469.
Lebraud et al., "Protein Degradation by In-Cell Self-Assembly of Proteolysis Targeting Chimeras," ACS Central Science, 2016, 2:927-934.
Li et al., "AF9 YEATS domain links histone acetylation to DOT1L-mediated H3K79 methylation," Cell, Oct. 2014, 159(3):558-571.
Li et al., "Discovery of MD-224 as a first-in-class, highly potent, and efficacious proteolysis targeting chimera Murine Double Minute 2 degrader capable of achieving complete and durable tumor regression," J. Med. Chem., 2019, 62(2):448-466.
Li et al., "Discovery of potent and noncovalent reversible EGFR kinase inhibitors of $EGFR^{L858R/T790M/C797S}$," ACS Med. Chem. Lett., Jun. 2019, 10(6):869-873.
Li et al., "High-affinity small molecular blockers of mixed lineage leukemia 1 (MLL1)-WDR5 interaction inhibit MILL1 complex H3K4 methyltransferase activity," European Journal of Medicinal Chemistry, Nov. 2016, 124:480-489.
Li et al., "Molecular Coupling of Histone Crotonylation and Active Transcription by AF9 YEATS Domain," Mol. Cell., Apr. 2016, 62(2):181-193.
Li et al., "RSEM: accurate transcript quantification from RNA-Seq data with or without a reference genome," Bmc Bioinformatics, 2011, 12:323.
Li et al., "Structure-based design and synthesis of small molecular inhibitors disturbing the interaction of MLL1-WDR5," European Journal of Medicinal Chemistry, Aug. 2016, 118:1-8.
Li et al., "Structure-guided development of YEATS domain inhibitors by targeting πππ stacking," Nat. Chem. Biol., Dec. 2018, 14:1140-1149.
Li et al., "The OncoPPi network of cancer-focused protein-protein interactions to inform biological insights and therapeutic strategies," Nat. Commun., Feb. 2017, 8:14356.
Li et al., "Understanding histone H3 lysine 36 methylation and its deregulation in disease," Cell. Mol. Life Sci., Aug. 2019, 76(15):2899-2916.
Li et al., "ZMYND11-MBTD1 induces leukemogenesis through hijacking NuA4/TIP60 acetyltransferase complex and a PWWP-mediated chromatin association mechanism," Nat. Commun., 2021, 12(1), 18 pages.
Lim et al., "CDK4/6 inhibitors: promising opportunities beyond breast cancer," Cancer Discovery, 2016, 6(7):697-699.
Lin et al., "AFF4, a component of the ELL/PTEFb elongation complex and a shared subunit of MLL chimeras, can link transcription elongation to leukemia," Mol. Cell., Feb. 2010, 37(3):429-437.
Lin et al., "Clinicopathologic features, patterns of recurrence, and survival among women with triple-negative breast cancer in the National Comprehensive Cancer Network," Cancer, 2012, 118(22):5463-5472.
Lin et al., "Targeting ALK: Precision Medicine Takes on Drug Resistance," Cancer Discovery, Feb. 2017, 7(2):137-155.
Ling et al., "Involvement of hematopoietic progenitor kinase 1 in T cell receptor signaling," The Journal of biological chemistry, Jun. 2001, 276:18908-18914.
Liou et al., "HPK1 is activated by lymphocyte antigen receptors and negatively regulates AP-1," Immunity, Apr. 2000, 12(4):399-408.
Liu et al., "Calcineurin is a common target of cyclophilin-cyclosporin A and FKBP-FK506 complexes," Cell, Aug. 1991, 66(4):807-815.
Liu et al., "Critical role of kinase activity of hematopoietic progenitor kinase 1 in anti-tumor immune surveillance, " PloS one, Mar. 2019, 14:e02 12670.
Liu et al., "METTL13 Methylation of eEF1A Increases Translational Output to Promote Tumorigenesis," Cell, Jan. 2019, 176:491-504.e421.
Liu et al., "Widening Synthesis Bottlenecks: Realization of Ultrafast and Continuous-Flow Synthesis of High-Silica Zeolite SSZ-13 for NOx Removal," Angew. Chem., May 4, 2015, 127(19):5775-5779.
Losada et al., "Binding of eEF1A2 to the RNA-dependent protein kinase PKR modulates its activity and promotes tumour cell survival," British Journal of Cancer, Nov. 2018, 119(11):1410-1420.
Lu et al., "Epigenetic Perturbations by Arg882-Mutated DNMT3A Potentiate Aberrant Stem Cell Gene-Expression Program and Acute Leukemia Development," Cancer Cell, 2016, 30:92-107.
Lu et al., "Hijacking the E3 ubiquitin ligase cereblon to efficiently target BRD4," Chemistry & Biology, Jun. 2015, 22(6):755-763.
Lu et al., "Targeting $EGFR^{L858R/T790M}$ and $EGFR^{L858R/T790M/C797S}$ resistance mutations in NSCLC: Current developments in medicinal chemistry," Med. Res. Rev., Jan. 2018, 38(5):1550-1581.
Mahara et al., "HIFI-α activation underlies a functional switch in the paradoxical role of Ezh2/PRC2 in breast cancer," PNAS, 2016, 113(26):E3735-E3744.
Mahmoud et al., "Discovery of 4-anilino α-carbolines as novel Brk inhibitors," Bioorganic & Medicinal Chemistry Letters, Apr. 2014, 24:1948-1951.
Majer et al., "A687V EZH2 is a gain-offunction mutation found in lymphoma patients," FEBS Lett., 2012, 586(19):3448-3451.

(56) References Cited

OTHER PUBLICATIONS

Maniaci et al., "Homo-PROTACs: bivalent small-molecule dimerizers of the VHL E3 ubiquitin ligase to induce self-degradation," Nature Communication, Oct. 2017, 8, 14 pages.
Manning et al., "AKT/PKB signaling: navigating the network," Cell, Apr. 2017, 169(3):381-405.
Marjon et al., "MTAP Deletions in Cancer Create Vulnerability to Targeting of the MAT2A/PRMT5/RIOK1 Axis," Cell Reports, Apr. 2016, 15:574-587.
Marschalek, "MLL Leukemia and Future Treatment Strategies," Arch. Pharm. Chem. Life Sci., Apr. 2015, 348(4):221-228.
Matsushime et al., "Identification and properties of an atypical catalytic subunit ($p34^{PSK-J3}$/cdk4) for mammalian D type G1 cyclins," Cell, 1992, 71(2):323-334.
Mavrakis et al., "Disordered methionine metabolism in MTAP/CDKN2A-deleted cancers leads to dependence on PRMT5," Science, Feb. 2016, 351(6278):1208-1213.
Mcalpine et al., "Abstract 4857: Discovery of PF-06855800, a SAM competitive PRMT5 inhibitor with potent antitumor activity," American Association for Cancer Research Annual Meeting, 2018, 78(13 Supplement), 4 pages.
McCabe et al., "EZH2 inhibition as a therapeutic strategy for lymphoma with EZH2-activating mutations," Nature, 2012, 492(7427):108-112.
McCabe et al., "Mutation of A677 in histone methyltransferase EZH2 in human B-cell lymphoma promotes hypertrimethylation of histone H3 on lysine 27 (H3K27)," Proc. Natl. Acad. Sci. USA, 2012, 109(8):2989-2994.
Meyer et al., "New insights to the MLL recombinome of acute leukemias," Leukemia, Aug. 2009, 23:1490-1499.
Meyer et al., "The MLL recombinome of acute leukemias in 2013," Leukemia, Nov. 2013, 27:2165-2176.
Meyer et al., "The MLL recombinome of acute leukemias," Leukemia, May 2006, 20:777-784.
Meyerson et al., "Identification of $G_1$ kinase activity for cdk6, a novel cyclin D partner," Molecular and Cellular Biology. 1994, 14(3):2077-2086.
Mi et al., "YEATS2 links histone acetylation to tumorigenesis of non-small cell lung cancer," Nat. Commun., Oct. 2017, 8:1088, 14 pages.
Migliori et al., "Symmetric dimethylation of H3R2 is a newly identified histone mark that supports euchromatin maintenance," Nature Structural and Molecular Biology, Feb. 2012, 19(2):136-144.
Miller et al., "COMPASS: a complex of proteins associated with atrithorax-related SET domain protein," Proceedings of the National Academy of Sciences, Nov. 2001, 98(23):12902-12907.
Mohan et al., "Licensed to elongate: a molecular mechanism for MLL-based leukaemogenesis," Nat. Rev. Cancer, Oct. 2010, 10:721-728.
Mohan et al., "Linking H3K79 trimethylation to Wnt signaling through a novel Dot1-containing complex (DotCom)," Genes Dev., 2010, 24:574-589.
Molander et al., "Efficient hydrolysis of organotrifluoroborates via silica gel and water," Journal of Organic Chemistry, Oct. 2009, 74(19):364-7369.
Morin et al., "Somatic mutations altering EZH2 (Y641) in follicular and diffuse large B-cell lymphomas of germinal-center origin," Nat. Genet., 2010, 42(2):181-185.
Morris et al., "ALK, the chromosome 2 gene locus altered by the t(2;5) in non-Hodgkin's lymphoma, encodes a novel neural receptor tyrosine kinase that is highly related to leukocyte tyrosine kinase (LTK)," Oncogene, Mar. 8, 1997, 14:2175-2188.
Morris et al., "Fusion of a kinase gene, ALK, to a nucleolar protein gene, NPM, in non-Hodgkin's lymphoma," Science, Mar. 4, 1994, 263(5151):1281-1284.
Moustakim et al., "Discovery of an MLLT1/3 Yeats Domain Chemical Probe," Angew. Chem. Int. Ed. Engl., Dec. 2018, 57(50):16302-16307.
Mueller et al., "A role for the MLL fusion partner ENL in transcriptional elongation and chromatin modification," Blood, Dec. 2007, 110(13):4445-4454.
Mueller et al., "Misguided Transcriptional Elongation Causes Mixed Lineage Leukemia," Plos Biol., Nov. 2009, 7(11):e1000249, 15 pages.
Müller et al., "Histone methyltransferase activity of a *Drosophila* Poly comb group repressor complex," Cell, 2002, 111(2):197-208.
MX Office Action in Mexican Appln. No. MX/a/2019/004950, dated Aug. 6, 2021, 6 pages (with English translation).
MX Office Action in Mexican Appln. No. MX/a/2019/004950, dated Nov. 23, 2021, 8 pages (with English Translation).
Nadeem Abbas et al., "Advances in targeting the epidermal growth factor receptor pathway by synthetic products and its regulation by epigenetic modulators as a therapy for glioblastoma," Cells, Apr. 2019, 8:350, 22 pages.
Neklesa et al., "Small-molecule hydrophobic tagging induced degradation of HaloTag fusion proteins," Nat. Chem. Biol., 2011, 7(8):538-543.
Ni et al., "Structural Insights into Interaction Mechanisms of Alternative Piperazine-urea YEATS Domain Binders in MLLTI," ACS Med. Chem. Lett., Dec. 2019, 10(12):1661-1666.
Nicholson et al., "EGFR and cancer prognosis," Eur. J. Cancer, Sep. 2001, 37(Supp. 4):9-15.
Noble et al., "Protein kinase inhibitors: insights into drug design from structure," Science, Mar. 2004, 303:1800-1805.
Odho et al., "Characterization of a novel WDR5-binding site that recruits RbBP5 through a conserved motif to enhance methylation of histone H3 lysine 4 by mixed lineage leukemia protein-1," Journal of Biological Chemistry, Oct. 2010, 285(43):32967-32976.
Ohoka et al., "In vivo knockdown of pathogenic proteins via specific and nongenetic inhibitor of apoptosis protein (IAP)-dependent protein erasers (SNIPERs)," Journal of Biological Chemistry, Mar. 2017, 292(11):4556-4570.
Okada et al., "hDOT1L links histone methylation to leukemogenesis," Cell, Apr. 2005, 121(2):167-178.
Okuhira et al., "Specific degradation of CRABP-II via cIAP1-mediated ubiquitylation induced by hybrid molecules that crosslink cIAP1 and the target protein," FEBS Lett., Apr. 2011, 585(8):1147-1152.
Olson et al., "Pharmacological perturbation of CDK9 using selective CDK9 inhibition or degradation," Nat. Chem. Biol., Feb. 2018, 14:163-170.
Ono et al., "PTK6 promotes cancer migration and invasion in pancreatic cancer cells dependent on ERK signaling," PLoS One, 2014, 9:e96060.
Ostrander et al., "Brk/PTK6 signaling in normal and cancer cell models," Curr. Opin. Phannacol., 2010, 10:662-669.
Ottis et al., "Proteolysis-targeting chimeras: induced protein degradation as a therapeutic strategy," ACS Chem. Biol., Mar. 2017, 12(4):892-898.
Paez et al., "EGFR mutations in lung cancer: correlation with clinical response to gefitinib therapy," Science, Jun. 2004, 304:1497-500.
Pao et al., "Acquired resistance of lung adenocarcinomas to gefitinib or erlotinib is associated with a second mutation in the EGFR kinase domain," PLoS Med., Feb. 2005, 2(3):e73.
Papazimas et al., "A General Strategy for the Preparation of Thalidomide-Conjugate Linkers," Synlett, Aug. 23, 2017, 28:2881-2885.
Park et al., "Discovery of EGF receptor inhibitors that are selective for the d746-750/T790M/C797S mutant through structure-based de novo design," Angew. Chem. Int. Ed., Jun. 2017, 56(26):7634-7638.
Park et al., "PTK6 inhibition promotes apoptosis of Lapatinib-resistant $Her2^+$ breast cancer cells by inducing Bim," Breast Cancer Res, 2015, 17:86.
Patel et al., "A conserved arginine-containing motif crucial for the assembly and enzymatic activity of the mixed lineage leukemia protein-I core complex," The Journal of Biological Chemistry, Nov. 2008, 283(47):32162-32175.
Patel et al., "Recent updates on third generation EGFR inhibitors and emergence of fourth generation EGFR inhibitors to combat C797S resistance," Eur. J. Med. Chem., Dec. 2017, 142:32-47.

(56) References Cited

OTHER PUBLICATIONS

Patel et al., "Structure of WDR5 bound to mixed lineage leukemia protein-I peptide," The Journal of Biological Chemistry, Nov. 2008, 283(47):32158-32161.
PCT International Preliminary Report on Patentability in International Appln No. PCT/US2018/063847, dated Jun. 18, 2020, 8 pages.
PCT International Preliminary Report on Patentability in International Appln. No. PCT/US2019/019123, dated Aug. 27, 2020, 10 pages.
PCT International Preliminary Report on Patentability in International Appln. No. PCT/US2019/038560, dated Dec. 30, 2020, 9 pages.
PCT International Preliminary Report on Patentability in International Appln. No. PCT/US2019/040507, dated Jan. 5, 2021, 7 pages.
PCT International Preliminary Report on Patentability in International Appln. No. PCT/US2020/031527, dated Nov. 2, 2021, 8 pages.
PCT International Search Report and Written Opinion in International Appln. No. PCT/US2017/058718, dated Jan. 28, 2018, 8 pages.
PCT International Search Report and Written Opinion in International Appln. No. PCT/US2017/065027, dated Mar. 6, 2018, 8 pages.
PCT International Search Report and Written Opinion in International Appln. No. PCT/US2018/063847, dated Mar. 27, 2019, 11 pages.
PCT International Search Report and Written Opinion in International Appln. No. PCT/US2019/019123, dated Jun. 20, 2019, 15 pages.
PCT International Search Report and Written Opinion in International Appln. No. PCT/US2019/021014, dated Jun. 27, 2019, 11 pages.
PCT International Search Report and Written Opinion in International Appln. No. PCT/US2019/038560, dated Oct. 10, 2019, 12 pages.
PCT International Search Report and Written Opinion in International Appln. No. PCT/US2019/040507, dated Nov. 12, 2019, 10 pages.
PCT International Search Report and Written Opinion in International Appln. No. PCT/US2020/031527, dated Sep. 14, 2020, 11 pages.
PCT International Search Report and Written Opinion in International Appln. No. PCT/US2021/055574, dated Feb. 25, 2022, 11 pages.
PCT Invitation to Pay Additional Fees in International Appln. No. PCT/US2019/019123, dated Apr. 8, 2019, 3 pages.
PCT Invitation to Pay Additional Fees in International Appln. No. PCT/US2019/021014, dated Apr. 22, 2019, 2 pages.
PCT Invitation to Pay Additional Fees in International Appln. No. PCT/US2019/038560, dated Aug. 14, 2019, 2 pages.
PCT Invitation to Pay Additional Fees in International Appln. No. PCT/US2021/055574, dated Dec. 22, 2021, 2 pages.
Pellegrino et al., "EEF1A2 inactivates p53 by way of PI3K/AKT/mTOR-dependent stabilization of MDM4 in hepatocellular carcinoma," Hepatology, May 2014, 59(5):1886-1899.
Peng et al., "Protein tyrosine kinase 6 promotes ERBB2-induced mammary gland tumorigenesis in the mouse," Cell Death Dis., 2015, 6:e1848.
Perlman et al., "MLLT1 YEATS domain mutations in clinically distinctive Favourable Histology Wilms tumours," Nat. Commun., Dec. 2015, 6:10013, 10 pages.
Peters et al., "Alectinib versus Crizotinib in Untreated ALK Positive Non-Small-Cell Lung Cancer," New England Journal of Medicine, Aug. 31, 2017, 377(9):829-838.
Pettersson et al., "PROteolysis TArgeting Chimeras (PROTACs)—past, present and future," Drug Discov. Today Technol., Apr. 2019, 31:15-27.
Pieters et al., "A treatment protocol for infants younger than 1 year with acute lymphoblastic leukaemia (Interfant-99): an observational study and a multicentre randomised trial," Lancet, Jul. 2007, 370:240-250.
Prabhu et al., "Adapting AlphaLISA high throughput screen to discover a novel small-molecule inhibitor targeting protein arginine methyltransferase 5 in pancreatic and colorectal cancers," Oncotarget, May 2017, 8(25):39963-39977.
Prêtre et al., "Inhibition of Akt and other AGC kinases: A target for clinical cancer therapy?," Accepted Manuscript, Seminars in Cancer Biology, 2018, 48:70-77.
PubChem-CID-44631912, NIH, National Center for Biotechnology Information, Create Date: Mar. 8, 2010, 30 pages.
Pui et al., "Treating Childhood Acute Lymphoblastic Leukemia without Cranial Irradiation," N. Engl. J. Med., Jun. 2009, 360(26):2730-2741.
Pulford et al., "Detection of anaplastic lymphoma kinase (ALK) and nucleolar protein nucleophosmin (NPM)-ALK proteins in normal and neoplastic cells with the monoclonal antibody ALK1," Blood, Feb. 15, 1997, 89(4):1394-1404.
Qi et al., "Selective inhibition of Ezh2 by a small molecule inhibitor blocks tumor cells proliferation," Proc. Natl. Acad. Sci. USA, 2012, 109(52):21360-21365.
Quentmeier et al., "EZH2 Y641 mutations in follicular lymphoma," Leukemia, 2011, 25(4):726-729.
Raina et al., "PROTACinduced BET protein degradation as a therapy for castration-resistant prostate cancer," Proceedings of the National Academy of Sciences of the United States of America, Jun. 2016, 113(26):7124-7129.
Rao et al., "Hijacked in cancer: the KMT2 (MLL) family of methyltransferases," Nat. Rev. Cancer, Jun. 2015, 15:334-346.
Ren et al., "PHF19 promotes multiple myeloma tumorigenicity through PRC2 activation and broad H3K27me3 domain formation," Blood, 2019, 134:1176-1189.
Ren et al., "Polycomb protein EZH2 regulates tumor invasion via the transcriptional repression of the metastasis suppressor RKIP in breast and prostate cancer," Cancer Res., 2012, 72(12):3091-3104.
Ribas et al., "Cancer immunotherapy using checkpoint blockade," Science (New York, NY), Mar. 2018, 359(6382):1350-1355.
Rikova et al., "Global survey of phosphotyrosine signaling identifies oncogenic kinases in lung cancer," Cell, Dec. 14, 2007, 131(6):1190-1203.
Ritchie et al., "limma powers differential expression analyses for RNA-sequencing and microarray studies," Nucleic Acids Res., 2015, 43(7):e47.
Rodrik-Outmezguine et al., "Overcoming mTOR resistance mutations with a new-generation mTOR inhibitor," Nature, Jun. 2016, 534:272-276.
Roguev et al., "The *Saccharomyces cerevisiae* Set1 complex includes an ash2 homologue and methylates histone 3 lysine," The EMBO journal, Dec. 2001, 20(24):7137-7148.
Rosati et al., "NUP98 is fused to the NSD3 gene in acute myeloid leukemia associated with t(8;11)(p11.2;p15)," Blood, 2002, 99:3857-3860.
Sakamoto et al., "Protacs: chimeric molecules that target proteins to the Skp1-Cullin-F box complex for ubiquitination and degradation," Proc. Natl. Acad. Sci. USA, Jul. 2001, 98(15):8554-8559.
Salami et al., "Waste disposal—An attractive strategy for cancer therapy," Science, Mar. 2017, 355:1163-1167.
Saura et al., "A first-in-human phase I study of the ATP-competitive AKT inhibitor ipatasertib demonstrates robust and safe targeting of AKT in patients with solid tumors," Cancer Discovery, Jan. 2017, 7(1):102-113.
Sauvageau et al., "Poly comb group proteins: multi-faceted regulators of somatic stem cells and cancer," Cell Stem Cell., 2010, 7(3):299-313.
Sawasdikosol et al., "Hematopoietic progenitor kinase 1 (HPK1) regulates prostaglandin $E_2$-induced fos gene transcription," Blood, May 2003, 101(9):3687-3689.
Sawasdikosol et al., "HPK1 as a novel target for cancer immunotherapy," Immunologic Research, Dec. 2012, 54(1-3):262-265.

(56) References Cited

OTHER PUBLICATIONS

Sawasdikosol et al., "Prostaglandin $E_2$ activates HPK 1 kinase activity via a PKA-dependent pathway," The Journal of biological chemistry, Nov. 2007, 282(48):34693-34699.
Schapira et al., "Targeted protein degradation: expanding the toolbox," Nat. Rev. Drug Discov., Dec. 2019, 18(12):949-963.
Schmandt et al., "The BRK tyrosine kinase is expressed in high-grade serous carcinoma of the ovary," Cancer Biol. Ther., 2006, 5:1136-1141.
Schneider et al. "Characterization of EBV-genome negative 'null ' and 'T' cell lines derived from children with acute lymphoblastic leukemia and leukemic transformed non-Hodgkin lymphoma," International Journal of Cancer, May 1977, 19(5): 621-626.
Schramm et al., "Novel BQCA- and TBPB-derived M1 receptor hybrid ligands: orthosteric carbachol differentially regulates partial agonism," ChemMedChem, Jul. 2019, 14(14):1349-1358.
Senisterra et al., "Small-molecule inhibition of MLL activity by disruption of its interaction with WDR5," Biochemical Journal, Jan. 2013, 449(1):151-159.
Seshacharyulu et al., "Targeting the EGFR signaling pathway in cancer therapy," Expert Opin. Ther. Targets, Jan. 2012, 16:15-31.
Shanle et al., "Association of Taf14 with acetylated histone H3 directs gene transcription and the DNA damage response," Genes Dev., 2015, 29:1795-1800.
Sharma et al., "Epidermal growth factor receptor mutations in lung cancer," Nat. Rev. Cancer, Mar. 2007, 7:169-181.
Shaw et al., "Ceritinib in ALK-rearranged non-small-cell lung cancer," New England Journal of Medicine, Mar. 27, 2014, 370(13):1189-1197.
Shen et al., "Identification of LEM-14 inhibitor of the oncoprotein NSD2," Biochem Biophys. Res. Commun., Jan. 2019, 508(1):102-108.
Shen et al., "NSD3-Short Is an Adaptor Protein that Couples BRD4 to the CHD8 Chromatin Remodeler," Mol. Cell., Dec. 2015, 60(6):847-859.
Shen et al., "Structure-based design of 5-methylpyrimidopyridone derivatives as new wild-type sparing inhibitors of the epidermal growth factor receptor triple mutant ($EGFR^{L858R/T790M/C797S}$)," J. Med. Chem., Jul. 2019, 62:7302-7308.
Sherr et al., "Targeting CDK4 and CDK6: from discovery to therapy," Cancer Discovery, 2016, 6(4):353-367.
Shibata et al., "Development of protein degradation inducers of oncogenic BCR-ABL protein by conjugation of ABL kinase inhibitors and IAP ligands," Cancer Science, Aug. 2017, 108(8):1657-1666.
Shimizu et al., "The protein arginine methyltransferase 5 promotes malignant phenotype of hepatocellular carcinoma cells and is associated with adverse patient outcomes after curative hepatectomy," International Journal of Oncology, Jan. 2017, 50(2):381-386.
Shiota et al., "Hyperphosphorylation of a novel 80 kDa protein-tyrosine kinase similar to Ltk in a human 40 Ki-1 lymphoma cell line, AMS3," Oncogene, Jun. 1994, 9(6):1567-1574.
Shui et al., "Hematopoietic progenitor kinase 1 negatively regulates T-cell receptor signaling and T cell-mediated immune responses," Nature Immunology, Jan. 2007, 8(1):84-91.
Slany, "When epigenetics kills: MLL fusion proteins in leukemia," Hematol. Oncol., Mar. 2005, 23:1-9.
Sneeringer et al., "Coordinated activities of wild-type plus mutant EZH2 drive tumor-associated hypertrimethylation of lysine 27 on histone H3 (H3K27) in human B-cell lymphomas," Proc. Natl. Acad. Sci. USA, Dec. 7, 2010, 107(49): 20980-20985.
Soda et al., "Identification of the transforming EML4-ALK fusion gene in non-small-cell lung cancer," Nature, Aug. 2, 2007,448:561-566.
Solomon et al., "First-line crizotinib versus chemotherapy in ALK-positive lung cancer," New England Journal of Medicine, Dec. 4, 2014, 371(23):2167-2177.
Song et al., "Selective inhibition of EZH2 by ZLD1039 blocks H3K27methylation and leads to potent anti-tumor activity in breast cancer," Sci. Rep., 2016, 6:20864.
Song et al., "WDR5 interacts with mixed lineage leukemia (MLL) protein via the histone HJ-binding pocket," The Journal of Biological Chemistry, Dec. 2008, 283(50):35258-35264.
Soucy et al., "An inhibitor of NEDD8-activating enzyme as a new approach to treat cancer," Nature, Apr. 2009, 458:732-736.
Subramanian et al., "Gene set enrichment analysis: a knowledge-based approach for interpreting genome-wide expression profiles," Proc. Natl. Acad. Sci. USA, Sep. 2005, 102(43):15545-15550.
Suda et al., "The structure of bestatin," The Journal of Antibiotic, Jan. 1976, 29(1):100-101.
Sun et al., "Discovery of AMG 232, a potent, selective, and orally bioavailable MDM2-p53 inhibitor in clinical development," Journal of Medicinal Chemistry, Feb. 2014, 57(4):1454-1472.
Sun et al., "PROTAC-induced BTK degradation as a novel therapy for mutated BTK C481S induced ibrutinib-resistant B-cell malignancies," Cell Research, Jul. 2018, 28(7):779-781.
Sun et al., "Up-regulated WDR5 promotes gastric cancer formation by induced cyclin D1 expression," Journal of Cellular Biochemistry, Apr. 2018, 119(4): 28 pages.
Sun et al., "WDR5 supports an N-Myc transcriptional complex that drives a protumorigenic gene expression signature in neuroblastoma," Cancer Research, Dec. 2015 75(23):5143-5154.
Tahirovic et al., "Discovery of N-alkyl piperazine side chain based CXCR4 antagonists with improved drug-like properties," ACS Med. Chem. Lett., May 2018, 9(5):446-451.
Takeuchi et al., "KIF5B-ALK, a novel fusion oncokinase identified by an immunohistochemistry-based diagnostic system for ALK-positive lung cancer," Clinical Cancer Research, May 1, 2009, 15(9):3143-3149.
Tan et al., "A kinase-independent role for EGF receptor in autophagy initiation," Cell, Jan. 2015, 160(1-2):145-160.
Tan et al., "Next-generation epidermal growth factor receptor tyrosine kinase inhibitors in epidermal growth factor receptor-mutant non-small cell lung cancer," Lung Cancer, Mar. 2016, 93:59-68.
Tan et al., "PBK/AKT-mediated upregulation of WDR5 promotes colorectal cancer metastasis by directly targeting ZNF407," Cell Death and Disease, Mar. 2017, 8(3): 12 pages.
Taniguchi et al., "Silencing of Kruppel-like factor 2 by the histone methyltransferase EZH2 in human cancer," Oncogene, 2012, 31(15):1988-1994.
Tarighat et al., "The dual epigenetic role of PRMT5 in acute myeloid leukemia: gene activation and repression via histone arginine methylation," Leukemia, Nov. 2016, 30:789-799.
Thomas et al., "Interaction with WDR5 promotes target gene recognition and tumorigenesis by MYC," Molecular Cell, May 2015, 58(3):440-452.
Thomas et al., "The MYC-WDR5 nexus and cancer," Cancer Research, Oct. 2015, 75(19):4012-4015.
Thress et al., "Acquired EGFR C797S mutation mediates resistance to AZD9291 in non-small cell lung cancer harboring EGFR T790M," Nat. Med., May 2015, 21:560-562.
Toure et al., "Small-Molecule PROTACS: New Approaches to Protein Degradation," Angewandte Chemie-International Edition, Feb. 2016, 55(6):1966-1973.
Trievel et al., "WDR5, a complexed protein," Nature Structural & Molecular Biology, Jul. 2009, 16(7):678-680.
Turner et al., "Palbociclib in hormone-receptor-positive advanced breast cancer," New England Journal of Medicine, 2015, 373(3):209-219.
Turner-Ivey et al., "Development of mammary hyperplasia, dysplasia, and invasive ductal carcinoma in transgenic mice expressing the 8p11 amplicon oncogene NSD3," Breast Cancer Res. Treat., Jul. 2017, 164(2):349-358.
Varambally et al., "The polycomb group protein EZH2 is involved in progression of prostate cancer," Nature, 2002, 419(6907):624-629.
Varfolomeev et al., "IAP antagonists induce autoubiquitination of c-IAPs, NF-κB activation, and TNFα-dependent apoptosis," Cell, Nov. 2007, 131(4):669-681.
Vassilev et al., "In vivo activation of the p53 pathway by small-molecule antagonists of MDM2," Science, Feb. 2004, 303(5659):844-848.

(56) References Cited

OTHER PUBLICATIONS

Verma et al., "Identification of Potent, Selective, Cell-Active Inhibitors of the Histone Lysine Methyltransferase EZH2," ACS Med. Chem. Lett., 2012, 3(12):1091-1096.
Vivanco et al., "A kinase-independent function of AKT promotes cancer cell survival," eLIFE, 2014, 3:e03751.
Vu et al., "Discovery of RG7112: a small-molecule MDM2 inhibitor in clinical development," ACS Medicinal Chemistry Letters, May 2013, 4(5):466-469.
Wakeling, "Use of pure antioestrogens to elucidate the mode of action of oestrogens," Biochemical Pharmacology, May 1995, 49(11):1545-1549.
Wan et al., "ENL links histone acetylation to oncogenic gene expression in acute myeloid leukaemia," Nature, Mar. 2017, 543:265-269.
Wan et al., "Impaired cell fate through gain-of-function mutations in a chromatin reader," Nature, Jan. 2020, 577:121-126.
Wang et al., "EAI045: The fourth-generation EGFR inhibitor overcoming T790M and C797S resistance," Cancer Lett., Jan. 2017, 385:51-54.
Wang et al., "MapSplice: accurate mapping of RNA-seq reads for splice junction discovery," Nucleic Acids Res., 2010, 38:e178.
Wang et al., "NUP98-NSD1 links H3K36 methylation to Hox-A gene activation and leukaemogenesis," Nat. Cell. Biol., Jul. 2007, 9(7):804-812.
Wang et al., "Polycomb genes, miRNA, and their deregulation in B-cell malignancies," Blood, 2015, 125(8):1217-1225.
Wei et al., "Protein arginine methylation of non-histone proteins and its role in diseases," Cell Cycle, 2014, 13(1):32-41.
Weisberg et al., "Smac mimetics: implications for enhancement of targeted therapies in leukemia," Leukemia, Dec. 2010, 24:2100-2109.
Weiss et al., "Anaplastic lymphoma kinase and leukocyte tyrosine kinase: functions and genetic interactions in learning, memory and adult neurogenesis," Pharmacology, Biochemistry and Behavior, Jan. 2012, 100(3):566-574.
Weiss et al., "The role of T3 surface molecules in the activation of human T cells: a two-stimulus requirement for IL 2 production reflects events occurring at a pre-translational level," Journal of Immunology, Aug. 1984, 133(1):123-128.
Wieduwilt et al., "The epidermal growth factor receptor family: biology driving targeted therapeutics," Cell. Mol. Life Sci., May 2008, 65(10):1566-1584.
Winter et al., "Phthalimide conjugation as a strategy for in vivo target protein degradation," Science, May 2015, 348(6241):1376-1381.
Wood et al., "Lack of the t(2;5) or other mutations resulting in expression of anaplastic lymphoma kinase catalytic domain in $CD30^+$ primary cutaneous lymphoproliferative disorders and Hodgkin's disease," Blood, Sep. 1, 1996, 88(5):1765-1770.
Wu et al., "Overexpression of WD repeat domain 5 associates with aggressive clinicopathological features and unfavorable prognosis in head neck squamous cell carcinoma," International Association of Oral Pathologists and the American Academy of Oral Pathology, Apr. 2018, 47(5): 27 pages.
Xie et al., "Pharmacological targeting of the pseudokinase Her3," Nature Chemical Biology, Dec. 2014, 10(12):1006-1012.
Xie et al., "WDR5 positively regulates p53 stability by inhibiting p53 ubiquitination," Biochemical and Biophysical Research Communications, May 2017, 487(2):333-338.
Xu et al., "eEF1A2 promotes cell migration, invasion and metastasis in pancreatic cancer by upregulating MMP-9 expression through Akt activation," Clin. Exp. Metastasis, May 2013, 30(7):933-944.
Xu et al., "Selective inhibition of EZH2 and EZH1 enzymatic activity by a small molecule suppresses MLL-rearranged leukemia," Blood, Jan. 2015, 125:346-357.
Xu et al., "Targeting EZH2 and PRC2 dependence as novel anticancer therapy," Exp. Hematol., 2015, 43(8):698-712.
Yang et al., "Structure-Activity Relationship Studies for Enhancer of Zeste Homologue 2 (EZH2) and Enhancer of Zeste Homologue 1 (EZH1) Inhibitors," J. Med. Chem., 2016, 59(16):7617-7633.
Yokoyama et al., "A Higher-Order Complex Containing AF4 and ENL Family Proteins with P-TEFb Facilitates Oncogenic and Physiologic MLL-Dependent Transcription," Cancer Cell, Feb. 2010, 17(2):198-212.
You et al., "Discovery of an AKT degrader with prolonged inhibition of downstream signaling," Cell Chemical Biology, 2020, 27(1):66-73.
Yu et al., "Altered Hox Expression and Segmental Identity in Mll-Mutant Mice," Nature, Nov. 1995, 378:505-508.
Yu et al., "Requirement for CDK4 kinase function in breast cancer," Cancer Cell, 2006, 9(1):23-32.
Yu et al., "Targeting AKT1-E17K and the PI3K/AKT pathway with an allosteric AKT inhibitor, ARQ 092," PLOS One, Oct. 2015, 10(10):e0140479.
Yun et al., "The T790M mutation in EGFR kinase causes drug resistance by increasing the affinity for ATP," Proc. Natl. Acad. Sci. USA, Feb. 2008, 105(6):2070-2075.
Zeng et al., "Discovery of novel imidazo[1,2-a]pyrazin-8-amines as Brk/PTK6 inhibitors," Bioorg. Med. Chem. Lett., Oct. 2011, 21(19):5870-5875.
Zengerle et al., "Selective Small Molecule Induced Degradation of the BET Bromodomain Protein BRD4," ACS Chemical Biology, Jun. 2015, 10(8):1770-1777.
Zhang et al., "Proteolysis targeting chimeras (PROTACs) of anaplastic lymphoma linase (ALK)," Eur. J. Med. Chem., May 2018, 151:304-314.
Zhang et al., "Structural Insights into Histone Crotonyl-Lysine Recognition by the AF9 YEATS Domain," Structure, Sep. 2016, 24(9):1606-1612.
Zhao et al., "PROTACs suppression of CDK4/6, crucial kinases for cell cycle regulation in cancer," Chem. Commun. (Camb)., 2019, 55:2704-2707.
Zhao et al., "The language of chromatin modification in human cancers," Nat. Rev. Cancer, Jul. 2021, 21:413-430.
Zheng et al., "PTK6 activation at the membrane regulates epithelial-mesenchymal transition in prostate cancer," Cancer Res., Sep. 2013, 73(17):5426-5437.
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistry, 2018, 61(2):462-481.
Zuber et al., "RNAi screen identifies Brd4 as a therapeutic target in acute myeloid leukaemia," Nature, 2011, 478:524-528.
CN Office Action in Chinese Appln. No. 201780085879.6, dated Jun. 27, 2022, 15 pages (with English Translation).
JP Office Action in Japanese Appln. No. 2019-522841, dated Jul. 12, 2022, 8 pages (with English Translation).
EP Office Action in European Appln. No. 17877800.7, dated May 24, 2022, 6 pages.
Office Action in U.S. Appl. No. 16/970,305, mailed on Sep. 8, 2023, 22 pages.
International Preliminary Report on Patentability Chapter II in International Appln. No. PCT/US2022/050929, mailed on Jun. 21, 2024, 6 pages.
International Preliminary Report on Patentability in International Appln. No. PCT/US2022/013225, mailed on Aug. 3, 2023, 21 pages.
Office Action in Australian Appln. No. 2019288740, mailed on Jun. 13, 2024, 4 pages.
Office Action in Chinese Appln. No. 202080049386.9, mailed on Sep. 4, 2024, 14 pages (with Machine translation).
Office Action in Chinese Appln. No. 202080049386.9, mailed on Feb. 13, 2025, 14 pages (with English translation).
Office Action in European Appln. No. 17877800.7, mailed Mar. 6, 2024, 6 pages.
Vaswani et al., "Identification of (R)-N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase

(56) References Cited

OTHER PUBLICATIONS

EZH2, Suitable for Phase I Clinical Trials for B-Cell Lymphomas," J Med Chem, Nov. 10, 2016, available online Oct. 28, 2016, 59(21):9928-9941.
Extended European Search Report in European Appln. No. 24222311.3, mailed on Mar. 31, 2025, 9 pages.
Getlik et al., "Structure-based optimization of a small molecule antagonist of the interaction between WD repeat-containing protein 5 (WDR5) and mixed-lineage leukemia 1 (MLL1)," Journal of Medicinal Chemistry, Mar. 2016, 59(6):2478-2496.
Github.com [online], "PreprocessCore," Oct. 26, 2021, retrieved on Mar. 17, 2022, retrieved from URL<Gihttps://github.com/bmbolstad/preprocessCore>, 1 page.
Kaniskan et al., "Inhibitors of Protein Methyltransferases and Demethylases," Chem. Rev., 2018, 118(3):989-1068.
Mitchell et al., "Cloning and characterisation of cDNAs encoding a novel non-receptor tyrosine kinase, brk, expressed in human breast tumours," Oncogene, Aug. 1994, 9:2383-2390.
U.S. Appl. No. 16/345,591, filed Apr. 26, 2019, Jian Jin.
U.S. Appl. No. 16/926,418 (U.S. Pat. No. 11,510,920), filed Jul. 10, 2020 (Nov. 29, 2022), Jian Jin.
U.S. Appl. No. 17/978,696, filed Nov. 1, 2022, Jian Jin.
U.S. Appl. No. 16/467,888 (U.S. Pat. No. 11,541,051), filed Jun. 7, 2019 (Jan. 3, 2023), Jian Jin.
U.S. Appl. No. 17/453,619, filed Nov. 4, 2021, Jian Jin.
U.S. Appl. No. 16/769,326, filed Jun. 3, 2020, Jian Jin.
U.S. Appl. No. 16/970,305, filed Aug. 14, 2020, Jian Jin.
U.S. Appl. No. 16/977,654 (U.S. Pat. No. 11,472,799), filed Sep. 2, 2020 (Oct. 18, 2022), Jian Jin.
U.S. Appl. No. 17/256,516, filed Dec. 28, 2020, Jian Jin.
U.S. Appl. No. 17/254,345 (U.S. Pat. No. 12,110,295), filed Dec. 21, 2020 (Oct. 8, 2024), Jian Jin.
U.S. Appl. No. 17/336,059 (U.S. Pat. No. 12,103,924), filed Jun. 1, 2021 (Oct. 1, 2024), Jian Jin.
U.S. Appl. No. 18/032,758, filed Apr. 19, 2023, Jian Jin.
U.S. Appl. No. 18/711,706, filed May 20, 2024, Jian Jin.

* cited by examiner

HC58 Series HPK1 Degraders

HC58 Series HPK1 Degraders

HC58 and HC65 Series HPK1 Degraders

| ANOVA table | SS | DF | MS | F(DFn, DFd) | P value |
|---|---|---|---|---|---|
| Interaction | 150.8 | 5 | 30.15 | F (5, 180) = 18.84 | P<0.0001 |
| Degrader concentrations (low VS high) | 212.2 | 5 | 42.45 | F (5, 180) = 26.52 | P<0.0001 |
| HC58-78 VS HC90-50 | 68.77 | 1 | 68.77 | F (1, 180) = 42.96 | P<0.0001 |

HETEROBIFUNCTIONAL COMPOUNDS AS DEGRADERS OF HPK1

TECHNICAL FIELD

This disclosure relates to bivalent compounds (e.g., heterobifunctional compounds) which degrade and/or disrupt Hematopoietic Progenitor Kinase 1 (HPK1), compositions comprising one or more of the bivalent compounds, and methods of use thereof for the treatment of HPK1-mediated diseases in a subject in need thereof. The disclosure also relates to methods for designing such bivalent compounds.

BACKGROUND OF THE INVENTION

Unlike traditional enzyme inhibitors, which only inhibit the catalytic activity of the target enzyme, heterobifunctional compounds, also known as proteolysis-targeted chimeras (PROTACs), bind and induce degradation of the enzyme, thus eliminating potential scaffolding functions of the protein, in addition to inhibiting its enzymatic activity (Buckley and Crews, 2014). The HPK1 degraders disclosed herein offer a novel mechanism for treating HPK1-mediated diseases. Additionally, the ability of the degraders to target HPK1 for degradation, as opposed to inhibiting the catalytic activity of HPK1, is expected to overcome resistance, regardless of whether due to the drugs used in prior treatments or whether acquired resistance was caused by gene mutation, amplification or otherwise.

Lewis Thomas and Frank Macfarlane Burnet are the first to introduce the concept that the immune system constantly surveil the host for the emergence of nascent cancer cells and eliminate them before they become tumors (Burnet, 1970). While several lines of evidence suggested that our immune system could accomplish such task (Corthay, 2014), the most direct support of such concept comes from the development of immuno-oncological drugs that target the inhibitory molecules that hinder the anti-tumor immunity effort, allowing immune system to vigorously engage and eliminate previously difficult to treat cancers. (Ribas and Wolchok, 2018) The success of the immune checkpoint inhibitor approach provides the roadmap as to how the exhausted immune systems could be provoked to re-engage the cancer cells. This theoretical framework spurs the search for novel immune checkpoint receptors that could serve as novel immune checkpoint targets.

Hematopoietic Progenitor Kinase 1 (HPK1, also known as MAP4K1), an intracellular negative regulator of the T cell antigen receptor (TCR) signal transduction pathways is a member of the KHS subfamily of Ste20 serine/threonine kinases (Hu et al., 1996; Kiefer et al., 1996). It is a multimodular-domain protein comprising proline-rich motifs and a C-terminal citron homology domain, in addition to its kinase domain. These additional domains suggest that HPK1 could perform functions other than its kinase function. HPK1 transcripts are detected in all embryonic tissues examined, but its expression profile shifts to a hematopoietic cell-restricted pattern post-partum at neonatal day 1 (Kiefer et al., 1996), leading to the speculation that HPK1 may perform a specialized function in hematopoietic cells. This cytosolic Ste20 kinase is recruited to the TCR complex (Ling et al., 2001) and its kinase activity is induced upon the engagement of the TCR (Liou et al., 2000). Overexpression of HPK1 suppresses TCR-induced activation of AP-1-dependent gene transcription in a kinase dependent manner, suggesting that the kinase activity of HPK1 is required to inhibit the Erk MAPK pathway (Liou et al., 2000). This blockage of the Erk MAPK pathway is thought to be the inhibitory mechanism that negatively regulates TCR-induced IL-2 gene transcription.

SUMMARY OF THE INVENTION

The present disclosure relates generally to bivalent compounds (e.g., bi-functional compounds) which degrade and/or disrupt HPK1 and to methods for the treatment of HPK1-mediated diseases (i.e., a disease which depends on HPK1; overexpresses HPK1; depends on HPK1 activity; or includes elevated levels of HPK1 activity relative to a wild-type tissue of the same species and tissue type). It is important to note, because the HPK1 degraders/disruptors have dual functions (enzyme inhibition plus protein degradation/disruption), the bivalent compounds of the present disclosure can be significantly more effective therapeutic agents than currently available HPK1 inhibitors, which inhibit the enzymatic activity of HPK1, but do not affect HPK1 protein levels. The present disclosure further provides methods for identifying HPK1 degraders/disruptors as described herein.

More specifically, the present disclosure provides a bivalent compound including a HPK1 ligand conjugated to a degradation/disruption tag.

In some aspects, the HPK1 degraders/disruptors have the form "PI-linker-EL", as shown below:

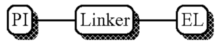

wherein PI (protein of interest) comprises an HPK1 ligand (e.g., an HPK1 inhibitor) and EL (E3 ligase) comprises a degradation/disruption tag (e.g., E3 ligase ligand). Exemplary HPK1 ligands (PI), exemplary degradation/disruption tags (EL), and exemplary linkers (Linker) are illustrated below:

HPK1 Ligands

In an embodiment, (HPK1) ligands include a moiety according to FORMULA 1A:

FORMULA 1A

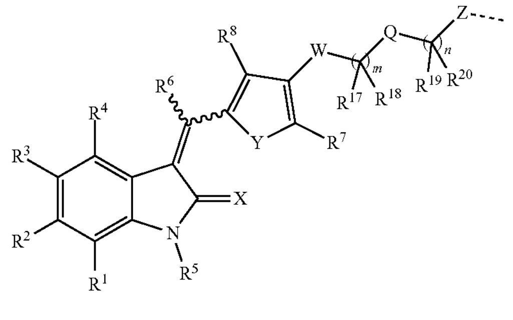

wherein, the "Linker" moiety of the bivalent compound is attached to Z;

X is selected from O or S; [not previously defined for FORMULA 1A; presume this is correct based on FORMULA 1]

$R^1$, $R^2$, $R^3$, $R^4$, $R^7$, and $R^8$ are selected from hydrogen, halogen, oxo, CN, $NO_2$, $OR^{11}$, $SR^{11}$, $NR^{11}R^{12}$, $C(O)R^{11}$, $C(O)OR^{11}$, $C(O)NR^{11}R^{12}$, $S(O)R^{11}$, $S(O)_2R^{11}$, $S(O)_2NR^{11}R^{12}$, $NR^{11}C(O)OR^{11}$, $NR^{13}C(O)R^{11}$, $NR^{13}C(O)NR^{11}R^{12}$, $NR^{13}S(O)R^{11}$, $NR^{13}S(O)_2R^{11}$, $NR^{13}S(O)_2NR^{11}R^{12}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^{11}$ and $R^{12}$, $R^{11}$ and $R^{13}$, $R^{12}$ and $R^{13}$ together with the atom to which they are connected form an optionally substituted 3-20 membered cycloalkyl or heterocyclyl ring;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl;

$R^{17}$, $R^{18}$, $R^{19}$, and $R^{20}$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

m, n, are independently selected from 0, 1, 2, 3, and 4; and

W, Q, and Z, at each occurrence, are independently selected from null, CO, $CO_2$, $CH_2$, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CR^{21}R^{22}$, $C(O)NR^{21}$, $C(S)NR^{21}$, O, S, SO, $SO_2$, $SO_2NR^{21}$, $NR^{21}$, $NR^{21}CO$, $NR^{121}CONR^{22}$, $NR^{21}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{21}$ and $R^{22}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

and pharmaceutically acceptable salts thereof.

In an embodiment, (HPK1) ligands include a moiety according to FORMULA 3A:

FORMULA 3A

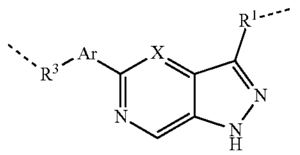

wherein the "Linker" moiety of the bivalent compound is attached independently to $R^1$ or $R^3$;

X is selected from $CR^2$ or N;

$R^1$ is selected from null, hydrogen, $C(O)R^6$, $C(O)OR^6$, $C(O)NR^6R^7$, $S(O)R^6$, $S(O)_2R^6$, $S(O)_2NR^6R^7$, $NR^8C(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^2$ is independently selected from hydrogen, halogen, oxo, CN, $NO_2$, $OR^9$, $SR^9$, $NR^9R^{10}$, $C(O)R^9$, $C(O)OR^9$, $C(O)NR^9R^{10}$, $S(O)R^9$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^9$ and $R^{10}$, $R^9$ and $R^{11}$, $R^{10}$ and $R^{11}$ together with the atom to which they are connected form an optionally substituted 3-20 membered cycloalkyl or heterocyclyl ring;

Ar is selected from null, aryl and heteroaryl, each of which is substituted with $R^3$ and optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCONR^{12}R^{13}$, $COR^{12}$, $CO_2R^{12}$, $CONR^{12}R^{13}$, $SOR^{12}$, $SO_2R^{12}$, $SO_2NR^{12}R^{13}$, $NR^{14}CO_2R^{12}$, $NR^{14}COR^{12}$, $NR^{14}C(O)NR^{12}R^{13}$, $NR^{14}SOR^{12}$, $NR^{14}SO_2R^{12}$, $NR^{14}SO_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{12}$ and $R^{13}$, $R^{12}$ and $R^{13}$ together with the atom to which they are connected form a 4-20 membered heterocyclyl ring;

$R^3$ is is selected from null, $OR^{15}$, $SR^{15}$, $NR^{15}R^{16}$, $OC(O)R^{15}$, $OC(O)OR^{15}$, $OCONR^{15}R^{16}$, $C(O)R^{15}$, $C(O)OR^{15}$, $CONR^{15}R^{16}$, $S(O)R^{15}$, $S(O)_2R^{15}$, $SO_2NR^{15}R^{16}$, $NR^{17}C(O)OR^{15}$, $NR^{17}C(O)R^{15}$, $NR^{17}C(O)NR^{15}R^{16}$, $NR^{14}S(O)R^{15}$, $NR^{17}S(O)_2R^{15}$, $NR^{17}S(O)_2NR^{15}R^{16}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{15}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{16}$ and $R^{17}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$, $R^{15b}$ and $R^{17}$, $R^{16}$ and $R^{17}$ together with the atom to which they are connected form a 3-20 membered cycloalkyl or heterocyclyl ring;

and pharmaceutically acceptable salts thereof.

In an embodiment, (HPK1) ligands include a moiety according to FORMULA 3B:

FORMULA 3B

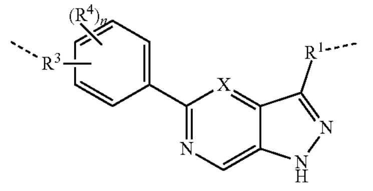

wherein the "Linker" moiety of the bivalent compound is attached independently to $R^1$ or $R^3$;

X is selected from $CR^2$ or N;

$R^1$ and $R^3$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NRIC(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$ is independently selected from hydrogen, halogen, oxo, CN, $NO_2$, $OR^9$, $SR^9$, $NR^9R^{10}$, $C(O)R^9$, $C(O)OR^9$, $C(O)NR^9R^{10}$, $S(O)R^9$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)$ $R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^9$ and $R^{10}$, $R^9$ and $R^{11}$, $R^{10}$ and $R^{11}$ together with the atom to which they are connected form an optionally substituted 3-20 membered cycloalkyl or heterocyclyl ring;

each $R^4$ is independently selected from null, hydrogen, halogen, oxo, CN, $NO_2$, $OR^{18}$, $SR^{18}$, $NR^{18}R^{19}$, $OCOR^{18}$, $OCO_2R^{18}$, $OCONR^{18}R^{19}$, $COR^{18}$, $CO_2R^{18}$, $CONR^{18}R^{19}$, $SOR^{18}$, $SO_2R^{18}$, $SO_2NR^{18}R^{19}$, $NR^{20}CO_2R^{18}$, $NR^{20}COR^{18}$, $NR^{20}C(O)NR^{18}R^{19}$, $NR^{20}SOR^{18}$, $NR^{20}SO_2R^{18}$, $NR^7SO_2NR^5R^6$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{18}$, $R^{19}$ and $R^{20}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{18}$ and $R^{19}$, $R^{18}$ and $R^{20}$ together with the atom to which they are connected form a 4-20 membered heterocyclyl ring; and n is independently selected from 0, 1, 2, 3, 4 and 5;

and pharmaceutically acceptable salts thereof.

In an embodiment, (HPK1) ligands include a moiety according to FORMULA 1:

FORMULA 1

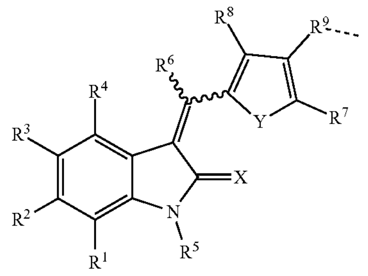

wherein the "Linker" moiety of the bivalent compound is attached to $R^9$;

X is selected from O or S;

Y is selected from O, S, $NR^{10}$; wherein $R^{10}$ is independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl;

$R^1$, $R^2$, $R^3$, $R^4$, $R^7$, and $R^8$ are selected from hydrogen, halogen, oxo, CN, $NO_2$, $OR^{11}$, $SR^{11}$, $NR^{11}R^{12}$, $C(O)R^{11}$, $C(O)OR^{11}$, $C(O)NR^{11}R^{12}$, $S(O)R^{11}$, $S(O)_2R^{11}$, $S(O)_2NR^{11}R^{12}$, $NR^{13}C(O)OR^{11}$, $NR^{13}C(O)R^{11}$, $NR^{13}C(O)NR^{11}R^{12}$, $NR^{13}S(O)R^{11}$, $NR^{13}S(O)_2R^{11}$, $NR^{13}S(O)_2NR^{11}R^{12}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^{11}$ and $R^{12}$, $R^{11}$ and $R^{13}$, $R^{12}$ and $R^{13}$ together with the atom to which they are connected form an optionally substituted 3-20 membered cycloalkyl or heterocyclyl ring;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl;

$R^9$ is selected from $OR^{14}$, $SR^{14}$, $NR^{14}R^{15}$, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{15}$ and $R^{16}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$, $R^{14}$ and $R^{16}$, $R^{15}$ and $R^{16}$ together with the atom to which they are connected form a 3-20 membered cycloalkyl or heterocyclyl ring.

In an embodiment, (HPK1) ligands include a moiety according to FORMULA 1A:

FORMULA 1A

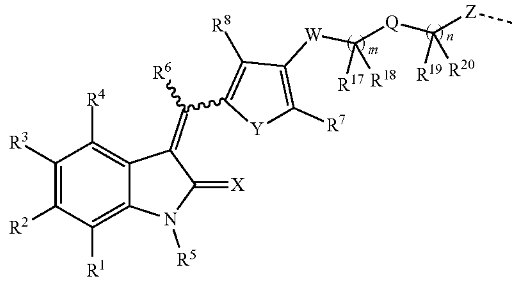

wherein, the "Linker" moiety of the bivalent compound is attached to Z;

the definitions of $R^1$, $R^2$, $R^3$, $R^4$, $R^5$, $R^6$, $R^7$ and $R^8$ are the same as for FORMULA 1;

$R^{17}$, $R^{18}$, $R^{19}$, and $R^{20}$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

m, n, are independently selected from 0, 1, 2, 3, and 4; and

W, Q, and Z, at each occurrence, are independently selected from null, CO, $CO_2$, $CH_2$, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CR^{21}R^{22}$, $C(O)NR^{21}$, $C(S)NR^{21}$, O, S, SO, $SO_2$, $SO_2NR^{21}$, $NR^{21}$, $NR^{21}CO$, $NR^{121}CONR^{22}$, $NR^{21}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{21}$ and $R^{22}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl.

In an embodiment, (HPK1) ligands include a moiety according to FORMULA 1B:

FORMULA 1B

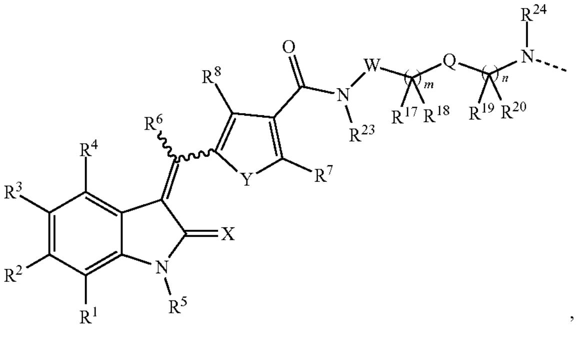

, wherein the definitions of X, Y, W, Q, $R^1$, $R^2$, $R^3$, $R^4$, $R^5$, $R^6$, $R^7$, $R^8$, $R^{17}$, $R^{18}$, $R^{19}$ and $R^{20}$ are the same as for FORMULA 1A;

the "Linker" moiety of the bivalent compound is attached to terminal N;

m, n, are independently selected from 0, 1, 2, 3, and 4;

$R^{23}$ and $R^{24}$ at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl.

In an embodiment, (HPK1) ligands include a moiety according to FORMULA 1C:

FORMULA 1C

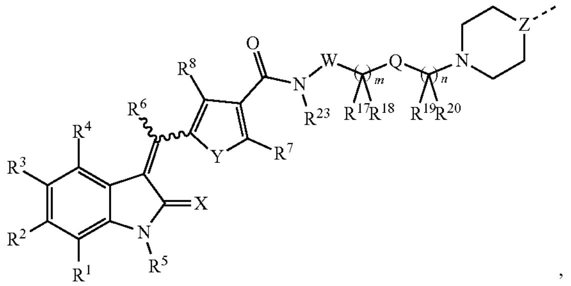

wherein;

the definitions of X, Y, W, Q, $R^1$, $R^2$, $R^3$, $R^4$, $R^5$, $R^6$, $R^7$, $R^8$, $R^{17}$, $R^{18}$, $R^{19}$, $R^{20}$ and $R^{23}$ are the same as for FORMULA 1B;

the "Linker" moiety of the bivalent compound is attached to Z;

m, n, are independently selected from 0, 1, 2, 3, and 4;

Z are independently selected from $CR^{25}$ or N; and $R^{25}$ is independently selected from null, hydrogen, C(O)$R^{26}$, C(O)O$R^{26}$, C(O)N$R^{26}R^{27}$, S(O)$R^{26}$, S(O)$_2R^{26}$, S(O)$_2$N$R^{26}R^{27}$, N$R^{28}$C(O)O$R^{26}$, N$R^{28}$C(O)$R^{26}$, N$R^{28}$C(O)N$R^{26}R^{27}$, N$R^{28}$S(O)$R^{26}$, N$R^{28}$S(O)$_2R^{26}$, N$R^{28}$S(O)$_2$N$R^{26}R^{27}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{26}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{27}$, and $R^{28}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{26}$ and $R^{27}$ together with the atom to which they are connected form an optionally substituted 3-20 membered cycloalkyl or heterocyclyl ring; and pharmaceutically acceptable salts thereof.

In an embodiment, (HPK1) ligands include a moiety according to FORMULA 2:

FORMULA 2

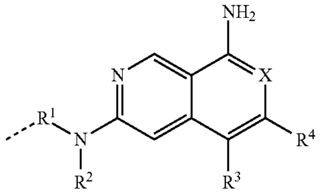

wherein the "Linker" moiety of the bivalent compound is attached to $R^1$ or $R^4$;

X is selected from $CR^5$ or N;

$R^1$, and $R^2$ are independently selected from null, hydrogen, C(O)$R^6$, C(O)O$R^6$, C(O)N$R^6R^7$, S(O)$R^6$, S(O)$_2R^6$, S(O)$_2$N$R^6R^7$, N$R^8$C(O)O$R^6$, N$R^8$C(O)$R^6$, N$R^8$C(O)N$R^6R^7$, N$R^8$S(O)$R^6$, N$R^8$S(O)$_2R^6$, N$R^8$S(O)$_2$N$R^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring; and $R^3$, $R^4$ and $R^5$ are independently selected from hydrogen, halogen, oxo, CN, $NO_2$, O$R^9$, S$R^9$, N$R^{10}R^{11}$, C(O)$R^9$, C(O)O$R^9$, C(O)N$R^{10}R^{11}$, S(O)$R^9$, S(O)$_2R^9$, S(O)$_2$N$R^{10}R^{11}$, N$R^{12}$C(O)O$R^{10}$, N$R^9$C(O)$R^{10}$, N$R^9$C(O)N$R^{10}R^{11}$, N$R^9$S(O)$R^{10}$, N$R^9$S(O)$_2R^{10}$, N$R^9$S(O)$_2$N$R^{10}R^{11}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^9$ and $R^{10}$, $R^{10}$ and $R^{11}$ together with the atom to which they are connected form an optionally substituted 3-20 membered cycloalkyl or heterocyclyl ring.

In an embodiment, (HPK1) ligands include a moiety according to FORMULA 2A or 2B:

FORMULA 2A

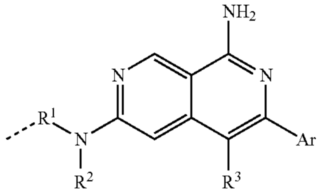

FORMULA 2B

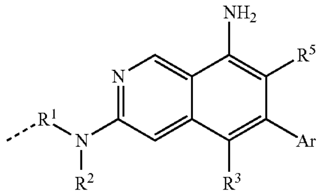

wherein the "Linker" moiety of the bivalent compound is attached to $R^1$;

the definitions of $R^1$, $R^2$, $R^3$ and $R^5$ are the same as for FORMULA 2;

Ar is selected from null, aryl and heteroaryl, each of which is optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCONR^{12}R^{13}$, $COR^{12}$, $CO_2R^{12}$, $CONR^{12}R^{13}$, $SOR^{12}$, $SO_2R^{12}$, $SO_2NR^{12}R^{13}$, $NR^{14}CO_2R^{12}$, $NR^{14}COR^{12}$, $NR^{14}C(O)NR^{12}R^{13}$, $NR^{14}SOR^{12}$, $NR^{14}SO_2R^{12}$, $NR^{14}SO_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{12}$ and $R^{13}$, $R^{13}$ and $R^{14}$ together with the atom to which they are connected form a 3-20 membered heterocyclyl ring.

In an embodiment, (HPK1) ligands include a moiety according to FORMULA 2C or 2D:

FORMULA 2C

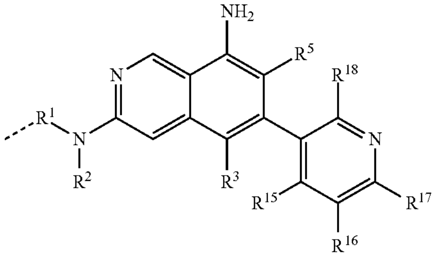

FORMULA 2D

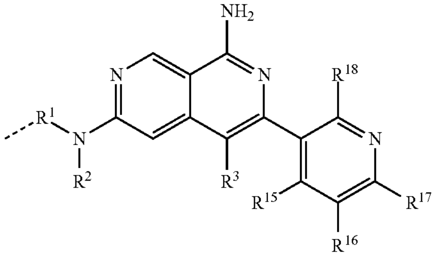

wherein the "Linker" moiety of the bivalent compound is attached to $R^1$;

the definitions of $R^1$, $R^2$, $R^3$ and $R^5$ are the same as for FORMULA 2;

$R^{15}$, $R^{16}$, $R^{17}$ and $R^{18}$ are independently selected hydrogen, halogen, oxo, CN, $NO_2$, $OR^{19}$, $SR^{19}$, $NR^{20}R^{21}$, $OCOR^{19}$, $OCO_2R^{19}$, $OCONR^{20}R^{21}$, $COR^{19}$, $CO_2R^{19}$, $CONR^{20}R^{21}$, $SOR^{19}$, $SO_2R^{19}$, $SO_2NR^{20}R^{21}$, $NR^{19}CO_2R^{20}$, $NR^{19}COR^{20}$, $NR^{19}C(O)NR^{20}R^{21}$, $NR^{19}SOR^{20}$, $NR^{19}SO_2R^{20}$, $NR^{19}SO_2NR^{20}R^{21}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{19}$, $R^{20}$, and $R^{21}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{19}$ and $R^{20}$, $R^{20}$ and $R^{21}$ together with the atom to which they are connected form a 3-20 membered heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2E or 2F:

FORMULA 2E

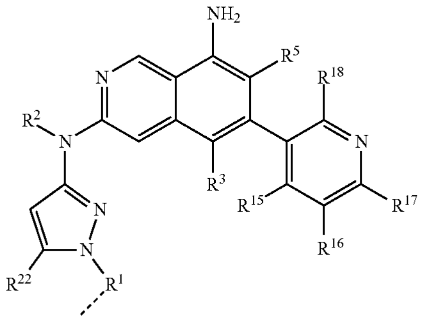

FORMULA 2F

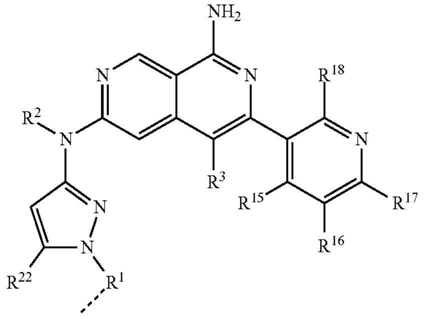

wherein the "Linker" moiety of the bivalent compound is attached to $R^1$;

the definitions of $R^1$, $R^2$, $R^3$, $R^5$, $R^{15}$, $R^{16}$, $R^{17}$ and $R^{18}$ are the same as for FORMULA 2C and 2D. $R^{22}$ is independently selected from hydrogen, halogen, oxo, aryl, CN, $NO_2$, $OR^{23}$, $SR^{23}$, $NR^{24}R^{25}$, $C(O)R^{23}$, $C(O)OR^{23}$, $C(O)NR^{24}R^{25}$, $S(O)R^{23}$, $S(O)_2R^{23}$, $S(O)_2NR^{24}R^{25}$, $NR^{24}C(O)OR^{23}$, $NR^{24}C(O)R^{23}$, $NR^{23}C(O)NR^{24}R^{25}$, $NR^{24}S(O)R^{23}$, $NR^{24}S(O)_2R^{23}$, $NR^{23}S(O)_2NR^{24}R^2$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{23}$, $R^{24}$, and $R^{25}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{23}$ and $R^{24}$, $R^{23}$ and $R^{25}$ together with the atom to which they are connected form an optionally substituted 3-20 membered cycloalkyl or heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2G or 2H:

FORMULA 2G

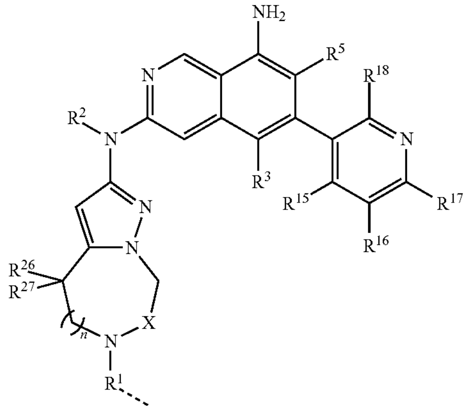

FORMULA 2H

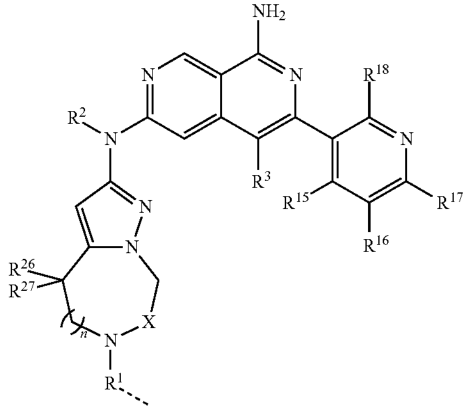

wherein the "Linker" moiety of the bivalent compound is attached to $R^1$;

the definitions of $R^1$, $R^2$, $R^3$, $R^5$, $R^{15}$, $R^{16}$, $R^{17}$ and $R^{18}$ are the same as for FORMULA 2C and 2D.

X is CO, $CH_2$ or SO2;

n is 0 to 1;

$R^{26}$ and $R^{27}$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{26}$ and $R^{27}$ together with the atom to which they are connected form an optionally substituted 3-20 membered cycloalkyl or heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2K, 2L, 2M and 2N.

FORMULA 2K

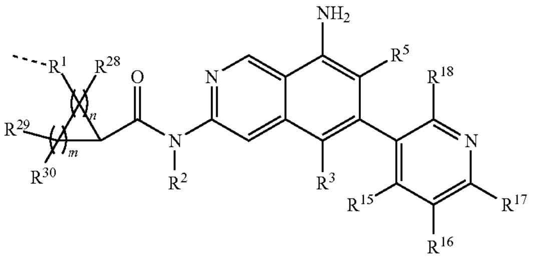

FORMULA 2L

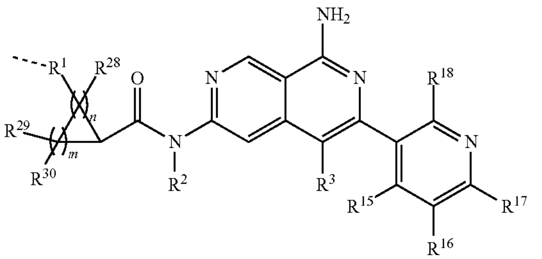

FORMULA 2M

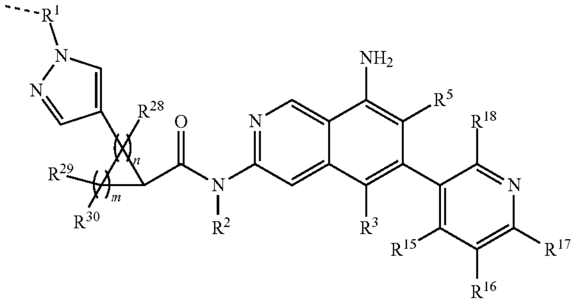

FORMULA 2N

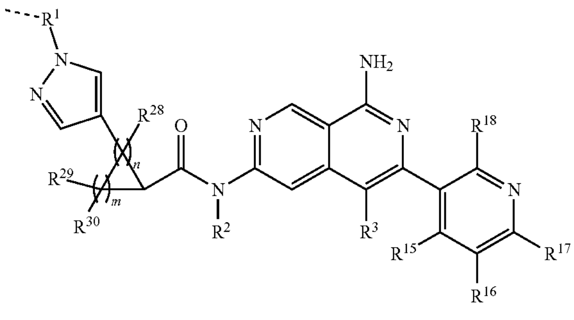

wherein the "Linker" moiety of the bivalent compound is attached to $R^9$;

the definitions of $R^1$, $R^2$, $R^3$, $R^5$, $R^{15}$, $R^{16}$, $R^{17}$ and $R^{18}$ are the same as for FORMULA 2C and 2D;

n and m are independently selected from 1, 2 and 3;

$R^{28}$, $R^{29}$ and $R^{30}$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^{29}$ and $R^{30}$ together with the atom to which they are connected form an optionally substituted 3-20 membered cycloalkyl or heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2O or 2P:

FORMULA 2O

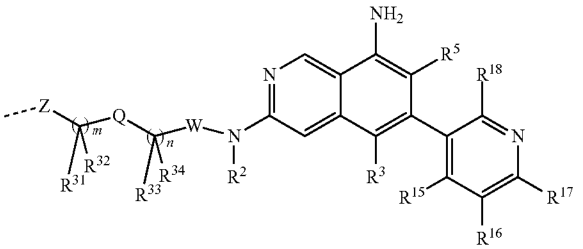

FORMULA 2P

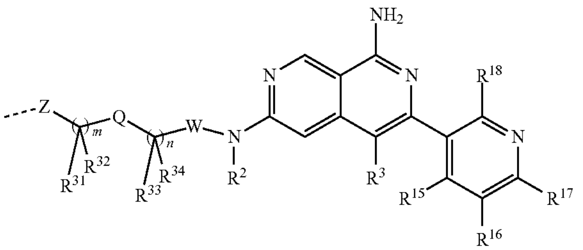

wherein the "Linker" moiety of the bivalent compound is attached to Z;

the definitions of $R^1$, $R^2$, $R^3$, $R^5$, $R^{15}$, $R^{16}$, $R^{17}$ and $R^{18}$ are the same as for FORMULA 2C and 2D; W, Q, and Z, at each occurrence, are independently selected from null, CO, $CO_2$, $CH_2$, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CR^{35}R^{36}$, $C(O)NR^{35}$, $C(S)NR^{35}$, O, S, SO, $SO_2$, $SO_2NR^{35}$, $NR^{35}$, $NR^{35}CO$, $NR^{35}CONR^{36}$, $NR^{35}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl, wherein $R^{35}$ and $R^{36}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

$R^{31}$, $R^{32}$, $R^{33}$, and $R^{34}$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{31}$ and $R^{32}$, $R^{33}$ and $R^{34}$ are together with the atom to which they are connected form an optionally substituted 3-20 membered cycloalkyl or heterocyclyl ring;

$R^{15}$ and $R^{16}$, $R^{16}$ and $R^{17}$ together with the atom to which they are connected form an optionally substituted 4-20 membered cycloalkyl or heterocyclyl ring; and m, n, are independently selected from 0, 1, 2, 3, and 4; and pharmaceutically acceptable salts thereof.

In an embodiment, (HPK1) ligands include a moiety according to FORMULA 3:

FORMULA 3

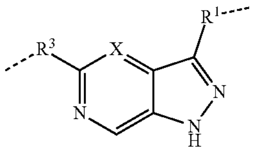

wherein the "Linker" moiety of the bivalent compound is attached independently to $R^1$ or $R^3$;

X is selected from $CR^2$ or N;

$R^1$ and $R^3$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NRIC(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$ is independently selected from hydrogen, halogen, oxo, CN, $NO_2$, $OR^9$, $SR^9$, $NR^9R^{10}$, $C(O)R^9$, $C(O)OR^9$, $C(O)NR^9R^{10}$, $S(O)R^9$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^9$ and $R^{10}$, $R^9$ and $R^{11}$, $R^{10}$ and $R^{11}$ together with the atom to which they are connected form an optionally substituted 3-20 membered cycloalkyl or heterocyclyl ring.

In an embodiment, (HPK1) ligands include a moiety according to FORMULA 3A:

FORMULA 3A

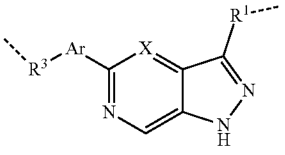

wherein the "Linker" moiety of the bivalent compound is attached independently to $R^1$ or $R^3$;

X is selected from $CR^2$ or N;

the definitions of $R^1$ and $R^2$ are the same as for FORMULA 3;

Ar is selected from null, aryl and heteroaryl, each of which is substituted with $R^3$ and optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCONR^{12}R^{13}$, $COR^{12}$, $CO_2R^{12}$, $CONR^{12}R^{13}$, $SOR^{12}$, $SO_2R^{12}$, $SO_2NR^{12}R^{13}$, $NR^{14}CO_2R^{12}$, $NR^{14}COR^{12}$, $NR^{14}C(O)NR^{12}R^{13}$, $NR^{14}SOR^{12}$, $NR^{14}SO_2R^{12}$, $NR^{14}SO_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{12}$ and $R^{13}$, $R^{12}$ and $R^{13}$ together with the atom to which they are connected form a 4-20 membered heterocyclyl ring;

$R^3$ is is selected from null, $OR^{15}$, $SR^{15}$, $NR^{15}R^{16}$, $OC(O)R^{15}$, $OC(O)OR^{15}$, $OCONR^{15}R^{16}$, $C(O)R^{15}$, $C(O)OR^{15}$, $CONR^{15}R^{16}$, $S(O)R^{15}$, $S(O)_2R^{15}$, $SO_2NR^{15}R^{16}$, $NR^{17}C(O)OR^{15}$, $NR^{17}C(O)R^{15}$, $NR^7C(O)NR^{15}R^{16}$, $NR^{14}S(O)R^{15}$, $NR^{17}S(O)_2R^{15}$, $NR^{17}S(O)_2NR^{15}R^{16}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{15}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{16}$ and $R^{17}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$, $R^{15b}$ and $R^{17}$, $R^{16}$ and $R^{17}$ together with the atom to which they are connected form a 3-20 membered cycloalkyl or heterocyclyl ring.

In an embodiment, (HPK1) ligands include a moiety according to FORMULA 3B:

FORMULA 3B

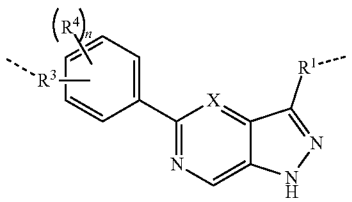

wherein the "Linker" moiety of the bivalent compound is attached independently to $R^1$ or $R^3$;

X is selected from $CR^2$ or N;

the definitions of $R^1$, $R^2$ and $R^3$ are the same as for FORMULA 3;

each $R^4$ is independently selected from null, hydrogen, halogen, oxo, CN, $NO_2$, $OR^{18}$, $SR^{18}$, $NR^{11}R^{19}$, $OCOR^{18}$, $OCO_2R^{18}$, $OCONR^{18}R^{19}$, $COR^{18}$, $CO_2R^{18}$, $CONR^{18}R^{19}$, $SOR^{18}$, $SO_2R^{18}$, $SO_2NR^{18}R^{19}$, $NR^{20}CO_2R^{18}$, $NR^{20}COR^{18}$, $NR^{20}C(O)NR^{18}R^{19}$, $NR^{20}SOR^{18}$, $NR^{20}SO_2R^{18}$, $NR^7SO_2NR^5R^6$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{18}$, $R^{19}$ and $R^{20}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{18}$ and $R^{19}$, $R^{18}$ and $R^{20}$ together with the atom to which they are connected form a 4-20 membered heterocyclyl ring; and n is independently selected from 0, 1, 2, 3, 4 and 5.

In an embodiment, (HPK1) ligands include a moiety according to FORMULAE 3C, 3D and 3E:

FORMULA 3C

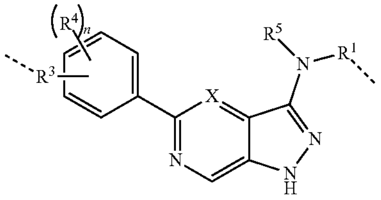

FORMULA 3D

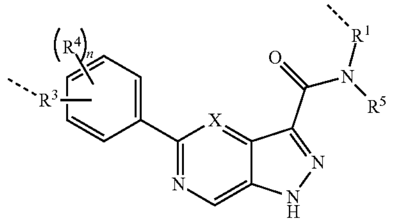

FORMULA 3E

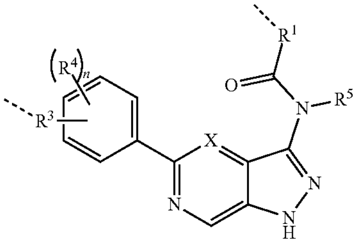

wherein the "Linker" moiety of the bivalent compound is attached independently to $R^1$ or $R^3$;

X is selected from $CR^2$ or N;

the definitions of $R^1$, $R^2$, $R^3$ and $R^4$ are the same as for FORMULA 3B;

$R^5$ at each occurrence, is independently selected from hydrogen, $C(O)R^{21}$, $C(O)OR^{21}$, $C(O)NR^{21}R^{22}$, $S(O)R^{21}$, $S(O)_2R^{21}$, $S(O)_2NR^{21}R^{22}$, $NR^{23}C(O)OR^{21}$, $NR^{23}C(O)R^{21}$, $NR^{23}C(O)NR^{21}R^{22}$, $NR^{23}S(O)R^{21}$, $NR^{23}S(O)_2R^{21}$, $NR^{23}S(O)_2NR^{21}R^{22}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{21}$, $R^{22}$ and $R^{23}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{21}$ and $R^{22}$, $R^{21}$ and $R^{23}$ together with the atom to which they are connected form a 3-20 membered heterocyclyl ring; and n is independently selected from 0, 1, 2, 3, 4 and 5.

In an embodiment, (HPK1) ligands include a moiety according to FORMULA 3F or 3G:

FORMULA 3F

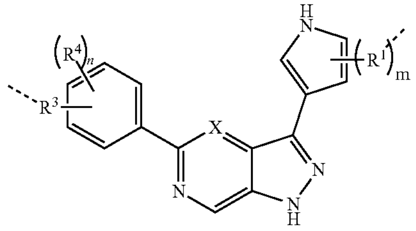

FORMULA 3G

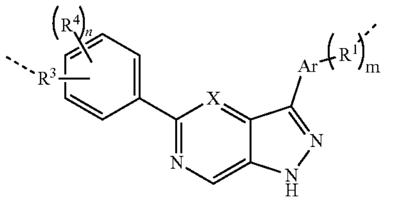

wherein the "Linker" moiety of the bivalent compound is attached independently to $R^3$ or independently to one of the $R^1$;

X is selected from $CR^2$ or N;

the definitions of $R^1$, $R^2$, $R^3$ and $R^4$ are the same as for FORMULA 3B.

Ar is selected from null, aryl and heteroaryl, each of which is substituted with $R^1$;

n and m are independently selected from 0, 1, 2, 3, 4 and 5.

In an embodiment, (HPK1) ligands include a moiety according to FORMULA 3H or 3K:

FORMULA 3H

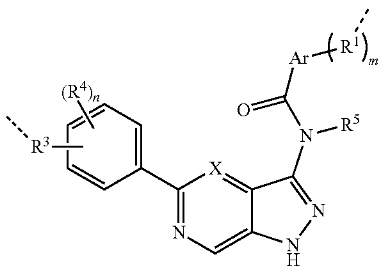

FORMULA 3K

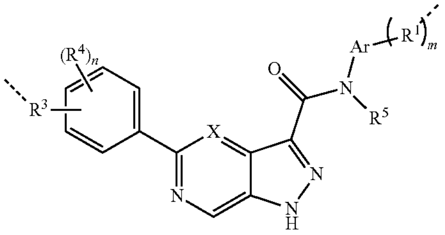

wherein the "Linker" moiety of the bivalent compound is attached independently to $R^1$ or $R^3$;

X is selected from $CR^2$ or N;

the definitions of $R^1$, $R^2$, $R^3$, $R^4$ and $R^5$ are the same as for FORMULA 3C, 3D, 3E;

Ar is selected from null, aryl and heteroaryl, each of which is substituted with $R^1$;

n and m are independently selected from 0, 1, 2, 3, 4 and 5.

In an embodiment, (HPK1) ligands include a moiety according to FORMULA 3L:

FORMULA 3L

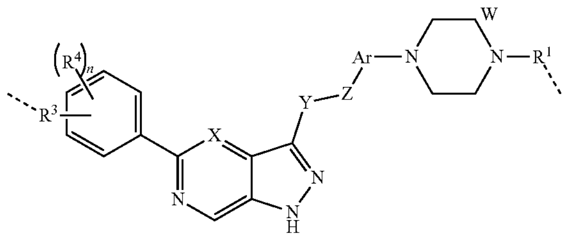

wherein the "Linker" moiety of the bivalent compound is attached independently to $R^1$ or $R^3$;

X is selected from $CR^2$ or N;

the definitions of $R^1$, $R^2$, $R^3$ and $R^4$ are the same as for FORMULA 3B;

Ar is selected from null, aryl and heteroaryl;

n is independently selected from 0, 1, 2, 3, 4 and 5;

Y, Z at each occurrence, are independently selected from null, CO, $CO_2$, $CH_2$, $CR^{24}R^{25}$, $C(O)NR^{24}$, $C(S)NR^{24}$, O, S, SO, $SO_2$, $SO_2NR^{24}$, $NR^{24}$, $NR^{24}CO$, $NR^{24}CONR^{24}$, $NR^{24}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{24}$ and $R^{25}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

W, at each occurrence, is independently selected from null, CO, $CH_2$, $(CH_2)_m$ $CR^{26}R^{27}$ $(CR^{26}R^{27})_m$, SO, $SO_2$ wherein $R^{26}$ and $R^{27}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

and m=0-5.

In an embodiment, (HPK1) ligands include a moiety according to FORMULA 3M:

FORMULA 3M

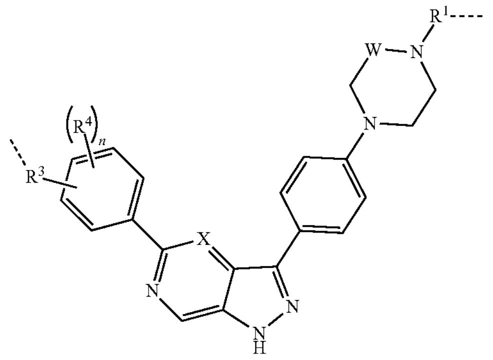

wherein the "Linker" moiety of the bivalent compound is attached independently to $R^1$ or $R^3$;

X is selected from $CR^2$ or N;

the definitions of W, $R^1$, $R^2$, $R^3$ and $R^4$ are the same as for FORMULA 3L.

n is independently selected from 0, 1, 2, 3, 4 and 5; and pharmaceutically acceptable salts thereof.

In an embodiment, (HPK1) ligands include a moiety according to FORMULA 4:

FORMULA 4

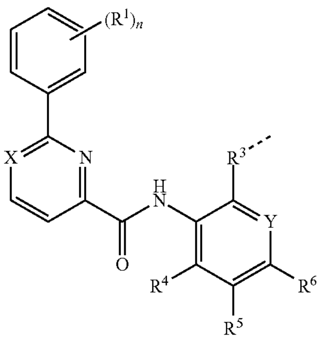

wherein the "Linker" moiety of the bivalent compound is attached to $R^3$;

X is selected from $CR^2$ or N;

Y is selected from $CR^7$ or N;

each $R^1$ is independently selected from null, hydrogen, halogen, oxo, CN, $NO_2$, $OR^8$, $SR^8$, $NR^8R^9$, $OCOR^8$, $OCO_2R^8$, $OCONR^8R^9$, $COR^8$, $CO_2R^8$, $CONR^8R^9$, $SOR^8$, $SO_2R^8$, $SO_2NR^8R^9$, $NR^{10}CO_2R^8$, $NR^{10}COR^8$, $NR^{10}C(O)NR^8R^9$, $NR^{10}SOR^8$, $NR^{10}SO_2R^8$, $NR^{10}SO_2NR^8R^9$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^8$, $R^9$ and $R^{10}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^8$ and $R^9$, $R^8$ and $R^{10}$ together with the atom to which they are connected form a 4-20 membered heterocyclyl ring; and n is independently selected from 0, 1, 2, 3, 4 and 5;

$R^2$ and $R^7$ are independently selected from hydrogen, halogen, oxo, CN, $NO_2$, $OR^{11}$, $SR^{11}$, $NR^{11}R^{12}$, $C(O)R^{11}$, $C(O)OR^{11}$, $C(O)NR^{11}R^{12}$, $S(O)R^{11}$, $S(O)_2R^{11}$, $S(O)_2NR^{11}R^{12}$, $NR^{13}C(O)OR^{10}$, $NR^{13}C(O)R^{11}$, $NR^{13}C(O)NR^{11}R^{12}$, $NR^{13}S(O)R^{11}$, $NR^{13}S(O)_2R^{11}$, $NR^{13}S(O)_2NR^{11}R^{12}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{11}$ and $R^{12}$, $R^{11}$ and $R^{12}$, $R^{12}$ and $R^{13}$ together with the atom to which they are connected form an optionally substituted 3-20 membered cycloalkyl or heterocyclyl ring;

$R^3$ is selected from null, hydrogen, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{15}$, and $R^{16}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$ together with the atom to which they are connected form an optionally substituted 3-20 membered cycloalkyl or heterocyclyl ring;

$R^4$, $R^5$ and $R^6$ are independently selected hydrogen, halogen, oxo, CN, $NO_2$, $OR^{17}$, $SR^{17}$, $NR^{18}R^{19}$, $OCOR^{17}$, $OCO_2R^{17}$, $OCONR^{18}R^{19}$, $COR^{17}$, $CO_2R^{17}$, $CONR^{18}R^{19}$, $SOR^{17}$, $SO_2R^{17}$, $SO_2NR^{18}R^{19}$, $NR^{17}CO_2R^{18}$, $NR^{17}COR^{18}$, $NR^{17}C(O)NR^{18}R^{19}$, $NR^{17}SOR^{18}$, $NR^{17}SO_2R^{18}$, $NR^{17}SO_2NR^{18}R^{19}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{17}$, $R^{18}$, and $R^{19}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{17}$ and $R^{18}$, $R^{18}$ and $R^{19}$ together with the atom to which they are connected form a 3-20 membered heterocyclyl ring.

In an embodiment, (HPK1) ligands include a moiety according to FORMULA 4A:

FORMULA 4A

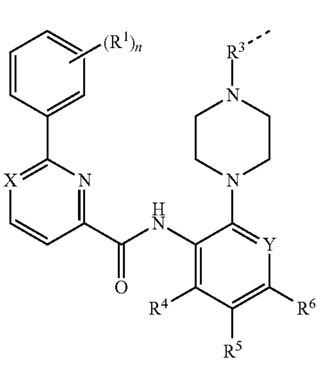

wherein the "Linker" moiety of the bivalent compound is attached to $R^3$;

X is selected from $CR^2$ or N;

Y is selected from $CR^7$ or N;

the definitions of $R^1$, $R^2$, $R^3$, $R^4$, $R^5$, $R^6$ and $R^7$ are the same as for FORMULA 4.

In an embodiment, (HPK1) ligands include a moiety according to FORMULA 4B:

FORMULA 4B

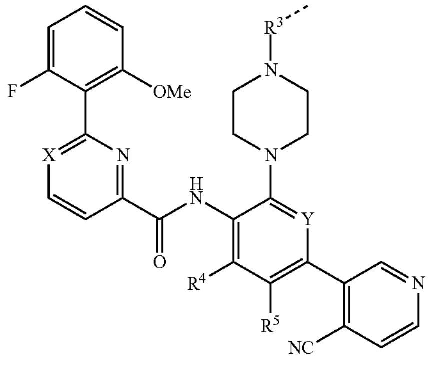

wherein the "Linker" moiety of the bivalent compound is attached to $R^3$;

X is selected from $CR^2$ or N;

Y is selected from $CR^7$ or N; and the definitions of $R^2$, $R^3$, $R^4$, $R^5$, and $R^7$ are the same as for FORMULA 4; and pharmaceutically acceptable salts thereof.

In an embodiment, (HPK1) ligands include a moiety according to FORMULA 5:

FORMULA 5

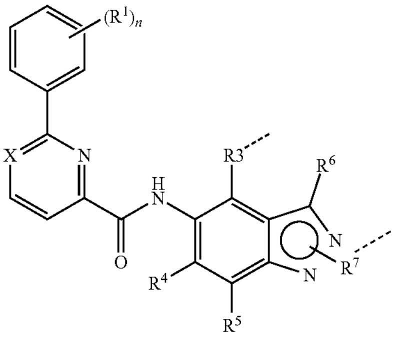

wherein the "Linker" moiety of the bivalent compound is attached to independently to $R^3$ or $R^7$;

X is selected from $CR^2$ or N;

each $R^1$ is independently selected from null, hydrogen, halogen, oxo, CN, $NO_2$, $OR^8$, $SR^8$, $NR^8R^9$, $OCOR^8$, $OCO_2R^8$, $OCONR^8R^9$, $COR^8$, $CO_2R^8$, $CONR^8R^9$, $SOR^8$, $SO_2R^8$, $SO_2NR^8R^9$, $NR^{10}CO_2R^8$, $NR^{10}COR^8$, $NR^{10}C(O)NR^8R^9$, $NR^{10}SOR^8$, $NR^{10}SO_2R^8$, $NR^{10}SO_2NR^8R^9$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^8$, $R^9$ and $R^{10}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^8$ and $R^9$, $R^8$ and $R^{10}$ together with the atom to which they are connected form a 4-20 membered heterocyclyl ring; and n is independently selected from 0, 1, 2, 3, 4 and 5;

$R^2$ is selected from hydrogen, halogen, oxo, CN, $NO_2$, $OR^{11}$, $SR^{11}$, $NR^{11}R^{12}$, $C(O)R^{11}$, $C(O)OR^{11}$, $C(O)NR^{11}R^{12}$, $S(O)R^{11}$, $S(O)_2R^{11}$, $S(O)_2NR^{11}R^{12}$, $NR^{13}C(O)OR^{10}$, $NR^{13}C(O)R^{11}$, $NR^{13}C(O)NR^{11}R^{12}$, $NR^{13}S(O)R^{11}$, $NR^{13}S(O)_2R^{11}$, $NR^{13}S(O)_2NR^{11}R^{12}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{11}$ and $R^{12}$, $R^{11}$ and $R^{12}$, $R^{12}$ and $R^{13}$ together with the atom to which they are connected form an optionally substituted 3-20 membered cycloalkyl or heterocyclyl ring;

$R^3$ and $R^7$ are independently selected from null, hydrogen, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{15}$, and $R^{16}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$ together with the atom to which they are connected form an optionally substituted 3-20 membered cycloalkyl or heterocyclyl ring;

$R^4$, $R^5$ and $R^6$ are independently selected hydrogen, halogen, oxo, CN, $NO_2$, $OR^{17}$, $SR^{17}$, $NR^{18}R^{19}$, $OCOR^{17}$, $OCO_2R^{17}$, $OCONR^{18}R^{19}$, $COR^{17}$, $CO_2R^{17}$, $CONR^{18}R^{19}$, $SOR^{17}$, $SO_2R^{17}$, $SO_2NR^{18}R^{19}$, $NR^{17}CO_2R^{18}$, $NR^{17}COR^{18}$, $NR^{17}C(O)NR^{18}R^{19}$, $NR^{17}SOR^{18}$, $NR^{17}SO_2R^{18}$, $NR^{17}SO_2NR^{18}R^{19}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{17}$, $R^{18}$, and $R^{19}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{17}$ and $R^{18}$, $R^{18}$ and $R^{19}$ together with the atom to which they are connected form a 3-20 membered heterocyclyl ring; and pharmaceutically acceptable salts thereof.

In an embodiment, (HPK1) ligands include a moiety according to FORMULA 6:

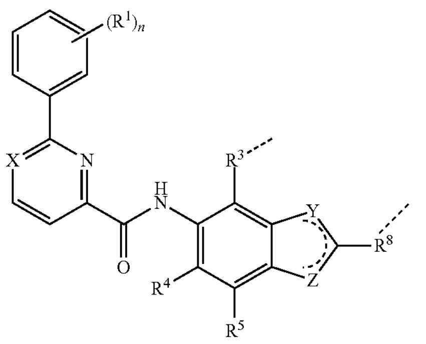

wherein the "Linker" moiety of the bivalent compound is attached to independently to $R^3$ or $R^8$;

X is selected from $CR^2$ or N;

Y is selected from $CR^6$ or N;

Z is selected from $CR^7$ or N or S;

each $R^1$ is independently selected from null, hydrogen, halogen, oxo, CN, $NO_2$, $OR^9$, $SR^9$, $NR^9R^{10}$, $OCOR^9$, $OCO_2R^9$, $OCONR^9R^{10}$, $COR^9$, $CO_2R^9$, $CONR^9R^{10}$, $SOR^9$, $SO_2R^9$, $SO_2NR^9R^{10}$, $NR^{11}CO_2R^9$, $NR^{11}COR^9$, $NR^{11}C(O)NR^9R^{10}$, $NR^{11}SOR^9$, $NR^{11}SO_2R^9$, $NR^{11}SO_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^9$, $R^{10}$ and $R^{11}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^9$ and $R^{10}$, $R^9$ and $R^{11}$ together with the atom to which they are connected form a 4-20 membered heterocyclyl ring; and n is independently selected from 0, 1, 2, 3, 4 and 5;

$R^2$, $R^6$ and $R^7$ are independently selected from hydrogen, halogen, oxo, CN, $NO_2$, $OR^{12}$, $SR^{12}$, $NR^{12}R^{13}$, $C(O)R^{12}$, $C(O)OR^1$, $C(O)NR^{12}R^{13}$, $S(O)R^{12}$, $S(O)_2R^{12}$, $S(O)_2NR^{12}R^{13}$, $NR^{14}C(O)OR^{11}$, $NR^{14}C(O)R^{12}$, $NR^{14}C(O)NR^{12}R^{13}$, $NR^{14}S(O)R^{12}$, $NR^{14}S(O)_2R^{12}$, $NR^{14}S(O)_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{13}$, $R^{13}$ and $R^{14}$ together with the atom to which they are connected form an optionally substituted 3-20 membered cycloalkyl or heterocyclyl ring;

$R^3$ and $R^8$ are independently selected from null, hydrogen, $C(O)R^{15}$, $C(O)OR^{15}$, $C(O)NR^{15}R^{16}$, $S(O)R^{15}$, $S(O)_2R^{15}$, $S(O)_2NR^{15}R^{16}$, $NR^{17}C(O)OR^{15}$, $NR^{16}C(O)R^{15}$, $NR^{17}C(O)NR^{15}R^{16}$, $NR^{17}S(O)R^{15}$, $NR^{17}S(O)_2R^{15}$, $NR^{17}S(O)_2NR^{15}R^{16}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{15}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{16}$, and $R^{17}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$ together with the atom to which they are connected form an optionally substituted 3-20 membered cycloalkyl or heterocyclyl ring;

$R^4$ and $R^5$ are independently selected hydrogen, halogen, oxo, CN, $NO_2$, $OR^{18}$, $SR^{18}$, $NR^{19}R^{20}$, $OCOR^{18}$, $OCO_2R^{18}$, $OCONR^{19}R^{20}$, $COR^{18}$, $CO_2R^{18}$, $CONR^{19}R^{20}$, $SOR^{18}$, $SO_2R^{18}$, $SO_2NR^{19}R^{20}$, $NR^{18}CO_2R^{19}$, $NR^{18}COR^{19}$, $NR^{18}C(O)NR^{19}R^{20}$, $NR^{18}SOR^{19}$, $NR^{18}SO_2R^{19}$, $NR^{19}SO_2NR^{19}R^{20}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{18}$, $R^{19}$, and $R^{20}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{18}$ and $R^{19}$, $R^{19}$ and $R^{20}$ together with the atom to which they are connected form a 3-20 membered heterocyclyl ring; and pharmaceutically acceptable salts thereof.

In an embodiment, (HPK1) ligands include a moiety according to FORMULA 7:

FORMULA 7

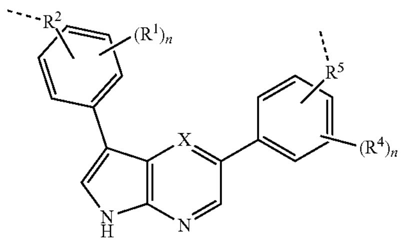

wherein the "Linker" moiety of the bivalent compound is attached to independently to $R^2$ or $R^5$;

X is selected from $CR^3$ or N;

each $R^1$ an d $R^4$ are independently selected from null, hydrogen, halogen, oxo, CN, $NO_2$, $OR^6$, $SR^6$, $NR^6R^7$, $OCOR^6$, $OCO_2R^6$, $OCONR^6R^7$, $COR^6$, $CO_2R^6$, $CONR^6R^7$, $SOR^6$, $SO_2R^6$, $SO_2NR^6R^7$, $NR^8CO_2R^6$, $NR^8COR^6$, $NR^8C(O)NR^6R^7$, $NR^8SOR^6$, $NR^8SO_2R^6$, $NR^8SO_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^6$, $R^7$ and $R^8$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^6$ and $R^7$, $R^6$ and $R^8$ together with the atom to which they are connected form a 4-20 membered heterocyclyl ring; and n is independently selected from 0, 1, 2, 3, 4 and 5;

$R^2$ and $R^5$ are independently selected from null, hydrogen, $C(O)R^{12}$, $C(O)OR^{12}$, $C(O)NR^{12}R^{13}$, $S(O)R^{12}$, $S(O)_2R^{12}$, $S(O)_2NR^{12}R^{13}$, $NR^{14}C(O)OR^{12}$, $NR^{13}C(O)R^{12}$, $NR^{14}C(O)NR^{12}R^{13}$, $NR^{14}S(O)R^{12}$, $NR^{14}S(O)_2R^{12}$, $NR^{14}S(O)_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{12}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{13}$, and $R^{14}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$ together with the atom to which they are connected form an optionally substituted 3-20 membered cycloalkyl or heterocyclyl ring;

$R^3$ is selected from hydrogen, halogen, oxo, CN, $NO_2$, $OR^{14}$, $SR^{14}$, $NR^{14}R^{15}$, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$, $R^{15}$, and $R^{16}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$, $R^{14}$ and $R^{15}$, $R^{15}$ and $R^{16}$ together with the atom to which they are connected form an optionally substituted 3-20 membered cycloalkyl or heterocyclyl ring.

In an embodiment, (HPK1) ligands include a moiety according to FORMULA 7A:

FORMULA 7A

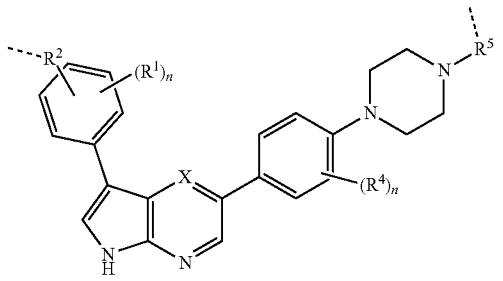

wherein the "Linker" moiety of the bivalent compound is attached to $R^2$ or $R^5$;

X is selected from $CR^3$ or N; and the definitions of $R^1$, $R^2$, $R^3$, $R^4$, and $R^5$ are the same as for FORMULA 7; and pharmaceutically acceptable salts thereof.

In an embodiment, (HPK1) ligands include a moiety according to FORMULA 8:

FORMULA 8

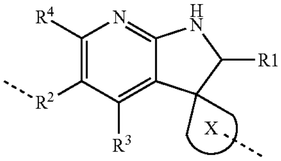

wherein the "Linker" moiety of the bivalent compound is attached to $R^2$ or X;

X is $C_{3-12}$ cycloalkyl, 3- to 14-membered heterocyclyl, $C_{6-14}$ aryl or 5- to- 14-membered heteroaryl, wherein $C_{3-12}$ cycloalkyl, 3- to 14-membered heterocyclyl, $C_{6-14}$ aryl or 5- to- 14-membered heteroaryl of X are each optionally substituted with 1, 2, 3, 4 or 5 substituents independently selected from $R^5$;

$R^1$ is selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl;

$R^2$ is selected from null, hydrogen, $C(O)R^7$, $C(O)OR^7$, $C(O)NR^7R^8$, $S(O)R^7$, $S(O)_2R^7$, $S(O)_2NR^7R^8$, $NR^9C(O)OR^7$, $NR^8C(O)R^7$, $NR^9C(O)NR^7R^8$, $NR^9S(O)R^7$, $NR^9S(O)_2R^7$, $NR^9S(O)_2NR^7R^8$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^7$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^8$, and $R^9$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^7$ and $R^8$ together with the atom to which they are connected form an optionally substituted 3-20 membered cycloalkyl or heterocyclyl ring;

$R^3$ and $R^4$ and $R^5$ are independently selected from null, hydrogen, halogen, oxo, CN, $NO_2$, $OR^{10}$, $SR^{10}$, $NR^{10}R^{11}$, $OCOR^{10}$, $OCO_2R^{10}$, $OCONR^{10}R^{11}$, $COR^{10}$, $CO_2R^{10}$, $CONR^{10}R^{11}$, $SOR^{10}$, $SO_2R^{10}$, $SO_2NR^{10}R^{11}$, $NR^{12}CO_2R^{10}$, $NR^{12}COR^{10}$, $NR^{12}C(O)NR^{10}R^{11}$, $NR^{12}SOR^{10}$, $NR^{12}SO_2R^{10}$, $NR^{12}SO_2NR^{10}R^{11}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{10}$, $R^{11}$ and $R^{12}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{10}$ and $R^{11}$, $R^{10}$ and $R^{12}$ together with the atom to which they are connected form a 4-20 membered heterocyclyl ring.

In an embodiment, (HPK1) ligands include a moiety according to FORMULA 8A:

FORMULA 8A

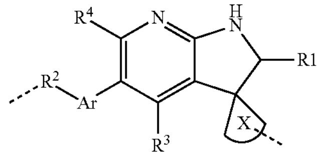

wherein the "Linker" moiety of the bivalent compound is attached to $R^2$ or X;

the definitions of X, $R^1$, $R^2$, $R^3$, $R^4$, and $R^5$ are the same as FORMULA 8;

Ar is selected from null, aryl and heteroaryl, each of which is substituted with $R^2$ and optionally substituted with one or more substituents independently selected from hydrogen, halogen, oxo, CN, $NO_2$, $OR^{11}$, $SR^{11}$, $NR^{11}R^{14}$, $OCOR^{13}$, $OCO_2R^{11}$, $OCONR^{11}R^{14}$, $COR^{13}$, $CO_2R^{11}$, $CONR^{13}R^{14}$, $SOR^{13}$, $SO_2R^{13}$, $SO_2NR^{13}R^{14}$, $NR^{15}CO_2R^{13}$, $NR^{15}COR^{13}$, $NR^{14}C(O)NR^{13}R^{14}$, $NR^5SOR^{13}$, $NR^{15}SO_2R^{13}$, $NR^{15}SO_2NR^{13}R^{14}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{13}$, $R^{14}$, and $R^{15}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{13}$ and $R^{14}$, $R^{13}$ and $R^{15}$ together with the atom to which they are connected form a 4-20 membered heterocyclyl ring.

In an embodiment, (HPK1) ligands include a moiety according to FORMULA 8B:

FORMULA 8B

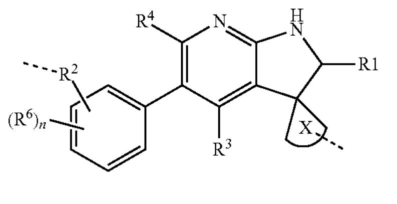

wherein the "Linker" moiety of the bivalent compound is attached to $R^2$ or X;

the definitions of X, $R^1$, $R^2$, $R^3$, $R^4$, and $R^5$ are the same as FORMULA 8;

Each $R^6$ is independently selected from null, hydrogen, halogen, oxo, CN, $NO_2$, $OR^{16}$, $SR^{16}$, $NR^{16}R^{17}$, $OCOR^{16}$, $OCO_2R^{16}$, $OCONR^{16}R^{17}$, $COR^{16}$, $CO_2R^{16}$, $CONR^{16}R^{17}$, $SOR^{16}$, $SO_2R^{16}$, $SO_2NR^{16}R^{17}$, $NR^{18}CO_2R^{16}$, $NR^{18}COR^{16}$, $NR^{18}C(O)NR^{16}R^{17}$, $NR^1SOR^{16}$, $NR^{18}SO_2R^{16}$, $NR^{18}SO_2NR^{16}R^{17}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{16}$, $R^{17}$ and $R^{18}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{16}$ and $R^{17}$, $R^{16}$ and $R^{18}$ together with the atom to which they are connected form a 4-20 membered heterocyclyl ring; and n is independently selected from 0, 1, 2, 3, 4 and 5; and pharmaceutically acceptable salts thereof.

In an embodiment, (HPK1) ligands include a moiety according to FORMULA 9:

FORMULA 9

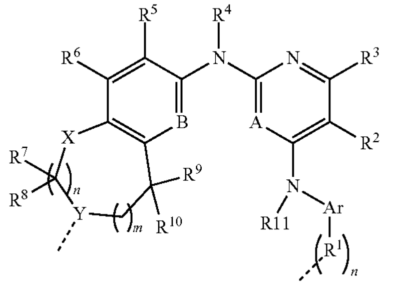

wherein the "Linker" moiety of the bivalent compound is attached independently to Y or independently one of the $R^1$;

each of $R^1$ is selected from null, $OR^{12}$, $SR^{11}$, $NR^{12}R^{13}$, $OC(O)R^{12}$, $OC(O)OR^{12}$, $OCONR^{12}R^{13}$, $C(O)R^{12}$, $C(O)OR^{12}$, $CONR^{12}R^{13}$, $S(O)R^{12}$, $S(O)_2R^{12}$, $SO_2NR^{12}R^{13}$, $NR^{14}C(O)OR^{12}$, $NR^{14}C(O)R^{12}$, $NR^{14}C(O)NR^{12}R^{13}$, $NR^{14}S(O)R^{12}$, $NR^{14}S(O)_2R^{12}$, $NR^{14}S(O)_2NR^{12}R^{13}$, $P(O)R^{12}R^{13}$, $P(O)(OR^{12})$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{12}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{13}$ and $R^{14}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{14}$, $R^{13}$ and $R^{14}$ together with the atom to which they are connected form a 3-20 membered cycloalkyl or heterocyclyl ring;

n and m are independently selected from 0, 1, 2, 3, 4 and 5;

Ar is selected from null, aryl and heteroaryl, each of which optionally is substituted with $R^1$; $R^2$, $R^3$, $R^5$ and $R^6$ are independently selected from hydrogen, halogen, $OR^{15}$, $SR^5$, $NR^{16}R^{17}$, $COR^{15}$, $CO_2R^{15}$, $C(O)NR^{16}R^{17}$, $SOR^{15}$, $SO_2R^{15}$, $SO_2NR^{16}R^{17}$, $NR^{15}C(O)R^{16}$, $NR^{15}C(O)NR^{16}R^{17}$, $NR^{15}SOR^{16}$, $NR^{15}SO_2R^{16}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{15}$, $R^{16}$, and $R^{17}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-10 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$, $R^{16}$ and $R^{17}$ together with the atom to which they are connected form an optionally substituted 3-20 membered cycloalkyl or heterocyclyl ring;

$R^7$, $R^8$, $R^9$, and $R^{10}$ are independently selected from null, hydrogen, halogen, $OR^{18}$, $NR^{19}R^{20}$ optionally substituted $C_1$-$C_8$ alkyl, optionally substituted $C_1$-$C_8$ alkoxy, optionally substituted $C_3$-$C_8$ cycloalkyl, optionally substituted $C_3$-$C_8$ cycloalkoxy; wherein $R^{18}$, $R^{19}$, and $R^{20}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-10 membered heterocyclyl, optionally substituted $C_2$-$C_8$ alkenyl, optionally substituted $C_2$-$C_8$ alkynyl; or $R^{19}$ and $R^{20}$ together with the atom to which they are connected form an an optionally substituted 3-20 membered cycloalkyl or heterocyclyl ring;

$R^{11}$ at each occurrence, is independently selected from hydrogen, $C(O)R^{21}$, $C(O)OR^{21}$, $C(O)NR^{21}R^{22}$, $S(O)R^{21}$, $S(O)_2R^{21}$, $S(O)_2NR^{21}R^{22}$, $NR^{23}C(O)OR^{21}$, $NR^{23}C(O)R^{21}$, $NR^{23}C(O)NR^{21}R^{22}$, $NR^{23}S(O)R^{21}$, $NR^{23}S(O)_2R^{21}$, $NR^{23}S(O)_2NR^{21}R^{22}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{21}$, $R^{22}$ and $R^{23}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{21}$ and $R^{22}$, $R^{21}$ and $R^{23}$ together with the atom to which they are connected form a 3-20 membered heterocyclyl ring; and X, Y at each occurrence, are independently selected from null, CO, $CO_2$, $CH_2$, $CR^{24}R^{25}$, $C(O)NR^{24}$, $C(S)NR^{24}$, O, S, SO, $SO_2$, $SO_2NR^{24}$, $NR^{24}$, $NR^{24}CO$, $NR^{24}CONR^{21}$, $NR^{24}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{24}$ and $R^{25}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl; and A and B are independently selected from C or N; and pharmaceutically acceptable salts thereof.

In an embodiment, (HPK1) ligands include a moiety according to FORMULA 10:

FORMULA 10

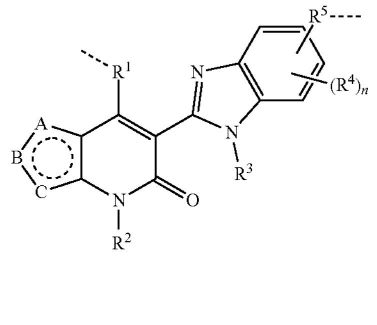

wherein the "Linker" moiety of the bivalent compound is attached independently to $R^1$ or $R^5$;

$R^1$ and $R^5$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NRIC(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$ and $R^3$ at each occurrence, is independently selected from hydrogen, $C(O)R^9$, $C(O)OR^9$, $C(O)NR^9R^{10}$, $S(O)R^{21}$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$ and $R^{11}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^9$ and $R^{10}$, $R^9$ and $R^{11}$ together with the atom to which they are connected form a 3-20 membered heterocyclyl ring;

each of $R^4$ is selected from null, $OR^{12}$, $SR^{12}$, $NR^{12}R^{13}$, $OC(O)R^{12}$, $OC(O)OR^{12}$, $OCONR^{12}R^{13}$, $C(O)R^{12}$, $C(O)OR^{12}$, $CONR^{12}R^{13}$, $S(O)R^{12}$, $S(O)_2R^{12}$, $SO_2NR^{12}R^{13}$, $NR^{14}C(O)OR^{12}$, $NR^{14}C(O)R^{12}$, $NR^{14}C(O)NR^{12}R^{13}$, $NR^{14}S(O)R^{12}$, $NR^{14}S(O)_2R^{12}$, $NR^{14}S(O)_2\ NR^{12}R^{13}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{12}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{13}$ and $R^{14}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{14}$, $R^{13}$ and $R^{14}$ together with the atom to which they are connected form a 3-20 membered cycloalkyl or heterocyclyl ring;

n is independently selected from 0, 1, 2, 3, 4 and 5;

one of A, B and C is S, the other two are each independently selected from $CR^{15}$ or N Wherein $R^{14}$ is independently selected from null, hydrogen, halogen, oxo, CN, $NO_2$, $OR^{16}$, $SR^{16}$, $NR^{16}R^{17}$, $OCOR^{16}$, $OCO_2R^{16}$, $OCONR^{16}R^{17}$, $COR^{16}$, $CO_2R^{16}$, $CONR^{16}R^{17}$, $SOR^{16}$, $SO_2R^{16}$, $SO_2NR^{16}R^{17}$, $NR^{15}CO_2R^{16}$, $NR^{18}COR^{16}$, $NR^{18}C(O)NR^{16}R^{17}$, $NR^{18}SOR^{16}$, $NR^{15}SO_2R^{16}$, $NR^{15}SO_2NR^{16}R^{17}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{16}$, $R^{17}$ and $R^{18}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{16}$ and $R^{17}$, $R^{16}$ and $R^{18}$ together with the atom to which they are connected form a 4-20 membered heterocyclyl ring; and pharmaceutically acceptable salts thereof.

In an embodiment, (HPK1) ligands include a moiety according to FORMULA 11:

FORMULA 11

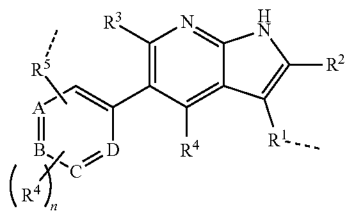

wherein the “Linker” moiety of the bivalent compound is attached independently to $R^1$ or $R^5$;

$R^1$ and $R^5$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NRIC(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$, $R^3$ and $R^4$ at each occurrence, is independently selected from hydrogen, $C(O)R^9$, $C(O)OR^9$, $C(O)NR^9R^{10}$, $S(O)R^{21}$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$ and $R^{11}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^9$ and $R^{10}$, $R^9$ and $R^{11}$ together with the atom to which they are connected form a 3-20 membered heterocyclyl ring;

A, B and C each independently selected from N or $CR^6$;

each of $R^6$ is independently selected from null, hydrogen, halogen, $OR^{12}$, $SR^{12}$, $NR^{12}R^{13}$, $OC(O)R^{12}$, $OC(O)OR^{12}$, $OCONR^{12}R^{13}$, $C(O)R^{12}$, $C(O)OR^{12}$, $CONR^{12}R^{13}$, $S(O)R^{12}$, $S(O)_2R^{12}$, $SO_2NR^{12}R^{13}$, $NR^{14}C(O)OR^{12}$, $NR^{14}C(O)R^{12}$, $NR^{14}C(O)NR^{12}R^{13}$, $NR^{14}S(O)R^{12}$, $NR^{14}S(O)_2R^{12}$, $NR^{14}S(O)_2NR^{12}R^{13}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl, wherein;

$R^{12}$, $R^{13}$ and $R^{14}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{14}$, $R^{13}$ and $R^{14}$ together with the atom to which they are connected form a 3-20 membered cycloalkyl or heterocyclyl ring; and n is independently selected from 0, 1, 2, 3, 4 and 5; and pharmaceutically acceptable salts thereof.

In an embodiment, (HPK1) ligands are selected from the group consisting of

FORMULA 110

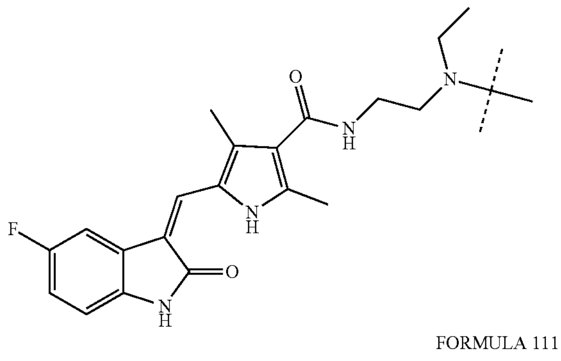

FORMULA 111

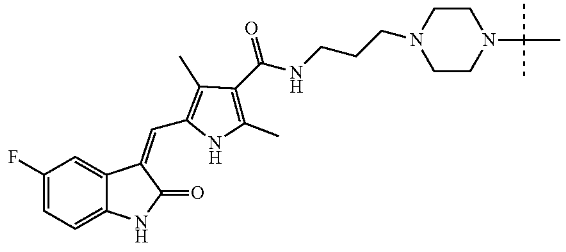

-continued
FORMULA 112
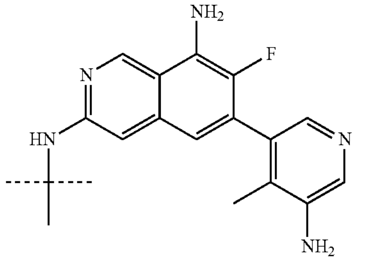
FORMULA 113
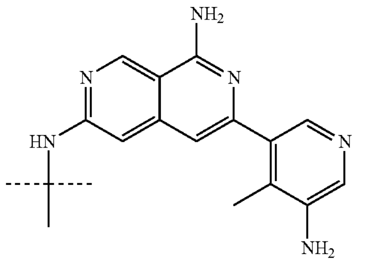
FORMULA 114
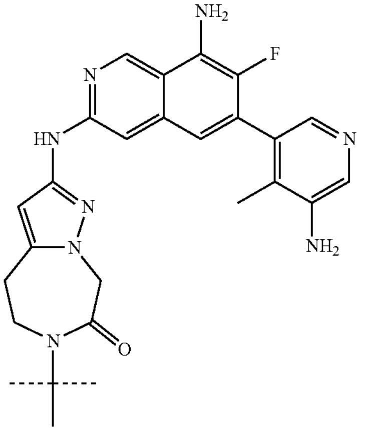
FORMULA 115
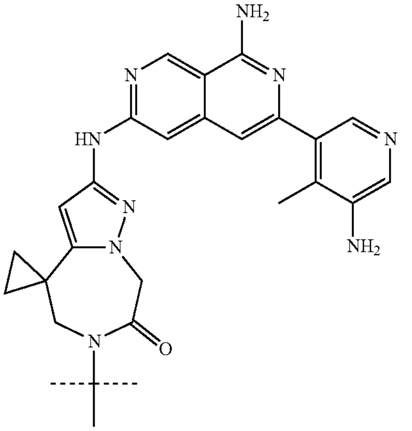
-continued
FORMULA 116
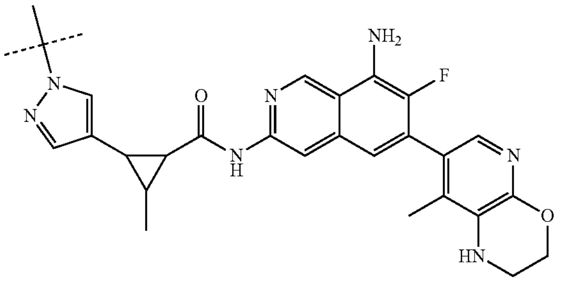
FORMULA 117
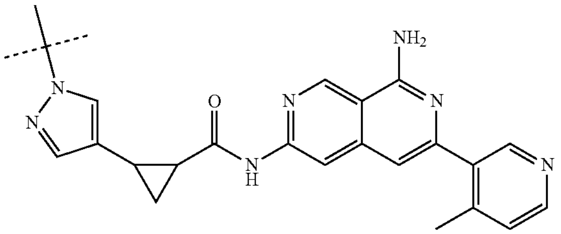
FORMULA 118
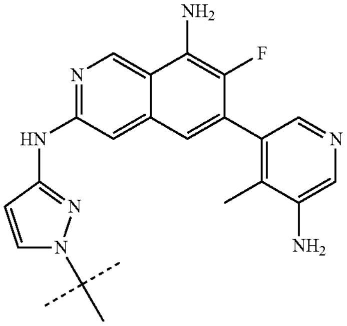
FORMULA 119
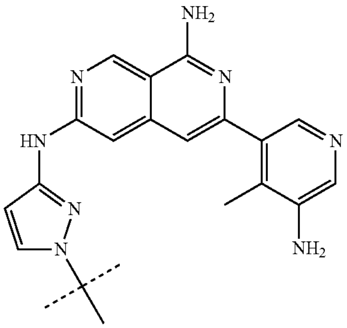
FORMULA 120
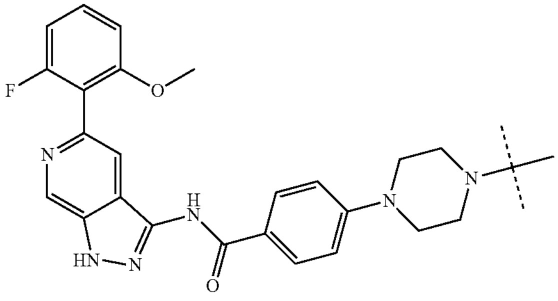

-continued
FORMULA 121
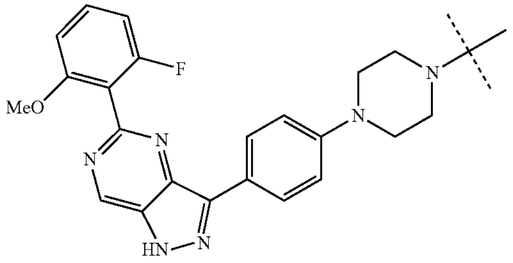
FORMULA 122
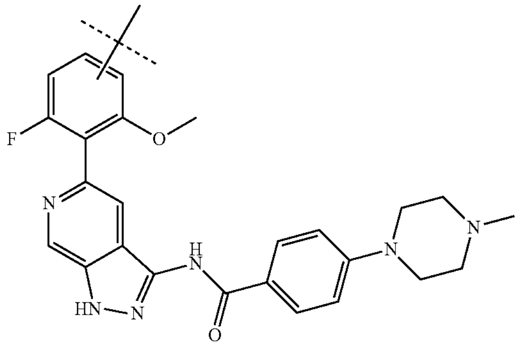
FORMULA 123
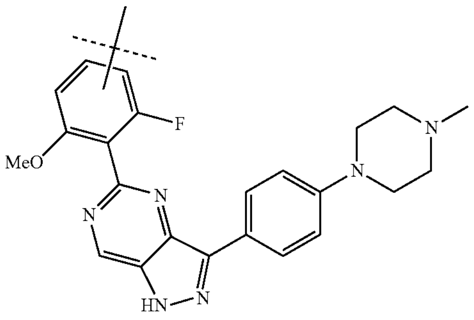
FORMULA 124
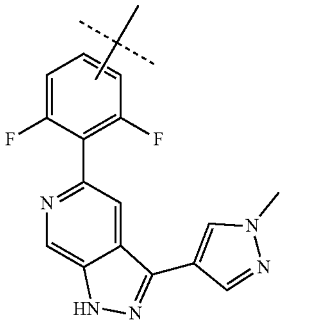
FORMULA 125
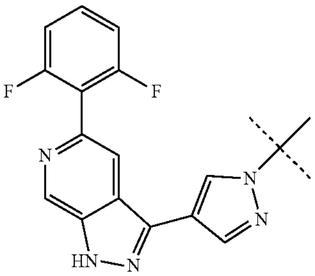
-continued
FORMULA 126
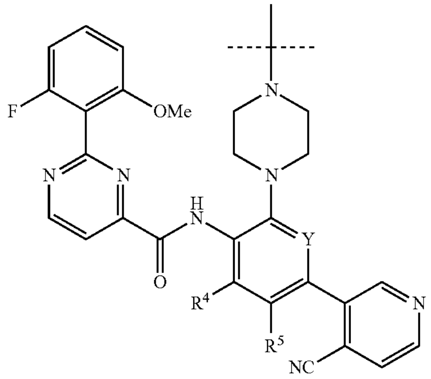
FORMULA 127
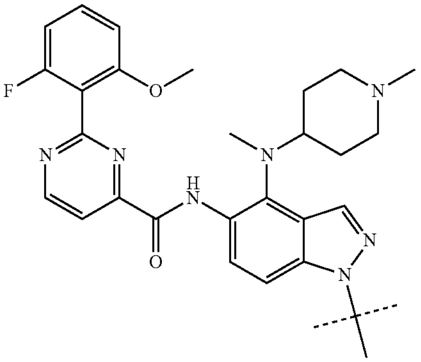
FORMULA 128
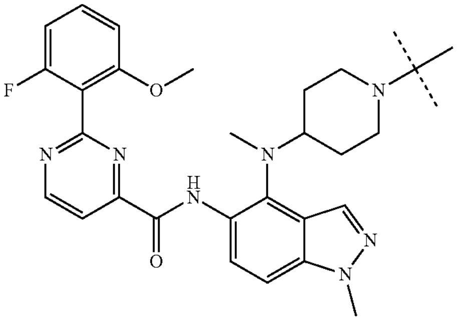
FORMULA 129
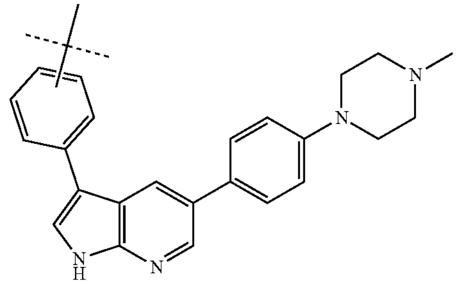

-continued
FORMULA 130
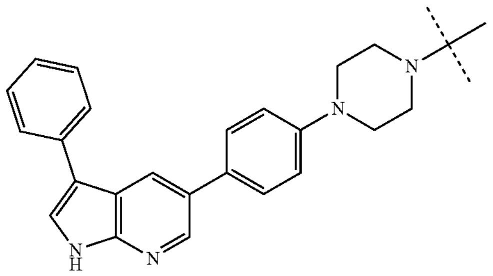
FORMULA 131
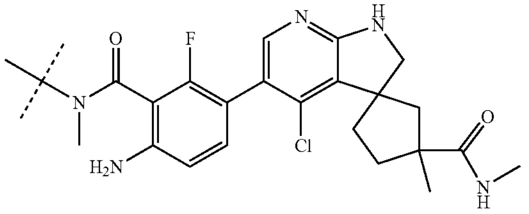
FORMULA 132
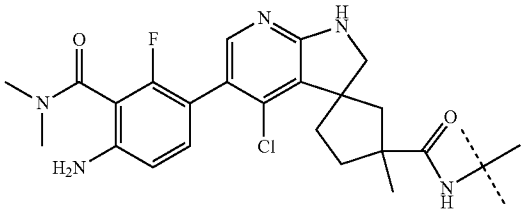
FORMULA 133
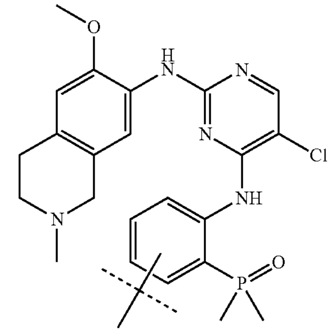
FORMULA 134
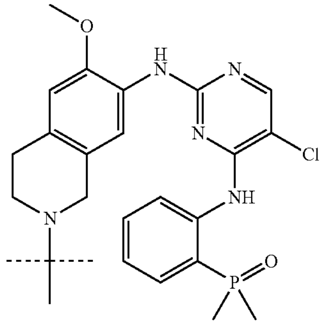
-continued
FORMULA 135
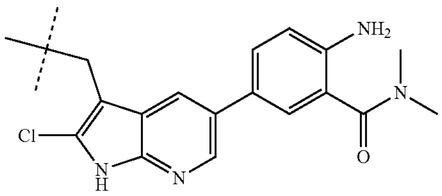
FORMULA 136
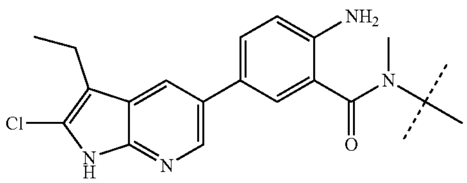
FORMULA 137
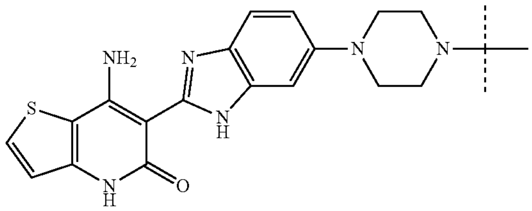
FORMULA 138
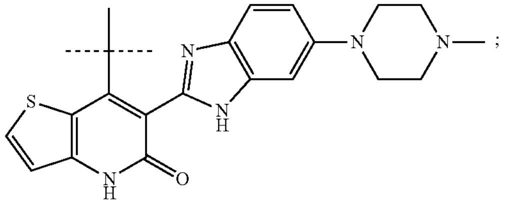
and
pharmaceutically acceptable salts thereof.
Degradation/Disruption Tags
Degradation/Disruption tags (EL) include, but are not limited to:
In an embodiment, degradation/disruption tags include a moiety according to FORMULAE 12A, 12B, 12C and 12D:
FORMULA 12A
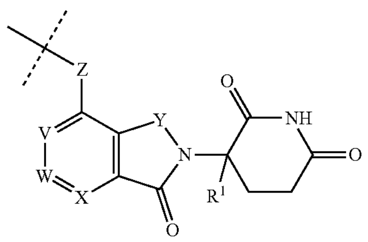

-continued

FORMULA 12B

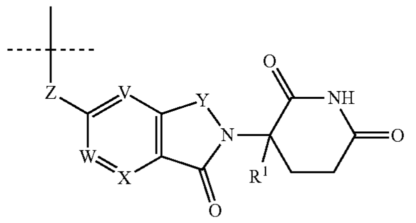

FORMULA 12C

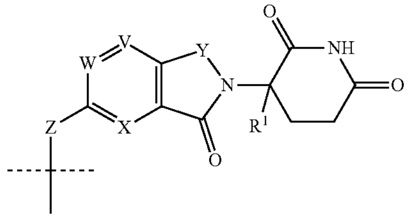

FORMULA 12D

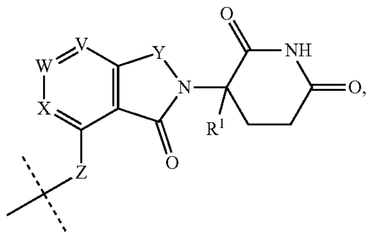

wherein

V, W, and X are independently selected from $CR^2$ and N;

Y is selected from CO, $CR^3R^4$, and N═N;

Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH═CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In an embodiment, degradation/disruption tags include a moiety according to one of FORMULAE 12E, 12F, 12G, 12H, and 12I:

FORMULA 12E

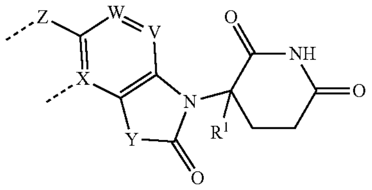

FORMULA 12F

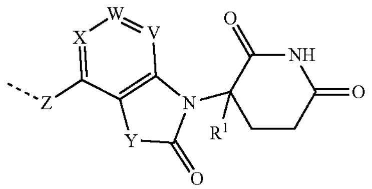

FORMULA 12G

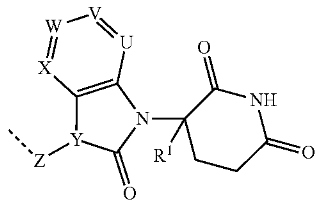

FORMULA 12H

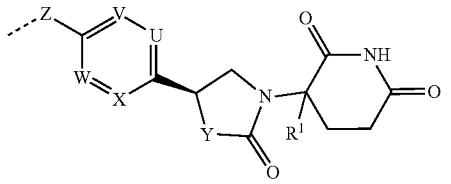

FORMULA 12I

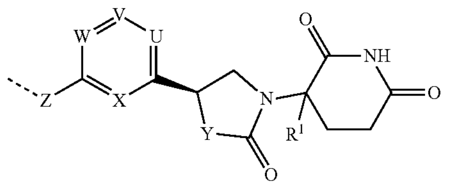

wherein

U, V, W, and X are independently selected from $CR^2$ and N;

Y is selected from $CR^3R^4$, $NR^3$ and O; preferably, Y is selected from $CH_2$, NH, $NCH_3$ and O;

Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH═CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl; and pharmaceutically acceptable salts thereof.

In an embodiment, degradation/disruption tags include a moiety according to FORMULA 13A:

FORMULA 13A

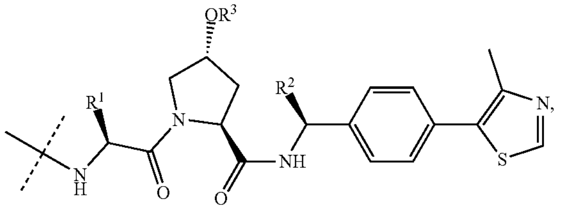

wherein $R^1$ and $R^2$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; and $R^3$ is hydrogen, optionally substituted C(O)$C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)$C_3$-$C_7$ cycloalkyl, optionally substituted C(O)(3-7 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O)O$C_1$-$C_8$alkylamino$C_1$-$C_8$alkyl, optionally substituted C(O)O$C_3$-$C_7$ cycloalkyl, optionally substituted C(O)O(3-7 membered heterocyclyl), optionally substituted C(O)O$C_2$-$C_8$ alkenyl, optionally substituted C(O)O$C_2$-$C_8$ alkynyl, optionally substituted C(O)N$C_1$-$C_8$alkoxy$C_1$-$C_8$alkyl, optionally substituted C(O)N$C_1$-$C_8$ haloalkyl, optionally substituted C(O)N$C_1$-$C_8$ hydroxyalkyl, optionally substituted C(O)N$C_1$-$C_8$ aminoalkyl, optionally substituted C(O)N$C_1$-$C_8$alkylamino$C_1$-$C_8$alkyl, optionally substituted C(O)N$C_3$-$C_7$ cycloalkyl, optionally substituted C(O)N(3-7 membered heterocyclyl), optionally substituted C(O)N$C_2$-$C_8$ alkenyl, optionally substituted C(O)N$C_2$-$C_8$ alkynyl, optionally substituted $P(O)(OH)_2$, optionally substituted P(O)(O$C_1$-$C_8$ $alkyl)_2$, and optionally substituted P(O)(O$C_1$-$C_8$ $aryl)_2$.

In an embodiment, degradation/disruption tags include a moiety according to FORMULAE 13B, 13C, 13D, 13E and 13F:

FORMULA 13B

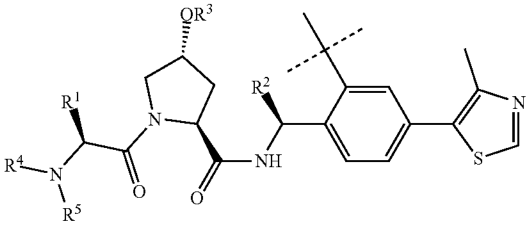

FORMULA 13C

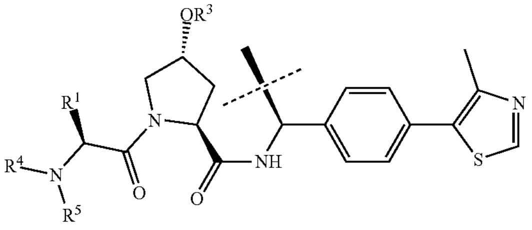

FORMULA 13D

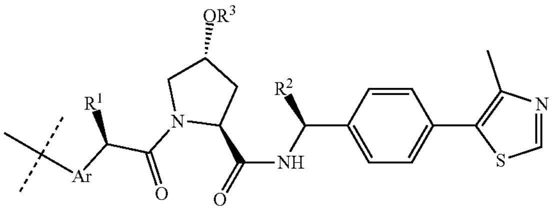

FORMULA 13E

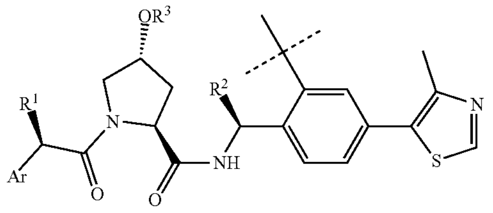

-continued

FORMULA 13F

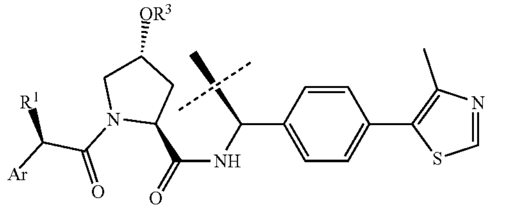

wherein $R^1$ and $R^2$ are independently selected from hydrogen, halogen, OH, $NH_2$, CN, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, $R^1$ is selected from iso-propyl or tert-butyl; and $R^2$ is selected from hydrogen or methyl);

$R^3$ is hydrogen, optionally substituted $C(O)C_1$-$C_8$ alkyl, optionally substituted $C(O)C_1$-$C_8$alkoxy$C_1$-$C_8$alkyl, optionally substituted $C(O)C_1$-$C_8$ haloalkyl, optionally substituted $C(O)C_1$-$C_8$ hydroxyalkyl, optionally substituted $C(O)C_1$-$C_8$ aminoalkyl, optionally substituted $C(O)C_1$-$C_8$alkylamino$C_1$-$C_8$alkyl, optionally substituted $C(O)C_3$-$C_7$ cycloalkyl, optionally substituted C(O)(3-7 membered heterocyclyl), optionally substituted $C(O)C_2$-$C_8$ alkenyl, optionally substituted C(O) $C_2$-$C_8$ alkynyl, optionally substituted $C(O)OC_1$-$C_8$alkoxy$C_1$-$C_8$alkyl, optionally substituted $C(O)OC_1$-$C_8$ haloalkyl, optionally substituted $C(O)OC_1$-$C_8$ hydroxyalkyl, optionally substituted $C(O)OC_1$-$C_8$ aminoalkyl, optionally substituted $C(O)OC_1$-$C_8$alkylamino$C_1$-$C_8$alkyl, optionally substituted C(O) $OC_3$-$C_7$ cycloalkyl, optionally substituted C(O)O(3-7 membered heterocyclyl), optionally substituted C(O) $OC_2$-$C_8$ alkenyl, optionally substituted $C(O)OC_2$-$C_8$ alkynyl, optionally substituted $C(O)NC_1$-$C_8$alkoxy$C_1$-$C_8$alkyl, optionally substituted $C(O)NC_1$-$C_8$ haloalkyl, optionally substituted $C(O)NC_1$-$C_8$ hydroxyalkyl, optionally substituted $C(O)NC_1$-$C_8$ aminoalkyl, optionally substituted $C(O)NC_1$-$C_8$alkylamino$C_1$-$C_8$alkyl, optionally substituted $C(O)NC_3$-$C_7$ cycloalkyl, optionally substituted C(O)N(3-7 membered heterocyclyl), optionally substituted $C(O)NC_2$-$C_8$ alkenyl, optionally substituted $C(O)NC_2$-$C_8$ alkynyl, optionally substituted $P(O)(OH)_2$, optionally substituted $P(O)(OC_1$-$C_8$ $alkyl)_2$, and optionally substituted $P(O)(OC_1$-$C_8$ $aryl)_2$; and $R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl; wherein $R^6$ and $R^7$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl; or $R^4$ and $R^5$; $R^6$ and $R^7$ together with the atom to which they are connected form a 4-8 membered cycloalkyl or heterocyclyl ring;

Ar is selected from aryl and heteroaryl, each of which is optionally substituted with one or more substituents independently selected from F, Cl, CN, $NO_2$, $OR^8$, $NR^8R^9$, $COR^8$, $CO_2R^8$, $CONR^8R^9$, $SOR^8$, $SO_2R^8$, $SO_2NR^9R^{10}$, $NR^9COR^{10}$, $NR^8C(O)NR^9R^{10}$, $NR^9SOR^{10}$, $NR^9SO_2R^{10}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl; wherein $R^8$, $R^9$, and $R^{10}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl; or $R^8$ and $R^9$; $R^9$ and $R^{10}$ together with the atom to which they are connected form a 4-8 membered cycloalkyl or heterocyclyl ring; and pharmaceutically acceptable salts thereof.

In an embodiment, degradation/disruption tags include a moiety according to FORMULA 14A:

FORMULA 14A

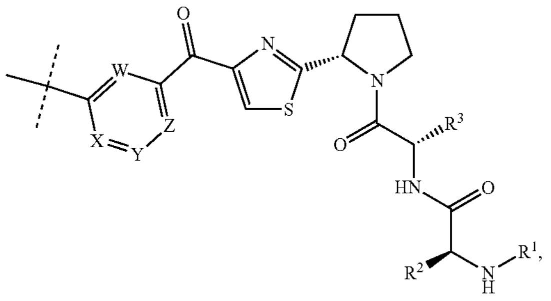

wherein

V, W, X, and Z are independently selected from $CR^4$ and N;

$R^1$, $R^2$, $R^3$, and $R^4$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl.

In an embodiment, degradation/disruption tags include a moiety according to FORMULA 14B:

FORMULA 14B

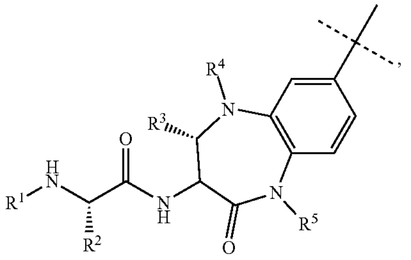

wherein $R^1$, $R^2$, and $R^3$ are independently selected from hydrogen, halogene, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl;

$R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted aryl-$C_1$-$C_8$alkyl, optionally substituted 3-8 membered cycloalkyl, optionally substituted 3-8 membered heterocyclyl, optionally substituted aryl, and optionally substituted heteroaryl; wherein $R^6$ and $R^7$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl; or $R^6$ and $R^7$ together with the atom to which they are connected form a 4-8 membered cycloalkyl or heterocyclyl ring; and pharmaceutically acceptable salts thereof.

In an embodiment, degradation/disruption tags are selected from the group consisting of:

FORMULA 15A

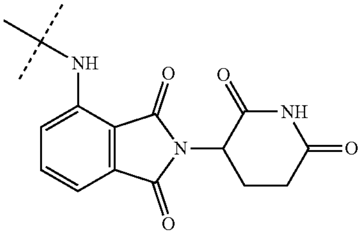

-continued

FORMULA 15B

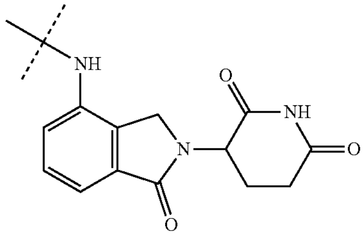

FORMULA 15C

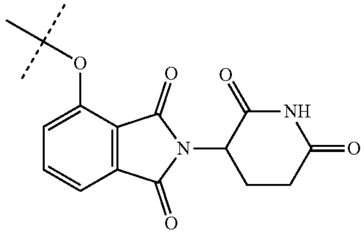

FORMULA 15D

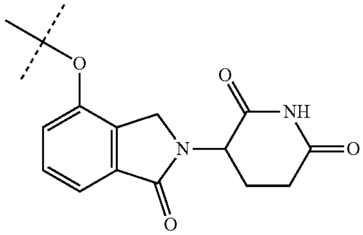

FORMULA 15E

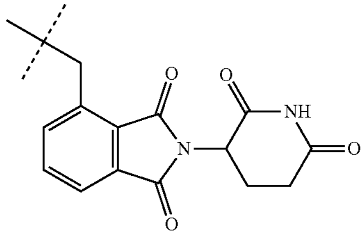

FORMULA 15F

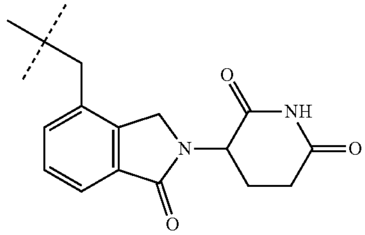

FORMULA 15G

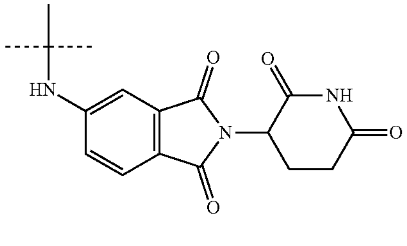

FORMULA 15H
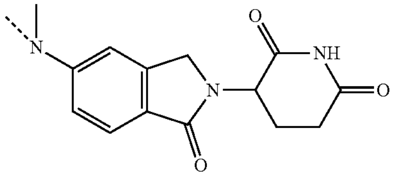
FORMULA 15I
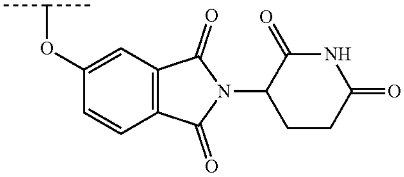
FORMULA 15J
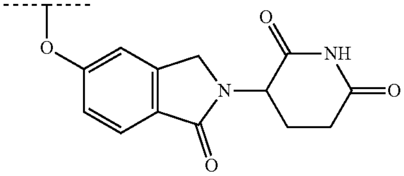
FORMULA 15K
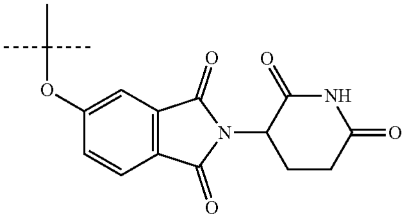
FORMULA 15L
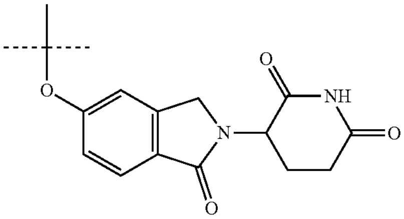
FORMULA 15M
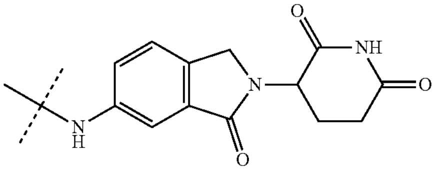
FORMULA 15N
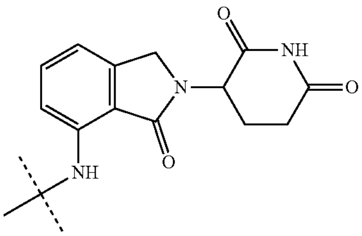
FORMULA 15O
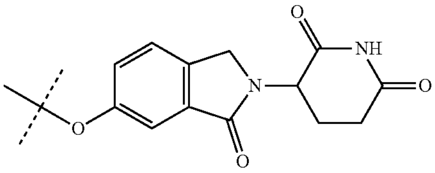
FORMULA 15P
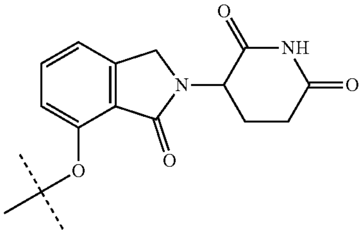
FORMULA 15Q
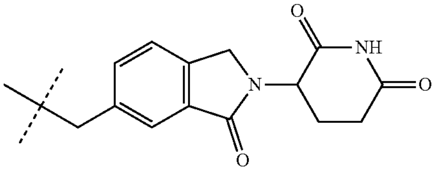
FORMULA 15R
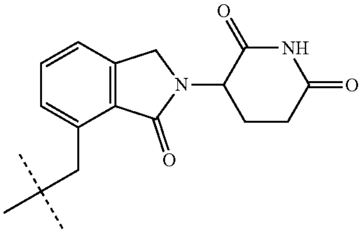
FORMULA 15S
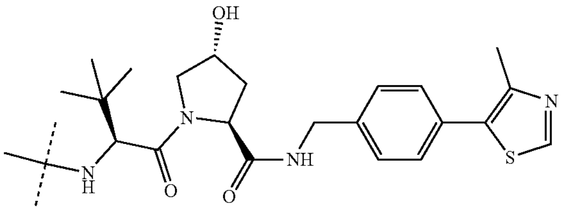
FORMULA 15T
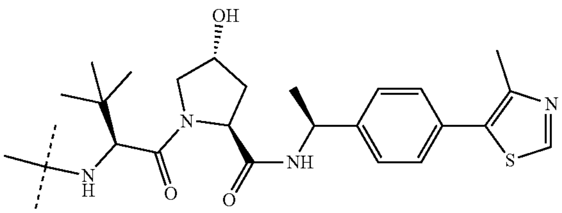

-continued
FORMULA 15U
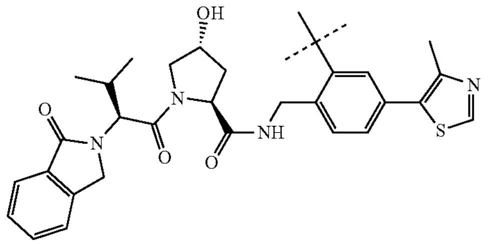
FORMULA 15V
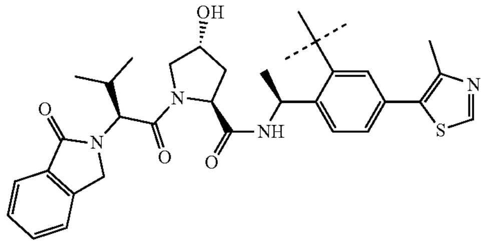
FORMULA 15W
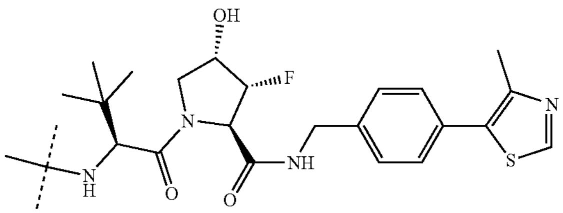
FORMULA 15X
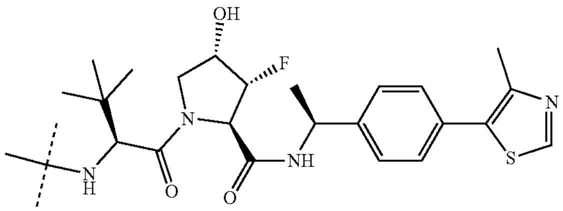
FORMULA 15Y
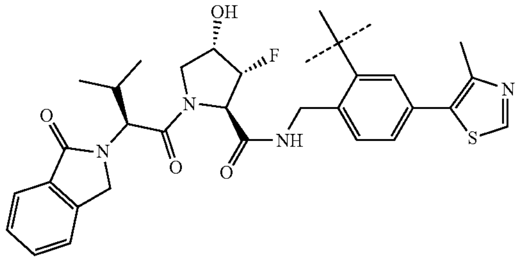
FORMULA 15Z
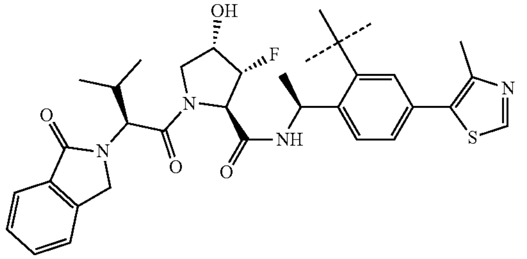
-continued
FORMULA 15AA
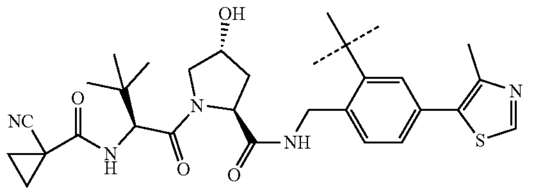
FORMULA 15AB
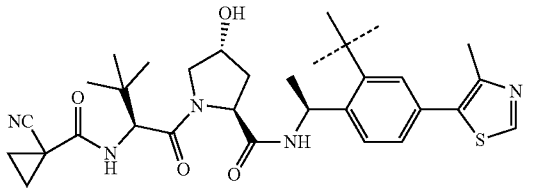
FORMULA 15AC
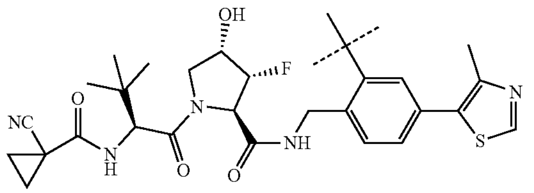
FORMULA 15AD
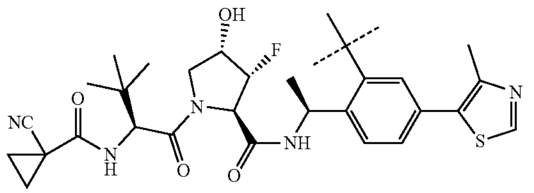
FORMULA 15AE
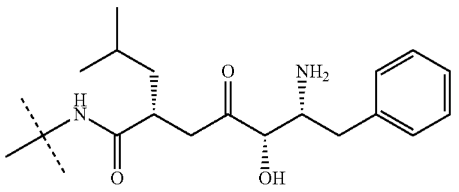
FORMULA 15AF
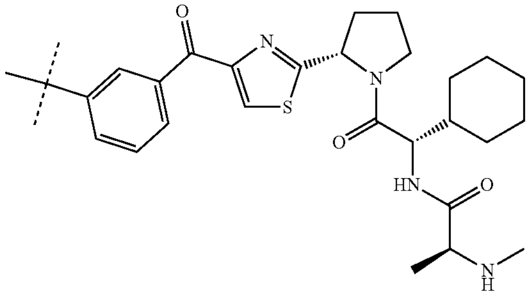

-continued
FORMULA 15AG
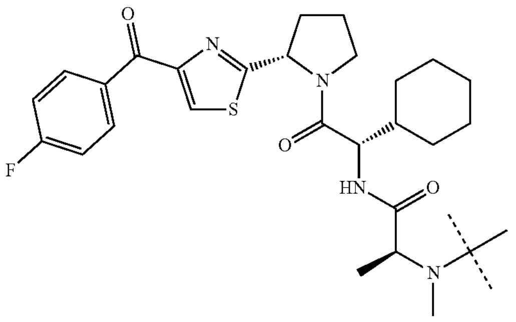
FORMULA 15AH
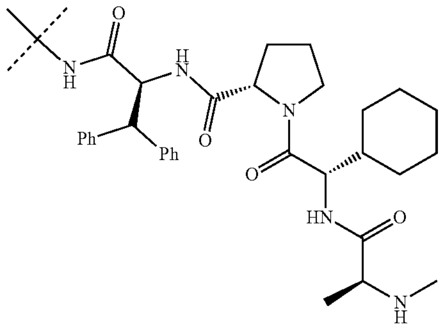
FORMULA 15AI
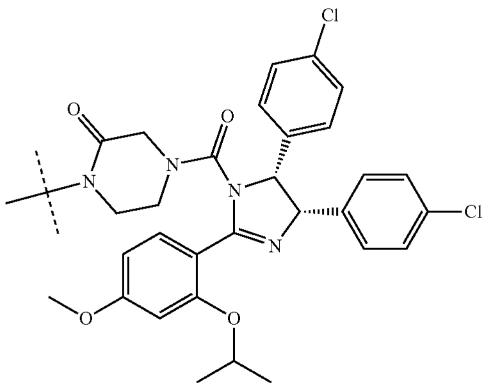
FORMULA 15AJ
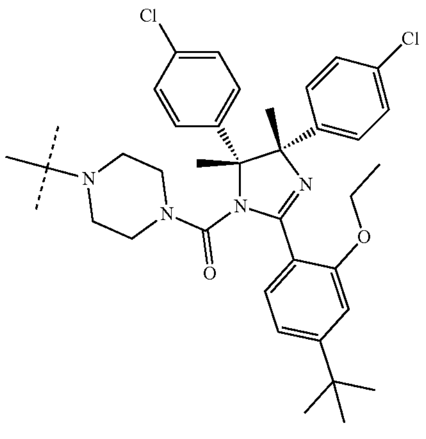
-continued
FORMULA 15AK
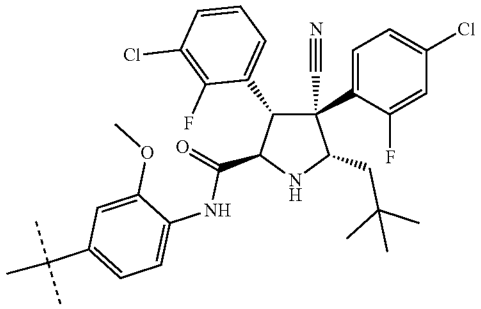
FORMULA 15AL
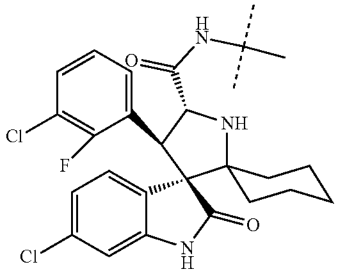
FORMULA 15AM
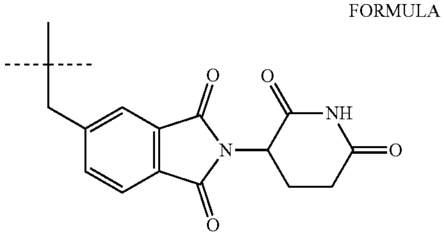
FORMULA 15AN
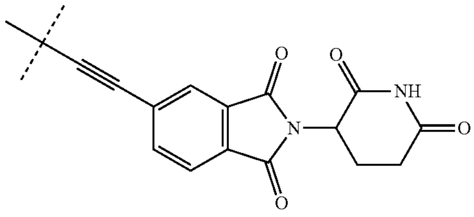
FORMULA 15AO
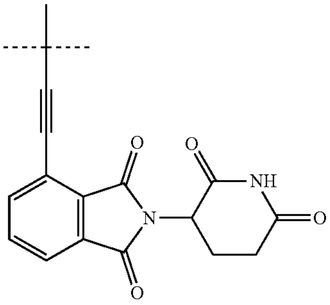
FORMULA 15AP
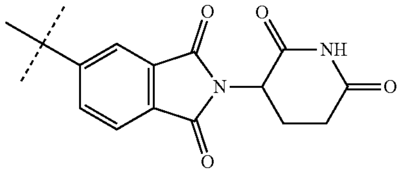

-continued
FORMULA 15AQ
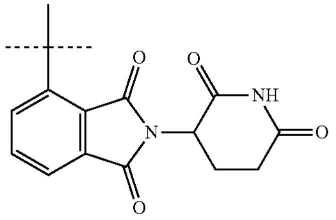
FORMULA 15AR
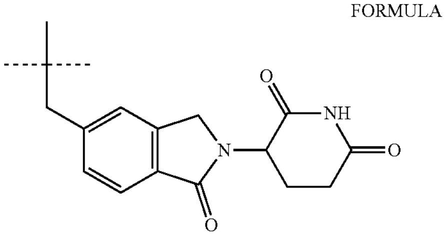
FORMULA 15AS
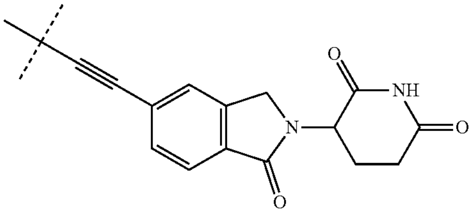
FORMULA 15AT
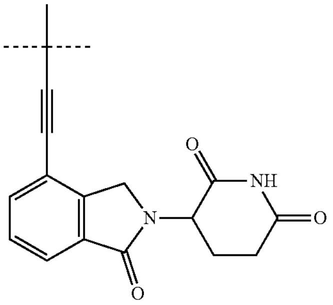
FORMULA 15AU
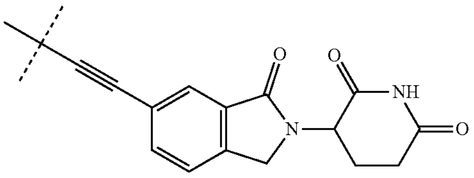
FORMULA 15AV
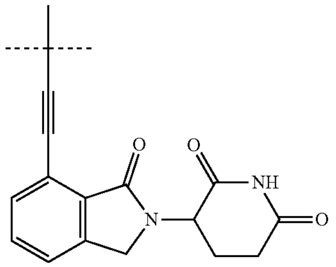
-continued
FORMULA 15AW
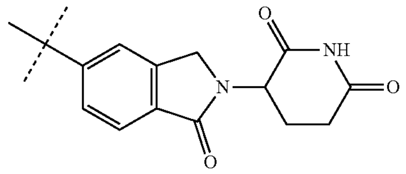
FORMULA 15AX
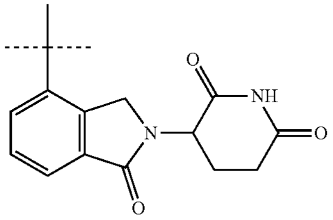
FORMULA 15AY
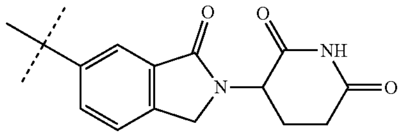
FORMULA 15AZ
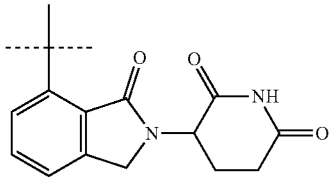
FORMULA 15BA
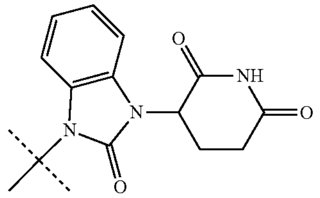
FORMULA 15BB
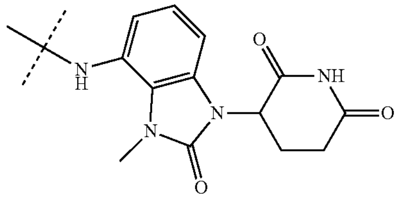
FORMULA 15BC
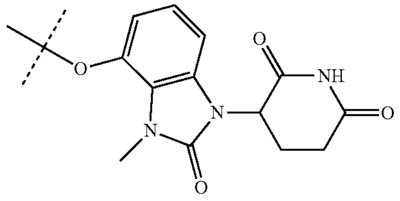

-continued
FORMULA 15BD
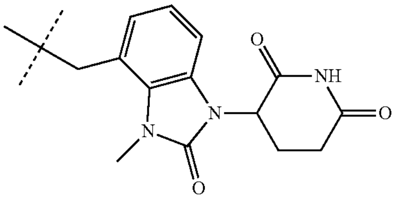
FORMULA 15BE
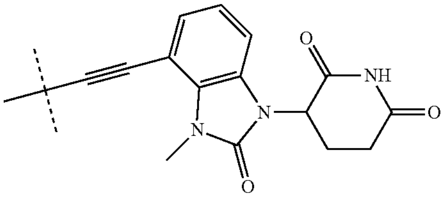
FORMULA 15BF
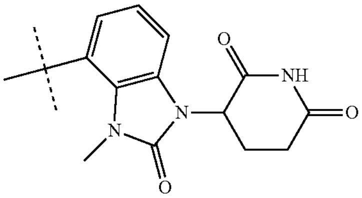
FORMULA 15BG
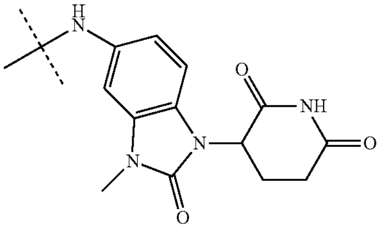
FORMULA 15BH
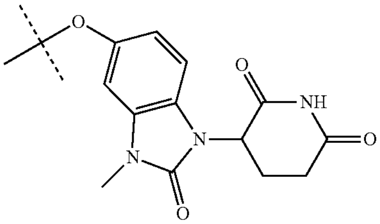
FORMULA 15BI
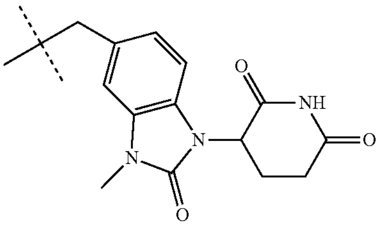
-continued
FORMULA 15BJ
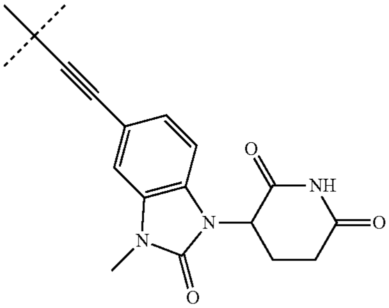
FORMULA 15BK
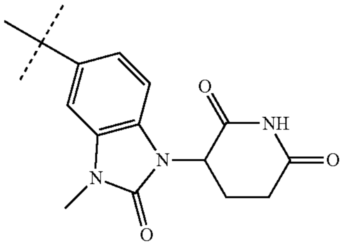
FORMULA 15BL
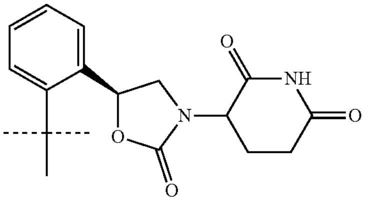
FORMULA 15BM
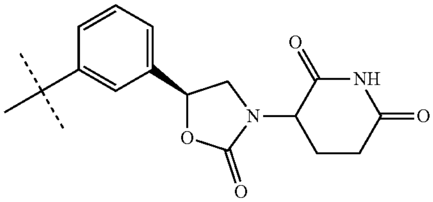
FORMULA 15BN
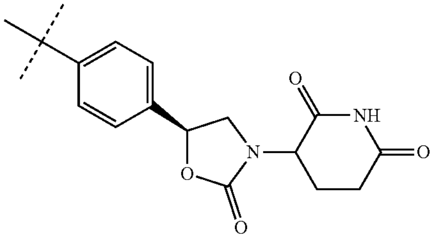
FORMULA 15BO
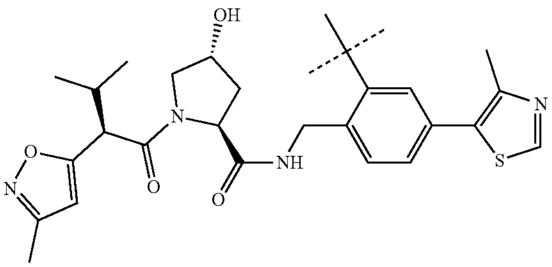

-continued
FORMULA 15BP
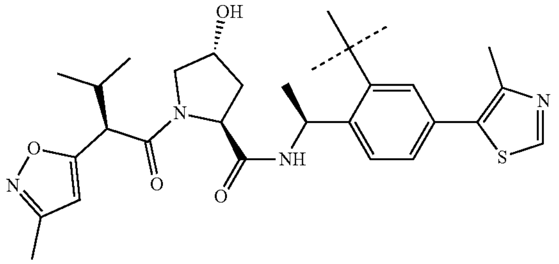
FORMULA 15BQ
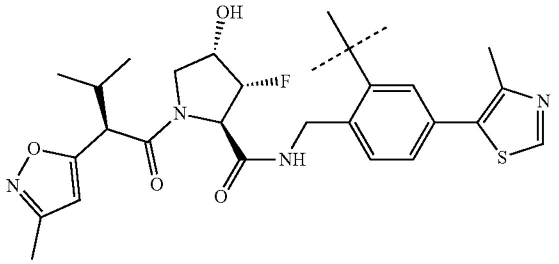
FORMULA 15BR
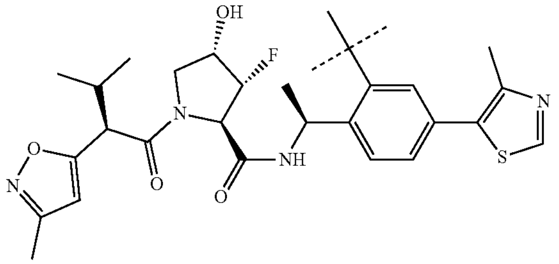
FORMULA 15BS
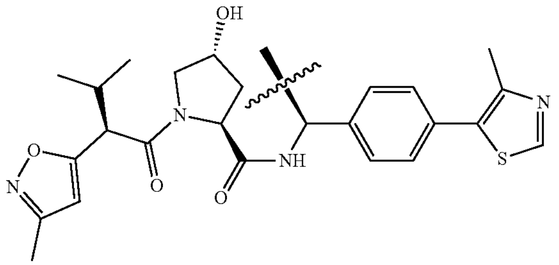
FORMULA 15BT
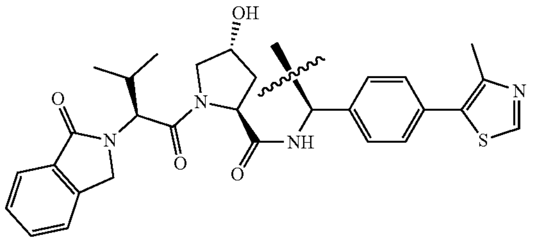
FORMULA 15BU
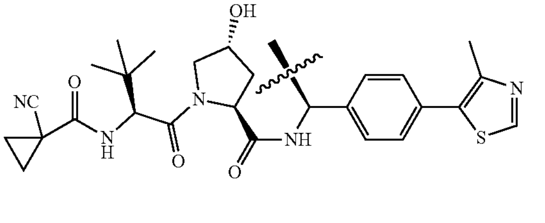
-continued
FORMULA 15BV
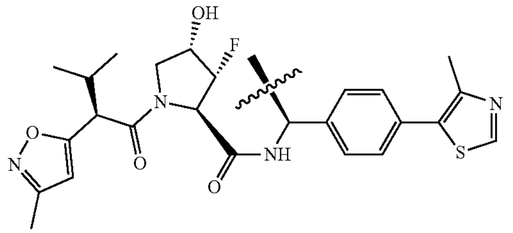
FORMULA 15BW
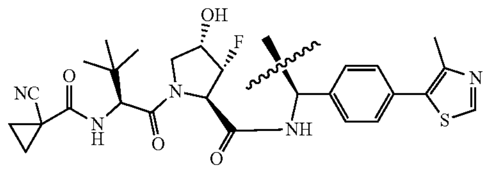
FORMULA 15BX
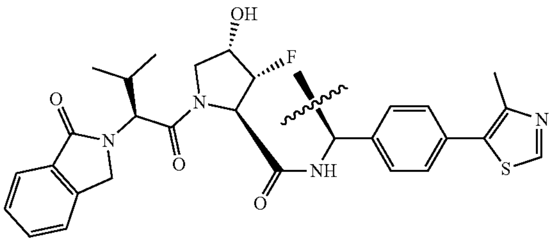
FORMULA 15BY
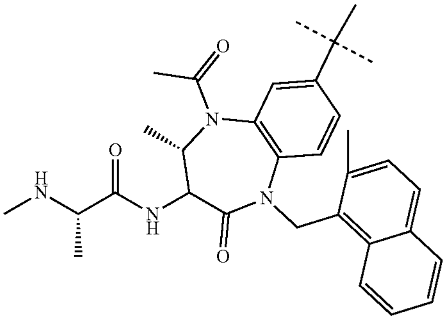
FORMULA 15BZ
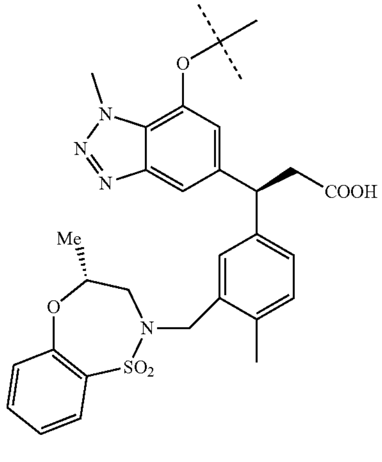

-continued
FORMULA 15CA
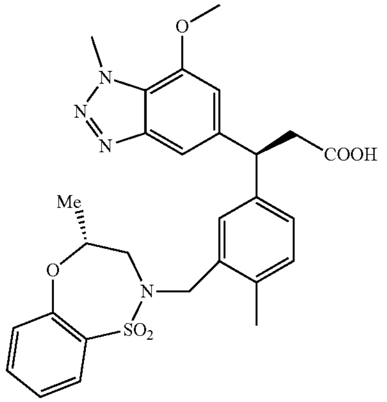
FORMULA 15CB
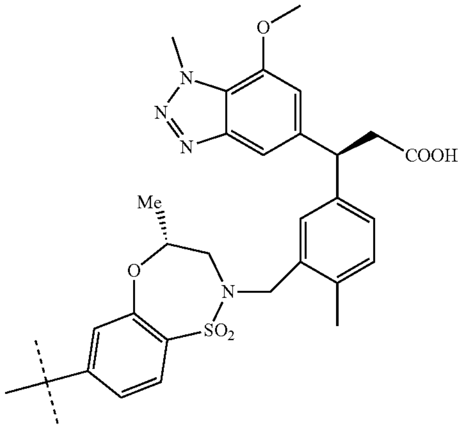
FORMULA 15CC
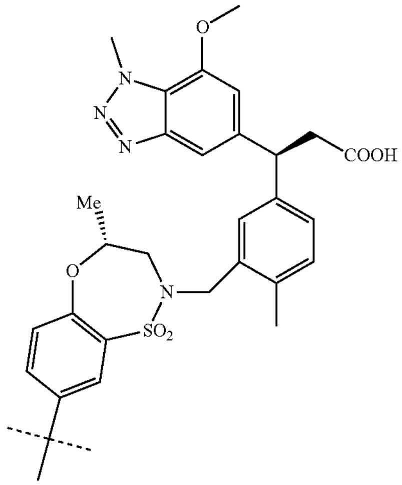
-continued
FORMULA 15CD
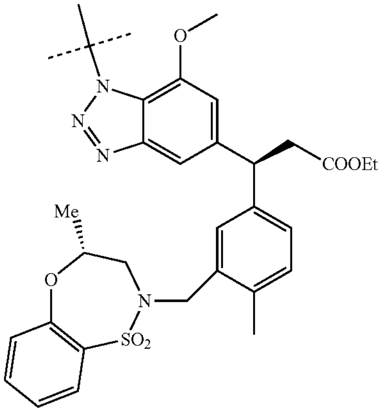
FORMULA 15CE
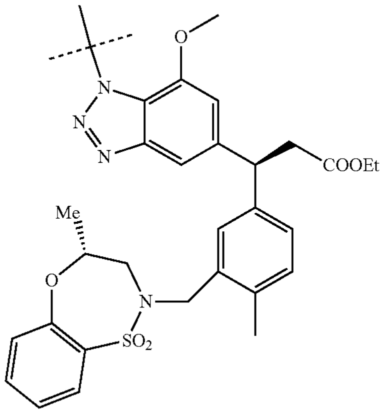
FORMULA 15CF
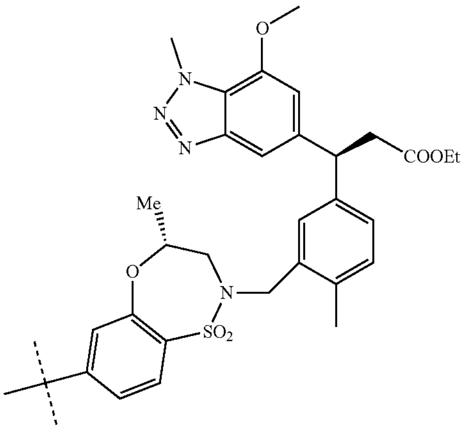

-continued

FORMULA 15CG

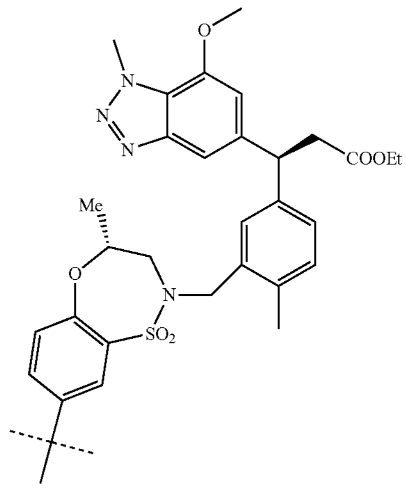

FORMULA 15CH

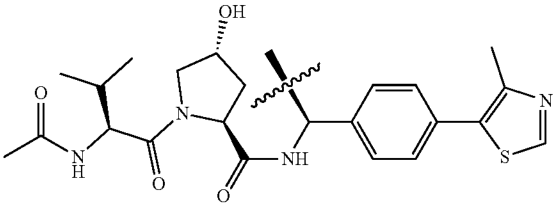

FORMULA 15CI

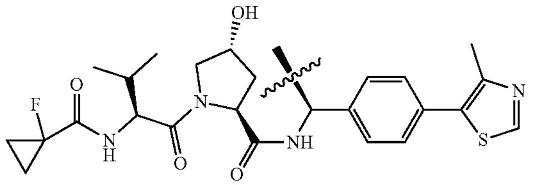

FORMULA 15CJ

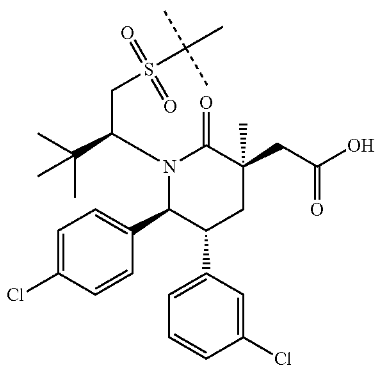

-continued

FORMULA 15CK

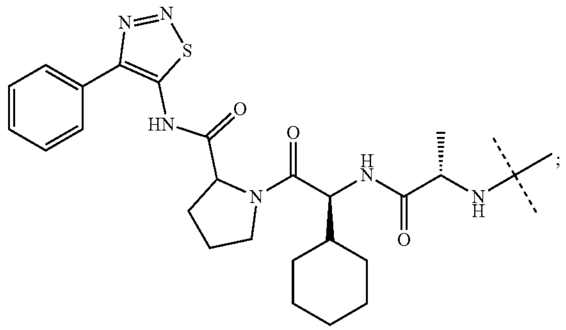

and pharmaceutically acceptable salts thereof.

Linkers

In any of the above-described compounds, the HPK1 ligand can be conjugated to the degradation/disruption tag through a linker. The linker can include, e.g., acyclic or cyclic saturated or unsaturated carbon, ethylene glycol, amide, amino, ether, urea, carbamate, aromatic, heteroaromatic, heterocyclic, and/or carbonyl containing groups with different lengths.

In an embodiment, the linker is a moiety according to FORMULA 16:

FORMULA 16

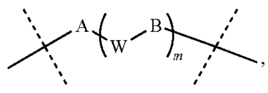

wherein

A, W, and B, at each occurrence, are independently selected from null, CO, $CO_2$, $C(O)NR^1$, $C(S)NR^1$, O, S, SO, $SO_2$, $SO_2NR^1$, $NR^1$, $NR^1CO$, $NR^1CONR^2$, $NR^8C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^1$ and $R^2$ are independently selected from hydrogen, optionally substituted $C_1$-$C_8$ alkyl, optionally substituted $C_3$-$C_8$ cycloalkyl, optionally substituted 3-8 membered cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl; and m is 0 to 15.

In an embodiment, the linker is a moiety according to FORMULA 16A:

FORMULA 16A

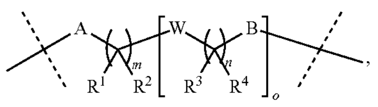

wherein $R^1$, $R^2$, $R^3$, and $R^4$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

A, W, and B, at each occurrence, are independently selected from null, CO, $CO_2$, C(O)$NR^5$, C(S)$NR^5$, O, S, SO, $SO_2$, $SO_2NR^5$, $NR^5$, $NR^5$CO, $NR^5CONR^6$, $NR^5$C(S), optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^5$ and $R^6$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

m is 0 to 15;

n, at each occurrence, is 0 to 15;

is 0 to 15.

In an embodiment, the linker is a moiety according to FORMULA 16B:

FORMULA 16B

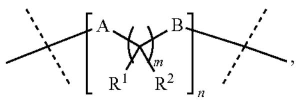

wherein $R^1$ and $R^2$, at each occurrence, are independently selected from hydrogen, halogen, CN, OH, $NH_2$, and optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, or $C_1$-$C_8$alkylamino$C_1$-$C_8$alkyl;

A and B, at each occurrence, are independently selected from null, CO, $CO_2$, C(O)$NR^3$, C(S)$NR^3$, O, S, SO, $SO_2$, $SO_2NR^3$, $NR^3$, $NR^3$CO, $NR^3CONR^4$, $NR^3$C(S), and optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, or $C_3$-$C_{13}$ spiro heterocyclyl; wherein $R^3$ and $R^4$ are independently selected from hydrogen, and optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, or $C_1$-$C_8$alkylamino$C_1$-$C_8$alkyl;

each m is 0 to 15; and n is 0 to 15.

In an embodiment, the linker is a moiety according to FORMULA 16C:

FORMULA 16C

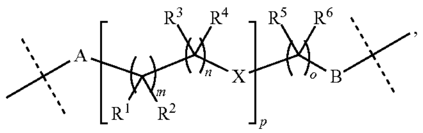

wherein

X is selected from O, NH, and $NR^7$;

$R^1$, $R^2$, $R^3$, $R^4$, $R^5$, and $R^6$, at each occurrence, are independently selected from hydrogen, halogen, CN, OH, $NH_2$, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

A and B, at each occurrence, are independently selected from null, CO, NH, NH—CO, CO—NH, $CH_2$—NH—CO, $CH_2$—CO—NH, NH—CO—$CH_2$, CO—NH—

$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CO_2$, C(O)$NR^7$, C(S)$NR^7$, O, S, SO, $SO_2$, $SO_2NR^7$, $NR^7$, $NR^7$CO, $NR^7CONR^8$, $NR^7$C(S), optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^7$ and $R^8$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

m, at each occurrence, is 0 to 15;

n, at each occurrence, is 0 to 15;

is 0 to 15; and p is 0 to 15; and pharmaceutically acceptable salts thereof.

In an embodiment, the linker is selected from the group consisting of a ring selected from the group consisting of a 3 to 13 membered ring; a 3 to 13 membered fused ring; a 3 to 13 membered bridged ring; and a 3 to 13 membered spiro ring; and pharmaceutically acceptable salts thereof.

In an embodiment, the linker is a moiety according to one of FORMULAE C1, C2, C3, C4 and C5:

FORMULA C1

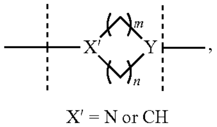

X' = N or CH
Y' = N or CH
m = 0-5
n = 0-5

FORMULA C2

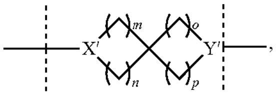

X' = N or CH
Y' = N or CH
m = 0-5
n = 0-5
o = 0-5
p = 0-5

-continued

FORMULA C3

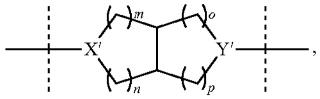

X' = N or CH
Y' = N or CH
m = 0-5
n = 0-5
o = 0-5
p = 0-5

FORMULA C4

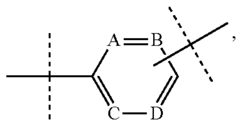

, and

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N

FORMULA C5

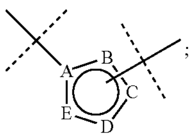

;

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3 alkyl), O, S and pharmaceutically acceptable salts thereof.

In an embodiment, the bivalent compound according to the present invention is selected from the group consisting of:

HC58-18, HC58-19, HC58-20, HC58-22, HC58-23, HC58-24, HC58-25, HC58-26, HC58-27, HC58-28, HC58-29, HC58-30, HC58-31, HC58-32, HC58-33, HC58-34, HC58-35, HC58-36, HC58-37, HC58-38, HC58-39, HC58-40, HC58-41, HC58-43, HC58-44, HC58-45, HC58-46, HC58-53, HC58-57, HC58-58, HC58-59, HC58-60, HC58-63, HC58-64, HC58-65, HC58-66, HC58-67, HC58-68, HC58-69, HC58-70, HC58-71, HC58-73, HC58-74, HC58-75, HC58-76, HC58-77, HC58-78, HC58-133, HC58-134, HC58-135, HC58-136, HC58-137, HC58-138, HC58-139, HC58-144, HC58-145, HC58-146, HC58-147, HC58-148, HC58-149, HC58-150, HC58-158, HC58-159, HC58-160, HC58-161, HC58-164, HC58-165, HC58-167, HC58-178, HC58-179, HC58-180, HC58-181, HC58-182, HC58-183, HC58-184, HC58-185, HC65-2, HC65-3, HC65-4, HC65-5, HC65-6, HC65-7, HC65-8, HC65-13, HC65-14, HC65-15, HC65-16, HC65-17, HC65-18, HC65-19, HC65-24, HC65-25, HC65-26, HC65-27, HC65-28, HC65-29, HC65-30, HC65-33, HC65-34, HC65-35, HC65-37, HC65-175, HC65-183, HC65-184, HC65-185, HC65-186, HC75-1, HC75-2, HC75-3, HC75-4, HC75-5, HC75-6, HC75-7, HC75-8, HC75-9, HC75-10, HC75-11, HC75-12, HC75-13, HC75-14, HC75-15, HC75-16, HC75-17, HC75-18, HC75-18, HC75-20, HC75-21, HC75-22, HC75-23, HC75-24, HC75-29, HC75-31, HC75-34, HC75-35, HC75-36, HC75-37, HC75-38,

HC75-39, HC75-40, HC75-41, HC75-42, HC75-43, HC75-44, HC75-45, HC75-46, HC75-47, HC75-48, HC75-49, HC75-50, HC75-52, HC75-53, HC75-54, HC75-55, HC75-56, HC75-57, HC75-58, HC75-59, HC75-60, HC75-61, HC75-62, HC90-33, HC90-34, HC90-35, HC90-36, HC90-37, HC90-41, HC90-42, HC90-43, HC90-44, HC90-45, HC90-46, HC90-47, HC90-49, HC90-50, HC90-51, HC90-52, HC90-53, HC90-54, HC90-55, HC90-56, HC90-57, HC90-58, HC90-59, HC90-61, HC90-66, HC90-69, HC90-70, HC90-71, HC90-72, HC90-73, HC90-74, HC90-84, HC90-85, HC90-86, HC90-87, HC90-88, HC90-89, HC90-90, HC90-91, HC90-92, HC90-93, HC90-94, HC90-95, HC90-96, HC90-97, HC90-102, HC90-103, HC90-104, HC90-105, HC90-106, HC90-107, HC90-108, HC90-109, HC90-110, HC90-111, HC90-112, HC90-113, HC90-117, HC90-119, HC90-120, HC90-121, HC90-122, HC90-123, HC90-124, HC90-125, HC90-126, HC90-127, HC90-128, HC90-129, HC90-130, HC90-131, HC90-132, HC90-133, HC90-134, HC90-135, HC90-136, HC90-60, HC90-62, HC90-63, HC90-64, HC90-65, HC90-67 and HC90-68 or analogs thereof, and pharmaceutically acceptable salts thereof.

In an embodiment, the bivalent compound according to the present invention is selected from the group consisting of: HC58-18, HC58-19, HC58-20, HC58-22, HC58-23, HC58-24, HC58-25, HC58-26, HC58-27, HC58-28, HC58-29, HC58-30, HC58-31, HC58-32, HC58-33, HC58-34, HC58-35, HC58-36, HC58-37, HC58-38, HC58-39, HC58-40, HC58-41, HC58-43, HC58-44, HC58-45, HC58-46, HC58-53, HC58-57, HC58-58, HC58-59, HC58-60, HC58-63, HC58-64, HC58-65, HC58-66, HC58-67, HC58-68, HC58-69, HC58-70, HC58-71, HC58-73, HC58-74, HC58-75, HC58-76, HC58-77, HC58-78, HC58-133, HC58-134, HC58-135, HC58-136, HC58-137, HC58-138, HC58-139, HC58-144, HC58-145, HC58-146, HC58-147, HC58-148, HC58-149, HC58-150, HC58-158, HC58-159, HC58-160, HC58-161, HC58-164, HC58-165, HC58-167, HC58-178, HC58-179, HC58-180, HC58-181, HC58-182, HC58-183, HC58-184, HC58-185, HC65-2, HC65-3, HC65-4, HC65-5, HC65-6, HC65-7, HC65-8, HC65-13, HC65-14, HC65-15, HC65-16, HC65-17, HC65-18, HC65-19, HC65-24, HC65-25, HC65-26, HC65-27, HC65-28, HC65-29, HC65-30, HC65-33, HC65-34, HC65-35 and HC65-37; and pharmaceutically acceptable salts thereof.

In an embodiment, the bivalent compound according to the present invention is selected from the group consisting of: HC65-175, HC65-183, HC65-184, HC65-185, HC65-186, HC75-1, HC75-2, HC75-3, HC75-4, HC75-5, HC75-6, HC75-7, HC75-8, HC75-9, HC75-10, HC75-11, HC75-12, HC75-13, HC75-14, HC75-15, HC75-16, HC75-17, HC75-18, HC75-18, HC75-20, HC75-21, HC75-22, HC75-23, HC75-24, HC75-29, HC75-31, HC75-34, HC75-35, HC75-36, HC75-37, HC75-38, HC75-39, HC75-40, HC75-41, HC75-42, HC75-43, HC75-44, HC75-45, HC75-46, HC75-47, HC75-48, HC75-49, HC75-50, HC75-52, HC75-53, HC75-54, HC75-55, HC75-56, HC75-57, HC75-58, HC75-59, HC75-60, HC75-61 and HC75-62; and pharmaceutically acceptable salts thereof.

In an embodiment, the bivalent compound according to the present invention is selected from the group consisting of:

HC90-33, HC90-34, HC90-35, HC90-36, HC90-37, HC90-41, HC90-42, HC90-43, HC90-44, HC90-45, HC90-46, HC90-47, HC90-49, HC90-50, HC90-51, HC90-52, HC90-53, HC90-54, HC90-55, HC90-56, HC90-57, HC90-58, HC90-59, HC90-61, HC90-66,

HC90-69, HC90-70, HC90-71, HC90-72, HC90-73, HC90-74, HC90-84, HC90-85, HC90-86, HC90-87, HC90-88, HC90-89, HC90-90, HC90-91, HC90-92, HC90-93, HC90-94, HC90-95, HC90-96, HC90-97, HC90-102, HC90-103, HC90-104, HC90-105, HC90-106, HC90-107, HC90-108, HC90-109, HC90-110, HC90-111, HC90-112, HC90-113, HC90-117, HC90-119, HC90-120, HC90-121, HC90-122, HC90-123, HC90-124, HC90-125, HC90-126, HC90-127, HC90-128, HC90-129, HC90-130, HC90-131, HC90-132, HC90-133, HC90-134, HC90-135, HC90-136, HC90-60, HC90-62, HC90-63, HC90-64, HC90-65, HC90-67 and HC90-68; and pharmaceutically acceptable salts thereof.

In one embodiment, preferred compounds according to the present invention include:

a. (Z)—N-(3-(4-(5-((2-(2,6-dioxopiperidin-3-yl)-1,3-dioxoisoindolin-4-yl)amino)pentanoyl)piperazin-1-yl)propyl)-5-((5-fluoro-2-oxoindolin-3-ylidene)methyl)-2,4-dimethyl-1H-pyrrole-3-carboxamide (HC58-38);
b. (Z)—N-(3-(4-(2-((5-((2-(2,6-dioxopiperidin-3-yl)-1,3-dioxoisoindolin-4-yl)amino)pentyl)amino)-2-oxoethyl)piperazin-1-yl)propyl)-5-((5-fluoro-2-oxoindolin-3-ylidene)methyl)-2,4-dimethyl-1H-pyrrole-3-carboxamide (HC58-75);
c. (Z)—N-(3-(4-(2-((6-((2-(2,6-dioxopiperidin-3-yl)-1,3-dioxoisoindolin-4-yl)amino)hexyl)amino)-2-oxoethyl)piperazin-1-yl)propyl)-5-((5-fluoro-2-oxoindolin-3-ylidene)methyl)-2,4-dimethyl-1H-pyrrole-3-carboxamide (HC58-76); and
d. (Z)—N-(3-(4-(2-((8-((2-(2,6-dioxopiperidin-3-yl)-1,3-dioxoisoindolin-4-yl)amino)octyl)amino)-2-oxoethyl)piperazin-1-yl)propyl)-5-((5-fluoro-2-oxoindolin-3-ylidene)methyl)-2,4-dimethyl-1H-pyrrole-3-carboxamide (HC58-78);
e. 2-(2,6-dioxopiperidin-3-yl)-4-((3-(4-(4-(5-(2-fluoro-6-methoxyphenyl)-1H-pyrazolo[4,3-d]pyrimidin-3-yl)phenyl)piperazin-1-yl)-3-oxopropyl)amino)isoindoline-1,3-dione (HC90-50); and
f. 2-(2,6-dioxopiperidin-3-yl)-4-((4-(4-(4-(5-(2-fluoro-6-methoxyphenyl)-1H-pyrazolo[4,3-d]pyrimidin-3-yl)phenyl)piperazin-1-yl)-4-oxobutyl)amino)isoindoline-1,3-dione (HC90-51), and pharmaceutically acceptable salts thereof.

In some aspects, this disclosure provides a method of treating the HPK1-mediated diseases, the method including administering to a subject in need thereof with an HPK1-mediated disease one or more bivalent compounds including an HPK1 ligand conjugated to a degradation/disruption tag. The HPK1-mediated diseases may be a disease resulting from HPK1 amplification. The HPK1-mediated diseases can have elevated HPK1 enzymatic activity relative to a wild-type tissue of the same species and tissue type. Non-limiting examples of HPK1-mediated diseases or diseases whose clinical symptoms could be treated by HPK1 degraders/disruptors-mediated therapy include: all solid and liquid cancer, chronic infections that produce exhausted immune response, infection-mediated immune suppression, age-related decline in immune response, age-related decline in cognitive function and infertility.

Exemplary types of cancer that could prevented, or therapeutically treated by manipulation of HPK1 level by degraders/disruptors should include all solid and liquid cancers, including, but not limited to, cancers of the breast, respiratory tract, brain, reproductive organs, digestive tract, urinary tract, eye, liver, skin, head and neck, thyroid, parathyroid and their distant metastases. Examples of liquid cancers include lymphomas, sarcomas, and leukaemias. Listed below are the type of cancers that immunotherapy using HPK1 degraders/disruptors should be able to prevent or treat.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to, prostate and testicular cancer.

Tumors of the female reproductive organs include, but are not limited to, endometrial, cervical, ovarian, vaginal, and vulvar cancer, as well as sarcoma of the uterus.

Examples of ovarian cancer include, but are not limited to, serous tumor, endometrioid tumor, mucinous cystadenocarcinoma, granulosa cell tumor, Sertoli-Leydig cell tumor and arrhenoblastoma.

Examples of cervical cancer include, but are not limited to, squamous cell carcinoma, adenocarcinoma, adenosquamous carcinoma, small cell carcinoma, neuroendocrine tumor, glassy cell carcinoma and villoglandular adenocarcinoma. Tumors of the digestive tract include, but are not limited to, anal, colon, colorectal, esophageal, gallbladder, gastric, pancreatic, rectal, small-intestine, and salivary gland cancers.

Examples of esophageal cancer include, but are not limited to, esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to, intestinal type and diffuse type gastric adenocarcinoma.

Examples of pancreatic cancer include, but are not limited to, ductal adenocarcinoma, adenosquamous carcinomas and pancreatic endocrine tumors.

Example of tumors of the urinary tract include, but are not limited to, bladder, penile, kidney, renal pelvis, ureter, urethral and human papillary renal cancers.

Examples of kidney cancer include, but are not limited to, renal cell carcinoma, urothelial cell carcinoma, juxtaglomerular cell tumor (reninoma), angiomyolipoma, renal oncocytoma, Bellini duct carcinoma, clear-cell sarcoma of the kidney, mesoblastic nephroma and Wilms' tumor.

Examples of bladder cancer include, but are not limited to, transitional cell carcinoma, squamous cell carcinoma, adenocarcinoma, sarcoma and small cell carcinoma. Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Example of skin cancers include, but are not limited to, squamous cell carcinoma, Kaposi's sarcoma, malignant melanoma, Merkel cell skin cancer, and non-melanoma skin cancer.

Example of head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Example of lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Example of sarcomas include, but are not limited to, sarcoma of the soft tissue, osteosarcoma, malignant fibrous histiocytoma, lymphosarcoma, and rhabdomyosarcoma.

Example of leukemias include, but are not limited to, acute myeloid leukemia, acute lymphoblastic leukemia, chronic lymphocytic leukemia, chronic myelogenous leukemia, and hairy cell leukemia.

The HPK1 degraders/disruptors should be able to treat the above cancer types as stand alone agents or used as an agent in combination with existing standards of treatment therapy and other FDA-approved cancer therapy.

Therapeutic use of HPK1 extends to include diseases and therapies that are amenable to treatment by stimulation/augmentation of immune response, including the prolongation of immune responses during vaccination for immunizable diseases such as influenza and coronaviruses, including Covid 19. Also, because HPK1 is expressed at high level in two other anatomical locations—brain and testes—the HPK1 degraders/disruptors should be able to treat or prevent diseases related to brain and testes that were caused by HPK1 or could be treated by HPK1 degraders/disruptors. These potential diseases include, but are not limited to, Alzheimer's disease, age-related dementia and infertility, regardless whether these possible diseases were caused by HPK1 or by other etiological causes.

Therapeutic use of HPK1 further extends to include therapies involving ex vivo treatment of immune cells, including, but not limited to, all T cell subsets, genetically engineered T cells, Chimeric Antigen Receptor (CAR) T cells, tumor infiltrating lymphocytes, dendritic cells, macrophage, mast cells, granulocytes (include basophils, eosinophils, and neutrophils), natural killer cells, NK T cells and B cells. Such cells would be therapeutically treated by HPK1 degraders and then re-introduced back to the patient being treated for conditions that would benefit from reduction in HPK1 expression. The sources of cells for such ex vivo treatment include, but are not limited to, the autologous bone marrow cells from the patient him/herself, or from the patient's frozen banked cord blood stem cells, peripheral blood or bone marrow stem cells from MHC-matched or MHC-mismatched donors.

Treating patients by administering specific immune cells that had been treated with HPK1 degraders offers many added advantages over in vivo use. By treating specific immune cells type with HPK1 degraders ex vivo, it is possible to specifically target the immune cell type that would receive the benefit of having the endogenous HPK1 level reduced by HPK1 degraders while sparing the HPK1 expression level in other immune cell types that are not involved in the disease condition.

This therapeutic approach would provide cell type-specific targeting of immune cells in a way that is not possible with the use of HPK1 degrader in the in vivo setting. Thus, the ex vivo approach would likely limit potential toxicity that may result from reduction of HPK1 level in immune cell types that do not benefit from a reduction in HPK1 levels.

Furthermore, by administering HPK1 degraders in the ex vivo cell setting, the risk of patients experiencing the toxicity or undesirable outcome that might occur should the HPK1 degraders were to be administered systemically would be eliminated.

It is known that HPK1 is also expressed in non-hematopoietically-derived tissues such as the brain and testes. Because of this tissue-specific expression pattern of HPK1, HPK1 degraders might be able to treat or prevent diseases related to the brain and testes that were caused by HPK1. These potential treatments include, but are not limited to, treatment of Alzheimer's disease, age-related dementia and infertility, irrespective to whether these possible diseases were caused by HPK1 or by other etiological causes.

The use of HPK1 expression status of the tumor as the biomarker would enable stratification of patients into appropriate therapeutic groups that would receive HPK1 degraders in vivo or ex vivo, based on HPK1 expression in the tumors.

Furthermore, using HPK1 degraders in an ex vivo setting offers additional advantages over gene-editing approaches such as CRISPR in that it allows therapeutic use of HPK1 degraders as a non-permanent treatment that allows a therapeutic regimen to be adjusted temporally through dosing levels and through alteration of the administration schedule.

In addition, HPK1 degraders could be used in settings whereby stimulation/augmentation of the immune response is required, or when the prolongation of immune responses is needed. Improving immune response to vaccination is one of the settings in which HPK1 degraders could be used therapeutically. HPK1 degraders could also be used to enhance the antigen presentation capability of dendritic cell-based cancer vaccines.

Other utilities of HPK1 degraders include treatment of dendritic cells with HPK1 degraders to increase resistance to maturation-induced apoptosis, thus increasing the yield of dendritic cell production.

In an embodiment, HPK1 degraders of the present invention may be employed in combination with treatments using checkpoint inhibitors, including, but not limited to anti-programmed cell death protein (anti-PD-1) and anti-programmed death ligand-1 (anti-PD-L1). Examples of anti-PD-1 and anti-PD-L1 agents include monoclonal antibodies that target either PD-1 or PD-L1. Such antibodies include, but are not limited to pembrolizumab (Keytruda), nivolumab (Opdivo), and cemiplimab (Libtayo) (PD-1 inhibitors); and atezolizumab (Tecentriq), avelumab (Bavencio), and durvalumab (Imfinzi) (PD-L1 inhibitors). Use of such anti-PD1 and/or anti-PD-L1 agents in immunotherapy, particularly cancer immunotherapy, may be enhanced by concomitant therapy with HPK1 degraders of the present invention. Such combination therapy of anti-PD-1 agents with HPK1 degraders of the present invention is particularly useful in the treatment of melanoma, lung cancer, renal cell carcinoma, Hodgkin lymphoma, head and neck cancer, colon cancer and liver cancer. Such combination therapy of anti-PD-L1 agents with HPK1 degraders of the present invention are particularly useful in the treatment of non-small cell lung carcinoma, multiple myeloma, urothelial cancer and head and neck cancer. (Hernandez 2018).

Similar combination therapy may employ HPK1 degraders of the present invention with an anti-CTLA-4 (cytotoxic T-lymphocyte-associated protein 4) agent, such as the monoclonal antibody ilimumab, particularly for the treatment of melanoma, lung cancer, renal cell carcinoma, glioblastoma, hepatocellular carcinoma large B cell lymphoma, Hodgkin lymphoma, head and neck cancer, colon cancer and liver cancer.

In an embodiment, the HPK1 degraders of the present invention may be used in the treatment of tumor types having elevated expression of cyclooxygenase-2 (COX-2). COX-2 elevation leads to over production of prostaglandin E2 (PGE2). PGE2 made by these tumors is known to inhibit the anti-tumor immune response. T cells lacking HPK1 are resistant to PGE2-mediated inhibition. (Alzabin 2010). Cancer types known to have high expression levels of COX-2 include, but not are not limited to colon cancer, lung cancer, sarcoma and breast cancer.

In any of the above-described methods, the bivalent compounds can be HC58-18, HC58-19, HC58-20, HC58-22, HC58-23, HC58-24, HC58-25, HC58-26, HC58-27, HC58-28, HC58-29, HC58-30, HC58-31, HC58-32, HC58-33, HC58-34, HC58-35, HC58-36, HC58-37, HC58-38, HC58-39, HC58-40, HC58-41, HC58-43, HC58-44, HC58-45, HC58-46, HC58-53, HC58-57, HC58-58, HC58-59, HC58-60, HC58-63, HC58-64, HC58-65, HC58-66, HC58-67, HC58-68, HC58-69, HC58-70, HC58-71, HC58-73, HC58-74, HC58-75, HC58-76, HC58-77, HC58-78, HC58-133, HC58-134, HC58-135, HC58-136, HC58-137, HC58-138, HC58-139, HC58-144, HC58-145, HC58-146, HC58-147, HC58-148, HC58-149, HC58-150, HC58-158, HC58-159, HC58-160, HC58-161, HC58-164, HC58-165, HC58-167, HC58-178, HC58-179, HC58-180, HC58-181, HC58-182, HC58-183, HC58-184, HC58-185, HC65-2, HC65-3, HC65-4, HC65-5, HC65-6, HC65-7, HC65-8, HC65-13, HC65-14, HC65-15, HC65-16, HC65-17, HC65-18, HC65-19, HC65-24, HC65-25, HC65-26, HC65-27, HC65-28, HC65-29, HC65-30, HC65-33, HC65-34, HC65-35, HC65-37, HC65-175, HC65-183, HC65-184, HC65-185, HC65-186, HC75-1, HC75-2, HC75-3, HC75-4, HC75-5, HC75-6, HC75-7, HC75-8, HC75-9, HC75-10, HC75-11, HC75-12, HC75-13, HC75-14, HC75-15, HC75-16, HC75-17, HC75-18, HC75-18, HC75-20, HC75-21, HC75-22, HC75-23, HC75-24, HC75-29, HC75-31, HC75-34, HC75-35, HC75-36, HC75-37, HC75-38, HC75-39, HC75-40, HC75-41, HC75-42, HC75-43, HC75-44, HC75-45, HC75-46, HC75-47, HC75-48, HC75-49, HC75-50, HC75-52, HC75-53, HC75-54, HC75-55, HC75-56, HC75-57, HC75-58, HC75-59, HC75-60, HC75-61, HC75-62, HC90-33, HC90-34, HC90-35, HC90-36, HC90-37, HC90-41, HC90-42, HC90-43, HC90-44, HC90-45, HC90-46, HC90-47, HC90-49, HC90-50, HC90-51, HC90-52, HC90-53, HC90-54, HC90-55, HC90-56, HC90-57, HC90-58, HC90-59, HC90-61, HC90-66, HC90-69, HC90-70, HC90-71, HC90-72, HC90-73, HC90-74, HC90-84, HC90-85, HC90-86, HC90-87, HC90-88, HC90-89, HC90-90, HC90-91, HC90-92, HC90-93, HC90-94, HC90-95, HC90-96, HC90-97, HC90-102, HC90-103, HC90-104, HC90-105, HC90-106, HC90-107, HC90-108, HC90-109, HC90-110, HC90-111, HC90-112, HC90-113, HC90-117, HC90-119, HC90-120, HC90-121, HC90-122, HC90-123, HC90-124, HC90-125, HC90-126, HC90-127, HC90-128, HC90-129, HC90-130, HC90-131, HC90-132, HC90-133, HC90-134, HC90-135, HC90-136, HC90-60, HC90-62, HC90-63, HC90-64, HC90-65, HC90-67, HC90-68 or analogs thereof.

In some aspects of the disclosed methods, the bivalent compounds can be administered by any of several routes of administration including, e.g., orally, parenterally, intradermally, subcutaneously, topically, and/or rectally.

Any of the above-described methods can further include treating the subject with one or more additional therapeutic regimens for treating cancer. The one or more additional therapeutic regimens for treating cancer can be, e.g., one or more of surgery, chemotherapy, radiation therapy, hormone therapy, or immunotherapy.

This disclosure additionally provides a method for identifying a bivalent compound which mediates degradation/disruption of HPK1, the method including providing a heterobifunctional test compound including a HPK1 ligand conjugated to a degradation/disruption tag, contacting the heterobifunctional test compound with a cell (e.g., a cancer cell such as a HPK1-mediated cancer cell) including a ubiquitin ligase and HPK1.

As used herein, the terms "about" and "approximately" are defined as being within plus or minus 10% of a given value or state, preferably within plus or minus 5% of said value or state. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
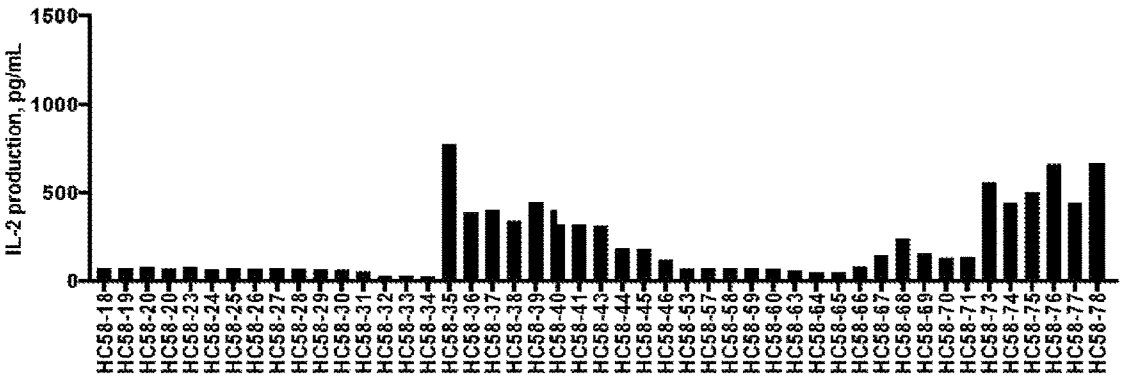
FIG. 1 is a series of graphs of screening of HC58 Series HPK1 Degraders for the enhancement of TCR-induced IL-2 production.
Figure 1B:
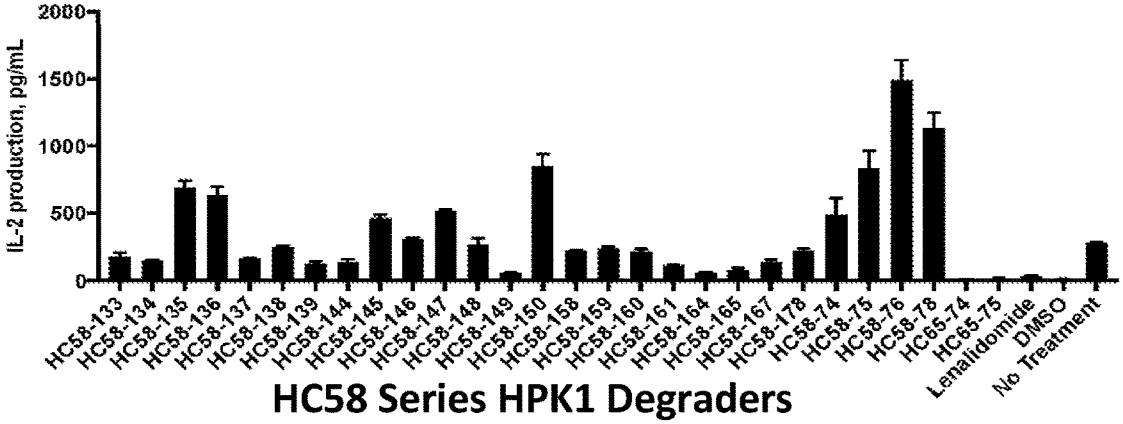
Figure 1C:
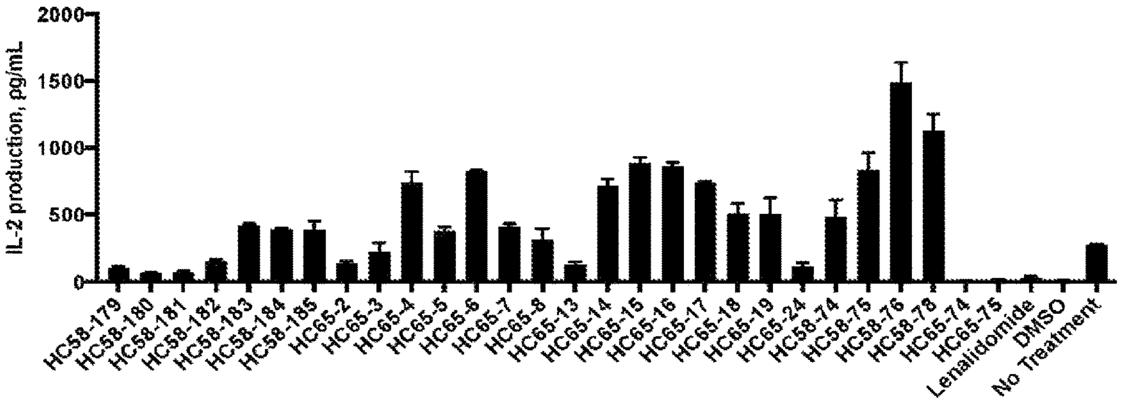
Figure 1D:
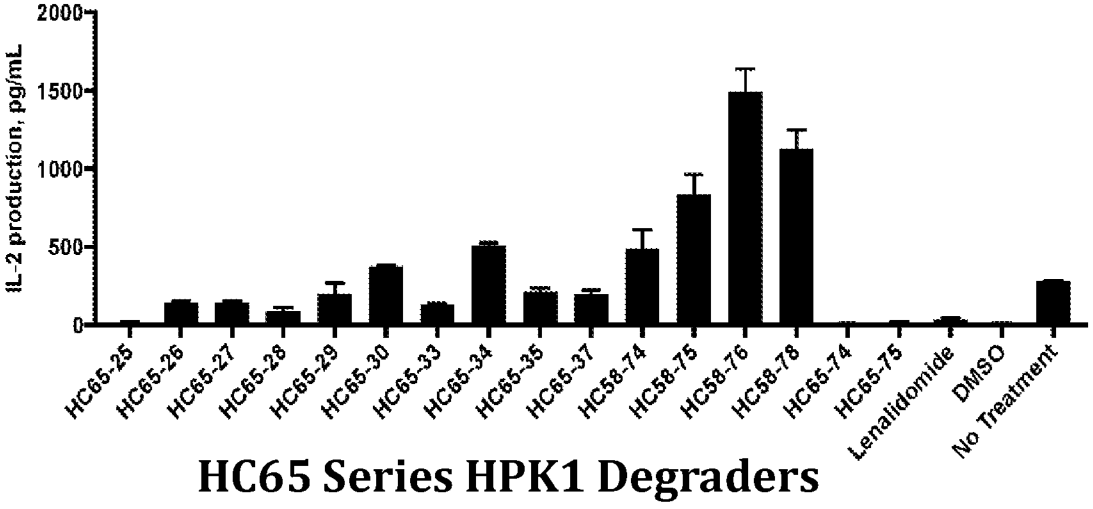
Figure 1E:
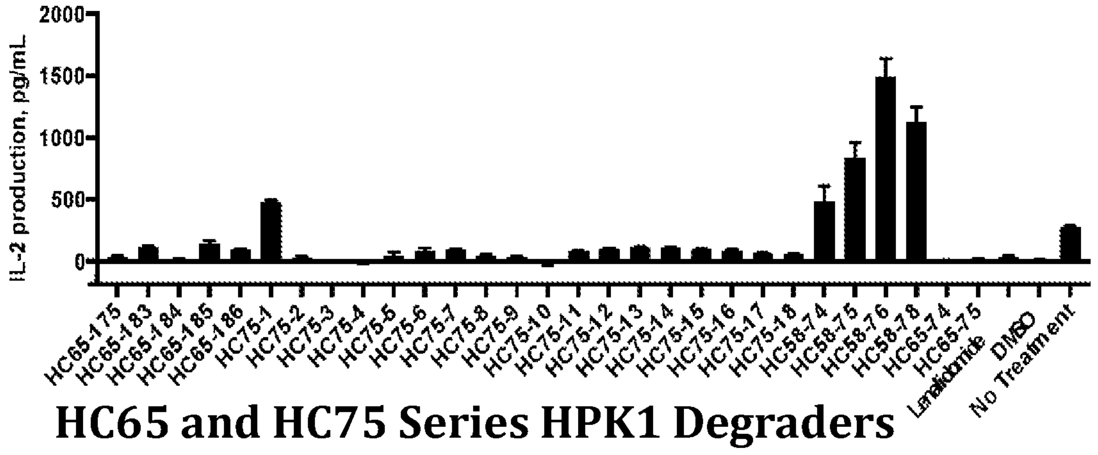
Figure 1F:
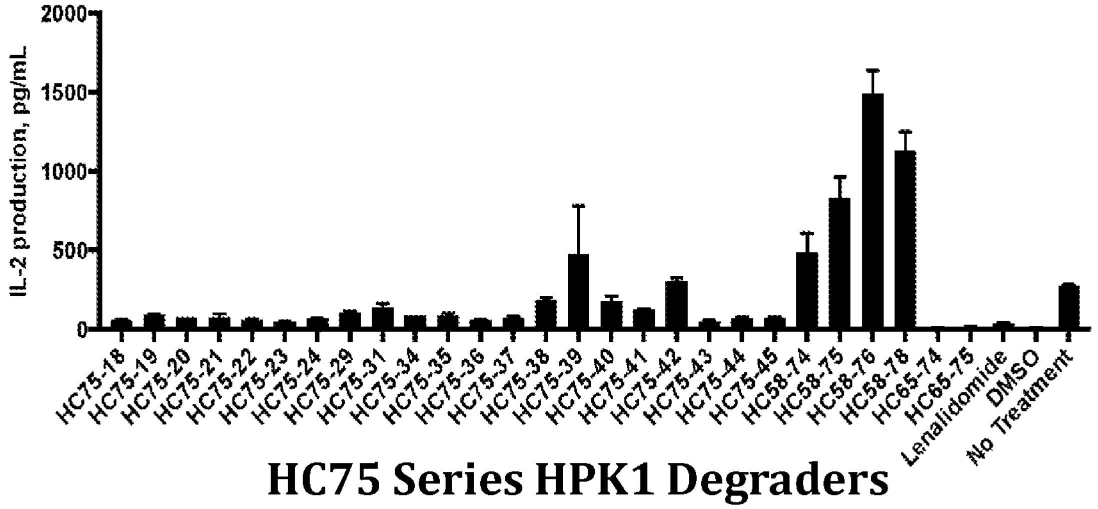

The present disclosure is based, in part, on the discovery that novel heterobifunctional molecules which degrade HPK1, HPK1 fusion proteins, and/or HPK1 mutant proteins are useful in the treatment of HPK1-mediated diseases.

Non-limiting examples of HPK1-mediated diseases or diseases whose clinical symptoms could be treated by HPK1 degraders/disruptors-mediated therapy include: all solid and liquid cancer, chronic infections that produce exhausted immune response, infection-mediated immune suppression, age-related decline in immune response, age-related decline in cognitive function and infertility Exemplary type of cancers that could be prevented, or therapeutically treated by manipulation of HPK1 level by degraders/disruptors should include all solid and liquid cancers, including, but not limited to, cancers of the breast, respiratory tract, brain, reproductive organs, digestive tract, urinary tract, eye, liver, skin, head and neck, thyroid, parathyroid and their distant metastases. Examples of liquid cancers include lymphomas, sarcomas, and leukaemias. Listed below are the type of cancers that immunotherapy using HPK1 degraders/disruptors should be able to prevent or treat.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to, prostate and testicular cancer.

Tumors of the female reproductive organs include, but are not limited to, endometrial, cervical, ovarian, vaginal, and vulvar cancer, as well as sarcoma of the uterus.

Examples of ovarian cancer include, but are not limited to, serous tumor, endometrioid tumor, mucinous cystadenocarcinoma, granulosa cell tumor, Sertoli-Leydig cell tumor and arrhenoblastoma.

Examples of cervical cancer include, but are not limited to, squamous cell carcinoma, adenocarcinoma, adenosquamous carcinoma, small cell carcinoma, neuroendocrine tumor, glassy cell carcinoma and villoglandular adenocarcinoma. Tumors of the digestive tract include, but are not limited to, anal, colon, colorectal, esophageal, gallbladder, gastric, pancreatic, rectal, small-intestine, and salivary gland cancers.

Examples of esophageal cancer include, but are not limited to, esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to, intestinal type and diffuse type gastric adenocarcinoma.

Examples of pancreatic cancer include, but are not limited to, ductal adenocarcinoma, adenosquamous carcinomas and pancreatic endocrine tumors.

Example of tumors of the urinary tract include, but are not limited to, bladder, penile, kidney, renal pelvis, ureter, urethral and human papillary renal cancers.

Examples of kidney cancer include, but are not limited to, renal cell carcinoma, urothelial cell carcinoma, juxtaglomerular cell tumor (reninoma), angiomyolipoma, renal oncocytoma, Bellini duct carcinoma, clear-cell sarcoma of the kidney, mesoblastic nephroma and Wilms' tumor.

Examples of bladder cancer include, but are not limited to, transitional cell carcinoma, squamous cell carcinoma, adenocarcinoma, sarcoma and small cell carcinoma. Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Example of skin cancers include, but are not limited to, squamous cell carcinoma, Kaposi's sarcoma, malignant melanoma, Merkel cell skin cancer, and non-melanoma skin cancer.

Example of head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Example of lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Example of sarcomas include, but are not limited to, sarcoma of the soft tissue, osteosarcoma, malignant fibrous histiocytoma, lymphosarcoma, and rhabdomyosarcoma.

Example of leukemias include, but are not limited to, acute myeloid leukemia, acute lymphoblastic leukemia, chronic lymphocytic leukemia, chronic myelogenous leukemia, and hairy cell leukemia.

The HPK1 degraders/disruptors should be able to treat the above cancer type as stand alone agent or used as agent in combination with existing standard of treatment therapy and other FDA-approved cancer therapy.

Therapeutic uses of HPK1 include diseases and therapies that are amenable to treatment by stimulation/augmentation of immune response, including the prolongation of immune responses during vaccination for immunizable diseases. Also, because HPK1 is expressed at high level in two other anatomical locations—brain and testes—the HPK1 degraders/disruptors should be able to treat or prevent diseases related to brain and testes that were caused by HPK1 or could be treated by HPK1 degraders/disruptors. These potential diseases include, but is not limited to, Alzheimer's disease, age-related dementia and infertility, regardless whether these possible diseases were caused by HPK1 or by other etiological causes.

Successful strategies for selective degradation/disruption of the target protein induced by a bifunctional molecule include recruiting an E3 ubiquitin ligase and mimicking protein misfolding with a hydrophobic tag (Buckley and Crews, 2014). PROTACs (PROteolysis TArgeting Chimeras) are bivalent molecules with one moiety that binds an E3 ubiquitin ligase and another moiety that binds the protein target of interest (Buckley and Crews, 2014). The induced proximity leads to selective ubiquitination of the target followed by its degradation at the proteasome. Several types of high affinity small-molecule E3 ligase ligands have been identified/developed: They include (1) immunomodulatory drugs (IMiDs) such as thalidomide and pomalidomide, which bind cereblon (CRBN or $CRL4^{CRBN}$), a component of a cullin-RING ubiquitin ligase (CRL) complex (Bondeson et al., 2015; Chamberlain et al., 2014; Fischer et al., 2014; Ito et al., 2010; Winter et al., 2015); (2) VHL-1, a hydroxyproline-containing ligand, which binds van Hippel-Lindau protein (VHL or $CRL2^{VHL}$), a component of another CRL complex (Bondeson et al., 2015; Buckley et al., 2012a; Buckley et al., 2012b; Galdeano et al., 2014; Zengerle et al., 2015); (3) compound 7, which selectively binds KEAP1, a component of a CRL3 complex (Davies et al., 2016); (4) AMG232, which selectively binds MDM2, a heterodimeric RING E3 ligase (Sun et al., 2014); and (5) LCL161, which selectively binds IAP, a homodimeric RING E3 ligase (Ohoka et al., 2017; Okuhira et al, 2011; Shibata et al., 2017). The degrader technology has been successfully applied to degradation of multiple targets (Bondeson et al., 2015; Buckley et al., 2015; Lai et al., 2016; Lu et al., 2015; Winter et al., 2015; Zengerle et al., 2015), but not to degradation of HPK1. In addition, a hydrophobic tagging approach, which utilizes a bulky and hydrophobic adamantyl group, has been developed to mimic protein misfolding, leading to the degradation of the target protein by proteasome (Buckley and Crews, 2014). This approach has also been successfully applied to selective degradation of the pseudokinase Her3 (Xie et al., 2014), but not to degradation of HPK1 proteins.

As discussed in the following examples, this disclosure provides specific examples of novel HPK1 degraders/disruptors, and examined the effect of exemplary degraders/disruptors on reducing HPK1 protein levels, inhibiting/disrupting HPK1 activity and increasing the TCR-induced IL-2 production by Jurkat T cells. The results indicated that these novel compounds can be beneficial in treating cancer. Exemplary type of cancers that could be prevented, or therapeutically treated by manipulation of HPK1 level by degraders/disruptors should include all solid and liquid cancers, including, but not limited to, cancers of the breast, respiratory tract, brain, reproductive organs, digestive tract, urinary tract, eye, liver, skin, head and neck, thyroid, parathyroid and their distant metastases. Examples of liquid cancers include lymphomas, sarcomas, and leukaemias. Listed below are the type of cancers that immunotherapy using HPK1 degraders/disruptors should be able to prevent or treat as mentioned above.

Current compounds targeting HPK1 generally focus on inhibition of its catalytic activity. In the present disclosure a different approach was taken: to develop compounds that directly and selectively target not only the catalytic function of HPK1, but also its protein level in cells. Strategies for inducing protein degradation include recruiting E3 ubiquitin ligases, mimicking protein misfolding with hydrophobic tags, and inhibiting chaperones. For example, a thalidomide-JQ1 bivalent compound has been used to hijack the cereblon E3 ligase, inducing highly selective BET protein degradation in vitro and in vivo and resulting in a demonstrated delay in leukemia progression in mice (Winter et al., 2015). Similarly, BET protein degradation has also been induced via another E3 ligase, VHL (Zengerle et al., 2015). Partial degradation of the Her3 protein has been induced using an adamantane-modified compound (Xie et al., 2014). Such an approach, based on the use of bivalent molecules, permits more flexible regulation of protein levels in vitro and in vivo compared with techniques such as gene knockout or knockdown via RNA interference. Unlike gene knockout or knockdown, this chemical approach provides an opportunity to study dose and time dependency in a disease model by varying the concentrations and frequencies of administration of the relevant compound.

This disclosure includes all stereoisomers, geometric isomers, tautomers and isotopes of the structures depicted and compounds named herein. This disclosure also includes compounds described herein, regardless of how they are prepared, e.g., synthetically, through biological process (e.g., metabolism or enzyme conversion), or a combination thereof.

This disclosure includes pharmaceutically acceptable salts of the structures depicted and compounds named herein.

One or more constituent atoms of the compounds presented herein can be replaced or substituted with isotopes of the atoms in natural or non-natural abundance. In some embodiments, the compound includes at least one deuterium atom In some embodiments, the compound includes two or more deuterium atoms. In some embodiments, the compound includes 1-2, 1-3, 1-4, 1-5, or 1-6 deuterium atoms. In some embodiments, all of the hydrogen atoms m a compound can be replaced or substituted by deuterium atoms. In some embodiments, the compound includes at least one fluorine atom In some embodiments, the compound includes two or more fluorine atoms. In some embodiments, the compound includes 1-2, 1-3, 1-4, 1-5, or 1-6 fluorine atoms. In some embodiments, all of the hydrogen atoms in a compound can be replaced or substituted by fluorine atoms.

Degraders

In some aspects, the present disclosure provides bivalent compounds, also referred to herein as degarders, comprising a HPK1 ligand (or targeting moiety) conjugated to a degradation tag. Linkage of the HPK1 ligand to the degradation tag can be direct, or indirect via a linker.

As used herein, the terms "protein arginine methyltransferase 5 (HPK1) ligand" or "HPK1 ligand" or "HPK1 targeting moiety" are to be construed broadly, and encompass a wide variety of molecules ranging from small molecules to large proteins that associate with or bind to HPK1. The HPK1 ligand or targeting moiety can be, for example, a small molecule compound (i.e., a molecule of molecular weight less than about 1.5 kilodaltons (kDa)), a peptide or polypeptide, nucleic acid or oligonucleotide, carbohydrate such as oligosaccharides, or an antibody or fragment thereof.

The HPK1 ligand or targeting moiety can be derived from a HPK1 inhibitor (e.g., sutent and analogs thereof), which is capable of interfering with the enzymatic activity of HPK1. As used herein, an "inhibitor" refers to an agent that restrains, retards, or otherwise causes inhibition of a physiological, chemical or enzymatic action or function. As used herein an inhibitor causes a decrease in enzyme activity of at least 5%. An inhibitor can also or alternatively refer to a drug, compound, or agent that prevents or reduces the expression, transcription, or translation of a gene or protein. An inhibitor can reduce or prevent the function of a protein, e.g., by binding to or activating/inactivating another protein or receptor.

Exemplary HPK1 ligands include, but are not limited to, the compounds listed below:

FORMULA 110

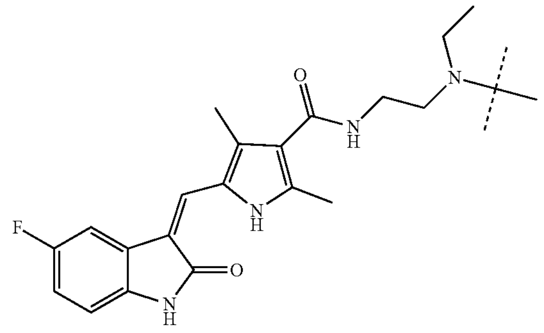

FORMULA 111

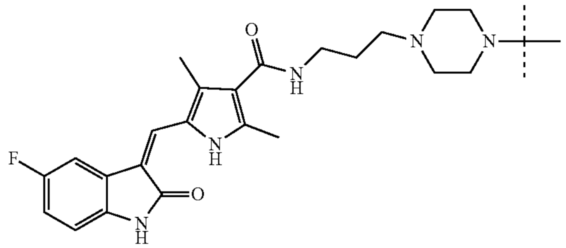

FORMULA 112

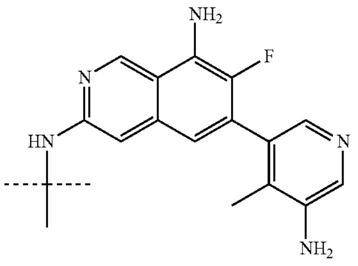

FORMULA 113

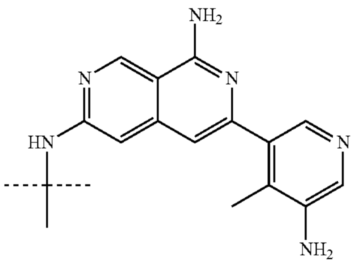

-continued
FORMULA 114
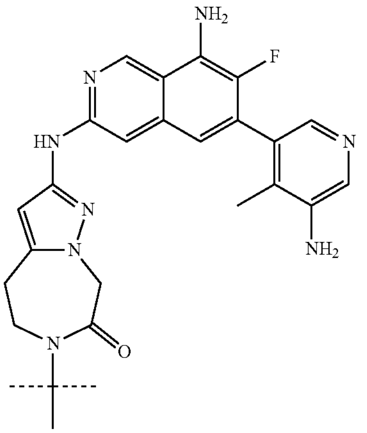
FORMULA 115
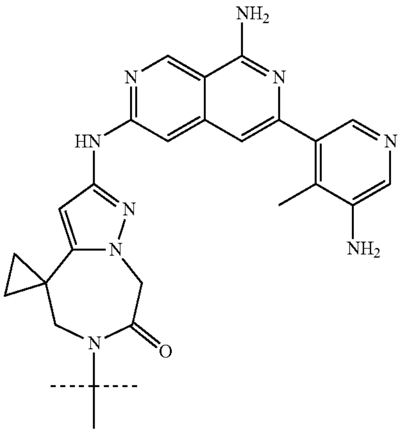
FORMULA 116
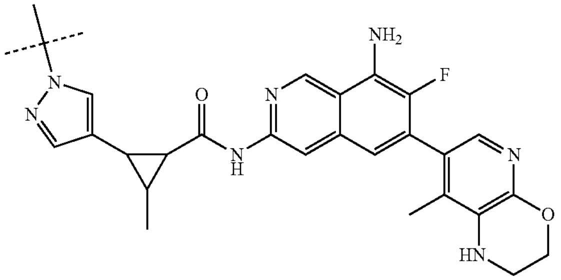
FORMULA 117
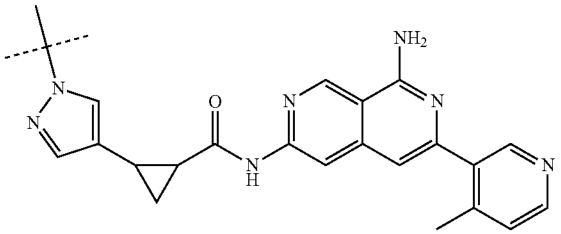
-continued
FORMULA 118
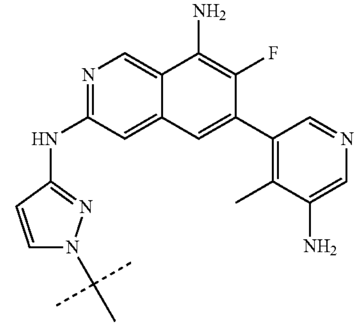
FORMULA 119
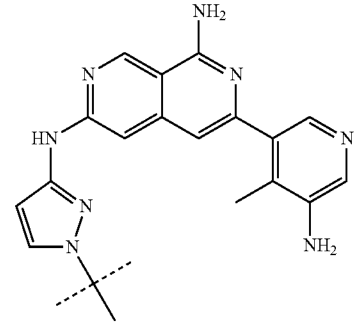
FORMULA 120
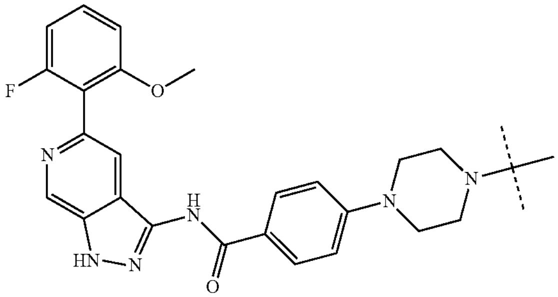
FORMULA 121
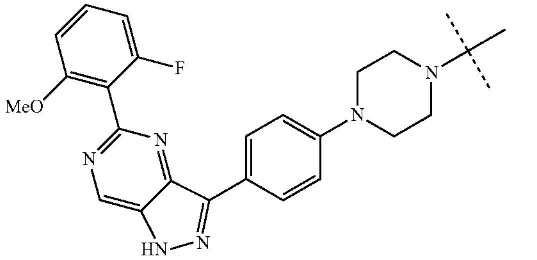
FORMULA 122
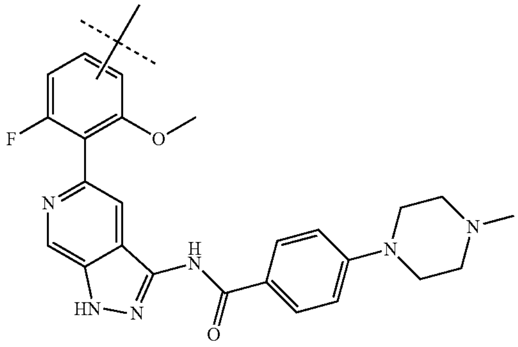

-continued
FORMULA 123
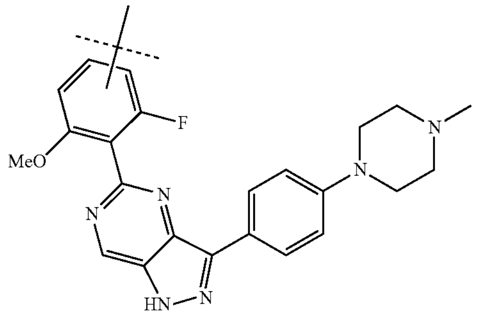
FORMULA 124
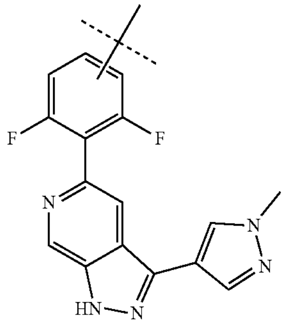
FORMULA 125
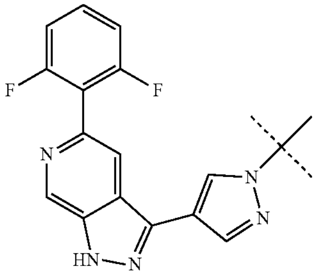
FORMULA 126
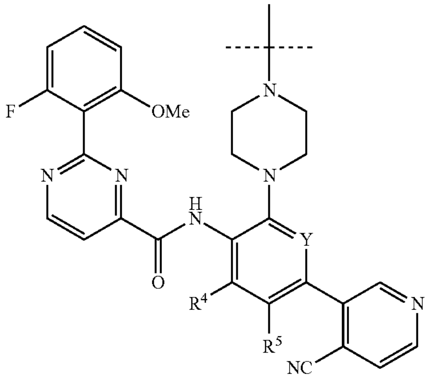
-continued
FORMULA 127
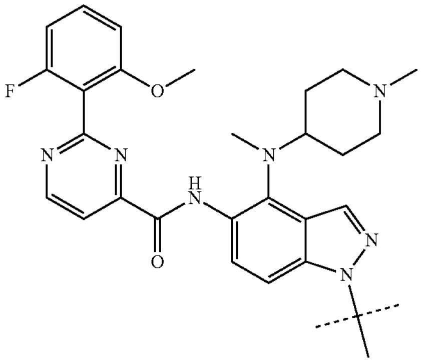
FORMULA 128
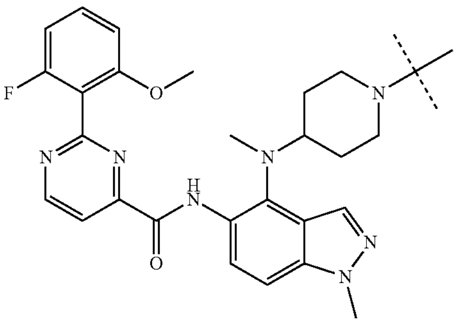
FORMULA 129
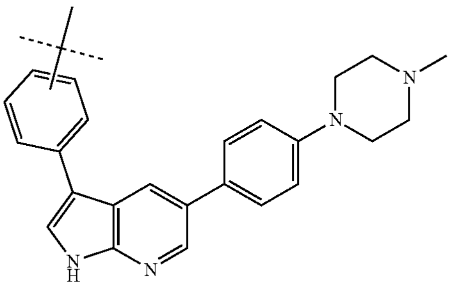
FORMULA 130
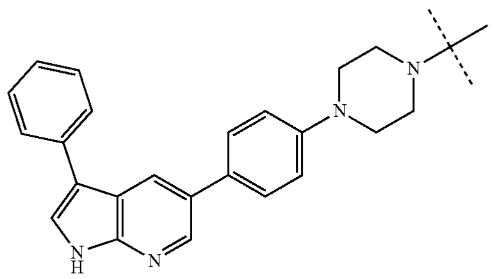
FORMULA 131
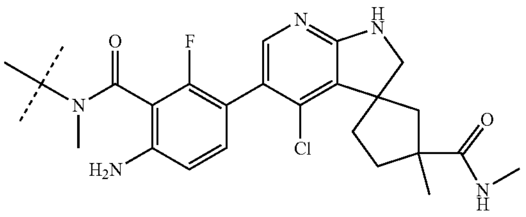

-continued

FORMULA 132

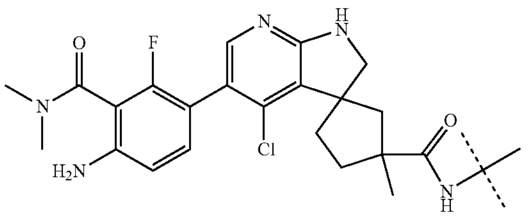

FORMULA 133

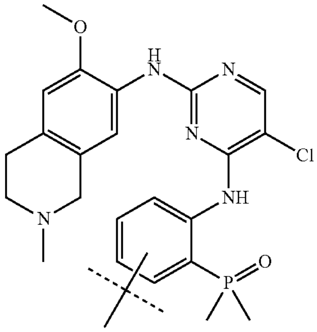

FORMULA 134

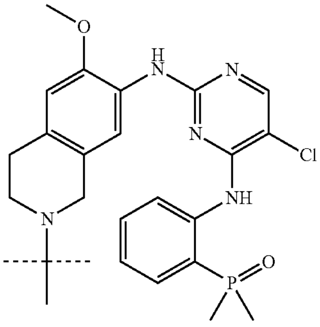

FORMULA 135

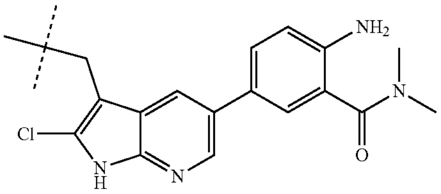

FORMULA 136

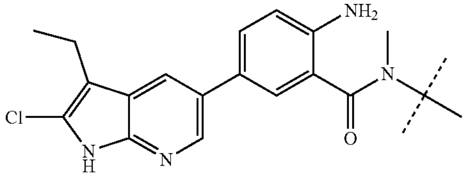

FORMULA 137

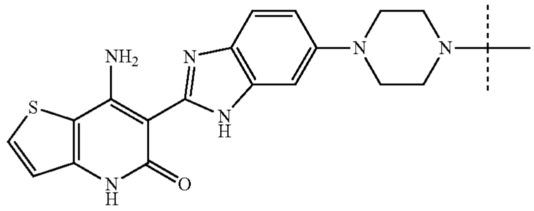

-continued

FORMULA 138

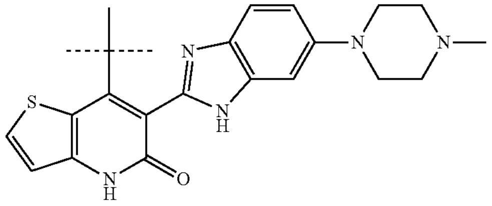

As used herein, the term "degradation/disruption tag" refers to a compound, which associates with or binds to a ubiquitin ligase for recruitment of the corresponding ubiquitination machinery to HPK1 or induces HPK1 protein misfolding and subsequent degradation at the proteasome or loss of function.

In some aspects, the degradation/disruption tags of the present disclosure include, e.g., thalidomide, pomalidomide, lenalidomide, VHL-1, adamantane, 1-((4,4,5,5,5-pentafluoropentyl)sulfinyl)nonane, nutlin-3a, RG7112, RG7338, AMG232, AA-115, bestatin, MV-1, LCL161, and/or analogs thereof.

As used herein, a "linker" is a bond, molecule, or group of molecules that binds two separate entities to one another. Linkers can provide for optimal spacing of the two entities. The term "linker" in some aspects refers to any agent or molecule that bridges the HPK1 ligand to the degradation/disruption tag. One of ordinary skill in the art recognizes that sites on the HPK1 ligand or the degradation/disruption tag, which are not necessary for the function of the degraders of the present disclosure, are ideal sites for attaching a linker, provided that the linker, once attached to the conjugate of the present disclosure, does not interfere with the function of the degrader, i.e., its ability to target HPK1 and its ability to recruit a ubiquitin ligase.

The length of the linker of the bivalent compound can be adjusted to minimize the molecular weight of the disruptors/degraders and avoid any potential clash of the HPK1 ligand or targeting moiety with either the ubiquitin ligase or the induction of HPK1 misfolding by the hydrophobic tag at the same time.

In some aspects, the degradation/disruption tags of the present disclosure include, for example, thalidomide, pomalidomide, lenalidomide, VHL-1, adamantane, 1-((4,4,5,5,5-pentafluoropentyl)sulfinyl)nonane, nutlin-3a, RG7112, RG7338, AMG 232, AA-115, bestatin, MV-1, LCL161, and analogs thereof. The degradation/disruption tags can be attached to any portion of the structure of a HPK1 ligand or targeting moiety (e.g., sutent) with linkers of different types and lengths in order to generate effective bivalent compounds. In particular, attaching VHL 1, pomalidomide, or LCL161 to any portion of the molecule can recruit the E3 ligase to HPK1.

The bivalent compounds disclosed herein can increasing the TCR-induced IL-2 production by Jurkat T cells.

Additional bivalent compounds (i.e., HPK1 degraders/disruptors) can be developed using the principles and methods disclosed herein. For example, other linkers, degradation tags, and HPK1 binding/inhibiting moieties can be synthesized and tested. Non-limiting examples of HPK1 disruptors/degraders (e.g., bivalent compounds) are shown in Table 1 (below). The left portion of each HPK1 disruptors/degrader compound as shown binds to HPK1 (as sutent (sunitinib) do), and the right portion of each compound recruits for the ubiquitination machinery to HPK1, which induces the poly-ubiquitination and degradation of HPK1 at the proteasome.

More specifically, the present disclosure provides a bivalent compound including a HPK1 ligand conjugated to a degradation/disruption tag.

In some aspects, the HPK1 degraders/disruptors have the form "PI-linker-EL", as shown below:

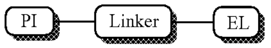

wherein PI (protein of interest) comprises an HPK1 ligand (e.g., an HPK1 inhibitor) and EL (E3 ligase) comprises a degradation/disruption tag (e.g., E3 ligase ligand). Exemplary HPK1 ligands (PI), exemplary degradation/disruption tags (EL), and exemplary linkers (Linker) are illustrated below:

HPK1 Ligands

In an embodiment, (HPK1) ligands include a moiety according to FORMULA 1A:

FORMULA 1A

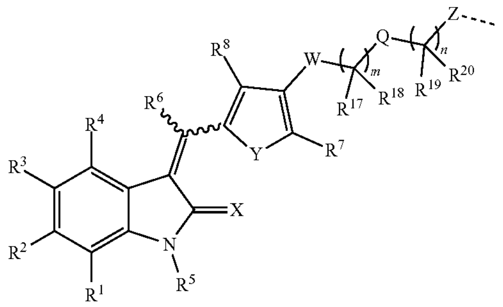

wherein, the "Linker" moiety of the bivalent compound is attached to Z;

X is selected from O or S; [not previously defined for FORMULA 1A; presume this is correct based on FORMULA 1]

$R^1$, $R^2$, $R^3$, $R^4$, $R^7$, and $R^8$ are selected from hydrogen, halogen, oxo, CN, $NO_2$, $OR^{11}$, $SR^{11}$, $NR^{11}R^{12}$, C(O)$R^{11}$, C(O)O$R^{11}$, C(O)N$R^{11}R^{12}$, S(O)$R^{11}$, $S(O)_2R^{11}$, $S(O)_2NR^{11}R^{12}$, $NR^{11}C(O)OR^{11}$, $NR^{13}C(O)R^{11}$, $NR^{13}C(O)NR^{11}R^{12}$, $NR^{13}S(O)R^{11}$, $NR^{13}S(O)_2R^{11}$, $NR^{13}S(O)_2NR^{11}R^{12}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^{11}$ and $R^{12}$, $R^{11}$ and $R^{13}$, $R^{12}$ and $R^{13}$ together with the atom to which they are connected form an optionally substituted 3-20 membered cycloalkyl or heterocyclyl ring;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl;

$R^{17}$, $R^{18}$, $R^{19}$, and $R^{20}$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

m, n, are independently selected from 0, 1, 2, 3, and 4; and

W, Q, and Z, at each occurrence, are independently selected from null, CO, $CO_2$, $CH_2$, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CR^{21}R^{22}$, C(O)$NR^{21}$, C(S)$NR^{21}$, O, S, SO, $SO_2$, $SO_2NR^{21}$, $NR^{21}$, $NR^{21}$CO, $NR^{121}CONR^{22}$, $NR^{21}$C(S), optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{21}$ and $R^{22}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

and pharmaceutically acceptable salts thereof.

In an embodiment, (HPK1) ligands include a moiety according to FORMULA 3A:

FORMULA 3A

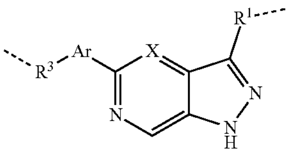

wherein the "Linker" moiety of the bivalent compound is attached independently to $R^1$ or $R^3$;

X is selected from $CR^2$ or N;

$R^1$ is selected from null, hydrogen, $C(O)R^6$, $C(O)OR^6$, $C(O)NR^6R^7$, $S(O)R^6$, $S(O)_2R^6$, $S(O)_2NR^6R^7$, $NR^8C(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^2$ is independently selected from hydrogen, halogen, oxo, CN, $NO_2$, $OR^9$, $SR^9$, $NR^9R^{10}$, $C(O)R^9$, $C(O)OR^9$, $C(O)NR^9R^{10}$, $S(O)R^9$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{10}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^9$ and $R^{10}$, $R^9$ and $R^{11}$, $R^{10}$ and $R^{11}$ together with the atom to which they are connected form an optionally substituted 3-20 membered cycloalkyl or heterocyclyl ring;

Ar is selected from null, aryl and heteroaryl, each of which is substituted with $R^3$ and optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCONR^{12}R^{13}$, $COR^{12}$, $CO_2R^{12}$, $CONR^{12}R^{13}$, $SOR^{12}$, $SO_2R^{12}$, $SO_2NR^{12}R^{13}$, $NR^{14}CO_2R^{12}$, $NR^{14}COR^{12}$, $NR^{14}C(O)NR^{12}R^{13}$, $NR^{14}SOR^{12}$, $NR^{14}SO_2R^{12}$, $NR^{14}SO_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{12}$ and $R^{13}$, $R^{12}$ and $R^{13}$ together with the atom to which they are connected form a 4-20 membered heterocyclyl ring;

$R^3$ is is selected from null, $OR^{15}$, $SR^{15}$, $NR^{15}R^{16}$, $OC(O)R^{15}$, $OC(O)OR^{15}$, $OCONR^{15}R^{16}$, $C(O)R^{15}$, $C(O)OR^{15}$, $CONR^{15}R^{16}$, $S(O)R^{15}$, $S(O)_2R^{15}$, $SO_2NR^{15}R^{16}$, $NR^{17}C(O)OR^{15}$, $NR^{17}C(O)R^{15}$, $NR^7C(O)NR^{15}R^{16}$, $NR^{14}S(O)R^{15}$, $NR^{17}S(O)_2R^{15}$, $NR^{17}S(O)_2NR^{15}R^{16}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{15}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{16}$ and $R^{17}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$, $R^{15b}$ and $R^{17}$, $R^{16}$ and $R^{17}$ together with the atom to which they are connected form a 3-20 membered cycloalkyl or heterocyclyl ring;

and pharmaceutically acceptable salts thereof.

In an embodiment, (HPK1) ligands include a moiety according to FORMULA 3B:

FORMULA 3B

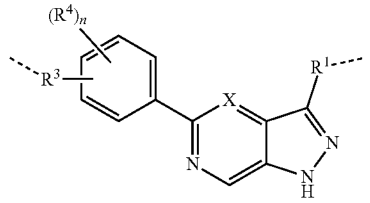

wherein the "Linker" moiety of the bivalent compound is attached independently to $R^1$ or $R^3$;

X is selected from $CR^2$ or N;

$R^1$ and $R^3$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NRIC(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$ is independently selected from hydrogen, halogen, oxo, CN, $NO_2$, $OR^9$, $SR^9$, $NR^9R^{10}$, $C(O)R^9$, $C(O)OR^9$, $C(O)NR^9R^{10}$, $S(O)R^9$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^9$ and $R^{10}$, $R^9$ and $R^{11}$, $R^{10}$ and $R^{11}$ together with the atom to which they are connected form an optionally substituted 3-20 membered cycloalkyl or heterocyclyl ring;

each $R^4$ is independently selected from null, hydrogen, halogen, oxo, CN, $NO_2$, $OR^{18}$, $SR^{18}$, $NR^{18}R^{19}$, $OCOR^{18}$, $OCO_2R^{18}$, $OCONR^{18}R^{19}$, $COR^{18}$, $CO_2R^{18}$, $CONRR^{19}$, $SOR^{18}$, $SO_2R^{18}$, $SO_2NR^{18}R^{19}$, $NR^{20}CO_2R^{18}$, $NR^{20}COR^{18}$, $NR^{20}C(O)NR^{18}R^{19}$, $NR^{20}SOR^{18}$, $NR^{20}SO_2R^{18}$, $NR^7SO_2NR^5R^6$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{18}$, $R^{19}$ and $R^{20}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{18}$ and $R^{19}$, $R^{18}$ and $R^{20}$ together with the atom to which they are connected form a 4-20 membered heterocyclyl ring; and n is independently selected from 0, 1, 2, 3, 4 and 5;

and pharmaceutically acceptable salts thereof.

In an embodiment, (HPK1) ligands include a moiety according to FORMULA 1:

FORMULA 1

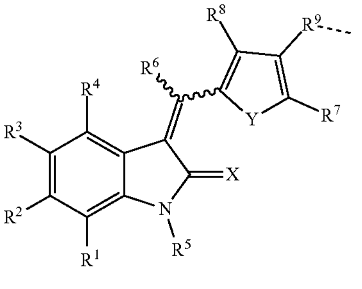

wherein the "Linker" moiety of the bivalent compound is attached to $R^9$;

X is selected from O or S;

Y is selected from O, S, $NR^{10}$; wherein $R^{10}$ is independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl;

$R^1$, $R^2$, $R^3$, $R^4$, $R^7$, and $R^8$ are selected from hydrogen, halogen, oxo, CN, $NO_2$, $OR^{11}$, $SR^{11}$, $NR^{11}R^{12}$, $C(O)R^{11}$, $C(O)OR^{11}$, $C(O)NR^{11}R^{12}$, $S(O)R^{11}$, $S(O)_2R^{11}$, $S(O)_2NR^{11}R^{12}$, $NR^{13}C(O)OR^{11}$, $NR^{13}C(O)R^{11}$, $NR^{13}C(O)NHR^{12}$, $NR^{13}S(O)R^{11}$, $NR^{13}S(O)_2R^{11}$, $NR^{13}S(O)_2NR^{11}R^{12}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^{11}$ and $R^{12}$, $R^{11}$ and $R^{13}$, $R^{12}$ and $R^{13}$ together with the atom to which they are connected form an optionally substituted 3-20 membered cycloalkyl or heterocyclyl ring;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl;

$R^9$ is selected from $OR^{14}$, $SR^{14}$, $NR^{14}R^{15}$, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{15}$ and $R^{16}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$, $R^{14}$ and $R^{16}$, $R^{15}$ and $R^{16}$ together with the atom to which they are connected form a 3-20 membered cycloalkyl or heterocyclyl ring.

In an embodiment, (HPK1) ligands include a moiety according to FORMULA 1A:

FORMULA 1A

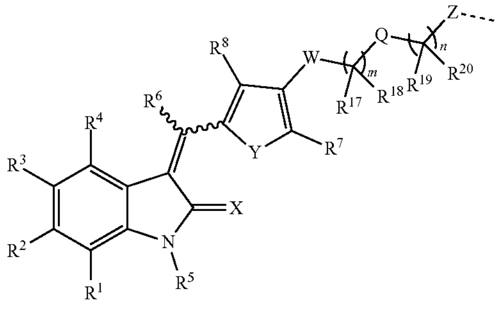

wherein, the "Linker" moiety of the bivalent compound is attached to Z;

the definitions of $R^1$, $R^2$, $R^3$, $R^4$, $R^5$, $R^6$, $R^7$ and $R^8$ are the same as for FORMULA 1;

$R^{17}$, $R^{18}$, $R^{19}$, and $R^{20}$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

m, n, are independently selected from 0, 1, 2, 3, and 4; and

W, Q, and Z, at each occurrence, are independently selected from null, CO, $CO_2$, $CH_2$, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CR^{21}R^{22}$, $C(O)NR^{21}$, $C(S)NR^{21}$, O, S, SO, $SO_2$, $SO_2NR^{21}$, $NR^{21}$, $NR^{21}CO$, $NR^{121}CONR^{22}$, $NR^{21}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{21}$ and $R^{22}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl.

In an embodiment, (HPK1) ligands include a moiety according to FORMULA 1B:

FORMULA 1B

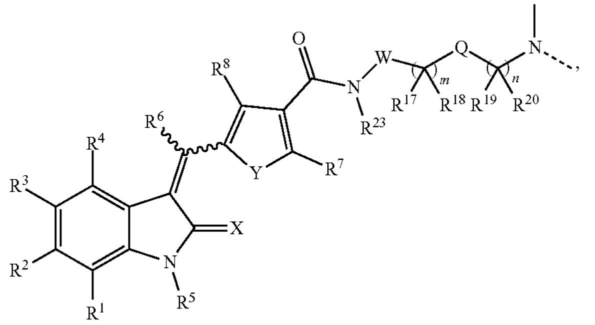

wherein the definitions of X, Y, W, Q, $R^1$, $R^2$, $R^3$, $R^4$, $R^5$, $R^6$, $R^7$, $R^8$, $R^{17}$, $R^{18}$, $R^{19}$ and $R^{20}$ are the same as for FORMULA 1A;

the "Linker" moiety of the bivalent compound is attached to terminal N;

m, n, are independently selected from 0, 1, 2, 3, and 4;

$R^{23}$ and $R^{24}$ at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl.

In an embodiment, (HPK1) ligands include a moiety according to FORMULA 1C:

FORMULA 1C

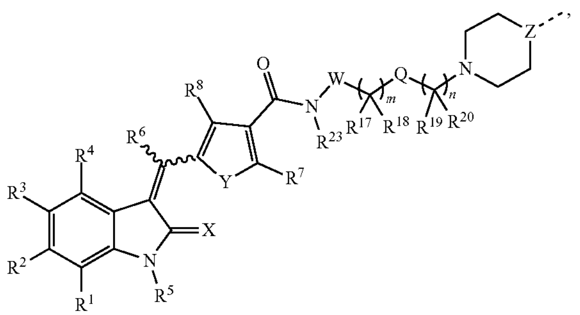

wherein;

the definitions of X, Y, W, Q, $R^1$, $R^2$, $R^3$, $R^4$, $R^5$, $R^6$, $R^7$, $R^8$, $R^{17}$, $R^{18}$, $R^{19}$, $R^{20}$ and $R^{23}$ are the same as for FORMULA 1B;

the "Linker" moiety of the bivalent compound is attached to Z;

m, n, are independently selected from 0, 1, 2, 3, and 4;

Z are independently selected from $CR^{25}$ or N; and $R^{25}$ is independently selected from null, hydrogen, C(O)$R^{26}$, C(O)O$R^{26}$, C(O)N$R^{26}R^{27}$, S(O)$R^{26}$, $S(O)_2R^{26}$, $S(O)_2NR^{26}R^{27}$, $NR^{28}C(O)OR^{26}$, $NR^{28}C(O)R^{26}$, $NR^{28}C(O)NR^{26}R^{27}$, $NR^{28}S(O)R^{26}$, $NR^{28}S(O)_2R^{26}$, $NR^{28}S(O)_2NR^{26}R^{27}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{26}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{27}$, and $R^{28}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{26}$ and $R^{27}$ together with the atom to which they are connected form an optionally substituted 3-20 membered cycloalkyl or heterocyclyl ring; and pharmaceutically acceptable salts thereof.

In an embodiment, (HPK1) ligands include a moiety according to FORMULA 2:

FORMULA 2

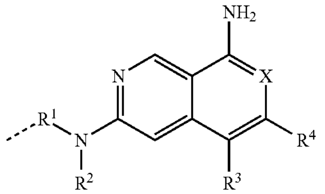

wherein the "Linker" moiety of the bivalent compound is attached to $R^1$ or $R^4$;

X is selected from $CR^5$ or N;

$R^1$, and $R^2$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NR^1C(O)OR^6$, $NR^1C(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring; and $R^3$, $R^4$ and $R^5$ are independently selected from hydrogen, halogen, oxo, CN, $NO_2$, $OR^9$, $SR^9$, $NR^{10}R^{11}$, $C(O)R^9$, $C(O)OR^9$, $C(O)NR^{10}R^{11}$, $S(O)R^9$, $S(O)_2R^9$, $S(O)_2NR^{10}R^{11}$, $NR^{12}C(O)OR^{10}$, $NR^9C(O)R^{10}$, $NR^9C(O)NR^{10}R^{11}$, $NR^9S(O)R^{10}$, $NR^9S(O)_2R^{10}$, $NR^9S(O)_2NR^{10}R^{11}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^9$ and $R^{10}$, $R^{10}$ and $R^{11}$ together with the atom to which they are connected form an optionally substituted 3-20 membered cycloalkyl or heterocyclyl ring.

In an embodiment, (HPK1) ligands include a moiety according to FORMULA 2A or 2B:

FORMULA 2A

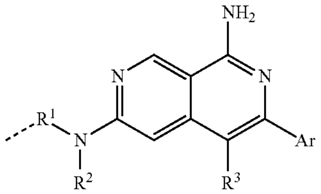

FORMULA 2B

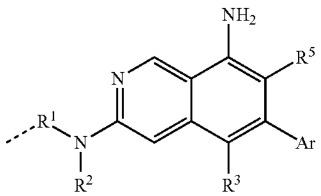

wherein the "Linker" moiety of the bivalent compound is attached to $R^1$;

the definitions of $R^1$, $R^2$, $R^3$ and $R^5$ are the same as for FORMULA 2;

Ar is selected from null, aryl and heteroaryl, each of which is optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCONR^{12}R^{13}$, $COR^{12}$, $CO_2R^{12}$, $CONR^{12}R^{13}$, $SOR^{12}$, $SO_2R^{12}$, $SO_2NR^{12}R^{13}$, $NR^{14}CO_2R^{12}$, $NR^{14}COR^{12}$, $NR^{14}C(O)NR^{12}R^{13}$, $NR^{14}SOR^{12}$, $NR^{14}SO_2R^{12}$, $NR^{14}SO_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{12}$ and $R^{13}$, $R^{13}$ and $R^{14}$ together with the atom to which they are connected form a 3-20 membered heterocyclyl ring.

In an embodiment, (HPK1) ligands include a moiety according to FORMULA 2C or 2D:

FORMULA 2C

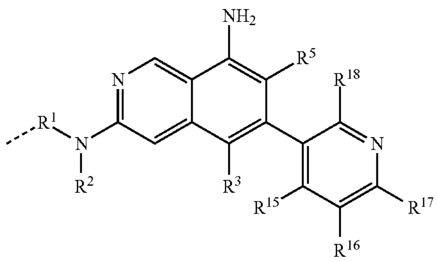

FORMULA 2D

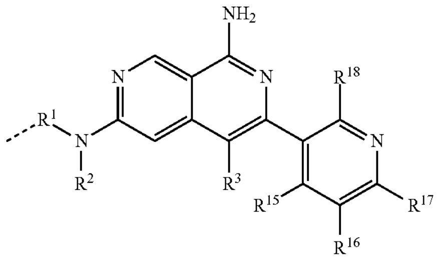

wherein the "Linker" moiety of the bivalent compound is attached to $R^1$;

the definitions of $R^1$, $R^2$, $R^3$ and $R^5$ are the same as for FORMULA 2;

$R^{15}$, $R^{16}$, $R^{17}$ and $R^{18}$ are independently selected hydrogen, halogen, oxo, CN, $NO_2$, $OR^{19}$, $SR^{19}$, $NR^{20}R^{21}$, $OCOR^{19}$, $OCO_2R^{19}$, $OCONR^{20}R^{21}$, $COR^{19}$, $CO_2R^{19}$, $CONR^{20}R^{21}$, $SOR^{19}$, $SO_2R^{19}$, $SO_2NR^{20}R^{21}$, $NR^{19}CO_2R^{20}$, $NR^{19}COR^{20}$, $NR^{19}C(O)NR^{20}R^{21}$, $NR^{19}SOR^{20}$, $NR^{19}SO_2R^{20}$, $NR^{19}SO_2NR^{20}R^{21}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{19}$, $R^{20}$, and $R^{21}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{19}$ and $R^{20}$, $R^{20}$ and $R^{21}$ together with the atom to which they are connected form a 3-20 membered heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2E or 2F:

FORMULA 2E

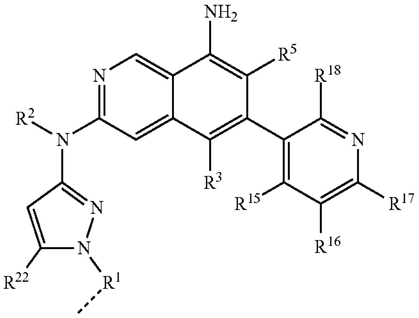

FORMULA 2F

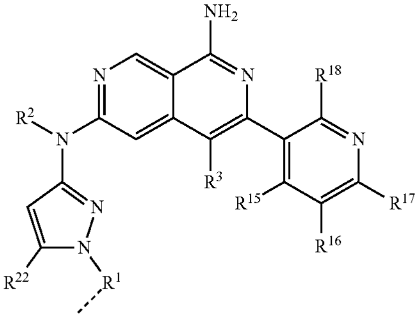

wherein the "Linker" moiety of the bivalent compound is attached to $R^1$;

the definitions of $R^1$, $R^2$, $R^3$, $R^5$, $R^{15}$, $R^{16}$, $R^{17}$ and $R^{18}$ are the same as for FORMULA 2C and 2D. $R^{22}$ is independently selected from hydrogen, halogen, oxo, aryl, CN, $NO_2$, $OR^{23}$, $SR^{23}$, $NR^{24}R^{25}$, $C(O)R^{23}$, $C(O)OR^{23}$, $C(O)NR^{24}R^{25}$, $S(O)R^{23}$, $S(O)_2R^{23}$, $S(O)_2NR^{24}R^{25}$, $NR^{24}C(O)OR^{23}$, $NR^{24}C(O)R^{23}$, $NR^{23}C(O)NR^{24}R^{25}$, $NR^{24}S(O)R^{23}$, $NR^{24}S(O)_2R^{23}$, $NR^{23}S(O)_2NR^{24}R^{2}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{23}$, $R^{24}$, and $R^{25}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{23}$ and $R^{24}$, $R^{23}$ and $R^{25}$ together with the atom to which they are connected form an optionally substituted 3-20 membered cycloalkyl or heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2G or 2H:

FORMULA 2G

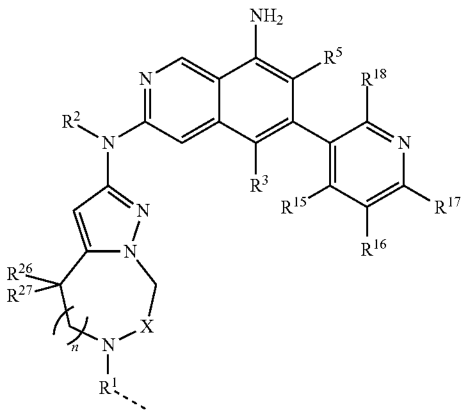

FORMULA 2H

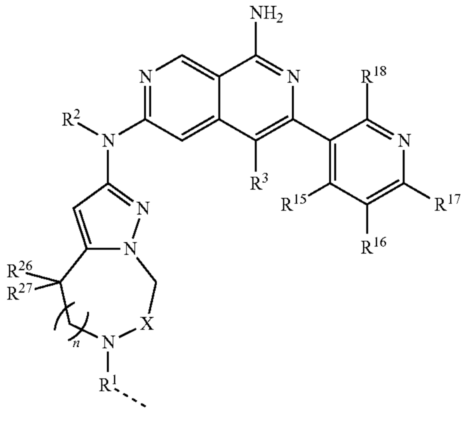

wherein the "Linker" moiety of the bivalent compound is attached to $R^1$;

the definitions of $R^1$, $R^2$, $R^3$, $R^5$, $R^{15}$, $R^{16}$, $R^{17}$ and $R^{18}$ are the same as for FORMULA 2C and 2D.

X is CO, $CH_2$ or SO2;

n is 0 to 1;

$R^{26}$ and $R^{27}$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{26}$ and $R^{27}$ together with the atom to which they are connected form an optionally substituted 3-20 membered cycloalkyl or heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2K, 2L, 2M and 2N:

FORMULA 2K

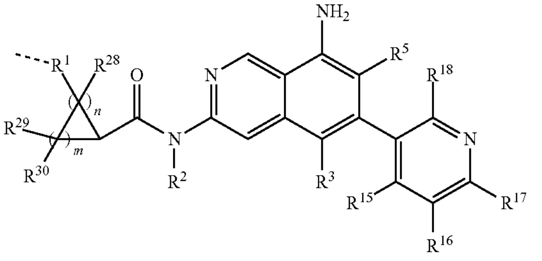

FORMULA 2L

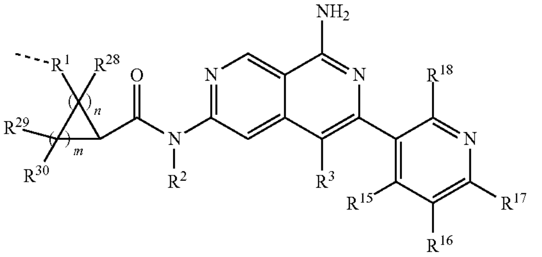

FORMULA 2M

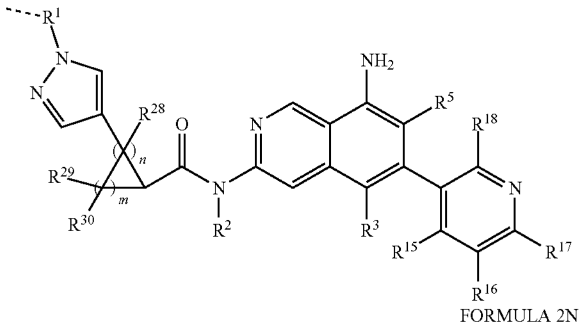

FORMULA 2N

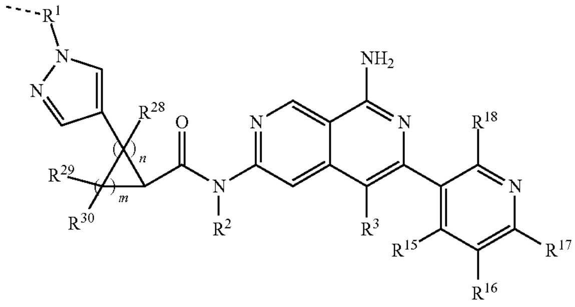

wherein the "Linker" moiety of the bivalent compound is attached to $R^9$;

the definitions of $R^1$, $R^2$, $R^3$, $R^5$, $R^{15}$, $R^{16}$, $R^{17}$ and $R^{18}$ are the same as for FORMULA 2C and 2D;

n and m are independently selected from 1, 2 and 3;

$R^{28}$, $R^{29}$ and $R^{30}$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl, or $R^{29}$ and $R^{30}$ together with the atom to which they are connected form an optionally substituted 3-20 membered cycloalkyl or heterocyclyl ring; and $R^{15}$ and $R^{16}$, $R^{16}$ and $R^{17}$ together with the atom to which they are connected form an optionally substituted 4-20 membered cycloalkyl or heterocyclyl ring.

In an embodiment, (HPK1) ligands include a moiety according to FORMULA 2O or 2P:

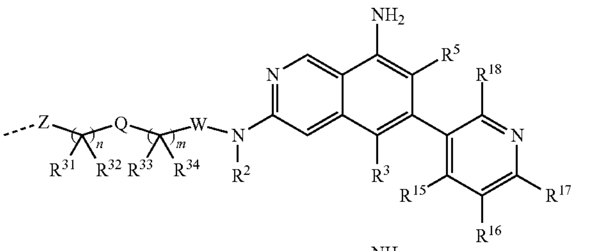

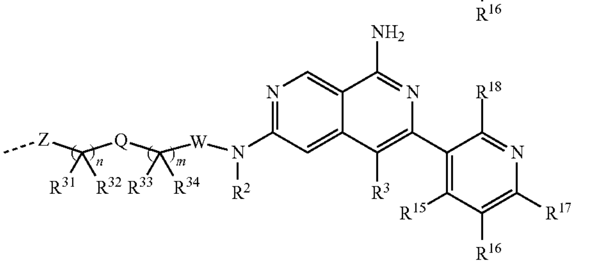

wherein the "Linker" moiety of the bivalent compound is attached to Z;

the definitions of $R^1$, $R^2$, $R^3$, $R^5$, $R^{15}$, $R^{16}$, $R^{17}$ and $R^{18}$ are the same as for FORMULA 2C and 2D; W, Q, and Z, at each occurrence, are independently selected from null, CO, $CO_2$, $CH_2$, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CR^{35}R^{36}$, $C(O)NR^{35}$, $C(S)NR^{35}$, O, S, SO, $SO_2$, $SO_2NR^{35}$, $NR^{35}$, $NR^{35}CO$, $NR^{35}CONR^{36}$, $NR^{35}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl, wherein $R^{35}$ and $R^{36}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

$R^{31}$, $R^{32}$, $R^{33}$, and $R^{34}$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{31}$ and $R^{32}$, $R^{33}$ and $R^{34}$ are together with the atom to which they are connected form an optionally substituted 3-20 membered cycloalkyl or heterocyclyl ring; $R^{15}$ and $R^{16}$, $R^{16}$ and $R^{17}$ together with the atom to which they are connected form an optionally substituted 4-20 membered cycloalkyl or heterocyclyl ring; and m, n, are independently selected from 0, 1, 2, 3, and 4; and pharmaceutically acceptable salts thereof.

In an embodiment, (HPK1) ligands include a moiety according to FORMULA 3:

FORMULA 3

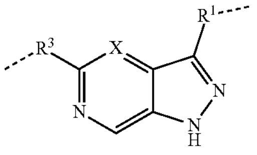

wherein the "Linker" moiety of the bivalent compound is attached independently to $R^1$ or $R^3$;

X is selected from $CR^2$ or N;

$R^1$ and $R^3$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NRIC(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$ is independently selected from hydrogen, halogen, oxo, CN, $NO_2$, $OR^9$, $SR^9$, $NR^9R^{10}$, $C(O)R^9$, $C(O)OR^9$, $C(O)NR^9R^{10}$, $S(O)R^9$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$, and $R^{11}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^9$ and $R^{10}$, $R^9$ and $R^{11}$, $R^{10}$ and $R^{11}$ together with the atom to which they are connected form an optionally substituted 3-20 membered cycloalkyl or heterocyclyl ring.

In an embodiment, (HPK1) ligands include a moiety according to FORMULA 3A:

FORMULA 3A

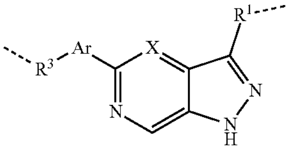

wherein the "Linker" moiety of the bivalent compound is attached independently to $R^1$ or $R^3$;

X is selected from $CR^2$ or N;

the definitions of $R^1$ and $R^2$ are the same as for FORMULA 3;

Ar is selected from null, aryl and heteroaryl, each of which is substituted with $R^3$ and optionally substituted with one or more substituents independently selected from hydrogen, halogen, oxo, CN, $NO_2$, $OR^{12}$, $SR^{12}$, $NR^{12}R^{13}$, $OCOR^{12}$, $OCO_2R^{12}$, $OCONR^{12}R^{13}$, $COR^{12}$, $CO_2R^{12}$, $CONR^{12}R^{13}$, $SOR^{12}$, $SO_2R^{12}$, $SO_2NR^{12}R^{13}$, $NR^{14}CO_2R^{12}$, $NR^{14}COR^{12}$, $NR^{14}C(O)NR^{12}R^{13}$, $NR^{14}SOR^{12}$, $NR^{14}SO_2R^{12}$, $NR^{14}SO_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{12}$ and $R^{13}$, $R^{12}$ and $R^{13}$ together with the atom to which they are connected form a 4-20 membered heterocyclyl ring;

$R^3$ is is selected from null, $OR^{15}$, $SR^{15}$, $NR^{15}R^{16}$, $OC(O)R^{15}$, $OC(O)OR^{15}$, $OCONR^{15}R^{16}$, $C(O)R^{15}$, $C(O)OR^{15}$, $CONR^{15}R^{16}$, $S(O)R^{15}$, $S(O)_2R^{15}$, $SO_2NR^{15}R^{16}$, $NR^{17}C(O)OR^{15}$, $NR^{17}C(O)R^{15}$, $NR^7C(O)NR^{15}R^{16}$, $NR^{14}S(O)R^{15}$, $NR^{17}S(O)_2R^{15}$, $NR^{17}S(O)_2NR^{15}R^{16}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{15}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{16}$ and $R^{17}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$, $R^{15b}$ and $R^{17}$, $R^{16}$ and $R^{17}$ together with the atom to which they are connected form a 3-20 membered cycloalkyl or heterocyclyl ring.

In an embodiment, (HPK1) ligands include a moiety according to FORMULA 3B:

FORMULA 3B

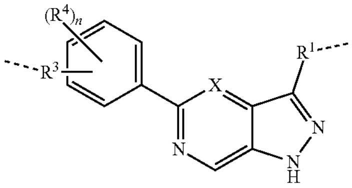

wherein the "Linker" moiety of the bivalent compound is attached independently to $R^1$ or $R^3$;

X is selected from $CR^2$ or N;

the definitions of $R^1$, $R^2$ and $R^3$ are the same as for FORMULA 3;

each $R^4$ is independently selected from null, hydrogen, halogen, oxo, CN, $NO_2$, $OR^{18}$, $SR^{18}$, $NR^{11}R^{19}$, $OCOR^{18}$, $OCO_2R^{18}$, $OCONR^{18}R^{19}$, $COR^{18}$, $CO_2R^{18}$, $CONR^{18}R^{19}$, $SOR^{18}$, $SO_2R^{18}$, $SO_2NR^{18}R^{19}$, $NR^{20}CO_2R^{18}$, $NR^{20}COR^{18}$, $NR^{20}C(O)NR^{18}R^{19}$, $NR^{20}SOR^{18}$, $NR^{20}SO_2R^{18}$, $NR^7SO_2NR^5R^6$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{18}$, $R^{19}$ and $R^{20}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{18}$ and $R^{19}$, $R^{18}$ and $R^{20}$ together with the atom to which they are connected form a 4-20 membered heterocyclyl ring; and n is independently selected from 0, 1, 2, 3, 4 and 5.

In an embodiment, (HPK1) ligands include a moiety according to FORMULAE 3C, 3D and 3E:

FORMULA 3C

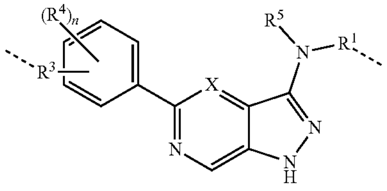

FORMULA 3D

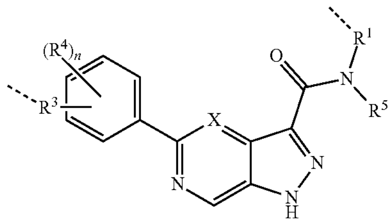

FORMULA 3E

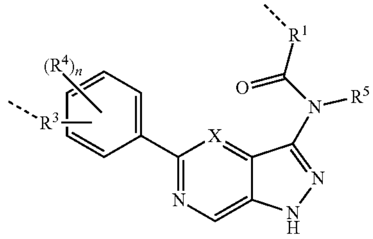

wherein the "Linker" moiety of the bivalent compound is attached independently to $R^1$ or $R^3$;

X is selected from $CR^2$ or N;

the definitions of $R^1$, $R^2$, $R^3$ and $R^4$ are the same as for FORMULA 3B;

$R^5$ at each occurrence, is independently selected from hydrogen, $C(O)R^{21}$, $C(O)OR^{21}$, $C(O)NR^{21}R^{22}$, $S(O)R^{21}$, $S(O)_2R^{21}$, $S(O)_2NR^{21}R^{22}$, $NR^{23}C(O)OR^{21}$, $NR^{23}C(O)R^{21}$, $NR^{23}C(O)NR^{21}R^{22}$, $NR^{23}S(O)R^{21}$, $NR^{23}S(O)_2R^{21}$, $NR^{23}S(O)_2NR^{21}R^{22}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{21}$, $R^{22}$ and $R^{23}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{21}$ and $R^{22}$, $R^{21}$ and $R^{23}$ together with the atom to which they are connected form a 3-20 membered heterocyclyl ring; and n is independently selected from 0, 1, 2, 3, 4 and 5.

In an embodiment, (HPK1) ligands include a moiety according to FORMULA 3F or 3G:

FORMULA 3F

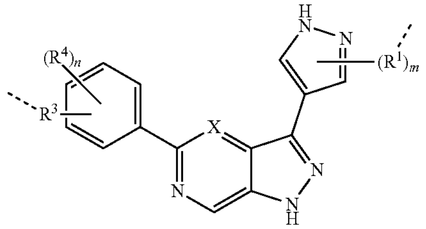

FORMULA 3G

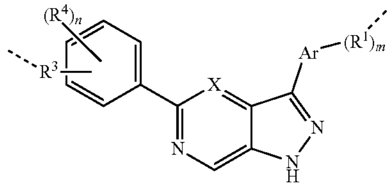

wherein the "Linker" moiety of the bivalent compound is attached independently to $R^3$ or independently to one of the $R^1$;

X is selected from $CR^2$ or N;

the definitions of $R^1$, $R^2$, $R^3$ and $R^4$ are the same as for FORMULA 3B.

Ar is selected from null, aryl and heteroaryl, each of which is substituted with $R^1$;

n and m are independently selected from 0, 1, 2, 3, 4 and 5.

In an embodiment, (HPK1) ligands include a moiety according to FORMULA 3H or 3K:

FORMULA 3H

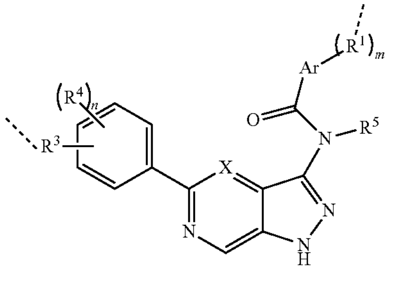

FORMULA 3K

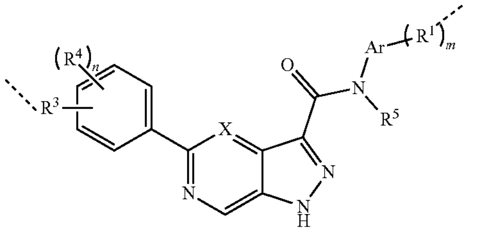

wherein the "Linker" moiety of the bivalent compound is attached independently to $R^1$ or $R^3$;

X is selected from $CR^2$ or N;

the definitions of $R^1$, $R^2$, $R^3$, $R^4$ and $R^5$ are the same as for FORMULA 3C, 3D, 3E;

Ar is selected from null, aryl and heteroaryl, each of which is substituted with $R^1$;

n and m are independently selected from 0, 1, 2, 3, 4 and 5.

In an embodiment, (HPK1) ligands include a moiety according to FORMULA 3L:

FORMULA 3L

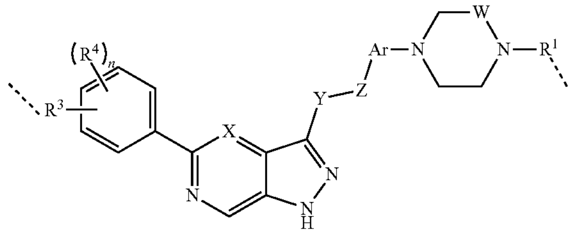

wherein the "Linker" moiety of the bivalent compound is attached independently to $R^1$ or $R^3$;

X is selected from $CR^2$ or N;

the definitions of $R^1$, $R^2$, $R^3$ and $R^4$ are the same as for FORMULA 3B3;

Ar is selected from null, aryl and heteroaryl;

n is independently selected from 0, 1, 2, 3, 4 and 5;

Y, Z at each occurrence, are independently selected from null, CO, $CO_2$, $CH_2$, $CR^{24}R^{25}$, $C(O)NR^{24}$, $C(S)NR^{24}$, O, S, SO, $SO_2$, $SO_2NR^{24}$, $NR^{24}$, $NR^{24}CO$, $NR^{24}CONR^{24}$, $NR^{24}C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{24}$ and $R^{25}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

W, at each occurrence, is independently selected from null, CO, $CH_2$, $(CH_2)_m$ $CR^{26}R^{27}$, $(CR^{26}R^{27})_m$, SO, $SO_2$ wherein $R^{26}$ and $R^{27}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

and m=0-5.

In an embodiment, (HPK1) ligands include a moiety according to FORMULA 3M:

FORMULA 3M

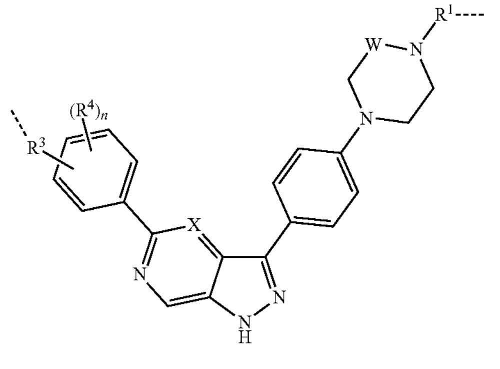

wherein the "Linker" moiety of the bivalent compound is attached independently to $R^1$ or $R^3$;

X is selected from $CR^2$ or N;

the definitions of W, $R^1$, $R^2$, $R^3$ and $R^4$ are the same as for FORMULA 3L.

n is independently selected from 0, 1, 2, 3, 4 and 5; and pharmaceutically acceptable salts thereof.

In an embodiment, (HPK1) ligands include a moiety according to FORMULA 4:

FORMULA 4

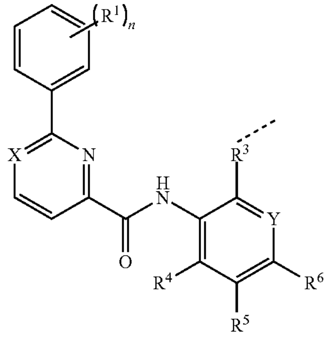

wherein the "Linker" moiety of the bivalent compound is attached to $R^3$;

X is selected from $CR^2$ or N;

Y is selected from $CR^7$ or N;

each $R^1$ is independently selected from null, hydrogen, halogen, oxo, CN, $NO_2$, $OR^8$, $SR^8$, $NR^8R^9$, $OCOR^8$, $OCO_2R^8$, $OCONR^8R^9$, $COR^8$, $CO_2R^8$, $CONR^8R^9$, $SOR^8$, $SO_2R^8$, $SO_2NR^8R^9$, $NR^1CO_2R^8$, $NR^{10}COR^8$, $NR^{10}C(O)NR^8R^9$, $NR^{10}SOR^8$, $NR^{10}SO_2R^8$, $NR^{10}SO_2NR^8R^9$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^8$, $R^9$ and $R^{10}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^8$ and $R^9$, $R^8$ and $R^{10}$ together with the atom to which they are connected form a 4-20 membered heterocyclyl ring; and n is independently selected from 0, 1, 2, 3, 4 and 5;

$R^2$ and $R^7$ are independently selected from hydrogen, halogen, oxo, CN, $NO_2$, $OR^{11}$, $SR^{11}$, $NR^{11}R^{12}$, $C(O)R^{11}$, $C(O)OR^{11}$, $C(O)NR^{11}R^{12}$, $S(O)R^{11}$, $S(O)_2R^{11}$, $S(O)_2NR^{11}R^{12}$, $NR^{13}C(O)OR^{10}$, $NR^{13}C(O)R^{11}$, $NR^{13}C(O)NR^{11}R^{12}$, $NR^{13}S(O)R^{11}$, $NR^{13}S(O)_2R^{11}$, $NR^{13}S(O)_2NR^{11}R^{12}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{11}$ and $R^{12}$, $R^{11}$ and $R^{12}$, $R^{12}$ and $R^{13}$ together with the atom to which they are connected form an optionally substituted 3-20 membered cycloalkyl or heterocyclyl ring;

$R^3$ is selected from null, hydrogen, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{15}$, and $R^{16}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$ together with the atom to which they are connected form an optionally substituted 3-20 membered cycloalkyl or heterocyclyl ring;

$R^4$, $R^5$ and $R^6$ are independently selected hydrogen, halogen, oxo, CN, $NO_2$, $OR^{17}$, $SR^{17}$, $NR^{18}R^{19}$, $OCOR^{17}$, $OCO_2R^{17}$, $OCONR^{18}R^{19}$, $COR^{17}$, $CO_2R^{17}$, $CONR^{18}R^{19}$, $SOR^{17}$, $SO_2R^{17}$, $SO_2NR^{18}R^{19}$, $NR^{17}CO_2R^{18}$, $NR^{17}COR^{18}$, $NR^{17}C(O)NR^{18}R^{19}$, $NR^{17}SOR^{18}$, $NR^{17}SO_2R^{18}$, $NR^{17}SO_2NR^{18}R^{19}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{17}$, $R^{18}$, and $R^{19}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{17}$ and $R^{18}$, $R^{18}$ and $R^{19}$ together with the atom to which they are connected form a 3-20 membered heterocyclyl ring.

In an embodiment, (HPK1) ligands include a moiety according to FORMULA 4A:

FORMULA 4A

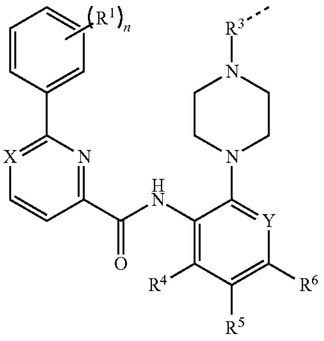

wherein the "Linker" moiety of the bivalent compound is attached to $R^3$;

X is selected from $CR^2$ or N;

Y is selected from $CR^7$ or N;

the definitions of $R^1$, $R^2$, $R^3$, $R^4$, $R^5$, $R^6$ and $R^7$ are the same as for FORMULA 4.

In an embodiment, (HPK1) ligands include a moiety according to FORMULA 4B:

FORMULA 4B

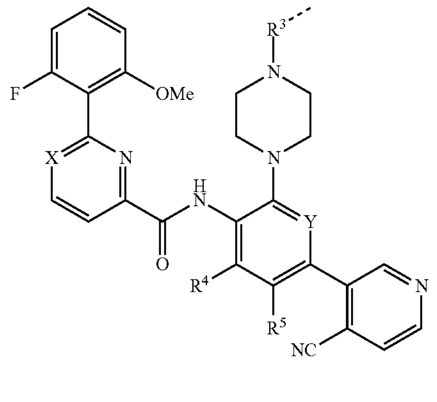

wherein the "Linker" moiety of the bivalent compound is attached to $R^3$;

X is selected from $CR^2$ or N;

Y is selected from $CR^7$ or N; and the definitions of $R^2$, $R^3$, $R^4$, $R^5$, and $R^7$ are the same as for FORMULA 4; and pharmaceutically acceptable salts thereof.

In an embodiment, (HPK1) ligands include a moiety according to FORMULA 5:

FORMULA 5

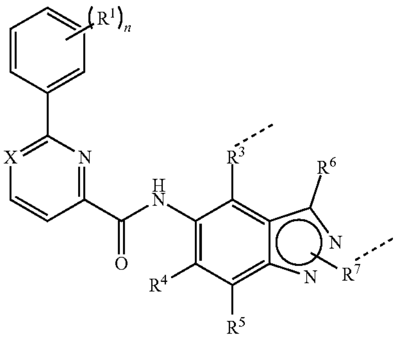

wherein the "Linker" moiety of the bivalent compound is attached to independently to $R^3$ or $R^7$;

X is selected from $CR^2$ or N;

each $R^1$ is independently selected from null, hydrogen, halogen, oxo, CN, $NO_2$, $OR^8$, $SR^8$, $NR^8R^9$, $OCOR^8$, $OCO_2R^8$, $OCONR^8R^9$, $COR^8$, $CO_2R^8$, $CONR^8R^9$, $SOR^8$, $SO_2R^8$, $SO_2NR^8R^9$, $NR^{10}CO_2R^8$, $NR^{10}COR^8$, $NR^{10}C(O)NR^8R^9$, $NR^{10}SOR^8$, $NR^{10}SO_2R^8$, $NR^{10}SO_2NR^8R^9$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^8$, $R^9$ and $R^{10}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^8$ and $R^9$, $R^8$ and $R^{10}$ together with the atom to which they are connected form a 4-20 membered heterocyclyl ring; and n is independently selected from 0, 1, 2, 3, 4 and 5;

$R^2$ is selected from hydrogen, halogen, oxo, CN, $NO_2$, $OR^{11}$, $SR^{11}$, $NR^{11}R^{12}$, $C(O)R^{11}$, $C(O)OR^{11}$, $C(O)NR^{11}R^{12}$, $S(O)R^{11}$, $S(O)_2R^1$, $S(O)_2NR^{11}R^{12}$, $NR^{13}C(O)OR^{10}$, $NR^{13}C(O)R^{11}$, $NR^{13}C(O)NR^{11}R^{12}$, $NR^{13}S(O)R^{11}$, $NR^{13}S(O)_2R^{11}$, $NR^{13}S(O)_2NR^{11}R^{12}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{11}$, $R^{12}$, and $R^{13}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{11}$ and $R^{12}$, $R^{11}$ and $R^{12}$, $R^{12}$ and $R^{13}$ together with the atom to which they are connected form an optionally substituted 3-20 membered cycloalkyl or heterocyclyl ring;

$R^3$ and $R^7$ are independently selected from null, hydrogen, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{15}$, and $R^{16}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$ together with the atom to which they are connected form an optionally substituted 3-20 membered cycloalkyl or heterocyclyl ring; $R^4$, $R^5$ and $R^6$ are independently selected hydrogen, halogen, oxo, CN, $NO_2$, $OR^{17}$, $SR^{17}$, $NR^{18}R^{19}$, $OCOR^{17}$, $OCO_2R^{17}$, $OCONR^{18}R^{19}$, $COR^{17}$, $CO_2R^{17}$, $CONR^{18}R^{19}$, $SOR^{17}$, $SO_2R^{17}$, $SO_2NR^{18}R^{19}$, $NR^{17}CO_2R^{18}$, $NR^{17}COR^{18}$, $NR^{17}C(O)NR^{18}R^{19}$, $NR^{17}SOR^{18}$, $NR^{17}SO_2R^{18}$, $NR^{17}SO_2NR^{18}R^{19}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{17}$, $R^{18}$, and $R^{19}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{17}$ and $R^{18}$, $R^{18}$ and $R^{19}$ together with the atom to which they are connected form a 3-20 membered heterocyclyl ring; and pharmaceutically acceptable salts thereof.

In an embodiment, (HPK1) ligands include a moiety according to FORMULA 6:

FORMULA 6

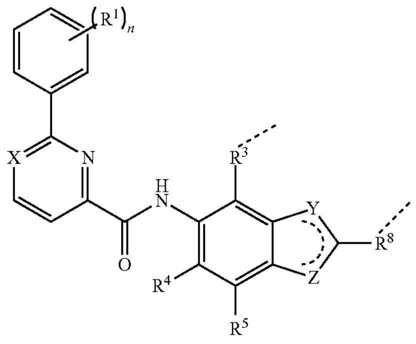

wherein the "Linker" moiety of the bivalent compound is attached to independently to $R^3$ or $R^8$;

X is selected from $CR^2$ or N;

Y is selected from $CR^6$ or N;

Z is selected from $CR^7$ or N or S;

each $R^1$ is independently selected from null, hydrogen, halogen, oxo, CN, $NO_2$, $OR^9$, $SR^9$, $NR^9R^{10}$, $OCOR^9$, $OCO_2R^9$, $OCONR^9R^{10}$, $COR^9$, $CO_2R^9$, $CONR^9R^{10}$, $SOR^9$, $SO_2R^9$, $SO_2NR^9R^{10}$, $NR^{11}CO_2R^9$, $NR^{11}COR^9$, $NR^{11}C(O)NR^9R^{10}$, $NR^{11}SOR^9$, $NR^{11}SO_2R^9$, $NR^{11}SO_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^9$, $R^{10}$ and $R^{11}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^9$ and $R^{10}$, $R^9$ and $R^{11}$ together with the atom to which they are connected form a 4-20 membered heterocyclyl ring; and n is independently selected from 0, 1, 2, 3, 4 and 5;

$R^2$, $R^6$ and $R^7$ are independently selected from hydrogen, halogen, oxo, CN, $NO_2$, $OR^{12}$, $SR^{12}$, $NR^{12}R^{13}$, C(O)

$R^{12}$, $C(O)OR^{12}$, $C(O)NR^{12}R^{13}$, $S(O)R^{12}$, $S(O)_2R^{12}$, $S(O)_2NR^{12}R^{13}$, $NR^{14}C(O)OR^{11}$, $NR^{14}C(O)R^{12}$, $NR^{14}C(O)NR^{12}R^{13}$, $NR^{14}S(O)R^{12}$, $NR^{14}S(O)_2R^{12}$, $NR^{14}S(O)_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{12}$, $R^{13}$, and $R^{14}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{13}$, $R^{13}$ and $R^{14}$ together with the atom to which they are connected form an optionally substituted 3-20 membered cycloalkyl or heterocyclyl ring;

$R^3$ and $R^8$ are independently selected from null, hydrogen, $C(O)R^{15}$, $C(O)OR^{15}$, $C(O)NR^{15}R^{16}$, $S(O)R^{15}$, $S(O)_2R^{15}$, $S(O)_2NR^{15}R^{16}$, $NR^{17}C(O)OR^{15}$, $NR^{16}C(O)R^{15}$, $NR^{17}C(O)NR^{15}R^{16}$, $NR^{17}S(O)R^{15}$, $NR^{17}S(O)_2R^{15}$, $NR^{17}S(O)_2NR^{15}R^{16}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{15}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{16}$, and $R^{17}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$ together with the atom to which they are connected form an optionally substituted 3-20 membered cycloalkyl or heterocyclyl ring;

$R^4$ and $R^5$ are independently selected hydrogen, halogen, oxo, CN, $NO_2$, $OR^{18}$, $SR^{18}$, $NR^{19}R^{20}$, $OCOR^{18}$, $OCO_2R^{18}$, $OCONR^{19}R^{20}$, $COR^{18}$, $CO_2R^{18}$, $CONR^{19}R^{20}$, $SOR^{18}$, $SO_2R^{18}$, $SO_2NR^{19}R^{20}$, $NR^{18}CO_2R^{19}$, $NR^{18}COR^{19}$, $NR^{18}C(O)NR^{19}R^{20}$, $NR^{18}SOR^{19}$, $NR^{18}SO_2R^{19}$, $NR^{19}SO_2NR^{19}R^{20}$ optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{18}$, $R^{19}$, and $R^{20}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{18}$ and $R^{19}$, $R^{19}$ and $R^{20}$ together with the atom to which they are connected form a 3-20 membered heterocyclyl ring; and pharmaceutically acceptable salts thereof.

In an embodiment, (HPK1) ligands include a moiety according to FORMULA 7:

FORMULA 7

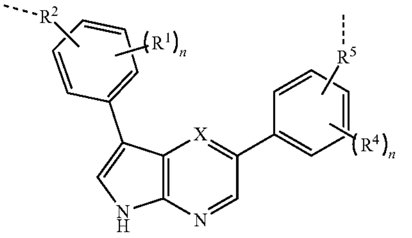

wherein the "Linker" moiety of the bivalent compound is attached to independently to $R^2$ or $R^5$;

X is selected from $CR^3$ or N;

each $R^1$ an d $R^4$ are independently selected from null, hydrogen, halogen, oxo, CN, $NO_2$, $OR^6$, $SR^6$, $NR^6R^7$, $OCOR^6$, $OCO_2R^6$, $OCONR^6R^7$, $COR^6$, $CO_2R^6$, $CONR^6R^7$, $SOR^6$, $SO_2R^6$, $SO_2NR^6R^7$, $NR^8CO_2R^6$, $NR^8COR^6$, $NR^8C(O)NR^6R^7$, $NR^8SOR^6$, $NR^8SO_2R^6$, $NR^8SO_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^6$, $R^7$ and $R^8$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^6$ and $R^7$, $R^6$ and $R^8$ together with the atom to which they are connected form a 4-20 membered heterocyclyl ring; and n is independently selected from 0, 1, 2, 3, 4 and 5;

$R^2$ and $R^5$ are independently selected from null, hydrogen, $C(O)R^{12}$, $C(O)OR^{12}$, $C(O)NR^{12}R^{13}$, $S(O)R^{12}$, $S(O)_2R^{12}$, $S(O)_2NR^{12}R^{13}$, $NR^{14}C(O)OR^{12}$, $NR^{13}C(O)R^{12}$, $NR^{14}C(O)NR^{12}R^{13}$, $NR^{14}S(O)R^{12}$, $NR^{14}S(O)_2R^{12}$, $NR^{14}S(O)_2NR^{12}R^{13}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{12}$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^{13}$, and $R^{14}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$ together with the atom to which they are connected form an optionally substituted 3-20 membered cycloalkyl or heterocyclyl ring;

$R^3$ is selected from hydrogen, halogen, oxo, CN, $NO_2$, $OR^{14}$, $SR^{14}$, $NR^{14}R^{15}$, $C(O)R^{14}$, $C(O)OR^{14}$, $C(O)NR^{14}R^{15}$, $S(O)R^{14}$, $S(O)_2R^{14}$, $S(O)_2NR^{14}R^{15}$, $NR^{16}C(O)OR^{14}$, $NR^{16}C(O)R^{14}$, $NR^{16}C(O)NR^{14}R^{15}$, $NR^{16}S(O)R^{14}$, $NR^{16}S(O)_2R^{14}$, $NR^{16}S(O)_2NR^{14}R^{15}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{14}$, $R^{15}$, and $R^{16}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^{14}$ and $R^{15}$, $R^{14}$ and $R^{15}$, $R^{15}$ and $R^{16}$ together with the atom to which they are connected form an optionally substituted 3-20 membered cycloalkyl or heterocyclyl ring.

In an embodiment, (HPK1) ligands include a moiety according to FORMULA 7A:

FORMULA 7A

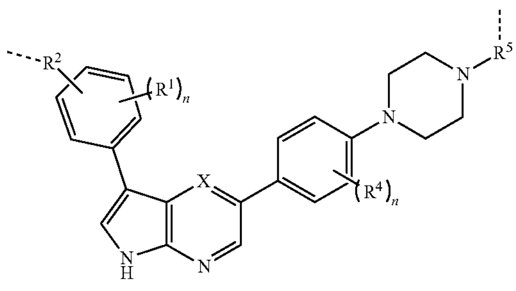

wherein the "Linker" moiety of the bivalent compound is attached to $R^2$ or $R^5$;

X is selected from $CR^3$ or N; and the definitions of $R^1$, $R^2$, $R^3$, $R^4$, and $R^5$ are the same as for FORMULA 7; and pharmaceutically acceptable salts thereof.

In an embodiment, (HPK1) ligands include a moiety according to FORMULA 8:

FORMULA 8

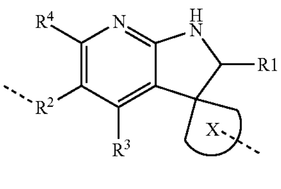

wherein the "Linker" moiety of the bivalent compound is attached to $R^2$ or X;

X is $C_{3-12}$ cycloalkyl, 3- to 14-membered heterocyclyl, $C_{6-14}$ aryl or 5- to- 14-membered heteroaryl, wherein $C_{3-12}$ cycloalkyl, 3- to 14-membered heterocyclyl, $C_{6-14}$ aryl or 5- to- 14-membered heteroaryl of X are each optionally substituted with 1, 2, 3, 4 or 5 substituents independently selected from $R^5$;

$R^1$ is selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl;

$R^2$ is selected from null, hydrogen, $C(O)R^7$, $C(O)OR^7$, $C(O)NR^7R^8$, $S(O)R^7$, $S(O)_2R^7$, $S(O)_2NR^7R^8$, $NR^9C(O)OR^7$, $NR^8C(O)R^7$, $NR^9C(O)NR^7R^8$, $NR^9S(O)R^7$, $NR^9S(O)_2R^7$, $NR^9S(O)_2NR^7R^8$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^7$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^8$, and $R^9$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^7$ and $R^8$ together with the atom to which they are connected form an optionally substituted 3-20 membered cycloalkyl or heterocyclyl ring;

$R^3$ and $R^4$ and $R^5$ are independently selected from null, hydrogen, halogen, oxo, CN, $NO_2$, $OR^{10}$, $SR^{10}$, $NR^{10}R^{11}$, $OCOR^{10}$, $OCO_2R^{10}$, $OCONR^{10}R^{11}$, $COR^{10}$, $CO_2R^{10}$, $CONR^{10}R^{11}$, $SOR^{10}$, $SO_2R^{10}$, $SO_2NR^{10}R^{11}$, $NR^{12}CO_2R^{10}$, $NR^{12}COR^{10}$, $NR^{12}C(O)NR^{10}R^{11}$, $NR^{12}SOR^{10}$, $NR^{12}SO_2R^{10}$, $NR^{12}SO_2NR^{10}R^{11}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{10}$, $R^{11}$ and $R^{12}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{10}$ and $R^{11}$, $R^{10}$ and $R^{12}$ together with the atom to which they are connected form a 4-20 membered heterocyclyl ring.

In an embodiment, (HPK1) ligands include a moiety according to FORMULA 8A:

FORMULA 8A

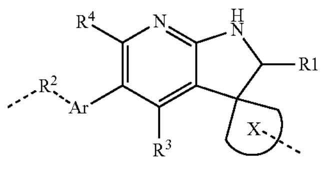

wherein the "Linker" moiety of the bivalent compound is attached to $R^2$ or X;

the definitions of X, $R^1$, $R^2$, $R^3$, $R^4$, and $R^5$ are the same as FORMULA 8;

Ar is selected from null, aryl and heteroaryl, each of which is substituted with $R^2$ and optionally substituted with one or more substituents independently selected from hydrogen, halogen, oxo, CN, $NO_2$, $OR^{13}$, $SR^{13}$, $NR^{13}R^{14}$, $OCOR^{13}$, $OCO_2R^{13}$, $OCONR^{13}R^{14}$, $COR^{13}$, $CO_2R^{13}$, $CONR^{13}R^{14}$, $SOR^{13}$, $SO_2R^{13}$, $SO_2NR^{13}R^{14}$, $NR^{15}CO_2R^{13}$, $NR^{15}COR^{13}$, $NR^{14}C(O)NR^{13}R^{14}$, $NR^{15}SOR^{13}$, $NR^{15}SO_2R^{13}$, $NR^{15}SO_2NR^{13}R^{14}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{13}$, $R^{14}$, and $R^{15}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{13}$ and $R^{14}$, $R^{13}$ and $R^{15}$ together with the atom to which they are connected form a 4-20 membered heterocyclyl ring.

In an embodiment, (HPK1) ligands include a moiety according to FORMULA 8B:

FORMULA 8B

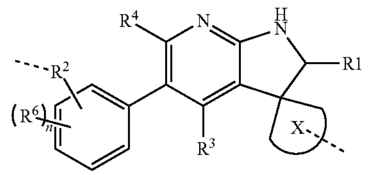

wherein the "Linker" moiety of the bivalent compound is attached to $R^2$ or X;

the definitions of X, $R^1$, $R^2$, $R^3$, $R^4$, and $R^5$ are the same as FORMULA 8;

Each $R^6$ is independently selected from null, hydrogen, halogen, oxo, CN, $NO_2$, $OR^{16}$, $SR^{16}$, $NR^{16}R^{17}$, $OCOR^{16}$, $OCO_2R^{16}$, $OCONR^{16}R^{17}$, $COR^{16}$, $CO_2R^{16}$, $CONR^{16}R^{17}$, $SOR^{16}$, $SO_2R^{16}$, $SO_2NR^{16}R^{17}$, $NR^{18}CO_2R^{16}$, $NR^{18}COR^{16}$, $NR^{18}C(O)NR^{16}R^{17}$, $NR^{18}SOR^{16}$, $NR^{18}SO_2R^{16}$, $NR^{18}SO_2NR^{16}R^{17}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{16}$, $R^{17}$ and $R^{18}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{16}$ and $R^{17}$, $R^{16}$ and $R^{18}$ together with the atom to which they are connected form a 4-20 membered heterocyclyl ring; and n is independently selected from 0, 1, 2, 3, 4 and 5; and pharmaceutically acceptable salts thereof.

In an embodiment, (HPK1) ligands include a moiety according to FORMULA 9:

FORMULA 9

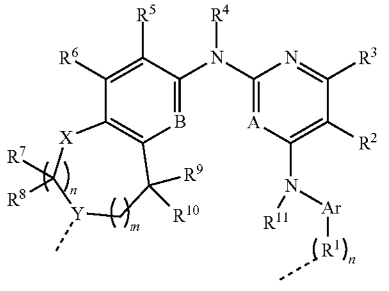

wherein the “Linker” moiety of the bivalent compound is attached independently to Y or independently one of the $R^1$;

each of $R^1$ is selected from null, $OR^{12}$, $SR^{12}$, $NR^{12}R^{13}$, $OC(O)R^{12}$, $OC(O)OR^{12}$, $OCONR^{12}R^{13}$, $C(O)R^{12}$, $C(O)OR^{12}$, $CONR^{12}R^{13}$, $S(O)R^1$, $S(O)_2R^{12}$, $SO_2NR^{12}R^{13}$, $NR^{14}C(O)OR^{12}$, $NR^{14}C(O)R^{12}$, $NR^{14}C(O)NR^{12}R^{13}$, $NR^{14}S(O)R^{12}$, $NR^{14}S(O)_2R^{12}$, $NR^{14}S(O)_2$ $NR^{12}R^{13}$, $P(O)R^{12}R^{13}$, $P(O)(OR^{12})$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{12}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{13}$ and $R^{14}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{14}$, $R^{13}$ and $R^{14}$ together with the atom to which they are connected form a 3-20 membered cycloalkyl or heterocyclyl ring;

n and m are independently selected from 0, 1, 2, 3, 4 and 5;

Ar is selected from null, aryl and heteroaryl, each of which optionally is substituted with $R^1$;

$R^2$, $R^3$, $R^5$ and $R^6$ are independently selected from hydrogen, halogen, $OR^{15}$, $SR^{15}$, $NR^{16}R^{17}$, $COR^{15}$, $CO_2R^{15}$, $C(O)NR^{16}R^{17}$, $SOR^{15}$, $SO_2R^{15}$, $SO_2NR^{16}R^{17}$, $NR^{15}C(O)R^{16}$, $NR^{15}C(O)NR^{16}R^{17}$, $NR^{15}SOR^{16}$, $NR^{15}SO_2R^{16}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{15}$, $R^{16}$, and $R^{17}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-10 membered heterocyclyl, optionally substituted $C_2$-$C_8$ alkenyl, optionally substituted $C_2$-$C_8$ alkynyl, optionally substituted aryl, and optionally substituted heteroaryl; or $R^{15}$ and $R^{16}$, $R^{16}$ and $R^{17}$ together with the atom to which they are connected form an optionally substituted 3-20 membered cycloalkyl or heterocyclyl ring; $R^7$, $R^8$, $R^9$, and $R^{10}$ are independently selected from null, hydrogen, halogen, $OR^{18}$, $NR^{19}R^{20}$ optionally substituted $C_1$-$C_8$ alkyl, optionally substituted $C_1$-$C_8$ alkoxy, optionally substituted $C_3$-$C_8$ cycloalkyl, optionally substituted $C_3$-$C_8$ cycloalkoxy; wherein $R^{18}$, $R^{19}$, and $R^{20}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-10 membered heterocyclyl, optionally substituted $C_2$-$C_8$ alkenyl, optionally substituted $C_2$-$C_8$ alkynyl; or $R^{19}$ and $R^{20}$ together with the atom to which they are connected form an an optionally substituted 3-20 membered cycloalkyl or heterocyclyl ring;

$R^{11}$ at each occurrence, is independently selected from hydrogen, $C(O)R^{21}$, $C(O)OR^{21}$, $C(O)NR^{21}R^{22}$, $S(O)R^{21}$, $S(O)_2R^{21}$, $S(O)_2NR^{21}R^{22}$, $NR^{23}C(O)OR^{21}$, $NR^{23}C(O)R^{21}$, $NR^{23}C(O)NR^{21}R^{22}$, $NR^{23}S(O)R^{21}$, $NR^{23}S(O)_2R^{21}$, $NR^{23}S(O)_2NR^{21}R^{22}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^{21}$, $R^{22}$ and $R^{23}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{21}$ and $R^{22}$, $R^{21}$ and $R^{23}$ together with the atom to which they are connected form a 3-20 membered heterocyclyl ring; and X, Y at each occurrence, are independently selected from null, CO, $CO_2$, $CH_2$, $CR^{24}R^{25}$, C(O)$NR^{24}$, C(S)$NR^{24}$, O, S, SO, $SO_2$, $SO_2NR^{24}$, $NR^{24}$, $NR^{24}$CO, $NR^{24}CONR^{21}$, $NR^{24}$C(S), optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^{24}$ and $R^{25}$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl; and A and B are independently selected from C or N; and pharmaceutically acceptable salts thereof.

In an embodiment, (HPK1) ligands include a moiety according to FORMULA 10:

FORMULA 10

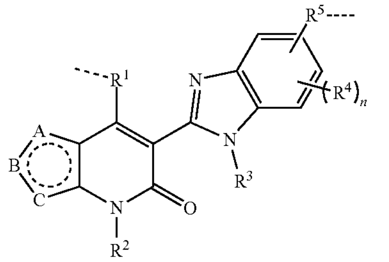

wherein the "Linker" moiety of the bivalent compound is attached independently to $R^1$ or $R^5$;

$R^1$ and $R^5$ are independently selected from null, hydrogen, C(O)$R^6$, C(O)O$R^6$, C(O)$NR^6R^7$, S(O)$R^6$, $S(O)_2R^6$, $S(O)_2NR^6R^7$, NRIC(O)O$R^6$, NRIC(O)$R^6$, NRIC(O)$NR^6R^7$, $NR^8$S(O)$R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$ and $R^3$ at each occurrence, is independently selected from hydrogen, C(O)$R^9$, C(O)O$R^9$, C(O)$NR^9R^{10}$, S(O)$R^{21}$, $S(O)_2R^9$, $S(O)_2NR^9R^{10}$, $NR^{11}$C(O)O$R^9$, $NR^{11}$C(O)$R^9$, $NR^{11}$C(O)$NR^9R^{10}$, $NR^{11}$S(O)$R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$ and $R^{11}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^9$ and $R^{10}$, $R^9$ and $R^{11}$ together with the atom to which they are connected form a 3-20 membered heterocyclyl ring;

each of $R^4$ is selected from null, O$R^{12}$, S$R^{12}$, $NR^{12}R^{13}$, OC(O)$R^{12}$, OC(O)O$R^{12}$, OCON$R^{12}R^{13}$, C(O)$R^{12}$, C(O)O$R^{12}$, CON$R^{12}R^{13}$, S(O)$R^{12}$, $S(O)_2R^{12}$, $SO_2NR^{12}R^{13}$, $NR^{14}$C(O)O$R^{12}$, $NR^{14}$C(O)$R^{12}$, $NR^{14}$C(O)$NR^{12}R^{13}$, $NR^{14}$S(O)$R^{12}$, $NR^{14}S(O)_2R^{12}$, $NR^{14}S(O)_2$ $NR^{12}R^{13}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl; wherein $R^{12}$ is null, or a bivalent moiety selected from optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl;

$R^{13}$ and $R^{14}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{14}$, $R^{13}$ and $R^{14}$ together with the atom to which they are connected form a 3-20 membered cycloalkyl or heterocyclyl ring;

n is independently selected from 0, 1, 2, 3, 4 and 5;

one of A, B and C is S, the other two are each independently selected from $CR^{15}$ or N Wherein $R^{1s}$ is independently selected from null, hydrogen, halogen, oxo, CN, $NO_2$, $OR^{16}$, $SR^{16}$, $NR^{16}R^{17}$, $OCOR^{16}$, $OCO_2R^{16}$, $OCONR^{16}R^{17}$, $COR^{16}$, $CO_2R^{16}$, $CONR^{16}R^{17}$, $SOR^{16}$, $SO_2R^{16}$, $SO_2NR^{16}R^{17}$, $NR^{18}CO_2R^{16}$, $NR^{18}COR^{16}$, $NR^1BC(O)NR^{16}R^{17}$, $NR^1SOR^{16}$, $NR^{15}SO_2R^{16}$, $NR^{18}SO_2NR^{16}R^{17}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; wherein $R^{16}$, $R^{17}$ and $R^{15}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^{16}$ and $R^{17}$, $R^{16}$ and $R^{18}$ together with the atom to which they are connected form a 4-20 membered heterocyclyl ring; and pharmaceutically acceptable salts thereof.

In an embodiment, (HPK1) ligands include a moiety according to FORMULA 11:

FORMULA 11

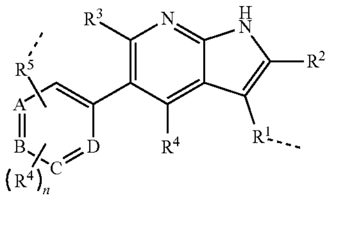

wherein the "Linker" moiety of the bivalent compound is attached independently to $R^1$ or $R^5$;

$R^1$ and $R^5$ are independently selected from null, hydrogen, $C(O)R^6$, $C(O)OR^6$, $C(O)NR^6R^7$, $S(O)R^6$, $S(O)_2R^6$, $S(O)_2NR^6R^7$, $NRIC(O)OR^6$, $NRIC(O)R^6$, $NR^8C(O)NR^6R^7$, $NR^8S(O)R^6$, $NR^8S(O)_2R^6$, $NR^8S(O)_2NR^6R^7$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^6$ is null, or a bivalent moiety selected from optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl;

$R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-20 membered heterocyclyl, optionally substituted $C_2$-$C_8$ alkenyl, optionally substituted $C_2$-$C_8$ alkynyl, optionally substituted aryl, and optionally substituted heteroaryl; or $R^6$ and $R^7$ together with the atom to which they are connected form an optionally substituted 3-20 membered cycloalkyl or heterocyclyl ring;

$R^2$, $R^3$ and $R^4$ at each occurrence, is independently selected from hydrogen, $C(O)R^9$, $C(O)OR^9$, $C(O)NR^9R^{10}$, $S(O)R^{21}$, $S(O)_2R^9$, $S(O)_2NR^9R^{10}$, $NR^{11}C(O)OR^9$, $NR^{11}C(O)R^9$, $NR^{11}C(O)NR^9R^{10}$, $NR^{11}S(O)R^9$, $NR^{11}S(O)_2R^9$, $NR^{11}S(O)_2NR^9R^{10}$, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 3-8 membered heterocyclyl, optionally substituted aryl, and optionally substituted heteroaryl; wherein $R^9$, $R^{10}$ and $R^{11}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted $C_3$-$C_8$ cycloalkoxy, optionally substituted 4-8 membered heterocyclyl, optionally substituted aryl, and optionally substituted heteroaryl; or $R^9$ and $R^{10}$, $R^9$ and $R^{11}$ together with the atom to which they are connected form a 3-20 membered heterocyclyl ring;

A, B and C each independently selected from N or $CR^6$;

each of $R^6$ is independently selected from null, hydrogen, halogen, $OR^{12}$, $SR^{12}$, $NR^{12}R^{13}$, $OC(O)R^{12}$, $OC(O)OR^{12}$, $OCONR^{12}R^{13}$, $C(O)R^{12}$, $C(O)OR^{12}$, $CONR^{12}R^{13}$, $S(O)R^{12}$, $S(O)_2R^{12}$, $SO_2NR^{12}R^{13}$, $NR^{14}C(O)OR^{12}$, $NR^{14}C(O)R^{12}$, $NR^{14}C(O)NR^{12}R^{13}$, $NR^{14}S(O)R^{12}$, $NR^{14}S(O)_2R^{12}$, $NR^{14}S(O)_2NR^{12}R^{13}$, optionally substituted $C_1$-$C_8$ alkylenyl, optionally substituted $C_2$-$C_8$ alkenylene, optionally substituted $C_2$-$C_8$ alkynylene, optionally substituted $C_3$-$C_8$ cycloalkylene, optionally substituted 3-8 membered heterocyclylene, optionally substituted aryl, and optionally substituted heteroaryl, wherein;

$R^{12}$, $R^{13}$ and $R^{14}$ are independently selected from optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl; or $R^{12}$ and $R^{13}$, $R^{12}$ and $R^{14}$, $R^{13}$ and $R^{14}$ together with the atom to which they are connected form a 3-20 membered cycloalkyl or heterocyclyl ring; and n is independently selected from 0, 1, 2, 3, 4 and 5; and pharmaceutically acceptable salts thereof.

In an embodiment, (HPK1) ligands are selected from the group consisting of

FORMULA 110

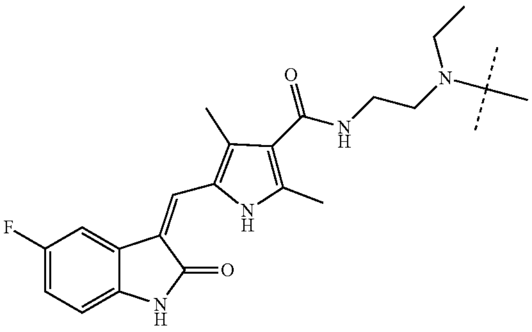

FORMULA 111

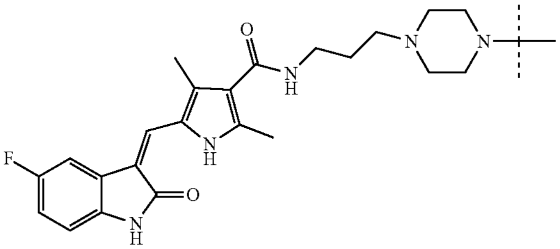

FORMULA 112

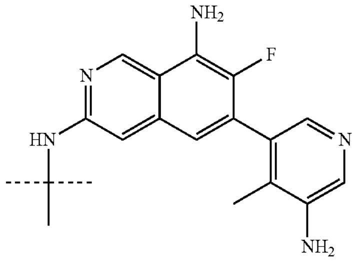

-continued

FORMULA 113

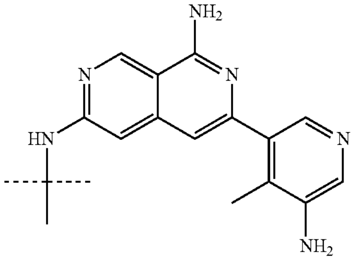

FORMULA 114

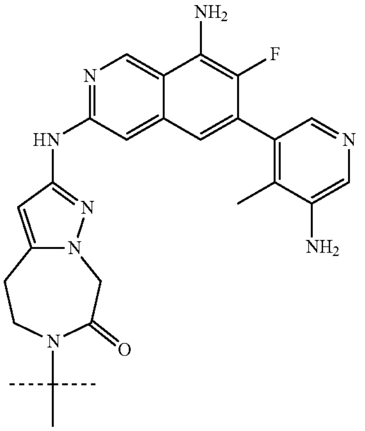

FORMULA 115

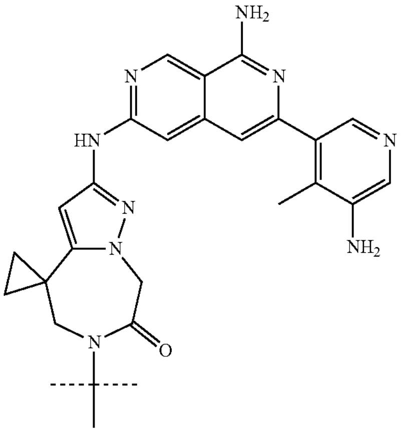

FORMULA 116

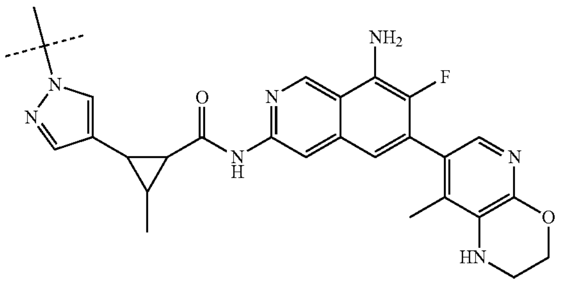

-continued
FORMULA 117
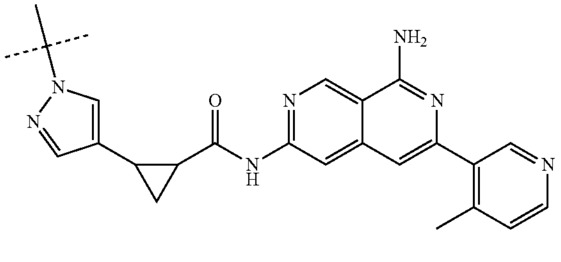
FORMULA 118
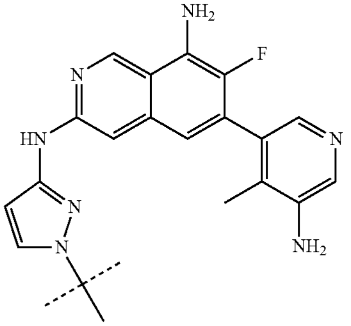
FORMULA 119
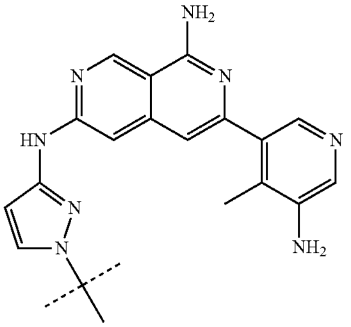
FORMULA 120
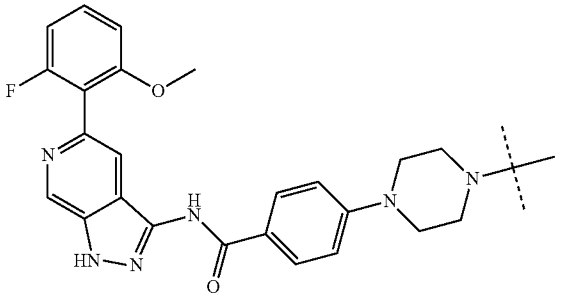
FORMULA 121
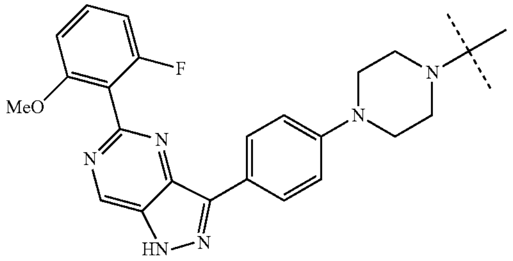
-continued
FORMULA 122
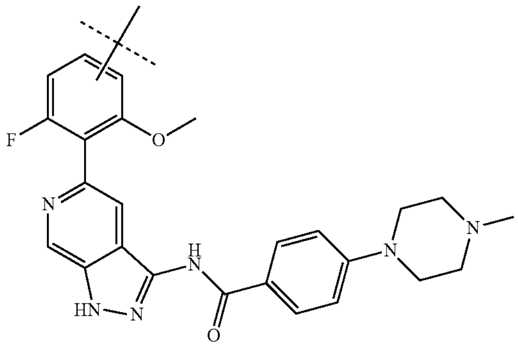
FORMULA 123
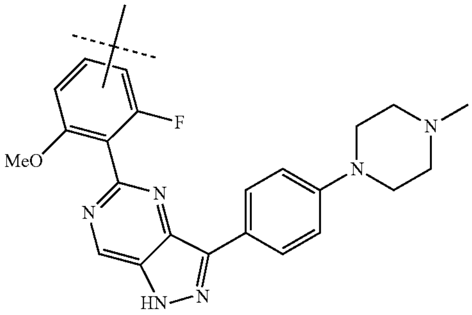
FORMULA 124
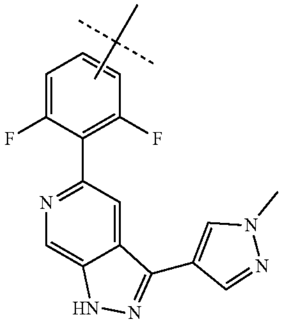
FORMULA 125
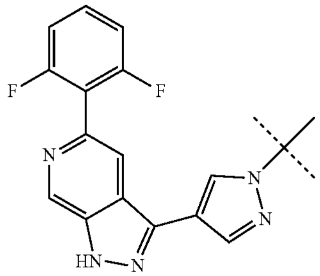

FORMULA 126
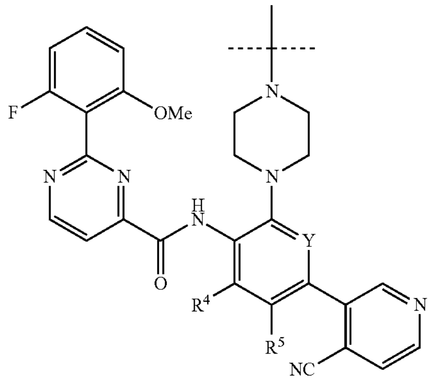
FORMULA 127
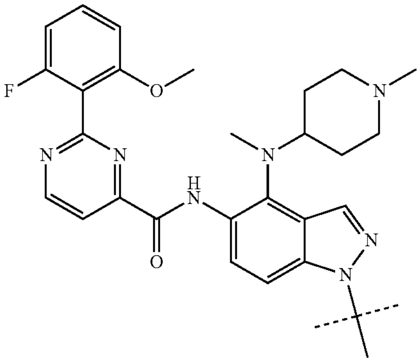
FORMULA 128
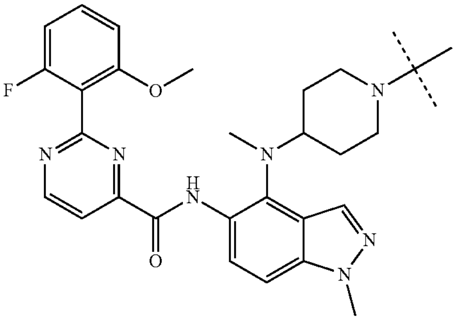
FORMULA 129
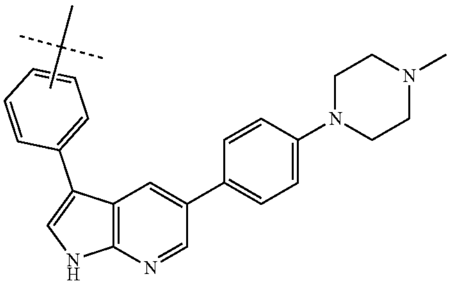
FORMULA 130
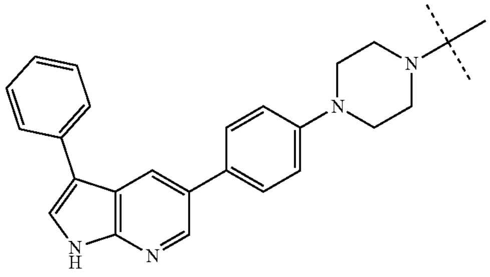
FORMULA 131
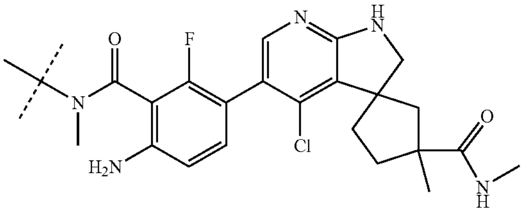
FORMULA 132
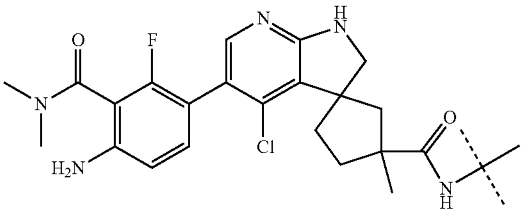
FORMULA 133
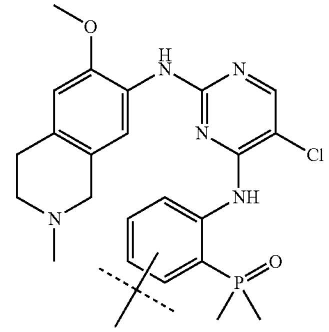
FORMULA 134
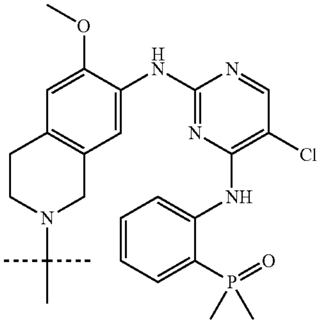

-continued

FORMULA 135

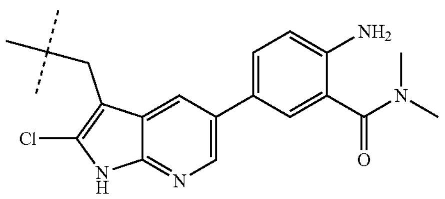

FORMULA 136

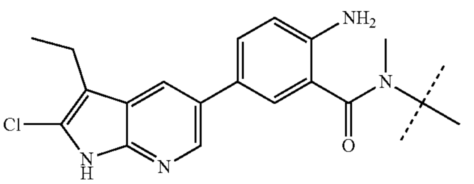

FORMULA 137

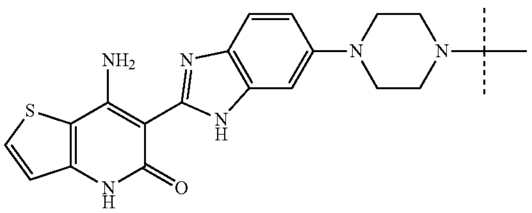

FORMULA 138

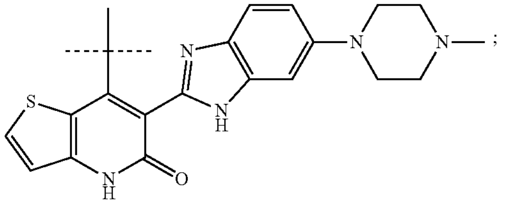

and pharmaceutically acceptable salts thereof.

Degradation/Disruption Tags

Degradation/Disruption tags (EL) include, but are not limited to:

In an embodiment, degradation/disruption tags include a moiety according to FORMULAE 12A, 12B, 12C and 12D:

FORMULA 12A

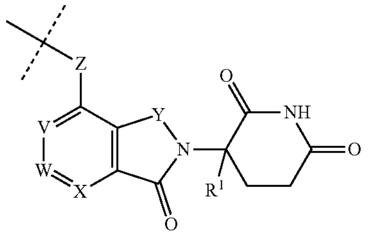

-continued

FORMULA 12B

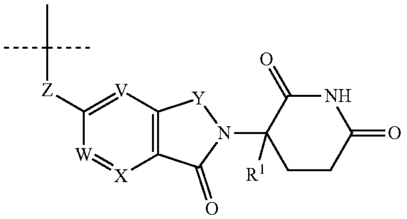

FORMULA 12C

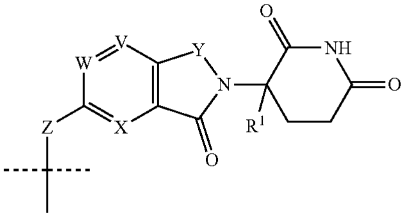

FORMULA 12D

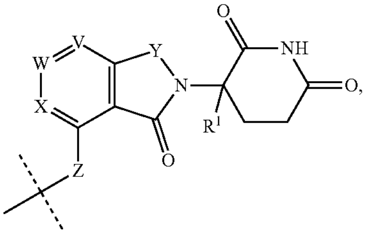

wherein

V, W, and X are independently selected from $CR^2$ and N;

Y is selected from CO, $CR^3R^4$, and N═N;

Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH═CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In an embodiment, degradation/disruption tags include a moiety according to one of FORMULAE 12E, 12F, 12G, 12H, and 12I:

FORMULA 12E

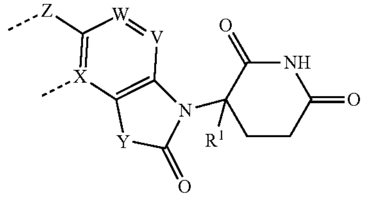

FORMULA 12F

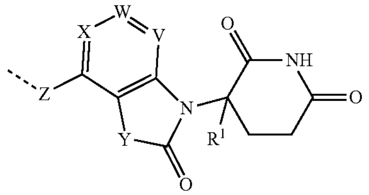

FORMULA 12G

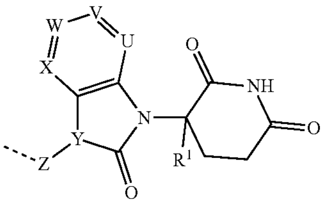

FORMULA 12H

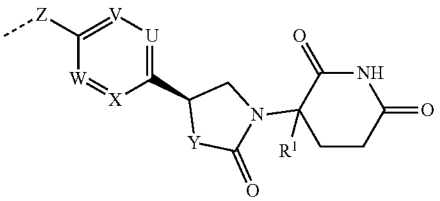

FORMULA 12I

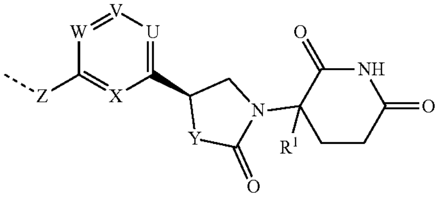

wherein

U, V, W, and X are independently selected from $CR^2$ and N;

Y is selected from $CR^3R^4$, $NR^3$ and O; preferably, Y is selected from $CH_2$, NH, $NCH_3$ and O;

Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH═CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl; and pharmaceutically acceptable salts thereof.

In an embodiment, degradation/disruption tags include a moiety according to FORMULA 13A:

FORMULA 13A

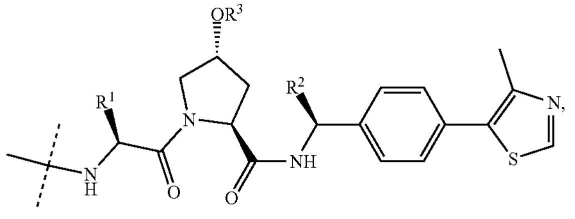

wherein $R^1$ and $R^2$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; and $R^3$ is hydrogen, optionally substituted C(O)$C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)$C_3$-$C_7$ cycloalkyl, optionally substituted C(O)(3-7 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O)O$C_1$-$C_8$alkylamino$C_1$-$C_8$alkyl, optionally substituted C(O)O$C_3$-$C_7$ cycloalkyl, optionally substituted C(O)O(3-7 membered heterocyclyl), optionally substituted C(O)$OC_2$-$C_8$ alkenyl, optionally substituted C(O)$OC_2$-$C_8$ alkynyl, optionally substituted C(O)$NC_1$-$C_8$alkoxy$C_1$-$C_8$alkyl, optionally substituted C(O)$NC_1$-$C_8$ haloalkyl, optionally substituted C(O)$NC_1$-$C_8$ hydroxyalkyl, optionally substituted C(O)$NC_1$-$C_8$ aminoalkyl, optionally substituted C(O)$NC_1$-$C_8$alkylamino$C_1$-$C_8$alkyl, optionally substituted C(O)$NC_3$-$C_7$ cycloalkyl, optionally substituted C(O)N(3-7 membered heterocyclyl), optionally substituted C(O)$NC_2$-$C_8$ alkenyl, optionally substituted C(O)$NC_2$-$C_8$ alkynyl, optionally substituted $P(O)(OH)_2$, optionally substituted P(O)($OC_1$-$C_8$ alkyl)$_2$, and optionally substituted P(O)($OC_1$-$C_8$ aryl)$_2$.

In an embodiment, degradation/disruption tags include a moiety according to FORMULAE 13B, 13C, 13D, 13E and 13F:

FORMULA 13B

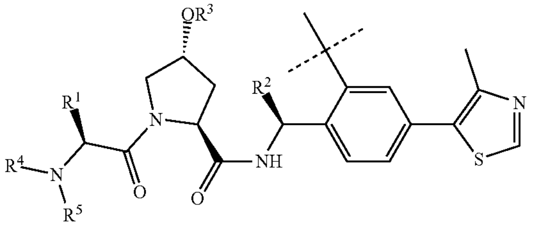

FORMULA 13C

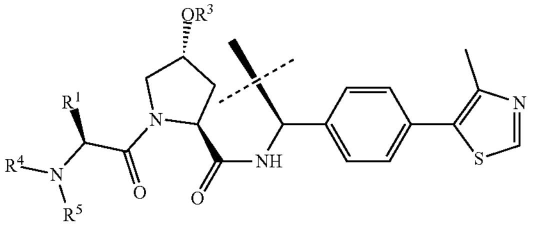

FORMULA 13D

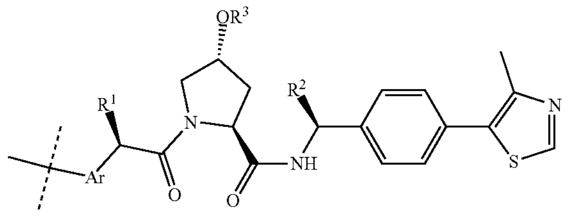

FORMULA 13E

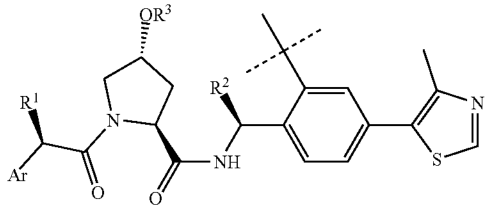

-continued

FORMULA 13F

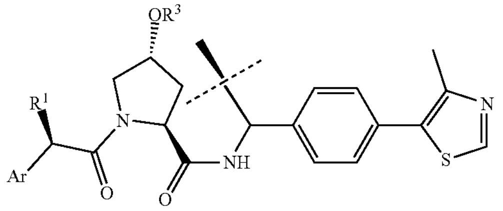

wherein $R^1$ and $R^2$ are independently selected from hydrogen, halogen, OH, $NH_2$, CN, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, $R^1$ is selected from iso-propyl or tert-butyl; and $R^2$ is selected from hydrogen or methyl);

$R^3$ is hydrogen, optionally substituted C(O)$C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)$C_3$-$C_7$ cycloalkyl, optionally substituted C(O)(3-7 membered heterocyclyl), optionally substituted C(O)$C_2$-$C_8$ alkenyl, optionally substituted C(O)$C_2$-$C_8$ alkynyl, optionally substituted C(O)$OC_1$-$C_8$alkoxy$C_1$-$C_8$alkyl, optionally substituted C(O)$OC_1$-$C_8$ haloalkyl, optionally substituted C(O)$OC_1$-$C_8$ hydroxyalkyl, optionally substituted C(O)$OC_1$-$C_8$ aminoalkyl, optionally substituted C(O)$OC_1$-$C_8$alkylamino$C_1$-$C_8$alkyl, optionally substituted C(O)$OC_3$-$C_7$ cycloalkyl, optionally substituted C(O)O(3-7 membered heterocyclyl), optionally substituted C(O)$OC_2$-$C_8$ alkenyl, optionally substituted C(O)$OC_2$-$C_8$ alkynyl, optionally substituted C(O)$NC_1$-$C_8$alkoxy$C_1$-$C_8$alkyl, optionally substituted C(O)$NC_1$-$C_8$ haloalkyl, optionally substituted C(O)$NC_1$-$C_8$ hydroxyalkyl, optionally substituted C(O)$NC_1$-$C_8$ aminoalkyl, optionally substituted C(O)$NC_1$-$C_8$alkylamino$C_1$-$C_8$alkyl, optionally substituted C(O)$NC_3$-$C_7$ cycloalkyl, optionally substituted C(O)N(3-7 membered heterocyclyl), optionally substituted C(O)$NC_2$-$C_8$ alkenyl, optionally substituted C(O)$NC_2$-$C_8$ alkynyl, optionally substituted $P(O)(OH)_2$, optionally substituted P(O)($OC_1$-$C_8$ alkyl)$_2$, and optionally substituted P(O)($OC_1$-$C_8$ aryl)$_2$; and $R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl; wherein $R^6$ and $R^7$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl; or $R^4$ and $R^5$; $R^6$ and $R^7$ together with the atom to which they are connected form a 4-8 membered cycloalkyl or heterocyclyl ring;

Ar is selected from aryl and heteroaryl, each of which is optionally substituted with one or more substituents independently selected from F, $C_1$, CN, $NO_2$, $OR^8$, $NR^8R^9$, $COR^8$, $CO_2R^8$, $CONR^8R^9$, $SOR^8$, $SO_2R^8$, $SO_2NR^9R^{10}$, $NR^9COR^{10}$, $NR^8C(O)NR^9R^{10}$, $NR^9SOR^{10}$, $NR^9SO_2R^{10}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl; wherein $R^8$, $R^9$, and $R^{10}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl; or $R^8$ and $R^9$; $R^9$ and $R^{10}$ together with the atom to which they are connected form a 4-8 membered cycloalkyl or heterocyclyl ring; and pharmaceutically acceptable salts thereof.

In an embodiment, degradation/disruption tags include a moiety according to FORMULA 14A:

FORMULA 14A

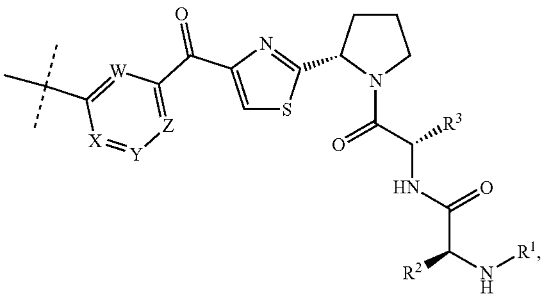

wherein

V, W, X, and Z are independently selected from $CR^4$ and N;

$R^1$, $R^2$, $R^3$, and $R^4$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl.

In an embodiment, degradation/disruption tags include a moiety according to FORMULA 14B:

FORMULA 14B

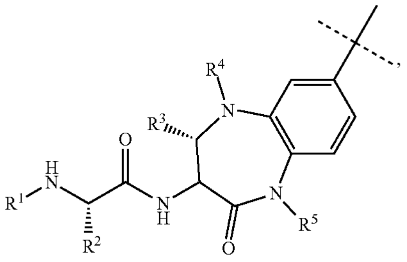

wherein $R^1$, $R^2$, and $R^3$ are independently selected from hydrogen, halogene, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl;

$R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted aryl-$C_1$-$C_8$alkyl, optionally substituted 3-8 membered cycloalkyl, optionally substituted 3-8 membered heterocyclyl, optionally substituted aryl, and optionally substituted heteroaryl; wherein $R^6$ and $R^7$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl; or $R^6$ and $R^7$ together with the atom to which they are connected form a 4-8 membered cycloalkyl or heterocyclyl ring; and pharmaceutically acceptable salts thereof.

In an embodiment, degradation/disruption tags are selected from the group consisting of:

FORMULA 15A

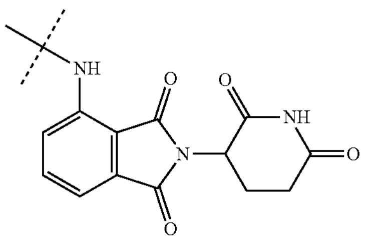

-continued
FORMULA 15B
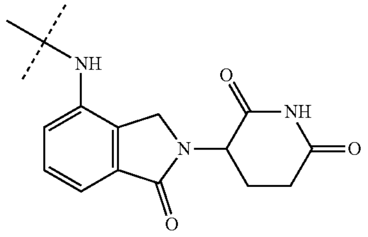
FORMULA 15C
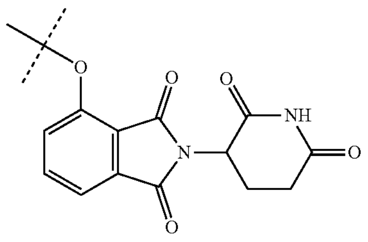
FORMULA 15D
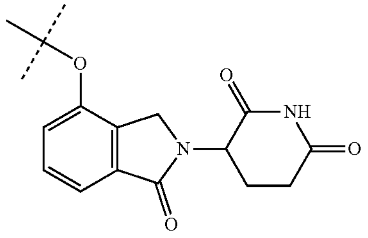
FORMULA 15E
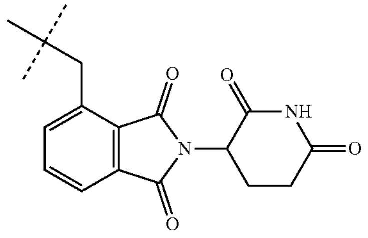
FORMULA 15F
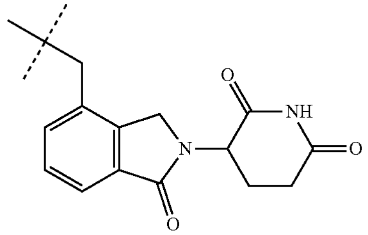
FORMULA 15G
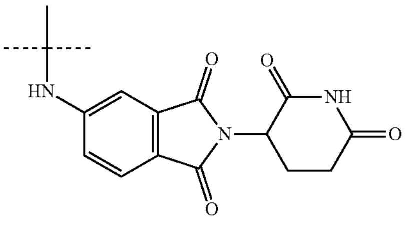
-continued
FORMULA 15H
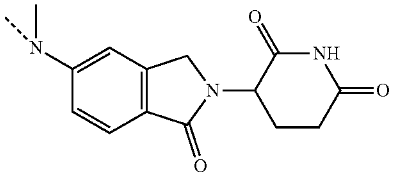
FORMULA 15I
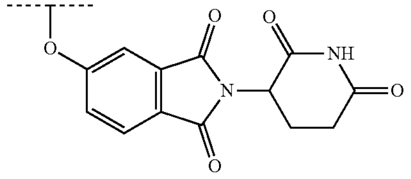
FORMULA 15J
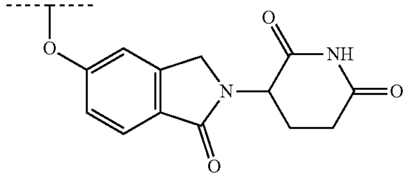
FORMULA 15K
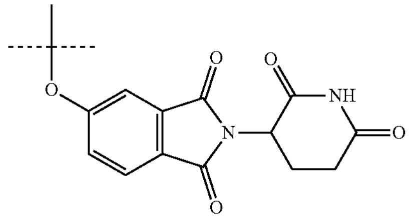
FORMULA 15L
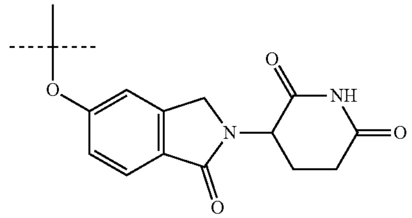
FORMULA 15M
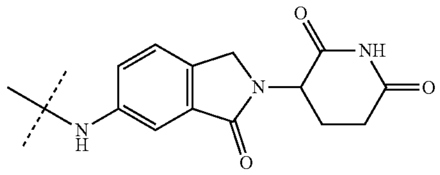
FORMULA 15N
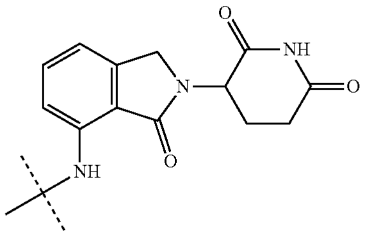

-continued
FORMULA 15O
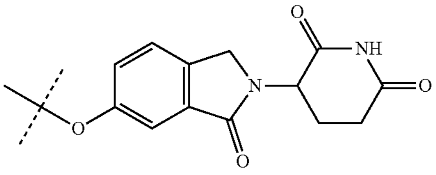
FORMULA 15P
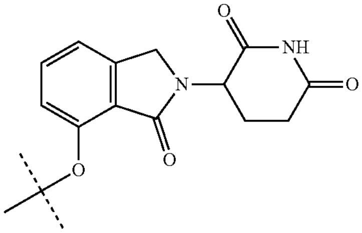
FORMULA 15Q
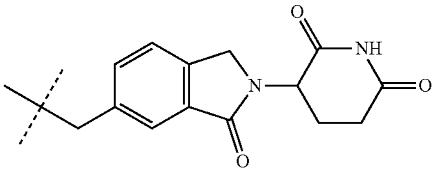
FORMULA 15R
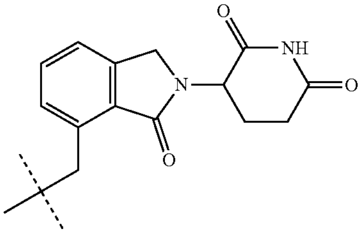
FORMULA 15S
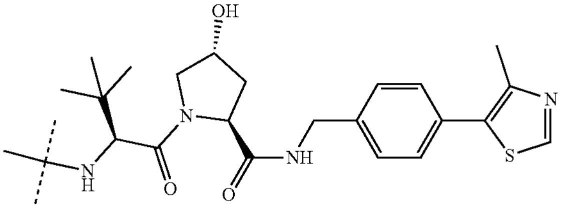
FORMULA 15T
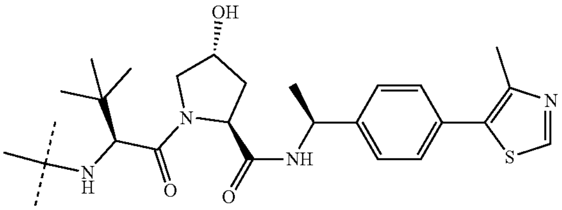
-continued
FORMULA 15U
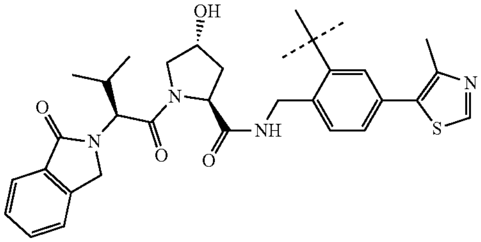
FORMULA 15V
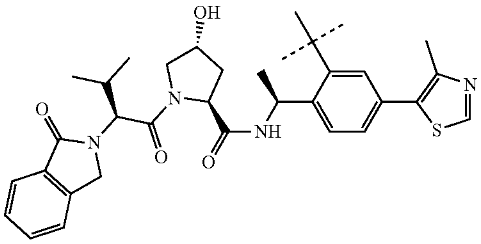
FORMULA 15W
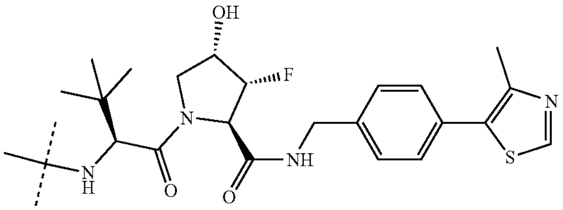
FORMULA 15X
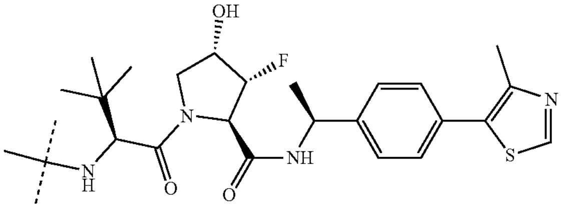
FORMULA 15Y
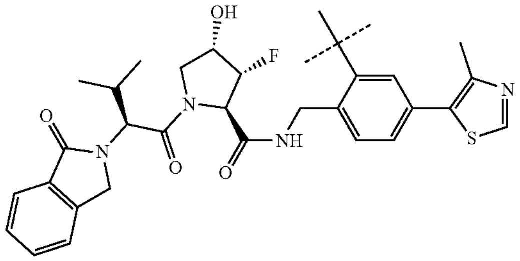
FORMULA 15Z
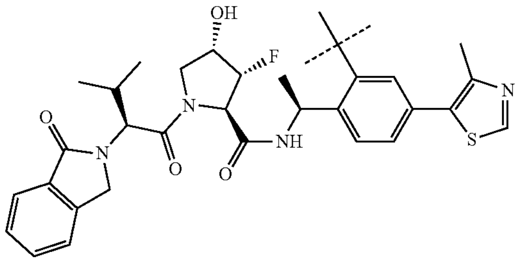

-continued
FORMULA 15AA
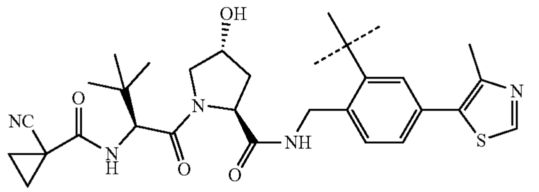
FORMULA 15AB
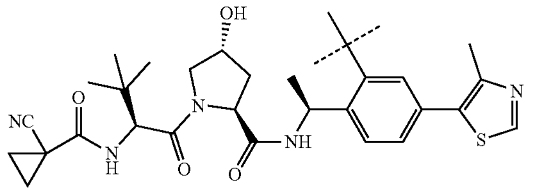
FORMULA 15AC
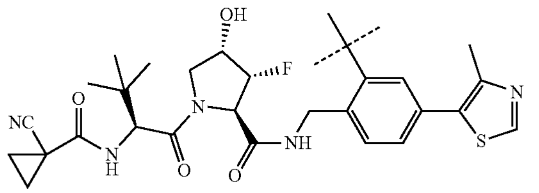
FORMULA 15AD
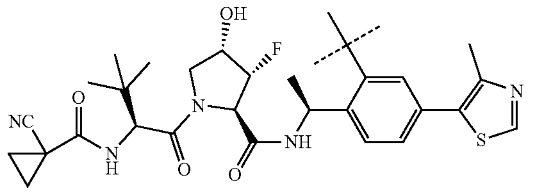
FORMULA 15AE
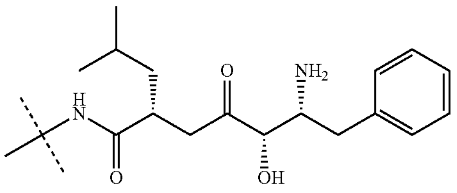
FORMULA 15AF
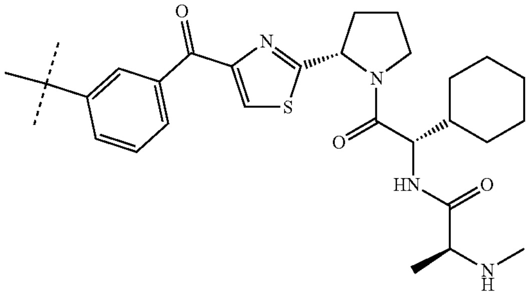
-continued
FORMULA 15AG
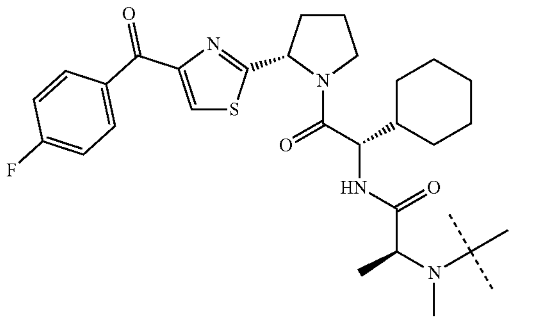
FORMULA 15AH
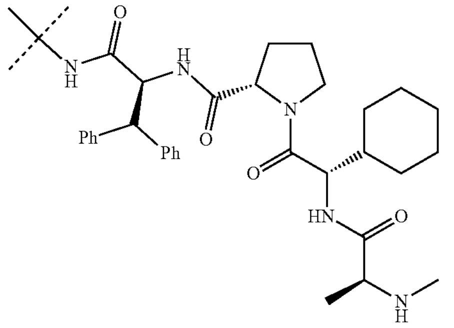
FORMULA 15AI
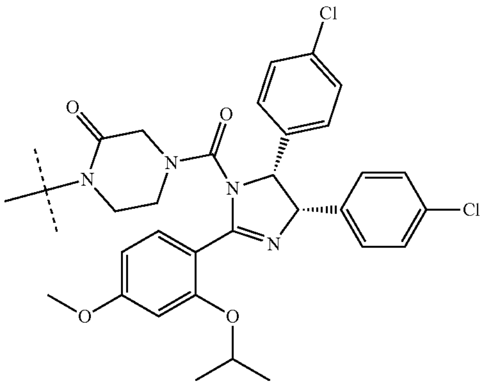
FORMULA 15AJ
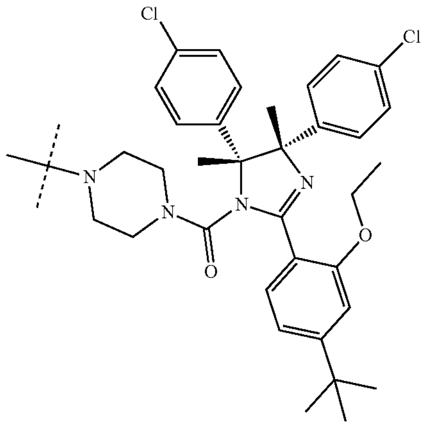

-continued
FORMULA 15AK
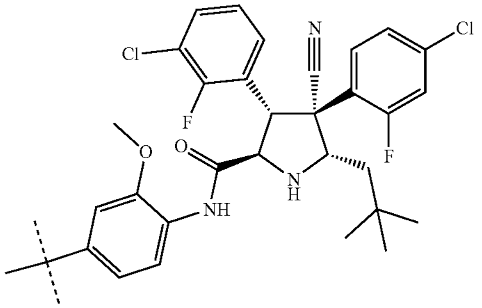
FORMULA 15AL
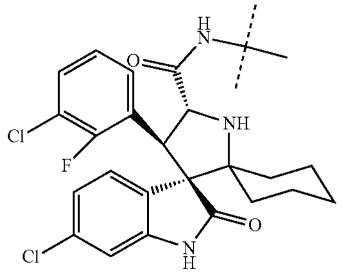
FORMULA 15AM
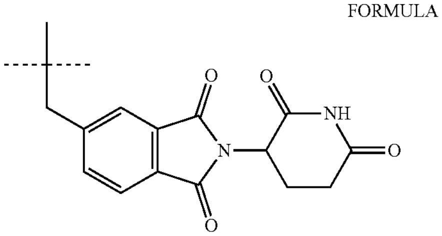
FORMULA 15AN
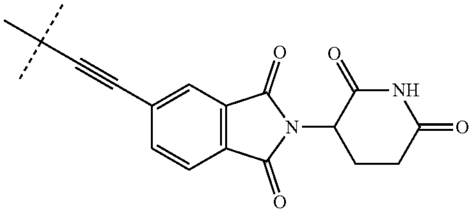
FORMULA 15AO
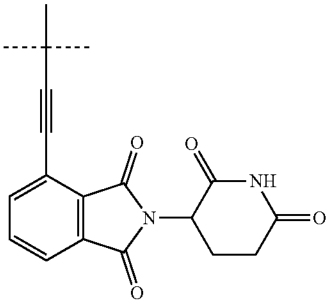
FORMULA 15AP
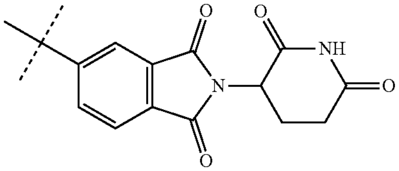
-continued
FORMULA 15AQ
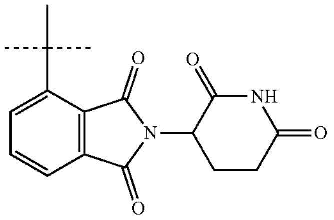
FORMULA 15AR
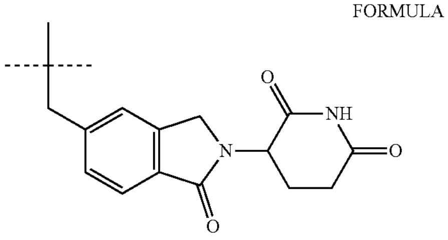
FORMULA 15AS
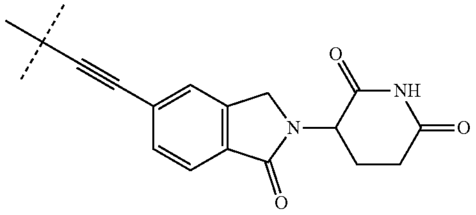
FORMULA 15AT
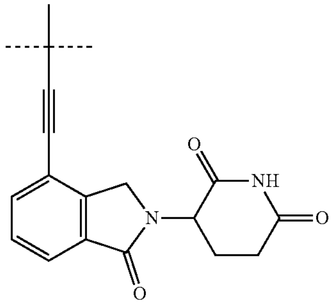
FORMULA 15AU
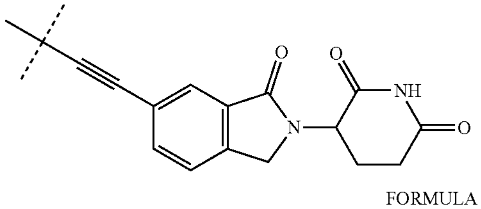
FORMULA 15AV
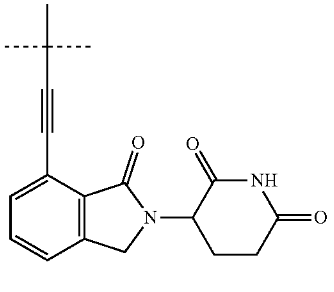

-continued
FORMULA 15AW
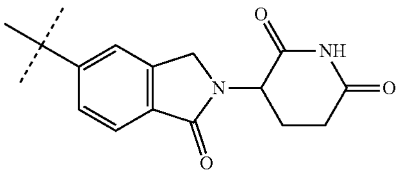
FORMULA 15AX
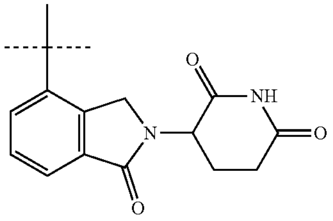
FORMULA 15AY
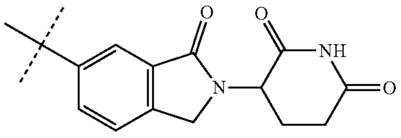
FORMULA 15AZ
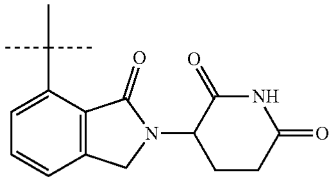
FORMULA 15BA
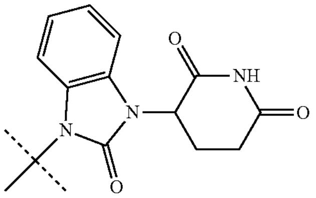
FORMULA 15BB
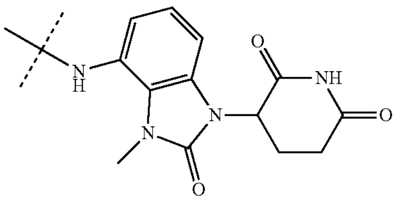
FORMULA 15BC
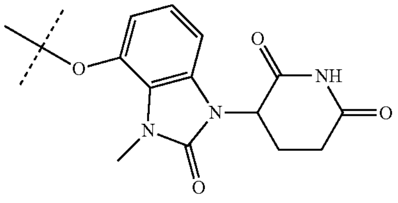
-continued
FORMULA 15BD
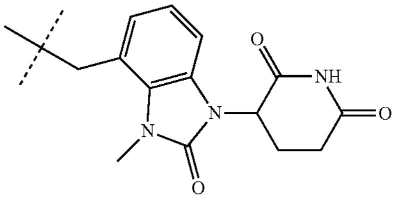
FORMULA 15BE
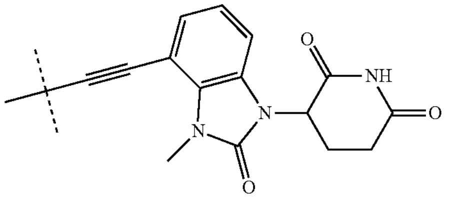
FORMULA 15BF
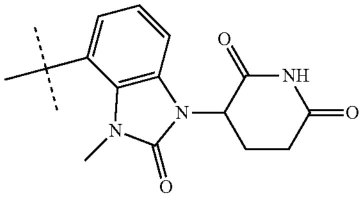
FORMULA 15BG
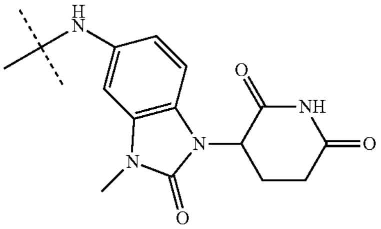
FORMULA 15BH
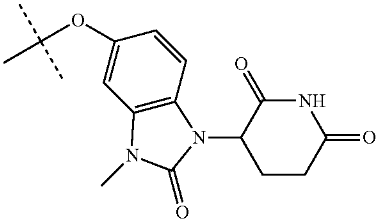
FORMULA 15BI
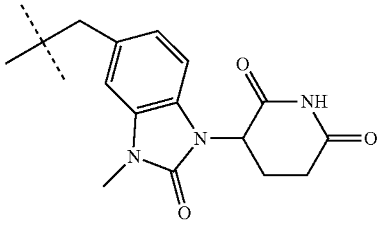

-continued
FORMULA 15BJ
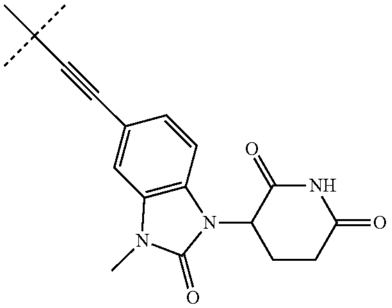
FORMULA 15BK
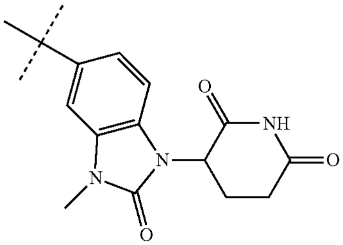
FORMULA 15BL
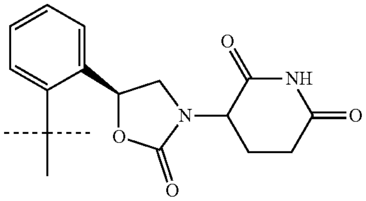
FORMULA 15BM
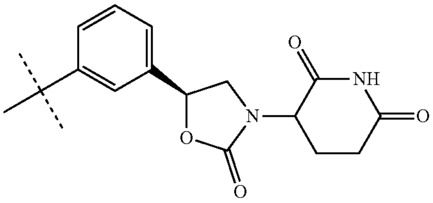
FORMULA 15BN
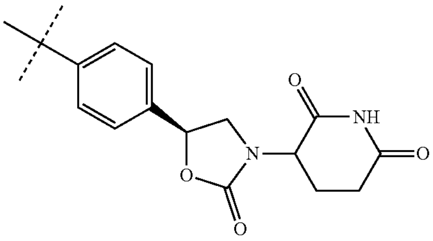
FORMULA 15BO
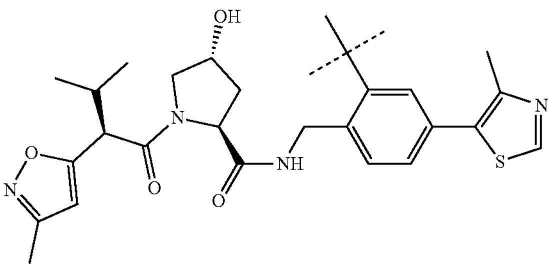
-continued
FORMULA 15BP
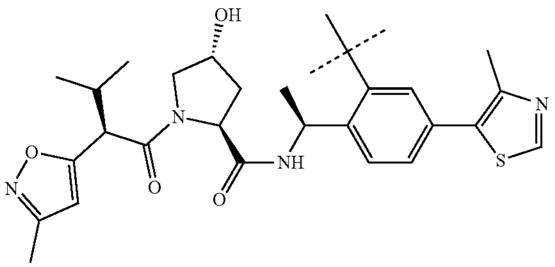
FORMULA 15BQ
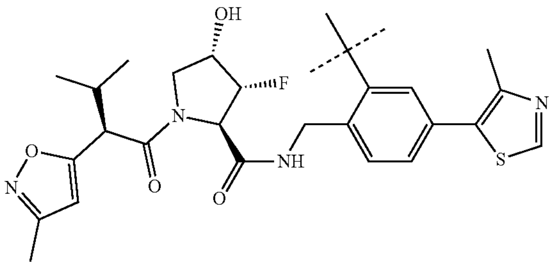
FORMULA 15BR
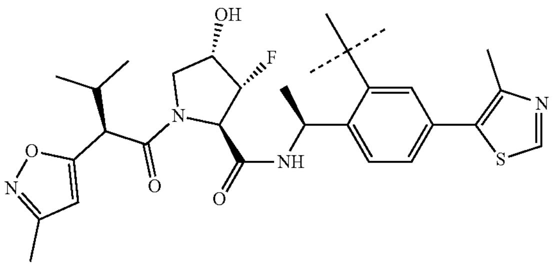
FORMULA 15BS
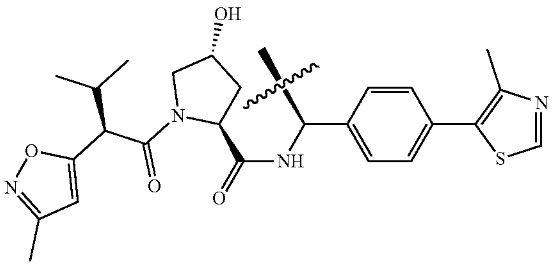
FORMULA 15BT
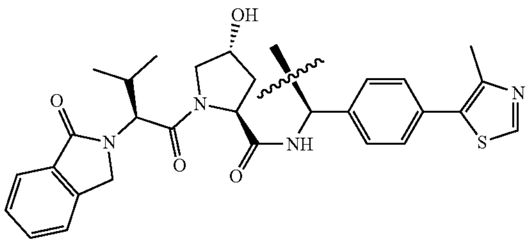
FORMULA 15BU
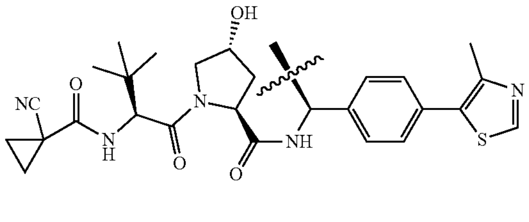

-continued
FORMULA 15BV
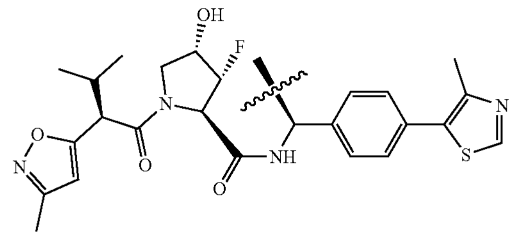
FORMULA 15BW
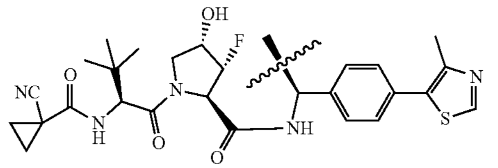
FORMULA 15BX
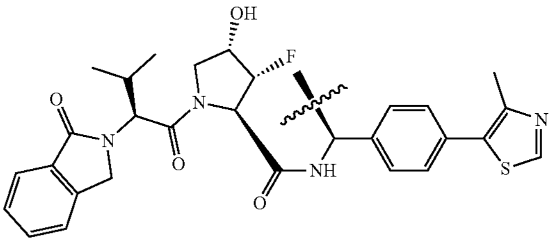
FORMULA 15BY
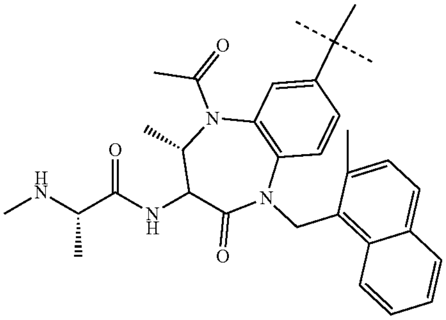
FORMULA 15BZ
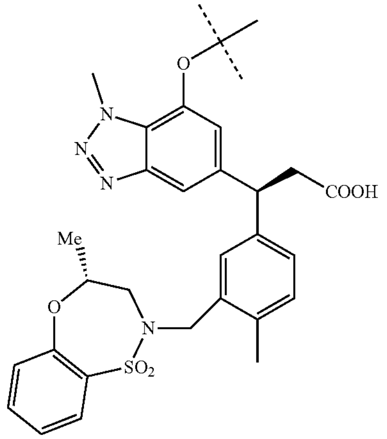
-continued
FORMULA 15CA
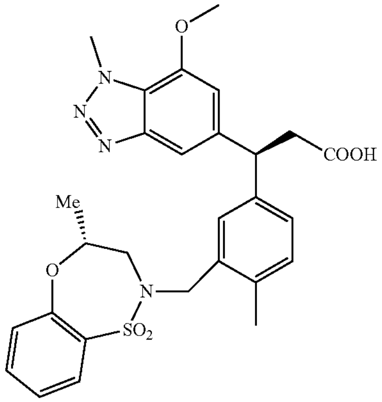
FORMULA 15CB
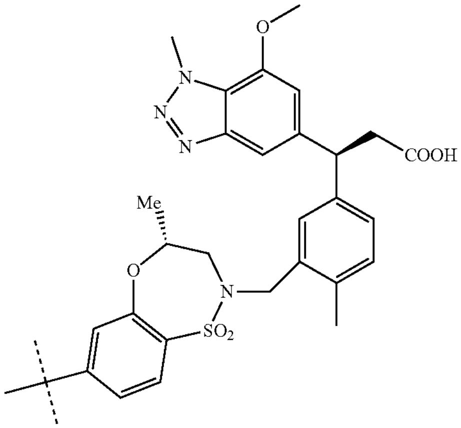
FORMULA 15CC
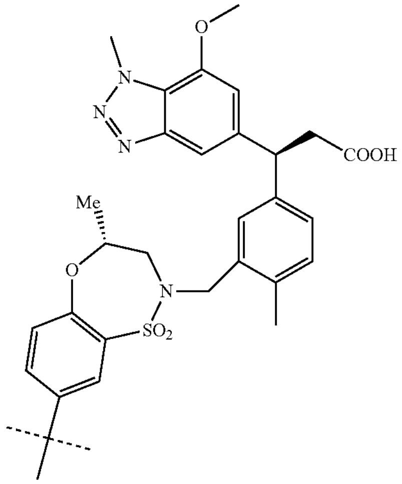

-continued
FORMULA 15CD
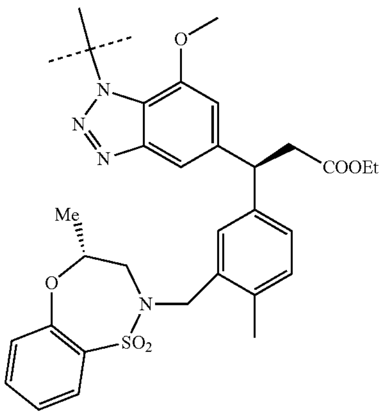
FORMULA 15CE
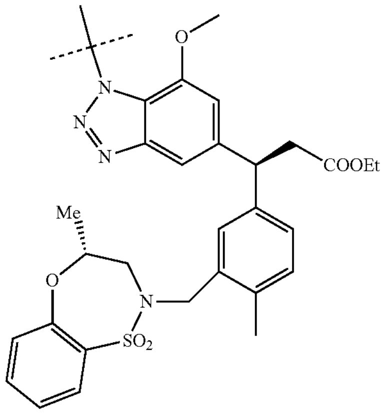
FORMULA 15CF
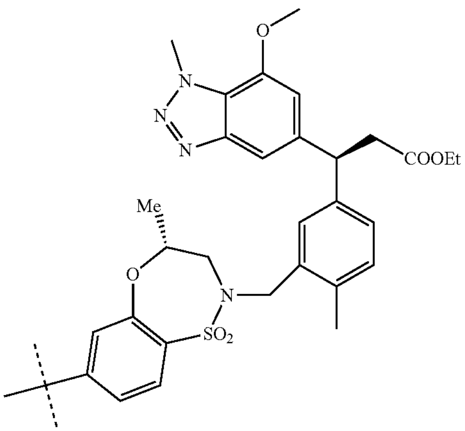
-continued
FORMULA 15CG
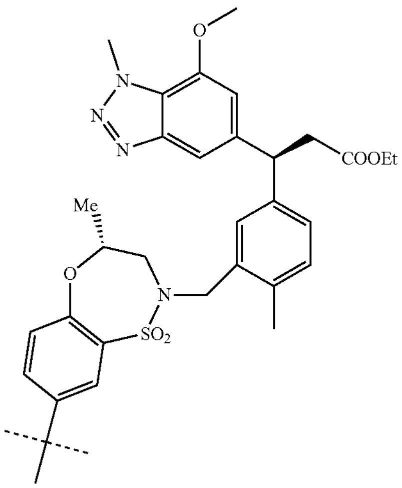
FORMULA 15CH
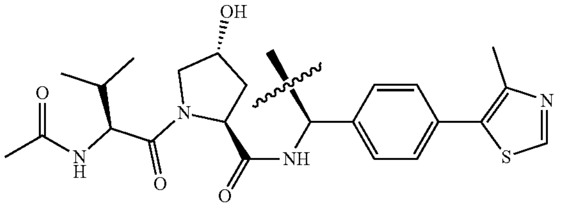
FORMULA 15CI
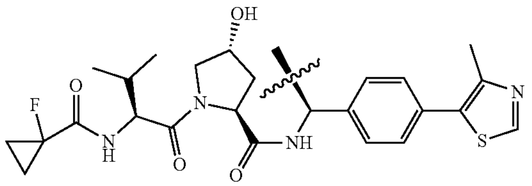
FORMULA 15CJ
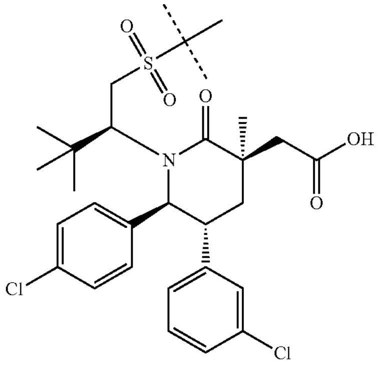

-continued

FORMULA 15CK

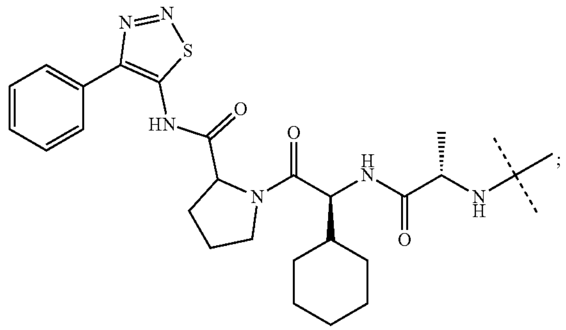

and pharmaceutically acceptable salts thereof.

Linkers

In any of the above-described compounds, the HPK1 ligand can be conjugated to the degradation/disruption tag through a linker. The linker can include, e.g., acyclic or cyclic saturated or unsaturated carbon, ethylene glycol, amide, amino, ether, urea, carbamate, aromatic, heteroaromatic, heterocyclic, and/or carbonyl containing groups with different lengths.

In an embodiment, the linker is a moiety according to FORMULA 16:

FORMULA 16

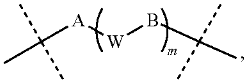

wherein

A, W, and B, at each occurrence, are independently selected from null, CO, $CO_2$, $C(O)NR^1$, $C(S)NR^1$, O, S, SO, $SO_2$, $SO_2NR^1$, $NR^1$, $NR^1CO$, $NR^1CONR^2$, $NR^1C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^1$ and $R^2$ are independently selected from hydrogen, optionally substituted $C_1$-$C_8$ alkyl, optionally substituted $C_3$-$C_8$ cycloalkyl, optionally substituted 3-8 membered cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl; and m is 0 to 15.

In an embodiment, the linker is a moiety according to FORMULA 16A:

FORMULA 16A

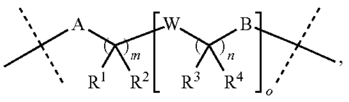

wherein $R^1$, $R^2$, $R^3$, and $R^4$, at each occurrence, are independently selected from hydrogen, halogen, CN, OH, $NH_2$, optionally substituted $C_1$-$C_8$ alkyl, optionally substituted $C_3$-$C_8$ cycloalkyl, optionally substituted $C_3$-$C_8$ cycloalkoxy, optionally substituted 3-8 membered membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

A, W, and B, at each occurrence, are independently selected from null, CO, $CO_2$, $C(O)NR^5$, $C(S)NR^5$, O, S, SO, $SO_2$, $SO_2NR^5$, $NR^5$, $NR^5CO$, $NR^5CONR^6$, $NR^5C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^5$ and $R^6$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$alkylamino$C_1$-$C_8$alkyl;

m is 0 to 15;

n, at each occurrence, is 0 to 15;

o is 0 to 15.

In an embodiment, the linker is a moiety according to FORMULA 16B:

FORMULA 16B

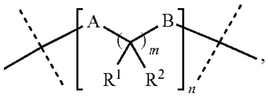

wherein $R^1$ and $R^2$, at each occurrence, are independently selected from hydrogen, halogen, CN, OH, $NH_2$, and optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, or $C_1$-$C_8$alkylamino$C_1$-$C_8$alkyl;

A and B, at each occurrence, are independently selected from null, CO, $CO_2$, C(O)$NR^3$, C(S)$NR^3$, O, S, SO, $SO_2$, $SO_2NR^3$, $NR^3$, $NR^3$CO, $NR^3CONR^4$, $NR^3$C(S), and optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, or $C_3$-$C_{13}$ spiro heterocyclyl; wherein $R^3$ and $R^4$ are independently selected from hydrogen, and optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, or $C_1$-$C_8$alkylamino$C_1$-$C_8$alkyl;

each m is 0 to 15; and n is 0 to 15.

In an embodiment, the linker is a moiety according to FORMULA 16C:

FORMULA 16C

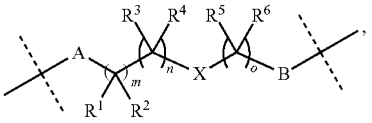

wherein

X is selected from O, NH, and $NR^7$;

$R^1$, $R^2$, $R^3$, $R^4$, $R^5$, and $R^6$, at each occurrence, are independently selected from hydrogen, halogen, CN, OH, $NH_2$, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

A and B, at each occurrence, are independently selected from null, CO, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, —CO—NH, CO—NH— $CH_2$—NH—$CH_2$, $CH_2$—NH—$CH_2$, $CO_2$, C(O)$NR^7$, C(S)$NR^7$, O, S, SO, $SO_2$, $SO_2NR^7$, $NR^7$, $NR^7$CO, $NR^7CONR^8$, $NR^7$C(S), optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted 3-8 membered cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl; wherein $R^7$ and $R^8$ are independently selected from hydrogen, optionally substituted $C_1$-$C_8$ alkyl, optionally substituted 3-8 membered cycloalkyl, optionally substituted $C_3$-$C_8$ cycloalkoxy, optionally substituted 3-8 membered heterocyclyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl;

m, at each occurrence, is 0 to 15;

n, at each occurrence, is 0 to 15;

is 0 to 15; and p is 0 to 15; and pharmaceutically acceptable salts thereof.

In an embodiment, the linker is selected from the group consisting of a ring selected from the group consisting of a 3 to 13 membered ring; a 3 to 13 membered fused ring; a 3 to 13 membered bridged ring; and a 3 to 13 membered spiro ring; and pharmaceutically acceptable salts thereof.

In an embodiment, the linker is a moiety according to one of FORMULAE C1, C2, C3, C4 and C5:

FORMULA C1

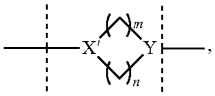

X′ = N or CH
Y′ = N or CH
m = 0-5
n = 0-5

FORMULA C2

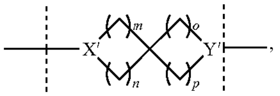

X′ = N or CH
Y′ = N or CH
m = 0-5
n = 0-5
o = 0-5
p = 0-5

-continued

FORMULA C3

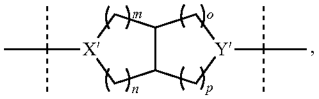,

X' = N or CH
Y' = N or CH
m = 0-5
n = 0-5
o = 0-5
p = 0-5

FORMULA C4

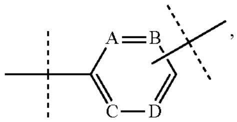, and

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N

FORMULA C5

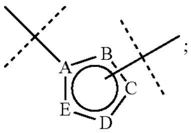;

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3 alkyl), O, S and pharmaceutically acceptable salts thereof.

Synthesis and Testing of Bivalent Compounds

The binding affinity of novel synthesized bivalent compounds (i.e., HPK1 degraders/disruptors) can be assessed using standard biophysical assays known in the art (e.g., isothermal titration calorimetry (ITC)). Cellular assays can then be used to assess the bivalent compound's ability to induce HPK1 degradation and inhibit cancer cell proliferation. Besides evaluating bivalent compound's-induced changes in the protein expression of HPK1, enzymatic activity can also be assessed. Assays suitable for use in any or all of these steps are known in the art, and include, e.g., Western blotting, quantitative mass spectrometry (MS) analysis, flow cytometry, enzymatic inhibition, ITC, SPR, cell growth inhibition and xenograft and PDX models. Suitable cell lines for use in any or all of these steps are known in the art and include, e.g., HPK1-deficient Jurkat clone that had been created by CRISPR-mediated frameshift mutation that resulted in the loss of HPK1 expression in Jurkat T cells. Such line could serve as a platform for counter screening the lead HPK1 degraders/disruptors for non-HPK1-specific effects. By way of non-limiting example, detailed synthesis protocols are described in the Examples for specific exemplary HPK1 degraders/disruptors.

Pharmaceutically acceptable isotopic variations of the compounds disclosed herein are contemplated and can be synthesized using conventional methods known in the art or methods corresponding to those described in the Examples (substituting appropriate reagents with appropriate isotopic variations of those reagents). Specifically, an isotopic variation is a compound in which at least one atom is replaced by an atom having the same atomic number, but an atomic mass different from the atomic mass usually found in nature. Useful isotopes are known in the art and include, for example, isotopes of hydrogen, carbon, nitrogen, oxygen, phosphorus, sulfur, fluorine, and chlorine. Exemplary isotopes thus include, e.g., $^{2}H$, $^{3}H$, C, $^{14}C$, $^{15}N$, $^{17}O$, $^{18}O$, $^{32}P$, $^{35}S$, $^{18}F$, and $^{36}Cl$.

Isotopic variations (e.g., isotopic variations containing $^{2}H$) can provide therapeutic advantages resulting from greater metabolic stability, e.g., increased in vivo half-life or reduced dosage requirements. In addition, certain isotopic variations (particularly those containing a radioactive isotope) can be used in drug or substrate tissue distribution studies. The radioactive isotopes tritium ($^{3}H$) and carbon-14 ($^{14}C$) are particularly useful for this purpose in view of their ease of incorporation and ready means of detection.

Pharmaceutically acceptable solvates of the compounds disclosed herein are contemplated. A solvate can be generated, e.g., by substituting a solvent used to crystallize a compound disclosed herein with an isotopic variation (e.g., $D_2O$ in place of $H_2O$, $d_6$-acetone in place of acetone, or $d_6$-DMSO in place of DMSO).

Pharmaceutically acceptable fluorinated variations of the compounds disclosed herein are contemplated and can be synthesized using conventional methods known in the art or methods corresponding to those described in the Examples (substituting appropriate reagents with appropriate fluorinated variations of those reagents). Specifically, a fluorinated variation is a compound in which at least one hydrogen atom is replaced by a fluoro atom. Fluorinated variations can provide therapeutic advantages resulting from greater metabolic stability, e.g., increased in vivo half-life or reduced dosage requirements Characterization of Exemplary HPK1 Degraders/Disruptors Specific exemplary HPK1 degraders/disruptors were characterized using (FIGS. 1-14). HC58-38, HC58-75, HC58-76, HC58-78, HC90-50, and HC90-51 in particular were found to be especially effective in reducing HPK1 protein levels.

Definition of Terms

As used herein, the terms "comprising" and "including" are used in their open, non-limiting sense.

"Alkyl" refers to a straight or branched hydrocarbon chain radical consisting solely of carbon and hydrogen atoms, containing no unsaturation. An alkyl may comprise one, two, three, four, five, six, seven, eight, nine, ten, eleven, twelve, thirteen, fourteen, fifteen, or sixteen carbon atoms. In certain embodiments, an alkyl comprises one to fifteen carbon atoms (e.g., $C_1$-$C_{15}$ alkyl).

In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), pentyl, 3-methylhexyl, 2-methylhexyl, and the like.

"Alkenyl" refers to a straight or branched hydrocarbon chain radical group consisting solely of carbon and hydrogen atoms, containing at least one double bond. An alkenyl may comprise two, three, four, five, six, seven, eight, nine, ten, eleven, twelve, thirteen, fourteen, fifteen, or sixteen carbon atoms. In certain embodiments, an alkenyl comprises two to twelve carbon atoms (e.g., $C_2$-$C_{12}$ alkenyl). In certain embodiments, an alkenyl comprises two to eight carbon atoms (e.g., $C_2$-$C_8$ alkenyl). In certain embodiments, an alkenyl comprises two to six carbon atoms (e.g., $C_2$-$C_6$ alkenyl). In other embodiments, an alkenyl comprises two to four carbon atoms (e.g., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "allyl," as used herein, means a $—CH_2CH═CH_2$ group.

As used herein, the term "alkynyl" refers to a straight or branched hydrocarbon chain radical group consisting solely of carbon and hydrogen atoms, containing at least one triple bond. An alkynyl may comprise two, three, four, five, six, seven, eight, nine, ten, eleven, twelve, thirteen, fourteen, fifteen, or sixteen carbon atoms. In certain embodiments, an alkynyl comprises two to twelve carbon atoms (e.g., $C_2$-$C_{12}$ alkynyl). In certain embodiments, an alkynyl comprises two to eight carbon atoms (e.g., $C_2$-$C_8$ alkynyl). In other embodiments, an alkynyl has two to six carbon atoms (e.g., $C_2$-$C_6$ alkynyl). In other embodiments, an alkynyl has two to four carbon atoms (e.g., $C_2$-$C_4$ alkynyl). The alkynyl is attached to the rest of the molecule by a single bond. Examples of such groups include, but are not limited to, ethynyl, propynyl, 1-butynyl, 2-butynyl, 1-pentynyl, 2-pentynyl, 1-hexynyl, 2-hexynyl, 3-hexynyl, and the like.

The term "alkoxy", as used herein, means an alkyl group as defined herein witch is attached to the rest of the molecule via an oxygen atom. Examples of such groups include, but are not limited to, methoxy, ethoxy, n-propyloxy, iso-propyloxy, n-butoxy, iso-butoxy, tert-butoxy, pentyloxy, hexyloxy, and the like.

The term "aryl", as used herein, "refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms. An aryl may comprise from six to eighteen carbon atoms, where at least one of the rings in the ring system is fully unsaturated, i.e., it contains a cyclic, delocalized $(4n+2)\pi$-electron system in accordance with the Hückel theory. In certain embodiments, an aryl comprises six to fourteen carbon atoms ($C_6$-$C_{14}$ aryl). In certain embodiments, an aryl comprises six to ten carbon atoms ($C_6$-$C_{10}$ aryl). Examples of such groups include, but are not limited to, phenyl, fluorenyl and naphthyl. The terms "Ph" and "phenyl," as used herein, mean a $—C_6H_5$ group.

The term "heteroaryl", refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized $(4n+2)\pi$-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of such groups include, but not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. In certain embodiments, an heteroaryl is attached to the rest of the molecule via a ring carbon atom. In certain embodiments, an heteroaryl is attached to the rest of the molecule via a nitrogen atom (N-attached) or a carbon atom (C-attached). For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "heterocyclyl", as used herein, means a non-aromatic, monocyclic, bicyclic, tricyclic, or tetracyclic radical having a total of from 4, 5, 6, 7, 8, 9, 10, 11, 12, or 13 atoms in its ring system, and containing from 3 to 12 carbon atoms and from 1 to 4 heteroatoms each independently selected from O, S and N, and with the proviso that the ring of said group does not contain two adjacent O atoms or two adjacent S atoms. A heterocyclyl group may include fused, bridged or spirocyclic ring systems. In certain embodiments, a hetercyclyl group comprises 3 to 10 ring atoms (3-10 membered heterocyclyl). In certain embodiments, a hetercyclyl group comprises 3 to 8 ring atoms (3-8 membered heterocyclyl). In certain embodiments, a hetercyclyl group comprises 4 to 8 ring atoms (4-8 membered heterocyclyl). In certain embodiments, a hetercyclyl group comprises 3 to 6 ring atoms (3-6 membered heterocyclyl). A heterocyclyl group may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocyclyl group contains a sulfur atom, said sulfur atom may be oxidized with one or two oxygen atoms to afford either a sulfoxide or sulfone. An example of a 4 membered heterocyclyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such heterocyclyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. A heteroaryl group may be attached to the rest of molecular via a carbon atom (C-attached) or a nitrogen atom (N-attached). For instance, a group derived from piperazine may be piperazin-1-yl (N-attached) or piperazin-2-yl (C-attached).

The term "cycloalkyl" means a saturated, monocyclic, bicyclic, tricyclic, or tetracyclic radical having a total of from 4, 5, 6, 7, 8, 9, 10, 11, 12, or 13 carbon atoms in its ring system. A cycloalkyl may be fused, bridged or spirocyclic. In certain embodiments, a cycloalkyl comprises 3 to 8 carbon ring atoms ($C_3$-$C_8$ cycloalkyl). In certain embodiments, a cycloalkyl comprises 3 to 6 carbon ring atoms ($C_3$-$C_6$ cycloalkyl). Examples of such groups include, but are not limited to, cyclopropyl, cyclobutyl, cyclopentyl, cyclopentenyl, cyclohexyl, cycloheptyl, adamantyl, and the like.

The term "cycloalkylene" is a bidentate radical obtained by removing a hydrogen atom from a cycloalkyl ring as defined above. Examples of such groups include, but are not limited to, cyclopropylene, cyclobutylene, cyclopentylene, cyclopentenylene, cyclohexylene, cycloheptylene, and the like.

The term "spirocyclic" as used herein has its conventional meaning, that is, any ring system containing two or more rings wherein two of the rings have one ring carbon in common. Each ring of the spirocyclic ring system, as herein defined, independently comprises 3 to 20 ring atoms. Preferably, they have 3 to 10 ring atoms. Non-limiting examples of a spirocyclic system include spiro[3.3]heptane, spiro[3.4]octane, and spiro[4.5]decane.

The term cyano" refers to a —C≡N group.

An "aldehyde" group refers to a —C(O)H group.

An "alkoxy" group refers to both an —O-alkyl, as defined herein.

An "alkoxycarbonyl" refers to a —C(O)-alkoxy, as defined herein.

An "alkylaminoalkyl" group refers to an -alkyl-NR-alkyl group, as defined herein.

An "alkylsulfonyl" group refer to a —$SO_2$alkyl, as defined herein.

An "amino" group refers to an optionally substituted —$NH_2$.

An "aminoalkyl" group refers to an -alky-amino group, as defined herein.

An "aminocarbonyl" refers to a —C(O)-amino, as defined herein.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)-aryloxy, as defined herein.

An "arylsulfonyl" group refers to a —$SO_2$aryl, as defined herein.

A "carbonyl" group refers to a —C(O)— group, as defined herein.

A "carboxylic acid" group refers to a —C(O)OH group.

A "cycloalkoxy" refers to a —O-cycloalkyl group, as defined herein.

A "halo" or "halogen" group refers to fluorine, chlorine, bromine or iodine.

A "haloalkyl" group refers to an alkyl group substituted with one or more halogen atoms.

A "hydroxy" group refers to an —OH group.

A "nitro" group refers to a —$NO_2$ group.

An "oxo" group refers to the =O substituent.

A "trihalomethyl" group refers to a methyl substituted with three halogen atoms.

The term "substituted," means that the specified group or moiety bears one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —$CO_2$H, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

The term "optionally substituted" means that the specified group may be either unsubstituted or substituted by one or more substituents as defined herein. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one at which the remainder of the compound of the present invention is attached to and an additional substituent, remaining 4 positions open). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

"Pharmaceutically acceptable salt" includes both acid and base addition salts. A pharmaceutically acceptable salt of any one of the bivalent compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety).

Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Pharmaceutical Compositions

In some aspects, the compositions and methods described herein include the manufacture and use of pharmaceutical compositions and medicaments that include one or more bivalent compounds as disclosed herein. Also included are the pharmaceutical compositions themselves.

In some aspects, the compositions disclosed herein can include other compounds, drugs, or agents used for the treatment of cancer. For example, in some instances, pharmaceutical compositions disclosed herein can be combined with one or more (e.g., one, two, three, four, five, or less than ten) compounds. Such additional compounds can include, e.g., conventional chemotherapeutic agents known in the art. When co-administered, HPK1 degraders/disruptors disclosed herein can operate in conjunction with conventional chemotherapeutic agents to produce mechanistically additive or synergistic therapeutic effects.

In some aspects, the pH of the compositions disclosed herein can be adjusted with pharmaceutically acceptable acids, bases, or buffers to enhance the stability of the HPK1 degraders/disruptor or its delivery form.

Pharmaceutical compositions typically include a pharmaceutically acceptable carrier, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable carrier, adjuvant, or vehicle is a composition that can be administered to a patient, together with a compound of the invention, and which does not destroy the pharmacological activity thereof and is nontoxic when administered in doses sufficient to deliver a therapeutic amount of the compound. Exemplary conventional nontoxic pharmaceutically acceptable carriers, adjuvants, and vehicles include saline, solvents, dispersion media, coatings, antibacterial and antifungal agents, isotonic and absorption delaying agents, and the like, compatible with pharmaceutical administration.

In particular, pharmaceutically acceptable carriers, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

As used herein, the HPK1 degraders/disruptors disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, $5^{th}$ Edition, Vol. 1: Principles and Practice, which is incorporated herein by reference to the extent of teaching such derivatives.

The HPK1 degraders/disruptors disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivative thereof.

In particular, pharmaceutically acceptable salts of the HPK1 degraders/disruptors disclosed herein include, e.g., those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, e.g., HPK1 alkali metal (e.g., sodium), HPK1 alkaline earth metal (e.g., magnesium), ammonium and N-(HPK1yl)4+ salts. The invention also envisions the quaternization of any basic nitrogen-containing groups of the HPK1 degraders/disruptors disclosed herein. Water or oil-soluble or dispersible products can be obtained by such quaternization.

In some aspects, the pharmaceutical compositions disclosed herein can include an effective amount of one or more HPK1 degraders/disruptors. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer). In some aspects, pharmaceutical compositions can further include one or more additional compounds, drugs, or agents used for the treatment of cancer (e.g., conventional chemotherapeutic agents) in amounts effective for causing an intended effect or physiological outcome (e.g., treatment or prevention of cell growth, cell proliferation, or cancer).

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/Forms-SubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, e.g., topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, e.g., as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. Fatty acids, such as oleic acid and its glyceride derivatives are useful in the preparation of injectables, as are natural pharmaceutically-acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of a compound of the formulae described herein (e.g., a HPK1 degraders/disruptors) and one or more additional compounds (e.g., one or more additional compounds, drugs, or agents used for the treatment of cancer or any other condition or disease, including conditions or diseases known to be associated with or caused by cancer), both the compound and the additional compound should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, the present disclosure provides methods for using a composition comprising a HPK1 degrader/disruptor, including pharmaceutical compositions (indicated below as 'X') disclosed herein in the following methods: Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of cancer.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition from which the subject is suffering (e.g., an HPK1-mediated cancer). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the compositions and methods of the present invention. In some aspects, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

As used herein, the term "treating cancer" means causing a partial or complete decrease in the rate of growth of a tumor, and/or in the size of the tumor and/or in the rate of local or distant tumor metastasis, and/or the overall tumor burden in a subject, and/or any decrease in tumor survival, in the presence of a degrader/disruptor (e.g., an HPK1 degrader/disruptor) described herein.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention.

Exemplary type of cancers that could be prevented, or therapeutically treated by manipulation of HPK1 level by degraders/disruptors should include all solid and liquid cancers, including, but not limited to, cancers of the breast, respiratory tract, brain, reproductive organs, digestive tract, urinary tract, eye, liver, skin, head and neck, thyroid, parathyroid and their distant metastases. Examples of liquid cancers include lymphomas, sarcomas, and leukaemias.

Listed below are the type of cancers that immunotherapy using HPK1 degraders/disruptors should be able to prevent or treat.

Examples of breast cancers include, but are not limited to, triple negative breast cancer, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to, prostate and testicular cancer.

Tumors of the female reproductive organs include, but are not limited to, endometrial, cervical, ovarian, vaginal, and vulvar cancer, as well as sarcoma of the uterus.

Examples of ovarian cancer include, but are not limited to, serous tumor, endometrioid tumor, mucinous cystadenocarcinoma, granulosa cell tumor, Sertoli-Leydig cell tumor and arrhenoblastoma.

Examples of cervical cancer include, but are not limited to, squamous cell carcinoma, adenocarcinoma, adenosquamous carcinoma, small cell carcinoma, neuroendocrine tumor, glassy cell carcinoma and villoglandular adenocarcinoma. Tumors of the digestive tract include, but are not limited to, anal, colon, colorectal, esophageal, gallbladder, gastric, pancreatic, rectal, small-intestine, and salivary gland cancers.

Examples of esophageal cancer include, but are not limited to, esophageal cell carcinomas and adenocarcinomas, as well as squamous cell carcinomas, leiomyosarcoma, malignant melanoma, rhabdomyosarcoma and lymphoma.

Examples of gastric cancer include, but are not limited to, intestinal type and diffuse type gastric adenocarcinoma.

Examples of pancreatic cancer include, but are not limited to, ductal adenocarcinoma, adenosquamous carcinomas and pancreatic endocrine tumors.

Example of tumors of the urinary tract include, but are not limited to, bladder, penile, kidney, renal pelvis, ureter, urethral and human papillary renal cancers.

Examples of kidney cancer include, but are not limited to, renal cell carcinoma, urothelial cell carcinoma, juxtaglomerular cell tumor (reninoma), angiomyolipoma, renal oncocytoma, Bellini duct carcinoma, clear-cell sarcoma of the kidney, mesoblastic nephroma and Wilms' tumor.

Examples of bladder cancer include, but are not limited to, transitional cell carcinoma, squamous cell carcinoma, adenocarcinoma, sarcoma and small cell carcinoma. Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Example of skin cancers include, but are not limited to, squamous cell carcinoma, Kaposi's sarcoma, malignant melanoma, Merkel cell skin cancer, and non-melanoma skin cancer.

Example of head-and-neck cancers include, but are not limited to, squamous cell cancer of the head and neck, laryngeal, hypopharyngeal, nasopharyngeal, oropharyngeal cancer, salivary gland cancer, lip and oral cavity cancer and squamous cell.

Example of lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Example of sarcomas include, but are not limited to, sarcoma of the soft tissue, osteosarcoma, malignant fibrous histiocytoma, lymphosarcoma, and rhabdomyosarcoma.

Example of leukemias include, but are not limited to, acute myeloid leukemia, acute lymphoblastic leukemia, chronic lymphocytic leukemia, chronic myelogenous leukemia, and hairy cell leukemia.

The HPK1 degraders/disruptors should be able to treat the above cancer type as stand alone agent or used as agent in combination with existing standard of treatment therapy and other FDA-approved cancer therapy.

Therapeutic uses of HPK1 include diseases and therapies that are amenable to treatment by stimulation/augmentation of immune response, including the prolongation of immune responses during vaccination for immunizable diseases. Also, because HPK1 is expressed at high level in two other anatomical locations—brain and testes—the HPK1 degraers/disruptors should be able to treat or prevent diseases related to brain and testes that were caused by HPK1 or could be treated by HPK1 degraders/disruptors. These potential diseases include, but is not limited to, Alzheimer's disease, age-related dementia and infertility, regarless whether these possible diseases were caused by HPK1 or by other eithiological causes.

As used herein, the term "preventing a disease" (e.g., preventing cancer) in a subject means for example, to stop the development of one or more symptoms of a disease in a subject before they occur or are detectable, e.g., by the patient or the patient's doctor. A blood test that measure the level of HPK1 in each of the immune cell sub-types, which could be achieved by intracellular staining by anti-HPK1 antibody and analyze by clinical FACS analysis. Such detection method could identify immune cell type possess aberrant level of HPK1 and may signify that such patient might be a good candidate for HPK1 degraders/disruptors-based therapy. This detection of aberrant expression level of HPK1 may be an early warning biomarker that may indicate which patient may respond well to their disease conditions if HPK1 degraders/disruptors were to used as stand alone or as part of combination therapy. Preferably, the disease (e.g., cancer) does not develop at all, i.e., no symptoms of the disease are detectable. However, it can also mean delaying or slowing of the development of one or more symptoms of the disease. Alternatively, or in addition, it can mean decreasing the severity of one or more subsequently developed symptoms.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

The HPK1 degraders/disruptors disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated and fluoro derivatives thereof.

EXAMPLES

The following Examples describe the synthesis of exemplary HPK1 degrader/disrupter compounds according to the present invention.

Examples

Example 1: Synthesis of Intermediate 2

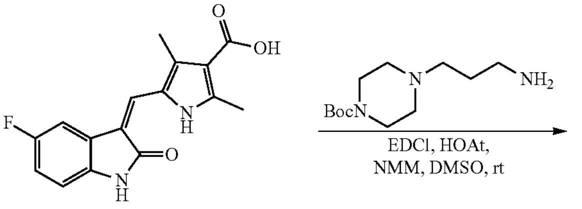

Intermediate 1

-continued

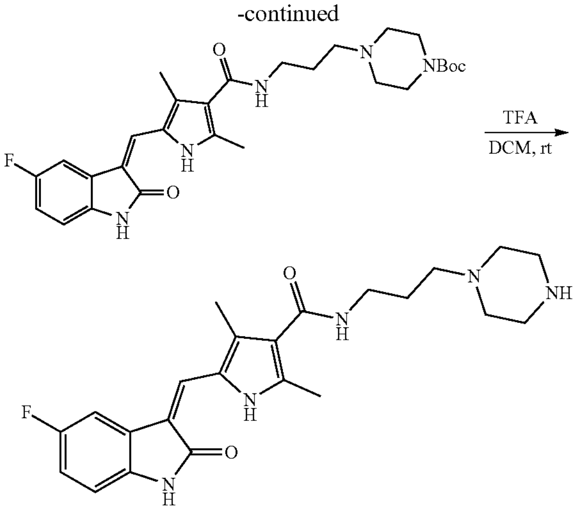

Intermediate 2

To a solution of Intermediate 1 (926 mg, 3.09 mmol) in DMSO (20 mL) were added tert-butyl 4-(3-aminopropyl) piperazine-1-carboxylate (899 mg, 3.70 mmol, 1.2 equiv), EDCI (1-ethyl-3-(3-dimethylaminopropyl)carbodiimide) (888 mg, 4.63 mmol, 1.5 equiv), HOAt (1-hydroxy-7-azabenzo-triazole) (630 mg, 4.63 mmol, 1.5 equiv), and NMM (N-Methylmorpholine) (625 mg, 6.18 mmol, 2.0 equiv). After being stirred overnight at room temperature, $H_2O$ (100 mL) was added to the solution and precipitates was filtered. The solid was washed with water and dried under vacuum. The obtained solid was dissolved in DCM (10 mL). To the resulting solution was added TFA (5 ml). After being stirred for 1 h at room temperature, the reaction mixture was concentrated and the residue was purified by reverse phase $C_{18}$ column (10%-100% methanol/0.1% TFA in $H_2O$) to afford intermediate 2 as yellow solid in TFA salt form (1.117 g, 55% yield for two step). $^1H$ NMR (600 MHz, DMSO-$d_6$) δ 13.72 (s, 1H), 10.93 (s, 1H), 7.80-7.75 (m, 2H), 7.73 (s, 1H), 6.94 (td, J=9.1, 2.6 Hz, 1H), 6.86 (dd, J=8.5, 4.5 Hz, 1H), 3.41-3.25 (m, 8H), 3.13-2.97 (m, 4H), 2.45 (s, 3H), 2.43 (s, 3H), 1.93-1.81 (m, 2H). ESI m/z=426.2 $[M+H^+]$.

Example 2

Synthesis of HC58-18

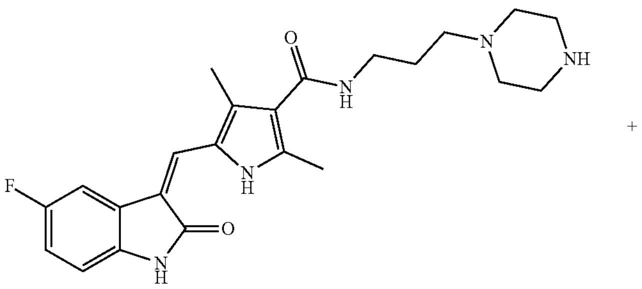

Intermediate 2

-continued

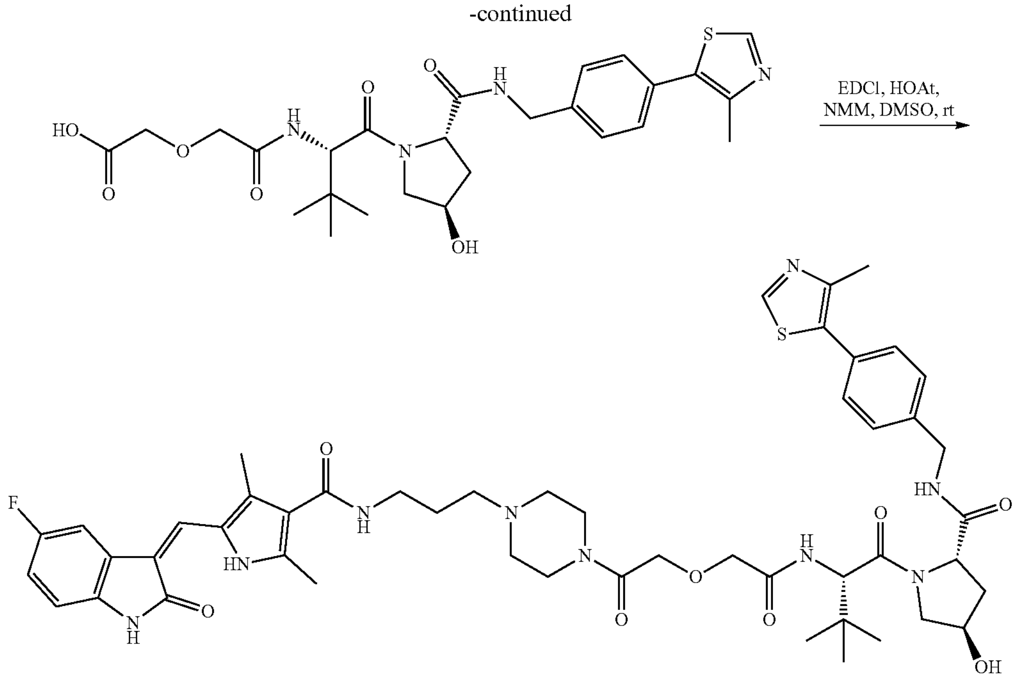

HC58-18

To a solution of Intermediate 2 (13.0 mg, 0.024 mmol, 1.2 equiv) in DMSO (1 mL) were added 2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetic acid (11 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirred overnight at room temperature, the resulting mixture was purified by preparative HPLC (10%-100% methanol/0.1% TFA in $H_2O$) to afford HC58-18 as white solid in TFA salt form (15.0 mg, 70%). $^1H$ NMR (600 MHz, Methanol-d4) δ 13.70 (s, 1H), 8.92 (s, 1H), 7.58 (s, 1H), 7.48-7.40 (m, 5H), 6.94-6.82 (m, 2H), 4.70 (s, 1H), 4.62-4.57 (m, 1H), 4.55-4.34 (m, 5H), 4.19 (d, J=15.1 Hz, 1H), 4.11 (d, J=15.0 Hz, 1H), 3.92 (d, J=11.0 Hz, 1H), 3.83 (dd, J=11.0, 3.8 Hz, 1H), 3.70-3.46 (m, 6H), 3.31-3.01 (m, 6H), 2.51 (s, 3H), 2.48 (s, 3H), 2.47 (s, 3H), 2.26 (dd, J=13.3, 7.7 Hz, 1H), 2.15-2.02 (m, 3H), 1.08 (s, 9H). HRMS calcd for $C_{49}H_{61}FN_9O_8S$ [M+H$^+$] 954.4348, found 954.4363.

Example 3

Synthesis of HC58-19

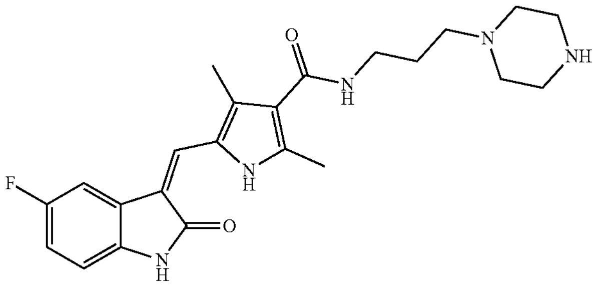

Intermediate 2

+

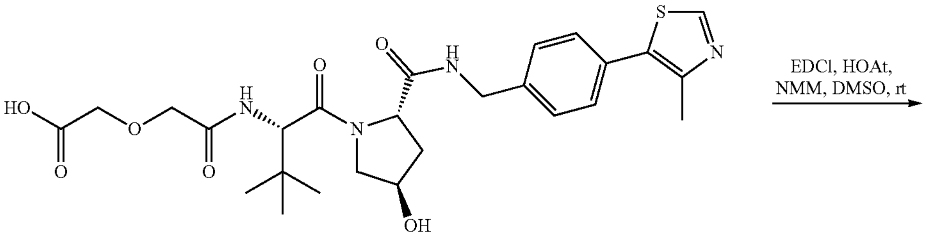

-continued

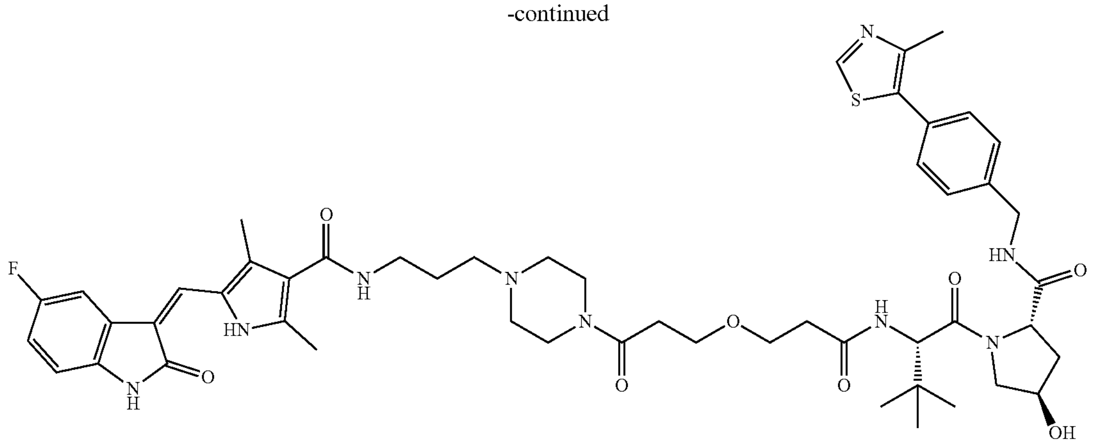

HC58-19

HC58-19 was synthesized following the standard procedure for preparing HC58-18 from Intermediate 2 (13.0 mg, 0.024 mmol, 1.2 equiv), 3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoic acid (11.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-19 was obtained as yellow solid in TFA salt form (13.8 mg, 63%). $^1H$ NMR (600 MHz, Methanol-d4) δ 13.69 (s, 1H), 8.94 (s, 1H), 7.56 (s, 1H), 7.42 (dt, J=11.3, 7.2 Hz, 5H), 6.97-6.79 (m, 2H), 4.67 (s, 1H), 4.56 (t, J=8.5 Hz, 1H), 4.51 (s, 1H), 4.47 (d, J=15.5 Hz, 1H), 4.40 (d, J=15.4 Hz, 1H), 3.91 (d, J=11.0 Hz, 1H), 3.81 (dd, J=11.0, 3.9 Hz, 1H), 3.79-3.57 (m, 8H), 3.53 (t, J=6.5 Hz, 2H), 3.30 (t, J=7.6 Hz, 3H), 3.23-2.98 (m, 4H), 2.55 (t, J=5.8 Hz, 2H), 2.50 (s, 3H), 2.49-2.45 (m, 7H), 2.27-2.22 (m, 1H), 2.16-2.04 (m, 3H), 1.05 (s, 9H). HRMS calcd for $C_{51}H_{65}FN_9O_8S$ [M+H$^+$] 982.4661, found 982.4669.

Example 4

Synthesis of HC58-20

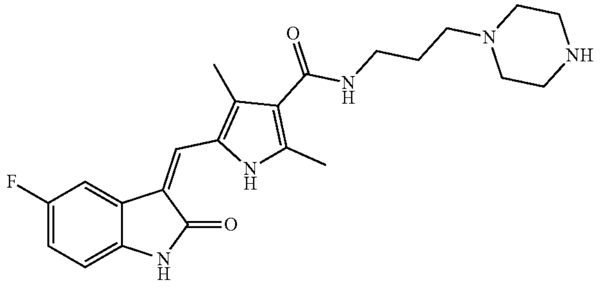

Intermediate 2

+

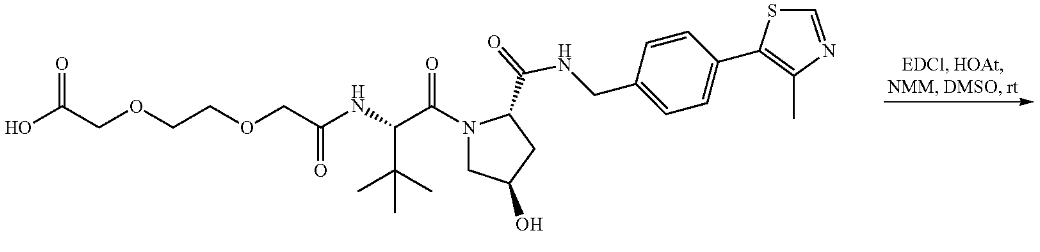

-continued

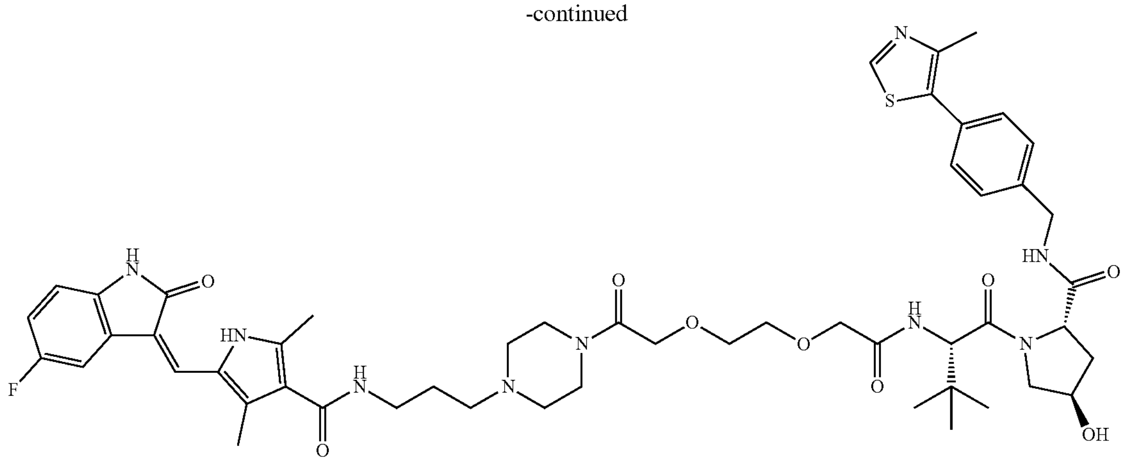

HC58-20

HC58-20 was synthesized following the standard procedure for preparing HC58-18 from Intermediate 2 (13.0 mg, 0.024 mmol, 1.2 equiv), 2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetic acid (11.8 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-20 was obtained as yellow solid in TFA salt form (10.7 mg, 48%). $^1$H NMR (600 MHz, Methanol-$d_4$) δ 13.65 (s, 1H), 8.92 (s, 1H), 7.71 (d, J=9.5 Hz, 1H), 7.52 (s, 1H), 7.46-7.33 (m, 6H), 6.95-6.78 (m, 2H), 4.76-4.70 (m, 1H), 4.62-4.55 (m, 1H), 4.51 (s, 1H), 4.42 (s, 2H), 4.08 (s, 2H), 3.90 (d, J=11.1 Hz, 1H), 3.82 (dd, J=11.1, 3.6 Hz, 1H), 3.80-3.72 (m, 6H), 3.68-3.45 (m, 6H), 3.31-3.02 (m, 6H), 2.49 (s, 3H), 2.47 (s, 3H), 2.44 (s, 3H), 2.29-2.22 (m, 1H), 2.16-2.03 (m, 3H), 1.06 (s, 9H). HRMS calcd for $C_{51}H_{65}FN_9O_9S$ [M+H$^+$] 998.4610, found 998.4625.

Example 5

Synthesis of HC58-22

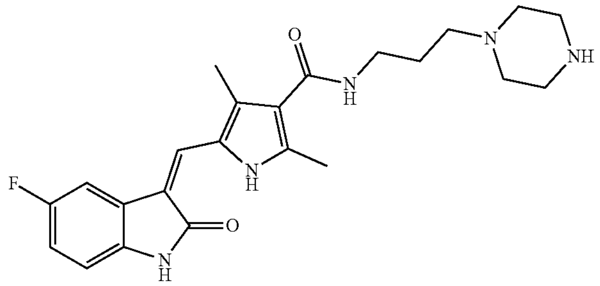

Intermediate 2

+

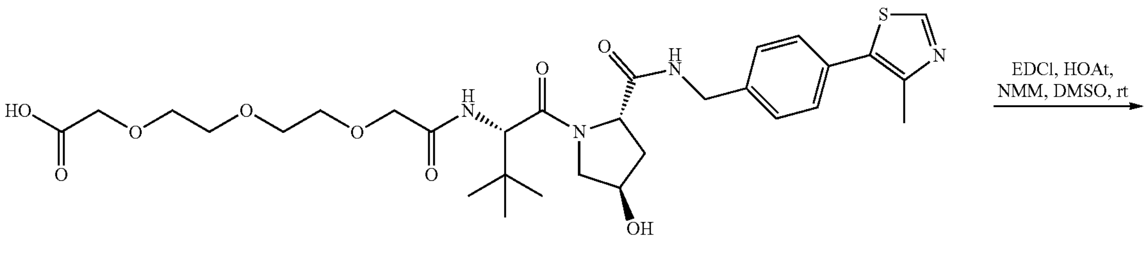

-continued

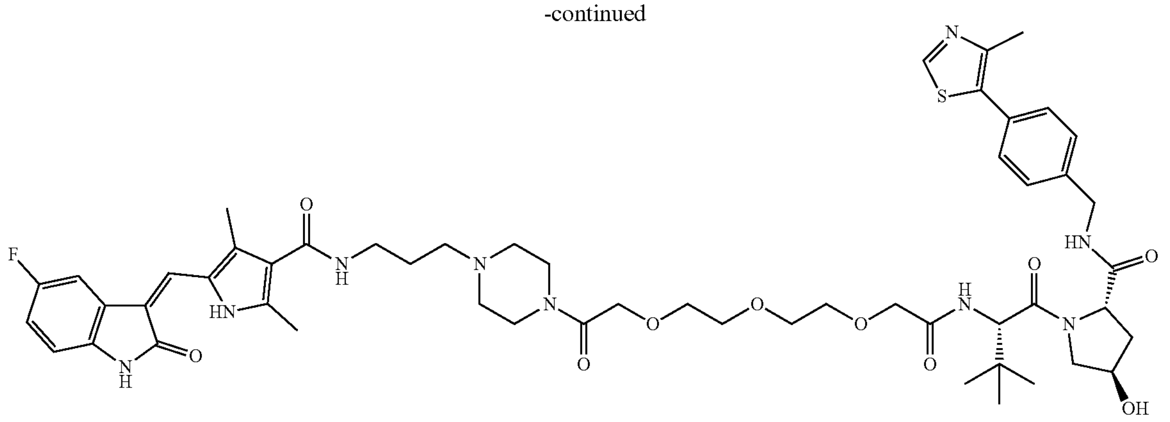

HC58-22

HC58-22 was synthesized following the standard procedure for preparing HC58-18 from Intermediate 2 (13.0 mg, 0.024 mmol, 1.2 equiv), (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoic acid (12.7 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-22 was obtained as yellow solid in TFA salt form (9.9 mg, 43%). $^1H$ NMR (600 MHz, Methanol-$d_4$) δ 13.68 (s, 1H), 8.98 (s, 1H), 7.71 (d, J=9.3 Hz, 1H), 7.56 (s, 1H), 7.45 (d, J=8.2 Hz, 2H), 7.43-7.39 (m, 3H), 6.89-6.83 (m, 2H), 4.72-4.68 (m, 1H), 4.62-4.49 (m, 3H), 4.39 (d, J=15.4 Hz, 1H), 4.36-4.21 (m, 2H), 4.09 (s, 2H), 3.90 (d, J=11.1 Hz, 1H), 3.81 (dd, J=11.0, 3.7 Hz, 1H), 3.78-3.45 (m, 14H), 3.28 (t, J=7.6 Hz, 2H), 3.24-3.03 (m, 4H), 2.51 (s, 3H), 2.49 (s, 3H), 2.47 (s, 3H), 2.29-2.22 (m, 1H), 2.10 (tt, J=8.4, 4.3 Hz, 3H), 1.06 (d, J=2.1 Hz, 9H). HRMS calcd for $C_{53}H_{69}FN_9O_{10}S$ [M+H$^+$] 1042.4872, found 1042.4868.

Example 6

Synthesis of HC58-23

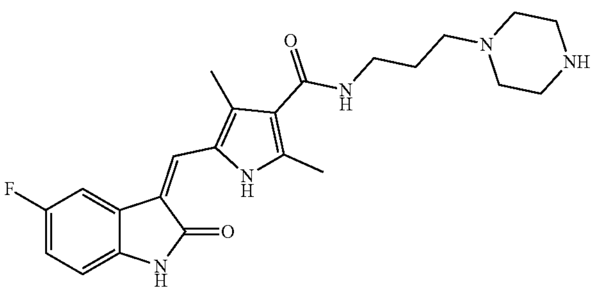

Intermediate 2

+

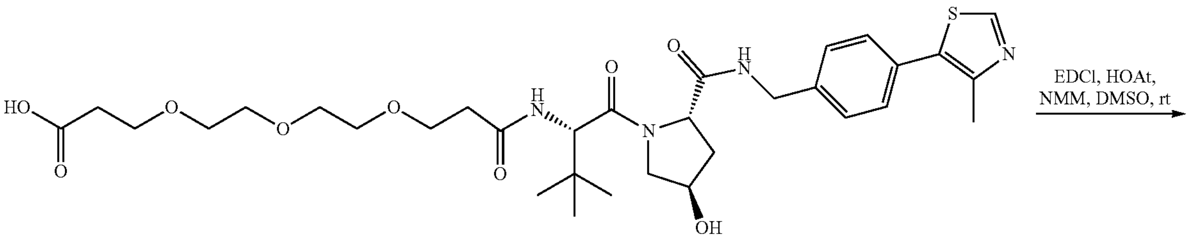

-continued

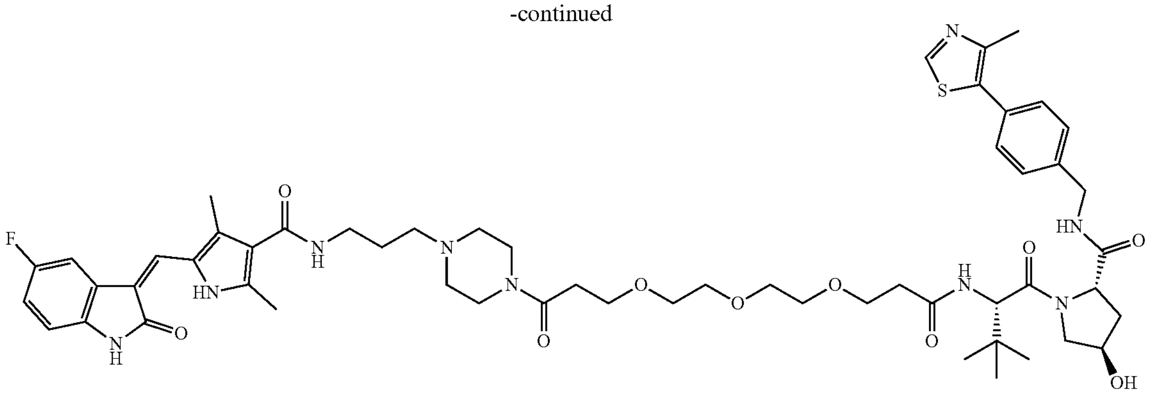

HC58-23

HC58-23 was synthesized following the standard procedure for preparing HC58-18 from Intermediate 2 (13.0 mg, 0.024 mmol, 1.2 equiv), (S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoic acid (13.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-23 was obtained as yellow solid in TFA salt form (9.9 mg, 43%). $^1$H NMR (600 MHz, Methanol-$d_4$) δ 13.69 (s, 1H), 8.95 (s, 1H), 7.93 (d, J=8.9 Hz, 1H), 7.57 (d, J=2.7 Hz, 1H), 7.46 (d, J=8.2 Hz, 2H), 7.43-7.39 (m, 3H), 6.93-6.83 (m, 2H), 4.65 (s, 1H), 4.61-4.53 (m, 1H), 4.53-4.49 (m, 2H), 4.37 (d, J=15.5 Hz, 1H), 3.90 (d, J=10.9 Hz, 1H), 3.81 (dd, J=11.0, 3.9 Hz, 1H), 3.79-3.71 (m, 4H), 3.69-3.57 (m, 13H), 3.53 (t, J=6.6 Hz, 2H), 3.28 (dd, J=10.8, 4.6 Hz, 2H), 3.24-2.98 (m, 4H), 2.59 (ddd, J=15.0, 7.1, 5.5 Hz, 1H), 2.55-2.45 (m, 11H), 2.28-2.20 (m, 1H), 2.17-2.06 (m, 3H), 1.05 (s, 9H). HRMS calcd for $C_{55}H_{73}FN_9O_{10}S$ [M+H$^+$] 1070.5185, found 1070.5197.

Example 7

Synthesis of HC58-24

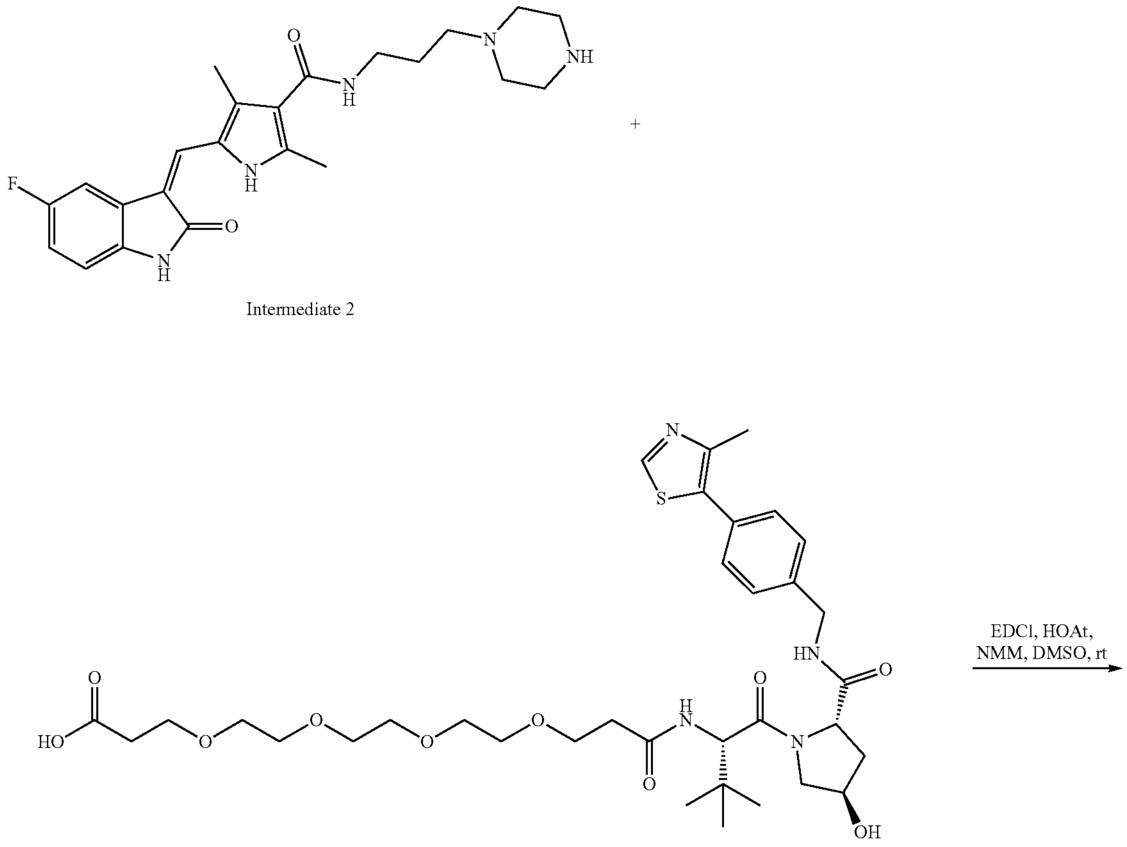

-continued

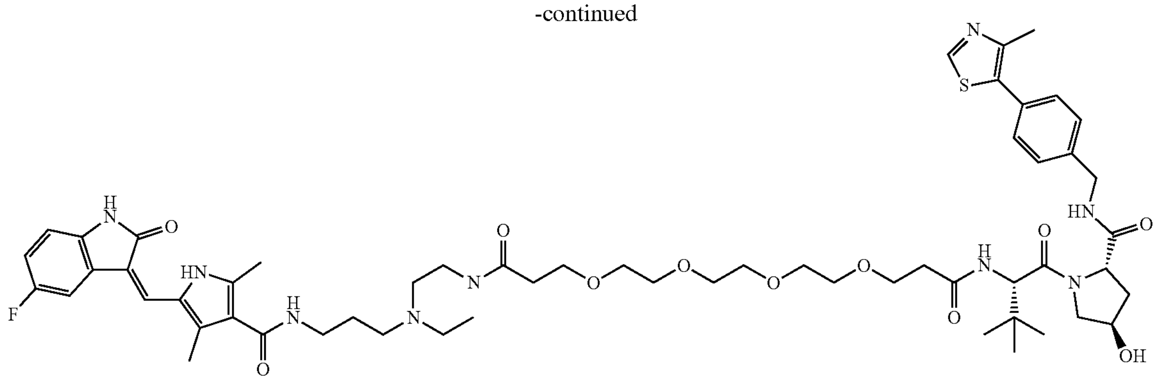

HC58-24

HC58-24 was synthesized following the standard procedure for preparing HC58-18 from Intermediate 2 (13.0 mg, 0.024 mmol, 1.2 equiv), (S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoic acid (14.1 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-24 was obtained as yellow solid in TFA salt form (9.6 mg, 39%). $^{1}H$ NMR (600 MHz, Methanol-$d_4$) δ 13.70 (s, 1H), 8.95 (s, 1H), 7.58 (s, 1H), 7.47 (d, J=8.2 Hz, 2H), 7.44-7.38 (m, 3H), 6.91-6.83 (m, 2H), 4.65 (s, 1H), 4.61-4.49 (m, 3H), 4.37 (d, J=15.6 Hz, 1H), 3.90 (d, J=10.8 Hz, 1H), 3.84-3.55 (m, 21H), 3.53 (t, J=6.5 Hz, 2H), 3.28 (t, J=7.6 Hz, 2H), 3.23-2.96 (m, 4H), 2.64-2.56 (m, 2H), 2.54-2.45 (m, 11H), 2.28-2.20 (m, 1H), 2.15-2.05 (m, 3H), 1.05 (s, 9H). HRMS calcd for $C_{57}H_{77}FN_9O_{11}S$ [M+H$^+$] 1114.5447, found 1114.5456.

Example 8

Synthesis of HC58-25

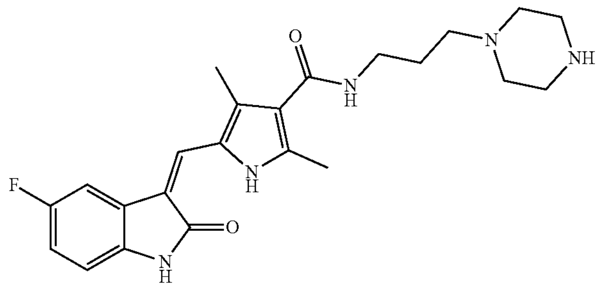

Intermediate 2

+

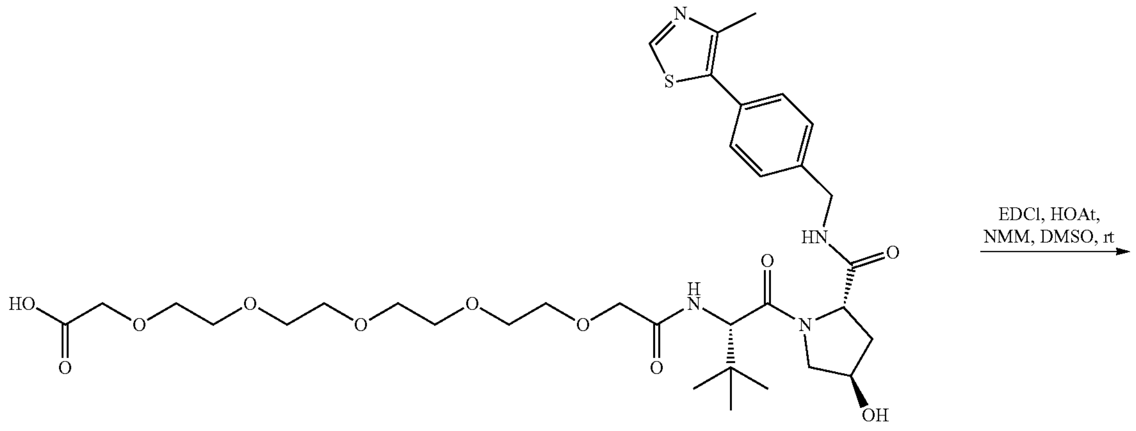

-continued

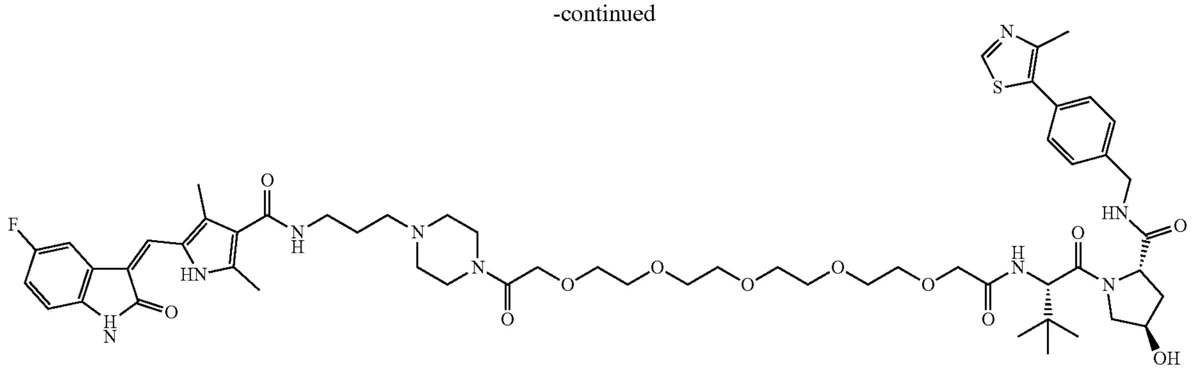

HC58-25

HC58-25 was synthesized following the standard procedure for preparing HC58-18 from Intermediate 2 (13.0 mg, 0.024 mmol, 1.2 equiv), (S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoic acid (14.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-25 was obtained as yellow solid in TFA salt form (8.9 mg, 36%). 1H NMR (600 MHz, Methanol-d4) δ 13.67 (s, 1H), 9.00 (s, 1H), 7.88 (d, J=8.6 Hz, 1H), 7.54 (s, 1H), 7.48-7.36 (m, 5H), 6.91-6.81 (m, 2H), 4.67-4.50 (m, 4H), 4.36 (d, J=15.5 Hz, 1H), 4.18-4.06 (m, 2H), 3.89 (d, J=10.9 Hz, 1H), 3.84-3.58 (m, 23H), 3.51 (t, J=6.7 Hz, 2H), 3.31-2.98 (m, 6H), 2.50 (s, 3H), 2.48 (s, 3H), 2.46 (s, 3H), 2.26 (dd, J=13.2, 7.4 Hz, 1H), 2.16-2.05 (m, 3H), 1.07 (s, 9H). HRMS calcd for $C_{57}H_{77}FN_9O_{12}S$ [M+H$^+$] 1130.5396, found 1130.5401.

Example 9

Synthesis of HC58-26

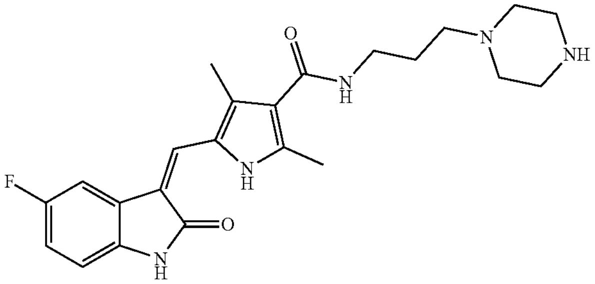

Intermediate 2

+

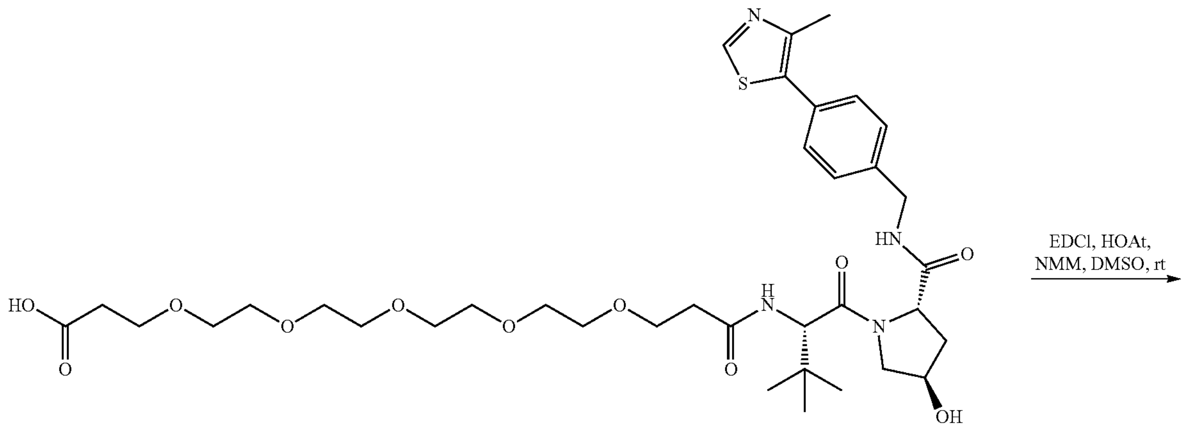

-continued

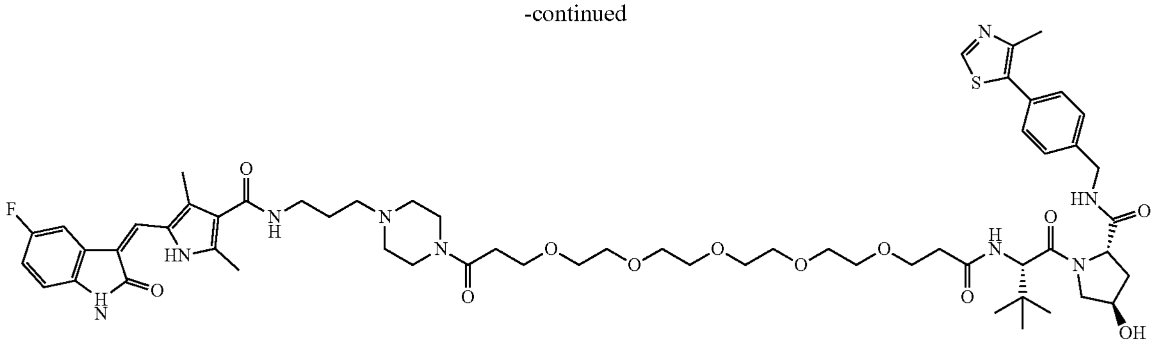

HC58-26

HC58-26 was synthesized following the standard procedure for preparing HC58-18 from Intermediate 2 (13.0 mg, 0.024 mmol, 1.2 equiv), (S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoic acid (15.0 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-26 was obtained as yellow solid in TFA salt form (12.2 mg, 48%). $^1$H NMR (600 MHz, Methanol-$d_4$) δ 13.68 (s, 1H), 9.01 (s, 1H), 7.95 (d, J=9.0 Hz, 1H), 7.55 (s, 1H), 7.50-7.34 (m, 5H), 6.92-6.80 (m, 2H), 4.65 (d, J=2.6 Hz, 1H), 4.61-4.49 (m, 3H), 4.36 (d, J=15.5 Hz, 1H), 3.90 (d, J=10.8 Hz, 1H), 3.84-3.56 (m, 25H), 3.52 (t, J=6.6 Hz, 2H), 3.28 (t, J=7.6 Hz, 2H), 3.24-2.99 (m, 4H), 2.64-2.55 (m, 2H), 2.53-2.43 (m, 11H), 2.28-2.20 (m, 1H), 2.10 (ddt, J=17.4, 9.2, 5.2 Hz, 3H), 1.05 (s, 9H). HRMS calcd for $C_{59}H_{81}FN_9O_{12}S$ [M+H$^+$] 1158.5709, found 1158.5704.

Example 10

Synthesis of HC58-27

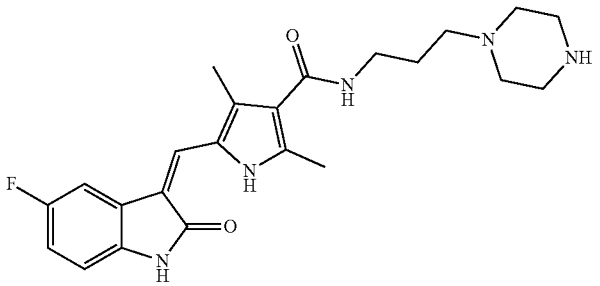

Intermediate 2

+

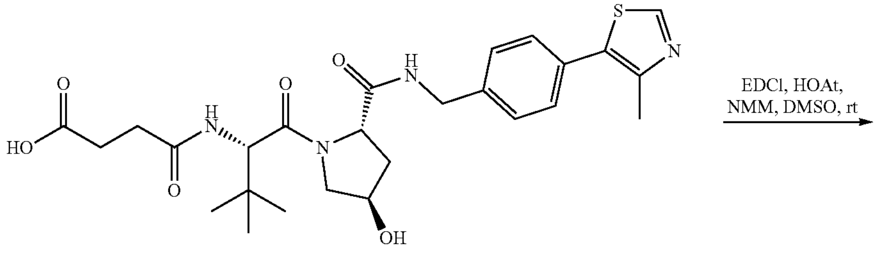

-continued

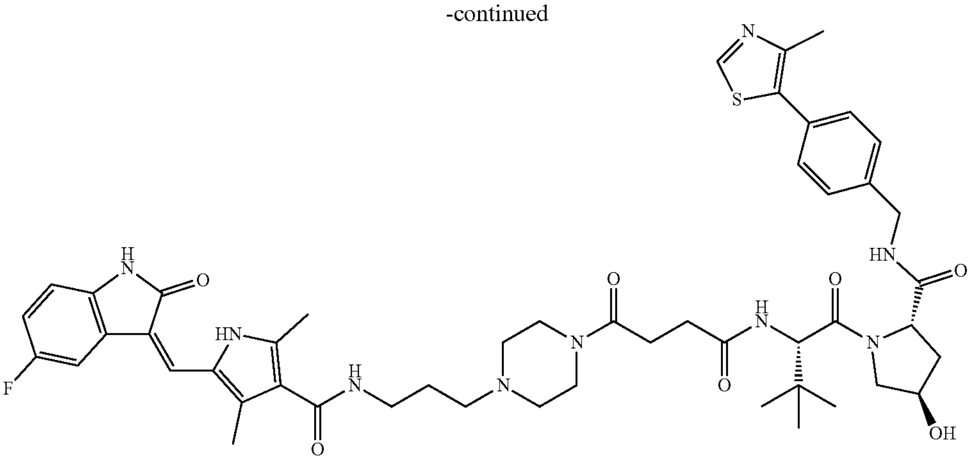

HC58-27

HC58-27 was synthesized following the standard procedure for preparing HC58-18 from Intermediate 2 (13.0 mg, 0.024 mmol, 1.2 equiv), 4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid (10.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-27 was obtained as yellow solid in TFA salt form (11.2 mg, 53%). $^1$H NMR (600 MHz, Methanol-d4) δ 13.68 (s, 1H), 8.91 (s, 1H), 7.97 (d, J=8.7 Hz, 1H), 7.56 (s, 1H), 7.47-7.39 (m, 5H), 6.96-6.79 (m, 2H), 4.63-4.56 (m, 2H), 4.56-4.47 (m, 2H), 4.36 (d, J=15.6 Hz, 1H), 3.92 (d, J=11.0 Hz, 1H), 3.81 (dd, J=10.9, 3.9 Hz, 1H), 3.73-3.44 (m, 6H), 3.31-3.00 (m, 6H), 2.75-2.59 (m, 4H), 2.51 (s, 3H), 2.48 (s, 3H), 2.47 (s, 3H), 2.32-2.20 (m, 1H), 2.16-2.05 (m, 3H), 1.06 (s, 9H). HRMS calcd for $C_{49}H_{61}FN_9O_7S$ [M+H$^+$] 938.4399, found 938.4408.

Example 11

Synthesis of HC58-28

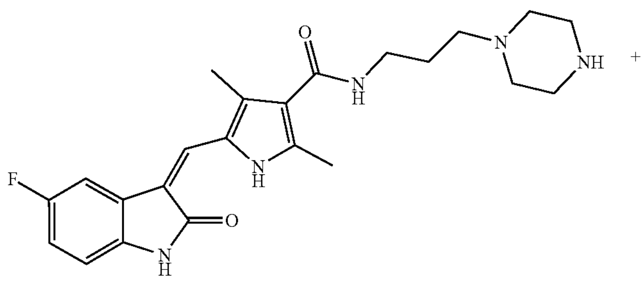

Intermediate 2

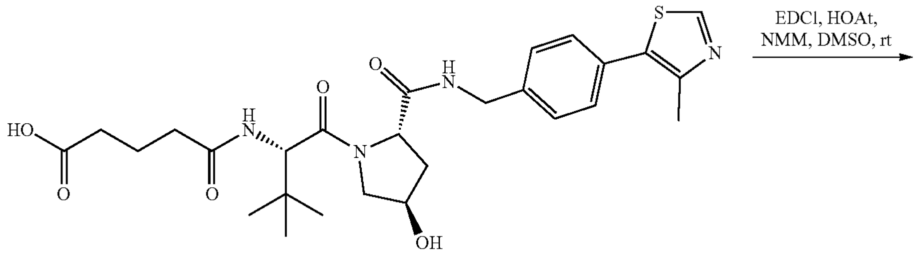

-continued

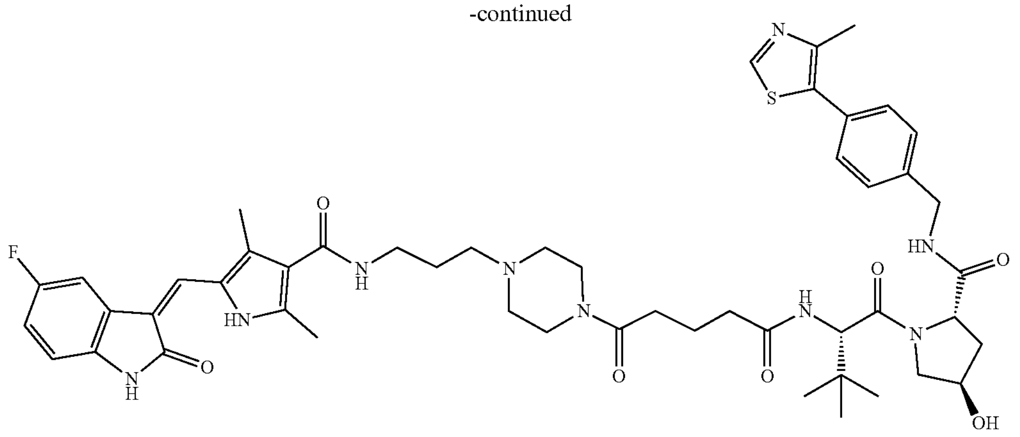

HC58-28

HC58-28 was synthesized following the standard procedure for preparing HC58-18 from Intermediate 2 (13.0 mg, 0.024 mmol, 1.2 equiv), 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid (10.9 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-28 was obtained as yellow solid in TFA salt form (11.9 mg, 56%). $^1$H NMR (600 MHz, Methanol-$d_4$) δ 13.68 (s, 1H), 8.90 (s, 1H), 7.94 (d, J=8.7 Hz, 1H), 7.56 (s, 1H), 7.49-7.37 (m, 5H), 6.97-6.83 (m, 2H), 4.64-4.61 (m, 1H), 4.57 (dd, J=9.3, 7.4 Hz, 1H), 4.53-4.47 (m, 2H), 4.36 (d, J=15.5 Hz, 1H), 3.95 (d, J=11.0 Hz, 1H), 3.82 (dd, J=10.9, 3.8 Hz, 1H), 3.72-3.46 (m, 6H), 3.30-2.95 (m, 6H), 2.54-2.44 (m, 11H), 2.38 (t, J=7.1 Hz, 2H), 2.29-2.21 (m, 1H), 2.16-2.07 (m, 3H), 1.93 (p, J=7.3 Hz, 2H), 1.06 (s, 9H). HRMS calcd for $C_{50}H_{63}FN_9O_7S$ [M+H$^+$] 952.4555, found 952.4568.

Example 12

Synthesis of HC58-29

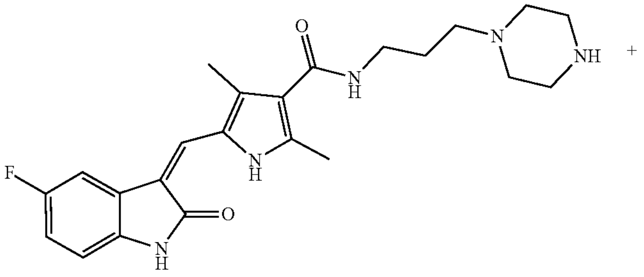

Intermediate 2

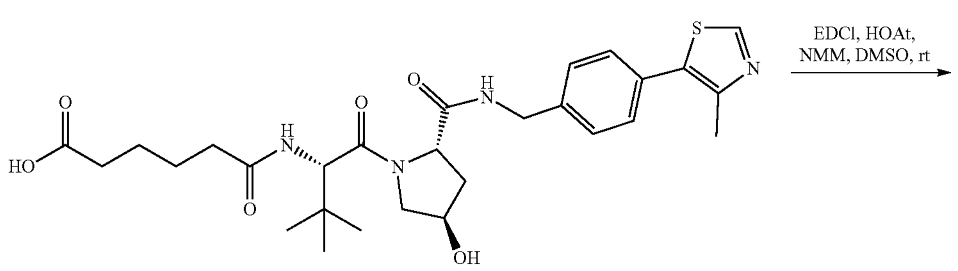

-continued

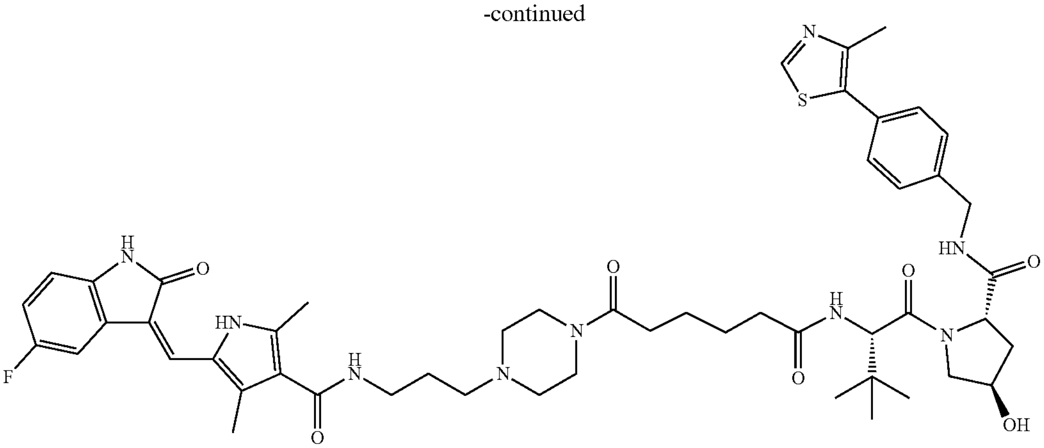

HC58-29

HC58-29 was synthesized following the standard procedure for preparing HC58-18 from Intermediate 2 (13.0 mg, 0.024 mmol, 1.2 equiv), 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid (11.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-29 was obtained as yellow solid in TFA salt form (13.2 mg, 61%). $^1$H NMR (600 MHz, Methanol-$d_4$) δ 13.68 (s, 1H), 9.02 (s, 1H), 7.56 (s, 1H), 7.47 (d, J=8.3 Hz, 2H), 7.44-7.39 (m, 3H), 6.95-6.82 (m, 2H), 4.64 (s, 1H), 4.58 (dd, J=9.1, 7.5 Hz, 1H), 4.55-4.48 (m, 2H), 4.37 (d, J=15.5 Hz, 1H), 3.92 (d, J=11.0 Hz, 1H), 3.82 (dd, J=10.9, 3.9 Hz, 1H), 3.73-3.47 (m, 6H), 3.28 (t, J=7.6 Hz, 2H), 3.22-3.00 (m, 4H), 2.55-2.45 (m, 11H), 2.39-2.29 (m, 2H), 2.27-2.21 (m, 1H), 2.15-2.05 (m, 3H), 1.78-1.56 (m, 4H), 1.05 (s, 9H). HRMS calcd for $C_{51}H_{65}FN_9O_7S$ [M+H$^+$] 966.4712, found 966.4723.

Example 13

Synthesis of HC58-30

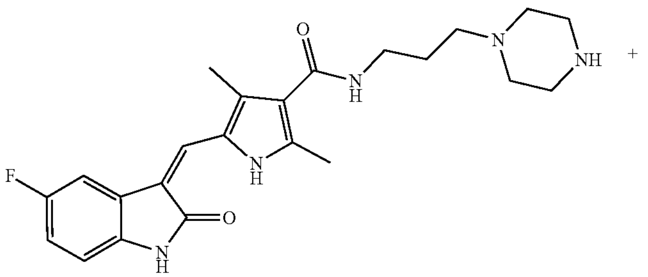

Intermediate 2

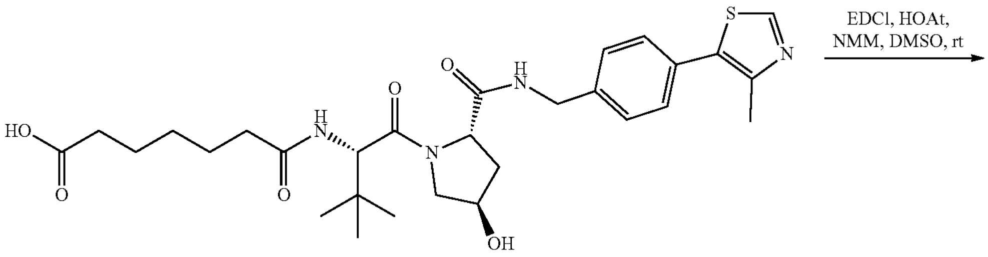

-continued

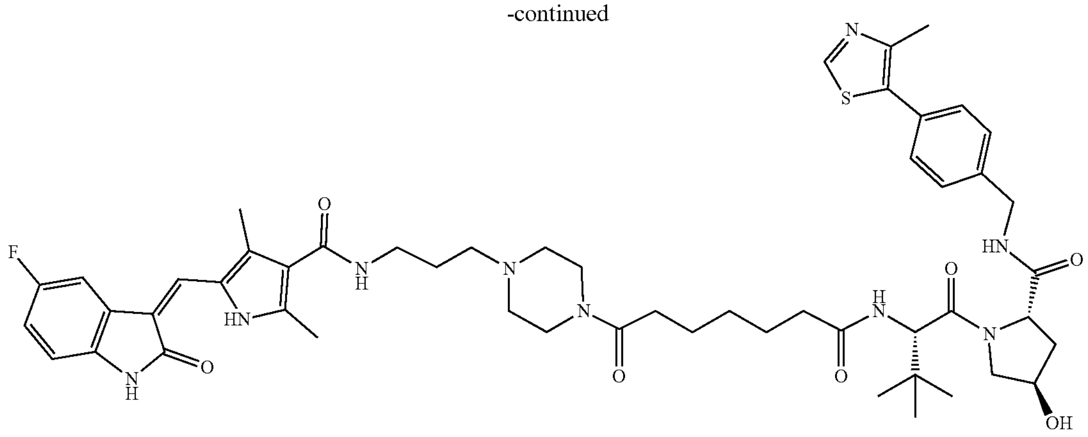

HC58-30

HC58-30 was synthesized following the standard procedure for preparing HC58-18 from Intermediate 2 (13.0 mg, 0.024 mmol, 1.2 equiv), 7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid (11.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-30 was obtained as yellow solid in TFA salt form (8.3 mg, 38%). $^1$H NMR (600 MHz, Methanol-$d_4$) δ 13.69 (s, 1H), 8.98 (d, J=2.5 Hz, 1H), 7.85 (d, J=8.6 Hz, 1H), 7.57 (d, J=2.7 Hz, 1H), 7.49-7.45 (m, 2H), 7.45-7.39 (m, 3H), 7.01-6.76 (m, 2H), 4.65 (d, J=2.7 Hz, 1H), 4.61-4.49 (m, 3H), 4.38 (dd, J=15.4, 2.6 Hz, 1H), 3.92 (d, J=10.9 Hz, 1H), 3.84-3.80 (m, 1H), 3.75-3.46 (m, 6H), 3.28 (t, J=7.1 Hz, 2H), 3.16 (d, J=61.8 Hz, 4H), 2.58-2.44 (m, 11H), 2.37-2.27 (m, 2H), 2.26-2.20 (m, 1H), 2.16-2.05 (m, 3H), 1.72-1.60 (m, 4H), 1.47-1.36 (m, 2H), 1.05 (s, 9H). HRMS calcd for $C_{52}H_{67}FN_9O_7S$ [M+H$^+$] 980.4868, found 980.4880.

Example 14

Synthesis of HC58-31

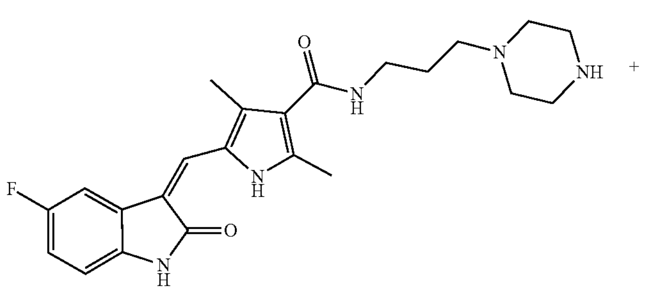

Intermediate 2

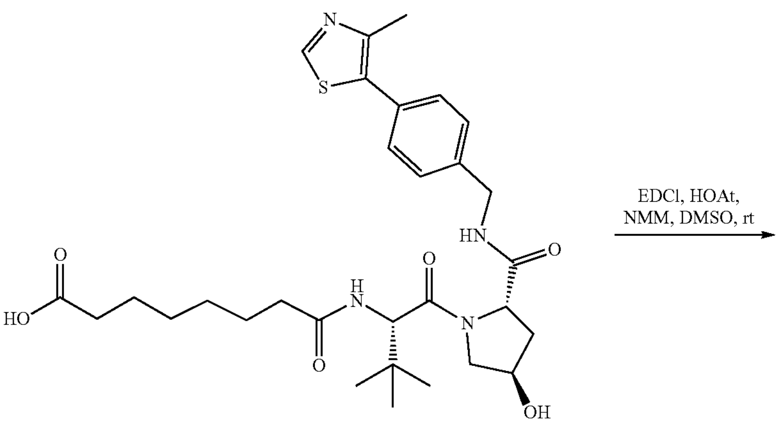

-continued

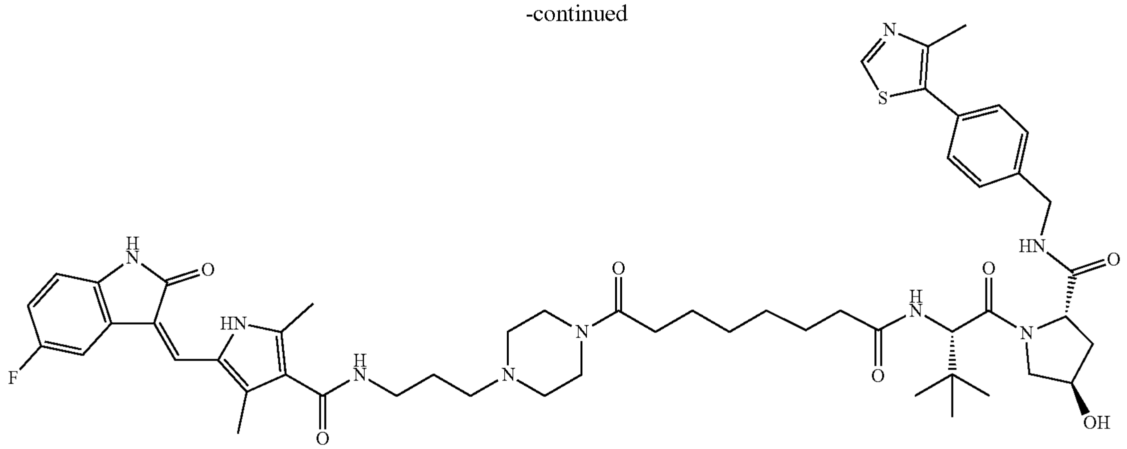

HC58-31

HC58-31 was synthesized following the standard procedure for preparing HC58-18 from Intermediate 2 (13.0 mg, 0.024 mmol, 1.2 equiv), 8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid (11.7 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-31 was obtained as yellow solid in TFA salt form (9.6 mg, 43%). $^1$H NMR (600 MHz, Methanol-d4) δ 13.69 (s, 1H), 9.04 (s, 1H), 7.56 (d, J=3.2 Hz, 1H), 7.48 (d, J=8.2 Hz, 2H), 7.45-7.40 (m, 3H), 6.92-6.80 (m, 2H), 4.65 (s, 1H), 4.60-4.50 (m, 3H), 4.38 (d, J=15.5 Hz, 1H), 3.92 (d, J=10.9 Hz, 1H), 3.82 (dd, J=10.9, 3.9 Hz, 1H), 3.73-3.56 (m, 4H), 3.52 (t, J=6.6 Hz, 2H), 3.28 (t, J=7.5 Hz, 2H), 3.23-2.98 (m, 4H), 2.51 (s, 3H), 2.49 (s, 3H), 2.48-2.44 (m, 5H), 2.36-2.19 (m, 3H), 2.16-2.06 (m, 3H), 1.69-1.59 (m, 4H), 1.46-1.33 (m, 4H), 1.05 (s, 9H). HRMS calcd for $C_{53}H_{69}FN_9O_7S$ [M+H$^+$] 994.5025, found 994.5029.

Example 15

Synthesis of HC58-32

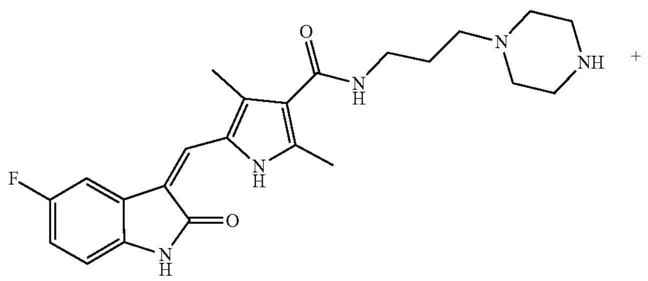

Intermediate 2

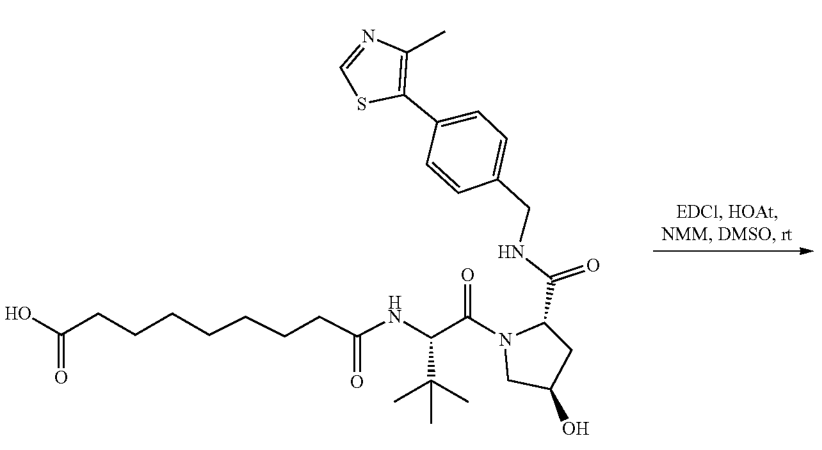

-continued

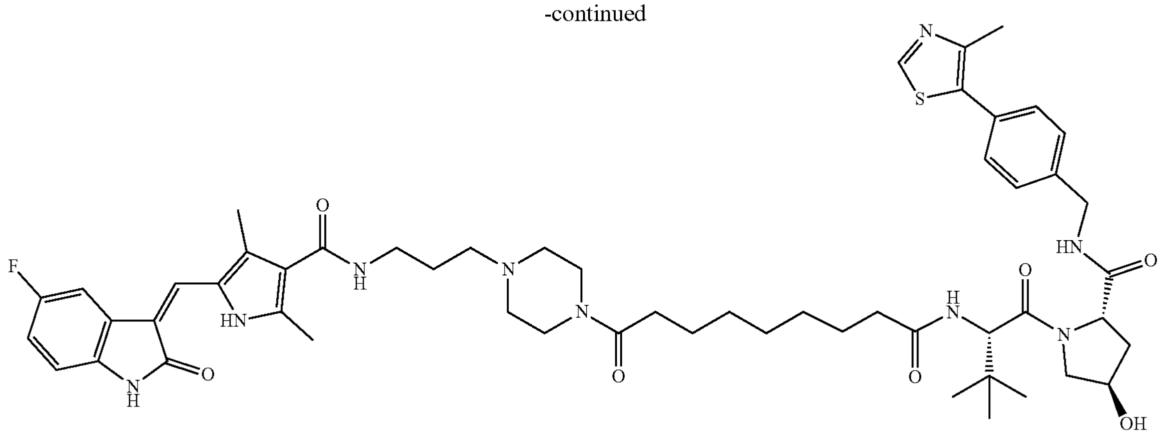

HC58-32

HC58-32 was synthesized following the standard procedure for preparing HC58-18 from Intermediate 2 (13.0 mg, 0.024 mmol, 1.2 equiv), 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid (12.0 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-32 was obtained as yellow solid in TFA salt form (10.8 mg, 48%). $^1$H NMR (600 MHz, Methanol-$d_4$) δ 8.95 (d, J=1.2 Hz, 1H), 7.84 (d, J=9.0 Hz, 1H), 7.59 (d, J=2.0 Hz, 1H), 7.48 (d, J=7.9 Hz, 2H), 7.46-7.40 (m, 3H), 6.94-6.83 (m, 2H), 4.70-4.63 (m, 1H), 4.62-4.49 (m, 3H), 4.38 (d, J=15.5 Hz, 1H), 3.93 (d, J=10.9 Hz, 1H), 3.82 (dd, J=10.9, 3.9 Hz, 1H), 3.74-3.46 (m, 6H), 3.28 (t, J=7.6 Hz, 2H), 3.23-2.99 (m, 4H), 2.52 (s, 3H), 2.51-2.44 (m, 8H), 2.37-2.21 (m, 3H), 2.17-2.07 (m, 3H), 1.69-1.58 (m, 4H), 1.44-1.33 (m, 6H), 1.05 (s, 9H). HRMS calcd for $C_{54}H_{71}FN_9O_7S$ [M+H$^+$] 1008.5181, found 1008.5189.

Example 16

Synthesis of HC58-33

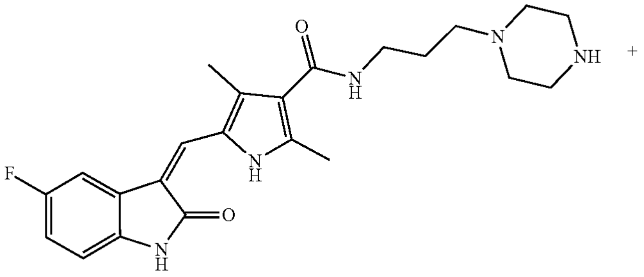

Intermediate 2

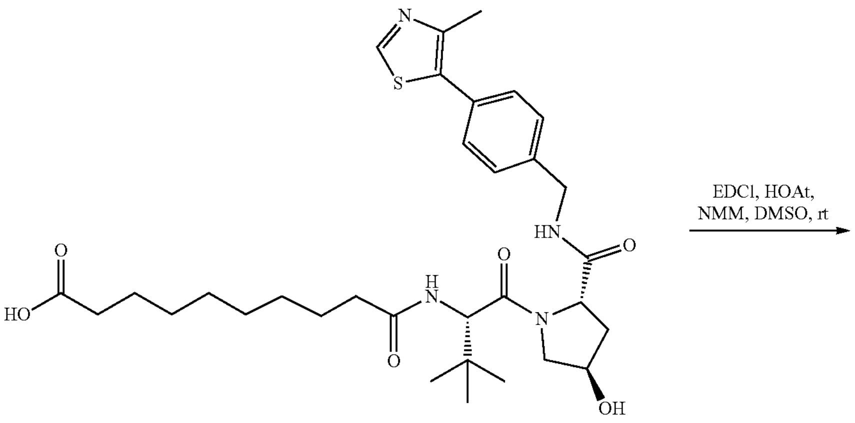

-continued

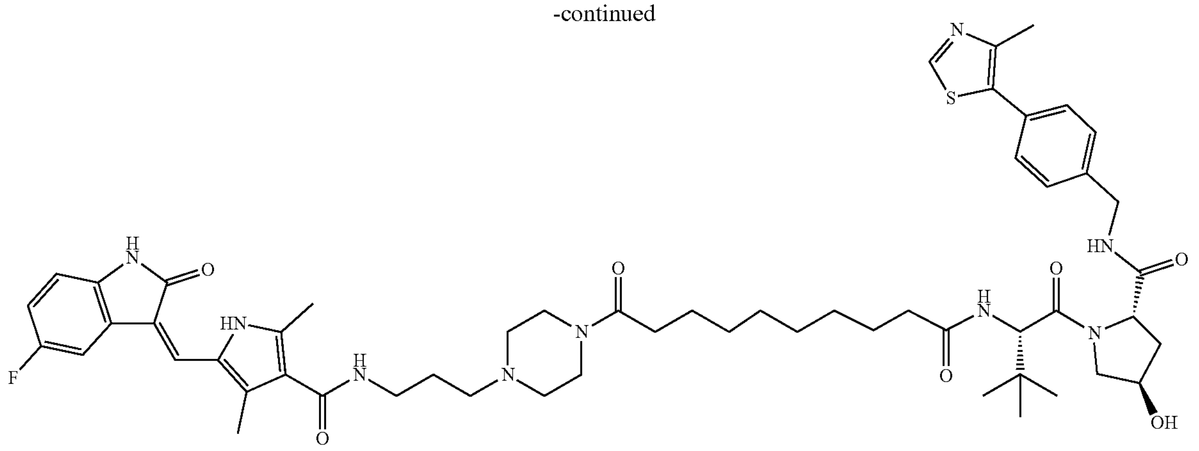

HC58-33

HC58-33 was synthesized following the standard procedure for preparing HC58-18 from Intermediate 2 (13.0 mg, 0.024 mmol, 1.2 equiv), 10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid (12.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-33 was obtained as yellow solid in TFA salt form (13.2 mg, 58%). $^1$H NMR (600 MHz, Methanol-$d_4$) δ 8.95 (s, 1H), 7.84 (d, J=9.0 Hz, 1H), 7.59 (s, 1H), 7.48 (d, J=8.2 Hz, 2H), 7.45-7.41 (m, 3H), 6.94-6.84 (m, 2H), 4.69-4.63 (m, 1H), 4.63-4.49 (m, 3H), 4.38 (d, J=15.4 Hz, 1H), 3.92 (d, J=10.9 Hz, 1H), 3.83 (dd, J=11.0, 3.9 Hz, 1H), 3.70-3.50 (m, 6H), 3.28 (t, J=7.6 Hz, 2H), 3.23-3.02 (m, 4H), 2.52 (s, 3H), 2.51-2.45 (m, 8H), 2.35-2.21 (m, 3H), 2.15-2.06 (m, 3H), 1.67-1.58 (m, 4H), 1.42-1.32 (m, 8H), 1.05 (s, 9H). HRMS calcd for $C_{55}H_{73}FN_9O_7S$ [M+H$^+$] 1022.5338, found 1022.5349.

Example 17

Synthesis of HC58-34

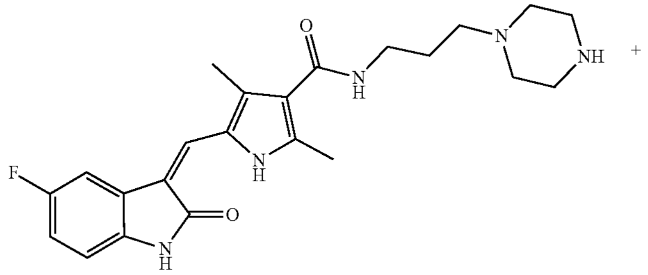

Intermediate 2

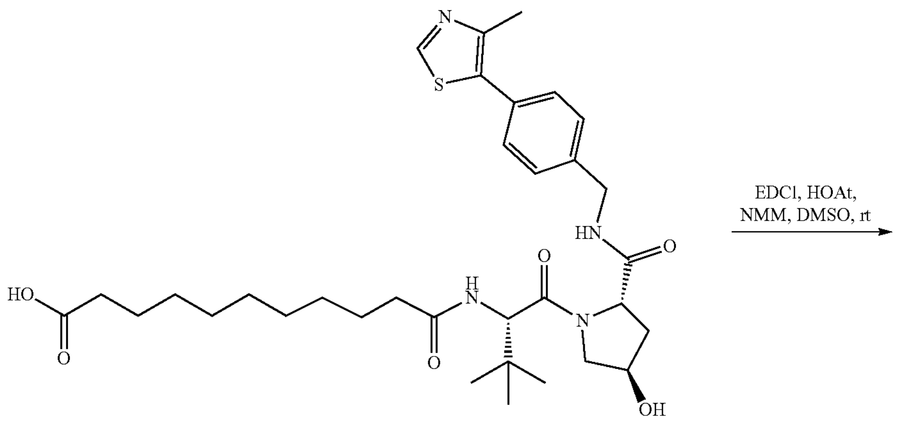

-continued

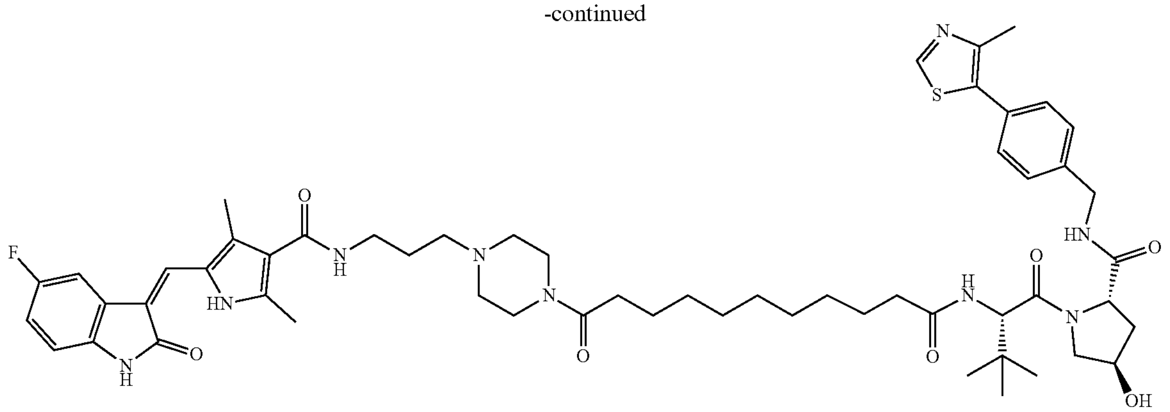

HC58-34

HC58-34 was synthesized following the standard procedure for preparing HC58-18 from Intermediate 2 (13.0 mg, 0.024 mmol, 1.2 equiv), 11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (12.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-34 was obtained as yellow solid in TFA salt form (10.1 mg, 44%). $^{1}$H NMR (600 MHz, Methanol-$d_4$) δ 13.68 (s, 1H), 9.04 (s, 1H), 7.55 (d, J=3.2 Hz, 1H), 7.48 (d, J=8.0 Hz, 2H), 7.44-7.37 (m, 3H), 6.90-6.83 (m, 2H), 4.65 (s, 1H), 4.62-4.48 (m, 3H), 4.37 (d, J=15.5 Hz, 1H), 3.92 (d, J=11.0 Hz, 1H), 3.82 (dd, J=10.9, 3.9 Hz, 1H), 3.78-3.47 (m, 6H), 3.28 (t, J=7.6 Hz, 2H), 3.22-2.97 (m, 4H), 2.52-2.43 (m, 11H), 2.36-2.20 (m, 3H), 2.14-2.05 (m, 3H), 1.67-1.55 (m, 4H), 1.42-1.28 (m, 10H), 1.05 (s, 9H). HRMS calcd for $C_{56}H_{75}FN_9O_7S$ [M+H$^+$] 1036.5494, found 1036.5499.

Example 18

Synthesis of HC58-35

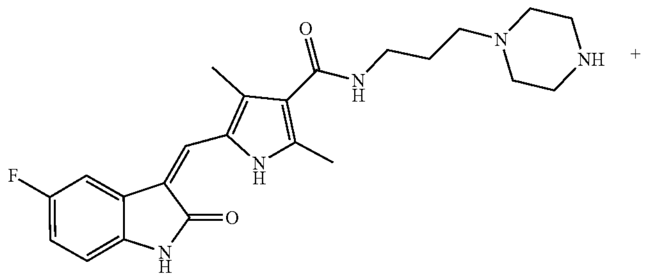

Intermediate 2

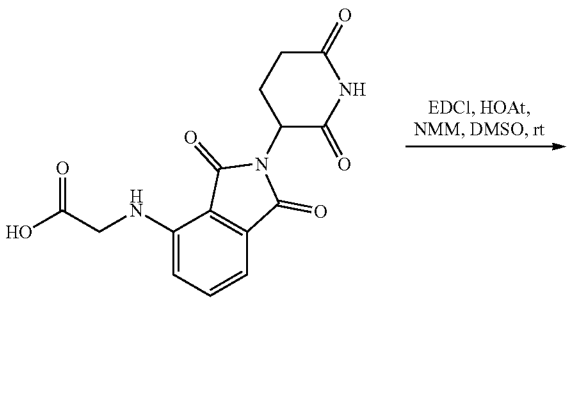

-continued

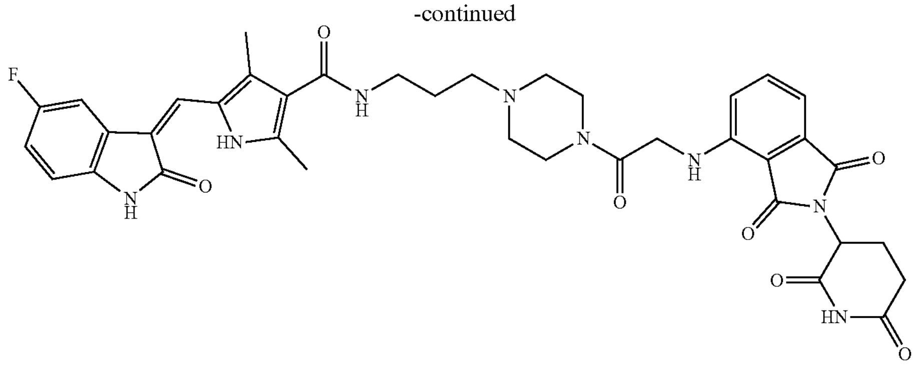

HC58-35

HC58-35 was synthesized following the standard procedure for preparing HC58-18 from Intermediate 2 (13.0 mg, 0.024 mmol, 1.2 equiv), (2-(2,6-dioxopiperidin-3-yl)-1,3-dioxoisoindolin-4-yl)glycine (6.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-35 was obtained as yellow solid in TFA salt form (9.7 mg, 57%). $^1$H NMR (600 MHz, DMSO-$d_6$) δ 13.73 (d, J=3.5 Hz, 1H), 11.13 (s, 1H), 10.94 (s, 1H), 7.81 (t, J=5.8 Hz, 1H), 7.79-7.76 (m, 1H), 7.73 (s, 1H), 7.64 (dd, J=8.5, 7.1 Hz, 1H), 7.11 (t, J=7.4 Hz, 2H), 7.03 (t, J=4.6 Hz, 1H), 6.94 (td, J=9.1, 2.6 Hz, 1H), 6.86 (dd, J=8.4, 4.6 Hz, 1H), 5.08 (dd, J=12.8, 5.5 Hz, 1H), 4.49 (s, 1H), 4.38-4.06 (m, 3H), 3.57 (s, 2H), 3.32 (q, J=6.3 Hz, 2H), 3.24-3.12 (m, 2H), 3.11-2.97 (m, 4H), 2.89 (ddd, J=17.0, 13.9, 5.4 Hz, 1H), 2.65-2.52 (m, 2H), 2.46 (s, 3H), 2.44 (s, 3H), 2.07-2.01 (m, 1H), 1.99-1.87 (m, 2H). HRMS calcd for $C_{38}H_{40}FN_8O_7$[M+H$^+$] 739.3004, found 739.3017.

Example 19

Synthesis of HC58-36

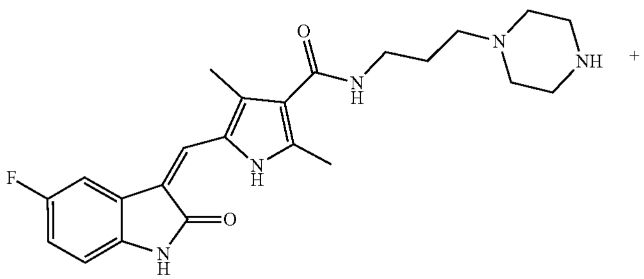

Intermediate 2

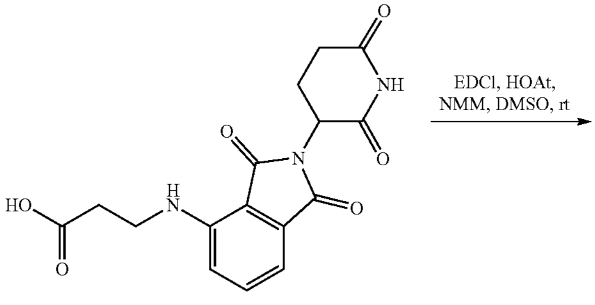

-continued

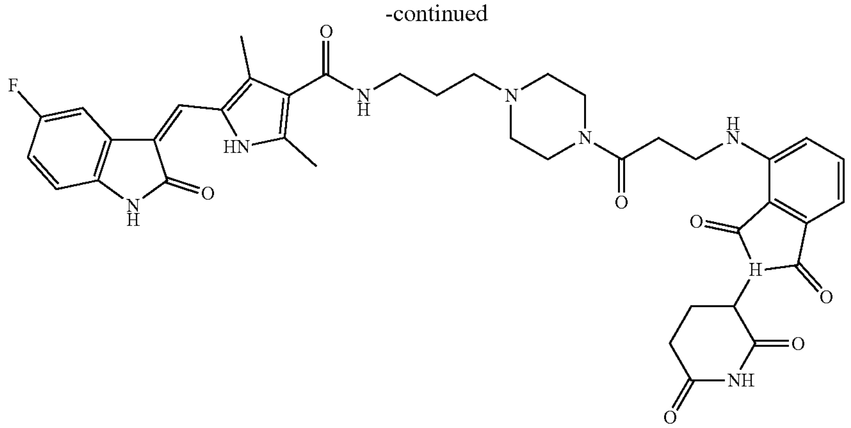

HC58-36

HC58-36 was synthesized following the standard procedure for preparing HC58-18 from Intermediate 2 (13.0 mg, 0.024 mmol, 1.2 equiv), 3-((2-(2,6-dioxopiperidin-3-yl)-1,3-dioxoisoindolin-4-yl)amino)propanoic acid (6.9 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-36 was obtained as yellow solid in TFA salt form (9.0 mg, 52%). 1H NMR (600 MHz, DMSO-d6) δ 13.72 (s, 1H), 11.11 (s, 1H), 10.93 (s, 1H), 7.79-7.75 (m, 2H), 7.73 (s, 1H), 7.64-7.55 (m, 1H), 7.16 (d, J=8.6 Hz, 1H), 7.04 (d, J=7.0 Hz, 1H), 6.94 (td, J=9.1, 2.6 Hz, 1H), 6.86 (dd, J=8.4, 4.5 Hz, 1H), 6.78 (t, J=6.3 Hz, 1H), 5.05 (dd, J=12.9, 5.5 Hz, 1H), 4.50 (s, 1H), 4.08 (d, J=6.9 Hz, 1H), 3.63-3.34 (m, 7H), 3.32-3.26 (m, 2H), 3.22-2.92 (m, 5H), 2.88 (ddd, J=17.1, 13.9, 5.4 Hz, 1H), 2.72 (s, 2H), 2.64-2.57 (m, 1H), 2.56-2.47 (m, 1H), 2.45 (s, 3H), 2.43 (s, 3H), 2.07-2.00 (m, 1H), 1.96-1.85 (m, 2H). HRMS calcd for $C_{39}H_{42}FN_8O_7[M+H^+]$ 753.3160, found 753.3178.

Example 20

Synthesis of HC58-37

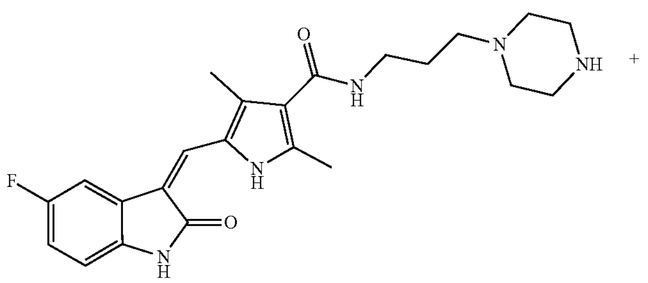

Intermediate 2

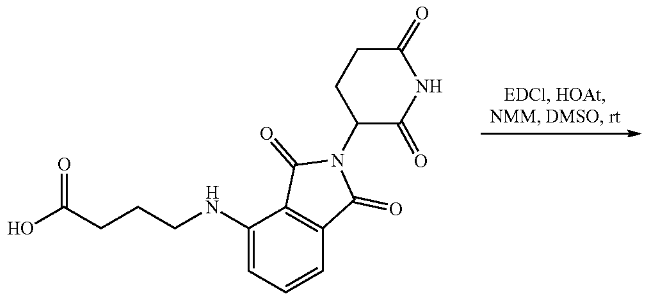

-continued

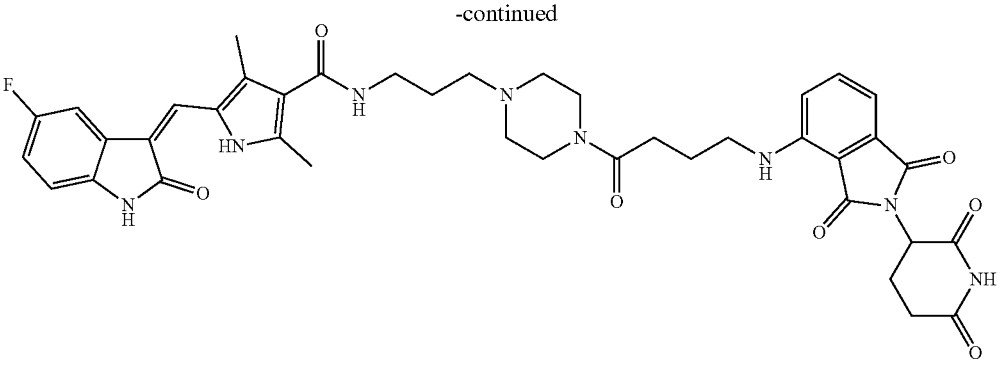

HC58-37

HC58-37 was synthesized following the standard procedure for preparing HC58-18 from Intermediate 2 (13.0 mg, 0.024 mmol, 1.2 equiv), 4-((2-(2,6-dioxopiperidin-3-yl)-1,3-dioxoisoindolin-4-yl)amino)butanoic acid (7.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-37 was obtained as yellow solid in TFA salt form (11.3 mg, 64%). $^1$H NMR (600 MHz, DMSO-$d_6$) δ 13.73 (s, 1H), 11.11 (s, 1H), 10.93 (s, 1H), 7.85-7.75 (m, 2H), 7.73 (s, 1H), 7.60 (t, J=7.8 Hz, 1H), 7.18 (d, J=8.6 Hz, 1H), 7.04 (d, J=7.0 Hz, 1H), 6.94 (td, J=9.1, 2.6 Hz, 1H), 6.86 (dd, J=8.5, 4.5 Hz, 1H), 6.68 (t, J=6.2 Hz, 1H), 5.06 (dd, J=12.8, 5.4 Hz, 1H), 4.56-4.44 (m, 1H), 4.17-4.01 (m, 1H), 3.51 (s, 2H), 3.43-3.27 (m, 7H), 3.19-3.10 (m, 2H), 3.10-3.00 (m, 1H), 3.00-2.84 (m, 3H), 2.63-2.57 (m, 1H), 2.57-2.52 (m, 1H), 2.46 (s, 3H), 2.43 (s, 3H), 2.07-1.99 (m, 1H), 1.96-1.86 (m, 2H), 1.85-1.76 (m, 2H). HRMS calcd for $C_{40}H_{44}FN_8O_7$[M+H$^+$] 767.3317, found 767.3332.

Example 21

Synthesis of HC58-38

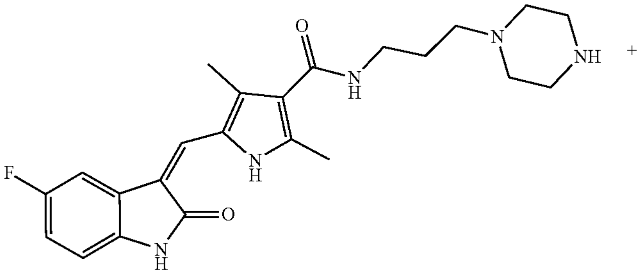

Intermediate 2

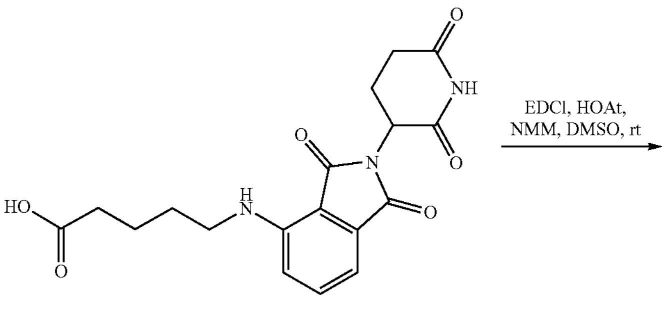

-continued

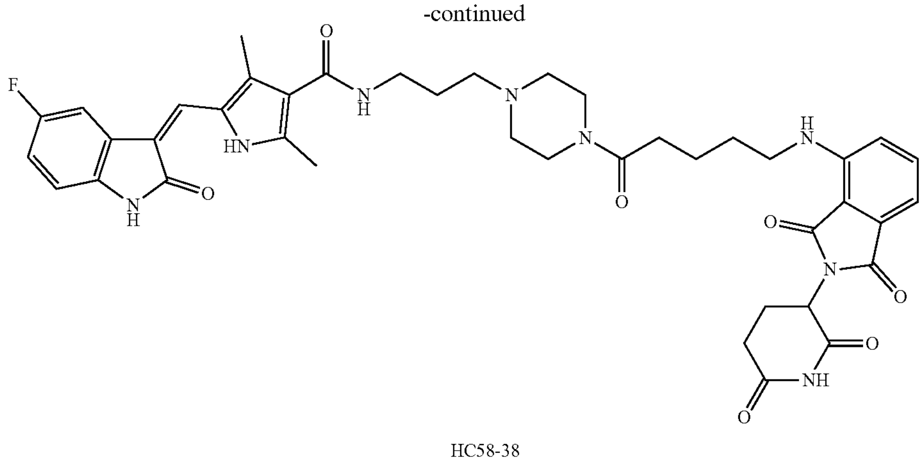

HC58-38

HC58-38 was synthesized following the standard procedure for preparing HC58-18 from Intermediate 2 (13.0 mg, 0.024 mmol, 1.2 equiv), 5-((2-(2,6-dioxopiperidin-3-yl)-1,3-dioxoisoindolin-4-yl)amino)pentanoic acid (7.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-38 was obtained as yellow solid in TFA salt form (11.5 mg, 61%). $^1$H NMR (600 MHz, DMSO-$d_6$) δ 13.72 (s, 1H), 11.11 (s, 1H), 10.93 (s, 1H), 7.86-7.74 (m, 2H), 7.73 (s, 1H), 7.64-7.54 (m, 1H), 7.11 (d, J=8.6 Hz, 1H), 7.03 (d, J=7.0 Hz, 1H), 6.94 (td, J=9.1, 2.7 Hz, 1H), 6.86 (dd, J=8.4, 4.5 Hz, 1H), 6.57 (t, J=5.9 Hz, 1H), 5.06 (dd, J=12.9, 5.4 Hz, 1H), 4.48 (s, 1H), 4.18-3.98 (m, 1H), 3.62-3.24 (m, 7H), 3.16 (d, J=15.7 Hz, 2H), 3.05 (s, 1H), 2.99-2.83 (m, 3H), 2.64-2.56 (m, 1H), 2.53 (d, J=4.6 Hz, 3H), 2.45 (s, 3H), 2.43 (s, 3H), 2.08-2.00 (m, 1H), 1.97-1.87 (m, 2H), 1.66-1.52 (m, 4H). HRMS calcd for $C_{41}H_{46}FN_8O_7$[M+H$^+$] 781.3473, found 781.3478.

Example 22

Synthesis of HC58-39

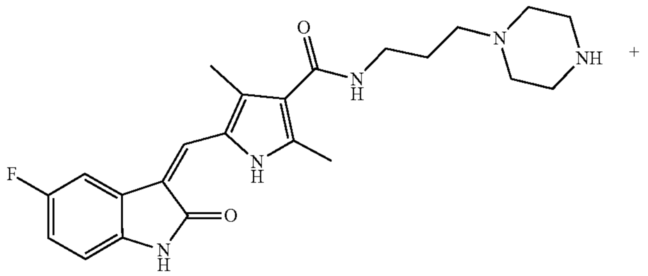

Intermediate 2

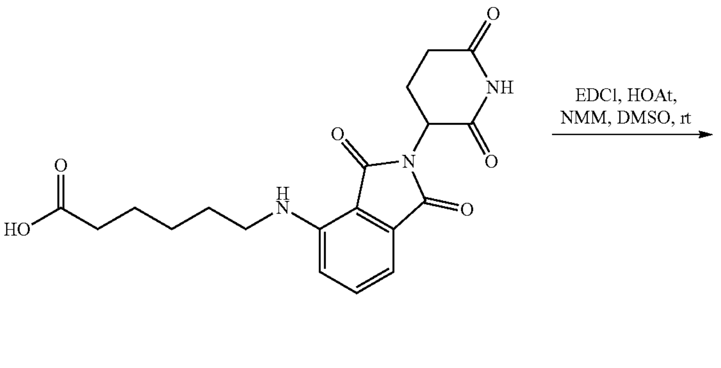

-continued

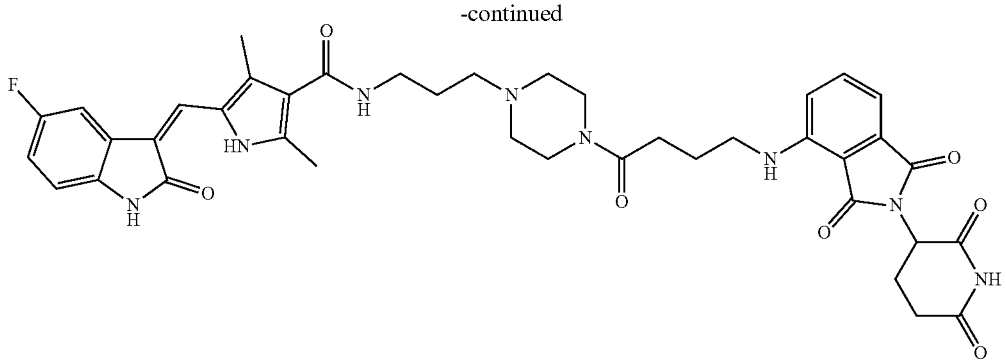

HC58-39

HC58-39 was synthesized following the standard procedure for preparing HC58-18 from Intermediate 2 (13.0 mg, 0.024 mmol, 1.2 equiv), 6-((2-(2,6-dioxopiperidin-3-yl)-1,3-dioxoisoindolin-4-yl)amino)hexanoic acid (7.8 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-39 was obtained as yellow solid in TFA salt form (9.8 mg, 54%). $^1$H NMR (600 MHz, DMSO-$d_6$) δ 13.72 (s, 1H), 11.11 (s, 1H), 10.93 (s, 1H), 7.84-7.76 (m, 2H), 7.73 (s, 1H), 7.59 (t, J=7.8 Hz, 1H), 7.10 (d, J=8.6 Hz, 1H), 7.03 (d, J=7.0 Hz, 1H), 6.94 (td, J=9.0, 2.6 Hz, 1H), 6.86 (dd, J=8.4, 4.5 Hz, 1H), 6.54 (d, J=5.9 Hz, 1H), 5.05 (dd, J=12.9, 5.5 Hz, 1H), 4.55-4.42 (m, 1H), 4.16-4.04 (m, 1H), 3.57-3.42 (m, 2H), 3.40-3.26 (m, 5H), 3.20-3.10 (m, 2H), 3.09-2.99 (m, 1H), 2.98-2.84 (m, 3H), 2.64-2.57 (m, 1H), 2.56-2.50 (m, 1H), 2.45 (s, 3H), 2.43 (s, 3H), 2.40-2.34 (m, 2H), 2.06-1.99 (m, 1H), 1.92 (p, J=7.0 Hz, 2H), 1.66-1.50 (m, 4H), 1.37 (p, J=7.8 Hz, 2H). HRMS calcd for $C_{42}H_{48}FN_8O_7$[M+H$^+$] 795.3630, found 795.3645.

Example 23

Synthesis of HC58-40

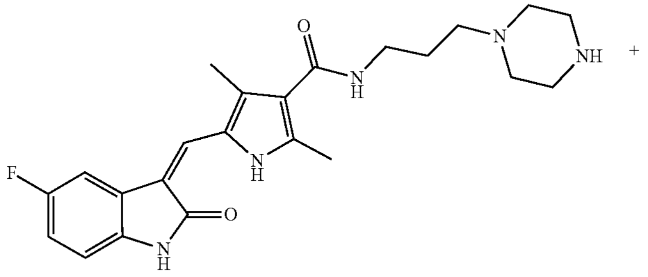

Intermediate 2

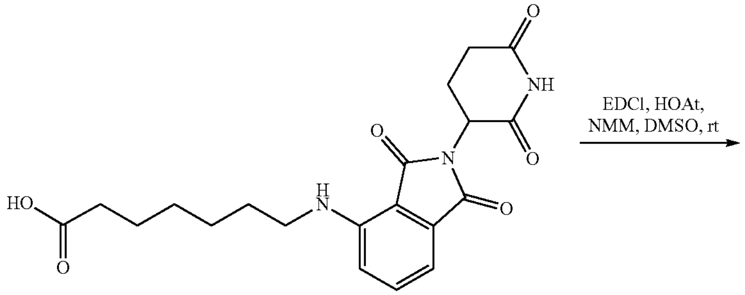

-continued

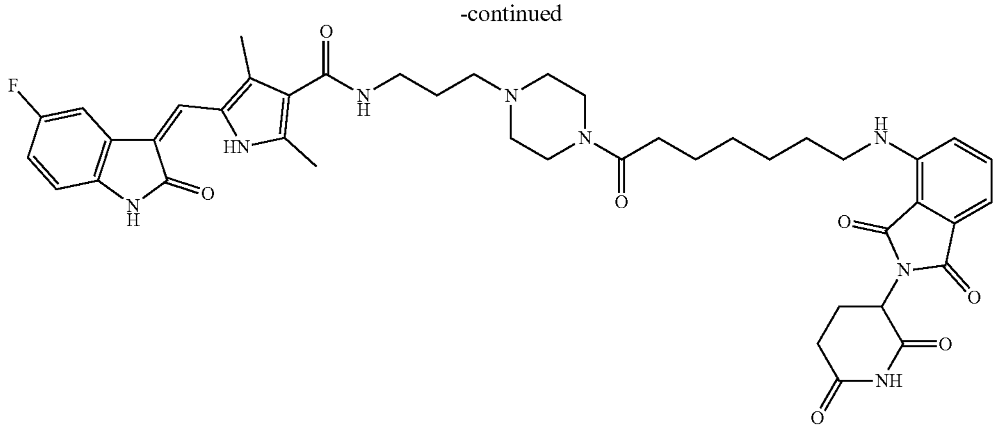

HC58-40

HC58-40 was synthesized following the standard procedure for preparing HC58-18 from Intermediate 2 (13.0 mg, 0.024 mmol, 1.2 equiv), 7-((2-(2,6-dioxopiperidin-3-yl)-1,3-dioxoisoindolin-4-yl)amino)heptanoic acid (8.0 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-40 was obtained as yellow solid in TFA salt form (7.8 mg, 42%). $^1$H NMR (600 MHz, DMSO-$d_6$) δ 13.73 (s, 1H), 11.11 (s, 1H), 10.93 (s, 1H), 7.84-7.76 (m, 2H), 7.73 (s, 1H), 7.58 (dd, J=9.2, 6.5 Hz, 1H), 7.10 (d, J=8.6 Hz, 1H), 7.03 (d, J=7.0 Hz, 1H), 6.94 (td, J=8.9, 2.5 Hz, 1H), 6.86 (dd, J=8.4, 4.5 Hz, 1H), 6.54 (s, 1H), 5.05 (dd, J=12.9, 5.5 Hz, 1H), 4.47 (s, 1H), 4.08 (d, J=14.3 Hz, 1H), 3.30 (p, J=6.1 Hz, 7H), 3.21-3.11 (m, 2H), 3.09-3.00 (m, 1H), 2.98-2.84 (m, 3H), 2.64-2.51 (m, 2H), 2.46 (s, 3H), 2.43 (s, 3H), 2.40-2.31 (m, 2H), 2.07-1.99 (m, 1H), 1.96-1.87 (m, 2H), 1.64-1.45 (m, 4H), 1.34 (d, J=10.1 Hz, 4H). HRMS calcd for $C_{43}H_{50}FN_8O_7$[M+H$^+$] 809.3786, found 809.3796.

Example 24

Synthesis of HC58-41

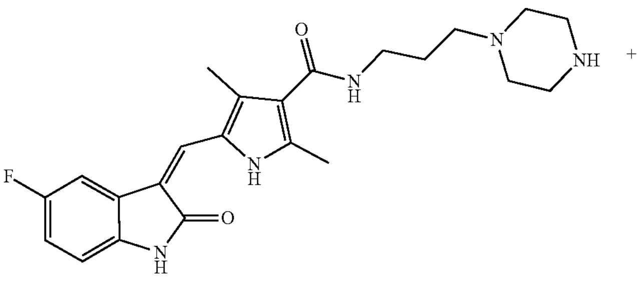

Intermediate 2

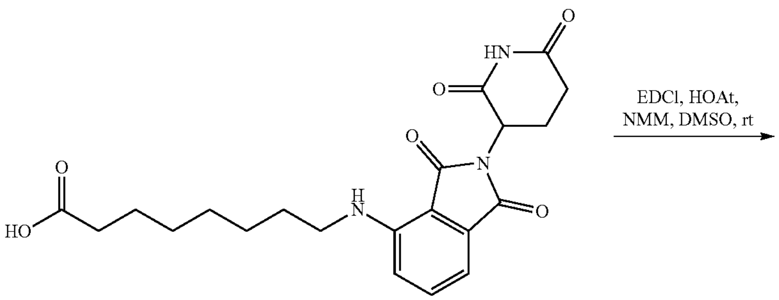

-continued

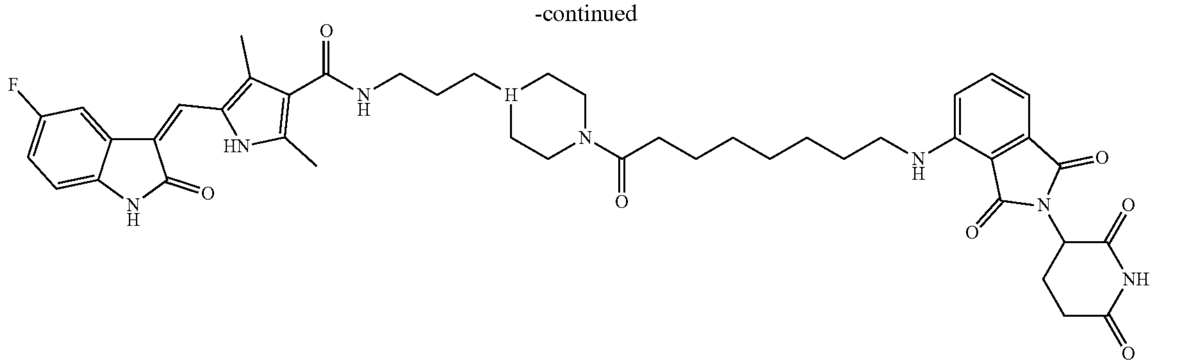

HC58-41

HC58-41 was synthesized following the standard procedure for preparing HC58-18 from Intermediate 2 (13.0 mg, 0.024 mmol, 1.2 equiv), 8-((2-(2,6-dioxopiperidin-3-yl)-1,3-dioxoisoindolin-4-yl)amino)octanoic acid (8.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-41 was obtained as yellow solid in TFA salt form (8.1 mg, 43%). $^1$H NMR (600 MHz, Methanol-d$_4$) δ 13.60 (s, 1H), 7.86 (s, 1H), 7.56-7.52 (m, 2H), 7.40-7.36 (m, 1H), 7.03 (d, J=7.1 Hz, 1H), 7.01 (d, J=8.6 Hz, 1H), 6.87-6.84 (m, 2H), 5.05 (dd, J=12.7, 5.5 Hz, 1H), 4.60 (s, 2H), 3.62 (s, 2H), 3.56 (t, J=5.2 Hz, 2H), 3.44 (t, J=6.8 Hz, 2H), 3.33-3.28 (m, 6H), 2.86 (ddd, J=17.3, 13.9, 5.2 Hz, 1H), 2.79-2.68 (m, 2H), 2.53 (t, J=7.3 Hz, 2H), 2.49 (s, 3H), 2.45 (s, 3H), 2.39 (t, J=7.6 Hz, 2H), 2.16-2.09 (m, 1H), 1.86 (p, J=7.0 Hz, 2H), 1.67 (p, J=7.0 Hz, 2H), 1.64-1.57 (m, 2H), 1.49-1.35 (m, 4H). HRMS calcd for $C_{44}H_{52}FN_8O_7$ [M+H$^+$] 823.3943, found 823.3952.

Example 25

Synthesis of HC58-43

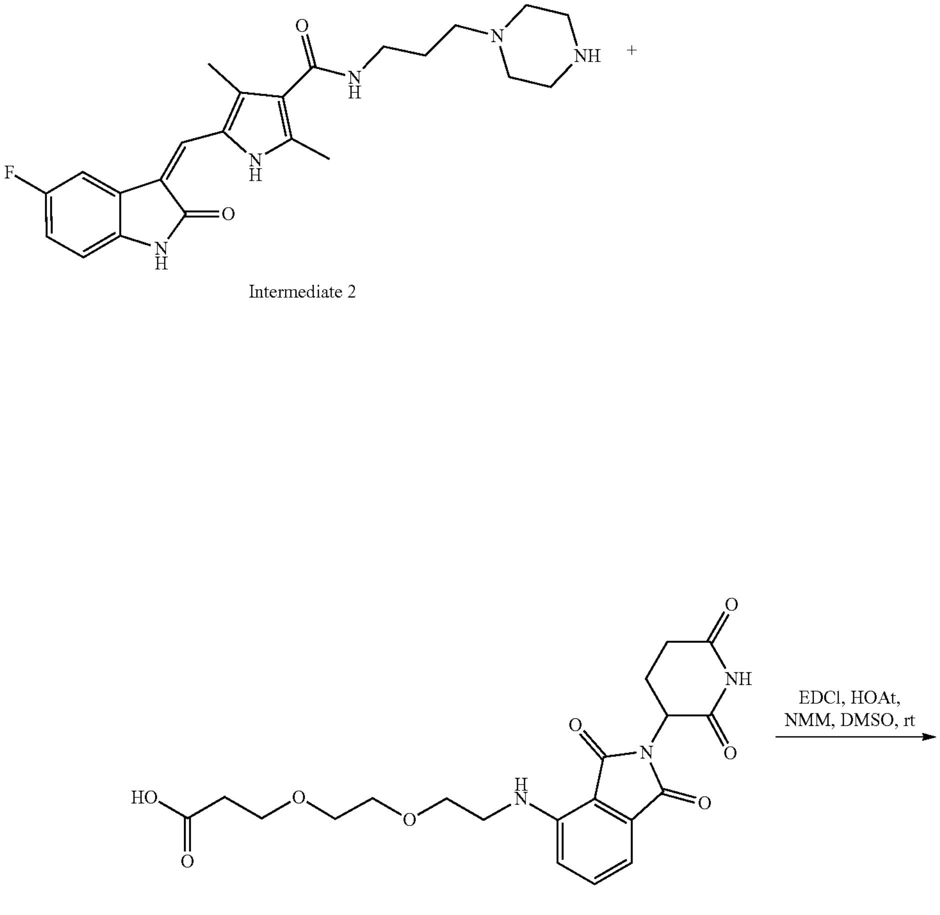

-continued

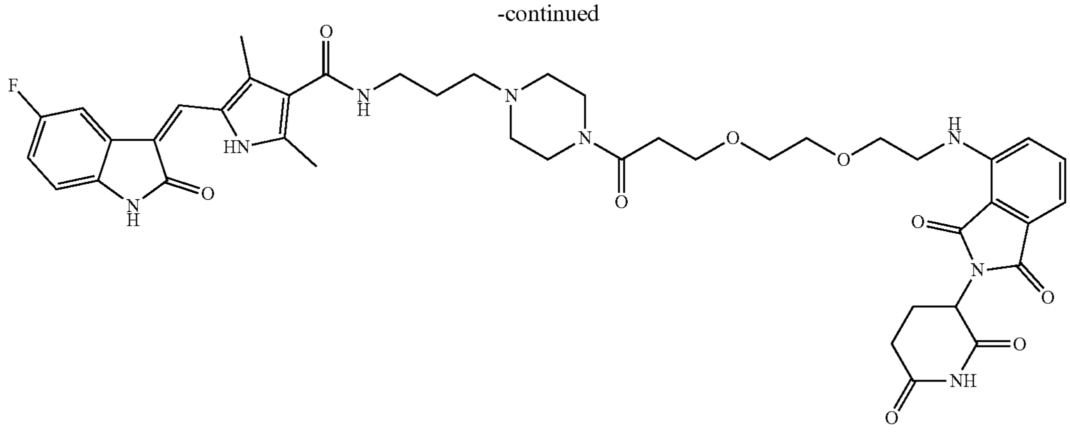

HC58-43

HC58-43 was synthesized following the standard procedure for preparing HC58-18 from Intermediate 2 (13.0 mg, 0.024 mmol, 1.2 equiv), 3-(2-(2-((2-(2,6-dioxopiperidin-3-yl)-1,3-dioxoisoindolin-4-yl)amino)ethoxy)ethoxy)propanoic acid (8.7 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-43 was obtained as yellow solid in TFA salt form (6.9 mg, 36%). $^{1}$H NMR (600 MHz, DMSO-$d_6$) δ 13.72 (s, 1H), 11.11 (s, 1H), 10.93 (s, 1H), 7.84-7.75 (m, 2H), 7.73 (s, 1H), 7.59 (dd, J=8.6, 7.1 Hz, 1H), 7.15 (d, J=8.6 Hz, 1H), 7.05 (d, J=7.0 Hz, 1H), 6.94 (td, J=9.0, 2.6 Hz, 1H), 6.86 (dd, J=8.5, 4.5 Hz, 1H), 6.61 (s, 1H), 5.06 (dd, J=12.9, 5.5 Hz, 1H), 4.51-4.42 (m, 1H), 4.09 (d, J=14.6 Hz, 1H), 3.68-3.59 (m, 4H), 3.59-3.27 (m, 11H), 3.18-3.10 (m, 2H), 3.07-2.98 (m, 1H), 2.96-2.83 (m, 3H), 2.71-2.47 (m, 4H), 2.45 (s, 3H), 2.43 (s, 3H), 2.08-2.00 (m, 1H), 1.96-1.86 (m, 2H). HRMS calcd for $C_{43}H_{50}FN_8O_9$[M+H$^+$] 841.3685, found 841.3692.

Example 26

Synthesis of HC58-44

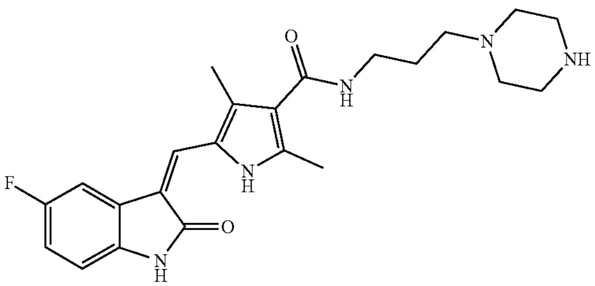

Intermediate 2

+

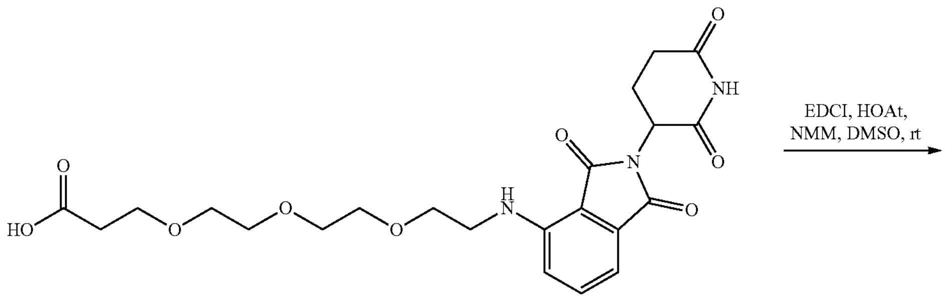

-continued

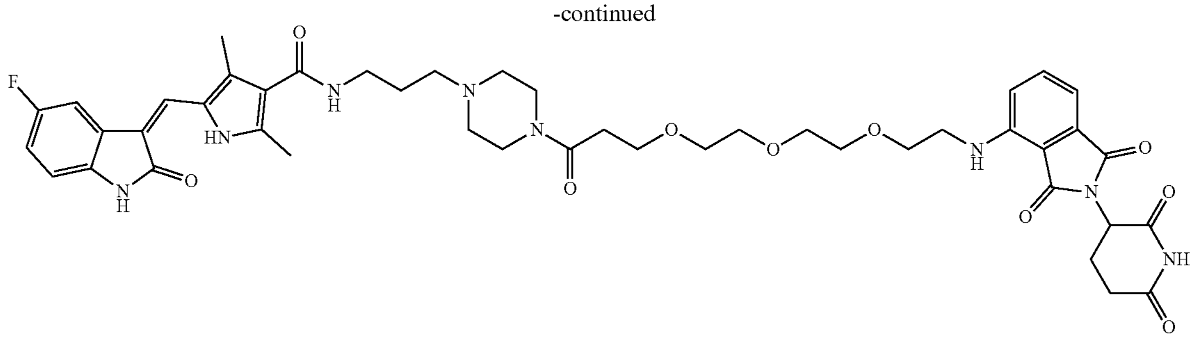

HC58-44

HC58-44 was synthesized following the standard procedure for preparing HC58-18 from Intermediate 2 (13.0 mg, 0.024 mmol, 1.2 equiv), 3-(2-(2-(2-((2-(2,6-dioxopiperidin-3-yl)-1,3-dioxoisoindolin-4-yl)amino)ethoxy)ethoxy)ethoxy)propanoic acid (9.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-44 was obtained as yellow solid in TFA salt form (90 mg, 45%). $^1$H NMR (600 MHz, DMSO-$d_6$) δ 13.72 (s, 1H), 11.11 (s, 1H), 10.93 (s, 1H), 7.82-7.75 (m, 2H), 7.73 (s, 1H), 7.58 (dd, J=8.5, 7.1 Hz, 1H), 7.14 (d, J=8.6 Hz, 1H), 7.04 (d, J=7.0 Hz, 1H), 6.94 (td, J=9.1, 2.6 Hz, 1H), 6.86 (dd, J=8.4, 4.5 Hz, 1H), 6.60 (s, 1H), 5.06 (dd, J=12.9, 5.4 Hz, 1H), 4.47 (s, 1H), 4.11 (d, J=14.4 Hz, 1H), 3.72-3.26 (m, 19H), 3.19-3.11 (m, 2H), 3.10-3.00 (m, 1H), 2.98-2.84 (m, 3H), 2.70-2.49 (m, 4H), 2.45 (s, 3H), 2.43 (s, 3H), 2.08-1.99 (m, 1H), 1.98-1.87 (m, 2H). HRMS calcd for $C_{45}H_{54}FN_8O_{10}$ [M+H$^+$]885.3947, found 885.3955.

Example 27

Synthesis of HC58-45

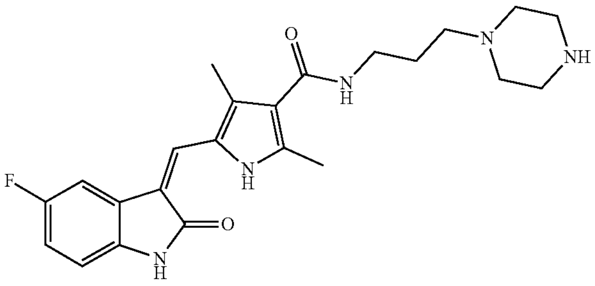

Intermediate 2

+

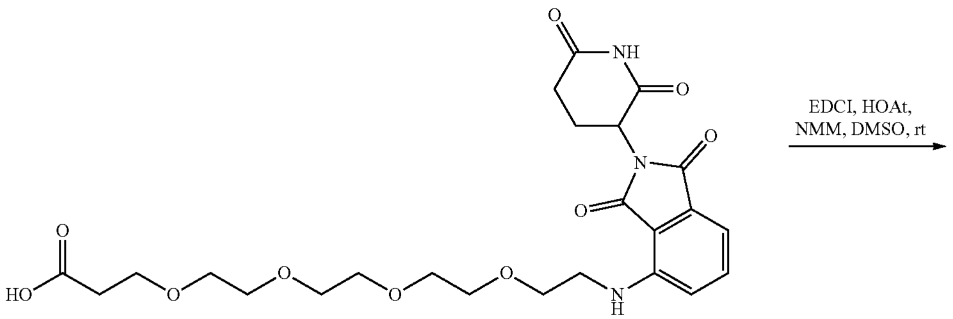

-continued

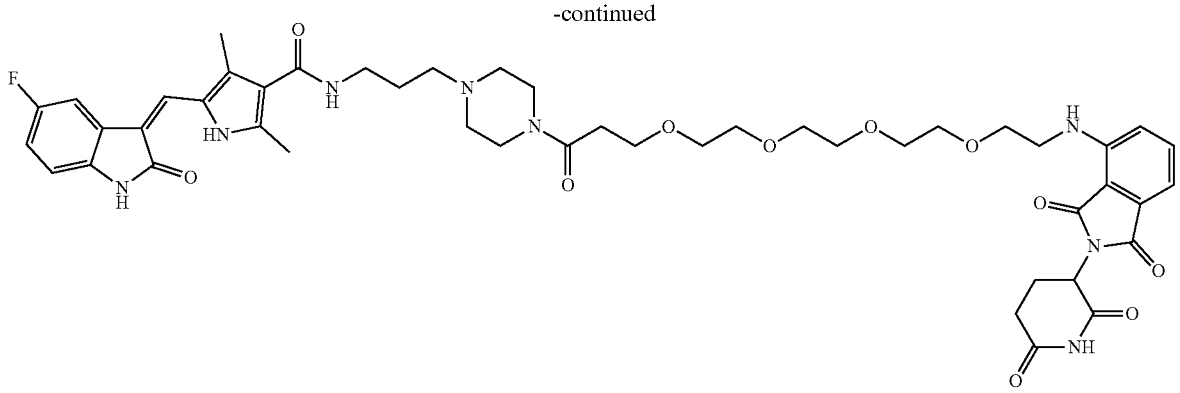

HC58-45

HC58-45 was synthesized following the standard procedure for preparing HC58-18 from Intermediate 2 (13.0 mg, 0.024 mmol, 1.2 equiv), 1-((2-(2,6-dioxopiperidin-3-yl)-1,3-dioxoisoindolin-4-yl)amino)-3,6,9,12-tetraoxapentadecan-15-oic acid (10.4 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-45 was obtained as yellow solid in TFA salt form (6.9 mg, 33%). $^1$H NMR (600 MHz, DMSO-$d_6$) δ 13.72 (s, 1H), 11.11 (s, 1H), 10.93 (s, 1H), 7.82-7.75 (m, 2H), 7.73 (s, 1H), 7.58 (t, J=7.8 Hz, 1H), 7.14 (d, J=8.6 Hz, 1H), 7.04 (d, J=7.0 Hz, 1H), 6.94 (td, J=9.1, 2.5 Hz, 1H), 6.86 (dd, J=8.5, 4.5 Hz, 1H), 6.60 (s, 1H), 5.06 (dd, J=12.9, 5.4 Hz, 1H), 4.47 (s, 1H), 4.12 (d, J=14.6 Hz, 1H), 3.65-3.42 (m, 20H), 3.42-3.26 (m, 3H), 3.19-3.12 (m, 2H), 3.09-2.98 (m, 1H), 2.98-2.83 (m, 3H), 2.73-2.52 (m, 4H), 2.45 (s, 3H), 2.43 (s, 3H), 2.06-1.99 (m, 1H), 1.96-1.87 (m, 2H). HRMS calcd for $C_{47}H_{58}FN_8O_{11}$ [M+H$^+$] 929.4209, found 929.4216.

Example 28

Synthesis of HC58-46

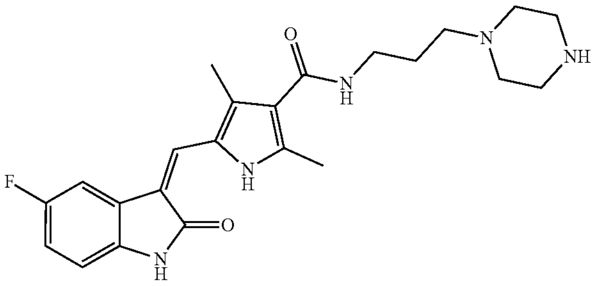

Intermediate 2

+

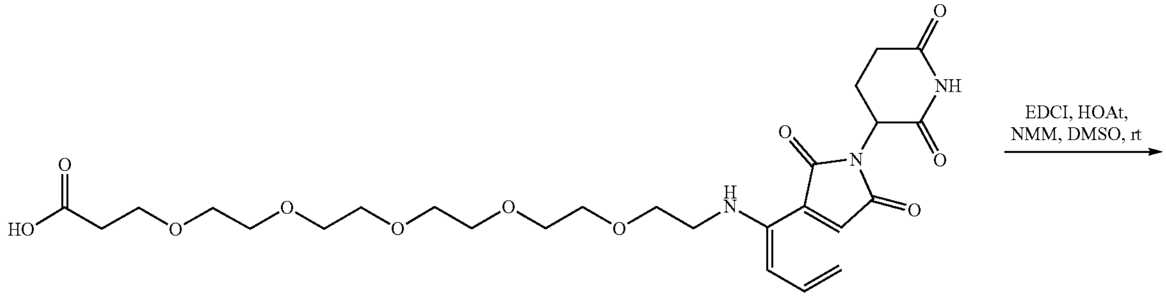

-continued

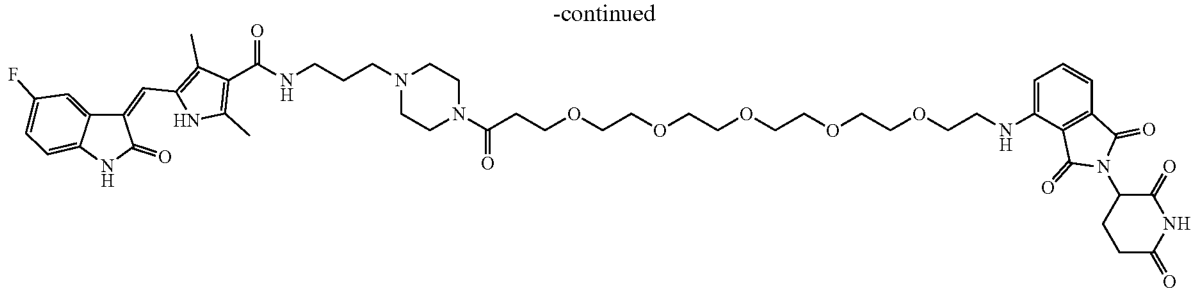

HC58-46

HC58-46 was synthesized following the standard procedure for preparing HC58-18 from Intermediate 2 (13.0 mg, 0.024 mmol, 1.2 equiv), 1-((2-(2,6-dioxopiperidin-3-yl)-1,3-dioxoisoindolin-4-yl)amino)-3,6,9,12,15-pentaoxaoctadecan-18-oic acid (11.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). HC58-46 was obtained as yellow solid in TFA salt form (8.9 mg, 41%). $^1H$ NMR (600 MHz, DMSO-$d_6$) δ 13.72 (s, 1H), 11.11 (s, 1H), 10.93 (s, 1H), 7.82-7.75 (m, 2H), 7.73 (s, 1H), 7.58 (dd, J=8.6, 7.0 Hz, 1H), 7.14 (d, J=8.7 Hz, 1H), 7.04 (d, J=7.1 Hz, 1H), 6.96-6.90 (m, 1H), 6.86 (dd, J=8.4, 4.6 Hz, 1H), 6.60 (t, J=5.9 Hz, 1H), 5.06 (dd, J=12.9, 5.5 Hz, 1H), 4.47 (s, 1H), 4.12 (d, J=14.5 Hz, 1H), 3.62 (td, J=6.0, 5.4, 3.9 Hz, 4H), 3.59-3.34 (m, 21H), 3.30 (q, J=6.5 Hz, 2H), 3.21-3.11 (m, 2H), 3.09-2.99 (m, 1H), 2.98-2.84 (m, 3H), 2.71-2.51 (m, 4H), 2.45 (s, 3H), 2.43 (s, 3H), 2.09-1.98 (m, 1H), 1.97-1.88 (m, 2H). HRMS calcd for $C_{49}H_{62}FN_8O_{12}$ [M+H$^+$] 973.4471, found 973.4479.

Example 29

Synthesis of Intermediate 3

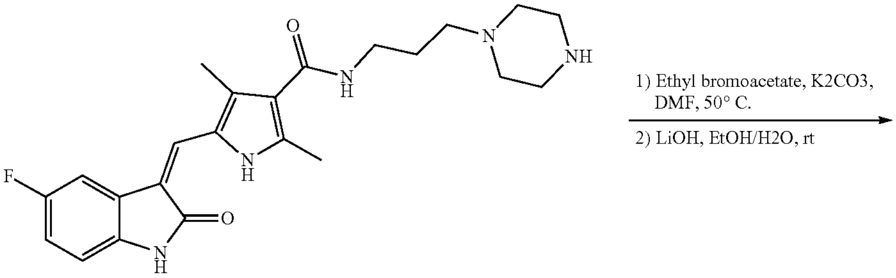

Intermediate 2

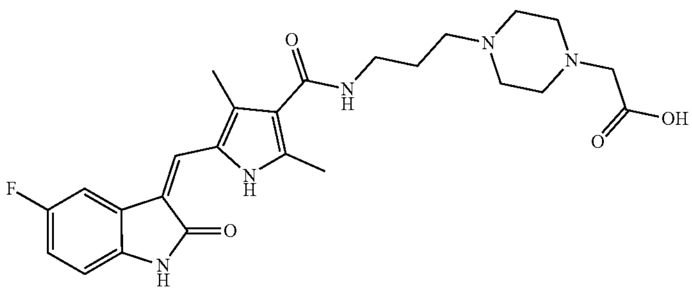

Intermediate 3

To a solution of intermediate 2 (540 mg, 0.83 mmol) in DMF (10 mL) was added potassium carbonate (280 mg, 2.03 mmol, 2.4 equiv) and ethyl bromoacetate (334 mg, 2.00 mmol, 2.41 equiv). Then the mixture was stirred at 50° C. overnight. Water (20 mL) was added to quench the reaction. The mixture was extracted with ethyl acetate (3×20 mL). The organic layer was combined and washed with brine. Dried over $Na_2SO_4$, filtered and evaporated. The resulting residue was purified by reverse phase C18 column (10%-100% methanol/0.1% TFA in $H_2O$) to afford yellow solid in TFA salt form. The obtained yellow solid was dissolved in EtOH/$H_2O$ (5:1). To the resulting solution was added lithium hydroxide (60 mg, 2.5 mmol, 3 equiv). After being stirred overnight at room temperature, the reaction mixture was concentrated and the residue was purified by reverse phase C18 column (10%-100% methanol/0.1% TFA in $H_2O$) to afford intermediate 3 as yellow solid in TFA salt form (395 mg, 67% yield for two steps). $^1H$ NMR (600 MHz, Methanol-$d_4$) δ 13.73 (s, 1H), 7.63 (s, 1H), 7.46 (d, J=8.9 Hz, 1H), 6.93-6.85 (m, 2H), 3.51 (t, J=6.6 Hz, 2H), 3.45 (s, 2H), 3.26-3.19 (m, 2H), 3.30-2.80 (m, 8H), 2.53 (s, 3H), 2.49 (s, 3H), 2.11-2.03 (m, 2H). ESI m/z=512.3 [M+H$^+$].

Example 30

Synthesis of HC58-53

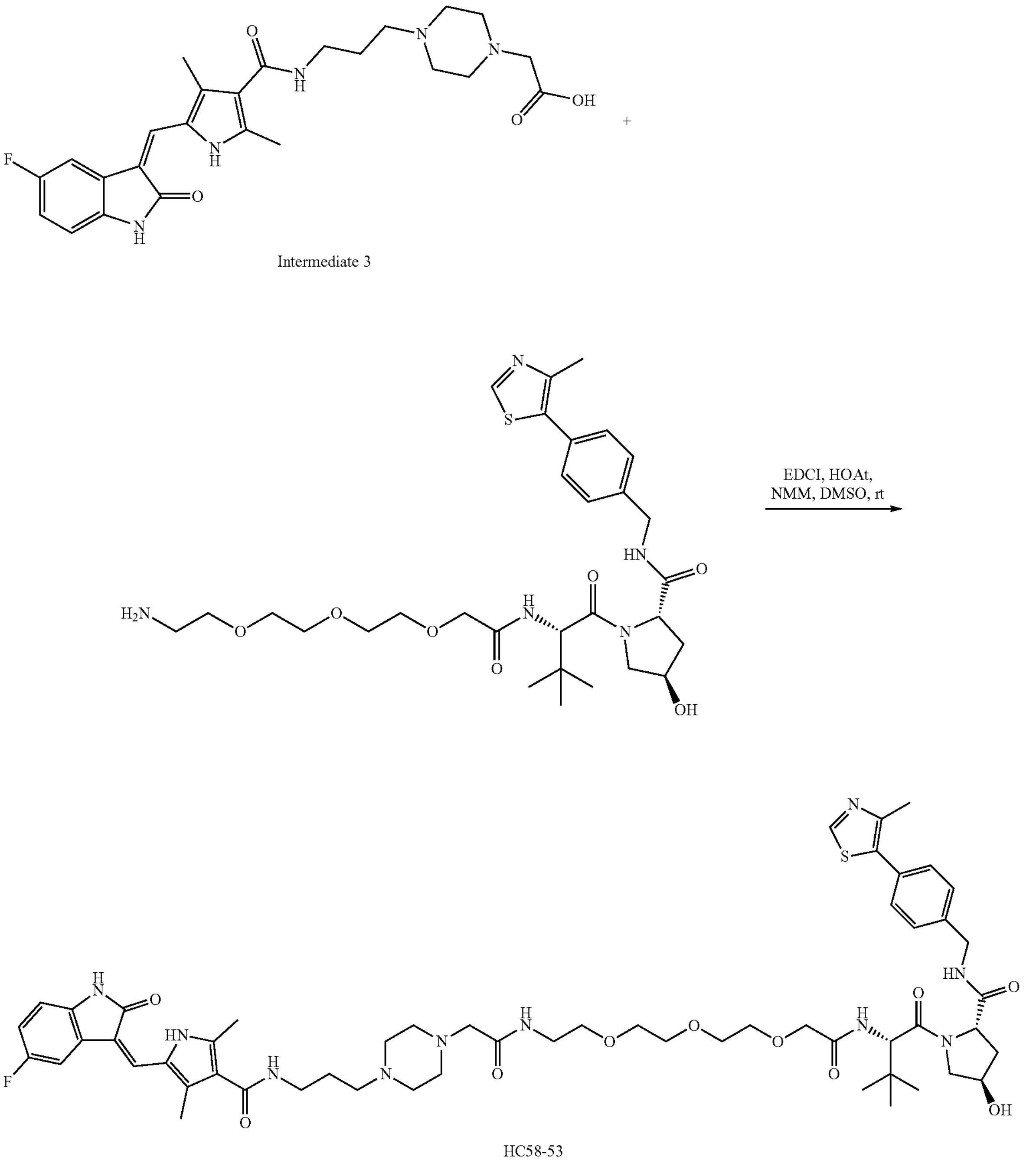

Intermediate 3

HC58-53

To a solution of Intermediate 3 (14.2 mg, 0.02 mmol, 1.0 equiv) in DMSO (1 mL) were added (2S,4R)-1-((S)-14-amino-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (16.9 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (12.1 mg, 0.12 mmol, 6.0 equiv). After being stirred overnight at room temperature, the resulting mixture was purified by preparative HPLC (10%-100% methanol/0.1% TFA in $H_2O$) to afford HC58-53 as yellow solid in TFA salt form (11.8 mg, 45%). $^1$H NMR (600 MHz, Methanol-$d_4$) δ 13.68 (s, 1H), 8.97 (s, 1H), 7.69

(d, J=9.3 Hz, 1H), 7.56 (s, 1H), 7.47-7.38 (m, 5H), 6.97-6.79 (m, 2H), 4.74-4.67 (m, 1H), 4.59 (dd, J=9.4, 7.5 Hz, 1H), 4.55-4.48 (m, 2H), 4.38 (d, J=15.4 Hz, 1H), 4.12-4.06 (m, 2H), 3.89 (d, J=11.1 Hz, 1H), 3.81 (dt, J=11.0, 3.2 Hz, 1H), 3.77-3.60 (m, 10H), 3.59-3.39 (m, 8H), 3.31-3.20 (m, 4H), 3.12-2.86 (m, 4H), 2.50 (s, 3H), 2.49 (s, 3H), 2.47 (s, 3H), 2.31-2.22 (m, 1H), 2.09 (tdd, J=13.2, 9.7, 4.1 Hz, 3H), 1.06 (d, J=1.7 Hz, 9H). HRMS calcd for $C_{55}H_{74}FN_{10}O_{10}S$ [M+H$^+$] 1085.5294, found 1085.5299.

Example 31

Synthesis of HC58-57

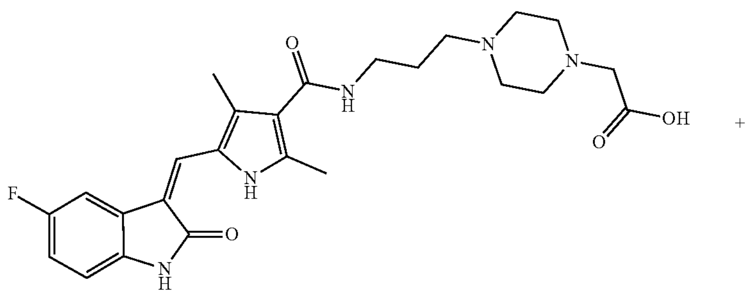

Intermediate 3

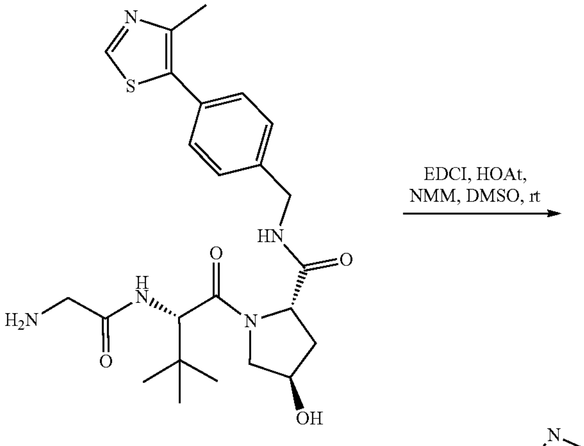

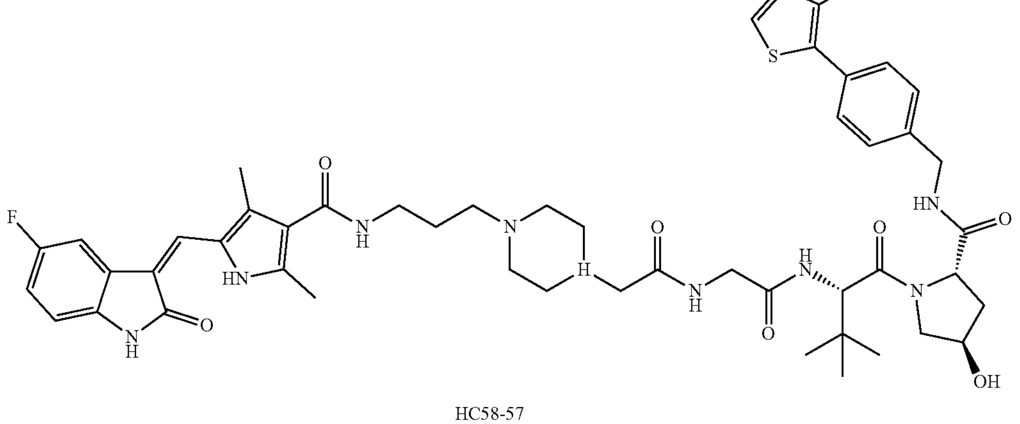

HC58-57

HC58-57 was synthesized following the standard procedure for preparing HC58-53 from Intermediate 3 (14.2 mg, 0.02 mmol, 1.0 equiv), (2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide (14.3 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-57 was obtained as yellow solid in TFA salt form (10.2 mg, 43%). $^1$H NMR (600 MHz, Methanol-$d_4$) δ 13.67 (s, 1H), 9.07 (s, 1H), 7.96 (s, 1H), 7.55 (s, 1H), 7.51-7.37 (m, 5H), 6.96-6.80 (m, 2H), 4.67-4.63 (m, 1H), 4.57 (t, J=8.2 Hz, 1H), 4.54-4.48 (m, 2H), 4.38 (d, J=15.5 Hz, 1H), 4.03 (d, J=16.8 Hz, 1H), 4.00-3.95 (m, 1H), 3.89 (d, J=10.9 Hz, 1H), 3.81 (dd, J=11.0, 3.8 Hz, 1H), 3.56-3.38 (m, 8H), 3.25 (t, J=7.6 Hz, 2H), 3.14-2.90 (m, 4H), 2.50 (s, 3H), 2.49 (s, 3H), 2.47 (s, 3H), 2.29-2.21 (m, 1H), 2.14-2.01 (m, 3H), 1.06 (s, 9H). HRMS calcd for $C_{49}H_{62}FN_{10}O_7S$ [M+H$^+$]953.4508, found 953.4516.

Example 32

Synthesis of HC58-58

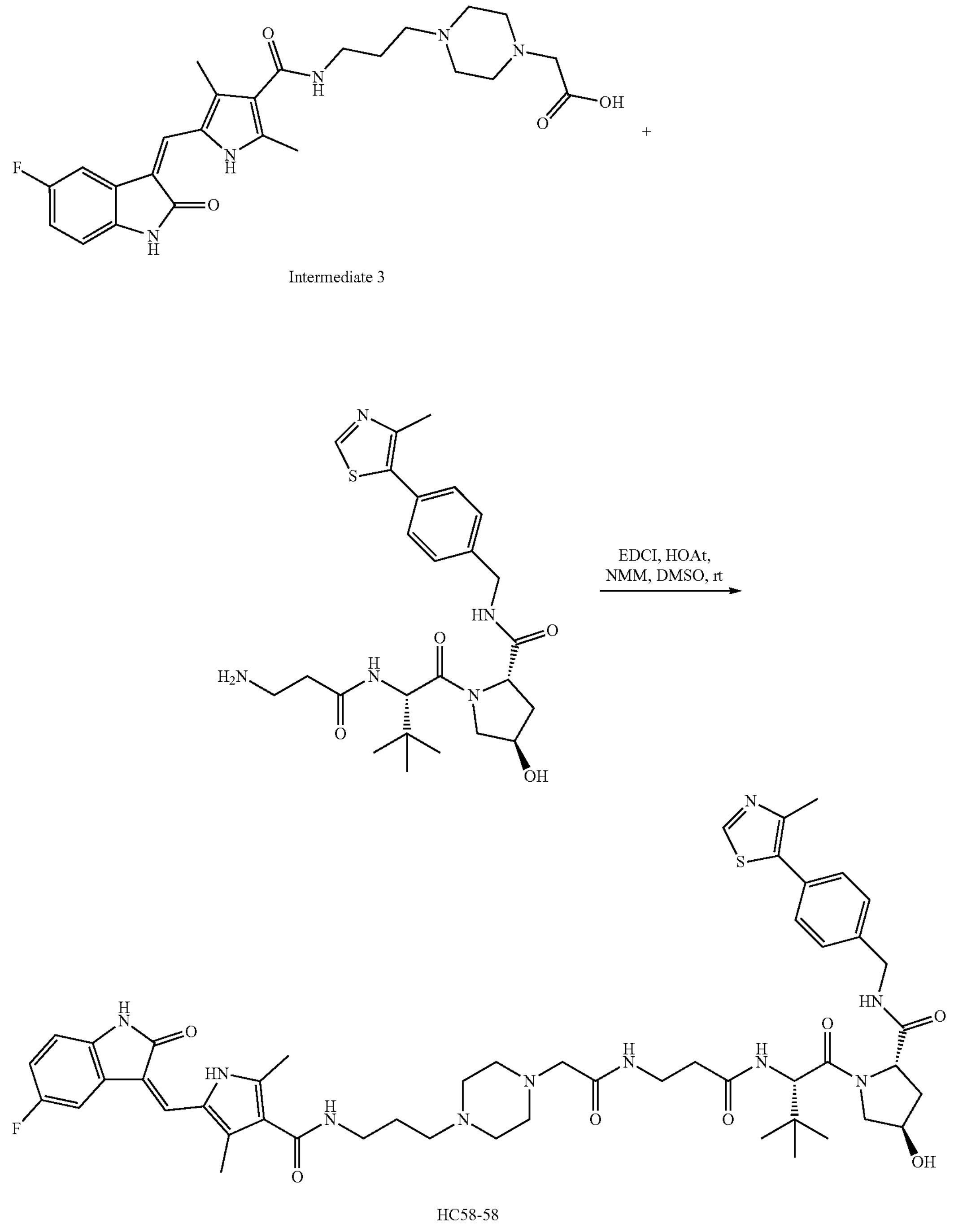

HC58-58 was synthesized following the standard procedure for preparing HC58-53 from Intermediate 3 (14.2 mg, 0.02 mmol, 1.0 equiv), (2S,4R)-1-((S)-2-(3-aminopropanamido)-3,3-dimethylbutanoyl)-4-hydroxy-N-(4-(4-methylthiazol-5-yl)benzyl)pyrrolidine-2-carboxamide (14.6 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-58 was obtained as yellow solid in TFA salt form (12.2 mg, 51%). $^1H$ NMR (600 MHz, Methanol-$d_4$) δ 13.68 (s, 1H), 9.01 (s, 1H), 8.00 (d, J=8.6 Hz, 1H), 7.55 (s, 1H), 7.50-7.38 (m, 5H), 6.94-6.82 (m, 2H), 4.65-4.56 (m, 2H), 4.54-4.48 (m, 2H), 4.37 (d, J=15.5 Hz, 1H), 3.95 (d, J=10.9 Hz, 1H), 3.81 (dd, J=10.8, 3.9 Hz, 1H), 3.58-3.36 (m, 8H), 3.29-3.20 (m, 4H), 3.14-2.81 (m, 4H), 2.58-2.51 (m, 2H), 2.50 (s, 3H), 2.48 (s, 3H), 2.46 (s, 3H), 2.32-2.23 (m, 1H), 2.14-2.05 (m, 3H), 1.06 (s, 9H). HRMS calcd for $C_{50}H_{64}FN_{10}O_7S$ [M+H$^+$] 967.4664, found 967.4672.

Example 33

Synthesis of HC58-59

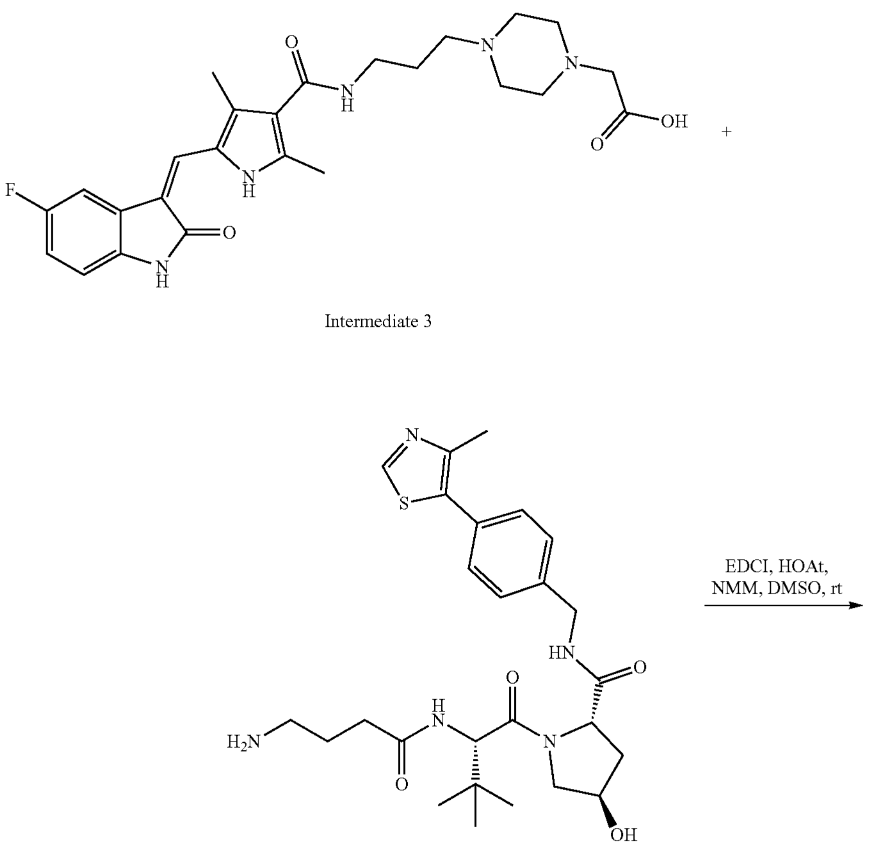

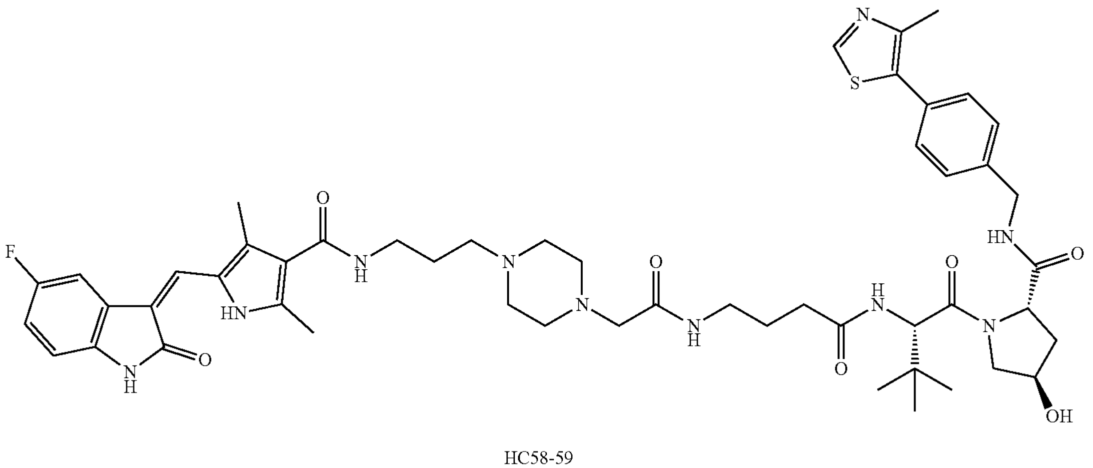

HC58-59

HC58-59 was synthesized following the standard procedure for preparing HC58-53 from Intermediate 3 (14.2 mg, 0.02 mmol, 1.0 equiv), (2S,4R)-1-((S)-2-(4-aminobutanamido)-3,3-dimethylbutanoyl)-4-hydroxy-N-(4-(4-methylthiazol-5-yl)benzyl)pyrrolidine-2-carboxamide (14.9 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-59 was obtained as yellow solid in TFA salt form (8.9 mg, 37%). $^1$H NMR (600 MHz, Methanol-$d_4$) δ 13.68 (s, 1H), 9.03 (s, 1H), 7.57 (s, 1H), 7.47 (d, J=8.0 Hz, 2H), 7.44-7.38 (m, 3H), 6.92-6.84 (m, 2H), 4.64 (s, 1H), 4.59 (dd, J=9.1, 7.6 Hz, 1H), 4.56-4.49 (m, 2H), 4.38 (d, J=15.5 Hz, 1H), 3.93 (d, J=11.0 Hz, 1H), 3.82 (dd, J=11.0, 3.9 Hz, 1H), 3.51 (t, J=6.4 Hz, 2H), 3.49-3.39 (m, 4H), 3.31-3.21 (m, 6H), 3.09-2.90 (m, 4H), 2.51 (s, 3H), 2.49 (s, 3H), 2.47 (s, 3H), 2.41-2.28 (m, 2H), 2.27-2.22 (m, 1H), 2.13-2.05 (m, 3H), 1.91-1.78 (m, 2H), 1.06 (s, 9H). HRMS calcd for $C_{51}H_{66}FN_{10}O_7S$ [M+H$^+$] 981.4821, found 981.4833.

Example 34

Synthesis of HC58-60

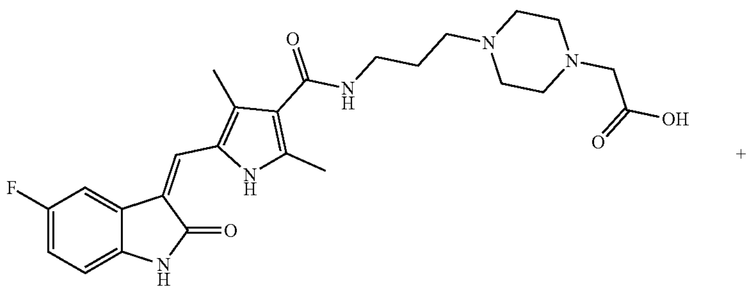

Intermediate 3

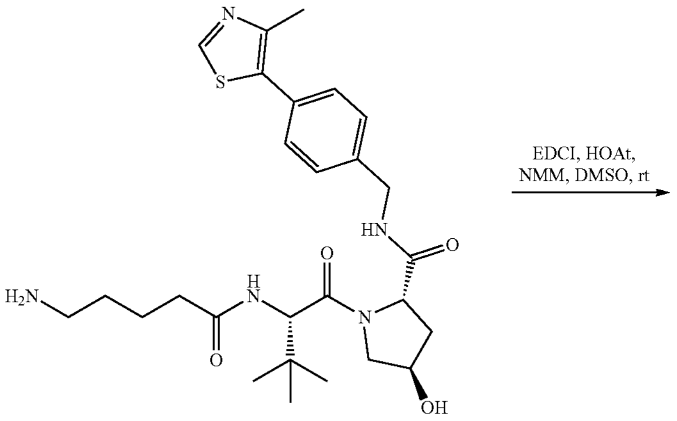

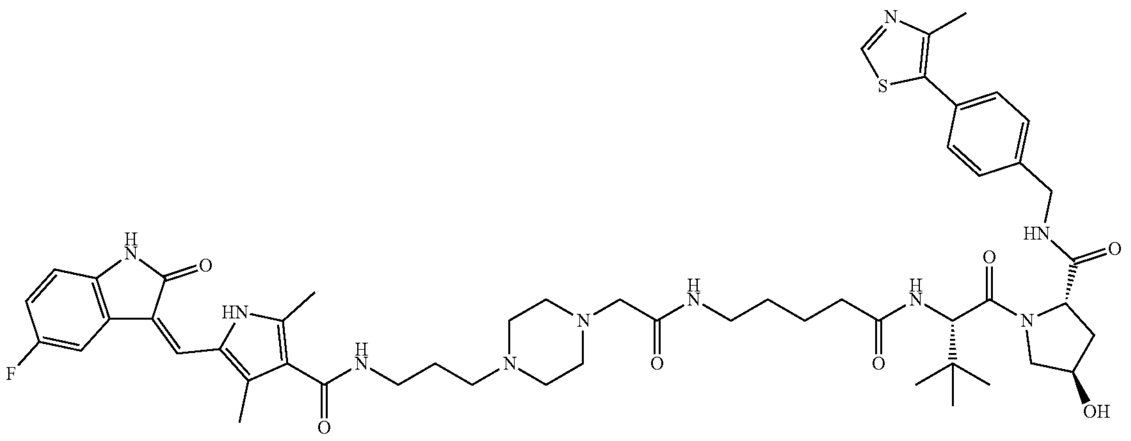

HC58-60

HC58-60 was synthesized following the standard procedure for preparing HC58-53 from Intermediate 3 (14.2 mg, 0.02 mmol, 1.0 equiv), (2S,4R)-1-((S)-2-(5-aminopentanamido)-3,3-dimethylbutanoyl)-4-hydroxy-N-(4-(4-methylthiazol-5-yl)benzyl)pyrrolidine-2-carboxamide (11.3 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-60 was obtained as yellow solid in TFA salt form (11.7 mg, 48%). $^1$H NMR (600 MHz, Methanol-$d_4$) δ 13.71 (s, 1H), 8.94 (s, 1H), 7.87 (d, J=8.9 Hz, 1H), 7.59 (s, 1H), 7.46 (d, J=8.2 Hz, 2H), 7.45-7.40 (m, 3H), 6.95-6.79 (m, 2H), 4.66-4.62 (m, 1H), 4.57 (t, J=8.3 Hz, 1H), 4.54-4.48 (m, 2H), 4.37 (d, J=15.4 Hz, 1H), 3.91 (d, J=11.0 Hz, 1H), 3.82 (dd, J=10.9, 3.9 Hz, 1H), 3.57-3.35 (m, 6H), 3.29-3.21 (m, 6H), 3.11-2.83 (m, 4H), 2.52 (s, 3H), 2.48 (s, 3H), 2.48 (s, 3H), 2.36-2.29 (m, 2H), 2.26-2.20 (m, 1H), 2.14-2.05 (m, 3H), 1.74-1.60 (m, 2H), 1.59-1.52 (m, 2H), 1.05 (s, 9H). HRMS calcd for $C_{52}H_{68}FN_{10}O_7S$ [M+H$^+$] 995.4977, found 995.4990.

Example 35

Synthesis of HC58-63

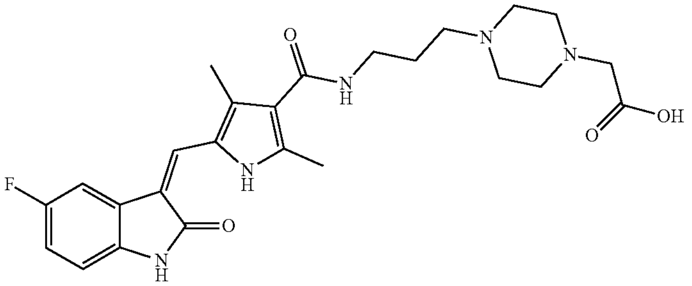

Intermediate 3

+

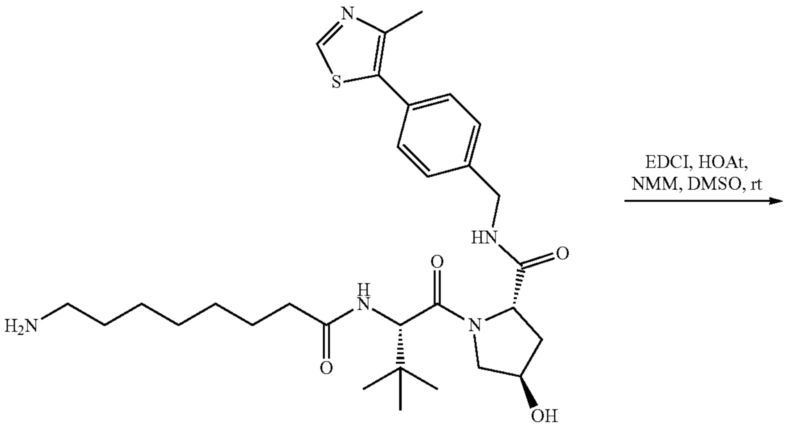

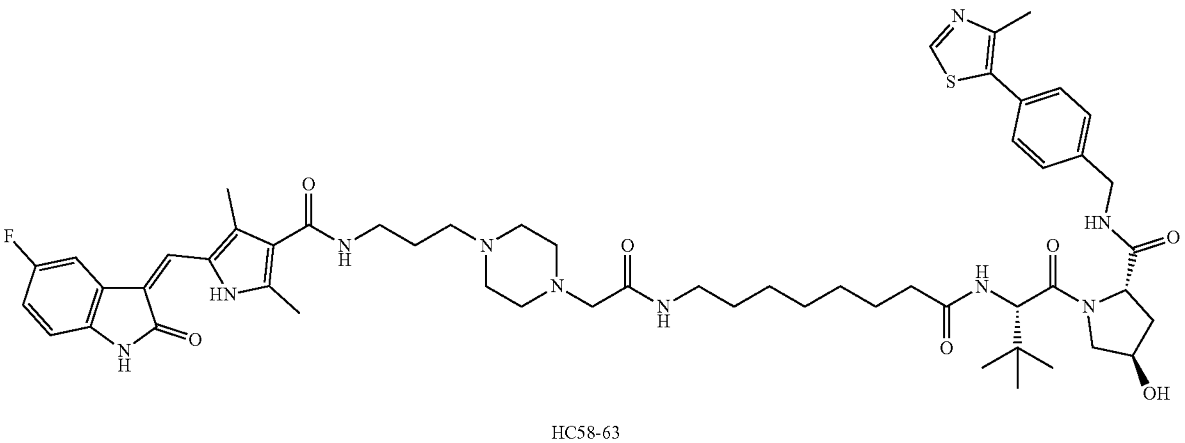

HC58-63

HC58-63 was synthesized following the standard procedure for preparing HC58-53 from Intermediate 3 (14.2 mg, 0.02 mmol, 1.0 equiv), (2S,4R)-1-((S)-2-(8-aminooctanamido)-3,3-dimethylbutanoyl)-4-hydroxy-N-(4-(4-methylthiazol-5-yl)benzyl)pyrrolidine-2-carboxamide (16.0 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-63 was obtained as yellow solid in TFA salt form (8.3 mg, 33%). $^1$H NMR (600 MHz, Methanol-$d_4$) δ 13.70 (s, 1H), 8.90 (s, 1H), 7.83 (d, J=9.0 Hz, 1H), 7.59 (s, 1H), 7.47 (d, J=8.1 Hz, 2H), 7.45-7.40 (m, 3H), 6.96-6.81 (m, 2H), 4.69-4.63 (m, 1H), 4.61-4.49 (m, 3H), 4.37 (d, J=15.4 Hz, 1H), 3.92 (d, J=11.0 Hz, 1H), 3.82 (dd, J=10.9, 3.9 Hz, 1H), 3.51 (t, J=6.6 Hz, 2H), 3.49-3.36 (m, 4H), 3.28-2.89 (m, 10H), 2.52 (s, 3H), 2.48 (s, 6H), 2.34-2.20 (m, 3H), 2.14-2.05 (m, 3H), 1.69-1.58 (m, 2H), 1.57-1.50 (m, 2H), 1.42-1.29 (m, 6H), 1.05 (s, 9H). HRMS calcd for $C_{55}H_{74}FN_{10}O_7S$ [M+H$^+$] 1037.5447, found 1037.5449.

Example 36

Synthesis of HC58-64

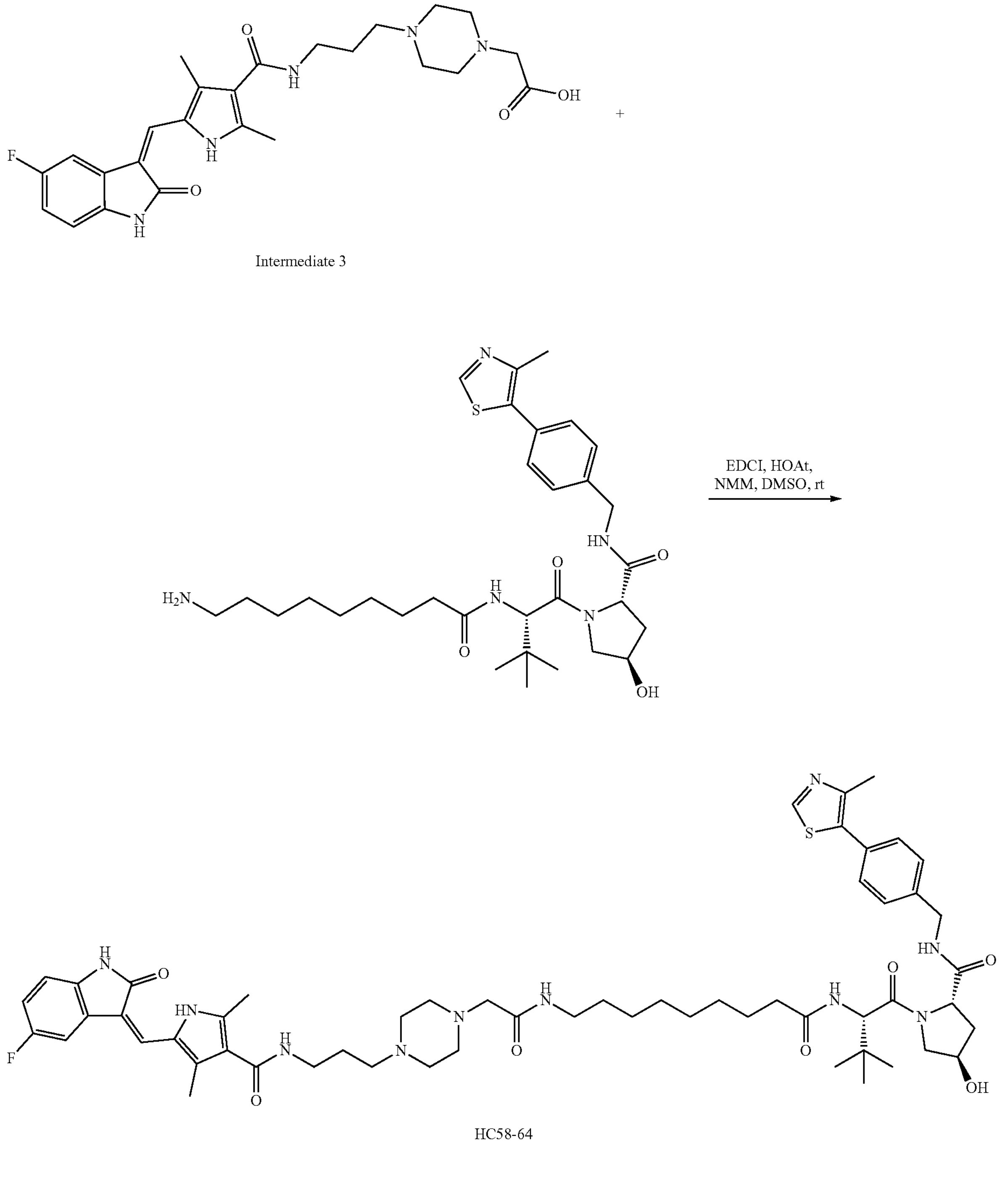 [SMILES: Cc1[nH]c(/C=C2\C(=O)Nc3ccc(F)cc32)c(C)c1C(=O)NCCCN1CCN(CC(=O)O)CC1 ; Cc1ncsc1-c1ccc(CNC(=O)[C@@H]2C[C@@H](O)CN2C(=O)[C@@H](NC(=O)CCCCCCCCN)C(C)(C)C)cc1 ; Cc1ncsc1-c1ccc(CNC(=O)[C@@H]2C[C@@H](O)CN2C(=O)[C@@H](NC(=O)CCCCCCCCNC(=O)CN2CCN(CCCNC(=O)c3c(C)[nH]c(/C=C4\C(=O)Nc5ccc(F)cc54)c3C)CC2)C(C)(C)C)cc1]

Intermediate 3

HC58-64

HC58-64 was synthesized following the standard procedure for preparing HC58-53 from Intermediate 3 (14.2 mg, 0.02 mmol, 1.0 equiv), (2S,4R)-1-((S)-2-(9-aminononanamido)-3,3-dimethylbutanoyl)-4-hydroxy-N-(4-(4-methylthiazol-5-yl)benzyl)pyrrolidine-2-carboxamide (12.4 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-64 was obtained as yellow solid in TFA salt form (10.2 mg, 39%). $^1$H NMR (600 MHz, Methanol-$d_4$) δ 13.70 (s, 1H), 8.91 (s, 1H), 7.84 (d, J=9.0 Hz, OH), 7.58 (s, 1H), 7.47 (d, J=8.2 Hz, 2H), 7.44-7.40 (m, 3H), 6.92-6.83 (m, 2H), 4.67-4.63 (m, 1H), 4.62-4.49 (m, 3H), 4.37 (d, J=15.5 Hz, 1H), 3.92 (d, J=11.0 Hz, 1H), 3.82 (dd, J=10.9, 3.9 Hz, 1H), 3.59-3.37 (m, 6H), 3.28-3.19 (m, 6H), 3.07-2.78 (m, 4H), 2.55-2.45 (m, 9H), 2.36-2.21 (m, 3H), 2.13-2.05 (m, 3H), 1.67-1.58 (m, 2H), 1.57-1.48 (m, 2H), 1.34 (s, 8H), 1.05 (s, 9H). HRMS calcd for $C_{56}H_{76}FN_{10}O_7S$ [M+H$^+$] 1051.5603, found 1051.5620.

Example 37

Synthesis of HC58-65

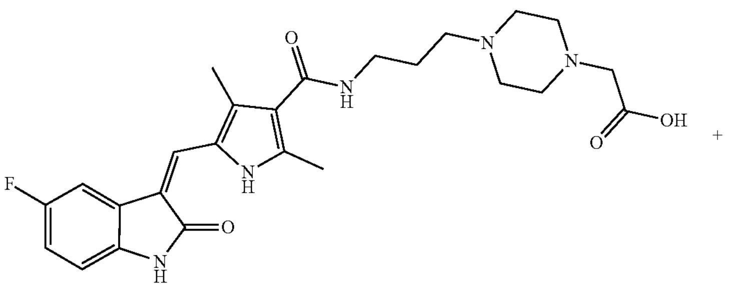

Intermediate 3

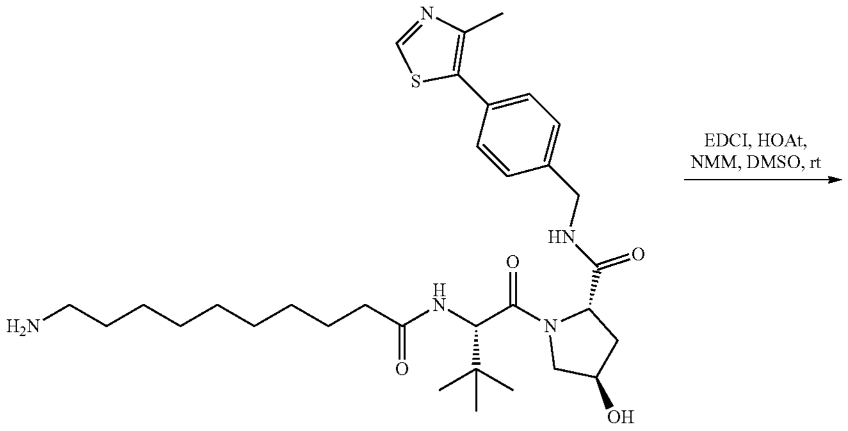

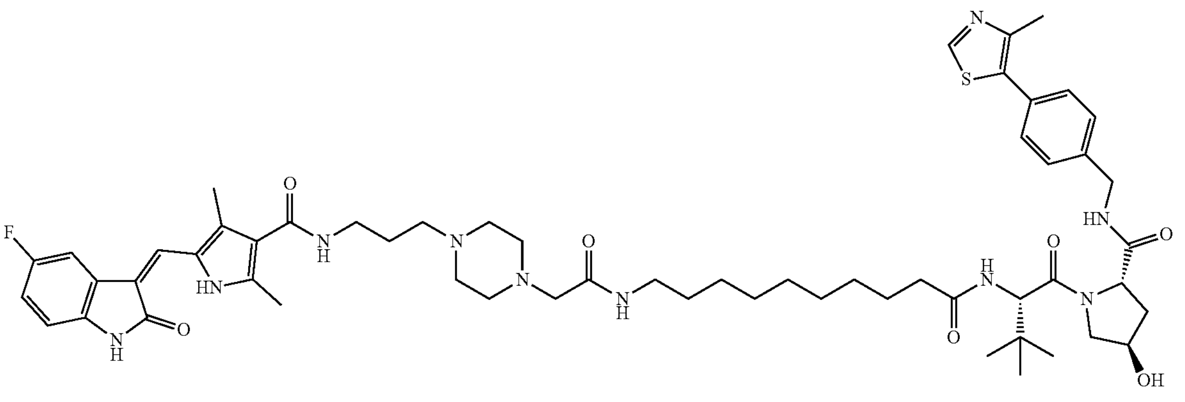

HC58-65

HC58-65 was synthesized following the standard procedure for preparing HC58-53 from Intermediate 3 (14.2 mg, 0.02 mmol, 1.0 equiv), (2S,4R)-1-((S)-2-(10-aminodecanamido)-3,3-dimethylbutanoyl)-4-hydroxy-N-(4-(4-methylthiazol-5-yl)benzyl)pyrrolidine-2-carboxamide (16.6 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-65 was obtained as yellow solid in TFA salt form (10.9 mg, 42%). $^1$H NMR (600 MHz, Methanol-$d_4$) δ 13.71 (s, 1H), 8.91 (s, 1H), 7.84 (d, J=9.0 Hz, 1H), 7.59 (s, 1H), 7.47 (d, J=8.3 Hz, 2H), 7.45-7.39 (m, 3H), 6.98-6.83 (m, 2H), 4.67-4.64 (m, 1H), 4.61-4.49 (m, 3H), 4.37 (d, J=15.4 Hz, 1H), 3.92 (d, J=11.0 Hz, 1H), 3.82 (dd, J=10.9, 3.9 Hz, 1H), 3.58-3.37 (m, 6H), 3.23 (dd, J=12.7, 5.3 Hz, 6H), 3.04-2.76 (m, 4H), 2.52 (s, 3H), 2.48 (s, 6H), 2.35-2.20 (m, 3H), 2.15-2.05 (m, 3H), 1.66-1.57 (m, 2H), 1.56-1.50 (m, 2H), 1.33 (s, 10H), 1.05 (s, 9H). HRMS calcd for $C_{57}H_{78}FN_{10}O_7S$ [M+H$^+$] 1065.5760, found 1065.5767.

Example 38

Synthesis of HC58-66

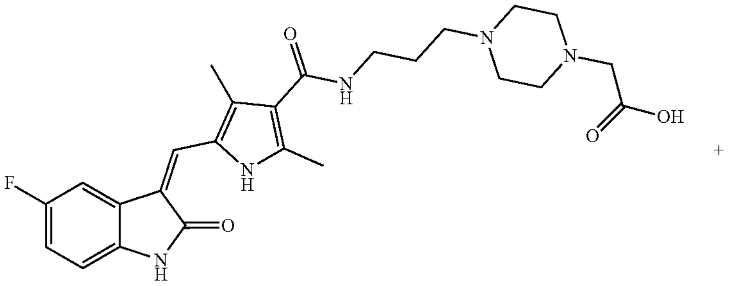

Intermediate 3

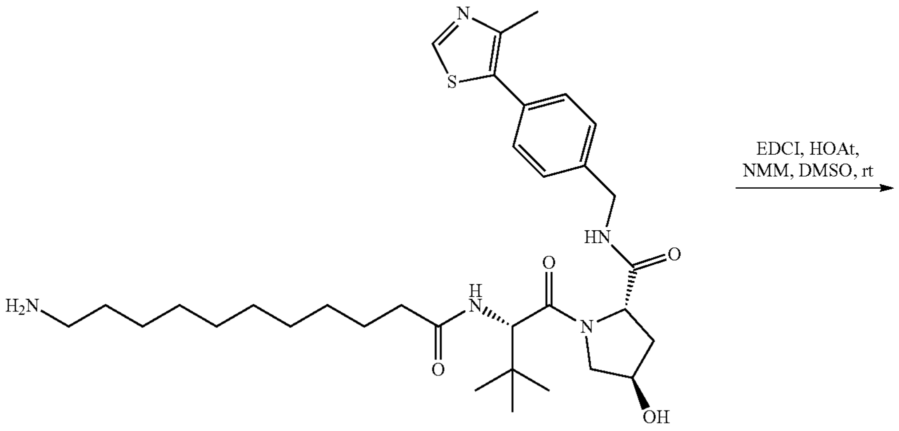

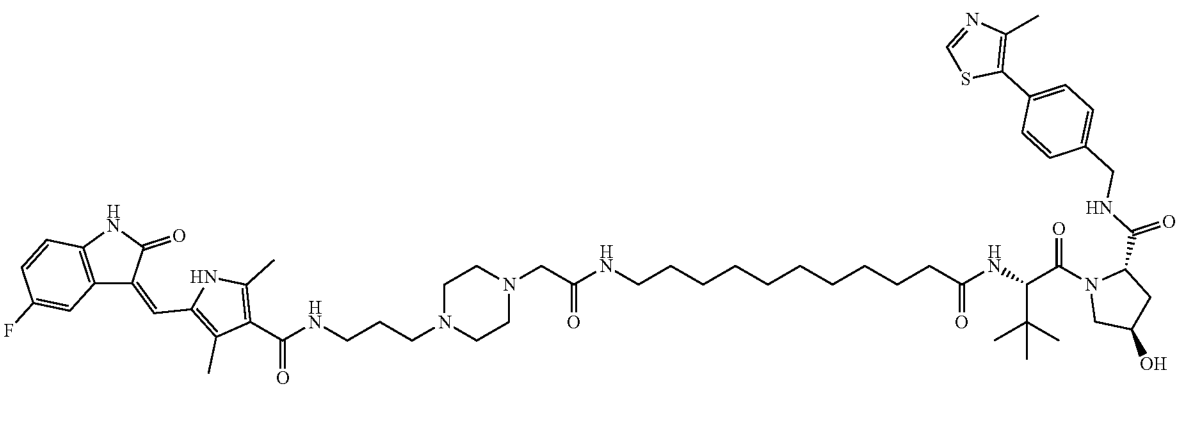

HC58-66

HC58-66 was synthesized following the standard procedure for preparing HC58-53 from Intermediate 3 (14.2 mg, 0.02 mmol, 1.0 equiv), (2S,4R)-1-((S)-2-(11-aminoundecanamido)-3,3-dimethylbutanoyl)-4-hydroxy-N-(4-(4-methylthiazol-5-yl)benzyl)pyrrolidine-2-carboxamide (14.3 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-66 was obtained as yellow solid in TFA salt form (8.4 mg, 32%). $^1$H NMR (600 MHz, Methanol-$d_4$) δ 13.73 (s, 1H), 8.89 (s, 1H), 7.83 (d, J=9.0 Hz, 1H), 7.62 (s, 1H), 7.49-7.41 (m, 5H), 6.95-6.85 (m, 2H), 4.69-4.63 (m, 1H), 4.60-4.49 (m, 3H), 4.37 (d, J=15.4 Hz, 1H), 3.92 (d, J=10.8 Hz, 1H), 3.82 (dd, J=10.9, 3.9 Hz, 1H), 3.65-3.55 (m, 4H), 3.51 (t, J=6.5 Hz, 2H), 3.28-3.18 (m, 6H), 3.16-3.05 (m, 4H), 2.53 (s, 3H), 2.49 (s, 3H), 2.48 (s, 3H), 2.36-2.20 (m, 3H), 2.13-2.04 (m, 3H), 1.62 (s, 2H), 1.56-1.49 (m, 2H), 1.37-1.27 (m, 12H), 1.05 (s, 9H). HRMS calcd for $C_{58}H_{80}FN_{10}O_7S$ [M+H$^+$] 1079.5916, found 1079.5928.

Example 39

Synthesis of HC58-67

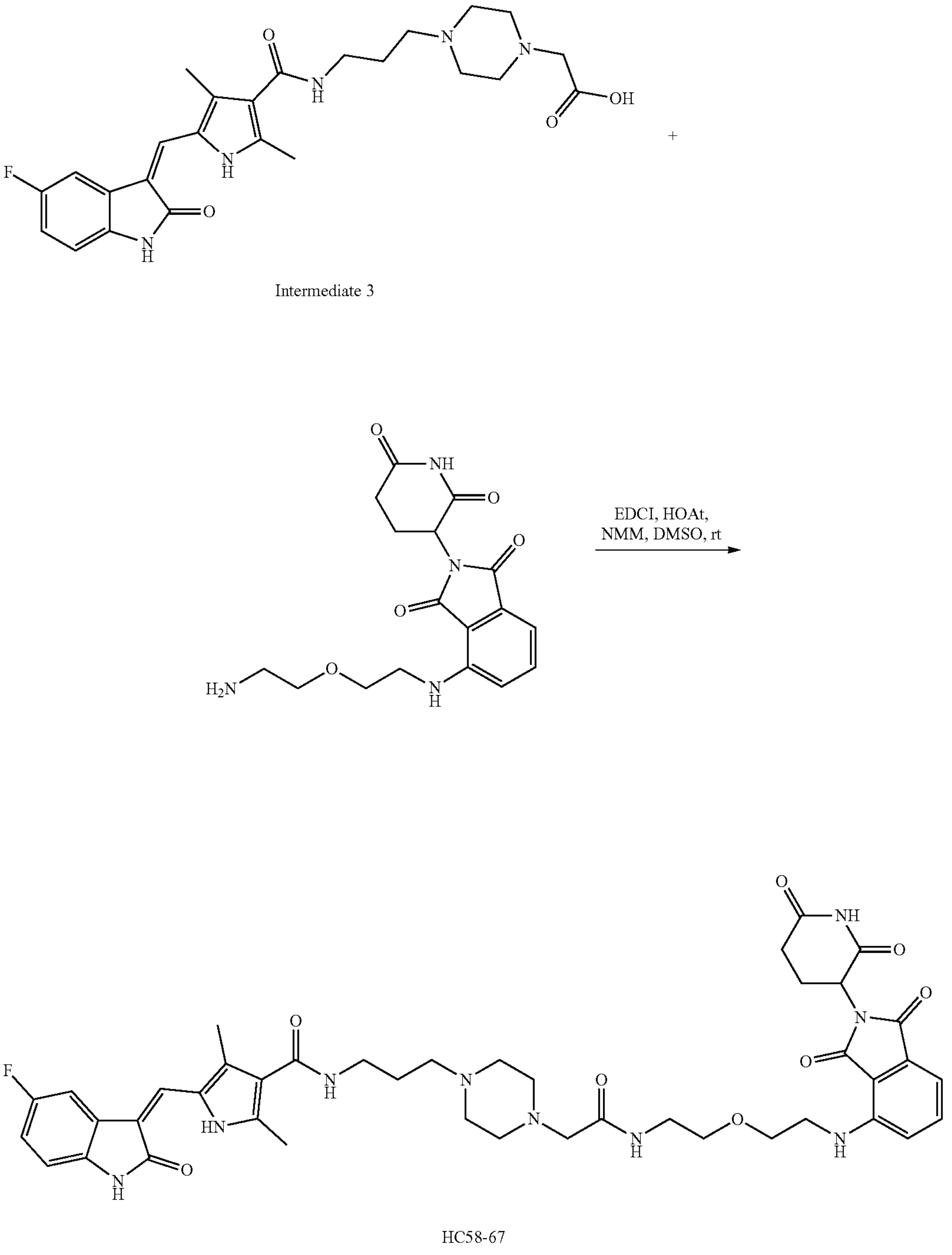

Intermediate 3

HC58-67

HC58-67 was synthesized following the standard procedure for preparing HC58-53 from Intermediate 3 (14.2 mg, 0.02 mmol, 1.0 equiv), 4-((2-(2-aminoethoxy)ethyl)amino)-2-(2,6-dioxopiperidin-3-yl)isoindoline-1,3-dione (9.5 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-67 was obtained as yellow solid in TFA salt form (11.0 mg, 52%). $^1$H NMR (600 MHz, Methanol-$d_4$) δ 13.68 (s, 1H), 7.59-7.54 (m, 2H), 7.42 (dd, J=8.9, 2.3 Hz, 1H), 7.10 (d, J=8.6 Hz, 1H), 7.07 (d, J=7.0 Hz, 1H), 6.91-6.84 (m, 2H), 5.06 (dd, J=12.8, 5.5 Hz, 1H), 3.73 (t, J=5.1 Hz, 2H), 3.63 (t, J=5.2 Hz, 2H), 3.49 (dt, J=13.9, 5.1 Hz, 6H), 3.41-3.31 (m, 4H), 3.25 (s, 2H), 3.17 (t, J=7.5 Hz, 2H), 3.02-2.80 (m, 5H), 2.79-2.69 (m, 2H), 2.50 (s, 3H), 2.46 (s, 3H), 2.16-2.10 (m, 1H), 2.07-1.99 (m, 2H). HRMS calcd for $C_{42}H_{49}FN_9O_8$ [M+H$^+$] 826.3688, found 826.3697.

Example 40

Synthesis of HC58-68

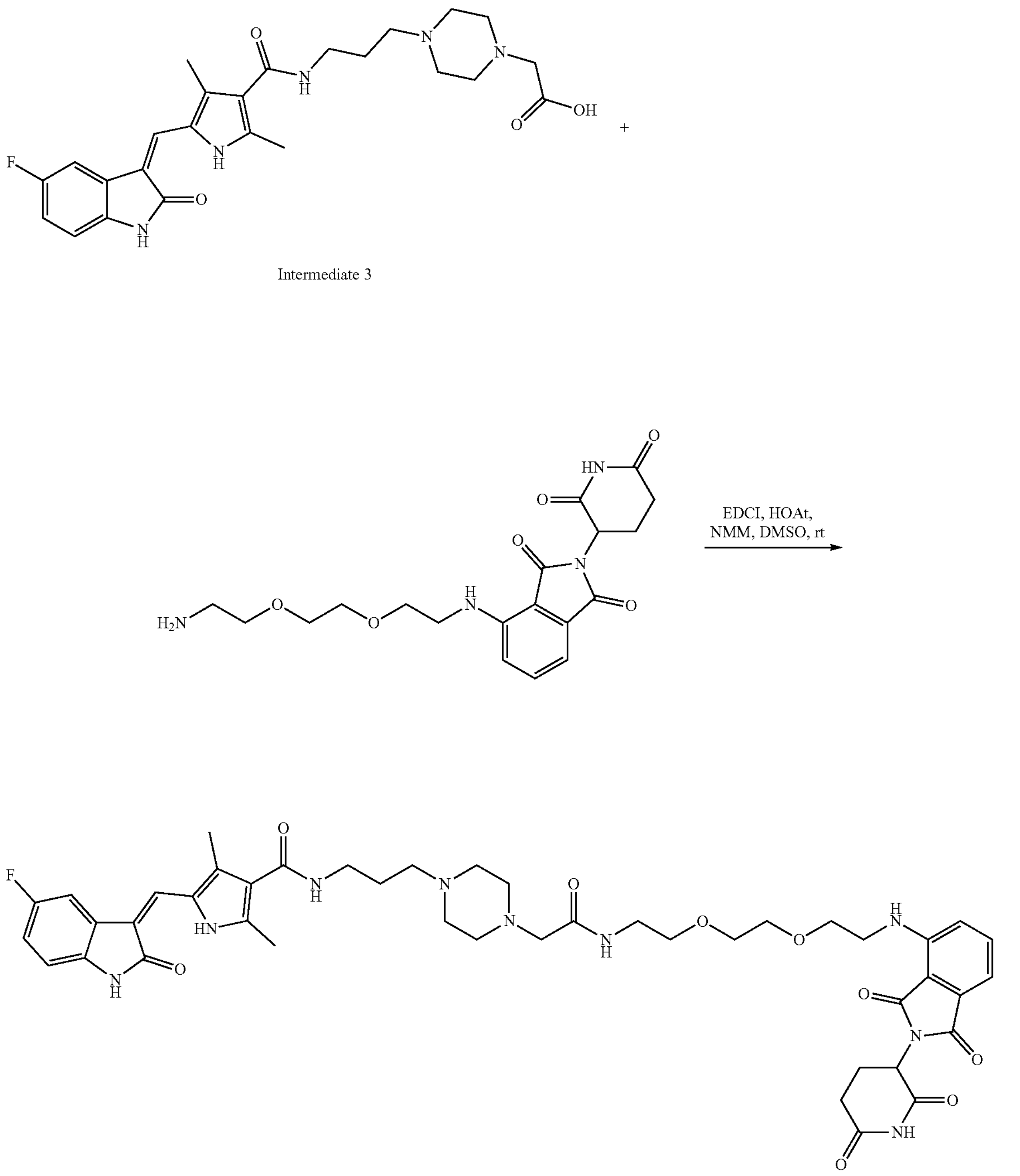

Intermediate 3

HC58-68

HC58-68 was synthesized following the standard procedure for preparing HC58-53 from Intermediate 3 (14.2 mg, 0.02 mmol, 1.0 equiv), 4-((2-(2-(2-aminoethoxy)ethoxy)ethyl)amino)-2-(2,6-dioxopiperidin-3-yl)isoindoline-1,3-dione (10.4 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-68 was obtained as yellow solid in TFA salt form (10.8 mg, 49%). $^1$H NMR (600 MHz, Methanol-$d_4$) δ 13.64 (s, 1H), 7.56-7.51 (m, 2H), 7.40 (dd, J=8.9, 2.3 Hz, 1H), 7.06 (d, J=8.6 Hz, 1H), 7.03 (d, J=7.0 Hz, 1H), 6.90-6.83 (m, 2H), 5.07 (dd, J=12.7, 5.4 Hz, 1H), 3.73 (t, J=5.1 Hz, 2H), 3.69-3.63 (m, 4H), 3.59 (t, J=5.3 Hz, 2H), 3.52-3.39 (m, 6H), 3.39-3.28 (m, 4H), 3.21 (d, J=2.6 Hz, 2H), 3.17 (t, J=7.5 Hz, 2H), 3.01-2.81 (m, 5H), 2.80-2.67 (m, 2H), 2.49 (s, 3H), 2.44 (s, 3H), 2.17-2.10 (m, 1H), 2.04 (p, J=6.7 Hz, 2H). HRMS calcd for $C_{44}H_{53}FN_9O_9$[M+H$^+$] 870.3950, found 870.3958.

Example 41

Synthesis of HC58-69

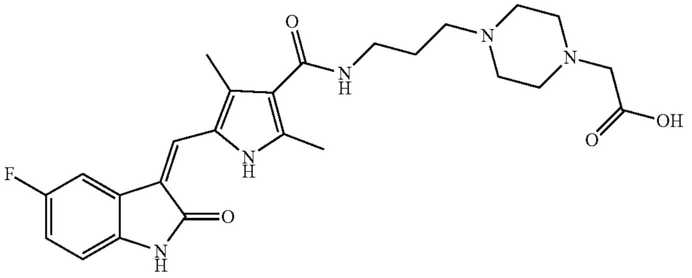

Intermediate 3

+

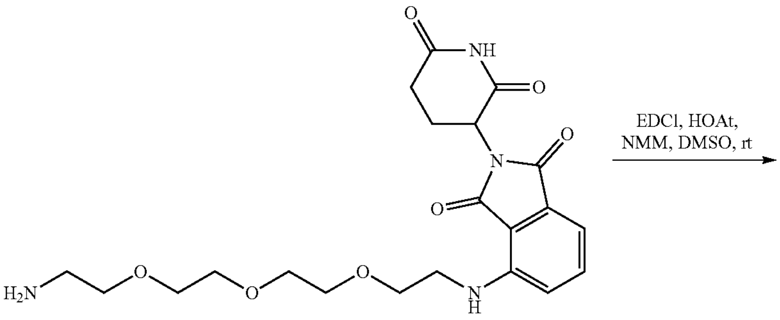

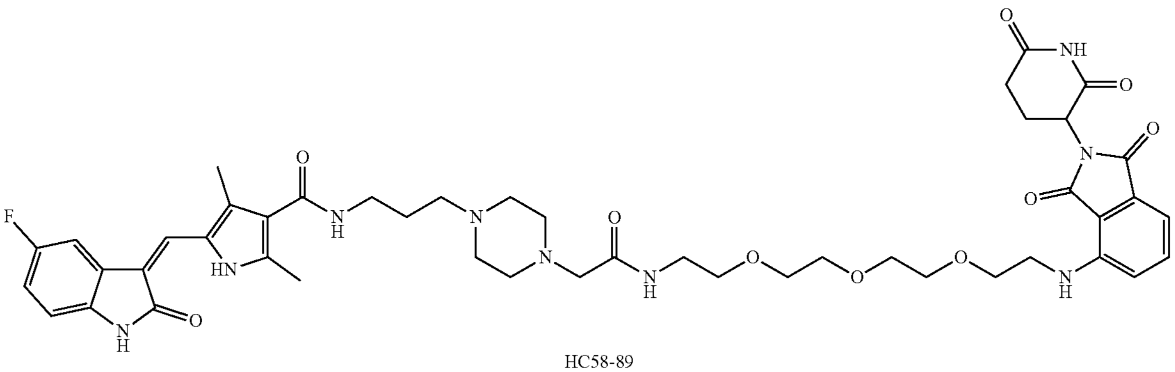

HC58-89

HC58-69 was synthesized following the standard procedure for preparing HC58-53 from Intermediate 3 (14.2 mg, 0.02 mmol, 1.0 equiv), 4-((2-(2-(2-(2-aminoethoxy)ethoxy)ethoxy)ethyl)amino)-2-(2,6-dioxopiperidin-3-yl)isoindoline-1,3-dione (11.2 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-69 was obtained as yellow solid in TFA salt form (13.2 mg, 58%). $^1$H NMR (600 MHz, Methanol-$d_4$) δ 13.65 (s, 1H), 7.55-7.50 (m, 2H), 7.40 (dd, J=9.0, 2.3 Hz, 1H), 7.05 (d, J=8.5 Hz, 1H), 7.01 (d, J=7.1 Hz, 1H), 6.90-6.82 (m, 2H), 5.06 (dd, J=12.7, 5.5 Hz, 1H), 3.71 (t, J=5.2 Hz, 2H), 3.68-3.63 (m, 6H), 3.60 (dt, J=6.4, 2.2 Hz, 2H), 3.56 (t, J=5.4 Hz, 2H), 3.52-3.46 (m, 4H), 3.42 (t, J=5.3 Hz, 2H), 3.41-3.35 (m, 4H), 3.26-3.19 (m, 4H), 3.04-2.81 (m, 5H), 2.79-2.66 (m, 2H), 2.49 (s, 3H), 2.45 (s, 3H), 2.15-2.10 (m, 1H), 2.06 (p, J=6.7 Hz, 2H). HRMS calcd for $C_{46}H_{57}FN_9O_{10}$ [M+H$^+$] 914.4212, found 914.4226.

Example 42

Synthesis of HC58-70

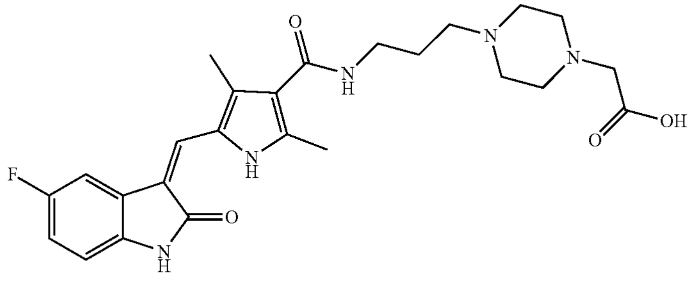

Intermediate 3

+

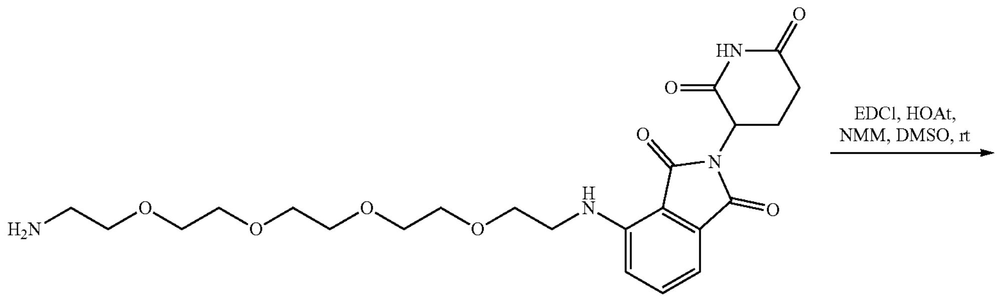

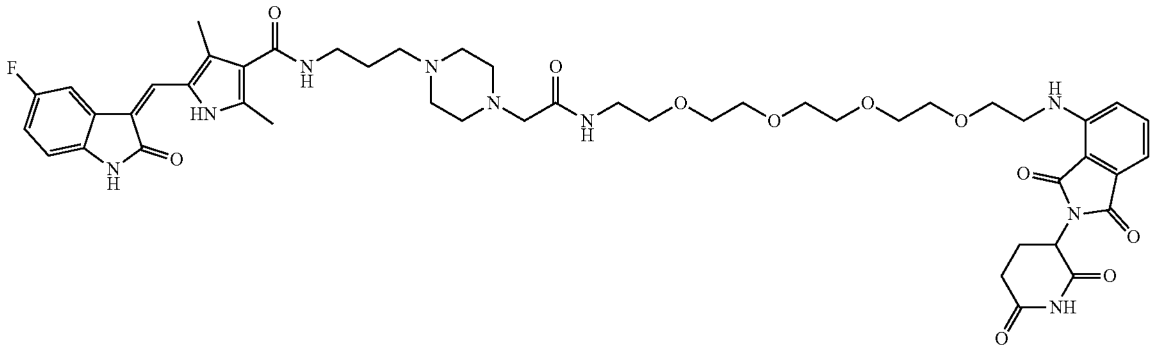

HC58-70

HC58-70 was synthesized following the standard procedure for preparing HC58-53 from Intermediate 3 (14.2 mg, 0.02 mmol, 1.0 equiv), 4-((14-amino-3,6,9,12-tetraoxatetradecyl)amino)-2-(2,6-dioxopiperidin-3-yl)isoindoline-1,3-dione (11.3 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-70 was obtained as yellow solid in TFA salt form (11.9 mg, 50%). $^1$H NMR (600 MHz, Methanol-d$_4$) δ 13.68 (s, 1H), 7.56 (s, 1H), 7.52 (dd, J=8.6, 7.1 Hz, 1H), 7.41 (dd, J=8.9, 2.4 Hz, 1H), 7.05 (d, J=8.6 Hz, 1H), 7.02 (d, J=7.0 Hz, 1H), 6.91-6.83 (m, 2H), 5.06 (dd, J=12.7, 5.5 Hz, 1H), 3.71 (t, J=5.2 Hz, 2H), 3.68-3.58 (m, 12H), 3.56 (t, J=5.3 Hz, 2H), 3.50 (t, J=6.5 Hz, 2H), 3.47 (t, J=5.2 Hz, 2H), 3.45-3.36 (m, 6H), 3.27-3.19 (m, 4H), 3.05-2.80 (m, 5H), 2.78-2.67 (m, 2H), 2.51 (s, 3H), 2.46 (s, 3H), 2.17-2.03 (m, 3H). HRMS calcd for $C_{48}H_{61}FN_9O_{11}$ [M+H$^+$] 958.4475, found 958.4488.

Example 43

Synthesis of HC58-71

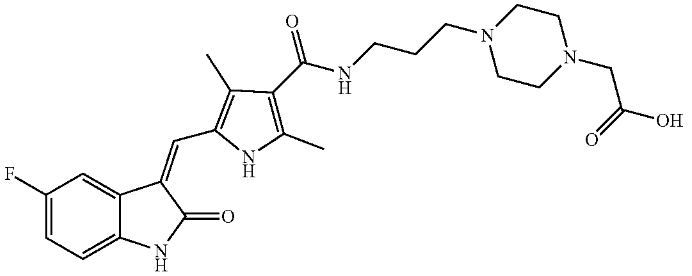

Intermediate 3

+

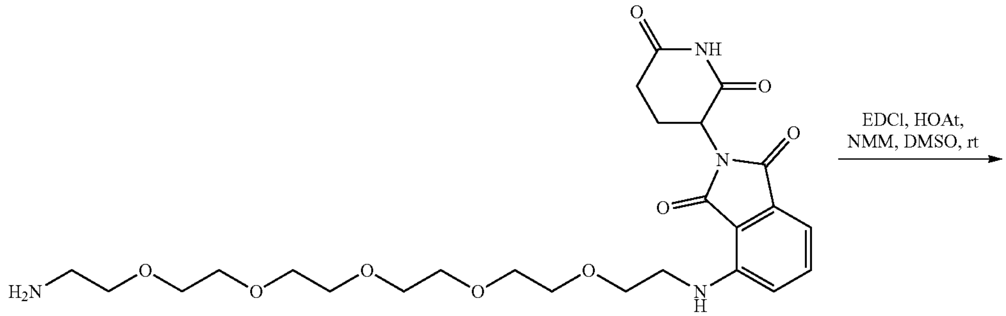

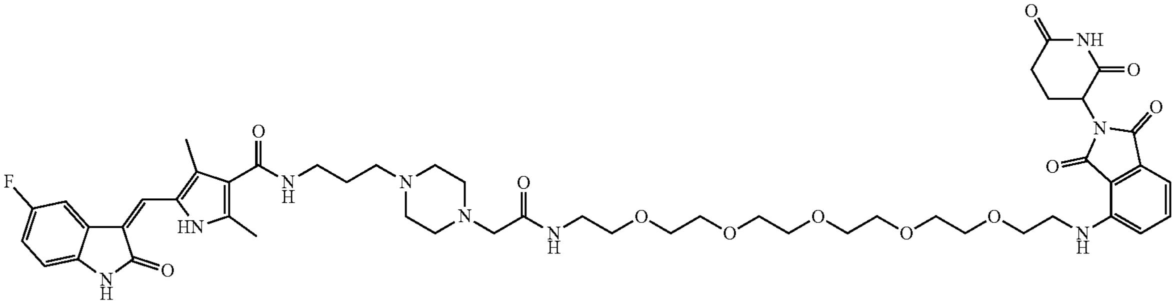

HC58-71

HC58-71 was synthesized following the standard procedure for preparing HC58-53 from Intermediate 3 (14.2 mg, 0.02 mmol, 1.0 equiv), 4-((17-amino-3,6,9,12,15-pentaoxaheptadecyl)amino)-2-(2,6-dioxopiperidin-3-yl)isoindoline-1,3-dione (12.2 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-71 was obtained as yellow solid in TFA salt form (11.8 mg, 48%). $^1$H NMR (600 MHz, Methanol-$d_4$) δ 13.65 (s, 1H), 7.54-7.49 (m, 2H), 7.39 (dd, J=8.9, 2.4 Hz, 1H), 7.04 (d, J=8.6 Hz, 1H), 7.01 (d, J=7.0 Hz, 1H), 6.90-6.82 (m, 3H), 5.05 (dd, J=12.8, 5.5 Hz, 1H), 3.70 (t, J=5.2 Hz, 2H), 3.67-3.59 (m, 16H), 3.56 (t, J=5.3 Hz, 2H), 3.50 (t, J=6.4 Hz, 2H), 3.48-3.38 (m, 8H), 3.28-3.21 (m, 4H), 3.08-2.82 (m, 5H), 2.79-2.66 (m, 2H), 2.49 (s, 3H), 2.45 (s, 3H), 2.17-2.04 (m, 3H). HRMS calcd for $C_{50}H_{65}FN_9O_{12}$ [M+H$^+$] 1002.4737, found 1002.4752.

Example 44

Synthesis of HC58-73

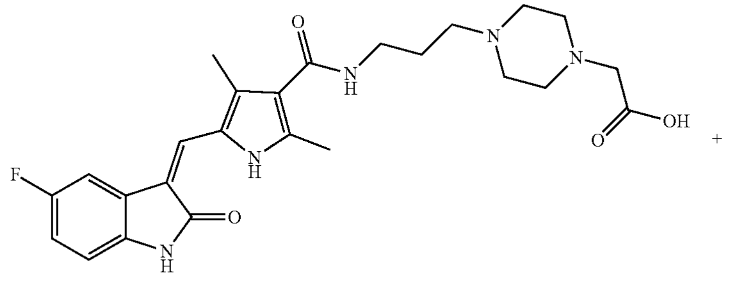

Intermediate 3

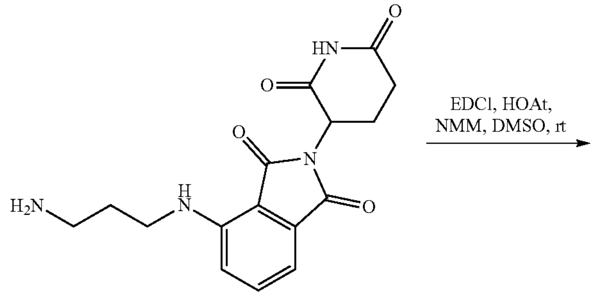

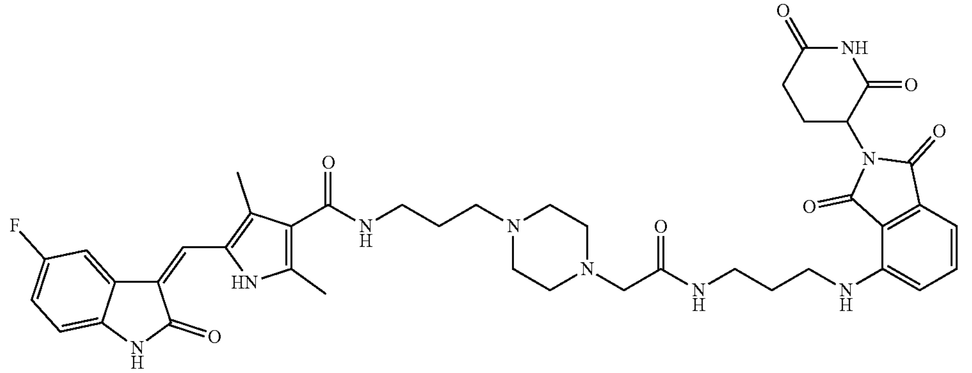

HC58-73

HC58-73 was synthesized following the standard procedure for preparing HC58-53 from Intermediate 3 (14.2 mg, 0.02 mmol, 1.0 equiv), 4-((3-aminopropyl)amino)-2-(2,6-dioxopiperidin-3-yl)isoindoline-1,3-dione (8.9 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-73 was obtained as yellow solid in TFA salt form (13.9 mg, 68%). $^1$H NMR (600 MHz, Methanol-$d_4$) δ 13.67 (s, 1H), 7.57-7.53 (m, 2H), 7.40 (dd, J=8.9, 2.4 Hz, 1H), 7.06 (d, J=5.6 Hz, 1H), 7.04 (d, J=4.1 Hz, 1H), 6.91-6.83 (m, 2H), 5.06 (dd, J=12.7, 5.5 Hz, 1H), 3.50 (t, J=6.5 Hz, 2H), 3.43-3.36 (m, 8H), 3.28 (s, 2H), 3.22 (dd, J=8.5, 6.6 Hz, 2H), 3.05-2.81 (m, 5H), 2.78-2.67 (m, 2H), 2.50 (s, 3H), 2.46 (s, 3H), 2.16-2.03 (m, 3H), 1.89 (p, J=6.6 Hz, 2H). HRMS calcd for $C_{41}H_{47}FN_9O_7$[M+H$^+$] 796.3582, found 796.3590.

Example 45

Synthesis of HC58-74

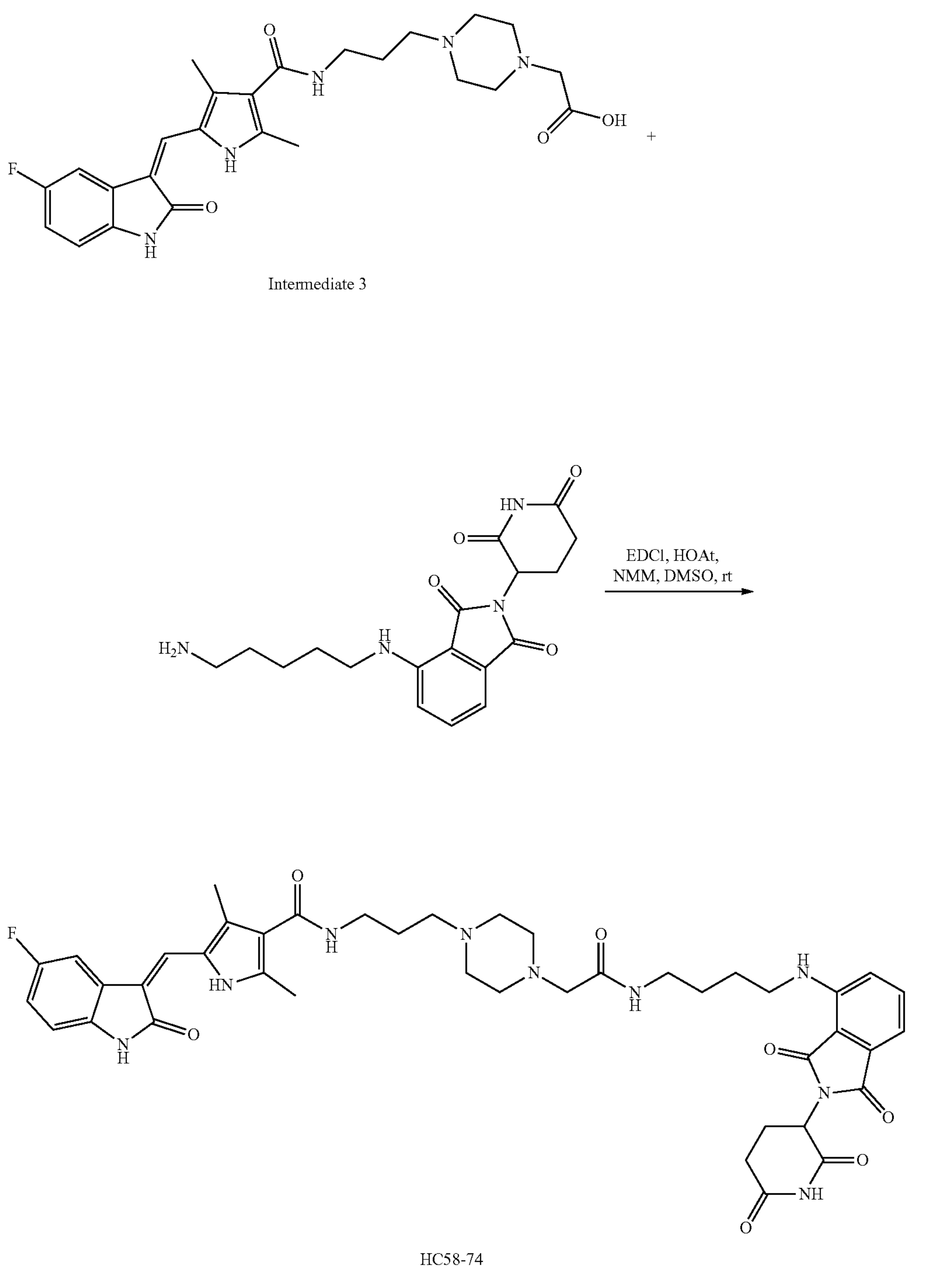

HC58-74 was synthesized following the standard procedure for preparing HC58-53 from Intermediate 3 (14.2 mg, 0.02 mmol, 1.0 equiv), 4-((4-aminobutyl)amino)-2-(2,6-dioxopiperidin-3-yl)isoindoline-1,3-dione (9.2 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-74 was obtained as yellow solid in TFA salt form (14.9 mg, 72%).

$^1$H NMR (600 MHz, Methanol-$d_4$) δ 13.67 (s, 1H), 7.59-7.52 (m, 2H), 7.41 (dd, J=8.9, 2.3 Hz, 1H), 7.08-7.02 (m, 2H), 6.91-6.83 (m, 2H), 5.05 (dd, J=12.7, 5.5 Hz, 1H), 3.50 (t, J=6.6 Hz, 2H), 3.40-3.31 (m, 8H), 3.24 (s, 2H), 3.21 (t, J=7.6 Hz, 2H), 3.01-2.80 (m, 5H), 2.79-2.68 (m, 2H), 2.50 (s, 3H), 2.46 (s, 3H), 2.16-2.01 (m, 3H), 1.73-1.62 (m, 4H). HRMS calcd for $C_{42}H_{49}FN_9O_7[M+H^+]$ 810.3739, found 810.3745.

Example 46

Synthesis of HC58-75

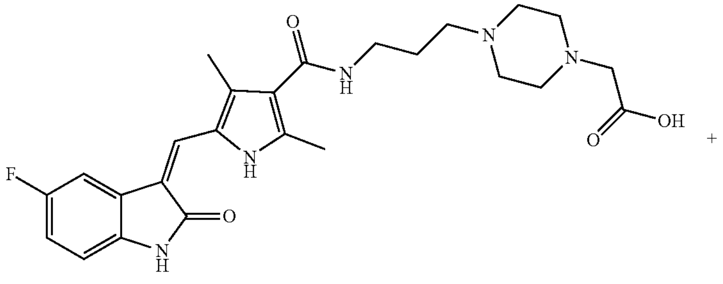

Intermediate 3

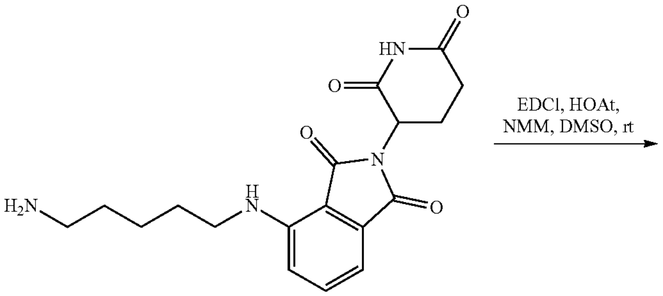

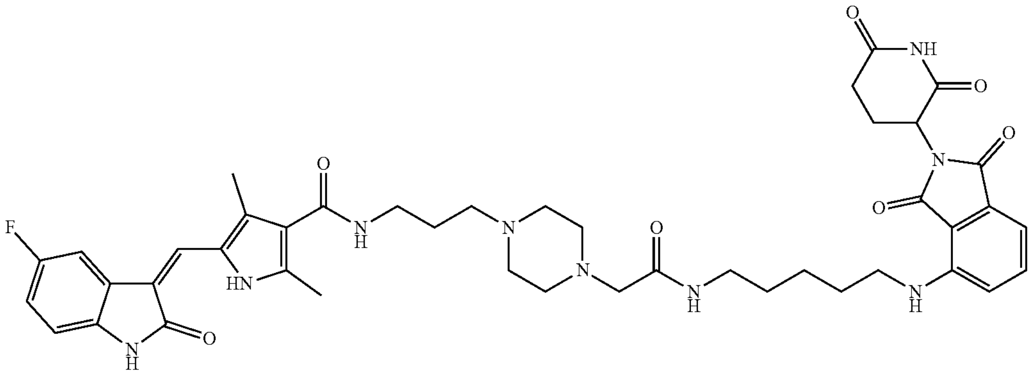

HC58-75

HC58-75 was synthesized following the standard procedure for preparing HC58-53 from Intermediate 3 (14.2 mg, 0.02 mmol, 1.0 equiv), 4-((5-aminopentyl)amino)-2-(2,6-dioxopiperidin-3-yl)isoindoline-1,3-dione (9.5 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-75 was obtained as yellow solid in TFA salt form (12.2 mg, 58%). $^1$H NMR (600 MHz, Methanol-$d_4$) δ 13.69 (s, 1H), 7.58 (s, 1H), 7.55 (dd, J=8.6, 7.1 Hz, 1H), 7.43 (dd, J=8.9, 2.3 Hz, 1H), 7.05 (d, J=6.4 Hz, 1H), 7.04 (d, J=4.9 Hz, 1H), 6.91-6.84 (m, 2H), 5.05 (dd, J=12.7, 5.5 Hz, 1H), 3.50 (t, J=6.5 Hz, 2H), 3.37-3.33 (m, 6H), 3.29 (t, J=6.8 Hz, 2H), 3.23-3.18 (m, 4H), 3.01-2.80 (m, 5H), 2.78-2.67 (m, 2H), 2.51 (s, 3H), 2.47 (s, 3H), 2.16-2.03 (m, 3H), 1.71 (p, J=6.9 Hz, 2H), 1.61 (p, J=7.0 Hz, 2H), 1.52-1.43 (m, 2H). HRMS calcd for $C_{43}H_{51}FN_9O_7$[M+H$^+$] 824.3895, found 824.3898.

Example 47

Synthesis of HC58-76

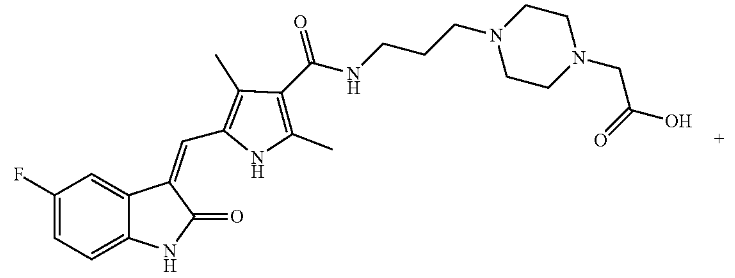

Intermediate 3

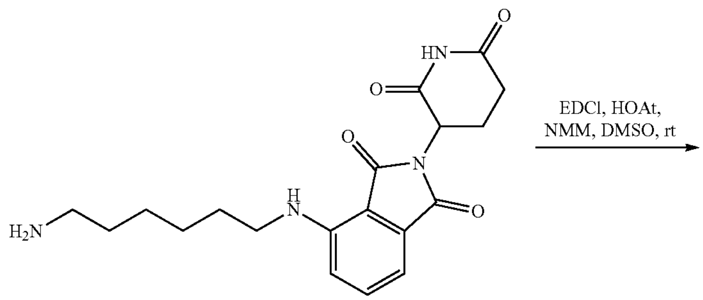

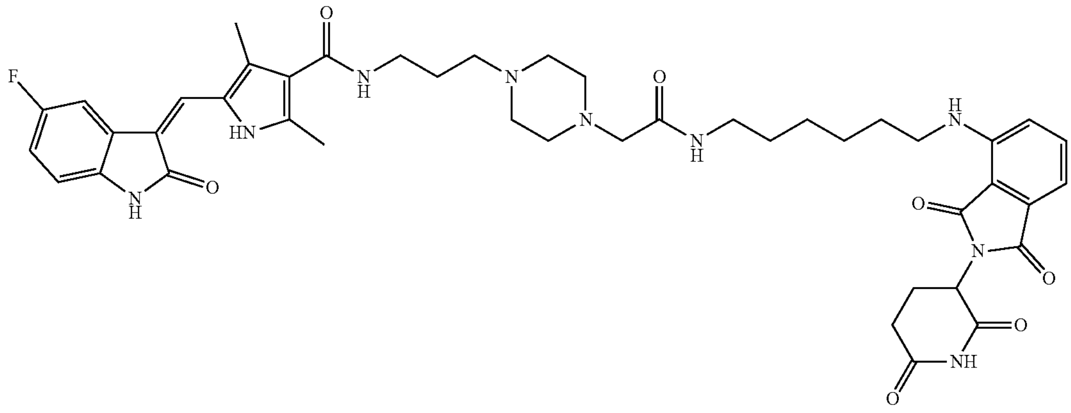

HC58-76

HC58-76 was synthesized following the standard procedure for preparing HC58-53 from Intermediate 3 (14.2 mg, 0.02 mmol, 1.0 equiv), 4-((6-aminohexyl)amino)-2-(2,6-dioxopiperidin-3-yl)isoindoline-1,3-dione (8.2 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-76 was obtained as yellow solid in TFA salt form (10.0 mg, 47%). $^{1}H$ NMR (600 MHz, Methanol-$d_4$) δ 13.71 (s, 1H), 7.59 (s, 1H), 7.55 (dd, J=8.6, 7.1 Hz, 1H), 7.44 (dd, J=8.9, 2.3 Hz, 1H), 7.04 (dd, J=7.8, 4.2 Hz, 2H), 6.93-6.84 (m, 2H), 5.06 (dd, J=12.7, 5.5 Hz, 1H), 3.51 (t, J=6.5 Hz, 2H), 3.39-3.32 (m, 6H), 3.26 (t, J=6.8 Hz, 2H), 3.23-3.19 (m, 4H), 3.01-2.81 (m, 5H), 2.79-2.66 (m, 2H), 2.52 (s, 3H), 2.48 (s, 3H), 2.16-2.02 (m, 3H), 1.69 (p, J=7.1 Hz, 2H), 1.57 (p, J=7.2 Hz, 2H), 1.48 (p, J=7.1 Hz, 2H), 1.45-1.37 (m, 2H). HRMS calcd for $C_{44}H_{53}FN_9O_7$[M+H$^{+}$] 838.4052, found 838.4030.

Example 48

Synthesis of HC58-77

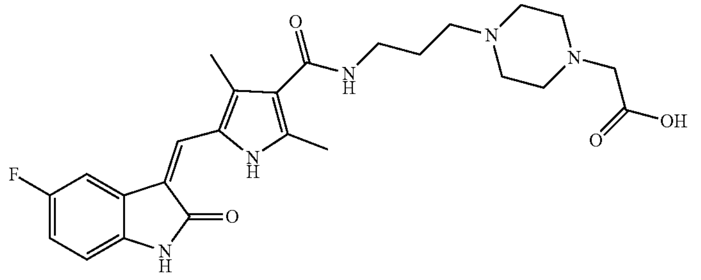

Intermediate 3

+

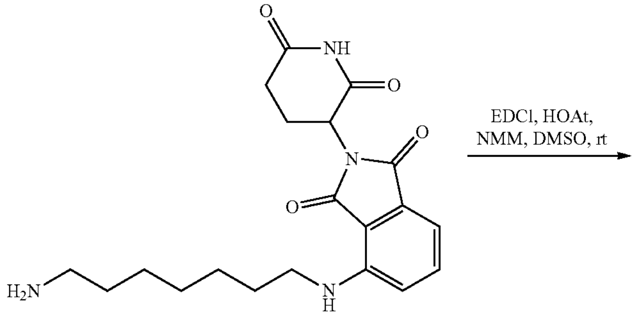

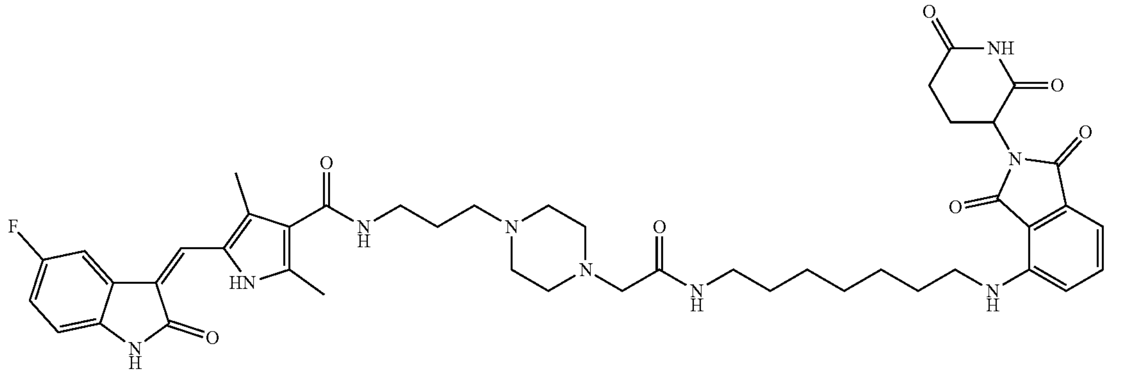

HC58-77

HC58-77 was synthesized following the standard procedure for preparing HC58-53 from Intermediate 3 (14.2 mg, 0.02 mmol, 1.0 equiv), 4-((7-aminoheptyl)amino)-2-(2,6-dioxopiperidin-3-yl)isoindoline-1,3-dione (10.0 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-77 was obtained as yellow solid in TFA salt form (9.7 mg, 45%). $^1$H NMR (600 MHz, Methanol-$d_4$) δ 13.70 (s, 1H), 7.58 (s, 1H), 7.54 (dd, J=8.6, 7.1 Hz, 1H), 7.43 (dd, J=9.0, 2.3 Hz, 1H), 7.03 (dd, J=7.8, 3.1 Hz, 2H), 6.92-6.85 (m, 2H), 5.06 (dd, J=12.7, 5.5 Hz, 1H), 3.51 (t, J=6.6 Hz, 2H), 3.33-3.29 (m, 6H), 3.27-3.19 (m, 6H), 3.02-2.81 (m, 5H), 2.78-2.66 (m, 2H), 2.52 (s, 3H), 2.48 (s, 3H), 2.16-2.04 (m, 3H), 1.67 (p, J=6.9 Hz, 2H), 1.55 (q, J=7.2 Hz, 2H), 1.48-1.33 (m, 6H). HRMS calcd for $C_{45}H_{55}FN_9O_7$[M+H$^+$] 852.4208, found 852.4201.

Example 49

Synthesis of HC58-78

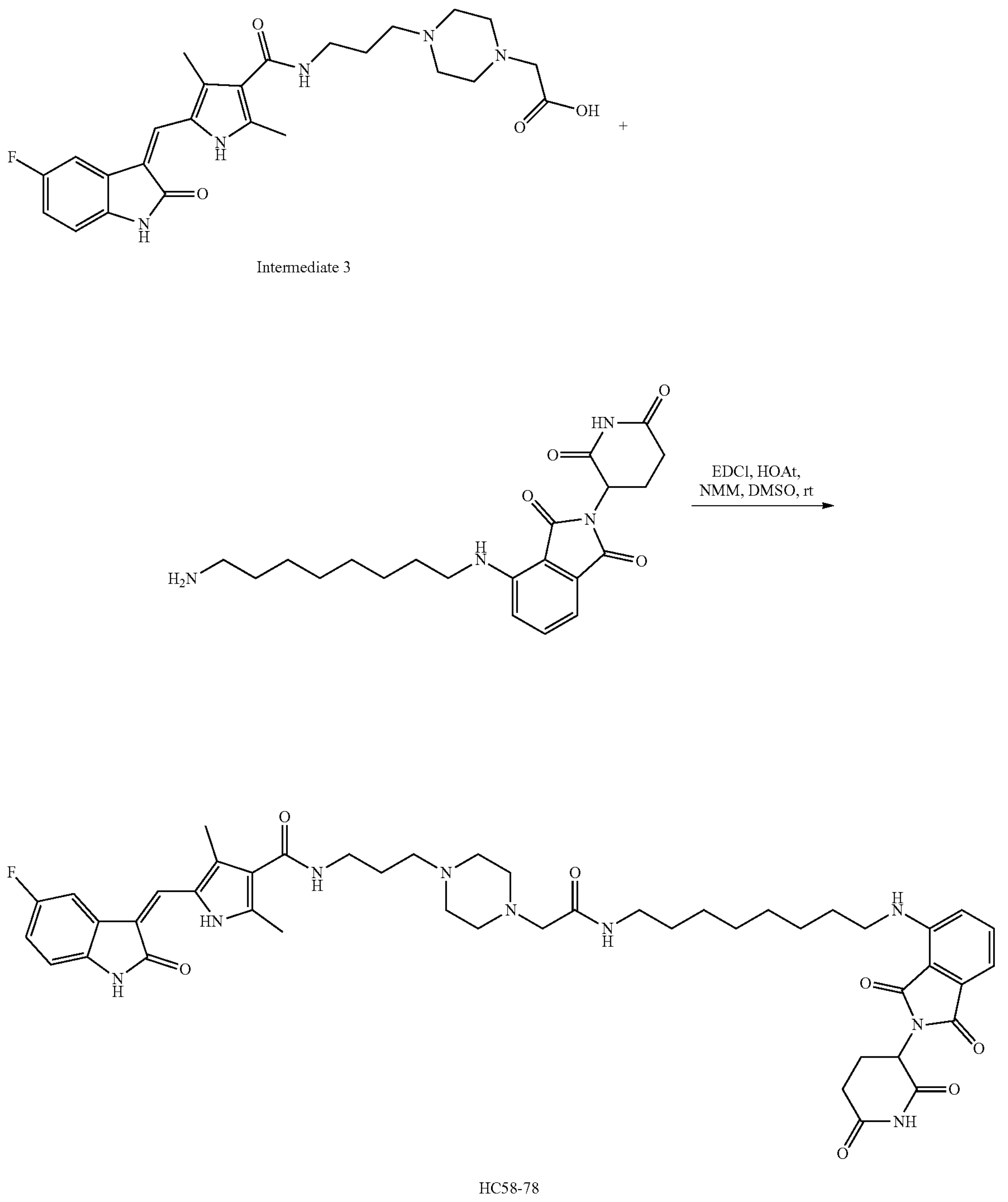

HC58-78 was synthesized following the standard procedure for preparing HC58-53 from Intermediate 3 (14.2 mg, 0.02 mmol, 1.0 equiv), 4-((8-aminooctyl)amino)-2-(2,6-dioxopiperidin-3-yl)isoindoline-1,3-dione (10.3 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-78 was obtained as yellow solid in TFA salt form (12.5 mg, 57%). $^1$H NMR (600 MHz, Methanol-$d_4$) δ 13.69 (s, 1H), 7.58 (s, 1H), 7.54 (dd, J=8.6, 7.1 Hz, 1H), 7.42 (dd, J=8.9, 2.3 Hz, 1H), 7.05-7.00 (m, 2H), 6.92-6.84 (m, 2H), 5.06 (dd, J=12.8, 5.5 Hz, 1H), 3.51 (t, J=6.6 Hz, 2H), 3.33-3.29 (m, 6H), 3.23 (dd, J=15.3, 8.1 Hz, 6H), 3.04-2.81 (m, 5H), 2.80-2.68 (m, 2H), 2.52 (s, 3H), 2.47 (s, 3H), 2.15-2.05 (m, 3H), 1.66 (p, J=7.1 Hz, 2H), 1.57-1.50 (m, 2H), 1.48-1.30 (m, 8H). HRMS calcd for $C_{46}H_{57}FN_9O_7[M+H^+]$ 866.4365, found 866.4346.

Example 50

Synthesis of intermediate 4

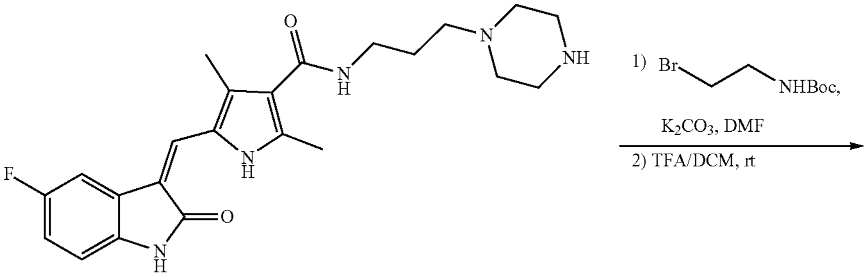

Intermediate 2

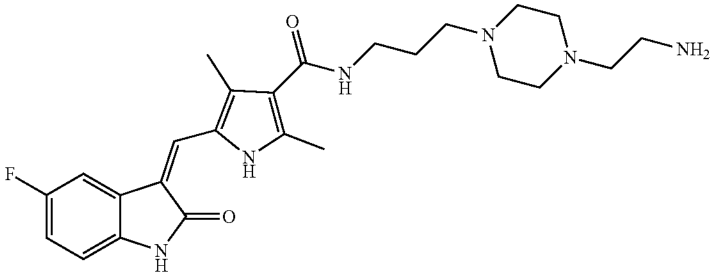

Intermediate 4

To a solution of intermediate 2 (196 mg, 0.3 mmol, 1.0 equiv) in DMF (4 mL) was added potassium carbonate (124 mg, 0.9 mmol, 3.0 equiv) and tert-butyl (2-bromoethyl) carbamate (140 mg, 0.6 mmol, 2.0 equiv). Then the mixture was stirred at 50° C. overnight. Water (10 mL) was added to quench the reaction. The mixture was extracted with ethyl acetate (3×15 mL). The organic layer was combined and washed with brine. Dried over $Na_2SO_4$, filtered, evaporated and afforded oil. The obtained oil was treated with DCM/TFA (2:1). After being stirred for 1 h at room temperature, the reaction mixture was concentrated and the residue was purified by reverse phase C18 column (10%-100% methanol/0.1% TFA in $H_2O$) to afford intermediate 4 as yellow solid in TFA salt form (164 mg, 67% yield for two steps). $^1H$ NMR (600 MHz, DMSO-$d_6$) δ 13.73 (s, 1H), 10.93 (s, 1H), 7.81 (t, J=5.9 Hz, 1H), 7.77 (dd, J=9.4, 2.6 Hz, 1H), 7.73 (s, 1H), 6.98-6.92 (m, 1H), 6.86 (dd, J=8.5, 4.6 Hz, 1H), 3.54-3.27 (m, 10H), 3.17-3.11 (m, 2H), 3.02-2.92 (m, 4H), 2.46 (s, 3H), 2.43 (s, 3H), 1.96-1.87 (m, 2H). ESI m/z=469.3 [M+H$^+$].

Example 51

Synthesis of HC58-133

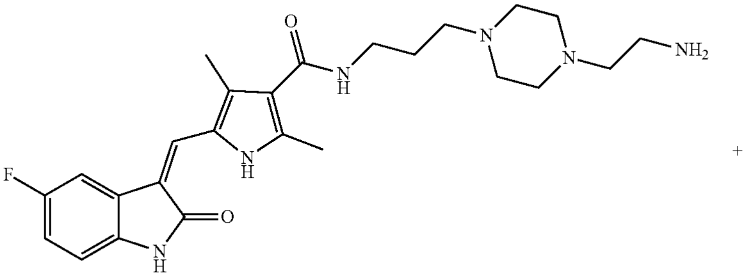

Intermediate 4

-continued

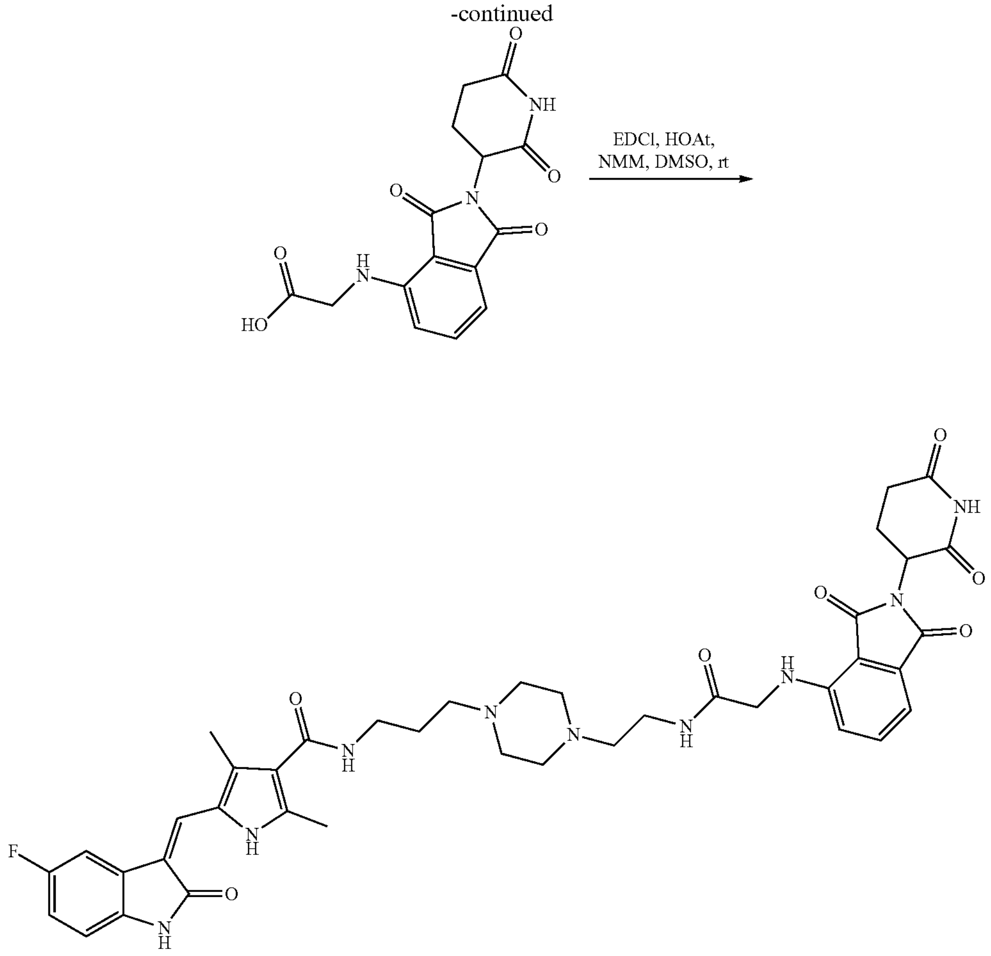

HC58-133

To a solution of Intermediate 4 (16.2 mg, 0.02 mmol, 1.0 equiv) in DMSO (1 mL) were added (2-(2,6-dioxopiperidin-3-yl)-1,3-dioxoisoindolin-4-yl)glycine (6.6 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (12.1 mg, 0.12 mmol, 6.0 equiv). After being stirred overnight at room temperature, the resulting mixture was purified by preparative HPLC (10%-100% MeCN/0.1% TFA in $H_2O$) to afford HC58-133 as yellow solid in TFA salt form (11.3 mg, 56%). $^1H$ NMR (600 MHz, Methanol-$d_4$) δ 13.65 (s, 1H), 7.63-7.57 (m, 1H), 7.55 (s, 1H), 7.40 (d, J=8.7 Hz, 1H), 7.15 (d, J=7.1 Hz, 1H), 6.93 (d, J=8.6 Hz, 1H), 6.90-6.78 (m, 2H), 5.08 (dd, J=12.6, 5.5 Hz, 1H), 4.04 (s, 2H), 3.54-3.41 (m, 6H), 3.36-3.22 (m, 4H), 3.17 (t, J=7.6 Hz, 2H), 3.11-2.92 (m, 4H), 2.87-2.70 (m, 3H), 2.50 (s, 3H), 2.46 (s, 3H), 2.18-2.07 (m, 1H), 2.08-1.96 (m, 2H). HRMS calcd for $C_{40}H_{45}FN_9O_7$[M+$H^+$] 782.3426, found 782.3418.

Example 52

Synthesis of HC58-134

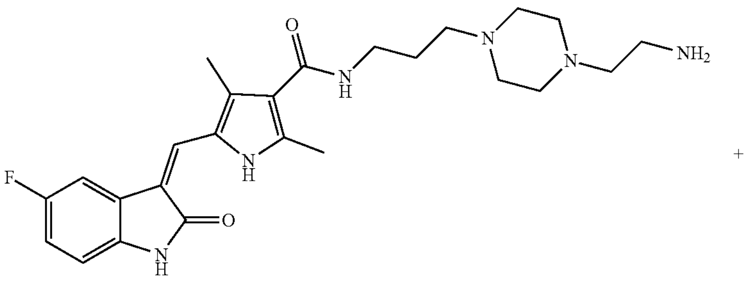

Intermediate 4

-continued

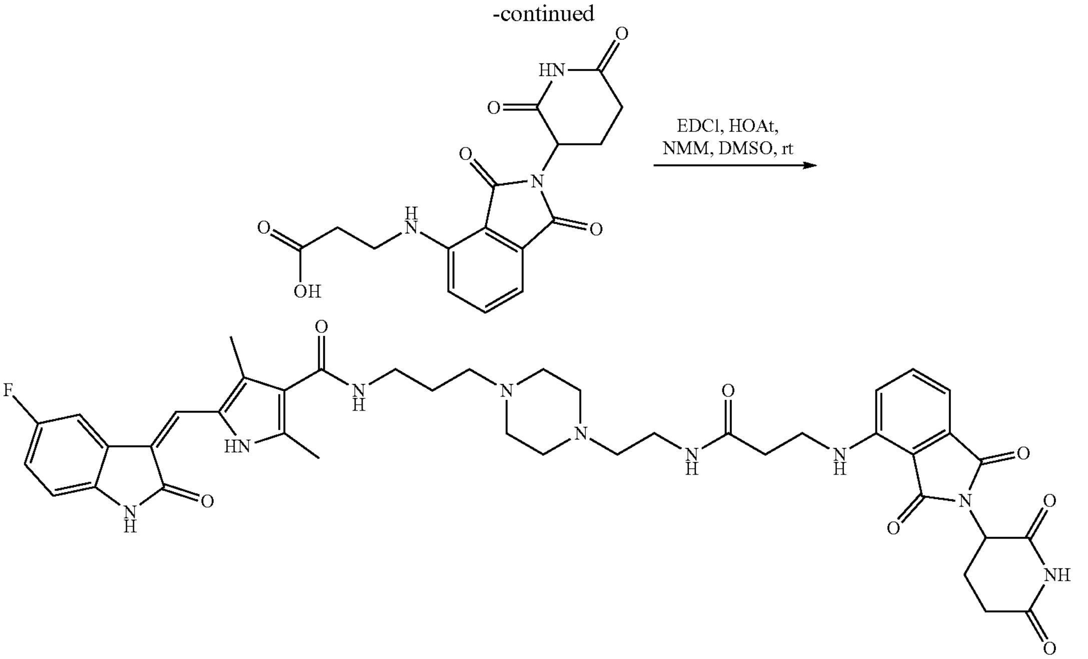

HC58-134

HC58-134 was synthesized following the standard procedure for preparing HC58-133 from Intermediate 4 (16.2 mg, 0.02 mmol, 1.0 equiv), 3-((2-(2,6-dioxopiperidin-3-yl)-1,3-dioxoisoindolin-4-yl)amino)propanoic acid (6.9 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-134 was obtained as yellow solid in TFA salt form (8.6 mg, 42%). $^1$H NMR (600 MHz, Methanol-$d_4$) δ 13.64 (s, 1H), 7.57 (dd, J=8.6, 7.1 Hz, 1H), 7.54 (s, 1H), 7.41-7.36 (m, 1H), 7.12 (d, J=8.5 Hz, 1H), 7.06 (d, J=7.1 Hz, 1H), 6.85 (q, J=5.0, 3.8 Hz, 2H), 5.06 (dd, J=12.7, 5.5 Hz, 1H), 3.66 (t, J=6.1 Hz, 2H), 3.52-3.35 (m, 8H), 3.27-3.12 (m, 6H), 2.92 (t, J=6.0 Hz, 2H), 2.84 (ddd, J=17.4, 13.9, 5.3 Hz, 1H), 2.77-2.67 (m, 2H), 2.57 (t, J=6.1 Hz, 2H), 2.50 (s, 3H), 2.46 (s, 3H), 2.14-2.08 (m, 1H), 2.04 (p, J=6.6 Hz, 2H). HRMS calcd for $C_{41}H_{47}FN_9O_7$[M+H$^+$] 796.3582, found 796.3598.

Example 53

Synthesis of HC58-135

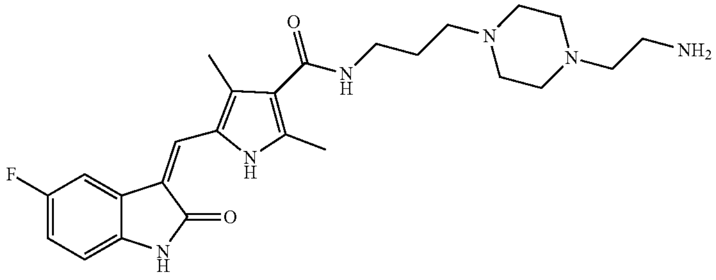

Intermediate 4

+

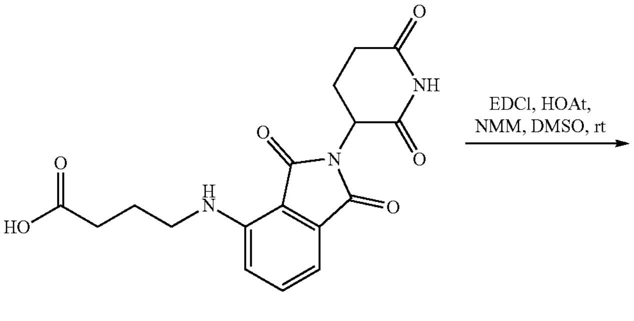

-continued

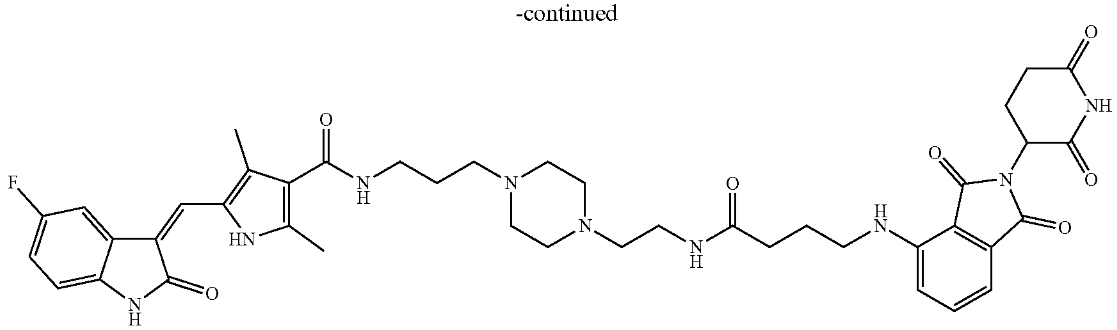

HC58-135

HC58-135 was synthesized following the standard procedure for preparing HC58-133 from Intermediate 4 (16.2 mg, 0.02 mmol, 1.0 equiv), 4-((2-(2,6-dioxopiperidin-3-yl)-1,3-dioxoisoindolin-4-yl)amino)butanoic acid (7.2 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-135 was obtained as yellow solid in TFA salt form (12.9 mg, 62%). $^1$H NMR (600 MHz, Methanol-$d_4$) δ 13.65 (s, 1H), 7.59-7.52 (m, 2H), 7.40 (d, J=8.9 Hz, 1H), 7.07 (d, J=8.6 Hz, 1H), 7.04 (d, J=7.1 Hz, 1H), 6.91-6.82 (m, 2H), 5.06 (ddd, J=12.8, 5.5, 1.9 Hz, 1H), 3.49 (t, J=6.4 Hz, 2H), 3.45-3.36 (m, 4H), 3.36-3.28 (m, 4H), 3.18-3.02 (m, 6H), 2.88-2.82 (m, 2H), 2.79-2.67 (m, 3H), 2.49 (s, 3H), 2.45 (s, 3H), 2.38-2.32 (m, 2H), 2.16-2.08 (m, 1H), 2.08-1.94 (m, 4H). HRMS calcd for $C_{42}H_{49}FN_9O_7$[M+H$^+$] 810.3739, found 810.3728.

Example 54

Synthesis of HC58-136

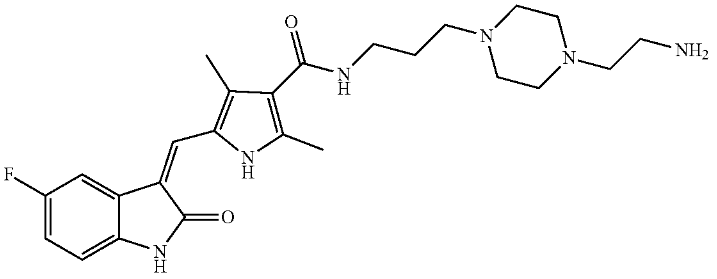

Intermediate 4

+

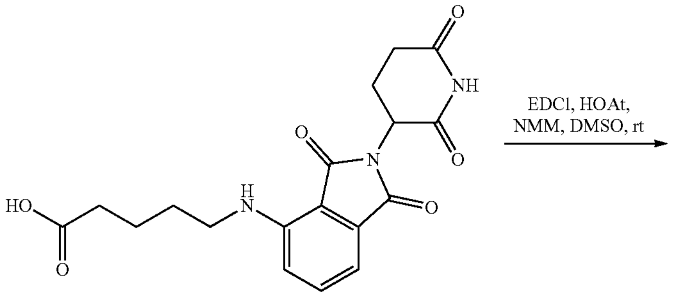

-continued

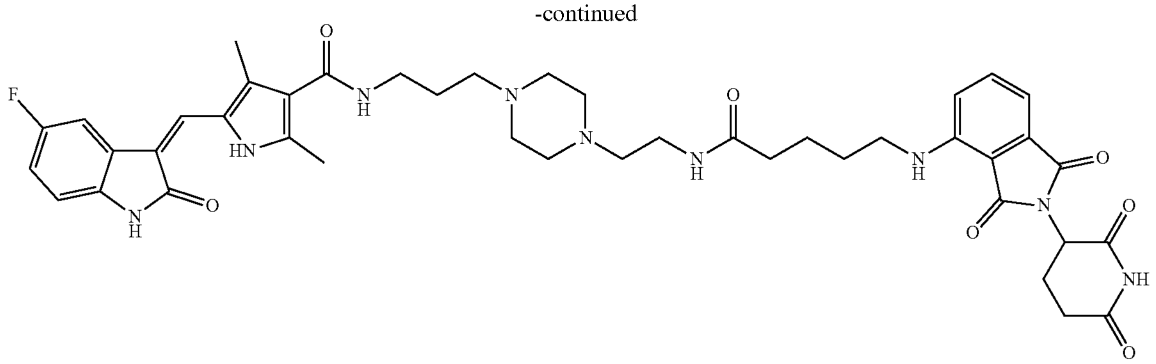

HC58-136

HC58-136 was synthesized following the standard procedure for preparing HC58-133 from Intermediate 4 (16.2 mg, 0.02 mmol, 1.0 equiv), 5-((2-(2,6-dioxopiperidin-3-yl)-1,3-dioxoisoindolin-4-yl)amino)pentanoic acid (7.5 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-136 was obtained as yellow solid in TFA salt form (9.9 mg, 47%). $^1$H NMR (600 MHz, Acetone-$d_6$) δ 13.54 (s, 1H), 9.80 (s, 1H), 9.74 (s, 1H), 7.51-7.44 (m, 2H), 7.34 (dd, J=9.1, 6.6 Hz, 1H), 7.30 (dd, J=9.1, 2.3 Hz, 1H), 7.04 (t, J=6.0 Hz, 1H), 6.84 (d, J=8.5 Hz, 1H), 6.79 (d, J=7.0 Hz, 1H), 6.70 (dd, J=8.4, 4.5 Hz, 1H), 6.68-6.63 (m, 1H), 6.20 (s, 1H), 4.85 (dd, J=12.4, 5.4 Hz, 1H), 3.62-3.45 (m, 8H), 3.43 (q, J=5.8 Hz, 2H), 3.31 (q, J=6.3 Hz, 2H), 3.19-3.03 (m, 6H), 2.78-2.67 (m, 1H), 2.59-2.48 (m, 2H), 2.29 (s, 3H), 2.25 (s, 3H), 2.03 (t, J=6.8 Hz, 2H), 2.00-1.88 (m, 3H), 1.55-1.41 (m, 4H). HRMS calcd for $C_{43}H_{51}FN_9O_7$ [M+H$^+$] 824.3895, found 824.3889.

Example 55

Synthesis of HC58-137

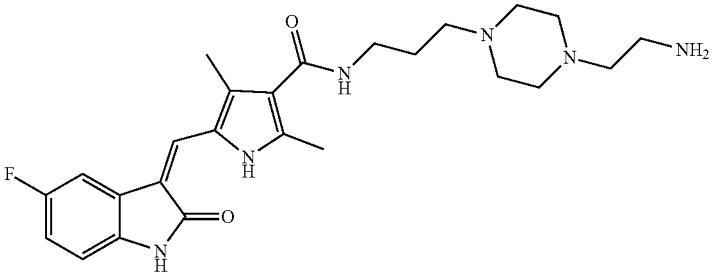

Intermediate 4

+

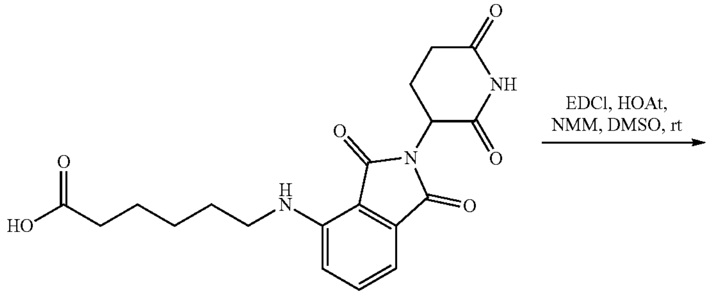

-continued

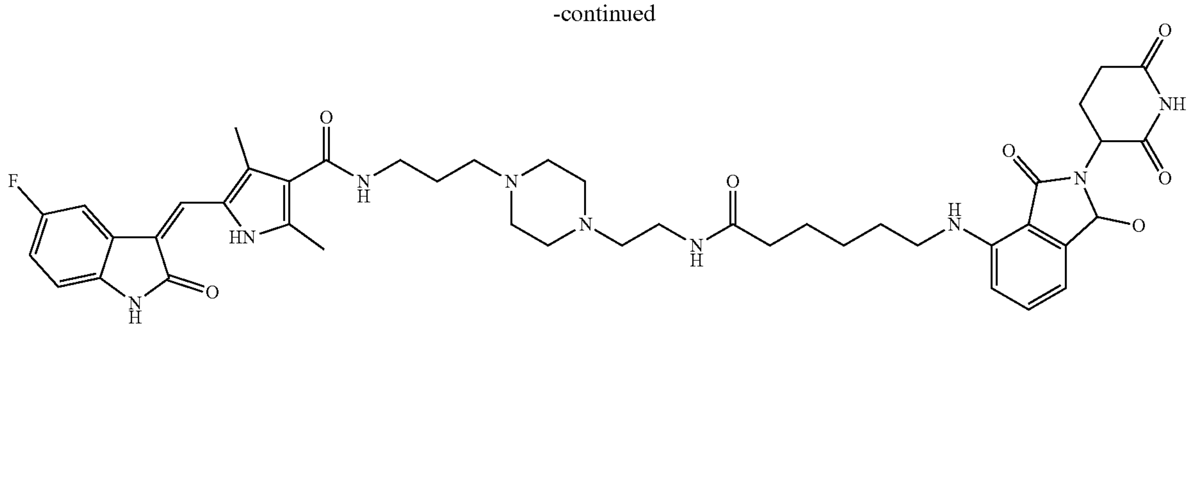

HC58-137

HC58-137 was synthesized following the standard procedure for preparing HC58-133 from Intermediate 4 (16.2 mg, 0.02 mmol, 1.0 equiv), 6-((2-(2,6-dioxopiperidin-3-yl)-1,3-dioxoisoindolin-4-yl)amino)hexanoic acid (7.8 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-137 was obtained as yellow solid in TFA salt form (11.3 mg, 53%). $^1$H NMR (600 MHz, Acetone-$d_6$) δ 13.78 (s, 1H), 10.03 (s, 1H), 9.98 (s, 1H), 7.74-7.67 (m, 2H), 7.58 (dd, J=8.6, 7.0 Hz, 1H), 7.54 (dd, J=9.2, 2.5 Hz, 1H), 7.31-7.25 (m, 1H), 7.08 (d, J=8.5 Hz, 1H), 7.03 (d, J=7.0 Hz, 1H), 6.94 (dd, J=8.4, 4.5 Hz, 1H), 6.90 (td, J=8.9, 2.5 Hz, 1H), 6.40 (s, 1H), 5.08 (dd, J=12.5, 5.5 Hz, 1H), 3.90-3.71 (m, 8H), 3.70-3.63 (m, 2H), 3.60-3.52 (m, 2H), 3.41-3.30 (m, 6H), 3.03-2.91 (m, 1H), 2.83-2.72 (m, 2H), 2.53 (s, 3H), 2.49 (s, 3H), 2.27-2.13 (m, 5H), 1.74-1.62 (m, 4H), 1.50-1.40 (m, 2H). HRMS calcd for $C_{44}H_{53}FN_9O_7$[M+H$^+$] 838.4052, found 838.4070.

Example 56

Synthesis of HC58-138

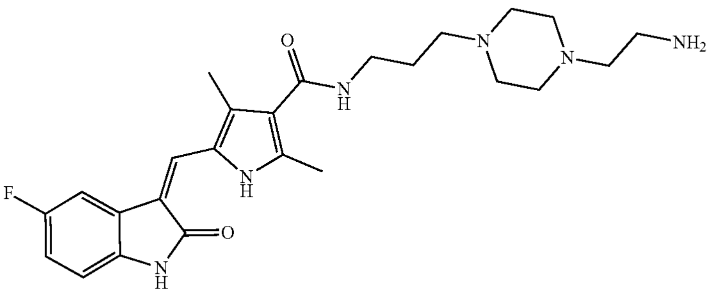

Intermediate 4

+

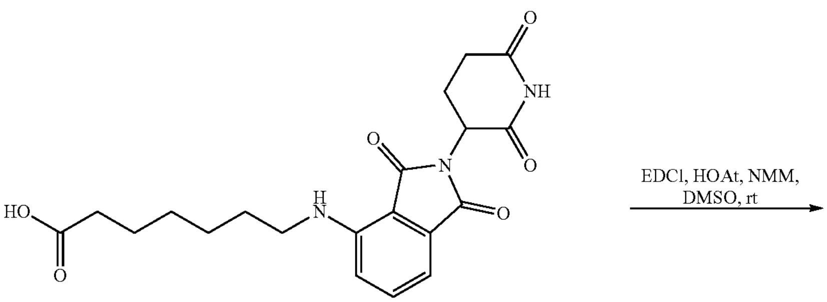

-continued

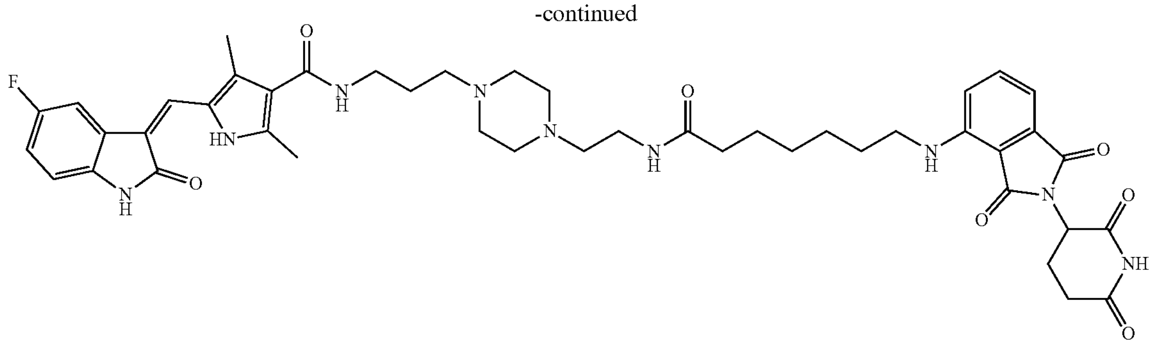

HC58-138

HC58-138 was synthesized following the standard procedure for preparing HC58-133 from Intermediate 4 (16.2 mg, 0.02 mmol, 1.0 equiv), 7-((2-(2,6-dioxopiperidin-3-yl)-1,3-dioxoisoindolin-4-yl)amino)heptanoic acid (8.0 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-138 was obtained as yellow solid in TFA salt form (11.7 mg, 54%). $^1$H NMR (600 MHz, Acetone-$d_6$) δ 13.78 (s, 1H), 10.01 (s, 1H), 9.98 (s, 1H), 7.71 (s, 1H), 7.61-7.53 (m, 2H), 7.24 (t, J=6.0 Hz, 1H), 7.09 (d, J=8.6 Hz, 1H), 7.03 (d, J=7.0 Hz, 1H), 6.94 (dd, J=8.4, 4.5 Hz, 1H), 6.90 (td, J=8.9, 2.5 Hz, 1H), 6.41 (s, 1H), 5.08 (dd, J=12.5, 5.5 Hz, 1H), 3.67-3.44 (m, 12H), 3.37 (t, J=7.1 Hz, 2H), 3.25 (t, J=7.7 Hz, 2H), 3.14 (t, J=5.8 Hz, 2H), 3.02-2.92 (m, 1H), 2.84-2.72 (m, 2H), 2.53 (s, 3H), 2.50 (s, 3H), 2.28-2.15 (m, 3H), 2.15-2.10 (m, 2H), 1.69 (p, J=7.3 Hz, 2H), 1.61 (p, J=7.5 Hz, 2H), 1.45 (p, J=7.1 Hz, 2H), 1.41-1.34 (m, 2H). HRMS calcd for $C_{45}H_{55}FN_9O_7$[M+H$^+$] 852.4208, found 852.4224.

Example 57

Synthesis of HC58-139

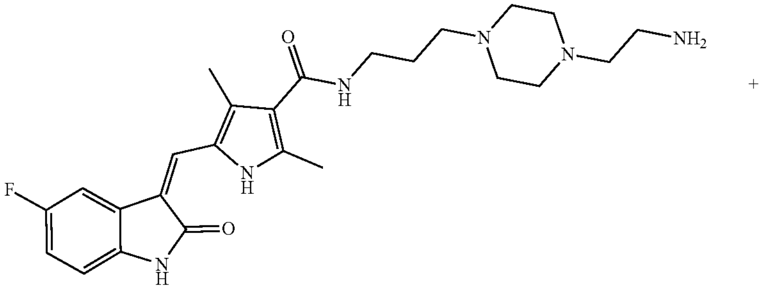

Intermediate 4

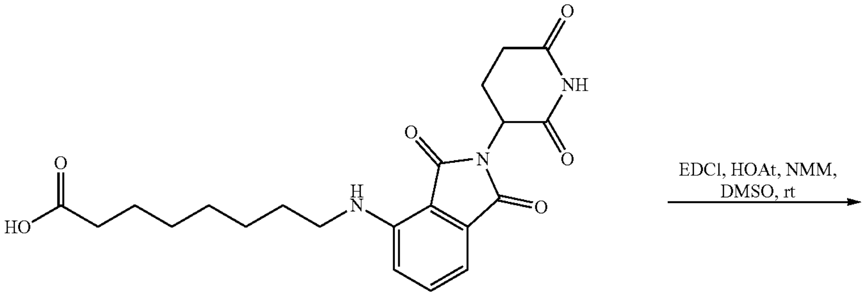

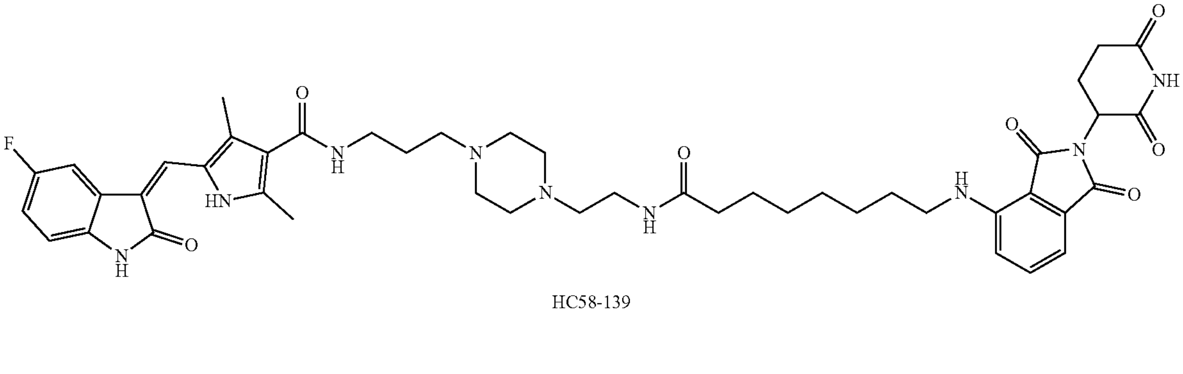

HC58-139

HC58-139 was synthesized following the standard procedure for preparing HC58-133 from Intermediate 4 (16.2 mg, 0.02 mmol, 1.0 equiv), 8-((2-(2,6-dioxopiperidin-3-yl)-1,3-dioxoisoindolin-4-yl)amino)octanoic acid (8.3 mg, 0.02 mmol, 1.0 equiv), EDCI (5.8 mg, 0.03 mmol, 1.5 equiv), HOAt (4.1 mg, 0.03 mmol, 1.5 equiv), and NMM (12.1 mg, 0.12 mmol, 6.0 equiv) in DMSO (1 mL). HC58-139 was obtained as yellow solid in TFA salt form (11.8 mg, 54%). $^1$H NMR (600 MHz, Acetone-$d_6$) δ 13.79 (s, 1H), 9.99 (s, 1H), 9.96 (s, 1H), 7.71 (s, 1H), 7.64-7.52 (m, 2H), 7.26 (s, 1H), 7.09 (d, J=8.6 Hz, 1H), 7.03 (d, J=7.1 Hz, 1H), 6.97-6.87 (m, 2H), 6.41 (s, 1H), 5.15-4.99 (m, 1H), 3.81-3.67 (m, 8H), 3.66-3.61 (m, 2H), 3.58-3.52 (m, 2H), 3.39-3.32 (m, 4H), 3.31-3.23 (m, 2H), 3.01-2.92 (m, 1H), 2.84-2.72 (m, 2H), 2.53 (s, 3H), 2.50 (s, 3H), 2.26-2.12 (m, 5H), 1.75-1.64 (m, 2H), 1.63-1.55 (m, 2H), 1.49-1.29 (m, 6H). HRMS calcd for $C_{46}H_{57}FN_9O_7$[M+H$^+$] 866.4365, found 866.4380.

Example 58

Synthesis of intermediate 5

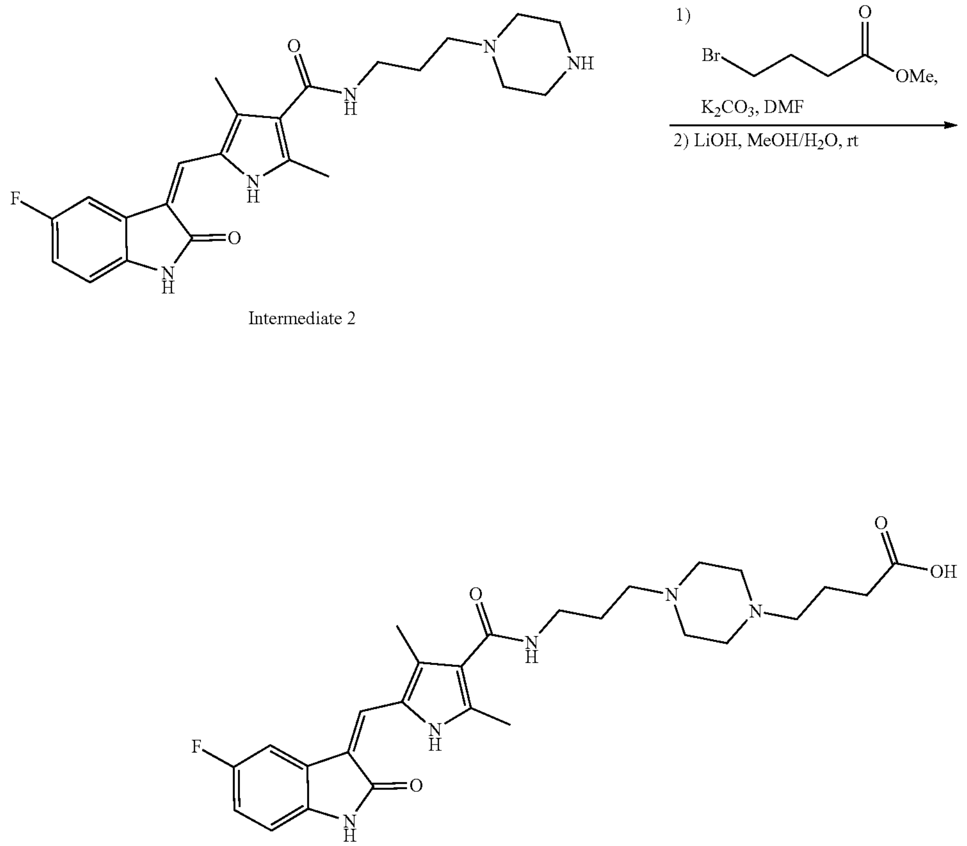

Intermediate 2

Intermediate 5

To a solution of intermediate 2 (196 mg, 0.3 mmol, 1.0 equiv) in DMF (4 mL) was added potassium carbonate (124 mg, 0.9 mmol, 3.0 equiv) and methyl 4-bromobutanoate (109 mg, 0.6 mmol, 2.0 equiv). Then the mixture was stirred at 60° C. overnight. Water (10 mL) was added to quench the reaction. The mixture was extracted with ethyl acetate (3×15 mL). The organic layer was combined and washed with brine. Dried over $Na_2SO_4$, filtered, evaporated and afforded solid. The obtained solid was dissolved in MeOH/$H_2O$ (2:1). To the solution was added LiOH (22 mg, 0.9 mmol, 3 equiv). After stirring overnight at room temperature, the reaction mixture was concentrated and the residue was purified by reverse phase $C_{18}$ column (10%-100% methanol/0.1% TFA in $H_2O$) to afford intermediate 5 as yellow solid in TFA salt form (154 mg, 69% yield for two steps). $^1$H NMR (600 MHz, Methanol-$d_4$) δ 7.59 (s, 1H), 7.42 (d, J=8.3 Hz, 1H), 6.92-6.85 (m, 2H), 3.51 (t, J=6.6 Hz, 2H), 3.48-3.36 (m, 8H), 3.15 (t, J=7.5 Hz, 2H), 3.09 (t, J=7.9 Hz, 2H), 2.52 (s, 3H), 2.50-2.44 (m, 5H), 2.09-1.96 (m, 4H).
ESI m/z=512.3 [M+H$^+$].

Example 59

Synthesis of HC58-144

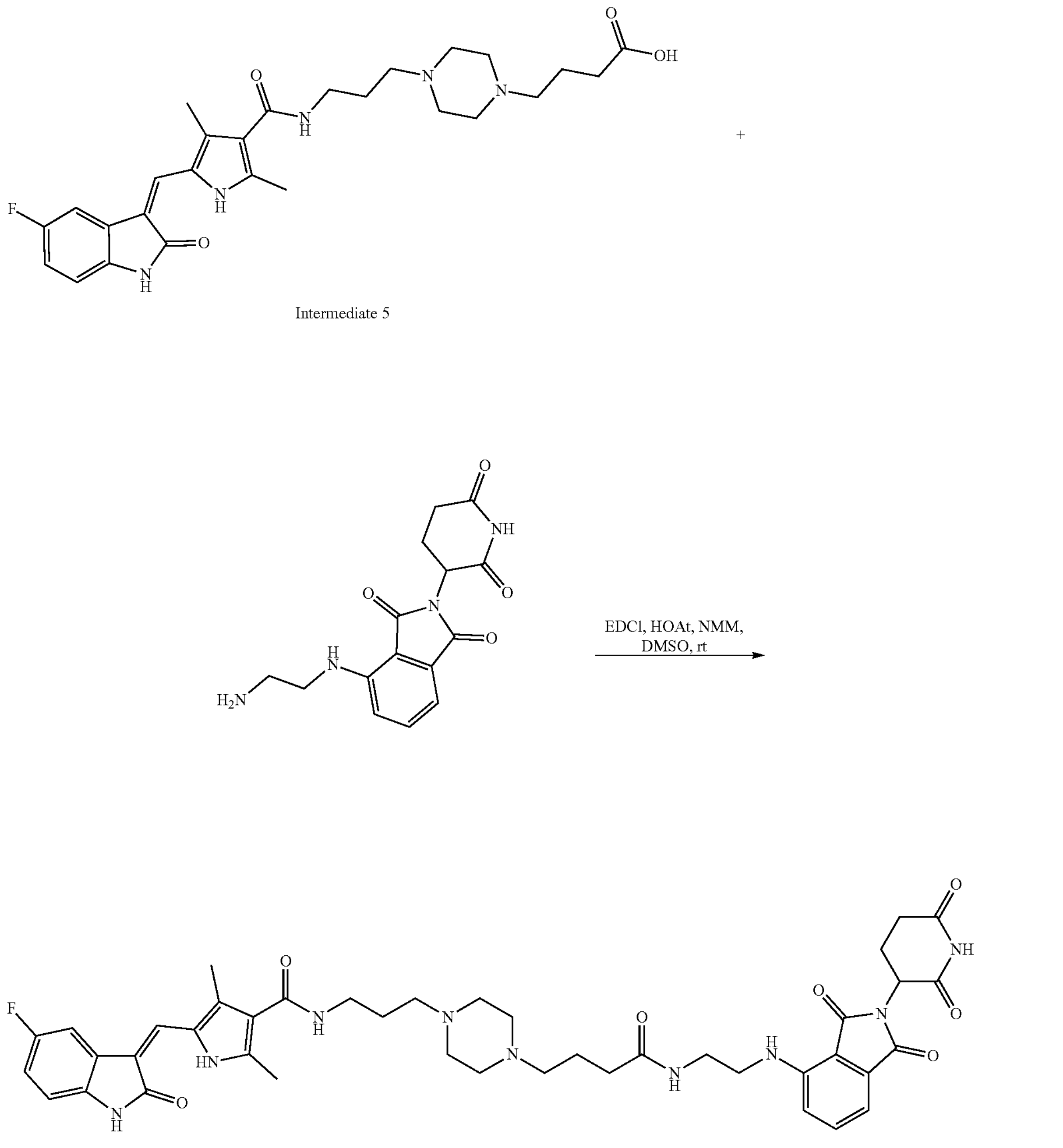

HC58-144

To a solution of Intermediate 5 (14.8 mg, 0.02 mmol, 1.0 equiv) in DMSO (1 mL) were added 4-((2-aminoethyl)amino)-2-(2,6-dioxopiperidin-3-yl)isoindoline-1,3-dione (9.5 mg, 0.022 mmol, 1.1 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (10.1 mg, 0.1 mmol, 5.0 equiv). After being stirred overnight at room temperature, the resulting mixture was purified by preparative HPLC (10%-100% MeOH/0.1% TFA in $H_2O$) to afford HC58-144 as yellow solid in TFA salt form (11.6 mg, 56%). $^1H$ NMR (600 MHz, Acetone-$d_6$) δ 13.82 (s, 1H), 10.10 (s, 1H), 9.95 (s, 1H), 7.99 (s, 1H), 7.72 (s, 1H), 7.60 (dd, J=8.6, 7.0 Hz, 1H), 7.55 (dd, J=9.1, 2.5 Hz, 1H), 7.35 (s, 1H), 7.16 (d, J=8.5 Hz, 1H), 7.06 (d, J=7.0 Hz, 1H), 7.00-6.86 (m, 2H), 5.11 (dd, J=12.7, 5.5 Hz, 1H), 3.99-3.72 (m, 8H), 3.64-3.50 (m, 6H), 3.49-3.38 (m, 4H), 3.02-2.91 (m, 1H), 2.81-2.71 (m, 2H), 2.54 (s, 3H), 2.51 (s, 3H), 2.27-2.16 (m, 2H), 2.14-2.01 (m, 5H). HRMS calcd for $C_{42}H_{49}FN_9O_7[M+H^+]$ 810.3739, found 810.3747.

Example 60

Synthesis of HC58-145

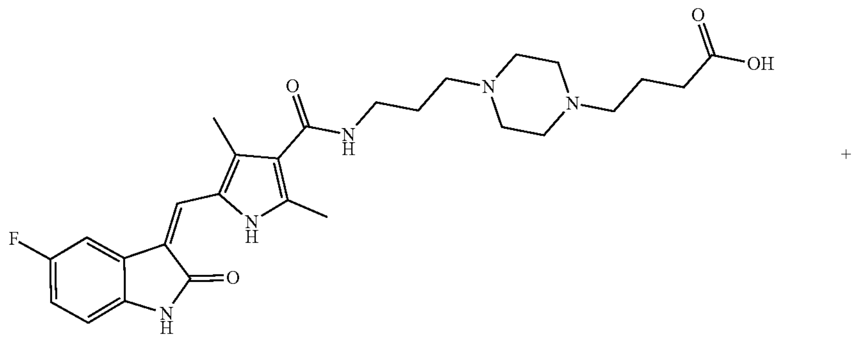

Intermediate 5

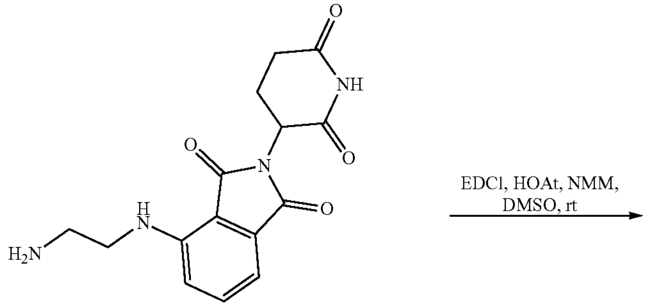

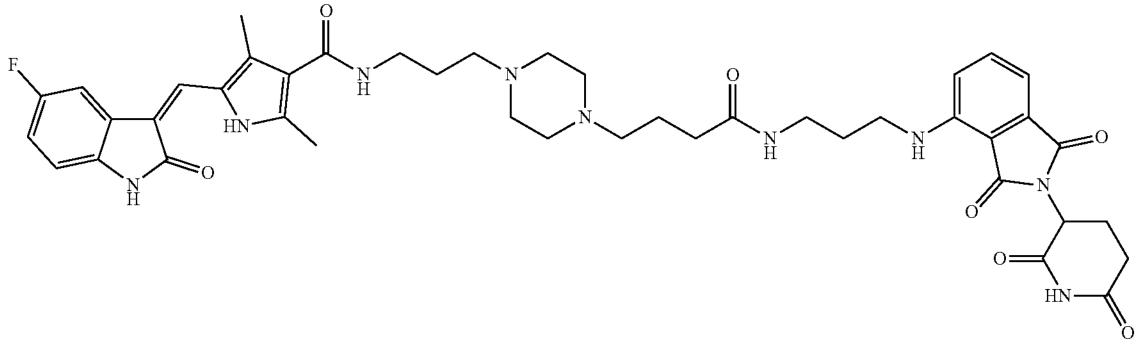

HC58-145

HC58-145 was synthesized following the standard procedure for preparing HC58-144 from Intermediate 5 (14.8 mg, 0.02 mmol, 1.0 equiv), 4-((3-aminopropyl)amino)-2-(2,6-dioxopiperidin-3-yl)isoindoline-1,3-dione (9.8 mg, 0.022 mmol, 1.1 equiv), EDCI (5.8 mg, 0.03 mmol, 1.5 equiv), HOAt (4.1 mg, 0.03 mmol, 1.5 equiv), and NMM (10.1 mg, 0.1 mmol, 5.0 equiv) in DMSO (1 mL). HC58-145 was obtained as yellow solid in TFA salt form (10.3 mg, 49%). $^1$H NMR (600 MHz, Acetone-$d_6$) δ 13.77 (s, 1H), 10.07 (s, 1H), 10.00 (s, 1H), 7.70 (s, 1H), 7.63 (s, 1H), 7.58 (dd, J=8.6, 7.0 Hz, 1H), 7.54 (dd, J=9.1, 2.5 Hz, 1H), 7.24-7.18 (m, 1H), 7.09 (d, J=8.6 Hz, 1H), 7.03 (d, J=7.1 Hz, 1H), 6.94 (dd, J=8.5, 4.5 Hz, 1H), 6.90 (td, J=8.9, 2.5 Hz, 1H), 6.61 (s, 1H), 5.09 (dd, J=12.5, 5.6 Hz, 1H), 3.65-3.48 (m, 10H), 3.46-3.40 (m, 2H), 3.38-3.32 (m, 2H), 3.23 (t, J=7.7 Hz, 2H), 3.18 (t, J=7.4 Hz, 2H), 2.96 (ddd, J=14.8, 10.5, 7.4 Hz, 1H), 2.82-2.71 (m, 2H), 2.52 (s, 3H), 2.49 (s, 3H), 2.41 (t, J=6.8 Hz, 2H), 2.26-2.18 (m, 1H), 2.12-2.08 (m, 4H), 1.89-1.77 (m, 2H). HRMS calcd for $C_{43}H_{51}FN_9O_7$[M+H$^+$] 824.3895, found 824.3889.

Example 61

Synthesis of HC58-146

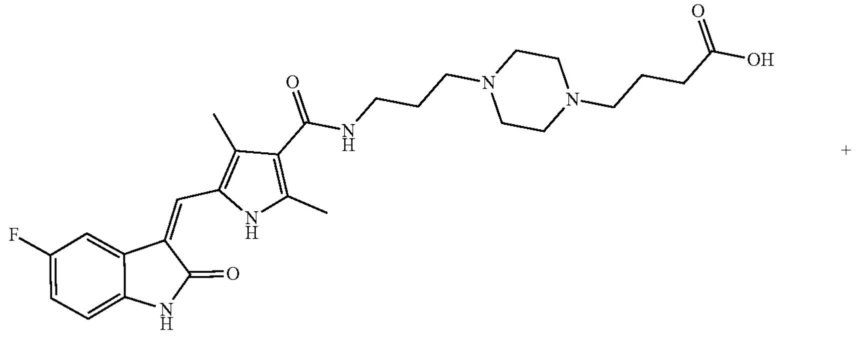

Intermediate 5

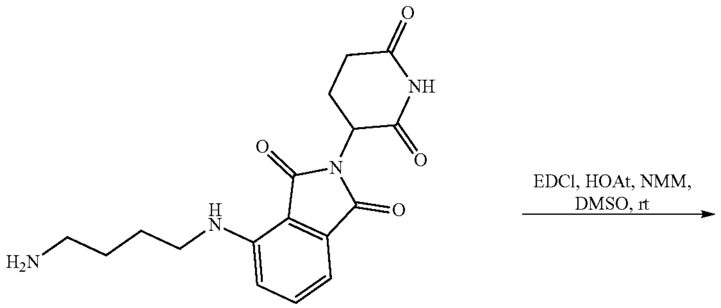

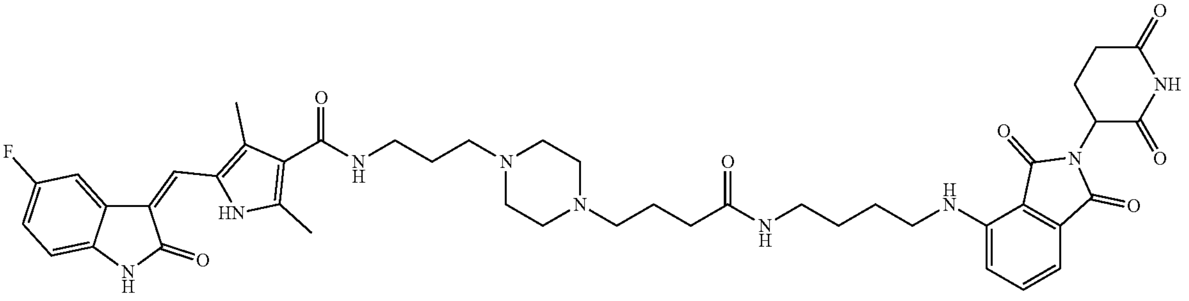

HC58-146

HC58-146 was synthesized following the standard procedure for preparing HC58-144 from Intermediate 5 (14.8 mg, 0.02 mmol, 1.0 equiv), 4-((4-aminobutyl)amino)-2-(2,6-dioxopiperidin-3-yl)isoindoline-1,3-dione (10.0 mg, 0.022 mmol, 1.1 equiv), EDCI (5.8 mg, 0.03 mmol, 1.5 equiv), HOAt (4.1 mg, 0.03 mmol, 1.5 equiv), and NMM (10.1 mg, 0.1 mmol, 5.0 equiv) in DMSO (1 mL). HC58-146 was obtained as yellow solid in TFA salt form (8.3 mg, 39%). $^1$H NMR (600 MHz, Acetone-$d_6$) δ 13.77 (s, 1H), 10.06 (s, 1H), 10.00 (s, 1H), 7.70 (s, 1H), 7.62-7.56 (m, 1H), 7.54 (dd, J=9.2, 2.5 Hz, 1H), 7.48 (t, J=5.8 Hz, 1H), 7.23 (t, J=6.0 Hz, 1H), 7.10 (d, J=8.6 Hz, 1H), 7.03 (d, J=7.1 Hz, 1H), 6.94 (dd, J=8.4, 4.5 Hz, 1H), 6.90 (td, J=9.0, 2.5 Hz, 1H), 6.42 (s, 1H), 5.09 (dd, J=12.5, 5.5 Hz, 1H), 3.68-3.49 (m, 10H), 3.40 (t, J=7.1 Hz, 2H), 3.28-3.20 (m, 4H), 3.15 (t, J=7.5 Hz, 2H), 2.97 (ddd, J=18.8, 14.7, 5.2 Hz, 1H), 2.83-2.72 (m, 2H), 2.52 (s, 3H), 2.49 (s, 3H), 2.36 (t, J=6.9 Hz, 2H), 2.21 (dt, J=10.8, 5.3 Hz, 1H), 2.14-2.02 (m, 4H), 1.72 (p, J=7.1 Hz, 2H), 1.63 (p, J=7.0 Hz, 2H). HRMS calcd for $C_{44}H_{53}FN_9O_7$[M+H$^+$] 838.4052, found 838.4068.

Example 62

Synthesis of HC58-147

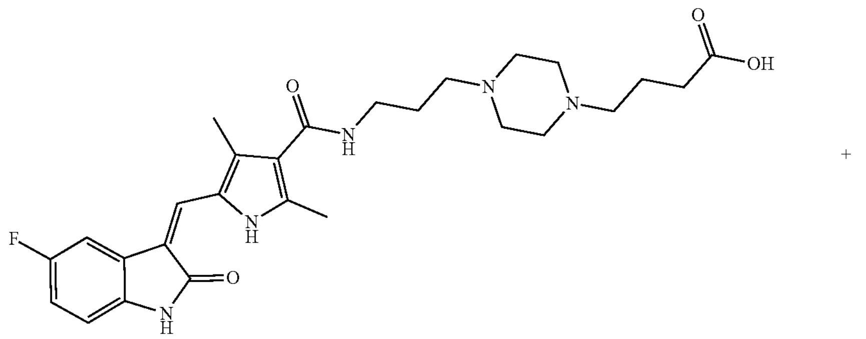

Intermediate 5

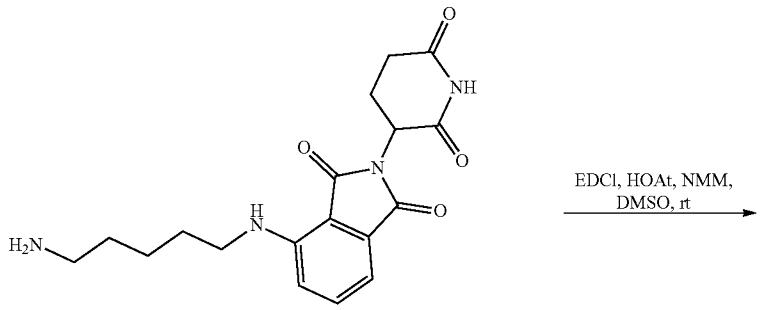

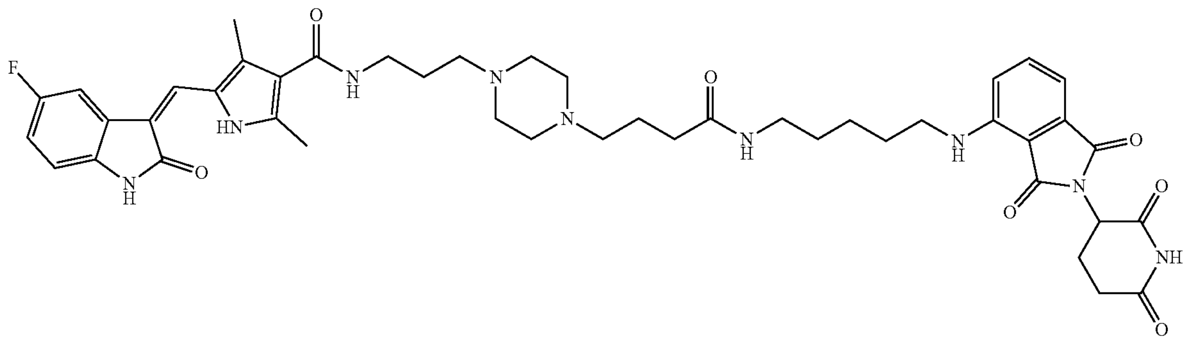

HC58-147

HC58-147 was synthesized following the standard procedure for preparing HC58-144 from Intermediate 5 (14.8 mg, 0.02 mmol, 1.0 equiv), 4-((5-aminopentyl)amino)-2-(2,6-dioxopiperidin-3-yl)isoindoline-1,3-dione (11.0 mg, 0.022 mmol, 1.1 equiv), EDCI (5.8 mg, 0.03 mmol, 1.5 equiv), HOAt (4.1 mg, 0.03 mmol, 1.5 equiv), and NMM (10.1 mg, 0.1 mmol, 5.0 equiv) in DMSO (1 mL). HC58-147 was obtained as yellow solid in TFA salt form (9.5 mg, 44%). $^1H$ NMR (600 MHz, Acetone-$d_6$) δ 13.79 (s, 1H), 10.02 (s, 1H), 9.97 (s, 1H), 7.72 (s, 1H), 7.59 (dd, J=8.6, 7.0 Hz, 1H), 7.55 (dd, J=9.2, 2.5 Hz, 1H), 7.42-7.36 (m, 1H), 7.25-7.18 (m, 1H), 7.09 (d, J=8.5 Hz, 1H), 7.04 (d, J=7.1 Hz, 1H), 6.94 (dd, J=8.4, 4.5 Hz, 1H), 6.90 (td, J=8.9, 2.5 Hz, 1H), 6.41 (s, 1H), 5.09 (dd, J=12.5, 5.4 Hz, 1H), 3.74-3.49 (m, 10H), 3.37 (t, J=7.1 Hz, 2H), 3.28-3.20 (m, 4H), 3.17 (t, J=7.5 Hz, 2H), 2.97 (ddd, J=18.1, 14.8, 5.3 Hz, 1H), 2.84-2.73 (m, 2H), 2.53 (s, 3H), 2.50 (s, 3H), 2.36 (t, J=6.8 Hz, 2H), 2.25-2.19 (m, 1H), 2.15-2.06 (m, 4H), 1.78-1.67 (m, 2H), 1.63-1.53 (m, 2H), 1.51-1.43 (m, 2H). HRMS calcd for $C_{45}H_{55}FN_9O_7$[M+$H^+$] 852.4208, found 852.4201.

Example 63

Synthesis of HC58-148

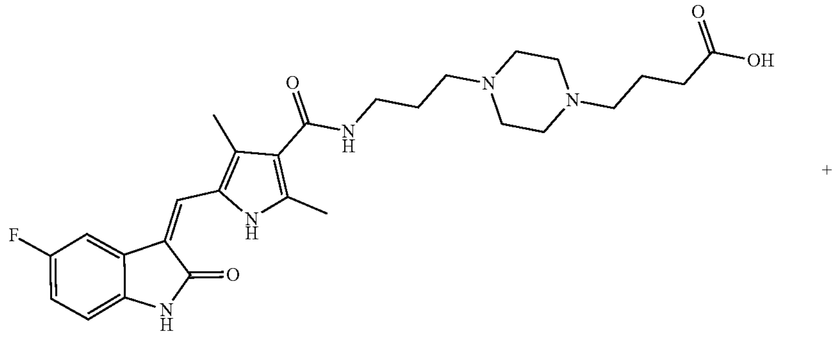

Intermediate 5

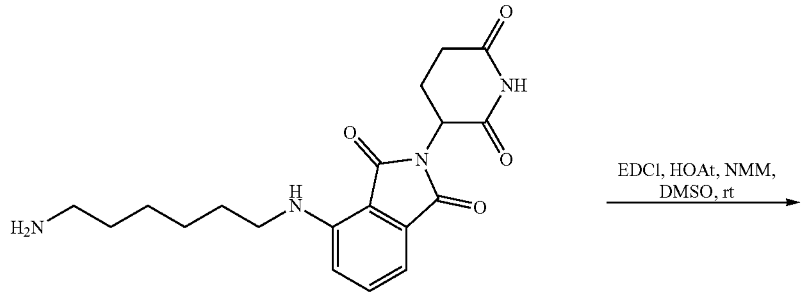

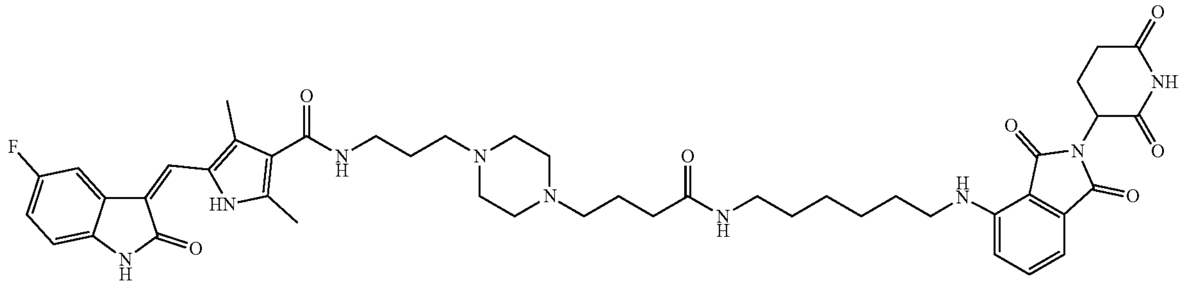

HC58-148

HC58-148 was synthesized following the standard procedure for preparing HC58-144 from Intermediate 5 (14.8 mg, 0.02 mmol, 1.0 equiv), 4-((6-aminohexyl)amino)-2-(2,6-dioxopiperidin-3-yl)isoindoline-1,3-dione (9.0 mg, 0.022 mmol, 1.1 equiv), EDCI (5.8 mg, 0.03 mmol, 1.5 equiv), HOAt (4.1 mg, 0.03 mmol, 1.5 equiv), and NMM (10.1 mg, 0.1 mmol, 5.0 equiv) in DMSO (1 mL). HC58-148 was obtained as yellow solid in TFA salt form (9.2 mg, 42%). $^1$H NMR (600 MHz, Acetone-$d_6$) δ 13.78 (s, 1H), 10.02 (s, 1H), 10.00 (s, 1H), 7.71 (s, 1H), 7.59 (dd, J=8.5, 7.1 Hz, 1H), 7.55 (dd, J=9.2, 2.5 Hz, 1H), 7.35 (s, 1H), 7.20 (t, J=5.9 Hz, 1H), 7.09 (d, J=8.5 Hz, 1H), 7.03 (d, J=7.1 Hz, 1H), 6.94 (dd, J=8.4, 4.5 Hz, 1H), 6.90 (td, J=9.0, 2.5 Hz, 1H), 6.42 (s, 1H), 5.08 (dd, J=12.4, 5.5 Hz, 1H), 3.59-3.43 (m, 10H), 3.40-3.34 (m, 2H), 3.23-3.15 (m, 4H), 3.08 (t, J=7.5 Hz, 2H), 2.97 (ddd, J=18.5, 15.0, 5.2 Hz, 1H), 2.82-2.72 (m, 2H), 2.53 (s, 3H), 2.50 (s, 3H), 2.33 (t, J=6.9 Hz, 2H), 2.26-2.18 (m, 1H), 2.11-2.07 (m, 2H), 2.04-1.99 (m, 2H), 1.69 (p, J=7.2 Hz, 2H), 1.55-1.35 (m, 6H). HRMS calcd for $C_{46}H_{57}FN_9O_7$[M+H$^+$]866.4365, found 866.4381.

Example 64

Synthesis of HC58-149

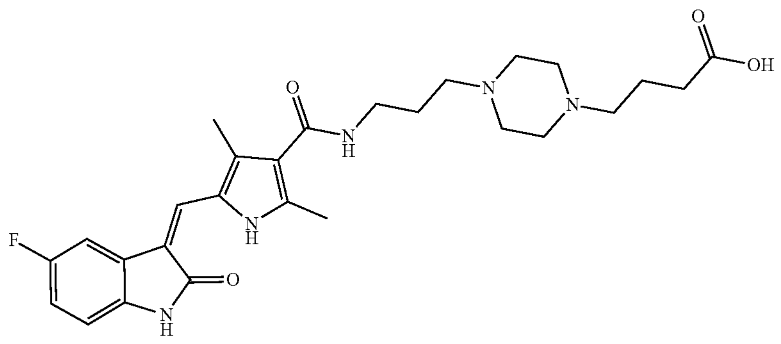

Intermediate 5

+

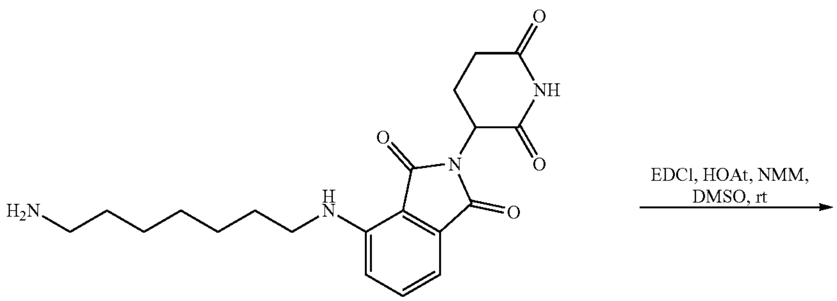

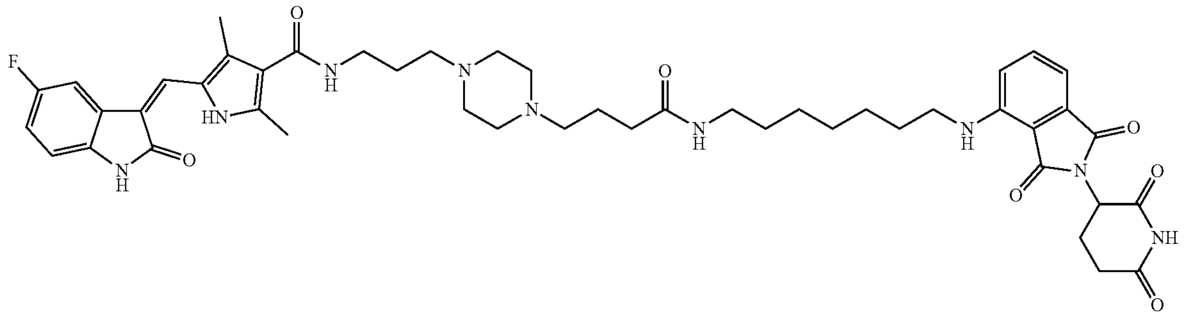

HC58-149

HC58-149 was synthesized following the standard procedure for preparing HC58-144 from Intermediate 5 (14.8 mg, 0.02 mmol, 1.0 equiv), 4-((7-aminoheptyl)amino)-2-(2,6-dioxopiperidin-3-yl)isoindoline-1,3-dione (11.0 mg, 0.022 mmol, 1.1 equiv), EDCI (5.8 mg, 0.03 mmol, 1.5 equiv), HOAt (4.1 mg, 0.03 mmol, 1.5 equiv), and NMM (10.1 mg, 0.1 mmol, 5.0 equiv) in DMSO (1 mL). HC58-149 was obtained as yellow solid in TFA salt form (9.8 mg, 44%). $^{1}H$ NMR (600 MHz, Acetone-$d_6$) δ 13.78 (s, 1H), 10.02 (s, 1H), 9.99 (s, 1H), 7.71 (s, 1H), 7.59 (t, J=7.8 Hz, 1H), 7.55 (dd, J=9.1, 2.4 Hz, 1H), 7.34 (s, 1H), 7.20 (s, 1H), 7.09 (d, J=8.5 Hz, 1H), 7.03 (d, J=7.0 Hz, 1H), 6.94 (dd, J=8.5, 4.5 Hz, 1H), 6.90 (td, J=9.0, 2.5 Hz, 1H), 6.41 (s, 1H), 5.08 (dd, J=12.4, 5.4 Hz, 1H), 3.60-3.43 (m, 10H), 3.37 (t, J=7.2 Hz, 2H), 3.22-3.16 (m, 4H), 3.09 (t, J=7.6 Hz, 2H), 2.97 (ddd, J=19.7, 15.2, 5.3 Hz, 1H), 2.84-2.72 (m, 2H), 2.53 (s, 3H), 2.50 (s, 3H), 2.33 (t, J=6.9 Hz, 2H), 2.22 (dt, J=10.9, 5.8 Hz, 1H), 2.11-2.00 (m, 4H), 1.69 (p, J=7.3 Hz, 2H), 1.53-1.31 (m, 8H). HRMS calcd for $C_{47}H_{59}FN_9O_7[M+H^+]$ 880.4521, found 880.4529.

Example 65

Synthesis of HC58-150

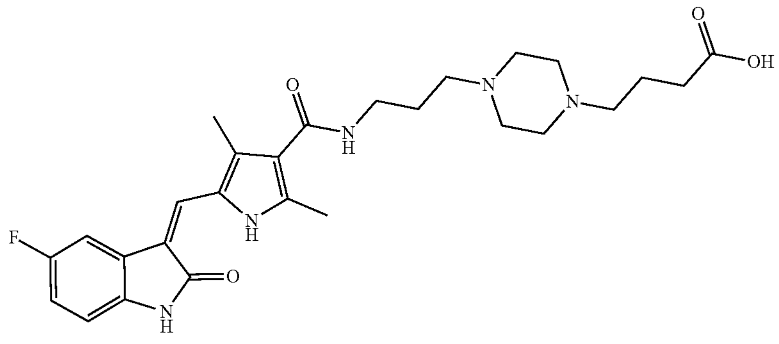

Intermediate 5

+

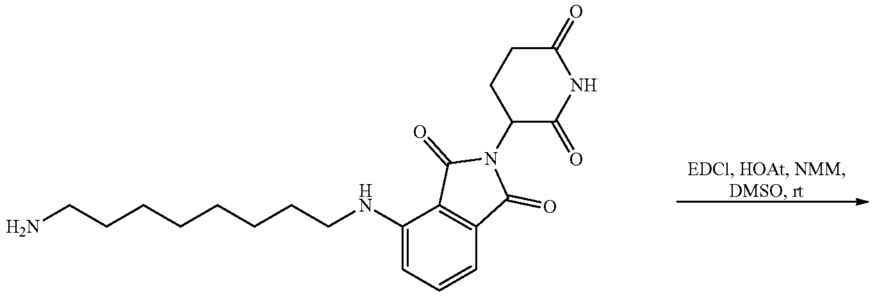

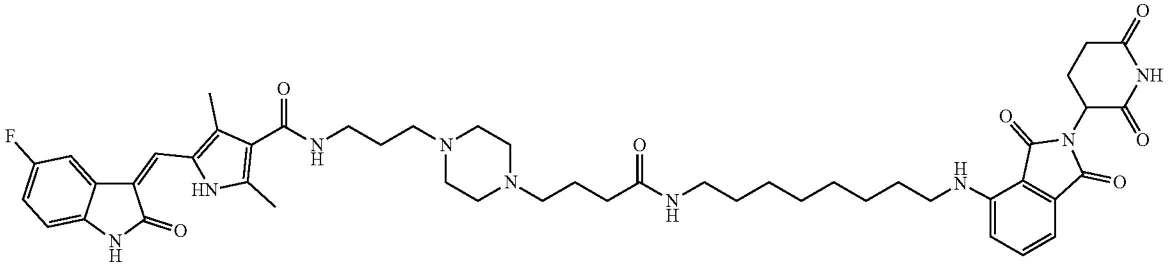

HC58-150

HC58-150 was synthesized following the standard procedure for preparing HC58-144 from Intermediate 5 (14.8 mg, 0.02 mmol, 1.0 equiv), 4-((8-aminooctyl)amino)-2-(2,6-dioxopiperidin-3-yl)isoindoline-1,3-dione (11.3 mg, 0.022 mmol, 1.1 equiv), EDCI (5.8 mg, 0.03 mmol, 1.5 equiv), HOAt (4.1 mg, 0.03 mmol, 1.5 equiv), and NMM (10.1 mg, 0.1 mmol, 5.0 equiv) in DMSO (1 mL). HC58-150 was obtained as yellow solid in TFA salt form (8.5 mg, 38%). $^1$H NMR (600 MHz, Acetone-$d_6$) δ 13.78 (s, 1H), 10.02 (s, 1H), 10.00 (s, 1H), 7.71 (s, 1H), 7.59 (dd, J=8.6, 7.0 Hz, 1H), 7.55 (dd, J=9.2, 2.5 Hz, 1H), 7.34 (s, 1H), 7.20 (t, J=5.9 Hz, 1H), 7.09 (d, J=8.5 Hz, 1H), 7.03 (d, J=7.0 Hz, 1H), 6.95 (dd, J=8.5, 4.5 Hz, 1H), 6.90 (td, J=9.0, 2.5 Hz, 1H), 6.42 (s, 1H), 5.08 (dd, J=12.6, 5.5 Hz, 1H), 3.56-3.32 (m, 12H), 3.21-3.13 (m, 4H), 3.07 (t, J=7.5 Hz, 2H), 3.01-2.92 (m, 1H), 2.83-2.73 (m, 2H), 2.53 (s, 3H), 2.50 (s, 3H), 2.33 (t, J=6.9 Hz, 2H), 2.27-2.19 (m, 1H), 2.13-2.06 (m, 2H), 2.01 (p, J=7.0 Hz, 2H), 1.69 (p, J=7.2 Hz, 2H), 1.53-1.28 (m, 10H). HRMS calcd for $C_{48}H_{61}FN_9O_7[M+H^+]$ 894.4678, found 894.4689.

Example 66

Synthesis of HC58-158

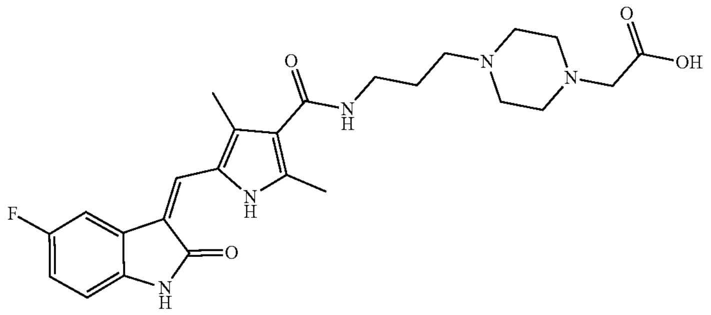

Intermediate 3

+

-continued

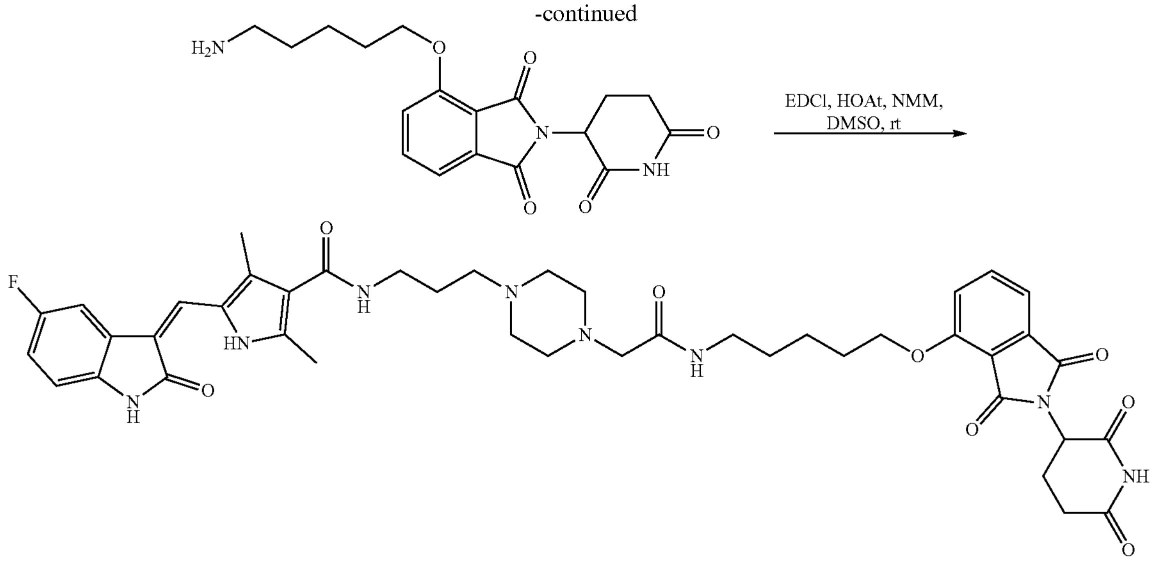

HC58-158

HC58-158 was synthesized following the standard procedure for preparing HC58-53 from Intermediate 3 (12.0 mg, 0.017 mmol, 1.0 equiv), 4-((5-aminopentyl)oxy)-2-(2,6-dioxopiperidin-3-yl)isoindoline-1,3-dione (9.5 mg, 0.02 mmol, 1.2 equiv), EDCI (5.0 mg, 0.026 mmol, 1.5 equiv), HOAt (4.0 mg, 0.026 mmol, 1.5 equiv), and NMM (8.6 mg, 0.085 mmol, 5.0 equiv) in DMSO (1 mL). HC58-158 was obtained as yellow solid in TFA salt form (8.2 mg, 46%). $^1$H NMR (600 MHz, Methanol-$d_4$) δ 13.63 (s, 1H), 7.74 (dd, J=8.4, 7.3 Hz, 1H), 7.51 (s, 1H), 7.43-7.35 (m, 3H), 6.89-6.81 (m, 2H), 5.10 (dd, J=12.7, 5.5 Hz, 1H), 4.20 (t, J=6.1 Hz, 2H), 3.49 (t, J=6.6 Hz, 2H), 3.44-3.29 (m, 8H), 3.22 (t, J=7.5 Hz, 2H), 3.07-2.91 (m, 4H), 2.87 (ddd, J=17.3, 13.9, 5.4 Hz, 1H), 2.79-2.68 (m, 2H), 2.48 (s, 3H), 2.44 (s, 3H), 2.19-2.10 (m, 1H), 2.06 (p, J=6.7 Hz, 2H), 1.87 (p, J=6.3 Hz, 2H), 1.68-1.55 (m, 4H). HRMS calcd for $C_{43}H_{50}FN_8O_8$[M+H$^+$] 825.3736, found 825.3749.

Example 67

Synthesis of HC58-159

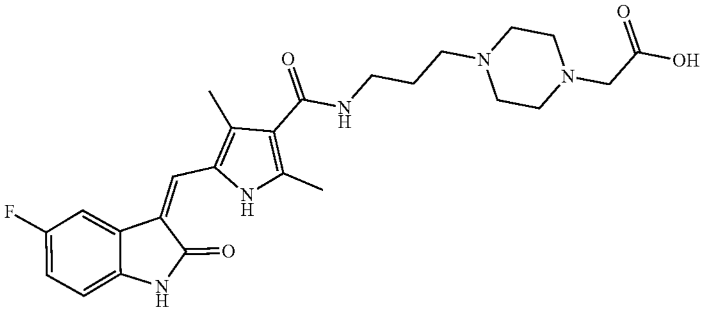

Intermediate 3

+

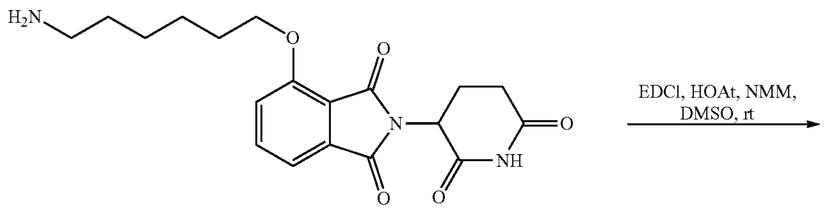

-continued

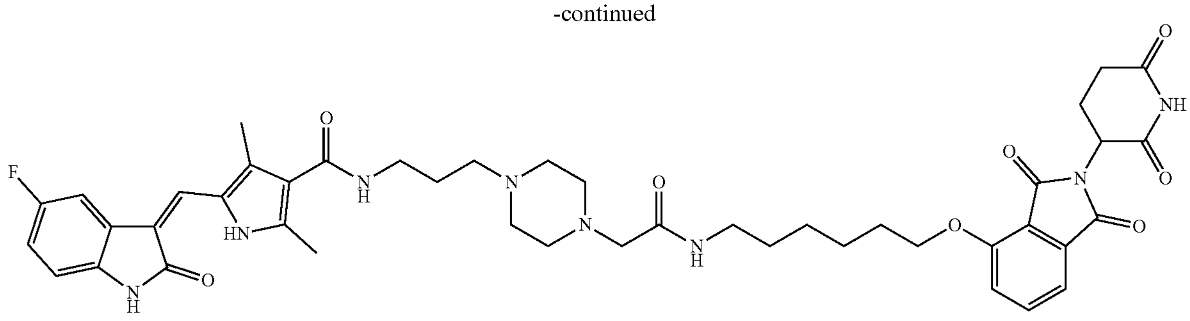

HC58-159

HC58-159 was synthesized following the standard procedure for preparing HC58-53 from Intermediate 3 (12.0 mg, 0.017 mmol, 1.0 equiv), 4-((6-aminohexyl)oxy)-2-(2,6-dioxopiperidin-3-yl)isoindoline-1,3-dione (9.7 mg, 0.02 mmol, 1.2 equiv), EDCI (5.0 mg, 0.026 mmol, 1.5 equiv), HOAt (4.0 mg, 0.026 mmol, 1.5 equiv), and NMM (8.6 mg, 0.085 mmol, 5.0 equiv) in DMSO (1 mL). HC58-159 was obtained as yellow solid in TFA salt form (8.0 mg, 44%). $^1$H NMR (600 MHz, Methanol-$d_4$) δ 13.63 (s, 1H), 7.73 (dd, J=8.5, 7.4 Hz, 1H), 7.52 (s, 1H), 7.43-7.34 (m, 3H), 6.90-6.81 (m, 2H), 5.10 (dd, J=12.8, 5.5 Hz, 1H), 4.20 (t, J=6.2 Hz, 2H), 3.58-3.38 (m, 6H), 3.35-3.33 (m, 2H), 3.29-3.21 (m, 4H), 3.03 (s, 4H), 2.87 (ddd, J=17.7, 14.1, 5.3 Hz, 1H), 2.79-2.67 (m, 2H), 2.48 (s, 3H), 2.44 (s, 3H), 2.18-2.03 (m, 3H), 1.85 (p, J=6.3 Hz, 2H), 1.63-1.53 (m, 4H), 1.49-1.40 (m, 2H). HRMS calcd for $C_{44}H_{52}FN_8O_8$[M+H$^+$] 839.3892, found 839.3881.

Example 68

Synthesis of HC58-160

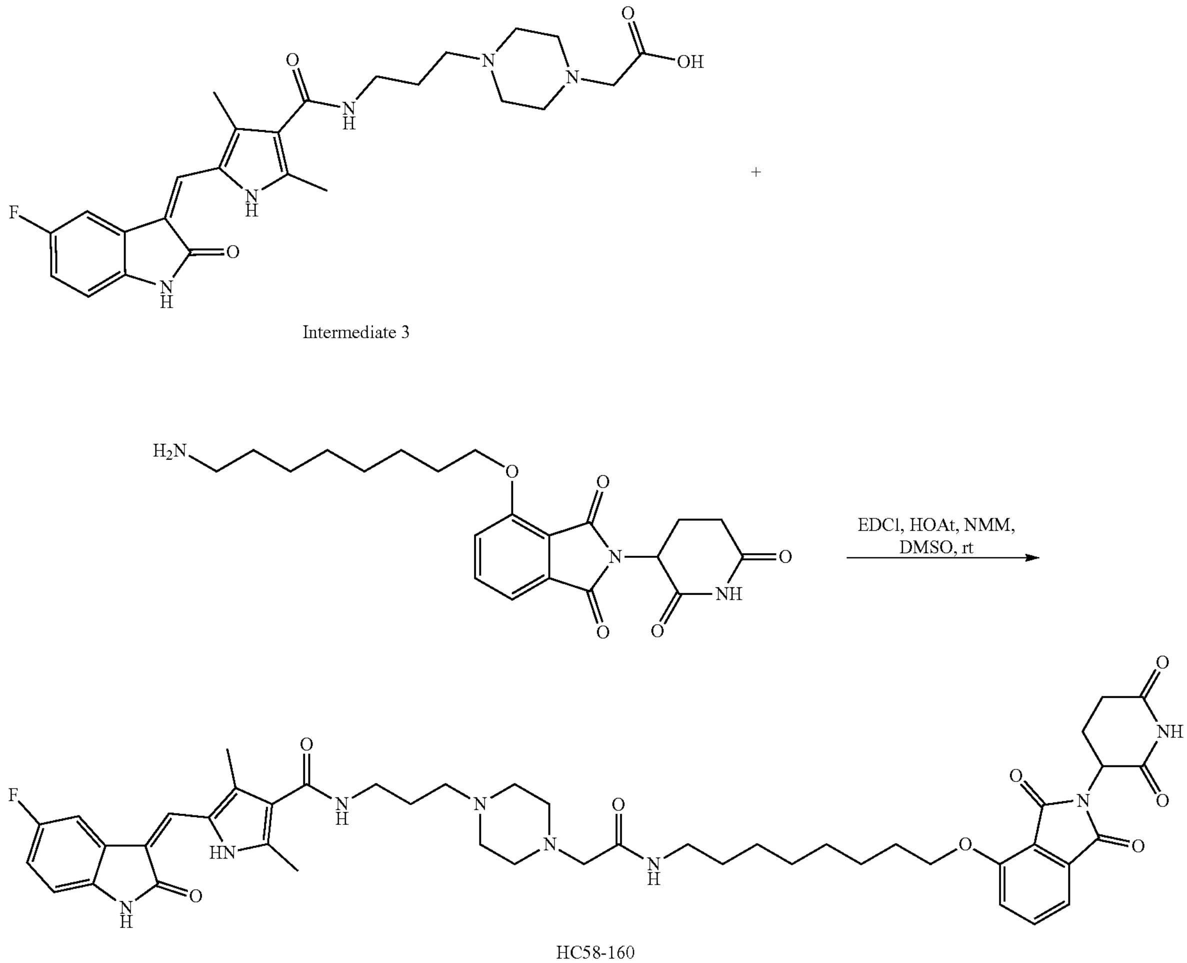

Intermediate 3

+

HC58-160

HC58-160 was synthesized following the standard procedure for preparing HC58-53 from Intermediate 3 (5.9 mg, 0.0083 mmol, 1.0 equiv), 4-((8-aminooctyl)oxy)-2-(2,6-dioxopiperidin-3-yl)isoindoline-1,3-dione (4.7 mg, 0.009 mmol, 1.1 equiv), EDCI (2.3 mg, 0.012 mmol, 1.5 equiv), HOAt (2.0 mg, 0.012 mmol, 1.5 equiv), and NMM (4.2 mg, 0.042 mmol, 5.0 equiv) in DMSO (0.6 mL). HC58-160 was obtained as yellow solid in TFA salt form (4.5 mg, 49%). $^1$H NMR (600 MHz, Methanol-$d_4$) δ 13.68 (s, 1H), 7.76-7.72 (m, 1H), 7.57 (s, 1H), 7.44-7.39 (m, 3H), 6.90-6.84 (m, 2H), 5.11 (dd, J=12.8, 5.5 Hz, 1H), 4.20 (t, J=6.3 Hz, 2H), 3.50 (t, J=6.5 Hz, 2H), 3.47-3.36 (m, 4H), 3.29-3.21 (m, 6H), 3.08-2.84 (m, 5H), 2.79-2.66 (m, 2H), 2.50 (s, 3H), 2.46 (s, 3H), 2.16-2.05 (m, 3H), 1.84 (p, J=6.5 Hz, 2H), 1.59-1.49 (m, 4H), 1.46-1.34 (m, 6H). HRMS calcd for $C_{46}H_{56}FN_8O_8$ [M+H$^+$] 867.4205, found 867.4221.

Example 69

Synthesis of HC58-161

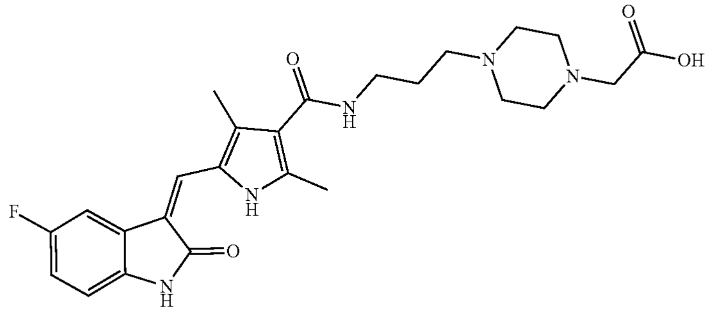

Intermediate 3

+

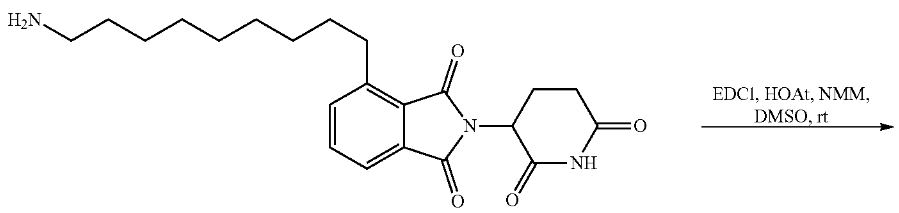

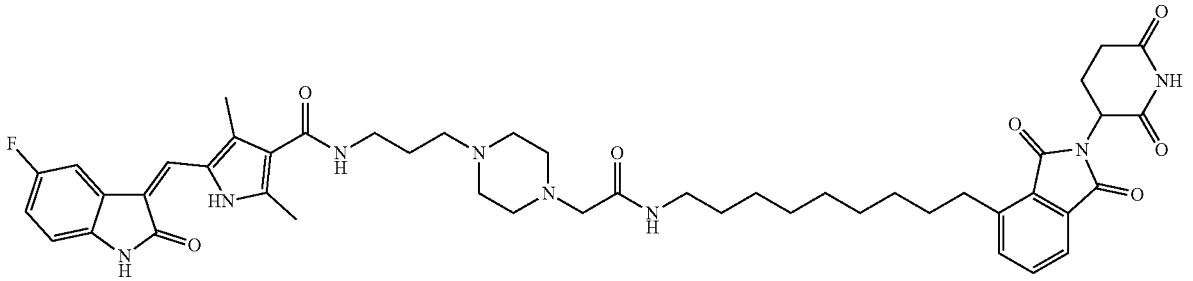

HC58-161

HC58-161 was synthesized following the standard procedure for preparing HC58-53 from Intermediate 3 (12.0 mg, 0.017 mmol, 1.0 equiv), 4-((5-aminopentyl)oxy)-2-(2,6-dioxopiperidin-3-yl)isoindoline-1,3-dione (9.4 mg, 0.018 mmol, 1.1 equiv), EDCI (5.0 mg, 0.026 mmol, 1.5 equiv), HOAt (4.0 mg, 0.026 mmol, 1.5 equiv), and NMM (8.6 mg, 0.085 mmol, 5.0 equiv) in DMSO (1 mL). HC58-161 was obtained as yellow solid in TFA salt form (6.5 mg, 35%). $^1$H NMR (600 MHz, Methanol-$d_4$) δ 13.66 (s, 1H), 7.71-7.67 (m, 2H), 7.62-7.58 (m, 1H), 7.53 (s, 1H), 7.39 (dd, J=8.9, 2.4 Hz, 1H), 6.90-6.82 (m, 2H), 5.13 (dd, J=12.7, 5.5 Hz, 1H), 3.55-3.39 (m, 6H), 3.28-3.21 (m, 4H), 3.14-2.95 (m, 6H), 2.89 (ddd, J=17.3, 13.8, 5.3 Hz, 1H), 2.80-2.69 (m, 2H), 2.50 (s, 3H), 2.46 (s, 3H), 2.19-2.04 (m, 3H), 1.65 (p, J=7.5 Hz, 2H), 1.57-1.49 (m, 2H), 1.43-1.27 (m, 12H). HRMS calcd for $C_{47}H_{58}FN_8O_7$ [M+H$^+$] 865.4412, found 865.4430.

Example 70

Synthesis of HC58-164

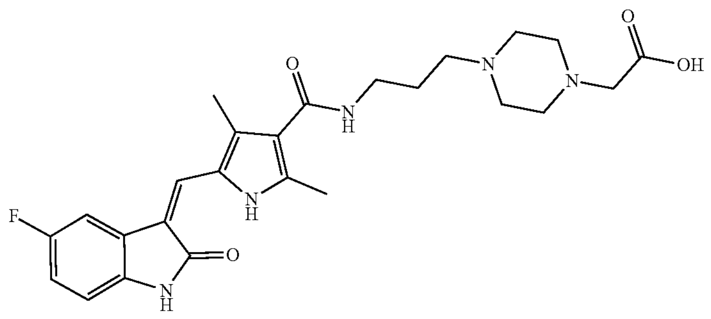

Intermediate 3

+

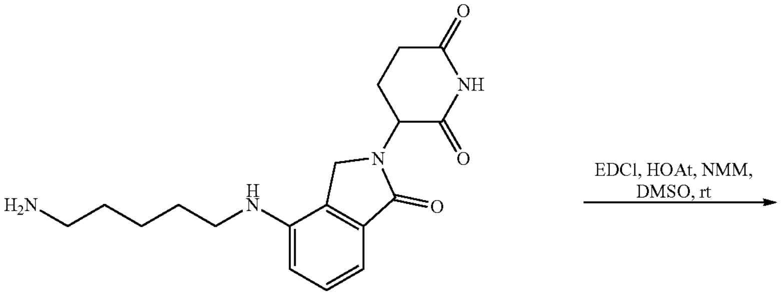

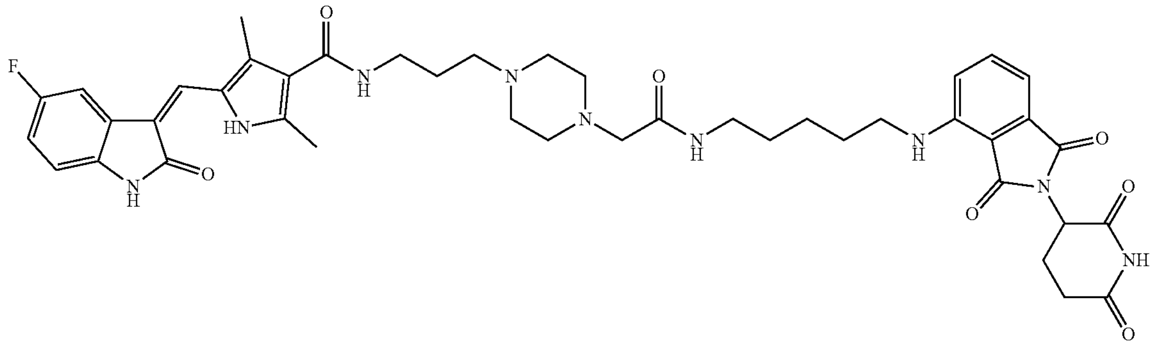

HC58-164

HC58-164 was synthesized following the standard procedure for preparing HC58-53 from Intermediate 3 (14.0 mg, 0.02 mmol, 1.0 equiv), 3-(4-((5-aminopentyl)amino)-1-oxoisoindolin-2-yl)piperidine-2,6-dione (10.0 mg, 0.022 mmol, 1.1 equiv), EDCI (5.8 mg, 0.03 mmol, 1.5 equiv), HOAt (4.1 mg, 0.03 mmol, 1.5 equiv), and NMM (10.1 mg, 0.1 mmol, 5.0 equiv) in DMSO (1 mL). HC58-164 was obtained as yellow solid in TFA salt form (8.9 mg, 35%). $^1$H NMR (600 MHz, Methanol-$d_4$) δ 13.70 (s, 1H), 7.58 (s, 1H), 7.46-7.41 (m, 2H), 7.39 (d, J=7.3 Hz, 1H), 7.20-7.15 (m, 1H), 6.92-6.84 (m, 2H), 5.17 (dd, J=13.5, 5.2 Hz, 1H), 4.46 (d, J=16.9 Hz, 1H), 4.38 (d, J=16.9 Hz, 1H), 3.86-3.73 (m, 2H), 3.51-3.44 (m, 2H), 3.40-3.21 (m, 8H), 3.15 (t, J=7.6 Hz, 2H), 3.06-2.88 (m, 7H), 2.51 (s, 3H), 2.48 (s, 3H), 2.24-2.16 (m, 1H), 2.02 (p, J=6.4 Hz, 2H), 1.65-1.51 (m, 4H), 1.39-1.27 (m, 2H). HRMS calcd for $C_{43}H_{53}FN_9O_6$[M+$H^+$]810.4103, found 810.4119.

Example 71

Synthesis of HC58-165

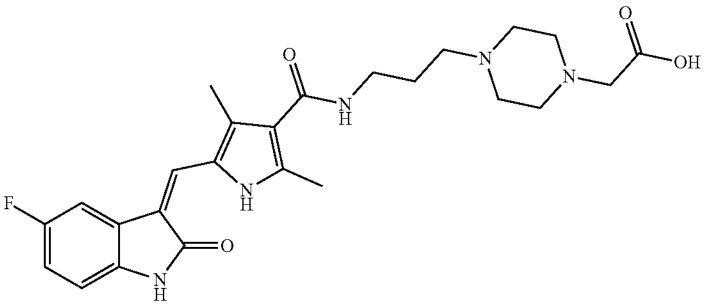

Intermediate 3

+

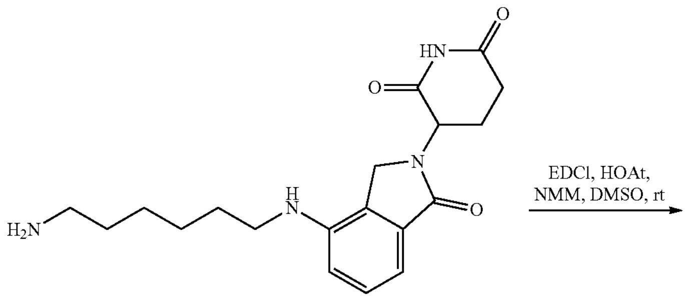

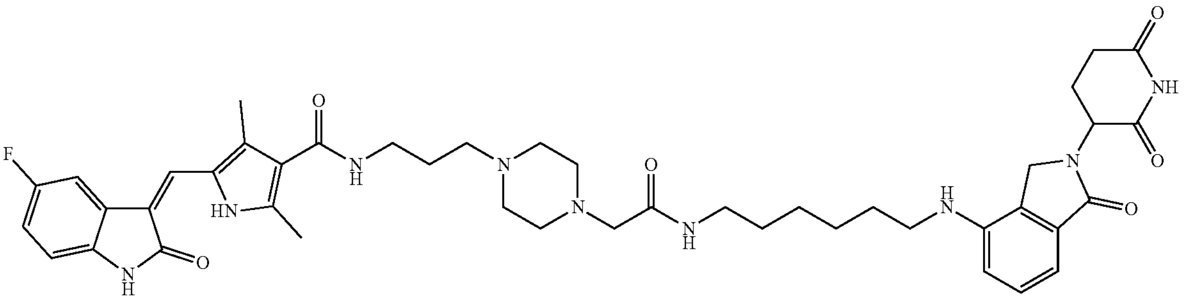

HC58-165

HC58-165 was synthesized following the standard procedure for preparing HC58-53 from Intermediate 3 (5.7 mg, 0.0085 mmol, 1.0 equiv), 3-(4-((6-aminohexyl)amino)-1-oxoisoindolin-2-yl)piperidine-2,6-dione (4.0 mg, 0.0085 mmol, 1.0 equiv), EDCI (2.5 mg, 0.013 mmol, 1.5 equiv), HOAt (2.0 mg, 0.013 mmol, 1.5 equiv), and NMM (4.3 mg, 0.043 mmol, 5.0 equiv) in DMSO (0.6 mL). HC58-165 was obtained as yellow solid in TFA salt form (3.4 mg, 38%). $^1$H NMR (600 MHz, Methanol-$d_4$) δ 13.73 (s, 1H), 7.62 (s, 1H), 7.48-7.43 (m, 1H), 7.32 (t, J=7.7 Hz, 1H), 7.20 (d, J=7.4 Hz, 1H), 7.00 (d, J=7.8 Hz, 1H), 6.95-6.85 (m, 2H), 5.15 (dd, J=13.5, 5.1 Hz, 1H), 4.38 (d, J=16.7 Hz, 1H), 4.29 (d, J=16.8 Hz, 1H), 3.85-3.75 (m, 2H), 3.50 (t, J=6.6 Hz, 2H), 3.41-3.33 (m, 4H), 3.26 (t, J=6.6 Hz, 2H), 3.22-3.16 (m, 4H), 3.03-2.79 (m, 7H), 2.53 (s, 3H), 2.49 (s, 3H), 2.24-2.17 (m, 1H), 2.10-2.02 (m, 2H), 1.63-1.50 (m, 4H), 1.45-1.28 (m, 4H). HRMS calcd for $C_{44}H_{55}FN_9O_6[M+H^+]$ 824.4259, found 824.4267.

Example 72

Synthesis of HC58-167

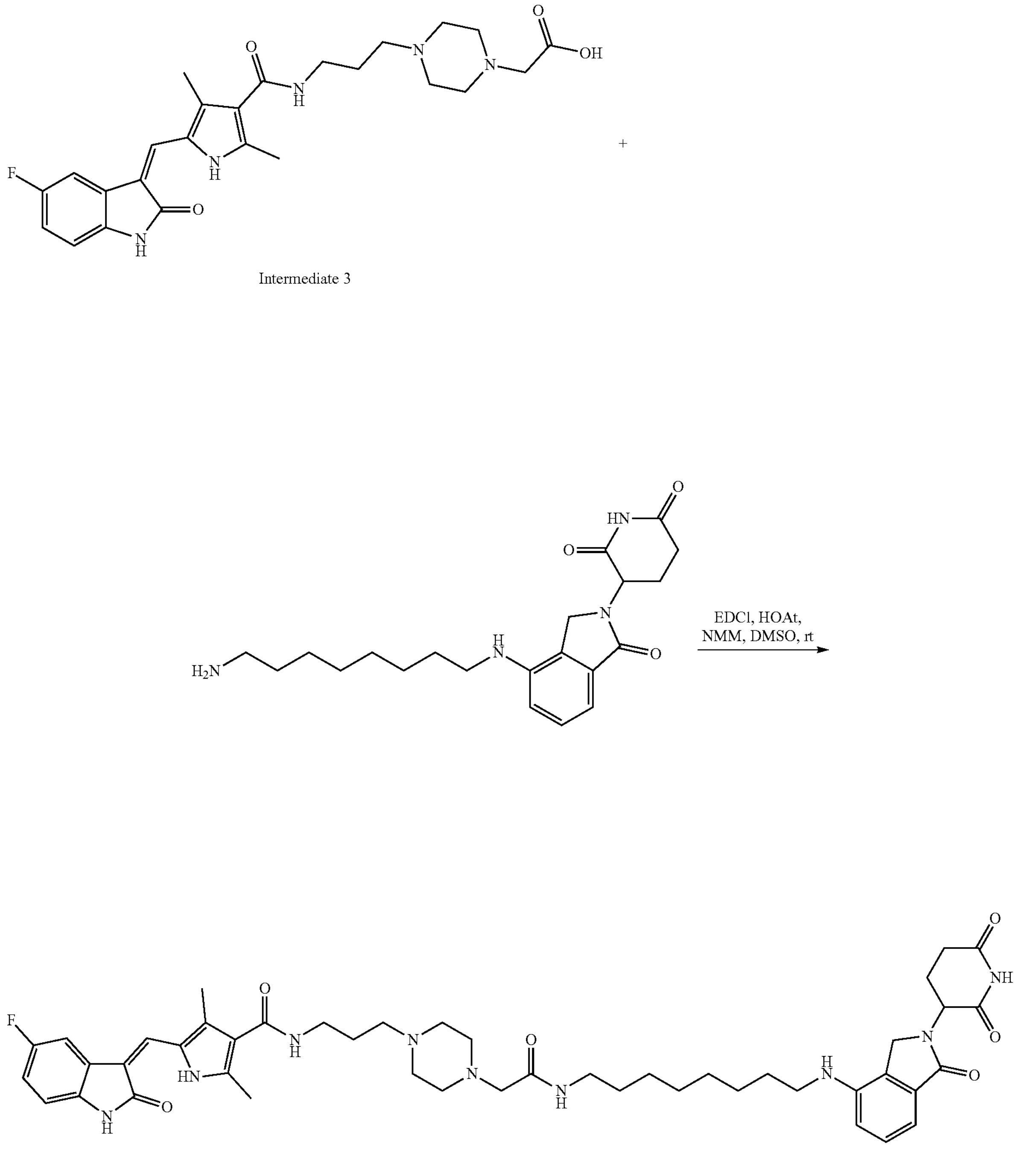

HC58-167

HC58-167 was synthesized following the standard procedure for preparing HC58-53 from Intermediate 3 (11.4 mg, 0.016 mmol, 1.0 equiv), 3-(4-((8-aminooctyl)amino)-1-oxoisoindolin-2-yl)piperidine-2,6-dione (9.0 mg, 0.018 mmol, 1.1 equiv), EDCI (4.6 mg, 0.024 mmol, 1.5 equiv), HOAt (3.3 mg, 0.024 mmol, 1.5 equiv), and NMM (8.1 mg, 0.08 mmol, 5.0 equiv) in DMSO (1 mL). HC58-167 was obtained as yellow solid in TFA salt form (9.3 mg, 54%). $^{1}$H NMR (600 MHz, Methanol-$d_4$) δ 13.69 (s, 1H), 7.57 (s, 1H), 7.45-7.40 (m, 1H), 7.40-7.34 (m, 1H), 7.33-7.29 (m, 1H), 7.10 (d, J=8.0 Hz, 1H), 6.93-6.83 (m, 2H), 5.15 (dd, J=13.3, 5.1 Hz, 1H), 4.41 (d, J=16.5 Hz, 1H), 4.33 (d, J=17.3 Hz, 1H), 3.83-3.69 (m, 2H), 3.56-3.28 (m, 8H), 3.27-3.20 (m, 4H), 3.10-2.87 (m, 7H), 2.51 (s, 3H), 2.47 (s, 3H), 2.24-2.14 (m, 1H), 2.12-2.01 (m, 2H), 1.53 (s, 4H), 1.45-1.26 (m, 8H). HRMS calcd for $C_{46}H_{59}FN_9O_6[M+H^+]$ 852.4572, found 852.4561.

Example 73

Synthesis of HC58-178

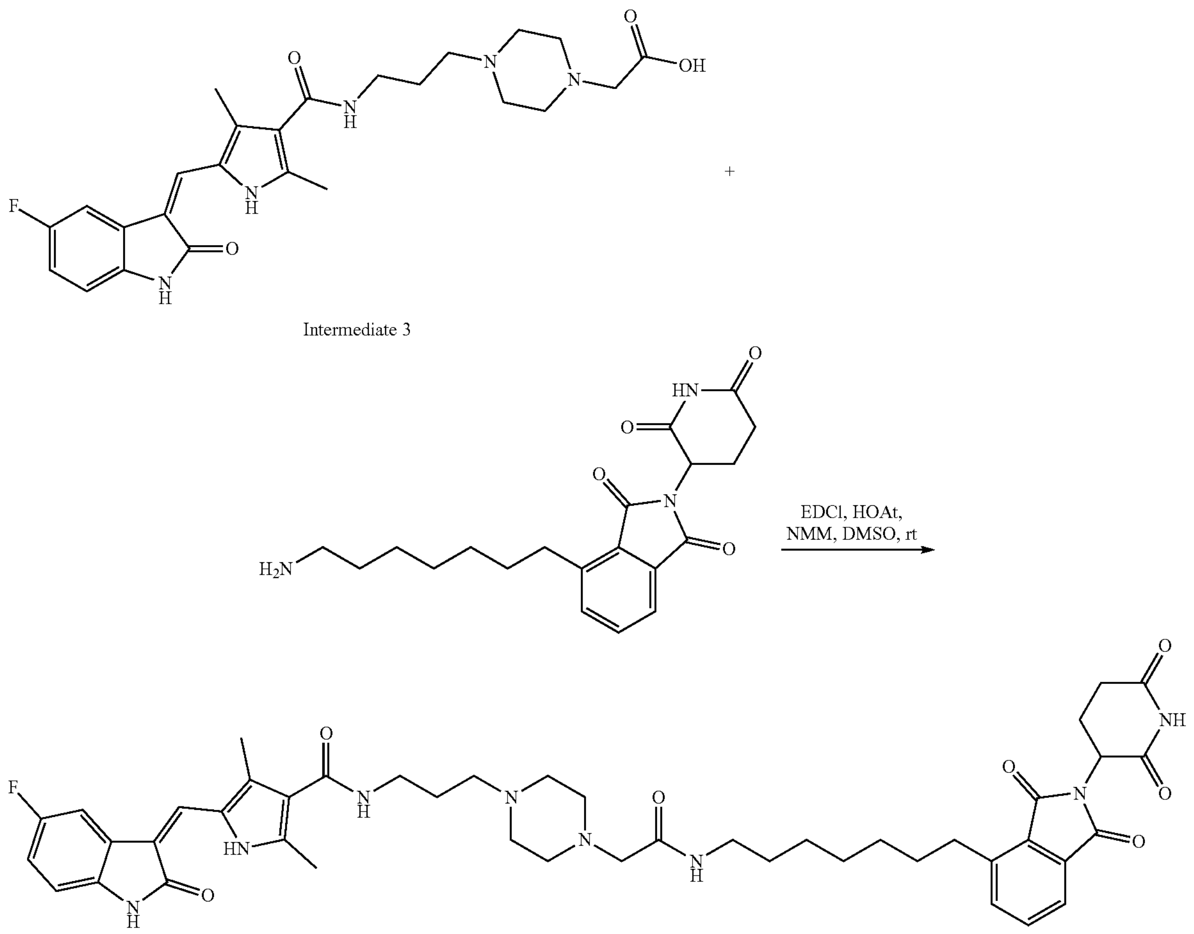

Intermediate 3

HC58-178

HC58-178 was synthesized following the standard procedure for preparing HC58-53 from Intermediate 3 (12.0 mg, 0.017 mmol, 1.0 equiv), 4-(7-aminoheptyl)-2-(2,6-dioxopiperidin-3-yl)isoindoline-1,3-dione (9.7 mg, 0.02 mmol, 1.2 equiv), EDCI (5.0 mg, 0.026 mmol, 1.5 equiv), HOAt (4.0 mg, 0.026 mmol, 1.5 equiv), and NMM (8.6 mg, 0.085 mmol, 5.0 equiv) in DMSO (1 mL). HC58-178 was obtained as yellow solid in TFA salt form (6.8 mg, 38%). $^1$H NMR (600 MHz, Methanol-d4) δ 13.65 (s, 1H), 7.71-7.67 (m, 2H), 7.63-7.59 (m, 1H), 7.53 (s, 1H), 7.39 (dd, J=9.0, 2.4 Hz, 1H), 6.89-6.82 (m, 2H), 5.13 (dd, J=12.8, 5.5 Hz, 1H), 3.51 (t, J=6.5 Hz, 2H), 3.47-3.37 (m, 4H), 3.27-3.21 (m, 4H), 3.12-2.94 (m, 6H), 2.88 (ddd, J=17.4, 13.9, 5.3 Hz, 1H), 2.80-2.69 (m, 2H), 2.50 (s, 3H), 2.45 (s, 3H), 2.18-2.04 (m, 3H), 1.71-1.62 (m, 2H), 1.52 (p, J=7.3 Hz, 2H), 1.44-1.30 (m, 8H). HRMS calcd for $C_{45}H_{54}FN_8O_7[M+H^+]$ 837.4099, found 837.4112.

Example 74

Synthesis of Intermediate 7

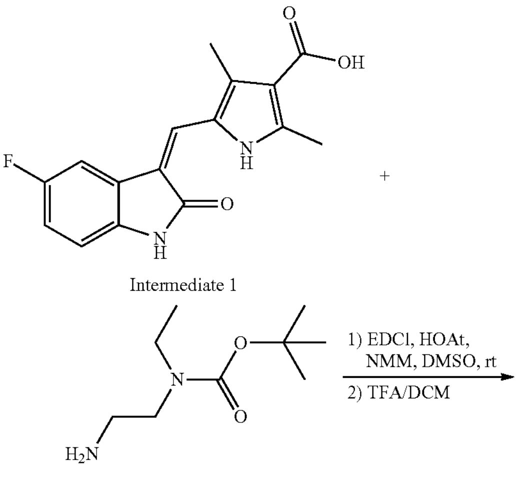

Intermediate 1

-continued

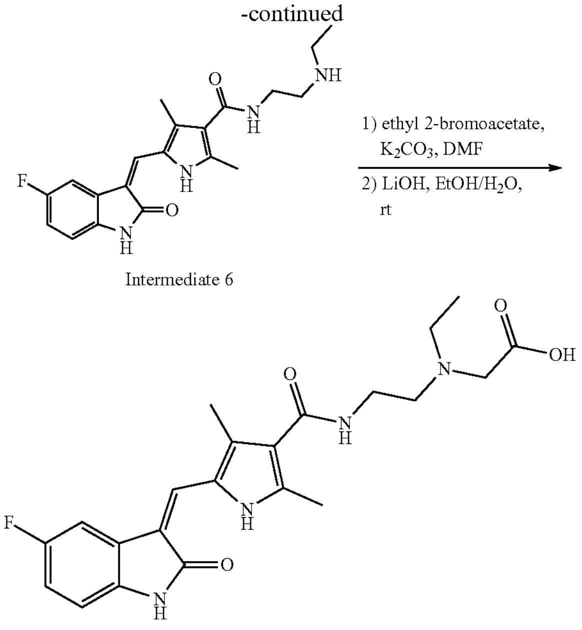

Intermediate 6

Intermediate 7

To a solution of Intermediate 1 (150 mg, 0.5 mmol) in DMSO (5 mL) were added tert-butyl (2-aminoethyl)(ethyl) carbamate (141.2 mg, 0.75 mmol, 1.5 equiv), EDCI (1-ethyl-3-(3-dimethylaminopropyl)carbodiimide) (144 mg, 0.75 mmol, 1.5 equiv), HOAt (1-hydroxy-7-azabenzo-triazole) (102 mg, 0.75 mmol, 1.5 equiv), and NMM (N-Methylmorpholine) (152 mg, 1.5 mmol, 3.0 equiv). After being stirred overnight at room temperature, the resulting mixture was purified by preparative HPLC (10%-100% methanol/0.1% TFA in $H_2O$) to afford yellow solid in TFA salt form. The obtained solid was dissolved in DCM (4 mL). To the resulting solution was added TFA (2 ml). After being stirred for 1 h at room temperature, the reaction mixture was concentrated and the residue was purified preparative HPLC (10%-100% methanol/0.1% TFA in $H_2O$) to afford intermediate 6 as yellow solid in TFA salt form (138 mg, 57% yield for two step). ESI m/z=371.2 [M+H$^+$]. To a solution of intermediate 6 (70 mg, 0.145 mmol) in DMF (2 mL) was added potassium carbonate (40 mg, 0.29 mmol, 2.0 equiv) and ethyl bromoacetate (48.3 mg, 0.29 mmol, 2.0 equiv). Then the mixture was stirred at 70° C. for 3 h. Water (20 mL) was added to quench the reaction. The mixture was extracted with ethyl acetate (3x20 mL). The organic layer was combined and washed with brine. Dried over $Na_2SO_4$, filtered and evaporated to afford yellow solid. The obtained yellow solid was dissolved in EtOH/$H_2O$ (2.5 mL/0.5 mL). To the resulting solution was added lithium hydroxide (11 mg, 0.46 mmol, 3 equiv). After being stirred overnight at room temperature, the reaction mixture was concentrated and the residue was purified by preparative HPLC (10%-100% methanol/0.1% TFA in $H_2O$) to afford intermediate 7 as yellow solid in TFA salt form (58.7 mg, 75% yield for two steps). $^1H$ NMR (600 MHz, Methanol-$d_4$) δ 7.60-7.54 (m, 1H), 7.44-7.38 (m, 1H), 6.92-6.83 (m, 2H), 4.08 (s, 2H), 3.81-3.72 (m, 2H), 3.51-3.43 (m, 4H), 2.53 (s, 3H), 2.49 (s, 3H), 1.44 (t, J=7.2 Hz, 3H). ESI m/z=429.2 [M+H$^+$].

Example 75

Synthesis of HC58-179

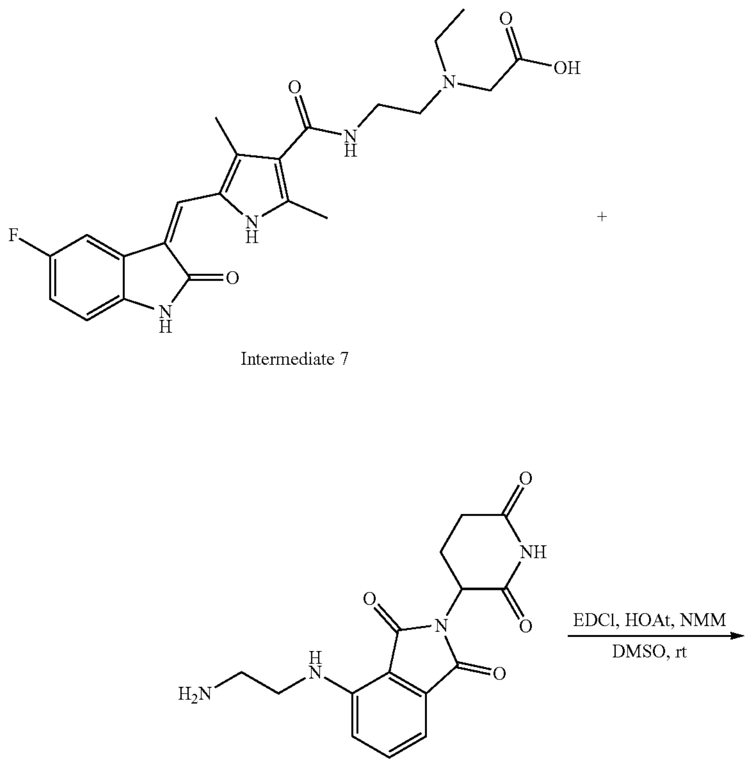

Intermediate 7

-continued

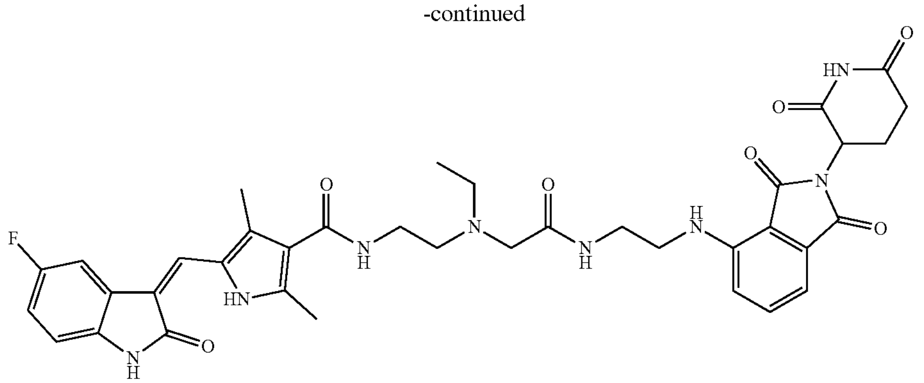

HC58-179

To a solution of Intermediate 7 (7.0 mg, 0.0129 mmol, 1.0 equiv) in DMSO (1 mL) were added 4-((2-aminoethyl) amino)-2-(2,6-dioxopiperidin-3-yl)isoindoline-1,3-dione (6.2 mg, 0.0143 mmol, 1.1 equiv), EDCI (1-ethyl-3-(3-dimethylaminopropyl)carbodiimide) (4.0 mg, 0.02 mmol, 1.5 equiv), HOAt (1-hydroxy-7-azabenzo-triazole) (3.0 mg, 0.02 mmol, 1.5 equiv), and NMM (N-Methylmorpholine) (5.3 mg, 0.052 mmol, 4.0 equiv). After being stirred overnight at room temperature, the resulting mixture was purified by preparative HPLC (10%-100% MeOH/0.1% TFA in $H_2O$) to afford HC58-179 as yellow solid in TFA salt form (4.7 mg, 43%). $^1H$ NMR (600 MHz, Methanol-d4) δ 13.63 (s, 1H), 7.52-7.47 (m, 2H), 7.37 (dd, J=8.9, 2.3 Hz, 1H), 7.10 (d, J=8.5 Hz, 1H), 6.97 (d, J=7.1 Hz, 1H), 6.90-6.82 (m, 2H), 5.04 (dd, J=12.8, 5.5 Hz, 1H), 4.16-3.94 (m, 2H), 3.93-3.75 (m, 1H), 3.73-3.34 (m, 9H), 2.84 (ddd, J=18.4, 13.7, 5.3 Hz, 1H), 2.78-2.62 (m, 2H), 2.47 (s, 3H), 2.42 (s, 3H), 2.14-2.04 (m, 1H), 1.41 (t, J=7.2 Hz, 3H). HRMS calcd for $C_{37}H_{40}FN_8O_7[M+H^+]$ 727.3004, found 727.3013.

Example 76

Synthesis of HC58-180

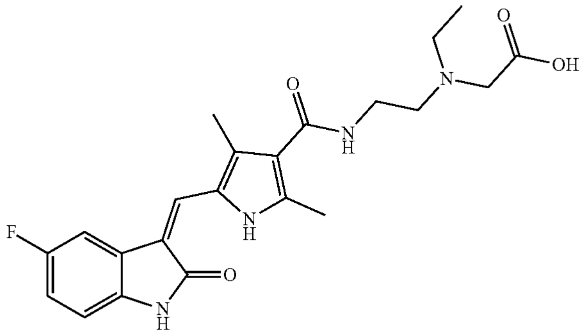

Intermediate 7

+

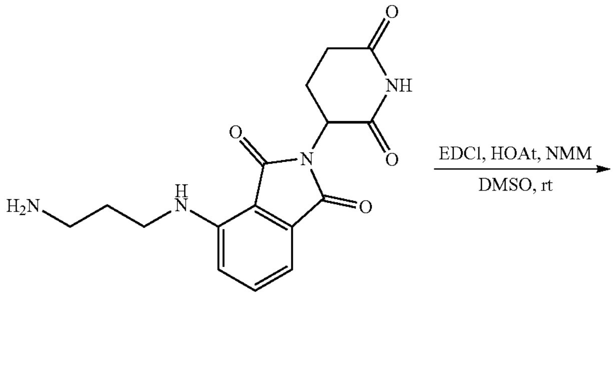

-continued

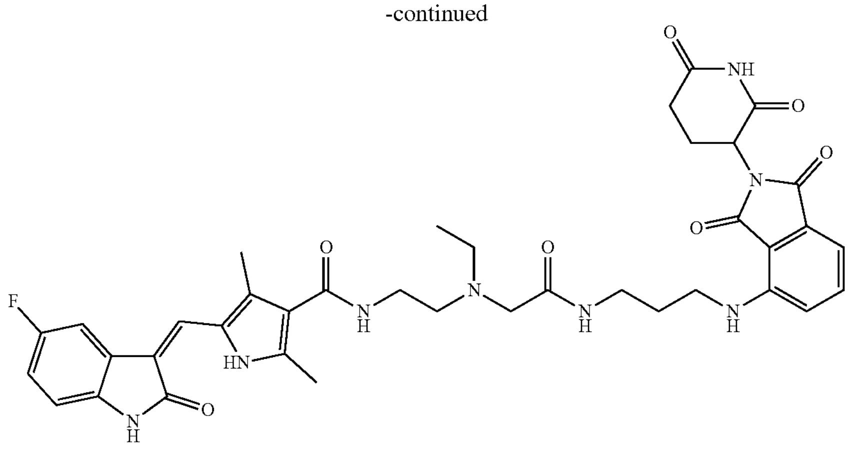

HC58-180

HC58-180 was synthesized following the standard procedure for preparing HC58-179 from Intermediate 7 (7.0 mg, 0.0129 mmol, 1.0 equiv), 4-((3-aminopropyl)amino)-2-(2,6-dioxopiperidin-3-yl)isoindoline-1,3-dione (6.4 mg, 0.0143 mmol, 1.1 equiv), EDCI (1-ethyl-3-(3-dimethylaminopropyl)carbodiimide) (4.0 mg, 0.02 mmol, 1.5 equiv), HOAt (1-hydroxy-7-azabenzo-triazole) (3.0 mg, 0.02 mmol, 1.5 equiv), and NMM (N-Methylmorpholine) (5.3 mg, 0.052 mmol, 4.0 equiv) in DMSO (1 mL). HC58-180 was obtained as yellow solid in TFA salt form (6.0 mg, 54%). $^1$H NMR (600 MHz, Methanol-d4) δ 13.64 (s, 1H), 7.51-7.45 (m, 2H), 7.37 (d, J=8.9 Hz, 1H), 7.00 (d, J=8.5 Hz, 1H), 6.94-6.83 (m, 3H), 5.05 (dd, J=12.8, 5.4 Hz, 1H), 4.18-3.98 (m, 2H), 3.91-3.77 (m, 1H), 3.73-3.61 (m, 1H), 3.58-3.40 (m, 8H), 2.86 (ddd, J=19.1, 14.0, 5.3 Hz, 1H), 2.79-2.68 (m, 2H), 2.53 (s, 3H), 2.46 (s, 3H), 2.19-2.10 (m, 1H), 1.93-1.79 (m, 2H), 1.44 (t, J=7.2 Hz, 3H). HRMS calcd for $C_{38}H_{42}FN_8O_7$[M+$H^+$] 741.3160, found 741.3152.

Example 77

Synthesis of HC58-181

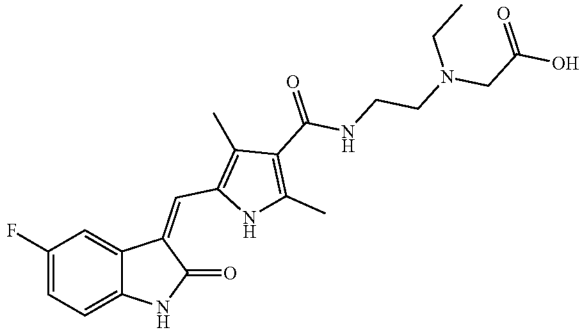

Intermediate 7

+

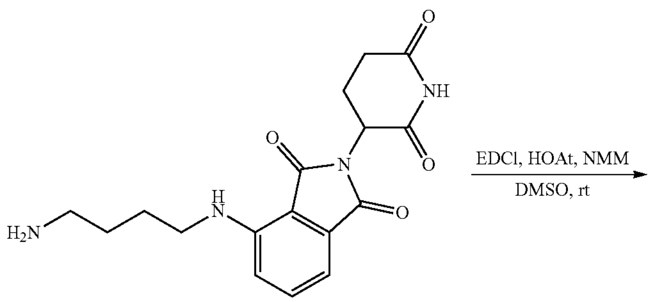

-continued

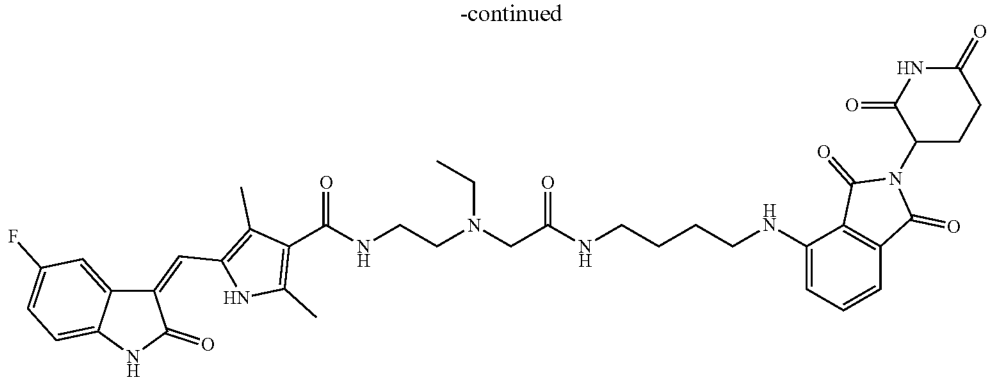

HC58-181

HC58-181 was synthesized following the standard procedure for preparing HC58-179 from Intermediate 7 (7.0 mg, 0.0129 mmol, 1.0 equiv), 4-((4-aminobutyl)amino)-2-(2,6-dioxopiperidin-3-yl)isoindoline-1,3-dione (6.6 mg, 0.0143 mmol, 1.1 equiv), EDCI (1-ethyl-3-(3-dimethylaminopropyl)carbodiimide) (4.0 mg, 0.02 mmol, 1.5 equiv), HOAt (1-hydroxy-7-azabenzo-triazole) (3.0 mg, 0.02 mmol, 1.5 equiv), and NMM (N-Methylmorpholine) (5.3 mg, 0.052 mmol, 4.0 equiv) in DMSO (1 mL). HC58-181 was obtained as yellow solid in TFA salt form (3.6 mg, 32%). $^1$H NMR (600 MHz, Methanol-$d_4$) δ 13.64 (s, 1H), 7.52-7.44 (m, 2H), 7.40-7.32 (m, 1H), 7.02-6.91 (m, 2H), 6.89-6.76 (m, 2H), 5.12-5.00 (m, 1H), 4.17-3.96 (m, 2H), 3.92-3.58 (m, 2H), 3.43 (s, 4H), 3.33-3.25 (m, 4H), 2.84 (ddd, J=18.0, 13.9, 5.3 Hz, 1H), 2.77-2.66 (m, 2H), 2.51 (s, 3H), 2.45 (s, 3H), 2.17-2.05 (m, 1H), 1.66 (s, 4H), 1.46-1.39 (m, 3H). HRMS calcd for $C_{39}H_{44}FN_8O_7$[M+H$^+$] 755.3317, found 755.3332.

Example 78

Synthesis of HC58-182

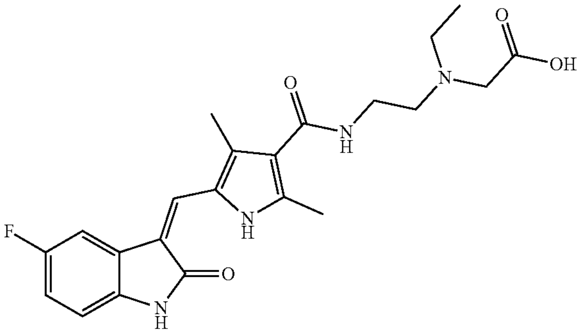

Intermediate 7

+

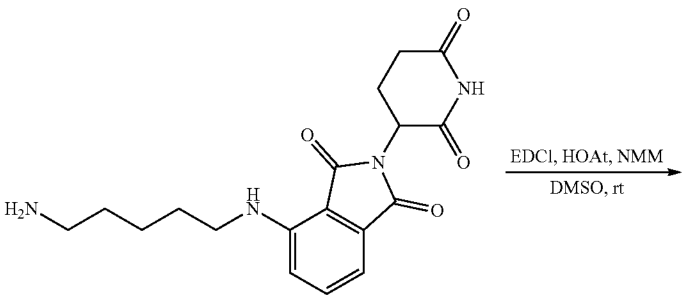

-continued

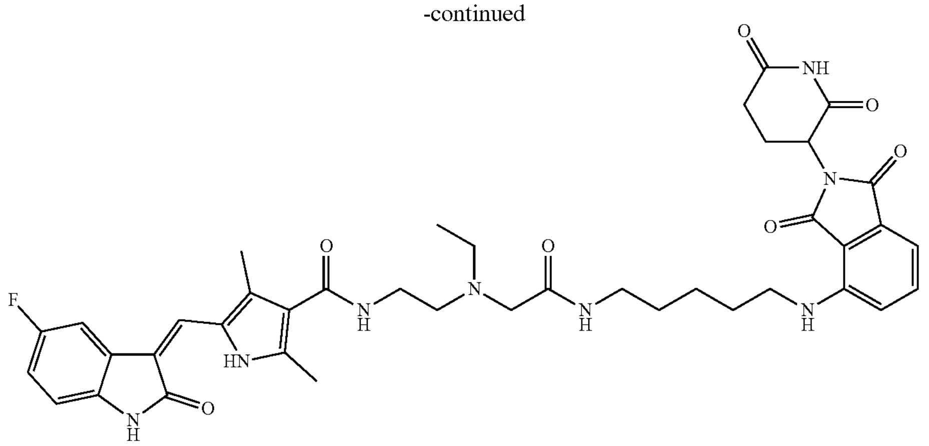

HC58-182

HC58-182 was synthesized following the standard procedure for preparing HC58-179 from Intermediate 7 (7.0 mg, 0.0129 mmol, 1.0 equiv), 4-((5-aminopentyl)amino)-2-(2,6-dioxopiperidin-3-yl)isoindoline-1,3-dione (6.8 mg, 0.0143 mmol, 1.1 equiv), EDCI (1-ethyl-3-(3-dimethylaminopropyl)carbodiimide) (4.0 mg, 0.02 mmol, 1.5 equiv), HOAt (1-hydroxy-7-azabenzo-triazole) (3.0 mg, 0.02 mmol, 1.5 equiv), and NMM (N-Methylmorpholine) (5.3 mg, 0.052 mmol, 4.0 equiv) in DMSO (1 mL). HC58-182 was obtained as yellow solid in TFA salt form (4.5 mg, 40%). $^1$H NMR (600 MHz, Methanol-$d_4$) δ 13.62 (s, 1H), 7.48-7.42 (m, 2H), 7.35 (dd, J=8.9, 2.4 Hz, 1H), 6.96-6.92 (m, 2H), 6.89-6.79 (m, 2H), 5.04 (dd, J=12.7, 5.5 Hz, 1H), 4.17-3.97 (m, 2H), 3.86 (s, 1H), 3.63 (s, 1H), 3.57-3.37 (m, 4H), 3.25 (t, J=6.9 Hz, 4H), 2.85 (ddd, J=17.0, 13.7, 5.2 Hz, 1H), 2.78-2.66 (m, 2H), 2.51 (s, 3H), 2.45 (s, 3H), 2.15-2.05 (m, 1H), 1.71-1.56 (m, 4H), 1.49-1.38 (m, 5H). HRMS calcd for $C_{40}H_{46}FN_8O_7$ [M+H$^+$]769.3473, found 769.3489.

Example 79

Synthesis of HC58-183

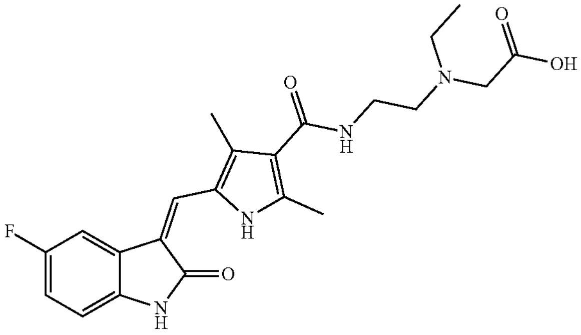

Intermediate 7

+

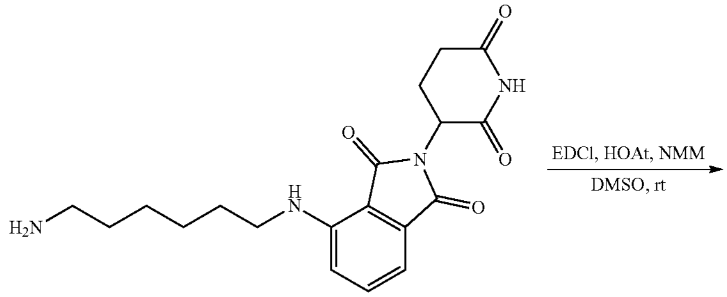

-continued

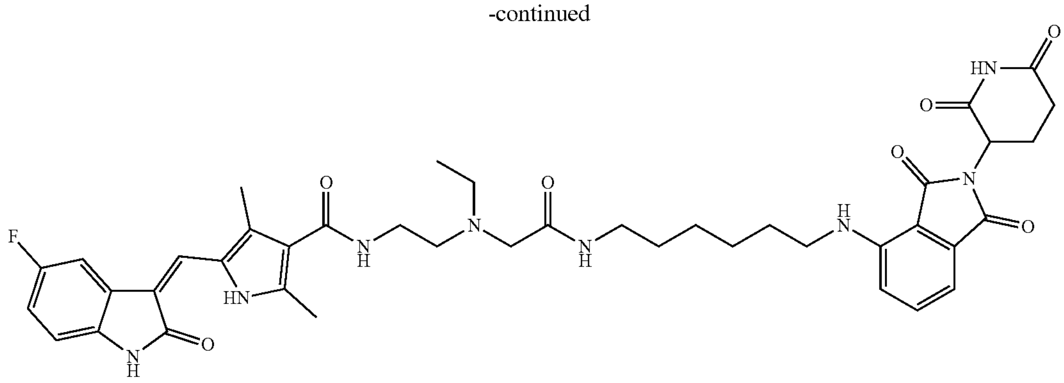

HC58-183

HC58-183 was synthesized following the standard procedure for preparing HC58-179 from Intermediate 7 (7.0 mg, 0.0129 mmol, 1.0 equiv), 4-((6-aminohexyl)amino)-2-(2,6-dioxopiperidin-3-yl)isoindoline-1,3-dione (5.9 mg, 0.0143 mmol, 1.1 equiv), EDCI (1-ethyl-3-(3-dimethylaminopropyl)carbodiimide) (4.0 mg, 0.02 mmol, 1.5 equiv), HOAt (1-hydroxy-7-azabenzo-triazole) (3.0 mg, 0.02 mmol, 1.5 equiv), and NMM (N-Methylmorpholine) (5.3 mg, 0.052 mmol, 4.0 equiv) in DMSO (1 mL). HC58-183 was obtained as yellow solid in TFA salt form (5.9 mg, 51%). $^1H$ NMR (600 MHz, Methanol-$d_4$) δ 13.66 (s, 1H), 7.50 (s, 1H), 7.46-7.43 (m, 1H), 7.37 (dd, J=9.0, 2.5 Hz, 1H), 6.93 (s, 1H), 6.91 (s, 1H), 6.88-6.80 (m, 2H), 5.04 (dd, J=12.8, 5.4 Hz, 1H), 4.17-3.95 (m, 2H), 3.87 (s, 1H), 3.63 (s, 1H), 3.57-3.37 (m, 4H), 3.27-3.17 (m, 4H), 2.92-2.81 (m, 1H), 2.77-2.64 (m, 2H), 2.53 (s, 3H), 2.46 (s, 3H), 2.16-2.07 (m, 1H), 1.67-1.51 (m, 4H), 1.48-1.36 (m, 7H). HRMS calcd for $C_{41}H_{48}FN_8O_7[M+H^+]$ 783.3630, found 783.3639.

Example 80

Synthesis of HC58-184

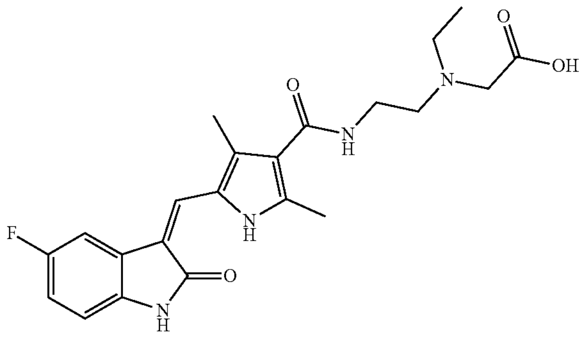

Intermediate 7

+

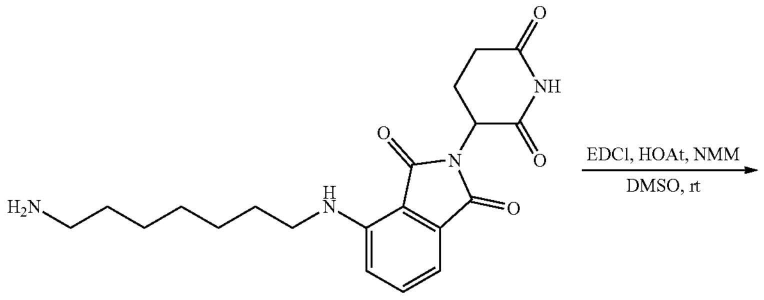

-continued

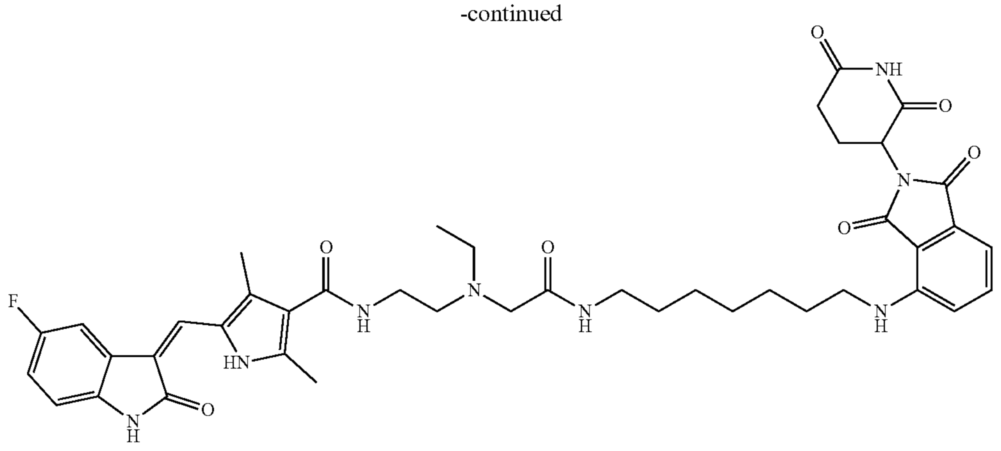

HC58-184

HC58-184 was synthesized following the standard procedure for preparing HC58-179 from Intermediate 7 (7.0 mg, 0.0129 mmol, 1.0 equiv), 4-((7-aminoheptyl)amino)-2-(2,6-dioxopiperidin-3-yl)isoindoline-1,3-dione (7.2 mg, 0.0143 mmol, 1.1 equiv), EDCI (1-ethyl-3-(3-dimethylaminopropyl)carbodiimide) (4.0 mg, 0.02 mmol, 1.5 equiv), HOAt (1-hydroxy-7-azabenzo-triazole) (3.0 mg, 0.02 mmol, 1.5 equiv), and NMM (N-Methylmorpholine) (5.3 mg, 0.052 mmol, 4.0 equiv) in DMSO (1 mL). HC58-184 was obtained as yellow solid in TFA salt form (4.8 mg, 41%). $^1H$ NMR (600 MHz, Methanol-$d_4$) δ 13.64 (s, 1H), 7.49-7.42 (m, 2H), 7.34 (dd, J=8.7, 2.7 Hz, 1H), 6.94 (dd, J=7.3, 2.9 Hz, 1H), 6.91 (dd, J=8.7, 2.8 Hz, 1H), 6.87-6.77 (m, 2H), 5.08-5.02 (m, 1H), 4.13-3.96 (m, 2H), 3.86 (s, 1H), 3.63 (s, 1H), 3.56-3.36 (m, 4H), 3.30-3.15 (m, 4H), 2.91-2.81 (m, 1H), 2.78-2.65 (m, 2H), 2.52 (s, 3H), 2.45 (s, 3H), 2.16-2.07 (m, 1H), 1.56 (d, J=30.8 Hz, 4H), 1.49-1.30 (m, 9H). HRMS calcd for $C_{42}H_{50}FN_8O_7$[M+H$^+$] 797.3786, found 797.3774.

Example 81

Synthesis of HC58-185

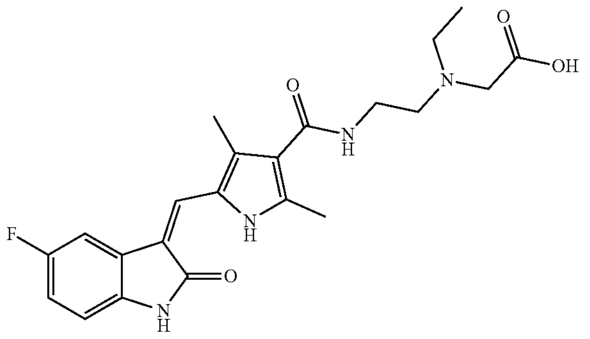

Intermediate 7

+

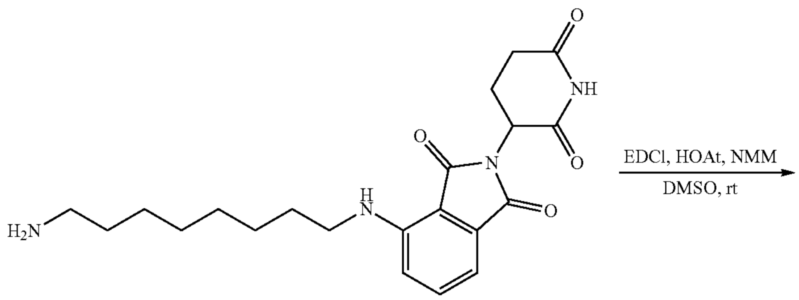

-continued

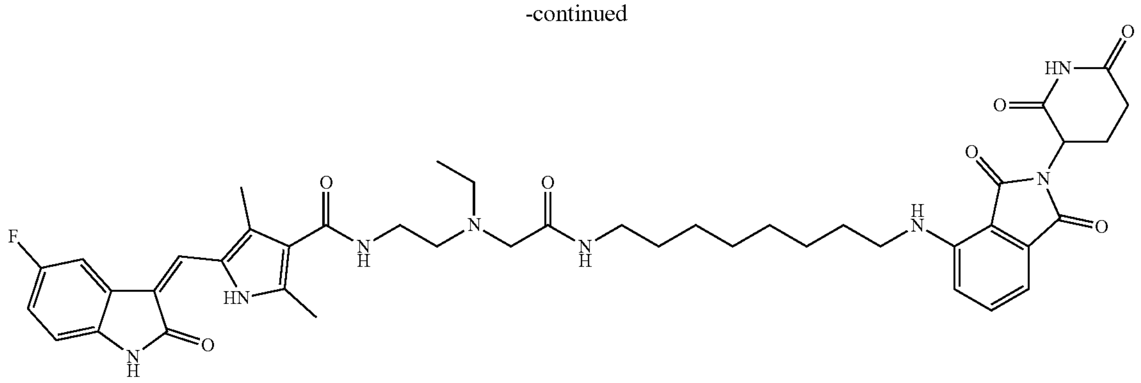

HC58-185

HC58-185 was synthesized following the standard procedure for preparing HC58-179 from Intermediate 7 (7.0 mg, 0.0129 mmol, 1.0 equiv), 4-((8-aminooctyl)amino)-2-(2,6-dioxopiperidin-3-yl)isoindoline-1,3-dione (7.4 mg, 0.0143 mmol, 1.1 equiv), EDCI (1-ethyl-3-(3-dimethylaminopropyl)carbodiimide) (4.0 mg, 0.02 mmol, 1.5 equiv), HOAt (1-hydroxy-7-azabenzo-triazole) (3.0 mg, 0.02 mmol, 1.5 equiv), and NMM (N-Methylmorpholine) (5.3 mg, 0.052 mmol, 4.0 equiv) in DMSO (1 mL). HC58-185 was obtained as yellow solid in TFA salt form (5.6 mg, 47%). $^1$H NMR (600 MHz, Methanol-$d_4$) δ 13.67 (s, 1H), 7.50 (s, 1H), 7.46 (dd, J=8.6, 7.1 Hz, 1H), 7.36 (dd, J=8.9, 2.4 Hz, 1H), 6.95 (d, J=7.1 Hz, 1H), 6.91 (d, J=8.6 Hz, 1H), 6.87-6.78 (m, 2H), 5.04 (dd, J=12.8, 5.5 Hz, 1H), 4.14-3.98 (m, 2H), 3.87 (s, 1H), 3.63 (s, 1H), 3.56-3.37 (m, 4H), 3.29-3.17 (m, 4H), 2.85 (ddd, J=17.6, 14.0, 5.3 Hz, 1H), 2.78-2.65 (m, 2H), 2.53 (s, 3H), 2.47 (s, 3H), 2.15-2.05 (m, 1H), 1.61-1.50 (m, 4H), 1.43 (t, J=7.2 Hz, 3H), 1.41-1.26 (m, 8H). HRMS calcd for $C_{43}H_{52}FN_8O_7$[M+H$^+$] 811.3943, found 811.3959.

Example 82

Synthesis of intermediate 8

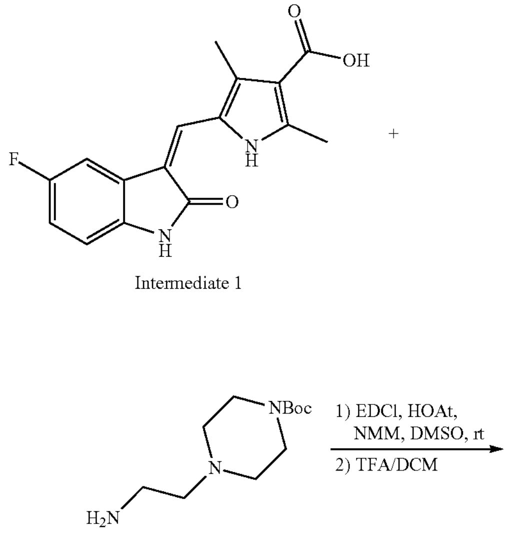

Intermediate 1

-continued

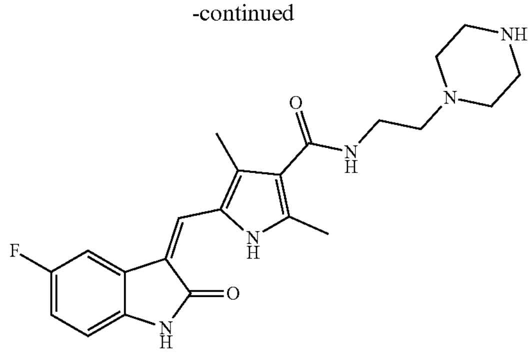

Intermediate 8

To a solution of intermediate 1 (150 mg, 0.5 mmol) in DMSO (5 mL) were added tert-butyl 4-(2-aminoethyl)piperazine-1-carboxylate (149 mg, 0.65 mmol, 1.3 equiv), EDCI (1-ethyl-3-(3-dimethylaminopropyl)carbodiimide) (144 mg, 0.75 mmol, 1.5 equiv), HOAt (1-hydroxy-7-azabenzo-triazole) (102 mg, 0.75 mmol, 1.5 equiv), and NMM (N-Methylmorpholine) (152 mg, 1.5 mmol, 3.0 equiv). After being stirred overnight at room temperature, the resulting mixture was purified by preparative HPLC (10%-100% methanol/0.1% TFA in $H_2O$) to afford yellow solid in TFA salt form. The obtained solid was dissolved in DCM (4 mL). To the resulting solution was added TFA (2 ml). After being stirred for 1 h at room temperature, the reaction mixture was concentrated and the residue was purified preparative HPLC (10%-100% methanol/0.1% TFA in $H_2O$) to afford intermediate 8 as yellow solid in TFA salt form (170 mg, 53% yield for two step). $^1$H NMR (600 MHz, Methanol-$d_4$) δ 7.60 (s, 1H), 7.46-7.42 (m, 1H), 6.93-6.86 (m, 2H), 3.62 (t, J=6.2 Hz, 2H), 3.39-3.34 (m, 4H), 3.05 (s, 4H), 2.94-2.87 (m, 2H), 2.53 (s, 3H), 2.49 (s, 3H). ESI m/z=412.2 [M+H$^+$].

Example 83

Synthesis of HC65-2

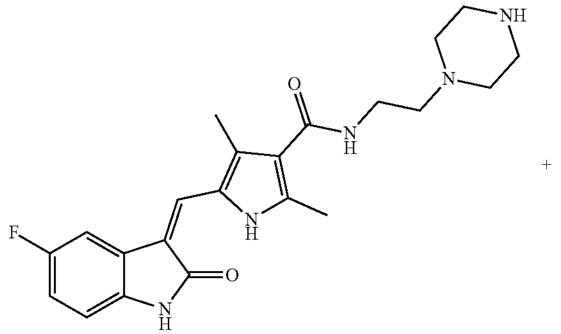

Intermediate 8

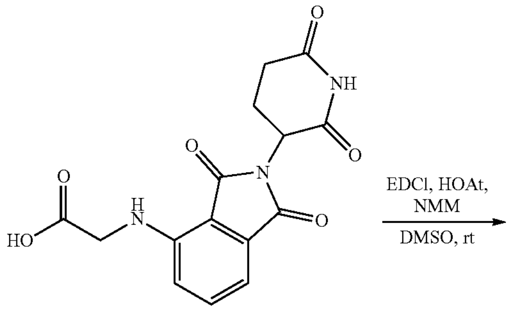

-continued

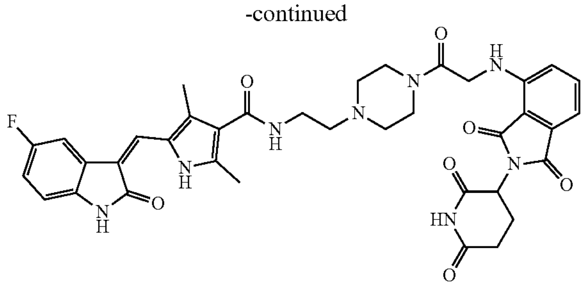

HC65-2

To a solution of Intermediate 8 (10 mg, 0.0156 mmol, 1.1 equiv) in DMSO (1 mL) were added (2-(2,6-dioxopiperidin-3-yl)-1,3-dioxoisoindolin-4-yl)glycine (4.9 mg, 0.0149 mmol, 1.0 equiv), EDCI (1-ethyl-3-(3-dimethylaminopropyl)carbodiimide) (4.3 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv). After being stirred overnight at room temperature, the resulting mixture was purified by preparative HPLC (10%-100% MeOH/0.1% TFA in $H_2O$) to afford HC65-2 as yellow solid in TFA salt form (7.0 mg, 56%). $^1H$ NMR (600 MHz, Acetone-$d_6$) δ 13.84 (s, 1H), 10.01 (s, 1H), 9.97 (s, 1H), 7.73 (s, 1H), 7.68 (s, 1H), 7.62-7.52 (m, 2H), 7.18 (s, 1H), 7.08-7.01 (m, 2H), 6.97-6.89 (m, 2H), 5.11 (dd, J=12.7, 5.4 Hz, 1H), 4.52-4.21 (m, 6H), 4.01-3.68 (m, 6H), 3.64-3.53 (m, 2H), 2.99 (ddd, J=17.4, 14.4, 5.8 Hz, 1H), 2.86-2.75 (m, 2H), 2.55 (s, 3H), 2.52 (s, 3H), 2.27-2.22 (m, 1H). HRMS calcd for $C_{37}H_{38}FN_8O_7[M+H^+]$ 725.2847, found 725.2842.

Example 84

Synthesis of HC65-3

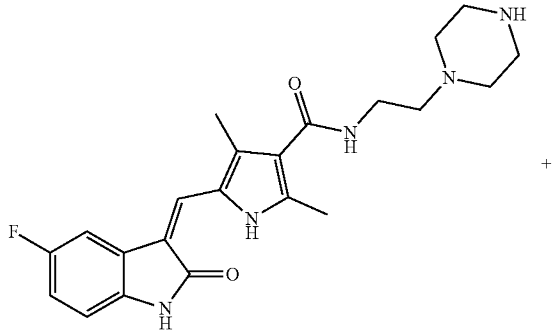

Intermediate 8

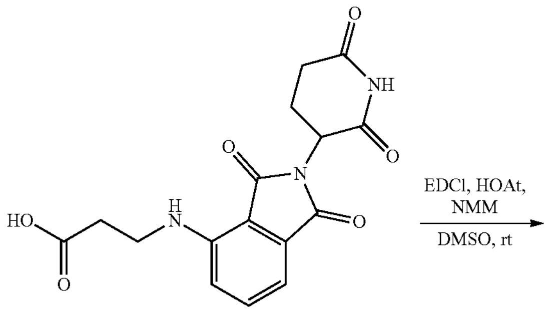

-continued

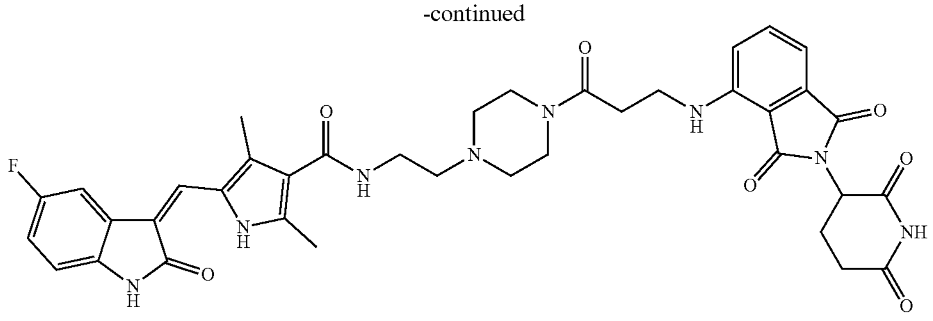

HC65-3

HC65-3 was synthesized following the standard procedure for preparing HC65-2 from Intermediate 8 (10 mg, 0.0156 mmol, 1.1 equiv), 3-((2-(2,6-dioxopiperidin-3-yl)-1,3-dioxoisoindolin-4-yl)amino)propanoic acid (5.1 mg, 0.0149 mmol, 1.0 equiv), EDCI (1-ethyl-3-(3-dimethylaminopropyl)carbodiimide) (4.3 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv) in DMSO (1 mL). HC65-3 was obtained as yellow solid in TFA salt form (7.4 mg, 58%). $^{1}H$ NMR (600 MHz, Acetone-$d_6$) δ 13.83 (s, 1H), 10.04 (s, 1H), 9.98 (s, 1H), 7.71 (s, 1H), 7.63-7.53 (m, 2H), 7.15 (d, J=8.5 Hz, 1H), 7.04 (d, J=7.0 Hz, 1H), 6.98-6.87 (m, 2H), 6.73 (s, 1H), 5.09 (dd, J=12.5, 5.4 Hz, 1H), 4.50-4.02 (m, 8H), 4.00-3.81 (m, 2H), 3.70 (s, 2H), 3.55 (s, 2H), 2.97 (ddd, J=18.1, 14.8, 5.0 Hz, 1H), 2.86 (s, 2H), 2.82-2.71 (m, 2H), 2.54 (s, 3H), 2.50 (s, 3H), 2.28-2.17 (m, 1H). HRMS calcd for $C_{38}H_{40}FN_8O_7[M+H^+]$ 739.3004, found 739.3021.

Example 85

Synthesis of HC65-4

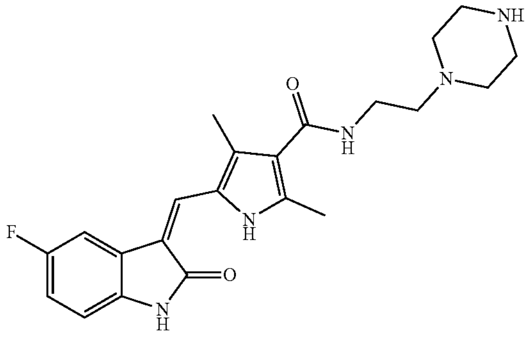

Intermediate 8

+

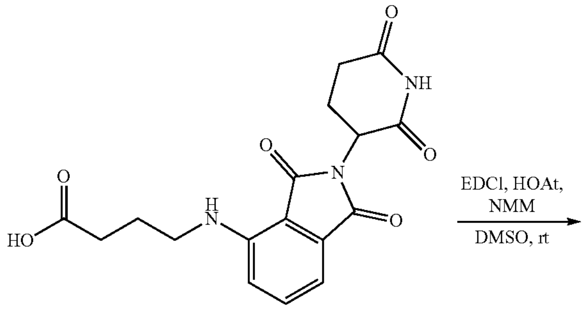

-continued

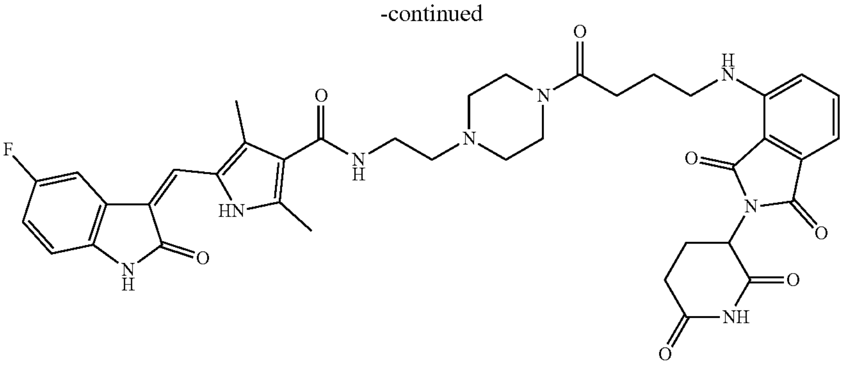

HC65-4

HC65-4 was synthesized following the standard procedure for preparing HC65-2 from Intermediate 8 (10 mg, 0.0156 mmol, 1.1 equiv), 4-((2-(2,6-dioxopiperidin-3-yl)-1,3-dioxoisoindolin-4-yl)amino)butanoic acid (5.4 mg, 0.0149 mmol, 1.0 equiv), EDCI (1-ethyl-3-(3-dimethylaminopropyl)carbodiimide) (4.3 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv) in DMSO (1 mL). HC65-4 was obtained as yellow solid in TFA salt form (6.5 mg, 50%). $^1$H NMR (600 MHz, Acetone-$d_6$) δ 13.84 (s, 1H), 10.04 (s, 1H), 9.97 (s, 1H), 7.74 (s, 1H), 7.70 (s, 1H), 7.64-7.55 (m, 2H), 7.19 (d, J=8.5 Hz, 1H), 7.05 (d, J=7.1 Hz, 1H), 6.98-6.88 (m, 2H), 6.53 (s, 1H), 5.09 (dd, J=12.6, 5.4 Hz, 1H), 4.02-3.72 (m, 10H), 3.58-3.51 (m, 2H), 3.45 (t, J=7.0 Hz, 2H), 3.01-2.93 (m, 1H), 2.83-2.71 (m, 2H), 2.61 (s, 2H), 2.55 (s, 3H), 2.52 (s, 3H), 2.25-2.19 (m, 1H), 2.02-1.98 (m, 2H). HRMS calcd for $C_{39}H_{42}FN_8O_7$ [M+H$^+$]753.3160, found 753.3167.

Example 86

Synthesis of HC65-5

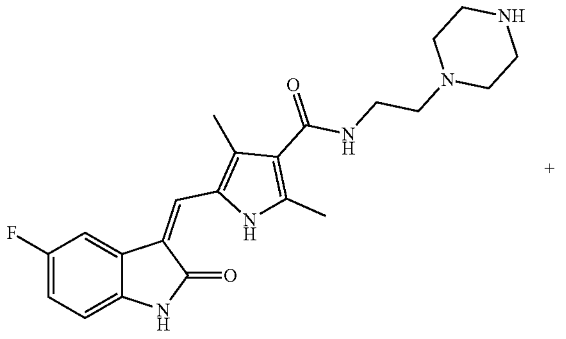

Intermediate 8

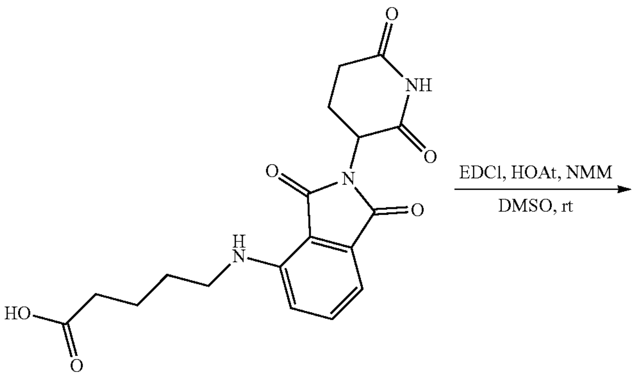

-continued

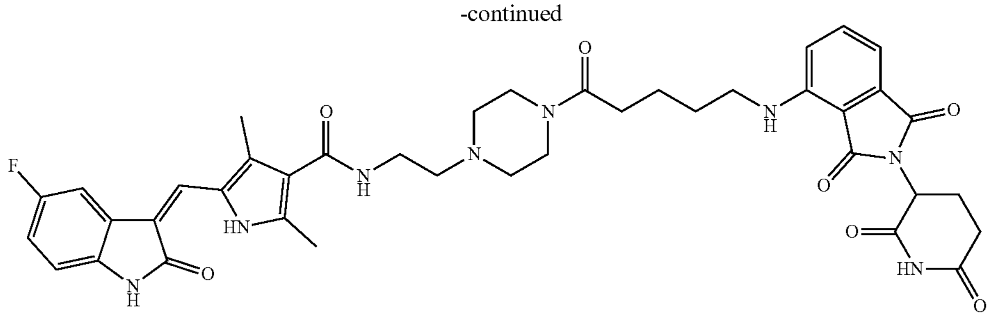

HC65-5

HC65-5 was synthesized following the standard procedure for preparing HC65-2 from Intermediate 8 (10 mg, 0.0156 mmol, 1.1 equiv), 5-((2-(2,6-dioxopiperidin-3-yl)-1,3-dioxoisoindolin-4-yl)amino)pentanoic acid (5.6 mg, 0.0149 mmol, 1.0 equiv), EDCI (1-ethyl-3-(3-dimethylaminopropyl)carbodiimide) (4.3 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv) in DMSO (1 mL). HC65-5 was obtained as yellow solid in TFA salt form (5.0 mg, 38%). $^1H$ NMR (600 MHz, Acetone-$d_6$) δ 13.85 (s, 1H), 10.04 (s, 1H), 9.98 (s, 1H), 7.73 (d, J=8.8 Hz, 1H), 7.62-7.52 (m, 2H), 7.10 (d, J=8.5 Hz, 1H), 7.04 (d, J=6.9 Hz, 1H), 6.98-6.88 (m, 2H), 5.10 (dd, J=12.7, 5.4 Hz, 1H), 4.08-3.64 (m, 6H), 3.61-3.51 (m, 2H), 3.47-3.08 (m, 6H), 3.02-2.91 (m, 1H), 2.81-2.70 (m, 4H), 2.55 (s, 3H), 2.52 (s, 3H), 2.28-2.18 (m, 1H), 1.81-1.70 (m, 4H). HRMS calcd for $C_{40}H_{44}FN_8O_7$ [M+H$^+$] 767.3317, found 767.3331.

Example 87

Synthesis of HC65-6

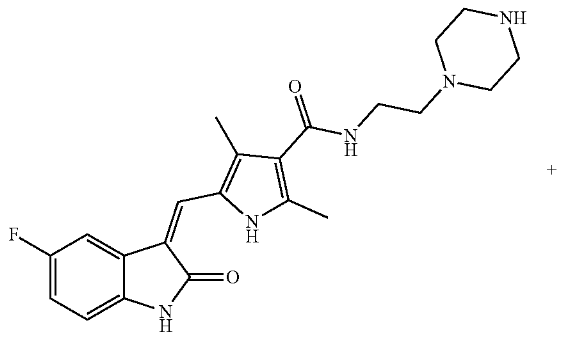

Intermediate 8

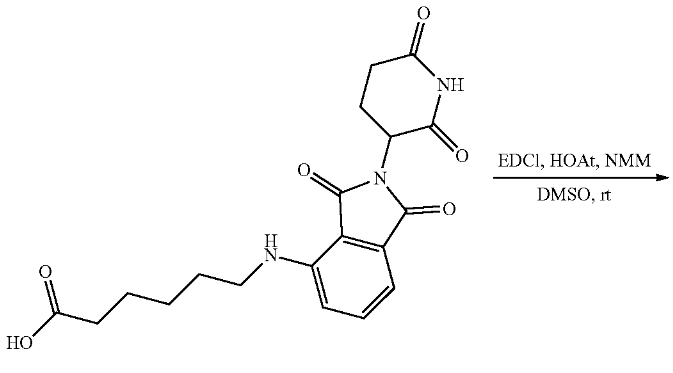

-continued

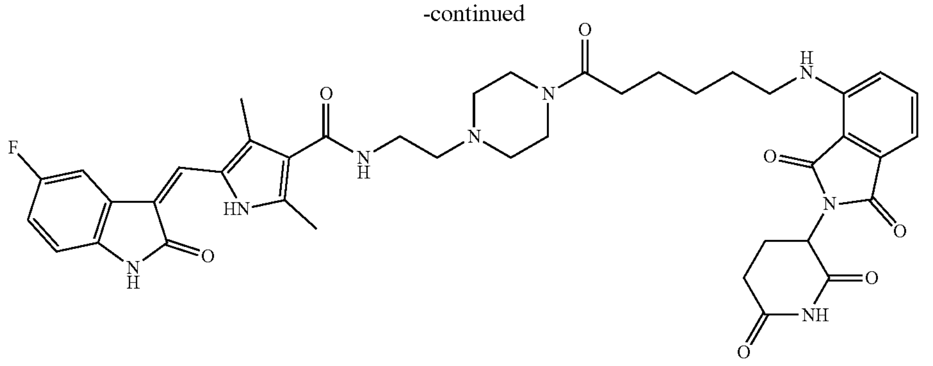

HC65-6

HC65-6 was synthesized following the standard procedure for preparing HC65-2 from Intermediate 8 (10 mg, 0.0156 mmol, 1.1 equiv), 6-((2-(2,6-dioxopiperidin-3-yl)-1,3-dioxoisoindolin-4-yl)amino)hexanoic acid (5.8 mg, 0.0149 mmol, 1.0 equiv), EDCI (1-ethyl-3-(3-dimethylaminopropyl)carbodiimide) (4.3 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv) in DMSO (1 mL). HC65-6 was obtained as yellow solid in TFA salt form (5.7 mg, 43%). $^1$H NMR (600 MHz, Acetone-d6) δ 13.85 (s, 1H), 10.02 (s, 1H), 9.98 (s, 1H), 7.74 (s, 1H), 7.73-7.68 (m, 1H), 7.62-7.55 (m, 2H), 7.10 (d, J=8.5 Hz, 1H), 7.04 (d, J=7.0 Hz, 1H), 6.97-6.88 (m, 2H), 5.09 (dd, J=12.7, 5.5 Hz, 1H), 3.99-3.66 (m, 6H), 3.56 (t, J=5.6 Hz, 2H), 3.39 (t, J=7.0 Hz, 2H), 3.34-3.10 (m, 4H), 3.04-2.92 (m, 1H), 2.83-2.73 (m, 2H), 2.55 (s, 3H), 2.52 (s, 3H), 2.48 (t, J=7.3 Hz, 2H), 2.27-2.19 (m, 1H), 1.79-1.63 (m, 4H), 1.49 (p, J=7.7 Hz, 2H). HRMS calcd for $C_{41}H_{46}FN_8O_7[M+H^+]$ 781.3473, found 781.3465.

Example 88

Synthesis of HC65-7

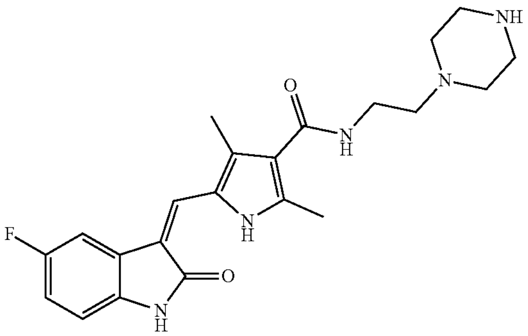

Intermediate 8

+

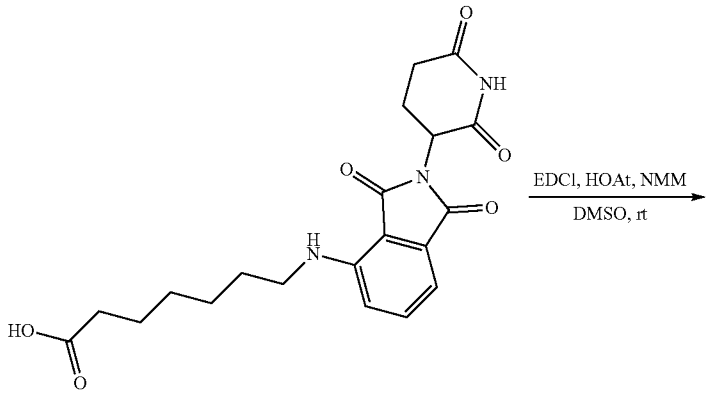

-continued

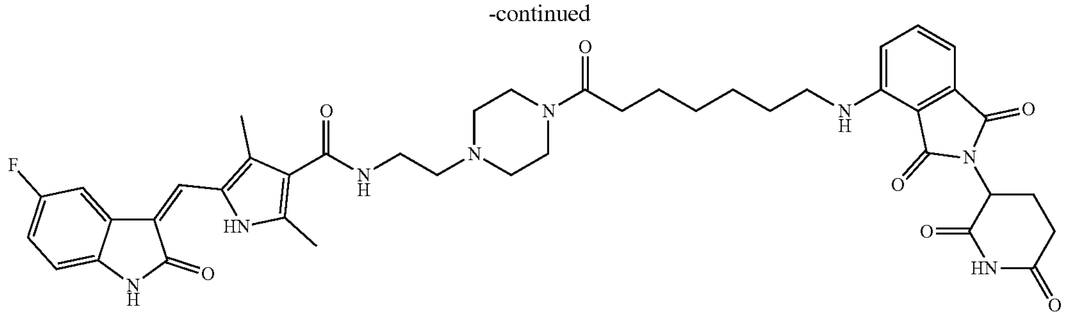

HC65-7

HC65-7 was synthesized following the standard procedure for preparing HC65-2 from Intermediate 8 (10 mg, 0.0156 mmol, 1.1 equiv), 7-((2-(2,6-dioxopiperidin-3-yl)-1,3-dioxoisoindolin-4-yl)amino)heptanoic acid (6.0 mg, 0.0149 mmol, 1.0 equiv), EDCI (1-ethyl-3-(3-dimethylaminopropyl)carbodiimide) (4.3 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv) in DMSO (1 mL). HC65-7 was obtained as yellow solid in TFA salt form (6.6 mg, 49%). $^{1}$H NMR (600 MHz, Acetone-$d_6$) δ 13.86 (s, 1H), 10.01 (s, 1H), 9.98 (s, 1H), 7.75 (s, 1H), 7.71 (s, 1H), 7.62-7.56 (m, 2H), 7.10 (d, J=8.5 Hz, 1H), 7.04 (d, J=7.0 Hz, 1H), 6.98-6.89 (m, 2H), 5.09 (dd, J=12.6, 5.5 Hz, 1H), 3.94-3.86 (m, 2H), 3.83-3.61 (m, 4H), 3.57 (s, 2H), 3.38 (t, J=7.0 Hz, 2H), 3.32-3.07 (m, 4H), 2.97 (ddd, J=17.9, 14.8, 5.3 Hz, 1H), 2.84-2.73 (m, 2H), 2.55 (s, 3H), 2.52 (s, 3H), 2.45 (t, J=7.4 Hz, 2H), 2.26-2.18 (m, 1H), 1.70 (p, J=7.2 Hz, 2H), 1.63 (p, J=7.4 Hz, 2H), 1.52-1.37 (m, 4H). HRMS calcd for $C_{42}H_{48}FN_8O_7$[M+H$^+$] 795.3630, found 795.3642.

Example 89

Synthesis of HC65-8

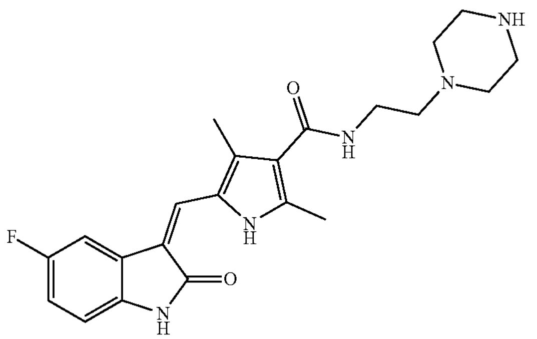

Intermediate 8

+

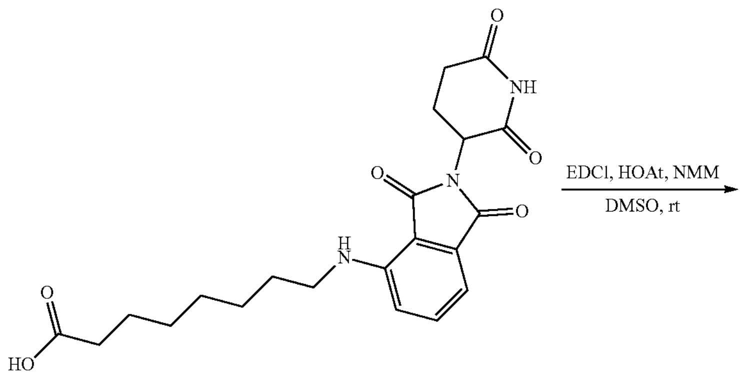

-continued

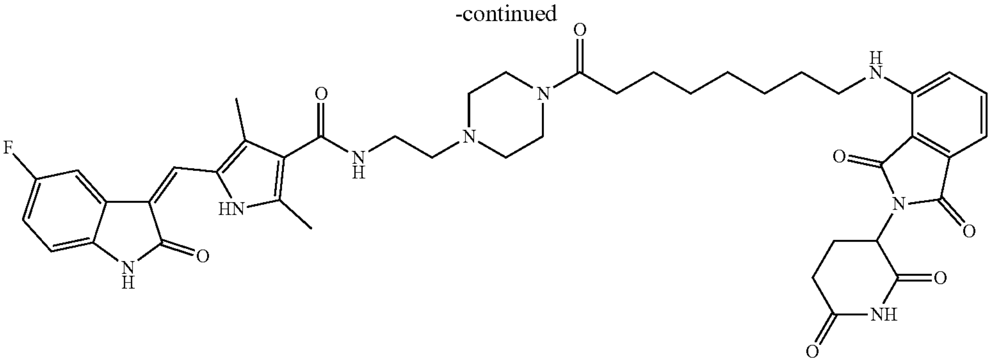

HC65-8

HC65-8 was synthesized following the standard procedure for preparing HC65-2 from Intermediate 8 (10 mg, 0.0156 mmol, 1.1 equiv), 8-((2-(2,6-dioxopiperidin-3-yl)-1,3-dioxoisoindolin-4-yl)amino)octanoic acid (6.2 mg, 0.0149 mmol, 1.0 equiv), EDCI (1-ethyl-3-(3-dimethylaminopropyl)carbodiimide) (4.3 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv) in DMSO (1 mL). HC65-8 was obtained as yellow solid in TFA salt form (7.3 mg, 53%). $^1$H NMR (600 MHz, Acetone-$d_6$) δ 13.86 (s, 1H), 9.99 (s, 1H), 9.98 (s, 1H), 7.75 (s, 1H), 7.71 (t, J=5.6 Hz, 1H), 7.63-7.55 (m, 2H), 7.10 (d, J=8.6 Hz, 1H), 7.04 (d, J=7.0 Hz, 1H), 6.98-6.88 (m, 2H), 5.09 (dd, J=12.6, 5.5 Hz, 1H), 3.92 (q, J=5.5 Hz, 6H), 3.58 (t, J=5.6 Hz, 2H), 3.38 (t, J=7.1 Hz, 2H), 3.34-3.15 (m, 4H), 2.97 (ddd, J=18.0, 14.7, 5.2 Hz, 1H), 2.83-2.73 (m, 2H), 2.55 (s, 3H), 2.52 (s, 3H), 2.44 (t, J=7.5 Hz, 2H), 2.28-2.19 (m, 1H), 1.70 (p, J=7.2 Hz, 2H), 1.61 (p, J=7.5 Hz, 2H), 1.48-1.34 (m, 6H). HRMS calcd for $C_{43}H_{50}FN_8O_7[M+H^+]$ 809.3786, found 809.3799.

Example 90

Synthesis of intermediate 9

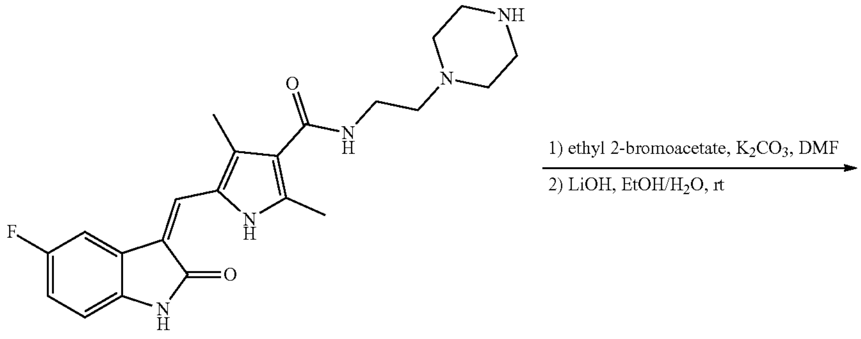

Intermediate 8

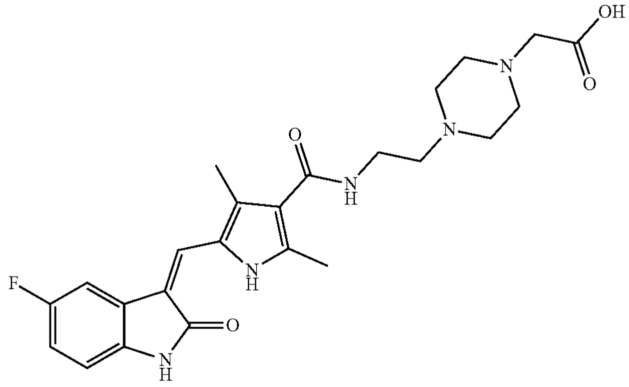

Intermediate 9

To a solution of intermediate 8 (80 mg, 0.125 mmol, 1.0 equiv) in DMF (2 mL) was added potassium carbonate (52 mg, 0.375 mmol, 3.0 equiv) and ethyl bromoacetate (42 mg, 0.25 mmol, 2.0 equiv). Then the mixture was stirred at 60° C. for 3 h. Water (10 mL) was added to quench the reaction. The mixture was extracted with ethyl acetate (3×10 mL). The organic layer was combined and washed with brine. Dried over $Na_2SO_4$, filtered and evaporated to afford yellow solid. The obtained yellow solid was dissolved in $EtOH/H_2O$ (2.5 mL/0.5 mL). To the resulting solution was added lithium hydroxide (9 mg, 0.375 mmol, 3 equiv). After being stirred overnight at room temperature, the reaction mixture was concentrated and the residue was purified by preparative HPLC (10%-100% methanol/0.1% TFA in $H_2O$) to afford intermediate 9 as yellow solid in TFA salt form (54.2 mg, 62% yield for two steps). $^1H$ NMR (600 MHz, Methanol-$d_4$) δ 7.61 (s, 1H), 7.44 (dd, J=8.8, 2.2 Hz, 1H), 6.93-6.85 (m, 2H), 3.73 (t, J=6.1 Hz, 2H), 3.60 (s, 2H), 3.36 (s, 4H), 3.26 (t, J=6.0 Hz, 2H), 3.12 (s, 4H), 2.54 (s, 3H), 2.50 (s, 3H). ESI m/z=470.2 [M+H$^+$].

Example 91

Synthesis of HC65-13

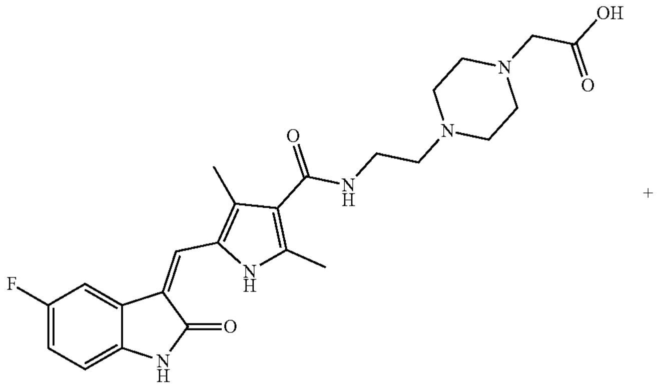

Intermediate 9

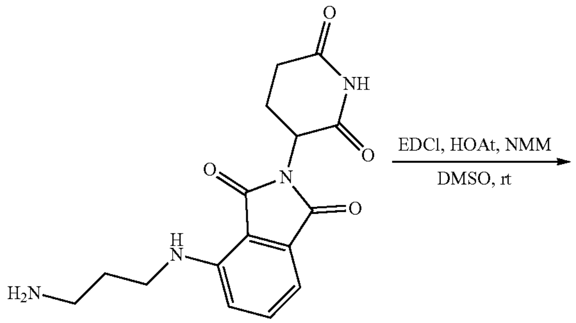

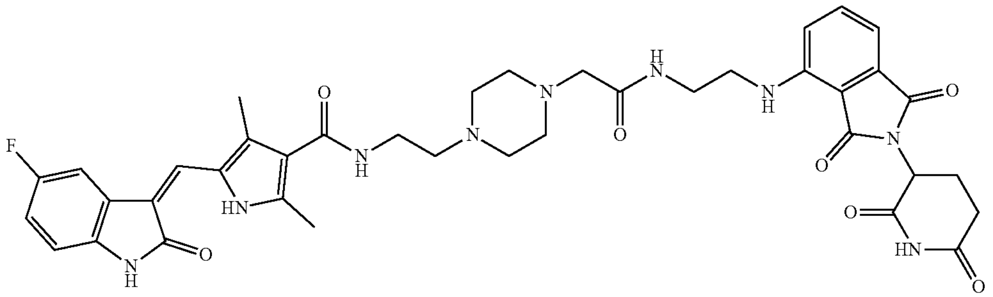

HC65-13

To a solution of Intermediate 9 (7 mg, 0.01 mmol, 1.1 equiv) in DMSO (1 mL) were added 4-((2-aminoethyl)amino)-2-(2,6-dioxopiperidin-3-yl)isoindoline-1,3-dione (4.8 mg, 0.011 mmol, 1.1 equiv), EDCI (1-ethyl-3-(3-dimethylaminopropyl)carbodiimide) (2.9 mg, 0.015 mmol, 1.5 equiv), HOAt (1-hydroxy-7-azabenzo-triazole) (2.0 mg, 0.015 mmol, 1.5 equiv), and NMM (N-Methylmorpholine) (5.0 mg, 0.05 mmol, 5.0 equiv). After being stirred overnight at room temperature, the resulting mixture was purified by preparative HPLC (10%-100% MeOH/0.1% TFA in $H_2O$) to afford HC65-13 as yellow solid in TFA salt form (5.8 mg, 58%). $^1$H NMR (600 MHz, Methanol-$d_4$) δ 13.70 (s, 1H), 7.60-7.55 (m, 2H), 7.43 (d, J=8.4 Hz, 1H), 7.14 (dd, J=8.7, 3.1 Hz, 1H), 7.08 (dd, J=7.1, 3.1 Hz, 1H), 6.92-6.84 (m, 2H), 5.17-5.06 (m, 1H), 3.80-3.70 (m, 2H), 3.60-3.51 (m, 2H), 3.46-3.28 (m, 10H), 3.02-2.80 (m, 5H), 2.79-2.61 (m, 2H), 2.52 (s, 3H), 2.47 (s, 3H), 2.21-2.08 (m, 1H). HRMS calcd for $C_{39}H_{43}FN_9O_7[M+H^+]$ 768.3269, found 768.3282.

Example 92

Synthesis of HC65-14

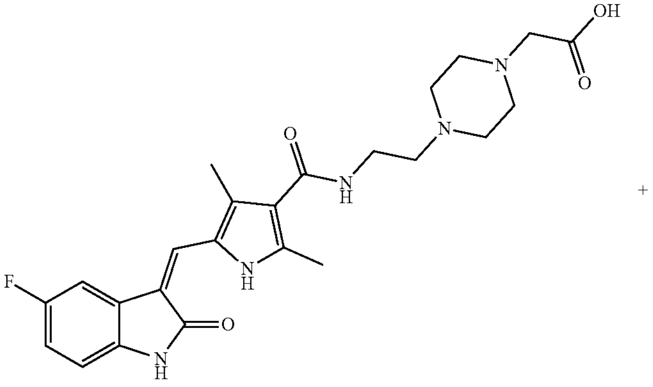

Intermediate 9

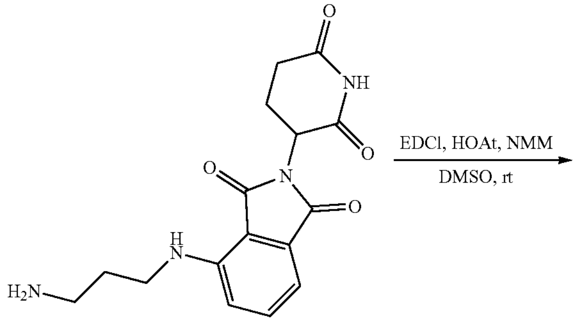

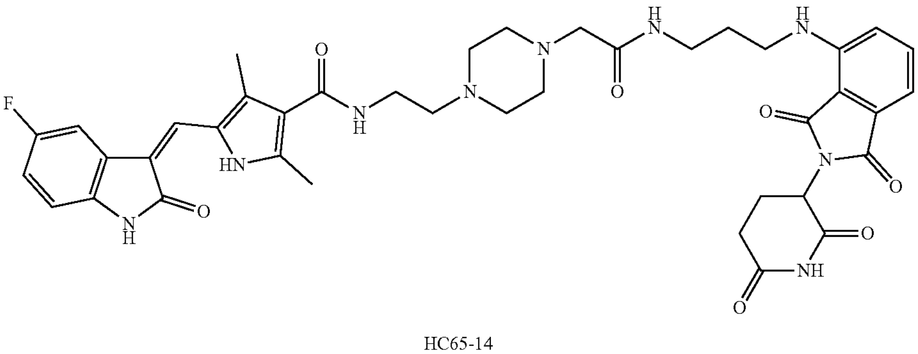

HC65-14

HC65-14 was synthesized following the standard procedure for preparing HC65-13 from Intermediate 9 (7 mg, 0.01 mmol, 1.1 equiv), 4-((3-aminopropyl)amino)-2-(2,6-dioxopiperidin-3-yl)isoindoline-1,3-dione (4.9 mg, 0.011 mmol, 1.1 equiv), EDCI (1-ethyl-3-(3-dimethylaminopropyl)carbodiimide) (2.9 mg, 0.015 mmol, 1.5 equiv), HOAt (1-hydroxy-7-azabenzo-triazole) (2.0 mg, 0.015 mmol, 1.5 equiv), and NMM (N-Methylmorpholine) (5.0 mg, 0.05 mmol, 5.0 equiv) in DMSO (1 mL). HC65-14 was obtained as yellow solid in TFA salt form (5.1 mg, 51%). $^1$H NMR (600 MHz, Methanol-$d_4$) δ 13.70 (s, 1H), 7.59-7.53 (m, 2H), 7.42 (d, J=8.9 Hz, 1H), 7.08-7.02 (m, 2H), 6.93-6.84 (m, 2H), 5.09-5.04 (m, 1H), 3.77-3.69 (m, 2H), 3.50-3.27 (m, 12H), 3.02 (s, 4H), 2.90-2.81 (m, 1H), 2.79-2.66 (m, 2H), 2.52 (s, 3H), 2.47 (s, 1H), 2.17-2.07 (m, 1H), 1.95-1.84 (m, 2H). HRMS calcd for $C_{40}H_{45}FN_9O_7$[M+H$^+$] 782.3426, found 782.3421.

Example 93

Synthesis of HC65-15

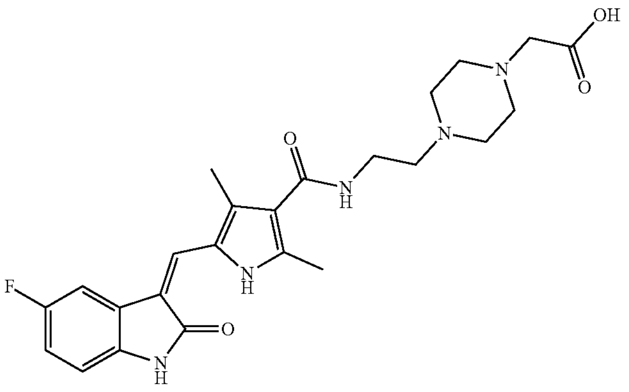

Intermediate 9

+

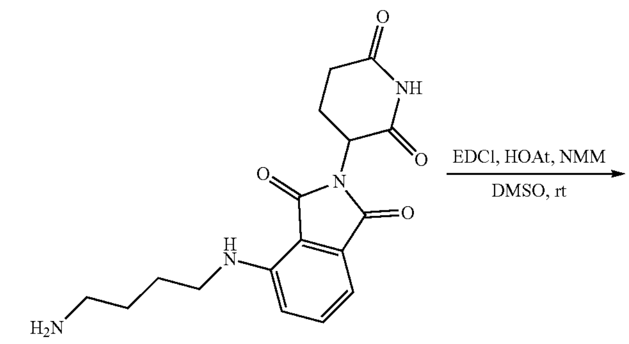

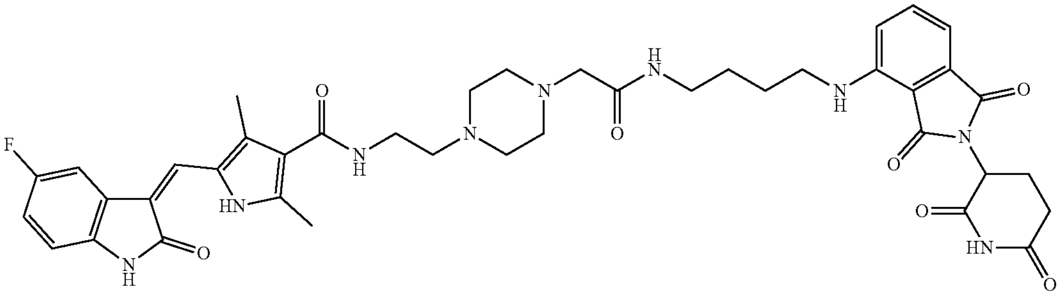

HC65-15

HC65-15 was synthesized following the standard procedure for preparing HC65-13 from Intermediate 9 (7 mg, 0.01 mmol, 1.1 equiv), 4-((4-aminobutyl)amino)-2-(2,6-dioxopiperidin-3-yl)isoindoline-1,3-dione (5.1 mg, 0.011 mmol, 1.1 equiv), EDCI (1-ethyl-3-(3-dimethylaminopropyl)carbodiimide) (2.9 mg, 0.015 mmol, 1.5 equiv), HOAt (1-hydroxy-7-azabenzo-triazole) (2.0 mg, 0.015 mmol, 1.5 equiv), and NMM (N-Methylmorpholine) (5.0 mg, 0.05 mmol, 5.0 equiv) in DMSO (1 mL). HC65-15 was obtained as yellow solid in TFA salt form (4.6 mg, 45%). $^1$H NMR (600 MHz, Methanol-$d_4$) δ 13.73 (s, 1H), 7.62-7.54 (m, 2H), 7.46-7.41 (m, 1H), 7.10-7.02 (m, 2H), 6.92-6.85 (m, 2H), 5.07 (dd, J=12.7, 5.7 Hz, 1H), 3.73 (t, J=6.0 Hz, 2H), 3.48-3.33 (m, 12H), 3.08-2.81 (m, 5H), 2.78-2.66 (m, 2H), 2.53 (s, 3H), 2.49 (s, 3H), 2.17-2.09 (m, 1H), 1.79-1.62 (m, 4H). HRMS calcd for $C_{41}H_{47}FN_9O_7$[M+H$^+$]796.3582, found 796.3595.

Example 94

Synthesis of HC65-16

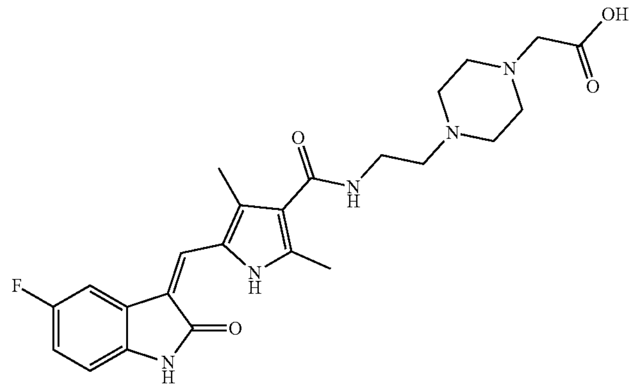

Intermediate 9

+

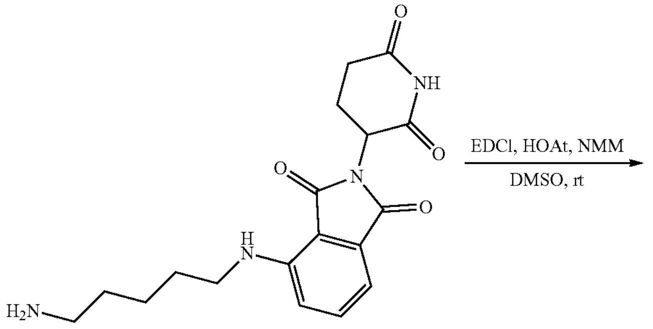

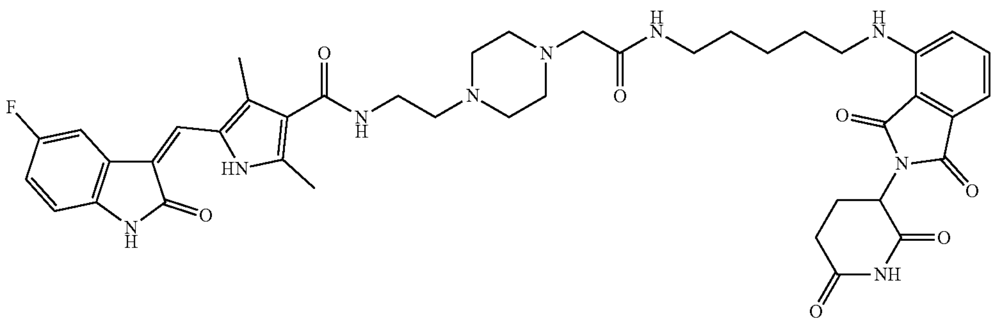

HC65-16

HC65-16 was synthesized following the standard procedure for preparing HC65-13 from Intermediate 9 (7 mg, 0.01 mmol, 1.1 equiv), 4-((5-aminopentyl)amino)-2-(2,6-dioxopiperidin-3-yl)isoindoline-1,3-dione (5.2 mg, 0.011 mmol, 1.1 equiv), EDCI (1-ethyl-3-(3-dimethylaminopropyl)carbodiimide) (2.9 mg, 0.015 mmol, 1.5 equiv), HOAt (1-hydroxy-7-azabenzo-triazole) (2.0 mg, 0.015 mmol, 1.5 equiv), and NMM (N-Methylmorpholine) (5.0 mg, 0.05 mmol, 5.0 equiv) in DMSO (1 mL). HC65-16 was obtained as yellow solid in TFA salt form (5.1 mg, 49%). $^1$H NMR (600 MHz, Methanol-$d_4$) δ 13.72 (s, 1H), 7.58 (s, 1H), 7.55 (dd, J=8.6, 7.1 Hz, 1H), 7.43 (dd, J=8.9, 2.4 Hz, 1H), 7.05 (d, J=4.7 Hz, 1H), 7.03 (d, J=3.2 Hz, 1H), 6.91-6.84 (m, 2H), 5.05 (dd, J=12.8, 5.5 Hz, 1H), 3.73 (t, J=6.0 Hz, 2H), 3.48-3.34 (m, 8H), 3.32-3.26 (m, 4H), 3.01 (s, 4H), 2.85 (ddd, J=17.6, 14.0, 5.3 Hz, 1H), 2.79-2.68 (m, 2H), 2.53 (s, 3H), 2.48 (s, 3H), 2.16-2.07 (m, 1H), 1.70 (p, J=6.9 Hz, 2H), 1.61 (p, J=7.0 Hz, 2H), 1.52-1.42 (m, 2H). HRMS calcd for $C_{42}H_{49}FN_9O_7[M+H^+]$ 810.3739, found 810.3747.

Example 95

Synthesis of HC65-17

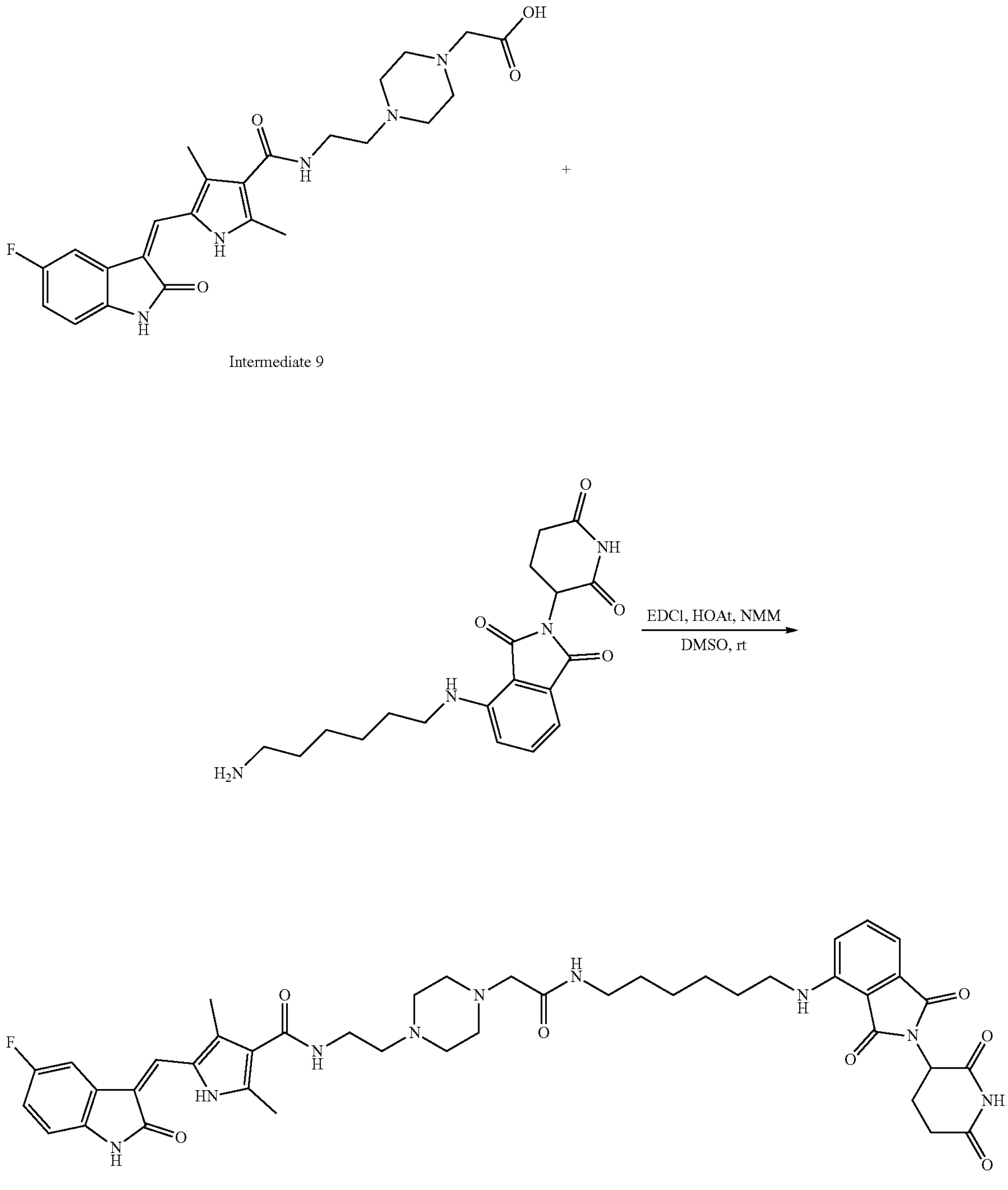

Intermediate 9

HC65-17

HC65-17 was synthesized following the standard procedure for preparing HC65-13 from Intermediate 9 (7 mg, 0.01 mmol, 1.1 equiv), 4-((6-aminohexyl)amino)-2-(2,6-dioxopiperidin-3-yl)isoindoline-1,3-dione (4.5 mg, 0.011 mmol, 1.1 equiv), EDCI (1-ethyl-3-(3-dimethylaminopropyl)carbodiimide) (2.9 mg, 0.015 mmol, 1.5 equiv), HOAt (1-hydroxy-7-azabenzo-triazole) (2.0 mg, 0.015 mmol, 1.5 equiv), and NMM (N-Methylmorpholine) (5.0 mg, 0.05 mmol, 5.0 equiv) in DMSO (1 mL). HC65-17 was obtained as yellow solid in TFA salt form (4.7 mg, 45%). $^1$H NMR (600 MHz, Methanol-$d_4$) δ 13.74 (s, 1H), 7.60 (s, 1H), 7.58-7.53 (m, 1H), 7.49-7.42 (m, 1H), 7.11-7.00 (m, 2H), 6.95-6.85 (m, 2H), 5.12-5.03 (m, 1H), 3.79-3.70 (m, 2H), 3.52-3.24 (m, 12H), 3.00 (s, 4H), 2.90-2.82 (m, 1H), 2.80-2.68 (m, 2H), 2.53 (s, 3H), 2.49 (d, J=1.4 Hz, 3H), 2.19-2.04 (m, 1H), 1.76-1.65 (m, 2H), 1.62-1.53 (m, 2H), 1.53-1.38 (m, 4H). HRMS calcd for $C_{43}H_{51}FN_9O_7$[M+H$^+$] 824.3895, found 824.3888.

Example 96

Synthesis of HC65-18

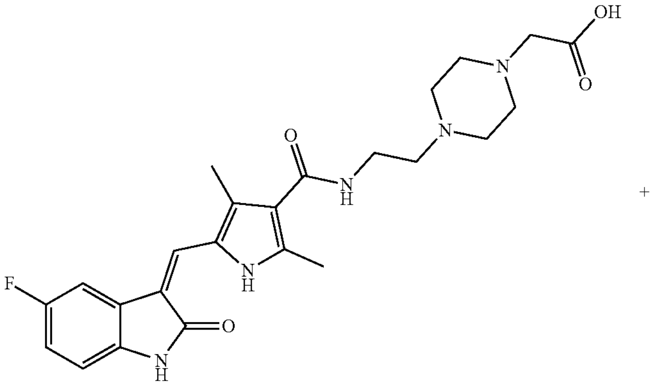

+

Intermediate 9

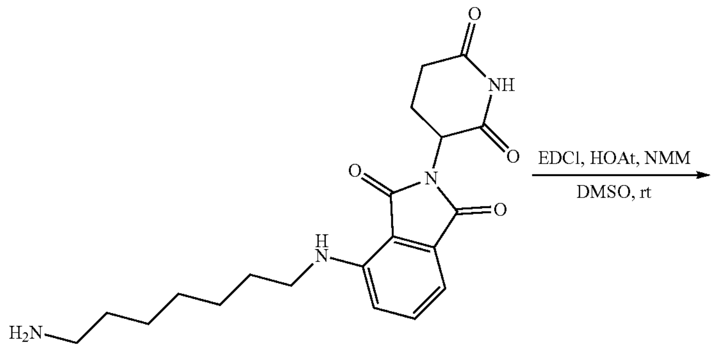

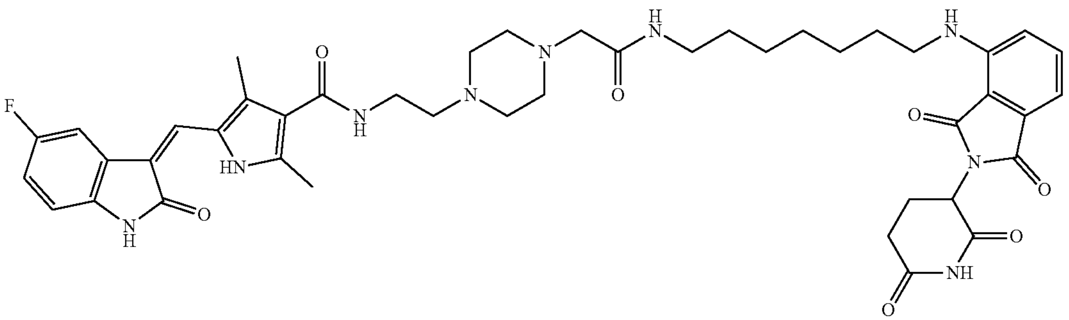

HC65-18

HC65-18 was synthesized following the standard procedure for preparing HC65-13 from Intermediate 9 (7 mg, 0.01 mmol, 1.1 equiv), 4-((7-aminoheptyl)amino)-2-(2,6-dioxopiperidin-3-yl)isoindoline-1,3-dione (5.5 mg, 0.011 mmol, 1.1 equiv), EDCI (1-ethyl-3-(3-dimethylaminopropyl)carbodiimide) (2.9 mg, 0.015 mmol, 1.5 equiv), HOAt (1-hydroxy-7-azabenzo-triazole) (2.0 mg, 0.015 mmol, 1.5 equiv), and NMM (N-Methylmorpholine) (5.0 mg, 0.05 mmol, 5.0 equiv) in DMSO (1 mL). HC65-18 was obtained as yellow solid in TFA salt form (4.2 mg, 39%). $^1$H NMR (600 MHz, Methanol-$d_4$) δ 13.71 (s, 1H), 7.58 (s, 1H), 7.56-7.52 (m, 1H), 7.43 (dd, J=8.9, 2.4 Hz, 1H), 7.03 (s, 1H), 7.02 (s, 1H), 6.92-6.84 (m, 2H), 5.06 (dd, J=12.8, 5.5 Hz, 1H), 3.74 (t, J=6.0 Hz, 2H), 3.43 (s, 4H), 3.39-3.28 (m, 6H), 3.25 (t, J=7.0 Hz, 2H), 3.02 (s, 4H), 2.86 (ddd, J=17.5, 13.9, 5.3 Hz, 1H), 2.79-2.67 (m, 2H), 2.52 (s, 3H), 2.48 (s, 3H), 2.16-2.08 (m, 1H), 1.67 (p, J=7.0 Hz, 2H), 1.55 (p, J=7.1 Hz, 2H), 1.48-1.34 (m, 6H). HRMS calcd for $C_{44}H_{53}FN_9O_7$[M+H$^+$] 838.4052, found 838.4069.

Example 97

Synthesis of HC65-19

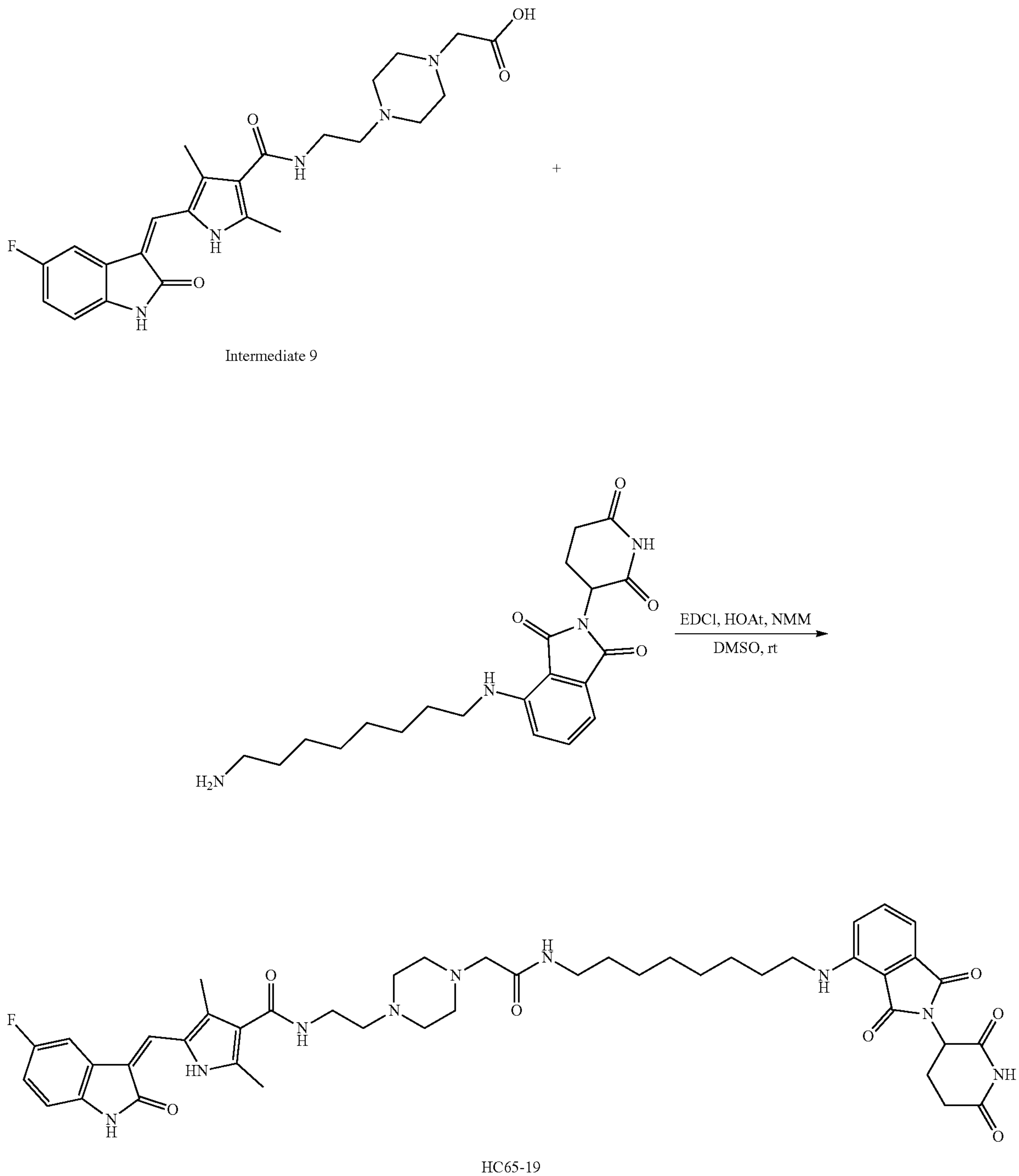 [SMILES: Cc1[nH]c(/C=C2\C(=O)Nc3ccc(F)cc32)c(C)c1C(=O)NCCN1CCN(CC(=O)O)CC1 ; NCCCCCCCCNc1cccc2c1C(=O)N(C1CCC(=O)NC1=O)C2=O ; Cc1[nH]c(/C=C2\C(=O)Nc3ccc(F)cc32)c(C)c1C(=O)NCCN1CCN(CC(=O)NCCCCCCCCNc2cccc3c2C(=O)N(C2CCC(=O)NC2=O)C3=O)CC1]

Intermediate 9

+

HC65-19

HC65-19 was synthesized following the standard procedure for preparing HC65-13 from Intermediate 9 (7 mg, 0.01 mmol, 1.1 equiv), 4-((8-aminooctyl)amino)-2-(2,6-dioxopiperidin-3-yl)isoindoline-1,3-dione (5.7 mg, 0.011 mmol, 1.1 equiv), EDCI (1-ethyl-3-(3-dimethylaminopropyl)carbodiimide) (2.9 mg, 0.015 mmol, 1.5 equiv), HOAt (1-hydroxy-7-azabenzo-triazole) (2.0 mg, 0.015 mmol, 1.5 equiv), and NMM (N-Methylmorpholine) (5.0 mg, 0.05 mmol, 5.0 equiv) in DMSO (1 mL). HC65-19 was obtained as yellow solid in TFA salt form (5.9 mg, 46%). $^1H$ NMR (600 MHz, Methanol-$d_4$) δ 13.74 (s, 1H), 7.60 (s, 1H), 7.57-7.52 (m, 1H), 7.45 (dd, J=8.9, 2.5 Hz, 1H), 7.03 (s, 1H), 7.02 (s, 2H), 6.92-6.84 (m, 2H), 5.07 (dd, J=12.7, 5.5 Hz, 1H), 3.73 (t, J=6.1 Hz, 2H), 3.51-3.27 (m, 10H), 3.24 (t, J=7.1 Hz, 2H), 3.01 (s, 4H), 2.91-2.83 (m, 1H), 2.80-2.67 (m, 2H), 2.53 (s, 3H), 2.49 (s, 3H), 2.19-2.07 (m, 1H), 1.72-1.61 (m, 2H), 1.59-1.50 (m, 2H), 1.48-1.31 (m, 8H). HRMS calcd for $C_{45}H_{55}FN_9O_7$[M+H$^+$]852.4208, found 852.4216.

Example 98

Synthesis of intermediate 10

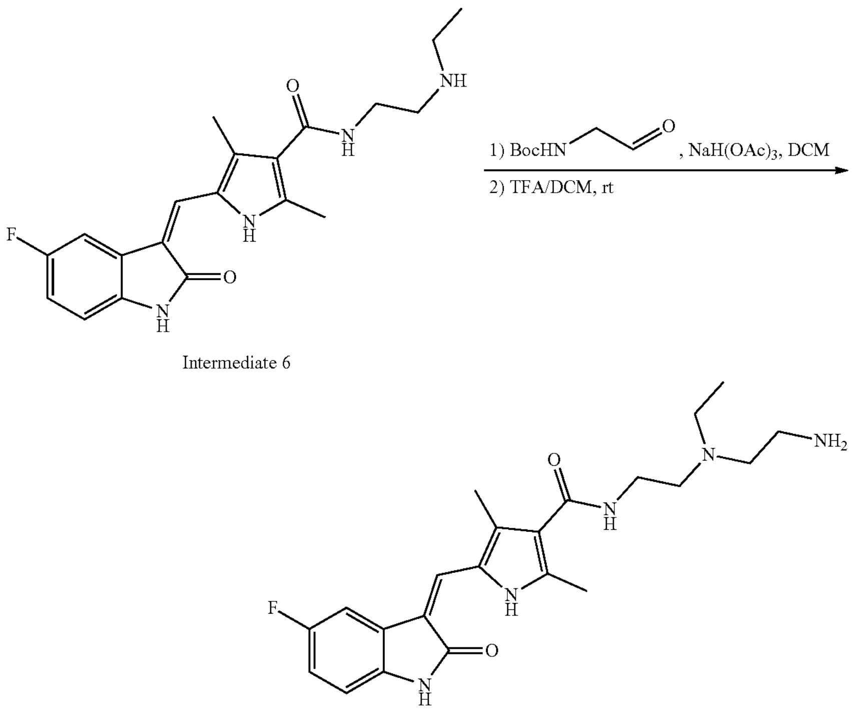

Intermediate 6

Intermediate 10

To a solution of intermediate 6 (60 mg, 0.124 mmol, 1.0 equiv) in DCM (2 mL) were added $Et_3N$ (19 mg, 0.186 mmol, 1.5 equiv), tert-butyl (2-oxoethyl)carbamate (30 mg, 0.186 mmol, 1.5 equiv), $NaH(OAc)_3$ (1-ethyl-3-(3-dimethylaminopropyl)carbodiimide) (144 mg, 0.75 mmol, 1.5 equiv), HOAt (1-hydroxy-7-azabenzo-triazole) (102 mg, 0.75 mmol, 1.5 equiv), and NMM (N-Methylmorpholine) (52 mg, 0.248 mmol, 2.0 equiv). After being stirred overnight at room temperature for 3 h, the reaction was quenched with water (1 mL) and concentrated under vacuum. the resulting mixture was purified by preparative HPLC (10%-100% methanol/0.1% TFA in $H_2O$) to afford yellow solid in TFA salt form. The obtained solid was dissolved in DCM (4 mL). To the resulting solution was added TFA (2 ml). After being stirred for 1 h at room temperature, the reaction mixture was concentrated and the residue was purified preparative HPLC (10%-100% methanol/0.1% TFA in $H_2O$) to afford intermediate 10 as yellow solid in TFA salt form (51 mg, 64% yield for two step). $^1H$ NMR (600 MHz, Methanol-$d_4$) δ 7.61 (s, 1H), 7.45 (dd, J=8.8, 2.1 Hz, 1H), 6.94-6.86 (m, 2H), 3.76 (t, J=6.2 Hz, 2H), 3.55 (s, 2H), 3.50-3.35 (m, 6H), 2.55 (s, 3H), 2.51 (s, 3H), 1.40 (t, J=7.2 Hz, 3H). ESI m/z=414.2 [M+H$^+$].

Example 99

Synthesis of HC65-24

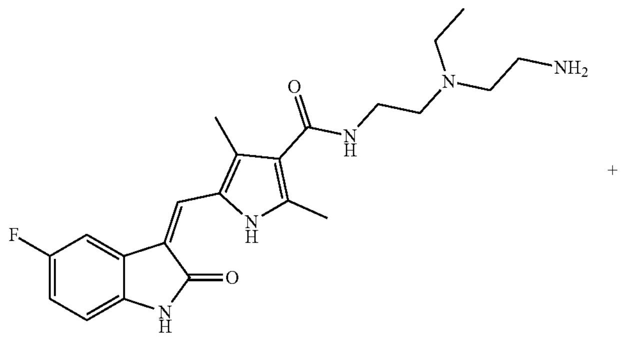

Intermediate 10

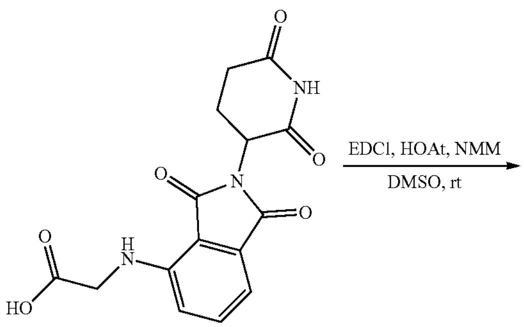

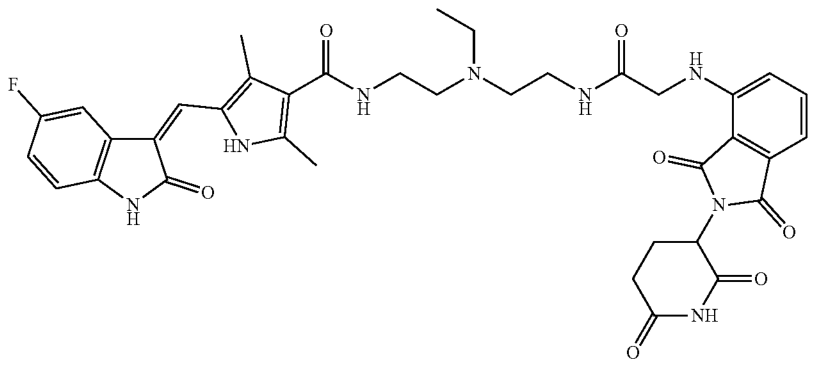

HC65-24

To a solution of Intermediate 10 (9.5 mg, 0.0148 mmol, 1.06 equiv) in DMSO (1 mL) were added (2-(2,6-dioxopiperidin-3-yl)-1,3-dioxoisoindolin-4-yl)glycine (4.6 mg, 0.014 mmol, 1.0 equiv), EDCI (1-ethyl-3-(3-dimethylaminopropyl)carbodiimide) (4.0 mg, 0.021 mmol, 1.5 equiv), HOAt (1-hydroxy-7-azabenzo-triazole) (2.9 mg, 0.021 mmol, 1.5 equiv), and NMM (N-Methylmorpholine) (5.7 mg, 0.056 mmol, 4.0 equiv). After being stirred overnight at room temperature, the resulting mixture was purified by preparative HPLC (10%-100% MeOH/0.1% TFA in $H_2O$) to afford HC65-24 as yellow solid in TFA salt form (7.4 mg, 63%). $^1H$ NMR (600 MHz, Methanol-$d_4$) δ 13.47 (s, 1H), 7.36 (t, J=7.8 Hz, 1H), 7.33-7.27 (m, 2H), 6.87 (dtd, J=19.1, 8.6, 3.3 Hz, 2H), 6.73-6.66 (m, 2H), 5.04-4.99 (m, 1H), 3.86 (s, 2H), 3.79-3.61 (m, 4H), 3.59-3.38 (m, 6H), 2.93-2.83 (m, 1H), 2.81-2.69 (m, 2H), 2.53 (s, 3H), 2.41 (s, 3H), 2.30-2.21 (m, 1H), 1.46 (t, J=7.2 Hz, 3H). HRMS calcd for $C_{37}H_{40}FN_8O_7[M+H^+]$ 727.3004, found 727.3013.

Example 100

Synthesis of HC65-25

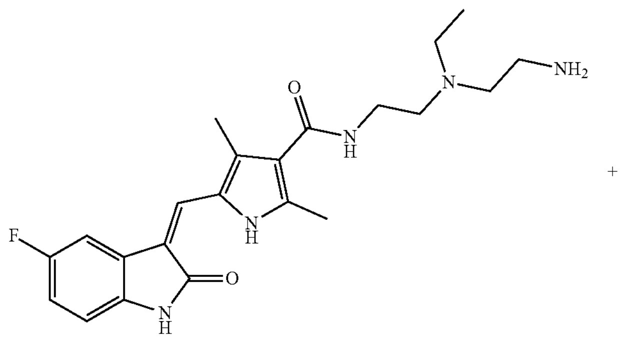

Intermediate 10

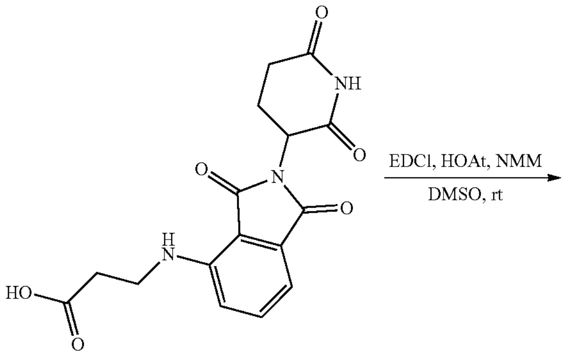

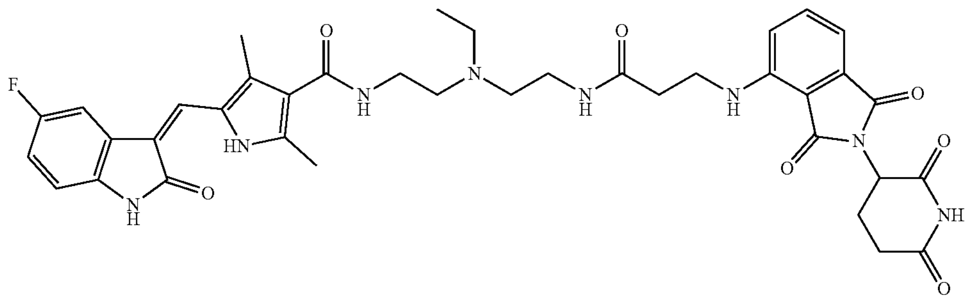

HC65-25

HC65-25 was synthesized following the standard procedure for preparing HC65-24 from Intermediate 10 (9.5 mg, 0.0148 mmol, 1.06 equiv), 3-((2-(2,6-dioxopiperidin-3-yl)-1,3-dioxoisoindolin-4-yl)amino)propanoic acid (4.9 mg, 0.014 mmol, 1.0 equiv), EDCI (1-ethyl-3-(3-dimethylaminopropyl)carbodiimide) (4.0 mg, 0.021 mmol, 1.5 equiv), HOAt (1-hydroxy-7-azabenzo-triazole) (2.9 mg, 0.021 mmol, 1.5 equiv), and NMM (N-Methylmorpholine) (5.7 mg, 0.056 mmol, 4.0 equiv) in DMSO (1 mL). HC65-25 was obtained as yellow solid in TFA salt form (8.0 mg, 67%). $^1H$ NMR (600 MHz, Methanol-$d_4$) δ 13.62 (s, 1H), 7.43 (s, 1H), 7.37-7.30 (m, 2H), 6.92-6.81 (m, 3H), 6.77-6.72 (m, 1H), 5.03 (d, J=13.2 Hz, 1H), 3.81-3.67 (m, 2H), 3.67-3.55 (m, 2H), 3.52-3.35 (m, 8H), 2.92-2.81 (m, 1H), 2.79-2.64 (m, 2H), 2.61-2.55 (m, 2H), 2.51 (s, 3H), 2.44 (s, 3H), 2.19-2.09 (m, 1H), 1.40 (t, J=7.2 Hz, 3H). HRMS calcd for $C_{38}H_{42}FN_8O_7$[M+H$^+$] 741.3160, found 741.3168.

Example 101

Synthesis of HC65-26

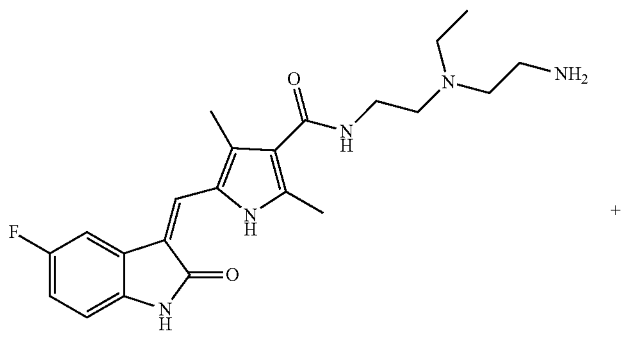

Intermediate 10

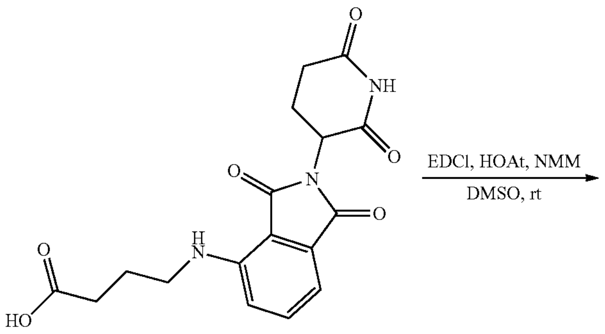

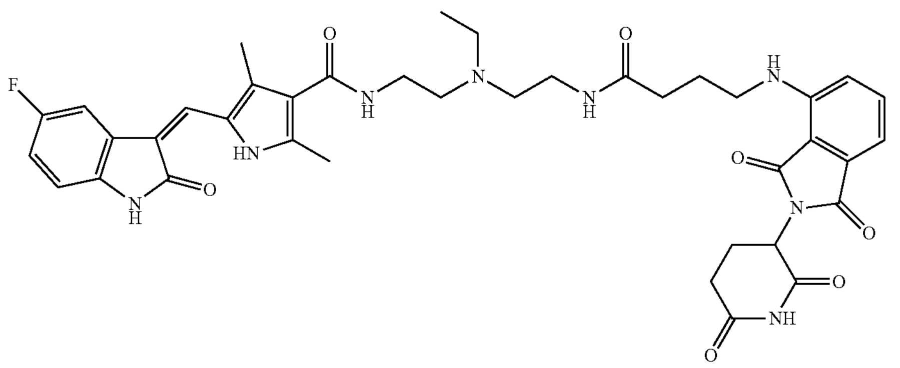

HC65-26

HC65-26 was synthesized following the standard procedure for preparing HC65-24 from Intermediate 10 (11.0 mg, 0.0172 mmol, 1.06 equiv), 4-((2-(2,6-dioxopiperidin-3-yl)-1,3-dioxoisoindolin-4-yl)amino)butanoic acid (5.8 mg, 0.016 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.3 mg, 0.024 mmol, 1.5 equiv), and NMM (N-Methylmorpholine) (8.1 mg, 0.08 mmol, 5.0 equiv) in DMSO (1 mL). HC65-26 was obtained as yellow solid in TFA salt form (7.9 mg, 57%). $^1$H NMR (600 MHz, Methanol-$d_4$) δ 13.65 (s, 1H), 7.44 (s, 1H), 7.39-7.31 (m, 2H), 6.90-6.78 (m, 4H), 5.03 (dd, J=12.7, 5.4 Hz, 1H), 3.79-3.70 (m, 2H), 3.63-3.55 (m, 2H), 3.52-3.32 (m, 6H), 3.17-3.09 (m, 2H), 2.86 (ddd, J=18.5, 13.8, 5.3 Hz, 1H), 2.79-2.64 (m, 2H), 2.53 (s, 3H), 2.47 (s, 3H), 2.36-2.30 (m, 2H), 2.16-2.08 (m, 1H), 1.88-1.69 (m, 2H), 1.47-1.36 (m, 3H). HRMS calcd for $C_{39}H_{44}FN_8O_7$[M+H$^+$] 755.3317, found 755.3312.

Example 102

Synthesis of HC65-27

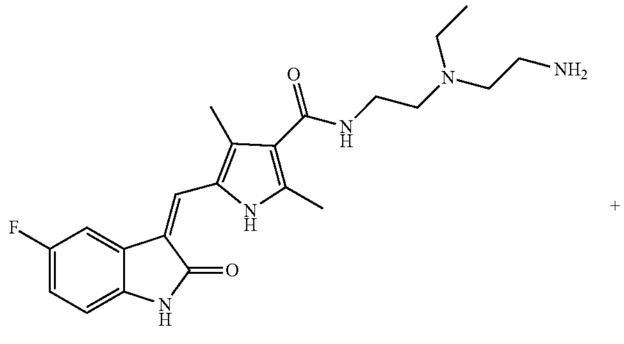

Intermediate 10

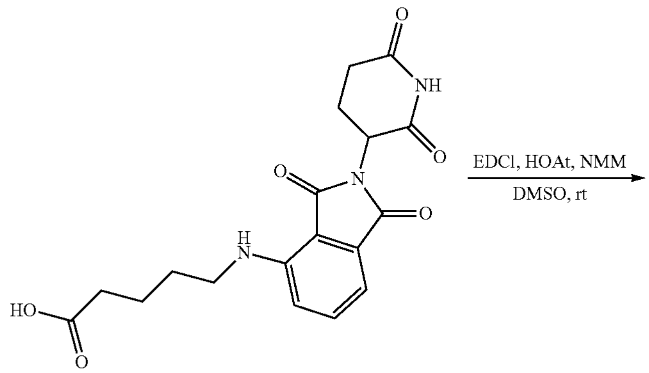

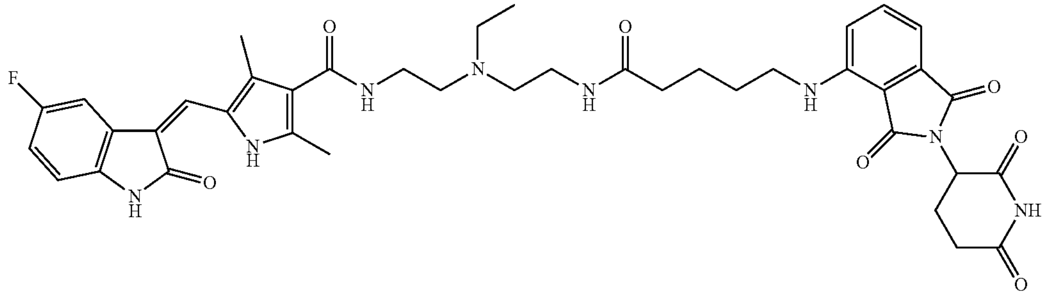

HC65-27

HC65-27 was synthesized following the standard procedure for preparing HC65-24 from Intermediate 10 (11.0 mg, 0.0172 mmol, 1.06 equiv), 5-((2-(2,6-dioxopiperidin-3-yl)-1,3-dioxoisoindolin-4-yl)amino)pentanoic acid (6.0 mg, 0.016 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.3 mg, 0.024 mmol, 1.5 equiv), and NMM (N-Methylmorpholine) (8.1 mg, 0.08 mmol, 5.0 equiv) in DMSO (1 mL). HC65-27 was obtained as yellow solid in TFA salt form (5.4 mg, 38%). $^1H$ NMR (600 MHz, Methanol-$d_4$) δ 13.70 (s, 1H), 7.48 (s, 1H), 7.36-7.29 (m, 2H), 6.82 (td, J=8.9, 2.5 Hz, 1H), 6.80-6.74 (m, 4H), 5.05 (dd, J=12.7, 5.6 Hz, 1H), 3.82-3.70 (m, 2H), 3.65-3.50 (m, 2H), 3.49-3.34 (m, 6H), 3.08-3.00 (m, 2H), 2.88 (ddd, J=17.0, 13.8, 5.2 Hz, 1H), 2.81-2.68 (m, 2H), 2.55 (s, 3H), 2.49 (s, 3H), 2.27 (t, J=7.0 Hz, 2H), 2.18-2.10 (m, 1H), 1.64-1.46 (m, 4H), 1.40 (t, J=7.2 Hz, 3H). HRMS calcd for $C_{40}H_{46}FN_8O_7[M+H^+]$ 769.3473, found 769.3489.

Example 103

Synthesis of HC65-28

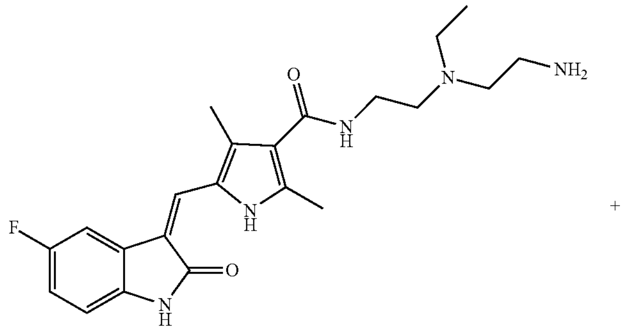

Intermediate 10

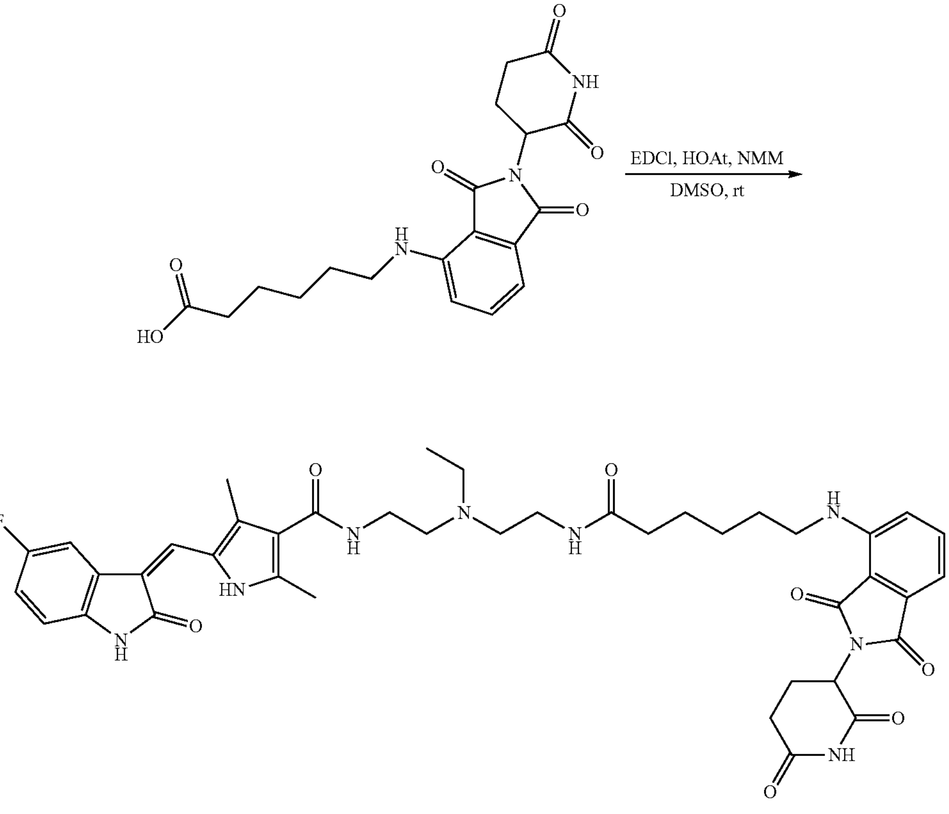

HC65-28

HC65-28 was synthesized following the standard procedure for preparing HC65-24 from Intermediate 10 (11.0 mg, 0.0172 mmol, 1.06 equiv), 6-((2-(2,6-dioxopiperidin-3-yl)-1,3-dioxoisoindolin-4-yl)amino)hexanoic acid (6.2 mg, 0.016 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.3 mg, 0.024 mmol, 1.5 equiv), and NMM (N-Methylmorpholine) (8.1 mg, 0.08 mmol, 5.0 equiv) in DMSO (1 mL). HC65-28 was obtained as yellow solid in TFA salt form (6.9 mg, 48%). $^1H$ NMR (600 MHz, Methanol-$d_4$) δ 13.72 (s, 1H), 7.50 (s, 1H), 7.38 (dd, J=8.5, 7.1 Hz, 1H), 7.33 (d, J=9.0 Hz, 1H), 6.86 (d, J=7.1 Hz, 1H), 6.83-6.72 (m, 3H), 5.05 (dd, J=12.7, 5.5 Hz, 1H), 3.74 (t, J=5.3 Hz, 2H), 3.66-3.53 (m, 3H), 3.52-3.30 (m, 5H), 3.05 (t, J=7.2 Hz, 2H), 2.87 (ddd, J=17.2, 13.8, 5.3 Hz, 1H), 2.80-2.66 (m, 2H), 2.56 (s, 3H), 2.50 (s, 3H), 2.23 (t, J=7.6 Hz, 2H), 2.18-2.10 (m, 1H), 1.60-1.43 (m, 4H), 1.41 (t, J=7.2 Hz, 3H), 1.34-1.25 (m, 2H). HRMS calcd for $C_{41}H_{48}FN_8O_7[M+H^+]$ 783.3630, found 783.3639.

Example 104

Synthesis of HC65-29

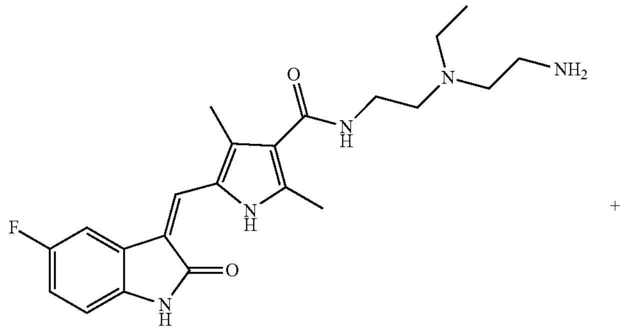

Intermediate 10

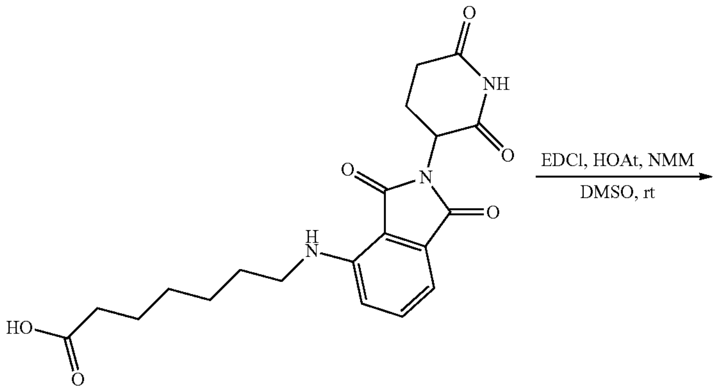

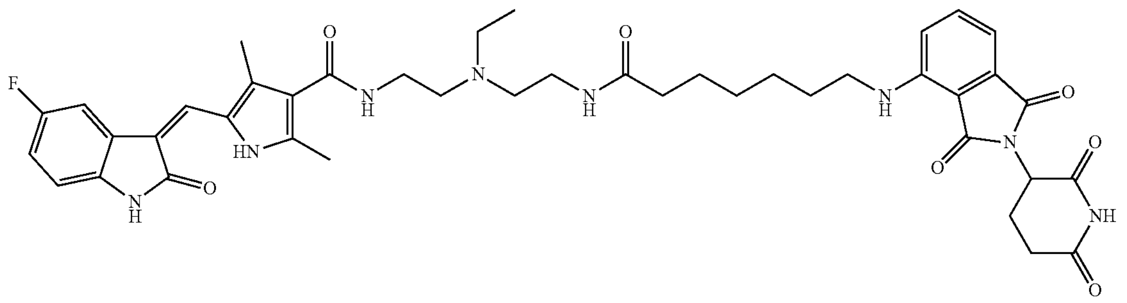

HC65-29

HC65-29 was synthesized following the standard procedure for preparing HC65-24 from Intermediate 10 (11.0 mg, 0.0172 mmol, 1.06 equiv), 7-((2-(2,6-dioxopiperidin-3-yl)-1,3-dioxoisoindolin-4-yl)amino)heptanoic acid (6.4 mg, 0.016 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.3 mg, 0.024 mmol, 1.5 equiv), and NMM (N-Methylmorpholine) (8.1 mg, 0.08 mmol, 5.0 equiv) in DMSO (1 mL). HC65-29 was obtained as yellow solid in TFA salt form (7.7 mg, 53%). $^1$H NMR (600 MHz, Methanol-d4) δ 13.75 (s, 1H), 7.55 (s, 1H), 7.41-7.35 (m, 2H), 6.92-6.87 (m, 1H), 6.82-6.73 (m, 3H), 5.06 (dd, J=12.8, 5.5 Hz, 1H), 3.80-3.68 (m, 2H), 3.67-3.52 (m, 1H), 3.52-3.32 (m, 7H), 3.05 (t, J=7.1 Hz, 2H), 2.88 (ddd, J=17.5, 14.0, 5.3 Hz, 1H), 2.80-2.68 (m, 2H), 2.56 (s, 3H), 2.50 (s, 3H), 2.21 (t, J=7.7 Hz, 2H), 2.16-2.10 (m, 1H), 1.56-1.43 (m, 4H), 1.40 (t, J=7.2 Hz, 3H), 1.30-1.20 (m, 4H). HRMS calcd for $C_{42}H_{50}FN_8O_7$[M+H$^+$] 797.3786, found 797.3798.

Example 105

Synthesis of HC65-30

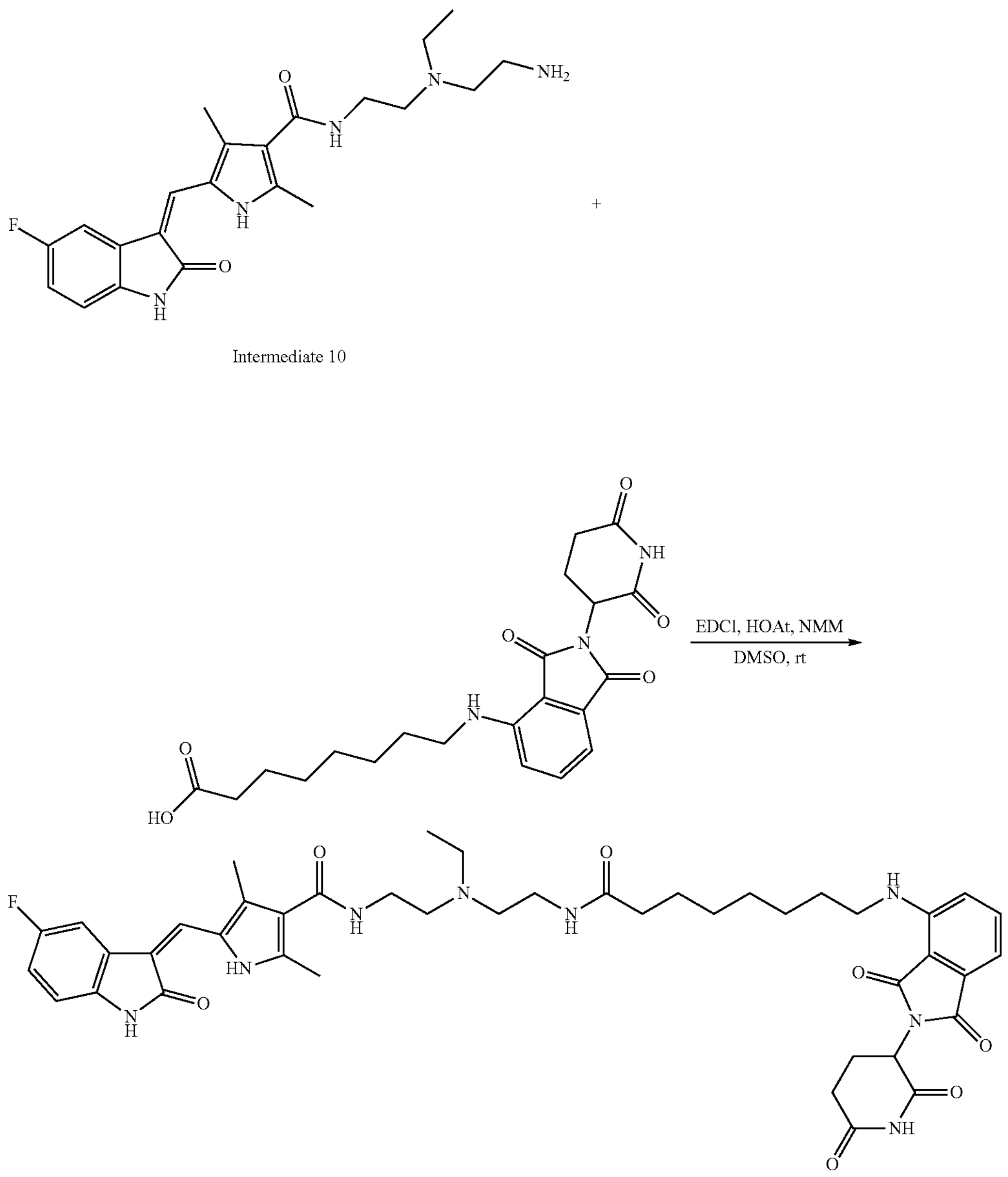

Intermediate 10

HC65-30

HC65-30 was synthesized following the standard procedure for preparing HC65-24 from Intermediate 10 (11.0 mg, 0.0172 mmol, 1.06 equiv), 8-((2-(2,6-dioxopiperidin-3-yl)-1,3-dioxoisoindolin-4-yl)amino)octanoic acid (6.7 mg, 0.016 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.3 mg, 0.024 mmol, 1.5 equiv), and NMM (N-Methylmorpholine) (8.1 mg, 0.08 mmol, 5.0 equiv) in DMSO (1 mL). HC65-30 was obtained as yellow solid in TFA salt form (6.2 mg, 42%). $^1$H NMR (600 MHz, Methanol-$d_4$) δ 13.75 (s, 1H), 7.55 (s, 1H), 7.44 (dd, J=8.6, 7.1 Hz, 1H), 7.37 (dd, J=8.9, 2.4 Hz, 1H), 6.95 (d, J=7.1 Hz, 1H), 6.82 (d, J=8.6 Hz, 1H), 6.81-6.74 (m, 2H), 5.06 (dd, J=12.8, 5.5 Hz, 1H), 3.74 (t, J=5.4 Hz, 2H), 3.60 (dd, J=13.9, 9.0 Hz, 1H), 3.52-3.30 (m, 7H), 3.07 (t, J=7.2 Hz, 2H), 2.88 (ddd, J=17.6, 13.9, 5.3 Hz, 1H), 2.81-2.66 (m, 2H), 2.55 (s, 3H), 2.50 (s, 3H), 2.20 (t, J=7.7 Hz, 2H), 2.16-2.10 (m, 1H), 1.55-1.42 (m, 4H), 1.40 (t, J=7.2 Hz, 3H), 1.29-1.17 (m, 6H). HRMS calcd for $C_{43}H_{52}FN_8O_7$[M+H$^+$] 811.3943, found 811.3939.

Example 106

Synthesis of HC65-33

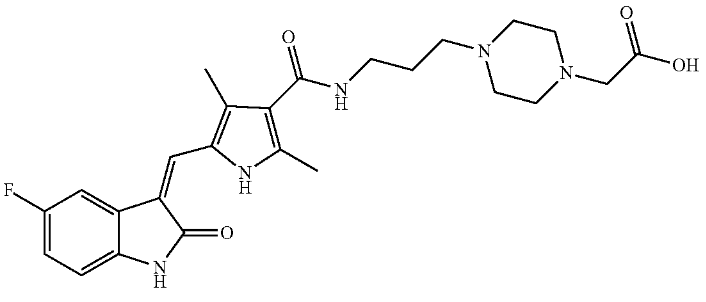

Intermediate 3

+

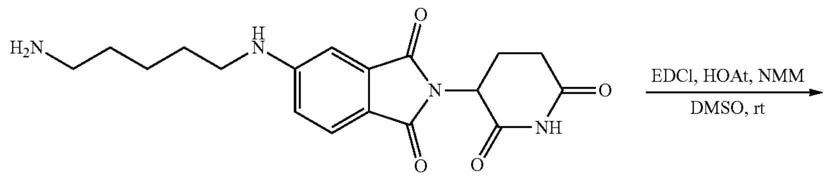

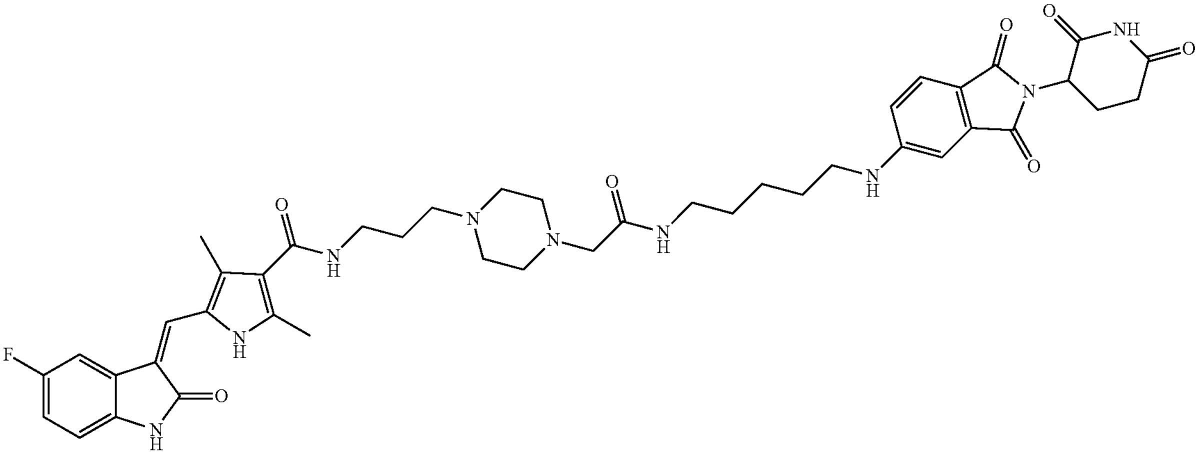

HC65-33

HC65-33 was synthesized following the standard procedure for preparing HC58-53 from Intermediate 3 (10.0 mg, 0.014 mmol, 1.0 equiv), 5-((5-aminopentyl)amino)-2-(2,6-dioxopiperidin-3-yl)isoindoline-1,3-dione (7.1 mg, 0.015 mmol, 1.1 equiv), EDCI (4.0 mg, 0.021 mmol, 1.5 equiv), HOAt (3.0 mg, 0.021 mmol, 1.5 equiv), and NMM (7.1 mg, 0.07 mmol, 5.0 equiv) in DMSO (1 mL). HC65-33 was obtained as yellow solid in TFA salt form (8.7 mg, 59%). $^1H$ NMR (600 MHz, Methanol-$d_4$) δ 13.67 (s, 1H), 7.60-7.51 (m, 2H), 7.40 (d, J=8.3 Hz, 1H), 6.95 (s, 1H), 6.90-6.79 (m, 4H), 5.04 (dd, J=12.8, 6.3 Hz, 1H), 3.62-3.35 (m, 6H), 3.31-3.17 (m, 8H), 2.99 (s, 4H), 2.90-2.80 (m, 1H), 2.79-2.65 (m, 2H), 2.50 (s, 3H), 2.46 (s, 3H), 2.15-2.03 (m, 3H), 1.77-1.65 (m, 2H), 1.63-1.54 (m, 2H), 1.52-1.39 (m, 2H). HRMS calcd for $C_{43}H_{51}FN_9O_7[M+H^+]$ 824.3895, found 824.3889.

Example 107

Synthesis of HC65-34

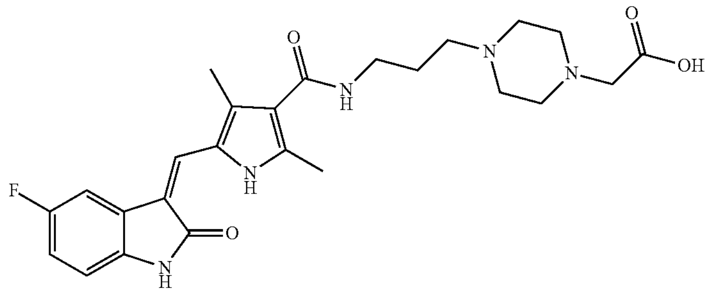

Intermediate 3

+

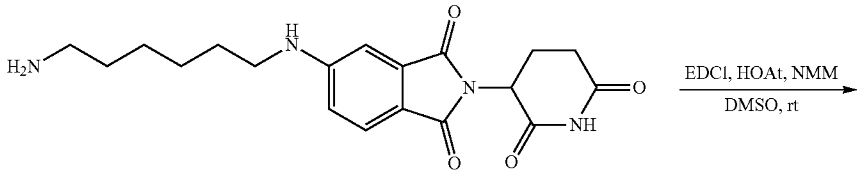

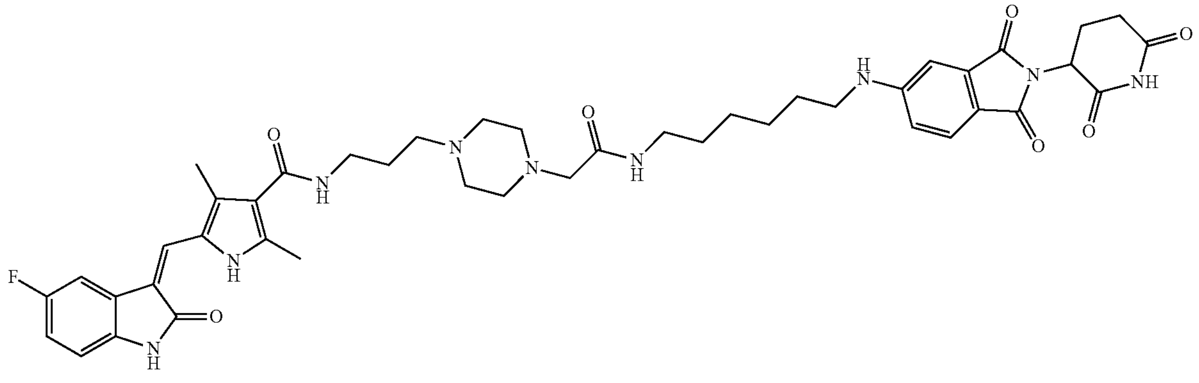

HC65-34

HC65-34 was synthesized following the standard procedure for preparing HC58-53 from Intermediate 3 (10.0 mg, 0.014 mmol, 1.0 equiv), 5-((6-aminohexyl)amino)-2-(2,6-dioxopiperidin-3-yl)isoindoline-1,3-dione (7.3 mg, 0.015 mmol, 1.1 equiv), EDCI (4.0 mg, 0.021 mmol, 1.5 equiv), HOAt (3.0 mg, 0.021 mmol, 1.5 equiv), and NMM (7.1 mg, 0.07 mmol, 5.0 equiv) in DMSO (1 mL). HC65-34 was obtained as yellow solid in TFA salt form (7.4 mg, 50%). $^1$H NMR (600 MHz, Methanol-d$_4$) δ 13.65 (s, 1H), 7.56-7.51 (m, 2H), 7.42-7.36 (m, 1H), 6.94 (d, J=2.1 Hz, 1H), 6.91-6.83 (m, 2H), 6.81 (dd, J=8.4, 2.1 Hz, 1H), 5.04 (dd, J=12.8, 5.5 Hz, 1H), 3.59-3.37 (m, 8H), 3.29-3.22 (m, 4H), 3.19 (t, J=7.0 Hz, 2H), 3.03 (s, 4H), 2.85 (ddd, J=18.6, 14.1, 5.3 Hz, 1H), 2.77-2.65 (m, 2H), 2.50 (s, 3H), 2.46 (s, 3H), 2.15-2.04 (m, 3H), 1.66 (p, J=7.2 Hz, 2H), 1.57 (p, J=7.2 Hz, 2H), 1.51-1.34 (m, 4H). HRMS calcd for $C_{44}H_{53}FN_9O_7$ [M+H$^+$] 838.4052, found 838.4064.

Example 108

Synthesis of HC65-35

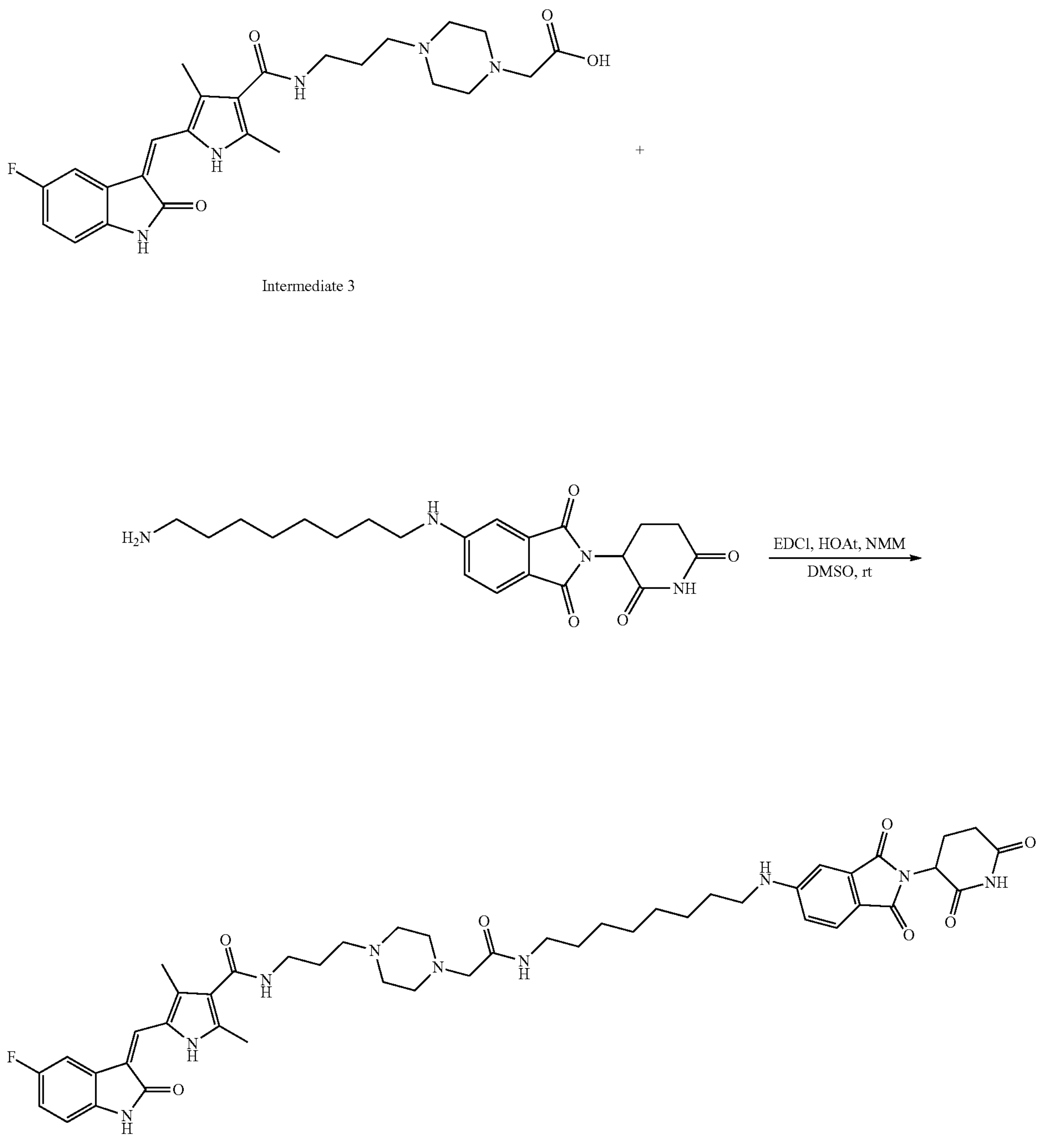

Intermediate 3

HC65-35

HC65-35 was synthesized following the standard procedure for preparing HC58-53 from Intermediate 3 (10.0 mg, 0.014 mmol, 1.0 equiv), 5-((8-aminooctyl)amino)-2-(2,6-dioxopiperidin-3-yl)isoindoline-1,3-dione (7.7 mg, 0.015 mmol, 1.1 equiv), EDCI (4.0 mg, 0.021 mmol, 1.5 equiv), HOAt (3.0 mg, 0.021 mmol, 1.5 equiv), and NMM (7.1 mg, 0.07 mmol, 5.0 equiv) in DMSO (1 mL). HC65-35 was obtained as yellow solid in TFA salt form (6.6 mg, 43%). $^1H$ NMR (600 MHz, Methanol-$d_4$) δ 13.66 (s, 1H), 7.55-7.51 (m, 2H), 7.39 (dd, J=8.8, 2.3 Hz, 1H), 6.93 (d, J=2.2 Hz, 1H), 6.89-6.83 (m, 2H), 6.80 (dd, J=8.4, 2.2 Hz, 1H), 5.04 (dd, J=12.8, 5.5 Hz, 1H), 3.57-3.37 (m, 8H), 3.29-3.21 (m, 4H), 3.18 (t, J=7.1 Hz, 2H), 3.10 (s, 4H), 2.85 (ddd, J=17.6, 14.0, 5.3 Hz, 1H), 2.79-2.64 (m, 2H), 2.50 (s, 3H), 2.46 (s, 3H), 2.14-2.05 (m, 3H), 1.64 (p, J=7.1 Hz, 2H), 1.54 (p, J=6.9 Hz, 2H), 1.40 (d, J=39.7 Hz, 8H). HRMS calcd for $C_{46}H_{57}FN_9O_7[M+H^+]$ 866.4365, found 866.4379.

Example 109

Synthesis of HC65-37

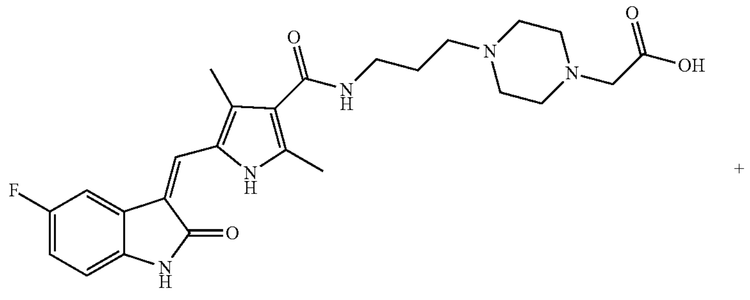

Intermediate 3

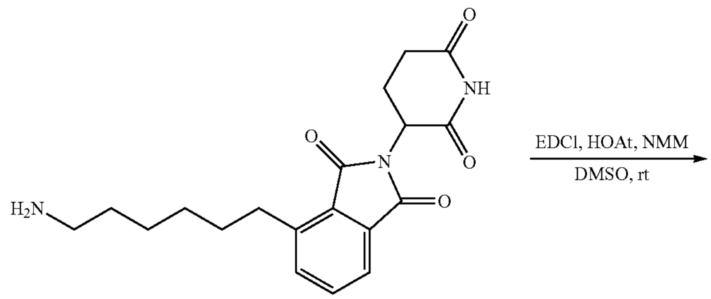

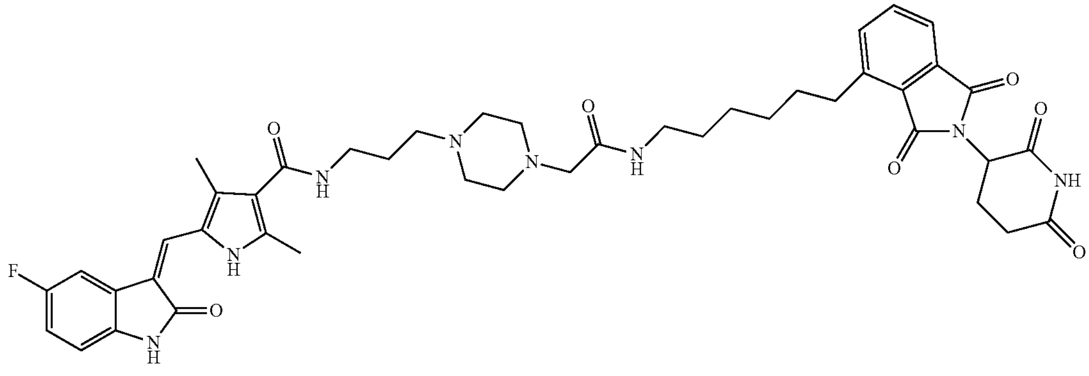

HC65-37

HC65-37 was synthesized following the standard procedure for preparing HC58-53 from Intermediate 3 (12.0 mg, 0.0169 mmol, 1.0 equiv), 4-(6-aminohexyl)-2-(2,6-dioxopiperidin-3-yl)isoindoline-1,3-dione (8.9 mg, 0.0185 mmol, 1.1 equiv), EDCI (4.9 mg, 0.0255 mmol, 1.5 equiv), HOAt (3.5 mg, 0.0255 mmol, 1.5 equiv), and NMM (8.6 mg, 0.085 mmol, 5.0 equiv) in DMSO (1 mL). HC65-37 was obtained as yellow solid in TFA salt form (9.3 mg, 52%). $^{1}$H NMR (600 MHz, Methanol-$d_4$) δ 13.64 (s, 1H), 7.70 (d, J=4.4 Hz, 2H), 7.61 (t, J=4.4 Hz, 1H), 7.52 (d, J=3.2 Hz, 1H), 7.38 (dd, J=8.9, 2.3 Hz, 1H), 6.91-6.81 (m, 2H), 5.13 (dd, J=12.8, 5.5 Hz, 1H), 3.55-3.37 (m, 6H), 3.24 (t, J=7.2 Hz, 4H), 3.13-2.97 (m, 6H), 2.88 (ddd, J=18.7, 13.9, 5.3 Hz, 1H), 2.81-2.67 (m, 2H), 2.48 (s, 3H), 2.44 (s, 3H), 2.19-2.00 (m, 3H), 1.67 (p, J=7.3 Hz, 2H), 1.54 (p, J=7.1 Hz, 2H), 1.40 (dt, J=9.8, 5.7 Hz, 6H). HRMS calcd for $C_{44}H_{52}FN_8O_7$ [M+H$^+$] 823.3943, found 823.3954.

Example 110

Synthesis of HC65-74

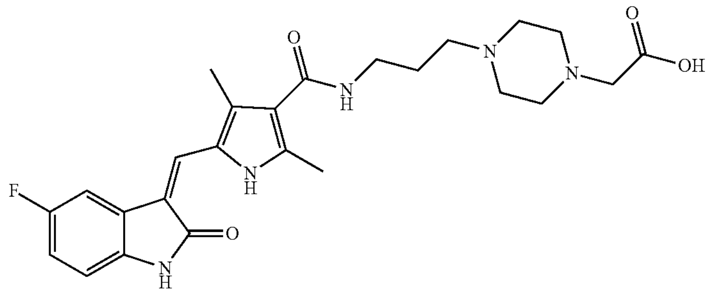

Intermediate 3

+

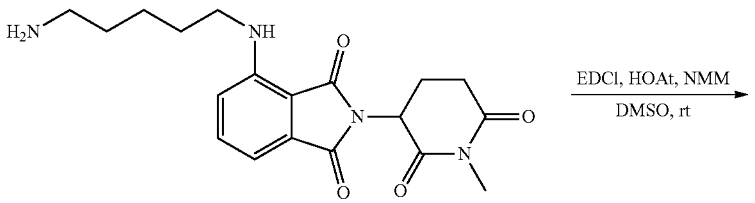

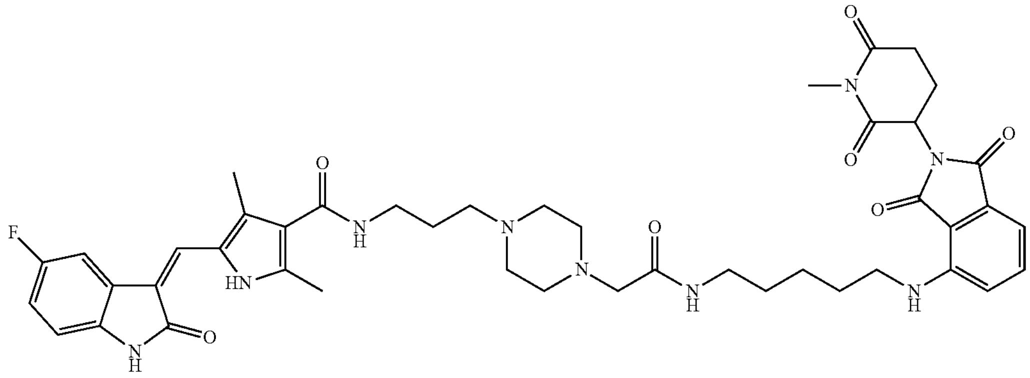

HC65-74

HC65-74 was synthesized following the standard procedure for preparing HC58-53 from Intermediate 3 (12.0 mg, 0.0169 mmol, 1.0 equiv), 4-((5-aminopentyl)amino)-2-(1-methyl-2,6-dioxopiperidin-3-yl)isoindoline-1,3-dione (9.0 mg, 0.0185 mmol, 1.1 equiv), EDCI (4.9 mg, 0.0255 mmol, 1.5 equiv), HOAt (3.5 mg, 0.0255 mmol, 1.5 equiv), and NMM (8.5 mg, 0.085 mmol, 5.0 equiv) in DMSO (1 mL). HC65-74 was obtained as yellow solid in TFA salt form (14.8 mg, 82%). $^1$H NMR (600 MHz, Acetone-$d_6$) δ 13.57 (s, 1H), 9.68 (s, 1H), 7.50-7.40 (m, 2H), 7.29 (dd, J=8.5, 7.0 Hz, 1H), 7.25 (dd, J=9.2, 2.2 Hz, 1H), 7.20 (t, J=6.0 Hz, 1H), 6.79 (d, J=8.5 Hz, 1H), 6.73 (d, J=7.0 Hz, 1H), 6.67-6.59 (m, 2H), 4.79 (dd, J=13.0, 5.4 Hz, 1H), 3.45-3.23 (m, 8H), 3.16-3.04 (m, 8H), 2.98 (q, J=6.6 Hz, 2H), 2.79 (s, 3H), 2.69 (ddd, J=18.6, 13.8, 5.3 Hz, 1H), 2.58 (dt, J=17.3, 3.6 Hz, 1H), 2.43 (qd, J=13.1, 4.5 Hz, 1H), 2.26 (s, 3H), 2.22 (s, 3H), 1.95-1.85 (m, 3H), 1.42 (p, J=7.3 Hz, 2H), 1.29 (p, J=7.2 Hz, 2H), 1.17 (p, J=7.7 Hz, 2H). HRMS calcd for $C_{44}H_{53}FN_9O_7[M+H^+]$ 838.4052, found 838.4059.

Example 111

Synthesis of HC65-75

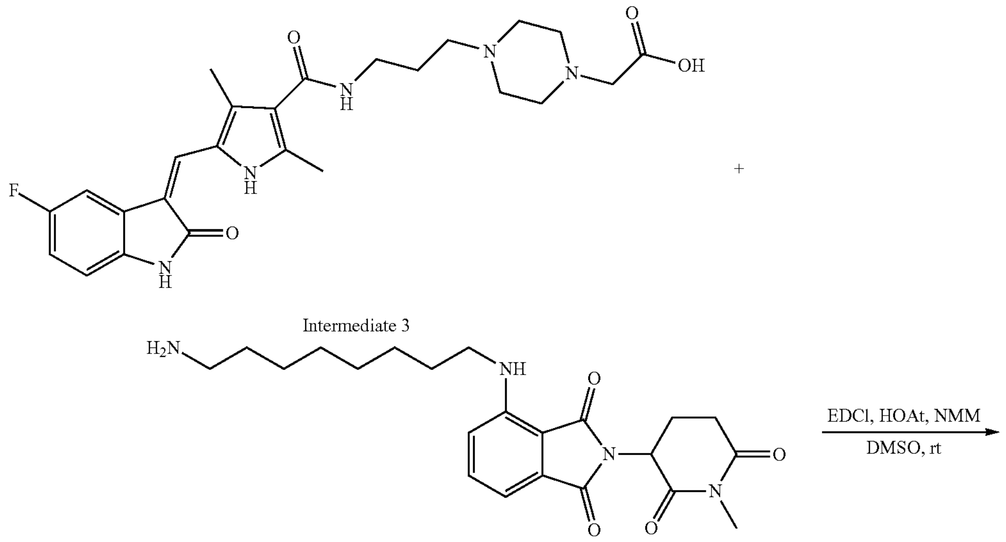

Intermediate 3

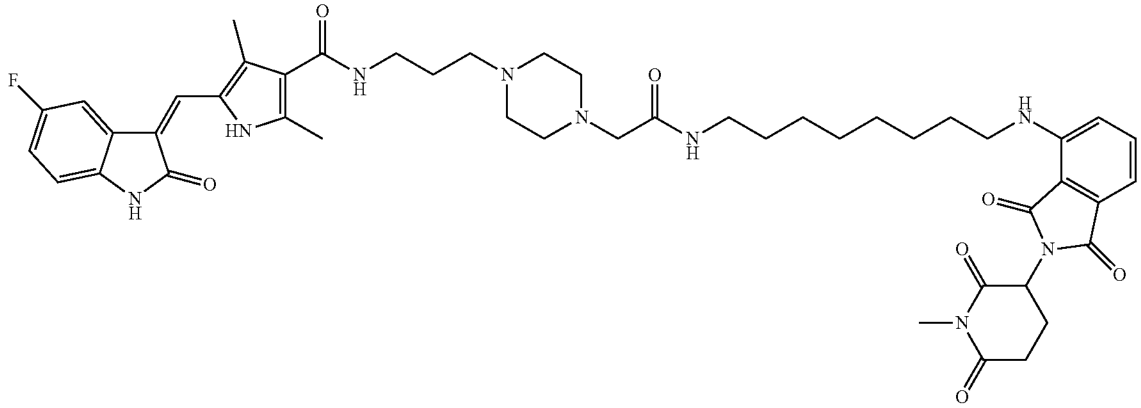

HC65-75

HC65-75 was synthesized following the standard procedure for preparing HC58-53 from Intermediate 3 (12.0 mg, 0.0169 mmol, 1.0 equiv), 4-((8-aminooctyl)amino)-2-(1-methyl-2,6-dioxopiperidin-3-yl)isoindoline-1,3-dione (9.9 mg, 0.0185 mmol, 1.1 equiv), EDCI (4.9 mg, 0.0255 mmol, 1.5 equiv), HOAt (3.5 mg, 0.0255 mmol, 1.5 equiv), and NMM (8.6 mg, 0.085 mmol, 5.0 equiv) in DMSO (1 mL). HC65-75 was obtained as yellow solid in TFA salt form (13.0 mg, 69%). $^1$H NMR (600 MHz, Acetone-$d_6$) δ 13.86 (s, 1H), 9.98 (s, 1H), 7.78-7.66 (m, 2H), 7.64-7.53 (m, 2H), 7.51-7.45 (m, 1H), 7.12-7.06 (m, 1H), 7.05-6.99 (m, 1H), 6.97-6.88 (m, 2H), 5.15-5.05 (m, 1H), 3.81-3.49 (m, 8H), 3.47-3.30 (m, 8H), 3.27-3.19 (m, 2H), 3.09 (s, 3H), 3.03-2.94 (m, 1H), 2.92-2.84 (m, 1H), 2.80-2.69 (m, 1H), 2.56 (s, 3H), 2.52 (s, 3H), 2.28-2.14 (m, 3H), 1.74-1.65 (m, 2H), 1.55-1.26 (m, 10H). HRMS calcd for $C_{47}H_{59}FN_9O_7$ [M+H$^+$] 880.4521, found 880.4533.

Example 112

Synthesis of tert-butyl N-tert-butoxycarbonyl-N-[4-methyl-5-(4,4,5,5-tetramethyl-1,3,2-dioxaborolan-2-yl)-3-pyridyl]carbamate

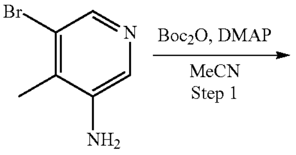

-continued

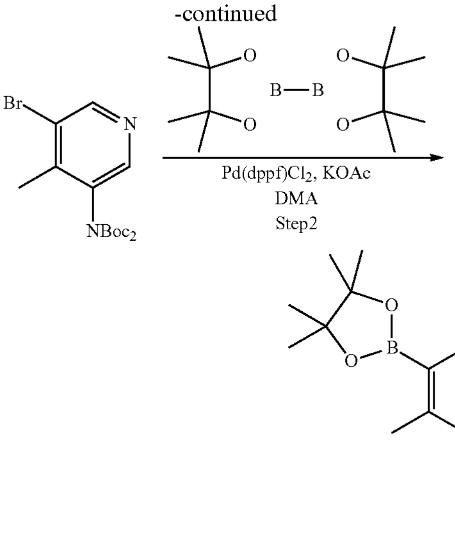

Step 1: N-tert-butoxycarbonyl-N-(4-methyl-5-bromo-3-pyridyl)carbamate

To a solution of 5-bromo-4-methylpyridin-3-amine (1.88 g, 10 mmol, 1.0 equiv) in MeCN (20 mL) were added DMAP (122 mg, 1.0 mmol, 0.1 equiv), di-tert-butyl dicarbonate (6.55 g, 30 mmol, 3.0 equiv). The mixture was heated to 60° C. and stirred overnight. The reaction was quenched with water (20 mL) and extracted with ethyl acetate (3×20 mL), dried over $Na_2SO_4$, filtered and evaporated. The resulting residue was purified by silica gel column (hexane/ethyl acetate=4:1) to afford N-tert-butoxycarbonyl-N-(4-methyl-5-bromo-3-pyridyl)carbamate (2.383 g, 62%). ESI m/z=387.2 [M+H$^+$].

Step 2: tert-butyl N-tert-butoxycarbonyl-N-[4-methyl-5-(4,4,5,5-tetramethyl-1,3,2-dioxaborolan-2-yl)-3-pyridyl]carbamate Dissolved the obtained N-tert-butoxycarbonyl-N-(4-methyl-5-bromo-3-pyridyl)carbamate (2.383 g, 6.16 mmol, 1 equiv) in dimethyl acetamide (24 mL). To the solution were added Bis(pinacolato)diboron (7.823 g, 30.8 mmol, 5 equiv), KOAc (1.813 g, 18.5 mmol, 3 equiv) and Pd(dppf) $Cl_2$ (454 mg, 0.62 mmol, 0.1 equiv) under $N_2$. The mixture was heated to 90° C. and stirred for 2 h. Cooled to room temperature, quenched with water (20 mL) and extracted with ethyl acetate (3×20 mL). Combined the organic layers, dried over $Na_2SO_4$, filtered and evaporated. The resulting residue was purified by silica gel column (hexane/ethyl acetate=1:2) to afford tert-butyl N-tert-butoxycarbonyl-N-[4-methyl-5-(4,4,5,5-tetramethyl-1,3,2-dioxaborolan-2-yl)-3-pyridyl]carbamate (2.077 g, 78%). ESI m/z=353.2 [M(Corresponding boric acid)+H$^+$].

Example 113

Synthesis of Intermediate 11

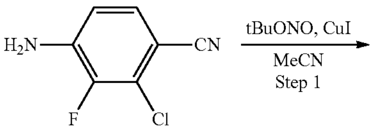

-continued

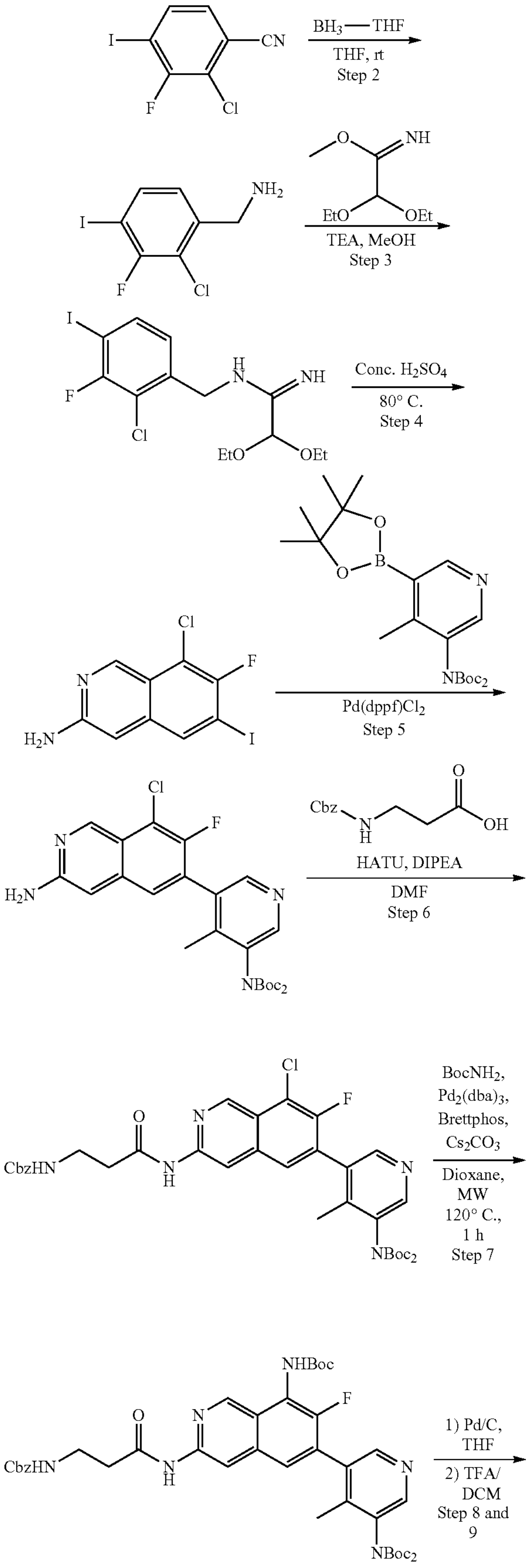

-continued

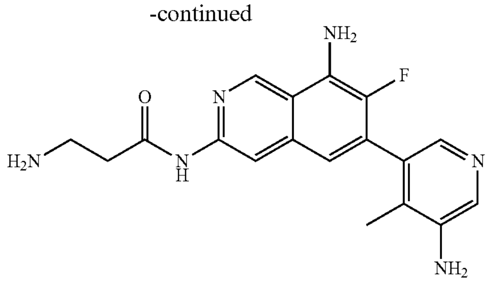

Intermediate 11

Step 1: 2-chloro-3-fluoro-4-iodobenzonitrile

To a suspension of CuI (9.24 g, 49 mmol) in acetonitrile (200 mL) was dropwise added 90% tert-butyl nitrite (6.95 mg, 60 mmol) at 65° C. The mixture was stirred at 65° C. for 10 minutes. Then 4-amino-2-chloro-3-fluorobenzonitrile (6.9 g, 40.4 mmol) was added to the reaction mixture for 1 h. The mixture was stirred at 65° C. for 2 h. The mixture was quenched with saturated aqueous $Na_2S_2O_4$ and extracted with ethyl acetate (3×300 mL). The combined organic layers was washed with brine, dried over $Na_2SO_4$ and filtered. The filtrate was concentrated to give crude product, which was purified by silica gel column (hexane/ethyl acetate=9:1) to give 2-chloro-3-fluoro-4-iodo-benzonitrile (6.66 g, 59%) as a yellow solid. $^1$H NMR (500 MHz, Chloroform-d) δ 7.82 (dd, J=8.3, 5.5 Hz, 1H), 7.24 (dd, J=8.3, 1.4 Hz, 1H).

Step 2: (2-chloro-3-fluoro-4-iodophenyl)methanamine

2-Chloro-3-fluoro-4-iodobenzonitrile (2 g, 7 mmol) was added to a solution of borane-THF (35 mL, 1 M in THF, 35 mmol) in THF (20 mL) at 0° C. The mixture was then warmed to room temperature and stirred overnight. The reaction solution was quenched by the dropwise addition of a solution of HCl (3 M, 8 mL). The mixture was neutralized with an aqueous solution of $NaHCO_3$ to pH=8 and extracted with dichloromethane (2×200 mL). The combined organic layer was washed with water and brine, dried over $Na_2SO_4$, filtered and concentrated to give (2-chloro-3-fluoro-4-iodo-phenyl)methanamine (1.287 g, crude yield 65%), which was used directly in the next step without further purification. ESI m/z=285.9 [M+H$^+$].

Step 3: N-(2-chloro-3-fluoro-4-iodobenzyl)-2,2-diethoxyacetimidamide

To a solution of methyl 2,2-diethoxyacetimidate (1 g, 6.4 mmol) in methanol (15 mL) was added (2-chloro-3-fluoro-4-iodophenyl)methanamine (1.287 mg, 4.5 mmol). The reaction mixture was stirred at room temperature for 1 hours, and then concentrated to dryness. The residue was diluted with DCM (50 mL), washed with water (50 mL) and brine (50 mL), dried over $Na_2SO_4$, filtered and concentrated to give N-(2-chloro-3-fluoro-4-iodobenzyl)-2,2-diethoxy-acetimidamide as a yellow solid. It was directly used to the next step without purification. ESI m/z=415.0 [M+H$^+$].

Step 4: 8-chloro-7-fluoro-6-iodoisoquinolin-3-amine

A solution of N-(2-chloro-3-fluoro-4-iodobenzyl)-2,2-diethoxyacetimidamide (from Step 3) and conc. $H2SO_4$ (8 mL) was stirred at 60° C. for overnight. The mixture was cooled to 0° C. and NaOH was added to adjust to pH=9. The residue was extracted with dichloromethane (4×80 mL). The combined organic layers were washed with brine, dried over $Na_2SO_4$, filtered and concentrated to give 8-chloro-7-fluoro-6-iodoisoquinolin-3-amine (1.01 g, 70% for two steps) as a yellow solid, which was directly used to the next step. ESI m/z=322.9 [M+H$^+$].

Step 5: tert-butyl N-[5-(3-amino-8-chloro-7-fluoro-6-isoquinolyl)-4-methyl-3-pyridyl]-N-tert-butoxy-carbony1-carbamate A mixture of 8-chloro-7-fluoro-6-iodo-isoquinolin-3-amine (636 mg, 2 mmol, 1.0 equiv), tert-butyl N-tert-butoxycarbonyl-N-[4-methyl-5-(4,4,5,5-tetramethyl-1,3,2-dioxaborolan-2-yl)-3-pyridyl]carbamate (1.04 g, 2.4 mmol, 1.2 equiv), Pd(dppf)$Cl_2$ (0.29 g, 0.4 mmol, 0.2 equiv), potassium carbonate (830 mg, 6 mmol, 3 equiv) in 1,4-dioxane (10 mL) and water (5 mL) was stirred at 80° C. (Microwave) for 30 min. The reaction was filtered. The product was extracted with ethyl acetate. The combined organic extracts were combined and concentrated under vacuum. The residue was purified by silica gel column (hexane/ethyl acetate=1:4) to give the tert-butyl N-[5-(3-amino-8-chloro-7-fluoro-6-isoquinolyl)-4-methyl-3-pyridyl]-N-tert-butoxycarbony1-carbamate as a yellow solid (690 mg, 62%). ESI m/z=503.2 [M+H$^+$].

Step 6: tert-butyl (5-(3-(3-(((benzyloxy)carbonyl) amino)propanamido)-8-chloro-7-fluoroisoquinolin-6-yl)-4-methylpyridin-3-yl)(tert-butoxycarbonyl) carbamate A mixture of tert-butyl N-[5-(3-amino-8-chloro-7-fluoro-6-isoquinolyl)-4-methyl-3-pyridyl]-N-tert-butoxycarbonyl-carbamate (300 mg, 0.6 mmol, 1.0 equiv), 3-(((benzyloxy) carbonyl)amino)propanoic acid (201 mg, 0.9 mmol, 1.5 equiv), HATU (342 mg, 0.9 mmol, 1.5 equiv) and DIPEA (232.2 mg, 1.8 mmol, 3 equiv) in DMF (6 mL) was stirred at 50° C. overnight. Cooled down and the mixture was purified preparative HPLC (10%-100% methanol/0.1% TFA in $H_2O$) to afford tert-butyl (5-(3-(3-(((benzyloxy)carbonyl) amino)propanamido)-8-chloro-7-fluoroisoquinolin-6-yl)-4-methylpyridin-3-yl)(tert-butoxycarbonyl)carbamate as yellow solid in TFA salt form (346 mg, 62%). ESI m/z=708.3 [M+H$^+$].

Step 7: tert-butyl (5-(3-(3-(((benzyloxy)carbonyl) amino)propanamido)-8-((tert-butoxycarbonyl) amino)-7-fluoroisoquinolin-6-yl)-4-methylpyridin-3-yl)(tert-butoxycarbonyl)carbamate A mixture of tert-butyl (5-(3-(3-(((benzyloxy)carbonyl) amino)propanamido)-8-chloro-7-fluoroisoquinolin-6-yl)-4-methylpyridin-3-yl)(tert-butoxycarbonyl)carbamate (276 mg, 0.3 mmol, 1.0 equiv), tert-butyl carbamate (518 mg, 4.4 mmol, 15 equiv), $Pd_2(dba)_2$ (61 mg, 0.06 mmol, 0.2 equiv), Brettphos (64 mg, 0.12 mmol, 0.4 equiv), cesium carbonate (482 mg, 1.5 mmol, 5 equiv) in 1,4-dioxane (10 mL) was stirred at 120° C. (Microwave) for 1 h. Cooled to room temperature and water was added. The product was extracted with ethyl acetate. The combined organic extracts were combined and concentrated under vacuum. The residue was purified by silica gel column (hexane/ethyl acetate=1:4) to give the tert-butyl (5-(3-(3-(((benzyloxy)carbonyl)amino) propanamido)-8-((tert-butoxycarbonyl)amino)-7-fluoroisoquinolin-6-yl)-4-methylpyridin-3-yl)(tert-butoxycarbonyl) carbamate as a yellow solid (114 mg, 48%). ESI m/z=789.4 [M+H$^+$].

Step 8 and 9: Intermediate 11

A mixture of tert-butyl (5-(3-(3-(((benzyloxy)carbonyl) amino)propanamido)-8-((tert-butoxycarbonyl)amino)-7-fluoroisoquinolin-6-yl)-4-methylpyridin-3-yl)(tert-butoxycarbonyl)carbamate (553 mg, 0.7 mmol, 1 equiv) and Pd/C (55 mg, 0.1 equiv) in THE (10 mL) under $H_2$ was stirred at room temperature overnight. Filtered and concentrated under vacuum to give a yellow solid. ESI m/z=655.3 [M+H$^+$]. Dissolved the obtained solid in DCM (4 mL). To the solution was added TFA (2 mL). Stirred at room temperature for 1 h and concentrated under vacuum. The residue was purified preparative HPLC (10%-100% methanol/0.1% TFA in $H_2O$) to afford intermediate 11 as a yellow solid (395 mg, 81% for two steps) in TFA salt form. $^1$H NMR (600 MHz, Methanol-d$_4$) δ 9.41 (s, 1H), 8.38 (s, 1H), 8.12 (s, 1H), 8.02 (s, 1H), 7.10 (d, J=5.9 Hz, 1H), 3.37-3.34 (m, 2H), 2.97 (t, J=6.4 Hz, 2H), 2.26 (s, 3H). ESI m/z=355.2 [M+H$^+$].

Example 114

Synthesis of Intermediate 12

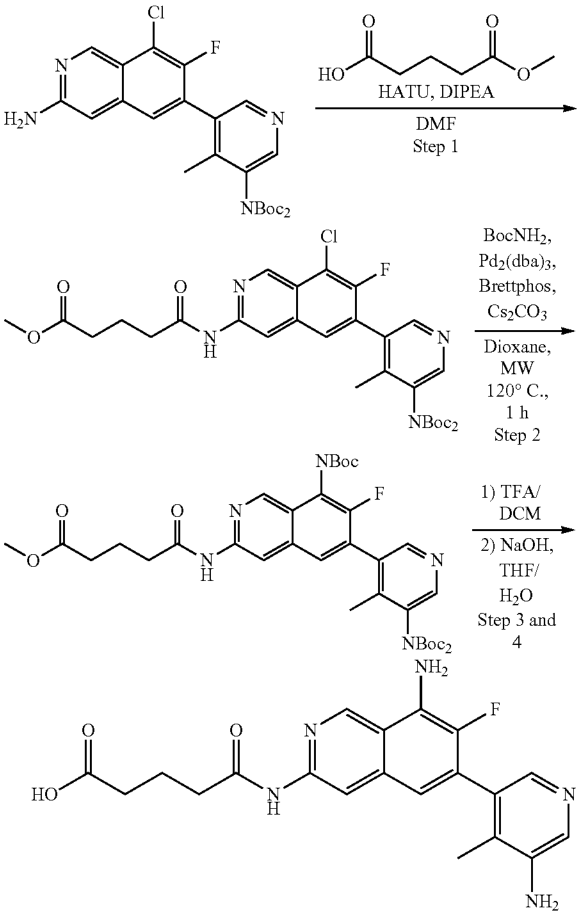

Intermediate 12

Step 1: methyl 5-((6-(5-(bis(tert-butoxycarbonyl) amino)-4-methylpyridin-3-yl)-8-chloro-7-fluoroisoquinolin-3-yl)amino)-5-oxopentanoate A mixture of tert-butyl N-[5-(3-amino-8-chloro-7-fluoro-6-isoquinolyl)-4-methyl-3-pyridyl]-N-tert-butoxycarbonyl-carbamate (800 mg, 1.6 mmol, 1.0 equiv), 5-methoxy-5-oxopentanoic acid (701 mg, 4.8 mmol, 3 equiv), HATU (1.82 g, 4.8 mmol, 3 equiv) and DIPEA (1.03 g, 8.0 mmol, 5 equiv) in DMF (8 mL) was stirred at room temperature overnight. Cooled down and the mixture was purified preparative HPLC (10%-100% methanol/0.1% TFA in $H_2O$) to afford methyl 5-((6-(5-(bis(tert-butoxycarbonyl)amino)-4-methylpyridin-3-yl)-8-chloro-7-fluoroisoquinolin-3-yl) amino)-5-oxopentanoate as yellow solid in TFA salt form (864 mg, 63%). ESI m/z=631.2 [M+H$^+$].

Step 2: methyl 5-((6-(5-(bis(tert-butoxycarbonyl) amino)-4-methylpyridin-3-yl)-8-((tert-butoxycarbonyl)amino)-7-fluoroisoquinolin-3-yl)amino)-5-oxopentanoate A mixture of methyl 5-((6-(5-(bis(tert-butoxycarbonyl) amino)-4-methylpyridin-3-yl)-8-chloro-7-fluoroisoquinolin-3-yl)amino)-5-oxopentanoate (864 mg, 1 mmol, 1.0 equiv), tert-butyl carbamate (1.76 mg, 15 mmol, 15 equiv), $Pd_2(dba)_2$·chloroform (207 mg, 0.2 mmol, 0.2 equiv), Brettphos (215 mg, 0.4 mmol, 0.4 equiv), cesium carbonate (1.63 mg, 5 mmol, 5 equiv) in 1,4-dioxane (15 mL) was stirred at 120° C. (Microwave) for 1 h. Cooled to room temperature and water was added. The product was extracted with ethyl acetate. The combined organic extracts were combined and concentrated under vacuum. The residue was purified by silica gel column (hexane/ethyl acetate=1:3) to give the methyl 5-((6-(5-(bis(tert-butoxycarbonyl)amino)-4-methylpyridin-3-yl)-8-((tert-butoxycarbonyl)amino)-7-fluoroisoquinolin-3-yl)amino)-5-oxopentanoate as a yellow solid (442 mg, 62%). ESI m/z=712.3 [M+H$^+$].

Step 3 and 4: Synthesis of Intermediate 12

To a solution of methyl 5-((6-(5-(bis(tert-butoxycarbonyl) amino)-4-methylpyridin-3-yl)-8-((tert-butoxycarbonyl) amino)-7-fluoroisoquinolin-3-yl)amino)-5-oxopentanoate (442 mg, 0.62 mmol, 1 equiv) in THE (10 mL) was added TFA (5 mL) and stirred at room temperature for 1 h. Concentrated under vacuum to remove all of the solvents and afforded yellow oil. ESI m/z=412.2 [M+H$^+$]. Dissolved the obtained solid in THF/$H_2O$ (4:2 mL). To the solution was added NaOH (124 mg, 3.1 mmol, 5 equiv). Stirred at room temperature for 2 h and concentrated under vacuum. The residue was purified preparative HPLC (10%-100% MeCN/ 0.1% TFA in $H_2O$) to afford intermediate 12 as a yellow solid (302 mg, 78% for two steps) in TFA salt form. $^1$H NMR (600 MHz, Methanol-d$_4$) δ 9.39 (s, 1H), 8.28 (s, 1H), 8.11 (s, 1H), 8.03 (s, 1H), 7.11 (d, J=5.9 Hz, 1H), 2.60 (t, J=7.5 Hz, 2H), 2.46 (t, J=7.4 Hz, 2H), 2.26 (s, 3H), 2.04 (p, J=7.4 Hz, 2H). ESI m/z=398.2 [M+H$^+$].

Example 115

Synthesis of HC65-175

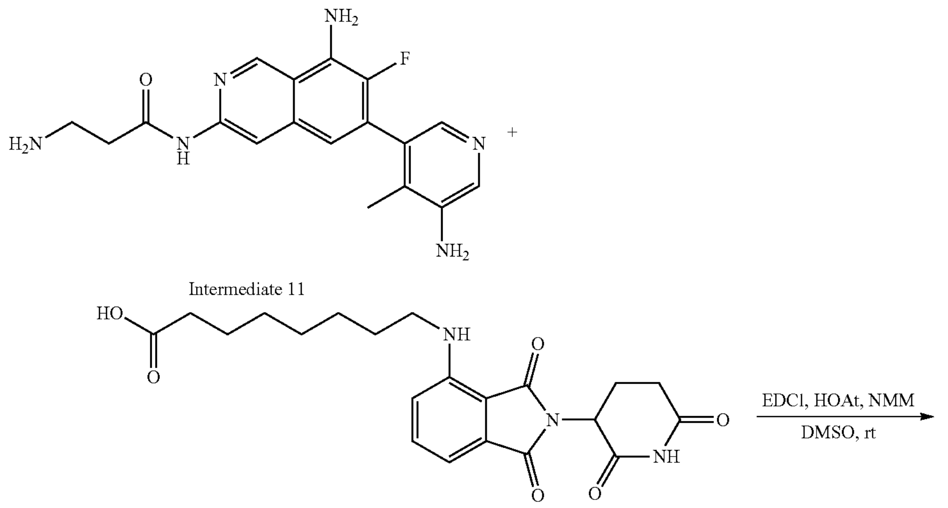

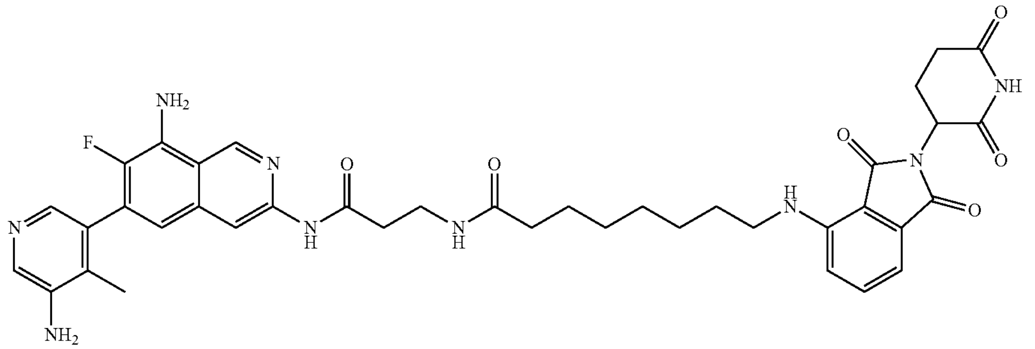

HC65-175

To a solution of Intermediate 11 (11 mg, 0.0158 mmol, 1.0 equiv) in DMSO (1 mL) were added 8-((2-(2,6-dioxopiperidin-3-yl)-1,3-dioxoisoindolin-4-yl)amino)octanoic acid (6.5 mg, 0.0158 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.2 mg, 0.024 mmol, 1.5 equiv), and NMM (N-Methylmorpholine) (8.0 mg, 0.079 mmol, 5.0 equiv). After being stirred overnight at room temperature, the resulting mixture was purified by preparative HPLC (10%-100% MeOH/0.1% TFA in $H_2O$) to afford HC65-175 as yellow solid in TFA salt form (7.6 mg, 49%). $^1H$ NMR (600 MHz, Methanol-$d_4$) δ 9.35 (s, 1H), 8.34 (s, 1H), 8.06 (s, 1H), 7.98 (s, 1H), 7.50 (t, J=7.8 Hz, 1H), 7.05 (d, J=5.8 Hz, 1H), 6.98 (d, J=7.1 Hz, 1H), 6.91 (d, J=8.6 Hz, 1H), 5.06 (dd, J=12.7, 5.5 Hz, 1H), 3.63-3.54 (m, 2H), 3.14 (t, J=7.1 Hz, 2H), 2.91-2.82 (m, 1H), 2.81-2.64 (m, 4H), 2.20 (s, 5H), 2.15-2.07 (m, 1H), 1.61 (t, J=7.0 Hz, 2H), 1.53 (t, J=6.9 Hz, 2H), 1.34-1.27 (m, 6H). HRMS calcd for $C_{39}H_{43}FN_9O_6[M+H^+]$ 752.3320, found 752.3328.

Example 116

Synthesis of HC65-183

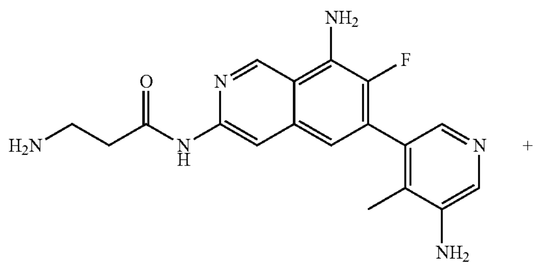

Intermediate 11

-continued

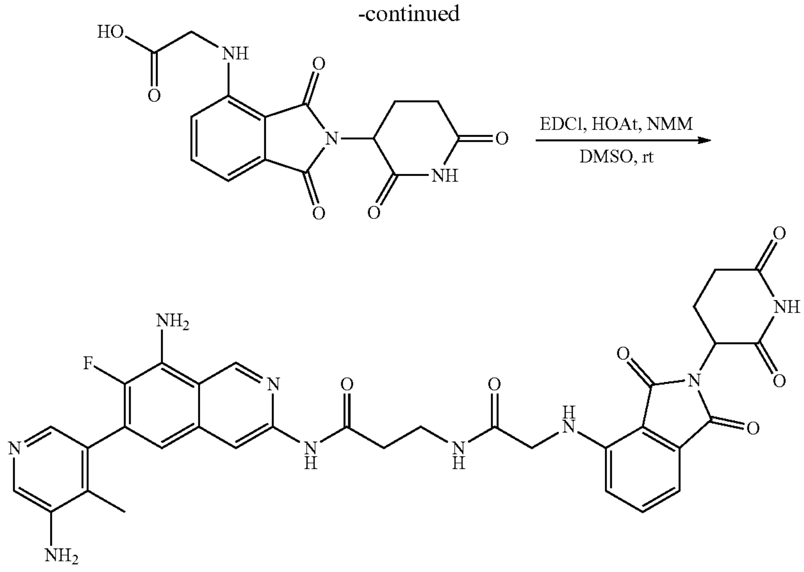

HC65-183

HC65-183 was synthesized following the standard procedure for preparing HC65-175 from Intermediate 11 (9.1 mg, 0.013 mmol, 1.0 equiv), (2-(2,6-dioxopiperidin-3-yl)-1,3-dioxoisoindolin-4-yl)glycine (4.3 mg, 0.013 mmol, 1.0 equiv), EDCI (3.8 mg, 0.02 mmol, 1.5 equiv), HOAt (2.7 mg, 0.02 mmol, 1.5 equiv), and NMM (6.6 mg, 0.065 mmol, 5.0 equiv) in DMSO (1 mL). HC65-183 was obtained as yellow solid in TFA salt form (5.8 mg, 50%). $^{1}$H NMR (600 MHz, Methanol-$d_4$) δ 9.34 (s, 1H), 8.09 (s, 1H), 8.06 (s, 1H), 8.03 (s, 1H), 7.36-7.24 (m, 1H), 6.99 (d, J=5.7 Hz, 1H), 6.80 (d, J=8.5 Hz, 1H), 6.69 (d, J=19.9 Hz, 1H), 5.02 (dd, J=12.9, 5.4 Hz, 1H), 4.00 (s, 2H), 3.71-3.56 (m, 2H), 2.85 (ddd, J=18.4, 13.9, 5.3 Hz, 1H), 2.79-2.63 (m, 4H), 2.27 (s, 3H), 2.12-2.04 (m, 1H). HRMS calcd for $C_{33}H_{31}FN_9O_6$[M+H$^+$] 668.2381, found 668.2388.

Example 117

Synthesis of HC65-184

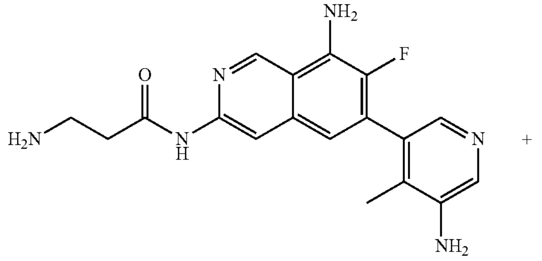

Intermediate 3

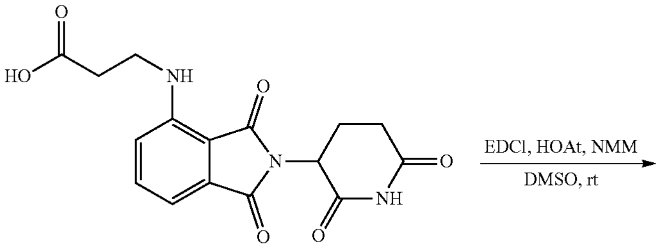

-continued

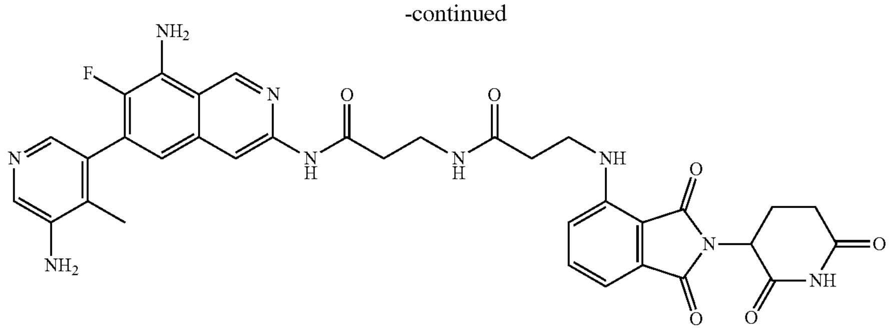

HC65-184

HC65-184 was synthesized following the standard procedure for preparing HC65-175 from Intermediate 11 (9.1 mg, 0.013 mmol, 1.0 equiv), 3-((2-(2,6-dioxopiperidin-3-yl)-1,3-dioxoisoindolin-4-yl)amino)propanoic acid (4.5 mg, 0.013 mmol, 1.0 equiv), EDCI (3.8 mg, 0.02 mmol, 1.5 equiv), HOAt (2.7 mg, 0.02 mmol, 1.5 equiv), and NMM (6.6 mg, 0.065 mmol, 5.0 equiv) in DMSO (1 mL). HC65-184 was obtained as yellow solid in TFA salt form (2.2 mg, 19%). $^1$H NMR (600 MHz, Methanol-$d_4$) δ 9.30 (s, 1H), 8.31 (s, 1H), 8.09 (s, OH), 8.04 (s, 1H), 7.52 (t, J=7.8 Hz, 1H), 7.08 (d, J=8.6 Hz, 1H), 7.02 (d, J=5.9 Hz, 1H), 6.97 (d, J=7.1 Hz, 1H), 5.07 (dd, J=12.8, 5.4 Hz, 1H), 3.67-3.64 (m, 3H), 3.52-3.47 (m, 1H), 2.87 (ddd, J=18.4, 13.8, 5.3 Hz, 1H), 2.80-2.67 (m, 1H), 2.71-2.68 (m, 3H), 2.62-2.49 (m, 2H), 2.26 (s, 3H), 2.13-2.07 (m, 1H). HRMS calcd for $C_{34}H_{33}FN_9O_6$[M+H$^+$] 682.2538, found 682.2551.

Example 118

Synthesis of HC65-185

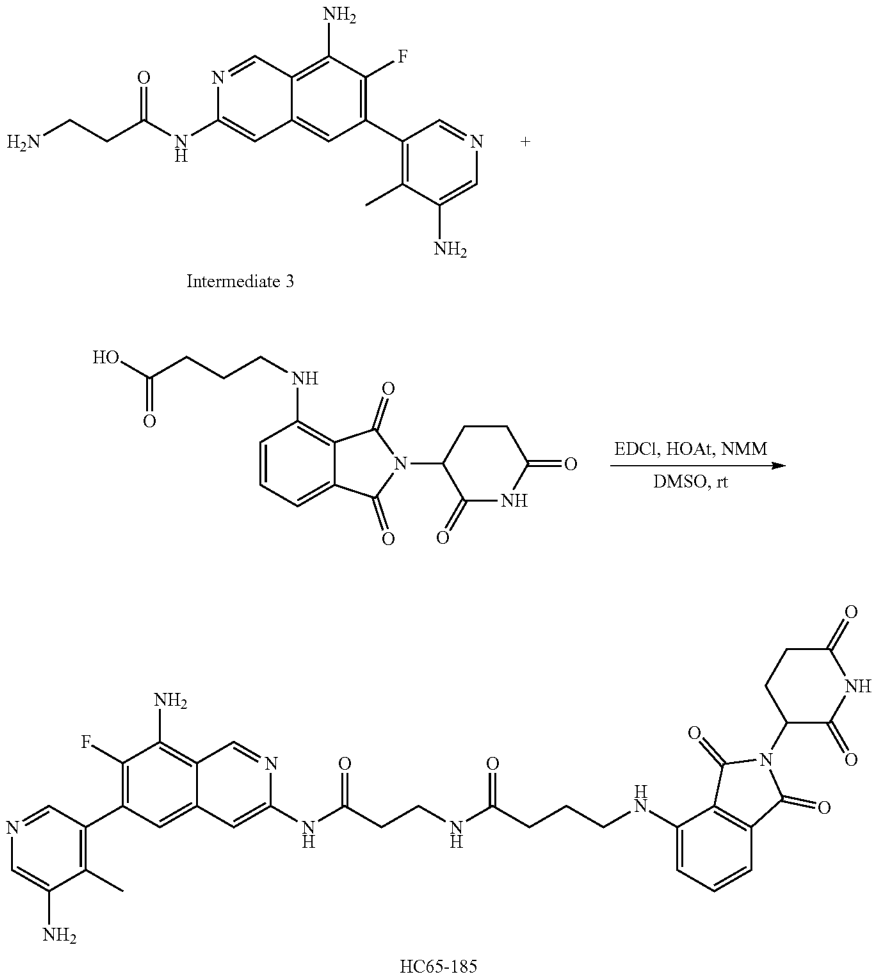 [SMILES: Cc1c(N)cncc1-c1cc2cc(NC(=O)CCN)ncc2c(N)c1F ; O=C(O)CCCNc1cccc2c1C(=O)N(C1CCC(=O)NC1=O)C2=O ; Cc1c(N)cncc1-c1cc2cc(NC(=O)CCNC(=O)CCCNc3cccc4c3C(=O)N(C3CCC(=O)NC3=O)C4=O)ncc2c(N)c1F]

Intermediate 3

HC65-185

HC65-185 was synthesized following the standard procedure for preparing HC65-175 from Intermediate 11 (9.1 mg, 0.013 mmol, 1.0 equiv), 4-((2-(2,6-dioxopiperidin-3-yl)-1,3-dioxoisoindolin-4-yl)amino)butanoic acid (4.7 mg, 0.013 mmol, 1.0 equiv), EDCI (3.8 mg, 0.02 mmol, 1.5 equiv), HOAt (2.7 mg, 0.02 mmol, 1.5 equiv), and NMM (6.6 mg, 0.065 mmol, 5.0 equiv) in DMSO (1 mL). HC65-185 was obtained as yellow solid in TFA salt form (4.1 mg, 34%). $^1$H NMR (600 MHz, Methanol-$d_4$) δ 9.30 (s, 1H), 8.24 (s, 1H), 8.09 (s, 1H), 8.01 (s, 1H), 7.40 (dd, J=8.5, 7.1 Hz, 1H), 6.97 (d, J=6.1 Hz, 1H), 6.95 (d, J=8.6 Hz, 1H), 6.87 (d, J=7.0 Hz, 1H), 5.04 (dd, J=12.7, 5.4 Hz, 1H), 3.64-3.56 (m, 2H), 3.30 (t, J=7.1 Hz, 2H), 2.85 (ddd, J=17.2, 13.8, 5.2 Hz, 1H), 2.79-2.65 (m, 4H), 2.33 (t, J=6.9 Hz, 2H), 2.24 (s, 3H), 2.14-2.06 (m, 1H), 1.95 (p, J=7.0 Hz, 2H). HRMS calcd for $C_{35}H_{35}FN_9O_6$[M+H$^+$] 696.2694, found 696.2688.

Example 119

Synthesis of HC65-186

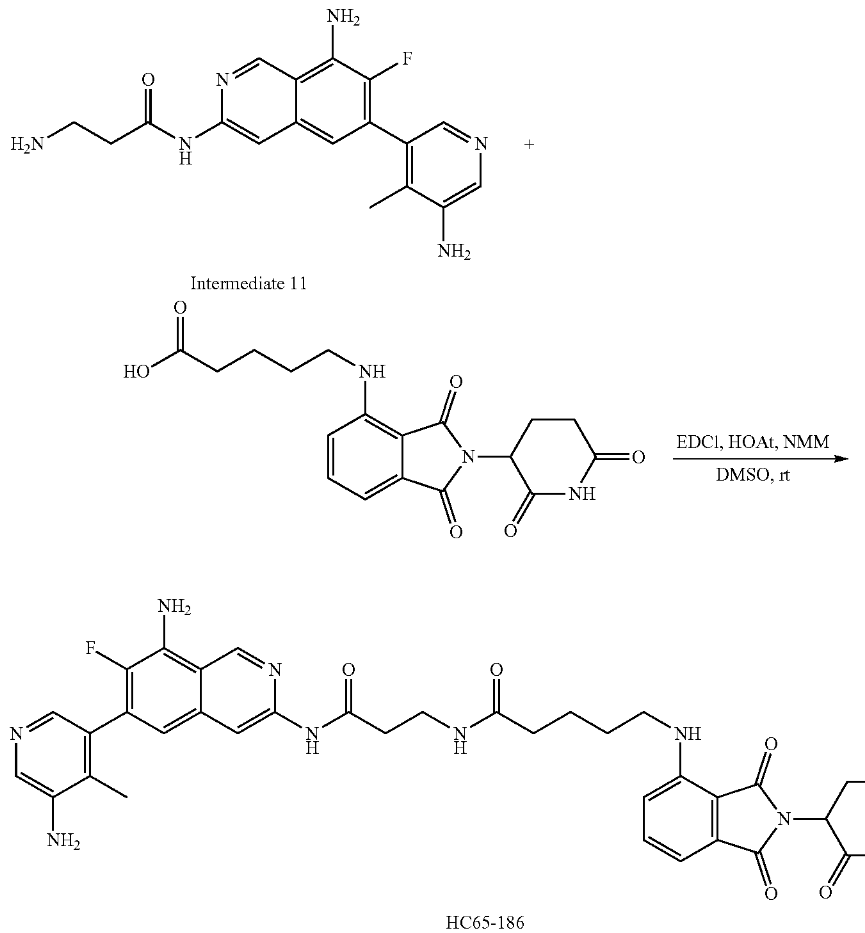

HC65-186

HC65-186 was synthesized following the standard procedure for preparing HC65-175 from Intermediate 11 (9.1 mg, 0.013 mmol, 1.0 equiv), 5-((2-(2,6-dioxopiperidin-3-yl)-1,3-dioxoisoindolin-4-yl)amino)pentanoic acid (4.9 mg, 0.013 mmol, 1.0 equiv), EDCI (3.8 mg, 0.02 mmol, 1.5 equiv), HOAt (2.7 mg, 0.02 mmol, 1.5 equiv), and NMM (6.6 mg, 0.065 mmol, 5.0 equiv) in DMSO (1 mL). HC65-186 was obtained as yellow solid in TFA salt form (5.5 mg, 45%). $^1$H NMR (600 MHz, Methanol-$d_4$) δ 9.31 (s, 1H), 8.27 (s, 1H), 8.09 (s, 1H), 8.00 (s, 1H), 7.45 (t, J=7.8 Hz, 1H), 7.00 (d, J=5.8 Hz, 1H), 6.91 (d, J=2.3 Hz, 1H), 6.90 (d, J=3.7 Hz, 1H), 5.05 (dd, J=12.7, 5.5 Hz, 1H), 3.61 (t, J=6.5 Hz, 2H), 3.22 (t, J=7.0 Hz, 2H), 2.86 (ddd, J=18.3, 13.7, 5.3 Hz, 1H), 2.80-2.63 (m, 4H), 2.28 (t, J=7.0 Hz, 2H), 2.22 (s, 3H), 2.17-2.04 (m, 1H), 1.74 (p, J=7.0 Hz, 2H), 1.66 (p, J=7.1 Hz, 2H). HRMS calcd for $C_{36}H_{37}FN_9O_6$[M+H$^+$] 710.2851, found 710.2867.

Example 120

Synthesis of HC75-1

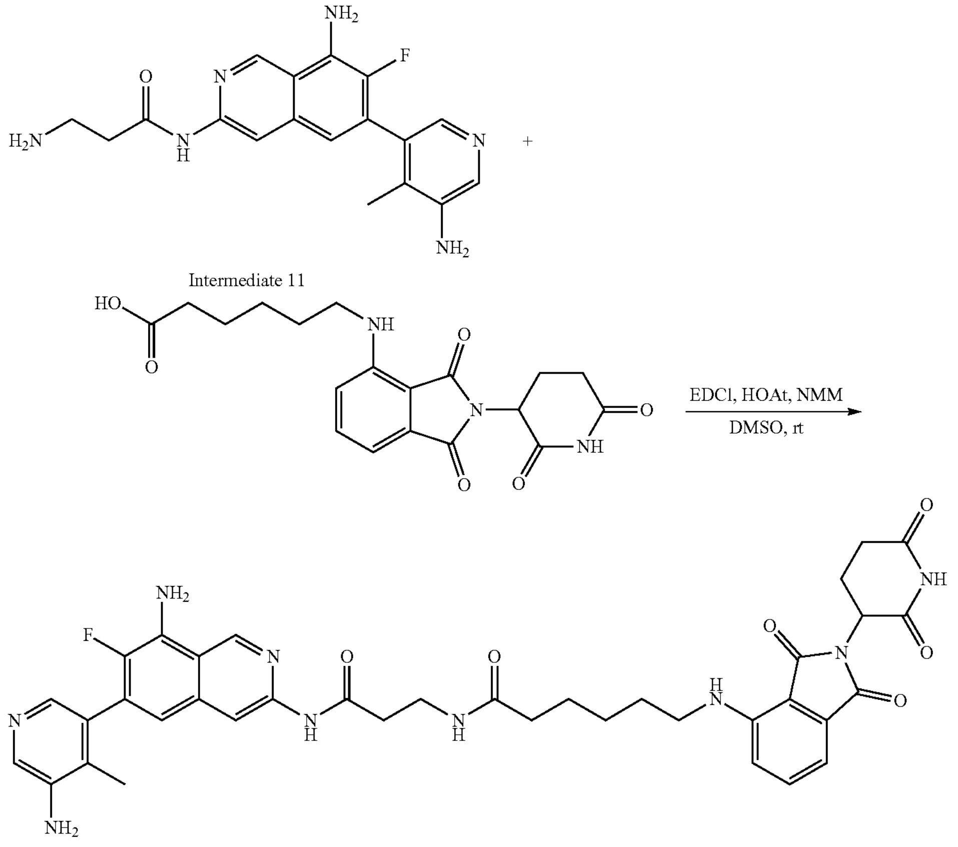

Intermediate 11

HC75-1

HC75-1 was synthesized following the standard procedure for preparing HC65-175 from Intermediate 11 (9.1 mg, 0.013 mmol, 1.0 equiv), 6-((2-(2,6-dioxopiperidin-3-yl)-1,3-dioxoisoindolin-4-yl)amino)hexanoic acid (5.1 mg, 0.013 mmol, 1.0 equiv), EDCI (3.8 mg, 0.02 mmol, 1.5 equiv), HOAt (2.7 mg, 0.02 mmol, 1.5 equiv), and NMM (6.6 mg, 0.065 mmol, 5.0 equiv) in DMSO (1 mL). HC75-1 was obtained as yellow solid in TFA salt form (7.1 mg, 51%). $^1$H NMR (600 MHz, Methanol-$d_4$) δ 9.33 (s, 1H), 8.27 (s, 1H), 8.08 (s, 1H), 8.00 (s, 1H), 7.45 (t, J=7.8 Hz, 1H), 7.03 (d, J=5.8 Hz, 1H), 6.93 (d, J=7.1 Hz, 1H), 6.87 (d, J=8.5 Hz, 1H), 5.05 (dd, J=12.8, 5.4 Hz, 1H), 3.60 (t, J=6.4 Hz, 2H), 3.17 (t, J=7.0 Hz, 2H), 2.85 (ddd, J=18.6, 14.0, 5.3 Hz, 1H), 2.72 (ddt, J=37.1, 13.5, 6.4 Hz, 4H), 2.24 (t, J=7.1 Hz, 2H), 2.21 (s, 3H), 2.15-2.06 (m, 1H), 1.68 (p, J=7.2 Hz, 2H), 1.61 (p, J=7.2 Hz, 2H), 1.45-1.37 (m, 2H). HRMS calcd for $C_{37}H_{39}FN_9O_6$[M+H$^+$] 724.3007, found 724.3016.

Example 121

Synthesis of HC75-2

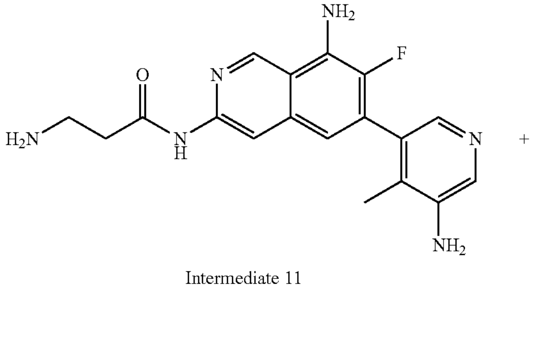

Intermediate 11

-continued

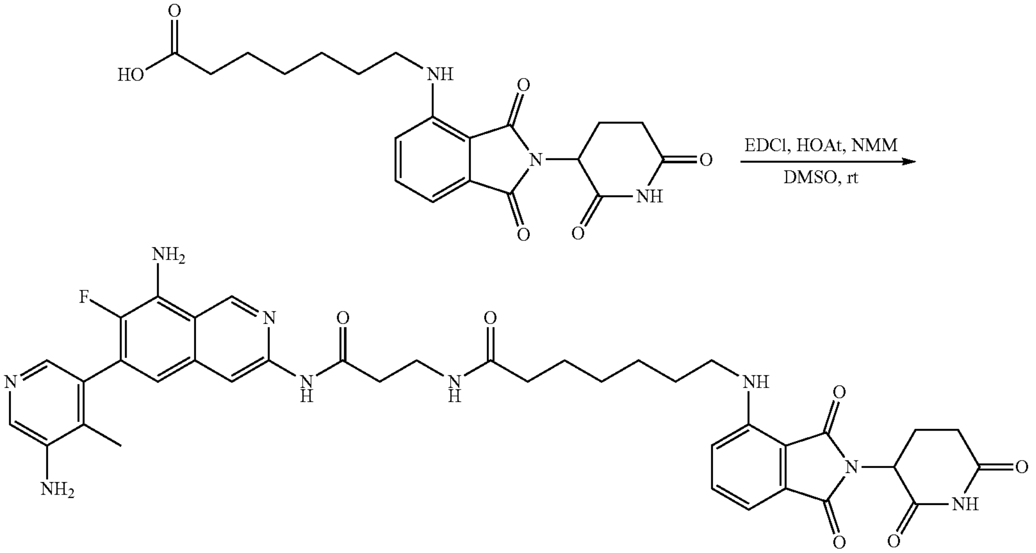

HC75-2

HC75-2 was synthesized following the standard procedure for preparing HC65-175 from Intermediate 11 (9.1 mg, 0.013 mmol, 1.0 equiv), 7-((2-(2,6-dioxopiperidin-3-yl)-1,3-dioxoisoindolin-4-yl)amino)heptanoic acid (5.2 mg, 0.013 mmol, 1.0 equiv), EDCI (3.8 mg, 0.02 mmol, 1.5 equiv), HOAt (2.7 mg, 0.02 mmol, 1.5 equiv), and NMM (6.6 mg, 0.065 mmol, 5.0 equiv) in DMSO (1 mL). HC75-2 was obtained as yellow solid in TFA salt form (4.5 mg, 36%). $^1H$ NMR (600 MHz, Methanol-$d_4$) δ 9.32 (s, 1H), 8.34 (s, 1H), 8.07 (s, 1H), 7.99 (s, 1H), 7.47 (dd, J=8.5, 7.0 Hz, 1H), 7.03 (d, J=5.8 Hz, 1H), 6.96 (d, J=7.0 Hz, 1H), 6.89 (d, J=8.5 Hz, 1H), 5.06 (dd, J=12.7, 5.4 Hz, 1H), 3.60 (t, J=6.4 Hz, 2H), 3.17 (t, J=7.0 Hz, 2H), 2.87 (ddd, J=17.0, 13.8, 5.2 Hz, 1H), 2.80-2.66 (m, 4H), 2.25-2.18 (m, 5H), 2.16-2.06 (m, 1H), 1.68-1.59 (m, 2H), 1.59-1.52 (m, 2H), 1.38 (h, J=5.4, 4.5 Hz, 4H). HRMS calcd for $C_{38}H_{41}FN_9O_6[M+H^+]$ 738.3164, found 738.3172.

Example 122

Synthesis of HC75-3

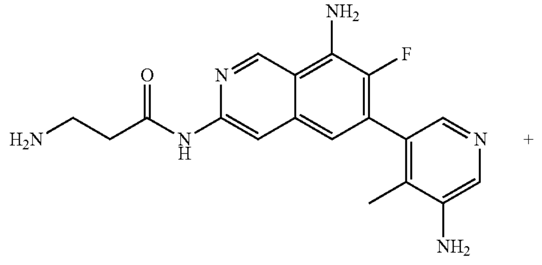

Intermediate 11

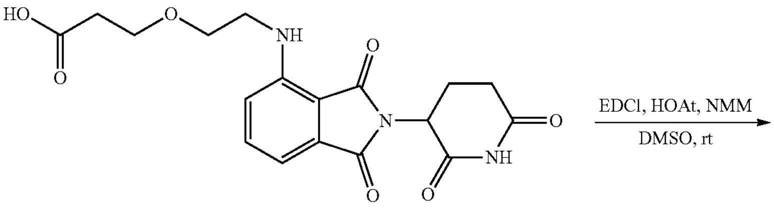

-continued

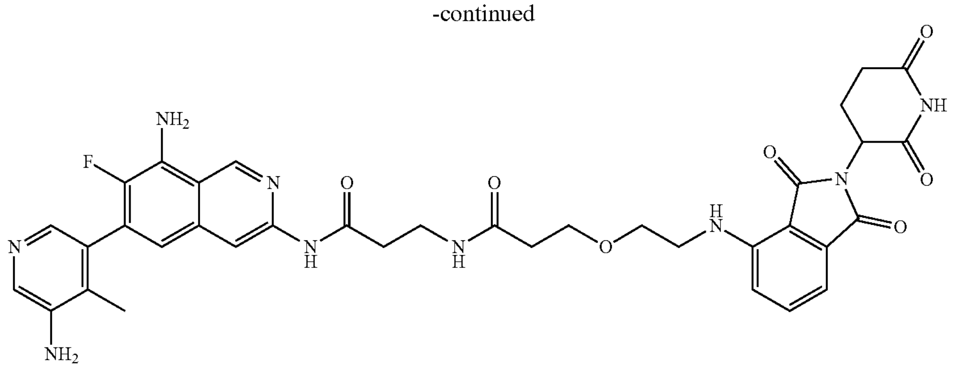

HC75-3

HC75-3 was synthesized following the standard procedure for preparing HC65-175 from Intermediate 11 (11.0 mg, 0.015 mmol, 1.0 equiv), 3-(2-((2-(2,6-dioxopiperidin-3-yl)-1,3-dioxoisoindolin-4-yl)amino)ethoxy)propanoic acid (6.0 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-3 was obtained as yellow solid in TFA salt form (3.6 mg, 25%). $^1$H NMR (600 MHz, Methanol-d4) δ 9.24 (s, 1H), 8.26 (s, 1H), 8.09 (s, 1H), 8.04 (s, 1H), 7.38 (t, J=7.9 Hz, 1H), 6.99 (s, 1H), 6.90 (d, J=8.6 Hz, 1H), 6.80 (s, 1H), 5.07 (dd, J=12.8, 5.5 Hz, 1H), 3.85-3.74 (m, 2H), 3.74-3.56 (m, 4H), 3.48-3.40 (m, 2H), 2.86 (ddd, J=17.5, 14.0, 5.4 Hz, 1H), 2.80-2.63 (m, 4H), 2.49 (s, 2H), 2.23 (s, 3H), 2.19-2.05 (m, 1H). HRMS calcd for $C_{36}H_{37}FN_9O_7[M+H^+]$ 726.2800, found 726.2810.

Example 123

Synthesis of HC75-4

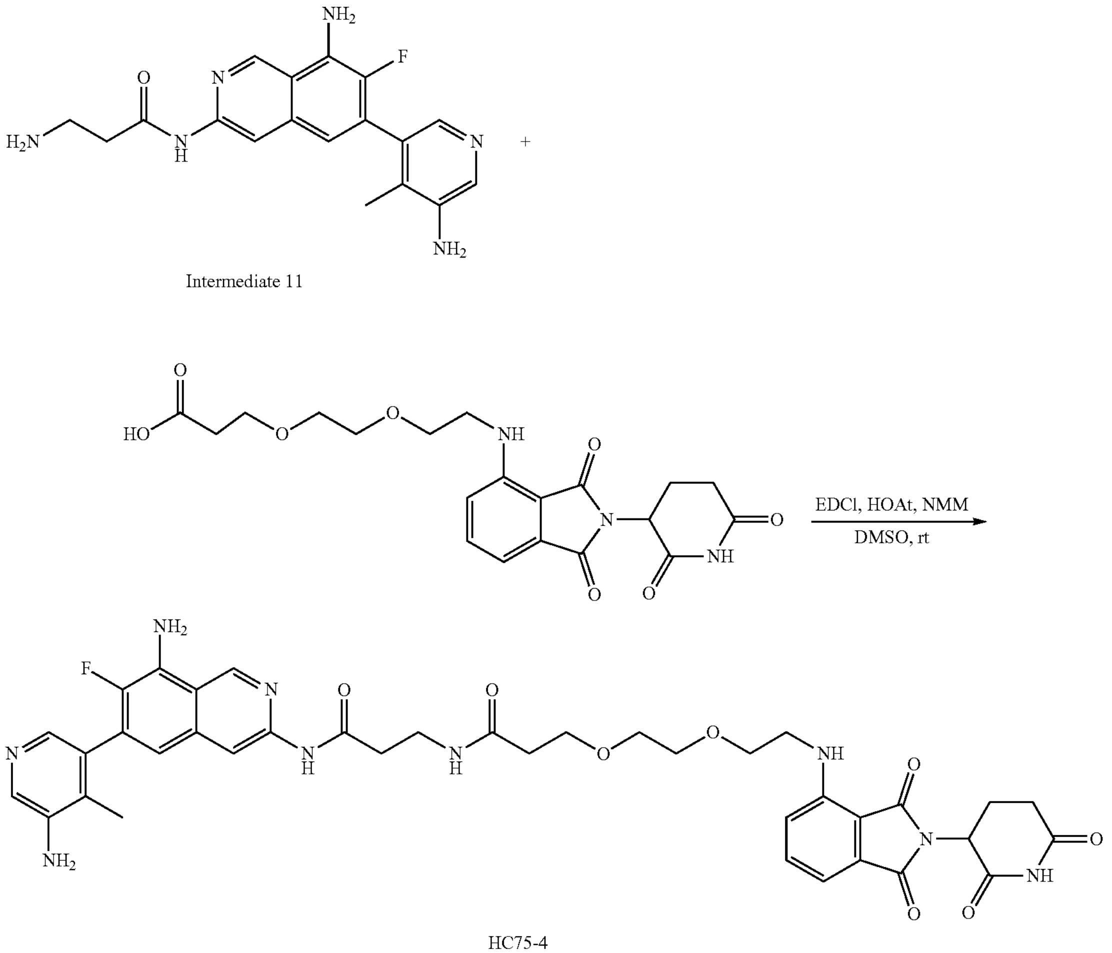

Intermediate 11

HC75-4

HC75-4 was synthesized following the standard procedure for preparing HC65-175 from Intermediate 11 (11.0 mg, 0.015 mmol, 1.0 equiv), 3-(2-(2-((2-(2,6-dioxopiperidin-3-yl)-1,3-dioxoisoindolin-4-yl)amino)ethoxy)ethoxy) propanoic acid (6.5 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-4 was obtained as yellow solid in TFA salt form (10.1 mg, 67%). $^1H$ NMR (600 MHz, Methanol-$d_4$) δ 9.31 (s, 1H), 8.15 (s, 1H), 8.10 (s, 1H), 8.04 (s, 1H), 7.41 (t, J=7.9 Hz, 1H), 7.07-7.02 (m, 1H), 6.93 (d, J=8.5 Hz, 1H), 6.88-6.75 (m, 1H), 5.05 (dd, J=12.7, 5.5 Hz, 1H), 3.78-3.68 (m, 4H), 3.68-3.57 (m, 6H), 3.42 (t, J=5.4 Hz, 2H), 2.87 (ddd, J=17.5, 13.8, 5.3 Hz, 1H), 2.80-2.69 (m, 4H), 2.54-2.41 (m, 2H), 2.23 (s, 3H), 2.18-2.09 (m, 1H). HRMS calcd for $C_{38}H_{41}FN_9O_8[M+H^+]$ 770.3062, found 770.3073.

Example 124

Synthesis of HC75-5

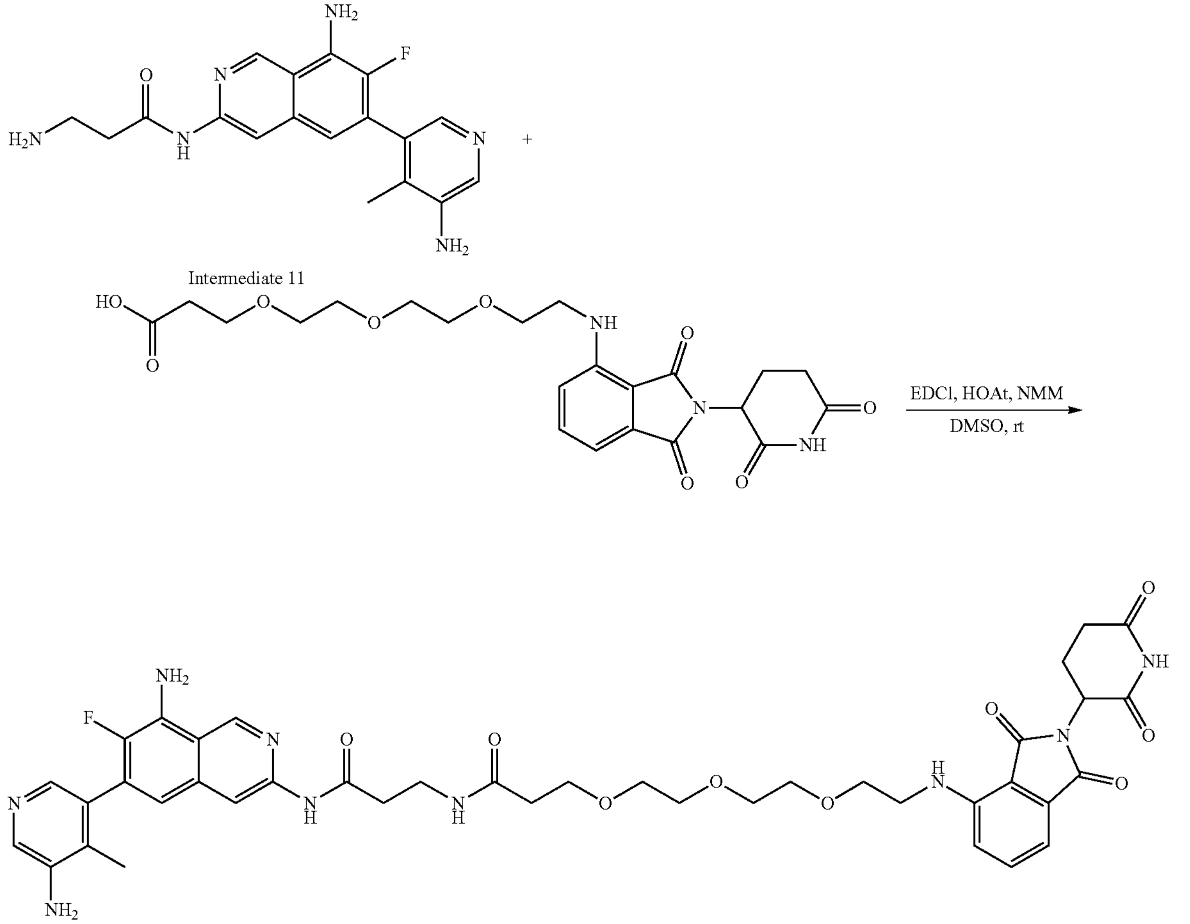

HC75-5

HC75-5 was synthesized following the standard procedure for preparing HC65-175 from Intermediate 11 (11.0 mg, 0.015 mmol, 1.0 equiv), 3-(2-(2-(2-((2-(2,6-dioxopiperidin-3-yl)-1,3-dioxoisoindolin-4-yl)amino)ethoxy) ethoxy)ethoxy)propanoic acid (7.2 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-5 was obtained as yellow solid in TFA salt form (10.5 mg, 67%). $^1H$ NMR (600 MHz, Methanol-$d_4$) δ 9.34 (s, 1H), 8.16 (s, 1H), 8.09 (s, 1H), 8.03 (s, 1H), 7.44 (t, J=7.7 Hz, 1H), 7.11-7.04 (m, 1H), 6.97 (d, J=8.6 Hz, 1H), 6.92-6.84 (m, 1H), 5.05 (dd, J=12.8, 5.5 Hz, 1H), 3.76-3.64 (m, 8H), 3.64-3.55 (m, 6H), 3.45 (q, J=4.8 Hz, 2H), 2.87 (ddd, J=17.5, 13.8, 5.4 Hz, 1H), 2.80-2.66 (m, 4H), 2.44 (t, J=5.9 Hz, 2H), 2.23 (s, 3H), 2.17-2.08 (m, 1H). HRMS calcd for $C_{40}H_{45}FN_9O_9[M+H^+]$ 814.3324, found 814.3318.

Example 125

Synthesis of HC75-6

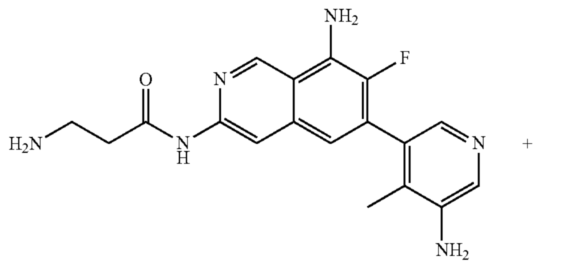

Intermediate 11

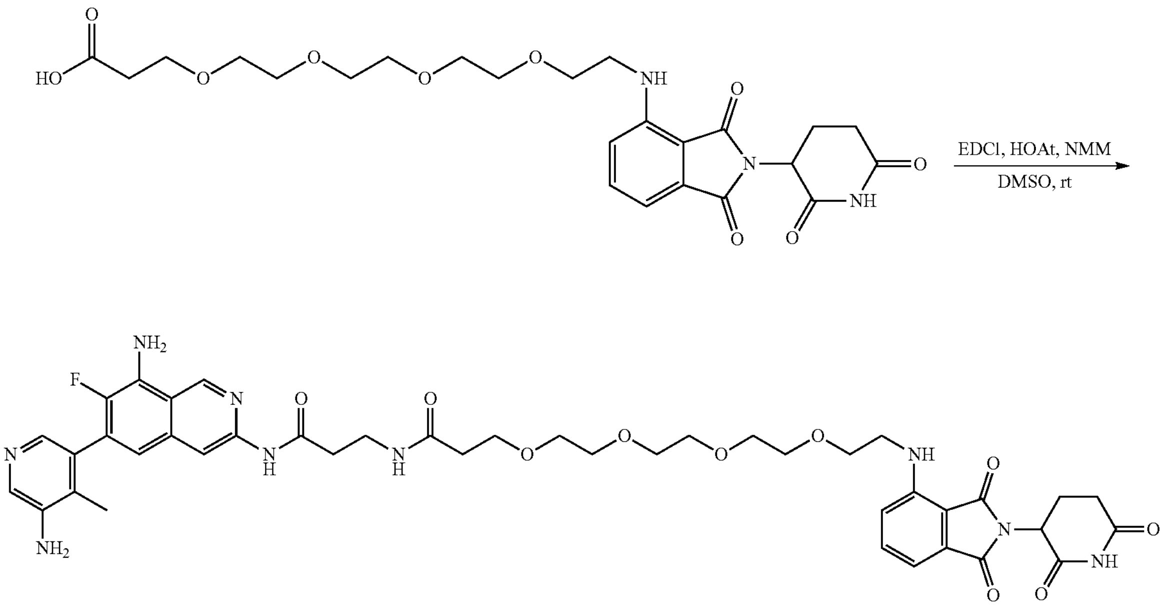

HC75-6

HC75-6 was synthesized following the standard procedure for preparing HC65-175 from Intermediate 11 (11.0 mg, 0.015 mmol, 1.0 equiv), 1-((2-(2,6-dioxopiperidin-3-yl)-1,3-dioxoisoindolin-4-yl)amino)-3,6,9,12-tetraoxapentadecan-15-oic acid (7.8 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-6 was obtained as yellow solid in TFA salt form (9.3 mg, 57%). $^1H$ NMR (600 MHz, Methanol-$d_4$) δ 9.35 (s, 1H), 8.19 (s, 1H), 8.09 (s, 1H), 8.03 (s, 1H), 7.46 (t, J=7.8 Hz, 1H), 7.08 (d, J=5.7 Hz, 1H), 6.98 (d, J=8.5 Hz, 1H), 6.92 (d, J=7.0 Hz, 1H), 5.05 (dd, J=12.8, 5.5 Hz, 1H), 3.71 (q, J=5.7 Hz, 4H), 3.67 (s, 4H), 3.65-3.57 (m, 6H), 3.55 (s, 4H), 3.49-3.40 (m, 2H), 2.87 (ddd, J=18.4, 13.8, 5.3 Hz, 1H), 2.80-2.65 (m, 4H), 2.45 (t, J=5.9 Hz, 2H), 2.23 (s, 3H), 2.16-2.07 (m, 1H). HRMS calcd for $C_{42}H_{49}FN_9O_{10}$ [M+H$^+$] 858.3586, found 858.3597.

Example 126

Synthesis of HC75-7

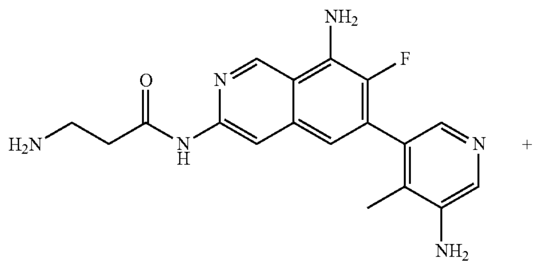

Intermediate 11

-continued

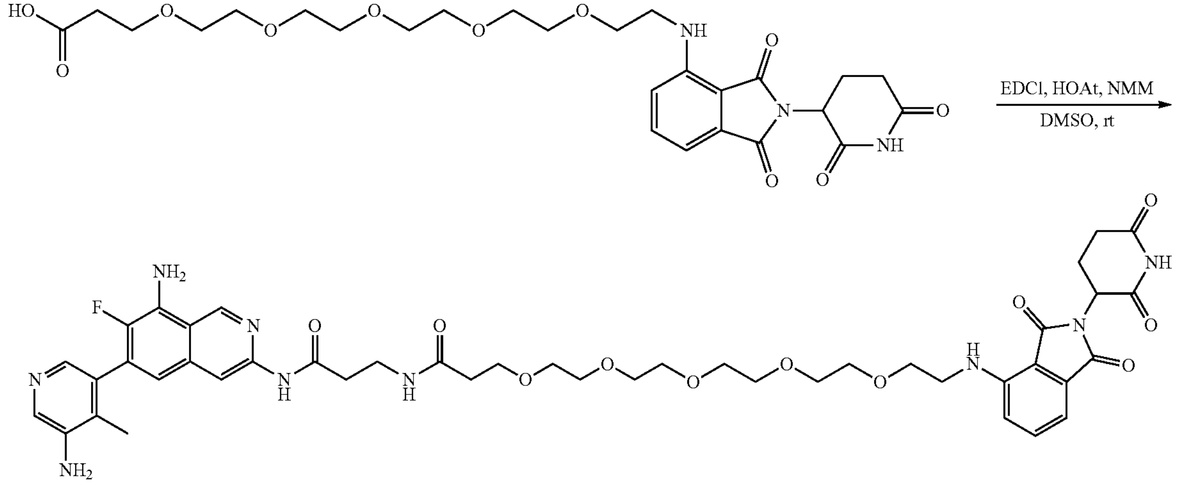

HC75-7

HC75-7 was synthesized following the standard procedure for preparing HC65-175 from Intermediate 11 (11.0 mg, 0.015 mmol, 1.0 equiv), 1-((2-(2,6-dioxopiperidin-3-yl)-1,3-dioxoisoindolin-4-yl)amino)-3,6,9,12,15-pentaoxaoctadecan-18-oic acid (8.5 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-7 was obtained as yellow solid in TFA salt form (11.0 mg, 65%). $^1$H NMR (600 MHz, Methanol-$d_4$) δ 9.35 (s, 1H), 8.26 (s, 1H), 8.09 (s, 1H), 8.03 (s, 1H), 7.49 (t, J=7.6 Hz, 1H), 7.07 (d, J=5.8 Hz, 1H), 7.00 (d, J=8.6 Hz, 1H), 6.96 (d, J=7.0 Hz, 1H), 5.06 (dd, J=12.7, 5.5 Hz, 1H), 3.71 (td, J=6.6, 5.3, 2.8 Hz, 4H), 3.68-3.59 (m, 9H), 3.56 (ddt, J=9.9, 6.2, 3.6 Hz, 9H), 3.44 (t, J=5.1 Hz, 2H), 2.87 (ddd, J=18.3, 13.9, 5.3 Hz, 1H), 2.79-2.66 (m, 4H), 2.51-2.41 (m, 2H), 2.23 (s, 3H), 2.15-2.09 (m, 1H). HRMS calcd for $C_{44}H_{53}FN_9O_{11}$[M+H$^+$] 902.3849, found 902.3860.

Example 127

Synthesis of HC75-8

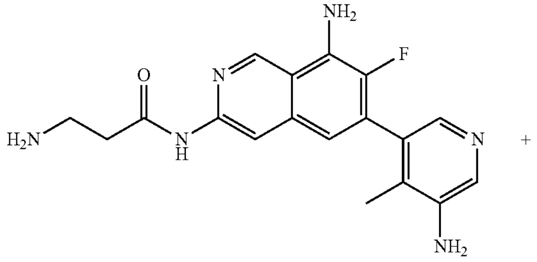

Intermediate 11

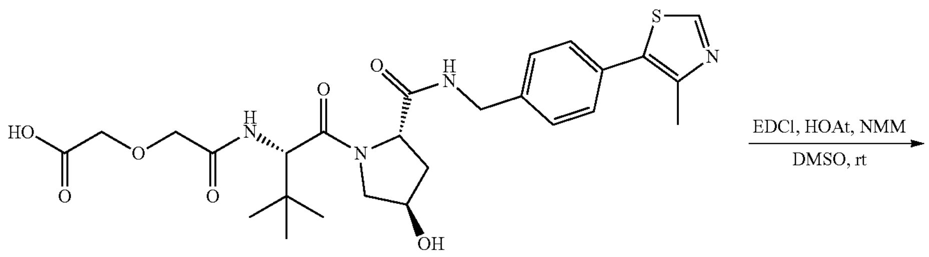

-continued

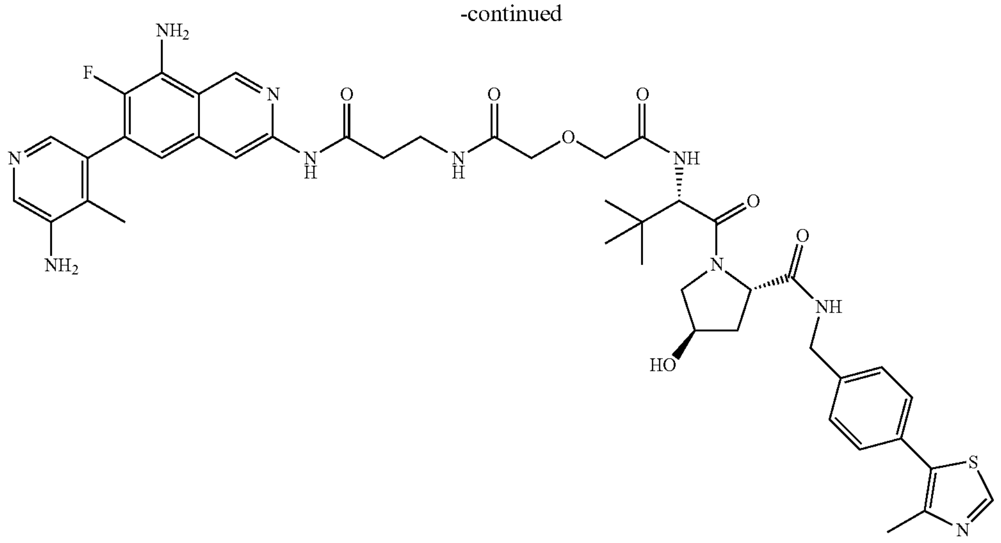

HC75-8

HC75-8 was synthesized following the standard procedure for preparing HC65-175 from Intermediate 11 (11.0 mg, 0.015 mmol, 1.0 equiv), 2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetic acid (8.2 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-8 was obtained as yellow solid in TFA salt form (11.2 mg, 67%). $^1$H NMR (600 MHz, Methanol-$d_4$) δ 9.37 (s, 1H), 8.98 (s, 1H), 8.22 (s, 1H), 8.10 (s, 1H), 7.99 (s, 1H), 7.45 (d, J=8.3 Hz, 2H), 7.38 (d, J=7.9 Hz, 2H), 7.02 (d, J=5.8 Hz, 1H), 4.72 (s, 1H), 4.66-4.56 (m, 2H), 4.53 (d, J=4.0 Hz, 1H), 4.32 (d, J=15.6 Hz, 1H), 4.21-4.11 (m, 2H), 4.10 (s, 2H), 3.92 (d, J=11.0 Hz, 1H), 3.82 (dd, J=11.0, 3.8 Hz, 1H), 3.74-3.62 (m, 2H), 2.84-2.74 (m, 2H), 2.46 (s, 3H), 2.33-2.26 (m, 1H), 2.23 (s, 3H), 2.11 (ddd, J=13.4, 9.5, 4.4 Hz, 1H), 1.03 (s, 9H). HRMS calcd for $C_{44}H_{52}FN_{10}O_7S$ [M+H$^+$] 883.3725, found 883.3733.

Example 128

Synthesis of HC75-9

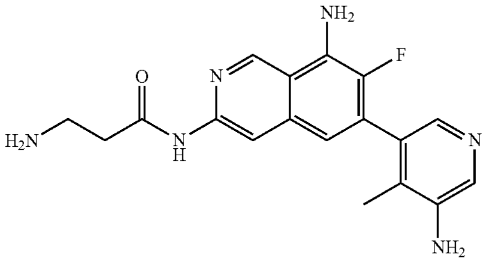

+

Intermediate 11

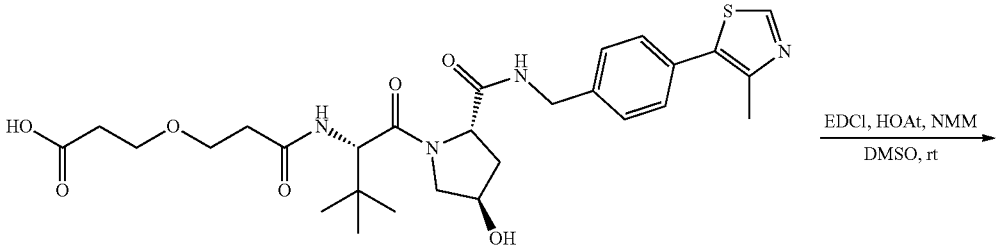

-continued

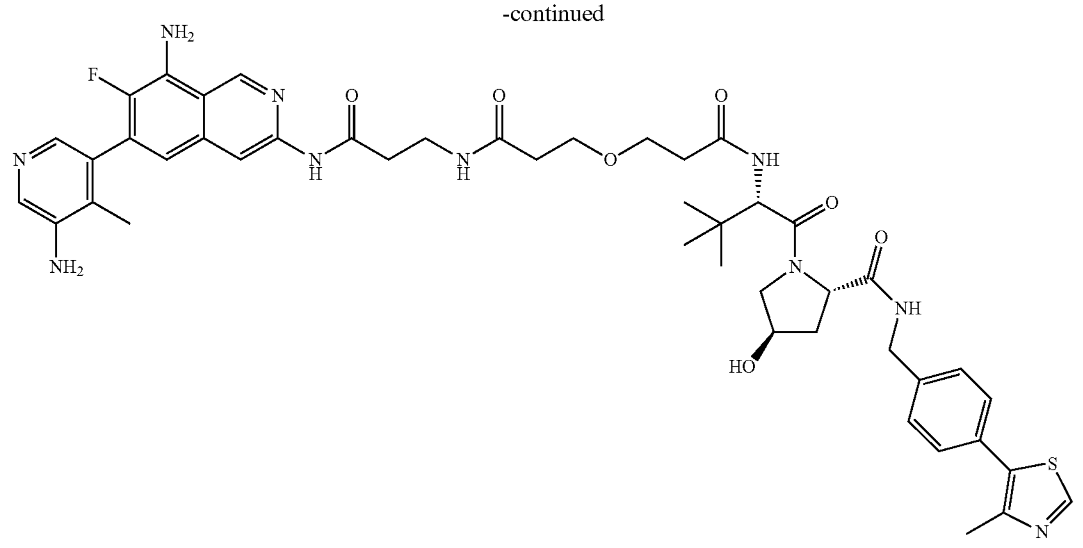

HC75-9

HC75-9 was synthesized following the standard procedure for preparing HC65-175 from Intermediate 11 (11.0 mg, 0.015 mmol, 1.0 equiv), 3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoic acid (8.6 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-9 was obtained as yellow solid in TFA salt form (8.9 mg, 52%). $^1$H NMR (600 MHz, Methanol-$d_4$) δ 9.46 (s, 1H), 9.13 (s, 1H), 8.14 (s, 1H), 8.11 (s, 1H), 8.02 (s, 1H), 7.47 (d, J=7.7 Hz, 2H), 7.39 (d, J=8.0 Hz, 2H), 7.09 (d, J=5.7 Hz, 1H), 4.68 (d, J=3.6 Hz, 1H), 4.59 (d, J=15.6 Hz, 1H), 4.54 (s, 1H), 4.34 (d, J=15.5 Hz, 1H), 3.95 (d, J=11.1 Hz, 1H), 3.83 (dd, J=11.0, 3.9 Hz, 1H), 3.74-3.66 (m, 5H), 3.60 (t, J=6.4 Hz, 2H), 2.83-2.70 (m, 2H), 2.56-2.41 (m, 7H), 2.33-2.22 (m, 4H), 2.16-2.06 (m, 1H), 1.05 (s, 9H). HRMS calcd for $C_{46}H_{56}FN_{10}O_7S$ [M+H$^+$] 911.4038, found 911.4049.

Example 129

Synthesis of HC75-10

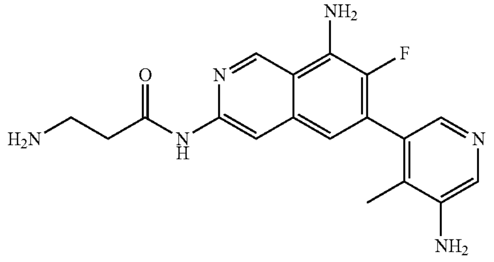

Intermediate 11

+

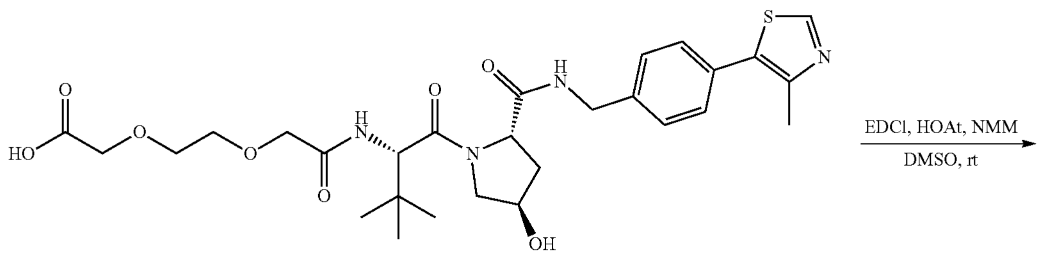

-continued

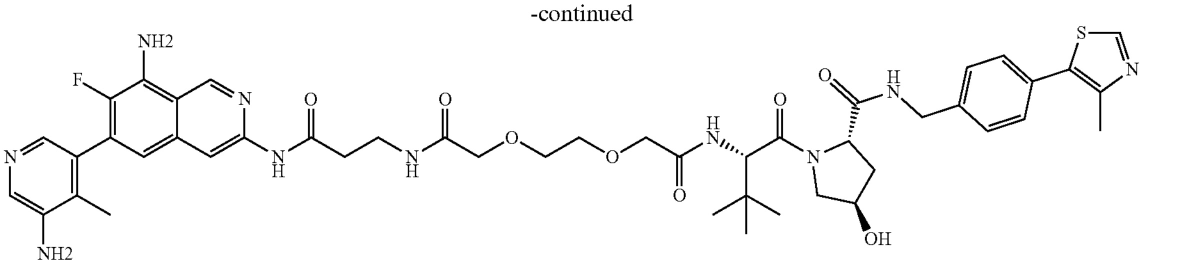

HC75-10

HC75-10 was synthesized following the standard procedure for preparing HC65-175 from Intermediate 11 (11.0 mg, 0.015 mmol, 1.0 equiv), 2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetic acid (8.9 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-10 was obtained as yellow solid in TFA salt form (10.8 mg, 62%). $^1$H NMR (600 MHz, Methanol-$d_4$) δ 9.44 (s, 1H), 9.14 (s, 1H), 8.17 (s, 1H), 8.11 (s, 1H), 8.03 (s, 1H), 7.46 (d, J=8.4 Hz, 2H), 7.41 (d, J=8.0 Hz, 2H), 7.11 (d, J=5.7 Hz, 1H), 4.72 (s, 1H), 4.58 (d, J=22.0 Hz, 1H), 4.53 (d, J=8.1 Hz, 2H), 4.40 (d, J=15.4 Hz, 1H), 4.12-4.05 (m, 2H), 4.00 (d, J=15.5 Hz, 1H), 3.88 (d, J=11.4 Hz, 1H), 3.82 (dd, J=11.0, 3.9 Hz, 1H), 3.79-3.60 (m, 7H), 2.84-2.70 (m, 2H), 2.49 (s, 3H), 2.30-2.20 (m, 4H), 2.11 (ddd, J=13.3, 9.2, 4.5 Hz, 1H), 1.04 (s, 9H). HRMS calcd for $C_{46}H_{56}FN_{10}O_8S$ [M+H$^+$] 927.3987, found 927.3978.

Example 130

Synthesis of HC75-11

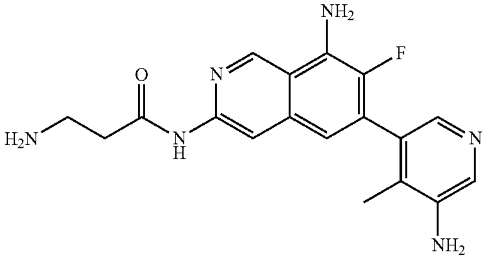

Intermediate 11

+

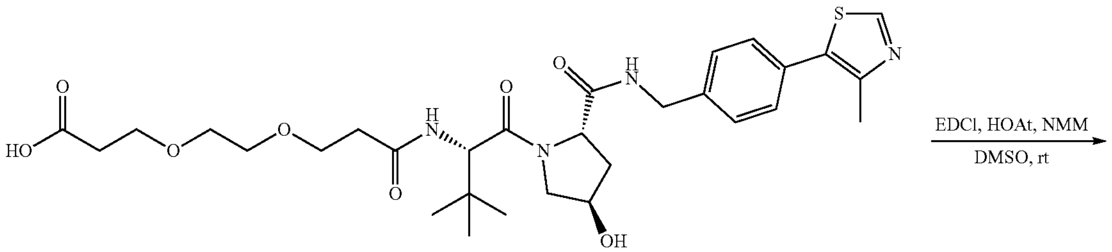

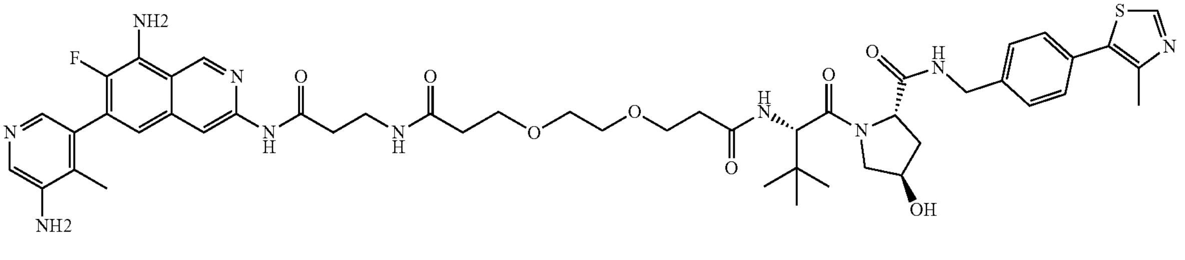

HC75-11

HC75-11 was synthesized following the standard procedure for preparing HC65-175 from Intermediate 11 (11.0 mg, 0.015 mmol, 1.0 equiv), 3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoic acid (9.3 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-11 was obtained as yellow solid in TFA salt form (9.9 mg, 56%). $^1$H NMR (600 MHz, Methanol-d$_4$) δ 9.42 (s, 1H), 9.04 (s, 1H), 8.26 (s, 1H), 8.10 (s, 1H), 8.01 (s, 1H), 7.48 (d, J=7.9 Hz, 2H), 7.40 (d, J=7.9 Hz, 2H), 7.08 (d, J=5.8 Hz, 1H), 4.71 (s, 1H), 4.63 (t, J=8.4 Hz, 1H), 4.57 (d, J=15.5 Hz, 1H), 4.55-4.51 (m, 1H), 4.38 (d, J=15.5 Hz, 1H), 3.93 (d, J=11.0 Hz, 1H), 3.83 (dd, J=11.0, 3.9 Hz, 1H), 3.77-3.65 (m, 4H), 3.62-3.52 (m, 6H), 2.79 (dt, J=15.6, 6.7 Hz, 1H), 2.67 (d, J=15.8 Hz, 1H), 2.56-2.38 (m, 7H), 2.30-2.22 (m, 4H), 2.11 (ddd, J=13.3, 9.2, 4.5 Hz, 1H), 1.05 (s, 9H). HRMS calcd for $C_{48}H_{60}FN_{10}O_8S$ [M+H$^+$]955.4300, found 955.4313.

Example 131

Synthesis of HC75-12

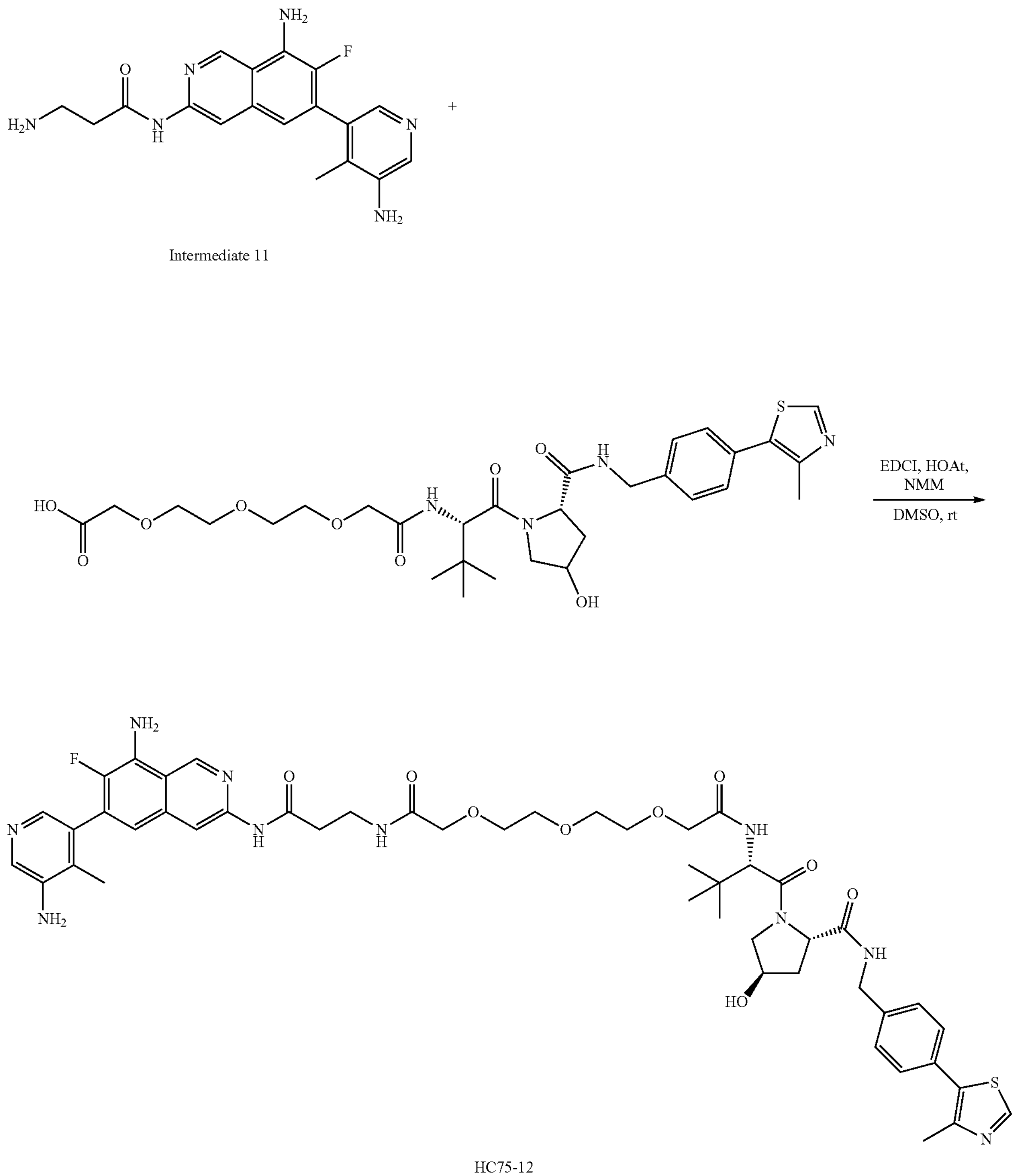

HC75-12

HC75-12 was synthesized following the standard procedure for preparing HC65-175 from Intermediate 11 (11.0 mg, 0.015 mmol, 1.0 equiv), (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoic acid (9.5 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-12 was obtained as yellow solid in TFA salt form (10.5 mg, 58%). $^1H$ NMR (600 MHz, Methanol-$d_4$) δ 9.40 (s, 1H), 9.02 (s, 1H), 8.27 (s, 1H), 8.10 (s, 1H), 8.02 (s, 1H), 7.47 (d, J=7.8 Hz, 2H), 7.40 (d, J=8.2 Hz, 2H), 7.07 (d, J=5.8 Hz, 1H), 4.71 (d, J=3.6 Hz, 1H), 4.65-4.60 (m, 1H), 4.58 (d, J=15.3 Hz, 1H), 4.53 (s, 1H), 4.35 (d, J=15.5 Hz, 1H), 4.04 (d, J=12.1 Hz, 1H), 3.98 (d, J=11.4 Hz, 1H), 3.90 (d, J=11.0 Hz, 1H), 3.82 (dd, J=11.0, 3.8 Hz, 1H), 3.75-3.62 (m, 12H), 2.82-2.72 (m, 2H), 2.47 (s, 3H), 2.29-2.21 (m, 4H), 2.12 (ddd, J=13.4, 9.4, 4.3 Hz, 1H), 1.04 (s, 9H). HRMS calcd for $C_{48}H_{60}FN_{10}O_9S$ [M+H$^+$] 971.4249, found 971.4262.

Example 132

Synthesis of HC75-13

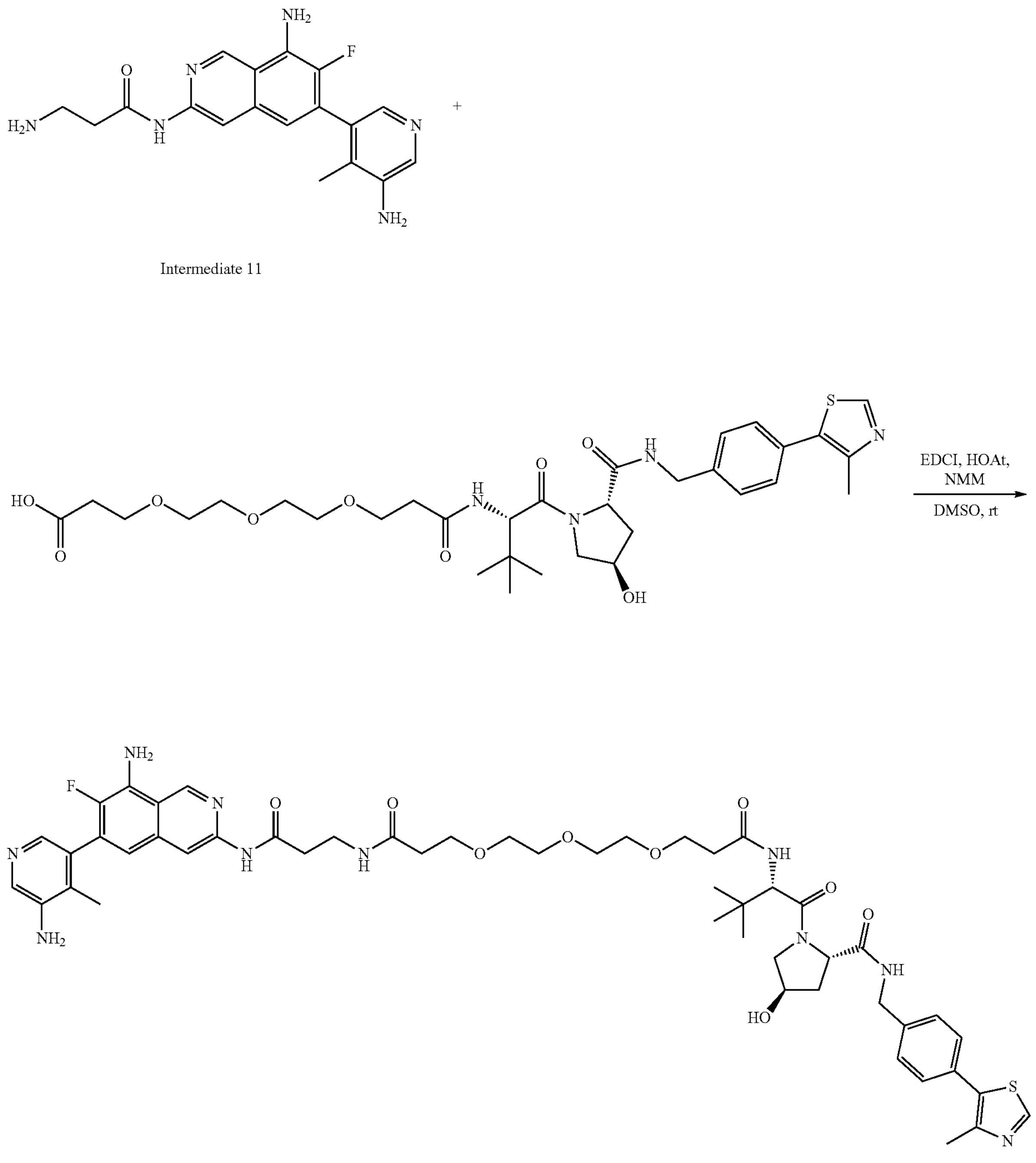

HC75-13

HC75-13 was synthesized following the standard procedure for preparing HC65-175 from Intermediate 11 (11.0 mg, 0.015 mmol, 1.0 equiv), (S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoic acid (9.9 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-13 was obtained as yellow solid in TFA salt form (8.4 mg, 46%). $^1$H NMR (600 MHz, Methanol-$d_4$) δ 9.44 (s, 1H), 9.08 (s, 1H), 8.22 (s, 1H), 8.11 (s, 1H), 8.01 (s, 1H), 7.48 (d, J=7.9 Hz, 2H), 7.40 (d, J=8.3 Hz, 2H), 7.09 (d, J=5.8 Hz, 1H), 4.69 (s, 1H), 4.63-4.60 (m, 1H), 4.58 (d, J=15.7 Hz, 1H), 4.54-4.50 (m, 1H), 4.37 (d, J=15.5 Hz, 1H), 3.92 (d, J=11.0 Hz, 1H), 3.83 (dd, J=11.0, 3.8 Hz, 1H), 3.75-3.67 (m, 4H), 3.62-3.54 (m, 10H), 2.75 (t, J=6.7 Hz, 2H), 2.62-2.53 (m, 1H), 2.52-2.43 (m, 6H), 2.30-2.22 (m, 4H), 2.10 (ddd, J=13.3, 9.3, 4.4 Hz, 1H), 1.05 (s, 9H). HRMS calcd for $C_{50}H_{64}FN_{10}O_9S$ [M+H$^+$] 999.4562, found 999.4569.

Example 133

Synthesis of HC75-14

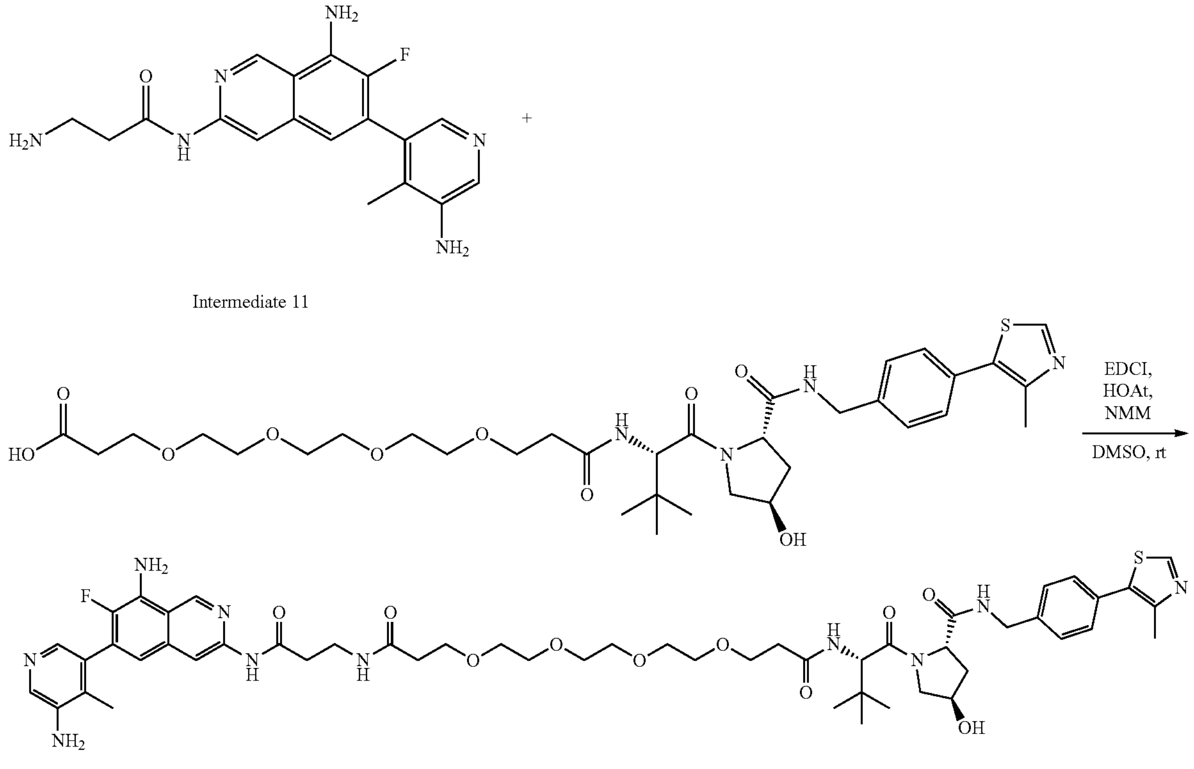

Intermediate 11

HC75-14

HC75-14 was synthesized following the standard procedure for preparing HC65-175 from Intermediate 11 (11.0 mg, 0.015 mmol, 1.0 equiv), (S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoic acid (11.0 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-14 was obtained as yellow solid in TFA salt form (6.4 mg, 34%). $^1$H NMR (600 MHz, Methanol-$d_4$) δ 9.41 (s, 1H), 9.00 (s, 1H), 8.29 (s, 1H), 8.10 (s, 1H), 8.01 (s, 1H), 7.48 (d, J=7.9 Hz, 2H), 7.41 (d, J=8.2 Hz, 2H), 7.07 (d, J=5.9 Hz, 1H), 4.68 (s, 1H), 4.61 (d, J=7.5 Hz, 1H), 4.57 (d, J=16.0 Hz, 1H), 4.54-4.51 (m, 1H), 4.37 (d, J=15.4 Hz, 1H), 3.91 (d, J=11.0 Hz, 1H), 3.82 (dd, J=11.0, 3.8 Hz, 1H), 3.71 (td, J=5.9, 3.2 Hz, 4H), 3.63-3.55 (m, 14H), 2.74 (t, J=6.6 Hz, 2H), 2.57 (ddd, J=14.9, 7.2, 5.4 Hz, 1H), 2.51-2.43 (m, 6H), 2.30-2.22 (m, 4H), 2.10 (ddd, J=13.4, 9.2, 4.5 Hz, 1H), 1.05 (s, 9H). HRMS calcd for $C_{52}H_{68}FN_{10}O_{10}S$ [M+H$^+$] 1043.4825, found 1043.4839.

Example 134

Synthesis of HC75-15

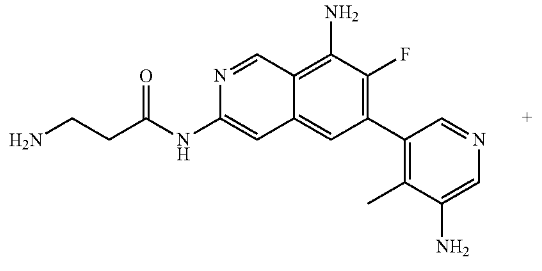

Intermediate 11

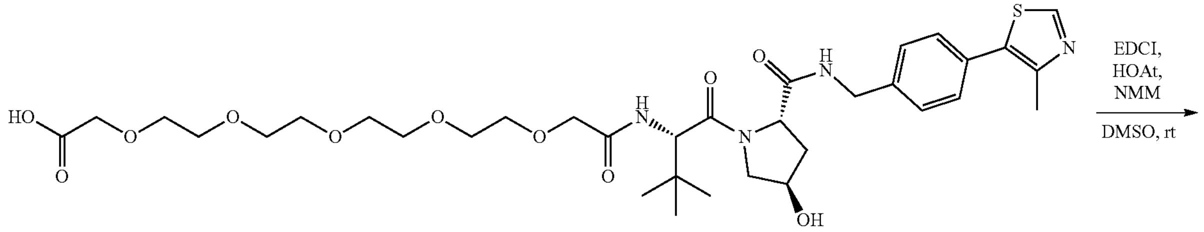

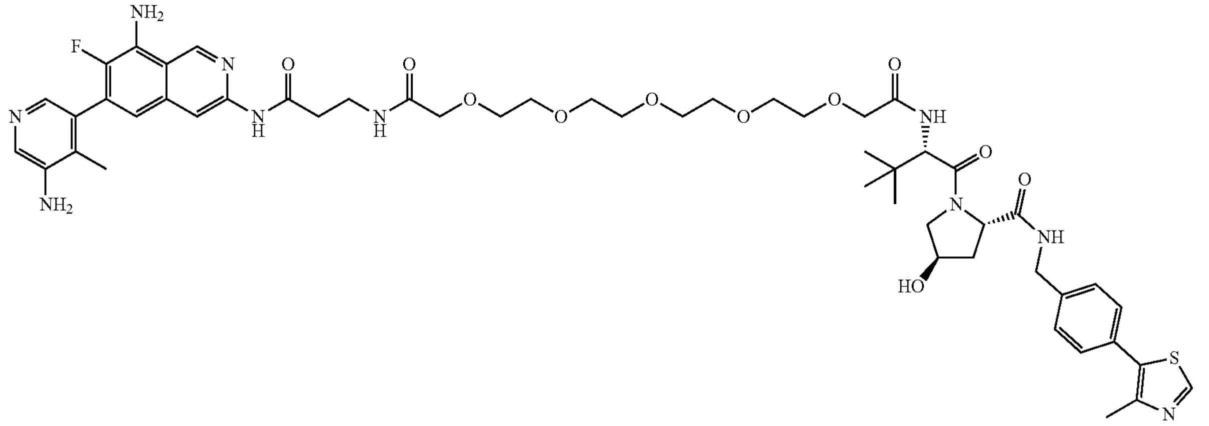

HC75-15

HC75-15 was synthesized following the standard procedure for preparing HC65-175 from Intermediate 11 (11.0 mg, 0.015 mmol, 1.0 equiv), (S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoic acid (11 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-15 was obtained as yellow solid in TFA salt form (9.8 mg, 51%). $^1$H NMR (600 MHz, Methanol-$d_4$) δ 9.46 (s, 1H), 9.15 (s, 1H), 8.19 (s, 1H), 8.12 (s, 1H), 8.01 (s, 1H), 7.49 (d, J=8.0 Hz, 2H), 7.43 (d, J=7.9 Hz, 2H), 7.11 (d, J=5.7 Hz, 1H), 4.71 (s, 1H), 4.61 (t, J=8.4 Hz, 1H), 4.57 (d, J=15.5 Hz, 1H), 4.54-4.51 (m, 1H), 4.38 (d, J=15.5 Hz, 1H), 4.06 (d, J=15.6 Hz, 1H), 4.02 (d, J=16.7 Hz, 1H), 3.91 (d, J=11.0 Hz, 1H), 3.82 (dd, J=11.0, 3.8 Hz, 1H), 3.70-3.60 (m, 20H), 2.79 (t, J=6.5 Hz, 2H), 2.50 (s, 3H), 2.29-2.21 (m, 4H), 2.11 (ddd, J=13.4, 9.4, 4.4 Hz, 1H), 1.05 (s, 9H). HRMS calcd for $C_{52}H_{68}FN_{10}O_{11}S$ [M+H$^+$] 1059.4774, found 1059.4788.

Example 135

Synthesis of HC75-16

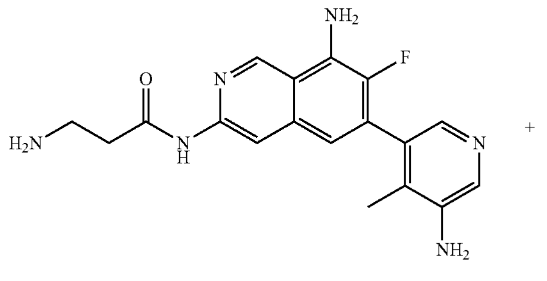

Intermediate 11

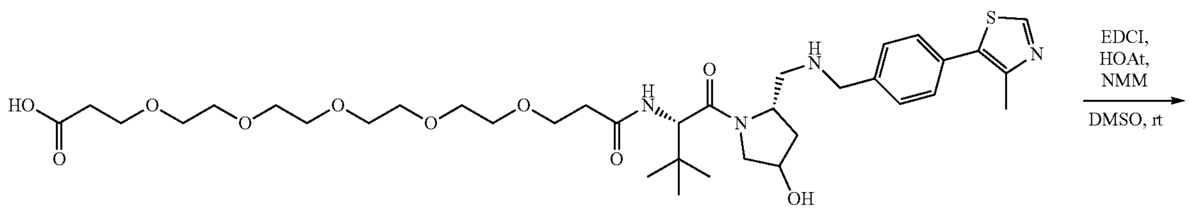

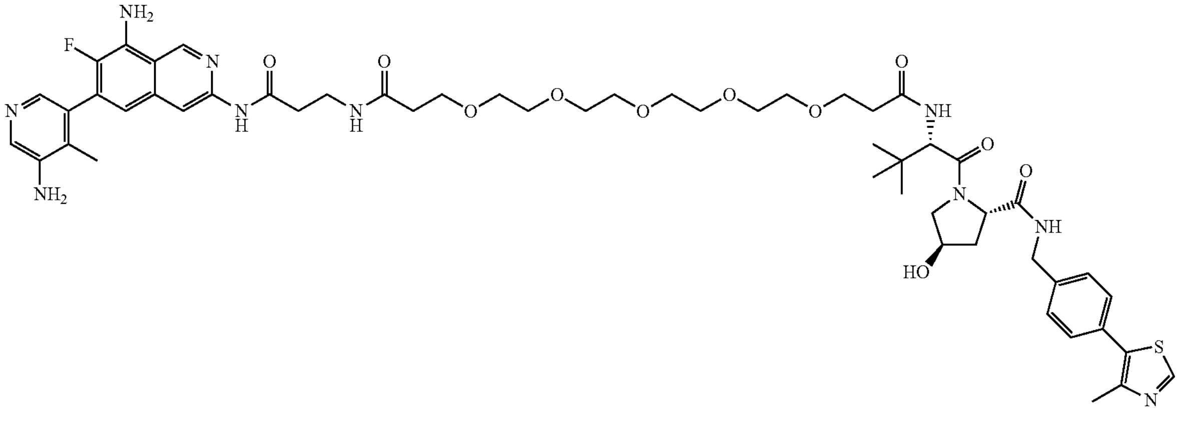

HC75-16

HC75-16 was synthesized following the standard procedure for preparing HC65-175 from Intermediate 11 (11.0 mg, 0.015 mmol, 1.0 equiv), (S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoic acid (11.3 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-16 was obtained as yellow solid in TFA salt form (8.9 mg, 45%). $^1$H NMR (600 MHz, Methanol-$d_4$) δ 9.44 (s, 1H), 9.06 (s, 1H), 8.25 (s, 1H), 8.11 (s, 1H), 8.02 (s, 1H), 7.49 (d, J=7.9 Hz, 2H), 7.42 (d, J=7.9 Hz, 2H), 7.10 (d, J=5.8 Hz, 1H), 4.68 (s, 1H), 4.60 (dd, J=9.4, 7.7 Hz, 1H), 4.57 (d, J=15.5 Hz, 1H), 4.54-4.50 (m, 1H), 4.38 (d, J=15.6 Hz, 1H), 3.92 (d, J=11.0 Hz, 1H), 3.82 (dd, J=11.0, 3.9 Hz, 1H), 3.76-3.67 (m, 4H), 3.62-3.55 (m, 18H), 2.75 (t, J=6.5 Hz, 2H), 2.57 (ddd, J=15.0, 7.6, 5.2 Hz, 1H), 2.52-2.43 (m, 6H), 2.25 (s, 4H), 2.10 (ddd, J=13.4, 9.3, 4.5 Hz, 1H), 1.05 (s, 9H). HRMS calcd for $C_{54}H_{72}FN_{10}O_{11}S$ [M+H$^+$] 1087.5087, found 1087.5096.

Example 136

Synthesis of HC75-17

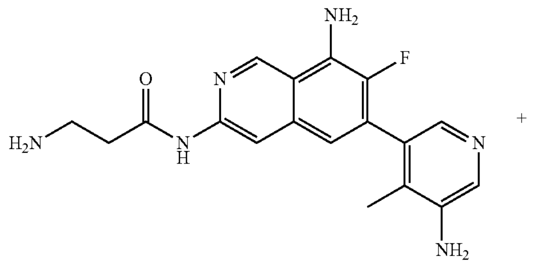

Intermediate 11

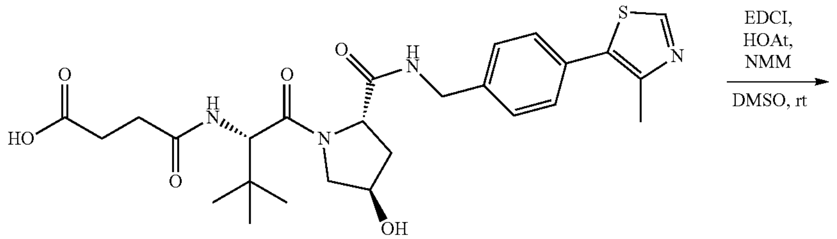

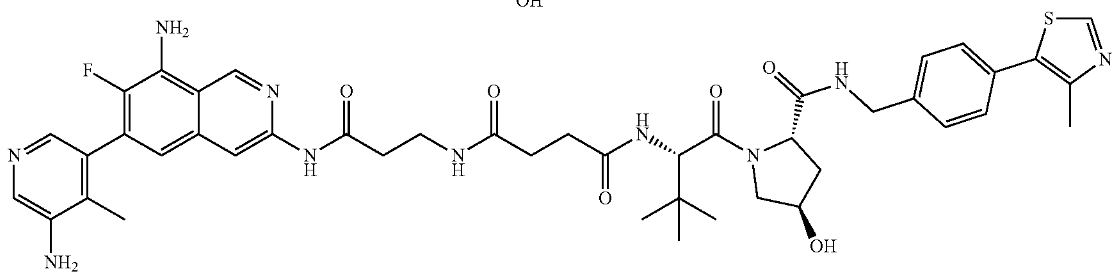

HC75-17

HC75-17 was synthesized following the standard procedure for preparing HC65-175 from Intermediate 11 (11.0 mg, 0.015 mmol, 1.0 equiv), 4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid (8.0 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-17 was obtained as yellow solid in TFA salt form (9.6 mg, 58%). $^1$H NMR (600 MHz, Methanol-$d_4$) δ 9.42 (s, 1H), 9.04 (s, 1H), 8.25 (s, 1H), 8.11 (s, 1H), 8.02 (s, 1H), 7.48 (d, J=8.0 Hz, 2H), 7.40 (d, J=8.0 Hz, 2H), 7.08 (d, J=5.8 Hz, 1H), 4.65-4.54 (m, 3H), 4.53-4.49 (m, 1H), 4.36 (d, J=15.5 Hz, 1H), 3.93 (d, J=11.0 Hz, 1H), 3.80 (dd, J=11.0, 3.9 Hz, 1H), 3.61 (dt, J=13.5, 6.5 Hz, 1H), 3.54 (dt, J=13.4, 6.5 Hz, 1H), 2.76-2.70 (m, 2H), 2.63-2.55 (m, 2H), 2.52-2.46 (m, 5H), 2.24 (d, J=5.1 Hz, 4H), 2.10 (ddd, J=13.4, 9.3, 4.4 Hz, 1H), 1.05 (s, 9H). HRMS calcd for $C_{44}H_{52}FN_{10}O_6S$ [M+H$^+$] 867.3776, found 867.3789.

Example 137

Synthesis of HC75-18

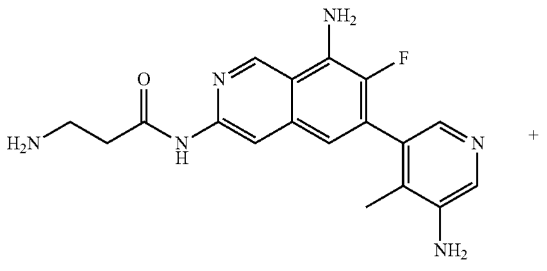

Intermediate 11

-continued

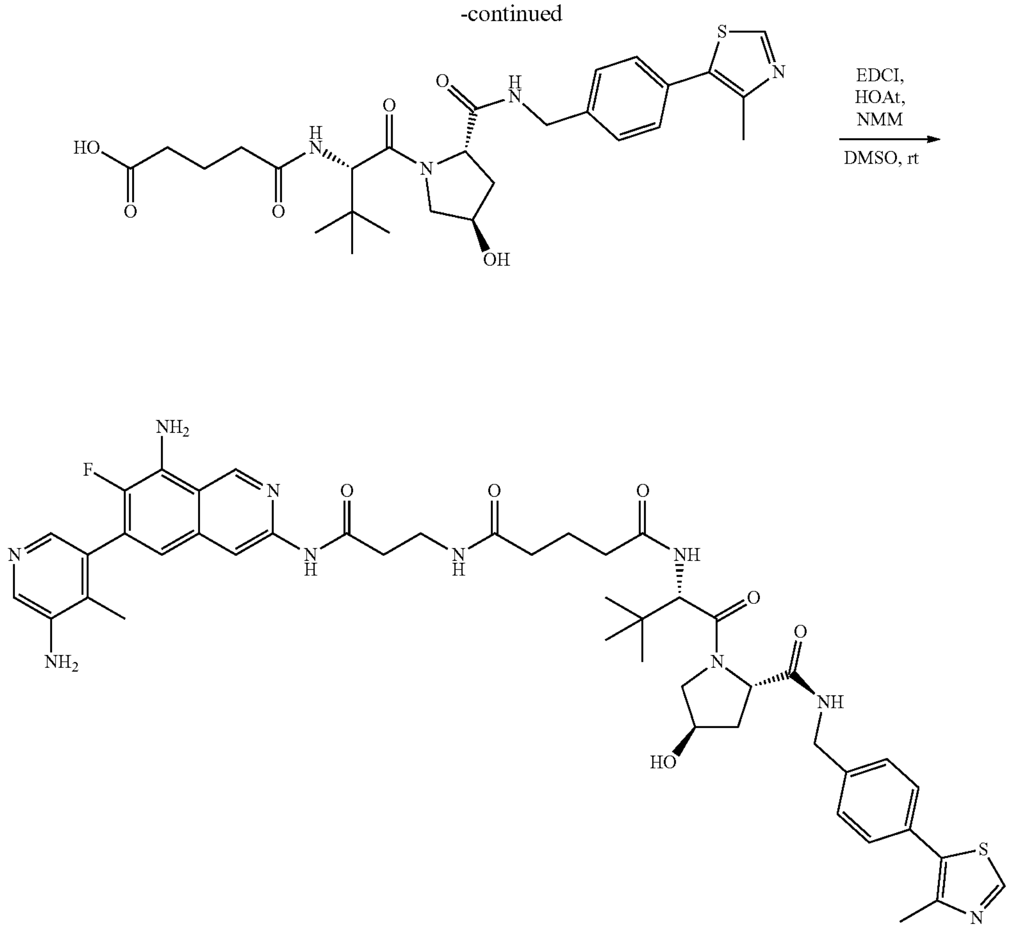

HC75-18

HC75-18 was synthesized following the standard procedure for preparing HC65-175 from Intermediate 11 (11.0 mg, 0.015 mmol, 1.0 equiv), 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid (8.2 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-18 was obtained as yellow solid in TFA salt form (9.1 mg, 55%). $^1$H NMR (600 MHz, Methanol-$d_4$) δ 9.45 (s, 1H), 9.10 (s, 1H), 8.17 (s, 1H), 8.11 (s, OH), 8.01 (s, 1H), 7.47 (d, J=7.9 Hz, 2H), 7.38 (d, J=7.9 Hz, 1H), 7.09 (d, J=5.8 Hz, 1H), 4.66 (s, 1H), 4.64-4.56 (m, 2H), 4.55-4.51 (m, 1H), 4.36 (d, J=15.5 Hz, 1H), 3.95 (d, J=11.0 Hz, 1H), 3.83 (dd, J=11.0, 3.8 Hz, 1H), 3.68-3.61 (m, 1H), 3.59-3.51 (m, 1H), 2.79-2.69 (m, 2H), 2.47 (s, 3H), 2.37-2.20 (m, 8H), 2.11 (ddd, J=13.4, 9.4, 4.4 Hz, 1H), 1.91 (p, J=7.3 Hz, 2H), 1.05 (s, 9H). HRMS calcd for $C_{45}H_{54}FN_{10}O_6S$ [M+H$^+$] 881.3933, found 881.3949.

Example 138

Synthesis of HC75-19

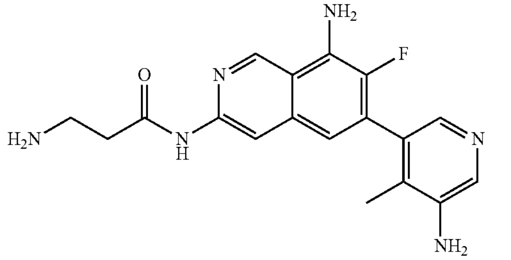

+

Intermediate 11

-continued

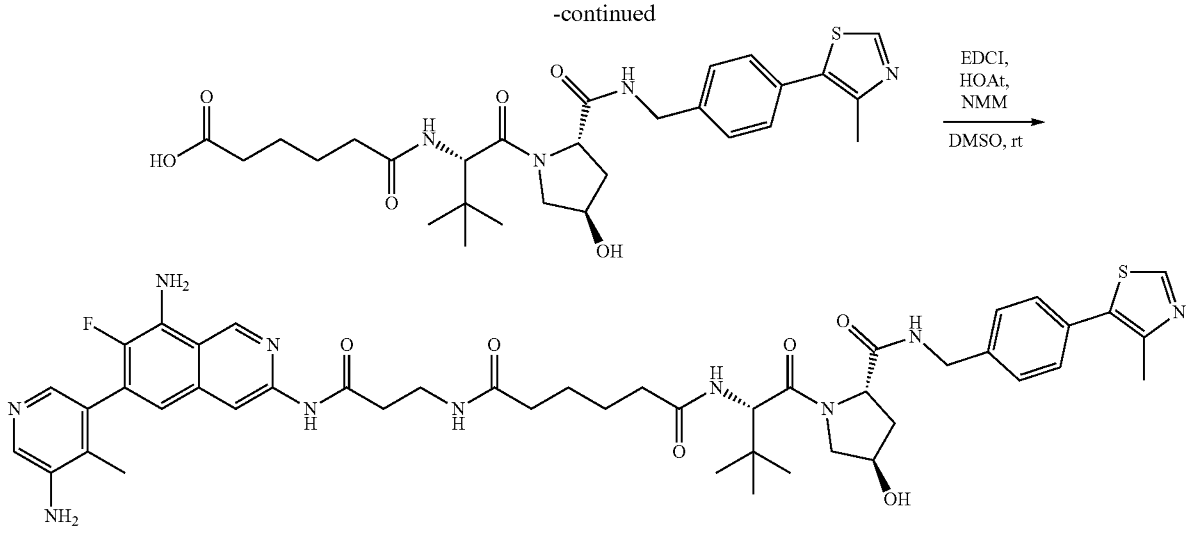

HC75-19

HC75-19 was synthesized following the standard procedure for preparing HC65-175 from Intermediate 11 (11.0 mg, 0.015 mmol, 1.0 equiv), 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid (8.4 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-19 was obtained as yellow solid in TFA salt form (8.1 mg, 48%). $^1$H NMR (600 MHz, Methanol-$d_4$) δ 9.43 (s, 1H), 9.01 (s, 1H), 8.26 (s, 1H), 8.11 (s, 1H), 8.03 (s, 1H), 7.48 (d, J=7.9 Hz, 2H), 7.38 (d, J=8.0 Hz, 2H), 7.06 (d, J=5.6 Hz, 1H), 4.71-4.62 (m, 2H), 4.59 (d, J=15.4 Hz, 1H), 4.54-4.50 (m, 1H), 4.34 (d, J=15.5 Hz, 1H), 3.95 (d, J=11.0 Hz, 1H), 3.84 (dd, J=11.0, 3.9 Hz, 1H), 3.62-3.52 (m, 2H), 2.82 (dt, J=14.3, 6.9 Hz, 1H), 2.60 (d, J=14.4 Hz, 1H), 2.46 (s, 3H), 2.36-2.16 (m, 8H), 2.11 (ddd, J=13.3, 9.3, 4.5 Hz, 1H), 1.69-1.54 (m, 4H), 1.06 (s, 9H). HRMS calcd for $C_{46}H_{56}FN_{10}O_6S$ [M+H$^+$] 895.4089, found 895.4096.

Example 139

Synthesis of HC75-20

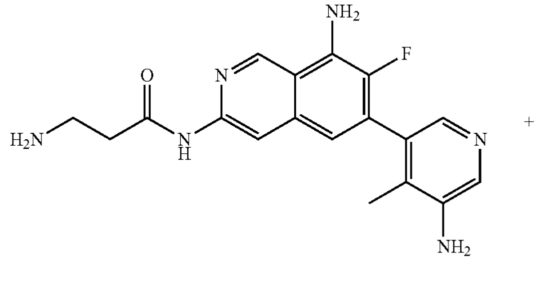

Intermediate 11

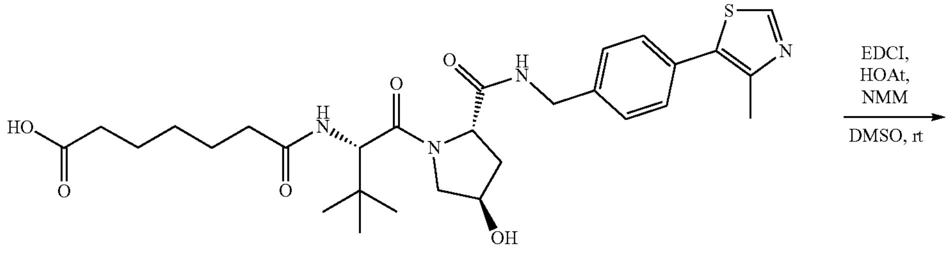

-continued

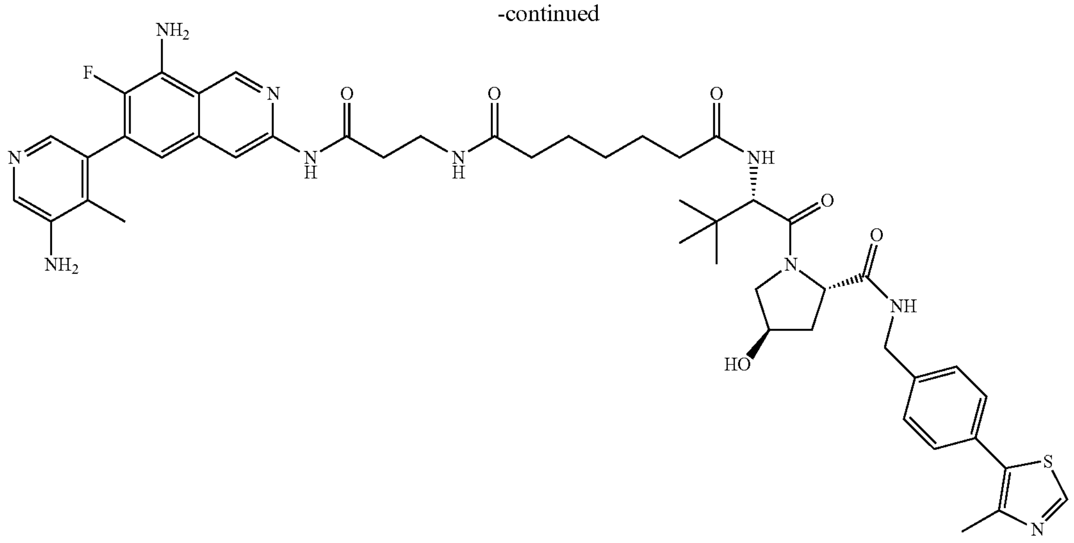

HC75-20

HC75-20 was synthesized following the standard procedure for preparing HC65-175 from Intermediate 11 (11.0 mg, 0.015 mmol, 1.0 equiv), 7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid (8.6 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-20 was obtained as yellow solid in TFA salt form (9.5 mg, 56%). $^1$H NMR (600 MHz, Methanol-$d_4$) δ 9.47 (s, 1H), 9.15 (s, 1H), 8.20 (s, 1H), 8.11 (s, 1H), 8.03 (s, 1H), 7.50 (d, J=7.9 Hz, 2H), 7.42 (d, J=8.2 Hz, 2H), 7.11 (d, J=5.8 Hz, 1H), 4.67 (s, 1H), 4.62 (dd, J=9.3, 7.4 Hz, 1H), 4.58 (d, J=15.5 Hz, 1H), 4.54-4.50 (m, 1H), 4.37 (d, J=15.5 Hz, 1H), 3.94 (d, J=11.0 Hz, 1H), 3.83 (dd, J=11.0, 3.9 Hz, 1H), 3.58 (t, J=6.5 Hz, 2H), 2.85-2.74 (m, 1H), 2.71-2.64 (m, 1H), 2.49 (s, 3H), 2.34-2.16 (m, 8H), 2.11 (ddd, J=13.3, 9.2, 4.5 Hz, 1H), 1.66-1.57 (m, 4H), 1.32 (p, J=7.8 Hz, 2H), 1.05 (s, 9H). HRMS calcd for $C_{47}H_{58}FN_{10}O_6S$ [M+H$^+$] 909.4246, found 909.4258.

Example 140

Synthesis of HC75-21

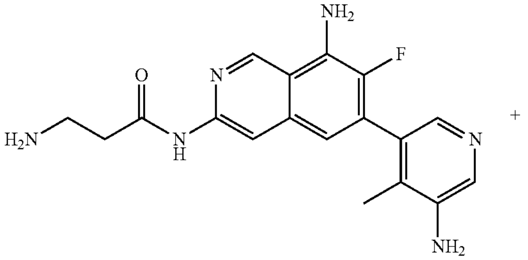

Intermediate 11

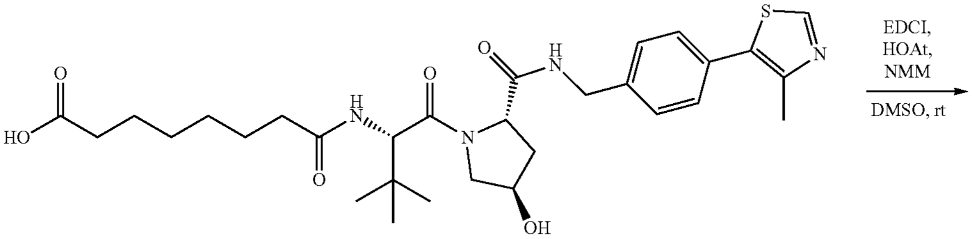

-continued

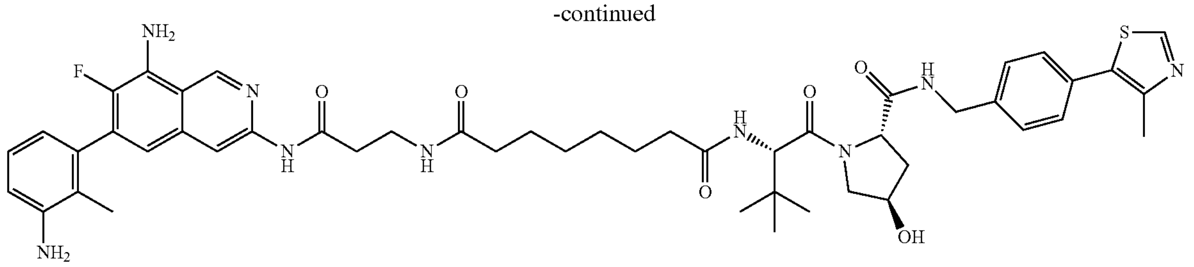

HC75-21

HC75-21 was synthesized following the standard procedure for preparing HC65-175 from Intermediate 11 (11.0 mg, 0.015 mmol, 1.0 equiv), 8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid (8.8 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-21 was obtained as yellow solid in TFA salt form (9.4 mg, 54%). $^1$H NMR (600 MHz, Methanol-$d_4$) δ 9.43 (s, 1H), 9.04 (s, 1H), 8.29 (s, 1H), 8.10 (s, 1H), 8.02 (s, 1H), 7.49 (d, J=7.9 Hz, 2H), 7.42 (d, J=8.0 Hz, 2H), 7.08 (d, J=5.8 Hz, 1H), 4.69 (s, 1H), 4.65-4.61 (m, 1H), 4.57 (d, J=15.5 Hz, 1H), 4.54-4.49 (m, 1H), 4.39 (d, J=15.5 Hz, 1H), 3.94 (d, J=10.9 Hz, 1H), 3.83 (dd, J=10.9, 3.9 Hz, 1H), 3.56 (t, J=6.4 Hz, 2H), 2.79 (dt, J=14.1, 6.7 Hz, 1H), 2.66-2.59 (m, 1H), 2.48 (s, 3H), 2.33-2.15 (m, 8H), 2.10 (ddd, J=13.4, 9.2, 4.5 Hz, 1H), 1.70-1.51 (m, 4H), 1.33-1.23 (m, 4H), 1.06 (s, 9H). HRMS calcd for $C_{48}H_{60}FN_{10}O_6S$ [M+H$^+$] 923.4402, found 923.4415.

Example 141

Synthesis of HC75-22

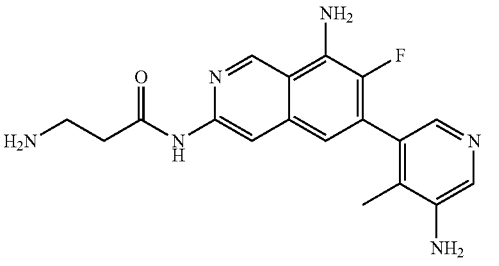

Intermediate 11

+

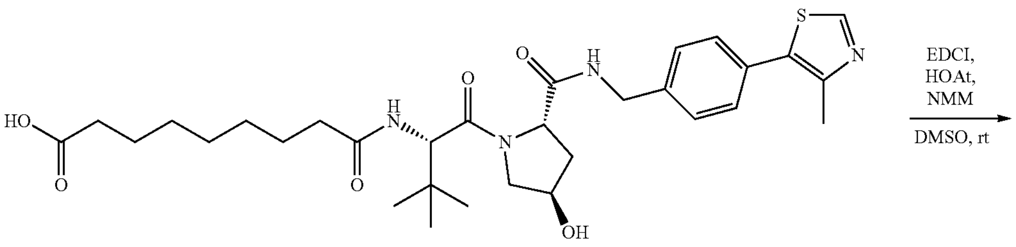

-continued

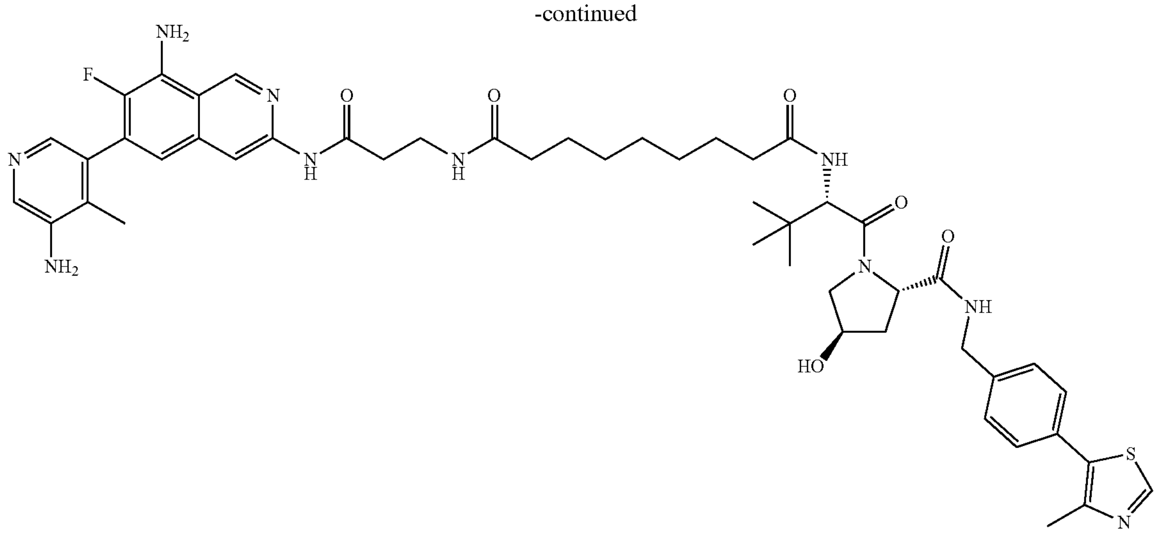

HC75-22

HC75-22 was synthesized following the standard procedure for preparing HC65-175 from Intermediate 11 (11.0 mg, 0.015 mmol, 1.0 equiv), 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid (9.0 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-22 was obtained as yellow solid in TFA salt form (7.8 mg, 45%). $^1$H NMR (600 MHz, Methanol-$d_4$) δ 9.45 (s, 1H), 9.09 (s, 1H), 8.27 (s, 1H), 8.11 (s, 1H), 8.02 (s, 1H), 7.50 (d, J=7.8 Hz, 2H), 7.45-7.42 (m, 2H), 7.10 (d, J=5.2 Hz, 1H), 4.69 (s, 1H), 4.62 (t, J=8.5 Hz, 1H), 4.58 (d, J=15.9 Hz, 1H), 4.53 (s, 1H), 4.41-4.37 (m, 1H), 3.95 (d, J=10.9 Hz, 1H), 3.83 (dd, J=11.0, 3.6 Hz, 1H), 3.56 (q, J=9.5, 6.9 Hz, 2H), 2.80 (dt, J=14.6, 6.9 Hz, 1H), 2.65-2.58 (m, 1H), 2.49 (d, J=3.0 Hz, 3H), 2.30-2.15 (m, 8H), 2.10 (ddt, J=13.1, 8.3, 3.8 Hz, 1H), 1.64-1.48 (m, 4H), 1.34-1.19 (m, 6H), 1.06 (s, 9H). HRMS calcd for $C_{49}H_{62}FN_{10}O_6S$ [M+H$^+$]937.4559, found 937.4567.

Example 142

Synthesis of HC75-23

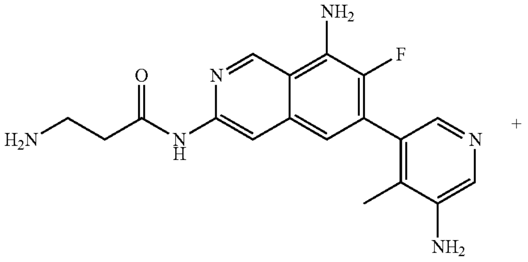

Intermediate 11

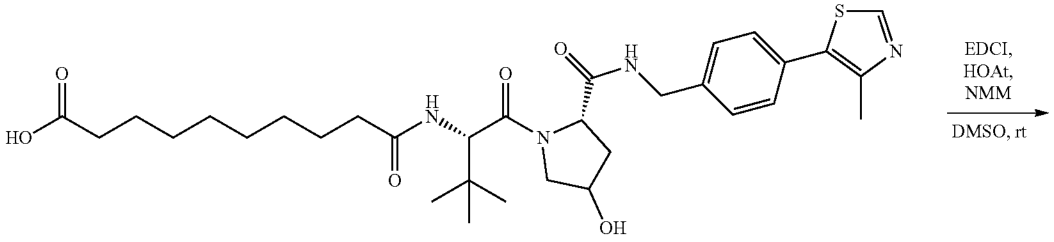

-continued

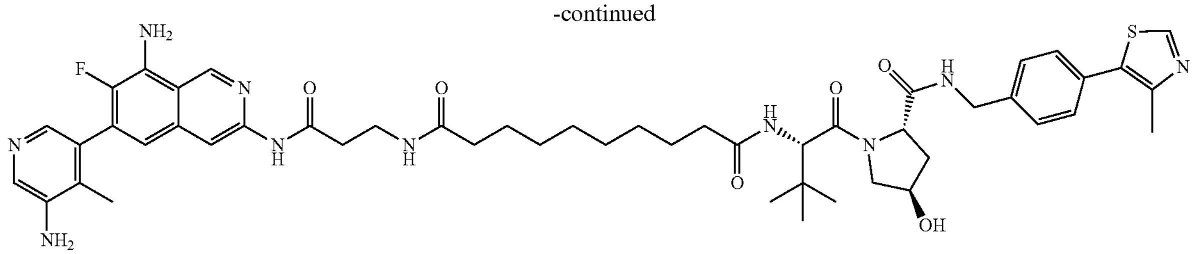

HC75-23

HC75-23 was synthesized following the standard procedure for preparing HC65-175 from Intermediate 11 (11.0 mg, 0.015 mmol, 1.0 equiv), 10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid (9.2 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-23 was obtained as yellow solid in TFA salt form (8.0 mg, 45%). $^1$H NMR (600 MHz, Methanol-$d_4$) δ 9.43 (s, 1H), 9.02 (s, 1H), 8.35 (s, 1H), 8.10 (s, 1H), 8.02 (s, 1H), 7.50 (d, J=8.0 Hz, 2H), 7.43 (d, J=8.0 Hz, 2H), 7.08 (d, J=5.8 Hz, 1H), 4.74 (s, 1H), 4.65-4.57 (m, 2H), 4.56-4.52 (m, 1H), 4.39 (d, J=15.4 Hz, 1H), 3.95 (d, J=11.0 Hz, 1H), 3.85 (dd, J=10.9, 3.9 Hz, 1H), 3.52 (t, J=6.3 Hz, 2H), 2.84 (dt, J=15.6, 6.8 Hz, 1H), 2.58-2.51 (m, 1H), 2.47 (s, 3H), 2.32-2.15 (m, 8H), 2.12 (ddd, J=13.3, 9.0, 4.5 Hz, 1H), 1.71-1.44 (m, 4H), 1.31-1.15 (m, 8H), 1.08 (s, 9H). HRMS calcd for $C_{50}H_{64}FN_{10}O_6S$ [M+H$^+$] 951.4715, found 951.4730.

Example 143

Synthesis of HC75-24

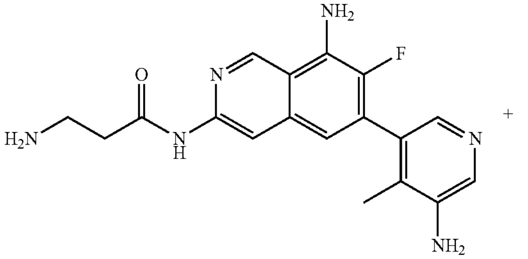

Intermediate 11

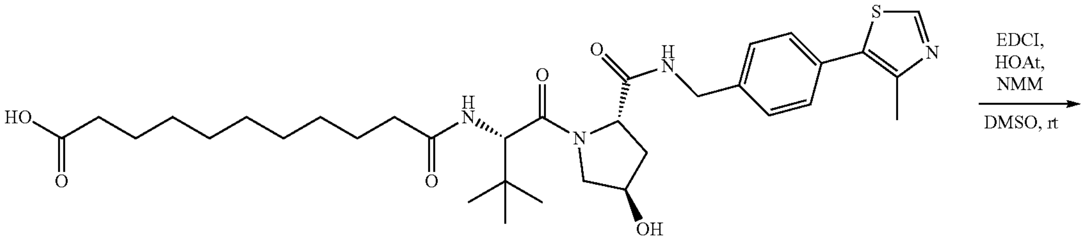

-continued

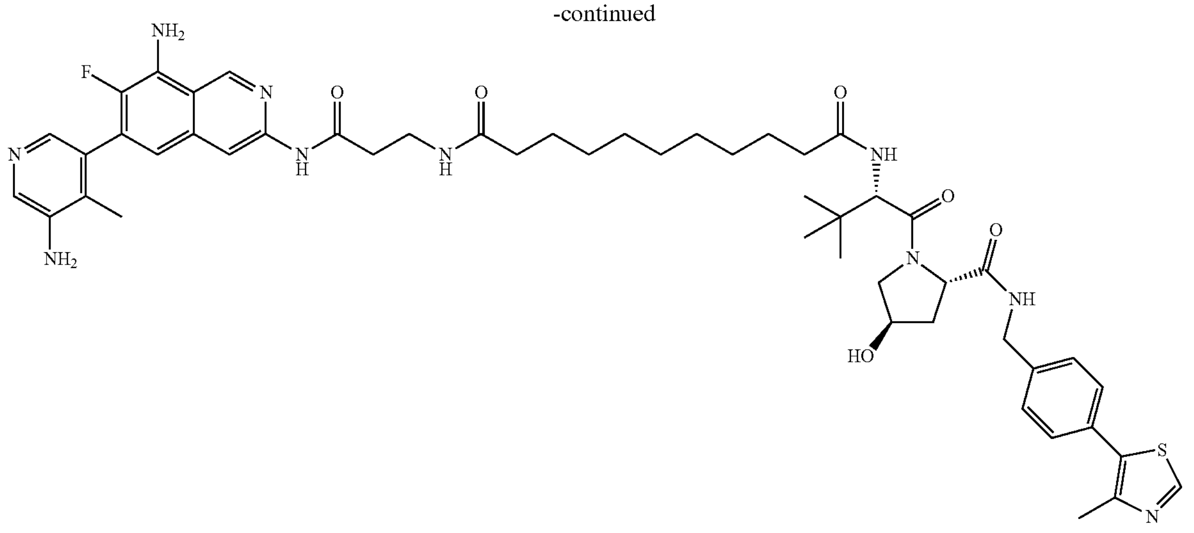

HC75-24

HC75-24 was synthesized following the standard procedure for preparing HC65-175 from Intermediate 11 (11.0 mg, 0.015 mmol, 1.0 equiv), 11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (9.4 mg, 0.015 mmol, 1.0 equiv), EDCI (4.3 mg, 0.0225 mmol, 1.5 equiv), HOAt (3.1 mg, 0.0225 mmol, 1.5 equiv), and NMM (7.6 mg, 0.075 mmol, 5.0 equiv) in DMSO (1 mL). HC75-24 was obtained as yellow solid in TFA salt form (9.1 mg, 51%). $^{1}H$ NMR (600 MHz, Methanol-$d_4$) δ 9.42 (s, 1H), 9.05 (s, 1H), 8.28 (s, 1H), 8.10 (s, 1H), 8.02 (s, 1H), 7.49 (d, J=8.0 Hz, 2H), 7.43 (d, J=8.1 Hz, 2H), 7.09 (d, J=5.8 Hz, 1H), 4.66 (s, 1H), 4.63-4.55 (m, 2H), 4.54-4.51 (m, 1H), 4.37 (d, J=15.5 Hz, 1H), 3.93 (d, J=11.0 Hz, 1H), 3.83 (dd, J=11.0, 3.9 Hz, 1H), 3.57 (t, J=6.5 Hz, 2H), 2.81-2.69 (m, 2H), 2.49 (s, 3H), 2.33-2.15 (m, 8H), 2.11 (ddd, J=13.4, 9.2, 4.5 Hz, 1H), 1.63-1.50 (m, 4H), 1.33-1.16 (m, 10H), 1.05 (s, 9H). HRMS calcd for $C_{51}H_{66}FN_{10}O_6S$ [M+H$^+$] 965.4872, found 965.4881.

Example 144

Synthesis of HC75-29

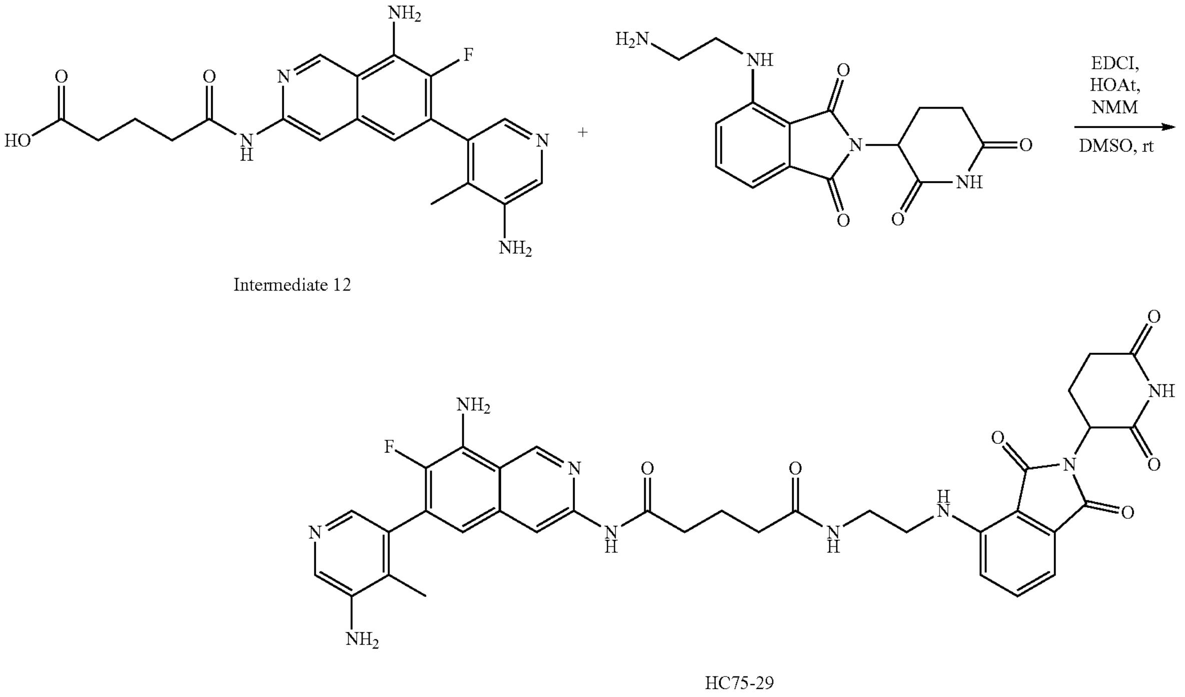

Intermediate 12

HC75-29

To a solution of Intermediate 12 (12 mg, 0.0192 mmol, 1.0 equiv) in DMSO (1 mL) were added 4-((2-aminoethyl) amino)-2-(2,6-dioxopiperidin-3-yl)isoindoline-1,3-dione (9.5 mg, 0.022 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (10.2 mg, 0.1 mmol, 5.0 equiv). After being stirred overnight at room temperature, the resulting mixture was purified by preparative HPLC (10%-100% MeOH/0.1% TFA in $H_2O$) to afford HC75-29 as yellow solid in TFA salt form (8.1 mg, 58%). $^1H$ NMR (600 MHz, Methanol-$d_4$) δ 9.37 (s, 1H), 8.19 (s, 1H), 8.10 (s, 1H), 8.05 (s, 1H), 7.52 (t, J=7.8 Hz, 1H), 7.12-7.05 (m, 2H), 6.96 (d, J=7.1 Hz, 1H), 5.04 (dd, J=12.3, 5.4 Hz, 1H), 3.48 (s, 4H), 2.86-2.75 (m, 1H), 2.74-2.64 (m, 2H), 2.55 (t, J=7.4 Hz, 2H), 2.34 (t, J=7.1 Hz, 2H), 2.25 (s, 3H), 2.13-2.00 (m, 3H). HRMS calcd for $C_{35}H_{35}FN_9O_6[M+H^+]$ 696.2694, found 696.2687.

Example 145

Synthesis of HC75-31

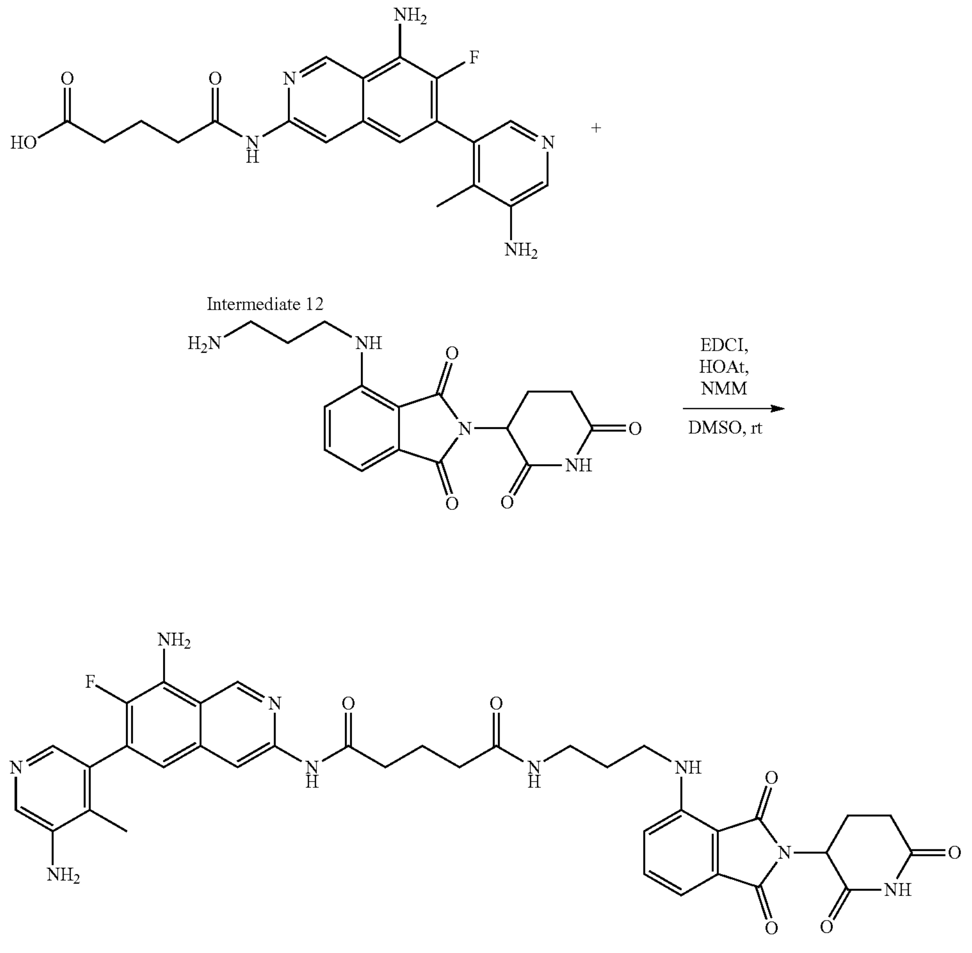

HC75-31

HC75-31 was synthesized following the standard procedure for preparing HC75-29 from Intermediate 12 (6.6 mg, 0.011 mmol, 1.0 equiv), 4-((3-aminopropyl)amino)-2-(2,6-dioxopiperidin-3-yl)isoindoline-1,3-dione (5.2 mg, 0.012 mmol, 1.1 equiv), EDCI (3.2 mg, 0.0165 mmol, 1.5 equiv), HOAt (2.2 mg, 0.0165 mmol, 1.5 equiv), and NMM (5.6 mg, 0.055 mmol, 5.0 equiv) in DMSO (0.8 mL). HC75-31 was obtained as yellow solid in TFA salt form (6.9 mg, 67%). $^1H$ NMR (600 MHz, Methanol-$d_4$) δ 9.38 (s, 1H), 8.19 (s, 1H), 8.10 (s, 1H), 8.03 (s, 1H), 7.50 (dd, J=8.6, 7.0 Hz, 1H), 7.08 (d, J=5.8 Hz, 1H), 7.01 (d, J=8.6 Hz, 1H), 6.97 (d, J=7.1 Hz, 1H), 5.06 (dd, J=12.8, 5.5 Hz, 1H), 3.38 (t, J=6.7 Hz, 2H), 3.33 (s, 2H), 2.86 (ddd, J=17.5, 13.9, 5.4 Hz, 1H), 2.79-2.66 (m, 2H), 2.58 (t, J=7.2 Hz, 2H), 2.36 (t, J=7.3 Hz, 2H), 2.24 (s, 3H), 2.16-2.02 (m, 3H), 1.85 (p, J=6.6 Hz, 2H). HRMS calcd for $C_{36}H_{37}FN_9O_6[M+H^+]$ 710.2851, found 710.2859.

Example 146

Synthesis of HC75-34

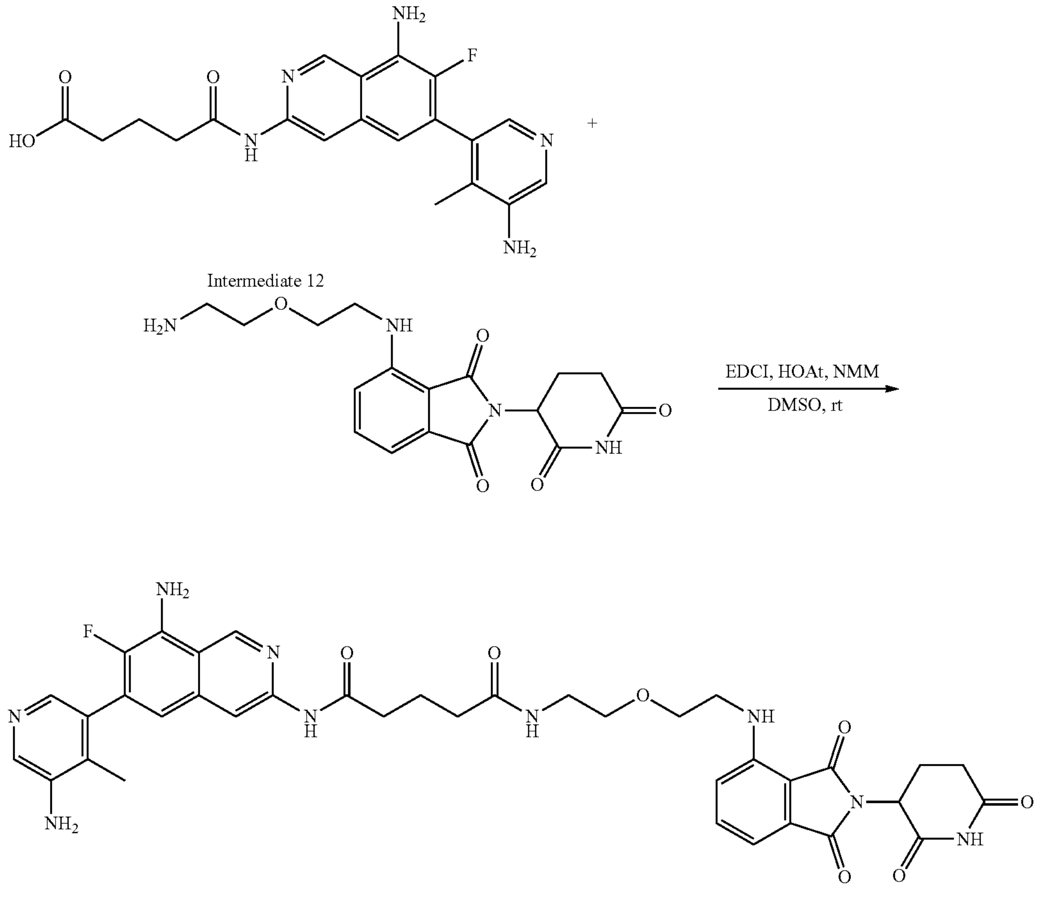

Intermediate 12

HC75-34

HC75-34 was synthesized following the standard procedure for preparing HC75-29 from Intermediate 12 (9.0 mg, 0.0144 mmol, 1.0 equiv), 4-((2-(2-aminoethoxy)ethyl)amino)-2-(2,6-dioxopiperidin-3-yl)isoindoline-1,3-dione (7.6 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-34 was obtained as yellow solid in TFA salt form (7.7 mg, 55%). $^1$H NMR (600 MHz, Methanol-$d_4$) δ 9.21 (s, 1H), 8.30 (s, 1H), 8.10 (s, 1H), 8.06 (s, 1H), 7.41 (t, J=7.8 Hz, 1H), 7.05-6.89 (m, 2H), 6.76 (s, 1H), 5.05 (dd, J=12.7, 5.5 Hz, 1H), 3.82-3.72 (m, 2H), 3.66 (t, J=5.0 Hz, 2H), 3.35-3.60 (m, 4H), 2.89 (ddd, J=17.5, 13.9, 5.4 Hz, 1H), 2.82-2.66 (m, 2H), 2.54 (t, J=7.0 Hz, 2H), 2.40 (s, 2H), 2.24 (s, 3H), 2.12-1.99 (m, 3H). HRMS calcd for $C_{37}H_{39}FN_9O_7$[M+H$^+$] 740.2956, found 740.2965.

Example 147

Synthesis of HC75-35

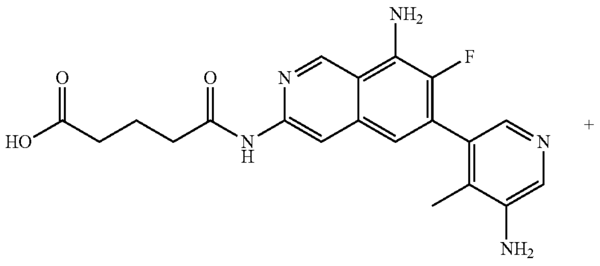

Intermediate 12

-continued

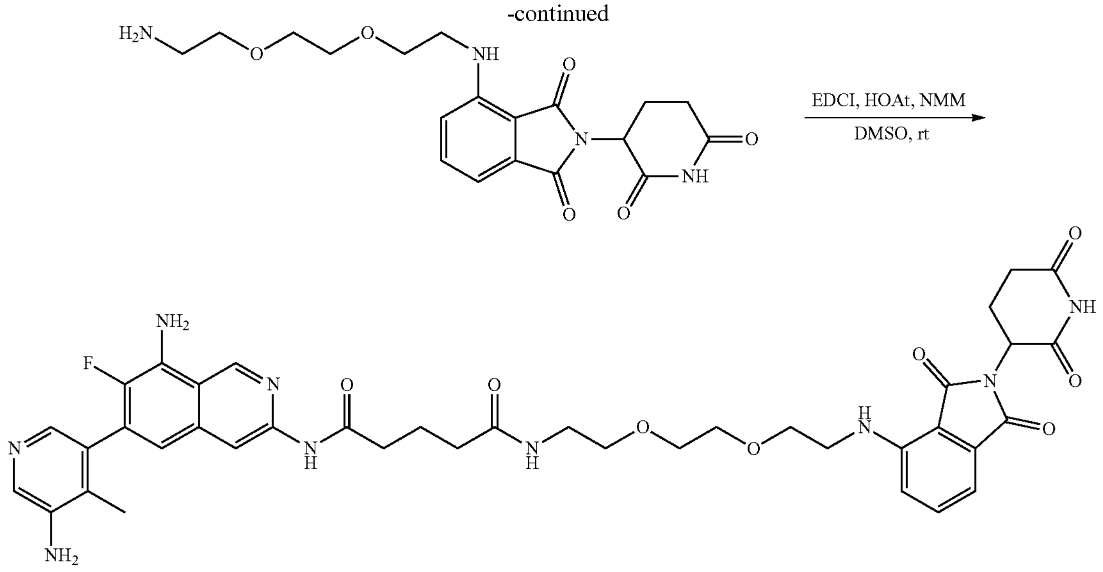

HC75-35

HC75-35 was synthesized following the standard procedure for preparing HC75-29 from Intermediate 12 (9.0 mg, 0.0144 mmol, 1.0 equiv), 4-((2-(2-(2-aminoethoxy)ethoxy)ethyl)amino)-2-(2,6-dioxopiperidin-3-yl)isoindoline-1,3-dione (8.3 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-35 was obtained as yellow solid in TFA salt form (9.7 mg, 67%). $^{1}$H NMR (600 MHz, Methanol-$d_4$) δ 9.29 (s, 1H), 8.24 (s, 1H), 8.09 (s, 1H), 8.03 (s, 1H), 7.45 (t, J=7.8 Hz, 1H), 7.02 (d, J=5.8 Hz, 1H), 6.98 (d, J=8.5 Hz, 1H), 6.89 (d, J=7.0 Hz, 1H), 5.05 (dd, J=12.7, 5.5 Hz, 1H), 3.77-3.70 (m, 2H), 3.70-3.63 (m, 4H), 3.59 (t, J=5.3 Hz, 2H), 3.47 (t, J=5.2 Hz, 2H), 3.39 (t, J=5.3 Hz, 2H), 2.88 (ddd, J=18.6, 13.8, 5.4 Hz, 1H), 2.81-2.66 (m, 2H), 2.55 (t, J=7.3 Hz, 2H), 2.33 (t, J=7.3 Hz, 2H), 2.23 (s, 3H), 2.17-2.10 (m, 1H), 2.05 (p, J=7.3 Hz, 2H). HRMS calcd for $C_{39}H_{43}FN_9O_8$[M+H$^+$] 784.3219, found 784.3211.

Example 148

Synthesis of HC75-36

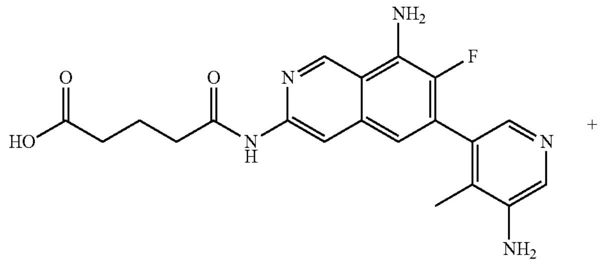

Intermediate 12

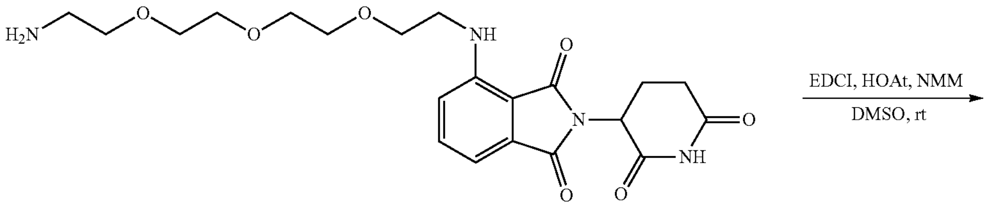

-continued

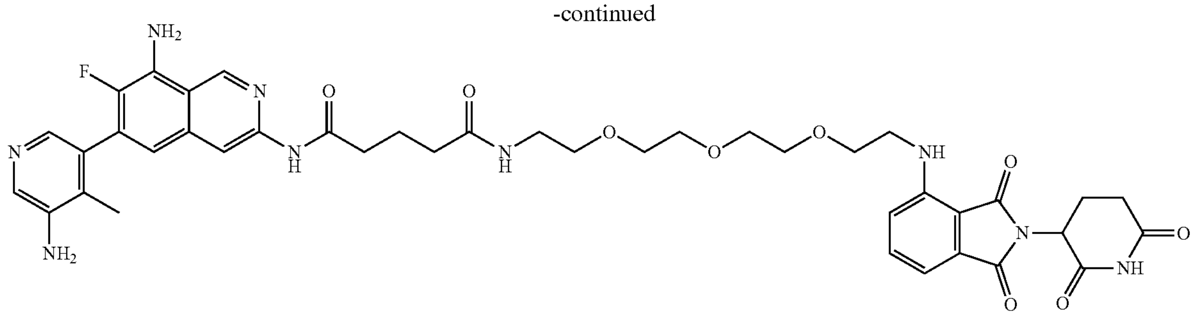

HC75-36

HC75-36 was synthesized following the standard procedure for preparing HC75-29 from Intermediate 12 (9.0 mg, 0.0144 mmol, 1.0 equiv), 4-((2-(2-(2-(2-aminoethoxy)ethoxy)ethoxy)ethyl)amino)-2-(2,6-dioxopiperidin-3-yl)isoindoline-1,3-dione (9.0 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-36 was obtained as yellow solid in TFA salt form (9.6 mg, 63%). $^1$H NMR (600 MHz, Methanol-$d_4$) δ 9.36 (s, 1H), 8.15 (s, 1H), 8.10 (s, 1H), 8.03 (s, 1H), 7.47 (t, J=7.8 Hz, 1H), 7.07 (s, 1H), 6.99 (d, J=8.5 Hz, 1H), 6.93 (s, 1H), 5.06 (dd, J=12.8, 5.5 Hz, 1H), 3.71 (t, J=5.2 Hz, 2H), 3.69-3.64 (m, 6H), 3.64-3.60 (m, 2H), 3.55 (t, J=5.3 Hz, 2H), 3.46 (t, J=5.2 Hz, 2H), 3.40-3.36 (m, 2H), 2.88 (ddd, J=18.5, 13.9, 5.4 Hz, 1H), 2.80-2.65 (m, 2H), 2.58 (s, 2H), 2.35 (t, J=7.2 Hz, 2H), 2.23 (s, 3H), 2.16-2.10 (m, 1H), 2.06 (t, J=7.3 Hz, 2H). HRMS calcd for $C_{41}H_{47}FN_9O_9$[M+H$^+$]828.3481, found 828.3488.

Example 149

Synthesis of HC75-37

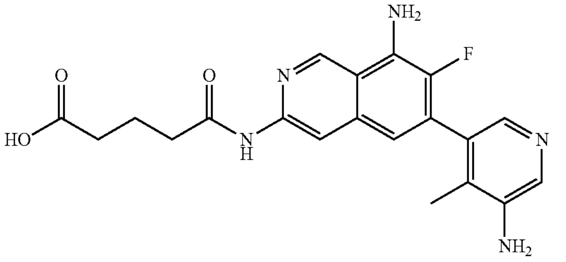

Intermediate 12

+

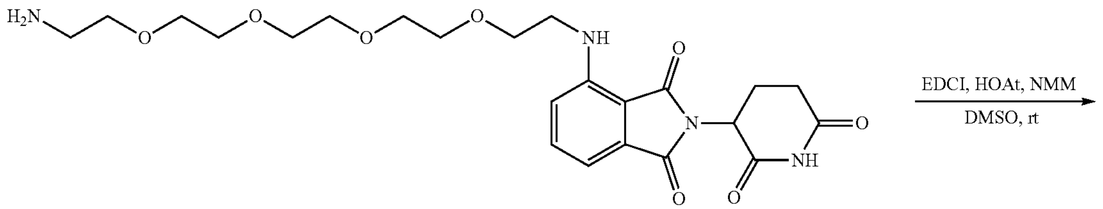

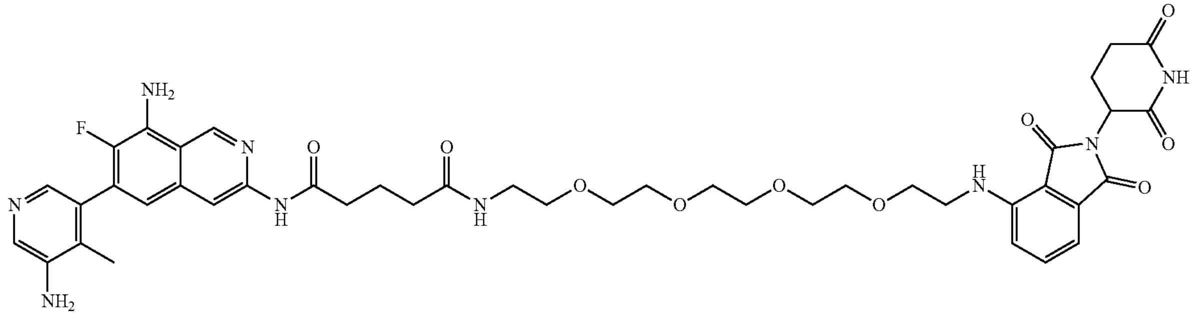

HC75-37

HC75-37 was synthesized following the standard procedure for preparing HC75-29 from Intermediate 12 (9.0 mg, 0.0144 mmol, 1.0 equiv), 4-((14-amino-3,6,9,12-tetraoxatetradecyl)amino)-2-(2,6-dioxopiperidin-3-yl)isoindoline-1,3-dione (9.0 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-37 was obtained as yellow solid in TFA salt form (5.6 mg, 35%). $^1$H NMR (600 MHz, Methanol-$d_4$) δ 9.34 (s, 1H), 8.27 (s, 1H), 8.08 (s, 1H), 8.02 (s, 1H), 7.50 (t, J=7.8 Hz, 1H), 7.08-7.00 (m, 2H), 6.97 (d, J=7.0 Hz, 1H), 5.06 (dd, J=12.7, 5.5 Hz, 1H), 3.71 (t, J=5.1 Hz, 2H), 3.67-3.57 (m, 12H), 3.55 (t, J=5.2 Hz, 2H), 3.46 (t, J=5.2 Hz, 2H), 3.38 (t, J=5.2 Hz, 2H), 2.87 (ddd, J=18.3, 13.9, 5.3 Hz, 1H), 2.80-2.66 (m, 2H), 2.57 (s, 2H), 2.36 (s, 2H), 2.23 (s, 3H), 2.16-2.09 (m, 1H), 2.09-2.00 (m, 2H). HRMS calcd for $C_{43}H_{51}FN_9O_{10}$ [M+H$^+$] 872.3743, found 872.3749.

Example 150

Synthesis of HC75-38

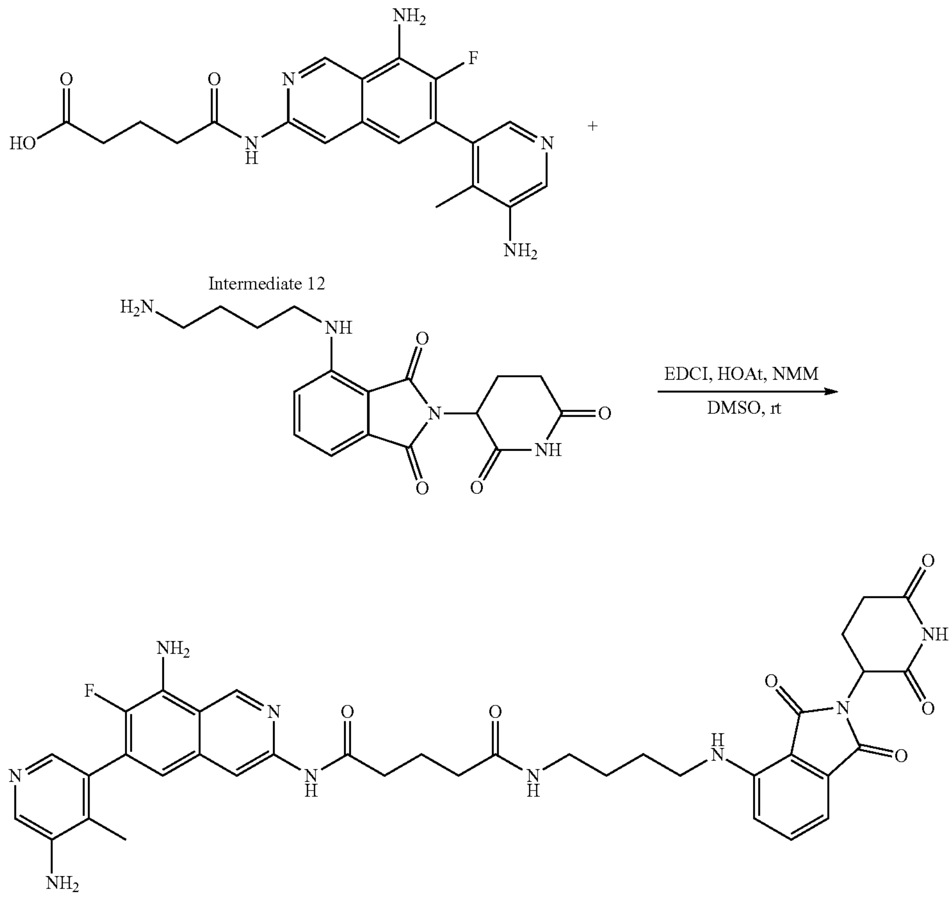

HC75-38

HC75-38 was synthesized following the standard procedure for preparing HC75-29 from Intermediate 12 (9.0 mg, 0.0144 mmol, 1.0 equiv), 4-((4-aminobutyl)amino)-2-(2,6-dioxopiperidin-3-yl)isoindoline-1,3-dione (7.4 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-38 was obtained as yellow solid in TFA salt form (8.1 mg, 59%). $^1$H NMR (600 MHz, Methanol-$d_4$) δ 9.37 (s, 1H), 8.23 (s, 1H), 8.10 (s, 1H), 8.03 (s, 1H), 7.51 (dd, J=8.6, 7.1 Hz, 1H), 7.08 (d, J=5.8 Hz, 1H), 7.02 (d, J=8.5 Hz, 1H), 6.96 (d, J=7.1 Hz, 1H), 5.04 (dd, J=12.7, 5.5 Hz, 1H), 3.35-3.31 (m, 2H), 3.26 (t, J=6.6 Hz, 2H), 2.85 (ddd, J=17.4, 13.9, 5.3 Hz, 1H), 2.79-2.63 (m, 2H), 2.55 (t, J=7.4 Hz, 2H), 2.34 (t, J=7.2 Hz, 2H), 2.24 (s, 3H), 2.14-2.00 (m, 3H), 1.74-1.59 (m, 4H). HRMS calcd for $C_{37}H_{39}FN_9O_6$[M+H$^+$] 724.3007, found 724.3014.

Example 151

Synthesis of HC75-39

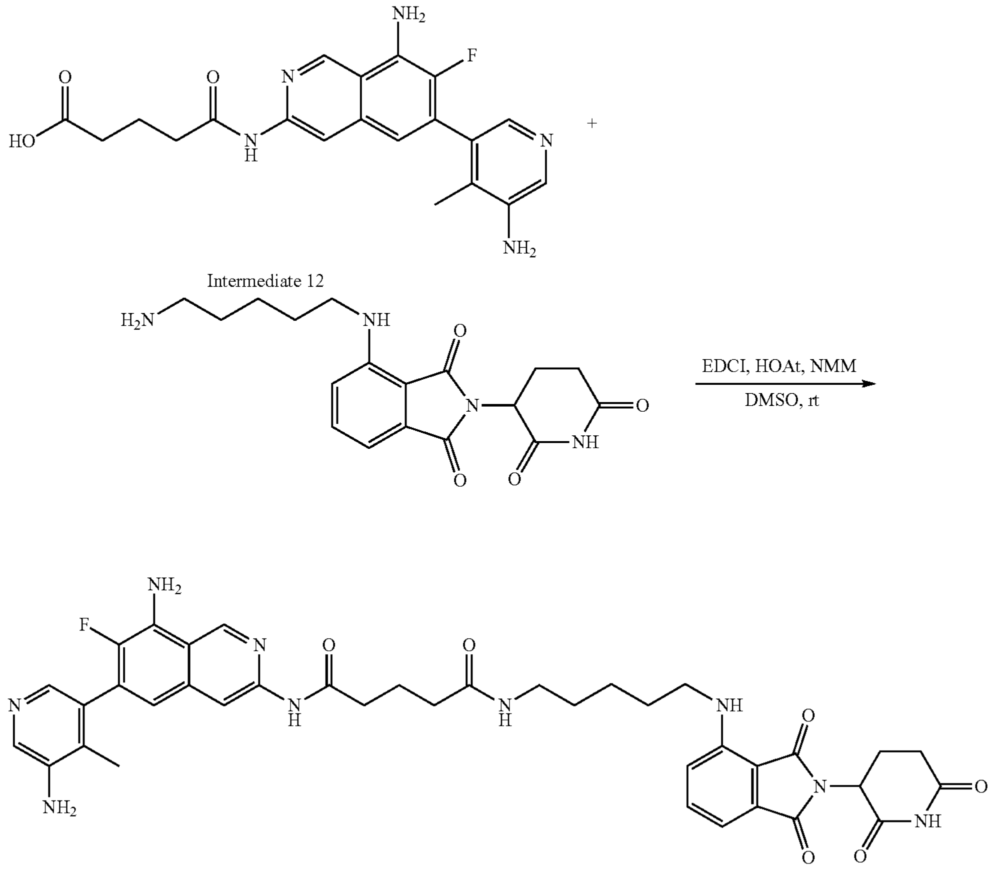

HC75-39

HC75-39 was synthesized following the standard procedure for preparing HC75-29 from Intermediate 12 (9.0 mg, 0.0144 mmol, 1.0 equiv), 4-((5-aminopentyl)amino)-2-(2,6-dioxopiperidin-3-yl)isoindoline-1,3-dione (7.6 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-39 was obtained as yellow solid in TFA salt form (9.6 mg, 69%). $^1$H NMR (600 MHz, Methanol-d$_4$) δ 9.36 (s, 1H), 8.24 (s, 1H), 8.10 (s, 1H), 8.03 (s, 1H), 7.52-7.48 (m, 1H), 7.07 (d, J=5.8 Hz, 1H), 6.99 (d, J=8.6 Hz, 1H), 6.95 (d, J=7.1 Hz, 1H), 5.05 (dd, J=12.8, 5.5 Hz, 1H), 3.30 (t, J=6.9 Hz, 2H), 3.23 (t, J=6.8 Hz, 2H), 2.86 (ddd, J=17.7, 14.0, 5.4 Hz, 1H), 2.79-2.67 (m, 2H), 2.55 (t, J=7.4 Hz, 2H), 2.33 (t, J=7.3 Hz, 2H), 2.24 (s, 3H), 2.15-2.09 (m, 1H), 2.05 (p, J=7.4 Hz, 2H), 1.68 (p, J=7.1 Hz, 2H), 1.58 (p, J=7.0 Hz, 2H), 1.52-1.40 (m, 2H). HRMS calcd for $C_{38}H_{41}FN_9O_6$[M+H$^+$] 738.3164, found 738.3169.

Example 152

Synthesis of HC75-40

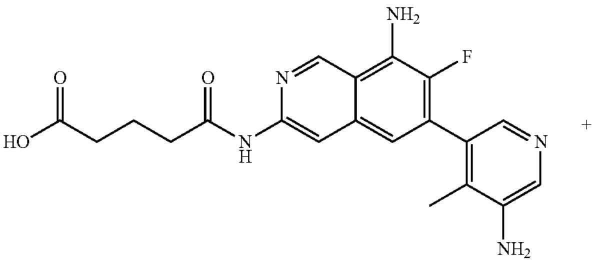

Intermediate 12

-continued

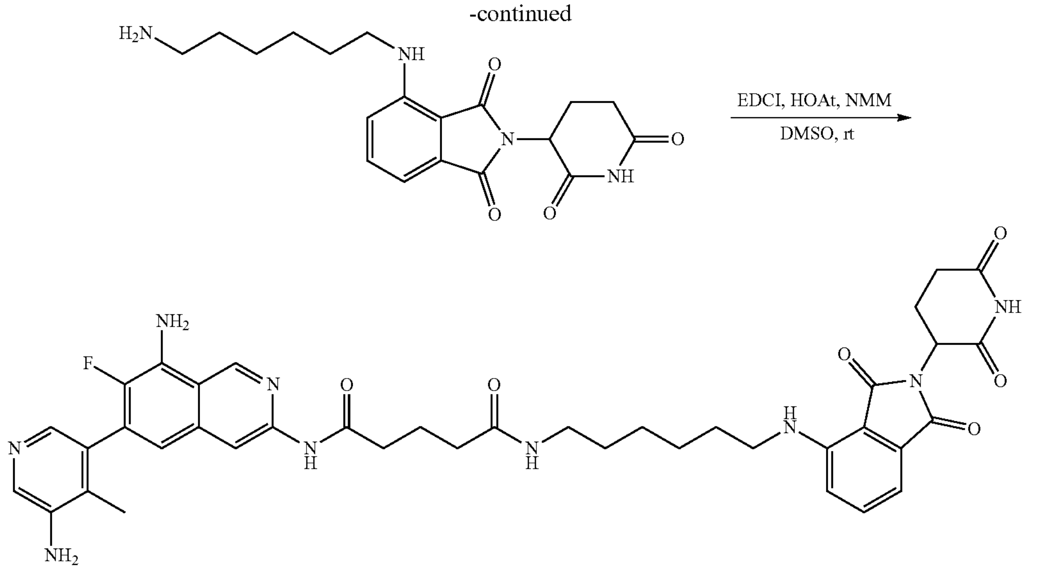

HC75-40

HC75-40 was synthesized following the standard procedure for preparing HC75-29 from Intermediate 12 (9.0 mg, 0.0144 mmol, 1.0 equiv), 4-((6-aminohexyl)amino)-2-(2,6-dioxopiperidin-3-yl)isoindoline-1,3-dione (6.5 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-40 was obtained as yellow solid in TFA salt form (9.8 mg, 69%). $^1$H NMR (600 MHz, Methanol-$d_4$) δ 9.40 (s, 1H), 8.17 (s, 1H), 8.10 (s, 1H), 8.03 (s, 1H), 7.55-7.46 (m, 1H), 7.09 (d, J=5.9 Hz, 1H), 6.99 (d, J=8.6 Hz, 1H), 6.95 (d, J=7.0 Hz, 1H), 5.05 (dd, J=12.6, 5.5 Hz, 1H), 3.29 (t, J=7.1 Hz, 2H), 3.21 (t, J=6.9 Hz, 2H), 2.87 (ddd, J=18.2, 13.8, 5.4 Hz, 1H), 2.80-2.66 (m, 2H), 2.57 (t, J=7.4 Hz, 2H), 2.34 (t, J=7.2 Hz, 2H), 2.24 (s, 3H), 2.16-2.09 (m, 1H), 2.06 (p, J=7.4 Hz, 2H), 1.66 (p, J=7.1 Hz, 2H), 1.59-1.49 (m, 2H), 1.49-1.33 (m, 4H). HRMS calcd for $C_{39}H_{43}FN_9O_6$[M+H$^+$] 752.3320, found 752.3329.

Example 153

Synthesis of HC75-41

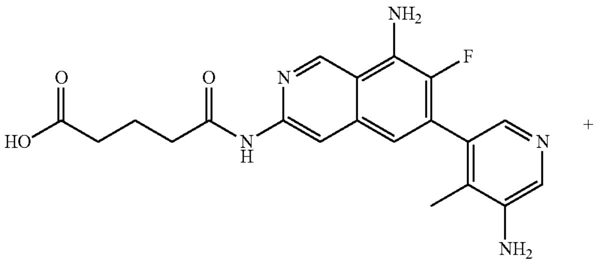

Intermediate 12

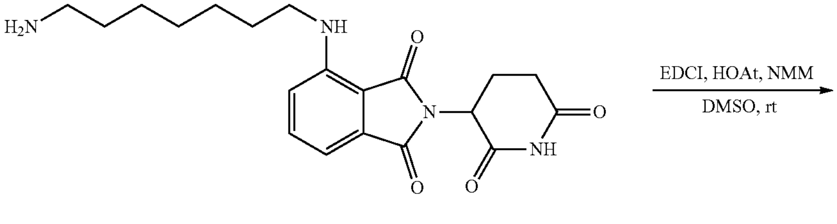

-continued

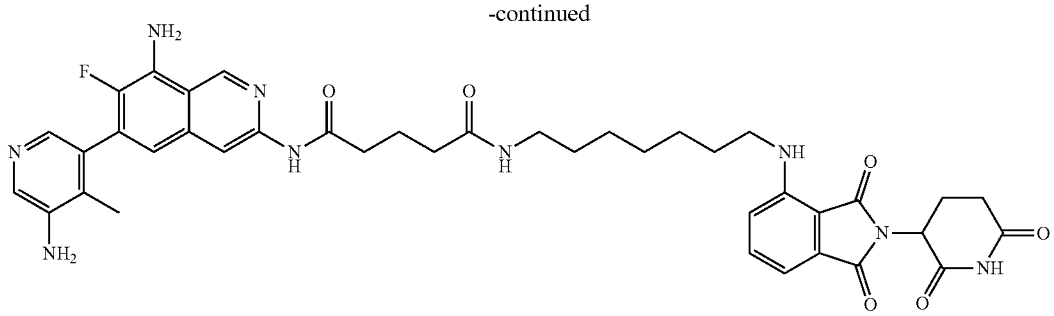

HC75-41

HC75-41 was synthesized following the standard procedure for preparing HC75-29 from Intermediate 12 (9.0 mg, 0.0144 mmol, 1.0 equiv), 4-((7-aminoheptyl)amino)-2-(2,6-dioxopiperidin-3-yl)isoindoline-1,3-dione (8.0 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-41 was obtained as yellow solid in TFA salt form (5.3 mg, 37%). $^1$H NMR (600 MHz, Methanol-$d_4$) δ 9.36 (s, 1H), 8.26 (s, 1H), 8.09 (s, 1H), 8.02 (s, 1H), 7.54-7.46 (m, 1H), 7.07 (d, J=5.8 Hz, 1H), 6.98 (d, J=8.6 Hz, 1H), 6.96 (d, J=7.1 Hz, 1H), 5.06 (dd, J=12.7, 5.5 Hz, 1H), 3.28 (t, J=7.0 Hz, 2H), 3.20 (t, J=6.9 Hz, 2H), 2.87 (ddd, J=17.4, 13.9, 5.3 Hz, 1H), 2.79-2.66 (m, 2H), 2.56 (t, J=7.4 Hz, 2H), 2.33 (t, J=7.3 Hz, 2H), 2.24 (s, 3H), 2.16-2.09 (m, 1H), 2.05 (p, J=7.4 Hz, 2H), 1.66 (p, J=7.1 Hz, 2H), 1.52 (p, J=7.0 Hz, 2H), 1.47-1.32 (m, 6H). HRMS calcd for $C_{40}H_{45}FN_9O_6[M+H^+]$ 766.3477, found 766.3489.

Example 154

Synthesis of HC75-42

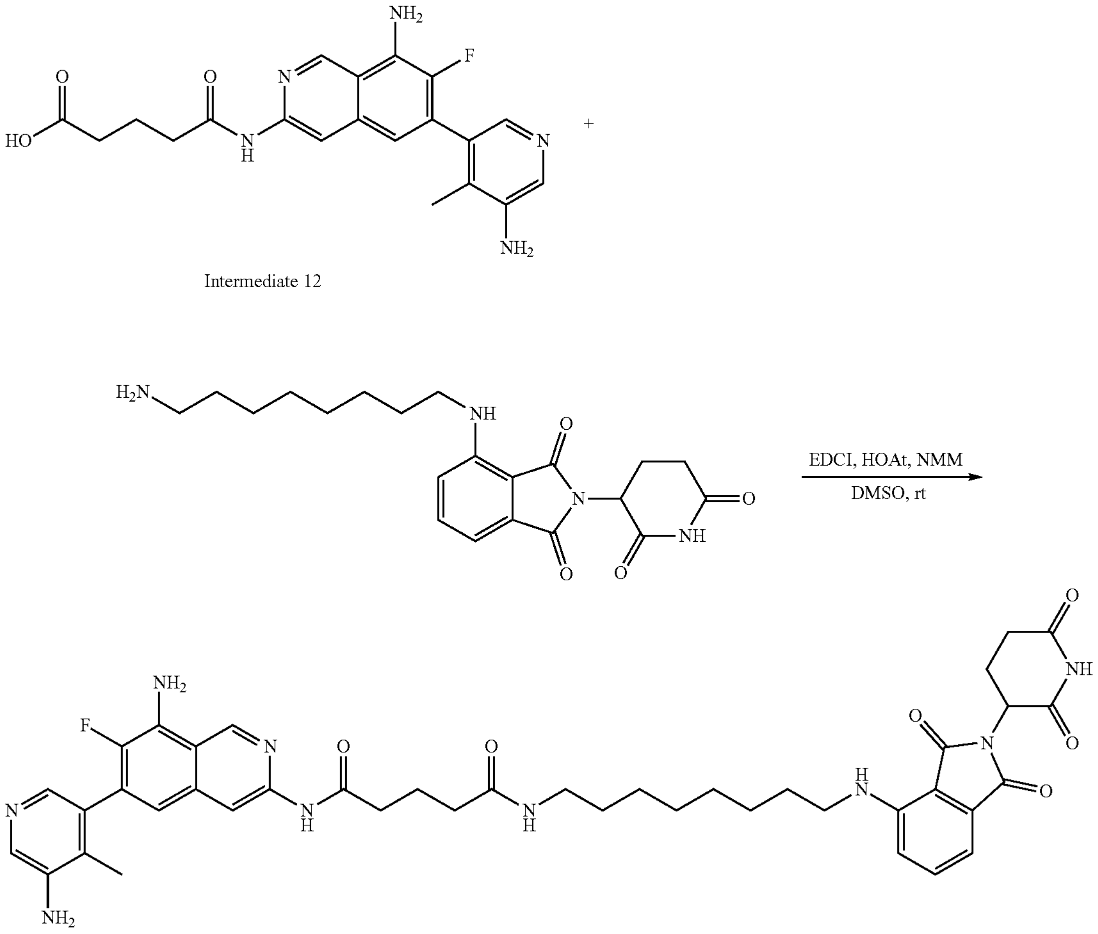

Intermediate 12

HC75-42

HC75-42 was synthesized following the standard procedure for preparing HC75-29 from Intermediate 12 (9.0 mg, 0.0144 mmol, 1.0 equiv), 4-((8-aminooctyl)amino)-2-(2,6-dioxopiperidin-3-yl)isoindoline-1,3-dione (8.2 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-42 was obtained as yellow solid in TFA salt form (9.9 mg, 68%). $^1$H NMR (600 MHz, Methanol-$d_4$) δ 9.40 (s, 1H), 8.17 (s, 1H), 8.10 (s, 1H), 8.02 (s, 1H), 7.50 (t, J=7.8 Hz, 1H), 7.09 (d, J=5.8 Hz, 1H), 7.00-6.94 (m, 2H), 5.06 (dd, J=12.7, 5.5 Hz, 1H), 3.28 (t, J=7.0 Hz, 2H), 3.19 (t, J=6.9 Hz, 2H), 2.87 (ddd, J=18.2, 13.7, 5.5 Hz, 1H), 2.80-2.65 (m, 2H), 2.58 (t, J=7.4 Hz, 2H), 2.34 (t, J=7.3 Hz, 2H), 2.24 (s, 3H), 2.17-2.09 (m, 1H), 2.06 (p, J=7.5 Hz, 2H), 1.63 (p, J=7.1 Hz, 2H), 1.56-1.49 (m, 2H), 1.46-1.30 (m, 8H). HRMS calcd for $C_{41}H_{47}FN_9O_6[M+H^+]$ 780.3633, found 780.3639.

Example 155

Synthesis of HC75-43

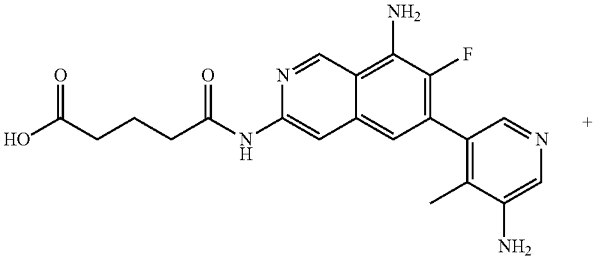

Intermediate 12

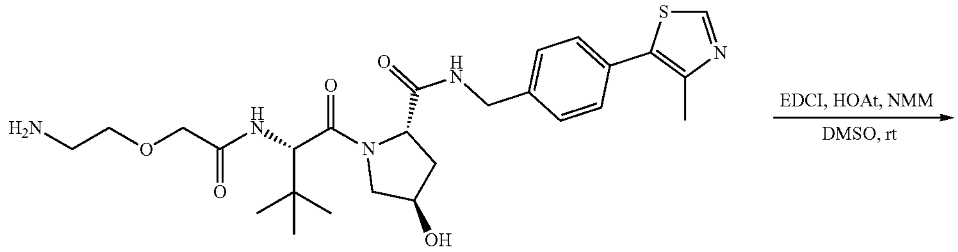

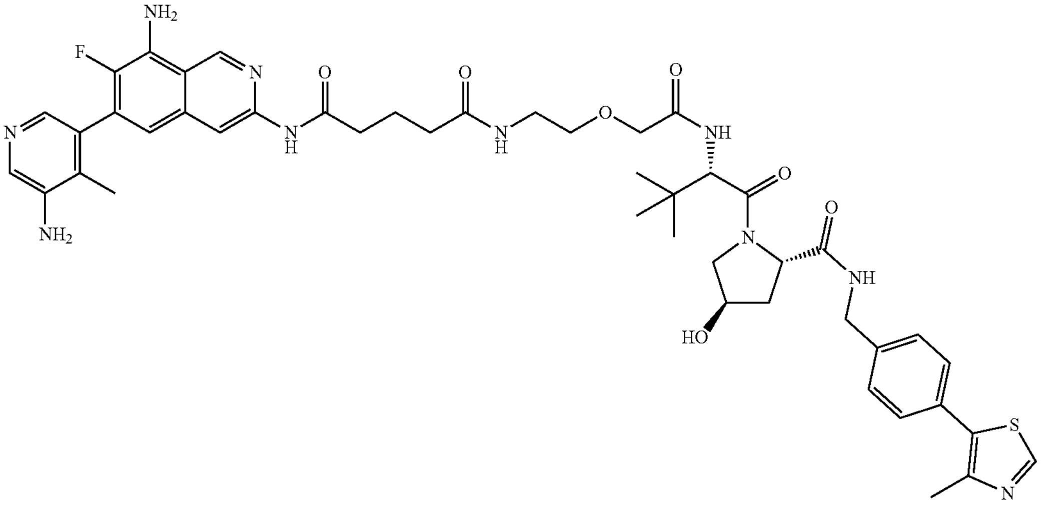

HC75-43

HC75-43 was synthesized following the standard procedure for preparing HC75-29 from Intermediate 12 (9.0 mg, 0.0144 mmol, 1.0 equiv), (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide (8.1 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-43 was obtained as yellow solid in TFA salt form (4.9 mg, 30%). $^1$H NMR (600 MHz, Methanol-$d_4$) δ 9.36 (s, 1H), 8.95 (s, 1H), 8.28 (s, 1H), 8.09 (s, 1H), 7.99 (s, 1H), 7.45 (d, J=7.4 Hz, 2H), 7.40 (d, J=8.0 Hz, 2H), 7.01 (d, J=5.9 Hz, 1H), 4.72 (s, 1H), 4.62 (dd, J=9.3, 7.6 Hz, 1H), 4.57-4.51 (m, 2H), 4.35 (d, J=15.6 Hz, 1H), 4.09 (d, J=15.3 Hz, 1H), 4.00 (d, J=15.2 Hz, 1H), 3.90 (d, J=11.1 Hz, 1H), 3.82 (dd, J=11.0, 3.8 Hz, 1H), 3.71-3.57 (m, 2H), 3.54-3.39 (m, 2H), 2.59-2.52 (m, 2H), 2.46 (s, 3H), 2.38 (t, J=7.4 Hz, 2H), 2.30-2.22 (m, 4H), 2.11 (ddd, J=13.4, 9.4, 4.4 Hz, 1H), 2.07-2.01 (m, 2H), 1.04 (s, 9H). HRMS calcd for $C_{46}H_{56}FN_{10}O_7S$ [M+H$^+$] 911.4038, found 911.4047.

Example 156

Synthesis of HC75-44

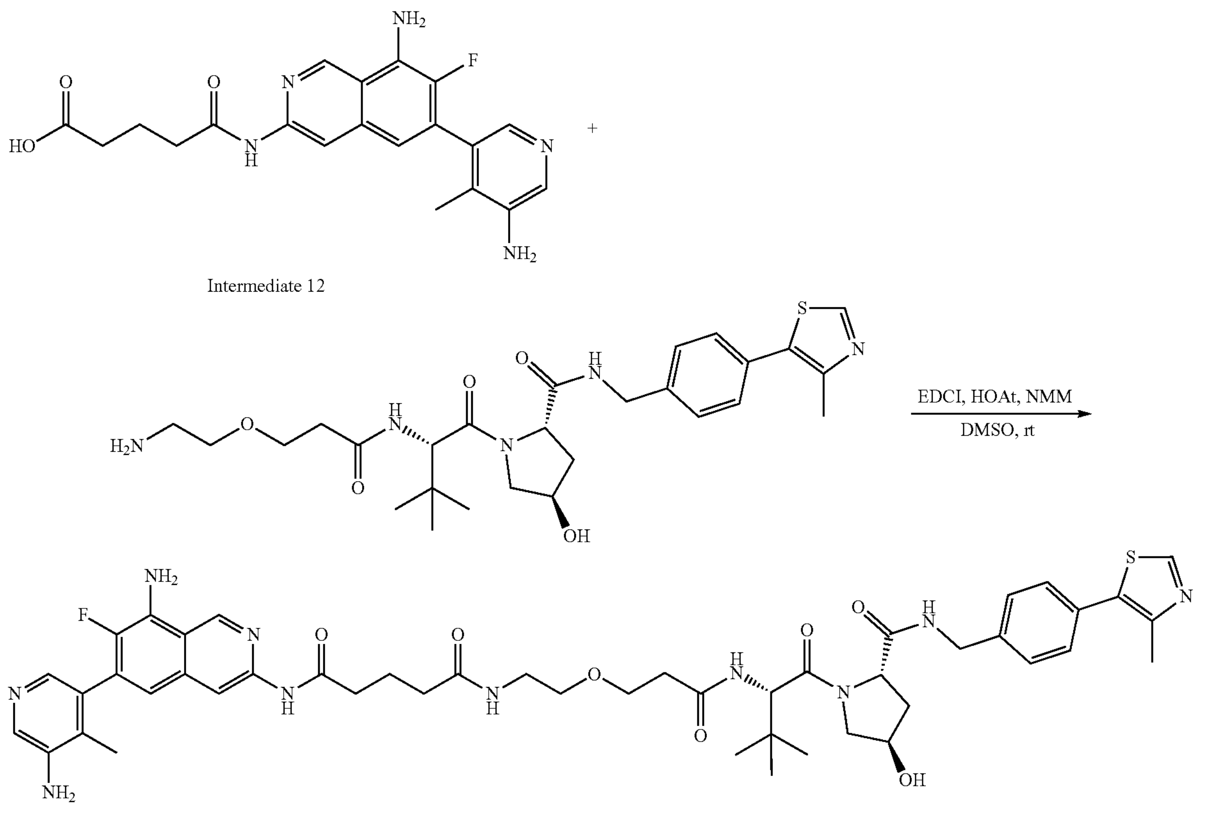

HC75-44

HC75-44 was synthesized following the standard procedure for preparing HC75-29 from Intermediate 12 (9.0 mg, 0.0144 mmol, 1.0 equiv), (2S,4R)-1-((S)-2-(3-(2-aminoethoxy)propanamido)-3,3-dimethylbutanoyl)-4-hydroxy-N-(4-(4-methylthiazol-5-yl)benzyl)pyrrolidine-2-carboxamide (12.4 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-44 was obtained as yellow solid in TFA salt form (11 mg, 73%). $^1$H NMR (600 MHz, Methanol-$d_4$) δ 9.41 (s, 1H), 9.01 (s, 1H), 8.24 (s, 1H), 8.10 (s, 1H), 8.00 (s, 1H), 7.46 (d, J=7.8 Hz, 2H), 7.39 (d, J=8.2 Hz, 2H), 7.06 (d, J=5.8 Hz, 1H), 4.70 (s, 1H), 4.63 (dd, J=9.2, 7.6 Hz, 1H), 4.57-4.49 (m, 2H), 4.40 (d, J=15.4 Hz, 1H), 3.92 (d, J=11.1 Hz, 1H), 3.82 (dd, J=11.0, 3.9 Hz, 1H), 3.78-3.69 (m, 2H), 3.59-3.51 (m, 2H), 3.46-3.35 (m, 2H), 2.62-2.51 (m, 4H), 2.47 (s, 3H), 2.35 (t, J=7.2 Hz, 2H), 2.30-2.21 (m, 4H), 2.09 (ddd, J=13.3, 9.3, 4.4 Hz, 1H), 2.06-1.99 (m, 2H), 1.05 (s, 9H). HRMS calcd for $C_{47}H_{58}FN_{10}O_7S$ [M+H$^+$] 925.4195, found 925.4191.

Example 157

Synthesis of HC75-45

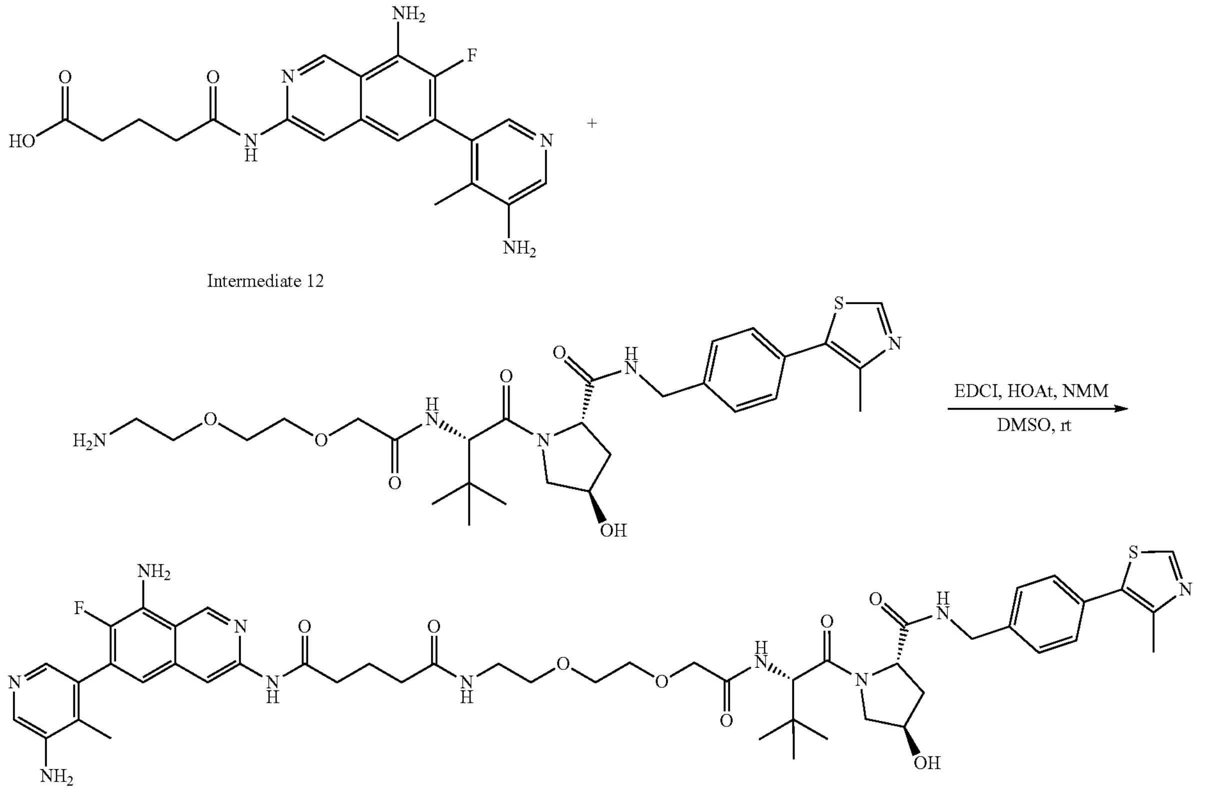

Intermediate 12

HC75-45

HC75-45 was synthesized following the standard procedure for preparing HC75-29 from Intermediate 12 (9.0 mg, 0.0144 mmol, 1.0 equiv), (2S,4R)-1-((S)-2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide (9.8 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-45 was obtained as yellow solid in TFA salt form (10.7 mg, 63%). $^1$H NMR (600 MHz, Methanol-$d_4$) δ 9.43 (s, 1H), 9.10 (s, 1H), 8.17 (s, 1H), 8.11 (s, 1H), 8.02 (s, 1H), 7.46 (d, J=8.2 Hz, 2H), 7.41 (d, J=8.0 Hz, 2H), 7.10 (d, J=5.8 Hz, 1H), 4.78 (s, 1H), 4.65 (t, J=8.2 Hz, 1H), 4.59-4.50 (m, 2H), 4.38 (d, J=15.5 Hz, 1H), 4.10-3.97 (m, 2H), 3.88 (d, J=11.0 Hz, 1H), 3.83 (dd, J=11.0, 3.8 Hz, 1H), 3.75-3.52 (m, 8H), 3.32-3.26 (m, 1H), 2.55 (t, J=7.3 Hz, 2H), 2.50 (s, 3H), 2.43-2.21 (m, 6H), 2.14-1.97 (m, 3H), 1.07 (s, 9H). HRMS calcd for $C_{48}H_{60}FN_{10}O_8S$ [M+H$^+$] 955.4300, found 955.4308.

Example 158

Synthesis of HC75-46

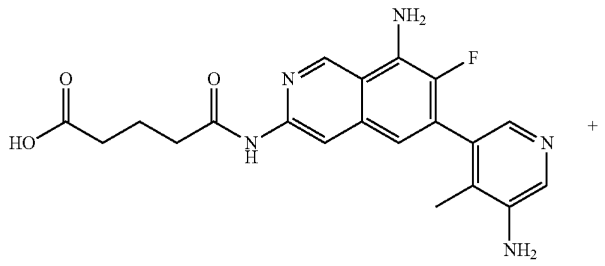

Intermediate 12

-continued

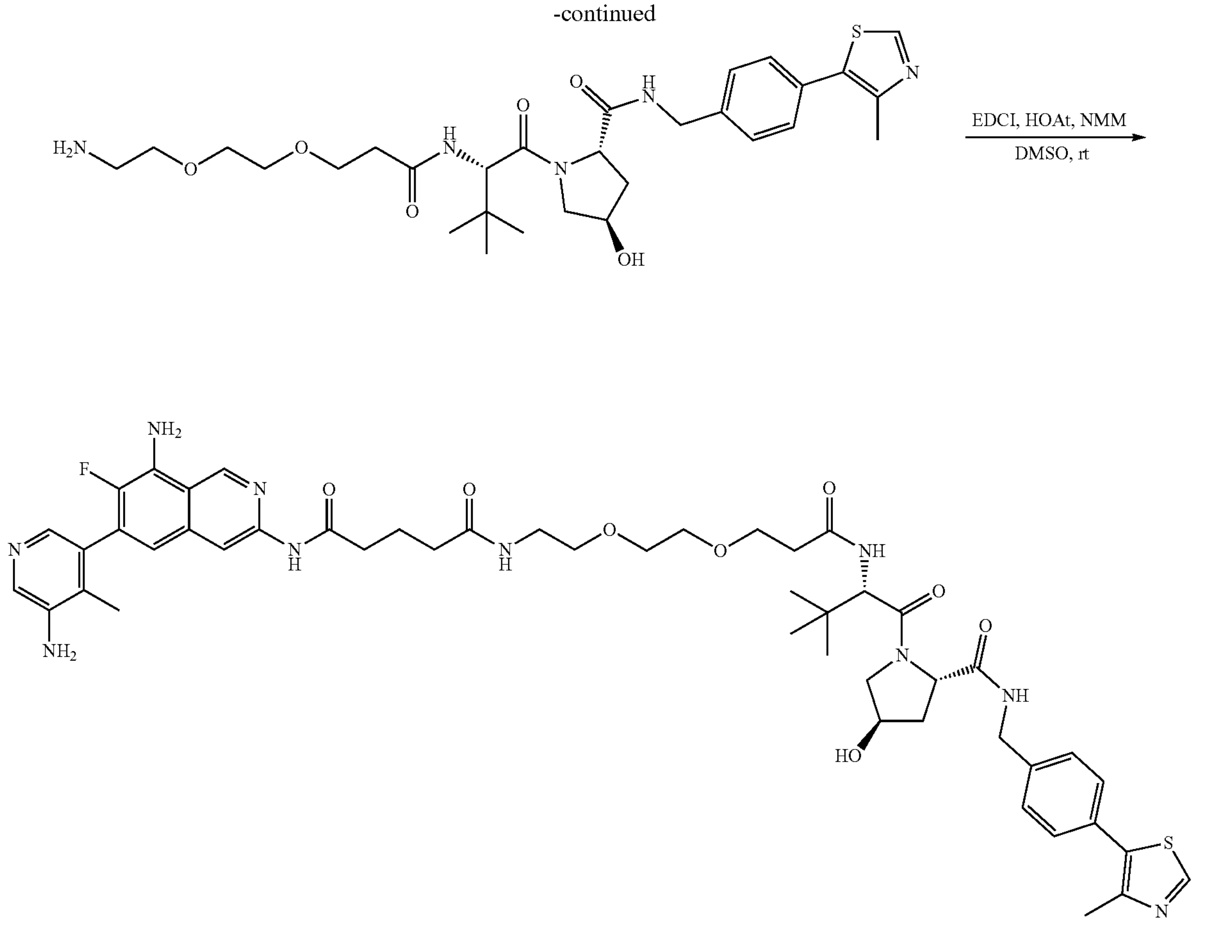

HC75-46

HC75-46 was synthesized following the standard procedure for preparing HC75-29 from Intermediate 12 (9.0 mg, 0.0144 mmol, 1.0 equiv), (2S,4R)-1-((S)-2-(3-(2-(2-aminoethoxy)ethoxy)propanamido)-3,3-dimethylbutanoyl)-4-hydroxy-N-(4-(4-methylthiazol-5-yl)benzyl)pyrrolidine-2-carboxamide (13.1 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-46 was obtained as yellow solid in TFA salt form (7.1 mg, 41%). $^1$H NMR (600 MHz, Methanol-$d_4$) δ 9.42 (s, 1H), 9.02 (s, 1H), 8.23 (s, 1H), 8.10 (s, 1H), 8.01 (s, 1H), 7.48 (d, J=8.0 Hz, 2H), 7.40 (d, J=8.2 Hz, 2H), 7.08 (d, J=5.8 Hz, 1H), 4.70 (s, 1H), 4.61 (dd, J=9.2, 7.5 Hz, 1H), 4.56 (d, J=15.5 Hz, 1H), 4.53-4.50 (m, 1H), 4.38 (d, J=15.5 Hz, 1H), 3.92 (d, J=11.0 Hz, 1H), 3.82 (dd, J=11.0, 3.9 Hz, 1H), 3.75 (t, J=5.9 Hz, 2H), 3.62 (s, 4H), 3.56 (t, J=5.5 Hz, 2H), 3.45-3.35 (m, 2H), 2.63-2.46 (m, 7H), 2.39-2.31 (m, 2H), 2.29-2.22 (m, 4H), 2.10 (ddd, J=13.4, 9.2, 4.5 Hz, 1H), 2.03 (p, J=7.9, 7.4 Hz, 2H), 1.05 (s, 9H). HRMS calcd for $C_{49}H_{62}FN_{10}O_8S$ [M+H$^+$] 969.4457, found 969.4451.

Example 159

Synthesis of HC75-47

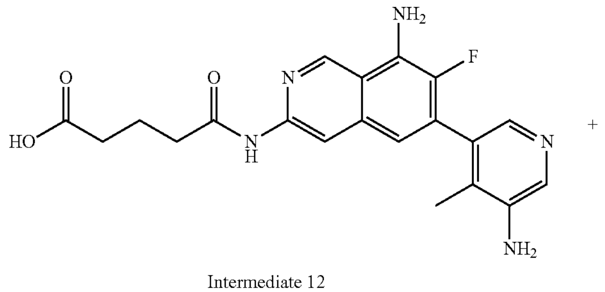

Intermediate 12

-continued

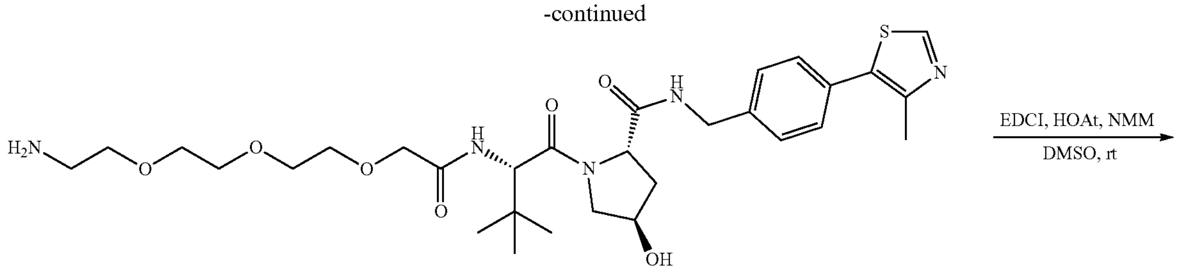

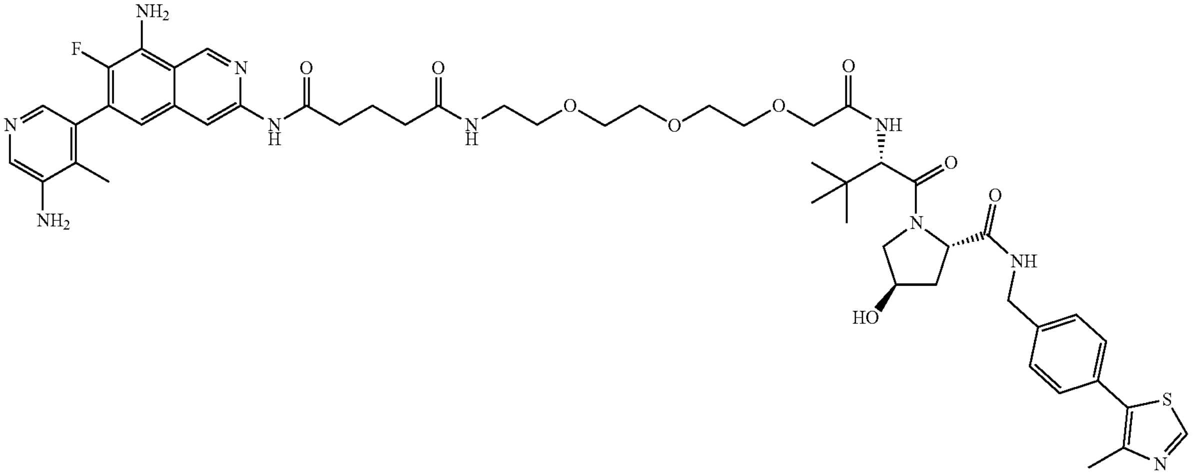

HC75-47

HC75-47 was synthesized following the standard procedure for preparing HC75-29 from Intermediate 12 (9.0 mg, 0.0144 mmol, 1.0 equiv), (2S,4R)-1-((S)-14-amino-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (13.6 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-47 was obtained as yellow solid in TFA salt form (9.8 mg, 55%). $^1$H NMR (600 MHz, Methanol-$d_4$) δ 9.42 (s, 1H), 9.04 (s, 1H), 8.23 (s, 1H), 8.11 (s, 1H), 8.01 (s, 1H), 7.48 (d, J=8.0 Hz, 2H), 7.42 (d, J=8.1 Hz, 2H), 7.09 (d, J=5.8 Hz, 1H), 4.72 (s, 1H), 4.64-4.59 (m, 1H), 4.57-4.50 (m, 2H), 4.38 (d, J=15.5 Hz, 1H), 4.11-4.01 (m, 2H), 3.90 (d, J=11.1 Hz, 1H), 3.82 (dd, J=11.0, 3.8 Hz, 1H), 3.75-3.61 (m, 8H), 3.54 (t, J=5.4 Hz, 2H), 3.39-3.35 (m, 2H), 2.56 (t, J=7.5 Hz, 2H), 2.49 (s, 3H), 2.34 (t, J=7.5 Hz, 2H), 2.30-2.22 (m, 4H), 2.11 (ddd, J=13.4, 9.3, 4.4 Hz, 1H), 2.04 (p, J=7.4 Hz, 2H), 1.05 (s, 9H). HRMS calcd for $C_{50}H_{64}FN_{10}O_9S$ [M+H$^+$]999.4562, found 999.4575.

Example 160

Synthesis of HC75-48

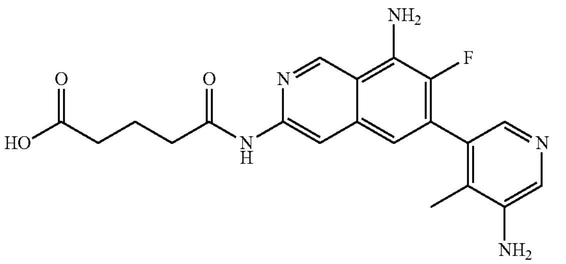

Intermediate 12

+

-continued

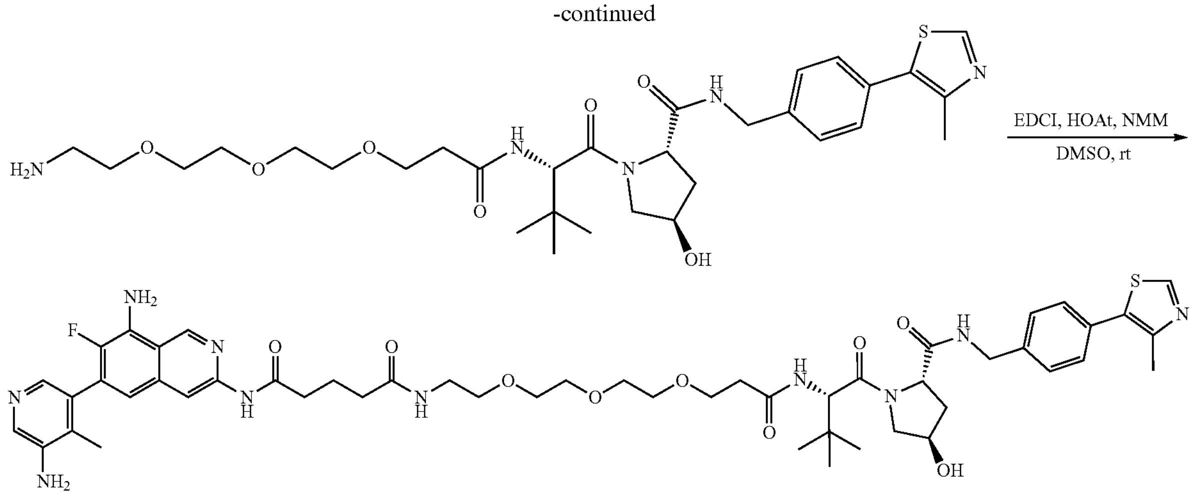

HC75-48

HC75-48 was synthesized following the standard procedure for preparing HC75-29 from Intermediate 12 (9.0 mg, 0.0144 mmol, 1.0 equiv), (2S,4R)-1-((S)-1-amino-14-(tert-butyl)-12-oxo-3,6,9-trioxa-13-azapentadecan-15-oyl)-4-hydroxy-N-(4-(4-methylthiazol-5-yl)benzyl)pyrrolidine-2-carboxamide (13.8 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-48 was obtained as yellow solid in TFA salt form (6.5 mg, 36%). $^1$H NMR (600 MHz, Methanol-$d_4$) δ 9.42 (s, 1H), 9.02 (s, 1H), 8.25 (s, 1H), 8.10 (s, 1H), 8.01 (s, 1H), 7.48 (d, J=8.0 Hz, 2H), 7.41 (d, J=8.1 Hz, 2H), 7.08 (d, J=5.9 Hz, 1H), 4.68 (s, 1H), 4.60 (dd, J=9.3, 7.5 Hz, 1H), 4.57 (d, J=15.5 Hz, 1H), 4.53-4.50 (m, 1H), 4.37 (d, J=15.5 Hz, 1H), 3.92 (d, J=10.9 Hz, 1H), 3.82 (dd, J=11.0, 3.9 Hz, 1H), 3.75-3.70 (m, 2H), 3.68-3.59 (m, 8H), 3.56 (t, J=5.4 Hz, 2H), 3.40-3.36 (m, 2H), 2.62-2.53 (m, 3H), 2.54-2.44 (m, 4H), 2.35 (t, J=7.3 Hz, 2H), 2.25 (s, 4H), 2.10 (ddd, J=13.3, 9.2, 4.4 Hz, 1H), 2.07-2.00 (m, 2H), 1.05 (s, 9H). HRMS calcd for $C_{51}H_{66}FN_{10}O_9S$ [M+H$^+$] 1013.4719, found 1013.4727.

Example 161

Synthesis of HC75-49

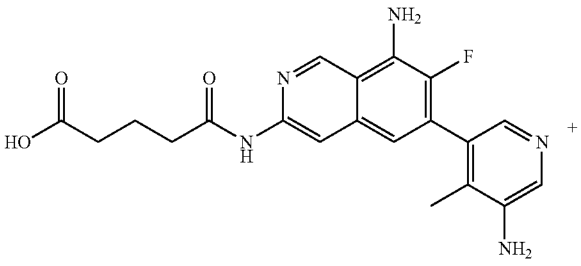

Intermediate 12

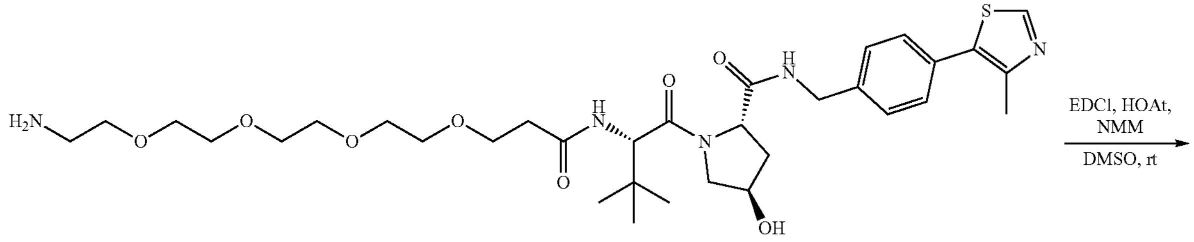

-continued

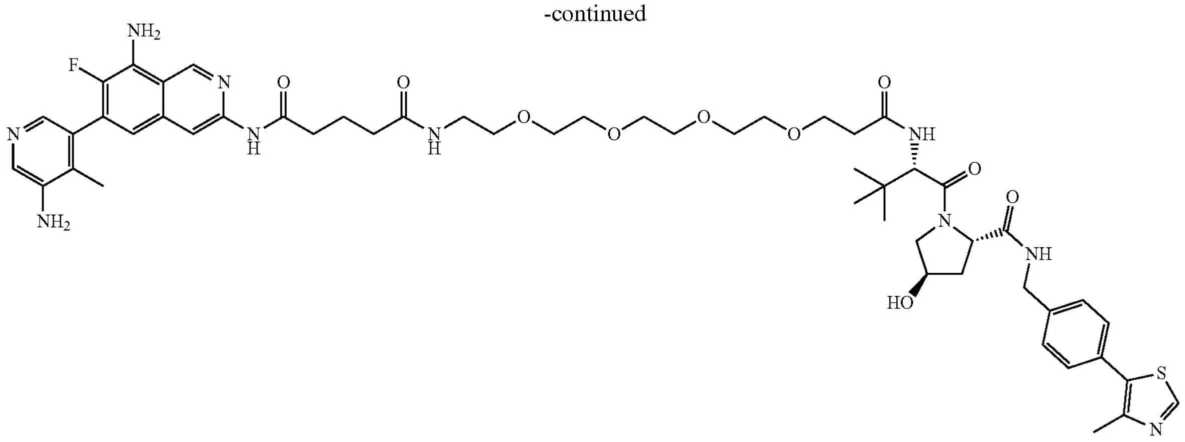

HC75-49

HC75-49 was synthesized following the standard procedure for preparing HC75-29 from Intermediate 12 (9.0 mg, 0.0144 mmol, 1.0 equiv), (2S,4R)-1-((S)-1-amino-17-(tert-butyl)-15-oxo-3,6,9,12-tetraoxa-16-azaoctadecan-18-oyl)-4-hydroxy-N-(4-(4-methylthiazol-5-yl)benzyl)pyrrolidine-2-carboxamide (11.5 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-49 was obtained as yellow solid in TFA salt form (9.3 mg, 50%). $^1$H NMR (600 MHz, Methanol-$d_4$) δ 9.43 (s, 1H), 9.05 (s, 1H), 8.22 (s, 1H), 8.11 (s, 1H), 8.01 (s, 1H), 7.49 (d, J=8.1 Hz, 2H), 7.42 (d, J=8.0 Hz, 2H), 7.10 (d, J=5.9 Hz, 1H), 4.67 (s, 1H), 4.63-4.50 (m, 3H), 4.38 (d, J=15.5 Hz, 1H), 3.92 (d, J=11.0 Hz, 1H), 3.82 (dd, J=11.0, 3.9 Hz, 1H), 3.77-3.68 (m, 2H), 3.66-3.58 (m, 12H), 3.56 (t, J=5.4 Hz, 2H), 3.39 (t, J=5.4 Hz, 2H), 2.62-2.54 (m, 3H), 2.53-2.45 (m, 4H), 2.35 (t, J=7.3 Hz, 2H), 2.25 (s, 4H), 2.16-2.00 (m, 3H), 1.05 (s, 9H). HRMS calcd for $C_{53}H_{70}FN_{10}O_{10}S$ [M+H$^+$] 1057.4981, found 1057.4987.

Example 162

Synthesis of HC75-50

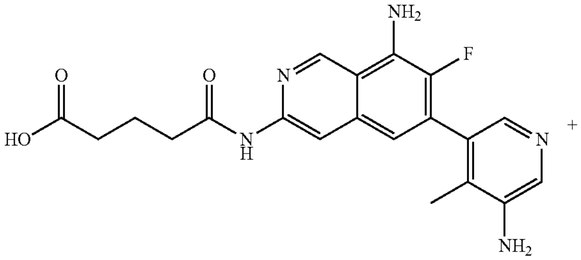

Intermediate 12

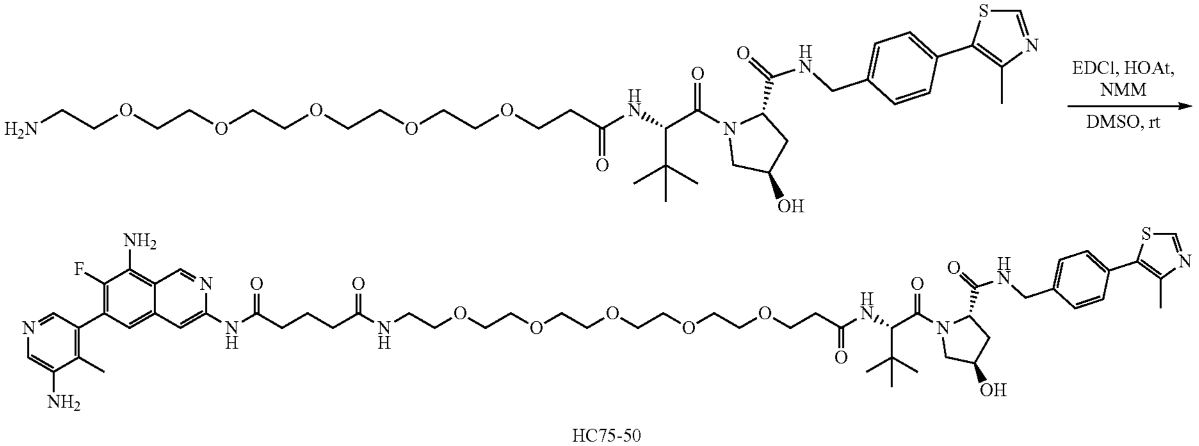

HC75-50

HC75-50 was synthesized following the standard procedure for preparing HC75-29 from Intermediate 12 (9.0 mg, 0.0144 mmol, 1.0 equiv), (2S,4R)-1-((S)-1-amino-20-(tert-butyl)-18-oxo-3,6,9,12,15-pentaoxa-19-azahenicosan-21-oyl)-4-hydroxy-N-(4-(4-methylthiazol-5-yl)benzyl)pyrrolidine-2-carboxamide (15.2 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-50 was obtained as yellow solid in TFA salt form (6.8 mg, 36%). $^1$H NMR (600 MHz, Methanol-$d_4$) δ 9.45 (s, 1H), 9.11 (d, J=8.1 Hz, 1H), 8.19 (s, 1H), 8.11 (s, 1H), 8.02 (s, 1H), 7.49 (d, J=8.0 Hz, 2H), 7.43 (d, J=7.9 Hz, 2H), 7.11 (d, J=5.7 Hz, 1H), 4.67 (s, 1H), 4.62-4.50 (m, 3H), 4.38 (d, J=15.6 Hz, 1H), 3.92 (d, J=10.9 Hz, 1H), 3.82 (dd, J=11.0, 3.9 Hz, 1H), 3.74 (ddq, J=19.4, 10.1, 4.7 Hz, 2H), 3.62 (dd, J=9.5, 6.3 Hz, 16H), 3.56 (t, J=5.4 Hz, 2H), 3.39 (t, J=5.4 Hz, 2H), 2.62-2.54 (m, 3H), 2.54-2.43 (m, 4H), 2.36 (t, J=7.2 Hz, 2H), 2.29-2.21 (m, 4H), 2.15-2.01 (m, 3H), 1.05 (s, 9H). HRMS calcd for $C_{55}H_{74}FN_{10}O_{11}S$ [M+H$^+$] 1101.5243, found 1101.5252.

Example 163

Synthesis of HC75-52

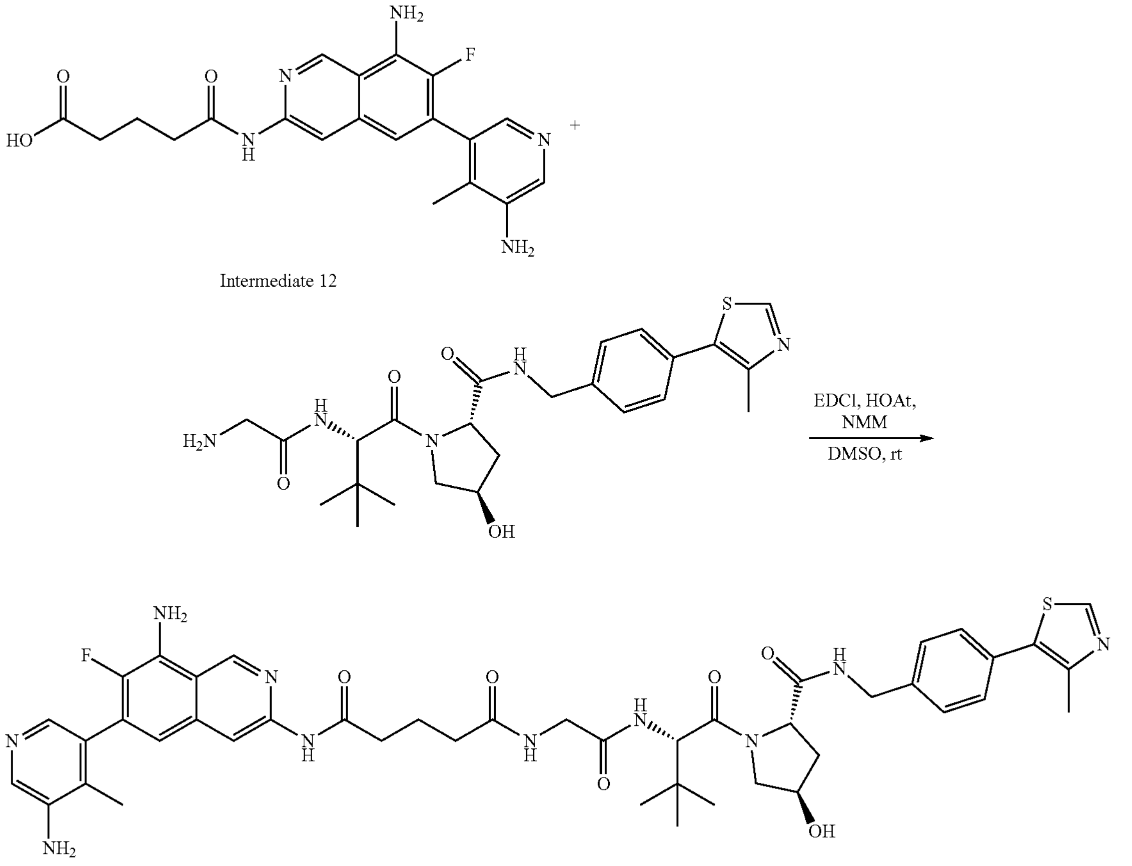

Intermediate 12

HC75-52

HC75-52 was synthesized following the standard procedure for preparing HC75-29 from Intermediate 12 (9.0 mg, 0.0144 mmol, 1.0 equiv), (2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide (10.3 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-52 was obtained as yellow solid in TFA salt form (4.3 mg, 27%). $^1$H NMR (600 MHz, Methanol-$d_4$) δ 9.40 (s, 1H), 9.02 (s, 1H), 8.21 (s, 1H), 8.10 (s, 1H), 8.01 (s, 1H), 7.43 (d, J=8.1 Hz, 2H), 7.37 (d, J=8.2 Hz, 2H), 7.08 (d, J=5.9 Hz, 1H), 4.72-4.64 (m, 2H), 4.60-4.50 (m, 2H), 4.34 (d, J=15.4 Hz, 1H), 4.01-3.91 (m, 2H), 3.90-3.82 (m, 2H), 2.67-2.54 (m, 2H), 2.49-2.37 (m, 5H), 2.30-2.21 (m, 4H), 2.19-2.06 (m, 3H), 1.07 (s, 9H). HRMS calcd for $C_{44}H_{52}FN_{10}O_6S$ [M+H$^+$] 867.3776, found 867.3788.

Example 164

Synthesis of HC75-53

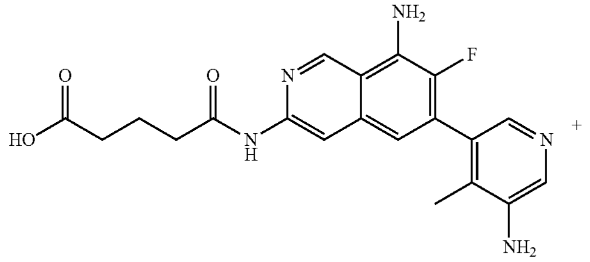

Intermediate 12

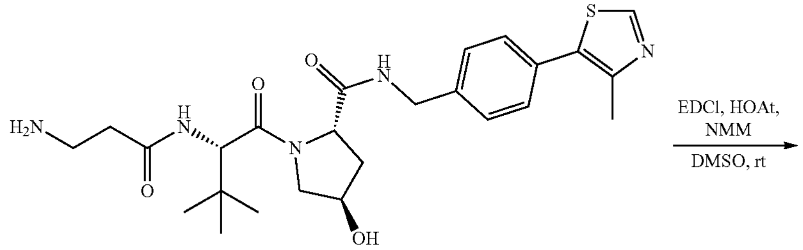

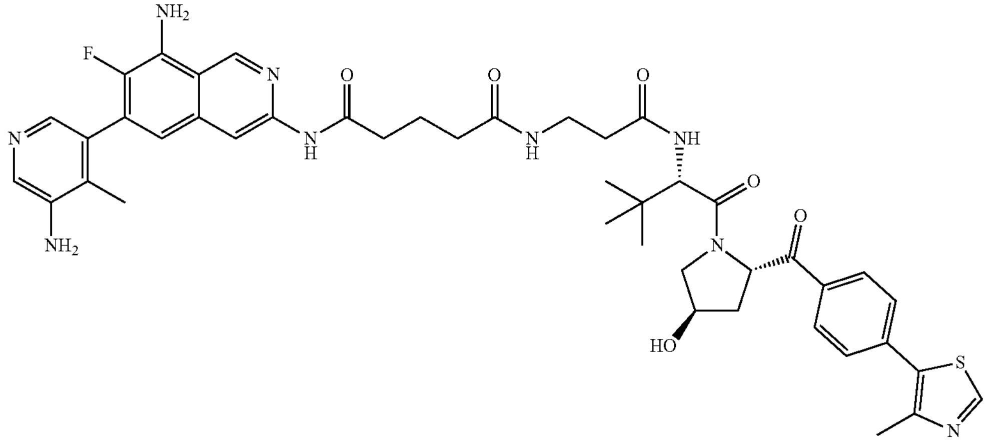

HC75-53

HC75-53 was synthesized following the standard procedure for preparing HC75-29 from Intermediate 12 (9.0 mg, 0.0144 mmol, 1.0 equiv), (2S,4R)-1-((S)-2-(3-aminopropanamido)-3,3-dimethylbutanoyl)-4-hydroxy-N-(4-(4-methylthiazol-5-yl)benzyl)pyrrolidine-2-carboxamide (10.5 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-53 was obtained as yellow solid in TFA salt form (4.9 mg, 31%). $^1$H NMR (600 MHz, Methanol-$d_4$) δ 9.38 (s, 1H), 8.97 (s, 1H), 8.25 (s, 1H), 8.09 (s, 1H), 8.00 (s, 1H), 7.45 (d, J=7.7 Hz, 2H), 7.36 (d, J=8.2 Hz, 2H), 7.01 (d, J=5.8 Hz, 1H), 4.69-4.51 (m, 4H), 4.35 (d, J=15.8 Hz, 1H), 3.98 (d, J=11.1 Hz, 1H), 3.81 (dd, J=11.0, 3.9 Hz, 1H), 3.56-3.48 (m, 1H), 3.45-3.37 (m, 1H), 2.57-2.43 (m, 7H), 2.33-2.29 (m, 2H), 2.28-2.21 (m, 4H), 2.16-1.98 (m, 3H), 1.06 (s, 9H). HRMS calcd for $C_{45}H_{54}FN_{10}O_6S$ [M+H$^+$] 881.3933, found 881.3939.

Example 165

Synthesis of HC75-54

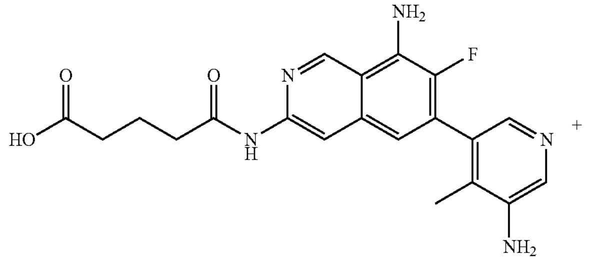

Intermediate 12

-continued

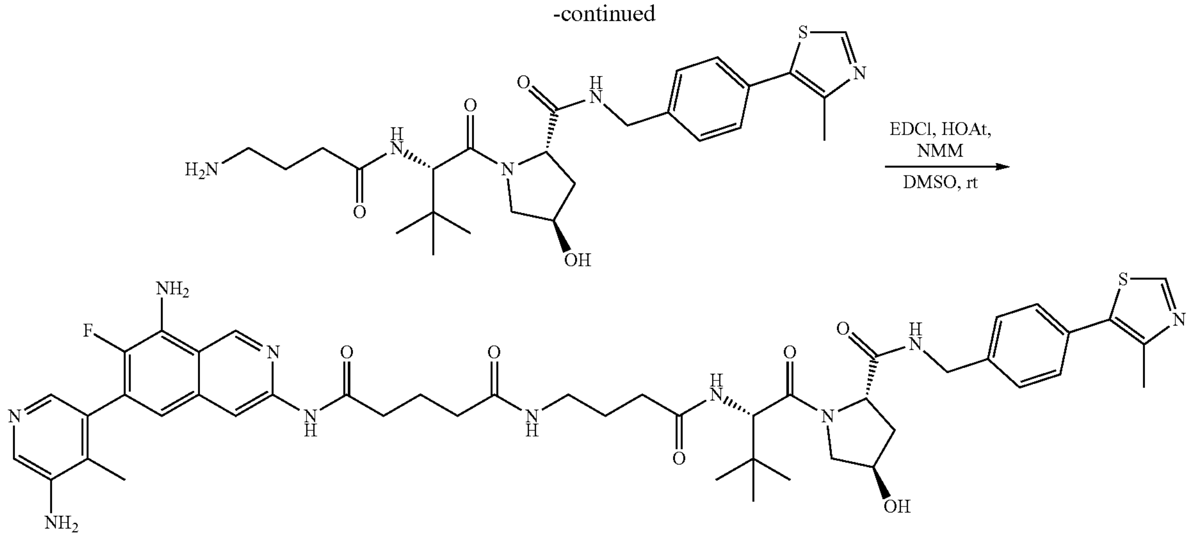

HC75-54

HC75-54 was synthesized following the standard procedure for preparing HC75-29 from Intermediate 12 (9.0 mg, 0.0144 mmol, 1.0 equiv), (2S,4R)-1-((S)-2-(4-aminobutanamido)-3,3-dimethylbutanoyl)-4-hydroxy-N-(4-(4-methylthiazol-5-yl)benzyl)pyrrolidine-2-carboxamide (10.7 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-54 was obtained as yellow solid in TFA salt form (5.6 mg, 35%). $^1$H NMR (600 MHz, Methanol-$d_4$) δ 9.40 (s, 1H), 9.00 (s, 1H), 8.25 (s, 1H), 8.10 (d, J=1.1 Hz, 1H), 8.01 (s, 1H), 7.47 (d, J=8.1 Hz, 2H), 7.40 (d, J=8.3 Hz, 2H), 7.07 (d, J=5.9 Hz, 1H), 4.66 (s, 1H), 4.61 (dd, J=9.3, 7.5 Hz, 1H), 4.56 (d, J=15.6 Hz, 1H), 4.54-4.50 (m, 1H), 4.36 (d, J=15.5 Hz, 1H), 3.94 (d, J=11.0 Hz, 1H), 3.83 (dd, J=11.0, 4.0 Hz, 1H), 3.23 (t, J=6.8 Hz, 2H), 2.57 (d, J=8.7 Hz, 2H), 2.47 (s, 3H), 2.39-2.30 (m, 4H), 2.26-2.21 (m, 4H), 2.15-2.02 (m, 3H), 1.85-1.76 (m, 2H), 1.06 (s, 9H). HRMS calcd for $C_{46}H_{56}FN_{10}O_6S$ [M+H$^+$] 895.4089, found 895.4098.

Example 166

Synthesis of HC75-55

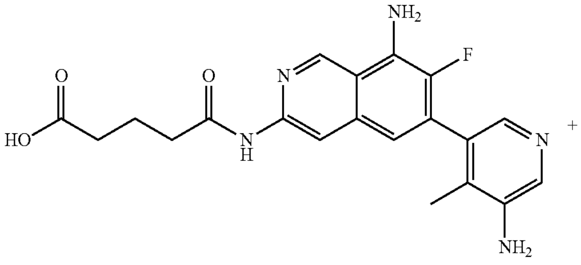

Intermediate 12

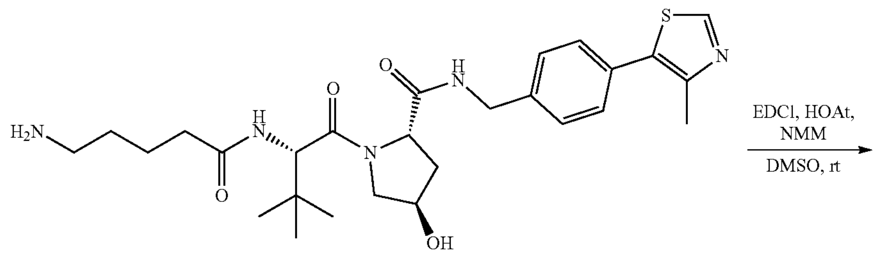

-continued

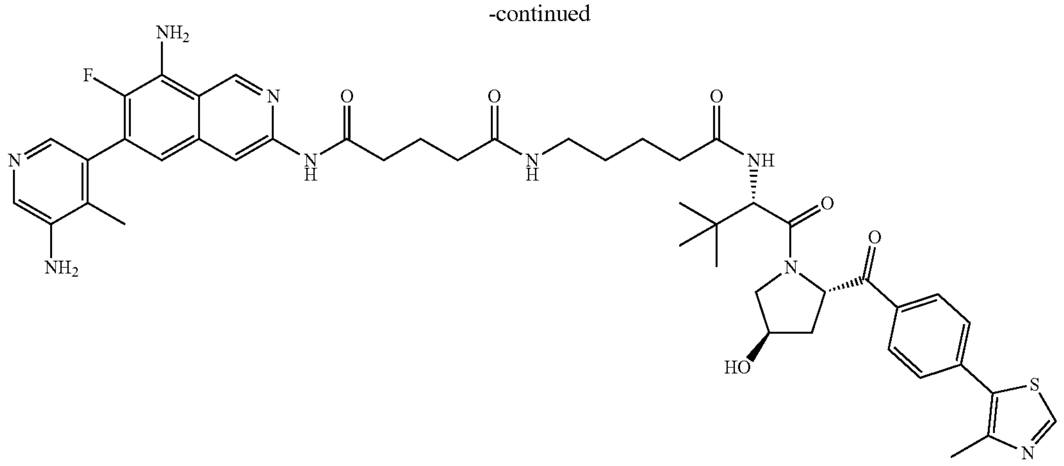

HC75-55

HC75-55 was synthesized following the standard procedure for preparing HC75-29 from Intermediate 12 (9.0 mg, 0.0144 mmol, 1.0 equiv), (2S,4R)-1-((S)-2-(5-aminopentanamido)-3,3-dimethylbutanoyl)-4-hydroxy-N-(4-(4-methylthiazol-5-yl)benzyl)pyrrolidine-2-carboxamide (8.5 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-55 was obtained as yellow solid in TFA salt form (3.7 mg, 23%). $^{1}$H NMR (600 MHz, Methanol-$d_4$) δ 9.41 (s, 1H), 9.02 (s, 1H), 8.26 (s, 1H), 8.10 (d, J=1.2 Hz, 1H), 8.02 (s, 1H), 7.51-7.46 (m, 2H), 7.42 (d, J=8.2 Hz, 2H), 7.08 (d, J=5.9 Hz, 1H), 4.67 (s, 1H), 4.63-4.49 (m, 3H), 4.37 (d, J=15.5 Hz, 1H), 3.92 (d, J=10.9 Hz, 1H), 3.82 (dd, J=10.9, 3.9 Hz, 1H), 3.26-3.15 (m, 2H), 2.60-2.51 (m, 2H), 2.49 (s, 3H), 2.35-2.28 (m, 4H), 2.25 (d, J=1.5 Hz, 4H), 2.14-1.99 (m, 3H), 1.70-1.62 (m, 2H), 1.53 (p, J=7.1 Hz, 2H), 1.05 (s, 9H). HRMS calcd for $C_{47}H_{58}FN_{10}O_6S$ [M+H$^+$]909.4246, found 909.4257.

Example 167

Synthesis of HC75-56

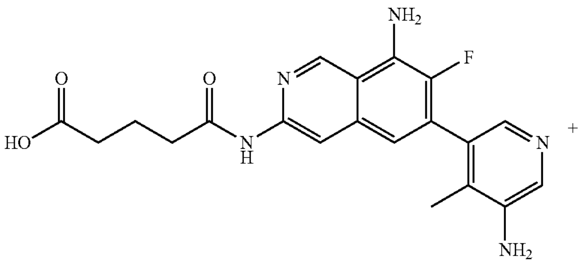

Intermediate 12

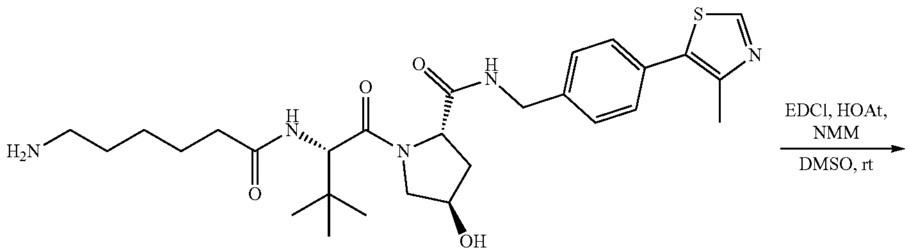

-continued

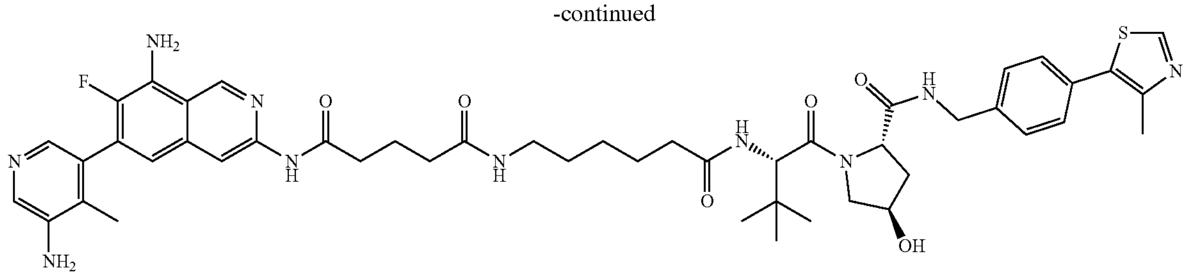

HC75-56

HC75-56 was synthesized following the standard procedure for preparing HC75-29 from Intermediate 12 (9.0 mg, 0.0144 mmol, 1.0 equiv), (2S,4R)-1-((S)-2-(6-aminohexanamido)-3,3-dimethylbutanoyl)-4-hydroxy-N-(4-(4-methylthiazol-5-yl)benzyl)pyrrolidine-2-carboxamide (8.7 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-56 was obtained as yellow solid in TFA salt form (4.7 mg, 28%). $^1$H NMR (600 MHz, Methanol-$d_4$) δ 9.43 (s, 1H), 9.05 (s, 1H), 8.26 (s, 1H), 8.10 (s, 1H), 8.02 (d, J=3.2 Hz, 1H), 7.49 (d, J=7.9 Hz, 2H), 7.42 (d, J=7.9 Hz, 2H), 7.09 (d, J=5.8 Hz, 1H), 4.70 (s, 1H), 4.66-4.61 (m, 1H), 4.56 (d, J=15.5 Hz, 1H), 4.52 (s, 1H), 4.39 (d, J=15.4 Hz, 1H), 3.95 (d, J=11.0 Hz, 1H), 3.82 (dd, J=10.9, 3.9 Hz, 1H), 3.28-3.22 (m, 1H), 3.19-3.11 (m, 1H), 2.65-2.56 (m, 1H), 2.49 (s, 4H), 2.38-2.22 (m, 8H), 2.10 (ddd, J=13.3, 9.2, 4.4 Hz, 1H), 2.06-1.99 (m, 2H), 1.69-1.60 (m, 2H), 1.56-1.47 (m, 2H), 1.41-1.29 (m, 2H), 1.06 (s, 9H). HRMS calcd for $C_{48}H_{60}FN_{10}O_6S$ [M+H$^+$] 923.4402, found 923.4410.

Example 168

Synthesis of HC75-57

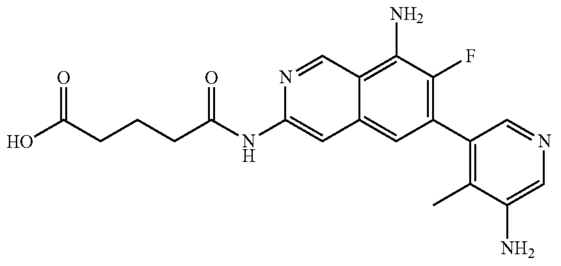

+

Intermediate 12

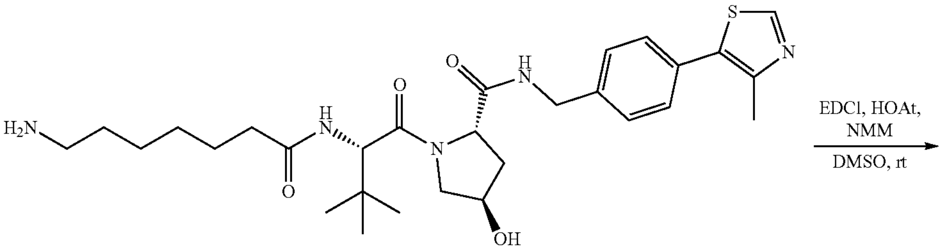

-continued

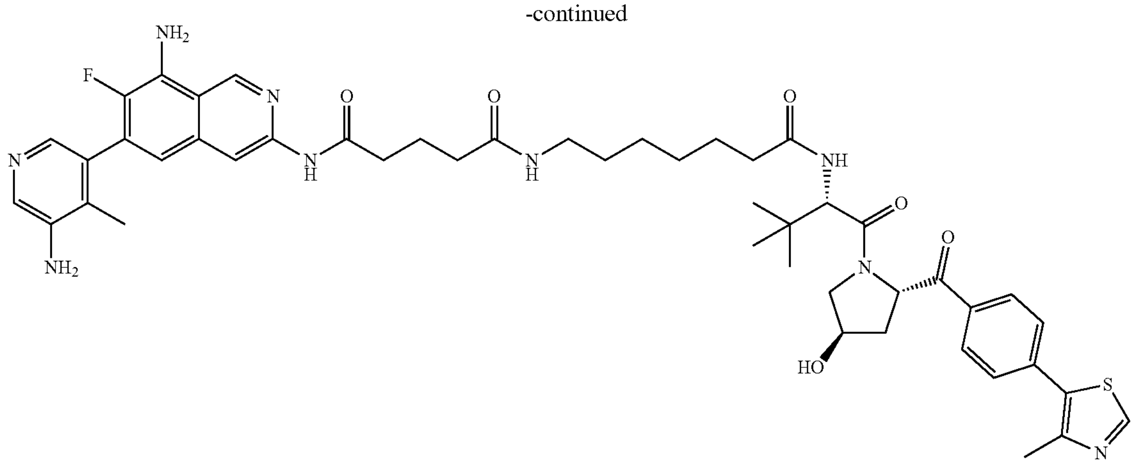

HC75-57

HC75-57 was synthesized following the standard procedure for preparing HC75-29 from Intermediate 12 (9.0 mg, 0.0144 mmol, 1.0 equiv), (2S,4R)-1-((S)-2-(7-aminoheptanamido)-3,3-dimethylbutanoyl)-4-hydroxy-N-(4-(4-methylthiazol-5-yl)benzyl)pyrrolidine-2-carboxamide (9.0 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-57 was obtained as yellow solid in TFA salt form (3.1 mg, 18%). $^1$H NMR (600 MHz, Methanol-$d_4$) δ 9.38 (s, 1H), 8.95 (s, 1H), 8.32 (s, 1H), 8.09 (s, 1H), 8.01 (s, 1H), 7.48 (d, J=8.0 Hz, 2H), 7.41 (d, J=8.2 Hz, 2H), 7.06 (d, J=5.9 Hz, 1H), 4.66 (s, 1H), 4.61 (dd, J=9.1, 7.5 Hz, 1H), 4.56 (d, J=15.4 Hz, 1H), 4.52 (s, 1H), 4.37 (d, J=15.5 Hz, 1H), 3.93 (d, J=11.0 Hz, 1H), 3.82 (dd, J=10.9, 3.9 Hz, 1H), 3.24-3.13 (m, 2H), 2.59-2.49 (m, 2H), 2.48 (s, 3H), 2.35-2.21 (m, 8H), 2.10 (ddd, J=13.3, 9.1, 4.4 Hz, 1H), 2.03 (p, J=7.4 Hz, 2H), 1.68-1.59 (m, 2H), 1.55-1.47 (m, 2H), 1.40-1.30 (m, 4H), 1.05 (s, 9H). HRMS calcd for $C_{49}H_{62}FN_{10}O_6S$ [M+H$^+$] 937.4559, found 937.4568.

Example 169

Synthesis of HC75-58

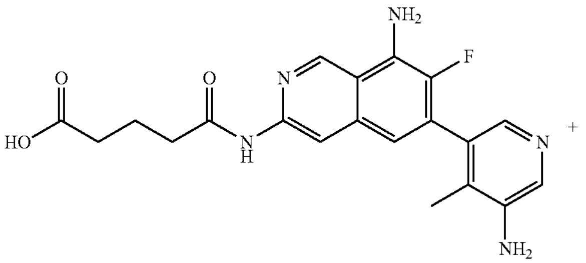

Intermediate 12

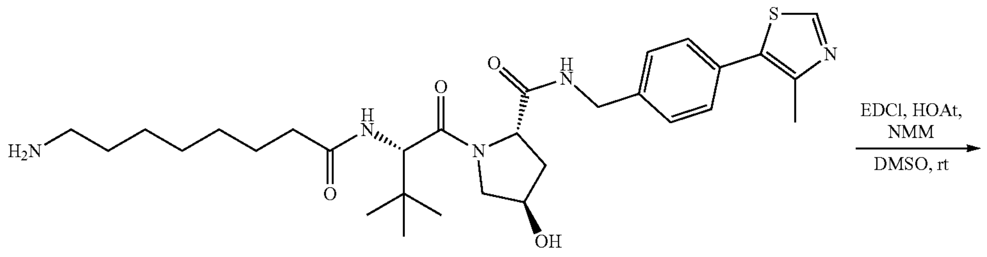

-continued

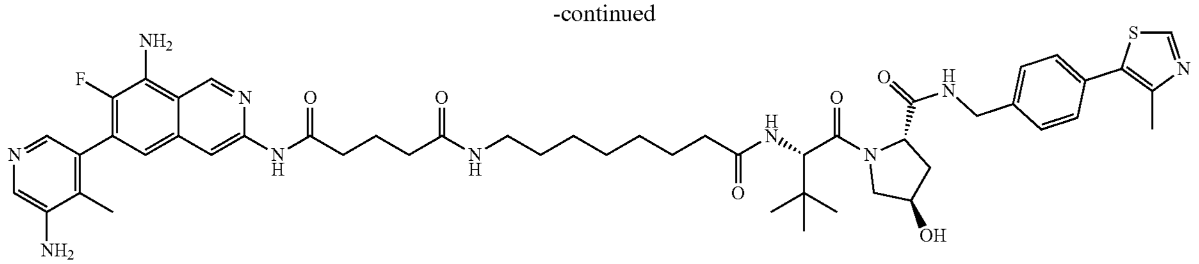

HC75-58

HC75-58 was synthesized following the standard procedure for preparing HC75-29 from Intermediate 12 (9.0 mg, 0.0144 mmol, 1.0 equiv), (2S,4R)-1-((S)-2-(8-aminooctanamido)-3,3-dimethylbutanoyl)-4-hydroxy-N-(4-(4-methylthiazol-5-yl)benzyl)pyrrolidine-2-carboxamide (11.5 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-58 was obtained as yellow solid in TFA salt form (4.2 mg, 25%). $^{1}$H NMR (600 MHz, Methanol-$d_4$) δ 9.42 (s, 1H), 9.01 (s, 1H), 8.26 (s, 1H), 8.10 (s, 1H), 8.03 (s, 1H), 7.50 (d, J=8.2 Hz, 2H), 7.41 (d, J=8.3 Hz, 2H), 7.07 (d, J=5.8 Hz, 1H), 4.71 (s, 1H), 4.65 (dd, J=9.1, 7.5 Hz, 1H), 4.61 (d, J=15.5 Hz, 1H), 4.55-4.50 (m, 1H), 4.36 (d, J=15.5 Hz, 1H), 3.94 (d, J=11.0 Hz, 1H), 3.83 (dd, J=11.0, 3.9 Hz, 1H), 3.32-3.25 (m, 1H), 3.10 (dt, J=13.4, 6.9 Hz, 1H), 2.60-2.52 (m, 1H), 2.52-2.42 (m, 4H), 2.40-2.22 (m, 8H), 2.10 (ddd, J=13.3, 9.2, 4.4 Hz, 1H), 2.03-1.97 (m, 2H), 1.66-1.57 (m, 2H), 1.54-1.42 (m, 2H), 1.37-1.26 (m, 6H), 1.06 (s, 9H). HRMS calcd for $C_{50}H_{64}FN_{10}O_6S$ [M+H$^+$] 951.4715, found 951.4719.

Example 170

Synthesis of HC75-59

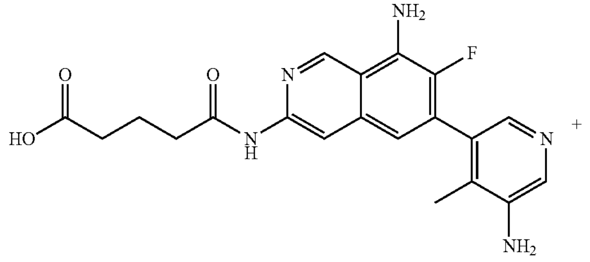

Intermediate 12

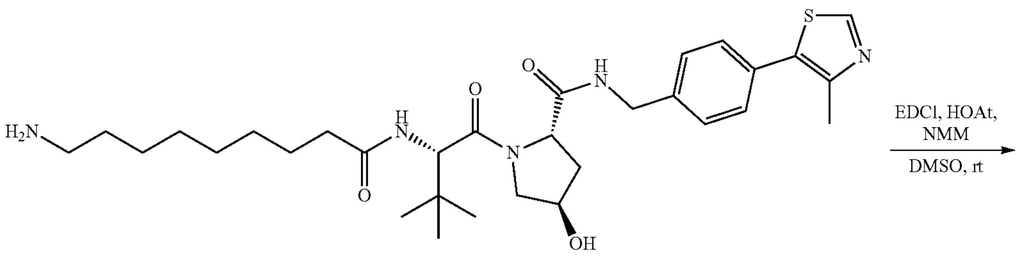

-continued

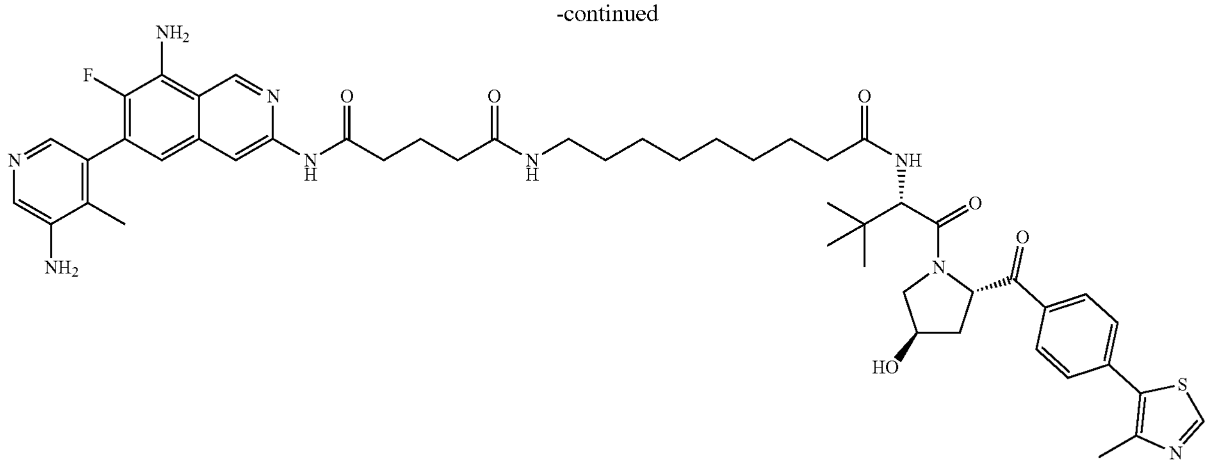

HC75-59

HC75-59 was synthesized following the standard procedure for preparing HC75-29 from Intermediate 12 (9.0 mg, 0.0144 mmol, 1.0 equiv), (2S,4R)-1-((S)-2-(9-aminononanamido)-3,3-dimethylbutanoyl)-4-hydroxy-N-(4-(4-methylthiazol-5-yl)benzyl)pyrrolidine-2-carboxamide (9.3 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-59 was obtained as yellow solid in TFA salt form (5.9 mg, 34%). $^1$H NMR (600 MHz, Methanol-$d_4$) δ 9.41 (s, 1H), 9.01 (s, 1H), 8.26 (s, 1H), 8.10 (s, 1H), 8.02 (s, 1H), 7.49 (d, J=8.0 Hz, 2H), 7.46-7.37 (m, 2H), 7.08 (d, J=5.9 Hz, 1H), 4.67 (s, 1H), 4.64-4.54 (m, 2H), 4.54-4.51 (m, 1H), 4.37 (d, J=15.5 Hz, 1H), 3.93 (d, J=11.0 Hz, 1H), 3.83 (dd, J=11.0, 3.9 Hz, 1H), 3.24-3.14 (m, 2H), 2.60-2.51 (m, 2H), 2.48 (s, 3H), 2.37-2.20 (m, 8H), 2.10 (ddd, J=13.3, 9.2, 4.5 Hz, 1H), 2.06-1.98 (m, 2H), 1.66-1.56 (m, 2H), 1.54-1.47 (m, 2H), 1.38-1.28 (m, 8H), 1.05 (s, 9H). HRMS calcd for $C_{51}H_{66}FN_{10}O_6S$ [M+H$^+$] 965.4872, found 965.4884.

Example 171

Synthesis of HC75-60

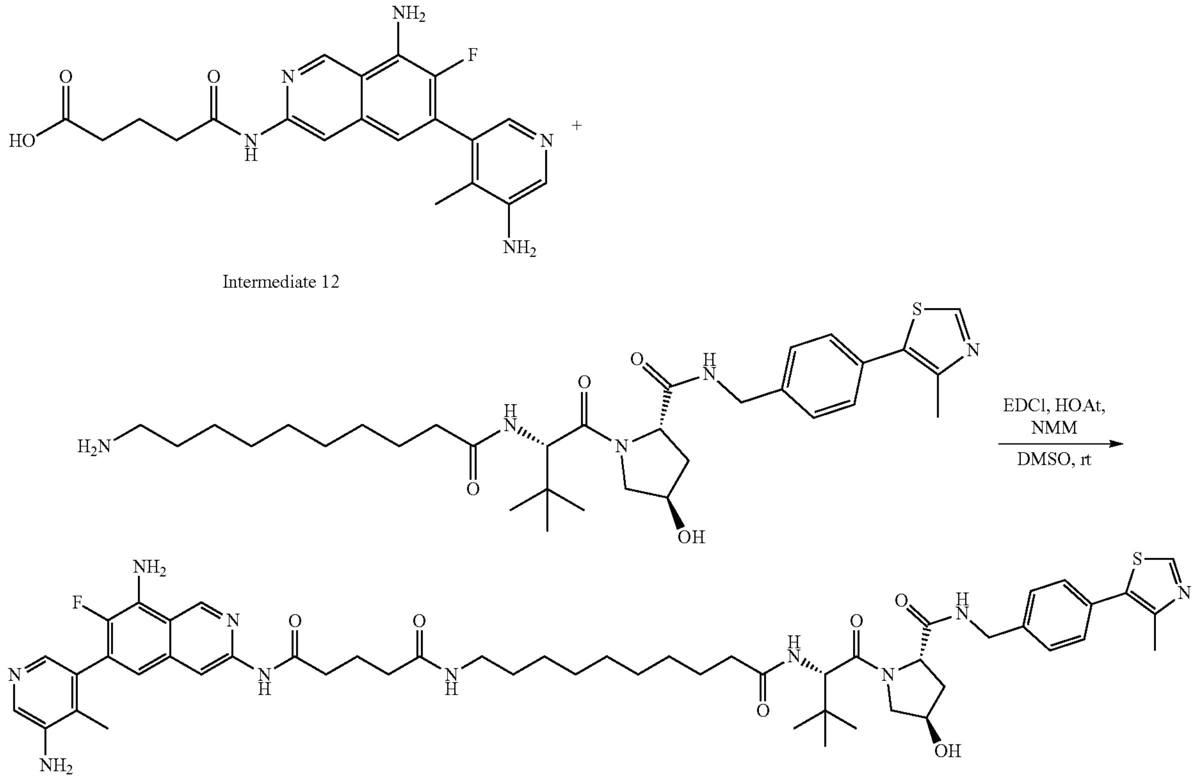

Intermediate 12

HC75-60

HC75-60 was synthesized following the standard procedure for preparing HC75-29 from Intermediate 12 (9.0 mg, 0.0144 mmol, 1.0 equiv), (2S,4R)-1-((S)-2-(10-aminodecanamido)-3,3-dimethylbutanoyl)-4-hydroxy-N-(4-(4-methylthiazol-5-yl)benzyl)pyrrolidine-2-carboxamide (11.9 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-60 was obtained as yellow solid in TFA salt form (4.3 mg, 25%). $^1H$ NMR (600 MHz, Methanol-$d_4$) δ 9.43 (s, 1H), 9.05 (s, 1H), 8.24 (s, 1H), 8.10 (s, 1H), 8.02 (s, 1H), 7.50 (d, J=8.1 Hz, 2H), 7.43 (d, J=8.2 Hz, 2H), 7.09 (d, J=5.9 Hz, 1H), 4.67 (s, 1H), 4.63-4.55 (m, 2H), 4.54-4.49 (m, 1H), 4.37 (d, J=15.6 Hz, 1H), 3.93 (d, J=11.0 Hz, 1H), 3.83 (dd, J=11.0, 3.9 Hz, 1H), 3.25-3.12 (m, 2H), 2.55 (t, J=7.3 Hz, 2H), 2.49 (s, 3H), 2.38-2.20 (m, 8H), 2.10 (ddd, J=13.2, 9.1, 4.5 Hz, 1H), 2.03 (p, J=7.4 Hz, 2H), 1.65-1.56 (m, 2H), 1.55-1.45 (m, 2H), 1.38-1.25 (m, 10H), 1.06 (s, 9H). HRMS calcd for $C_{52}H_{68}FN_{10}O_6S$ [M+H$^+$] 979.5028, found 979.5042.

Example 172

Synthesis of HC75-61

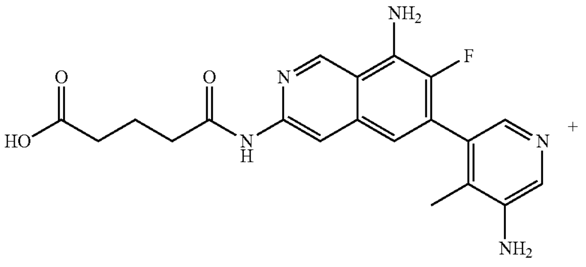

Intermediate 12

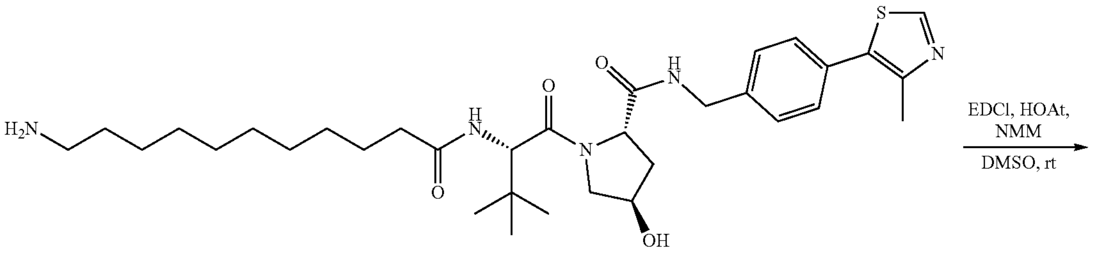

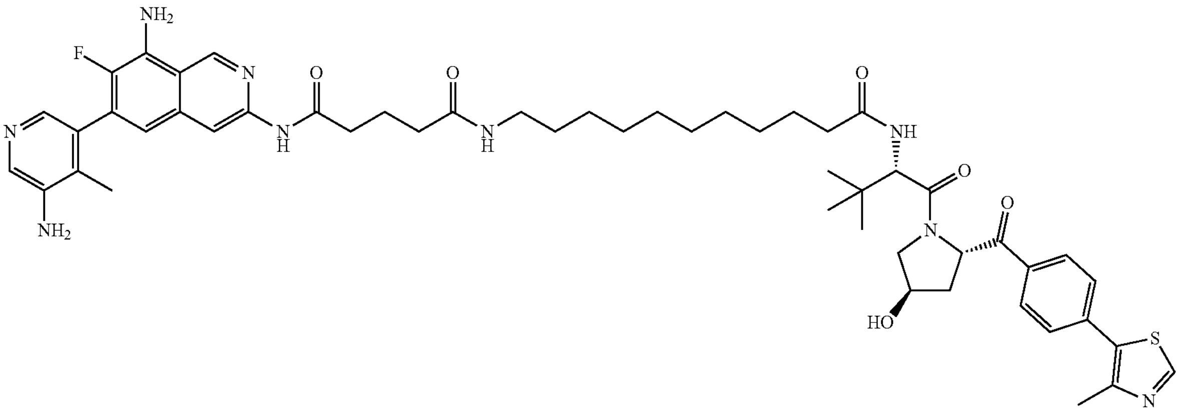

HC75-61

HC75-61 was synthesized following the standard procedure for preparing HC75-29 from Intermediate 12 (9.0 mg, 0.0144 mmol, 1.0 equiv), (2S,4R)-1-((S)-2-(11-aminoundecanamido)-3,3-dimethylbutanoyl)-4-hydroxy-N-(4-(4-methylthiazol-5-yl)benzyl)pyrrolidine-2-carboxamide (9.8 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-61 was obtained as yellow solid in TFA salt form (6.3 mg, 36%). $^1$H NMR (600 MHz, Methanol-$d_4$) δ 9.42 (s, 1H), 9.04 (s, 1H), 8.25 (s, 1H), 8.10 (s, 1H), 8.02 (s, 1H), 7.49 (d, J=8.0 Hz, 2H), 7.43 (d, J=8.2 Hz, 2H), 7.10 (d, J=5.8 Hz, 1H), 4.66 (s, 1H), 4.63-4.54 (m, 2H), 4.54-4.49 (m, 1H), 4.37 (d, J=15.5 Hz, 1H), 3.93 (d, J=11.0 Hz, 1H), 3.82 (dd, J=11.0, 3.9 Hz, 1H), 3.22-3.13 (m, 2H), 2.56 (t, J=7.4 Hz, 2H), 2.50 (s, 3H), 2.35-2.21 (m, 8H), 2.10 (ddd, J=13.3, 9.2, 4.5 Hz, 1H), 2.06-2.00 (m, 2H), 1.65-1.56 (m, 2H), 1.54-1.47 (m, 2H), 1.37-1.26 (m, 12H), 1.05 (s, 9H). HRMS calcd for $C_{53}H_{70}FN_{10}O_6S$ [M+H$^+$] 993.5185, found 993.5189.

Example 173

Synthesis of HC75-62

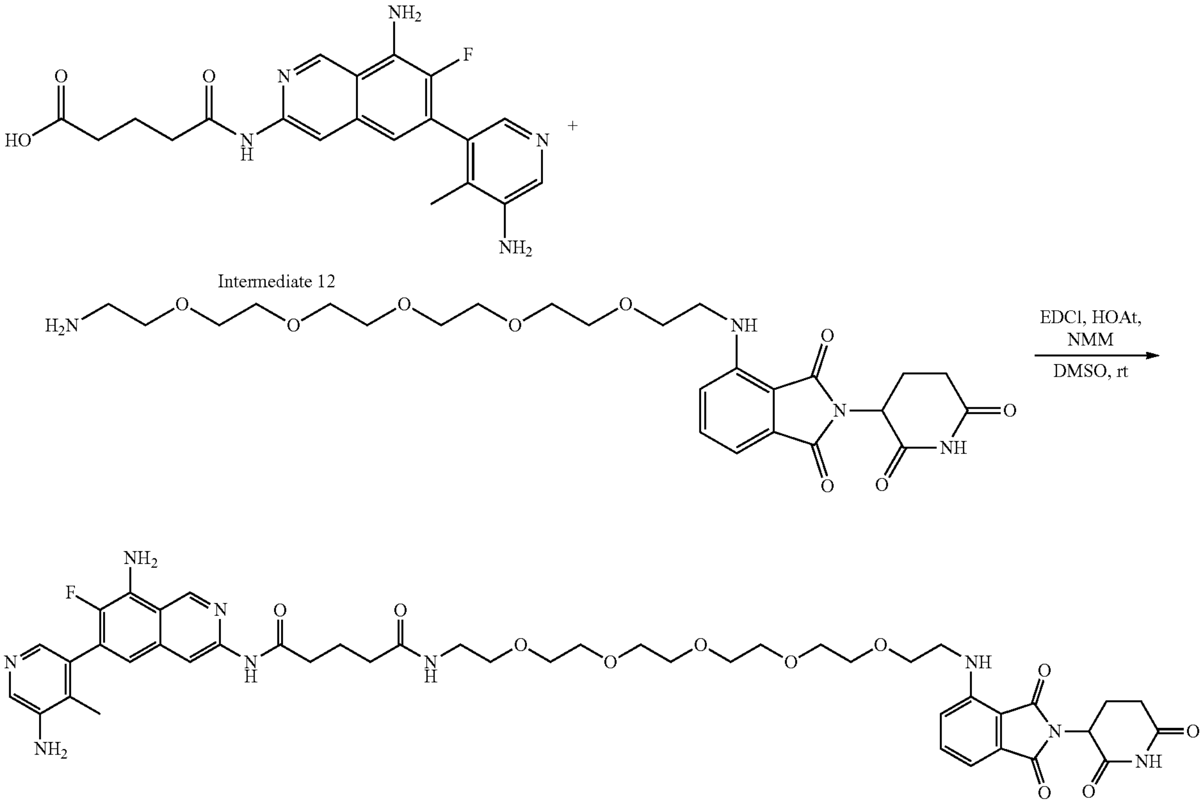

HC75-62

HC75-62 was synthesized following the standard procedure for preparing HC75-29 from Intermediate 12 (9.0 mg, 0.0144 mmol, 1.0 equiv), 4-((17-amino-3,6,9,12,15-pentaoxaheptadecyl)amino)-2-(2,6-dioxopiperidin-3-yl)isoindoline-1,3-dione (10.4 mg, 0.016 mmol, 1.1 equiv), EDCI (4.2 mg, 0.0216 mmol, 1.5 equiv), HOAt (3.0 mg, 0.0216 mmol, 1.5 equiv), and NMM (9.0 mg, 0.0864 mmol, 6.0 equiv) in DMSO (1 mL). HC75-62 was obtained as yellow solid in TFA salt form (8.2 mg, 48%). $^1$H NMR (600 MHz, Methanol-$d_4$) δ 9.35 (s, 1H), 8.24 (s, 1H), 8.09 (s, 1H), 8.03 (s, 1H), 7.50 (dd, J=8.5, 7.0 Hz, 1H), 7.07 (d, J=5.8 Hz, 1H), 7.02 (d, J=8.6 Hz, 1H), 6.97 (d, J=7.0 Hz, 1H), 5.06 (dd, J=12.7, 5.5 Hz, 1H), 3.71 (t, J=5.2 Hz, 2H), 3.65 (s, 4H), 3.64-3.58 (m, 12H), 3.55 (t, J=5.4 Hz, 2H), 3.46 (t, J=5.2 Hz, 2H), 3.38 (t, J=5.4 Hz, 2H), 2.88 (ddd, J=17.1, 13.8, 5.3 Hz, 1H), 2.81-2.65 (m, 2H), 2.57 (t, J=7.4 Hz, 2H), 2.35 (t, J=7.3 Hz, 2H), 2.23 (d, J=1.5 Hz, 3H), 2.16-2.09 (m, 1H), 2.05 (p, J=7.3 Hz, 2H). HRMS calcd for $C_{45}H_{55}FN_9O_{11}$ [M+H$^+$] 916.4005, found 916.4016.

Example 174

Synthesis of Intermediate 13

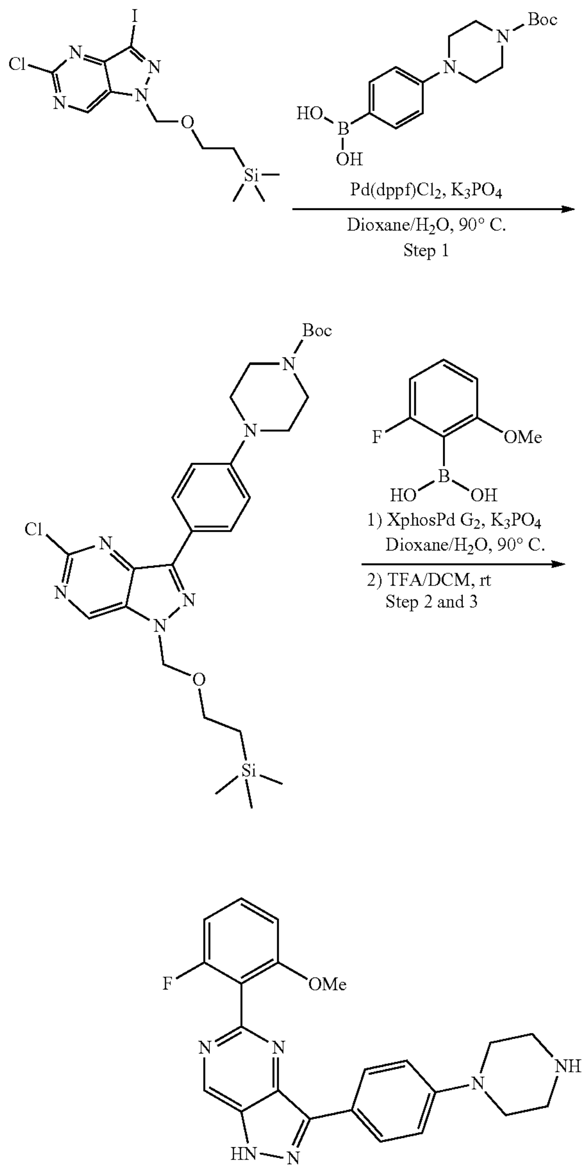

Intermediate 13

Step 1: tert-butyl 4-(4-(5-chloro-1-((2-(trimethylsilyl)ethoxy)methyl)-1H-pyrazolo[4,3-d]pyrimidin-3-yl)phenyl)piperazine-1-carboxylate A mixture of 5-chloro-3-iodo-1-((2-(trimethylsilyl) ethoxy)methyl)-1H-pyrazolo[4,3-d]pyrimidine (411 mg, 1 mmol, 1.0 equiv), (4-(4-(tert-butoxycarbonyl)piperazin-1-yl)phenyl)boronic acid (306 mg, 1 mmol, 1.0 equiv), Pd(dppf)$Cl_2$ (110 mg, 0.15 mmol, 0.15 equiv), $K_3PO_4$ (424 mg, 2.0 mmol, 2.0 equiv) in 1,4-dioxane (8 mL) and water (1.3 mL) was stirred at 90° C. for 5 h. The reaction was filtered and extracted with ethyl acetate. The combined organic extracts were combined and concentrated under vacuum. The residue was purified by silica gel column (hexane/ethyl acetate=3:2) to give the tert-butyl 4-(4-(5-chloro-1-((2-(trimethylsilyl)ethoxy)methyl)-1H-pyrazolo[4,3-d]pyrimidin-3-yl)phenyl)piperazine-1-carboxylate as a yellow solid (345 mg, 63%). ESI m/z=545.3 [M+H$^+$].

Step 2 and 3: Intermediate 13

A mixture of tert-butyl 4-(4-(5-chloro-1-((2-(trimethylsilyl)ethoxy)methyl)-1H-pyrazolo[4,3-d]pyrimidin-3-yl)phenyl)piperazine-1-carboxylate (345 mg, 0.63 mmol, 1.0 equiv), (2-fluoro-6-methoxyphenyl)boronic acid (306 mg, 1 mmol, 1.0 equiv), XphosPd G2 (50 mg, 0.06 mmol, 0.1 equiv), $K_3PO_4$ (400 mg, 1.9 mmol, 3.0 equiv) in 1,4-dioxane (6.4 mL) and water (0.8 mL) was stirred at 90° C. for 1.5 h. The reaction was filtered and extracted with ethyl acetate. The combined organic extracts were combined and concentrated under vacuum. The obtained residue was dissolved in DCM (4 mL). To the solution was added TFA (2 mL). Stirred at room temperature for 1 h and concentrated under vacuum. The residue was purified preparative HPLC (10%-100% methanol/0.1% TFA in $H_2O$) to afford intermediate 13 as a yellow solid (280 mg, 86% for two steps) in TFA salt form. $^1$H NMR (800 MHz, Methanol-d$_4$) δ 9.32 (s, 1H), 8.43 (d, J=8.4 Hz, 2H), 7.50 (q, J=7.9 Hz, 1H), 7.17 (d, J=8.4 Hz, 2H), 7.02 (d, J=8.5 Hz, 1H), 6.90 (t, J=8.6 Hz, 1H), 3.81 (s, 3H), 3.53 (t, J=5.2 Hz, 4H), 3.41 (t, J=5.2 Hz, 4H). ESI m/z=405.3 [M+H$^+$].

Example 175

Synthesis of HC90-33

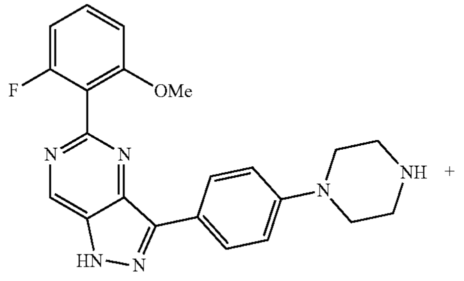

Intermediate 13

-continued

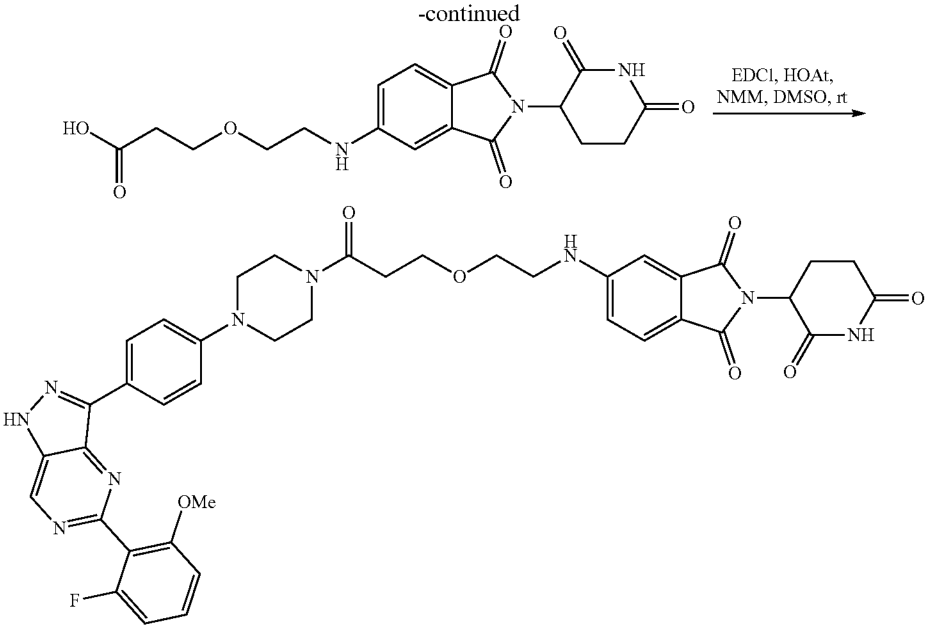

HC90-33

To a solution of Intermediate 13 (7.8 mg, 0.015 mmol, 1.0 equiv) in DMSO (1 mL) were added 3-(2-((2-(2,6-dioxopiperidin-3-yl)-1,3-dioxoisoindolin-5-yl)amino)ethoxy)propanoic acid (7.6 mg, 0.015 mmol, 1.0 equiv), EDCI (1-ethyl-3-(3-dimethylaminopropyl)carbodiimide) (4.2 mg, 0.0225 mmol, 1.5 equiv), HOAt (1-hydroxy-7-azabenzo-triazole) (3.1 mg, 0.0225 mmol, 1.5 equiv), and NMM (N-Methylmorpholine) (6.1 mg, 0.06 mmol, 4.0 equiv). After being stirred overnight at room temperature, the resulting mixture was purified by preparative HPLC (10%-100% methanol/0.1% TFA in $H_2O$) to afford HC90-33 as yellow solid in TFA salt form (8.2 mg, 61%). $^1H$ NMR (600 MHz, Acetone-$d_6$) δ 9.88 (s, 1H), 9.41 (s, 1H), 8.45 (d, J=8.9 Hz, 2H), 7.57 (d, J=8.3 Hz, 1H), 7.50 (td, J=8.5, 6.7 Hz, 1H), 7.11 (d, J=8.9 Hz, 2H), 7.08 (d, J=2.1 Hz, 1H), 7.02 (d, J=8.5 Hz, 1H), 6.99 (dd, J=8.3, 2.2 Hz, 1H), 6.91 (t, J=8.7 Hz, 1H), 5.05 (dd, J=12.6, 5.4 Hz, 1H), 3.90-3.71 (m, 11H), 3.45 (t, J=5.2 Hz, 2H), 3.33 (dd, J=6.4, 4.0 Hz, 2H), 3.28 (t, J=5.3 Hz, 2H), 3.00-2.90 (m, 1H), 2.82-2.69 (m, 4H), 2.20-2.13 (m, 1H). HRMS calcd for $C_{40}H_{39}FN_9O_7^+$ [M+H$^+$] 776.2951, found 776.2940.

Example 176

Synthesis of HC90-34

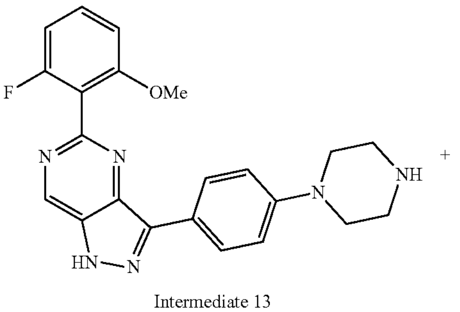

Intermediate 13

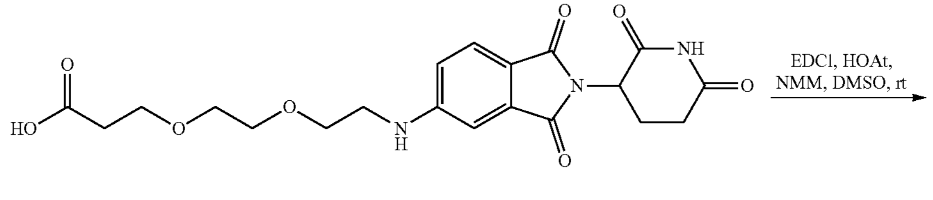

-continued

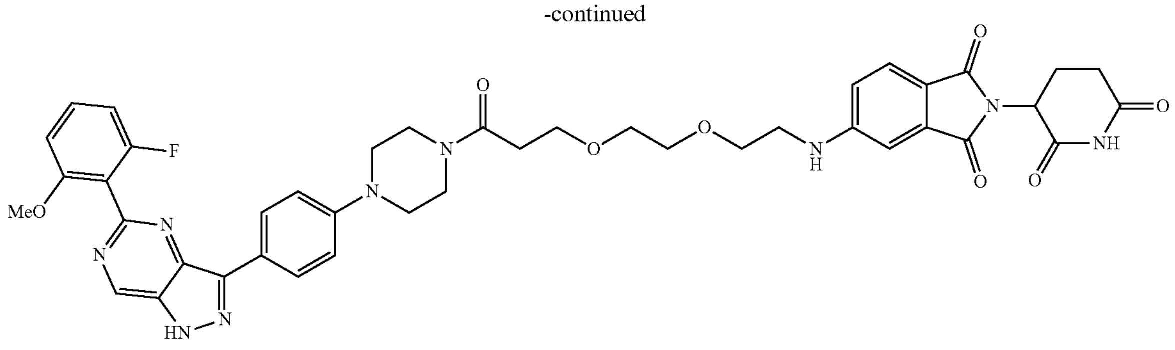

HC90-34

HC90-34 was synthesized following the standard procedure for preparing HC90-33 from Intermediate 13 (7.8 mg, 0.015 mmol, 1.0 equiv), 3-(2-(2-((2-(2,6-dioxopiperidin-3-yl)-1,3-dioxoisoindolin-5-yl)amino)ethoxy)ethoxy)propanoic acid (8.2 mg, 0.015 mmol, 1.0 equiv), EDCI (4.2 mg, 0.0225 mmol, 1.5 equiv), HOAt (3.1 mg, 0.0225 mmol, 1.5 equiv), and NMM (6.1 mg, 0.06 mmol, 4.0 equiv) in DMSO (1 mL). HC90-34 was obtained as yellow solid in TFA salt form (8.4 mg, 60%). $^1H$ NMR (600 MHz, Acetone-$d_6$) δ 9.89 (s, 1H), 9.41 (s, 1H), 8.45 (d, J=8.9 Hz, 2H), 7.55 (d, J=8.3 Hz, 1H), 7.50 (td, J=8.5, 6.7 Hz, 1H), 7.14 (d, J=8.9 Hz, 2H), 7.10 (d, J=2.1 Hz, 1H), 7.02 (d, J=8.5 Hz, 1H), 6.98 (dd, J=8.3, 2.2 Hz, 1H), 6.91 (t, J=8.7 Hz, 1H), 5.05 (dd, J=12.7, 5.4 Hz, 1H), 3.84-3.73 (m, 9H), 3.72 (t, J=5.2 Hz, 2H), 3.66-3.57 (m, 4H), 3.44 (t, J=5.3 Hz, 2H), 3.35 (t, J=5.2 Hz, 2H), 3.28 (t, J=5.3 Hz, 2H), 2.99-2.91 (m, 1H), 2.82-2.71 (m, 2H), 2.68 (t, J=6.3 Hz, 2H), 2.19-2.14 (m, 1H). HRMS calcd for $C_{42}H_{43}FN_9O_8^+$ [M+H$^+$] 820.3213, found 820.3201.

Example 177

Synthesis of HC90-35

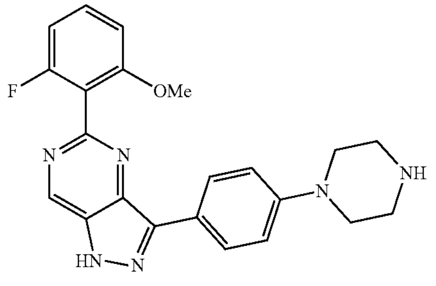

Intermediate 13

+

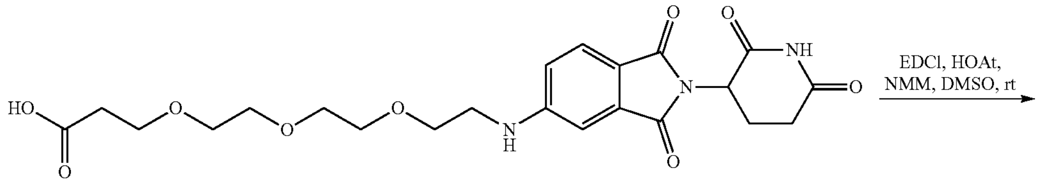

-continued

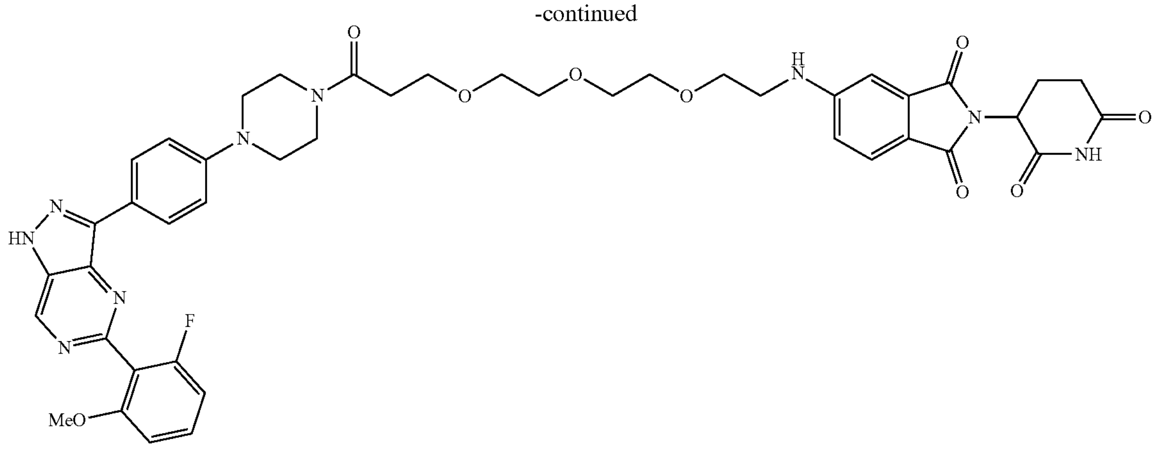

HC90-35

HC90-35 was synthesized following the standard procedure for preparing HC90-33 from Intermediate 13 (7.8 mg, 0.015 mmol, 1.0 equiv), 3-(2-(2-(2-((2-(2,6-dioxopiperidin-3-yl)-1,3-dioxoisoindolin-5-yl)amino)ethoxy)ethoxy) ethoxy)propanoic acid (8.9 mg, 0.015 mmol, 1.0 equiv), EDCI (4.2 mg, 0.0225 mmol, 1.5 equiv), HOAt (3.1 mg, 0.0225 mmol, 1.5 equiv), and NMM (6.1 mg, 0.06 mmol, 4.0 equiv) in DMSO (1 mL). HC90-35 was obtained as yellow solid in TFA salt form (9.6 mg, 74%). $^1$H NMR (600 MHz, Acetone-$d_6$) δ 9.89 (s, 1H), 9.42 (s, 1H), 8.46 (d, J=8.9 Hz, 2H), 7.55 (d, J=8.3 Hz, 1H), 7.50 (td, J=8.4, 6.6 Hz, 1H), 7.15 (d, J=8.9 Hz, 2H), 7.06 (d, J=2.2 Hz, 1H), 7.03 (d, J=8.5 Hz, 1H), 6.95 (dd, J=8.3, 2.2 Hz, 1H), 6.91 (t, J=8.7 Hz, 1H), 5.06 (dd, J=12.7, 5.5 Hz, 1H), 3.81-3.73 (m, 9H), 3.70 (t, J=5.4 Hz, 2H), 3.60 (s, 8H), 3.44 (t, J=5.4 Hz, 2H), 3.35 (t, J=5.2 Hz, 2H), 3.28 (t, J=5.2 Hz, 2H), 3.00-2.89 (m, 1H), 2.83-2.72 (m, 2H), 2.68 (t, J=6.5 Hz, 2H), 2.25-2.13 (m, 1H). HRMS calcd for $C_{44}H_{47}FN_9O_9^+$ [M+H$^+$] 864.3475, found 864.3458.

Example 178

Synthesis of HC90-36

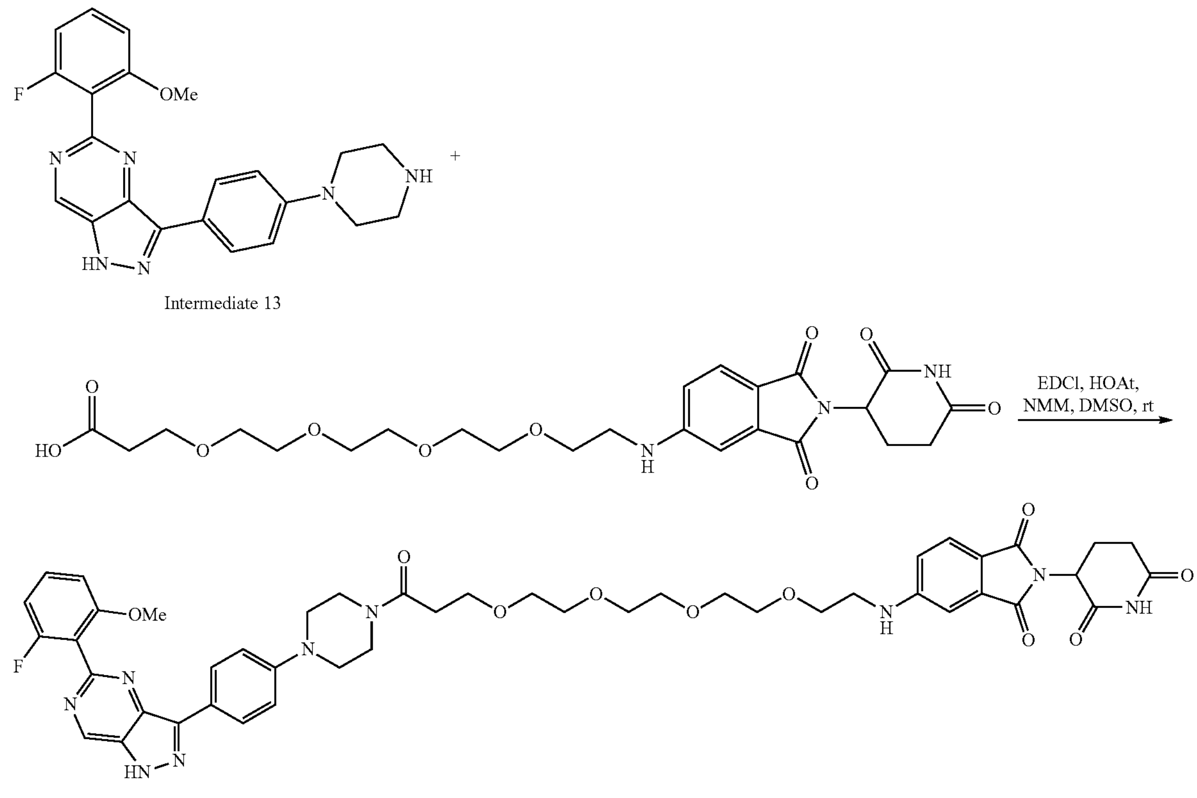

Intermediate 13

HC90-38

HC90-36 was synthesized following the standard procedure for preparing HC90-33 from Intermediate 13 (7.8 mg, 0.015 mmol, 1.0 equiv), 1-((2-(2,6-dioxopiperidin-3-yl)-1,3-dioxoisoindolin-5-yl)amino)-3,6,9,12-tetraoxapentadecan-15-oic acid (9.5 mg, 0.015 mmol, 1.0 equiv), EDCI (4.2 mg, 0.0225 mmol, 1.5 equiv), HOAt (3.1 mg, 0.0225 mmol, 1.5 equiv), and NMM (6.1 mg, 0.06 mmol, 4.0 equiv) in DMSO (1 mL). HC90-36 was obtained as yellow solid in TFA salt form (9.5 mg, 62%). $^1$H NMR (600 MHz, Acetone-$d_6$) δ 9.89 (s, 1H), 9.41 (s, 1H), 8.46 (d, J=8.9 Hz, 2H), 7.57 (d, J=8.3 Hz, 1H), 7.50 (td, J=8.5, 6.7 Hz, 1H), 7.13 (d, J=9.0 Hz, 2H), 7.07 (d, J=2.1 Hz, 1H), 7.02 (d, J=8.5 Hz, 1H), 6.96 (dd, J=8.3, 2.2 Hz, 1H), 6.93-6.89 (m, 1H), 5.06 (dd, J=12.7, 5.4 Hz, 1H), 3.79 (s, 3H), 3.77-3.70 (m, 8H), 3.62-3.57 (m, 12H), 3.46 (t, J=5.3 Hz, 2H), 3.34 (t, J=5.1 Hz, 2H), 3.27 (t, J=5.2 Hz, 2H), 3.00-2.92 (m, 1H), 2.82-2.72 (m, 2H), 2.67 (t, J=6.5 Hz, 2H), 2.20-2.14 (m, 1H). HRMS calcd for $C_{46}H_{51}FN_9O_{10}^+$ [M+H$^+$] 908.3737, found 908.3721.

Example 179

Synthesis of HC90-37

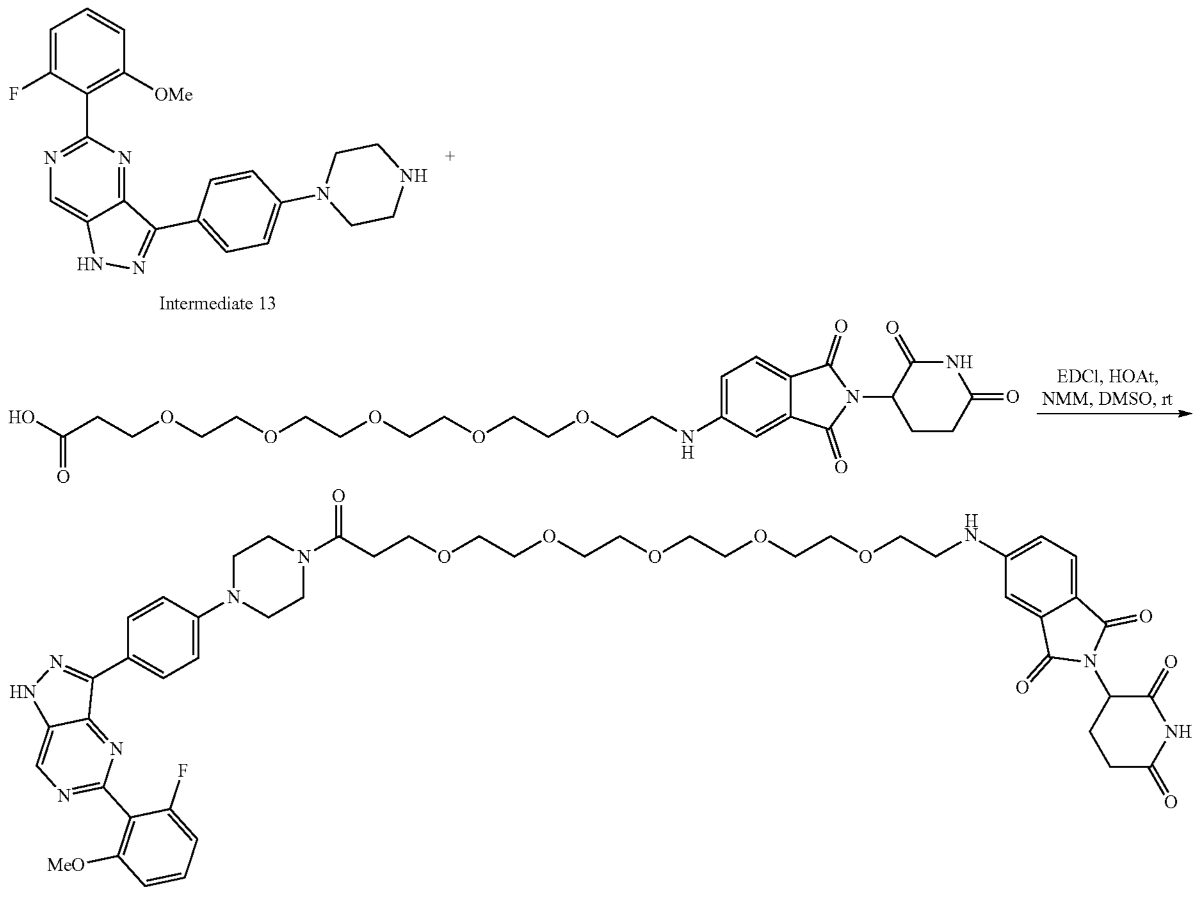

HC90-37

HC90-37 was synthesized following the standard procedure for preparing HC90-33 from Intermediate 13 (7.8 mg, 0.015 mmol, 1.0 equiv), 1-((2-(2,6-dioxopiperidin-3-yl)-1,3-dioxoisoindolin-5-yl)amino)-3,6,9,12,15-pentaoxaoctadecan-18-oic acid (10.2 mg, 0.015 mmol, 1.0 equiv), EDCI (4.2 mg, 0.0225 mmol, 1.5 equiv), HOAt (3.1 mg, 0.0225 mmol, 1.5 equiv), and NMM (6.1 mg, 0.06 mmol, 4.0 equiv) in DMSO (1 mL). HC90-37 was obtained as yellow solid in TFA salt form (8.9 mg, 56%). $^1$H NMR (600 MHz, Acetone-$d_6$) δ 9.90 (s, 1H), 9.40 (s, 1H), 8.46 (d, J=9.0 Hz, 2H), 7.57 (d, J=8.3 Hz, 1H), 7.49 (td, J=8.5, 6.7 Hz, 1H), 7.13 (d, J=9.0 Hz, 2H), 7.07 (d, J=2.2 Hz, 1H), 7.02 (d, J=8.5 Hz, 1H), 6.97 (dd, J=8.3, 2.2 Hz, 1H), 6.91 (t, J=8.7 Hz, 1H), 5.06 (dd, J=12.6, 5.5 Hz, 1H), 3.79 (s, 3H), 3.77-3.71 (m, 8H), 3.63-3.56 (m, 16H), 3.46 (t, J=5.3 Hz, 2H), 3.34 (t, J=5.2 Hz, 2H), 3.27 (t, J=5.4 Hz, 2H), 3.02-2.92 (m, 1H), 2.84-2.73 (m, 2H), 2.68 (t, J=6.4 Hz, 2H), 2.23-2.14 (m, 1H). HRMS calcd for $C_{48}H_{55}FN_9O_{11}^+$ [M+H$^+$] 952.4000, found 952.3988.

Example 180

Synthesis of HC90-41

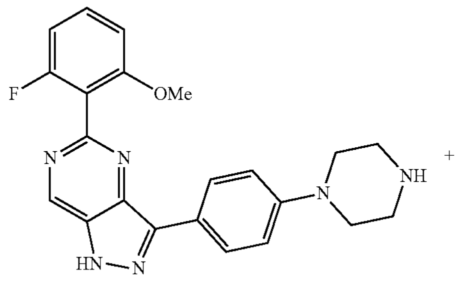

Intermediate 13

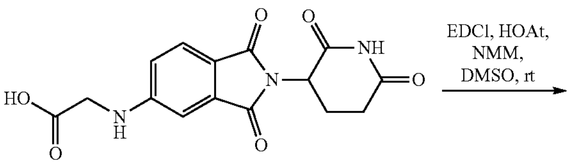

-continued

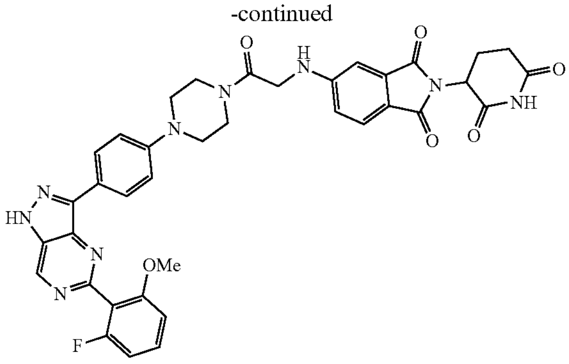

HC90-41

HC90-41 was synthesized following the standard procedure for preparing HC90-33 from Intermediate 13 (6.5 mg, 0.0125 mmol, 1.0 equiv), (2-(2,6-dioxopiperidin-3-yl)-1,3-dioxoisoindolin-5-yl)glycine (5.6 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-41 was obtained as yellow solid in TFA salt form (4.8 mg, 46%). $^1$H NMR (800 MHz, Acetone-$d_6$) δ 9.40 (s, 1H), 8.47 (d, J=8.2 Hz, 2H), 7.62 (d, J=8.1 Hz, 1H), 7.50 (q, J=8.3 Hz, 1H), 7.20 (s, 1H), 7.18-7.11 (m, 3H), 7.03 (d, J=8.4 Hz, 1H), 6.91 (t, J=8.5 Hz, 1H), 5.07 (dd, J=12.9, 5.8 Hz, 1H), 4.30 (s, 3H), 3.91-3.76 (m, 6H), 3.43 (t, J=5.1 Hz, 2H), 3.39-3.31 (m, 2H), 3.05-2.92 (m, 1H), 2.85-2.74 (m, 2H), 2.27-2.18 (m, 1H). HRMS calcd for $C_{37}H_{33}FN_9O_6^+$ [M+H$^+$] 718.2532, found 718.2514.

Example 181

Synthesis of HC90-42

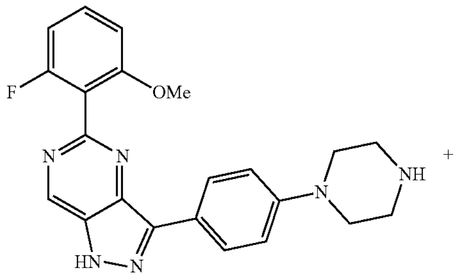

Intermediate 13

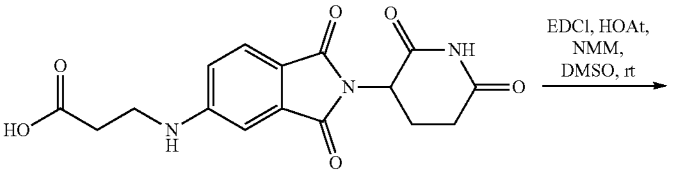

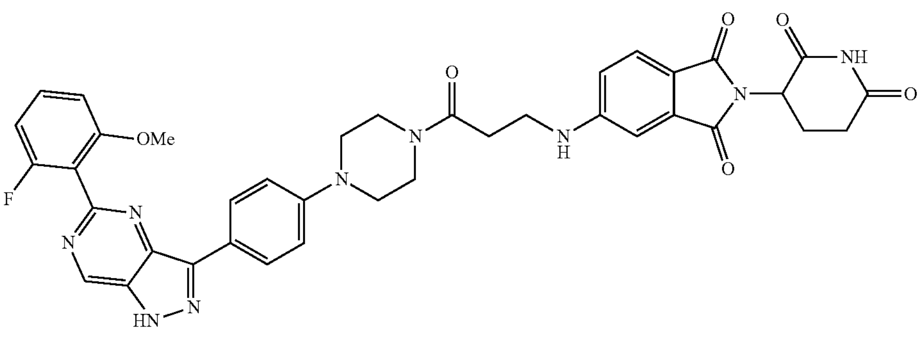

HC90-42

HC90-42 was synthesized following the standard procedure for preparing HC90-33 from Intermediate 13 (6.5 mg, 0.0125 mmol, 1.0 equiv), 3-((2-(2,6-dioxopiperidin-3-yl)-1,3-dioxoisoindolin-5-yl)amino)propanoic acid (5.7 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-42 was obtained as yellow solid in TFA salt form (3.3 mg, 28%). $^{1}$H NMR (800 MHz, Acetone-$d_6$) δ 9.40 (s, 1H), 8.45 (d, J=8.5 Hz, 2H), 7.59 (d, J=8.3 Hz, 1H), 7.50 (q, J=8.0 Hz, 1H), 7.11 (d, J=8.5 Hz, 2H), 7.08 (s, 1H), 7.03 (d, J=8.5 Hz, 1H), 7.00 (d, J=8.6 Hz, 1H), 6.91 (t, J=8.6 Hz, 1H), 5.06 (dd, J=12.7, 5.7 Hz, 1H), 3.79 (s, 3H), 3.78-3.71 (m, 4H), 3.65 (t, J=6.3 Hz, 2H), 3.35-3.29 (m, 2H), 3.27 (t, J=5.4 Hz, 2H), 2.98-2.74 (m, 5H), 2.20-2.14 (m, 1H). HRMS calcd for $C_{38}H_{35}FN_9O_6^+$ [M+H$^+$] 732.2689, found 732.2672.

Example 182

Synthesis of HC90-43

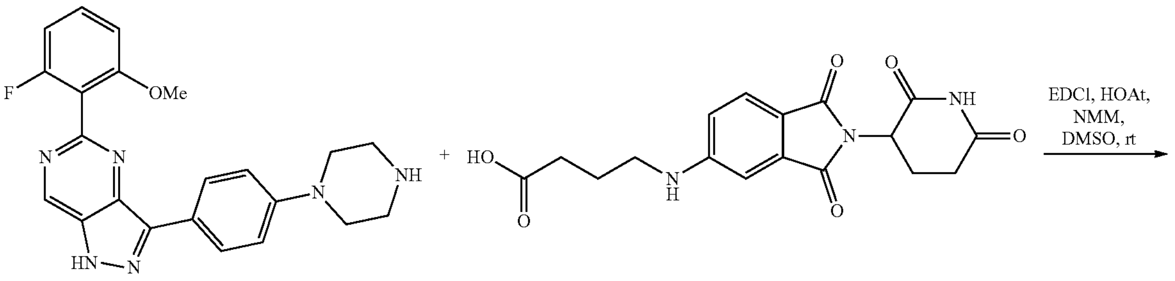

Intermediate 13

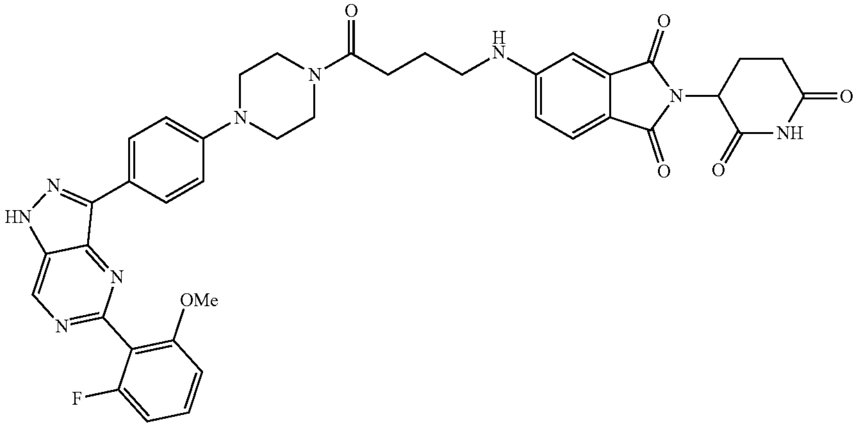

HC90-43

HC90-43 was synthesized following the standard procedure for preparing HC90-33 from Intermediate 13 (6.5 mg, 0.0125 mmol, 1.0 equiv), 4-((2-(2,6-dioxopiperidin-3-yl)-1,3-dioxoisoindolin-5-yl)amino)butanoic acid (5.9 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-43 was obtained as yellow solid in TFA salt form (3.6 mg, 33%). $^{1}$H NMR (600 MHz, Acetone-$d_6$) δ 9.87 (s, 1H), 9.41 (d, J=1.7 Hz, 1H), 8.45 (d, J=7.7 Hz, 2H), 7.61-7.56 (m, 1H), 7.53-7.46 (m, 1H), 7.11 (d, J=7.1 Hz, 2H), 7.06-7.01 (m, 2H), 6.99-6.95 (m, 1H), 6.91 (t, J=8.6 Hz, 1H), 6.52 (s, 1H), 5.04 (dd, J=12.7, 5.6 Hz, 1H), 3.79 (s, 3H), 3.77-3.72 (m, 4H), 3.42-3.37 (m, 2H), 3.32-3.25 (m, 4H), 2.81-2.71 (m, 3H), 2.62 (t, J=6.9 Hz, 2H), 2.20-2.13 (m, 1H), 2.04-1.99 (m, 2H). HRMS calcd for $C_{39}H_{37}FN_9O_6^+$ [M+H$^+$]746.2845, found 746.2832.

Example 183

Synthesis of HC90-44

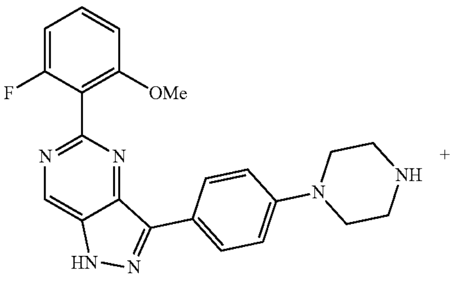

Intermediate 13

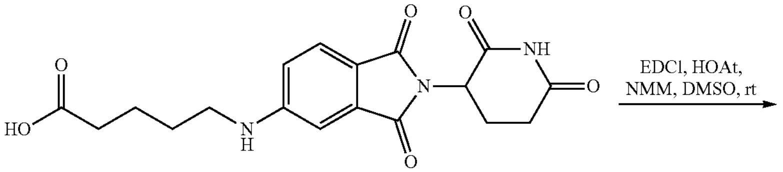

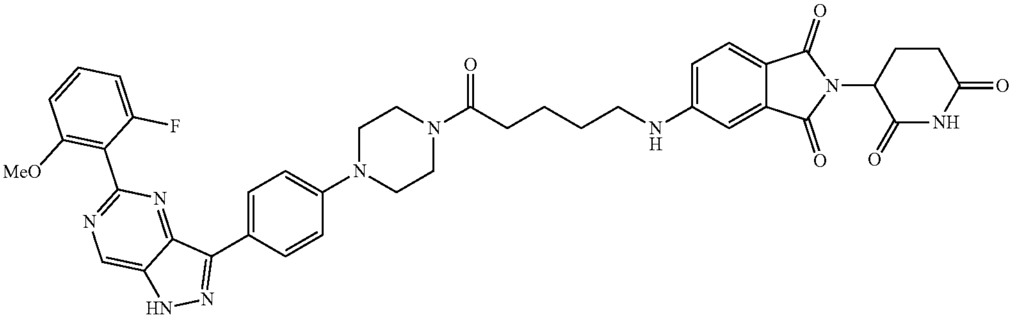

HC90-44

HC90-44 was synthesized following the standard procedure for preparing HC90-33 from Intermediate 13 (6.5 mg, 0.0125 mmol, 1.0 equiv), 5-((2-(2,6-dioxopiperidin-3-yl)-1,3-dioxoisoindolin-5-yl)amino)pentanoic acid (6.1 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-44 was obtained as yellow solid in TFA salt form (5.2 mg, 46%). $^1$H NMR (800 MHz, Acetone-$d_6$) δ 9.40 (s, 1H), 8.46 (d, J=8.3 Hz, 1H), 7.58 (d, J=8.4 Hz, 1H), 7.50 (q, J=8.3 Hz, 1H), 7.12 (d, J=8.3 Hz, 2H), 7.06-7.01 (m, 3H), 6.96 (d, J=8.0 Hz, 1H), 6.91 (t, J=8.5 Hz, 1H), 5.05 (dd, J=12.6, 5.7 Hz, 1H), 3.79 (s, 3H), 3.76-3.69 (m, 4H), 3.40-3.30 (m, 4H), 3.26 (t, J=5.6 Hz, 2H), 3.01-2.92 (m, 1H), 2.84-2.73 (m, 2H), 2.53 (t, J=6.6 Hz, 2H), 2.21-2.15 (m, 1H), 1.84-1.74 (m, 4H). HRMS calcd for $C_{40}H_{39}FN_9O_6^+$ [M+H$^+$] 760.3002, found 760.2988.

Example 184

Synthesis of HC90-45

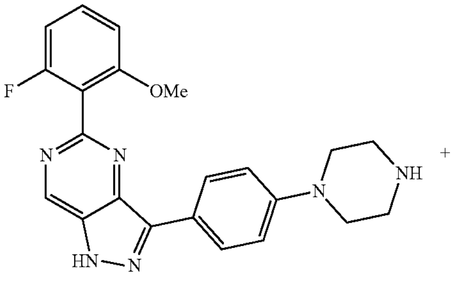

Intermediate 13

-continued

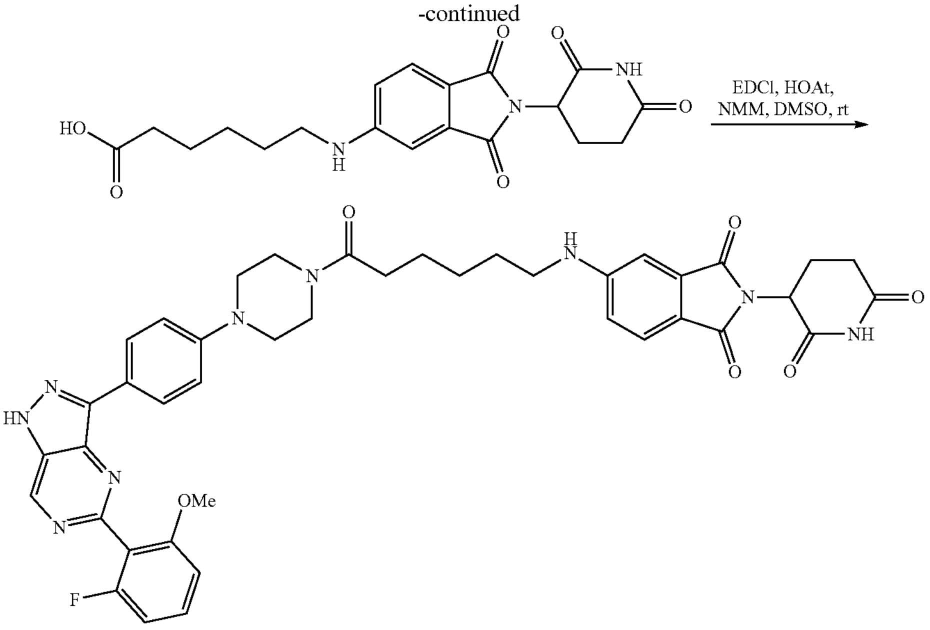

HC90-45

HC90-45 was synthesized following the standard procedure for preparing HC90-33 from Intermediate 13 (6.5 mg, 0.0125 mmol, 1.0 equiv), 6-((2-(2,6-dioxopiperidin-3-yl)-1,3-dioxoisoindolin-5-yl)amino)hexanoic acid (6.3 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-45 was obtained as yellow solid in TFA salt form (5.8 mg, 52%). $^1$H NMR (800 MHz, Acetone-$d_6$) δ 9.40 (s, 1H), 8.46 (d, J=8.4 Hz, 2H), 7.58 (d, J=8.2 Hz, 1H), 7.54-7.46 (m, 1H), 7.12 (d, J=8.3 Hz, 2H), 7.07-7.01 (m, 2H), 6.95 (d, J=8.3 Hz, 1H), 6.91 (t, J=8.4 Hz, 1H), 5.05 (dd, J=12.8, 5.7 Hz, 1H), 3.79 (s, 3H), 3.76-3.71 (m, 4H), 3.36-3.29 (m, 4H), 3.29-3.24 (m, 2H), 3.02-2.93 (m, 1H), 2.82-2.73 (m, 2H), 2.46 (t, J=7.3 Hz, 2H), 2.22-2.15 (m, 1H), 1.72 (dq, J=28.5, 7.3 Hz, 4H), 1.52 (t, J=7.7 Hz, 2H). HRMS calcd for $C_{41}H_{41}FN_9O_6^+$ [M+H$^+$] 774.3158, found 774.3144.

Example 185

Synthesis of HC90-46

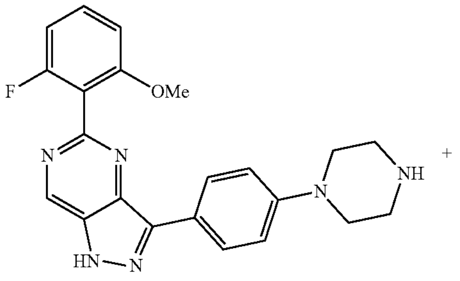

Intermediate 13

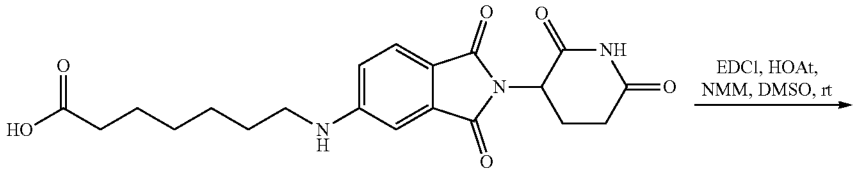

-continued

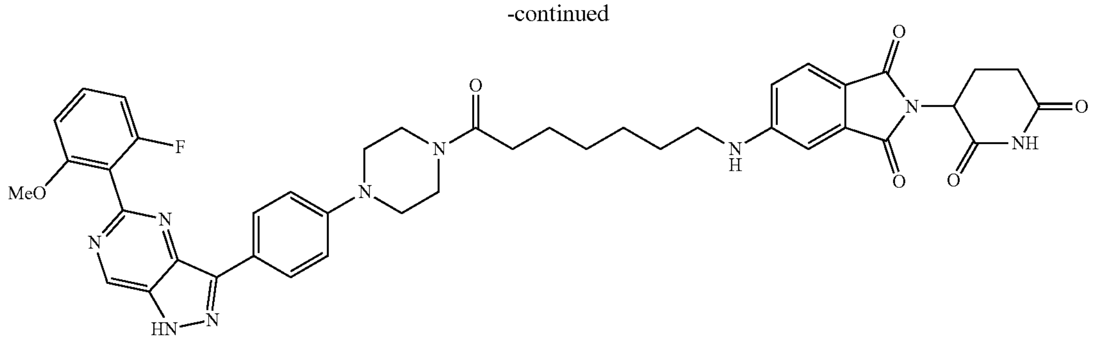

HC90-46

HC90-46 was synthesized following the standard procedure for preparing HC90-33 from Intermediate 13 (6.5 mg, 0.0125 mmol, 1.0 equiv), 7-((2-(2,6-dioxopiperidin-3-yl)-1,3-dioxoisoindolin-5-yl)amino)heptanoic acid (6.4 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-46 was obtained as yellow solid in TFA salt form (4.7 mg, 42%). $^1$H NMR (600 MHz, Acetone-$d_6$) δ 9.87 (s, 1H), 9.41 (s, 1H), 8.46 (d, J=8.9 Hz, 2H), 7.58 (d, J=8.4 Hz, 1H), 7.50 (td, J=8.5, 6.7 Hz, 1H), 7.13 (d, J=9.0 Hz, 2H), 7.03 (dd, J=5.3, 3.2 Hz, 2H), 6.94 (dd, J=8.4, 2.2 Hz, 1H), 6.91 (t, J=8.7 Hz, 1H), 5.05 (dd, J=12.7, 5.5 Hz, 1H), 3.79 (s, 3H), 3.75-3.69 (m, 4H), 3.34-3.22 (m, 6H), 3.01-2.92 (m, 1H), 2.82-2.73 (m, 2H), 2.44 (t, J=7.4 Hz, 2H), 2.22-2.14 (m, 1H), 1.72 (p, J=7.2 Hz, 2H), 1.66 (p, J=7.5 Hz, 2H), 1.51 (p, J=7.2 Hz, 2H), 1.47-1.41 (m, 2H). HRMS calcd for $C_{42}H_{43}FN_9O_6^+$ [M+H$^+$] 788.3315, found 788.3302.

Example 186

Synthesis of HC90-47

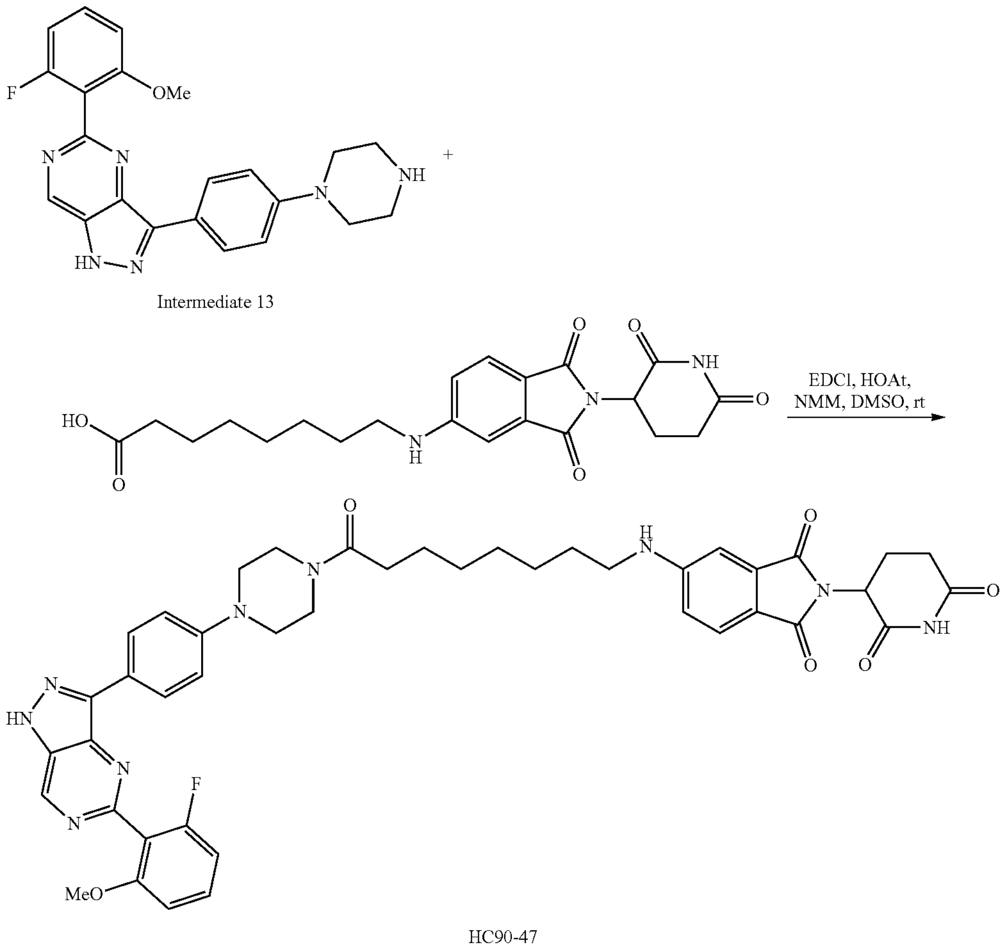

HC90-47

HC90-47 was synthesized following the standard procedure for preparing HC90-33 from Intermediate 13 (6.5 mg, 0.0125 mmol, 1.0 equiv), 8-((2-(2,6-dioxopiperidin-3-yl)-1,3-dioxoisoindolin-5-yl)amino)octanoic acid (6.6 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-47 was obtained as yellow solid in TFA salt form (4.2 mg, 37%). $^1$H NMR (800 MHz, Acetone-$d_6$) δ 9.40 (s, 1H), 8.46 (d, J=8.5 Hz, 2H), 7.57 (d, J=8.2 Hz, 1H), 7.50 (q, J=8.0 Hz, 1H), 7.13 (d, J=8.5 Hz, 2H), 7.07-7.01 (m, 2H), 6.98-6.89 (m, 2H), 5.06 (dd, J=12.8, 5.7 Hz, 1H), 3.79 (s, 3H), 3.76-3.70 (m, 4H), 3.36-3.24 (m, 6H), 3.01-2.93 (m, 1H), 2.81-2.73 (m, 2H), 2.43 (t, J=7.4 Hz, 2H), 2.22-2.15 (m, 1H), 1.71 (t, J=7.5 Hz, 2H), 1.64 (t, J=7.3 Hz, 2H), 1.48 (t, J=7.6 Hz, 2H), 1.45-1.39 (m, 4H). HRMS calcd for $C_{43}H_{45}FN_9O_6^+$ [M+H$^+$] 802.3471, found 802.3457.

Example 187

Synthesis of HC90-49

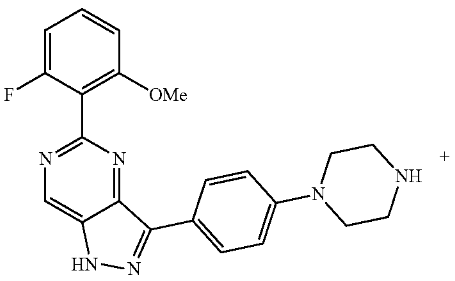

Intermediate 13

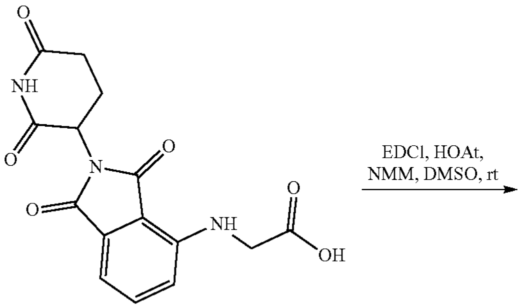

-continued

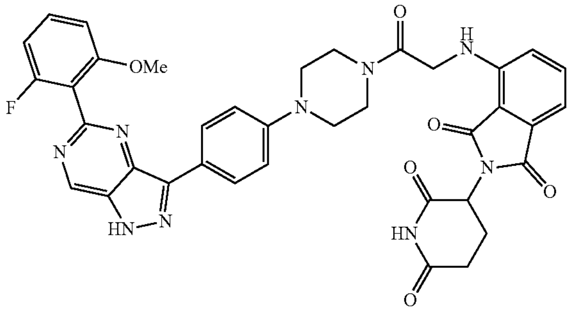

HC90-49

HC90-49 was synthesized following the standard procedure for preparing HC90-33 from Intermediate 13 (6.5 mg, 0.0125 mmol, 1.0 equiv), (2-(2,6-dioxopiperidin-3-yl)-1,3-dioxoisoindolin-4-yl)glycine (4.2 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-49 was obtained as yellow solid in TFA salt form (5.3 mg, 51%). $^1$H NMR (800 MHz, Acetone-$d_6$) δ 9.40 (s, 1H), 8.47 (d, J=8.4 Hz, 2H), 7.62 (t, J=7.7 Hz, 1H), 7.50 (q, J=7.9 Hz, 1H), 7.21-7.12 (m, 3H), 7.09 (d, J=6.9 Hz, 1H), 7.03 (d, J=8.4 Hz, 1H), 6.92 (t, J=8.6 Hz, 1H), 5.11 (dd, J=12.6, 5.7 Hz, 1H), 4.35 (s, 2H), 3.87-3.77 (m, 7H), 3.43 (t, J=5.5 Hz, 2H), 3.36 (t, J=5.5 Hz, 2H), 3.03-2.96 (m, 1H), 2.88-2.76 (m, 2H), 2.31-2.20 (m, 1H). HRMS calcd for $C_{37}H_{33}FN_9O_6^+$ [M+H$^+$] 718.2532, found 718.2520.

Example 188

Synthesis of HC90-50

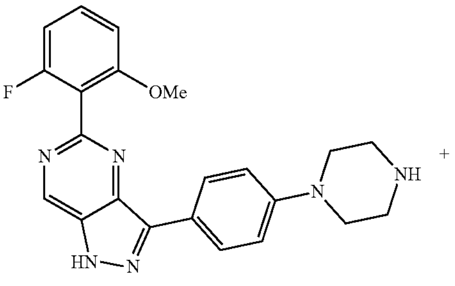

Intermediate 13

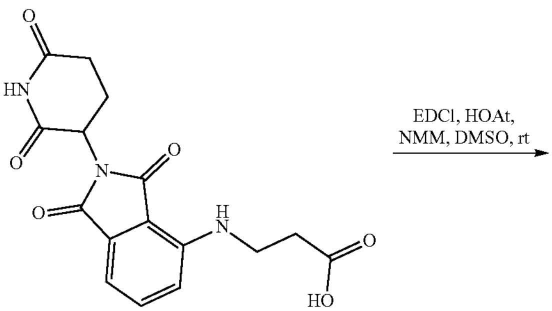

-continued

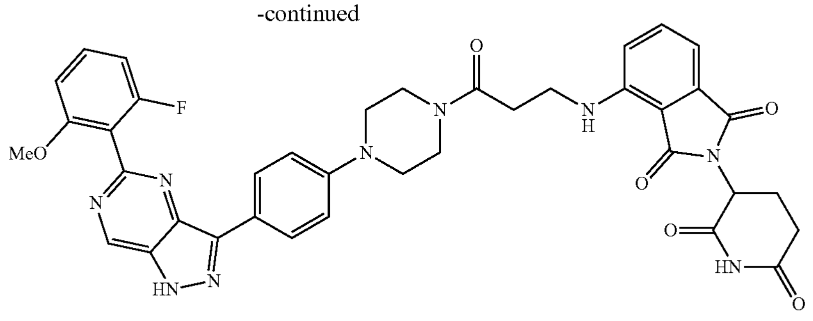

HC90-50

HC90-50 was synthesized following the standard procedure for preparing HC90-33 from Intermediate 13 (6.5 mg, 0.0125 mmol, 1.0 equiv), 3-((2-(2,6-dioxopiperidin-3-yl)-1,3-dioxoisoindolin-4-yl)amino)propanoic acid (4.4 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-50 was obtained as yellow solid in TFA salt form (6.4 mg, 610%). $^{1}H$ NMR (800 MHz, Acetone-$d_6$) δ 9.40 (s, 1H), 8.45 (d, J=8.5 Hz, 2H), 7.61 (t, J=7.8 Hz, 1H), 7.54-7.46 (m, 1H), 7.18 (d, J=8.6 Hz, 1H), 7.12 (d, J=8.4 Hz, 2H), 7.08-7.00 (m, 2H), 6.91 (t, J=8.6 Hz, 1H), 5.06 (dd, J=12.9, 5.7 Hz, 1H), 3.84-3.69 (m, 9H), 3.31 (t, J=5.4 Hz, 2H), 3.27 (t, J=5.5 Hz, 2H), 3.00-2.91 (m, 1H), 2.85 (t, J=6.3 Hz, 2H), 2.81-2.72 (m, 2H), 2.26-2.16 (m, 1H). HRMS calcd for $C_{38}H_{35}FN_9O_6^+$ [M+H$^+$] 732.2689, found 732.2671.

Example 189

Synthesis of HC90-51

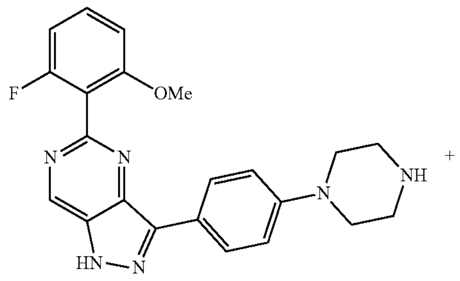

Intermediate 13

-continued

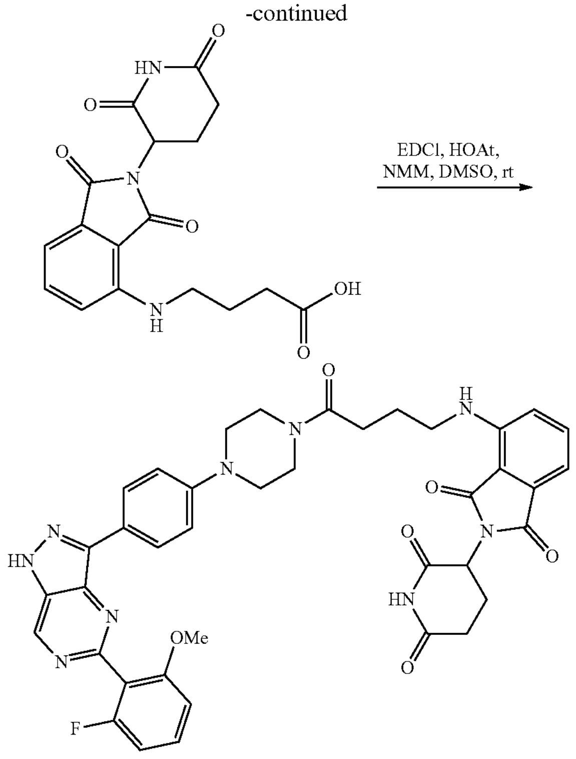

HC90-51

HC90-51 was synthesized following the standard procedure for preparing HC90-33 from Intermediate 13 (6.5 mg, 0.0125 mmol, 1.0 equiv), 4-((2-(2,6-dioxopiperidin-3-yl)-1,3-dioxoisoindolin-4-yl)amino)butanoic acid (4.5 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-51 was obtained as yellow solid in TFA salt form (6.8 mg, 63%). $^{1}H$ NMR (800 MHz, Acetone-$d_6$) δ 9.40 (s, 1H), 8.46 (d, J=8.4 Hz, 2H), 7.61 (t, J=7.8 Hz, 1H), 7.54-7.45 (m, 1H), 7.23 (d, J=8.6 Hz, 1H), 7.12 (d, J=8.4 Hz, 2H), 7.07-7.00 (m, 2H), 6.91 (t, J=8.6 Hz, 1H), 5.08 (dd, J=12.8, 5.8 Hz, 1H), 3.79 (s, 3H), 3.78-3.71 (m, 4H), 3.48 (t, J=7.2 Hz, 2H), 3.34-3.23 (m, 4H), 3.00-2.91 (m, 1H), 2.84-2.77 (m, 2H), 2.59 (t, J=6.8 Hz, 2H), 2.24-2.19 (m, 1H), 2.02 (t, J=7.0 Hz, 2H). HRMS calcd for $C_{39}H_{37}FN_9O_6^+$ [M+H$^+$]746.2845, found 746.2828.

Example 190

Synthesis of HC90-52

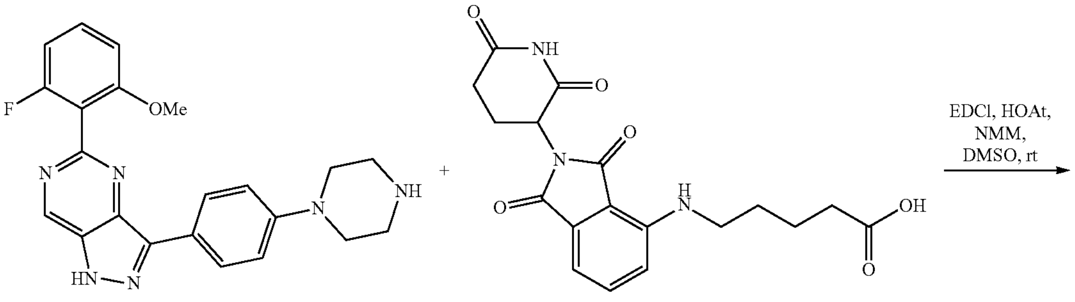

Intermediate 13

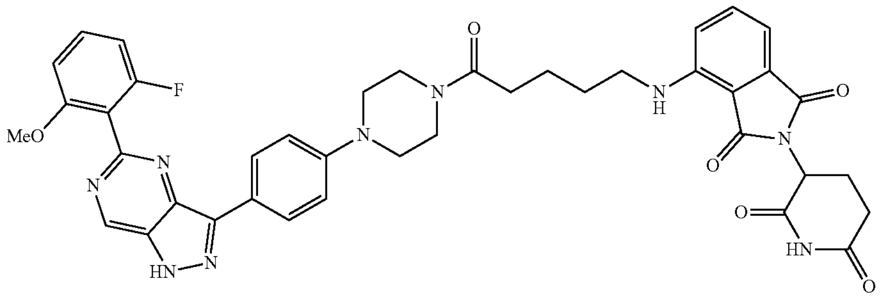

HC90-52

HC90-52 was synthesized following the standard procedure for preparing HC90-33 from Intermediate 13 (6.5 mg, 0.0125 mmol, 1.0 equiv), 5-((2-(2,6-dioxopiperidin-3-yl)-1,3-dioxoisoindolin-4-yl)amino)pentanoic acid (4.7 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-52 was obtained as yellow solid in TFA salt form (6.2 mg, 57%). $^1$H NMR (800 MHz, Acetone-$d_6$) δ 9.40 (s, 1H), 8.46 (d, J=8.4 Hz, 2H), 7.60 (t, J=7.8 Hz, 1H), 7.50 (q, J=8.4 Hz, 1H), 7.17-7.09 (m, 3H), 7.07-7.00 (m, 2H), 6.91 (t, J=8.7 Hz, 1H), 5.07 (dd, J=12.7, 5.7 Hz, 1H), 3.79 (s, 3H), 3.76-3.70 (m, 4H), 3.48-3.42 (m, 2H), 3.35-3.29 (m, 2H), 3.29-3.22 (m, 2H), 3.00-2.92 (m, 1H), 2.81-2.74 (m, 2H), 2.57-2.50 (m, 2H), 2.24-2.19 (m, 1H), 1.84-1.75 (m, 4H). HRMS calcd for $C_{40}H_{39}FN_9O_6^+$ [M+H$^+$] 760.3002, found 760.2988.

Example 191

Synthesis of HC90-53

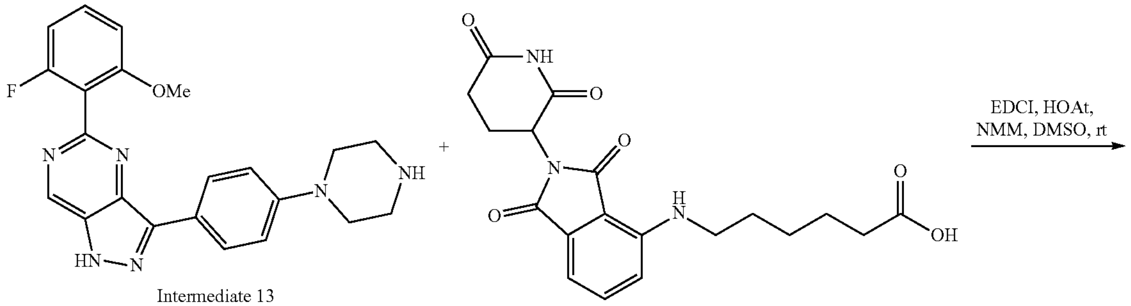

Intermediate 13

-continued

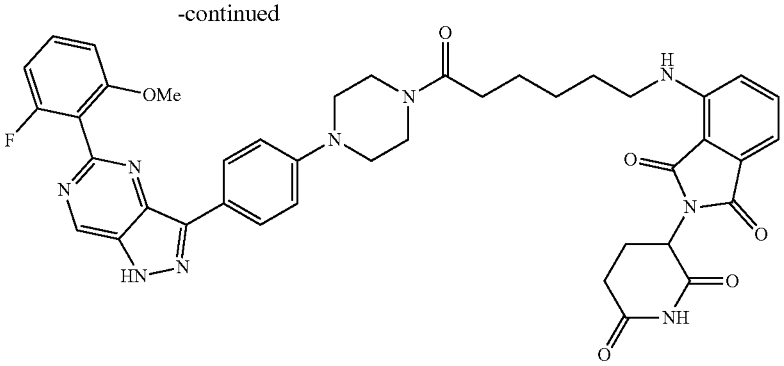

HC90-53

HC90-53 was synthesized following the standard procedure for preparing HC90-33 from Intermediate 13 (6.5 mg, 0.0125 mmol, 1.0 equiv), 6-((2-(2,6-dioxopiperidin-3-yl)-1,3-dioxoisoindolin-4-yl)amino)hexanoic acid (4.9 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-53 was obtained as yellow solid in TFA salt form (4.9 mg, 44%). $^1$H NMR (800 MHz, Acetone-$d_6$) δ 9.40 (s, 1H), 8.46 (d, J=8.4 Hz, 2H), 7.60 (t, J=7.8 Hz, 1H), 7.50 (q, J=8.3 Hz, 1H), 7.19-7.10 (m, 3H), 7.03 (t, J=8.2 Hz, 2H), 6.91 (t, J=8.6 Hz, 1H), 5.08 (dd, J=12.8, 5.7 Hz, 1H), 3.79 (s, 3H), 3.75-3.70 (m, 4H), 3.41 (t, J=7.1 Hz, 2H), 3.35-3.29 (m, 2H), 3.28-3.23 (m, 2H), 3.00-2.92 (m, 1H), 2.83-2.75 (m, 2H), 2.47 (t, J=7.4 Hz, 2H), 2.27-2.19 (m, 1H), 1.80-1.70 (m, 4H), 1.57-1.50 (m, 2H). HRMS calcd for $C_{41}H_{41}FN_9O_6^+$ [M+H$^+$] 774.3158, found 774.3141.

Example 192

Synthesis of HC90-54

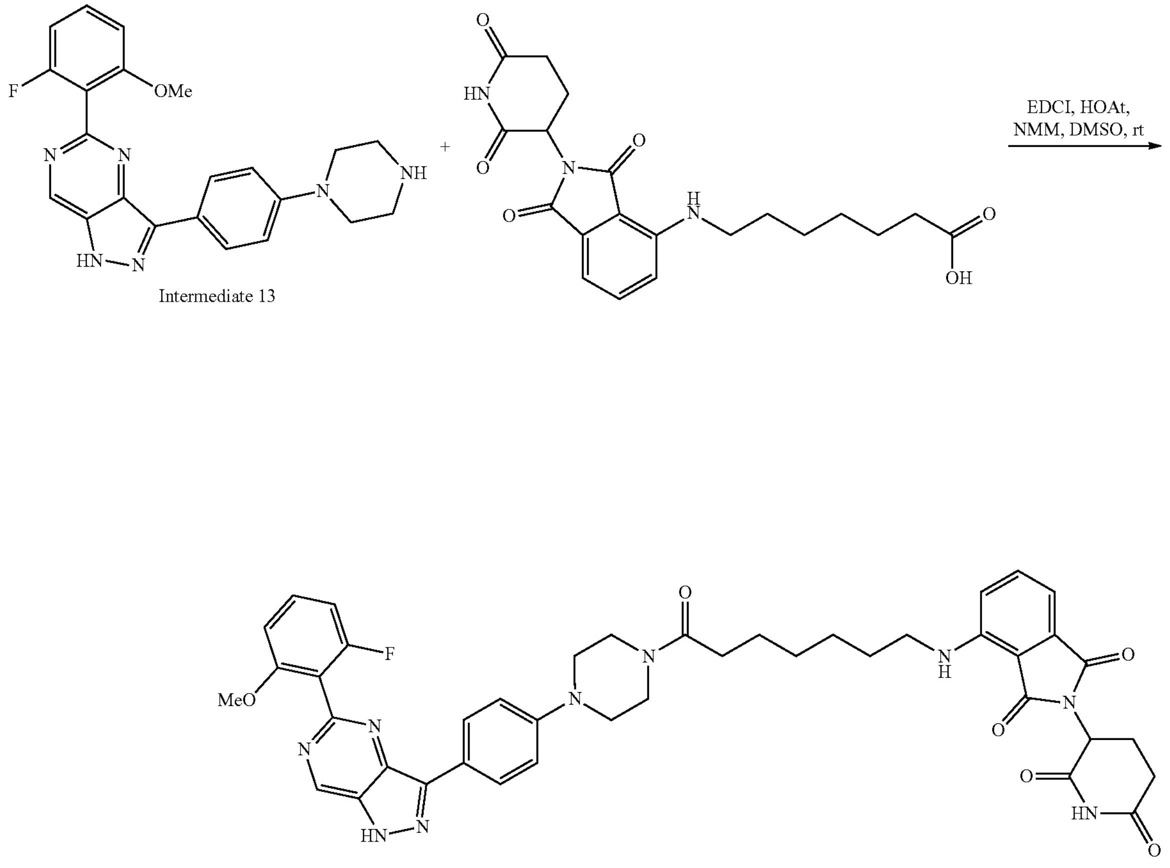

HC90-54

HC90-54 was synthesized following the standard procedure for preparing HC90-33 from Intermediate 13 (6.5 mg, 0.0125 mmol, 1.0 equiv), 7-((2-(2,6-dioxopiperidin-3-yl)-1,3-dioxoisoindolin-4-yl)amino)heptanoic acid (5.1 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-54 was obtained as yellow solid in TFA salt form (5.5 mg, 49%). $^1$H NMR (800 MHz, Acetone-$d_6$) δ 9.40 (s, 1H), 8.46 (d, J=8.5 Hz, 2H), 7.60 (t, J=7.8 Hz, 1H), 7.50 (d, J=7.7 Hz, 1H), 7.16-7.09 (m, 3H), 7.07-7.01 (m, 2H), 6.91 (t, J=8.6 Hz, 1H), 5.08 (dd, J=12.8, 5.8 Hz, 1H), 3.79 (s, 3H), 3.75-3.70 (m, 4H), 3.40 (t, J=7.1 Hz, 2H), 3.34-3.29 (m, 2H), 3.28-3.23 (m, 2H), 3.00-2.94 (m, 1H), 2.81-2.76 (m, 2H), 2.44 (t, J=7.4 Hz, 2H), 2.23-2.20 (m, 1H), 1.77-1.71 (m, 2H), 1.67 (t, J=7.5 Hz, 2H), 1.54-1.45 (m, 4H). HRMS calcd for $C_{42}H_{43}FN_9O_6^+$ [M+H$^+$] 788.3315, found 788.3301.

Example 193

Synthesis of HC90-55

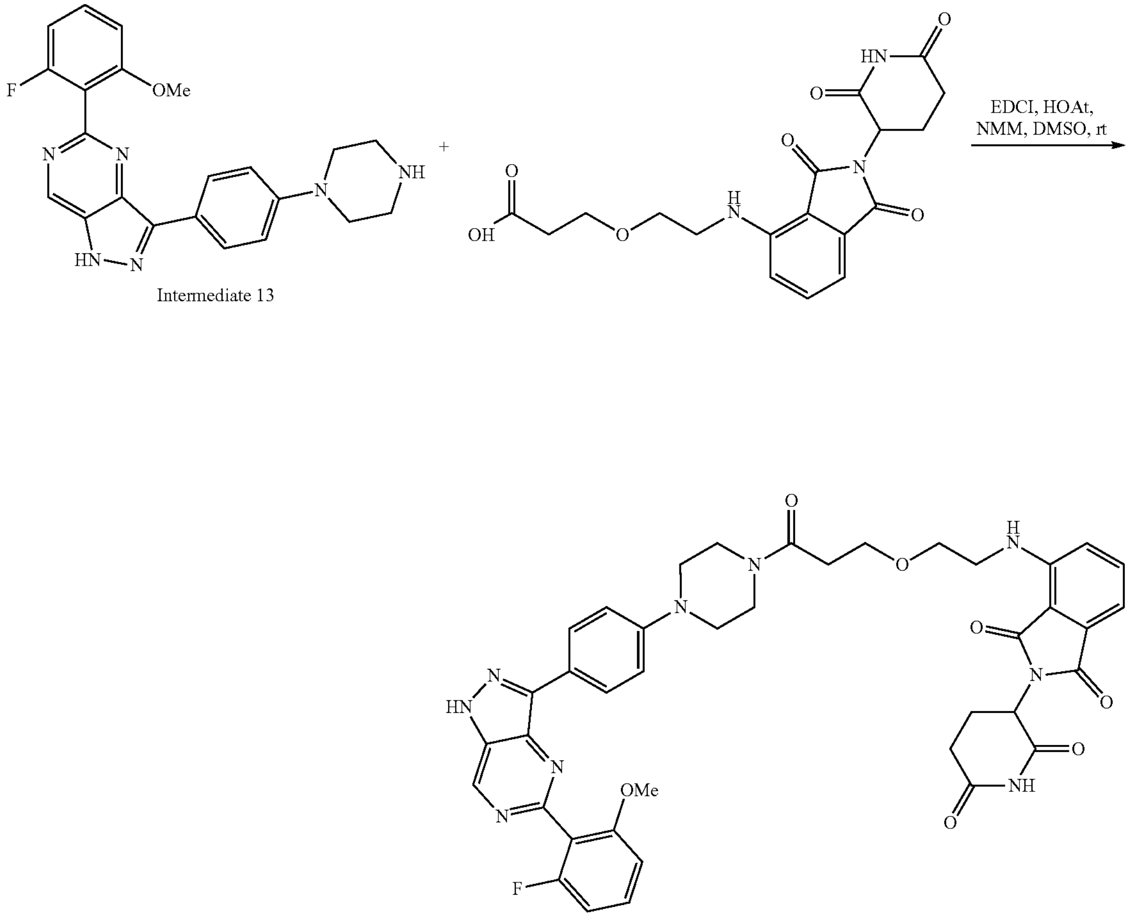

HC90-55

HC90-55 was synthesized following the standard procedure for preparing HC90-33 from Intermediate 13 (6.5 mg, 0.0125 mmol, 1.0 equiv), 3-(2-((2-(2,6-dioxopiperidin-3-yl)-1,3-dioxoisoindolin-4-yl)amino)ethoxy)propanoic acid (4.9 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-55 was obtained as yellow solid in TFA salt form (5.4 mg, 49%). $^1$H NMR (800 MHz, Acetone-$d_6$) δ 9.40 (s, 1H), 8.43 (d, J=8.4 Hz, 2H), 7.58 (t, J=7.8 Hz, 1H), 7.55-7.48 (m, 1H), 7.13 (d, J=8.6 Hz, 1H), 7.07 (d, J=8.3 Hz, 2H), 7.03 (dd, J=7.9, 4.3 Hz, 2H), 6.92 (t, J=8.5 Hz, 1H), 5.07 (dd, J=12.9, 5.7 Hz, 1H), 3.83 (t, J=6.4 Hz, 2H), 3.80 (s, 3H), 3.77-3.72 (m, 6H), 3.59-3.54 (m, 2H), 3.32-3.23 (m, 4H), 2.96-2.90 (m, 1H), 2.82-2.69 (m, 4H), 2.23-2.18 (m, 1H). HRMS calcd for $C_{40}H_{39}FN_9O_7^+$ [M+H$^+$] 776.2951, found 776.2935.

Example 194

Synthesis of HC90-56

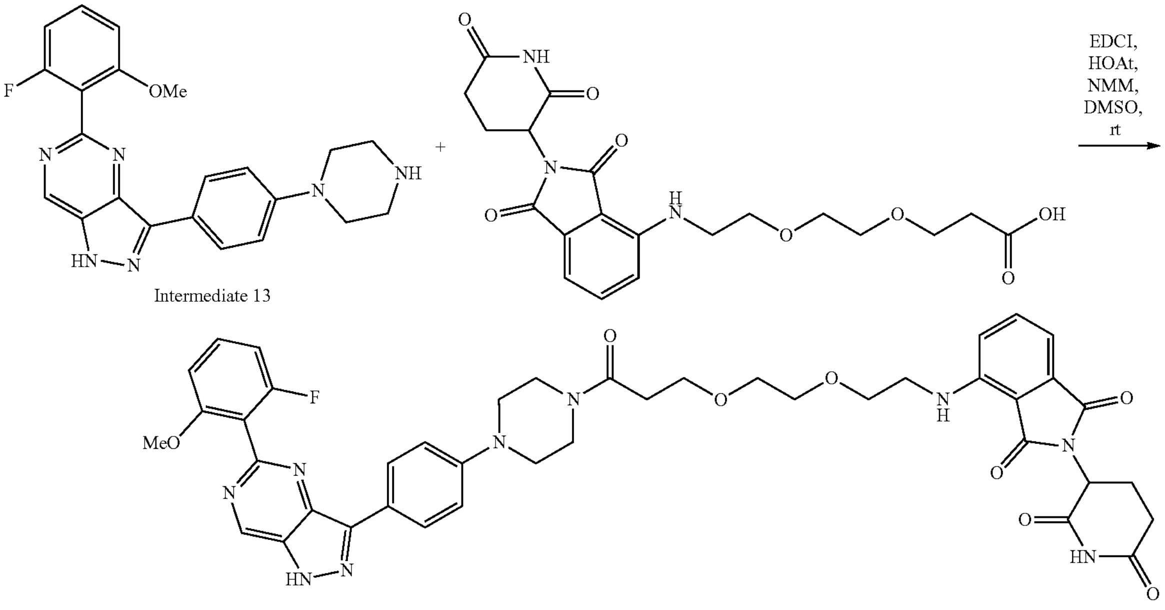

Intermediate 13

HC90-56

HC90-56 was synthesized following the standard procedure for preparing HC90-33 from Intermediate 13 (6.5 mg, 0.0125 mmol, 1.0 equiv), 3-(2-(2-((2-(2,6-dioxopiperidin-3-yl)-1,3-dioxoisoindolin-4-yl)amino)ethoxy)ethoxy)propanoic acid (5.5 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-56 was obtained as yellow solid in TFA salt form (6.7 mg, 57%). $^1H$ NMR (600 MHz, Acetone-$d_6$) δ 9.94 (s, 1H), 9.39 (s, 1H), 8.47-8.41 (m, 2H), 7.61-7.52 (m, 1H), 7.52-7.46 (m, 1H), 7.17-7.06 (m, 2H), 7.02 (dd, J=7.8, 4.3 Hz, 2H), 6.91 (t, J=8.4 Hz, 1H), 6.62 (s, 1H), 5.19-5.05 (m, 1H), 3.79 (s, 3H), 3.77-3.69 (m, 8H), 3.68-3.59 (m, 4H), 3.54-3.47 (m, 2H), 3.38-3.19 (m, 4H), 2.99-2.92 (m, 1H), 2.84-2.71 (m, 2H), 2.69-2.62 (m, 2H), 2.28-2.17 (m, 1H). HRMS calcd for $C_{42}H_{43}FN_9O_8^+$ [M+H$^+$] 820.3213, found 820.3201.

Example 195

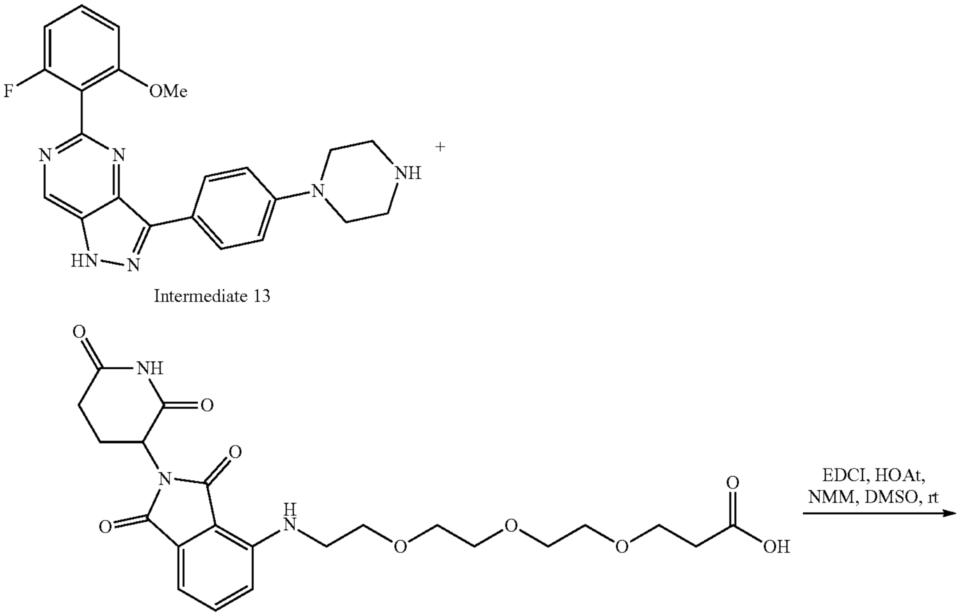

Intermediate 13

-continued

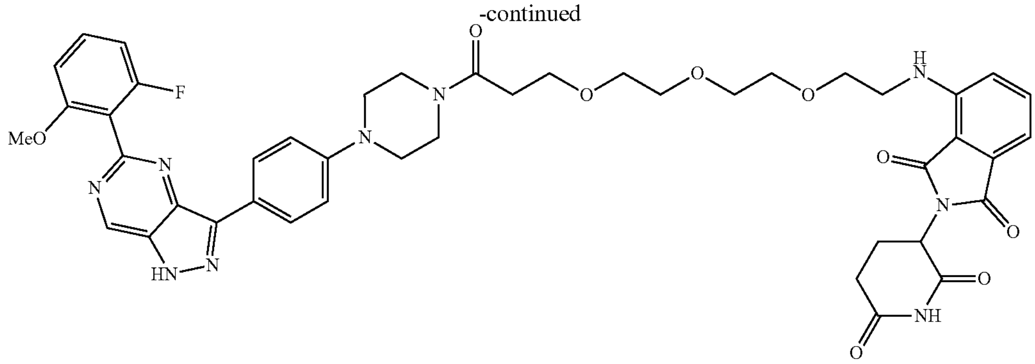

HC90-57

HC90-57 was synthesized following the standard procedure for preparing HC90-33 from Intermediate 13 (6.5 mg, 0.0125 mmol, 1.0 equiv), 3-(2-(2-(2-((2-(2,6-dioxopiperidin-3-yl)-1,3-dioxoisoindolin-4-yl)amino)ethoxy)ethoxy)ethoxy)propanoic acid (6.0 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-57 was obtained as yellow solid in TFA salt form (6.1 mg, 57%). $^1H$ NMR (800 MHz, Acetone-$d_6$) δ 9.39 (s, 1H), 8.45 (d, J=8.5 Hz, 2H), 7.56 (t, J=7.8 Hz, 1H), 7.50 (q, J=8.0 Hz, 1H), 7.16-7.08 (m, 3H), 7.03 (t, J=7.4 Hz, 2H), 6.91 (t, J=8.6 Hz, 1H), 5.09 (dd, J=13.0, 5.7 Hz, 1H), 3.79 (s, 3H), 3.78-3.70 (m, 8H), 3.65-3.57 (m, 8H), 3.50 (t, J=5.4 Hz, 2H), 3.37-3.30 (m, 2H), 3.25 (t, J=5.4 Hz, 2H), 3.01-2.94 (m, 1H), 2.84-2.74 (m, 2H), 2.66 (t, J=6.5 Hz, 2H), 2.26-2.20 (m, 1H). HRMS calcd for $C_{44}H_{47}FN_9O_9^+$ [M+H$^+$] 864.3475, found 864.3459.

Example 196

Synthesis of HC90-58

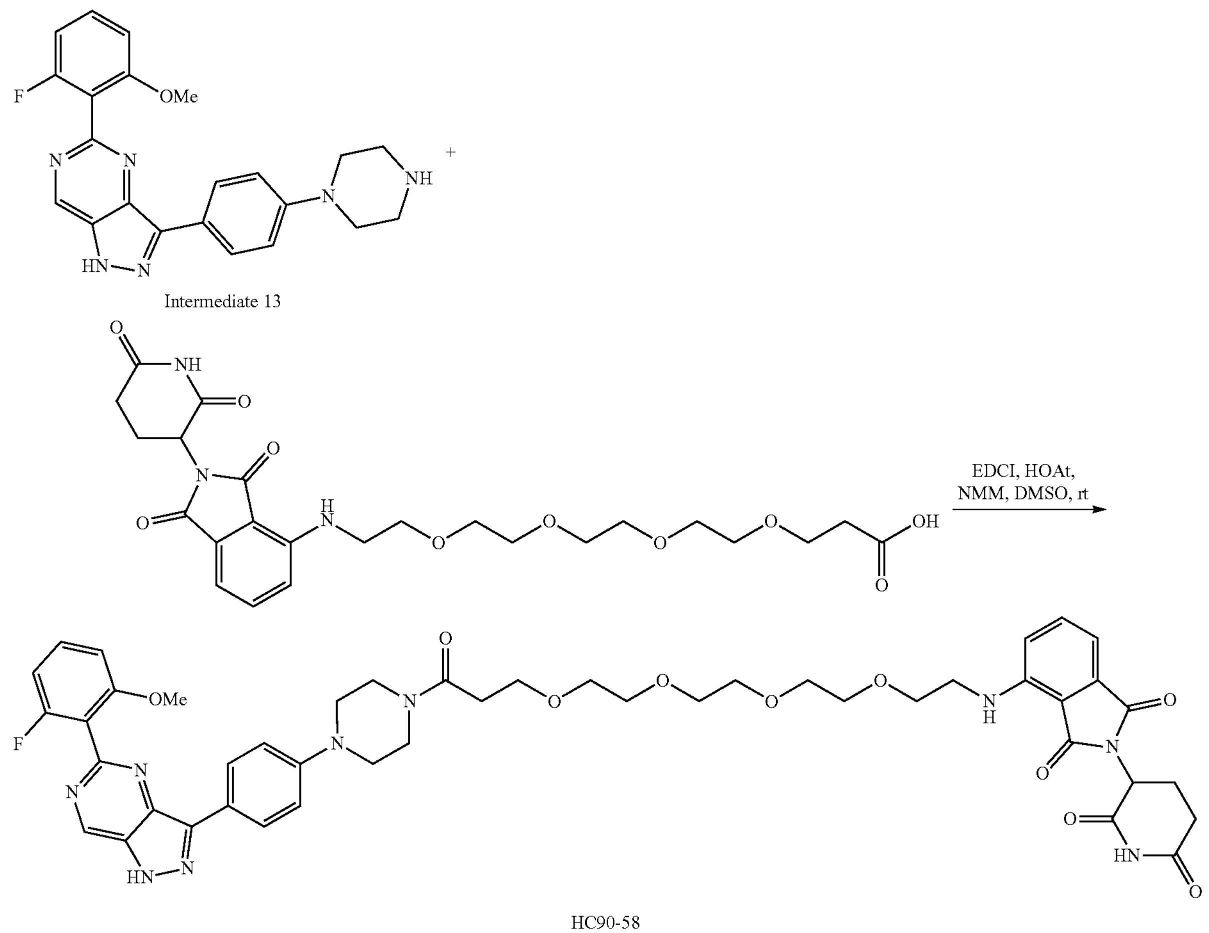

HC90-58

HC90-58 was synthesized following the standard procedure for preparing HC90-33 from Intermediate 13 (6.5 mg, 0.0125 mmol, 1.0 equiv), 1-((2-(2,6-dioxopiperidin-3-yl)-1,3-dioxoisoindolin-4-yl)amino)-3,6,9,12-tetraoxapentadecan-15-oic acid (6.6 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-58 was obtained as yellow solid in TFA salt form (6.5 mg, 51%). $^1$H NMR (600 MHz, Acetone-$d_6$) δ 9.95 (s, 1H), 9.40 (s, 1H), 8.45 (d, J=8.8 Hz, 2H), 7.59-7.55 (m, 1H), 7.53-7.47 (m, 1H), 7.14-7.09 (m, 2H), 7.07-7.01 (m, 2H), 6.91 (t, J=8.7 Hz, 1H), 6.61 (s, 1H), 5.08 (dd, J=12.8, 5.5 Hz, 1H), 3.79 (s, 3H), 3.77-3.48 (m, 22H), 3.33 (d, J=5.9 Hz, 2H), 3.24 (t, J=5.3 Hz, 2H), 3.01-2.92 (m, 1H), 2.84-2.74 (m, 2H), 2.68 (t, J=6.4 Hz, 2H), 2.29-2.19 (m, 1H). HRMS calcd for $C_{46}H_{51}FN_9O_{10}^+$ [M+H$^+$] 908.3737, found 908.3721.

Example 197

Synthesis of HC90-59

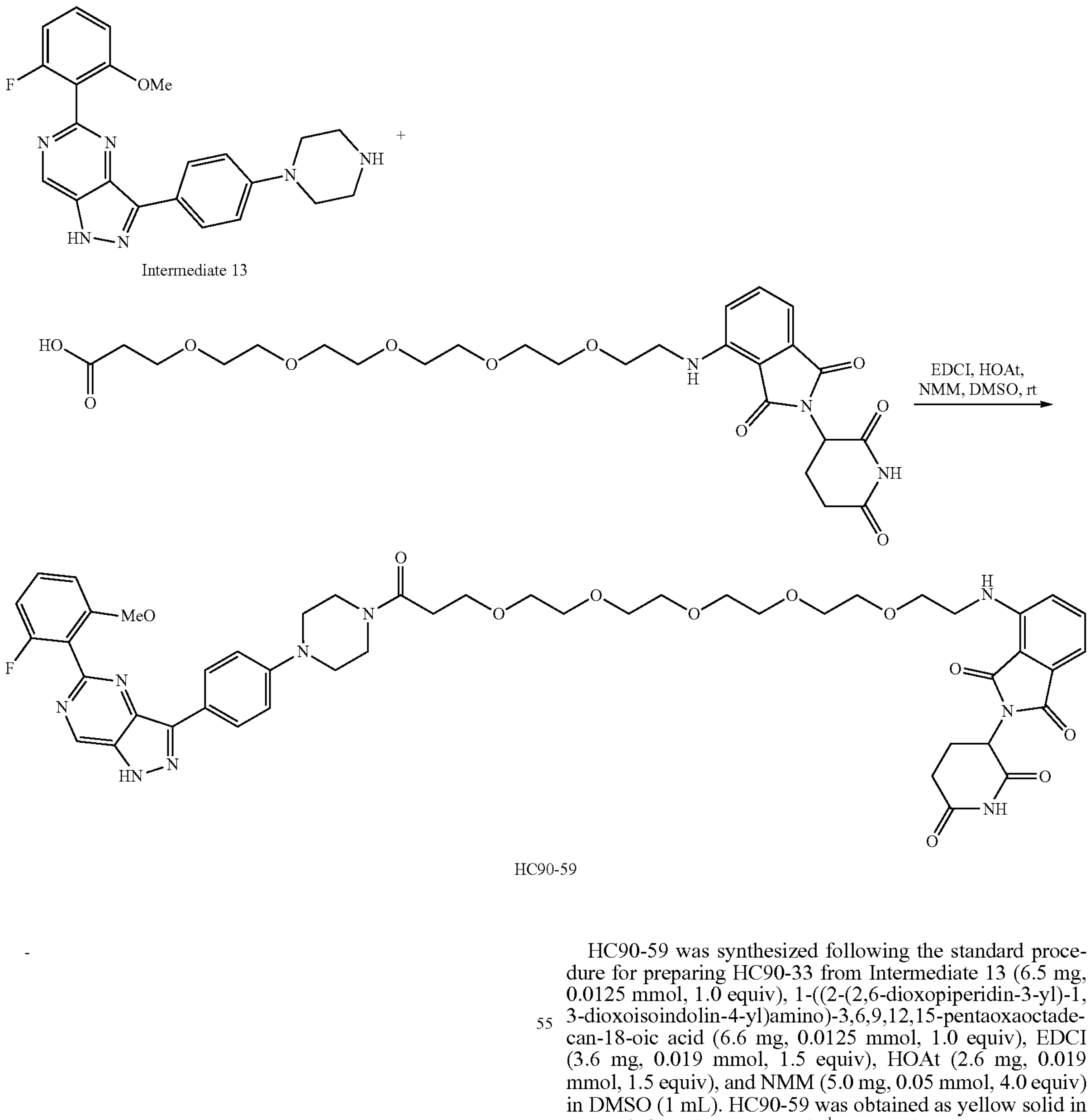

Intermediate 13

HC90-59

HC90-59 was synthesized following the standard procedure for preparing HC90-33 from Intermediate 13 (6.5 mg, 0.0125 mmol, 1.0 equiv), 1-((2-(2,6-dioxopiperidin-3-yl)-1,3-dioxoisoindolin-4-yl)amino)-3,6,9,12,15-pentaoxaoctadecan-18-oic acid (6.6 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-59 was obtained as yellow solid in TFA salt form (5.9 mg, 44%). $^1$H NMR (800 MHz, Acetone-$d_6$) δ 9.40 (s, 1H), 8.45 (d, J=8.5 Hz, 2H), 7.58 (t, J=7.8 Hz, 1H), 7.54-7.48 (m, 1H), 7.12 (t, J=9.7 Hz, 3H), 7.07-7.02 (m, 2H), 6.91 (t, J=8.4 Hz, 1H), 5.09 (dd, J=12.6, 5.7 Hz, 1H), 3.79 (s, 3H), 3.78-3.72 (m, 8H), 3.69-3.52 (m, 18H), 3.37-3.31 (m, 2H), 3.30-3.24 (m, 2H), 3.01-2.92 (m, 1H), 2.85-2.75 (m, 2H), 2.69 (t, J=6.4 Hz, 2H), 2.27-2.20 (m, 1H). HRMS calcd for $C_{48}H_{55}FN_9O_{11}^+$ [M+H$^+$]952.4000, found 952.3983.

Example 198

Synthesis of HC90-61

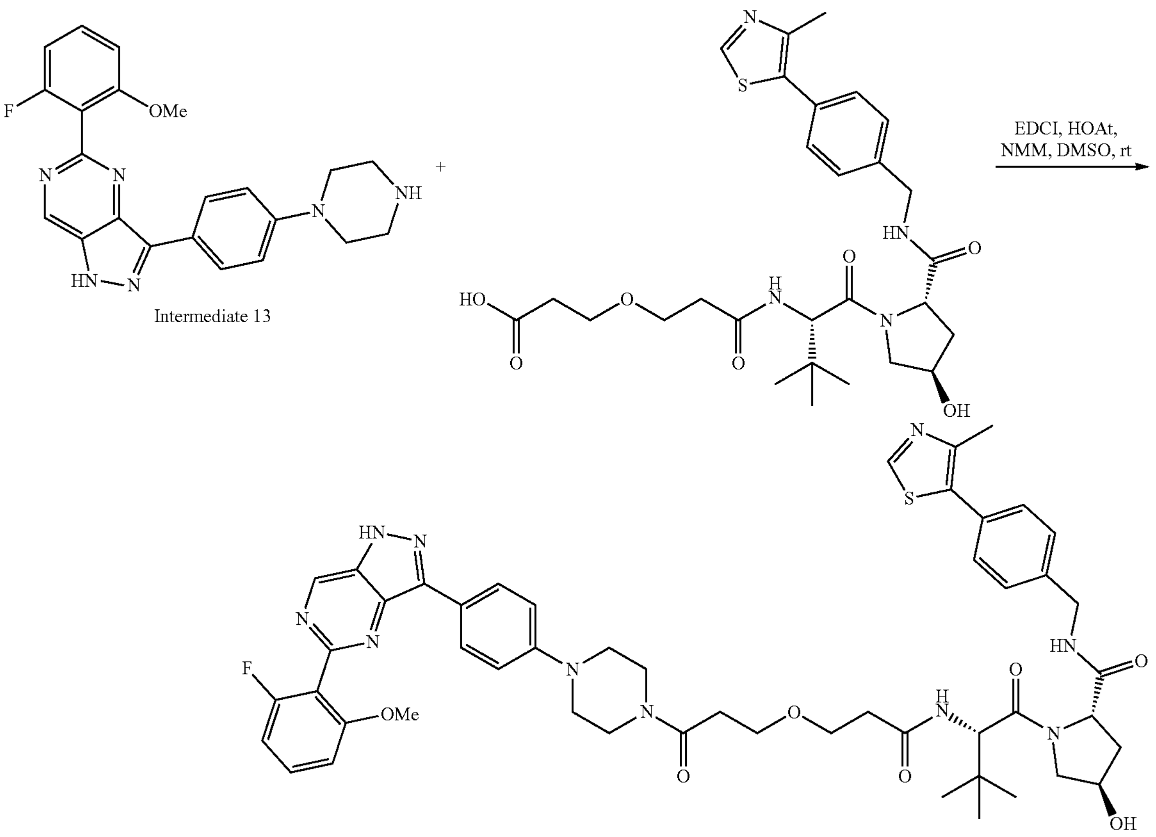

HC90-61

HC90-61 was synthesized following the standard procedure for preparing HC90-33 from Intermediate 13 (6.5 mg, 0.0125 mmol, 1.0 equiv), 3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy) propanoic acid (7.2 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-61 was obtained as yellow solid in TFA salt form (7.1 mg, 53%). $^1$H NMR (800 MHz, Methanol-$d_4$) δ 9.29 (s, 1H), 8.84 (s, 1H), 8.36 (d, J=8.3 Hz, 2H), 7.49 (q, J=7.8 Hz, 1H), 7.40 (d, J=7.9 Hz, 2H), 7.34 (d, J=7.8 Hz, 2H), 7.08 (d, J=8.5 Hz, 2H), 7.00 (d, J=8.4 Hz, 1H), 6.89 (t, J=8.5 Hz, 1H), 4.68 (s, 1H), 4.57 (t, J=8.4 Hz, 1H), 4.51 (s, 2H), 4.48 (d, J=15.4 Hz, 1H), 4.32 (d, J=15.4 Hz, 1H), 3.90 (d, J=11.1 Hz, 1H), 3.83-3.70 (m, 10H), 3.31-3.23 (m, 2H), 2.74 (t, J=6.2 Hz, 2H), 2.59-2.50 (m, 2H), 2.43 (s, 3H), 2.26-2.19 (m, 1H), 2.08 (ddd, J=13.2, 9.1, 4.6 Hz, 1H), 1.05 (s, 9H). HRMS calcd for $C_{50}H_{58}FN_{10}O_7S^+$ [M+H$^+$] 961.4189, found 961.4172.

Example 199

Synthesis of HC90-66

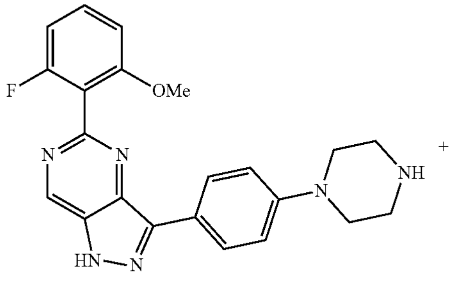

Intermediate 13

-continued

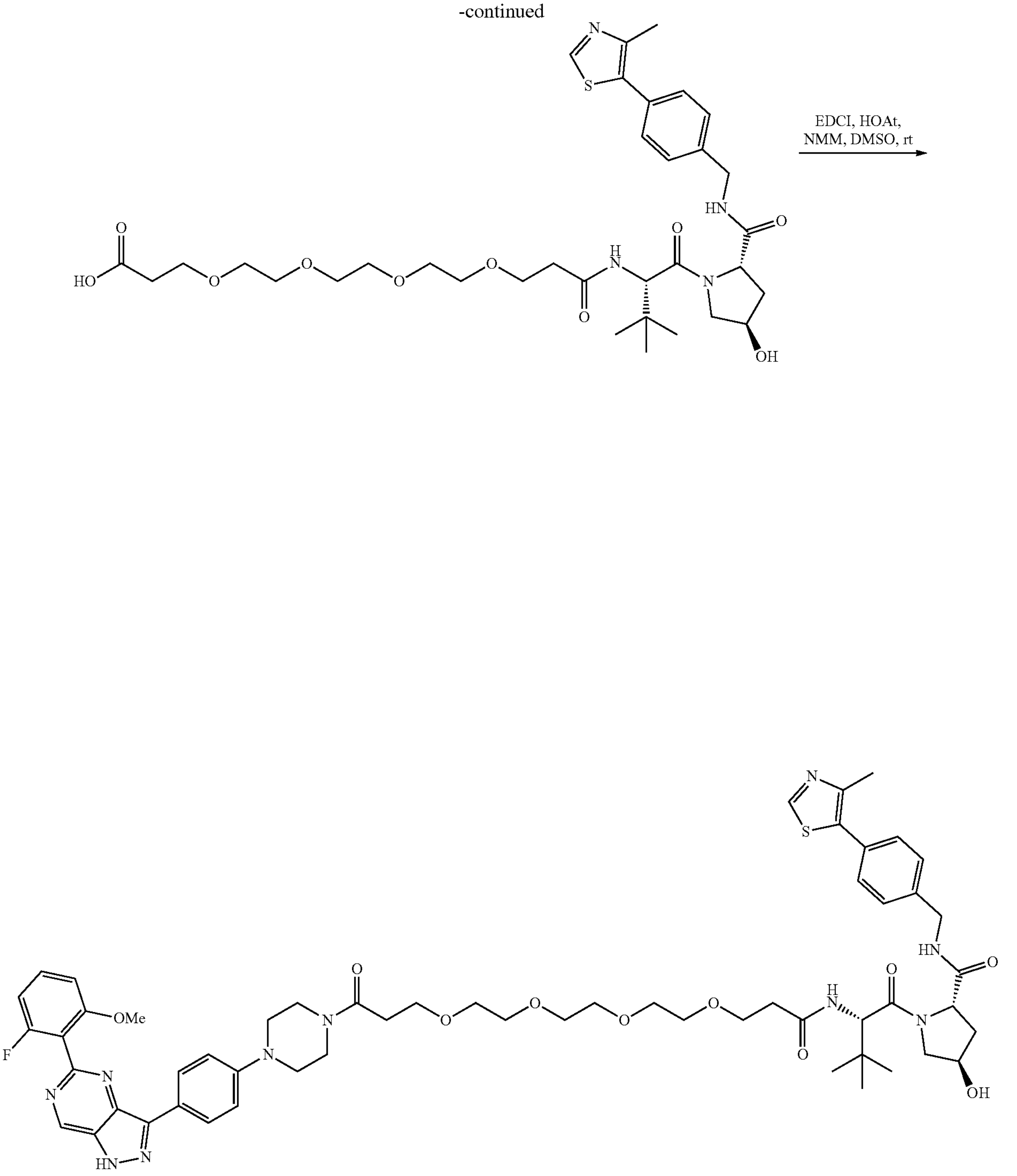

HC90-66

HC90-66 was synthesized following the standard procedure for preparing HC90-33 from Intermediate 13 (6.5 mg, 0.0125 mmol, 1.0 equiv), (S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoic acid (8.9 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-66 was obtained as yellow solid in TFA salt form (7.5 mg, 50%). $^1H$ NMR (800 MHz, Methanol-$d_4$) δ 9.29 (s, 1H), 8.90 (s, 1H), 8.38 (d, J=8.3 Hz, 2H), 7.53-7.48 (m, 1H), 7.47 (d, J=8.0 Hz, 2H), 7.41 (d, J=7.8 Hz, 2H), 7.12 (d, J=8.4 Hz, 3H), 7.00 (d, J=8.4 Hz, 1H), 6.89 (t, J=8.6 Hz, 1H), 4.65 (s, 1H), 4.60-4.57 (m, 1H), 4.55 (d, J=15.3 Hz, 1H), 4.51 (s, 1H), 4.35 (d, J=15.4 Hz, 1H), 3.90 (d, J=11.2 Hz, 2H), 3.85-3.76 (m, 6H), 3.72-3.52 (m, 21H), 2.72 (t, J=6.1 Hz, 2H), 2.55 (ddd, J=13.7, 7.8, 4.7 Hz, 1H), 2.49-2.44 (m, 4H), 2.23 (t, J=10.4 Hz, 1H), 2.09 (ddd, J=13.2, 8.8, 4.4 Hz, 1H), 1.04 (s, 9H). HRMS calcd for $C_{56}H_{70}FN_{10}O_{10}S^+$ [M+H$^+$] 1093.4976, found 1093.4960.

Example 200

Synthesis of HC90-69

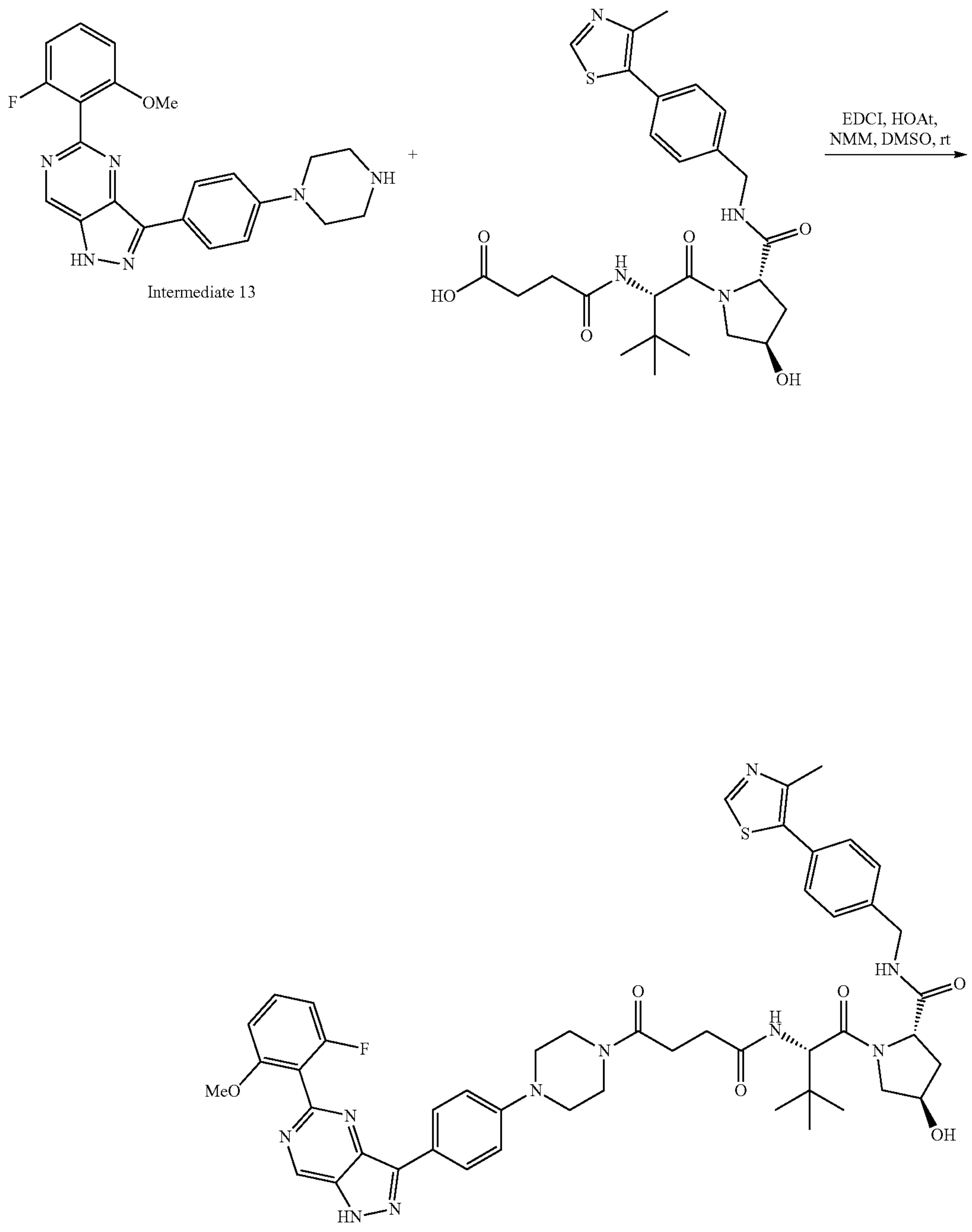

HC90-69

HC90-69 was synthesized following the standard procedure for preparing HC90-33 from Intermediate 13 (6.5 mg, 0.0125 mmol, 1.0 equiv), 4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid (6.7 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-69 was obtained as yellow solid in TFA salt form (6.8 mg, 53%). $^1$H NMR (800 MHz, Methanol-$d_4$) δ 9.29 (s, 1H), 8.90 (s, 1H), 8.37 (d, J=8.4 Hz, 2H), 7.48 (d, J=8.3 Hz, 1H), 7.45 (d, J=8.1 Hz, 2H), 7.41 (d, J=7.8 Hz, 2H), 7.11 (d, J=8.5 Hz, 2H), 7.01 (d, J=8.5 Hz, 1H), 6.90 (t, J=8.6 Hz, 1H), 4.62 (s, 1H), 4.59-4.49 (m, 3H), 4.36 (d, J=15.4 Hz, 1H), 3.92 (d, J=11.0 Hz, 1H), 3.83-3.77 (m, 4H), 3.75-3.71 (m, 4H), 3.33-3.26 (m, 4H), 2.79-2.70 (m, 2H), 2.69-2.58 (m, 2H), 2.49 (s, 3H), 2.28-2.20 (m, 1H), 2.13-2.04 (m, 1H), 1.06 (s, 9H). HRMS calcd for $C_{48}H_{54}FN_{10}O_6S^+$ [M+H$^+$] 917.3927, found 917.3911.

Example 201

Synthesis of HC90-70

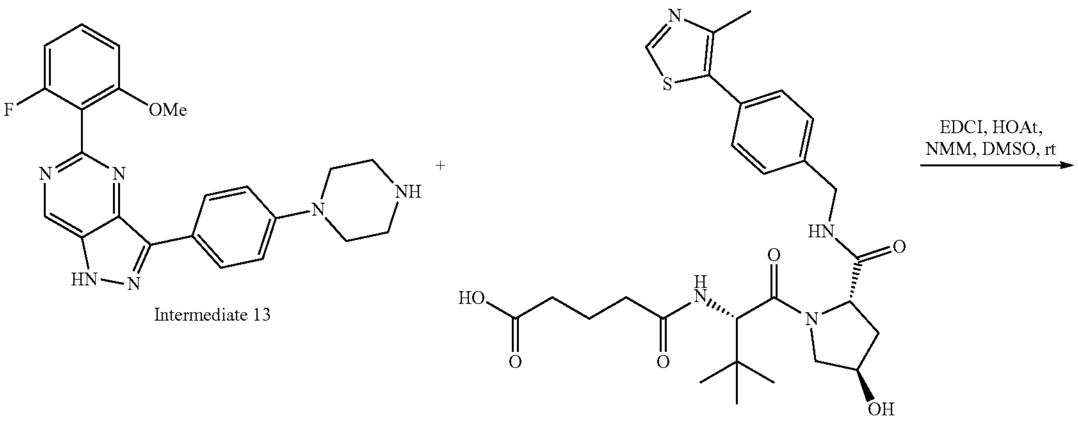

Intermediate 13

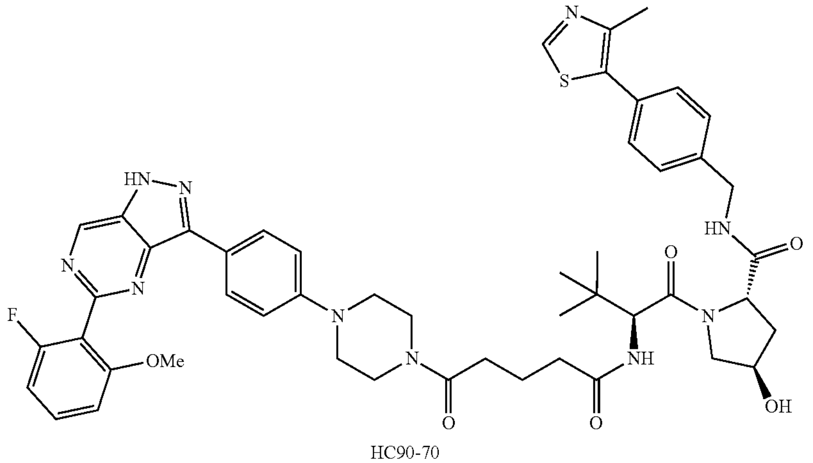

HC90-70

HC90-70 was synthesized following the standard procedure for preparing HC90-33 from Intermediate 13 (6.5 mg, 0.0125 mmol, 1.0 equiv), 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid (6.8 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-70 was obtained as yellow solid in TFA salt form (6.8 mg, 52%). $^1$H NMR (800 MHz, Methanol-$d_4$) δ 9.29 (s, 1H), 8.89 (s, 1H), 8.36 (d, J=8.4 Hz, 2H), 7.51-7.48 (m, 1H), 7.44 (d, J=7.8 Hz, 2H), 7.38 (d, J=7.8 Hz, 2H), 7.08 (d, J=8.4 Hz, 2H), 7.01 (d, J=8.4 Hz, 1H), 6.90 (t, J=8.5 Hz, 1H), 4.64 (s, 1H), 4.57-4.49 (m, 3H), 4.33 (d, J=15.5 Hz, 1H), 3.96 (d, J=11.2 Hz, 1H), 3.86-3.79 (m, 4H), 3.76-3.68 (m, 4H), 3.32-3.26 (m, 4H), 2.53-2.47 (m, 2H), 2.46 (s, 3H), 2.38 (t, J=7.1 Hz, 2H), 2.24 (dd, J=12.2, 7.6 Hz, 1H), 2.12-2.05 (m, 1H), 2.00-1.90 (m, 2H), 1.07 (s, 9H). HRMS calcd for $C_{49}H_{56}FN_{10}O_6S^+$ [M+H$^+$] 931.4084, found 931.4071.

Example 202

Synthesis of HC90-71

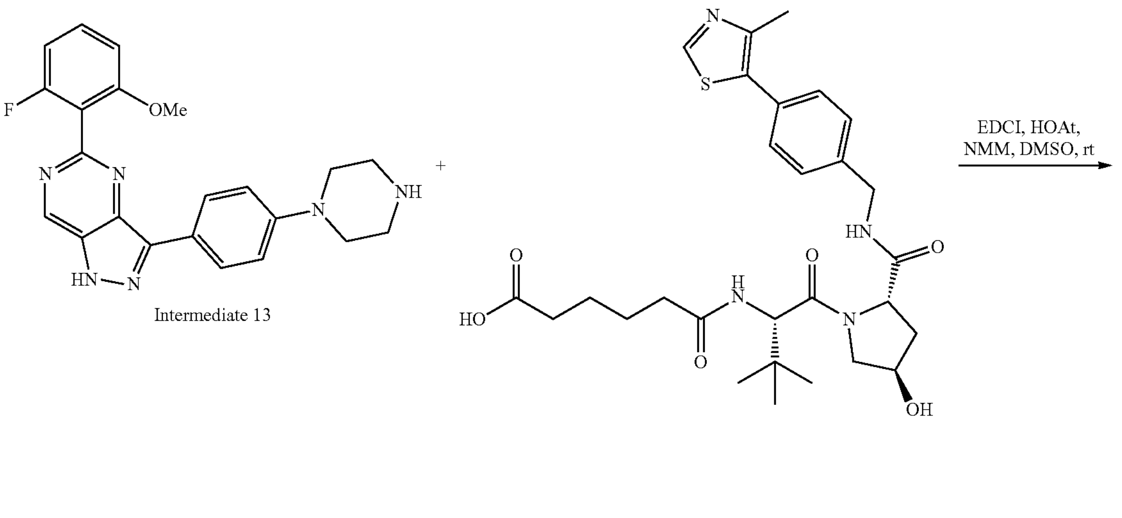

Intermediate 13

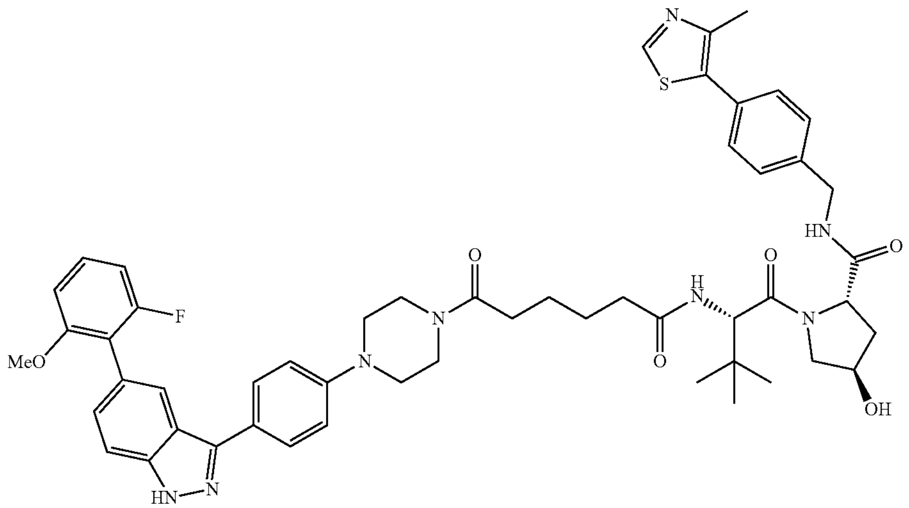

HC90-71

HC90-71 was synthesized following the standard procedure for preparing HC90-33 from Intermediate 13 (6.5 mg, 0.0125 mmol, 1.0 equiv), 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid (7.0 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-71 was obtained as yellow solid in TFA salt form (9.2 mg, 69%). $^1$H NMR (800 MHz, Methanol-$d_4$) δ 9.29 (s, 1H), 8.90 (s, 1H), 8.38 (d, J=8.4 Hz, 2H), 7.54-7.47 (m, 1H), 7.45 (d, J=7.7 Hz, 2H), 7.39 (d, J=7.8 Hz, 2H), 7.11 (d, J=8.4 Hz, 2H), 7.00 (d, J=8.4 Hz, 1H), 6.89 (t, J=8.5 Hz, 1H), 4.64 (s, 1H), 4.57 (t, J=8.4 Hz, 1H), 4.54-4.50 (m, 2H), 4.35 (d, J=15.4 Hz, 1H), 3.92 (d, J=10.8 Hz, 1H), 3.83-3.78 (m, 4H), 3.78-3.69 (m, 4H), 3.32-3.25 (m, 4H), 2.50-2.44 (m, 5H), 2.38-2.30 (m, 2H), 2.23 (dd, J=13.3, 7.3 Hz, 1H), 2.08 (ddd, J=13.7, 9.3, 4.9 Hz, 1H), 1.74-1.62 (m, 4H), 1.05 (s, 9H). HRMS calcd for $C_{50}H_{58}FN_{10}O_6S^+$ [M+H$^+$] 945.4240, found 945.4222.

Example 203

Synthesis of HC90-72

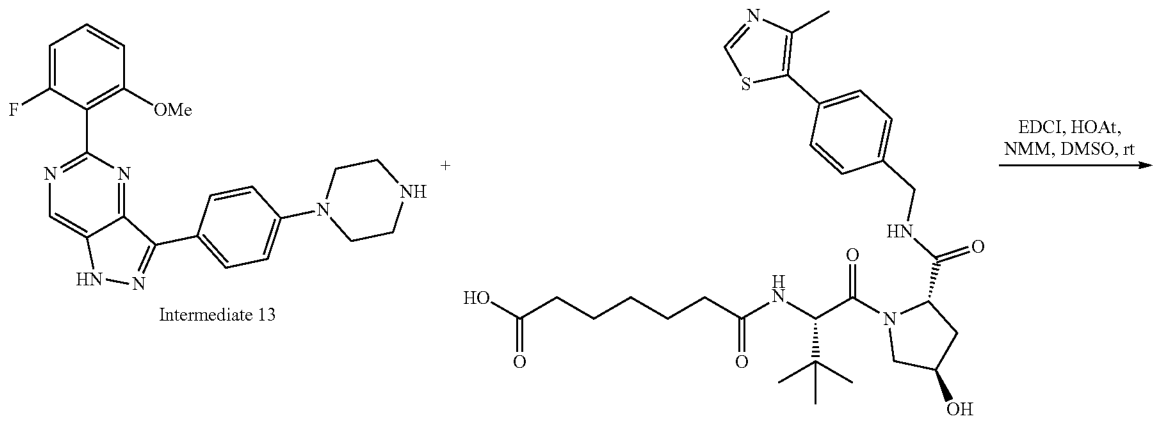

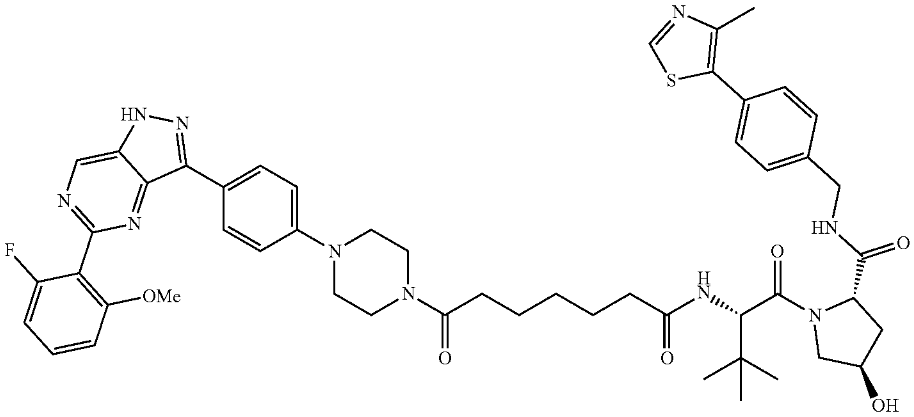

HC90-72

HC90-72 was synthesized following the standard procedure for preparing HC90-33 from Intermediate 13 (6.5 mg, 0.0125 mmol, 1.0 equiv), 7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid (7.2 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-72 was obtained as yellow solid in TFA salt form (7.2 mg, 54%). $^1$H NMR (800 MHz, Methanol-$d_4$) δ 9.30 (s, 1H), 8.89 (s, 1H), 8.38 (d, J=8.4 Hz, 2H), 7.51-7.45 (m, 3H), 7.41 (d, J=7.9 Hz, 2H), 7.11 (d, J=8.6 Hz, 2H), 7.00 (d, J=8.4 Hz, 1H), 6.89 (t, J=8.6 Hz, 1H), 4.65 (s, 1H), 4.58 (t, J=8.3 Hz, 1H), 4.54 (d, J=15.4 Hz, 1H), 4.52-4.50 (m, 1H), 4.36 (d, J=15.3 Hz, 1H), 3.95-3.90 (m, 1H), 3.86-3.78 (m, 4H), 3.78-3.71 (m, 4H), 3.32-3.23 (m, 4H), 2.49-2.44 (m, 5H), 2.36-2.28 (m, 2H), 2.23 (dd, J=13.4, 7.4 Hz, 1H), 2.12-2.06 (m, 1H), 1.67 (hept, J=7.1 Hz, 4H), 1.41 (p, J=7.8 Hz, 2H), 1.05 (s, 9H). HRMS calcd for $C_{51}H_{60}FN_{10}O_6S^+$ [M+H$^+$] 959.4397, found 959.4381.

Example 204

Synthesis of HC90-73

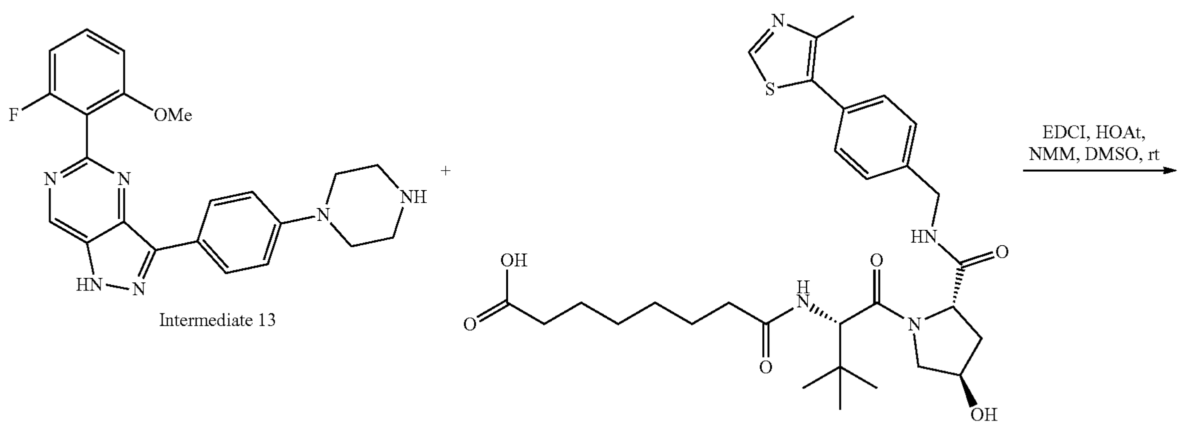

Intermediate 13

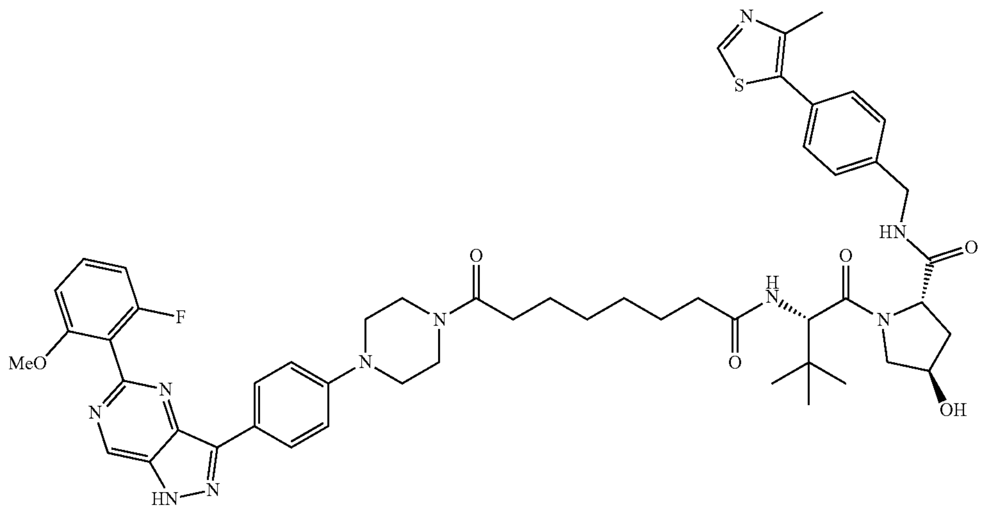

HC90-73

HC90-73 was synthesized following the standard procedure for preparing HC90-33 from Intermediate 13 (6.5 mg, 0.0125 mmol, 1.0 equiv), 8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid (7.4 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-73 was obtained as yellow solid in TFA salt form (7.4 mg, 54%). $^1$H NMR (800 MHz, Methanol-$d_4$) δ 9.30 (s, 1H), 8.90 (s, 1H), 8.38 (d, J=8.4 Hz, 2H), 7.52-7.46 (m, 3H), 7.42 (d, J=7.9 Hz, 2H), 7.11 (d, J=8.6 Hz, 2H), 7.00 (d, J=8.4 Hz, 1H), 6.89 (t, J=8.6 Hz, 1H), 4.65 (s, 1H), 4.59 (t, J=8.2 Hz, 1H), 4.55 (d, J=15.4 Hz, 1H), 4.51 (s, 1H), 4.36 (d, J=15.4 Hz, 1H), 3.93 (d, J=11.1 Hz, 1H), 3.85-3.79 (m, 4H), 3.77-3.71 (m, 4H), 3.31-3.24 (m, 4H), 2.49-2.43 (m, 5H), 2.34-2.26 (m, 2H), 2.24-2.21 (m, 1H), 2.13-2.07 (m, 1H), 1.68-1.61 (m, 4H), 1.45-1.34 (m, 4H), 1.05 (s, 9H). HRMS calcd for $C_{52}H_{62}FN_{10}O_6S^+$ [M+H$^+$] 973.4553, found 973.4538.

Example 205

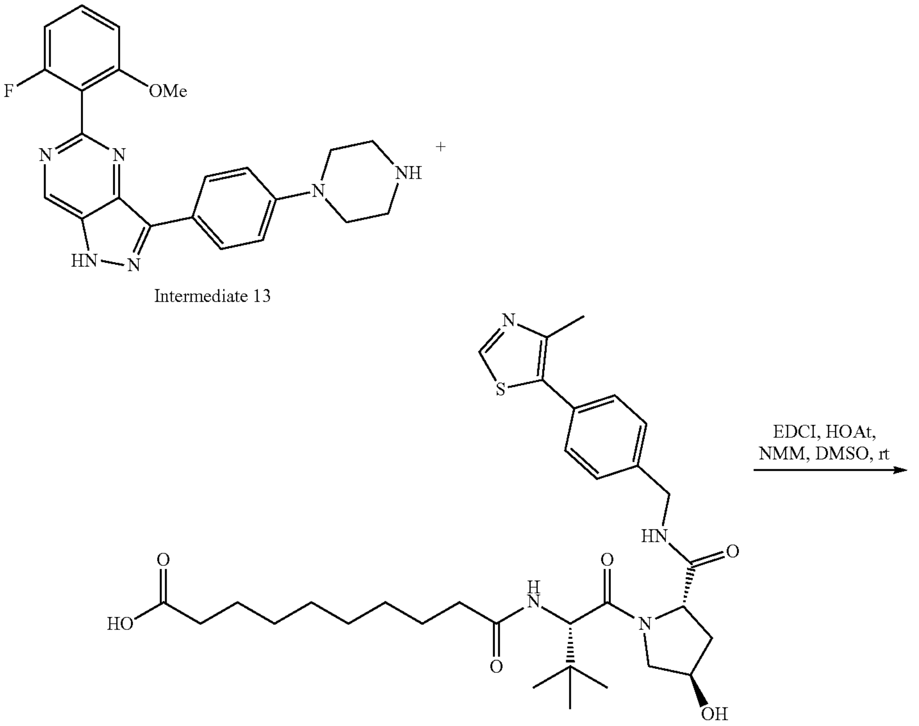

Intermediate 13

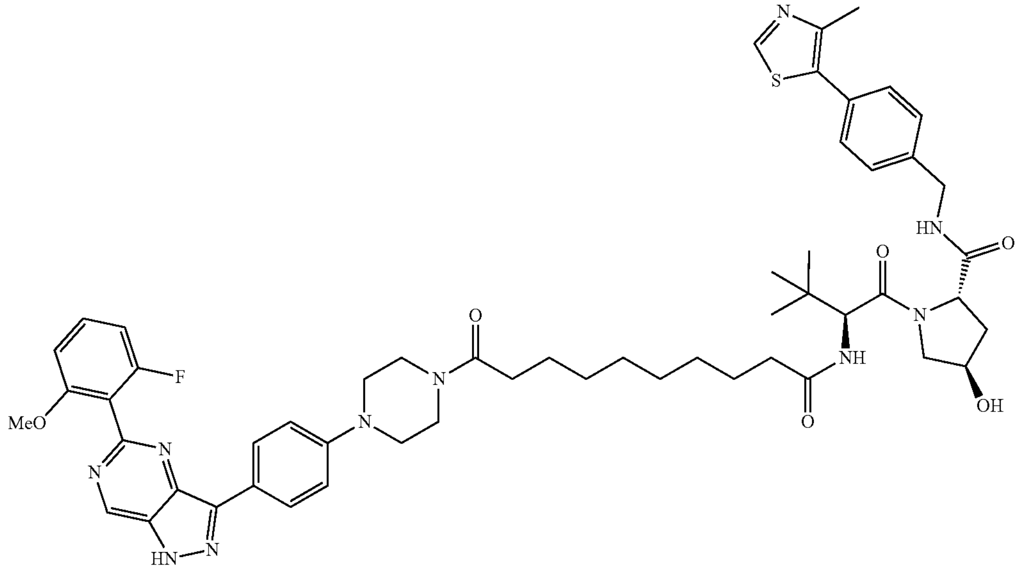

HC90-74

HC90-74 was synthesized following the standard procedure for preparing HC90-33 from Intermediate 13 (6.5 mg, 0.0125 mmol, 1.0 equiv), 10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid (7.7 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-74 was obtained as yellow solid in TFA salt form (5.5 mg, 39%). $^1$H NMR (800 MHz, Methanol-$d_4$) δ 9.30 (s, 1H), 8.90 (s, 1H), 8.38 (d, J=8.4 Hz, 2H), 7.52-7.46 (m, 3H), 7.43 (d, J=7.8 Hz, 2H), 7.11 (d, J=8.6 Hz, 2H), 7.01 (d, J=8.6 Hz, 1H), 6.90 (t, J=8.6 Hz, 1H), 4.66 (s, 1H), 4.59 (t, J=8.7 Hz, 1H), 4.55 (d, J=15.5 Hz, 1H), 4.51 (s, 1H), 4.37 (d, J=15.6 Hz, 1H), 3.92 (d, J=11.0 Hz, 1H), 3.85-3.79 (m, 4H), 3.78-3.71 (m, 4H), 3.32-3.22 (m, 4H), 2.52-2.43 (m, 5H), 2.34-2.21 (m, 3H), 2.10 (ddd, J=13.1, 8.7, 4.4 Hz, 1H), 1.68-1.60 (m, 4H), 1.44-1.32 (m, 8H), 1.05 (s, 9H). HRMS calcd for $C_{54}H_{66}FN_{10}O_6S^+$ [M+H$^+$] 1001.4866, found 1001.4850.

Example 206

Synthesis of HC90-84

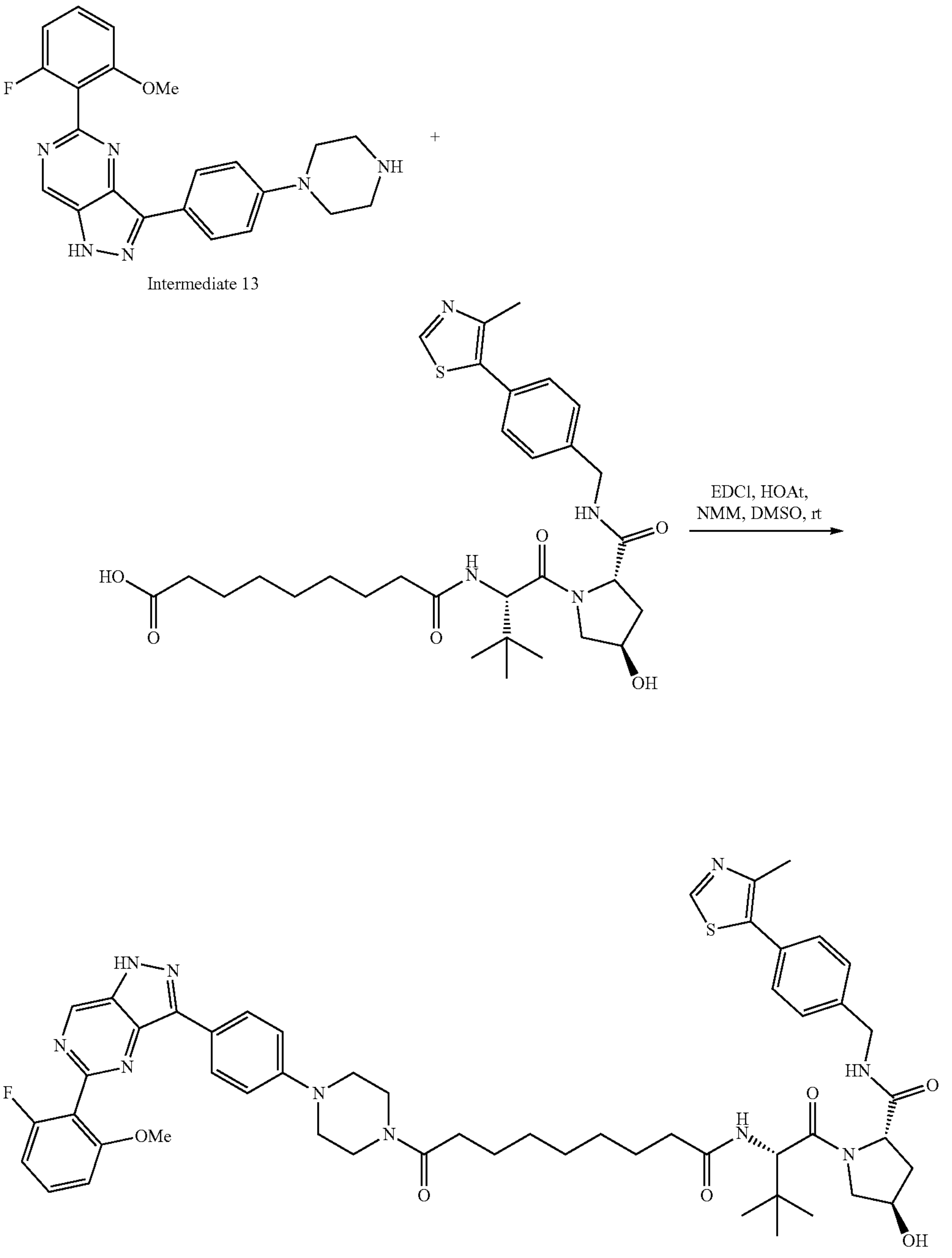

Intermediate 13

HC90-84

HC90-84 was synthesized following the standard procedure for preparing HC90-33 from Intermediate 13 (6.5 mg, 0.0125 mmol, 1.0 equiv), 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid (7.5 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-84 was obtained as yellow solid in TFA salt form (7.2 mg, 50%). $^1$H NMR (800 MHz, Methanol-$d_4$) δ 9.30 (s, 1H), 8.92 (s, 1H), 8.38 (d, J=8.2 Hz, 2H), 7.51-7.47 (m, 3H), 7.42 (d, J=8.0 Hz, 2H), 7.10 (d, J=8.5 Hz, 2H), 7.00 (d, J=8.5 Hz, 1H), 6.90 (t, J=8.5 Hz, 1H), 4.65 (s, 1H), 4.60 (t, J=8.4 Hz, 1H), 4.55 (d, J=15.3 Hz, 1H), 4.51 (s, 1H), 4.37 (d, J=15.4 Hz, 1H), 3.92 (d, J=10.9 Hz, 1H), 3.85-3.79 (m, 4H), 3.78-3.70 (m, 4H), 3.32-3.21 (m, 4H), 2.54-2.40 (m, 5H), 2.37-2.21 (m, 3H), 2.10 (ddd, J=13.3, 9.2, 4.7 Hz, 1H), 1.69-1.60 (m, 4H), 1.42-1.33 (m, 6H), 1.05 (s, 9H). HRMS calcd for $C_{53}H_{64}FN_{10}O_6S^+$ [M+H$^+$] 987.4710, found 987.4693.

9Example 207

Synthesis of HC90-85

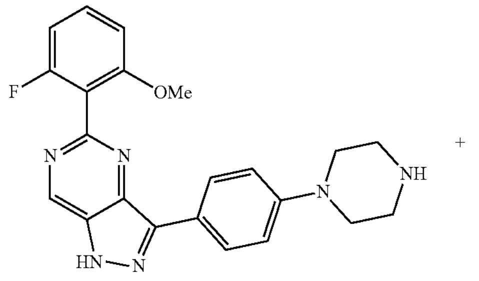

Intermediate 13

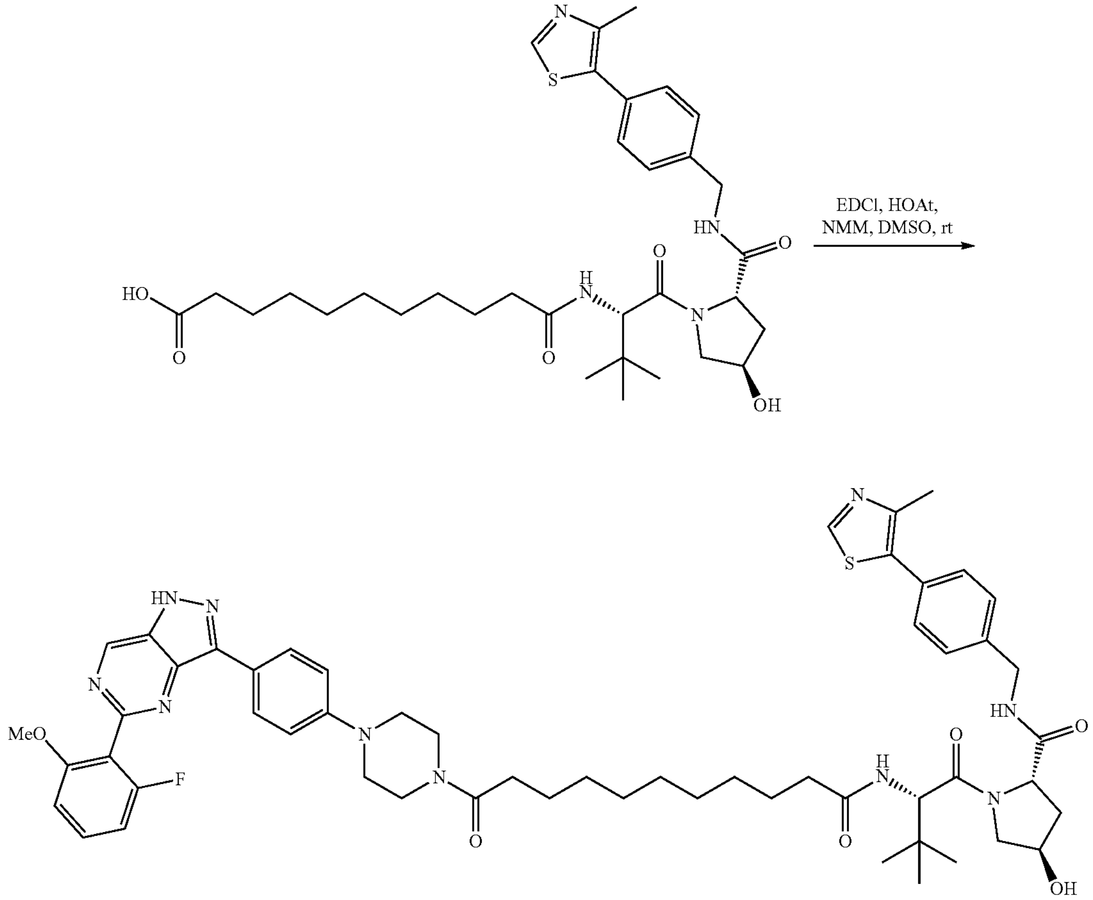

HC90-85

HC90-85 was synthesized following the standard procedure for preparing HC90-33 from Intermediate 13 (6.5 mg, 0.0125 mmol, 1.0 equiv), 11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (7.8 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-85 was obtained as yellow solid in TFA salt form (4.3 mg, 30%). $^1H$ NMR (800 MHz, Methanol-$d_4$) δ 9.30 (s, 1H), 8.91 (s, 1H), 8.38 (d, J=8.4 Hz, 2H), 7.52-7.46 (m, 3H), 7.43 (d, J=7.8 Hz, 2H), 7.12 (d, J=8.3 Hz, 2H), 7.01 (d, J=8.6 Hz, 1H), 6.90 (t, J=8.6 Hz, 1H), 4.66 (s, 1H), 4.59 (t, J=8.0 Hz, 1H), 4.55 (d, J=15.3 Hz, 1H), 4.51 (s, 1H), 4.37 (d, J=15.6 Hz, 1H), 3.92 (d, J=10.9 Hz, 1H), 3.85-3.79 (m, 4H), 3.78-3.73 (m, 4H), 3.33-3.23 (m, 4H), 2.49 (s, 3H), 2.46 (t, J=7.6 Hz, 2H), 2.31 (dt, J=14.9, 7.5 Hz, 1H), 2.29-2.20 (m, 2H), 2.10 (ddd, J=13.2, 8.9, 4.6 Hz, 1H), 1.69-1.60 (m, 4H), 1.43-1.29 (m, 10H), 1.05 (s, 9H). HRMS calcd for $C_{55}H_{68}FN_{10}O_6S^+$ [M+H$^+$] 1015.5023, found 1015.5009.

Example 208
Synthesis of Intermediate 14
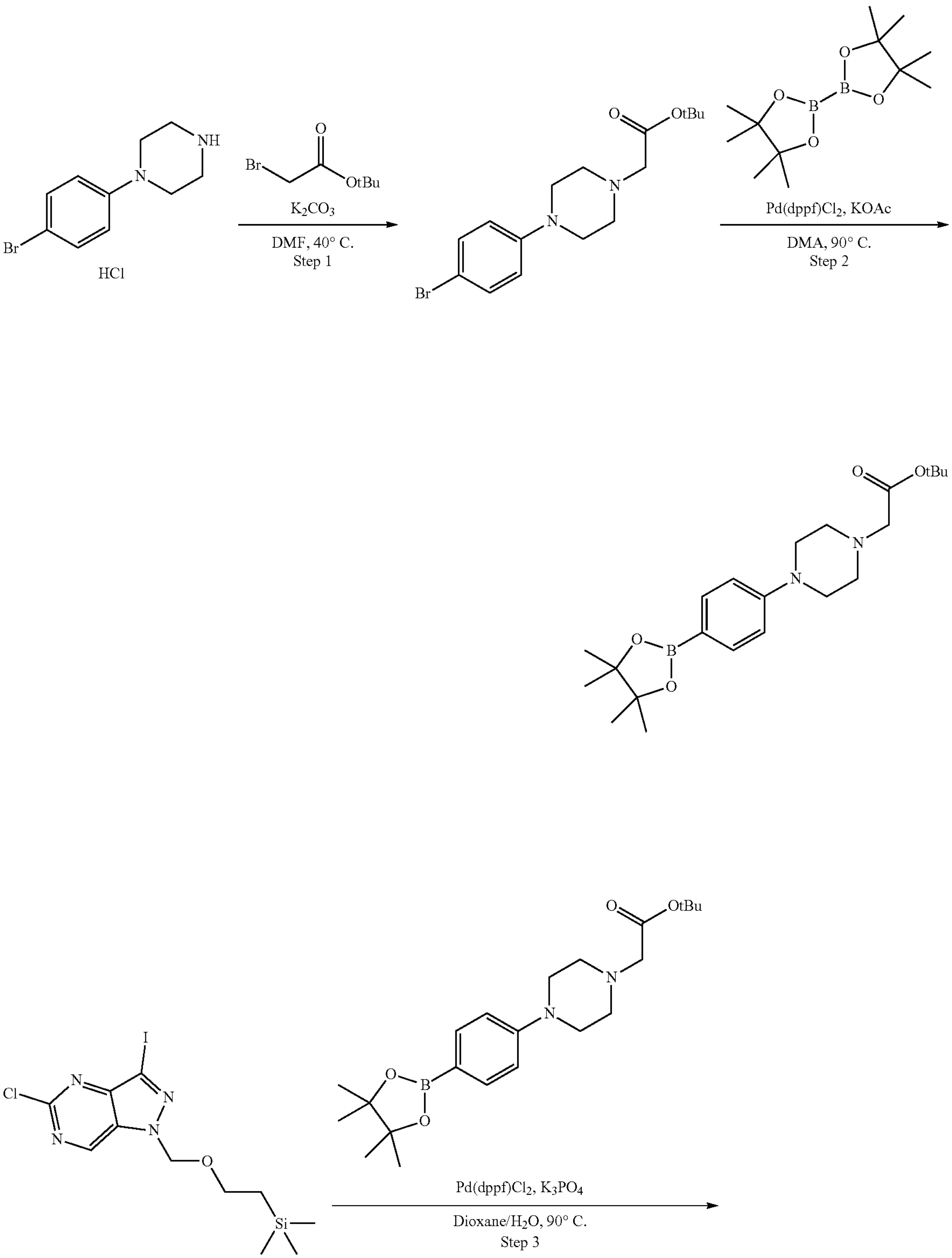

-continued

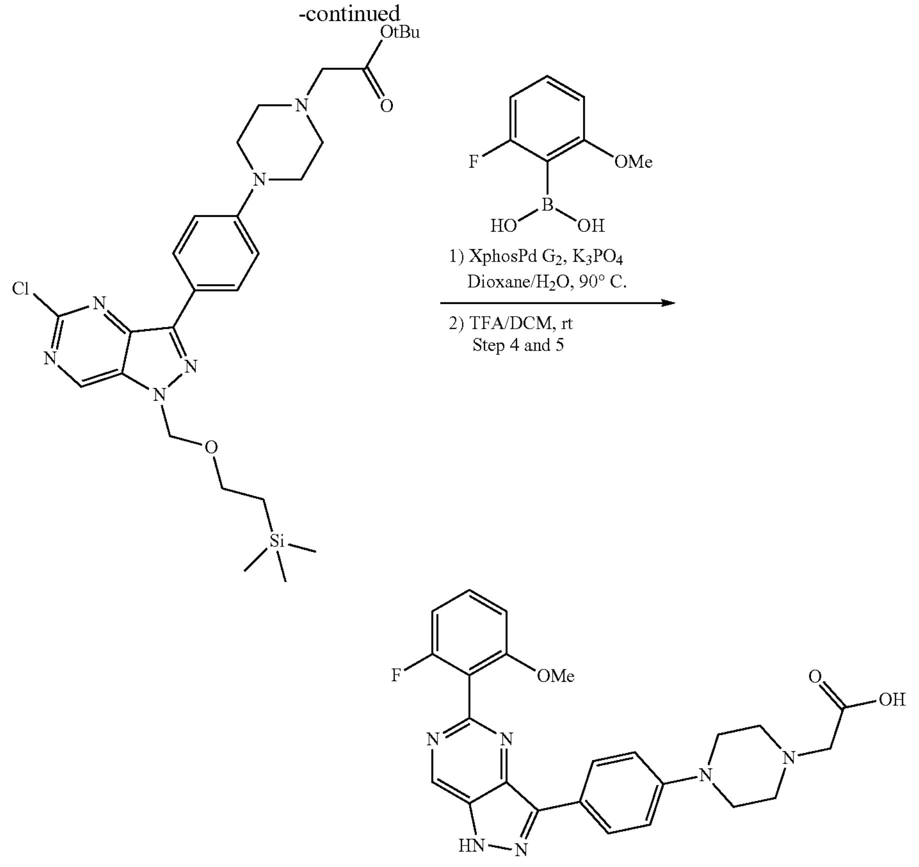

Intermediate 14

Step 1: tert-butyl 2-(4-(4-bromophenyl)piperazin-1-yl)acetate

To a solution of 1-(4-Bromophenyl)piperazine hydrochloride (813 mg, 2.93 mmol, 1.0 equiv) in DMF (8 mL) was added potassium carbonate (1.7 g, 11.72 mmol, 4.0 equiv) and tert-butyl bromoacetate (686 mg, 3.52 mmol, 1.2 equiv). Then the mixture was stirred at 40° C. for 2 h. Water (20 mL) was added to quench the reaction. The mixture was extracted with ethyl acetate (3×20 mL). The organic layer was combined and washed with brine. Dried over $Na_2SO_4$, filtered and evaporated to afford oil. ESI m/z=355.1 [M+H$^+$]. The oil was not further purified and directly used in next step.

Step 2: tert-butyl 2-(4-(4-(4,4,5,5-tetramethyl-1,3,2-dioxaborolan-2-yl)phenyl)piperazin-1-yl)acetate A mixture of tert-butyl 2-(4-(4-bromophenyl)piperazin-1-yl)acetate (3.0 mmol, 1.0 equiv), 4,4,4',4',5,5,5',5'-octamethyl-2,2'-bi(1,3,2-dioxaborolane) (4.6 g, 18 mmol, 6.0 equiv), Pd(dppf)$Cl_2$ (330 mg, 0.45 mmol, 0.15 equiv), KOAc (1.2 mg, 12 mmol, 4.0 equiv) in DMA (10 mL) was stirred at 90° C. for 18 h. The mixture was purified preparative HPLC (10%-100% methanol/0.1% TFA in $H_2O$) to afford tert-butyl 2-(4-(4-(4,4,5,5-tetramethyl-1,3,2-dioxaborolan-2-yl)phenyl)piperazin-1-yl)acetate as a white solid (1.43 g, 91% for two steps) in TFA salt form. ESI m/z=403.4 [M+H$^+$].

Step 3: tert-butyl 2-(4-(4-(5-chloro-1-((2-(trimethylsilyl)ethoxy)methyl)-1H-pyrazolo[4,3-d]pyrimidin-3-yl)phenyl)piperazin-1-yl)acetate A mixture of 5-chloro-3-iodo-1-((2-(trimethylsilyl)ethoxy)methyl)-1H-pyrazolo[4,3-d]pyrimidine (411 mg, 1 mmol, 1.0 equiv), tert-butyl 2-(4-(4-(4,4,5,5-tetramethyl-1,3,2-dioxaborolan-2-yl)phenyl)piperazin-1-yl)acetate (516 mg, 1 mmol, 1.0 equiv), Pd(dppf)$Cl_2$ (110 mg, 0.15 mmol, 0.15 equiv), $K_3PO_4$ (530 mg, 2.5 mmol, 2.5 equiv) in 1,4-dioxane (8 mL) and water (1.3 mL) was stirred at 90° C. for 18 h. The reaction was filtered and extracted with ethyl acetate. The combined organic extracts were combined and concentrated under vacuum. The residue was purified by silica gel column (hexane/ethyl acetate=3:2) to give tert-butyl 2-(4-(4-(5-chloro-1-((2-(trimethylsilyl)ethoxy)methyl)-1H-pyrazolo[4,3-d]pyrimidin-3-yl)phenyl)piperazin-1-yl)acetate as a yellow solid (306 mg, 55%). ESI m/z=559.3 [M+H$^+$].

Step 4 and 5: Intermediate 14

A mixture of tert-butyl 2-(4-(4-(5-chloro-1-((2-(trimethylsilyl)ethoxy)methyl)-1H-pyrazolo[4,3-d]pyrimidin-3-yl)phenyl)piperazin-1-yl)acetate (207 mg, 0.31 mmol, 1.0 equiv), (2-fluoro-6-methoxyphenyl)boronic acid (105 mg, 0.62 mmol, 2.0 equiv), XphosPd G2 (37 mg, 0.05 mmol, 0.15 equiv), $K_3PO_4$ (255 mg, 1.2 mmol, 4.0 equiv) in 1,4-dioxane (4.0 mL) and water (0.5 mL) was stirred at 90° C. for 1.5 h. The reaction was filtered and extracted with ethyl acetate. The combined organic extracts were combined and concentrated under vacuum. The obtained residue was dissolved in DCM (4 mL). To the solution was added TFA (2 mL). Stirred at room temperature for 3 h and concentrated under vacuum. The residue was purified preparative HPLC (10%-100% acetonitrile/0.1% TFA in $H_2O$) to afford intermediate 14 as a yellow solid (154 mg, 86% for two steps) in TFA salt form. $^1H$ NMR (800 MHz, Methanol-d4) δ 9.32 (s, 1H), 8.43 (d, J=8.3 Hz, 2H), 7.50 (q, J=7.9 Hz, 1H), 7.18 (d, J=8.4 Hz, 2H), 7.02 (d, J=8.5 Hz, 1H), 6.90 (t, J=8.6 Hz, 1H), 4.20 (s, 2H), 3.81 (s, 3H), 3.74-3.49 (m, 8H). ESI m/z=463.3 [M+H⁺].

Example 209

Synthesis of HC90-86

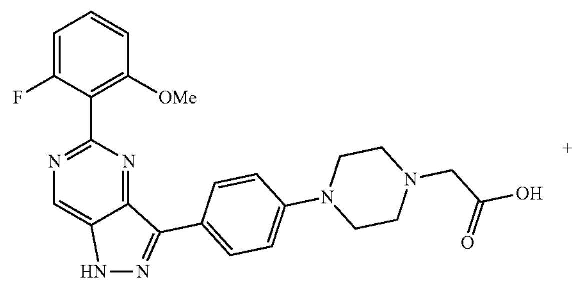

Intermediate 14

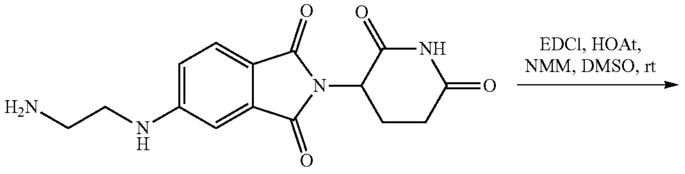

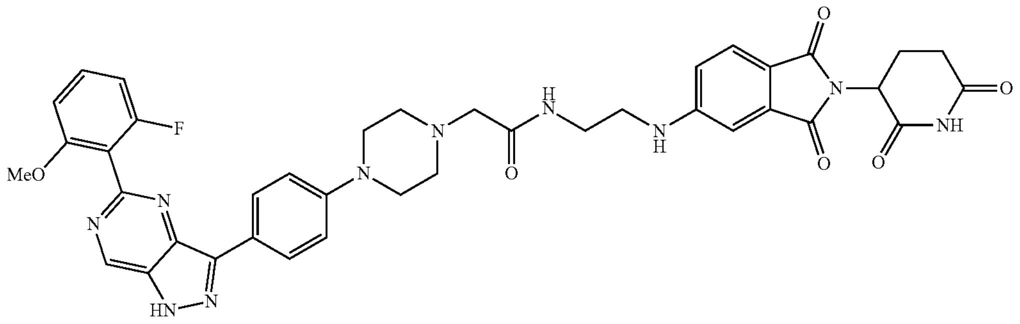

HC90-86

To a solution of Intermediate 14 (5.8 mg, 0.01 mmol, 1.0 equiv) in DMSO (1 mL) were added 5-((2-aminoethyl)amino)-2-(2,6-dioxopiperidin-3-yl)isoindoline-1,3-dione (4.8 mg, 0.011 mmol, 1.1 equiv), EDCI (1-ethyl-3-(3-dimethylaminopropyl)carbodiimide) (3.8 mg, 0.02 mmol, 2.0 equiv), HOAt (1-hydroxy-7-azabenzo-triazole) (2.7 mg, 0.02 mmol, 2.0 equiv), and NMM (N-Methylmorpholine) (5.1 mg, 0.05 mmol, 5.0 equiv). After being stirred overnight at room temperature, the resulting mixture was purified by preparative HPLC (10%-100% methanol/0.1% TFA in $H_2O$) to afford HC90-86 as yellow solid in TFA salt form (5.3 mg, 61%). $^1H$ NMR (800 MHz, Methanol-$d_4$) δ 9.32 (s, 1H), 8.42 (d, J=8.3 Hz, 2H), 7.62 (d, J=8.3 Hz, 1H), 7.50 (q, J=7.9 Hz, 1H), 7.15 (d, J=8.4 Hz, 2H), 7.08 (s, 1H), 7.01 (d, J=8.5 Hz, 1H), 6.94 (d, J=8.5 Hz, 1H), 6.90 (t, J=8.6 Hz, 1H), 5.06 (dd, J=12.5, 5.3 Hz, 1H), 3.93-3.88 (m, 2H), 3.81 (s, 3H), 3.54 (t, J=6.0 Hz, 2H), 3.51-3.40 (m, 10H), 2.89-2.80 (m, 1H), 2.76-2.68 (m, 2H), 2.13-2.05 (m, 1H). HRMS calcd for $C_{39}H_{38}FN_{10}O_6^+$ [M+H$^+$] 761.2954, found 761.2940.

Example 210

Synthesis of HC90-87

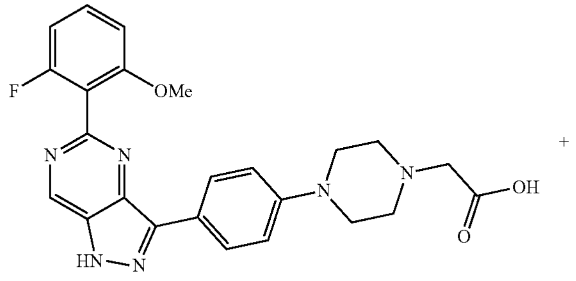

Intermediate 14

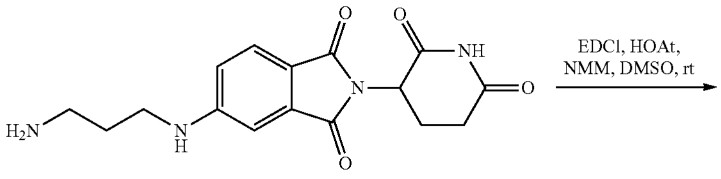

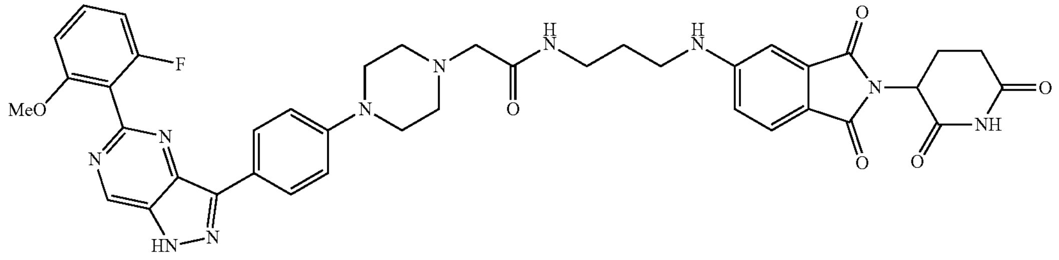

HC90-87

HC90-87 was synthesized following the standard procedure for preparing HC90-86 from Intermediate 14 (5.8 mg, 0.01 mmol, 1.0 equiv), 5-((3-aminopropyl)amino)-2-(2,6-dioxopiperidin-3-yl)isoindoline-1,3-dione (4.9 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-87 was obtained as yellow solid in TFA salt form (5.9 mg, 66%). $^1H$ NMR (800 MHz, Methanol-$d_4$) δ 9.32 (s, 1H), 8.42 (d, J=8.3 Hz, 2H), 7.60 (d, J=8.3 Hz, 1H), 7.50 (q, J=7.9 Hz, 1H), 7.15 (d, J=8.4 Hz, 2H), 7.03-7.00 (m, 2H), 6.96-6.86 (m, 2H), 5.06 (dd, J=12.9, 5.4 Hz, 1H), 4.03-3.96 (m, 2H), 3.81 (s, 3H), 3.57-3.38 (m, 10H), 3.32 (t, J=7.2 Hz, 2H), 2.89-2.80 (m, 1H), 2.76-2.67 (m, 2H), 2.13-2.07 (m, 1H), 1.92 (p, J=7.2 Hz, 2H). HRMS calcd for $C_{40}H_{40}FN_{10}O_6^+$ [M+H$^+$] 775.3111, found 775.3096.

Example 211

Synthesis of HC90-88

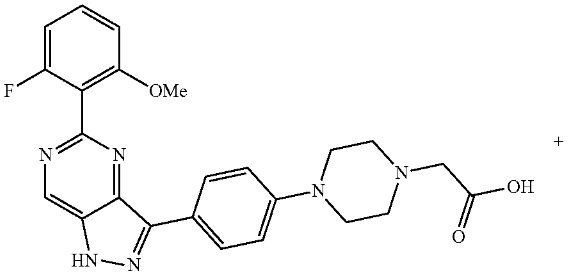

Intermediate 14

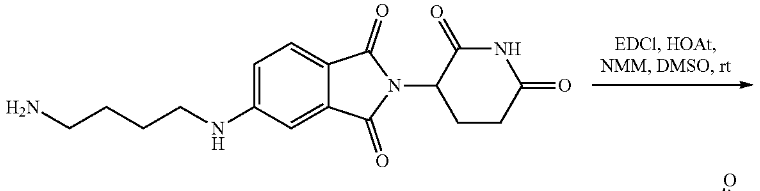

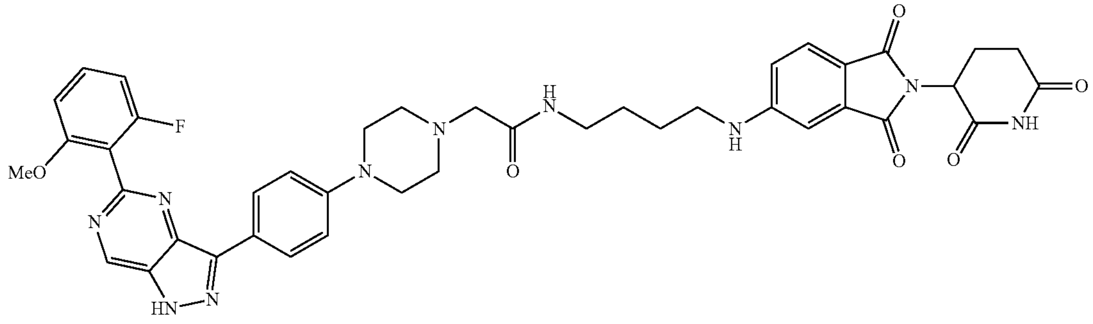

HC90-88

HC90-88 was synthesized following the standard procedure for preparing HC90-86 from Intermediate 14 (5.8 mg, 0.01 mmol, 1.0 equiv), 5-((4-aminobutyl)amino)-2-(2,6-dioxopiperidin-3-yl)isoindoline-1,3-dione (5.1 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-88 was obtained as yellow solid in TFA salt form (5.9 mg, 65%). $^1$H NMR (800 MHz, Methanol-$d_4$) δ 9.32 (s, 1H), 8.42 (d, J=8.3 Hz, 2H), 7.59 (d, J=8.3 Hz, 1H), 7.50 (q, J=8.0 Hz, 1H), 7.16 (d, J=8.4 Hz, 2H), 7.03-6.99 (m, 2H), 6.90 (t, J=8.6 Hz, 1H), 6.87 (d, J=8.5 Hz, 1H), 5.05 (dd, J=12.4, 5.4 Hz, 1H), 3.98 (s, 2H), 3.81 (s, 3H), 3.56-3.43 (m, 8H), 3.37 (t, J=6.6 Hz, 2H), 3.30 (t, J=6.7 Hz, 2H), 2.87-2.78 (m, 1H), 2.76-2.65 (m, 2H), 2.12-2.05 (m, 1H), 1.78-1.67 (m, 4H). HRMS calcd for $C_{41}H_{42}FN_{10}O_6^+$ [M+H$^+$] 789.3267, found 789.3251.

Example 212

Synthesis of HC90-89

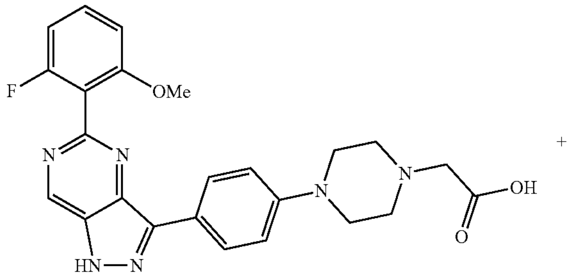

Intermediate 14

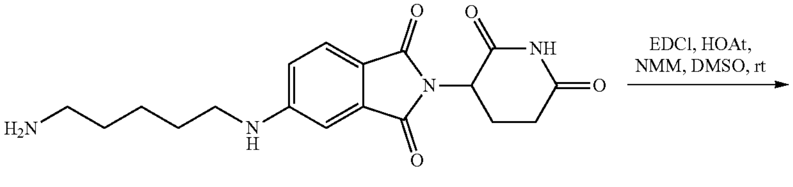

-continued

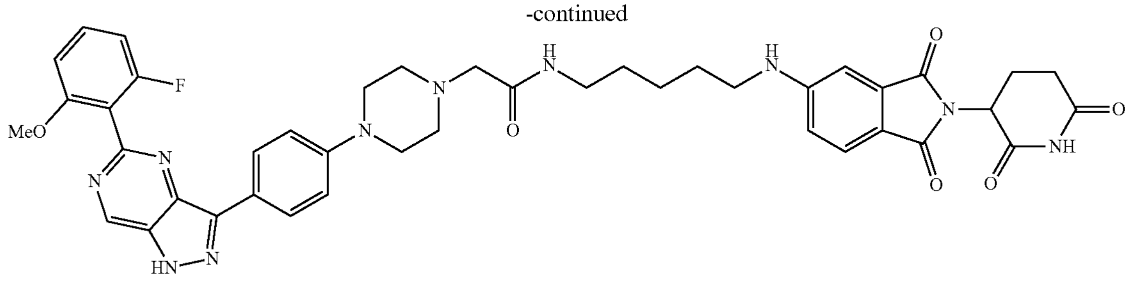

HC90-89

HC90-89 was synthesized following the standard procedure for preparing HC90-86 from Intermediate 14 (5.8 mg, 0.01 mmol, 1.0 equiv), 5-((5-aminopentyl)amino)-2-(2,6-dioxopiperidin-3-yl)isoindoline-1,3-dione (5.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-89 was obtained as yellow solid in TFA salt form (4.2 mg, 46%). $^1$H NMR (800 MHz, Methanol-$d_4$) δ 9.32 (s, 1H), 8.42 (d, J=8.3 Hz, 2H), 7.59 (d, J=8.3 Hz, 1H), 7.50 (q, J=7.9 Hz, 1H), 7.16 (d, J=8.4 Hz, 2H), 7.08-6.98 (m, 2H), 6.90 (t, J=8.6 Hz, 1H), 6.87 (d, J=8.6 Hz, 1H), 5.05 (dd, J=12.8, 5.3 Hz, 1H), 3.92 (s, 2H), 3.81 (s, 3H), 3.67-3.33 (m, 10H), 3.26 (t, J=7.1 Hz, 2H), 2.86-2.79 (m, 1H), 2.76-2.66 (m, 2H), 2.11-2.04 (m, 1H), 1.73 (p, J=7.2 Hz, 2H), 1.64 (p, J=7.3 Hz, 2H), 1.52 (q, J=7.9 Hz, 2H). HRMS calcd for $C_{42}H_{44}FN_{10}O_6^+$ [M+H$^+$] 803.3424, found 803.3410.

Example 213

Synthesis of HC90-90

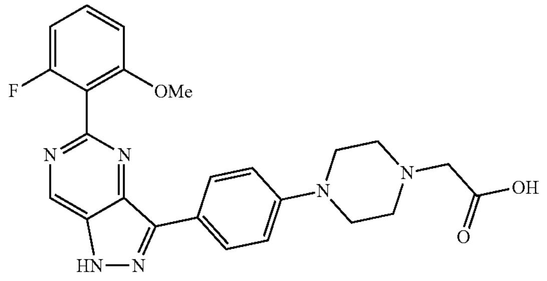

Intermediate 14

+

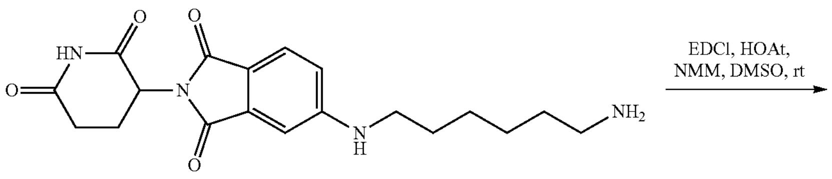

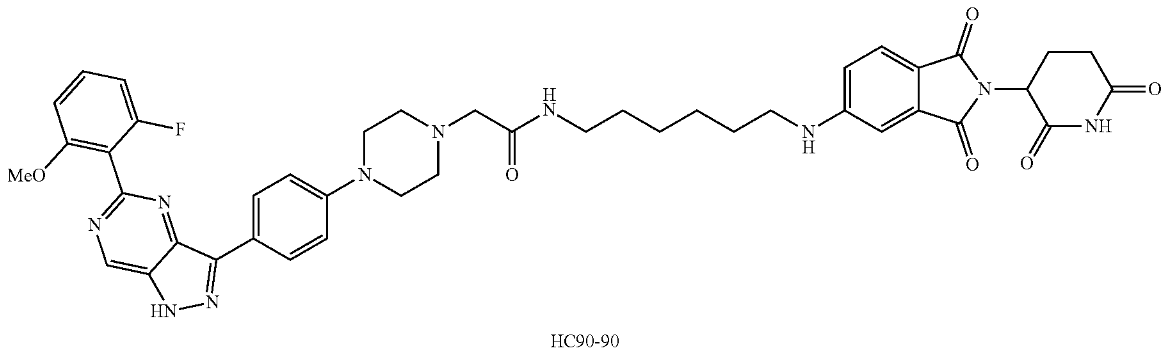

HC90-90

HC90-90 was synthesized following the standard procedure for preparing HC90-86 from Intermediate 14 (5.8 mg, 0.01 mmol, 1.0 equiv), 5-((6-aminohexyl)amino)-2-(2,6-dioxopiperidin-3-yl)isoindoline-1,3-dione (5.4 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-90 was obtained as yellow solid in TFA salt form (7.1 mg, 76%). $^1$H NMR (800 MHz, Methanol-$d_4$) δ 9.32 (s, 1H), 8.42 (d, J=8.3 Hz, 2H), 7.58 (d, J=8.3 Hz, 1H), 7.50 (q, J=8.0 Hz, 1H), 7.16 (d, J=8.4 Hz, 2H), 7.01 (d, J=8.5 Hz, 1H), 6.99 (s, 1H), 6.90 (t, J=8.6 Hz, 1H), 6.86 (d, J=8.5 Hz, 1H), 5.05 (dd, J=12.9, 5.3 Hz, 1H), 4.00 (s, 2H), 3.81 (s, 3H), 3.62-3.45 (m, 8H), 3.31 (t, J=7.2 Hz, 2H), 3.24 (t, J=7.1 Hz, 2H), 2.88-2.80 (m, 1H), 2.76-2.65 (m, 2H), 2.12-2.06 (m, 1H), 1.70 (p, J=7.3 Hz, 2H), 1.60 (p, J=7.3 Hz, 2H), 1.54-1.42 (m, 4H). HRMS calcd for $C_{43}H_{46}FN_{10}O_6^+$ [M+H$^+$] 817.3580, found 817.3566.

Example 214

Synthesis of HC90-91

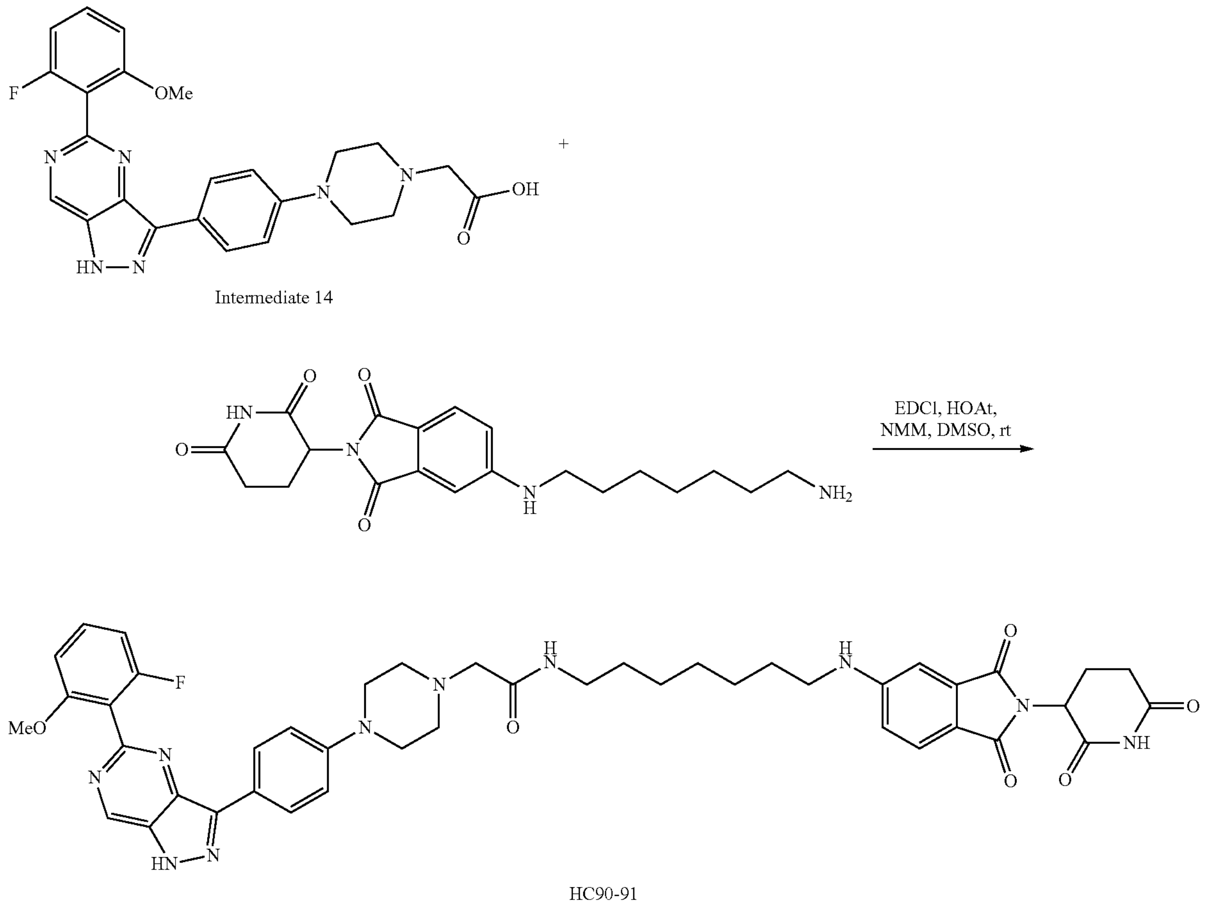 [SMILES: COc1cccc(F)c1-c1ncc2[nH]nc(-c3ccc(N4CCN(CC(=O)O)CC4)cc3)c2n1 ; NCCCCCCCNc1ccc2c(c1)C(=O)N(C1CCC(=O)NC1=O)C2=O ; COc1cccc(F)c1-c1ncc2[nH]nc(-c3ccc(N4CCN(CC(=O)NCCCCCCCNc5ccc6c(c5)C(=O)N(C5CCC(=O)NC5=O)C6=O)CC4)cc3)c2n1]

HC90-91 was synthesized following the standard procedure for preparing HC90-86 from Intermediate 14 (5.8 mg, 0.01 mmol, 1.0 equiv), 5-((7-aminoheptyl)amino)-2-(2,6-dioxopiperidin-3-yl)isoindoline-1,3-dione (5.5 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-91 was obtained as yellow solid in TFA salt form (6.4 mg, 68%). $^1$H NMR (800 MHz, Methanol-$d_4$) δ 9.32 (s, 1H), 8.42 (d, J=8.3 Hz, 2H), 7.58 (d, J=8.3 Hz, 1H), 7.50 (q, J=8.0 Hz, 1H), 7.17 (d, J=8.4 Hz, 2H), 7.02 (d, J=8.5 Hz, 1H), 7.00 (s, 1H), 6.90 (t, J=8.6 Hz, 1H), 6.85 (d, J=8.5 Hz, 1H), 5.05 (dd, J=12.8, 5.4 Hz, 1H), 3.99 (s, 2H), 3.81 (s, 3H), 3.63-3.39 (m, 8H), 3.30 (t, J=7.2 Hz, 2H), 3.24 (t, J=7.1 Hz, 2H), 2.92-2.81 (m, 1H), 2.79-2.66 (m, 2H), 2.14-2.07 (m, 1H), 1.69 (p, J=7.2 Hz, 2H), 1.59 (p, J=7.3 Hz, 2H), 1.52-1.38 (m, 6H). HRMS calcd for $C_{44}H_{48}FN_{10}O_6^+$ [M+H$^+$] 831.3737, found 831.3721.

Example 215

Synthesis of HC90-92

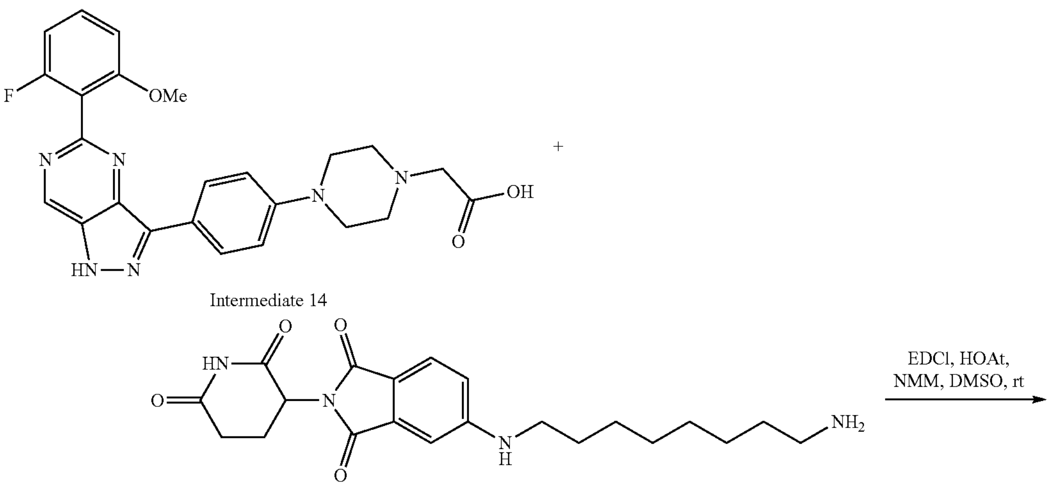

Intermediate 14

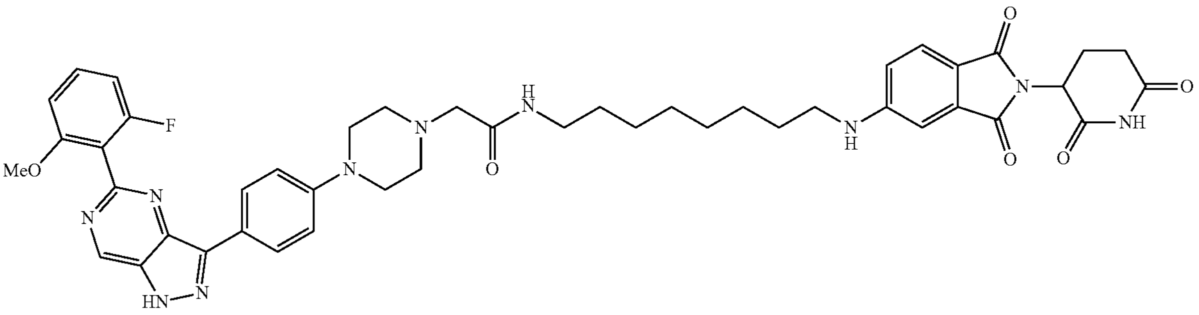

HC90-92

HC90-92 was synthesized following the standard procedure for preparing HC90-86 from Intermediate 14 (5.8 mg, 0.01 mmol, 1.0 equiv), 5-((8-aminooctyl)amino)-2-(2,6-dioxopiperidin-3-yl)isoindoline-1,3-dione (5.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-92 was obtained as yellow solid in TFA salt form (5.3 mg, 55%). $^1$H NMR (800 MHz, Methanol-$d_4$) δ 9.31 (s, 1H), 8.42 (d, J=8.3 Hz, 2H), 7.57 (d, J=8.3 Hz, 1H), 7.50 (q, J=7.9 Hz, 1H), 7.16 (d, J=8.4 Hz, 2H), 7.02 (d, J=8.5 Hz, 1H), 6.99 (s, 1H), 6.90 (t, J=8.6 Hz, 1H), 6.85 (d, J=8.4 Hz, 1H), 5.05 (dd, J=12.9, 5.3 Hz, 1H), 3.95 (s, 2H), 3.81 (s, 3H), 3.60-3.40 (m, 8H), 3.29 (t, J=7.2 Hz, 2H), 3.23 (t, J=7.1 Hz, 2H), 2.92-2.81 (m, 1H), 2.78-2.66 (m, 2H), 2.18-2.04 (m, 1H), 1.69 (p, J=7.2 Hz, 2H), 1.57 (t, J=7.0 Hz, 2H), 1.47 (t, J=7.4 Hz, 2H), 1.41 (q, J=7.3, 5.1 Hz, 6H). HRMS calcd for $C_{45}H_{50}FN_{10}O_6^+$ [M+H$^+$] 845.3893, found 845.3879.

Example 216

Synthesis of HC90-93

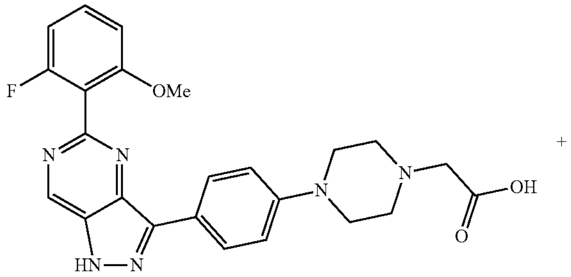

Intermediate 14

-continued

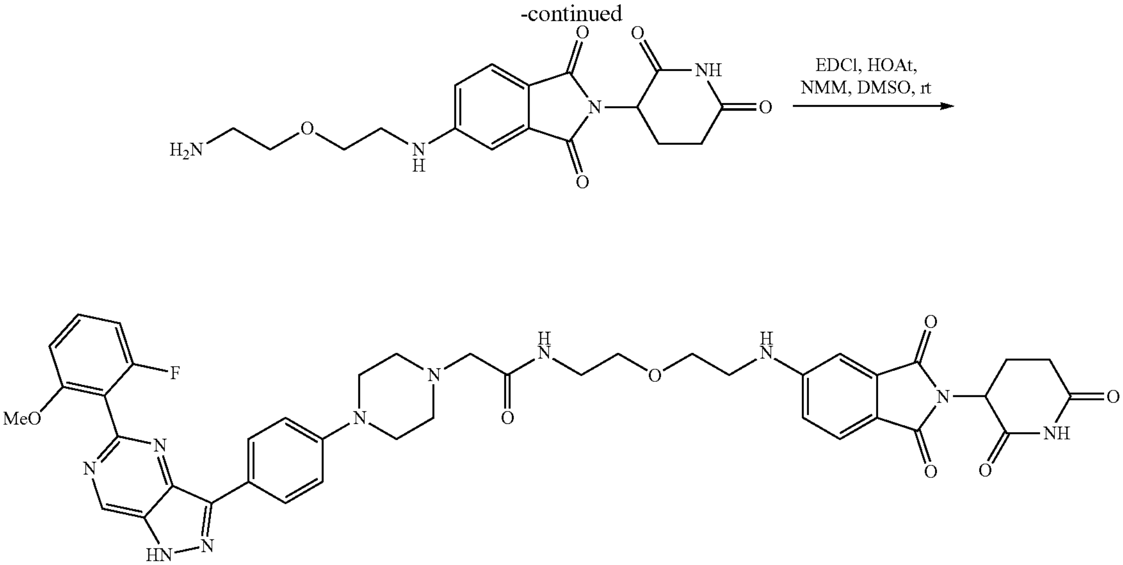

HC90-93

HC90-93 was synthesized following the standard procedure for preparing HC90-86 from Intermediate 14 (5.8 mg, 0.01 mmol, 1.0 equiv), 5-((2-(2-aminoethoxy)ethyl)amino)-2-(2,6-dioxopiperidin-3-yl)isoindoline-1,3-dione (5.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-93 was obtained as yellow solid in TFA salt form (7.4 mg, 81%). $^1$H NMR (800 MHz, Methanol-$d_4$) δ 9.32 (s, 1H), 8.41 (d, J=8.3 Hz, 2H), 7.61 (d, J=8.3 Hz, 1H), 7.50 (q, J=7.9 Hz, 1H), 7.13 (d, J=8.4 Hz, 2H), 7.11 (s, 1H), 7.01 (d, J=8.5 Hz, 1H), 6.93 (d, J=8.4 Hz, 1H), 6.90 (t, J=8.6 Hz, 1H), 5.03 (dd, J=12.8, 5.5 Hz, 1H), 3.98 (s, 2H), 3.81 (s, 3H), 3.73 (t, J=5.2 Hz, 2H), 3.63 (t, J=5.2 Hz, 2H), 3.56-3.42 (m, 12H), 2.85-2.74 (m, 1H), 2.72-2.62 (m, 2H), 2.14-2.00 (m, 1H). HRMS calcd for $C_{41}H_{42}FN_{10}O_7^+$ [M+H$^+$] 805.3216, found 805.3202.

Example 217

Synthesis of HC90-94

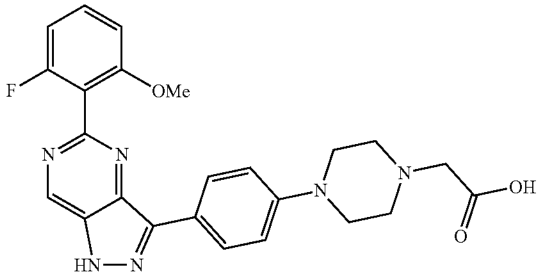

Intermediate 14

+

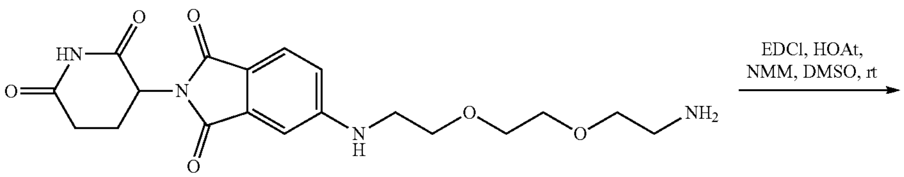

-continued

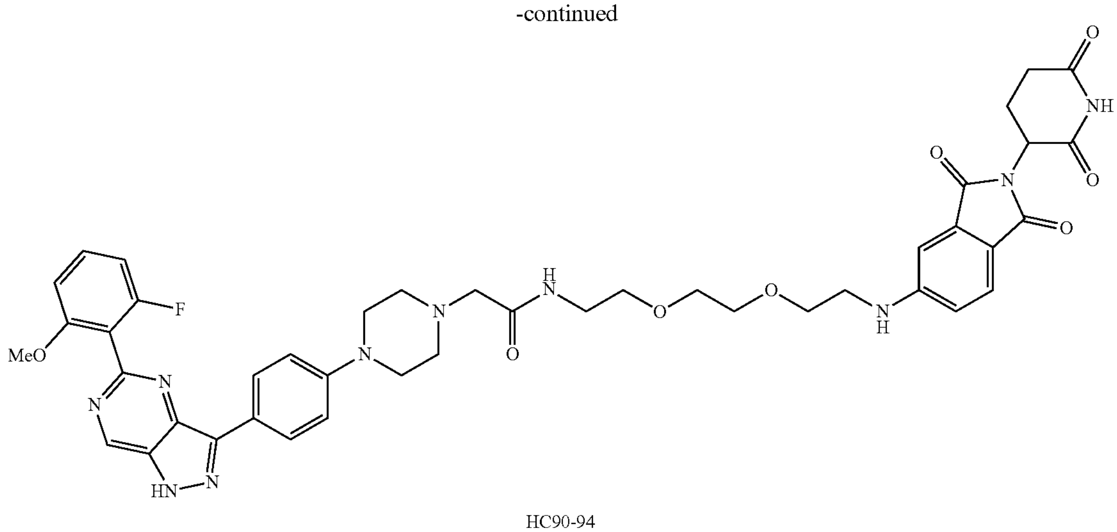

HC90-94

HC90-94 was synthesized following the standard procedure for preparing HC90-86 from Intermediate 14 (5.8 mg, 0.01 mmol, 1.0 equiv), 5-((2-(2-(2-aminoethoxy)ethoxy)ethyl)amino)-2-(2,6-dioxopiperidin-3-yl)isoindoline-1,3-dione (5.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-94 was obtained as yellow solid in TFA salt form (7.1 mg, 74%). $^{1}$H NMR (800 MHz, Methanol-$d_4$) δ 9.32 (s, 1H), 8.41 (d, J=8.4 Hz, 2H), 7.58 (d, J=8.3 Hz, 1H), 7.50 (q, J=7.9 Hz, 1H), 7.14 (d, J=8.4 Hz, 2H), 7.07 (s, 1H), 7.01 (d, J=8.6 Hz, 1H), 6.95-6.86 (m, 2H), 5.03 (dd, J=12.9, 5.4 Hz, 1H), 3.98 (s, 2H), 3.81 (s, 3H), 3.73 (t, J=5.3 Hz, 2H), 3.70-3.66 (m, 4H), 3.61 (t, J=5.3 Hz, 2H), 3.53-3.41 (m, 12H), 2.85-2.77 (m, 1H), 2.74-2.65 (m, 2H), 2.20-1.92 (m, 1H). HRMS calcd for $C_{43}H_{46}FN_{10}O_8^+$ [M+H$^+$] 849.3479, found 849.3463.

Example 218

Synthesis of HC90-95

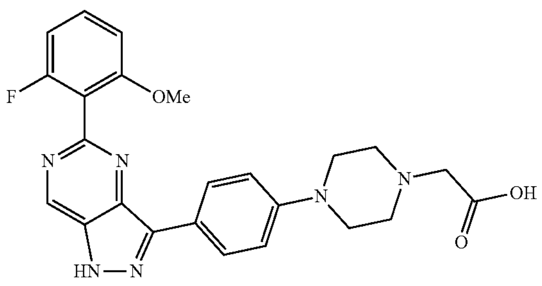

Intermediate 14

+

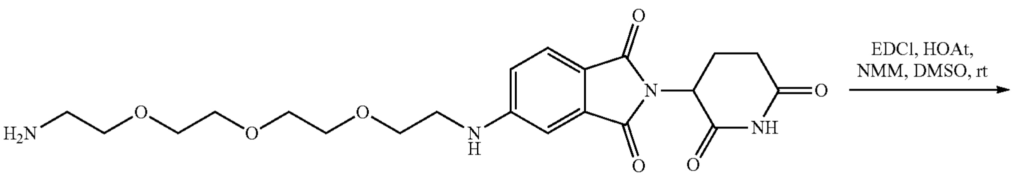

-continued

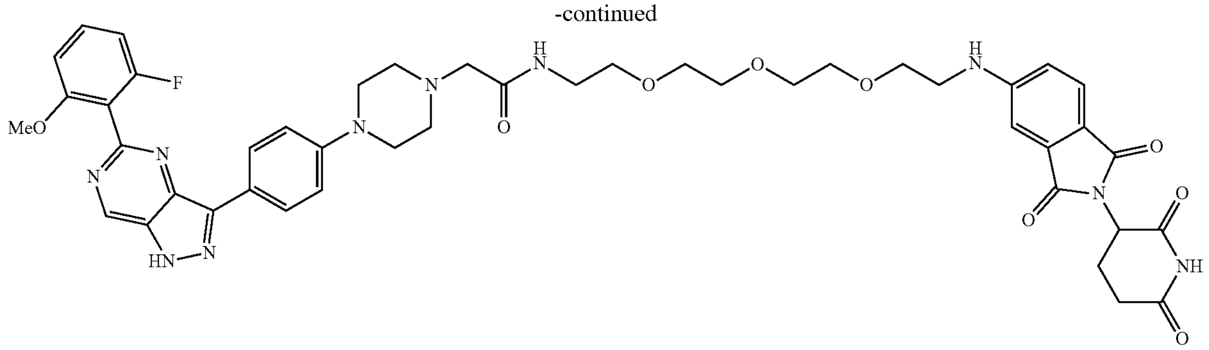

HC90-95

HC90-95 was synthesized following the standard procedure for preparing HC90-86 from Intermediate 14 (5.8 mg, 0.01 mmol, 1.0 equiv), 5-((2-(2-(2-(2-aminoethoxy)ethoxy)ethoxy)ethyl)amino)-2-(2,6-dioxopiperidin-3-yl)isoindoline-1,3-dione (6.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-95 was obtained as yellow solid in TFA salt form (6.5 mg, 65%). $^1$H NMR (800 MHz, Methanol-$d_4$) δ 9.31 (s, 1H), 8.40 (d, J=8.4 Hz, 2H), 7.55 (d, J=8.3 Hz, 1H), 7.50 (q, J=7.9 Hz, 1H), 7.14 (d, J=8.4 Hz, 2H), 7.04 (s, 1H), 7.01 (d, J=8.5 Hz, 1H), 6.90 (t, J=8.6 Hz, 1H), 6.87 (d, J=8.5 Hz, 1H), 5.04 (dd, J=12.8, 5.4 Hz, 1H), 3.93 (s, 2H), 3.81 (s, 3H), 3.70 (t, J=5.3 Hz, 2H), 3.69-3.63 (m, 8H), 3.60 (t, J=5.3 Hz, 2H), 3.48 (t, J=5.3 Hz, 2H), 3.46-3.43 (m, 8H), 3.41 (t, J=5.3 Hz, 2H), 2.82 (ddd, J=18.5, 13.8, 5.3 Hz, 1H), 2.75-2.65 (m, 2H), 2.13-2.05 (m, 1H). HRMS calcd for $C_{45}H_{50}FN_{10}O_9^+$ [M+H$^+$] 893.3741, found 893.3730.

Example 219

Synthesis of HC90-96

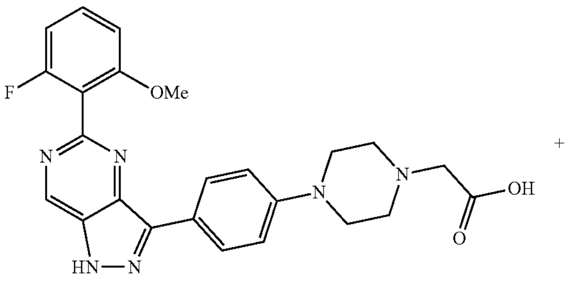

Intermediate 14

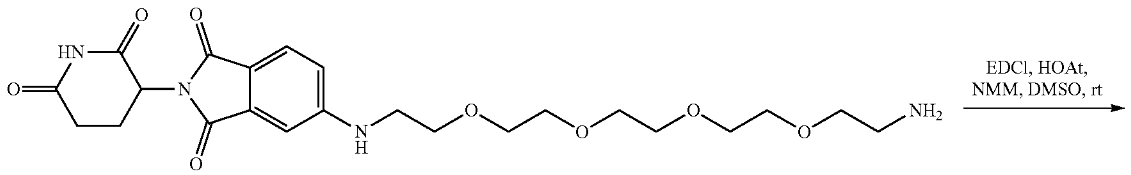

-continued

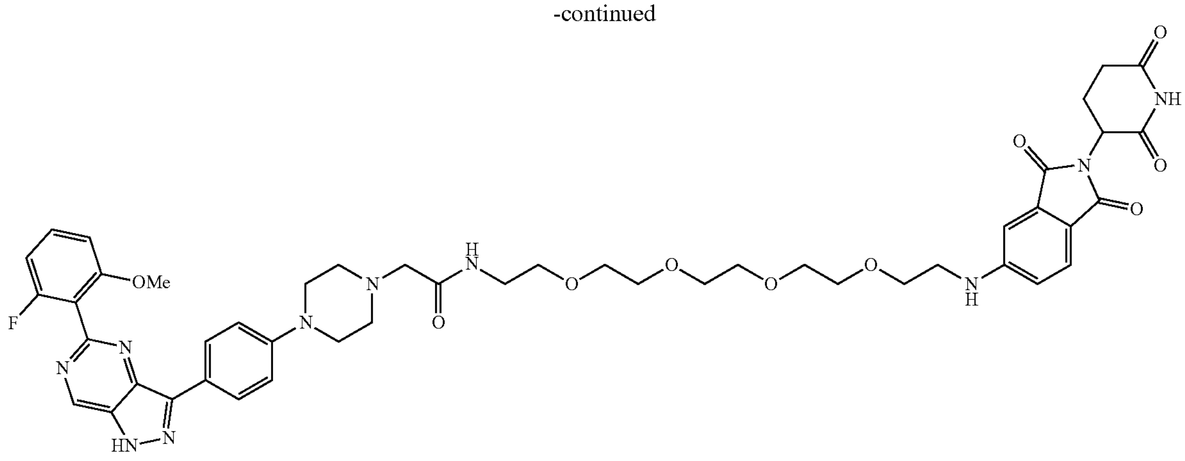

HC90-96

HC90-96 was synthesized following the standard procedure for preparing HC90-86 from Intermediate 14 (5.8 mg, 0.01 mmol, 1.0 equiv), 5-((14-amino-3,6,9,12-tetraoxatetradecyl)amino)-2-(2,6-dioxopiperidin-3-yl)isoindoline-1,3-dione (6.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-96 was obtained as yellow solid in TFA salt form (6.7 mg, 64%). $^{1}$H NMR (800 MHz, Methanol-$d_4$) δ 9.31 (s, 1H), 8.40 (d, J=8.3 Hz, 2H), 7.55 (d, J=8.3 Hz, 1H), 7.50 (q, J=7.9 Hz, 1H), 7.14 (d, J=8.4 Hz, 2H), 7.02 (s, 1H), 7.01 (d, J=8.6 Hz, 1H), 6.90 (t, J=8.6 Hz, 1H), 6.86 (d, J=8.4 Hz, 1H), 5.04 (dd, J=12.9, 5.4 Hz, 1H), 3.98 (s, 2H), 3.81 (s, 3H), 3.68 (t, J=5.2 Hz, 2H), 3.67-3.63 (m, 12H), 3.59 (t, J=5.2 Hz, 2H), 3.53-3.44 (m, 10H), 3.39 (t, J=5.3 Hz, 2H), 2.83 (ddd, J=18.5, 13.9, 5.4 Hz, 1H), 2.76-2.62 (m, 2H), 2.18-1.99 (m, 1H). HRMS calcd for $C_{47}H_{54}FN_{10}O_{10}^{+}$ [M+H$^{+}$] 937.4003, found 937.3987.

Example 220

Synthesis of HC90-97

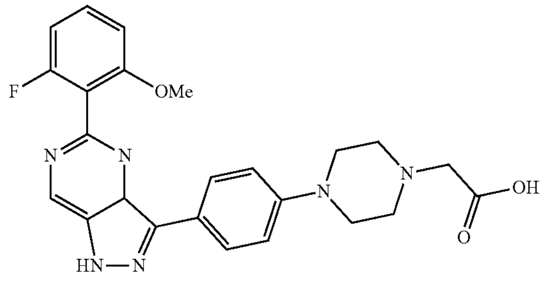

Intermediate 14

+

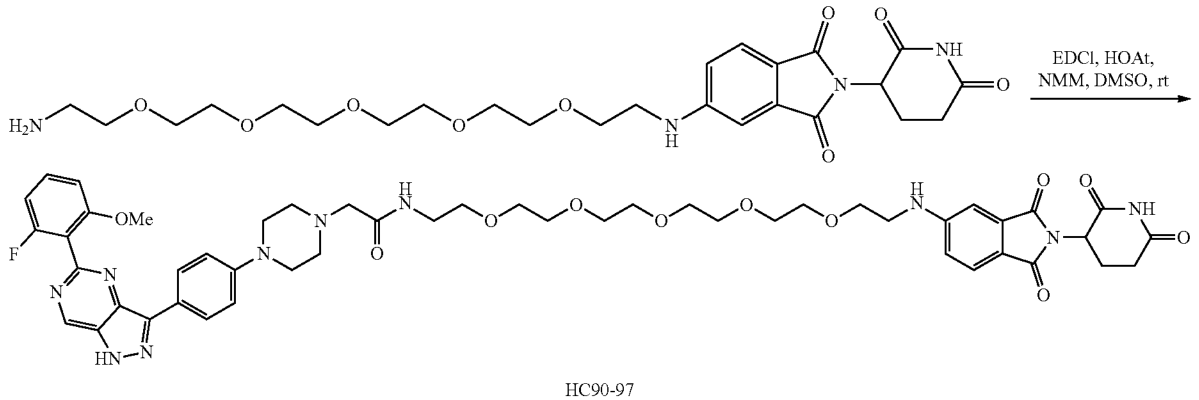

HC90-97

HC90-97 was synthesized following the standard procedure for preparing HC90-86 from Intermediate 14 (5.8 mg, 0.01 mmol, 1.0 equiv), 5-((17-amino-3,6,9,12,15-pentaoxaheptadecyl)amino)-2-(2,6-dioxopiperidin-3-yl)isoindoline-1,3-dione (7.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-97 was obtained as yellow solid in TFA salt form (6.8 mg, 62%). $^1$H NMR (800 MHz, Methanol-$d_4$) δ 9.31 (s, 1H), 8.41 (d, J=8.4 Hz, 2H), 7.55 (d, J=8.3 Hz, 1H), 7.50 (q, J=8.0 Hz, 1H), 7.14 (d, J=8.4 Hz, 2H), 7.02 (s, 1H), 7.01 (d, J=8.6 Hz, 1H), 6.90 (t, J=8.6 Hz, 1H), 6.86 (d, J=8.5 Hz, 1H), 5.05 (dd, J=13.0, 5.3 Hz, 1H), 4.00 (s, 2H), 3.81 (s, 3H), 3.68 (t, J=5.3 Hz, 2H), 3.64 (d, J=6.4 Hz, 16H), 3.60 (t, J=5.2 Hz, 2H), 3.52-3.44 (m, 10H), 3.38 (t, J=5.3 Hz, 2H), 2.84 (ddd, J=18.6, 14.0, 5.3 Hz, 1H), 2.78-2.60 (m, 2H), 2.18-1.95 (m, 1H). HRMS calcd for $C_{49}H_{58}FN_{10}O_{11}^+$ [M+H$^+$]981.4265, found 981.4250.

Example 221

Synthesis of HC90-102

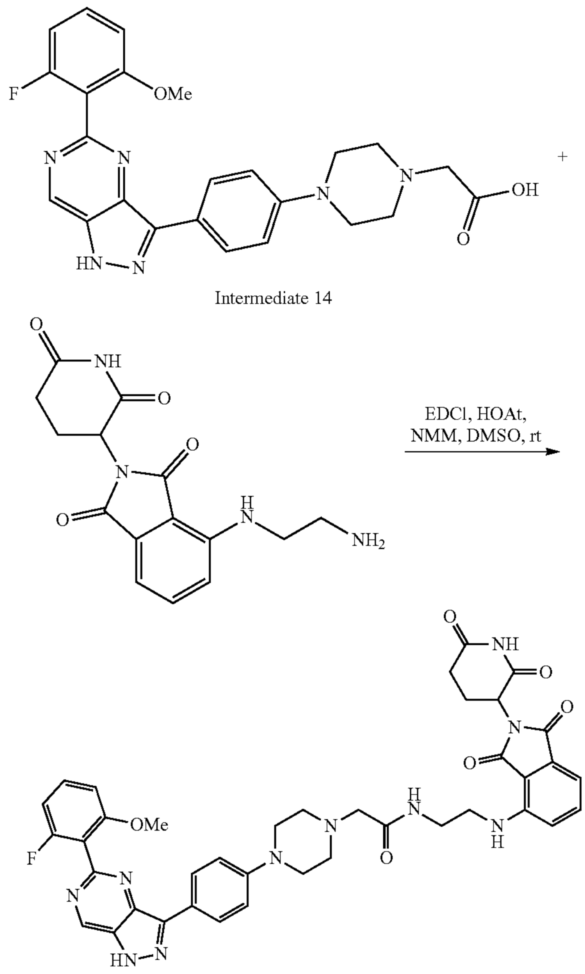

Intermediate 14

HC90-102

HC90-102 was synthesized following the standard procedure for preparing HC90-86 from Intermediate 14 (5.8 mg, 0.01 mmol, 1.0 equiv), 4-((2-aminoethyl)amino)-2-(2,6-dioxopiperidin-3-yl)isoindoline-1,3-dione (4.8 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-102 was obtained as yellow solid in TFA salt form (5.7 mg, 65%). $^1$H NMR (800 MHz, Methanol-$d_4$) δ 9.32 (s, 1H), 8.42 (d, J=8.3 Hz, 2H), 7.61 (t, J=7.8 Hz, 1H), 7.50 (q, J=7.9 Hz, 1H), 7.18 (d, J=8.5 Hz, 1H), 7.15 (d, J=8.4 Hz, 2H), 7.12 (d, J=7.2 Hz, 1H), 7.01 (d, J=8.5 Hz, 1H), 6.90 (t, J=8.6 Hz, 1H), 5.09 (dd, J=12.9, 5.4 Hz, 1H), 3.98 (s, 2H), 3.81 (s, 3H), 3.62-3.58 (m, 2H), 3.57-3.54 (m, 2H), 3.52-3.42 (m, 8H), 2.86 (ddd, J=18.4, 13.8, 5.4 Hz, 1H), 2.78-2.62 (m, 2H), 2.18-2.04 (m, 1H). HRMS calcd for $C_{39}H_{38}FN_{10}O_6^+$ [M+H$^+$] 761.2954, found 761.2939.

Example 222

Synthesis of HC90-103

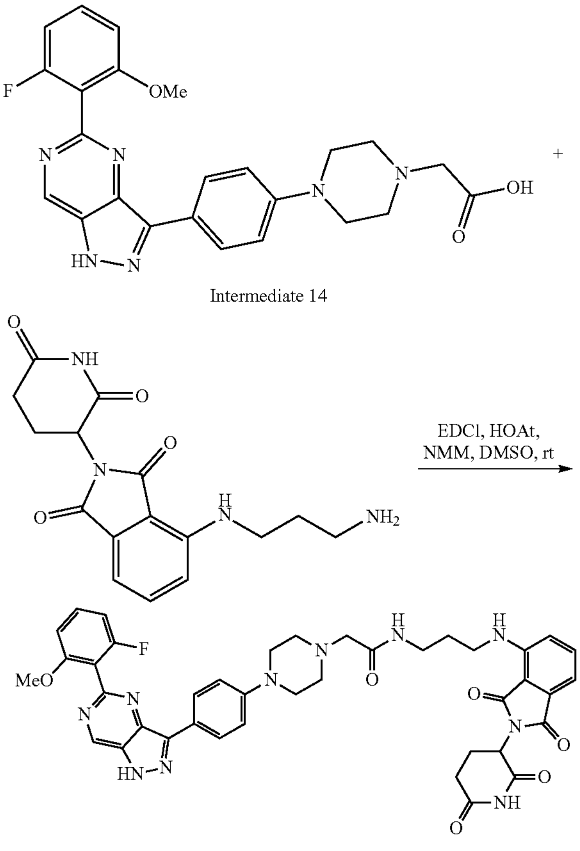

Intermediate 14

HC90-103

HC90-103 was synthesized following the standard procedure for preparing HC90-86 from Intermediate 14 (5.8 mg, 0.01 mmol, 1.0 equiv), 4-((3-aminopropyl)amino)-2-(2,6-dioxopiperidin-3-yl)isoindoline-1,3-dione (4.9 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-103 was obtained as yellow solid in TFA salt form (4.4 mg, 50%). $^1$H NMR (800 MHz, Methanol-$d_4$) δ 9.32 (s, 1H), 8.42 (d, J=8.3 Hz, 2H), 7.60 (t, J=7.8 Hz, 1H), 7.50 (q, J=7.9 Hz, 1H), 7.16 (d, J=8.4 Hz, 2H), 7.10 (d, J=7.9 Hz, 2H), 7.02 (d, J=8.5 Hz, 1H), 6.90 (t, J=8.6 Hz, 1H), 5.09 (dd, J=12.9, 5.5 Hz, 1H), 3.96 (s, 2H), 3.81 (s, 3H), 3.56-3.39 (m, 12H), 2.86 (ddd, J=18.5, 13.9, 5.4 Hz, 1H), 2.79-2.67 (m, 2H), 2.15-2.10 (m, 1H), 1.98-1.89 (m, 2H). HRMS calcd for $C_{40}H_{40}FN_{10}O_6^+$ [M+H$^+$] 775.3111, found 775.3094.

Example 223

Synthesis of HC90-104

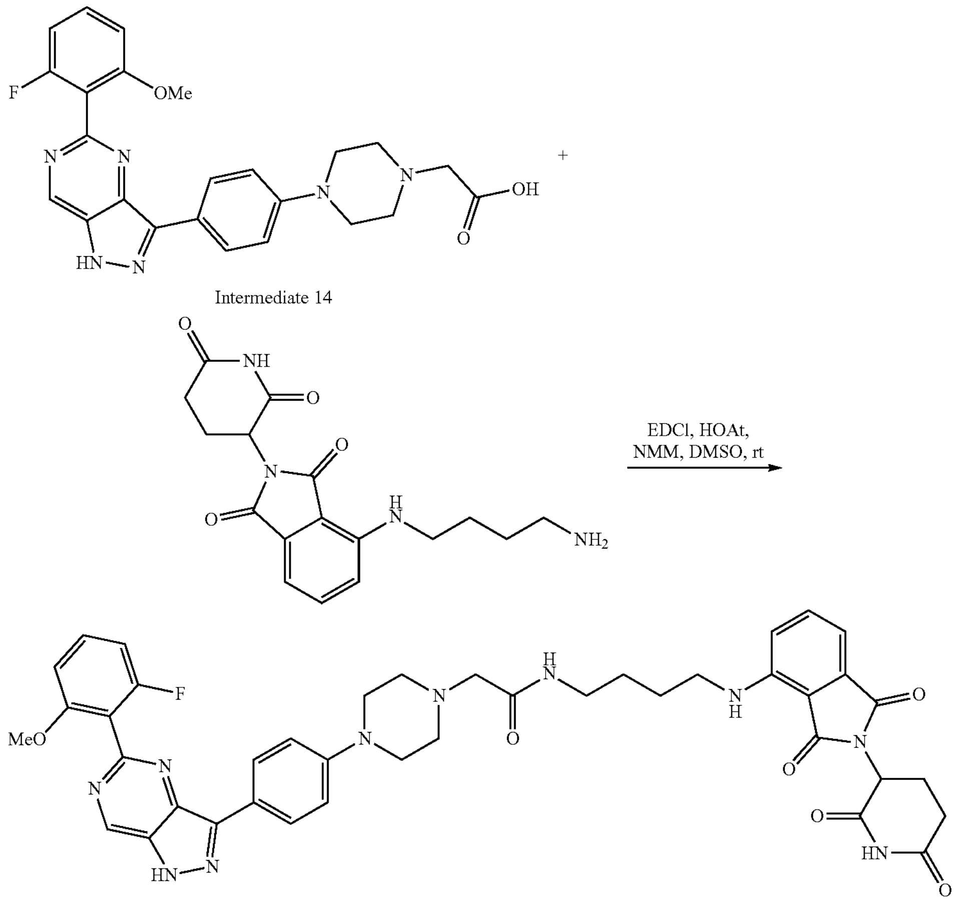

Intermediate 14

HC90-104

HC90-104 was synthesized following the standard procedure for preparing HC90-86 from Intermediate 14 (5.8 mg, 0.01 mmol, 1.0 equiv), 4-((4-aminobutyl)amino)-2-(2,6-dioxopiperidin-3-yl)isoindoline-1,3-dione (5.1 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-104 was obtained as yellow solid in TFA salt form (6.1 mg, 68%). $^1$H NMR (800 MHz, Methanol-$d_4$) δ 9.32 (s, 1H), 8.42 (d, J=8.3 Hz, 2H), 7.58 (t, J=7.8 Hz, 1H), 7.50 (q, J=7.9 Hz, 1H), 7.16 (d, J=8.4 Hz, 2H), 7.12-7.06 (m, 2H), 7.01 (d, J=8.5 Hz, 1H), 6.90 (t, J=8.6 Hz, 1H), 5.07 (dd, J=12.8, 5.4 Hz, 1H), 3.98 (s, 2H), 3.81 (s, 3H), 3.58-3.44 (m, 8H), 3.40 (t, J=6.7 Hz, 2H), 3.36 (t, J=6.7 Hz, 2H), 2.85 (ddd, J=18.3, 13.7, 5.4 Hz, 1H), 2.78-2.68 (m, 2H), 2.14-2.08 (m, 1H), 1.77-1.68 (m, 4H). HRMS calcd for $C_{41}H_{42}FN_{10}O_6^+$ [M+H$^+$] 789.3267, found 789.3251.

Example 224

Synthesis of HC90-105

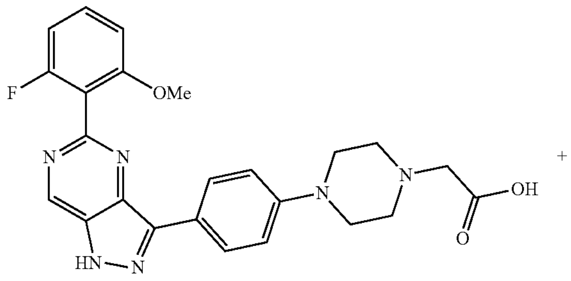

Intermediate 14

-continued

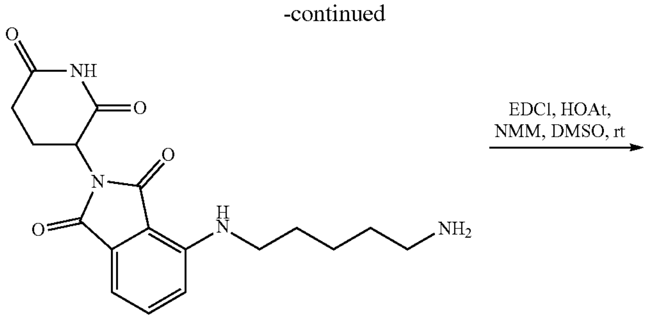

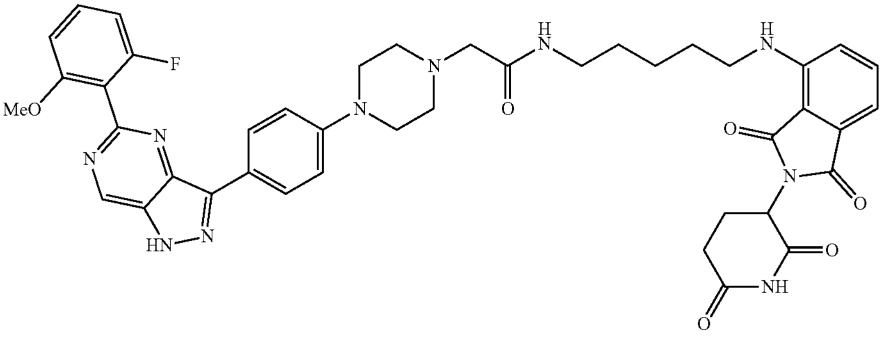

HC90-105

HC90-105 was synthesized following the standard procedure for preparing HC90-86 from Intermediate 14 (5.8 mg, 0.01 mmol, 1.0 equiv), 4-((5-aminopentyl)amino)-2-(2,6-dioxopiperidin-3-yl)isoindoline-1,3-dione (5.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-105 was obtained as yellow solid in TFA salt form (6.9 mg, 75%). $^1$H NMR (800 MHz, Methanol-$d_4$) δ 9.32 (s, 1H), 8.43 (d, J=8.4 Hz, 2H), 7.57 (t, J=7.8 Hz, 1H), 7.50 (q, J=7.9 Hz, 1H), 7.17 (d, J=8.4 Hz, 2H), 7.09-7.05 (m, 2H), 7.01 (d, J=8.5 Hz, 1H), 6.90 (t, J=8.6 Hz, 1H), 5.18-4.97 (m, 1H), 3.98 (q, J=15.3 Hz, 2H), 3.81 (s, 3H), 3.61-3.45 (m, 8H), 3.42-3.32 (m, 4H), 2.79-2.65 (m, 3H), 2.15-2.05 (m, 1H), 1.79-1.70 (m, 2H), 1.67-1.58 (m, 2H), 1.57-1.45 (m, 2H). HRMS calcd for $C_{42}H_{44}FN_{10}O_6^+$ [M+H$^+$] 803.3424, found 803.3411.

Example 225

Synthesis of HC90-106

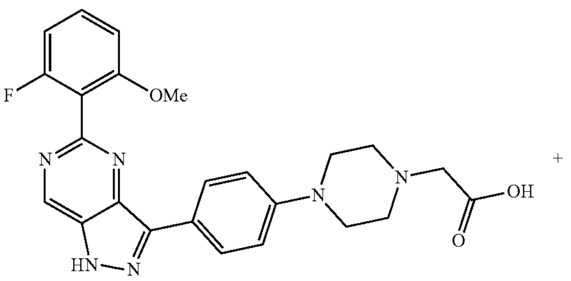

Intermediate 14

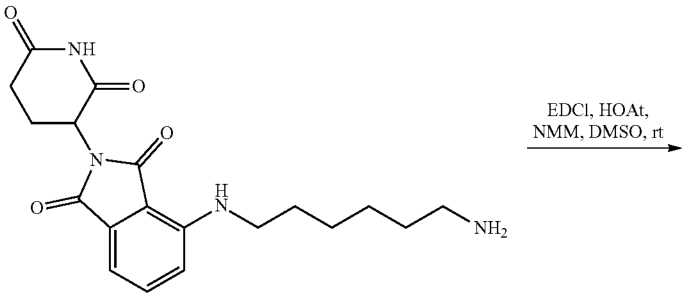

-continued

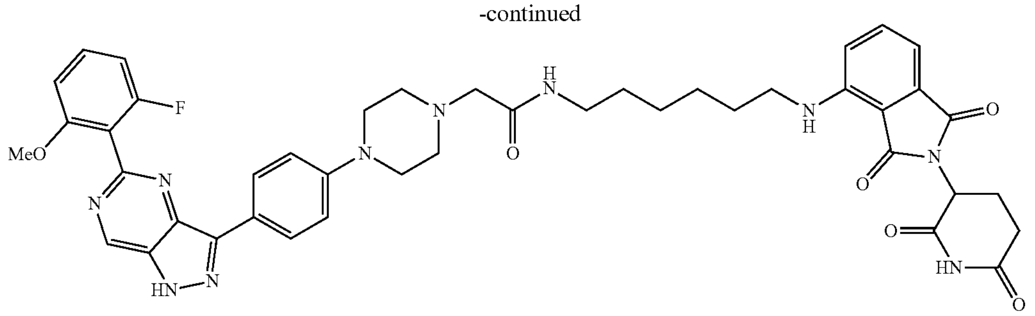

HC90-106

HC90-106 was synthesized following the standard procedure for preparing HC90-86 from Intermediate 14 (5.8 mg, 0.01 mmol, 1.0 equiv), 4-((6-aminohexyl)amino)-2-(2,6-dioxopiperidin-3-yl)isoindoline-1,3-dione (5.4 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-106 was obtained as yellow solid in TFA salt form (6.2 mg, 67%). $^1$H NMR (800 MHz, Methanol-$d_4$) δ 9.32 (s, 1H), 8.42 (d, J=8.3 Hz, 2H), 7.57 (t, J=7.8 Hz, 1H), 7.50 (q, J=7.9 Hz, 1H), 7.16 (d, J=8.4 Hz, 2H), 7.09-7.04 (m, 2H), 7.01 (d, J=8.5 Hz, 1H), 6.90 (t, J=8.6 Hz, 1H), 5.07 (dd, J=12.9, 5.3 Hz, 1H), 3.98 (s, 2H), 3.81 (s, 3H), 3.56-3.45 (m, 8H), 3.36 (t, J=7.1 Hz, 2H), 3.30 (t, J=7.1 Hz, 2H), 2.86 (ddd, J=18.4, 13.8, 5.4 Hz, 1H), 2.78-2.69 (m, 2H), 2.17-2.09 (m, 1H), 1.75-1.67 (m, 2H), 1.64-1.57 (m, 2H), 1.54-1.43 (m, 4H). HRMS calcd for $C_{43}H_{46}FN_{10}O6^+$ [M+H$^+$] 817.3580, found 817.3567.

Example 226

Synthesis of HC90-107

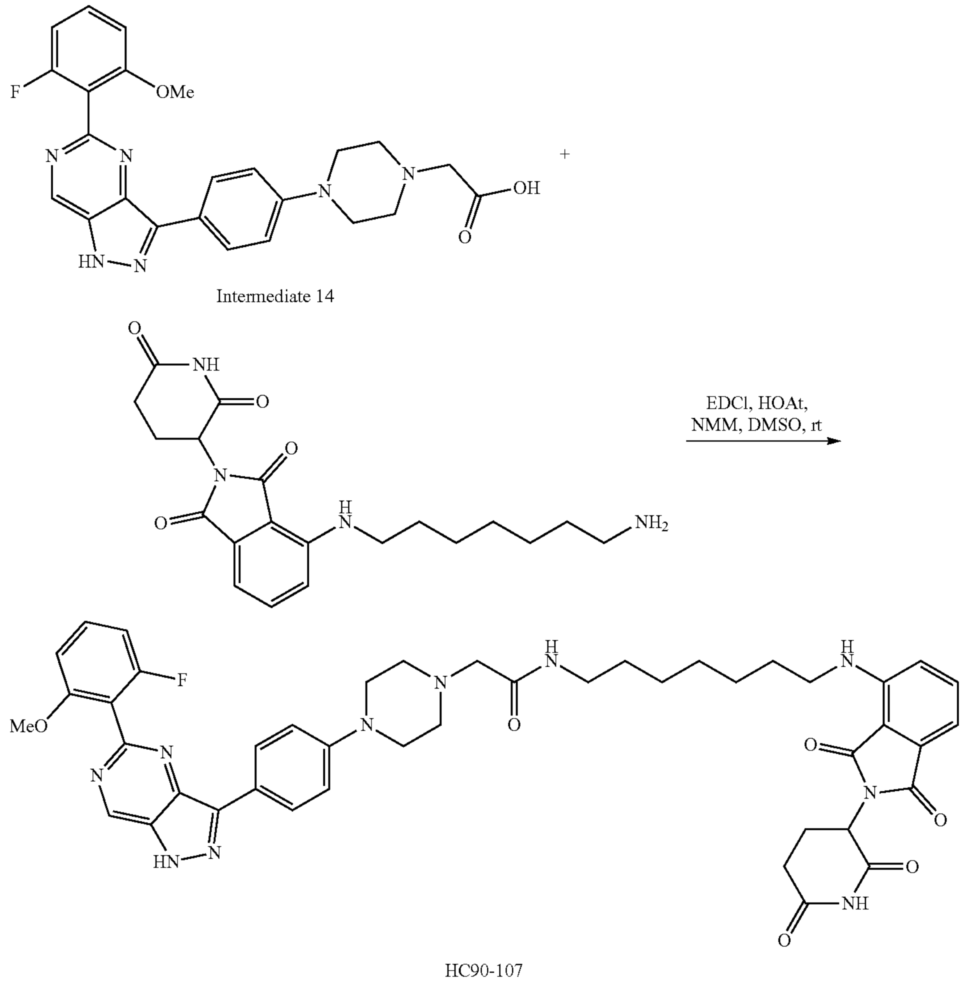

HC90-107

HC90-107 was synthesized following the standard procedure for preparing HC90-86 from Intermediate 14 (5.8 mg, 0.01 mmol, 1.0 equiv), 4-((7-aminoheptyl)amino)-2-(2,6-dioxopiperidin-3-yl)isoindoline-1,3-dione (5.5 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-107 was obtained as yellow solid in TFA salt form (6.6 mg, 70%). $^1$H NMR (800 MHz, Methanol-$d_4$) δ 9.32 (s, 1H), 8.42 (d, J=8.3 Hz, 2H), 7.56 (t, J=7.8 Hz, 1H), 7.50 (q, J=7.8 Hz, 1H), 7.16 (d, J=8.4 Hz, 2H), 7.08-7.03 (m, 2H), 7.01 (d, J=8.5 Hz, 1H), 6.90 (t, J=8.6 Hz, 1H), 5.05 (dd, J=12.2, 5.1 Hz, 1H), 3.98 (s, 2H), 3.81 (s, 3H), 3.63-3.43 (m, 8H), 3.35 (t, J=7.3 Hz, 2H), 3.29 (t, J=7.1 Hz, 2H), 2.83 (ddd, J=18.8, 13.9, 5.3 Hz, 1H), 2.77-2.67 (m, 2H), 2.18-2.05 (m, 1H), 1.75-1.66 (m, 2H), 1.61-1.55 (m, 2H), 1.52-1.37 (m, 6H). HRMS calcd for $C_{44}H_{48}FN_{10}O_6^+$ [M+H$^+$] 831.3737, found 831.3725.

Example 227

Synthesis of HC90-108

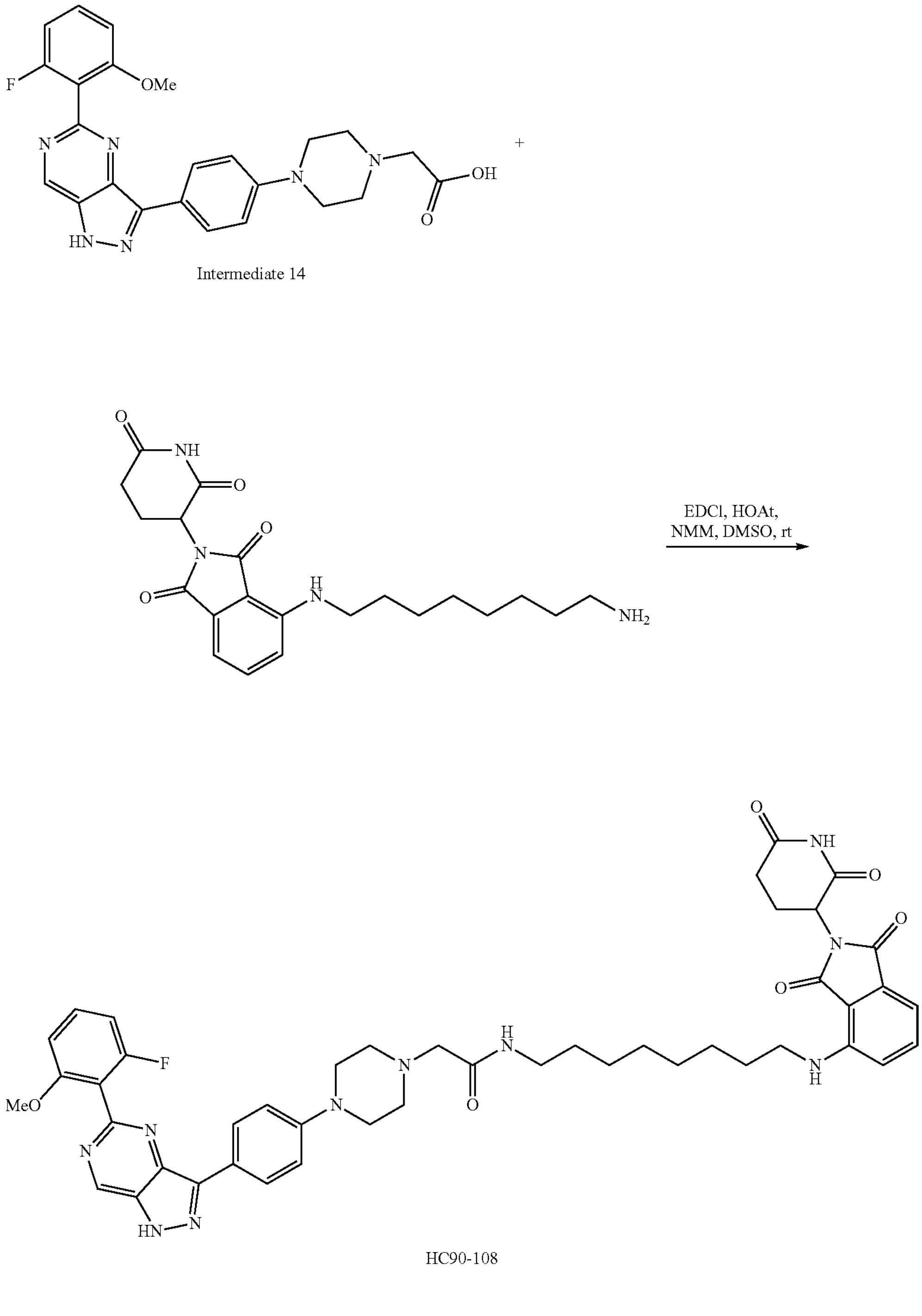

Intermediate 14

HC90-108

HC90-108 was synthesized following the standard procedure for preparing HC90-86 from Intermediate 14 (5.8 mg, 0.01 mmol, 1.0 equiv), 4-((8-aminooctyl)amino)-2-(2,6-dioxopiperidin-3-yl)isoindoline-1,3-dione (5.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-108 was obtained as yellow solid in TFA salt form (5.9 mg, 62%). $^1$H NMR (800 MHz, Methanol-$d_4$) δ 9.31 (s, 1H), 8.42 (d, J=8.3 Hz, 2H), 7.55 (t, J=7.8 Hz, 1H), 7.50 (q, J=7.9 Hz, 1H), 7.16 (d, J=8.4 Hz, 2H), 7.04 (d, J=7.8 Hz, 2H), 7.01 (d, J=8.5 Hz, 1H), 6.90 (t, J=8.6 Hz, 1H), 5.07 (dd, J=12.9, 5.3 Hz, 1H), 3.97 (s, 2H), 3.81 (s, 3H), 3.60-3.42 (m, 8H), 3.36-3.33 (m, 2H), 3.29 (t, J=7.1 Hz, 2H), 2.86 (ddd, J=18.5, 13.8, 5.4 Hz, 1H), 2.80-2.68 (m, 2H), 2.16-2.06 (m, 1H), 1.69 (p, J=7.2 Hz, 2H), 1.57 (t, J=7.0 Hz, 2H), 1.47 (t, J=7.5 Hz, 2H), 1.44-1.36 (m, 6H). HRMS calcd for $C_{45}H_{50}FN_{10}O_6^+$ [M+H$^+$] 845.3893, found 845.3881.

Example 228

Synthesis of HC90-109

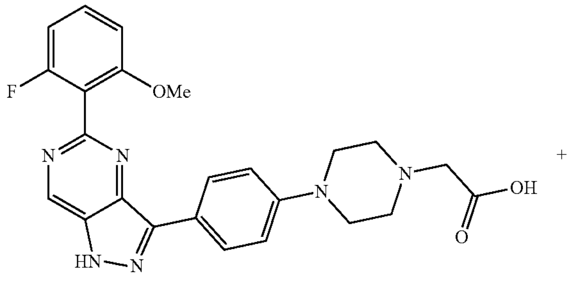

Intermediate 14

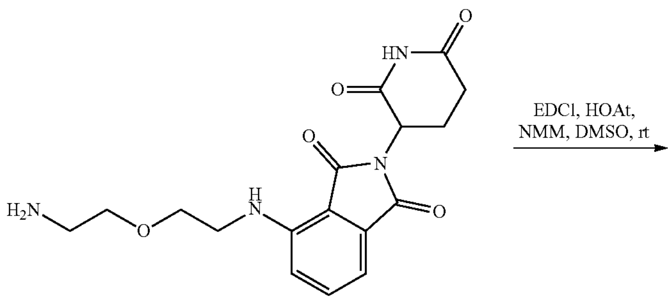

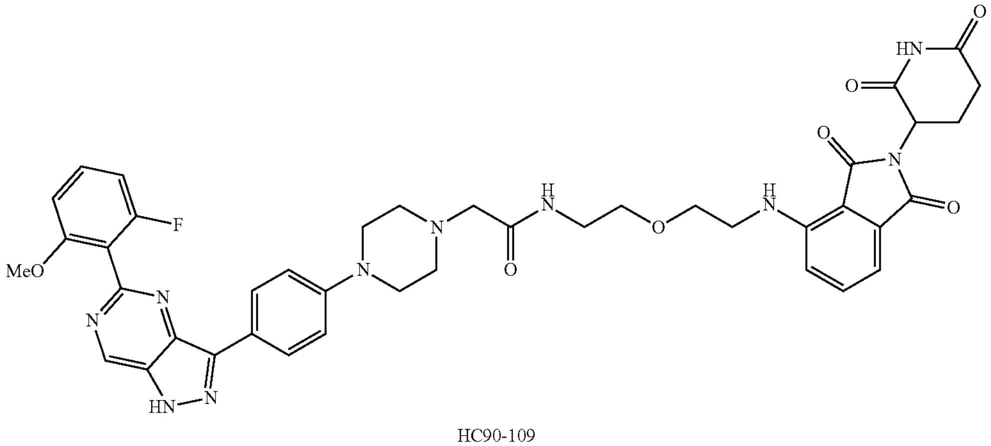

HC90-109

HC90-109 was synthesized following the standard procedure for preparing HC90-86 from Intermediate 14 (5.8 mg, 0.01 mmol, 1.0 equiv), 4-((2-(2-aminoethoxy)ethyl) amino)-2-(2,6-dioxopiperidin-3-yl)isoindoline-1,3-dione (5.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-109 was obtained as yellow solid in TFA salt form (5.5 mg, 60%). $^1$H NMR (800 MHz, Methanol-d$_4$) δ 9.32 (s, 1H), 8.41 (d, J=8.3 Hz, 2H), 7.59 (t, J=7.8 Hz, 1H), 7.50 (q, J=7.9 Hz, 1H), 7.14 (d, J=8.6 Hz, 2H), 7.12 (d, J=8.7 Hz, 1H), 7.09 (d, J=7.1 Hz, 1H), 7.01 (d, J=8.5 Hz, 1H), 6.90 (t, J=8.6 Hz, 1H), 5.05 (dd, J=12.5, 5.5 Hz, 1H), 3.96 (s, 2H), 3.81 (s, 3H), 3.75 (t, J=5.0 Hz, 2H), 3.66 (t, J=5.2 Hz, 2H), 3.58-3.40 (m, 12H), 2.78 (ddd, J=18.7, 14.8, 6.0 Hz, 1H), 2.73-2.66 (m, 2H), 2.12-2.07 (m, 1H). HRMS calcd for $C_{41}H_{42}FN_{10}O_7^+$ [M+H$^+$] 805.3216, found 805.3201.

Example 229

Synthesis of HC90-110

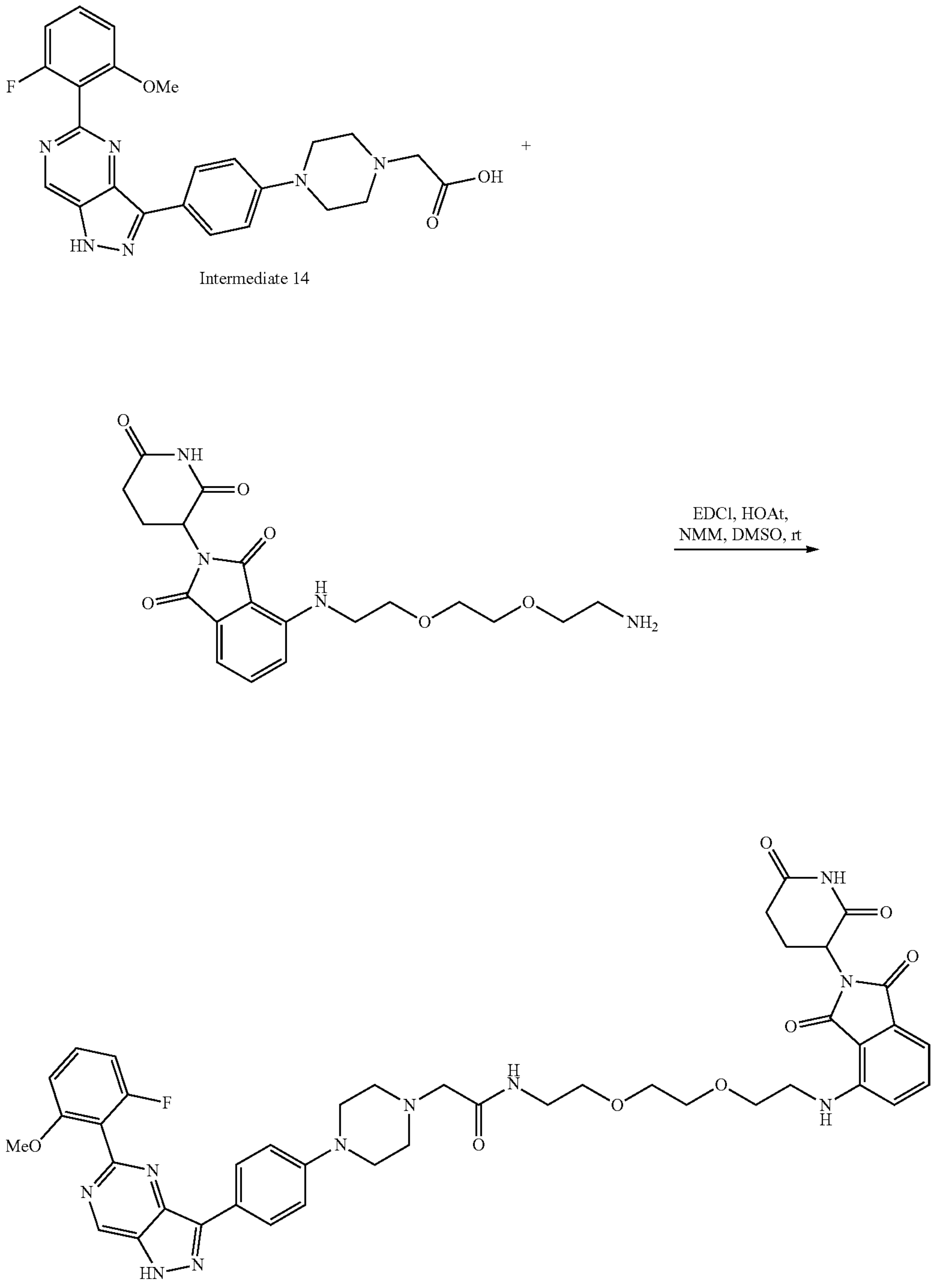

Intermediate 14

HC90-110

HC90-110 was synthesized following the standard procedure for preparing HC90-86 from Intermediate 14 (5.8 mg, 0.01 mmol, 1.0 equiv), 4-((2-(2-(2-aminoethoxy)ethoxy)ethyl)amino)-2-(2,6-dioxopiperidin-3-yl)isoindoline-1,3-dione (5.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-110 was obtained as yellow solid in TFA salt form (6.8 mg, 71%). $^1$H NMR (800 MHz, Methanol-$d_4$) δ 9.32 (s, 1H), 8.40 (d, J=8.3 Hz, 2H), 7.54 (t, J=7.8 Hz, 1H), 7.50 (q, J=7.9 Hz, 1H), 7.13 (d, J=8.4 Hz, 2H), 7.08 (d, J=8.5 Hz, 1H), 7.05 (d, J=7.2 Hz, 1H), 7.01 (d, J=8.5 Hz, 1H), 6.90 (t, J=8.6 Hz, 1H), 5.07 (dd, J=12.9, 5.4 Hz, 1H), 3.95 (s, 2H), 3.81 (s, 3H), 3.75 (t, J=5.1 Hz, 2H), 3.71-3.67 (m, 4H), 3.63 (t, J=5.3 Hz, 2H), 3.54-3.42 (m, 12H), 2.85 (ddd, J=18.7, 13.9, 5.4 Hz, 1H), 2.78-2.68 (m, 2H), 2.18-2.10 (m, 1H). HRMS calcd for $C_{43}H_{46}FN_{10}O_8^+$ [M+H$^+$] 849.3479, found 849.3465.

Example 230

Synthesis of HC90-111

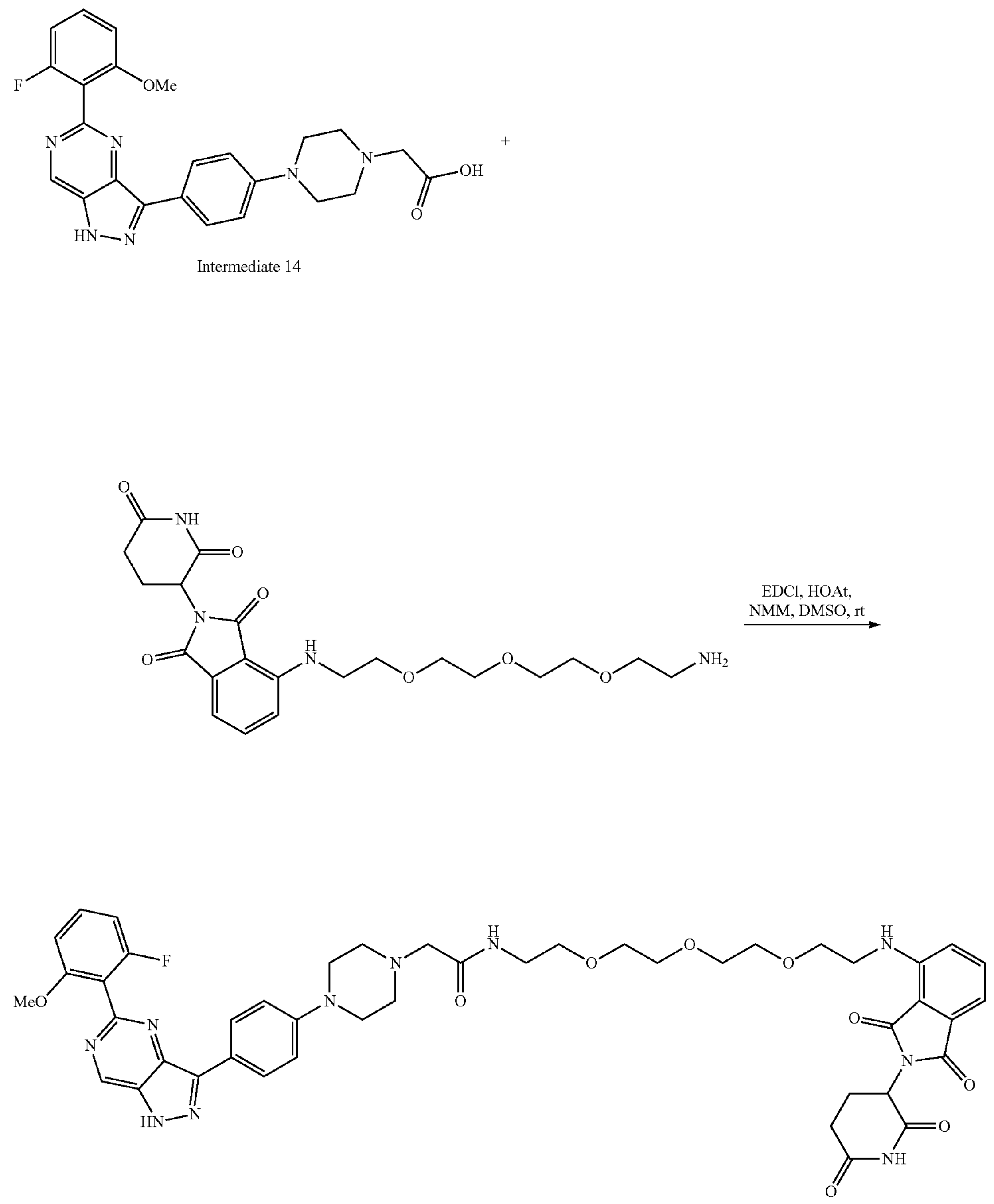

Intermediate 14

HC90-111

HC90-111 was synthesized following the standard procedure for preparing HC90-86 from Intermediate 14 (5.8 mg, 0.01 mmol, 1.0 equiv), 4-((2-(2-(2-(2-aminoethoxy)ethoxy)ethoxy)ethyl)amino)-2-(2,6-dioxopiperidin-3-yl)isoindoline-1,3-dione (6.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-111 was obtained as yellow solid in TFA salt form (8.6 mg, 85%). $^1$H NMR (800 MHz, Methanol-d$_4$) δ 9.32 (s, 1H), 8.39 (d, J=8.3 Hz, 2H), 7.52-7.47 (m, 2H), 7.11 (d, J=8.4 Hz, 2H), 7.06-7.02 (m, 2H), 7.01 (d, J=8.6 Hz, 1H), 6.90 (t, J=8.6 Hz, 1H), 5.06 (dd, J=12.7, 5.4 Hz, 1H), 3.99 (s, 2H), 3.81 (s, 3H), 3.72 (t, J=5.1 Hz, 2H), 3.68 (d, J=7.9 Hz, 6H), 3.65-3.63 (m, 2H), 3.59 (t, J=5.2 Hz, 2H), 3.53-3.41 (m, 12H), 2.86 (ddd, J=18.1, 13.7, 5.3 Hz, 1H), 2.78-2.68 (m, 2H), 2.15-2.09 (m, 1H). HRMS calcd for $C_{45}H_{50}FN_{10}O_9^+$ [M+H$^+$] 893.3741, found 893.3724.

Example 231

Synthesis of HC90-112

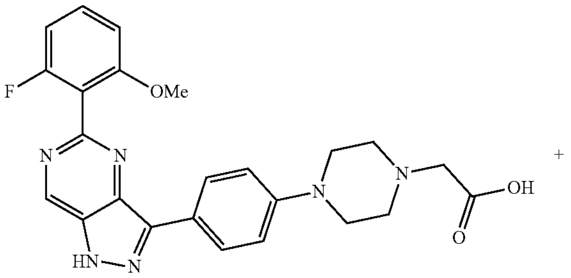

Intermediate 14

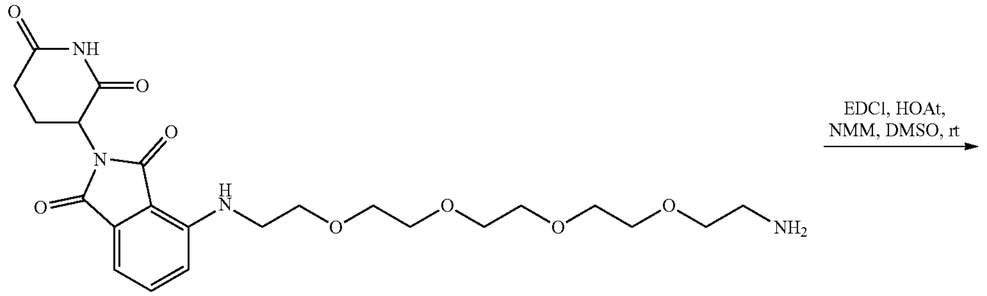

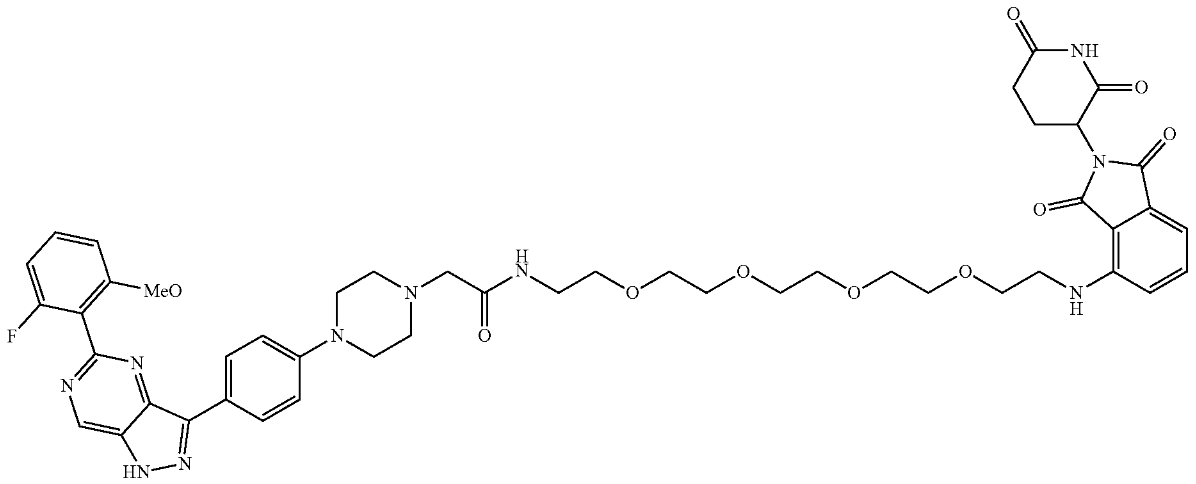

HC90-112

HC90-112 was synthesized following the standard procedure for preparing HC90-86 from Intermediate 14 (5.8 mg, 0.01 mmol, 1.0 equiv), 4-((14-amino-3,6,9,12-tetraoxatetradecyl)amino)-2-(2,6-dioxopiperidin-3-yl)isoindoline-1,3-dione (6.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-112 was obtained as yellow solid in TFA salt form (4.8 mg, 46%). $^1$H NMR (800 MHz, Methanol-$d_4$) δ 9.32 (s, 1H), 8.38 (d, J=8.3 Hz, 2H), 7.55-7.46 (m, 2H), 7.11 (d, J=8.4 Hz, 2H), 7.05-7.00 (m, 3H), 6.90 (t, J=8.6 Hz, 1H), 5.06 (dd, J=12.8, 5.3 Hz, 1H), 4.01 (s, 2H), 3.81 (s, 3H), 3.72-3.62 (m, 14H), 3.60 (t, J=5.2 Hz, 2H), 3.51-3.44 (m, 12H), 2.85 (ddd, J=18.1, 13.7, 5.3 Hz, 1H), 2.80-2.66 (m, 2H), 2.17-2.07 (m, 1H). HRMS calcd for $C_{47}H_{54}FN_{10}O_{10}^+$ [M+H$^+$] 937.4003, found 937.3991.

Example 232

Synthesis of HC90-113

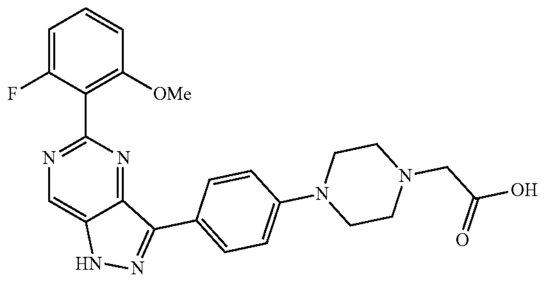

Intermediate 14

+

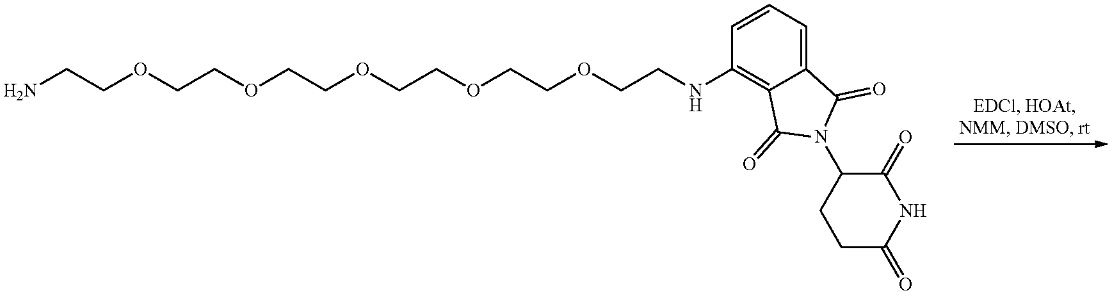

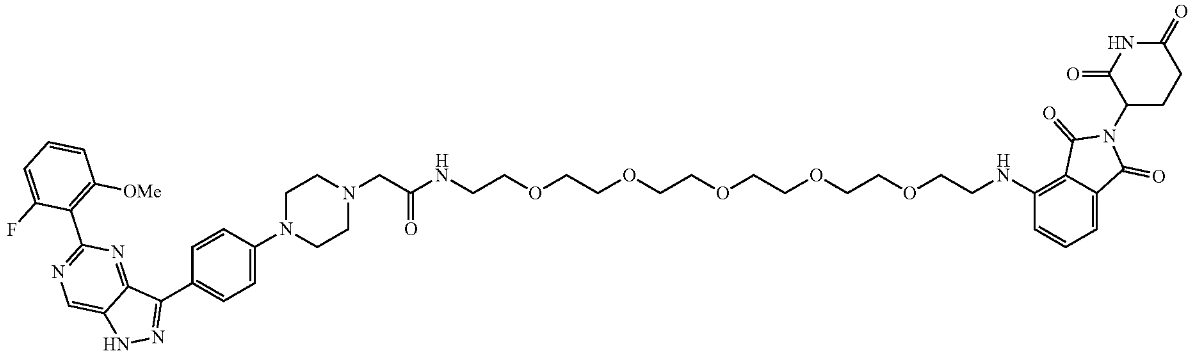

HC90-113

HC90-113 was synthesized following the standard procedure for preparing HC90-86 from Intermediate 14 (5.8 mg, 0.01 mmol, 1.0 equiv), 4-((17-amino-3,6,9,12,15-pentaoxaheptadecyl)amino)-2-(2,6-dioxopiperidin-3-yl)isoindoline-1,3-dione (7.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-113 was obtained as yellow solid in TFA salt form (5.7 mg, 52%). $^1$H NMR (800 MHz, Methanol-$d_4$) δ 9.31 (s, 1H), 8.38 (d, J=8.3 Hz, 2H), 7.53-7.45 (m, 2H), 7.11 (d, J=8.4 Hz, 2H), 7.06-6.99 (m, 3H), 6.90 (t, J=8.6 Hz, 1H), 5.06 (dd, J=12.7, 5.4 Hz, 1H), 4.03 (s, 2H), 3.81 (s, 3H), 3.69 (t, J=5.1 Hz, 2H), 3.65 (d, J=7.9 Hz, 16H), 3.61 (t, J=5.2 Hz, 2H), 3.51-3.43 (m, 12H), 2.85 (ddd, J=18.1, 13.7, 5.3 Hz, 1H), 2.79-2.64 (m, 2H), 2.16-2.08 (m, 1H). HRMS calcd for $C_{49}H_{58}FN_{10}O_{11}^+$ [M+H$^+$]981.4265, found 981.4251.

Example 233

Synthesis of HC90-117

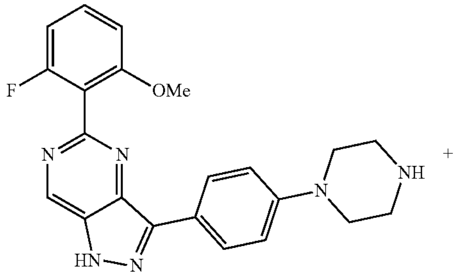

Intermediate 13

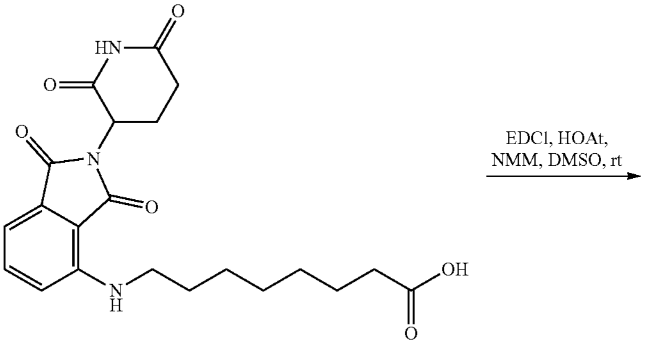

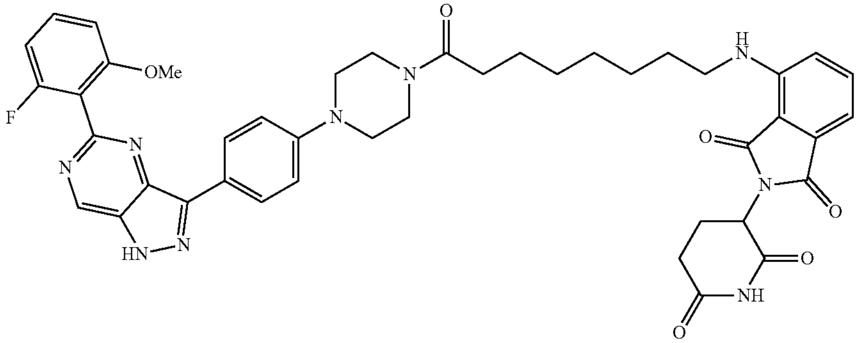

HC90-117

HC90-117 was synthesized following the standard procedure for preparing HC90-33 from Intermediate 13 (6.5 mg, 0.0125 mmol, 1.0 equiv), 8-((2-(2,6-dioxopiperidin-3-yl)-1,3-dioxoisoindolin-4-yl)amino)octanoic acid (6.6 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-117 was obtained as yellow solid in TFA salt form (4.2 mg, 37%). $^1$H NMR (800 MHz, Acetone-$d_6$) δ 9.40 (s, 1H), 8.46 (d, J=8.4 Hz, 2H), 7.60 (t, J=7.8 Hz, 1H), 7.50 (q, J=8.1 Hz, 1H), 7.12 (t, J=8.9 Hz, 3H), 7.07-7.00 (m, 2H), 6.91 (t, J=8.7 Hz, 1H), 5.08 (dd, J=12.8, 5.6 Hz, 1H), 3.79 (s, 3H), 3.76-3.64 (m, 4H), 3.40 (t, J=7.1 Hz, 2H), 3.32 (s, 2H), 3.26 (s, 2H), 2.88-2.76 (m, 3H), 2.43 (t, J=7.5 Hz, 2H), 2.29-2.20 (m, 1H), 1.73 (t, J=7.3 Hz, 2H), 1.65 (t, J=7.2 Hz, 2H), 1.54-1.37 (m, 6H). HRMS calcd for $C_{43}H_{45}FN_9O_6^+$ [M+H$^+$] 802.3471, found 802.3456.

Example 234

Synthesis of HC90-119

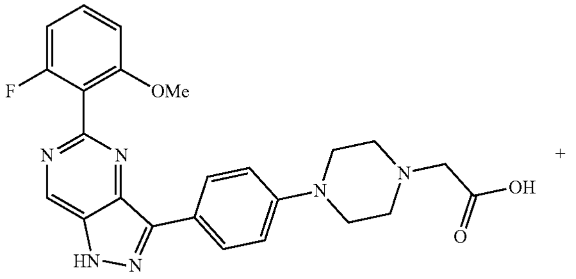

Intermediate 14

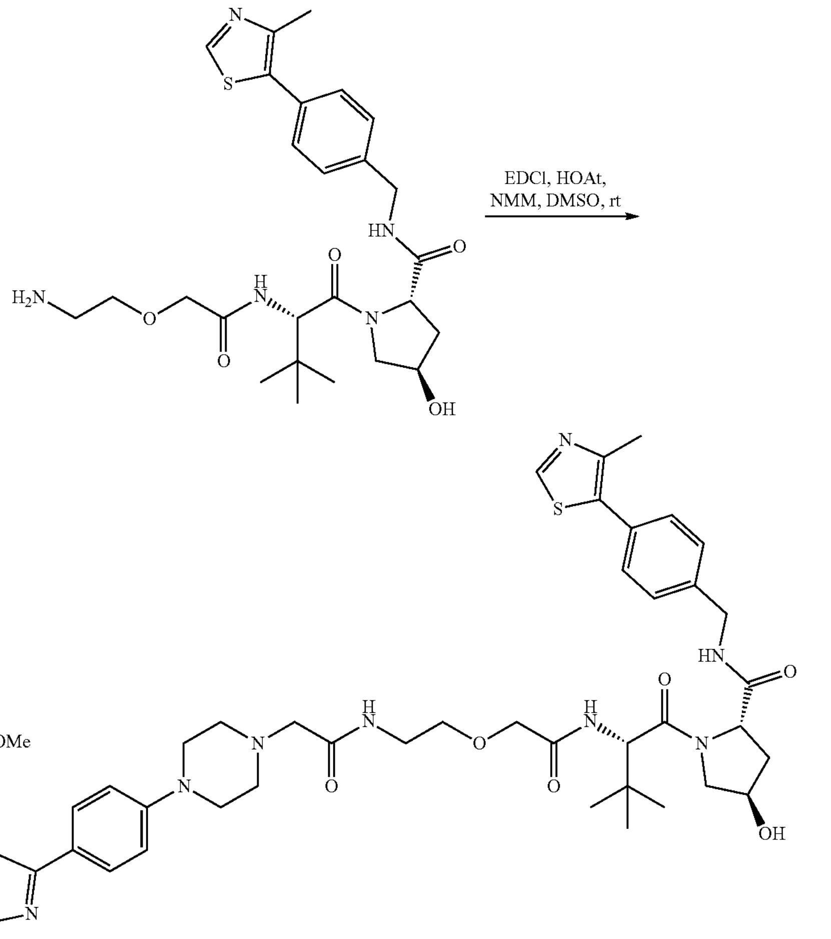

HC90-119

HC90-119 was synthesized following the standard procedure for preparing HC90-86 from Intermediate 14 (5.8 mg, 0.01 mmol, 1.0 equiv), (2S,4R)-1-((S)-2-(2-(2-aminoethoxy)acetamido)-3,3-dimethylbutanoyl)-4-hydroxy-N-(4-(4-methylthiazol-5-yl)benzyl)pyrrolidine-2-carboxamide (7.1 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-119 was obtained as yellow solid in TFA salt form (5.8 mg, 53%). $^{1}$H NMR (800 MHz, Methanol-$d_4$) δ 9.31 (s, 1H), 8.85 (s, 1H), 8.41 (d, J=8.2 Hz, 2H), 7.52-7.45 (m, 1H), 7.32 (s, 4H), 7.14 (d, J=8.4 Hz, 2H), 7.01 (d, J=8.5 Hz, 1H), 6.89 (t, J=8.6 Hz, 1H), 4.77 (s, 1H), 4.58 (t, J=8.3 Hz, 1H), 4.52 (t, J=3.6 Hz, 1H), 4.43 (d, J=15.4 Hz, 1H), 4.29 (d, J=15.4 Hz, 1H), 4.15-4.10 (m, 3H), 4.01 (d, J=15.3 Hz, 1H), 3.93 (d, J=11.1 Hz, 1H), 3.85 (dd, J=11.2, 3.8 Hz, 1H), 3.79 (s, 3H), 3.73 (dd, J=10.3, 3.9 Hz, 1H), 3.68-3.55 (m, 10H), 3.48 (dd, J=11.7, 5.6 Hz, 1H), 2.41 (s, 3H), 2.30 (dd, J=12.8, 8.0 Hz, 1H), 2.08 (ddd, J=13.3, 9.0, 4.4 Hz, 1H), 1.10 (s, 9H). HRMS calcd for $C_{50}H_{59}FN_{11}O_7S^+$ [M+H$^+$] 976.4298, found 976.4273.

Example 235

Synthesis of HC90-120 PGP-355 $C_3$

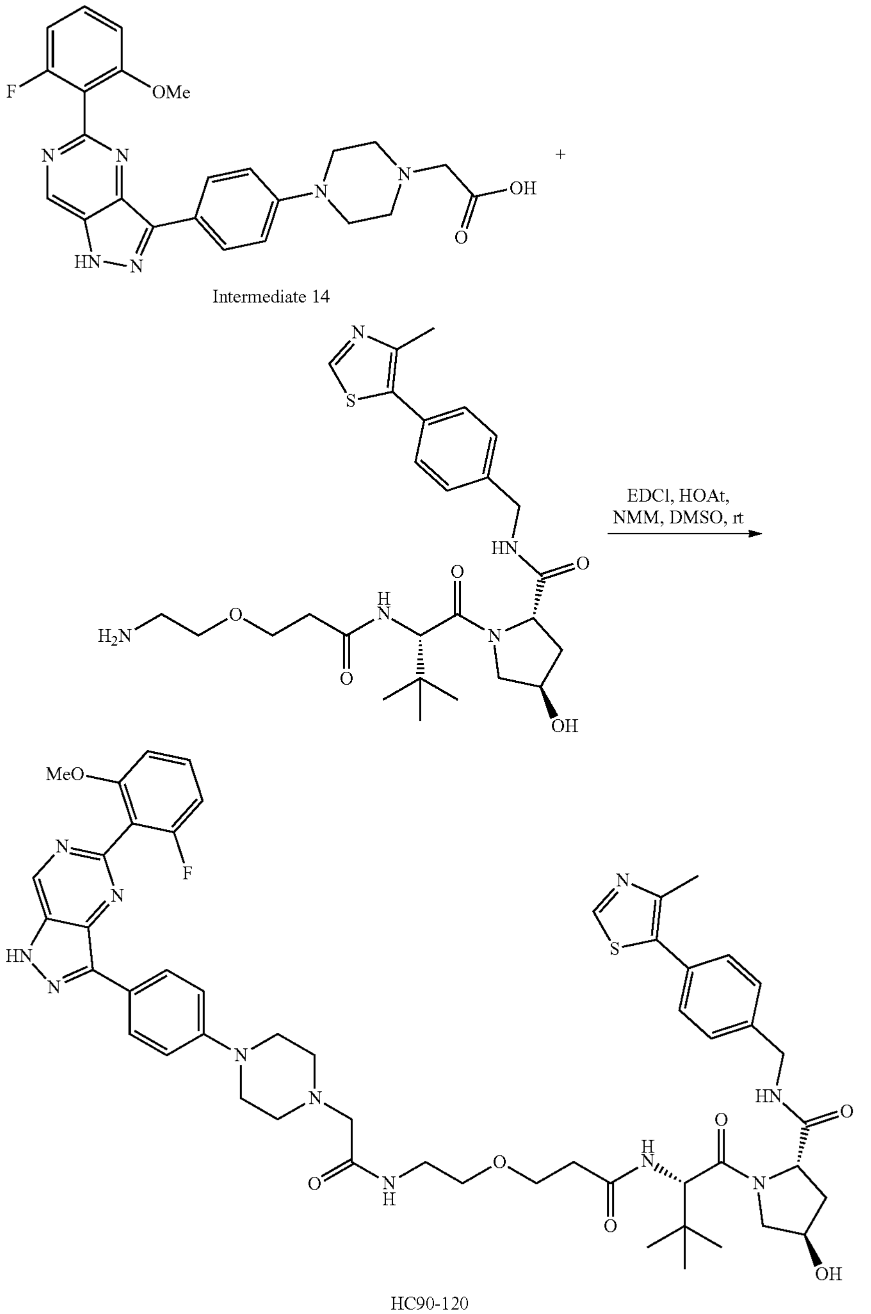

Intermediate 14

HC90-120

HC90-120 was synthesized following the standard procedure for preparing HC90-86 from Intermediate 14 (5.8 mg, 0.01 mmol, 1.0 equiv), (2S,4R)-1-((S)-2-(3-(2-aminoethoxy)propanamido)-3,3-dimethylbutanoyl)-4-hydroxy-N-(4-(4-methylthiazol-5-yl)benzyl)pyrrolidine-2-carboxamide (8.5 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-120 was obtained as yellow solid in TFA salt form (8.2 mg, 74%). $^1$H NMR (800 MHz, Methanol-$d_4$) δ 9.31 (s, 1H), 8.88 (s, 1H), 8.42 (d, J=8.4 Hz, 2H), 7.50 (q, J=7.9 Hz, 1H), 7.42 (d, J=8.7 Hz, 2H), 7.39 (d, J=7.9 Hz, 2H), 7.15 (d, J=8.4 Hz, 2H), 7.01 (d, J=8.5 Hz, 1H), 6.90 (t, J=8.6 Hz, 1H), 4.69 (s, 1H), 4.59 (t, J=8.4 Hz, 1H), 4.52 (s, 1H), 4.46 (d, J=15.4 Hz, 1H), 4.41 (d, J=15.4 Hz, 1H), 4.06 (s, 2H), 3.94 (d, J=11.0 Hz, 1H), 3.84 (dd, J=11.0, 3.8 Hz, 1H), 3.80 (s, 3H), 3.77-3.74 (m, 2H), 3.66-3.46 (m, 12H), 2.61-2.52 (m, 2H), 2.46 (s, 3H), 2.27 (dd, J=13.2, 7.6 Hz, 1H), 2.10 (ddd, J=13.4, 9.2, 4.5 Hz, 1H), 1.07 (s, 9H). HRMS calcd for $C_{51}H_{61}FN_{11}O_7S^+$ [M+H$^+$] 990.4455, found 990.4441.

Example 236

Synthesis of HC90-121

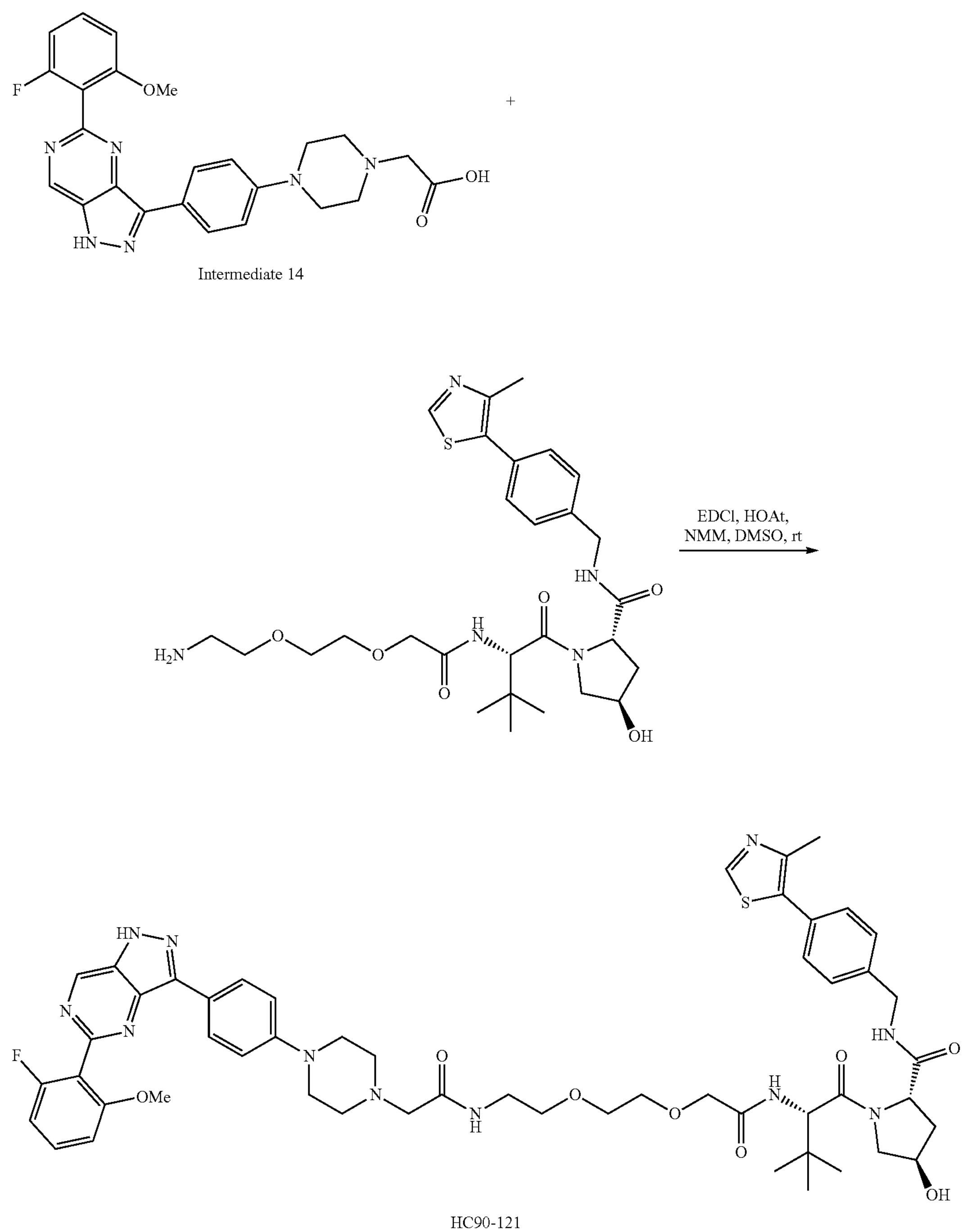 [SMILES: COc1cccc(F)c1-c1ncc2[nH]nc(-c3ccc(N4CCN(CC(=O)O)CC4)cc3)c2n1 ; Cc1ncsc1-c1ccc(CNC(=O)[C@@H]2C[C@@H](O)CN2C(=O)[C@@H](NC(=O)CCCCCCCN)C(C)(C)C)cc1 ; COc1cccc(F)c1-c1ncc2[nH]nc(-c3ccc(N4CCN(CC(=O)NCCCCCCCC(=O)N[C@H](C(=O)N5C[C@H](O)C[C@H]5C(=O)NCc5ccc(-c6scnc6C)cc5)C(C)(C)C)CC4)cc3)c2n1]

Intermediate 14

HC90-121

HC90-121 was synthesized following the standard procedure for preparing HC90-86 from Intermediate 14 (5.8 mg, 0.01 mmol, 1.0 equiv), (2S,4R)-1-((S)-2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide (6.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-121 was obtained as yellow solid in TFA salt form (7.5 mg, 66%). $^1$H NMR (800 MHz, Methanol-$d_4$) δ 9.31 (s, 1H), 8.89 (s, 1H), 8.42 (d, J=8.3 Hz, 2H), 7.50 (q, J=7.9, 7.3 Hz, 1H), 7.41 (d, J=8.0 Hz, 2H), 7.39 (d, J=8.0 Hz, 2H), 7.15 (d, J=8.4 Hz, 2H), 7.01 (d, J=8.5 Hz, 1H), 6.90 (t, J=8.6 Hz, 1H), 4.79 (s, 1H), 4.56 (t, J=8.7 Hz, 1H), 4.52 (t, J=3.5 Hz, 1H), 4.45 (d, J=15.3 Hz, 1H), 4.41 (d, J=15.4 Hz, 1H), 4.15-4.06 (m, 4H), 3.92 (d, J=11.2 Hz, 1H), 3.86 (dd, J=11.1, 3.7 Hz, 1H), 3.81 (s, 3H), 3.76-3.38 (m, 16H), 2.47 (s, 3H), 2.30 (dd, J=13.4, 7.5 Hz, 1H), 2.14-2.07 (m, 1H), 1.07 (s, 9H). HRMS calcd for $C_{52}H_{63}FN_{10}O_8S^+$ [M+H$^+$]1020.4560, found 1020.4549.

Example 237

Synthesis of HC90-122

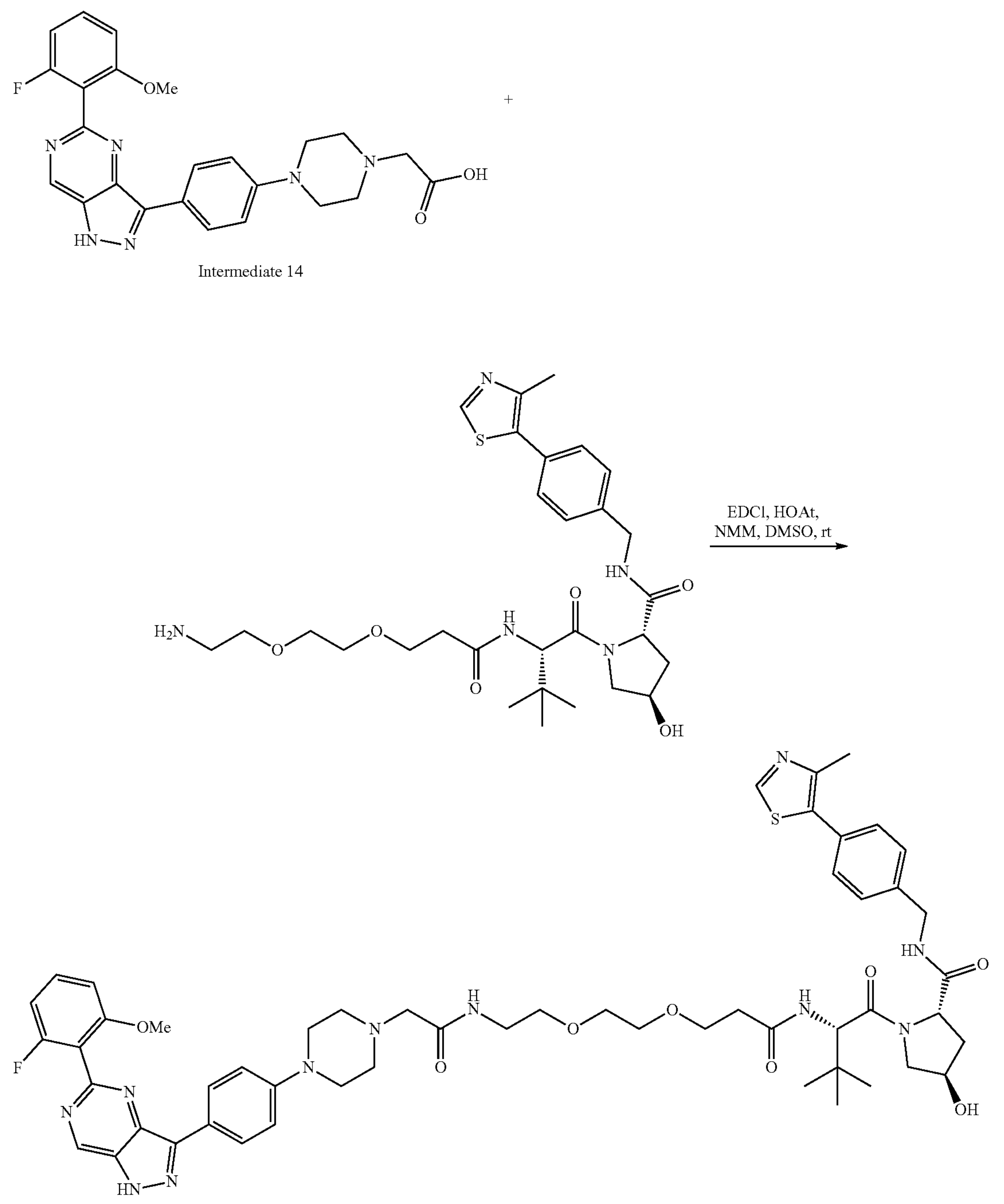

HC90-122

HC90-122 was synthesized following the standard procedure for preparing HC90-86 from Intermediate 14 (5.8 mg, 0.01 mmol, 1.0 equiv), (2S,4R)-1-((S)-2-(3-(2-(2-aminoethoxy)ethoxy)propanamido)-3,3-dimethylbutanoyl)-4-hydroxy-N-(4-(4-methylthiazol-5-yl)benzyl)pyrrolidine-2-carboxamide (9.0 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-122 was obtained as yellow solid in TFA salt form (8.9 mg, 78%). $^1$H NMR (800 MHz, Methanol-$d_4$) δ 9.32 (s, 1H), 8.89 (s, 1H), 8.42 (d, J=8.4 Hz, 2H), 7.50 (q, J=7.9 Hz, 1H), 7.45 (d, J=7.8 Hz, 2H), 7.41 (d, J=7.8 Hz, 2H), 7.16 (d, J=8.4 Hz, 2H), 7.01 (d, J=8.5 Hz, 1H), 6.90 (t, J=8.6 Hz, 1H), 4.68 (s, 1H), 4.57 (t, J=8.4 Hz, 1H), 4.53-4.48 (m, 1H), 4.40 (d, J=15.4 Hz, 1H), 4.06 (s, 1H), 3.92 (d, J=10.9 Hz, 1H), 3.85-3.74 (m, 6H), 3.70-3.46 (m, 18H), 2.63-2.58 (m, 1H), 2.55-2.50 (m, 1H), 2.47 (s, 3H), 2.25 (dd, J=13.1, 7.6 Hz, 1H), 2.09 (ddd, J=13.3, 9.0, 4.5 Hz, 1H), 1.06 (s, 9H). HRMS calcd for $C_{53}H_{65}FN_{11}O_8S^+$ [M+H$^+$] 1034.4717, found 1034.4707.

Example 238

Synthesis of HC90-123

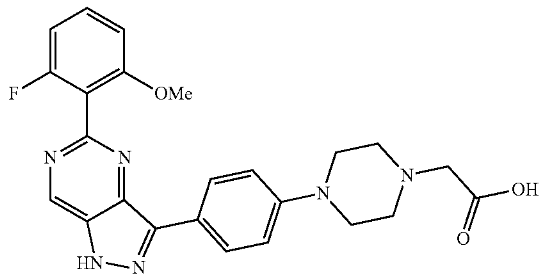

Intermediate 14

+

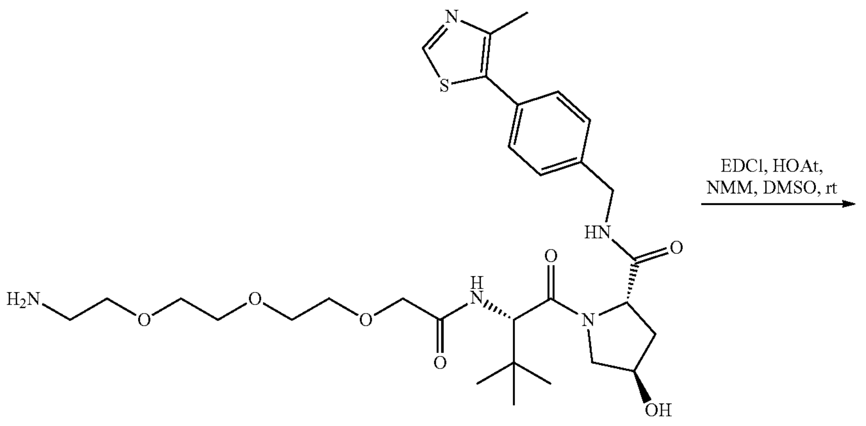

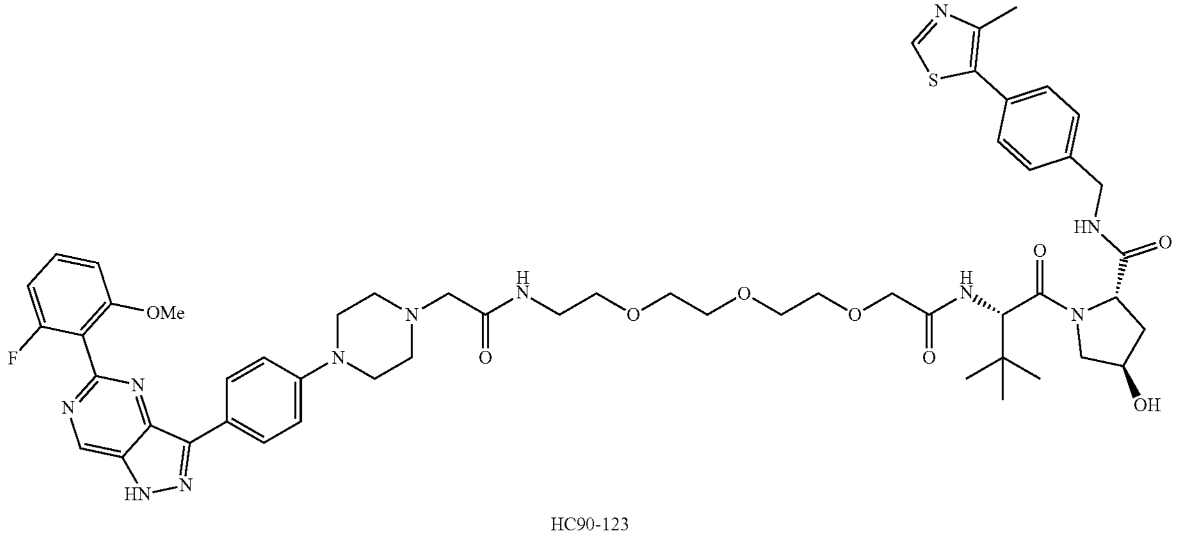

HC90-123

HC90-123 was synthesized following the standard procedure for preparing HC90-86 from Intermediate 14 (5.8 mg, 0.01 mmol, 1.0 equiv), (2S,4R)-1-((S)-14-amino-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (9.3 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-123 was obtained as yellow solid in TFA salt form (7.3 mg, 62%). $^1$H NMR (800 MHz, Methanol-d$_4$) δ 9.31 (s, 1H), 8.90 (s, 1H), 8.42 (d, J=8.4 Hz, 2H), 7.50 (q, J=8.0 Hz, 1H), 7.45 (d, J=7.9 Hz, 2H), 7.41 (d, J=7.9 Hz, 2H), 7.16 (d, J=8.4 Hz, 2H), 7.01 (d, J=8.5 Hz, 1H), 6.90 (t, J=8.6 Hz, 1H), 4.71 (s, 1H), 4.61-4.56 (m, 1H), 4.54-4.48 (m, 2H), 4.40 (d, J=15.4 Hz, 1H), 4.15-4.07 (m, 2H), 4.05 (s, 2H), 3.89 (d, J=10.9 Hz, 1H), 3.83-3.79 (m, 4H), 3.75 (t, J=4.4 Hz, 2H), 3.74-3.71 (m, 2H), 3.70-3.68 (m, 2H), 3.67-3.64 (m, 2H), 3.63-3.44 (m, 12H), 2.48 (s, 3H), 2.26 (dd, J=13.4, 7.6 Hz, 1H), 2.09 (ddd, J=13.4, 9.3, 4.5 Hz, 1H), 1.06 (s, 9H). HRMS calcd for $C_{54}H_{67}FN_{11}O_9S^+$ [M+H$^+$] 1064.4822, found 1064.4808.

Example 239

Synthesis of HC90-124

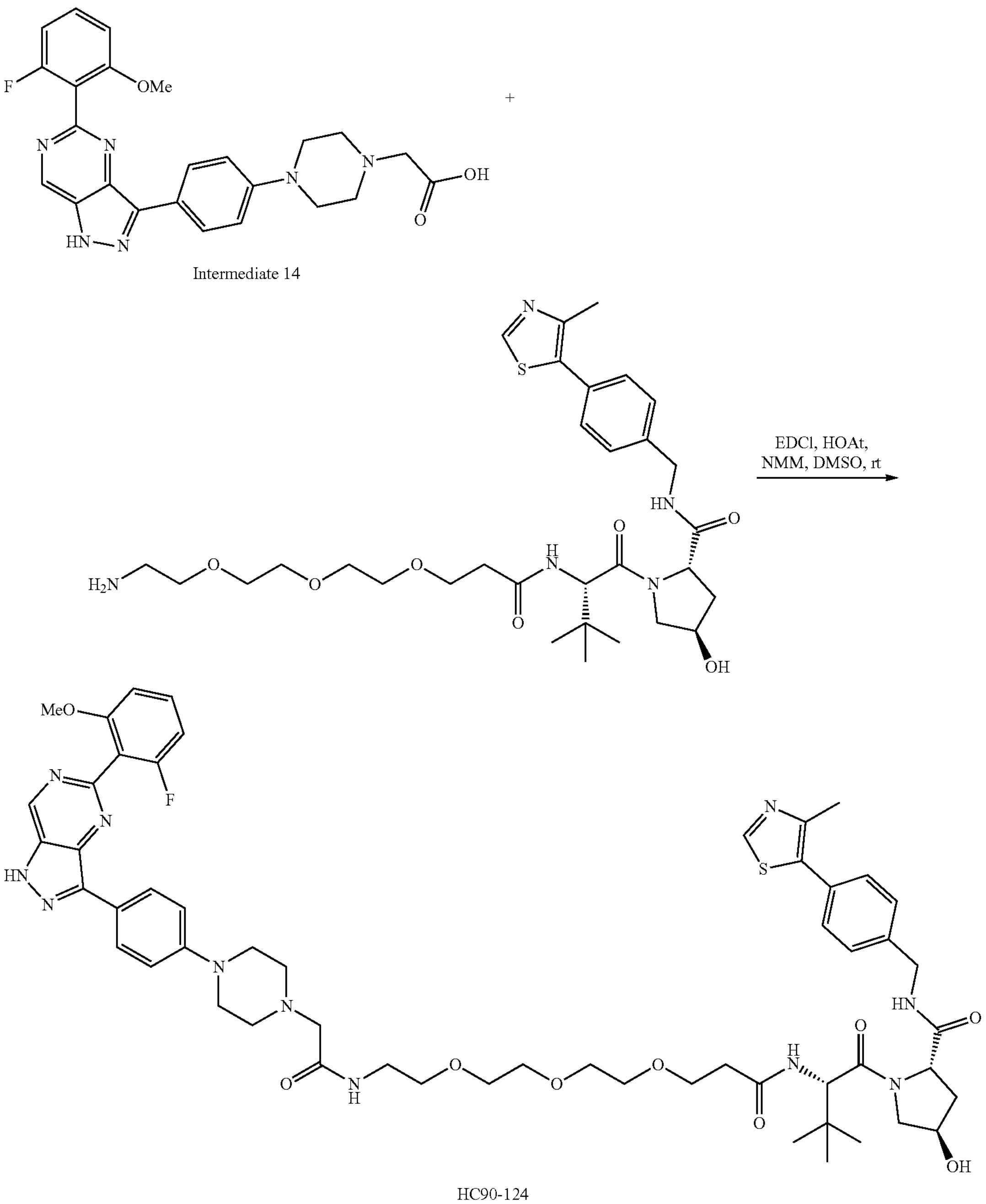

Intermediate 14

HC90-124

HC90-124 was synthesized following the standard procedure for preparing HC90-86 from Intermediate 14 (5.8 mg, 0.01 mmol, 1.0 equiv), (2S,4R)-1-((S)-1-amino-14-(tert-butyl)-12-oxo-3,6,9-trioxa-13-azapentadecan-15-oyl)-4-hydroxy-N-(4-(4-methylthiazol-5-yl)benzyl)pyrrolidine-2-carboxamide (9.5 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-124 was obtained as yellow solid in TFA salt form (7.4 mg, 62%). $^1$H NMR (800 MHz, Methanol-$d_4$) δ 9.31 (s, 1H), 8.90 (s, 1H), 8.42 (d, J=8.3 Hz, 2H), 7.50 (q, J=8.0 Hz, 1H), 7.45 (d, J=7.9 Hz, 2H), 7.41 (d, J=7.8 Hz, 2H), 7.16 (d, J=8.4 Hz, 2H), 7.01 (d, J=8.5 Hz, 1H), 6.90 (t, J=8.6 Hz, 1H), 4.67 (s, 1H), 4.58 (t, J=8.3 Hz, 1H), 4.54-4.48 (m, 2H), 4.38 (d, J=15.4 Hz, 1H), 4.05 (s, 2H), 3.91 (d, J=11.0 Hz, 1H), 3.84-3.73 (m, 6H), 3.70-3.46 (m, 20H), 2.64-2.59 (m, 1H), 2.53-2.45 (m, 4H), 2.27-2.22 (m, 1H), 2.09 (ddd, J=13.3, 9.1, 4.6 Hz, 1H), 1.06 (s, 10H). HRMS calcd for $C_{55}H_{69}FN_{10}O_9S^+$ [M+H$^+$] 1078.4979, found 1078.4966.

Example 240

Synthesis of HC90-125

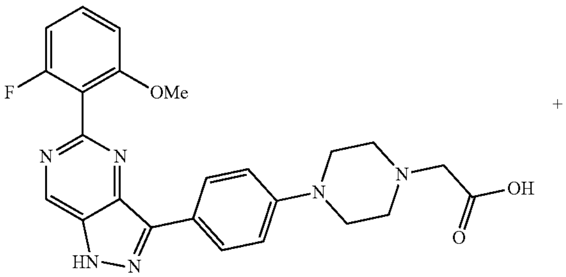

Intermediate 14

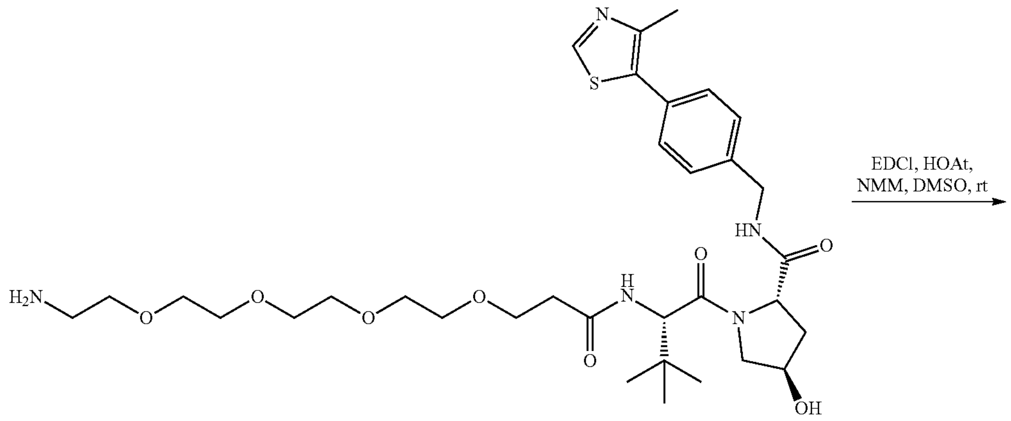

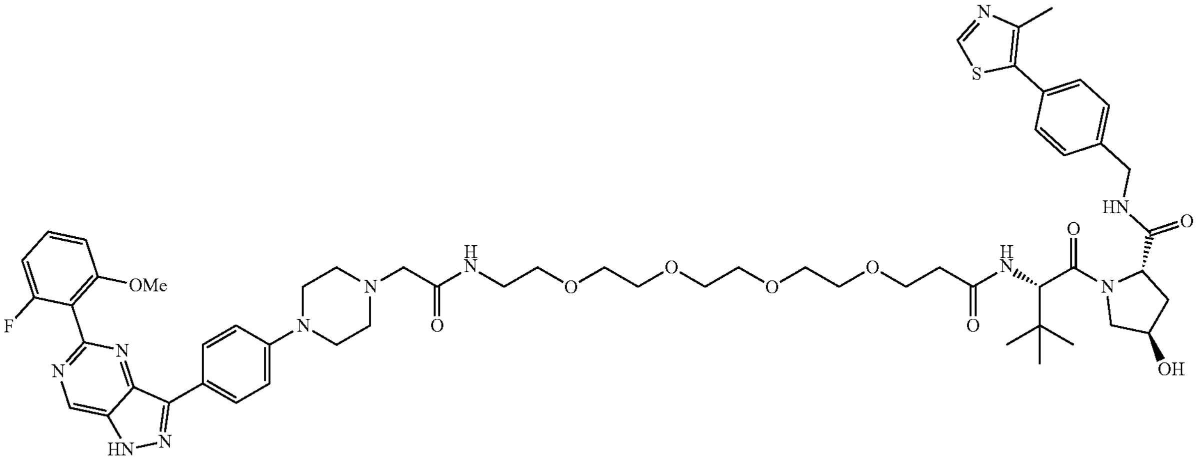

HC90-125

HC90-125 was synthesized following the standard procedure for preparing HC90-86 from Intermediate 14 (5.8 mg, 0.01 mmol, 1.0 equiv), (2S,4R)-1-((S)-1-amino-17-(tert-butyl)-15-oxo-3,6,9,12-tetraoxa-16-azaoctadecan-18-oyl)-4-hydroxy-N-(4-(4-methylthiazol-5-yl)benzyl)pyrrolidine-2-carboxamide (8.0 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-125 was obtained as yellow solid in TFA salt form (9.8 mg, 79%). $^1$H NMR (800 MHz, Methanol-$d_4$) δ 9.31 (s, 1H), 8.90 (s, 1H), 8.42 (d, J=8.4 Hz, 2H), 7.50 (q, J=8.0 Hz, 1H), 7.46 (d, J=7.8 Hz, 2H), 7.41 (d, J=7.8 Hz, 2H), 7.17 (d, J=8.4 Hz, 2H), 7.01 (d, J=8.5 Hz, 1H), 6.90 (t, J=8.6 Hz, 1H), 4.67 (s, 1H), 4.58 (t, J=8.3 Hz, 1H), 4.54-4.50 (m, 2H), 4.38 (d, J=15.4 Hz, 1H), 4.05 (s, 2H), 3.91 (d, J=11.0 Hz, 1H), 3.83-3.78 (m, 4H), 3.74 (ddd, J=16.0, 8.7, 4.6 Hz, 2H), 3.69-3.56 (m, 22H), 3.49 (t, J=5.2 Hz, 2H), 2.64-2.56 (m, 1H), 2.51-2.46 (m, 4H), 2.24 (dd, J=13.3, 7.6 Hz, 1H), 2.09 (ddd, J=13.3, 9.0, 4.5 Hz, 1H), 1.05 (s, 9H). HRMS calcd for $C_{57}H_{73}FN_{11}O_{10}S^+$ [M+H$^+$] 1122.5241, found 1122.5230.

Example 241

Synthesis of HC90-126

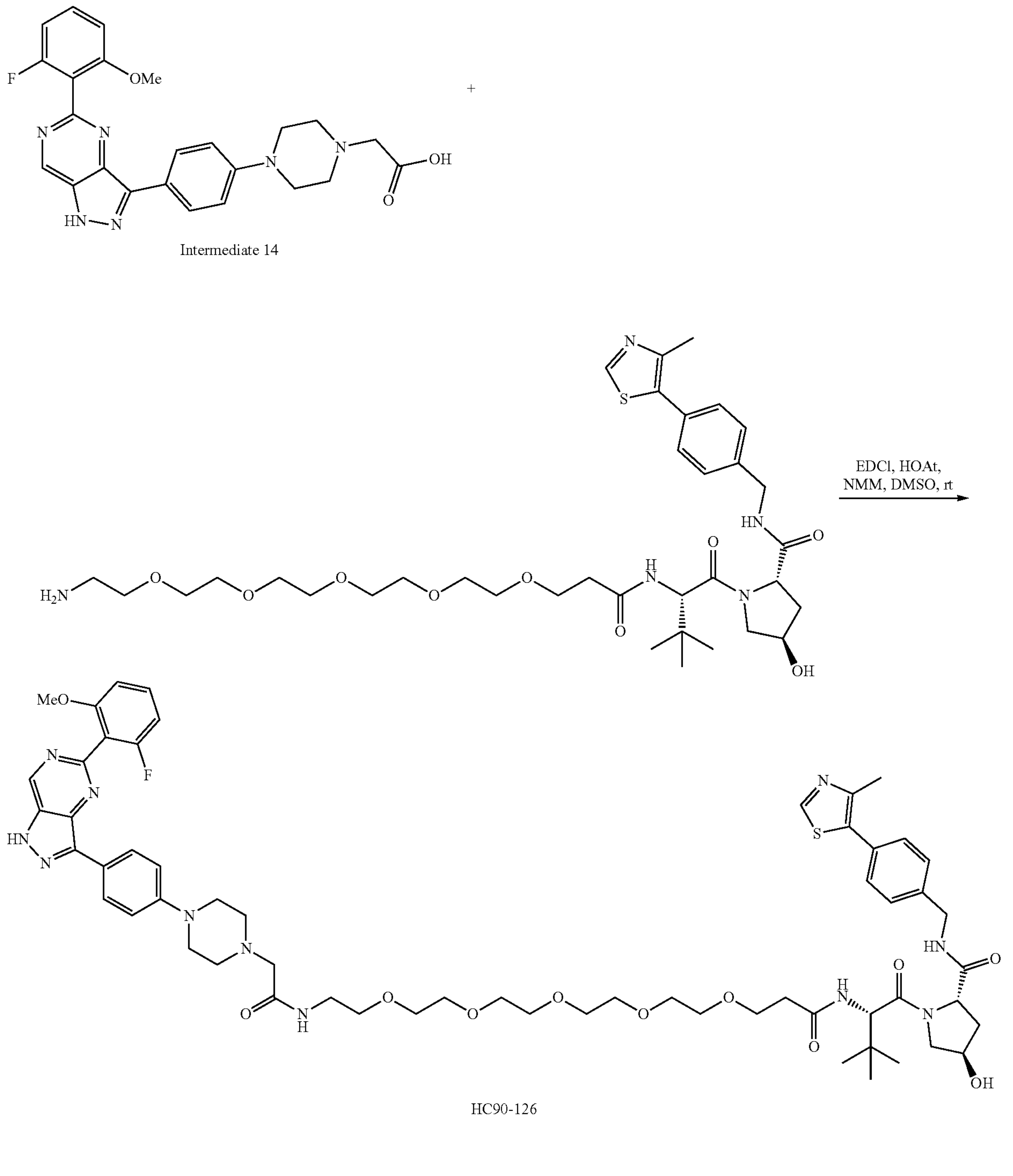

Intermediate 14

HC90-126

HC90-126 was synthesized following the standard procedure for preparing HC90-86 from Intermediate 14 (5.8 mg, 0.01 mmol, 1.0 equiv), (2S,4R)-1-((S)-1-amino-20-(tert-butyl)-18-oxo-3,6,9,12,15-pentaoxa-19-azahenicosan-21-oyl)-4-hydroxy-N-(4-(4-methylthiazol-5-yl)benzyl)pyrrolidine-2-carboxamide (10.5 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-126 was obtained as yellow solid in TFA salt form (6.3 mg, 49%). $^1$H NMR (800 MHz, Methanol-$d_4$) δ 9.31 (s, 1H), 8.90 (s, 1H), 8.43 (d, J=8.4 Hz, 2H), 7.50 (q, J=8.0 Hz, 1H), 7.46 (d, J=7.8 Hz, 2H), 7.41 (d, J=7.8 Hz, 2H), 7.17 (d, J=8.5 Hz, 2H), 7.01 (d, J=8.5 Hz, 1H), 6.90 (t, J=8.6 Hz, 1H), 4.67 (s, 1H), 4.58 (t, J=8.5 Hz, 1H), 4.53 (d, J=15.8 Hz, 1H), 4.52-4.50 (m, 1H), 4.38 (d, J=15.4 Hz, 1H), 4.06 (s, 2H), 3.91 (d, J=11.1 Hz, 1H), 3.81-3.78 (m, 4H), 3.74 (ddt, J=19.3, 9.9, 4.1 Hz, 2H), 3.69-3.54 (m, 26H), 3.49 (t, J=5.2 Hz, 2H), 2.59 (dt, J=13.5, 6.6 Hz, 1H), 2.52-2.46 (m, 4H), 2.24 (dd, J=13.2, 7.7 Hz, 1H), 2.09 (ddd, J=13.2, 8.8, 4.5 Hz, 1H), 1.05 (s, 9H). HRMS calcd for $C_{59}H_{77}FN_{11}O_{11}S^+$ [M+H$^+$]1166.5503, found 1166.5491.

Example 242

Synthesis of HC90-127

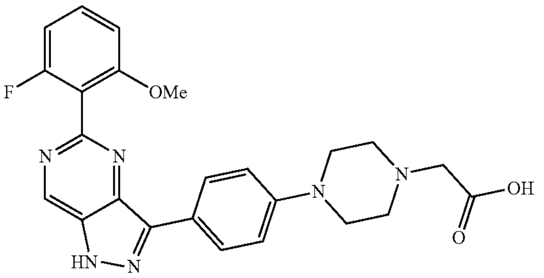

Intermediate 14

+

-continued

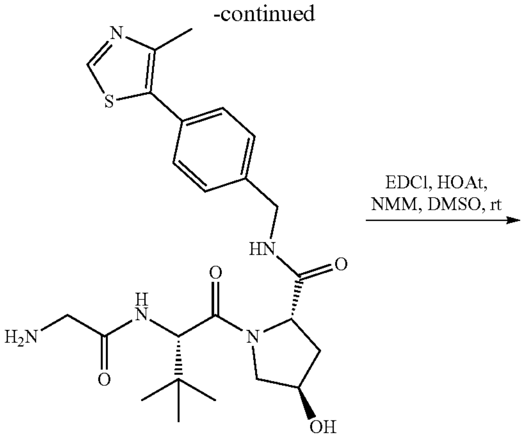

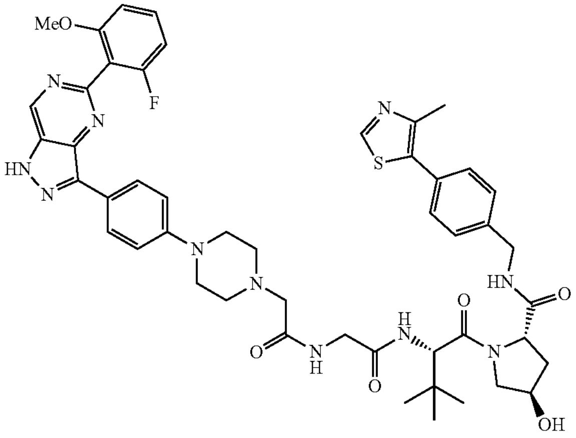

HC90-127

HC90-127 was synthesized following the standard procedure for preparing HC90-86 from Intermediate 14 (5.8 mg, 0.01 mmol, 1.0 equiv), (2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide (7.9 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-127 was obtained as yellow solid in TFA salt form (6.1 mg, 58%). $^1$H NMR (800 MHz, Methanol-$d_4$) δ 9.32 (s, 1H), 8.89 (s, 1H), 8.41 (d, J=8.3 Hz, 2H), 7.49 (dd, J=21.6, 7.6 Hz, 3H), 7.41 (d, J=7.8 Hz, 2H), 7.11 (d, J=8.4 Hz, 2H), 7.01 (d, J=8.5 Hz, 1H), 6.90 (t, J=8.6 Hz, 1H), 4.69 (s, 1H), 4.61-4.55 (m, 2H), 4.54 (d, J=4.3 Hz, 1H), 4.36 (d, J=15.4 Hz, 1H), 4.13-4.02 (m, 4H), 3.90 (d, J=10.9 Hz, 1H), 3.84 (dd, J=11.1, 3.9 Hz, 1H), 3.81 (s, 3H), 3.67-3.49 (m, 8H), 2.46 (s, 3H), 2.25 (dd, J=13.2, 7.8 Hz, 1H), 2.12 (ddd, J=13.2, 8.9, 4.5 Hz, 1H), 1.08 (s, 9H). HRMS calcd for $C_{48}H_{55}FN_{11}O_6S^+$ [M+H$^+$] 932.4036, found 932.4026.

Example 243

Synthesis of HC90-128

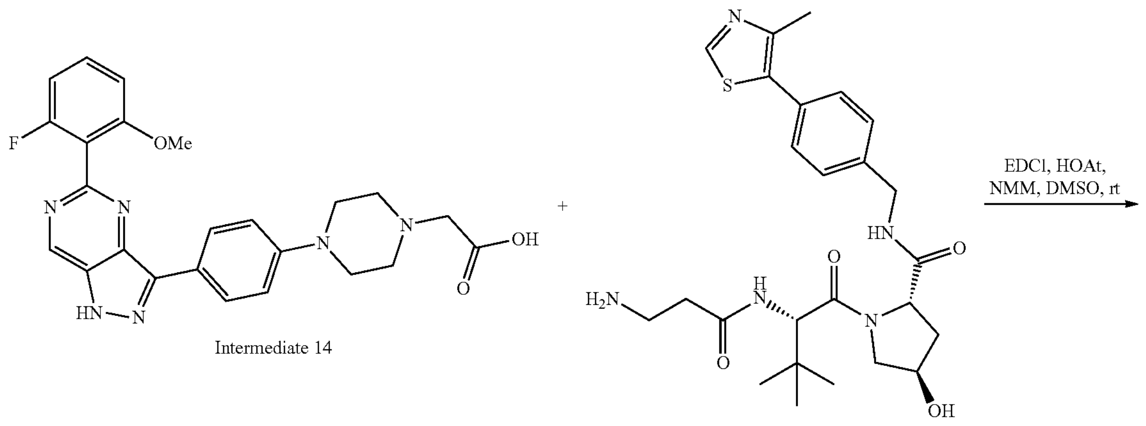

Intermediate 14

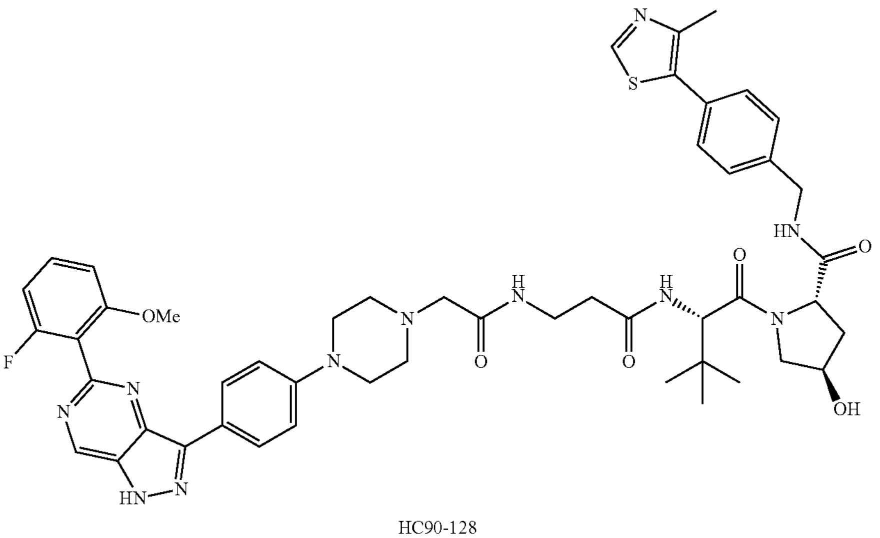

HC90-128

HC90-128 was synthesized following the standard procedure for preparing HC90-86 from Intermediate 14 (5.8 mg, 0.01 mmol, 1.0 equiv), (2S,4R)-1-((S)-2-(3-aminopropanamido)-3,3-dimethylbutanoyl)-4-hydroxy-N-(4-(4-methylthiazol-5-yl)benzyl)pyrrolidine-2-carboxamide (8.1 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-128 was obtained as yellow solid in TFA salt form (7.2 mg, 68%). $^{1}H$ NMR (800 MHz, Methanol-$d_4$) δ 9.31 (s, 1H), 8.86 (s, 1H), 8.40 (d, J=8.3 Hz, 2H), 7.53-7.46 (m, 1H), 7.41 (d, J=7.8 Hz, 2H), 7.36 (d, J=7.8 Hz, 2H), 7.12 (d, J=8.4 Hz, 2H), 7.01 (d, J=8.3 Hz, 1H), 6.90 (t, J=8.4 Hz, 1H), 4.64 (s, 1H), 4.60-4.53 (m, 2H), 4.48 (d, J=15.5 Hz, 1H), 4.34 (d, J=15.2 Hz, 1H), 4.03-3.93 (m, 3H), 3.84-3.78 (m, 4H), 3.68-3.41 (m, 10H), 2.70-2.60 (m, 1H), 2.53-2.48 (m, 1H), 2.44 (s, 3H), 2.31-2.24 (m, 1H), 2.15-2.08 (m, 1H), 1.08 (s, 9H). HRMS calcd for $C_{49}H_{57}FN_{11}O_6S^+$ [M+H$^+$] 946.4193, found 946.4182.

Example 244

Synthesis of HC90-129

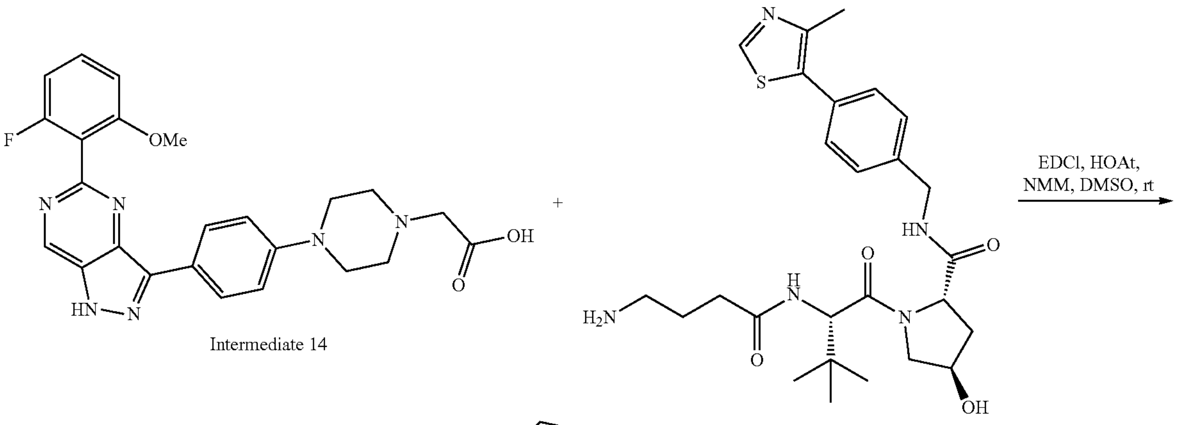

Intermediate 14

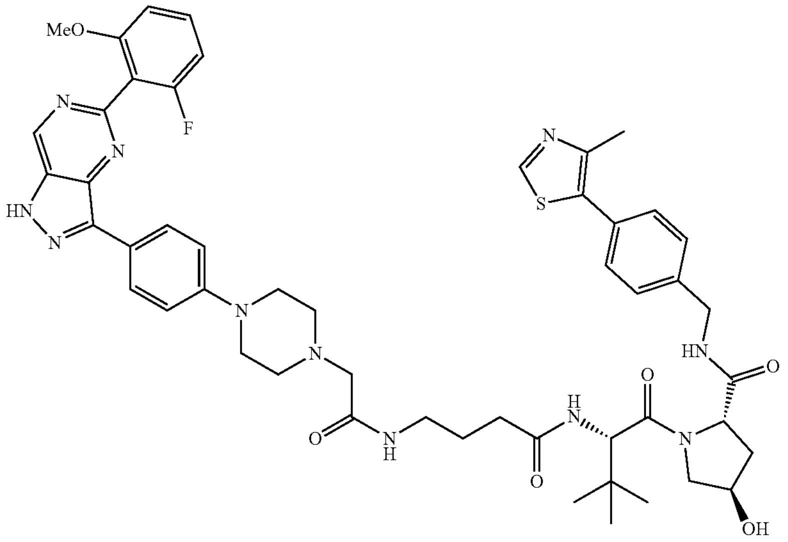

HC90-129

HC90-129 was synthesized following the standard procedure for preparing HC90-86 from Intermediate 14 (5.8 mg, 0.01 mmol, 1.0 equiv), (2S,4R)-1-((S)-2-(4-aminobutanamido)-3,3-dimethylbutanoyl)-4-hydroxy-N-(4-(4-methylthiazol-5-yl)benzyl)pyrrolidine-2-carboxamide (8.2 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-129 was obtained as yellow solid in TFA salt form (5.8 mg, 54%). $^1$H NMR (800 MHz, Methanol-$d_4$) δ 9.32 (s, 1H), 8.88 (s, 1H), 8.42 (d, J=8.3 Hz, 2H), 7.50 (q, J=8.3 Hz, 1H), 7.46 (d, J=7.8 Hz, 2H), 7.41 (d, J=7.8 Hz, 2H), 7.15 (d, J=8.4 Hz, 2H), 7.01 (d, J=8.6 Hz, 1H), 6.90 (t, J=8.6 Hz, 1H), 4.65 (s, 1H), 4.61-4.57 (m, 1H), 4.56-4.51 (m, 2H), 4.37 (d, J=15.5 Hz, 1H), 4.03 (s, 2H), 3.95 (d, J=11.0 Hz, 1H), 3.84 (dd, J=10.9, 3.8 Hz, 1H), 3.81 (s, 3H), 3.70-3.42 (m, 10H), 2.47 (s, 3H), 2.41-2.32 (m, 2H), 2.29-2.22 (m, 1H), 2.11 (ddd, J=13.3, 8.9, 4.5 Hz, 1H), 1.92-1.82 (m, 2H), 1.08 (s, 9H). HRMS calcd for $C_{50}H_{59}FN_{11}O_6S^+$ [M+H$^+$] 960.4349, found 960.4336.

Example 245

Synthesis of HC90-130

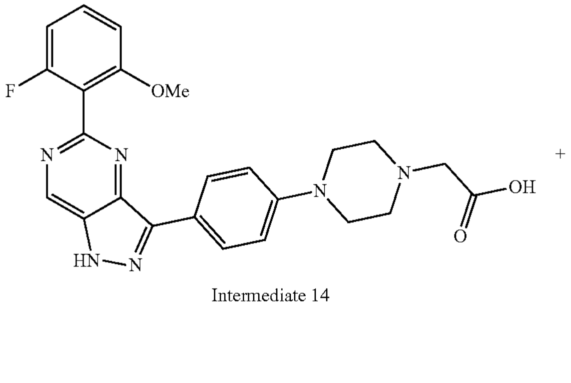

Intermediate 14

-continued

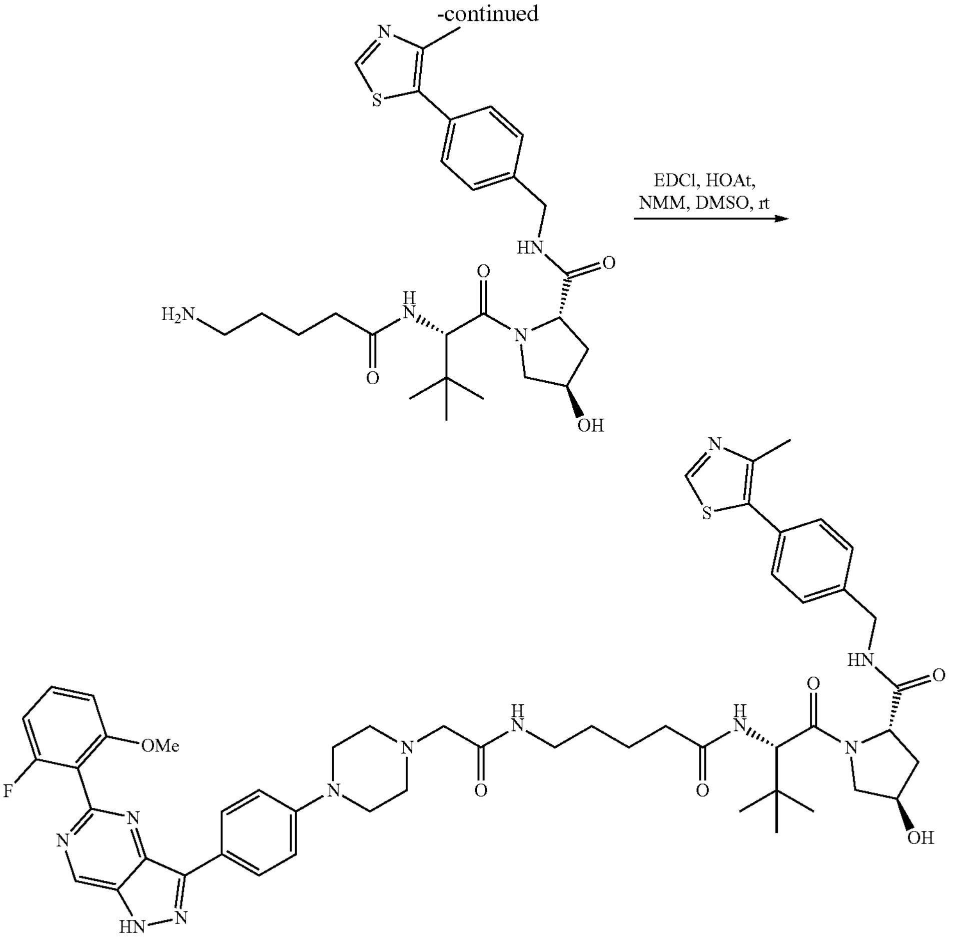

HC90-130

HC90-130 was synthesized following the standard procedure for preparing HC90-86 from Intermediate 14 (5.8 mg, 0.01 mmol, 1.0 equiv), (2S,4R)-1-((S)-2-(5-aminopentanamido)-3,3-dimethylbutanoyl)-4-hydroxy-N-(4-(4-methylthiazol-5-yl)benzyl)pyrrolidine-2-carboxamide (7.1 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-130 was obtained as yellow solid in TFA salt form (6.0 mg, 55%). $^1$H NMR (800 MHz, Methanol-$d_4$) δ 9.31 (s, 1H), 8.87 (s, 1H), 8.42 (d, J=8.5 Hz, 2H), 7.50 (q, J=7.9 Hz, 1H), 7.45 (d, J=7.8 Hz, 2H), 7.40 (d, J=7.9 Hz, 2H), 7.16 (d, J=8.4 Hz, 2H), 7.01 (dd, J=8.4, 3.8 Hz, 1H), 6.89 (t, J=8.6 Hz, 1H), 4.66 (s, 1H), 4.60-4.56 (m, 1H), 4.54-4.52 (m, 1H), 4.49 (d, J=15.6 Hz, 1H), 4.39 (d, J=15.5 Hz, 1H), 4.01 (s, 2H), 3.93 (d, J=11.0 Hz, 1H), 3.83 (dd, J=11.2, 3.9 Hz, 1H), 3.81 (d, J=4.3 Hz, 3H), 3.62-3.44 (m, 8H), 3.33-3.28 (m, 2H), 2.47 (s, 3H), 2.39-2.31 (m, 2H), 2.26 (dd, J=12.7, 7.5 Hz, 1H), 2.10 (ddd, J=13.2, 8.8, 4.4 Hz, 1H), 1.74-1.55 (m, 4H), 1.07 (s, 9H). HRMS calcd for $C_{51}H_{61}FN_{11}O_6S^+$ [M+H$^+$] 974.4506, found 974.4498.

Example 246

Synthesis of HC90-131

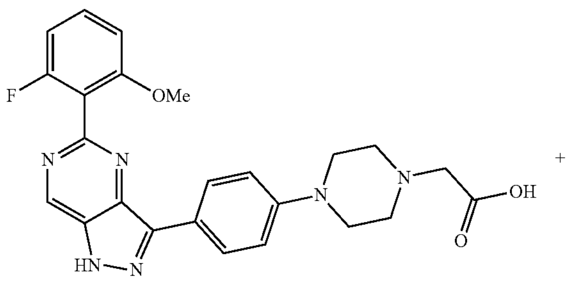

Intermediate 14

-continued

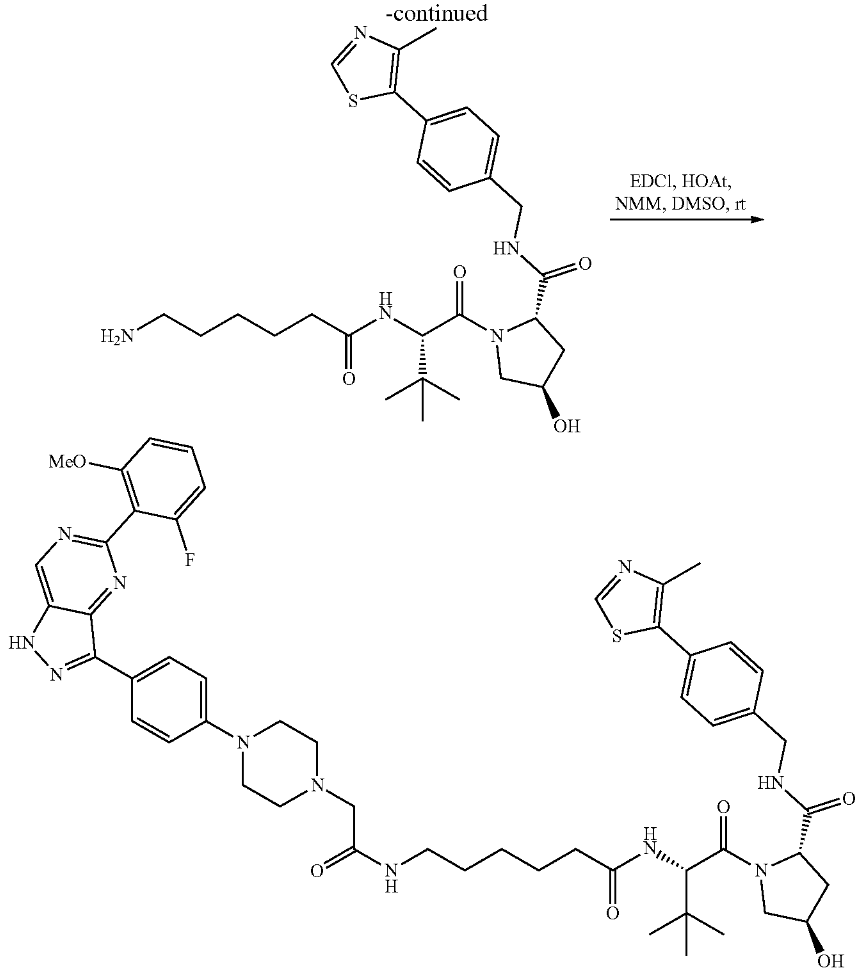

HC90-131

HC90-131 was synthesized following the standard procedure for preparing HC90-86 from Intermediate 14 (5.8 mg, 0.01 mmol, 1.0 equiv), (2S,4R)-1-((S)-2-(6-aminohexanamido)-3,3-dimethylbutanoyl)-4-hydroxy-N-(4-(4-methylthiazol-5-yl)benzyl)pyrrolidine-2-carboxamide (7.3 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-131 was obtained as yellow solid in TFA salt form (7.7 mg, 70%). $^1$H NMR (800 MHz, Methanol-$d_4$) δ 9.31 (s, 1H), 8.88 (s, 1H), 8.42 (d, J=8.3 Hz, 2H), 7.55-7.48 (m, 1H), 7.46 (d, J=7.7 Hz, 2H), 7.41 (d, J=7.8 Hz, 2H), 7.16 (d, J=8.4 Hz, 2H), 7.01 (d, J=8.5 Hz, 1H), 6.90 (t, J=8.6 Hz, 1H), 4.66 (s, 1H), 4.59 (t, J=8.3 Hz, 1H), 4.55-4.50 (m, 2H), 4.38 (d, J=15.5 Hz, 1H), 4.02 (s, 2H), 3.93 (d, J=11.0 Hz, 1H), 3.85-3.78 (m, 4H), 3.64-3.45 (m, 8H), 3.32-3.28 (m, 2H), 2.48 (s, 3H), 2.37-2.28 (m, 2H), 2.25 (dd, J=13.4, 7.7 Hz, 1H), 2.11 (ddd, J=13.3, 9.0, 4.6 Hz, 1H), 1.67 (p, J=7.5 Hz, 2H), 1.59 (p, J=7.1 Hz, 2H), 1.40 (p, J=7.7 Hz, 2H), 1.06 (s, 9H). HRMS calcd for $C_{52}H_{63}FN_{11}O_6S^+$ [M+H$^+$] 988.4662, found 988.4649.

Example 247

Synthesis of HC90-132

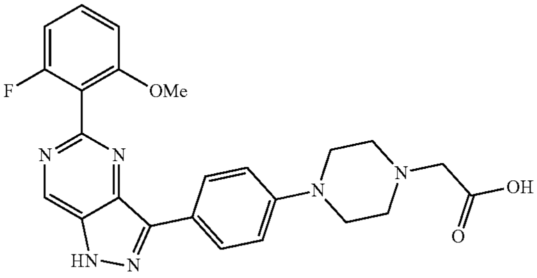

Intermediate 14

+

-continued

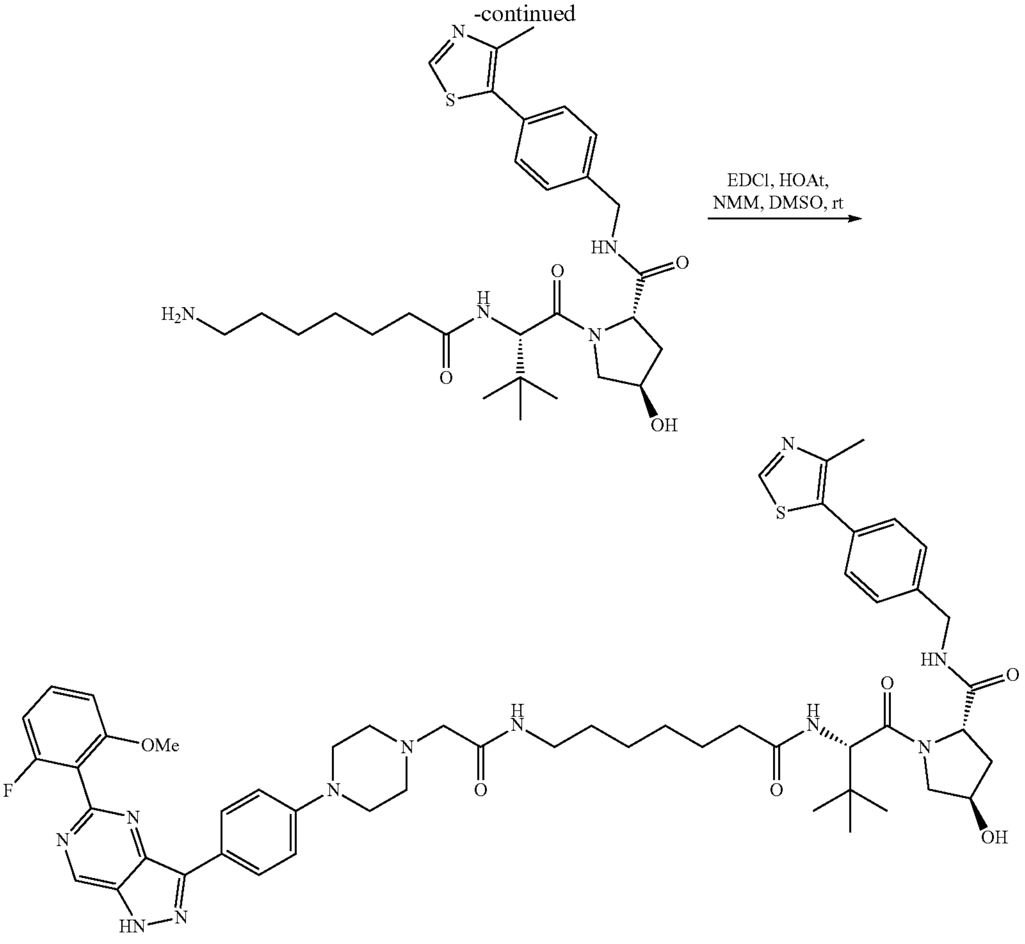

HC90-132

HC90-132 was synthesized following the standard procedure for preparing HC90-86 from Intermediate 14 (5.8 mg, 0.01 mmol, 1.0 equiv), (2S,4R)-1-((S)-2-(7-aminoheptanamido)-3,3-dimethylbutanoyl)-4-hydroxy-N-(4-(4-methylthiazol-5-yl)benzyl)pyrrolidine-2-carboxamide (7.4 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-132 was obtained as yellow solid in TFA salt form (4.3 mg, 39%). $^1$H NMR (800 MHz, Methanol-d$_4$) δ 9.31 (s, 1H), 8.89 (s, 1H), 8.42 (d, J=8.3 Hz, 2H), 7.50 (q, J=8.1 Hz, 1H), 7.47 (d, J=7.9 Hz, 2H), 7.42 (d, J=7.9 Hz, 2H), 7.16 (d, J=8.5 Hz, 2H), 7.01 (d, J=8.5 Hz, 1H), 6.90 (t, J=8.6 Hz, 1H), 4.67 (s, 1H), 4.59 (t, J=8.3 Hz, 1H), 4.55-4.51 (m, 2H), 4.39 (d, J=15.5 Hz, 1H), 4.00 (s, 2H), 3.93 (d, J=10.9 Hz, 1H), 3.83 (dd, J=10.9, 3.8 Hz, 1H), 3.81 (s, 3H), 3.62-3.42 (m, 8H), 3.31-3.28 (m, 2H), 2.48 (s, 3H), 2.36-2.27 (m, 2H), 2.27-2.21 (m, 1H), 2.11 (ddd, J=13.2, 8.9, 4.4 Hz, 1H), 1.71-1.62 (m, 2H), 1.58 (t, J=7.3 Hz, 2H), 1.39 (d, J=5.8 Hz, 4H), 1.06 (s, 9H). HRMS calcd for $C_{53}H_{65}FN_{11}O_6S^+$ [M+H$^+$] 1002.4819, found 1002.4808.

Example 248

Synthesis of HC90-133

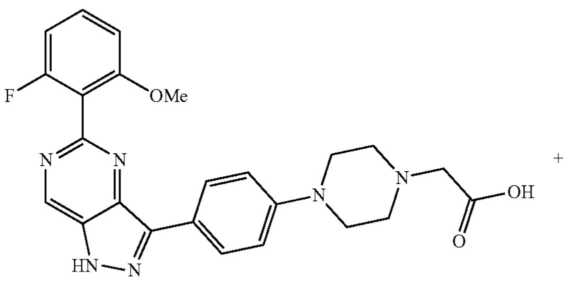

Intermediate 14

-continued

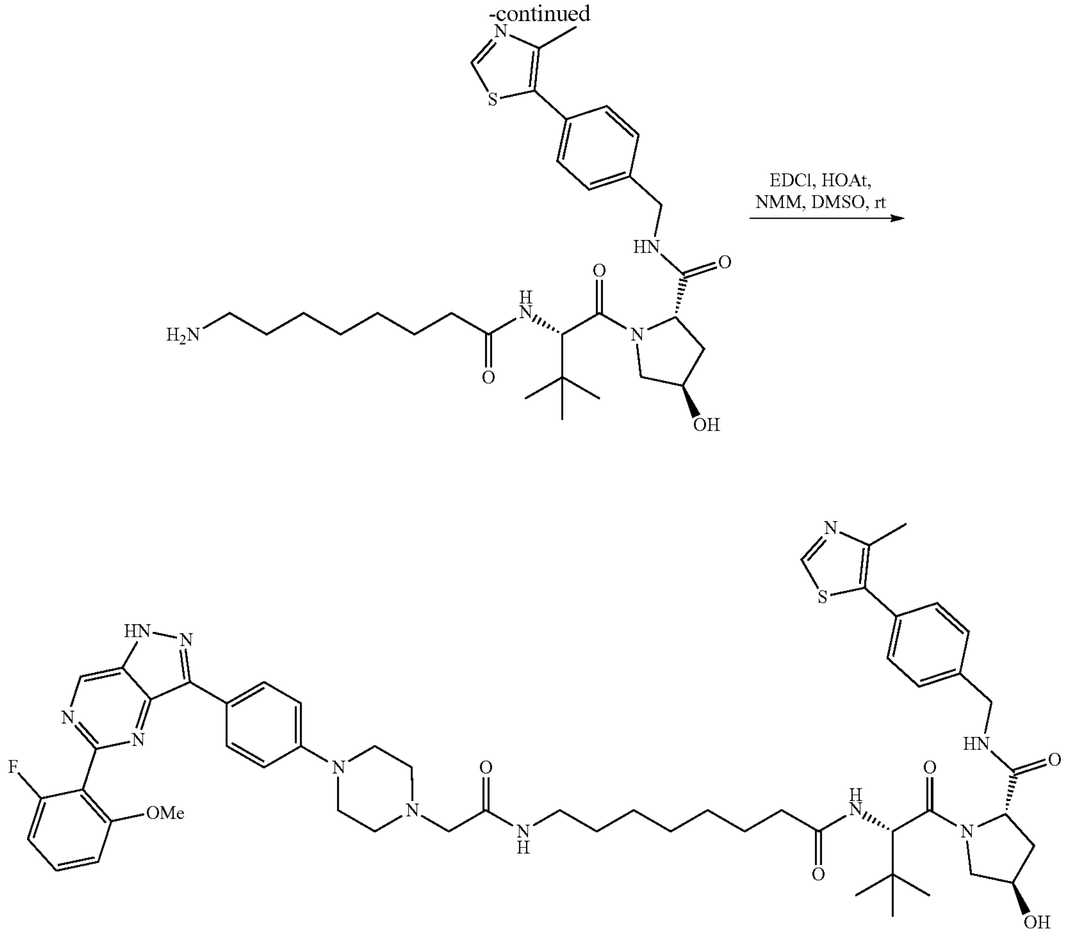

HC90-133

HC90-133 was synthesized following the standard procedure for preparing HC90-86 from Intermediate 14 (5.8 mg, 0.01 mmol, 1.0 equiv), (2S,4R)-1-((S)-2-(8-aminooctanamido)-3,3-dimethylbutanoyl)-4-hydroxy-N-(4-(4-methylthiazol-5-yl)benzyl)pyrrolidine-2-carboxamide (7.5 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-133 was obtained as yellow solid in TFA salt form (4.7 mg, 42%). $^1$H NMR (800 MHz, Methanol-$d_4$) δ 9.31 (s, 1H), 8.89 (s, 1H), 8.43 (d, J=8.3 Hz, 2H), 7.50 (q, J=8.2 Hz, 1H), 7.47 (d, J=7.8 Hz, 2H), 7.42 (d, J=7.9 Hz, 2H), 7.17 (d, J=8.5 Hz, 2H), 7.01 (d, J=8.5 Hz, 1H), 6.90 (t, J=8.7 Hz, 1H), 4.66 (s, 1H), 4.58 (t, J=8.1 Hz, 1H), 4.56-4.51 (m, 2H), 4.38 (d, J=15.5 Hz, 1H), 4.01 (s, 2H), 3.92 (d, J=10.9 Hz, 1H), 3.85-3.79 (m, 4H), 3.65-3.43 (m, 8H), 3.30 (t, J=7.1 Hz, 2H), 2.48 (s, 3H), 2.36-2.21 (m, 3H), 2.10 (ddd, J=13.4, 9.1, 4.5 Hz, 1H), 1.69-1.61 (m, 2H), 1.61-1.54 (m, 2H), 1.38 (s, 6H), 1.05 (s, 9H). HRMS calcd for $C_{54}H_{67}FN_{11}O_6S^+$ [M+H$^+$] 1016.4975, found 1016.4961.

Example 249

Synthesis of HC90-134

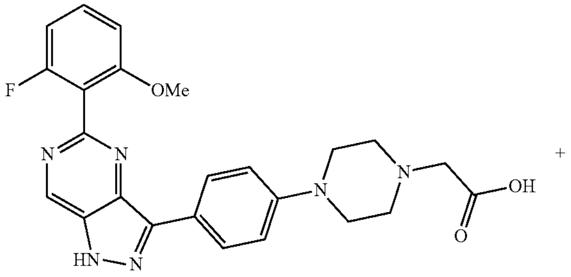

Intermediate 14

-continued

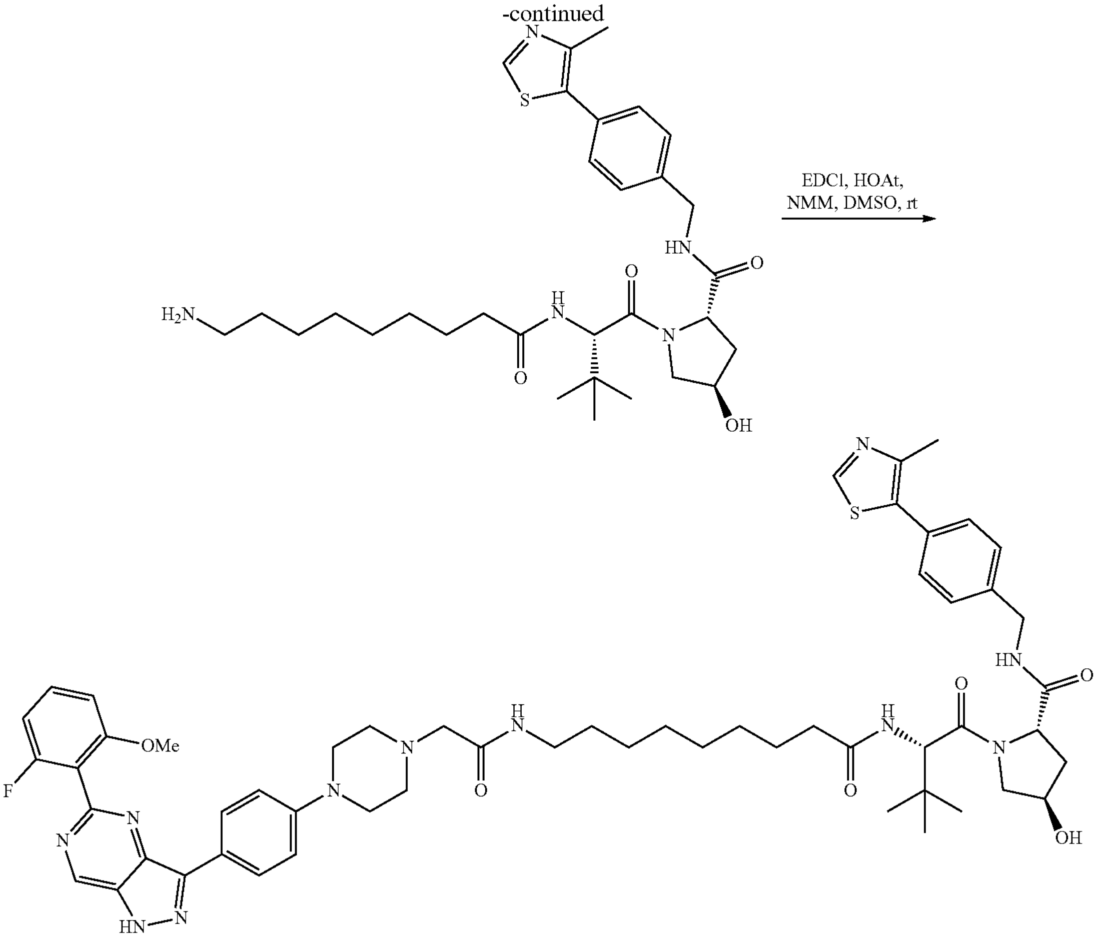

HC90-134

HC90-134 was synthesized following the standard procedure for preparing HC90-86 from Intermediate 14 (5.8 mg, 0.01 mmol, 1.0 equiv), (2S,4R)-1-((S)-2-(9-aminononanamido)-3,3-dimethylbutanoyl)-4-hydroxy-N-(4-(4-methylthiazol-5-yl)benzyl)pyrrolidine-2-carboxamide (7.7 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-134 was obtained as yellow solid in TFA salt form (9.5 mg, 83%). $^1$H NMR (800 MHz, Methanol-$d_4$) δ 9.31 (s, 1H), 8.89 (s, 1H), 8.42 (d, J=8.3 Hz, 2H), 7.50 (q, J=7.9 Hz, 1H), 7.47 (d, J=8.0 Hz, 2H), 7.42 (d, J=7.8 Hz, 2H), 7.16 (d, J=8.3 Hz, 2H), 7.01 (d, J=8.5 Hz, 1H), 6.90 (t, J=8.6 Hz, 1H), 4.67 (s, 1H), 4.59 (t, J=8.3 Hz, 1H), 4.56-4.50 (m, 2H), 4.38 (d, J=15.4 Hz, 1H), 4.02 (s, 2H), 3.92 (d, J=11.0 Hz, 1H), 3.83 (dd, J=11.5, 3.9 Hz, 1H), 3.81 (s, 3H), 3.63-3.48 (m, 8H), 3.29 (t, J=7.2 Hz, 2H), 2.48 (s, 3H), 2.37-2.29 (m, 1H), 2.29-2.22 (m, 2H), 2.10 (ddd, J=13.4, 9.1, 4.6 Hz, 1H), 1.68-1.60 (m, 2H), 1.59-1.54 (m, 2H), 1.37 (s, 8H), 1.06 (s, 9H). HRMS calcd for $C_{55}H_{69}FN_{11}O_6S^+$ [M+H$^+$] 1030.5132, found 1030.5119.

Example 250

Synthesis of HC90-135

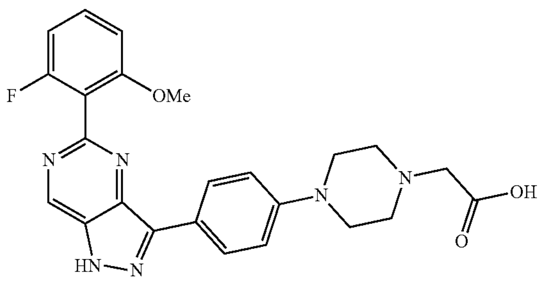

Intermediate 14

+

-continued

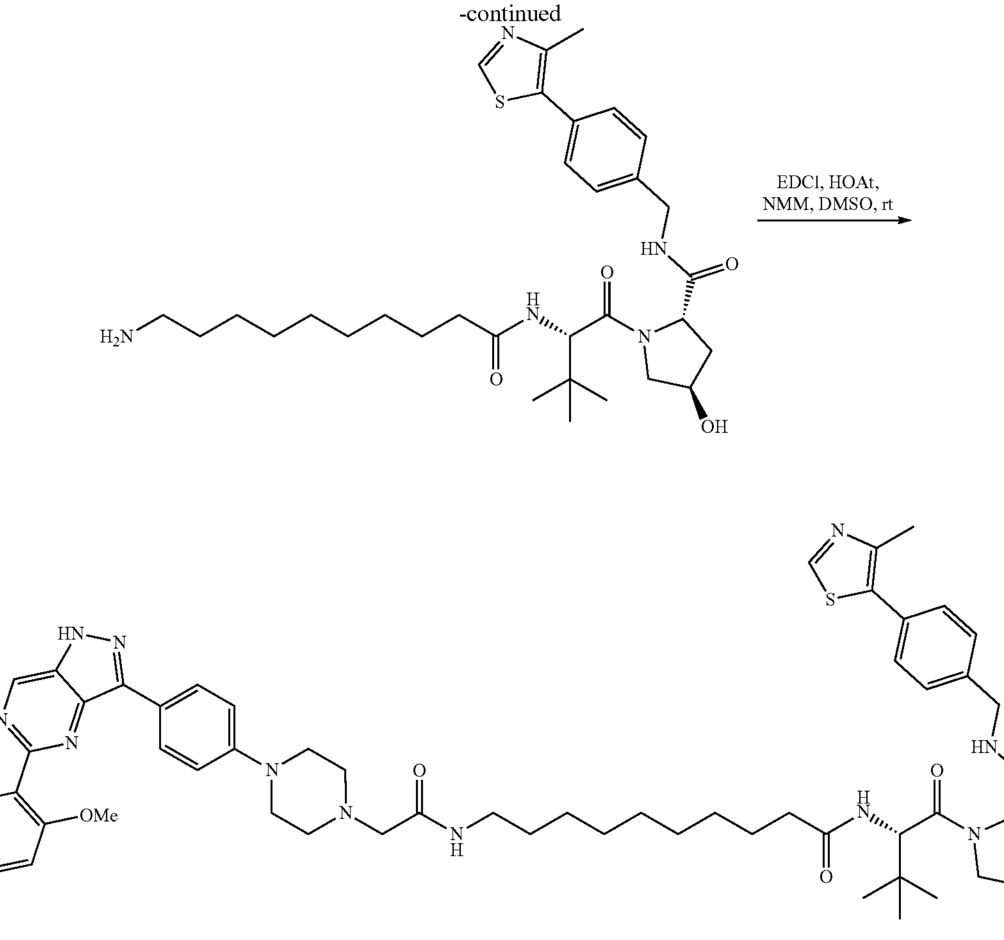

HC90-135

HC90-135 was synthesized following the standard procedure for preparing HC90-86 from Intermediate 14 (5.8 mg, 0.01 mmol, 1.0 equiv), (2S,4R)-1-((S)-2-(10-aminodecanamido)-3,3-dimethylbutanoyl)-4-hydroxy-N-(4-(4-methylthiazol-5-yl)benzyl)pyrrolidine-2-carboxamide (7.8 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-135 was obtained as yellow solid in TFA salt form (8.1 mg, 70%). $^1$H NMR (800 MHz, Methanol-$d_4$) δ 9.31 (s, 1H), 8.90 (s, 1H), 8.43 (d, J=8.3 Hz, 2H), 7.54-7.45 (m, 3H), 7.42 (d, J=7.8 Hz, 2H), 7.17 (d, J=8.4 Hz, 2H), 7.01 (d, J=8.5 Hz, 1H), 6.90 (t, J=8.6 Hz, 1H), 4.66 (s, 1H), 4.59 (t, J=8.4 Hz, 1H), 4.55 (d, J=15.5 Hz, 1H), 4.53-4.50 (m, 1H), 4.38 (d, J=15.4 Hz, 1H), 4.02 (s, 2H), 3.92 (d, J=11.0 Hz, 1H), 3.86-3.78 (m, 4H), 3.67-3.42 (m, 8H), 3.29 (t, J=7.2 Hz, 2H), 2.49 (s, 3H), 2.37-2.29 (m, 1H), 2.29-2.21 (m, 2H), 2.10 (ddd, J=13.2, 8.9, 4.5 Hz, 1H), 1.68-1.53 (m, 4H), 1.41-1.32 (m, 10H), 1.06 (s, 9H). HRMS calcd for $C_{56}H_{71}FN_{11}O_6S^+$ [M+H$^+$]1044.5288, found 1044.5279.

Example 251

Synthesis of HC90-136

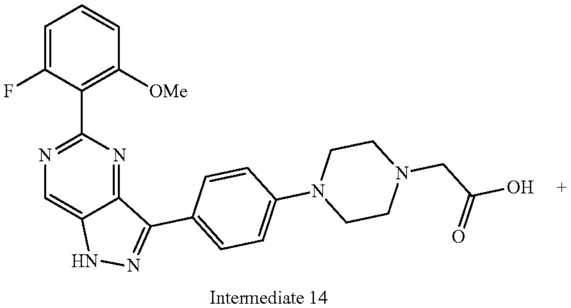

Intermediate 14

-continued

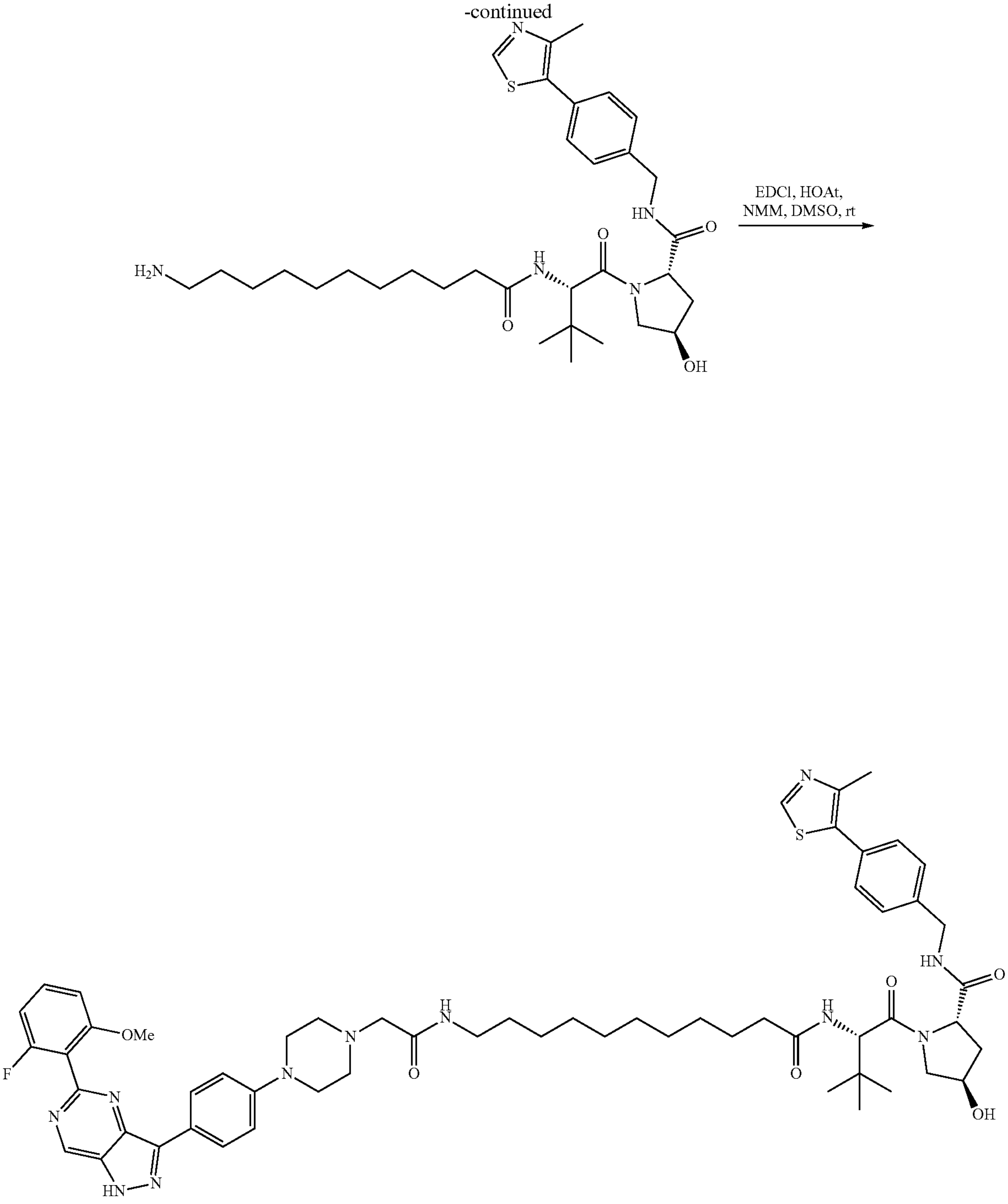

HC90-136

HC90-136 was synthesized following the standard procedure for preparing HC90-86 from Intermediate 14 (5.8 mg, 0.01 mmol, 1.0 equiv), (2S,4R)-1-((S)-2-(11-aminoundecanamido)-3,3-dimethylbutanoyl)-4-hydroxy-N-(4-(4-methylthiazol-5-yl)benzyl)pyrrolidine-2-carboxamide (8.0 mg, 0.011 mmol, 1.1 equiv), EDCI (3.8 mg, 0.02 mmol, 2.0 equiv), HOAt (2.7 mg, 0.02 mmol, 2.0 equiv), and NMM (5.1 mg, 0.05 mmol, 5.0 equiv) in DMSO (1 mL). HC90-136 was obtained as yellow solid in TFA salt form (9.1 mg, 78%). $^1$H NMR (800 MHz, Methanol-$d_4$) δ 9.31 (s, 1H), 8.90 (s, 1H), 8.43 (d, J=8.3 Hz, 2H), 7.53-7.46 (m, 3H), 7.42 (d, J=7.8 Hz, 2H), 7.17 (d, J=8.4 Hz, 2H), 7.01 (d, J=8.5 Hz, 1H), 6.90 (t, J=8.6 Hz, 1H), 4.66 (s, 1H), 4.59 (t, J=8.3 Hz, 1H), 4.55 (d, J=15.4 Hz, 1H), 4.52 (s, 1H), 4.38 (d, J=15.4 Hz, 1H), 4.02 (s, 2H), 3.92 (d, J=10.9 Hz, 1H), 3.83 (dd, J=11.2, 4.0 Hz, 1H), 3.81 (s, 3H), 3.66-3.44 (m, 8H), 3.29 (t, J=7.2 Hz, 2H), 2.49 (s, 3H), 2.36-2.29 (m, 1H), 2.30-2.22 (m, 2H), 2.11 (ddd, J=13.3, 9.1, 4.6 Hz, 1H), 1.59 (dtd, J=52.8, 15.7, 8.2 Hz, 4H), 1.41-1.29 (m, 12H), 1.06 (s, 9H). HRMS calcd for $C_{57}H_{73}FN_{11}O_6S^+$ [M+H$^+$] 1058.5445, found 1058.5434.

Example 252

Synthesis of HC90-60

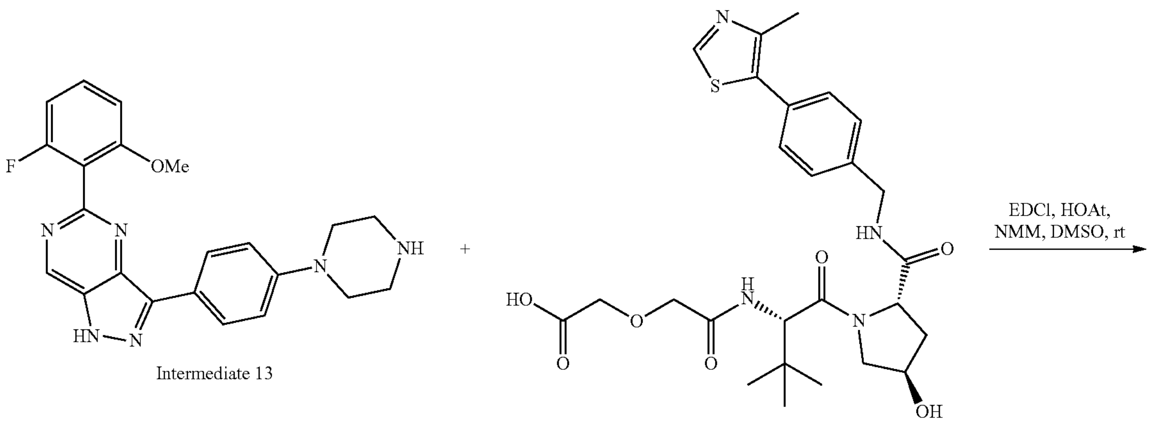

Intermediate 13

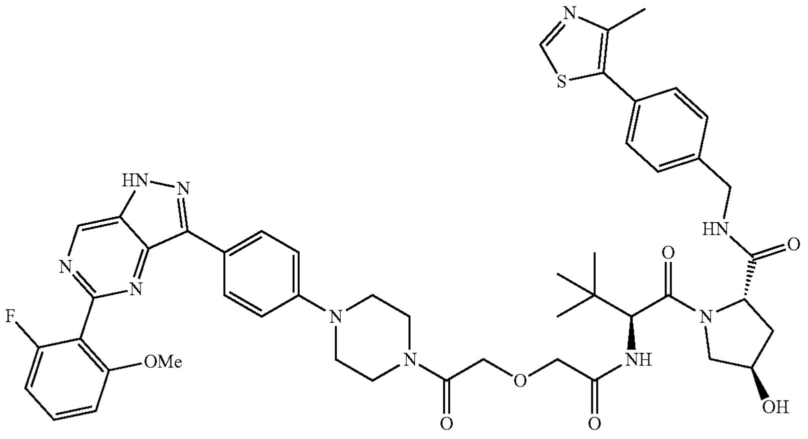

HC90-60

HC90-60 was synthesized following the standard procedure for preparing HC90-33 from Intermediate 13 (6.5 mg, 0.0125 mmol, 1.0 equiv), 2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetic acid (6.9 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-60 was obtained as yellow solid in TFA salt form (7.4 mg, 57%). HRMS calcd for $C_{48}H_{54}FN_{10}O_7S^+$ [M+H$^+$] 933.3876, found 933.3865.

Example 253

Synthesis of HC90-62

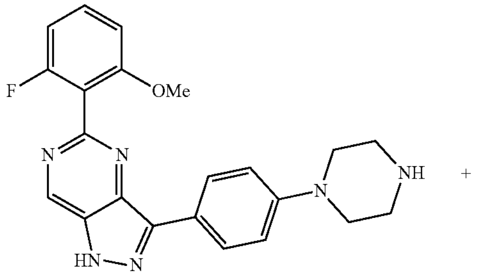

Intermediate 13

-continued

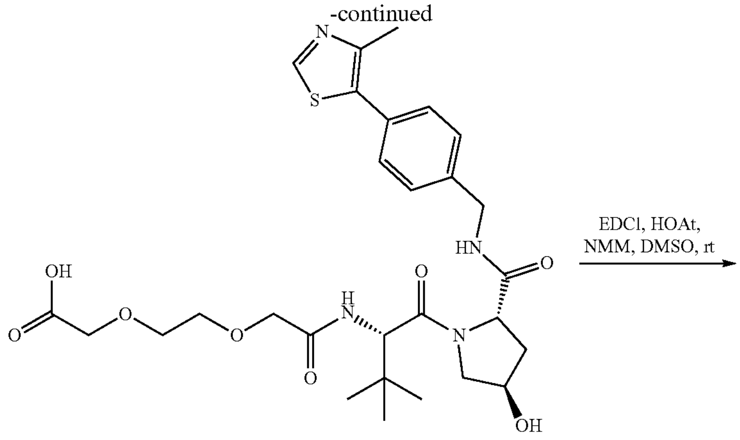

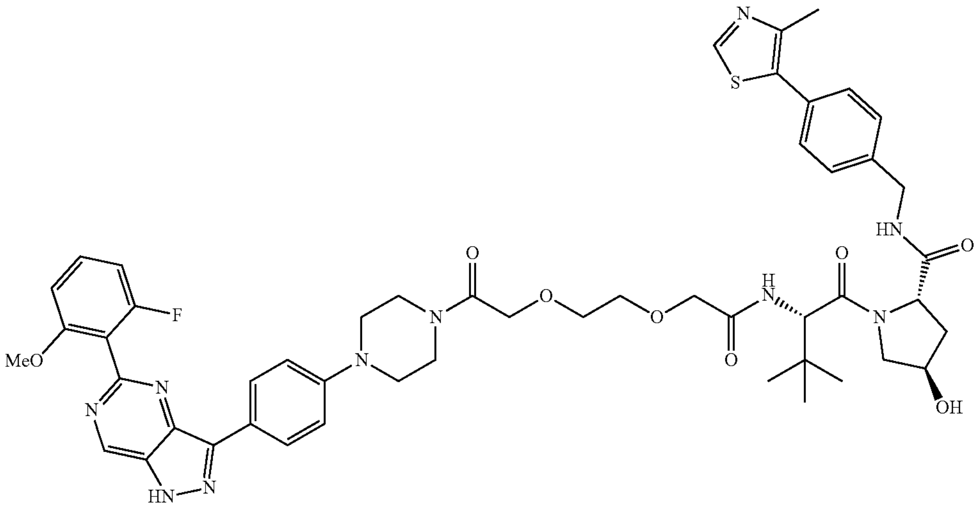

HC90-62

HC90-62 was synthesized following the standard procedure for preparing HC90-33 from Intermediate 13 (6.5 mg, 0.0125 mmol, 1.0 equiv), 2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetic acid (7.4 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-62 was obtained as yellow solid in TFA salt form (8.0 mg, 59%). HRMS calcd for $C_{50}H_{58}FN_{10}O_8S^+$ [M+H$^+$] 977.4138, found 977.4129.

Example 254

Synthesis of HC90-63

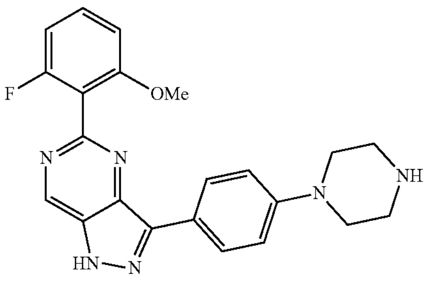

+

Intermediate 13

-continued

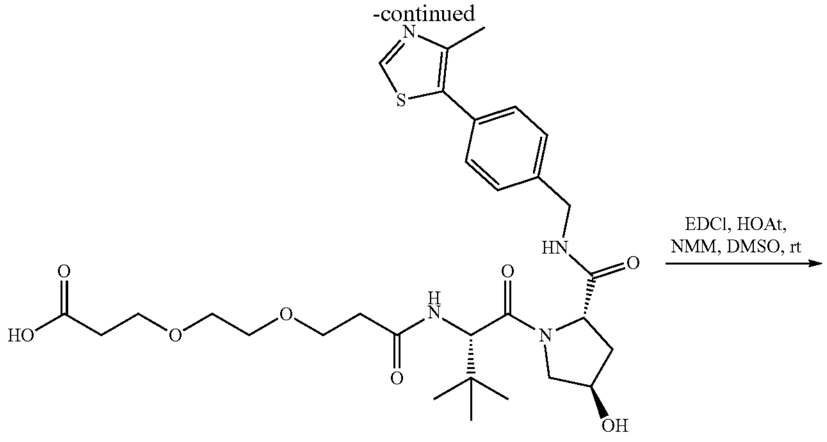

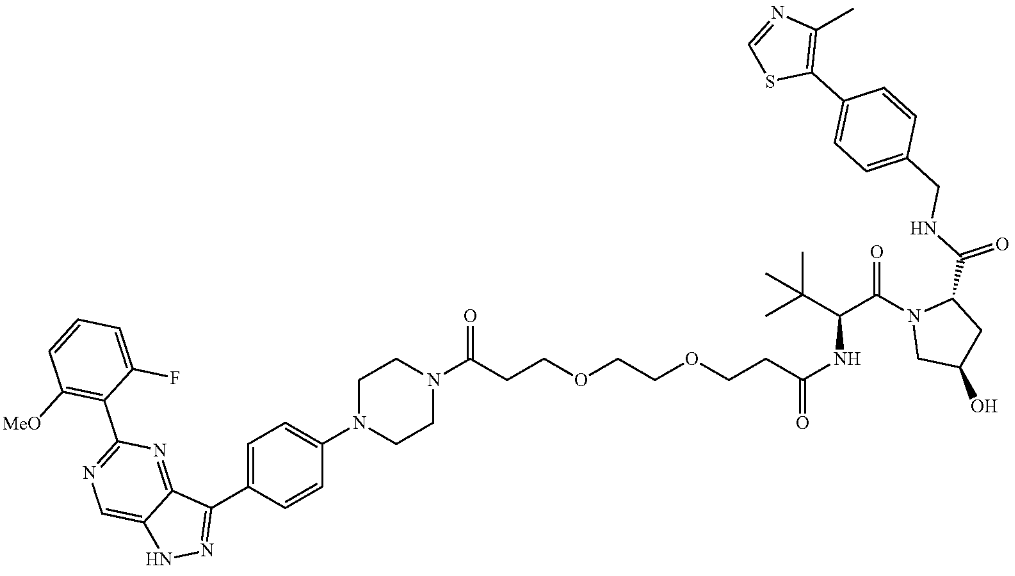

HC90-63

HC90-63 was synthesized following the standard procedure for preparing HC90-33 from Intermediate 13 (6.5 mg, 0.0125 mmol, 1.0 equiv), 3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoic acid (7.8 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-63 was obtained as yellow solid in TFA salt form (6.6 mg, 47%). HRMS calcd for $C_{52}H_{62}FN_{10}O_8S^+$ [M+H$^+$] 1005.4451, found 1005.4440.

Example 255

Synthesis of HC90-64

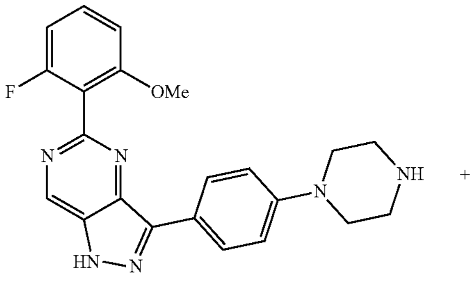

Intermediate 13

-continued

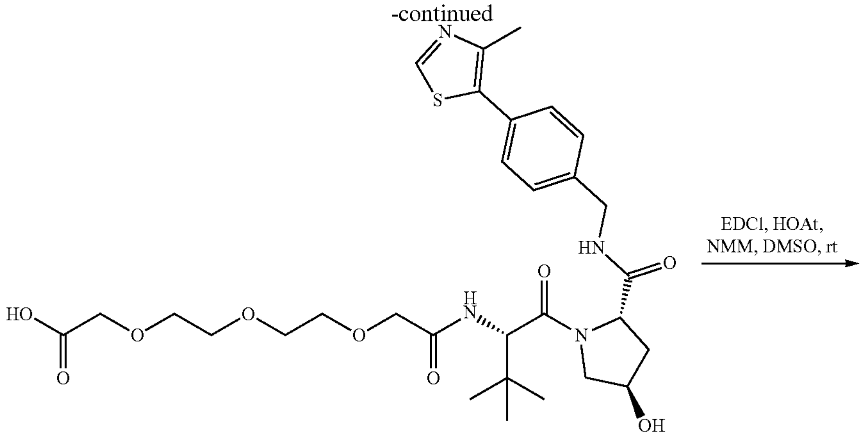

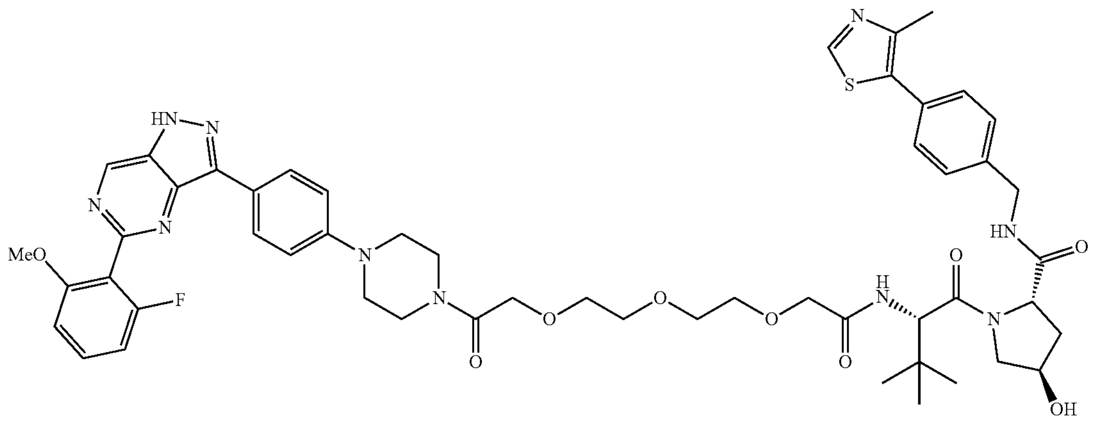

HC90-64

HC90-64 was synthesized following the standard procedure for preparing HC90-33 from Intermediate 13 (6.5 mg, 0.0125 mmol, 1.0 equiv), (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoic acid (8.0 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-64 was obtained as yellow solid in TFA salt form (8.8 mg, 62%). HRMS calcd for $C_{52}H_{62}FN_{10}O_9S^+$ [M+H+] 1021.4400, found 1021.4388.

Example 256

Synthesis of HC90-65

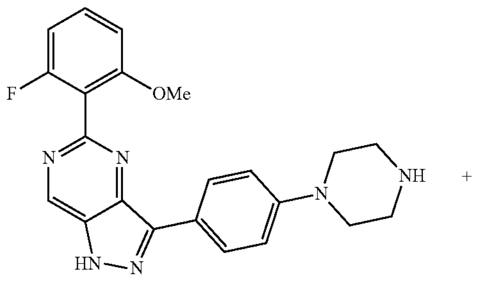

Intermediate 13

-continued

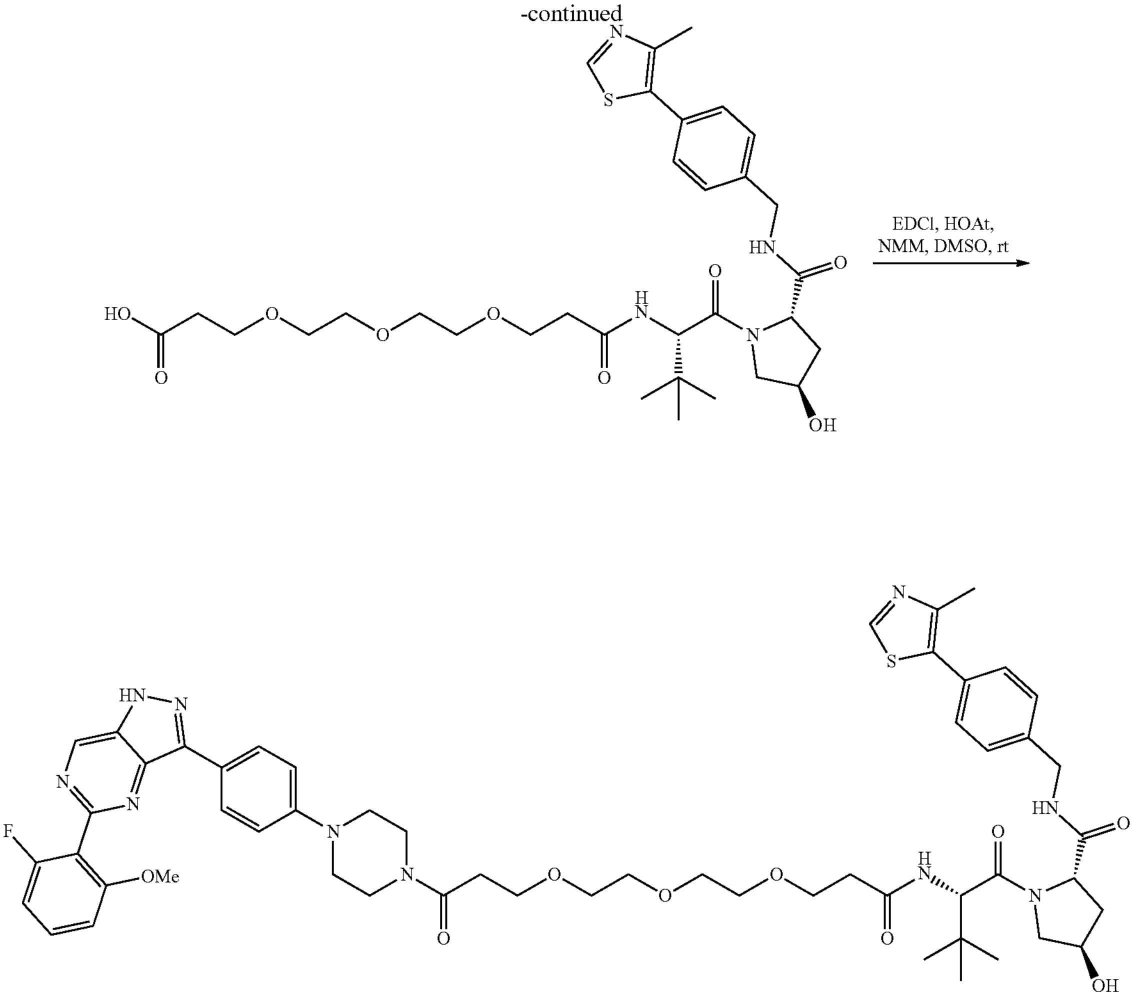

HC90-65

HC90-65 was synthesized following the standard procedure for preparing HC90-33 from Intermediate 13 (6.5 mg, 0.0125 mmol, 1.0 equiv), (S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoic acid (8.3 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-65 was obtained as yellow solid in TFA salt form (7.2 mg, 50%). HRMS calcd for $C_{54}H_{66}FN_{10}O_9S^+$ [M+H$^+$] 1049.4713, found 1049.4703.

Example 257

Synthesis of HC90-67

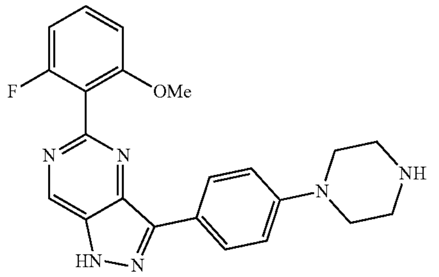

+

Intermediate 13

-continued

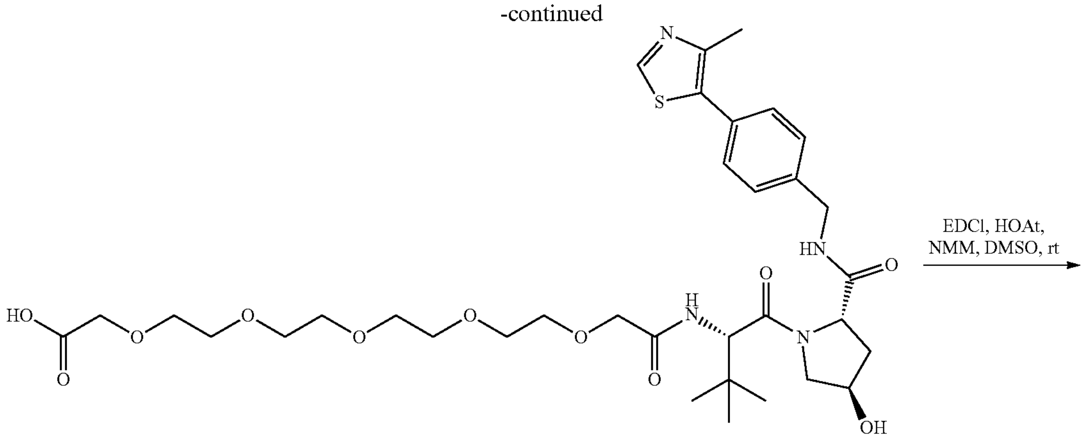

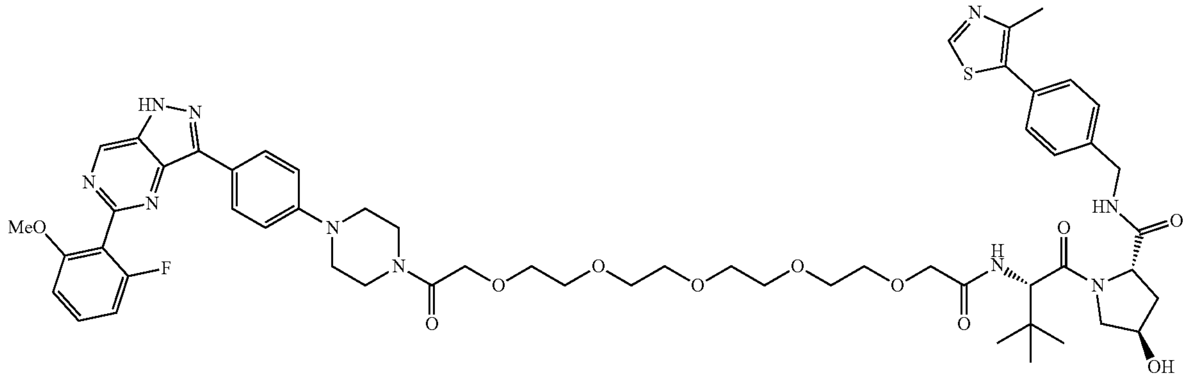

HC90-67

HC90-67 was synthesized following the standard procedure for preparing HC90-33 from Intermediate 13 (6.5 mg, 0.0125 mmol, 1.0 equiv), (S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoic acid (9.1 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-67 was obtained as yellow solid in TFA salt form (9.4 mg, 61%). HRMS calcd for $C_{56}H_{74}FN_{10}O_{11}S^+$ [M+H$^+$] 1109.4925, found 1109.4918.

Example 258

Synthesis of HC90-68

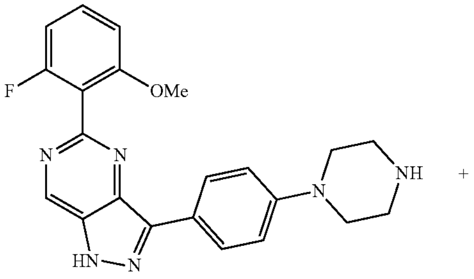

Intermediate 13

-continued

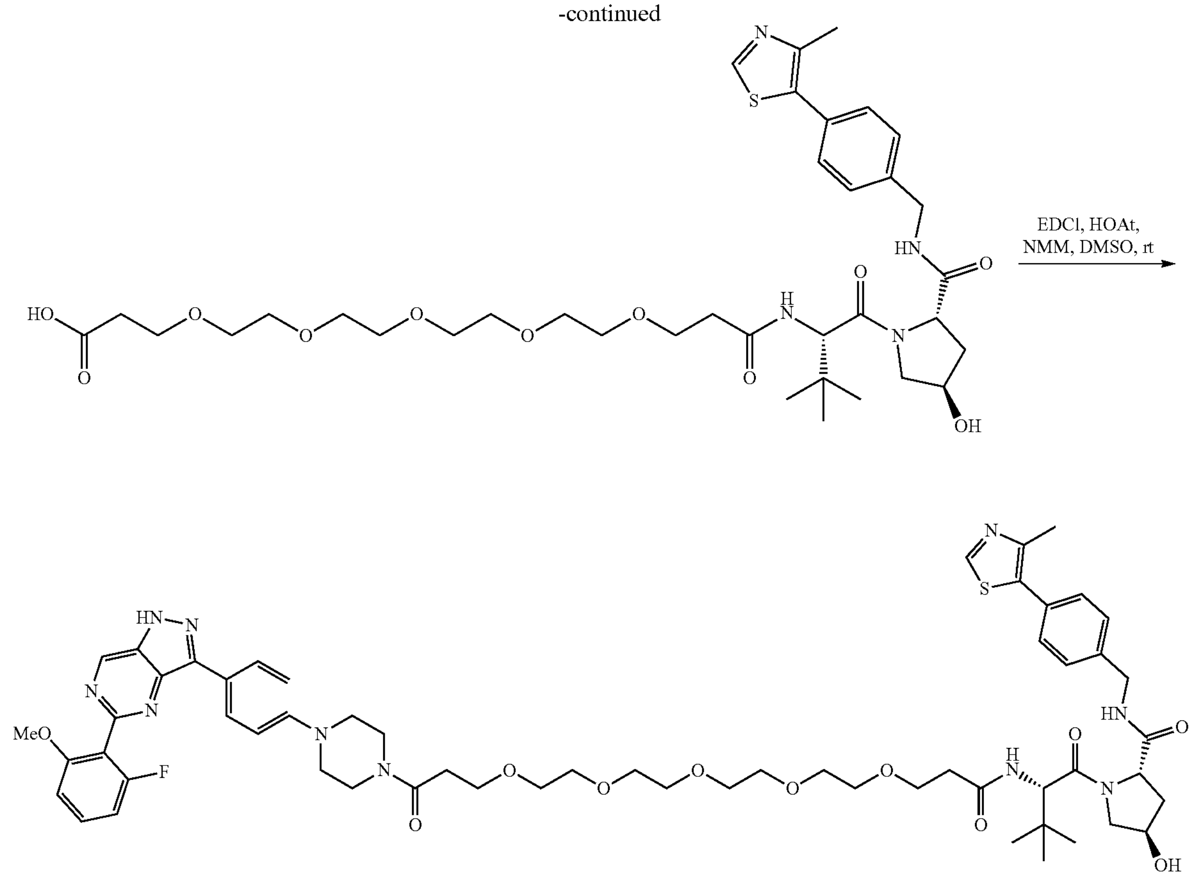

HC90-68

HC90-68 was synthesized following the standard procedure for preparing HC90-33 from Intermediate 13 (6.5 mg, 0.0125 mmol, 1.0 equiv), (S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoic acid (9.4 mg, 0.0125 mmol, 1.0 equiv), EDCI (3.6 mg, 0.019 mmol, 1.5 equiv), HOAt (2.6 mg, 0.019 mmol, 1.5 equiv), and NMM (5.0 mg, 0.05 mmol, 4.0 equiv) in DMSO (1 mL). HC90-68 was obtained as yellow solid in TFA salt form (8.8 mg, 56%). HRMS calcd for $C_{58}H_{74}FN_{10}O_{11}S^+$ [M+H$^+$] 1137.5238, found 1137.5229.

Example 259

Synthesis of Intermediate 15

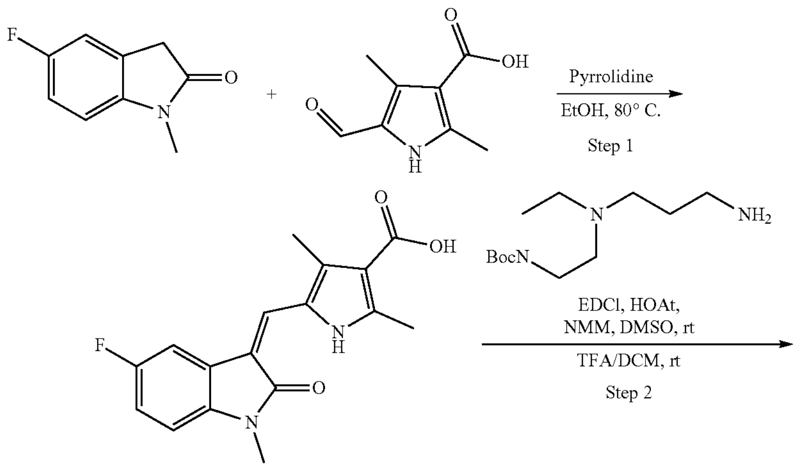

-continued

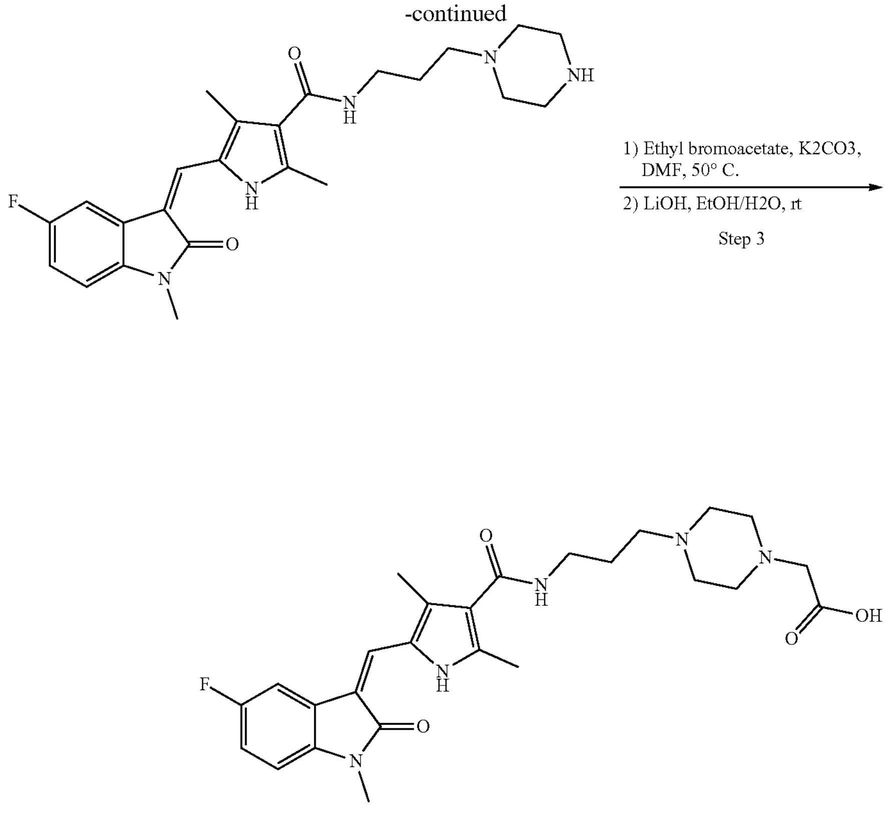

Intermediate 15

Step 1: (Z)-5-((5-fluoro-1-methyl-2-oxoindolin-3-ylidene)methyl)-2,4-dimethyl-1H-pyrrole-3-carboxylic acid A solution of 5-fluoro-1-methylindolin-2-one (82 mg, 0.5 mmol, 1.0 eq), 5-formyl-2,4-dimethyl-1H-pyrrole-3-carboxylic acid (84 g, 0.5 mmol, 1.0 eq), and pyrrolidine (71 mg, 1.0 mmol, 2.0 eq) in ethanol (2 mL) was heated to 80° C. for 3 h. Upon cooling to room temperature, HCl (1 M, 1.5 mL) was added to the suspension and the resulted crude precipitate was recovered by suction filtration, washed with ethanol (2 mL) and petroleum ether (10 mL) to afford (Z)-5-((5-fluoro-1-methyl-2-oxoindolin-3-ylidene)methyl)-2,4-dimethyl-1H-pyrrole-3-carboxylic acid as a yellow powder (155 mg, 99% yield). ESI m/z=315.1 [M+H$^+$].

Step 2: (Z)-5-((5-fluoro-1-methyl-2-oxoindolin-3-ylidene)methyl)-2,4-dimethyl-N-(3-(piperazin-1-yl)propyl)-1H-pyrrole-3-carboxamide To a solution of (Z)-5-((5-fluoro-1-methyl-2-oxoindolin-3-ylidene)methyl)-2,4-dimethyl-1H-pyrrole-3-carboxylic acid (79 mg, 0.25 mmol, 1.0 equiv) in DMSO (2 mL) were added tert-butyl 4-(3-aminopropyl)piperazine-1-carboxylate (73 mg, 0.30 mmol, 1.2 equiv), EDCI (1-ethyl-3-(3-dimethylaminopropyl)carbodiimide) (96 mg, 0.50 mmol, 2.0 equiv), HOAt (1-hydroxy-7-azabenzo-triazole) (68 mg, 0.50 mmol, 2.0 equiv), and NMM (N-Methylmorpholine) (101 mg, 1.00 mmol, 4.0 equiv). After being stirred overnight at room temperature, $H_2O$ (10 mL) was added to the solution and precipitates was filtered. The solid was washed with water and dried under vacuum. The obtained solid was dissolved in DCM (4 mL). To the resulting solution was added TFA (2 ml). After being stirred for 1 h at room temperature, the reaction mixture was concentrated and the residue was purified by reverse phase C18 column (10%-100% methanol/0.1% TFA in $H_2O$) to afford (Z)-5-((5-fluoro-1-methyl-2-oxoindolin-3-ylidene)methyl)-2,4-dimethyl-N-(3-(piperazin-1-yl)propyl)-1H-pyrrole-3-carboxamide as yellow solid in TFA salt form (127 mg, 76% for two steps). ESI m/z=440.2 [M+H$^+$].

Step 3: Intermediate 15

To a solution of (Z)-5-((5-fluoro-1-methyl-2-oxoindolin-3-ylidene)methyl)-2,4-dimethyl-N-(3-(piperazin-1-yl)propyl)-1H-pyrrole-3-carboxamide (127 mg, 0.19 mmol, 1.0 equiv) in DMF (2 mL) was added potassium carbonate (131 mg, 0.95 mmol, 5.0 equiv) and tert-butyl bromoacetate (44 mg, 0.23 mmol, 1.2 equiv). Then the mixture was stirred at 40° C. for 2 h. Water (10 mL) was added to quench the reaction. The mixture was extracted with ethyl acetate (3×10 mL). The organic layer was combined and washed with brine. Dried over $Na_2SO_4$, filtered and evaporated to afford oil. The obtained residue was dissolved in DCM (4 mL). To the solution was added TFA (2 mL). Stirred at room temperature for 1 h and concentrated under vacuum. The residue was purified preparative HPLC (10%-100% acetonitrile/0.1% TFA in $H_2O$) to afford intermediate 15 as a yellow solid (82 mg, 59% for two steps) in TFA salt form. $^1H$ NMR (600 MHz, Methanol-$d_4$) δ 7.64 (s, 1H), 7.51 (d, J=8.8 Hz, 1H), 7.04-6.95 (m, 2H), 3.51 (t, J=6.5 Hz, 2H), 3.46 (s, 2H), 3.38 (s, 3H), 3.35-3.26 (m, 8H), 3.22 (t, J=7.5 Hz, 2H), 2.55 (s, 3H), 2.50 (s, 3H), 2.12-2.04 (m, 2H). ESI m/z=498.3 [M+H$^+$].

Example 260

Synthesis of HC90-114

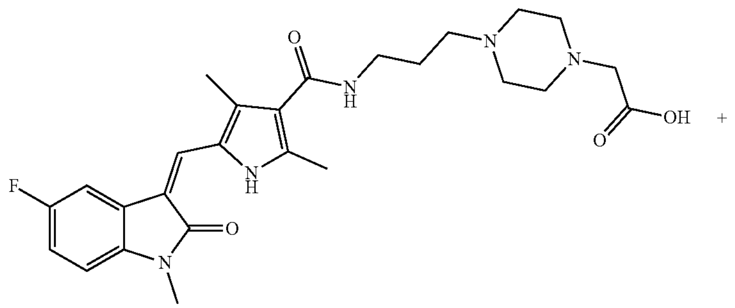

Intermediate 15

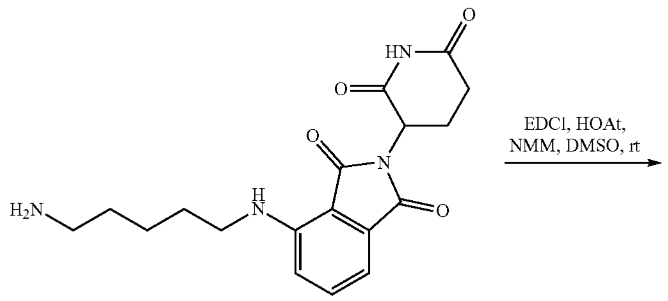

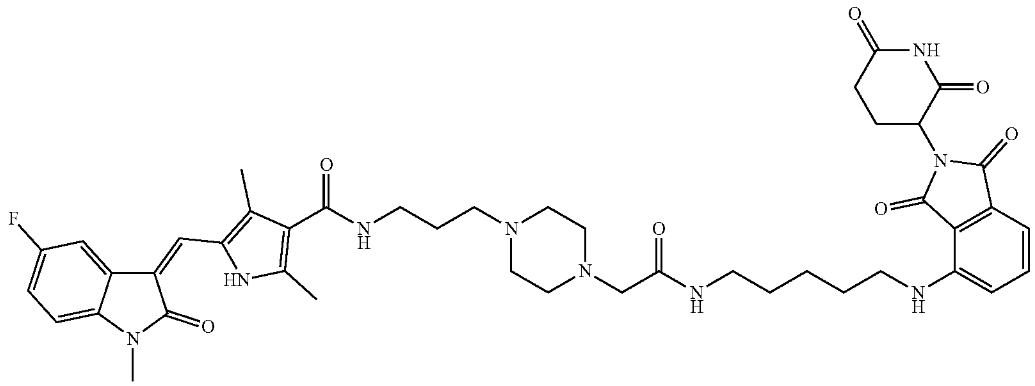

HC90-114

HC90-114 was synthesized following the standard procedure for preparing HC58-53 from Intermediate 15 (9.4 mg, 0.013 mmol, 1.0 equiv), 4-((5-aminooctyl)amino)-2-(2,6-dioxopiperidin-3-yl)isoindoline-1,3-dione (6.8 mg, 0.0143 mmol, 1.1 equiv), EDCI (5.0 mg, 0.026 mmol, 2.0 equiv), HOAt (3.5 mg, 0.026 mmol, 2.0 equiv), and NMM (8.0 mg, 0.078 mmol, 6.0 equiv) in DMSO (1 mL). HC90-114 was obtained as yellow solid in TFA salt form (8.9 mg, 64%). $^1$H NMR (600 MHz, Methanol-$d_4$) δ 7.58-7.53 (m, 2H), 7.45 (dd, J=8.9, 2.2 Hz, 1H), 7.04 (t, J=7.5 Hz, 2H), 6.98-6.92 (m, 2H), 5.06 (dd, J=12.7, 5.5 Hz, 1H), 3.51 (t, J=6.5 Hz, 2H), 3.39-3.31 (m, 13H), 3.29 (t, J=6.7 Hz, 2H), 3.24-3.19 (m, 4H), 2.85 (ddd, J=17.5, 13.9, 5.3 Hz, 1H), 2.79-2.66 (m, 2H), 2.53 (s, 3H), 2.47 (s, 3H), 2.15-2.02 (m, 3H), 1.71 (p, J=6.9 Hz, 2H), 1.62 (p, J=7.0 Hz, 2H), 1.52-1.43 (m, 2H). HRMS calcd for $C_{44}H_{53}FN_9O_7^+$ [M+H$^+$] 838.4046, found 838.4037.

Example 261

Synthesis of HC90-115

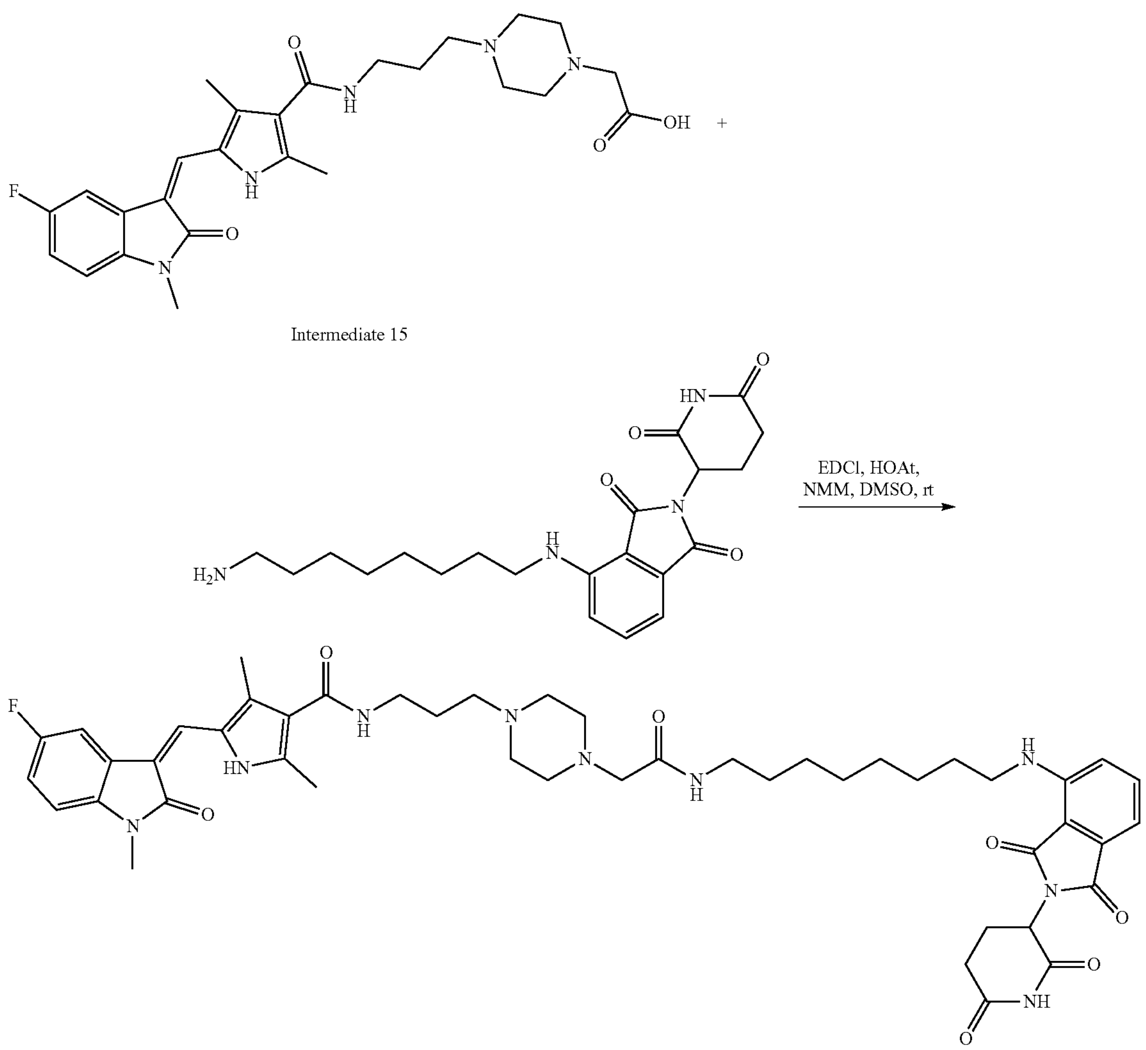

Intermediate 15

HC90-115

HC90-115 was synthesized following the standard procedure for preparing HC58-53 from Intermediate 15 (9.4 mg, 0.013 mmol, 1.0 equiv), 4-((8-aminooctyl)amino)-2-(2,6-dioxopiperidin-3-yl)isoindoline-1,3-dione (7.4 mg, 0.0143 mmol, 1.1 equiv), EDCI (5.0 mg, 0.026 mmol, 2.0 equiv), HOAt (3.5 mg, 0.026 mmol, 2.0 equiv), and NMM (8.0 mg, 0.078 mmol, 6.0 equiv) in DMSO (1 mL). HC90-115 was obtained as yellow solid in TFA salt form (9.3 mg, 65%). $^1$H NMR (600 MHz, Methanol-$d_4$) δ 7.57-7.48 (m, 2H), 7.43 (dd, J=8.8, 2.3 Hz, 1H), 7.01 (dd, J=7.8, 2.4 Hz, 2H), 6.97-6.88 (m, 2H), 5.06 (dd, J=12.8, 5.5 Hz, 1H), 3.51 (t, J=6.6 Hz, 2H), 3.37 (s, 3H), 3.34-3.28 (m, 10H), 3.26-3.19 (m, 6H), 2.87 (ddd, J=17.5, 13.9, 5.3 Hz, 1H), 2.80-2.69 (m, 2H), 2.51 (s, 3H), 2.46 (s, 3H), 2.15-2.05 (m, 3H), 1.66 (p, J=7.1 Hz, 2H), 1.54 (p, J=7.1 Hz, 2H), 1.47-1.29 (m, 8H). HRMS calcd for $C_{47}H_{59}FN_9O_7^+$ [M+H$^+$] 880.4516, found 880.4515.

Example 262

Synthesis of HC90-118

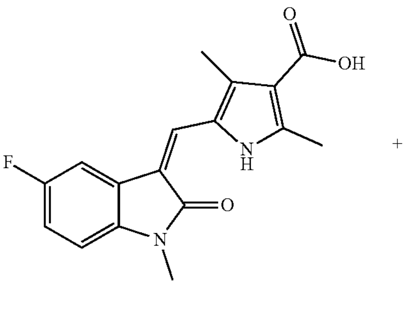

-continued

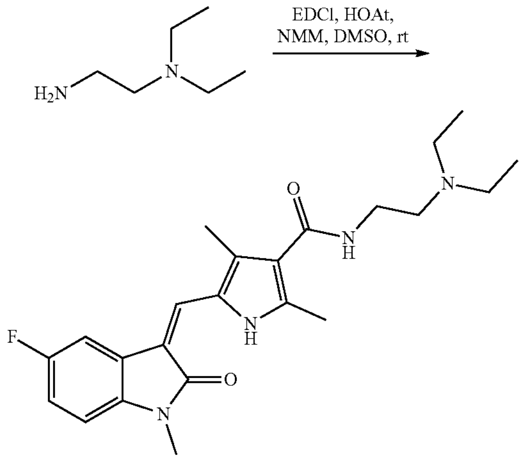

HC90-118

To a solution of (Z)-5-((5-fluoro-1-methyl-2-oxoindolin-3-ylidene)methyl)-2,4-dimethyl-1H-pyrrole-3-carboxylic acid (9.4 mg, 0.03 mmol, 1.0 equiv) in DMSO (1 mL) were added $N^1$,$N^1$-diethylethane-1,2-diamine (7.0 mg, 0.06 mmol, 2.0 equiv), EDCI (1-ethyl-3-(3-dimethylaminopropyl)carbodiimide) (11.5 mg, 0.06 mmol, 2.0 equiv), HOAt (1-hydroxy-7-azabenzo-triazole) (8.2 mg, 0.06 mmol, 2.0 equiv), and NMM (N-Methylmorpholine) (9.1 mg, 0.09 mmol, 3.0 equiv). After being stirred overnight at room temperature, the resulting mixture was purified by preparative HPLC (10%-100% methanol/0.1% TFA in $H_2O$) to afford HC90-118 as yellow solid in TFA salt form (12.0 mg, 76%). $^1$H NMR (600 MHz, Acetone-$d_6$) δ 10.67 (s, 1H), 7.89 (s, 1H), 7.74 (s, 1H), 7.67-7.54 (m, 1H), 7.02-6.98 (m, 2H), 3.90 (q, J=5.5 Hz, 2H), 3.61-3.54 (m, 2H), 3.52-3.44 (m, 4H), 3.36 (s, 3H), 2.59 (s, 3H), 2.53 (s, 3H), 1.44 (t, J=7.2 Hz, 6H). ESI m/z=413.2 [M+H$^+$].

Example 263

Synthesis of HC90-168

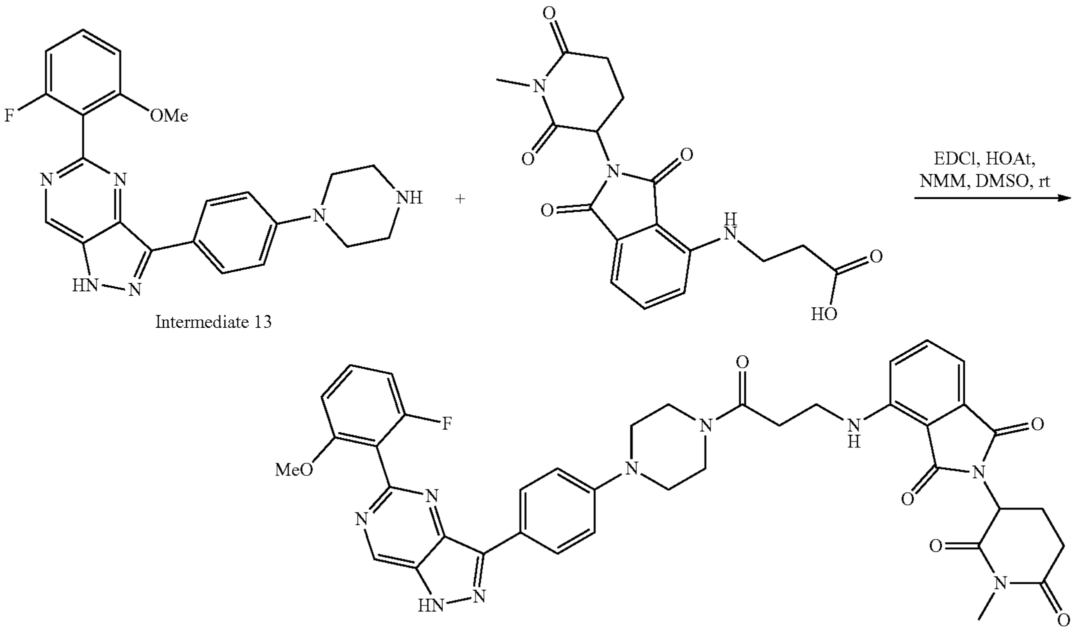

Intermediate 13

HC90-168

HC90-168 was synthesized following the standard procedure for preparing HC90-33 from Intermediate 13 (5.2 mg, 0.01 mmol, 1.0 equiv), 3-((2-(1-methyl-2,6-dioxopiperidin-3-yl)-1,3-dioxoisoindolin-4-yl)amino)propanoic acid (3.6 mg, 0.01 mmol, 1.0 equiv), EDCI (3.8 mg, 0.02 mmol, 2.0 equiv), HOAt (2.7 mg, 0.02 mmol, 2.0 equiv), and NMM (4.0 mg, 0.04 mmol, 4.0 equiv) in DMSO (1 mL). HC90-168 was obtained as yellow solid in TFA salt form (4.8 mg, 64%). $^1$H NMR (600 MHz, Acetone-$d_6$) δ 9.40 (s, 1H), 8.45 (d, J=8.9 Hz, 2H), 7.61 (dd, J=8.6, 7.1 Hz, 1H), 7.50 (td, J=8.5, 6.7 Hz, 1H), 7.18 (d, J=8.6 Hz, 1H), 7.15-7.09 (m, 2H), 7.08-7.00 (m, 2H), 6.91 (t, J=8.7 Hz, 1H), 5.07 (dd, J=13.1, 5.4 Hz, 1H), 3.79 (s, 3H), 3.77-3.68 (m, 6H), 3.31 (t, J=5.3 Hz, 2H), 3.27 (t, J=5.3 Hz, 2H), 3.09 (s, 3H), 2.97 (ddd, J=17.3, 14.0, 5.3 Hz, 1H), 2.90-2.83 (m, 3H), 2.73 (qd, J=13.2, 4.6 Hz, 1H), 2.23-2.13 (m, 1H). HRMS calcd for $C_{39}H_{37}FN_9O_6^+$ [M+H$^+$] 746.2845, found 746.2834.

Example 264

Synthesis of HC90-169

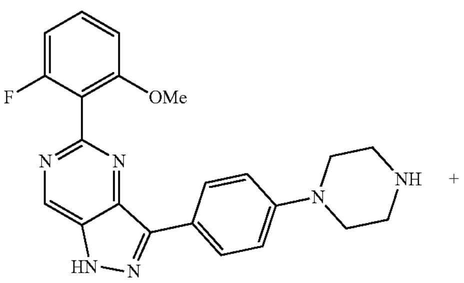

Intermediate 13

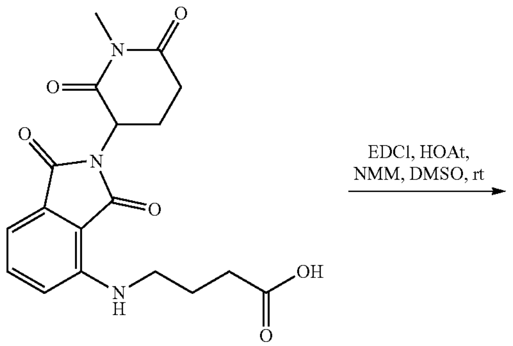

-continued

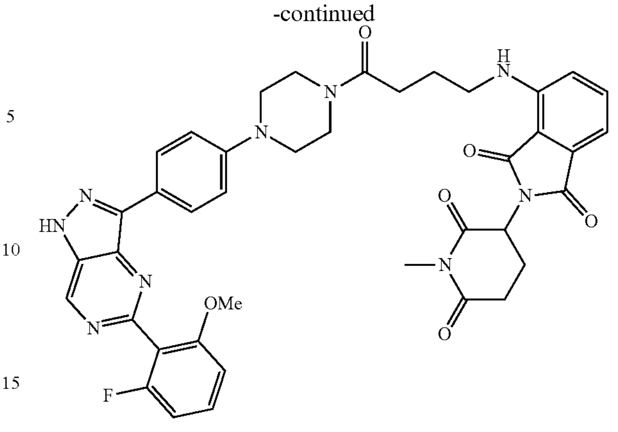

HC90-169

HC90-169 was synthesized following the standard procedure for preparing HC90-33 from Intermediate 13 (5.2 mg, 0.01 mmol, 1.0 equiv), 4-((2-(1-methyl-2,6-dioxopiperidin-3-yl)-1,3-dioxoisoindolin-4-yl)amino)butanoic acid (3.8 mg, 0.01 mmol, 1.0 equiv), EDCI (3.8 mg, 0.02 mmol, 2.0 equiv), HOAt (2.7 mg, 0.02 mmol, 2.0 equiv), and NMM (4.0 mg, 0.04 mmol, 4.0 equiv) in DMSO (1 mL). HC90-169 was obtained as yellow solid in TFA salt form (4.7 mg, 54%). $^1$H NMR (600 MHz, Acetone-$d_6$) δ 9.41 (s, 1H), 8.48-8.44 (m, 2H), 7.61 (ddd, J=8.4, 6.9, 1.2 Hz, 1H), 7.50 (dt, J=9.4, 7.6 Hz, 1H), 7.23 (d, J=8.5 Hz, 1H), 7.13 (d, J=8.4 Hz, 2H), 7.03 (t, J=7.3 Hz, 2H), 6.91 (t, J=8.7 Hz, 1H), 5.08 (dd, J=13.0, 5.4 Hz, 1H), 3.79 (s, 3H), 3.77-3.72 (m, 4H), 3.49 (t, J=7.1 Hz, 2H), 3.34-3.25 (m, 4H), 3.10 (s, 3H), 2.99 (ddd, J=18.6, 13.9, 5.3 Hz, 1H), 2.89 (dt, J=17.4, 3.5 Hz, 1H), 2.75 (qd, J=13.3, 4.5 Hz, 1H), 2.60 (t, J=6.8 Hz, 2H), 2.24-2.15 (m, 1H), 2.02 (p, J=7.0 Hz, 2H). HRMS calcd for $C_{40}H_{39}FN_9O_6^+$ [M+H$^+$] 760.3002, found 760.2991.

Certain compounds disclosed herein have the structures shown in Table 1.

TABLE 1

| Examples | Compound code | Structure | Chemical Name |
| --- | --- | --- | --- |
| 2 | HC58-18 | 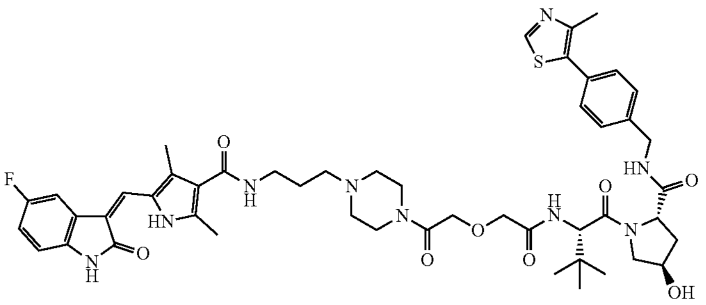 | 5-(((Z)-5-fluoro-2-oxoindolin-3-ylidene)methyl)-N-(3-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)piperazin-1-yl)propyl)-2,4-dimethyl-1H-pyrrole-3-carboxamide |

TABLE 1-continued

| Ex am- ples | Com- pound code | Structure | Chemical Name |
|---|---|---|---|
| 3 | HC58-19 | 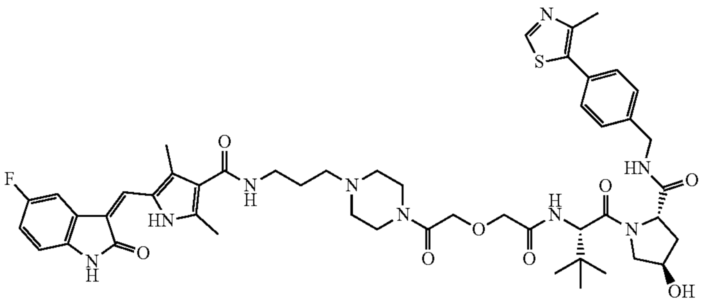 [SMILES: Cc1ncsc1-c1ccc(CNC(=O)[C@@H]2C[C@@H](O)CN2C(=O)[C@@H](NC(=O)COCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)piperazin-1-yl)propyl)-2,4-dimethyl-1H-pyrrole-3-carboxamide |
| 4 | HC58-20 | 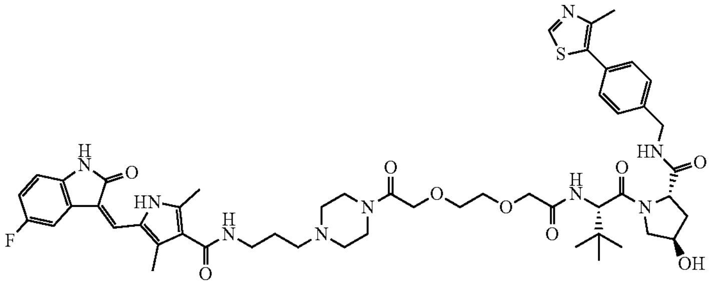 [SMILES: Cc1ncsc1-c1ccc(CNC(=O)[C@@H]2C[C@@H](O)CN2C(=O)[C@@H](NC(=O)COCCOCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)propyl)-2,4-dimethyl-1H-pyrrole-3-carboxamide |
| 5 | HC58-22 | 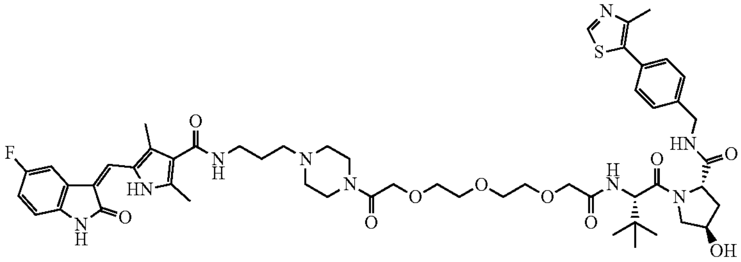 [SMILES: Cc1ncsc1-c1ccc(CNC(=O)[C@@H]2C[C@@H](O)CN2C(=O)[C@@H](NC(=O)COCCOCCOCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)piperazin-1-yl)propyl)-2,4-dimethyl-1H-pyrrole-3-carboxamide |
| 6 | HC58-23 | 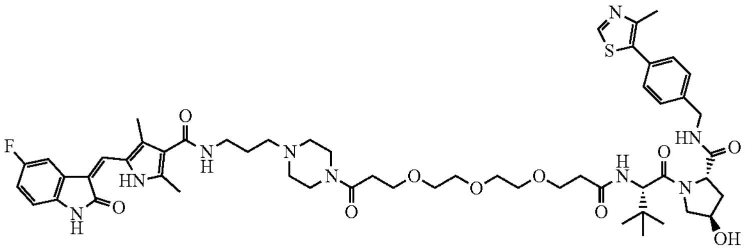 [SMILES: Cc1ncsc1-c1ccc(CNC(=O)[C@@H]2C[C@@H](O)CN2C(=O)[C@@H](NC(=O)CCOCCOCCOCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)propyl)-2,4-dimethyl-1H-pyrrole-3-carboxamide |
| 7 | HC58-24 | 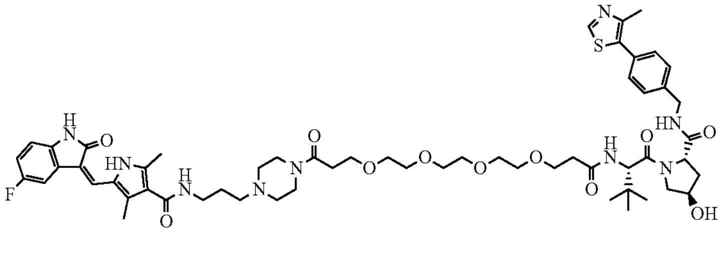 [SMILES: Cc1ncsc1-c1ccc(CNC(=O)[C@@H]2C[C@@H](O)CN2C(=O)[C@@H](NC(=O)CCOCCOCCOCCOCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)propyl)-2,4-dimethyl-1H-pyrrole-3-carboxamide |

TABLE 1-continued

| Examples | Compound code | Structure | Chemical Name |
|---|---|---|---|
| 8 | HC58-25 | 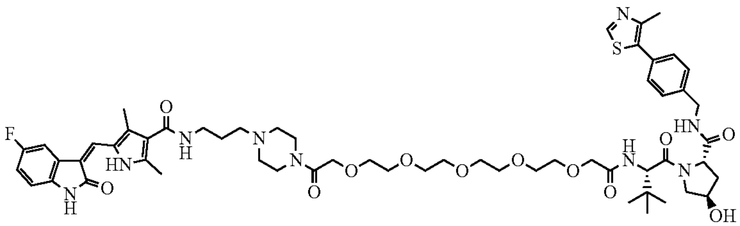 [SMILES: Cc1ncsc1-c1ccc(CNC(=O)[C@@H]2C[C@@H](O)CN2C(=O)[C@@H](NC(=O)COCCOCCOCCOCCOCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoyl)piperazin-1-yl)propyl)-2,4-dimethyl-1H-pyrrole-3-carboxamide |
| 9 | HC58-26 | 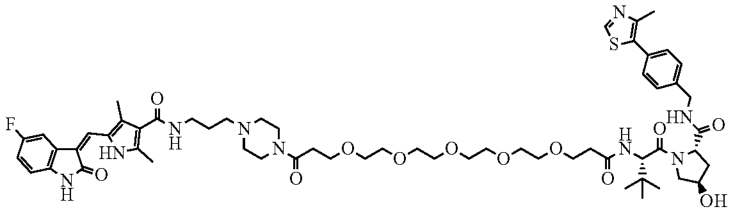 [SMILES: Cc1ncsc1-c1ccc(CNC(=O)[C@@H]2C[C@@H](O)CN2C(=O)[C@@H](NC(=O)CCOCCOCCOCCOCCOCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)piperazin-1-yl)propyl)-2,4-dimethyl-1H-pyrrole-3-carboxamide |
| 10 | HC58-27 | 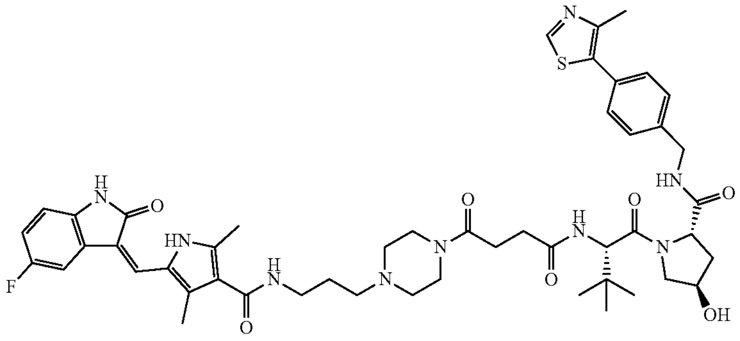 [SMILES: Cc1ncsc1-c1ccc(CNC(=O)[C@@H]2C[C@@H](O)CN2C(=O)[C@@H](NC(=O)CCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)propyl)-2,4-dimethyl-1H-pyrrole-3-carboxamide |
| 11 | HC58-28 | 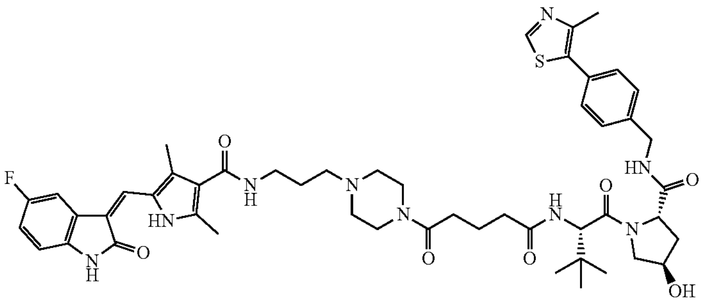 | 5-(((Z)-5-fluoro-2-oxoindolin-3-ylidene)methyl)-N-(3-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)propyl)-2,4-dimethyl-1H-pyrrole-3-carboxamide |
| 12 | HC58-29 | 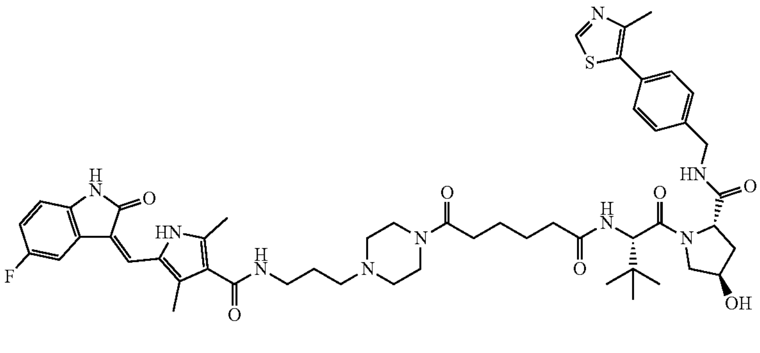 [SMILES: Cc1ncsc1-c1ccc(CNC(=O)[C@@H]2C[C@@H](O)CN2C(=O)[C@@H](NC(=O)CCCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)propyl)-2,4-dimethyl-1H-pyrrole-3-carboxamide |

TABLE 1-continued

| Ex am- ples | Com- pound code | Structure | Chemical Name |
|---|---|---|---|
| 13 | HC58-30 | 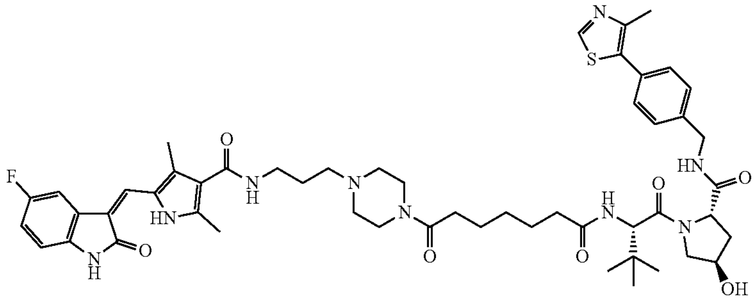 [SMILES: Cc1ncsc1-c1ccc(CNC(=O)[C@@H]2C[C@@H](O)CN2C(=O)[C@@H](NC(=O)CCCCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)propyl)-2,4-dimethyl-1H-pyrrole-3-carboxamide |
| 14 | HC58-31 | 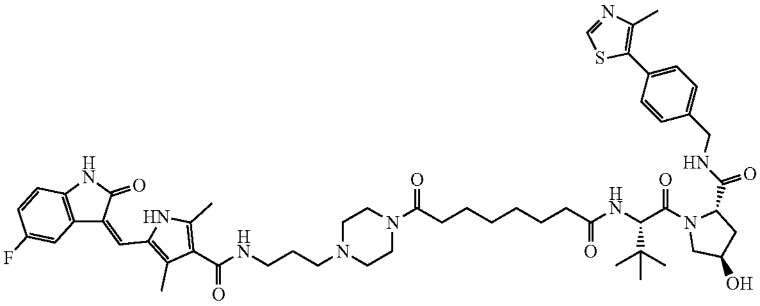 [SMILES: Cc1ncsc1-c1ccc(CNC(=O)[C@@H]2C[C@@H](O)CN2C(=O)[C@@H](NC(=O)CCCCCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)propyl)-2,4-dimethyl-1H-pyrrole-3-carboxamide |
| 15 | HC58-32 | 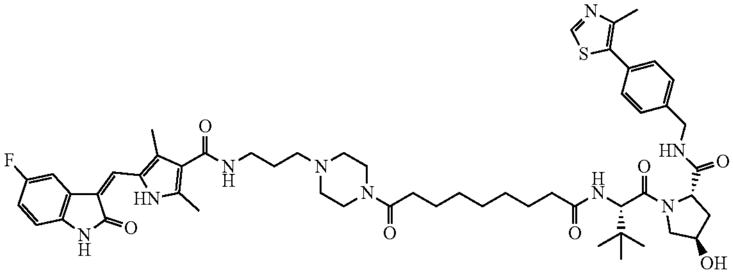 [SMILES: Cc1ncsc1-c1ccc(CNC(=O)[C@@H]2C[C@@H](O)CN2C(=O)[C@@H](NC(=O)CCCCCCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)propyl)-2,4-dimethyl-1H-pyrrole-3-carboxamide |
| 16 | HC58-33 | 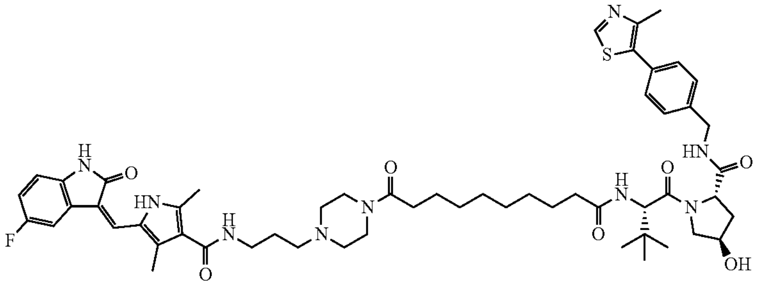 [SMILES: Cc1ncsc1-c1ccc(CNC(=O)[C@@H]2C[C@@H](O)CN2C(=O)[C@@H](NC(=O)CCCCCCCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)propyl)-2,4-dimethyl-1H-pyrrole-3-carboxamide |
| 17 | HC58-34 | 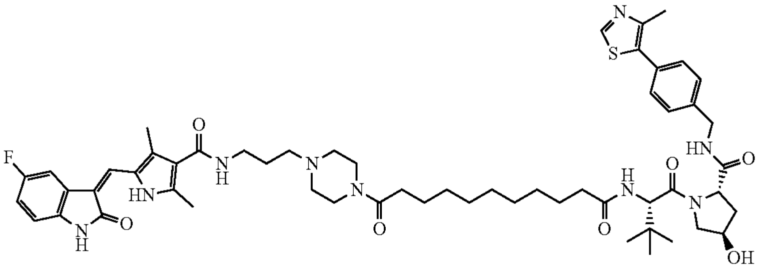 [SMILES: Cc1ncsc1-c1ccc(CNC(=O)[C@@H]2C[C@@H](O)CN2C(=O)[C@@H](NC(=O)CCCCCCCCCC(=O)N2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)propyl)-2,4-dimethyl-1H-pyrrole-3-carboxamide |

TABLE 1-continued

| Examples | Compound code | Structure | Chemical Name |
|---|---|---|---|
| 18 | HC58-35 | 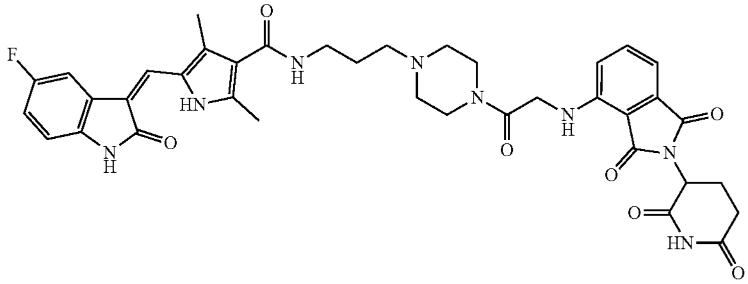 [SMILES: Cc1[nH]c(/C=C2\C(=O)Nc3ccc(F)cc32)c(C)c1C(=O)NCCCN1CCN(C(=O)CNc2cccc3c2C(=O)N(C2CCC(=O)NC2=O)C3=O)CC1] | (Z)-N-(3-(4-((2-(2,6-dioxopiperidin-3-yl)-1,3-dioxoisoindolin-4-yl)glycyl)piperazin-1-yl)propyl)-5-((5-fluoro-2-oxoindolin-3-ylidene)methyl)-2,4-dimethyl-1H-pyrrole-3-carboxamide |
| 19 | HC58-36 | 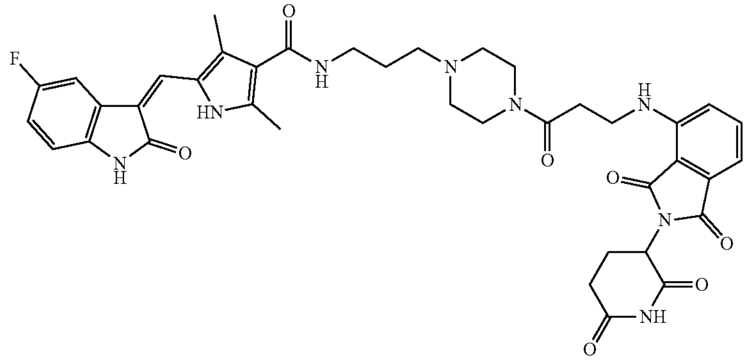 [SMILES: Cc1[nH]c(/C=C2\C(=O)Nc3ccc(F)cc32)c(C)c1C(=O)NCCCN1CCN(C(=O)CCNc2cccc3c2C(=O)N(C2CCC(=O)NC2=O)C3=O)CC1] | (Z)-N-(3-(4-(3-((2-(2,6-dioxopiperidin-3-yl)-1,3-dioxoisoindolin-4-yl)amino)propanoyl)piperazin-1-yl)propyl)-5-((5-fluoro-2-oxoindolin-3-ylidene)methyl)-2,4-dimethyl-1H-pyrrole-3-carboxamide |
| 20 | HC58-37 | 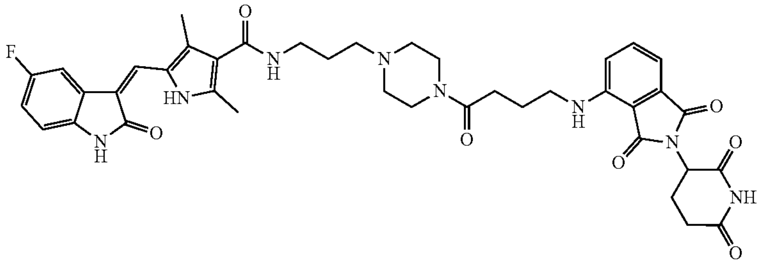 [SMILES: Cc1[nH]c(/C=C2\C(=O)Nc3ccc(F)cc32)c(C)c1C(=O)NCCCN1CCN(C(=O)CCCNc2cccc3c2C(=O)N(C2CCC(=O)NC2=O)C3=O)CC1] | (Z)-N-(3-(4-(4-((2-(2,6-dioxopiperidin-3-yl)-1,3-dioxoisoindolin-4-yl)amino)butanoyl)piperazin-1-yl)propyl)-5-((5-fluoro-2-oxoindolin-3-ylidene)methyl)-2,4-dimethyl-1H-pyrrole-3-carboxamide |
| 21 | HC58-38 | 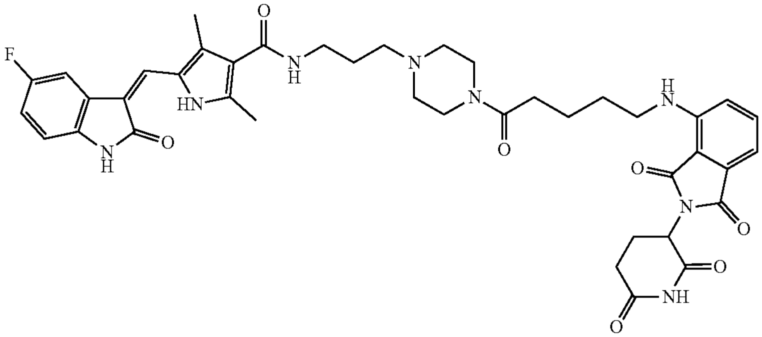 [SMILES: Cc1[nH]c(/C=C2\C(=O)Nc3ccc(F)cc32)c(C)c1C(=O)NCCCN1CCN(C(=O)CCCCNc2cccc3c2C(=O)N(C2CCC(=O)NC2=O)C3=O)CC1] | (Z)-N-(3-(4-(5-((2-(2,6-dioxopiperidin-3-yl)-1,3-dioxoisoindolin-4-yl)amino)pentanoyl)piperazin-1-yl)propyl)-5-((5-fluoro-2-oxoindolin-3-ylidene)methyl)-2,4-dimethyl-1H-pyrrole-3-carboxamide |
| 22 | HC58-39 | 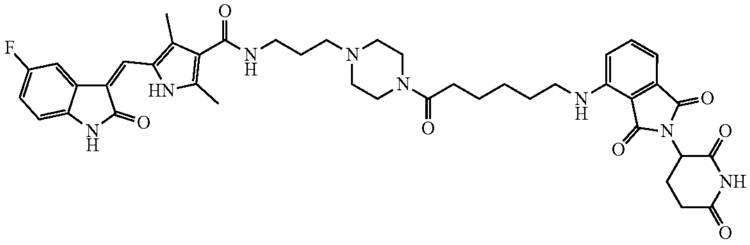 [SMILES: Cc1[nH]c(/C=C2\C(=O)Nc3ccc(F)cc32)c(C)c1C(=O)NCCCN1CCN(C(=O)CCCCCNc2cccc3c2C(=O)N(C2CCC(=O)NC2=O)C3=O)CC1] | (Z)-N-(3-(4-(6-((2-(2,6-dioxopiperidin-3-yl)-1,3-dioxoisoindolin-4-yl)amino)hexanoyl)piperazin-1-yl)propyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 23 | HC58-40 | 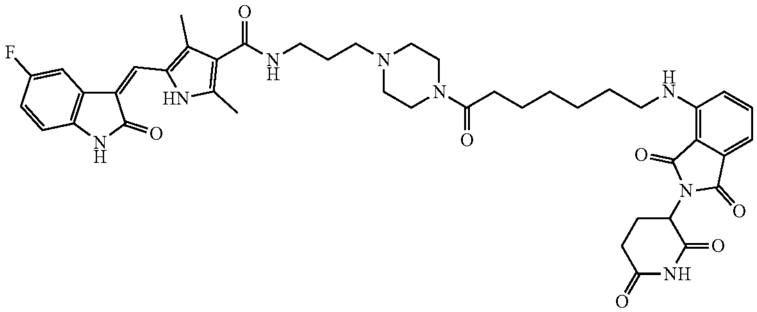 [SMILES: Cc1[nH]c(/C=C2\C(=O)Nc3ccc(F)cc32)c(C)c1C(=O)NCCCN1CCN(C(=O)CCCCCCNc2cccc3c2C(=O)N(C2CCC(=O)NC2=O)C3=O)CC1] | (Z)-N-(3-(4-(7-((2-(2,6-dioxopiperidin-3-yl)-1,3-dioxoisoindolin-4-yl)amino)heptanoyl)piperazin-1-yl)propyl)-5-((5-fluoro-2-oxoindolin-3-ylidene)methyl)-2,4-dimethyl-1H-pyrrole-3-carboxamide |
| 24 | HC58-41 | 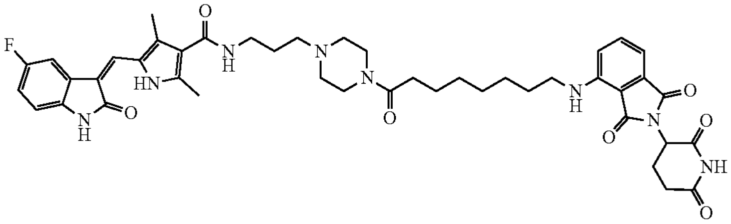 [SMILES: Cc1[nH]c(/C=C2\C(=O)Nc3ccc(F)cc32)c(C)c1C(=O)NCCCN1CCN(C(=O)CCCCCCCNc2cccc3c2C(=O)N(C2CCC(=O)NC2=O)C3=O)CC1] | (Z)-N-(3-(4-(8-((2-(2,6-dioxopiperidin-3-yl)-1,3-dioxoisoindolin-4-yl)amino)octanoyl)piperazin-1-yl)propyl)-5-((5-fluoro-2-oxoindolin-3-ylidene)methyl)-2,4-dimethyl-1H-pyrrole-3-carboxamide |
| 25 | HC58-43 | 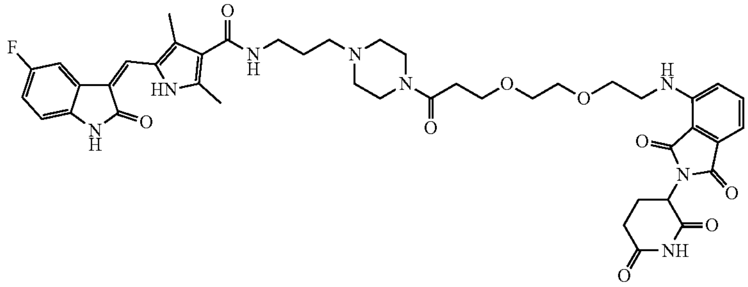 [SMILES: Cc1[nH]c(/C=C2\C(=O)Nc3ccc(F)cc32)c(C)c1C(=O)NCCCN1CCN(C(=O)CCOCCOCCNc2cccc3c2C(=O)N(C2CCC(=O)NC2=O)C3=O)CC1] | (Z)-N-(3-(4-(3-(2-(2-((2-(2,6-dioxopiperidin-3-yl)-1,3-dioxoisoindolin-4-yl)amino)ethoxy)ethoxy)propanoyl)piperazin-1-yl)propyl)-5-((5-fluoro-2-oxoindolin-3-ylidene)methyl)-2,4-dimethyl-1H-pyrrole-3-carboxamide |
| 26 | HC58-44 | 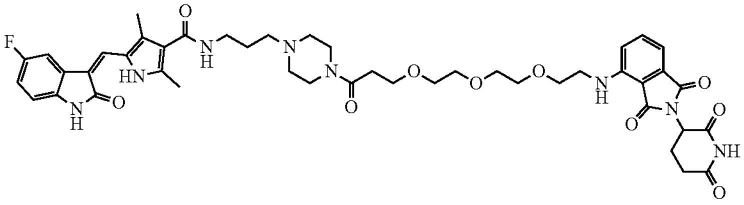 [SMILES: Cc1[nH]c(/C=C2\C(=O)Nc3ccc(F)cc32)c(C)c1C(=O)NCCCN1CCN(C(=O)CCOCCOCCOCCNc2cccc3c2C(=O)N(C2CCC(=O)NC2=O)C3=O)CC1] | (Z)-N-(3-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)propyl)-5-((5-fluoro-2-oxoindolin-3-ylidene)methyl)-2,4-dimethyl-1H-pyrrole-3-carboxamide |
| 27 | HC58-45 | 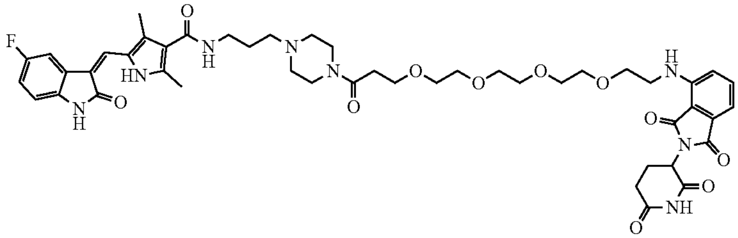 [SMILES: Cc1[nH]c(/C=C2\C(=O)Nc3ccc(F)cc32)c(C)c1C(=O)NCCCN1CCN(C(=O)CCOCCOCCOCCOCCNc2cccc3c2C(=O)N(C2CCC(=O)NC2=O)C3=O)CC1] | (Z)-N-(3-(4-(1-((2-(2,6-dioxopiperidin-3-yl)-1,3-dioxoisoindolin-4-yl)amino)-3,6,9,12-tetraoxapentadecan-15-oyl)piperazin-1-yl)propyl)-5-((5-fluoro-2-oxoindolin-3-ylidene)methyl)-2,4-dimethyl-1H-pyrrole-3-carboxamide |
| 28 | HC58-46 | 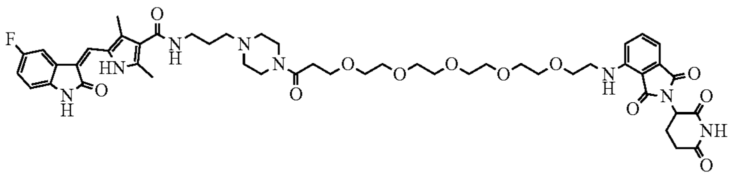 [SMILES: Cc1[nH]c(/C=C2\C(=O)Nc3ccc(F)cc32)c(C)c1C(=O)NCCCN1CCN(C(=O)CCOCCOCCOCCOCCOCCNc2cccc3c2C(=O)N(C2CCC(=O)NC2=O)C3=O)CC1] | (Z)-N-(3-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)propyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 30 | HC58-53 | 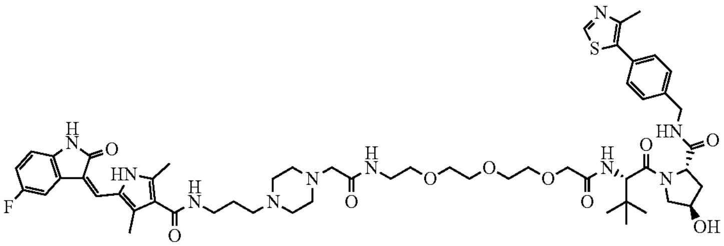 [SMILES: Cc1ncsc1-c1ccc(CNC(=O)[C@@H]2C[C@@H](O)CN2C(=O)[C@@H](NC(=O)COCCOCCOCCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-((S)-16-((2S,4R)-4-hydroxy-2-((4-(4-methylthiazol-5-yl)benzyl)carbamoyl)pyrrolidine-1-carbonyl)-17,17-dimethyl-2,14-dioxo-6,9,12-trioxa-3,15-diazaoctadecyl)piperazin-1-yl)propyl)-2,4-dimethyl-1H-pyrrole-3-carboxamide |
| 31 | HC58-57 | 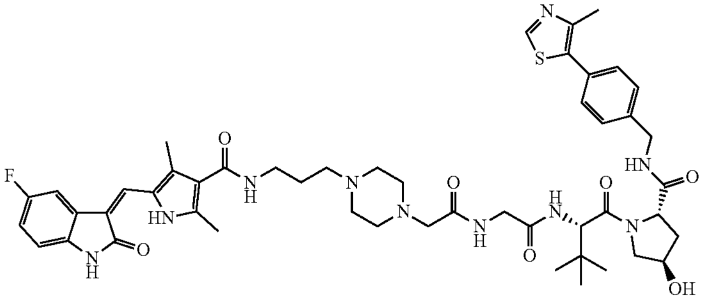 [SMILES: Cc1ncsc1-c1ccc(CNC(=O)[C@@H]2C[C@@H](O)CN2C(=O)[C@@H](NC(=O)CNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)amino)-2-oxoethyl)piperazin-1-yl)propyl)-2,4-dimethyl-1H-pyrrole-3-carboxamide |
| 32 | HC58-58 | 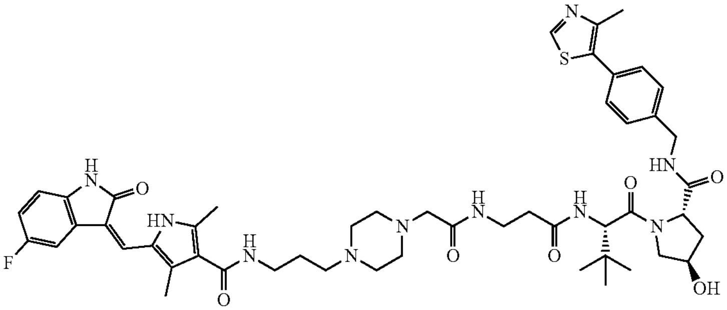 [SMILES: Cc1ncsc1-c1ccc(CNC(=O)[C@@H]2C[C@@H](O)CN2C(=O)[C@@H](NC(=O)CCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-2-oxoethyl)piperazin-1-yl)propyl)-2,4-dimethyl-1H-pyrrole-3-carboxamide |
| 33 | HC58-59 | 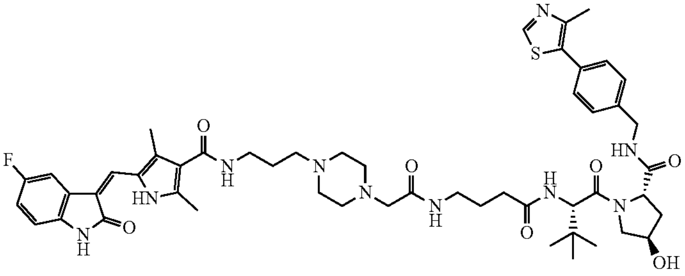 [SMILES: Cc1ncsc1-c1ccc(CNC(=O)[C@@H]2C[C@@H](O)CN2C(=O)[C@@H](NC(=O)CCCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)amino)-2-oxoethyl)piperazin-1-yl)propyl)-2,4-dimethyl-1H-pyrrole-3-carboxamide |
| 34 | HC58-60 | 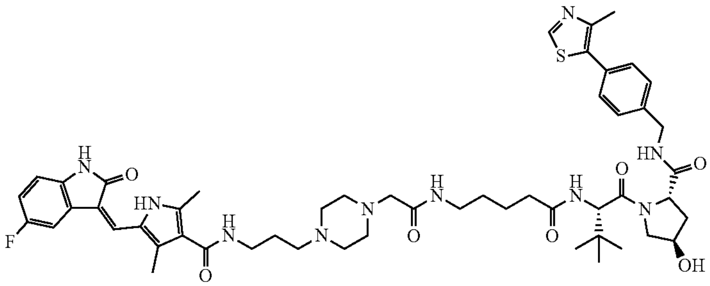 [SMILES: Cc1ncsc1-c1ccc(CNC(=O)[C@@H]2C[C@@H](O)CN2C(=O)[C@@H](NC(=O)CCCCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-2-oxoethyl)piperazin-1-yl)propyl)-2,4-dimethyl-1H-pyrrole-3-carboxamide |

TABLE 1-continued

| Ex am- ples | Com- pound code | Structure | Chemical Name |
|---|---|---|---|
| 35 | HC58-63 | 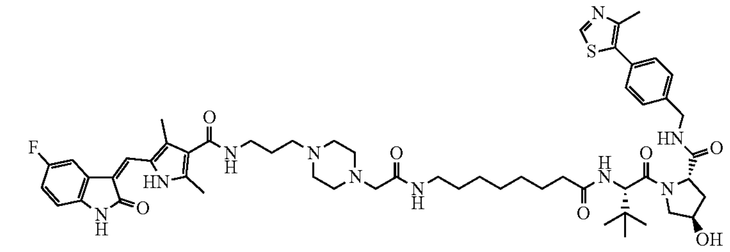 [SMILES: Cc1ncsc1-c1ccc(CNC(=O)[C@@H]2C[C@@H](O)CN2C(=O)[C@@H](NC(=O)CCCCCCCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)amino)-2-oxoethyl)piperazin-1-yl)propyl)-2,4-dimethyl-1H-pyrrole-3-carboxamide |
| 36 | HC58-64 | 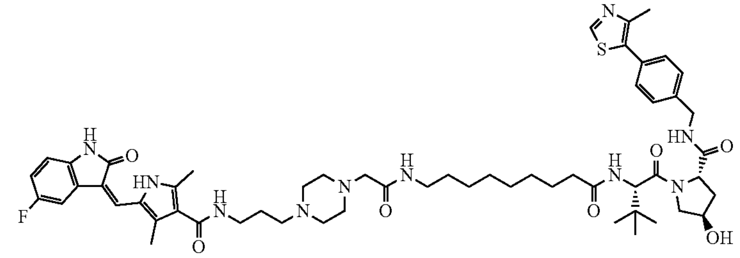 [SMILES: Cc1ncsc1-c1ccc(CNC(=O)[C@@H]2C[C@@H](O)CN2C(=O)[C@@H](NC(=O)CCCCCCCCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-2-oxoethyl)piperazin-1-yl)propyl)-2,4-dimethyl-1H-pyrrole-3-carboxamide |
| 37 | HC58-65 | 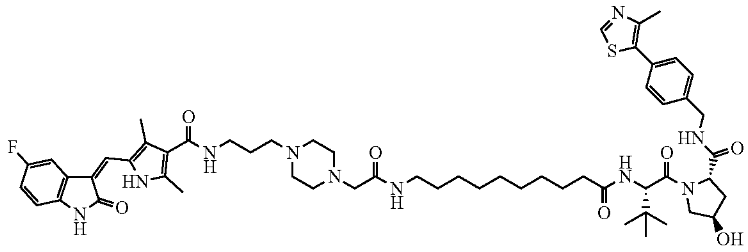 [SMILES: Cc1ncsc1-c1ccc(CNC(=O)[C@@H]2C[C@@H](O)CN2C(=O)[C@@H](NC(=O)CCCCCCCCCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)amino)-2-oxoethyl)piperazin-1-yl)propyl)-2,4-dimethyl-1H-pyrrole-3-carboxamide |
| 38 | HC58-66 | 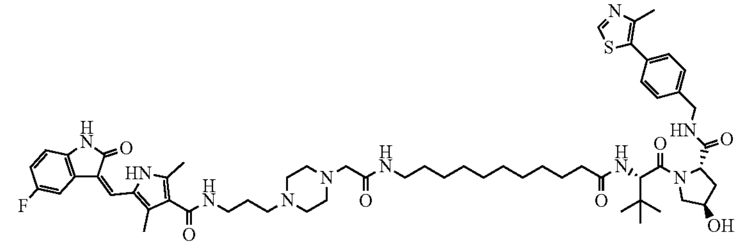 [SMILES: Cc1ncsc1-c1ccc(CNC(=O)[C@@H]2C[C@@H](O)CN2C(=O)[C@@H](NC(=O)CCCCCCCCCCNC(=O)CN2CCN(CCCNC(=O)c3c(C)[nH]c(/C=C4\C(=O)Nc5ccc(F)cc54)c3C)CC2)C(C)(C)C)cc1] | 5-(((Z)-5-fluoro-2-oxoindolin-3-ylidene)methyl)-N-(3-(4-(2-((11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)amino)-2-oxoethyl)piperazin-1-yl)propyl)-2,4-dimethyl-1H-pyrrole-3-carboxamide |
| 39 | HC58-67 | 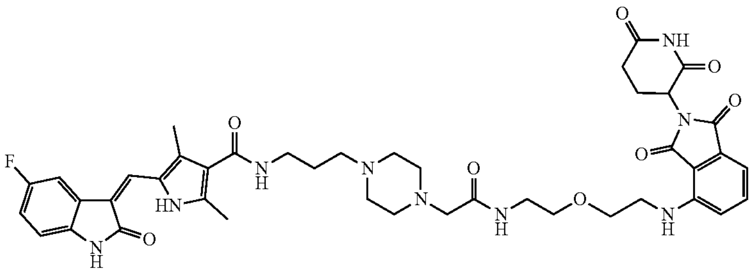 [SMILES: Cc1[nH]c(/C=C2\C(=O)Nc3ccc(F)cc32)c(C)c1C(=O)NCCCN1CCN(CC(=O)NCCOCCNc2cccc3c2C(=O)N(C2CCC(=O)NC2=O)C3=O)CC1] | (Z)-N-(3-(4-(2-((2-(2-((2-(2,6-dioxopiperidin-3-yl)-1,3-dioxoisoindolin-4-yl)amino)ethoxy)ethyl)amino)-2-oxoethyl)piperazin-1-yl)propyl)-5-((5-fluoro-2-oxoindolin-3-ylidene)methyl)-2,4-dimethyl-1H-pyrrole-3-carboxamide |

TABLE 1-continued

| Ex am- ples | Com- pound code | Structure | Chemical Name |
|---|---|---|---|
| 40 | HC58-68 | 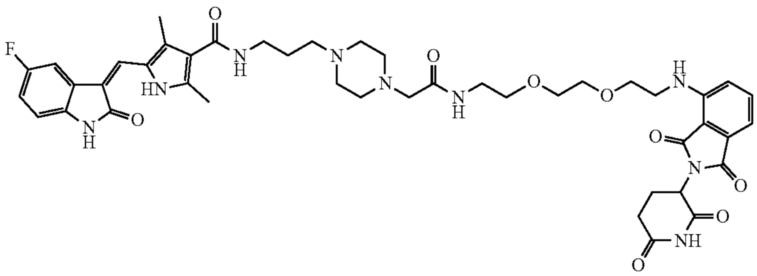 [SMILES: Cc1[nH]c(/C=C2\C(=O)Nc3ccc(F)cc32)c(C)c1C(=O)NCCCN1CCN(CC(=O)NCCOCCOCCNc2cccc3c2C(=O)N(C2CCC(=O)NC2=O)C3=O)CC1] | (Z)-N-(3-(4-(2-((2-(2-(2-((2-(2,6-dioxopiperidin-3-yl)-1,3-dioxoisoindolin-4-yl)amino)ethoxy)ethoxy)ethyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 41 | HC58-69 | 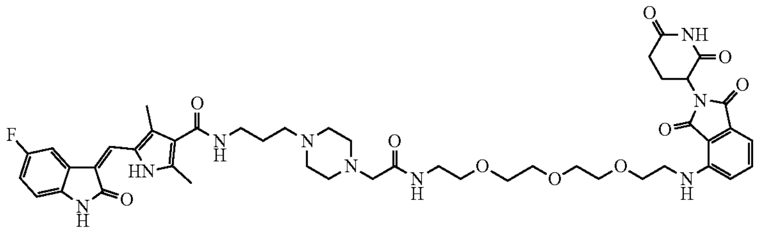 [SMILES: Cc1[nH]c(/C=C2\C(=O)Nc3ccc(F)cc32)c(C)c1C(=O)NCCCN1CCN(CC(=O)NCCOCCOCCOCCNc2cccc3c2C(=O)N(C2CCC(=O)NC2=O)C3=O)CC1] | (Z)-N-(3-(4-(14-((2-(2,6-dioxopiperidin-3-yl)-1,3-dioxoisoindolin-4-yl)amino)-2-oxo-6,9,12-trioxa-3-azatetradecyl)piperazin-1-yl)propyl)-5-((5-fluoro-2-oxoindolin-3-ylidene)methyl)-2,4-dimethyl-1H-pyrrole-3-carboxamide |
| 42 | HC58-70 | 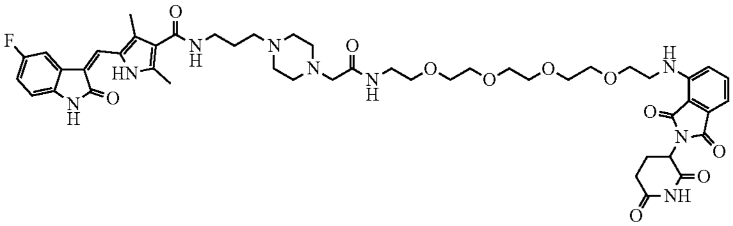 [SMILES: Cc1[nH]c(/C=C2\C(=O)Nc3ccc(F)cc32)c(C)c1C(=O)NCCCN1CCN(CC(=O)NCCOCCOCCOCCOCCNc2cccc3c2C(=O)N(C2CCC(=O)NC2=O)C3=O)CC1] | (Z)-N-(3-(4-(17-((2-(2,6-dioxopiperidin-3-yl)-1,3-dioxoisoindolin-4-yl)amino)-2-oxo-6,9,12,15-tetraoxa-3-azaheptadecyl)piperazin-1-yl)propyl)-5-((5-fluoro-2-oxoindolin-3-ylidene)methyl)-2,4-dimethyl-1H-pyrrole-3-carboxamide |
| 43 | HC58-71 | 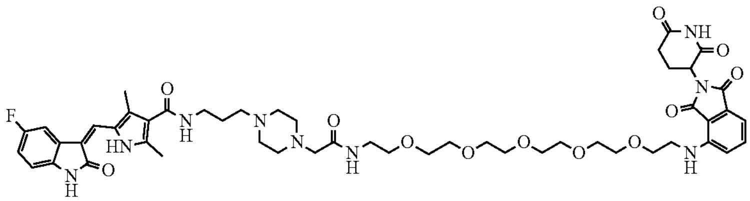 [SMILES: Cc1[nH]c(/C=C2\C(=O)Nc3ccc(F)cc32)c(C)c1C(=O)NCCCN1CCN(CC(=O)NCCOCCOCCOCCOCCOCCNc2cccc3c2C(=O)N(C2CCC(=O)NC2=O)C3=O)CC1] | (Z)-N-(3-(4-(20-((2-(2,6-dioxopiperidin-3-yl)-1,3-dioxoisoindolin-4-yl)amino)-2-oxo-6,9,12,15,18-pentaoxa-3-azaicosyl)piperazin-1-yl)propyl)-5-((5-fluoro-2-oxoindolin-3-ylidene)methyl)-2,4-dimethyl-1H-pyrrole-3-carboxamide |
| 44 | HC58-73 | 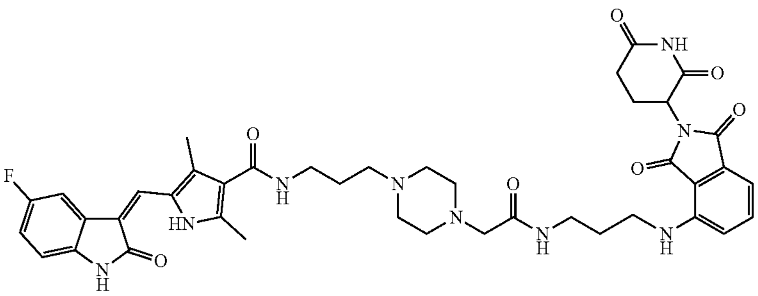 [SMILES: Cc1[nH]c(/C=C2\C(=O)Nc3ccc(F)cc32)c(C)c1C(=O)NCCCN1CCN(CC(=O)NCCCNc2cccc3c2C(=O)N(C2CCC(=O)NC2=O)C3=O)CC1] | (Z)-N-(3-(4-(2-((3-((2-(2,6-dioxopiperidin-3-yl)-1,3-dioxoisoindolin-4-yl)amino)propyl)amino)-2-oxoethyl)piperazin-1-yl)propyl)-5-((5-fluoro-2-oxoindolin-3-ylidene)methyl)-2,4-dimethyl-1H-pyrrole-3-carboxamide |

TABLE 1-continued

| Ex amples | Compound code | Structure | Chemical Name |
|---|---|---|---|
| 45 | HC58-74 | 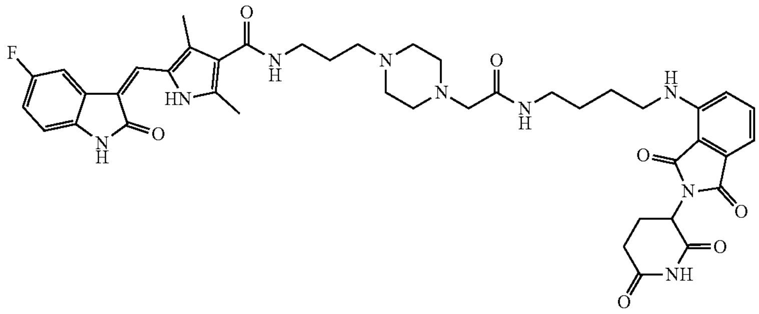 [SMILES: Cc1[nH]c(/C=C2\C(=O)Nc3ccc(F)cc32)c(C)c1C(=O)NCCCN1CCN(CC(=O)NCCCCNc2cccc3c2C(=O)N(C2CCC(=O)NC2=O)C3=O)CC1] | (Z)-N-(3-(4-(2-((4-((2-(2,6-dioxopiperidin-3-yl)-1,3-dioxoisoindolin-4-yl)amino)butyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 46 | HC58-75 | 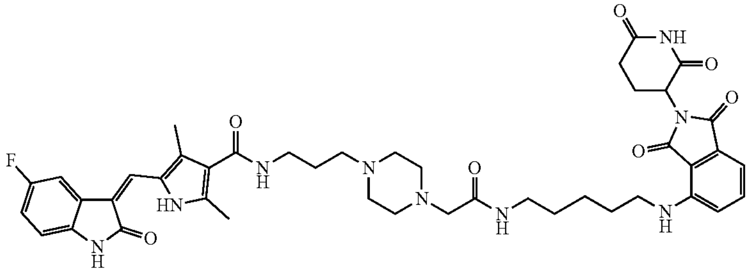 [SMILES: Cc1[nH]c(/C=C2\C(=O)Nc3ccc(F)cc32)c(C)c1C(=O)NCCCN1CCN(CC(=O)NCCCCCNc2cccc3c2C(=O)N(C2CCC(=O)NC2=O)C3=O)CC1] | (Z)-N-(3-(4-(2-((5-((2-(2,6-dioxopiperidin-3-yl)-1,3-dioxoisoindolin-4-yl)amino)pentyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 47 | HC58-76 | 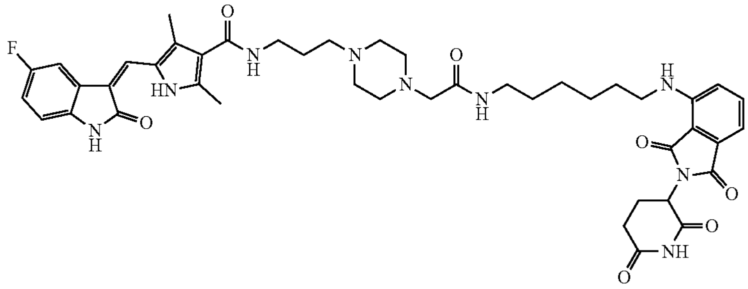 [SMILES: Cc1[nH]c(/C=C2\C(=O)Nc3ccc(F)cc32)c(C)c1C(=O)NCCCN1CCN(CC(=O)NCCCCCCNc2cccc3c2C(=O)N(C2CCC(=O)NC2=O)C3=O)CC1] | (Z)-N-(3-(4-(2-((6-((2-(2,6-dioxopiperidin-3-yl)-1,3-dioxoisoindolin-4-yl)amino)hexyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 48 | HC58-77 | 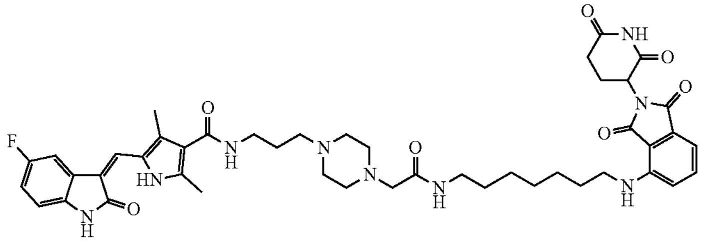 [SMILES: Cc1[nH]c(/C=C2\C(=O)Nc3ccc(F)cc32)c(C)c1C(=O)NCCCN1CCN(CC(=O)NCCCCCCCNc2cccc3c2C(=O)N(C2CCC(=O)NC2=O)C3=O)CC1] | (Z)-N-(3-(4-(2-((7-((2-(2,6-dioxopiperidin-3-yl)-1,3-dioxoisoindolin-4-yl)amino)heptyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 49 | HC58-78 | 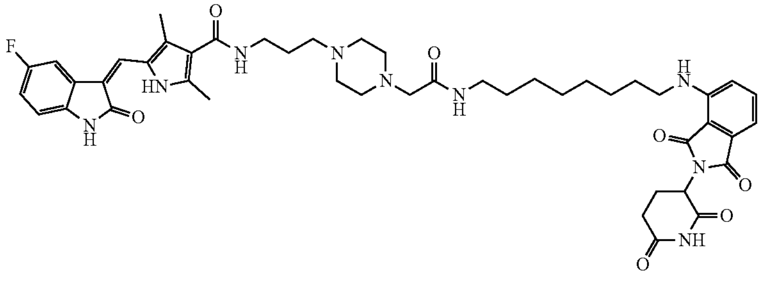 [SMILES: Cc1[nH]c(/C=C2\C(=O)Nc3ccc(F)cc32)c(C)c1C(=O)NCCCN1CCN(CC(=O)NCCCCCCCCNc2cccc3c2C(=O)N(C2CCC(=O)NC2=O)C3=O)CC1] | (Z)-N-(3-(4-(2-((8-((2-(2,6-dioxopiperidin-3-yl)-1,3-dioxoisoindolin-4-yl)amino)octyl)amino)-2-oxoethyl)piperazin-1-yl)propyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 51 | HC58-133 | 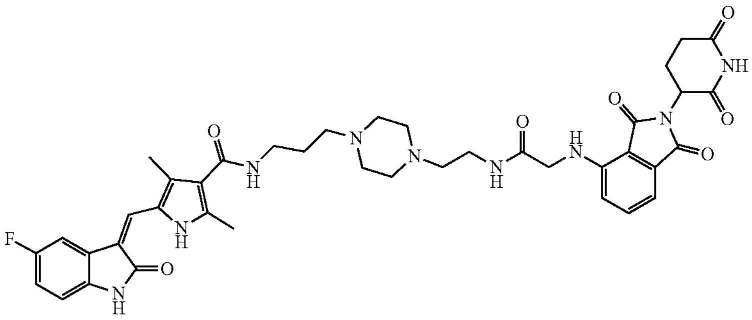 [SMILES: Cc1[nH]c(/C=C2\C(=O)Nc3ccc(F)cc32)c(C)c1C(=O)NCCCN1CCN(CCNC(=O)CNc2cccc3c2C(=O)N(C2CCC(=O)NC2=O)C3=O)CC1] | (Z)-N-(3-(4-(2-(2-((2-(2,6-dioxopiperidin-3-yl)-1,3-dioxoisoindolin-4-yl)amino)acetamido)ethyl)piperazin-1-yl)propyl)-5-((5-fluoro-2-oxoindolin-3-ylidene)methyl)-2,4-dimethyl-1H-pyrrole-3-carboxamide |
| 52 | HC58-134 | 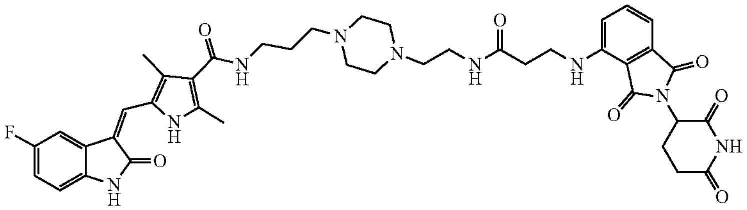 [SMILES: Cc1[nH]c(/C=C2\C(=O)Nc3ccc(F)cc32)c(C)c1C(=O)NCCCN1CCN(CCNC(=O)CCNc2cccc3c2C(=O)N(C2CCC(=O)NC2=O)C3=O)CC1] | (Z)-N-(3-(4-(2-(3-((2-(2,6-dioxopiperidin-3-yl)-1,3-dioxoisoindolin-4-yl)amino)propanamido)ethyl)piperazin-1-yl)propyl)-5-((5-fluoro-2-oxoindolin-3-ylidene)methyl)-2,4-dimethyl-1H-pyrrole-3-carboxamide |
| 53 | HC58-135 | 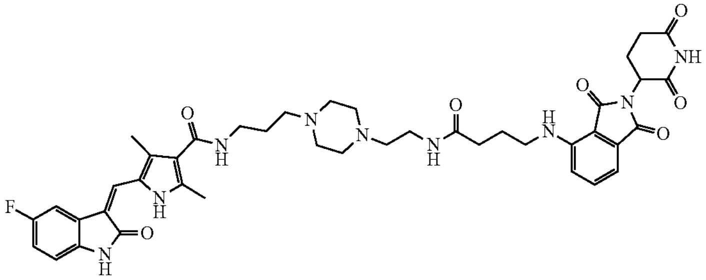 [SMILES: Cc1[nH]c(/C=C2\C(=O)Nc3ccc(F)cc32)c(C)c1C(=O)NCCCN1CCN(CCNC(=O)CCCNc2cccc3c2C(=O)N(C2CCC(=O)NC2=O)C3=O)CC1] | (Z)-N-(3-(4-(2-(4-((2-(2,6-dioxopiperidin-3-yl)-1,3-dioxoisoindolin-4-yl)amino)butanamido)ethyl)piperazin-1-yl)propyl)-5-((5-fluoro-2-oxoindolin-3-ylidene)methyl)-2,4-dimethyl-1H-pyrrole-3-carboxamide |
| 54 | HC58-136 | 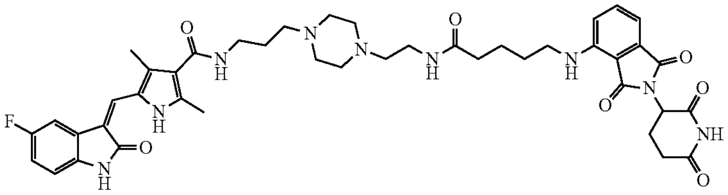 [SMILES: Cc1[nH]c(/C=C2\C(=O)Nc3ccc(F)cc32)c(C)c1C(=O)NCCCN1CCN(CCNC(=O)CCCCNc2cccc3c2C(=O)N(C2CCC(=O)NC2=O)C3=O)CC1] | (Z)-N-(3-(4-(2-(5-((2-(2,6-dioxopiperidin-3-yl)-1,3-dioxoisoindolin-4-yl)amino)pentanamido)ethyl)piperazin-1-yl)propyl)-5-((5-fluoro-2-oxoindolin-3-ylidene)methyl)-2,4-dimethyl-1H-pyrrole-3-carboxamide |
| 55 | HC58-137 | 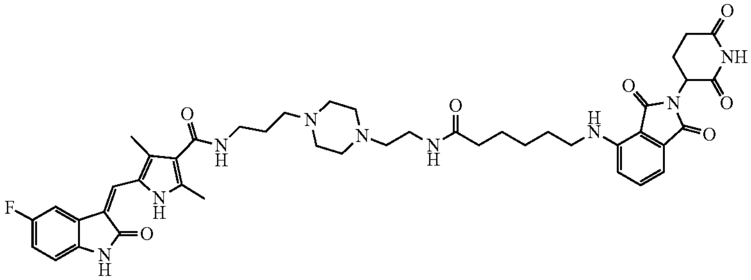 [SMILES: Cc1[nH]c(/C=C2\C(=O)Nc3ccc(F)cc32)c(C)c1C(=O)NCCCN1CCN(CCNC(=O)CCCCCNc2cccc3c2C(=O)N(C2CCC(=O)NC2=O)C3=O)CC1] | (Z)-N-(3-(4-(2-(6-((2-(2,6-dioxopiperidin-3-yl)-1,3-dioxoisoindolin-4-yl)amino)hexanamido)ethyl)piperazin-1-yl)propyl)-5-((5-fluoro-2-oxoindolin-3-ylidene)methyl)-2,4-dimethyl-1H-pyrrole-3-carboxamide |
| 56 | HC58-138 | 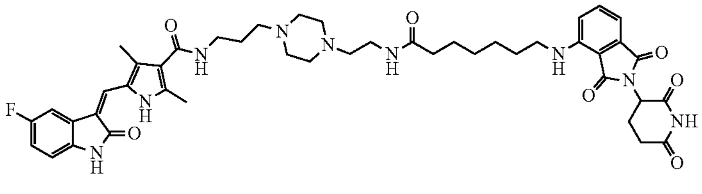 [SMILES: Cc1[nH]c(/C=C2\C(=O)Nc3ccc(F)cc32)c(C)c1C(=O)NCCCN1CCN(CCNC(=O)CCCCCCNc2cccc3c2C(=O)N(C2CCC(=O)NC2=O)C3=O)CC1] | (Z)-N-(3-(4-(2-(7-((2-(2,6-dioxopiperidin-3-yl)-1,3-dioxoisoindolin-4-yl)amino)heptanamido)ethyl)piperazin-1-yl)propyl)-5-((5-fluoro-2-oxoindolin-3-ylidene)methyl)-2,4-dimethyl-1H-pyrrole-3-carboxamide |

TABLE 1-continued

| Ex am- ples | Com- pound code | Structure | Chemical Name |
|---|---|---|---|
| 57 | HC58- 139 | 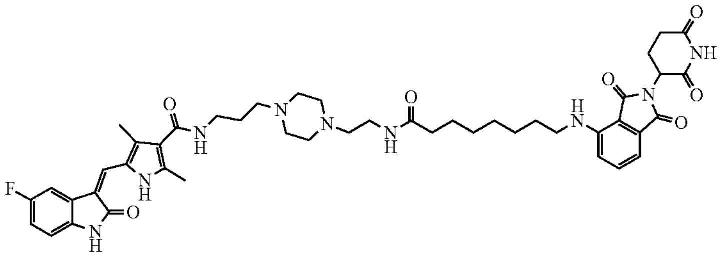 [SMILES: Cc1[nH]c(/C=C2\C(=O)Nc3ccc(F)cc32)c(C)c1C(=O)NCCCN1CCN(CCNC(=O)CCCCCCCNc2cccc3c2C(=O)N(C2CCC(=O)NC2=O)C3=O)CC1] | (Z)-N-(3-(4-(2-(8-((2-(2,6-dioxopiperidin-3-yl)-1,3-dioxoisoindolin-4-yl)amino)octanamido)ethyl) piperazin-1-yl)propyl)-5-((5-fluoro-2-oxoindolin-3-ylidene)methyl)-2,4-dimethyl-1H-pyrrole-3-carboxamide |
| 59 | HC58- 144 | 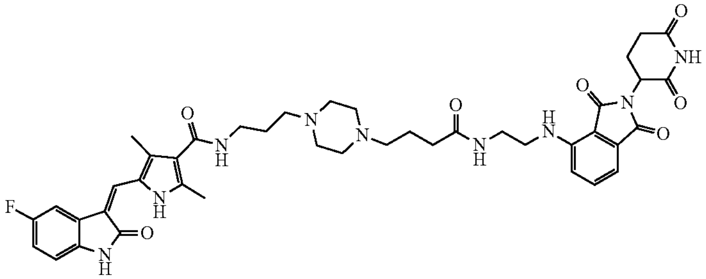 [SMILES: Cc1[nH]c(/C=C2\C(=O)Nc3ccc(F)cc32)c(C)c1C(=O)NCCCN1CCN(CCCC(=O)NCCNc2cccc3c2C(=O)N(C2CCC(=O)NC2=O)C3=O)CC1] | (Z)-N-(3-(4-(4-((2-((2-(2,6-dioxopiperidin-3-yl)-1,3-dioxoisoindolin-4-yl)amino)ethyl)amino)-4-oxobutyl)piperazin-1-yl)propyl)-5-((5-fluoro-2-oxoindolin-3-ylidene)methyl)-2,4-dimethyl-1H-pyrrole-3-carboxamide |
| 60 | HC58- 145 | 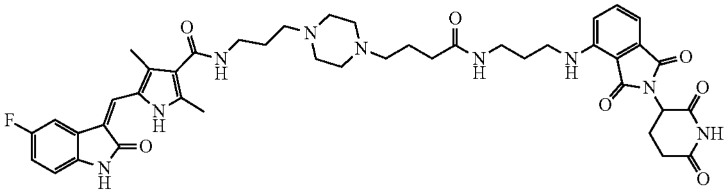 [SMILES: Cc1[nH]c(/C=C2\C(=O)Nc3ccc(F)cc32)c(C)c1C(=O)NCCCN1CCN(CCCC(=O)NCCCNc2cccc3c2C(=O)N(C2CCC(=O)NC2=O)C3=O)CC1] | (Z)-N-(3-(4-(4-((3-((2-(2,6-dioxopiperidin-3-yl)-1,3-dioxoisoindolin-4-yl)amino)propyl)amino)-4-oxobutyl)piperazin-1-yl)propyl)-5-((5-fluoro-2-oxoindolin-3-ylidene)methyl)-2,4-dimethyl-1H-pyrrole-3-carboxamide |
| 61 | HC58- 146 | 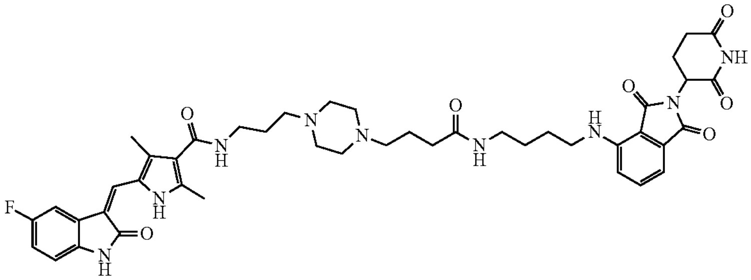 [SMILES: Cc1[nH]c(/C=C2\C(=O)Nc3ccc(F)cc32)c(C)c1C(=O)NCCCN1CCN(CCCC(=O)NCCCCNc2cccc3c2C(=O)N(C2CCC(=O)NC2=O)C3=O)CC1] | (Z)-N-(3-(4-(4-((4-((2-(2,6-dioxopiperidin-3-yl)-1,3-dioxoisoindolin-4-yl)amino)butyl)amino)-4-oxobutyl)piperazin-1-yl)propyl)-5-((5-fluoro-2-oxoindolin-3-ylidene)methyl)-2,4-dimethyl-1H-pyrrole-3-carboxamide |
| 62 | HC58- 147 | 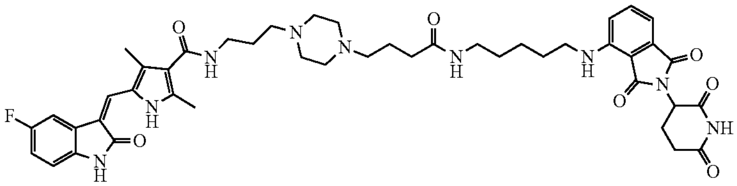 [SMILES: Cc1[nH]c(/C=C2\C(=O)Nc3ccc(F)cc32)c(C)c1C(=O)NCCCN1CCN(CCCC(=O)NCCCCCNc2cccc3c2C(=O)N(C2CCC(=O)NC2=O)C3=O)CC1] | (Z)-N-(3-(4-(4-((5-((2-(2,6-dioxopiperidin-3-yl)-1,3-dioxoisoindolin-4-yl)amino)pentyl)amino)-4-oxobutyl)piperazin-1-yl)propyl)-5-((5-fluoro-2-oxoindolin-3-ylidene)methyl)-2,4-dimethyl-1H-pyrrole-3-carboxamide |
| 63 | HC58- 148 | 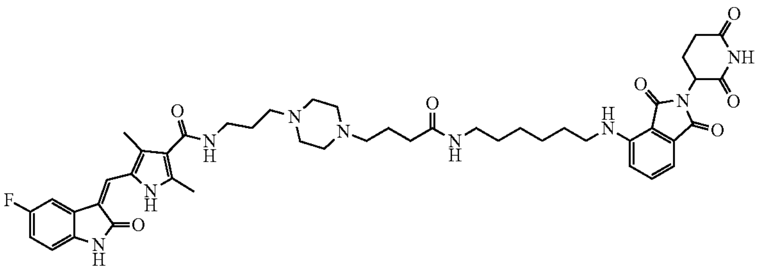 [SMILES: Cc1[nH]c(/C=C2\C(=O)Nc3ccc(F)cc32)c(C)c1C(=O)NCCCN1CCN(CCCC(=O)NCCCCCCNc2cccc3c2C(=O)N(C2CCC(=O)NC2=O)C3=O)CC1] | (Z)-N-(3-(4-(4-((6-((2-(2,6-dioxopiperidin-3-yl)-1,3-dioxoisoindolin-4-yl)amino)hexyl)amino)-4-oxobutyl)piperazin-1-yl)propyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 64 | HC58-149 | 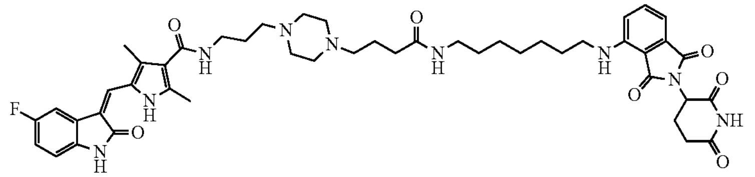 [SMILES: Cc1[nH]c(/C=C2\C(=O)Nc3ccc(F)cc32)c(C)c1C(=O)NCCCN1CCN(CCCC(=O)NCCCCCCCNc2cccc3c2C(=O)N(C2CCC(=O)NC2=O)C3=O)CC1] | (Z)-N-(3-(4-(4-((7-((2-(2,6-dioxopiperidin-3-yl)-1,3-dioxoisoindolin-4-yl)amino)heptyl)amino)-4-oxobutyl)piperazin-1-yl)propyl)-5-((5-fluoro-2-oxoindolin-3-ylidene)methyl)-2,4-dimethyl-1H-pyrrole-3-carboxamide |
| 65 | HC58-150 | 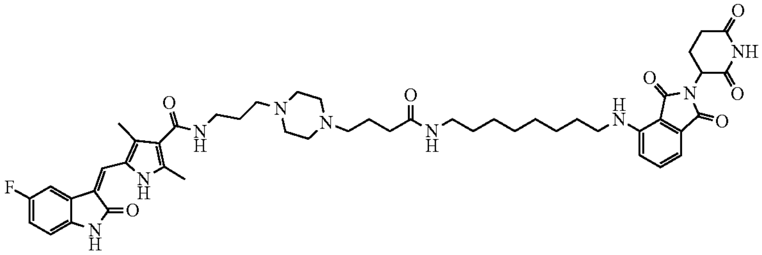 [SMILES: Cc1[nH]c(/C=C2\C(=O)Nc3ccc(F)cc32)c(C)c1C(=O)NCCCN1CCN(CCCC(=O)NCCCCCCCCNc2cccc3c2C(=O)N(C2CCC(=O)NC2=O)C3=O)CC1] | (Z)-N-(3-(4-(4-((8-((2-(2,6-dioxopiperidin-3-yl)-1,3-dioxoisoindolin-4-yl)amino)octyl)amino)-4-oxobutyl)piperazin-1-yl)propyl)-5-((5-fluoro-2-oxoindolin-3-ylidene)methyl)-2,4-dimethyl-1H-pyrrole-3-carboxamide |
| 66 | HC58-158 | 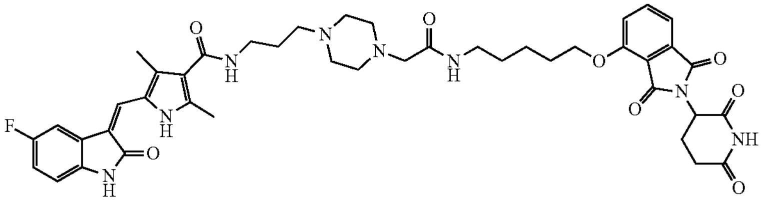 [SMILES: Cc1[nH]c(/C=C2\C(=O)Nc3ccc(F)cc32)c(C)c1C(=O)NCCCN1CCN(CC(=O)NCCCCCOc2cccc3c2C(=O)N(C2CCC(=O)NC2=O)C3=O)CC1] | (Z)-N-(3-(4-(2-((5-((2-(2,6-dioxopiperidin-3-yl)-1,3-dioxoisoindolin-4-yl)oxy)pentyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 67 | HC58-159 | 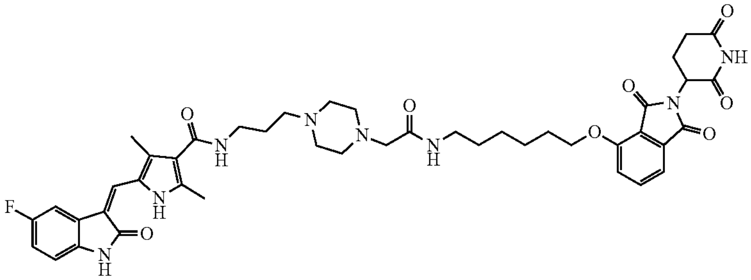 [SMILES: Cc1[nH]c(/C=C2\C(=O)Nc3ccc(F)cc32)c(C)c1C(=O)NCCCN1CCN(CC(=O)NCCCCCCOc2cccc3c2C(=O)N(C2CCC(=O)NC2=O)C3=O)CC1] | (Z)-N-(3-(4-(2-((6-((2-(2,6-dioxopiperidin-3-yl)-1,3-dioxoisoindolin-4-yl)oxy)hexyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 68 | HC58-160 | 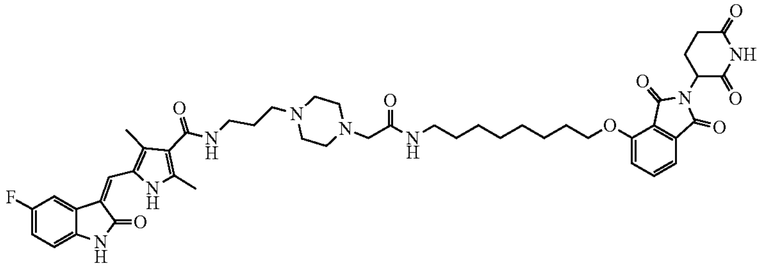 [SMILES: Cc1[nH]c(/C=C2\C(=O)Nc3ccc(F)cc32)c(C)c1C(=O)NCCCN1CCN(CC(=O)NCCCCCCCCOc2cccc3c2C(=O)N(C2CCC(=O)NC2=O)C3=O)CC1] | (Z)-N-(3-(4-(2-((8-((2-(2,6-dioxopiperidin-3-yl)-1,3-dioxoisoindolin-4-yl)oxy)octyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 69 | HC58-161 | 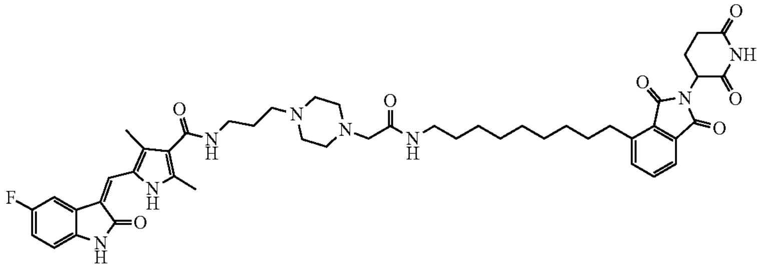 [SMILES: Cc1[nH]c(/C=C2\C(=O)Nc3ccc(F)cc32)c(C)c1C(=O)NCCCN1CCN(CC(=O)NCCCCCCCCCc2cccc3c2C(=O)N(C2CCC(=O)NC2=O)C3=O)CC1] | (Z)-N-(3-(4-(2-((9-(2-(2,6-dioxopiperidin-3-yl)-1,3-dioxoisoindolin-4-yl)nonyl)amino)-2-oxoethyl)piperazin-1-yl)propyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 70 | HC58-164 | 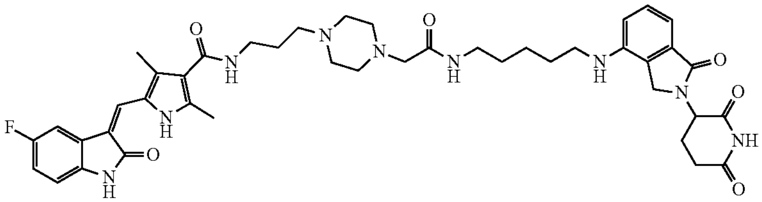 [SMILES: Cc1[nH]c(/C=C2\C(=O)Nc3ccc(F)cc32)c(C)c1C(=O)NCCCN1CCN(CC(=O)NCCCCCNc2cccc3c2CN(C2CCC(=O)NC2=O)C3=O)CC1] | (Z)-N-(3-(4-(2-((5-((2-(2,6-dioxopiperidin-3-yl)-1-oxoisoindolin-4-yl)amino)pentyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 71 | HC58-165 | 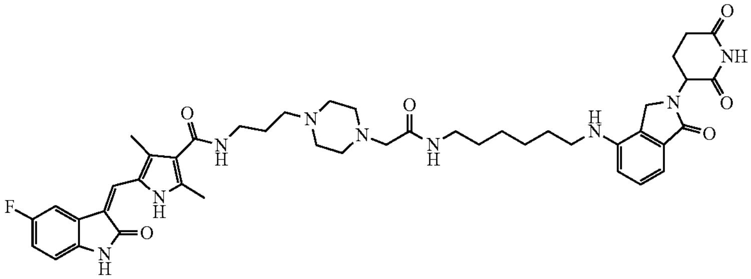 [SMILES: Cc1[nH]c(/C=C2\C(=O)Nc3ccc(F)cc32)c(C)c1C(=O)NCCCN1CCN(CC(=O)NCCCCCCNc2cccc3c2CN(C2CCC(=O)NC2=O)C3=O)CC1] | (Z)-N-(3-(4-(2-((6-((2-(2,6-dioxopiperidin-3-yl)-1-oxoisoindolin-4-yl)amino)hexyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 72 | HC58-167 | 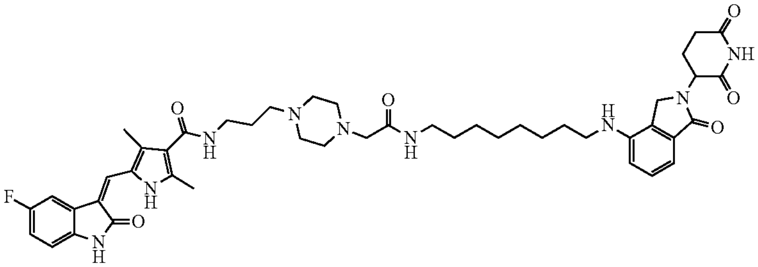 [SMILES: Cc1[nH]c(/C=C2\C(=O)Nc3ccc(F)cc32)c(C)c1C(=O)NCCCN1CCN(CC(=O)NCCCCCCCCNc2cccc3c2CN(C2CCC(=O)NC2=O)C3=O)CC1] | (Z)-N-(3-(4-(2-((8-((2-(2,6-dioxopiperidin-3-yl)-1-oxoisoindolin-4-yl)amino)octyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 73 | HC58-178 | 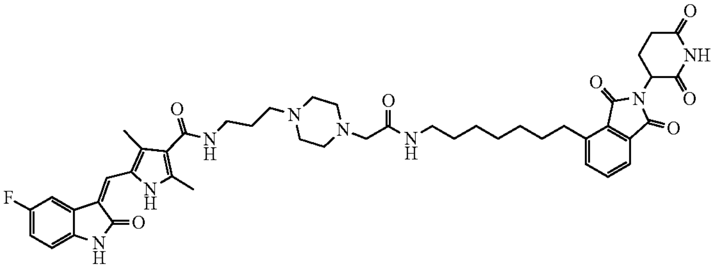 [SMILES: Cc1[nH]c(/C=C2\C(=O)Nc3ccc(F)cc32)c(C)c1C(=O)NCCCN1CCN(CC(=O)NCCCCCCCc2cccc3c2C(=O)N(C2CCC(=O)NC2=O)C3=O)CC1] | (Z)-N-(3-(4-(2-((7-(2-(2,6-dioxopiperidin-3-yl)-1,3-dioxoisoindolin-4-yl)heptyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 75 | HC58-179 | 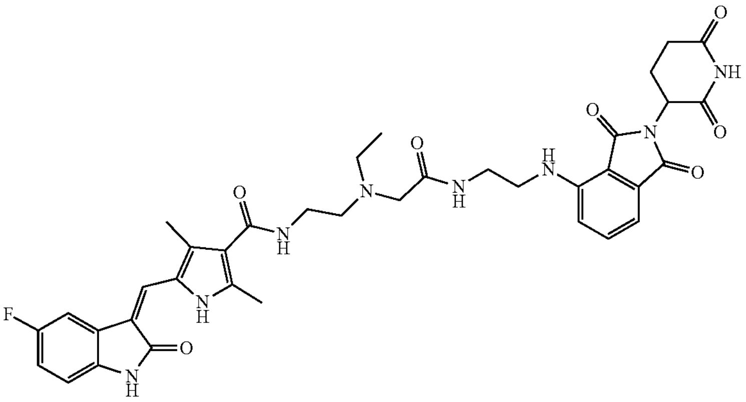 [SMILES: CCN(CCNC(=O)c1c(C)[nH]c(/C=C2\C(=O)Nc3ccc(F)cc32)c1C)CC(=O)NCCNc1cccc2c1C(=O)N(C1CCC(=O)NC1=O)C2=O] | (Z)-N-(2-((2-((2-((2-(2,6-dioxopiperidin-3-yl)-1,3-dioxoisoindolin-4-yl)amino)ethyl)amino)-2-oxoethyl)(ethyl)amino)ethyl)-5-((5-fluoro-2-oxoindolin-3-ylidene)methyl)-2,4-dimethyl-1H-pyrrole-3-carboxamide |

TABLE 1-continued

| Ex am- ples | Com- pound code | Structure | Chemical Name |
|---|---|---|---|
| 76 | HC58-180 | 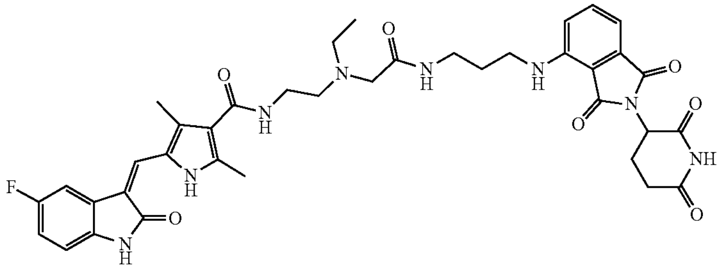 [SMILES: CCN(CCNC(=O)c1c(C)[nH]c(/C=C2\C(=O)Nc3ccc(F)cc32)c1C)CC(=O)NCCCNc1cccc2c1C(=O)N(C1CCC(=O)NC1=O)C2=O] | (Z)-N-(2-((2-((3-((2-(2,6-dioxopiperidin-3-yl)-1,3-dioxoisoindolin-4-yl)amino)propyl)amino)-2-oxoethyl)(ethyl)amino)ethyl)-5-((5-fluoro-2-oxoindolin-3-ylidene)methyl)-2,4-dimethyl-1H-pyrrole-3-carboxamide |
| 77 | HC58-181 | 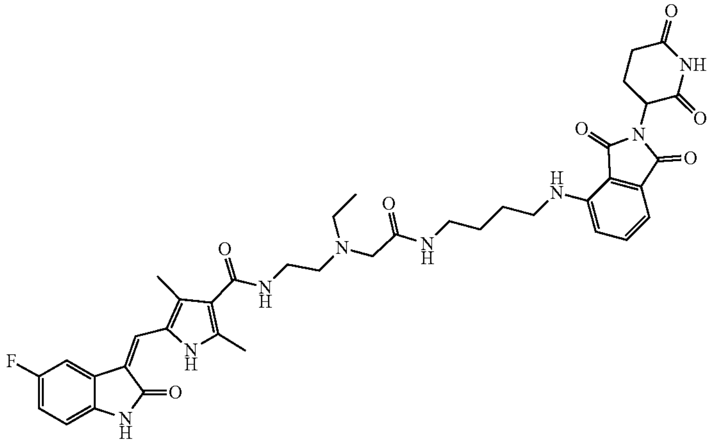 [SMILES: CCN(CCNC(=O)c1c(C)[nH]c(/C=C2\C(=O)Nc3ccc(F)cc32)c1C)CC(=O)NCCCCNc1cccc2c1C(=O)N(C1CCC(=O)NC1=O)C2=O] | (Z)-N-(2-((2-((4-((2-(2,6-dioxopiperidin-3-yl)-1,3-dioxoisoindolin-4-yl)amino)butyl)amino)-2-oxoethyl)(ethyl)amino)ethyl)-5-((5-fluoro-2-oxoindolin-3-ylidene)methyl)-2,4-dimethyl-1H-pyrrole-3-carboxamide |
| 78 | HC58-182 | 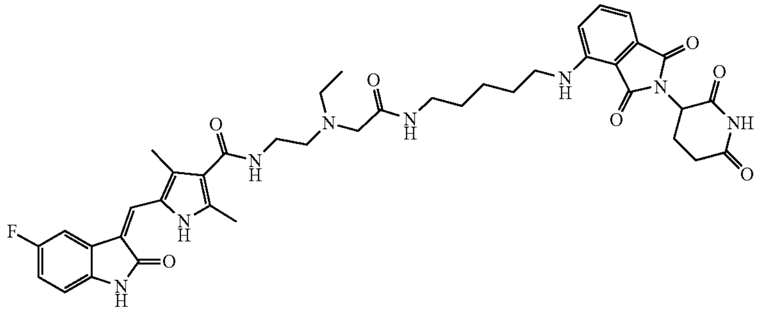 [SMILES: CCN(CCNC(=O)c1c(C)[nH]c(/C=C2\C(=O)Nc3ccc(F)cc32)c1C)CC(=O)NCCCCCNc1cccc2c1C(=O)N(C1CCC(=O)NC1=O)C2=O] | (Z)-N-(2-((2-((5-((2-(2,6-dioxopiperidin-3-yl)-1,3-dioxoisoindolin-4-yl)amino)pentyl)amino)-2-oxoethyl)(ethyl)amino)ethyl)-5-((5-fluoro-2-oxoindolin-3-ylidene)methyl)-2,4-dimethyl-1H-pyrrole-3-carboxamide |
| 79 | HC58-183 | 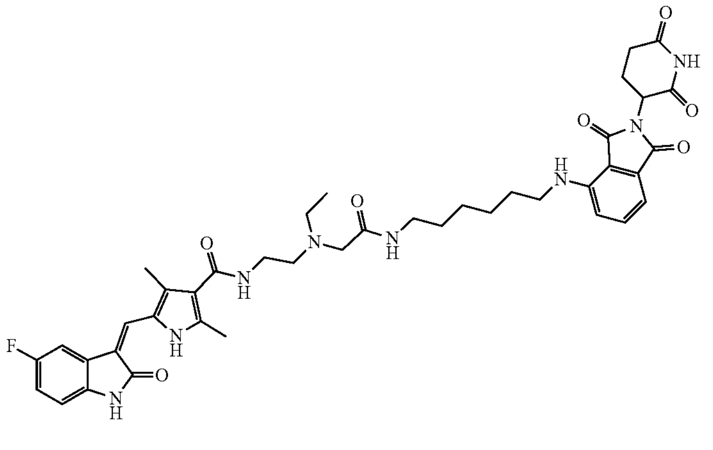 [SMILES: CCN(CCNC(=O)c1c(C)[nH]c(/C=C2\C(=O)Nc3ccc(F)cc32)c1C)CC(=O)NCCCCCCNc1cccc2c1C(=O)N(C1CCC(=O)NC1=O)C2=O] | (Z)-N-(2-((2-((6-((2-(2,6-dioxopiperidin-3-yl)-1,3-dioxoisoindolin-4-yl)amino)hexyl)amino)-2-oxoethyl)(ethyl)amino)ethyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 80 | HC58-184 | 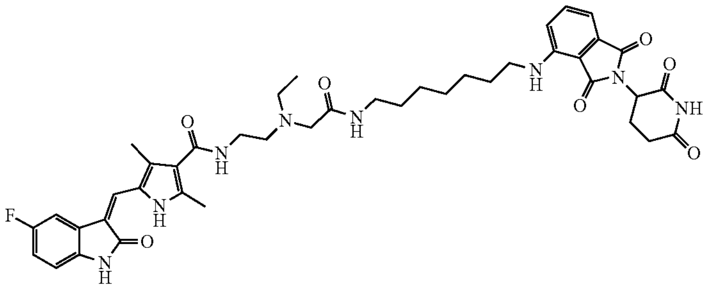 [SMILES: CCN(CCNC(=O)c1c(C)[nH]c(/C=C2\C(=O)Nc3ccc(F)cc32)c1C)CC(=O)NCCCCCCCNc1cccc2c1C(=O)N(C1CCC(=O)NC1=O)C2=O] | (Z)-N-(2-((2-((7-((2-(2,6-dioxopiperidin-3-yl)-1,3-dioxoisoindolin-4-yl)amino)heptyl)amino)-2-oxoethyl)(ethyl)amino)ethyl)-5-((5-fluoro-2-oxoindolin-3-ylidene)methyl)-2,4-dimethyl-1H-pyrrole-3-carboxamide |
| 81 | HC58-185 | 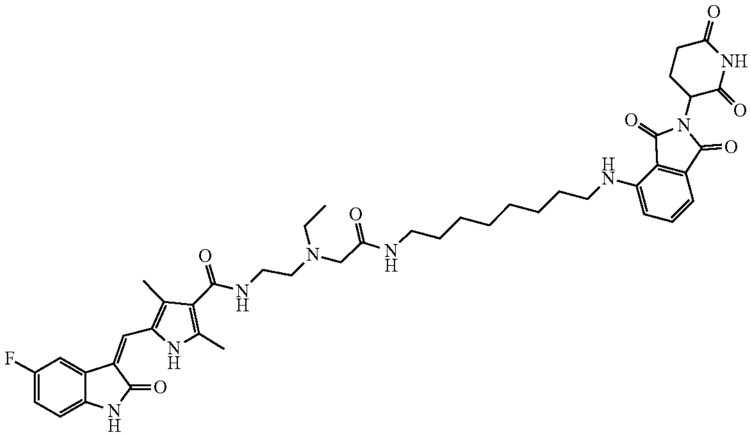 [SMILES: CCN(CCNC(=O)c1c(C)[nH]c(/C=C2\C(=O)Nc3ccc(F)cc32)c1C)CC(=O)NCCCCCCCCNc1cccc2c1C(=O)N(C1CCC(=O)NC1=O)C2=O] | (Z)-N-(2-((2-((8-((2-(2,6-dioxopiperidin-3-yl)-1,3-dioxoisoindolin-4-yl)amino)octyl)amino)-2-oxoethyl)(ethyl)amino)ethyl)-5-((5-fluoro-2-oxoindolin-3-ylidene)methyl)-2,4-dimethyl-1H-pyrrole-3-carboxamide |
| 83 | HC65-2 | 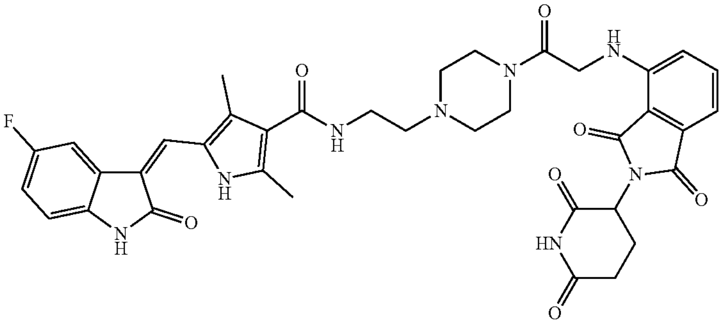 [SMILES: Cc1[nH]c(/C=C2\C(=O)Nc3ccc(F)cc32)c(C)c1C(=O)NCCN1CCN(C(=O)CNc2cccc3c2C(=O)N(C2CCC(=O)NC2=O)C3=O)CC1] | (Z)-N-(2-(4-((2-(2,6-dioxopiperidin-3-yl)-1,3-dioxoisoindolin-4-yl)glycyl)piperazin-1-yl)ethyl)-5-((5-fluoro-2-oxoindolin-3-ylidene)methyl)-2,4-dimethyl-1H-pyrrole-3-carboxamide |
| 84 | HC65-3 | 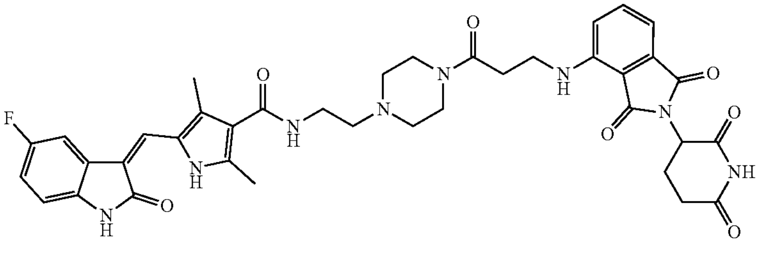 [SMILES: Cc1[nH]c(/C=C2\C(=O)Nc3ccc(F)cc32)c(C)c1C(=O)NCCN1CCN(C(=O)CCNc2cccc3c2C(=O)N(C2CCC(=O)NC2=O)C3=O)CC1] | (Z)-N-(2-(4-(3-((2-(2,6-dioxopiperidin-3-yl)-1,3-dioxoisoindolin-4-yl)amino)propanoyl)piperazin-1-yl)ethyl)-5-((5-fluoro-2-oxoindolin-3-ylidene)methyl)-2,4-dimethyl-1H-pyrrole-3-carboxamide |

TABLE 1-continued

| Ex am- ples | Com- pound code | Structure | Chemical Name |
|---|---|---|---|
| 85 | HC65- 4 | 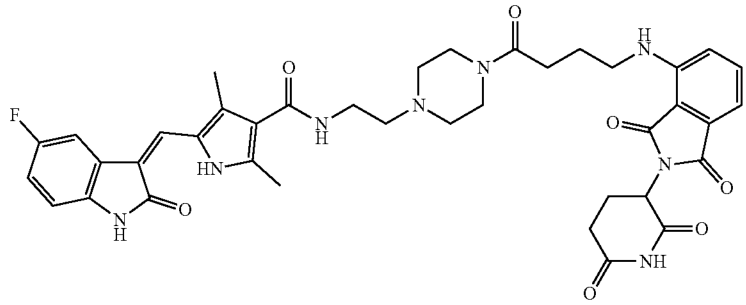 [SMILES: Cc1[nH]c(/C=C2\C(=O)Nc3ccc(F)cc32)c(C)c1C(=O)NCCN1CCN(C(=O)CCCNc2cccc3c2C(=O)N(C2CCC(=O)NC2=O)C3=O)CC1] | (Z)-N-(2-(4-(4-((2-(2,6-dioxopiperidin-3-yl)-1,3-dioxoisoindolin-4-yl)amino)butanoyl)piperazin-1-yl)ethyl)-5-((5-fluoro-2-oxoindolin-3-ylidene)methyl)-2,4-dimethyl-1H-pyrrole-3-carboxamide |
| 86 | HC65- 5 | 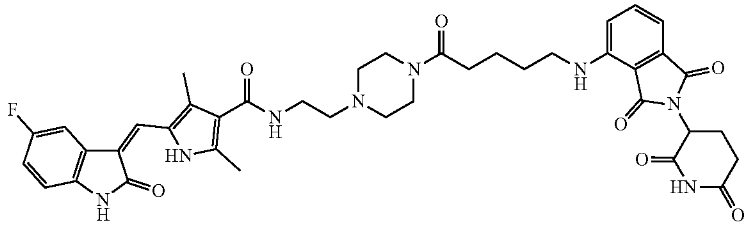 [SMILES: Cc1[nH]c(/C=C2\C(=O)Nc3ccc(F)cc32)c(C)c1C(=O)NCCN1CCN(C(=O)CCCCNc2cccc3c2C(=O)N(C2CCC(=O)NC2=O)C3=O)CC1] | (Z)-N-(2-(4-(5-((2-(2,6-dioxopiperidin-3-yl)-1,3-dioxoisoindolin-4-yl)amino)pentanoyl)piperazin-1-yl)ethyl)-5-((5-fluoro-2-oxoindolin-3-ylidene)methyl)-2,4-dimethyl-1H-pyrrole-3-carboxamide |
| 87 | HC65- 6 | 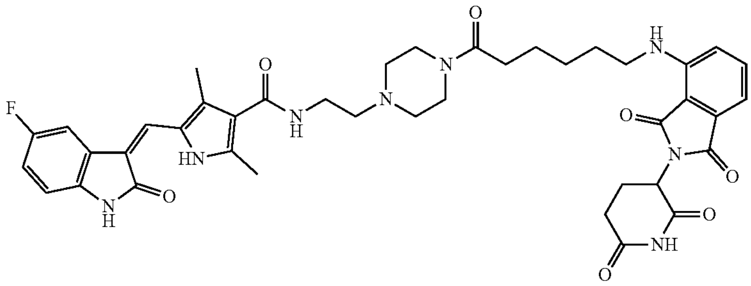 [SMILES: Cc1[nH]c(/C=C2\C(=O)Nc3ccc(F)cc32)c(C)c1C(=O)NCCN1CCN(C(=O)CCCCCNc2cccc3c2C(=O)N(C2CCC(=O)NC2=O)C3=O)CC1] | (Z)-N-(2-(4-(6-((2-(2,6-dioxopiperidin-3-yl)-1,3-dioxoisoindolin-4-yl)amino)hexanoyl)piperazin-1-yl)ethyl)-5-((5-fluoro-2-oxoindolin-3-ylidene)methyl)-2,4-dimethyl-1H-pyrrole-3-carboxamide |
| 88 | HC65- 7 | 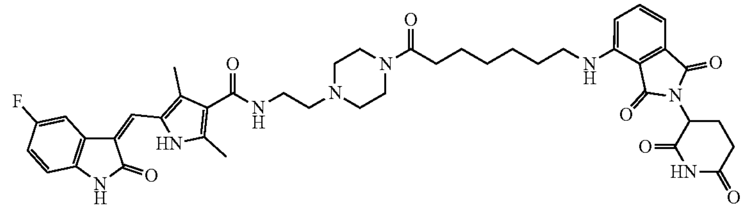 [SMILES: Cc1[nH]c(/C=C2\C(=O)Nc3ccc(F)cc32)c(C)c1C(=O)NCCN1CCN(C(=O)CCCCCCNc2cccc3c2C(=O)N(C2CCC(=O)NC2=O)C3=O)CC1] | (Z)-N-(2-(4-(7-((2-(2,6-dioxopiperidin-3-yl)-1,3-dioxoisoindolin-4-yl)amino)heptanoyl)piperazin-1-yl)ethyl)-5-((5-fluoro-2-oxoindolin-3-ylidene)methyl)-2,4-dimethyl-1H-pyrrole-3-carboxamide |
| 89 | HC65- 8 | 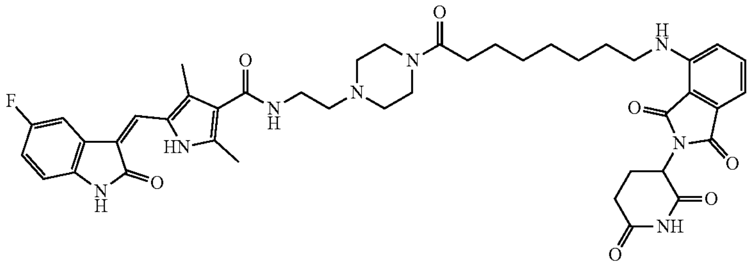 [SMILES: Cc1[nH]c(/C=C2\C(=O)Nc3ccc(F)cc32)c(C)c1C(=O)NCCN1CCN(C(=O)CCCCCCCNc2cccc3c2C(=O)N(C2CCC(=O)NC2=O)C3=O)CC1] | (Z)-N-(2-(4-(8-((2-(2,6-dioxopiperidin-3-yl)-1,3-dioxoisoindolin-4-yl)amino)octanoyl)piperazin-1-yl)ethyl)-5-((5-fluoro-2-oxoindolin-3-ylidene)methyl)-2,4-dimethyl-1H-pyrrole-3-carboxamide |
| 91 | HC65- 13 | 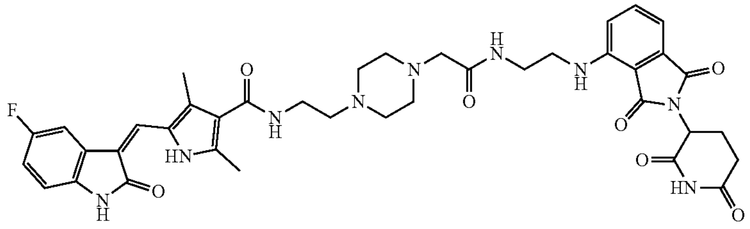 [SMILES: Cc1[nH]c(/C=C2\C(=O)Nc3ccc(F)cc32)c(C)c1C(=O)NCCN1CCN(CC(=O)NCCNc2cccc3c2C(=O)N(C2CCC(=O)NC2=O)C3=O)CC1] | (Z)-N-(2-(4-(2-((2-((2-(2,6-dioxopiperidin-3-yl)-1,3-dioxoisoindolin-4-yl)amino)ethyl)amino)-2-oxoethyl)piperazin-1-yl)ethyl)-5-((5-fluoro-2-oxoindolin-3-ylidene)methyl)-2,4-dimethyl-1H-pyrrole-3-carboxamide |

TABLE 1-continued

| Ex am- ples | Com- pound code | Structure | Chemical Name |
|---|---|---|---|
| 92 | HC65-14 | 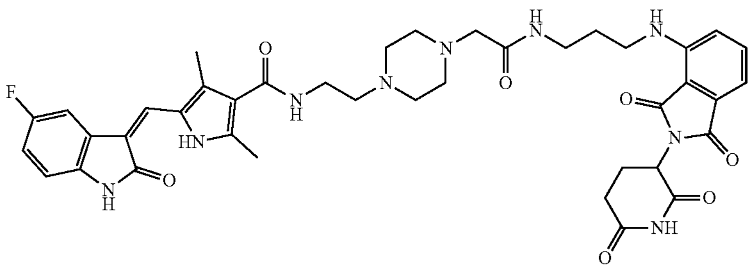 [SMILES: Cc1[nH]c(/C=C2\C(=O)Nc3ccc(F)cc32)c(C)c1C(=O)NCCN1CCN(CC(=O)NCCCNc2cccc3c2C(=O)N(C2CCC(=O)NC2=O)C3=O)CC1] | (Z)-N-(2-(4-(2-((3-((2-(2,6-dioxopiperidin-3-yl)-1,3-dioxoisoindolin-4-yl)amino)propyl)amino)-2-oxoethyl)piperazin-1-yl)ethyl)-5-((5-fluoro-2-oxoindolin-3-ylidene)methyl)-2,4-dimethyl-1H-pyrrole-3-carboxamide |
| 93 | HC65-15 | 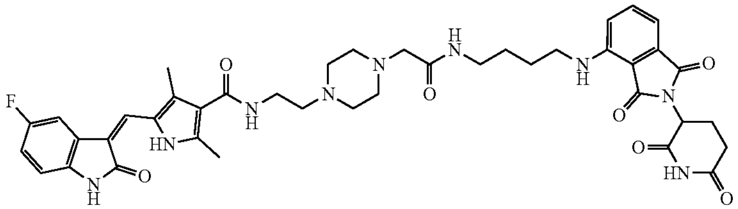 [SMILES: Cc1[nH]c(/C=C2\C(=O)Nc3ccc(F)cc32)c(C)c1C(=O)NCCN1CCN(CC(=O)NCCCCNc2cccc3c2C(=O)N(C2CCC(=O)NC2=O)C3=O)CC1] | (Z)-N-(2-(4-(2-((4-((2-(2,6-dioxopiperidin-3-yl)-1,3-dioxoisoindolin-4-yl)amino)butyl)amino)-2-oxoethyl)piperazin-1-yl)ethyl)-5-((5-fluoro-2-oxoindolin-3-ylidene)methyl)-2,4-dimethyl-1H-pyrrole-3-carboxamide |
| 94 | HC65-16 | 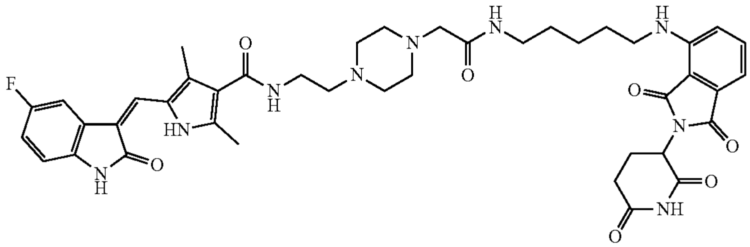 [SMILES: Cc1[nH]c(/C=C2\C(=O)Nc3ccc(F)cc32)c(C)c1C(=O)NCCN1CCN(CC(=O)NCCCCCNc2cccc3c2C(=O)N(C2CCC(=O)NC2=O)C3=O)CC1] | (Z)-N-(2-(4-(2-((5-((2-(2,6-dioxopiperidin-3-yl)-1,3-dioxoisoindolin-4-yl)amino)pentyl)amino)-2-oxoethyl)piperazin-1-yl)ethyl)-5-((5-fluoro-2-oxoindolin-3-ylidene)methyl)-2,4-dimethyl-1H-pyrrole-3-carboxamide |
| 95 | HC65-17 | 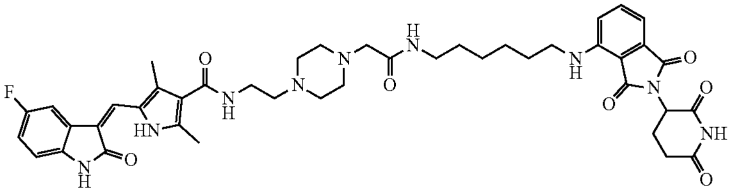 [SMILES: Cc1[nH]c(/C=C2\C(=O)Nc3ccc(F)cc32)c(C)c1C(=O)NCCN1CCN(CC(=O)NCCCCCCNc2cccc3c2C(=O)N(C2CCC(=O)NC2=O)C3=O)CC1] | (Z)-N-(2-(4-(2-((6-((2-(2,6-dioxopiperidin-3-yl)-1,3-dioxoisoindolin-4-yl)amino)hexyl)amino)-2-oxoethyl)piperazin-1-yl)ethyl)-5-((5-fluoro-2-oxoindolin-3-ylidene)methyl)-2,4-dimethyl-1H-pyrrole-3-carboxamide |
| 96 | HC65-18 | 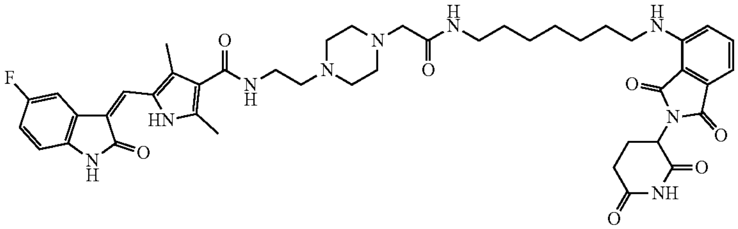 [SMILES: Cc1[nH]c(/C=C2\C(=O)Nc3ccc(F)cc32)c(C)c1C(=O)NCCN1CCN(CC(=O)NCCCCCCCNc2cccc3c2C(=O)N(C2CCC(=O)NC2=O)C3=O)CC1] | (Z)-N-(2-(4-(2-((7-((2-(2,6-dioxopiperidin-3-yl)-1,3-dioxoisoindolin-4-yl)amino)heptyl)amino)-2-oxoethyl)piperazin-1-yl)ethyl)-5-((5-fluoro-2-oxoindolin-3-ylidene)methyl)-2,4-dimethyl-1H-pyrrole-3-carboxamide |
| 97 | HC65-19 | 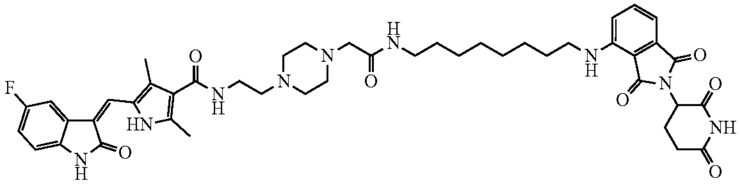 [SMILES: Cc1[nH]c(/C=C2\C(=O)Nc3ccc(F)cc32)c(C)c1C(=O)NCCN1CCN(CC(=O)NCCCCCCCCNc2cccc3c2C(=O)N(C2CCC(=O)NC2=O)C3=O)CC1] | (Z)-N-(2-(4-(2-((8-((2-(2,6-dioxopiperidin-3-yl)-1,3-dioxoisoindolin-4-yl)amino)octyl)amino)-2-oxoethyl)piperazin-1-yl)ethyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 99 | HC65-24 | 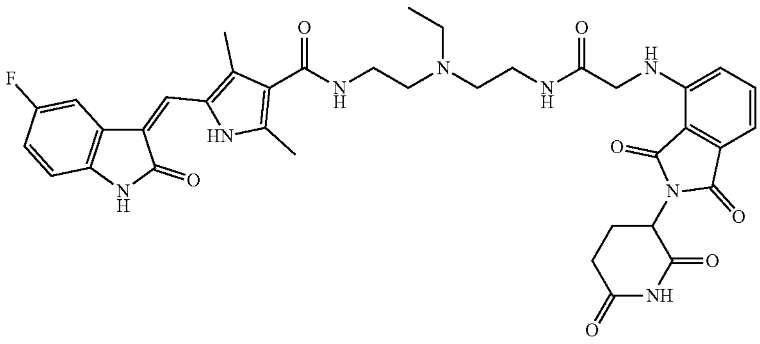 [SMILES: CCN(CCNC(=O)CNc1cccc2c1C(=O)N(C1CCC(=O)NC1=O)C2=O)CCNC(=O)c1c(C)[nH]c(/C=C2\C(=O)Nc3ccc(F)cc32)c1C] | (Z)-N-(2-((2-(2-((2-(2,6-dioxopiperidin-3-yl)-1,3-dioxoisoindolin-4-yl)amino)acetamido)ethyl)(ethyl)amino)ethyl)-5-((5-fluoro-2-oxoindolin-3-ylidene)methyl)-2,4-dimethyl-1H-pyrrole-3-carboxamide |
| 100 | HC65-25 | 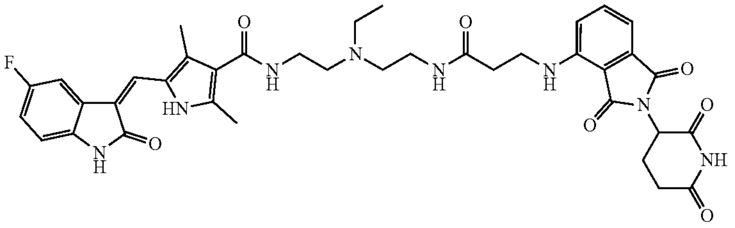 [SMILES: CCN(CCNC(=O)CCNc1cccc2c1C(=O)N(C1CCC(=O)NC1=O)C2=O)CCNC(=O)c1c(C)[nH]c(/C=C2\C(=O)Nc3ccc(F)cc32)c1C] | (Z)-N-(2-((2-(3-((2-(2,6-dioxopiperidin-3-yl)-1,3-dioxoisoindolin-4-yl)amino)propanamido)ethyl)(ethyl)amino)ethyl)-5-((5-fluoro-2-oxoindolin-3-ylidene)methyl)-2,4-dimethyl-1H-pyrrole-3-carboxamide |
| 101 | HC65-26 | 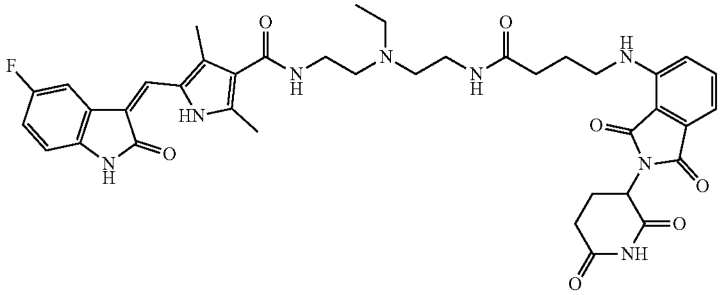 [SMILES: CCN(CCNC(=O)CCCNc1cccc2c1C(=O)N(C1CCC(=O)NC1=O)C2=O)CCNC(=O)c1c(C)[nH]c(/C=C2\C(=O)Nc3ccc(F)cc32)c1C] | (Z)-N-(2-((2-(4-((2-(2,6-dioxopiperidin-3-yl)-1,3-dioxoisoindolin-4-yl)amino)butanamido)ethyl)(ethyl)amino)ethyl)-5-((5-fluoro-2-oxoindolin-3-ylidene)methyl)-2,4-dimethyl-1H-pyrrole-3-carboxamide |
| 102 | HC65-27 | 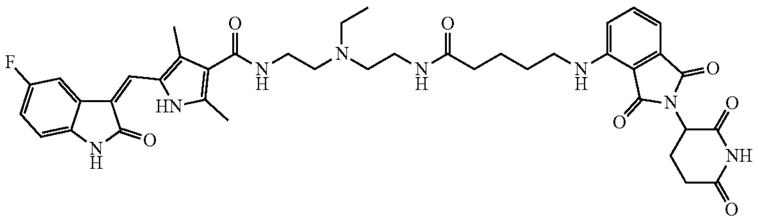 [SMILES: CCN(CCNC(=O)CCCCNc1cccc2c1C(=O)N(C1CCC(=O)NC1=O)C2=O)CCNC(=O)c1c(C)[nH]c(/C=C2\C(=O)Nc3ccc(F)cc32)c1C] | (Z)-N-(2-((2-(5-((2-(2,6-dioxopiperidin-3-yl)-1,3-dioxoisoindolin-4-yl)amino)pentanamido)ethyl)(ethyl)amino)ethyl)-5-((5-fluoro-2-oxoindolin-3-ylidene)methyl)-2,4-dimethyl-1H-pyrrole-3-carboxamide |
| 103 | HC65-28 | 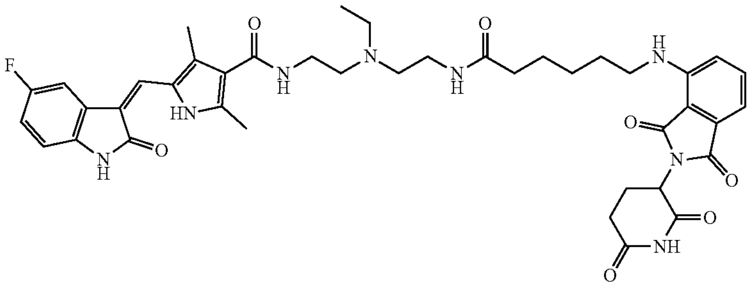 [SMILES: CCN(CCNC(=O)CCCCCNc1cccc2c1C(=O)N(C1CCC(=O)NC1=O)C2=O)CCNC(=O)c1c(C)[nH]c(/C=C2\C(=O)Nc3ccc(F)cc32)c1C] | (Z)-N-(2-((2-(6-((2-(2,6-dioxopiperidin-3-yl)-1,3-dioxoisoindolin-4-yl)amino)hexanamido)ethyl)(ethyl)amino)ethyl)-5-((5-fluoro-2-oxoindolin-3-ylidene)methyl)-2,4-dimethyl-1H-pyrrole-3-carboxamide |

TABLE 1-continued

| Ex am- ples | Com- pound code | Structure | Chemical Name |
|---|---|---|---|
| 104 | HC65-29 | 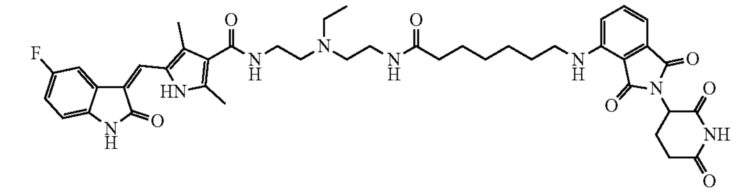 [SMILES: CCN(CCNC(=O)CCCCCCNc1cccc2c1C(=O)N(C1CCC(=O)NC1=O)C2=O)CCNC(=O)c1c(C)[nH]c(/C=C2\C(=O)Nc3ccc(F)cc32)c1C] | (Z)-N-(2-((2-(7-((2-(2,6-dioxopiperidin-3-yl)-1,3-dioxoisoindolin-4-yl)amino)heptanamido)ethyl)(ethyl)amino)ethyl)-5-((5-fluoro-2-oxoindolin-3-ylidene)methyl)-2,4-dimethyl-1H-pyrrole-3-carboxamide |
| 105 | HC65-30 | 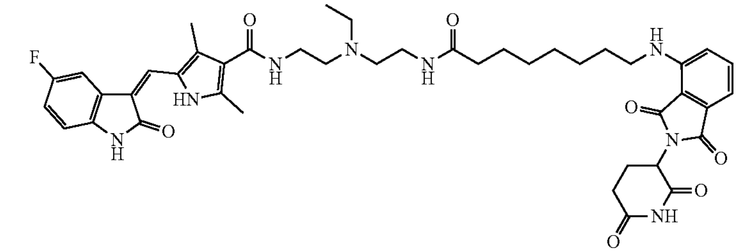 [SMILES: CCN(CCNC(=O)CCCCCCCNc1cccc2c1C(=O)N(C1CCC(=O)NC1=O)C2=O)CCNC(=O)c1c(C)[nH]c(/C=C2\C(=O)Nc3ccc(F)cc32)c1C] | (Z)-N-(2-((2-(8-((2-(2,6-dioxopiperidin-3-yl)-1,3-dioxoisoindolin-4-yl)amino)octanamido)ethyl)(ethyl)amino)ethyl)-5-((5-fluoro-2-oxoindolin-3-ylidene)methyl)-2,4-dimethyl-1H-pyrrole-3-carboxamide |
| 106 | HC65-33 | 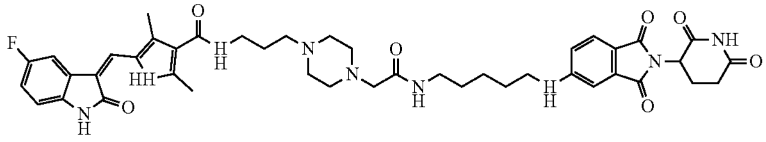 | (Z)-N-(3-(4-(2-((5-((2-(2,6-dioxopiperidin-3-yl)-1,3-dioxoisoindolin-5-yl)amino)pentyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 107 | HC65-34 | 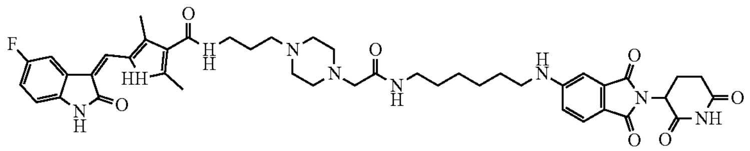 | (Z)-N-(3-(4-(2-((6-((2-(2,6-dioxopiperidin-3-yl)-1,3-dioxoisoindolin-5-yl)amino)hexyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 108 | HC65-35 | 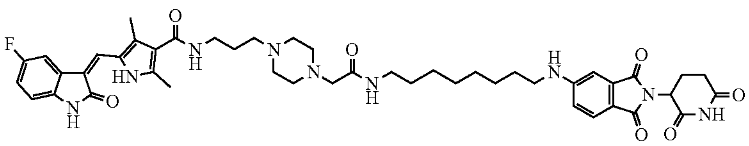 [SMILES: Cc1[nH]c(/C=C2\C(=O)Nc3ccc(F)cc32)c(C)c1C(=O)NCCCN1CCN(CC(=O)NCCCCCCCCNc2ccc3c(c2)C(=O)N(C2CCC(=O)NC2=O)C3=O)CC1] | (Z)-N-(3-(4-(2-((8-((2-(2,6-dioxopiperidin-3-yl)-1,3-dioxoisoindolin-5-yl)amino)octyl)amino)-2-oxoethyl)piperazin-1-yl)propyl)-5-((5-fluoro-2-oxoindolin-3-ylidene)methyl)-2,4-dimethyl-1H-pyrrole-3-carboxamide |
| 109 | HC65-37 | 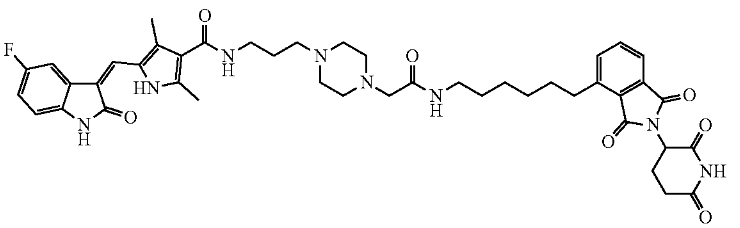 [SMILES: Cc1[nH]c(/C=C2\C(=O)Nc3ccc(F)cc32)c(C)c1C(=O)NCCCN1CCN(CC(=O)NCCCCCCc2cccc3c2C(=O)N(C2CCC(=O)NC2=O)C3=O)CC1] | (Z)-N-(3-(4-(2-((6-(2-(2,6-dioxopiperidin-3-yl)-1,3-dioxoisoindolin-4-yl)hexyl)amino)-2-oxoethyl)piperazin-1-yl)propyl)-5-((5-fluoro-2-oxoindolin-3-ylidene)methyl)-2,4-dimethyl-1H-pyrrole-3-carboxamide |

TABLE 1-continued

| Examples | Compound code | Structure | Chemical Name |
|---|---|---|---|
| 110 | HC65-74 | 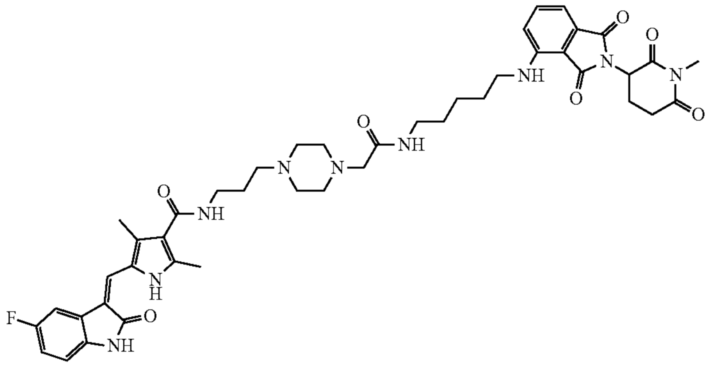 [SMILES: Cc1[nH]c(/C=C2\C(=O)Nc3ccc(F)cc32)c(C)c1C(=O)NCCCN1CCN(CC(=O)NCCCCCNc2cccc3c2C(=O)N(C2CCC(=O)N(C)C2=O)C3=O)CC1] | (Z)-5-((5-fluoro-2-oxoindolin-3-ylidene)methyl)-2,4-dimethyl-N-(3-(4-(2-((5-((2-(1-methyl-2,6-dioxopiperidin-3-yl)-1,3-dioxoisoindolin-4-yl)amino)pentyl)amino)-2-oxoethyl)piperazin-1-yl)propyl)-1H-pyrrole-3-carboxamide |
| 111 | HC65-75 | 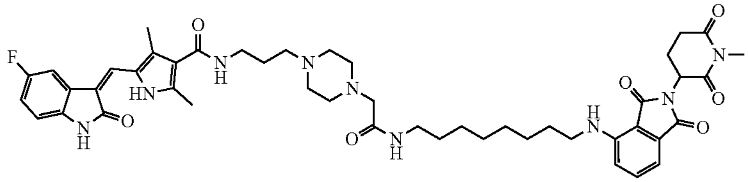 [SMILES: Cc1[nH]c(/C=C2\C(=O)Nc3ccc(F)cc32)c(C)c1C(=O)NCCCN1CCN(CC(=O)NCCCCCCCCNc2cccc3c2C(=O)N(C2CCC(=O)N(C)C2=O)C3=O)CC1] | (Z)-5-((5-fluoro-2-oxoindolin-3-ylidene)methyl)-2,4-dimethyl-N-(3-(4-(2-((8-((2-(1-methyl-2,6-dioxopiperidin-3-yl)-1,3-dioxoisoindolin-4-yl)amino)octyl)amino)-2-oxoethyl)piperazin-1-yl)propyl)-1H-pyrrole-3-carboxamide |
| 115 | HC65-175 | 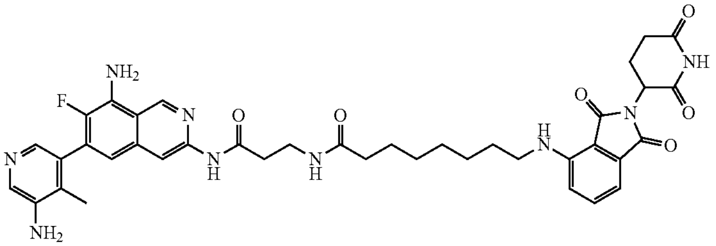 [SMILES: Cc1c(N)cncc1-c1cc2cc(NC(=O)CCNC(=O)CCCCCCCNc3cccc4c3C(=O)N(C3CCC(=O)NC3=O)C4=O)ncc2c(N)c1F] | N-(3-((8-amino-6-(5-amino-4-methylpyridin-3-yl)-7-fluoroisoquinolin-3-yl)amino)-3-oxopropyl)-8-((2-(2,6-dioxopiperidin-3-yl)-1,3-dioxoisoindolin-4-yl)amino)octanamide |
| 116 | HC65-183 | 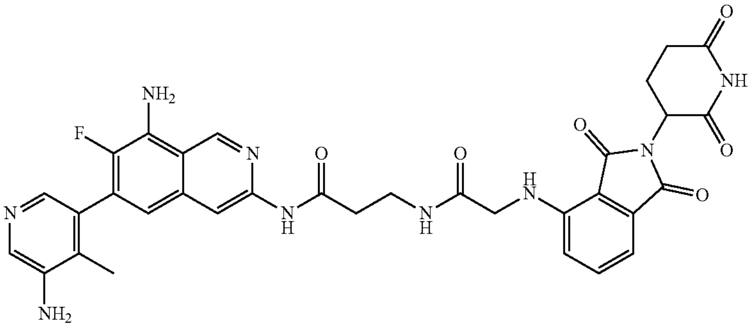 [SMILES: Cc1c(N)cncc1-c1cc2cc(NC(=O)CCNC(=O)CNc3cccc4c3C(=O)N(C3CCC(=O)NC3=O)C4=O)ncc2c(N)c1F] | N-(8-amino-6-(5-amino-4-methylpyridin-3-yl)-7-fluoroisoquinolin-3-yl)-3-(2-((2-(2,6-dioxopiperidin-3-yl)-1,3-dioxoisoindolin-4-yl)amino)acetamido)propanamide |
| 117 | HC65-184 | 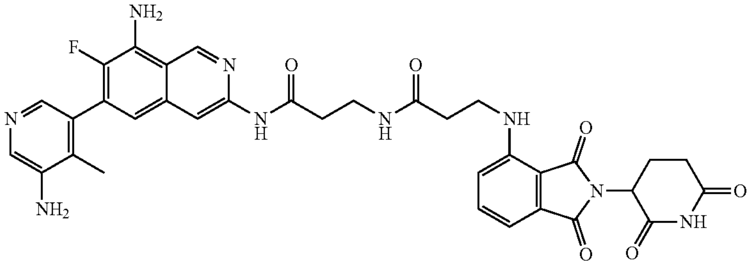 [SMILES: Cc1c(N)cncc1-c1cc2cc(NC(=O)CCNC(=O)CCNc3cccc4c3C(=O)N(C3CCC(=O)NC3=O)C4=O)ncc2c(N)c1F] | N-(8-amino-6-(5-amino-4-methylpyridin-3-yl)-7-fluoroisoquinolin-3-yl)-3-(3-((2-(2,6-dioxopiperidin-3-yl)-1,3-dioxoisoindolin-4-yl)amino)propanamido)propanamide |

TABLE 1-continued

| Examples | Compound code | Structure | Chemical Name |
|---|---|---|---|
| 118 | HC65-185 | 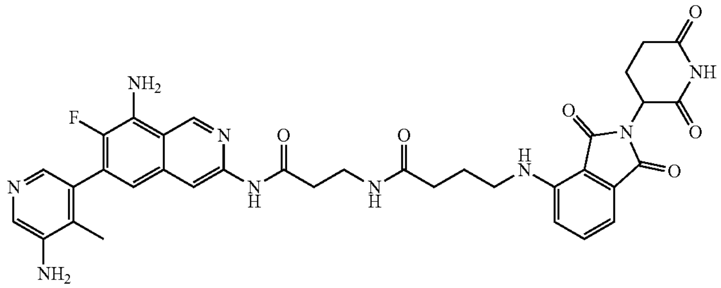 [SMILES: Cc1c(N)cncc1-c1cc2cc(NC(=O)CCNC(=O)CCCNc3cccc4c3C(=O)N(C3CCC(=O)NC3=O)C4=O)ncc2c(N)c1F] | N-(3-((8-amino-6-(5-amino-4-methylpyridin-3-yl)-7-fluoroisoquinolin-3-yl)amino)-3-oxopropyl)-4-((2-(2,6-dioxopiperidin-3-yl)-1,3-dioxoisoindolin-4-yl)amino)butanamide |
| 119 | HC65-186 | 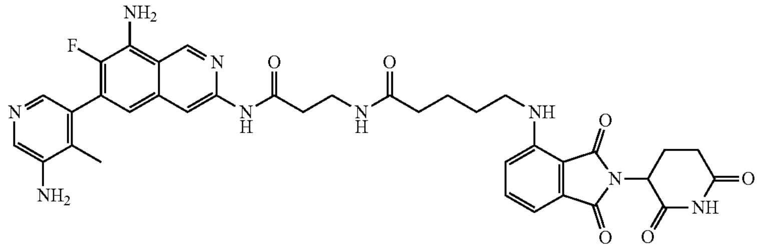 [SMILES: Cc1c(N)cncc1-c1cc2cc(NC(=O)CCNC(=O)CCCCNc3cccc4c3C(=O)N(C3CCC(=O)NC3=O)C4=O)ncc2c(N)c1F] | N-(3-((8-amino-6-(5-amino-4-methylpyridin-3-yl)-7-fluoroisoquinolin-3-yl)amino)-3-oxopropyl)-5-((2-(2,6-dioxopiperidin-3-yl)-1,3-dioxoisoindolin-4-yl)amino)pentanamide |
| 120 | HC75-1 | 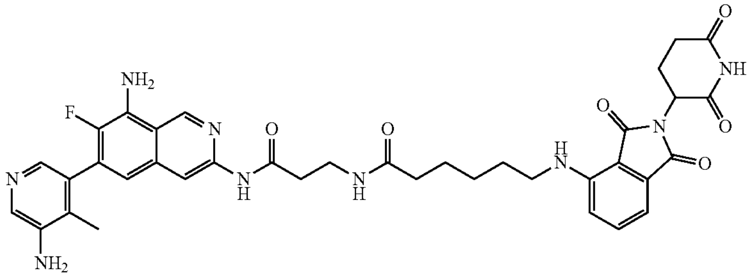 | N-(3-((8-amino-6-(5-amino-4-methylpyridin-3-yl)-7-fluoroisoquinolin-3-yl)amino)-3-oxopropyl)-6-((2-(2,6-dioxopiperidin-3-yl)-1,3-dioxoisoindolin-4-yl)amino)hexanamide |
| 121 | HC75-2 | 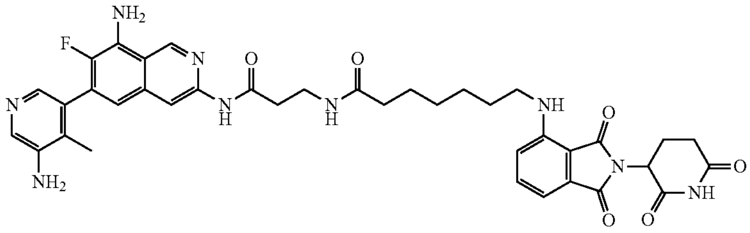 [SMILES: Cc1c(N)cncc1-c1cc2cc(NC(=O)CCNC(=O)CCCCCCNc3cccc4c3C(=O)N(C3CCC(=O)NC3=O)C4=O)ncc2c(N)c1F] | N-(3-((8-amino-6-(5-amino-4-methylpyridin-3-yl)-7-fluoroisoquinolin-3-yl)amino)-3-oxopropyl)-7-((2-(2,6-dioxopiperidin-3-yl)-1,3-dioxoisoindolin-4-yl)amino)heptanamide |
| 122 | HC75-3 | 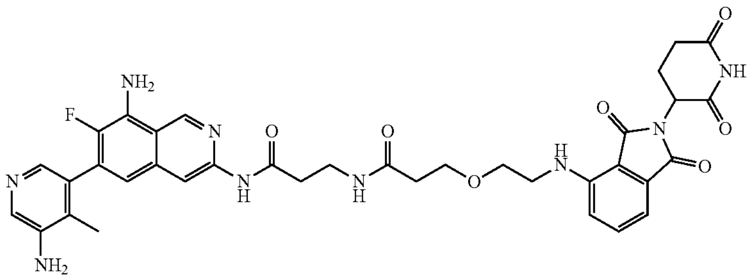 [SMILES: Cc1c(N)cncc1-c1cc2cc(NC(=O)CCNC(=O)CCOCCNc3cccc4c3C(=O)N(C3CCC(=O)NC3=O)C4=O)ncc2c(N)c1F] | N-(8-amino-6-(5-amino-4-methylpyridin-3-yl)-7-fluoroisoquinolin-3-yl)-3-(3-(2-((2-(2,6-dioxopiperidin-3-yl)-1,3-dioxoisoindolin-4-yl)amino)ethoxy)propanamido)propanamide |
| 123 | HC75-4 | 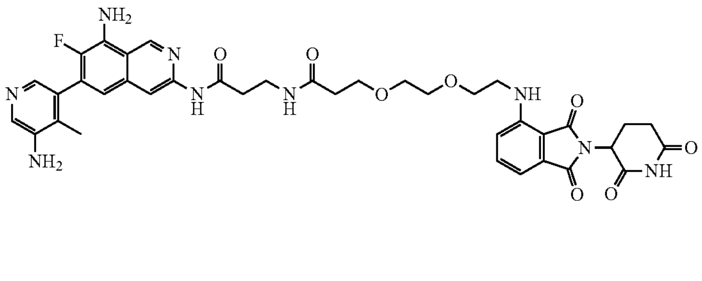 [SMILES: Cc1c(N)cncc1-c1cc2cc(NC(=O)CCNC(=O)CCOCCOCCNc3cccc4c3C(=O)N(C3CCC(=O)NC3=O)C4=O)ncc2c(N)c1F] | N-(8-amino-6-(5-amino-4-methylpyridin-3-yl)-7-fluoroisoquinolin-3-yl)-3-(3-(2-(2-((2-(2,6-dioxopiperidin-3-yl)-1,3-dioxoisoindolin-4-yl)amino)ethoxy)ethoxy)propanamido)propanamide |

TABLE 1-continued

| Ex am- ples | Com- pound code | Structure | Chemical Name |
|---|---|---|---|
| 124 | HC75- 5 | 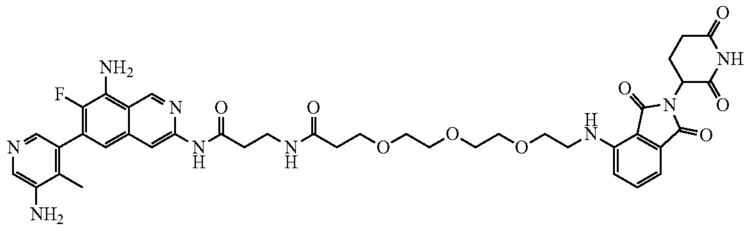 [SMILES: Cc1c(N)cncc1-c1cc2cc(NC(=O)CCNC(=O)CCOCCOCCOCCNc3cccc4c3C(=O)N(C3CCC(=O)NC3=O)C4=O)ncc2c(N)c1F] | N-(8-amino-6-(5-amino-4-methylpyridin-3-yl)-7-fluoroisoquinolin-3-yl)-3-(3-(2-(2-(2-((2-(2,6-dioxopiperidin-3-yl)-1,3-dioxoisoindolin-4-yl)amino)ethoxy)ethoxy)ethoxy) propanamido)propanamide |
| 125 | HC75- 6 | 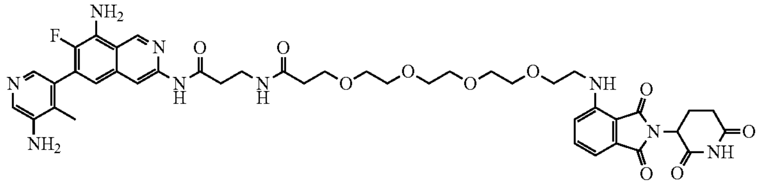 [SMILES: Cc1c(N)cncc1-c1cc2cc(NC(=O)CCNC(=O)CCOCCOCCOCCOCCNc3cccc4c3C(=O)N(C3CCC(=O)NC3=O)C4=O)ncc2c(N)c1F] | N-(3-((8-amino-6-(5-amino-4-methylpyridin-3-yl)-7-fluoroisoquinolin-3-yl)amino)-3-oxopropyl)-1-((2-(2,6-dioxopiperidin-3-yl)-1,3-dioxoisoindolin-4-yl)amino)-3,6,9,12-tetraoxapentadecan-15-amide |
| 126 | HC75- 7 | 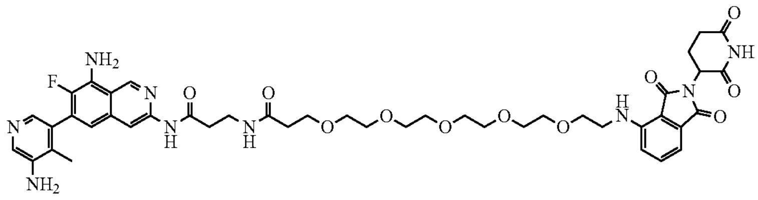 [SMILES: Cc1c(N)cncc1-c1cc2cc(NC(=O)CCNC(=O)CCOCCOCCOCCOCCOCCNc3cccc4c3C(=O)N(C3CCC(=O)NC3=O)C4=O)ncc2c(N)c1F] | N-(3-((8-amino-6-(5-amino-4-methylpyridin-3-yl)-7-fluoroisoquinolin-3-yl)amino)-3-oxopropyl)-1-((2-(2,6-dioxopiperidin-3-yl)-1,3-dioxoisoindolin-4-yl)amino)-3,6,9,12,15-pentaoxaoctadecan-18-amide |
| 127 | HC75- 8 | 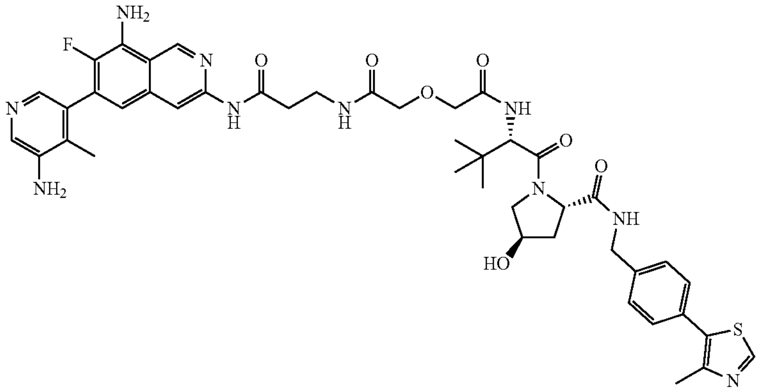 [SMILES: Cc1ncsc1-c1ccc(CNC(=O)[C@@H]2C[C@@H](O)CN2C(=O)[C@@H](NC(=O)COCC(=O)NCCC(=O)Nc2cc3cc(-c4cncc(N)c4C)c(F)c(N)c3cn2)C(C)(C)C)cc1] | (2S,4R)-1-((S)-2-(2-(2-((3-((8-amino-6-(5-amino-4-methylpyridin-3-yl)-7-fluoroisoquinolin-3-yl)amino)-3-oxopropyl)amino)-2-oxoethoxy)acetamido)-3,3-dimethylbutanoyl)-4-hydroxy-N-(4-(4-methylthiazol-5-yl)benzyl)pyrrolidine-2-carboxamide |
| 128 | HC75- 9 | 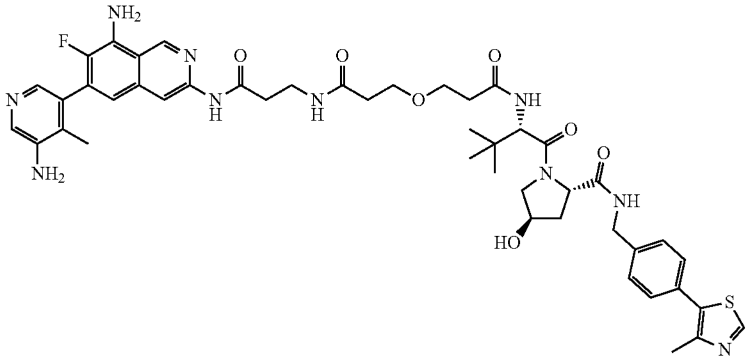 [SMILES: Cc1ncsc1-c1ccc(CNC(=O)[C@@H]2C[C@@H](O)CN2C(=O)[C@@H](NC(=O)CCOCCC(=O)NCCC(=O)Nc2cc3cc(-c4cncc(N)c4C)c(F)c(N)c3cn2)C(C)(C)C)cc1] | (28,4R)-1-((S)-2-(3-(3-((3-((8-amino-6-(5-amino-4-methylpyridin-3-yl)-7-fluoroisoquinolin-3-yl)amino)-3-oxopropyl)amino)-3-oxopropoxy)propanamido)-3,3-dimethylbutanoyl)-4-hydroxy-N-(4-(4-methylthiazol-5-yl)benzyl)pyrrolidine-2-carboxamide |

TABLE 1-continued

| Ex am- ples | Com- pound code | Structure | Chemical Name |
|---|---|---|---|
| 129 | HC75-10 | 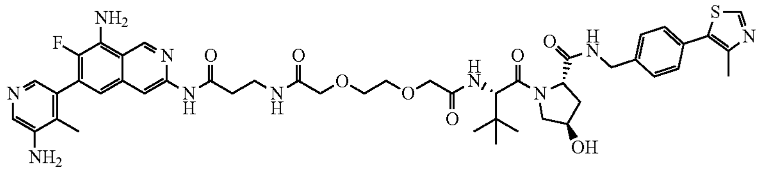 [SMILES: Cc1ncsc1-c1ccc(CNC(=O)[C@@H]2C[C@@H](O)CN2C(=O)[C@@H](NC(=O)COCCOCC(=O)NCCC(=O)Nc2cc3cc(-c4cncc(N)c4C)c(F)c(N)c3cn2)C(C)(C)C)cc1] | (2S,4R)-1-((S)-15-((8-amino-6-(5-amino-4-methylpyridin-3-yl)-7-fluoroisoquinolin-3-yl)amino)-2-(tert-butyl)-4,11,15-trioxo-6,9-dioxa-3,12-diazapentadecanoyl)-4-hydroxy-N-(4-(4-methylthiazol-5-yl)benzyl)pyrrolidine-2-carboxamide |
| 130 | HC75-11 | 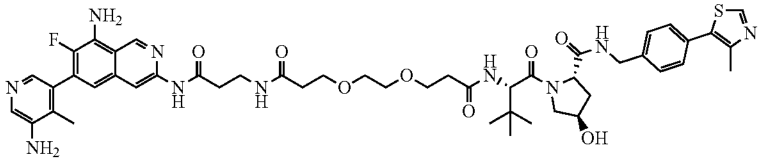 [SMILES: Cc1ncsc1-c1ccc(CNC(=O)[C@@H]2C[C@@H](O)CN2C(=O)[C@@H](NC(=O)CCOCCOCCC(=O)NCCC(=O)Nc2cc3cc(-c4cncc(N)c4C)c(F)c(N)c3cn2)C(C)(C)C)cc1] | (2S,4R)-1-((S)-17-((8-amino-6-(5-amino-4-methylpyridin-3-yl)-7-fluoroisoquinolin-3-yl)amino)-2-(tert-butyl)-4,13,17-trioxo-7,10-dioxa-3,14-diazaheptadecanoyl)-4-hydroxy-N-(4-(4-methylthiazol-5-yl)benzyl)pyrrolidine-2-carboxamide |
| 131 | HC75-12 | 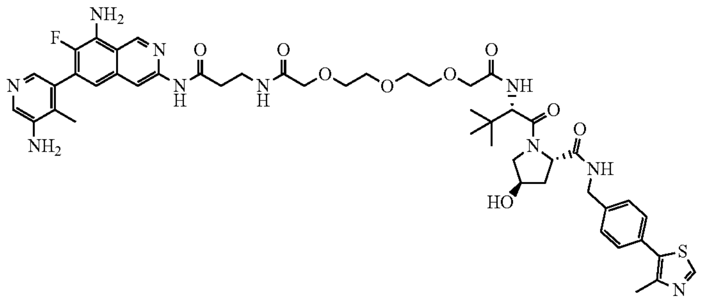 [SMILES: Cc1ncsc1-c1ccc(CNC(=O)[C@@H]2C[C@@H](O)CN2C(=O)[C@@H](NC(=O)COCCOCCOCC(=O)NCCC(=O)Nc2cc3cc(-c4cncc(N)c4C)c(F)c(N)c3cn2)C(C)(C)C)cc1] | (2S,4R)-1-((S)-18-((8-amino-6-(5-amino-4-methylpyridin-3-yl)-7-fluoroisoquinolin-3-yl)amino)-2-(tert-butyl)-4,14,18-trioxo-6,9,12-trioxa-3,15-diazaoctadecanoyl)-4-hydroxy-N-(4-(4-methylthiazol-5-yl)benzyl)pyrrolidine-2-carboxamide |
| 132 | HC75-13 | 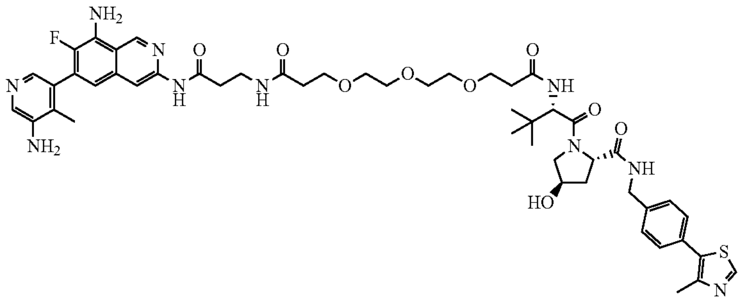 [SMILES: Cc1ncsc1-c1ccc(CNC(=O)[C@@H]2C[C@@H](O)CN2C(=O)[C@@H](NC(=O)CCOCCOCCOCCC(=O)NCCC(=O)Nc2cc3cc(-c4cncc(N)c4C)c(F)c(N)c3cn2)C(C)(C)C)cc1] | (2S,4R)-1-((S)-20-((8-amino-6-(5-amino-4-methylpyridin-3-yl)-7-fluoroisoquinolin-3-yl)amino)-2-(tert-butyl)-4,16,20-trioxo-7,10,13-trioxa-3,17-diazaicosanoyl)-4-hydroxy-N-(4-(4-methylthiazol-5-yl)benzyl)pyrrolidine-2-carboxamide |
| 133 | HC75-14 | 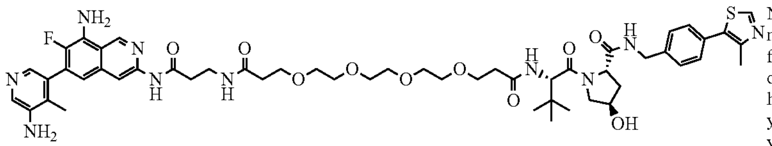 | $N^1$-(3-((8-amino-6-(5-amino-4-methylpyridin-3-yl)-7-fluoroisoquinolin-3-yl)amino)-3-oxopropyl)-$N^{16}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |
| 134 | HC75-15 | 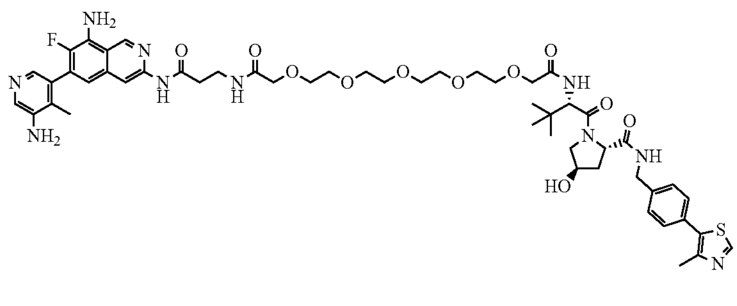 [SMILES: Cc1ncsc1-c1ccc(CNC(=O)[C@@H]2C[C@@H](O)CN2C(=O)[C@@H](NC(=O)COCCOCCOCCOCCOCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^{17}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide |

TABLE 1-continued

| Ex am- ples | Com- pound code | Structure | Chemical Name |
|---|---|---|---|
| 135 | HC75-16 | 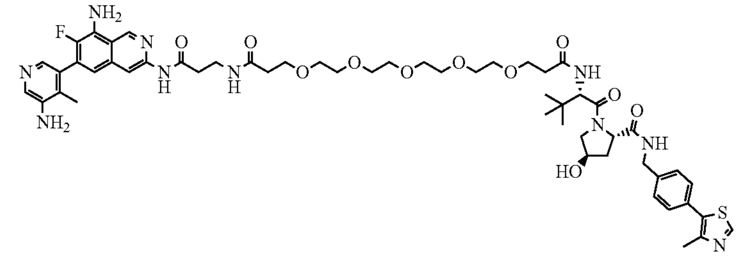 [SMILES: Cc1ncsc1-c1ccc(CNC(=O)[C@@H]2C[C@@H](O)CN2C(=O)[C@@H](NC(=O)CCOCCOCCOCCOCCOCCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^{19}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| 136 | HC75-17 | 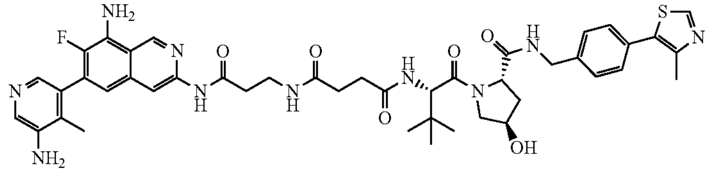 [SMILES: Cc1ncsc1-c1ccc(CNC(=O)[C@@H]2C[C@@H](O)CN2C(=O)[C@@H](NC(=O)CCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^4$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |
| 137 | HC75-18 | 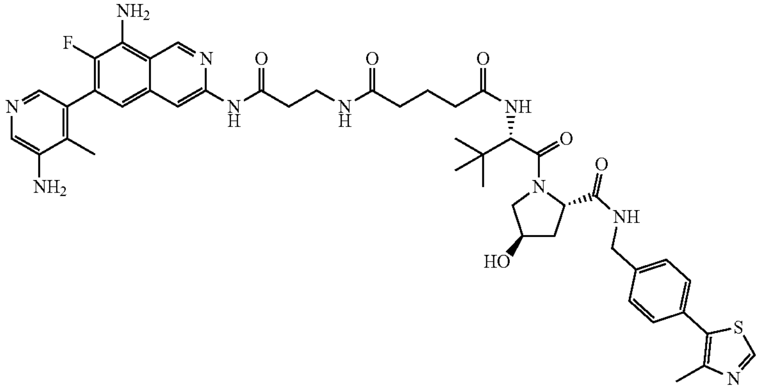 [SMILES: Cc1ncsc1-c1ccc(CNC(=O)[C@@H]2C[C@@H](O)CN2C(=O)[C@@H](NC(=O)CCCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^5$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |
| 138 | HC75-19 | 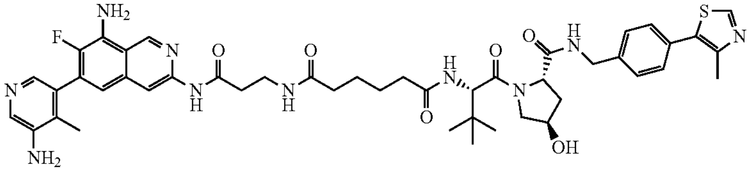 [SMILES: Cc1ncsc1-c1ccc(CNC(=O)[C@@H]2C[C@@H](O)CN2C(=O)[C@@H](NC(=O)CCCCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^6$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |
| 139 | HC75-20 | 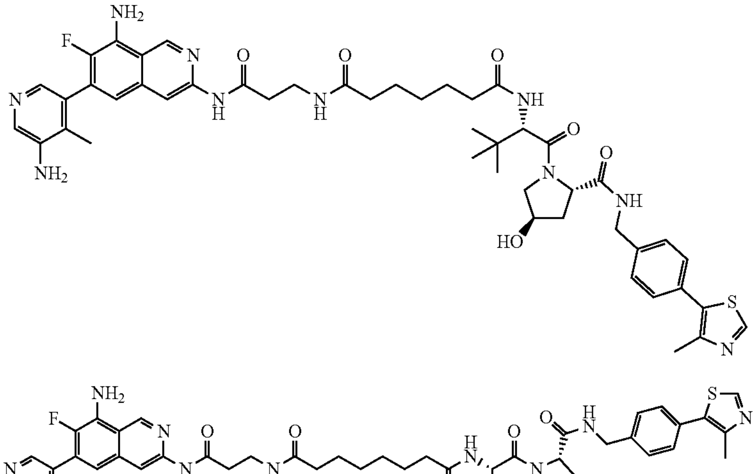 | $N^1$-(3-((8-amino-6-(5-amino-4-methylpyridin-3-yl)-7-fluoroisoquinolin-3-yl)amino)-3-oxopropyl)-$N^7$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |
| 140 | HC75-21 | 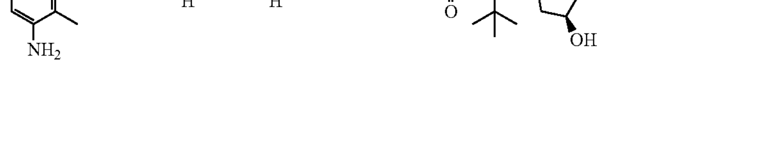 | $N^1$-(3-((8-amino-6-(5-amino-4-methylpyridin-3-yl)-7-fluoroisoquinolin-3-yl)amino)-3-oxopropyl)-$N^8$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |

TABLE 1-continued

| Examples | Compound code | Structure | Chemical Name |
|---|---|---|---|
| 141 | HC75-22 | 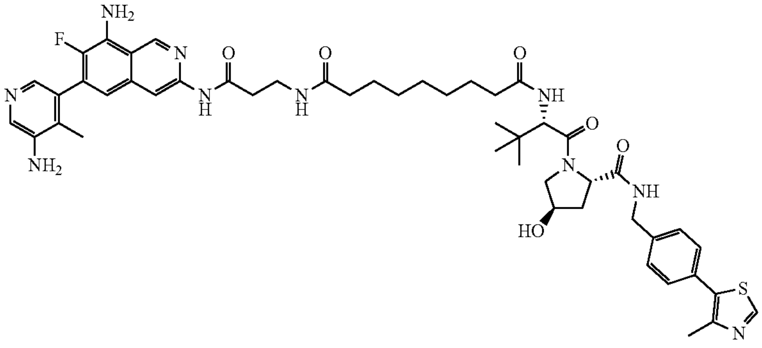 [SMILES: Cc1ncsc1-c1ccc(CNC(=O)[C@@H]2C[C@@H](O)CN2C(=O)[C@@H](NC(=O)CCCCCCCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^9$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |
| 142 | HC75-23 | 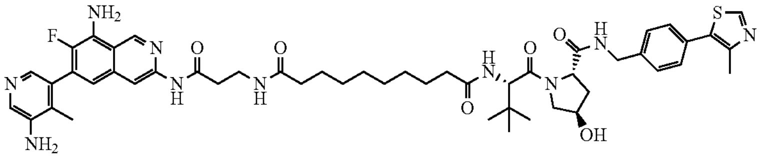 [SMILES: Cc1ncsc1-c1ccc(CNC(=O)[C@@H]2C[C@@H](O)CN2C(=O)[C@@H](NC(=O)CCCCCCCCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^{10}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |
| 143 | HC75-24 | 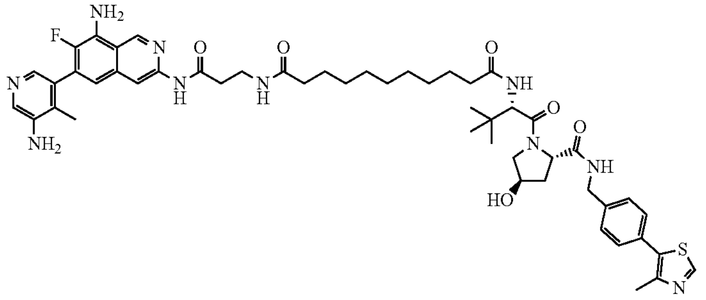 [SMILES: Cc1ncsc1-c1ccc(CNC(=O)[C@@H]2C[C@@H](O)CN2C(=O)[C@@H](NC(=O)CCCCCCCCCC(=O)NCCC(=O)Nc2cc3cc(-c4cncc(N)c4C)c(F)c(N)c3cn2)C(C)(C)C)cc1] | $N^1$-(3-((8-amino-6-(5-amino-4-methylpyridin-3-yl)-7-fluoroisoquinolin-3-yl)amino)-3-oxopropyl)-$N^{11}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| 144 | HC75-29 | 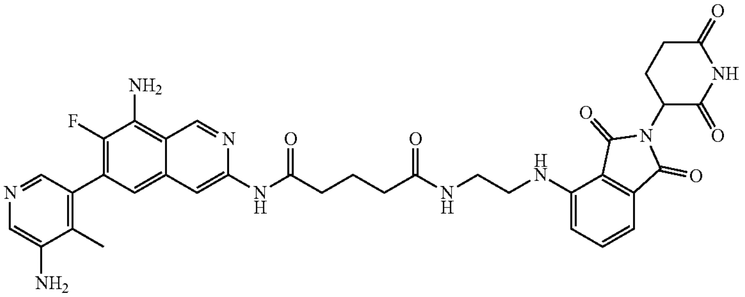 [SMILES: Cc1c(N)cncc1-c1cc2cc(NC(=O)CCCC(=O)NCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(2-((2-(2,6-dioxopiperidin-3-yl)-1,3-dioxoisoindolin-4-yl)amino)ethyl)glutaramide |
| 145 | HC75-31 | 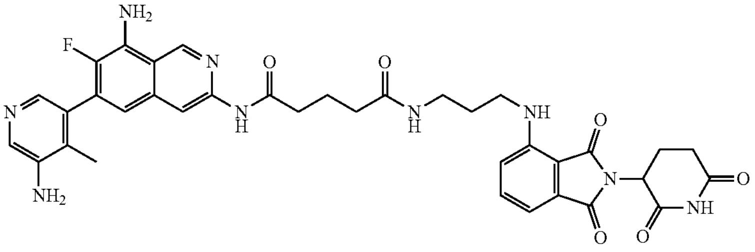 [SMILES: Cc1c(N)cncc1-c1cc2cc(NC(=O)CCCC(=O)NCCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(3-((2-(2,6-dioxopiperidin-3-yl)-1,3-dioxoisoindolin-4-yl)amino)propyl)glutaramide |

TABLE 1-continued

| Ex am- ples | Com- pound code | Structure | Chemical Name |
|---|---|---|---|
| 146 | HC75-34 | 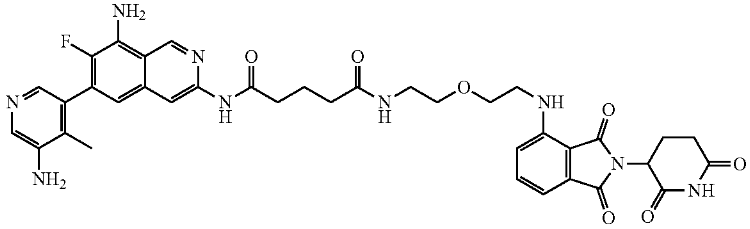 | $N^1$-(8-amino-6-(5-amino-4-methylpyridin-3-yl)-7-fluoroisoquinolin-3-yl)-$N^5$-(2-(2-((2-(2,6-dioxopiperidin-3-yl)-1,3-dioxoisoindolin-4-yl)amino)ethoxy)ethyl)glutaramide |
| 147 | HC75-35 | 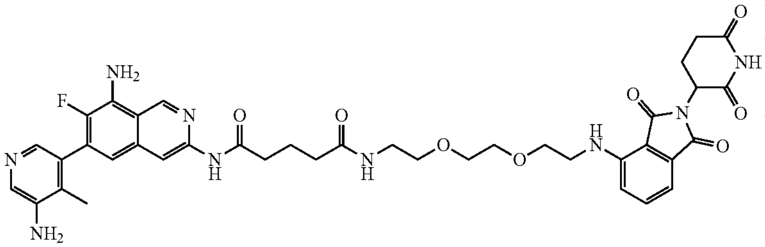 [SMILES: Cc1c(N)cncc1-c1cc2cc(NC(=O)CCCC(=O)NCCOCCOCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(2-(2-(2-((2-(2,6-dioxopiperidin-3-yl)-1,3-dioxoisoindolin-4-yl)amino)ethoxy)ethoxy)ethyl) glutaramide |
| 148 | HC75-36 | 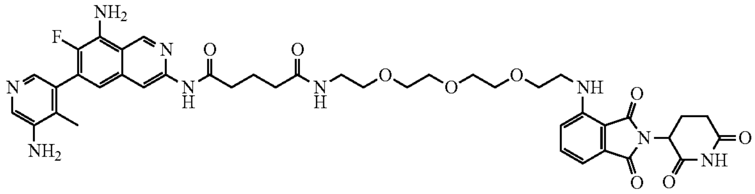 [SMILES: Cc1c(N)cncc1-c1cc2cc(NC(=O)CCCC(=O)NCCOCCOCCOCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(2-(2-(2-(2-((2-(2,6-dioxopiperidin-3-yl)-1,3-dioxoisoindolin-4-yl)amino)ethoxy)ethoxy)ethoxy) ethyl)glutaramide |
| 149 | HC75-37 | 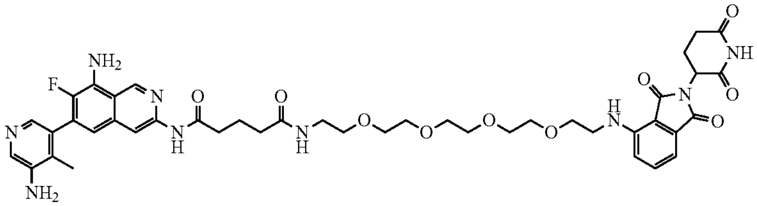 [SMILES: Cc1c(N)cncc1-c1cc2cc(NC(=O)CCCC(=O)NCCOCCOCCOCCOCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(14-((2-(2,6-dioxopiperidin-3-yl)-1,3-dioxoisoindolin-4-yl)amino)-3,6,9,12-tetraoxatetradecyl)glutaramide |
| 150 | HC75-38 | 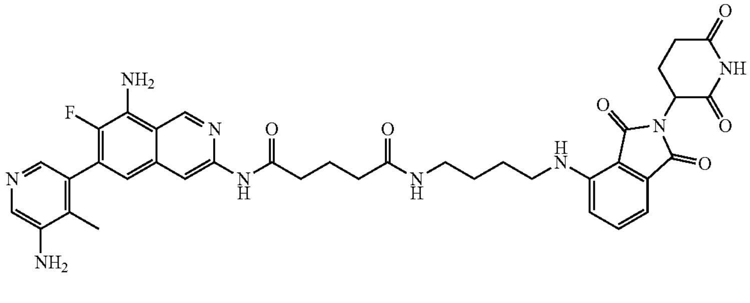 [SMILES: Cc1c(N)cncc1-c1cc2cc(NC(=O)CCCC(=O)NCCCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(4-((2-(2,6-dioxopiperidin-3-yl)-1,3-dioxoisoindolin-4-yl)amino)butyl)glutaramide |
| 151 | HC75-39 | 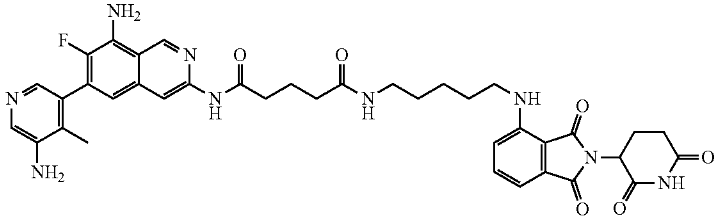 [SMILES: Cc1c(N)cncc1-c1cc2cc(NC(=O)CCCC(=O)NCCCCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(5-((2-(2,6-dioxopiperidin-3-yl)-1,3-dioxoisoindolin-4-yl)amino)pentyl)glutaramide |

TABLE 1-continued

| Examples | Compound code | Structure | Chemical Name |
|---|---|---|---|
| 152 | HC75-40 | 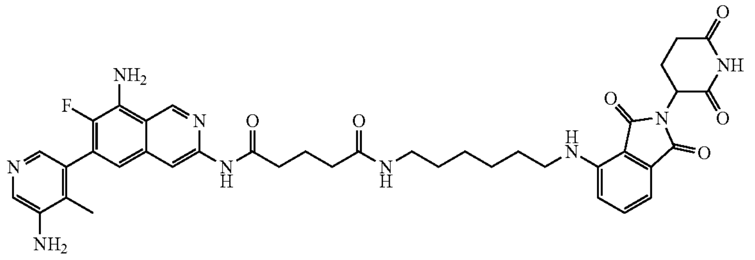 [SMILES: Cc1c(N)cncc1-c1cc2cc(NC(=O)CCCC(=O)NCCCCCCNc3cccc4c3C(=O)N(C3CCC(=O)NC3=O)C4=O)ncc2c(N)c1F] | N[1]-(8-amino-6-(5-amino-4-methylpyridin-3-yl)-7-fluoroisoquinolin-3-yl)-N[5]-(6-((2-(2,6-dioxopiperidin-3-yl)-1,3-dioxoisoindolin-4-yl)amino)hexyl)glutaramide |
| 153 | HC75-41 | 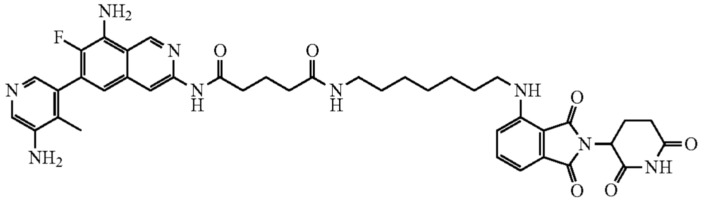 [SMILES: Cc1c(N)cncc1-c1cc2cc(NC(=O)CCCC(=O)NCCCCCCCNc3cccc4c3C(=O)N(C3CCC(=O)NC3=O)C4=O)ncc2c(N)c1F] | N[1]-(8-amino-6-(5-amino-4-methylpyridin-3-yl)-7-fluoroisoquinolin-3-yl)-N[5]-(7-((2-(2,6-dioxopiperidin-3-yl)-1,3-dioxoisoindolin-4-yl)amino)heptyl)glutaramide |
| 154 | HC75-42 | 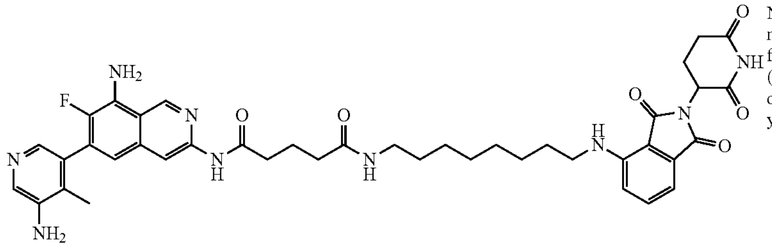 | N[1]-(8-amino-6-(5-amino-4-methylpyridin-3-yl)-7-fluoroisoquinolin-3-yl)-N[5]-(8-((2-(2,6-dioxopiperidin-3-yl)-1,3-dioxoisoindolin-4-yl)amino)octyl)glutaramide |
| 155 | HC75-43 | 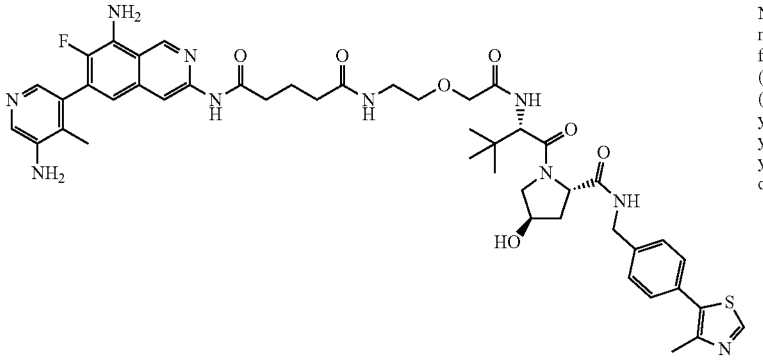 | N[1]-(8-amino-6-(5-amino-4-methylpyridin-3-yl)-7-fluoroisoquinolin-3-yl)-N[5]-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)glutaramide |
| 156 | HC75-44 | 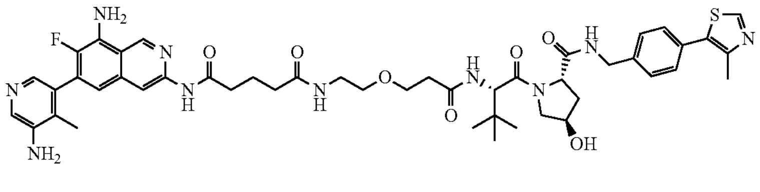 | N[1]-(8-amino-6-(5-amino-4-methylpyridin-3-yl)-7-fluoroisoquinolin-3-yl)-N[5]-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl) glutaramide |
| 157 | HC75-45 | 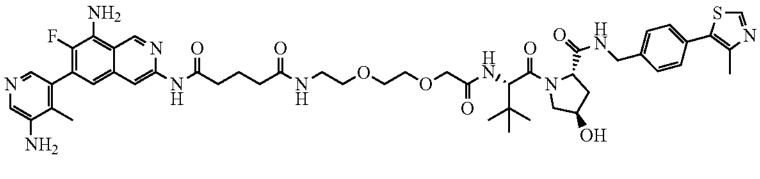 [SMILES: Cc1ncsc1-c1ccc(CNC(=O)[C@@H]2C[C@@H](O)CN2C(=O)[C@@H](NC(=O)COCCOCCNC(=O)CCCC(=O)Nc2cc3cc(-c4cncc(N)c4C)c(F)c(N)c3cn2)C(C)(C)C)cc1] | N[1]-(8-amino-6-(5-amino-4-methylpyridin-3-yl)-7-fluoroisoquinolin-3-yl)-N[5]-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)ethyl) glutaramide |

TABLE 1-continued

| Ex am- ples | Com- pound code | Structure | Chemical Name |
|---|---|---|---|
| 158 | HC75-46 | 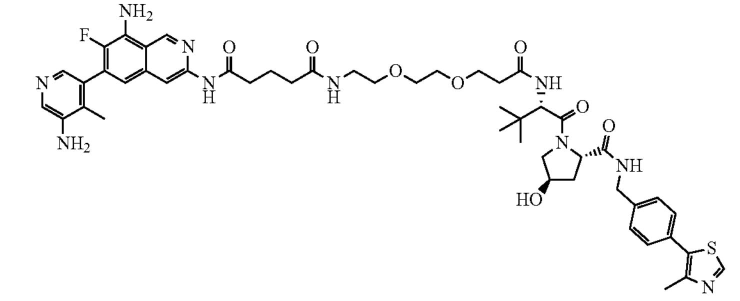 [SMILES: Cc1ncsc1-c1ccc(CNC(=O)[C@@H]2C[C@@H](O)CN2C(=O)[C@@H](NC(=O)CCOCCOCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(2-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)ethyl) glutaramide |
| 159 | HC75-47 | 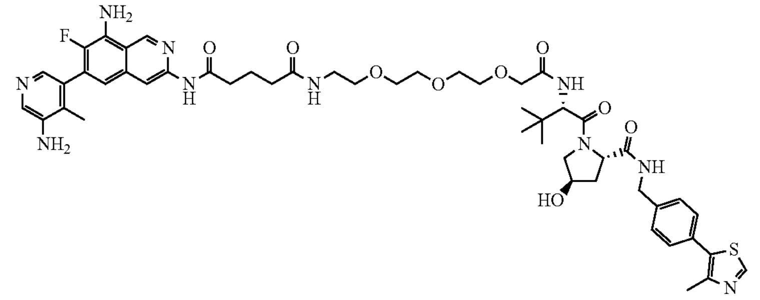 [SMILES: Cc1ncsc1-c1ccc(CNC(=O)[C@@H]2C[C@@H](O)CN2C(=O)[C@@H](NC(=O)COCCOCCOCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)glutaramide |
| 160 | HC75-48 | 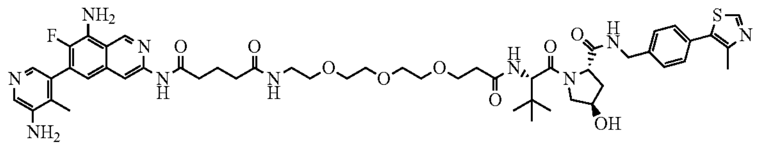 [SMILES: Cc1ncsc1-c1ccc(CNC(=O)[C@@H]2C[C@@H](O)CN2C(=O)[C@@H](NC(=O)CCOCCOCCOCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-((S)-14-((2S,4R)-4-hydroxy-2-((4-(4-methylthiazol-5-yl)benzyl)carbamoyl)pyrrolidine-1-carbonyl)-15,15-dimethyl-12-oxo-3,6,9-trioxa-13-azahexadecyl)glutaramide |
| 161 | HC75-49 | 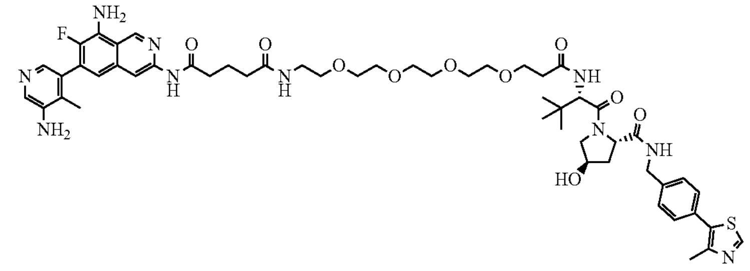 [SMILES: Cc1ncsc1-c1ccc(CNC(=O)[C@@H]2C[C@@H](O)CN2C(=O)[C@@H](NC(=O)CCOCCOCCOCCOCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-((S)-17-((2S,4R)-4-hydroxy-2-((4-(4-methylthiazol-5-yl)benzyl)carbamoyl)pyrrolidine-1-carbonyl)-18,18-dimethyl-15-oxo-3,6,9,12-tetraoxa-16-azanonadecyl)glutaramide |
| 162 | HC75-50 | 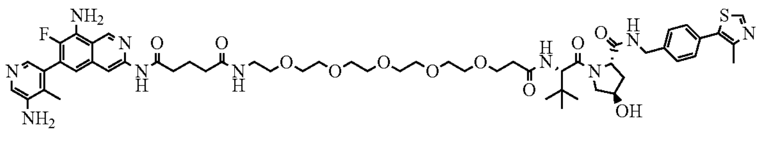 [SMILES: Cc1ncsc1-c1ccc(CNC(=O)[C@@H]2C[C@@H](O)CN2C(=O)[C@@H](NC(=O)CCOCCOCCOCCOCCOCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-((S)-20-((2S,4R)-4-hydroxy-2-((4-(4-methylthiazol-5-yl)benzyl)carbamoyl)pyrrolidine-1-carbonyl)-21,21-dimethyl-18-oxo-3,6,9,12,15-pentaoxa-19-azadocosyl)glutaramide |
| 163 | HC75-52 | 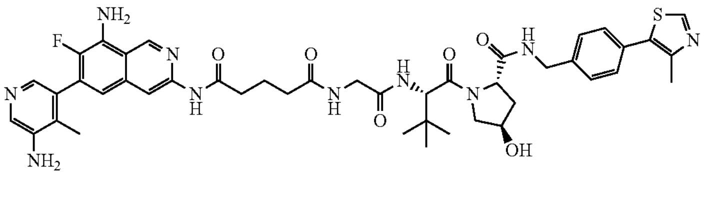 [SMILES: Cc1ncsc1-c1ccc(CNC(=O)[C@@H]2C[C@@H](O)CN2C(=O)[C@@H](NC(=O)CNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)glutaramide |

TABLE 1-continued

| Examples | Compound code | Structure | Chemical Name |
|---|---|---|---|
| 164 | HC75-53 | 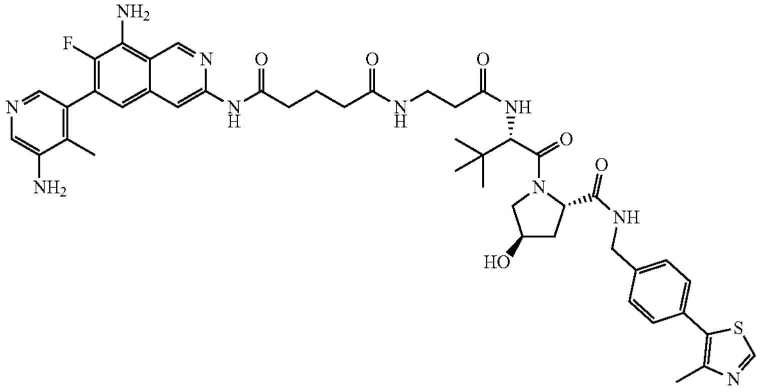 [SMILES: Cc1ncsc1-c1ccc(CNC(=O)[C@@H]2C[C@@H](O)CN2C(=O)[C@@H](NC(=O)CCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)glutaramide |
| 165 | HC75-54 | 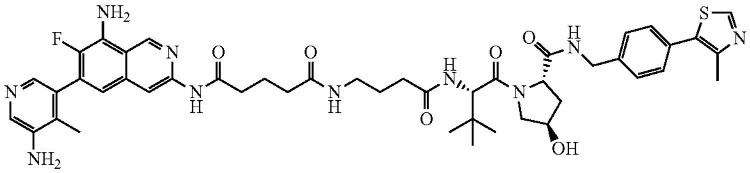 [SMILES: Cc1ncsc1-c1ccc(CNC(=O)[C@@H]2C[C@@H](O)CN2C(=O)[C@@H](NC(=O)CCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)glutaramide |
| 166 | HC75-55 | 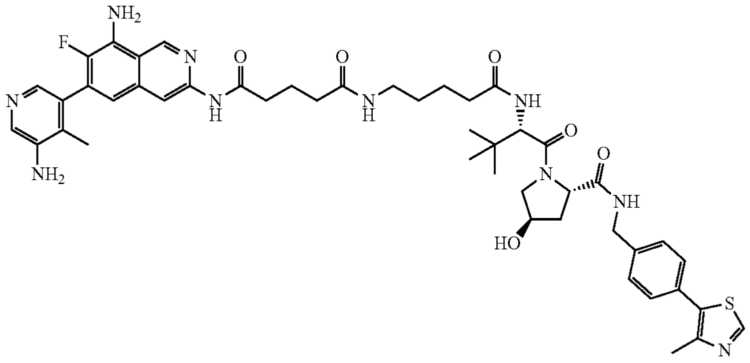 [SMILES: Cc1ncsc1-c1ccc(CNC(=O)[C@@H]2C[C@@H](O)CN2C(=O)[C@@H](NC(=O)CCCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)glutaramide |
| 167 | HC75-56 | 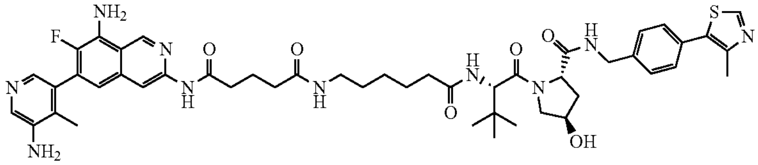 [SMILES: Cc1ncsc1-c1ccc(CNC(=O)[C@@H]2C[C@@H](O)CN2C(=O)[C@@H](NC(=O)CCCCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)glutaramide |
| 168 | HC75-57 | 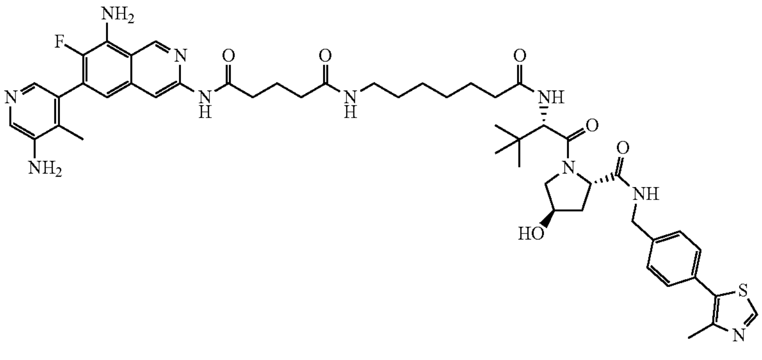 [SMILES: Cc1ncsc1-c1ccc(CNC(=O)[C@@H]2C[C@@H](O)CN2C(=O)[C@@H](NC(=O)CCCCCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)glutaramide |

TABLE 1-continued

| Ex amples | Compound code | Structure | Chemical Name |
|---|---|---|---|
| 169 | HC75-58 | 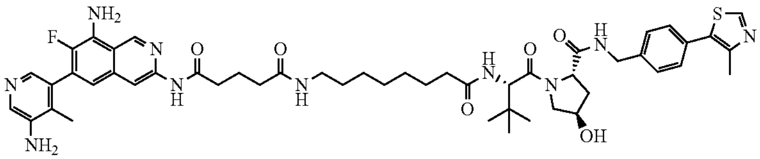 [SMILES: Cc1ncsc1-c1ccc(CNC(=O)[C@@H]2C[C@@H](O)CN2C(=O)[C@@H](NC(=O)CCCCCCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)glutaramide |
| 170 | HC75-59 | 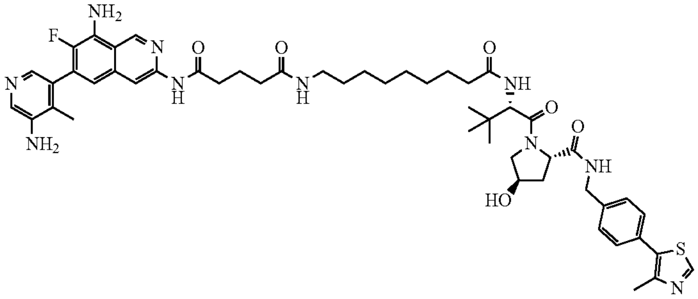 [SMILES: Cc1ncsc1-c1ccc(CNC(=O)[C@@H]2C[C@@H](O)CN2C(=O)[C@@H](NC(=O)CCCCCCCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)glutaramide |
| 171 | HC75-60 | 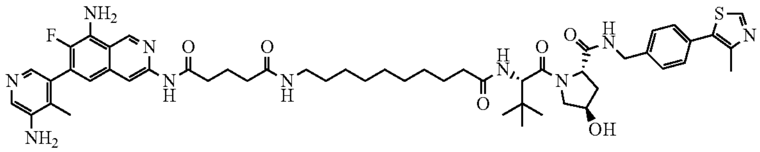 [SMILES: Cc1ncsc1-c1ccc(CNC(=O)[C@@H]2C[C@@H](O)CN2C(=O)[C@@H](NC(=O)CCCCCCCCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)glutaramide |
| 172 | HC75-61 | 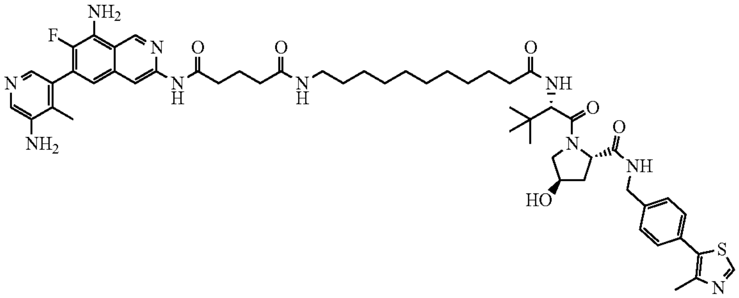 [SMILES: Cc1ncsc1-c1ccc(CNC(=O)[C@@H]2C[C@@H](O)CN2C(=O)[C@@H](NC(=O)CCCCCCCCCCNC(=O)CCCC(=O)Nc2cc3cc(-c4cncc(N)c4C)c(F)c(N)c3cn2)C(C)(C)C)cc1] | $N^1$-(8-amino-6-(5-amino-4-methylpyridin-3-yl)-7-fluoroisoquinolin-3-yl)-$N^5$-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)glutaramide |
| 173 | HC75-62 | 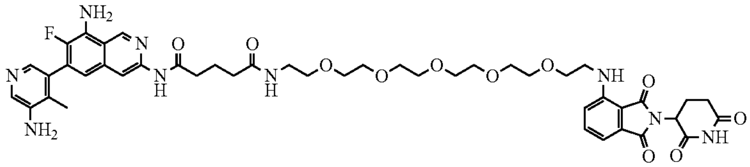 [SMILES: Cc1c(N)cncc1-c1cc2cc(NC(=O)CCCC(=O)NCCOCCOCCOCCOCCOCCNc3cccc4c3C(=O)N(C3CCC(=O)NC3=O)C4=O)ncc2c(N)c1F] | $N^1$-(8-amino-6-(5-amino-4-methylpyridin-3-yl)-7-fluoroisoquinolin-3-yl)-$N^5$-(17-((2-(2,6-dioxopiperidin-3-yl)-1,3-dioxoisoindolin-4-yl)amino)-3,6,9,12,15-pentaoxaheptadecyl)glutaramide |
| 175 | HC90-33 | 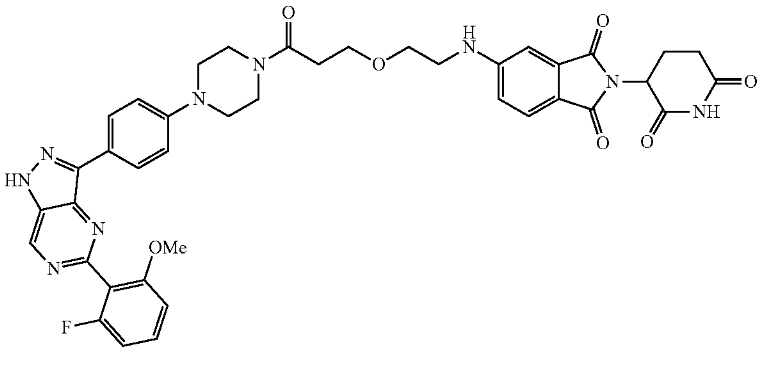 [SMILES: COc1cccc(F)c1-c1ncc2[nH]nc(-c3ccc(N4CCN(C(=O)CCOCCNc5ccc6c(c5)C(=O)N(C5CCC(=O)NC5=O)C6=O)CC4)cc3)c2n1] | 2-(2,6-dioxopiperidin-3-yl)-5-((2-(3-(4-(4-(5-(2-fluoro-6-methoxyphenyl)-1H-pyrazolo[4,3-d]pyrimidin-3-yl)phenyl)piperazin-1-yl)-3-oxopropoxy)ethyl)amino)isoindoline-1,3-dione |

TABLE 1-continued

| Examples | Compound code | Structure | Chemical Name |
|---|---|---|---|
| 176 | HC90-34 | 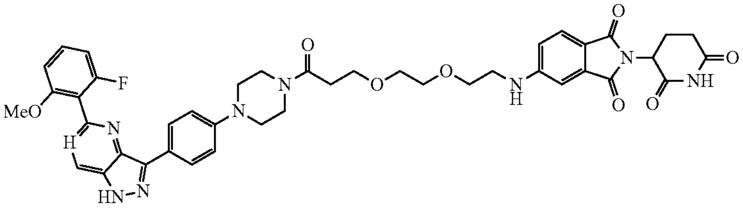 | 2-(2,6-dioxopiperidin-3-yl)-5-((2-(2-(3-(4-(4-(5-(2-fluoro-6-methoxyphenyl)-1H-pyrazolo[4,3-d]pyrimidin-3-yl)phenyl)piperazin-1-yl)-3-oxopropoxy)ethoxy)ethyl)amino)isoindoline-1,3-dione |
| 177 | HC90-35 | 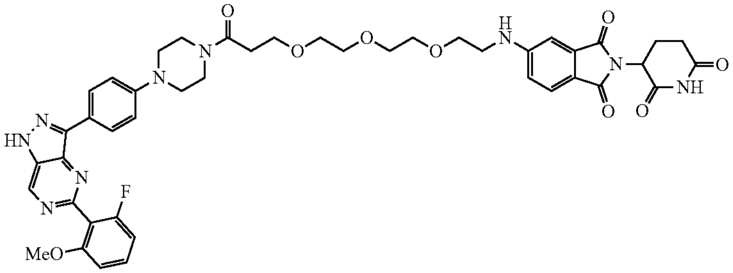 [SMILES: COc1cccc(F)c1-c1ncc2[nH]nc(-c3ccc(N4CCN(C(=O)CCOCCOCCOCCNc5ccc6c(c5)C(=O)N(C5CCC(=O)NC5=O)C6=O)CC4)cc3)c2n1] | 2-(2,6-dioxopiperidin-3-yl)-5-((2-(2-(2-(3-(4-(4-(5-(2-fluoro-6-methoxyphenyl)-1H-pyrazolo[4,3-d]pyrimidin-3-yl)phenyl)piperazin-1-yl)-3-oxopropoxy)ethoxy)ethoxy)ethyl)amino)isoindoline-1,3-dione |
| 178 | HC90-36 | 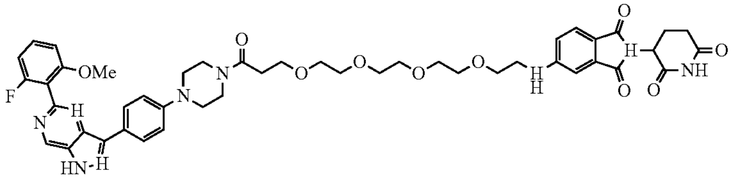 | 2-(2,6-dioxopiperidin-3-yl)-5-((15-(4-(4-(5-(2-fluoro-6-methoxyphenyl)-1H-pyrazolo[4,3-d]pyrimidin-3-yl)phenyl)piperazin-1-yl)-15-oxo-3,6,9,12-tetraoxapentadecyl)amino)isoindoline-1,3-dione |
| 179 | HC90-37 | 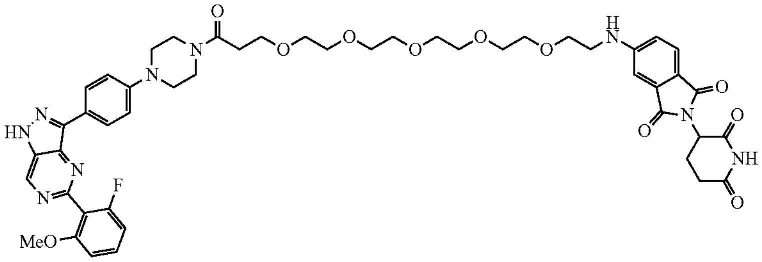 [SMILES: COc1cccc(F)c1-c1ncc2[nH]nc(-c3ccc(N4CCN(C(=O)CCOCCOCCOCCOCCOCCNc5ccc6c(c5)C(=O)N(C5CCC(=O)NC5=O)C6=O)CC4)cc3)c2n1] | 2-(2,6-dioxopiperidin-3-yl)-5-((18-(4-(4-(5-(2-fluoro-6-methoxyphenyl)-1H-pyrazolo[4,3-d]pyrimidin-3-yl)phenyl)piperazin-1-yl)-18-oxo-3,6,9,12,15-pentaoxaoctadecyl)amino)isoindoline-1,3-dione |
| 180 | HC90-41 | 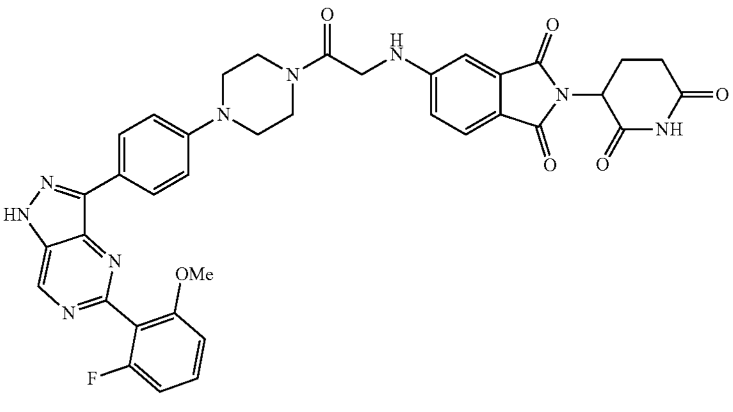 [SMILES: COc1cccc(F)c1-c1ncc2[nH]nc(-c3ccc(N4CCN(C(=O)CNc5ccc6c(c5)C(=O)N(C5CCC(=O)NC5=O)C6=O)CC4)cc3)c2n1] | 2-(2,6-dioxopiperidin-3-yl)-5-((2-(4-(4-(5-(2-fluoro-6-methoxyphenyl)-1H-pyrazolo[4,3-d]pyrimidin-3-yl)phenyl)piperazin-1-yl)-2-oxoethyl)amino)isoindoline-1,3-dione |

TABLE 1-continued

| Ex am- ples | Com- pound code | Structure | Chemical Name |
|---|---|---|---|
| 181 | HC90-42 | 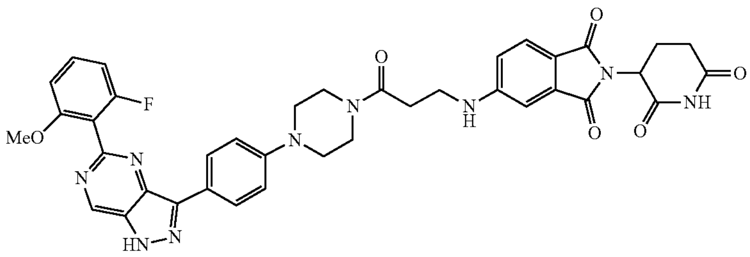 [SMILES: COc1cccc(F)c1-c1ncc2[nH]nc(-c3ccc(N4CCN(C(=O)CCNc5ccc6c(c5)C(=O)N(C5CCC(=O)NC5=O)C6=O)CC4)cc3)c2n1] | 2-(2,6-dioxopiperidin-3-yl)-5-((3-(4-(4-(5-(2-fluoro-6-methoxyphenyl)-1H-pyrazolo[4,3-d]pyrimidin-3-yl)phenyl)piperazin-1-yl)-3-oxopropyl)amino)isoindoline-1,3-dione |
| 182 | HC90-43 | 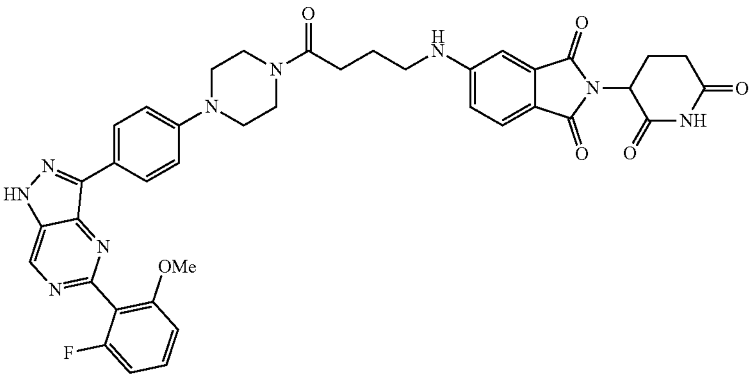 [SMILES: COc1cccc(F)c1-c1ncc2[nH]nc(-c3ccc(N4CCN(C(=O)CCCNc5ccc6c(c5)C(=O)N(C5CCC(=O)NC5=O)C6=O)CC4)cc3)c2n1] | 2-(2,6-dioxopiperidin-3-yl)-5-((4-(4-(4-(5-(2-fluoro-6-methoxyphenyl)-1H-pyrazolo[4,3-d]pyrimidin-3-yl)phenyl)piperazin-1-yl)-4-oxobutyl)amino)isoindoline-1,3-dione |
| 183 | HC90-44 | 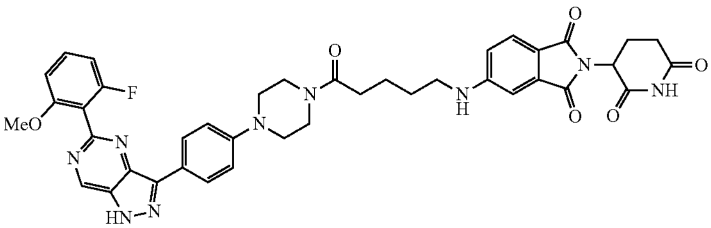 [SMILES: COc1cccc(F)c1-c1ncc2[nH]nc(-c3ccc(N4CCN(C(=O)CCCCNc5ccc6c(c5)C(=O)N(C5CCC(=O)NC5=O)C6=O)CC4)cc3)c2n1] | 2-(2,6-dioxopiperidin-3-yl)-5-((5-(4-(4-(5-(2-fluoro-6-methoxyphenyl)-1H-pyrazolo[4,3-d]pyrimidin-3-yl)phenyl)piperazin-1-yl)-5-oxopentyl)amino)isoindoline-1,3-dione |
| 184 | HC90-45 | 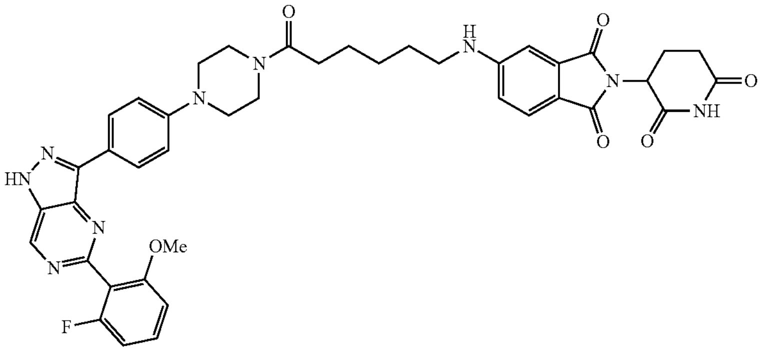 [SMILES: COc1cccc(F)c1-c1ncc2[nH]nc(-c3ccc(N4CCN(C(=O)CCCCCNc5ccc6c(c5)C(=O)N(C5CCC(=O)NC5=O)C6=O)CC4)cc3)c2n1] | 2-(2,6-dioxopiperidin-3-yl)-5-((6-(4-(4-(5-(2-fluoro-6-methoxyphenyl)-1H-pyrazolo[4,3-d]pyrimidin-3-yl)phenyl)piperazin-1-yl)-6-oxohexyl)amino)isoindoline-1,3-dione |
| 185 | HC90-46 | 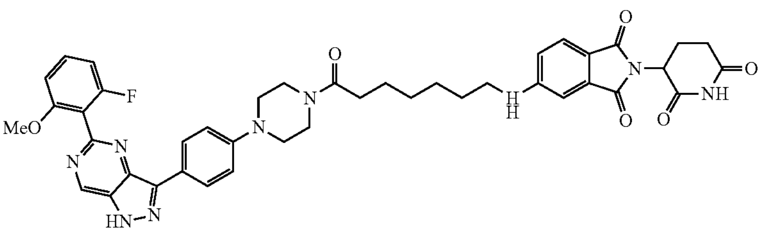 | 2-(2,6-dioxopiperidin-3-yl)-5-((7-(4-(4-(5-(2-fluoro-6-methoxyphenyl)-1H-pyrazolo[4,3-d]pyrimidin-3-yl)phenyl)piperazin-1-yl)-7-oxoheptyl)amino)isoindoline-1,3-dione |

TABLE 1-continued

| Examples | Compound code | Structure | Chemical Name |
|---|---|---|---|
| 186 | HC90-47 | 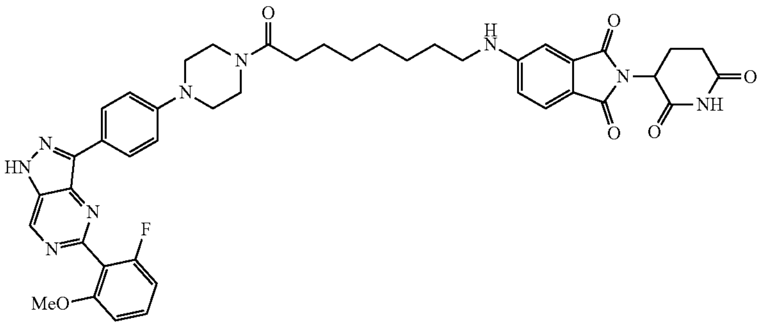 [SMILES: COc1cccc(F)c1-c1ncc2[nH]nc(-c3ccc(N4CCN(C(=O)CCCCCCCNc5ccc6c(c5)C(=O)N(C5CCC(=O)NC5=O)C6=O)CC4)cc3)c2n1] | 2-(2,6-dioxopiperidin-3-yl)-5-((8-(4-(4-(5-(2-fluoro-6-methoxyphenyl)-1H-pyrazolo[4,3-d]pyrimidin-3-yl)phenyl)piperazin-1-yl)-8-oxooctyl)amino)isoindoline-1,3-dione |
| 187 | HC90-49 | 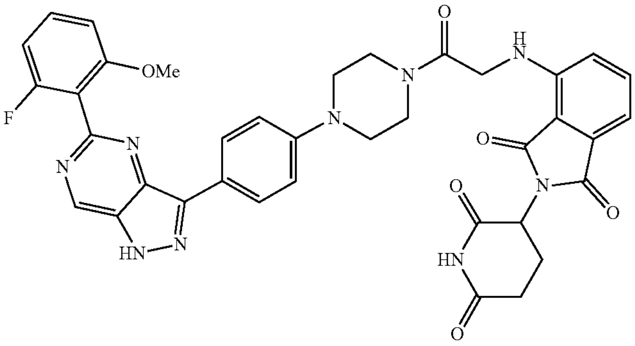 [SMILES: COc1cccc(F)c1-c1ncc2[nH]nc(-c3ccc(N4CCN(C(=O)CNc5cccc6c5C(=O)N(C5CCC(=O)NC5=O)C6=O)CC4)cc3)c2n1] | 2-(2,6-dioxopiperidin-3-yl)-4-((2-(4-(4-(5-(2-fluoro-6-methoxyphenyl)-1H-pyrazolo[4,3-d]pyrimidin-3-yl)phenyl)piperazin-1-yl)-2-oxoethyl)amino)isoindoline-1,3-dione |
| 188 | HC90-50 | 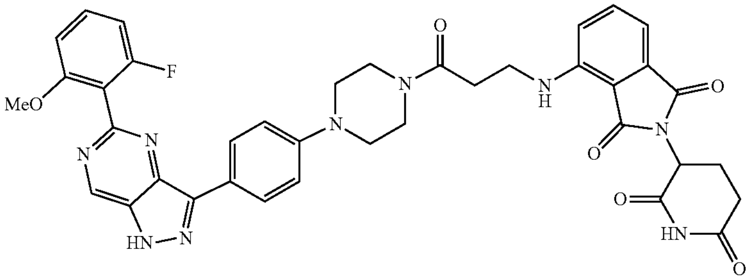 [SMILES: COc1cccc(F)c1-c1ncc2[nH]nc(-c3ccc(N4CCN(C(=O)CCNc5cccc6c5C(=O)N(C5CCC(=O)NC5=O)C6=O)CC4)cc3)c2n1] | 2-(2,6-dioxopiperidin-3-yl)-4-((3-(4-(4-(5-(2-fluoro-6-methoxyphenyl)-1H-pyrazolo[4,3-d]pyrimidin-3-yl)phenyl)piperazin-1-yl)-3-oxopropyl)amino)isoindoline-1,3-dione |
| 189 | HC90-51 | 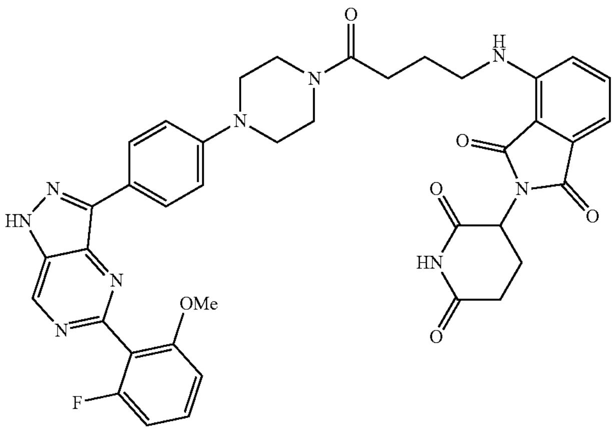 [SMILES: COc1cccc(F)c1-c1ncc2[nH]nc(-c3ccc(N4CCN(C(=O)CCCNc5cccc6c5C(=O)N(C5CCC(=O)NC5=O)C6=O)CC4)cc3)c2n1] | 2-(2,6-dioxopiperidin-3-yl)-4-((4-(4-(4-(5-(2-fluoro-6-methoxyphenyl)-1H-pyrazolo[4,3-d]pyrimidin-3-yl)phenyl)piperazin-1-yl)-4-oxobutyl)amino)isoindoline-1,3-dione |

TABLE 1-continued

| Examples | Compound code | Structure | Chemical Name |
|---|---|---|---|
| 190 | HC90-52 | 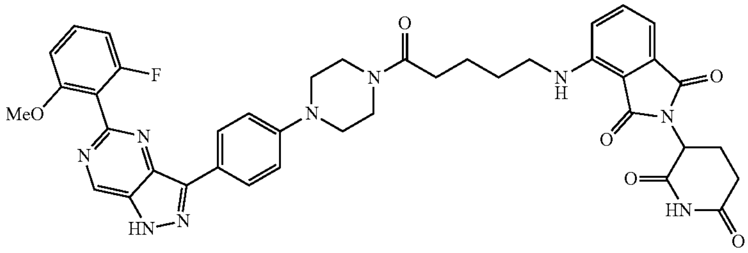 [SMILES: COc1cccc(F)c1-c1ncc2[nH]nc(-c3ccc(N4CCN(C(=O)CCCCNc5cccc6c5C(=O)N(C5CCC(=O)NC5=O)C6=O)CC4)cc3)c2n1] | 2-(2,6-dioxopiperidin-3-yl)-4-((5-(4-(4-(5-(2-fluoro-6-methoxyphenyl)-1H-pyrazolo[4,3-d]pyrimidin-3-yl)phenyl)piperazin-1-yl)-5-oxopentyl)amino)isoindoline-1,3-dione |
| 191 | HC90-53 | 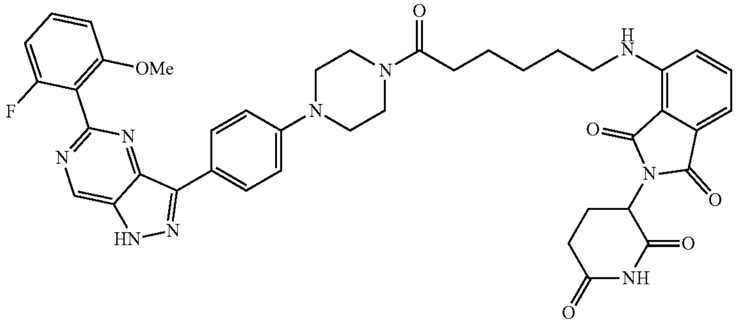 [SMILES: COc1cccc(F)c1-c1ncc2[nH]nc(-c3ccc(N4CCN(C(=O)CCCCCNc5cccc6c5C(=O)N(C5CCC(=O)NC5=O)C6=O)CC4)cc3)c2n1] | 2-(2,6-dioxopiperidin-3-yl)-4-((6-(4-(4-(5-(2-fluoro-6-methoxyphenyl)-1H-pyrazolo[4,3-d]pyrimidin-3-yl)phenyl)piperazin-1-yl)-6-oxohexyl)amino)isoindoline-1,3-dione |
| 192 | HC90-54 | 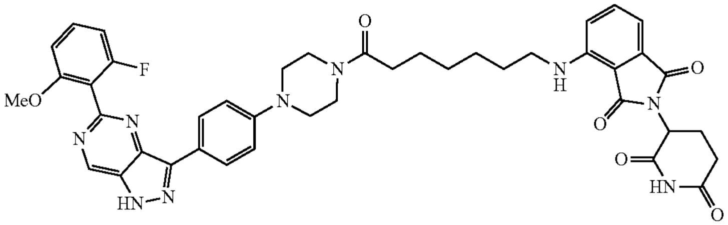 [SMILES: COc1cccc(F)c1-c1ncc2[nH]nc(-c3ccc(N4CCN(C(=O)CCCCCCNc5cccc6c5C(=O)N(C5CCC(=O)NC5=O)C6=O)CC4)cc3)c2n1] | 2-(2,6-dioxopiperidin-3-yl)-4-((7-(4-(4-(5-(2-fluoro-6-methoxyphenyl)-1H-pyrazolo[4,3-d]pyrimidin-3-yl)phenyl)piperazin-1-yl)-7-oxoheptyl)amino)isoindoline-1,3-dione |
| 193 | HC90-55 | 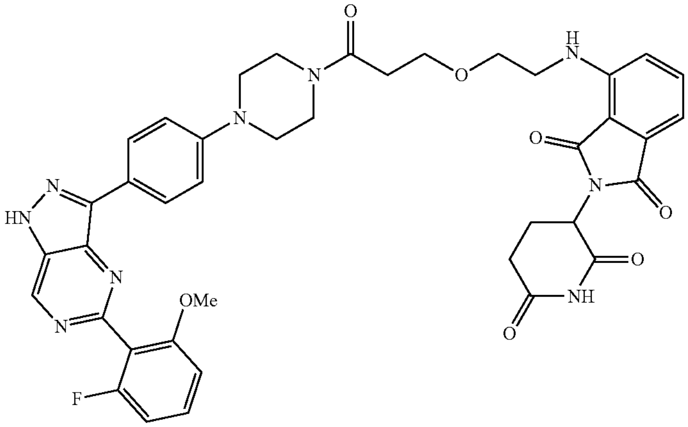 [SMILES: COc1cccc(F)c1-c1ncc2[nH]nc(-c3ccc(N4CCN(C(=O)CCOCCNc5cccc6c5C(=O)N(C5CCC(=O)NC5=O)C6=O)CC4)cc3)c2n1] | 2-(2,6-dioxopiperidin-3-yl)-4-((2-(3-(4-(4-(5-(2-fluoro-6-methoxyphenyl)-1H-pyrazolo[4,3-d]pyrimidin-3-yl)phenyl)piperazin-1-yl)-3-oxopropoxy)ethyl)amino) isoindoline-1,3-dione |
| 194 | HC90-56 | 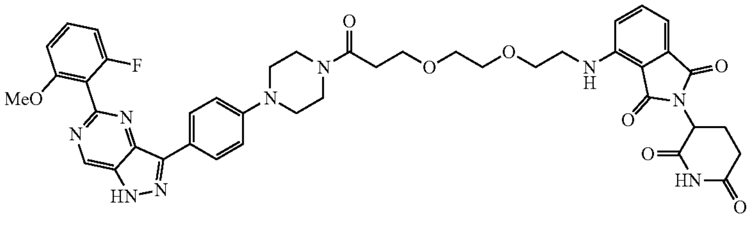 [SMILES: COc1cccc(F)c1-c1ncc2[nH]nc(-c3ccc(N4CCN(C(=O)CCOCCOCCNc5cccc6c5C(=O)N(C5CCC(=O)NC5=O)C6=O)CC4)cc3)c2n1] | 2-(2,6-dioxopiperidin-3-yl)-4-((2-(2-(3-(4-(4-(5-(2-fluoro-6-methoxyphenyl)-1H-pyrazolo[4,3-d]pyrimidin-3-yl)phenyl)piperazin-1-yl)-3-oxopropoxy)ethoxy)ethyl)amino) isoindoline-1,3-dione |

TABLE 1-continued

| Examples | Compound code | Structure | Chemical Name |
| --- | --- | --- | --- |
| 195 | HC90-57 | 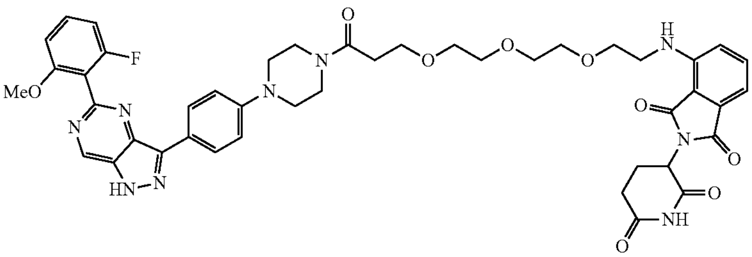 [SMILES: COc1cccc(F)c1-c1ncc2[nH]nc(-c3ccc(N4CCN(C(=O)CCOCCOCCOCCNc5cccc6c5C(=O)N(C5CCC(=O)NC5=O)C6=O)CC4)cc3)c2n1] | 2-(2,6-dioxopiperidin-3-yl)-4-((2-(2-(2-(3-(4-(4-(5-(2-fluoro-6-methoxyphenyl)-1H-pyrazolo[4,3-d]pyrimidin-3-yl)phenyl)piperazin-1-yl)-3-oxopropoxy)ethoxy)ethoxy)ethyl)amino)isoindoline-1,3-dione |
| 196 | HC90-58 | 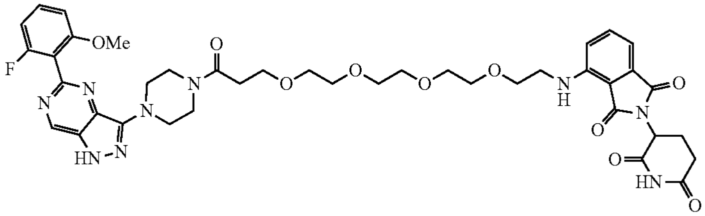 [SMILES: COc1cccc(F)c1-c1ncc2[nH]nc(N3CCN(C(=O)CCOCCOCCOCCOCCNc4cccc5c4C(=O)N(C4CCC(=O)NC4=O)C5=O)CC3)c2n1] | 2-(2,6-dioxopiperidin-3-yl)-4-((15-(4-(4-(5-(2-fluoro-6-methoxyphenyl)-1H-pyrazolo[4,3-d]pyrimidin-3-yl)phenyl)piperazin-1-yl)-15-oxo-3,6,9,12-tetraoxapentadecyl)amino)isoindoline-1,3-dione |
| 197 | HC90-59 | 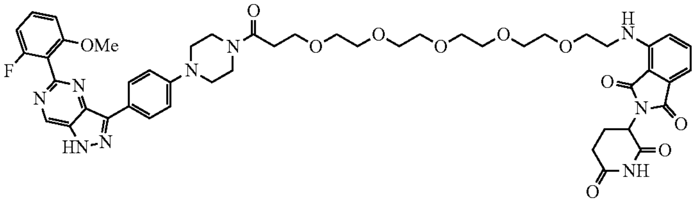 [SMILES: COc1cccc(F)c1-c1ncc2[nH]nc(-c3ccc(N4CCN(C(=O)CCOCCOCCOCCOCCOCCNc5cccc6c5C(=O)N(C5CCC(=O)NC5=O)C6=O)CC4)cc3)c2n1] | 2-(2,6-dioxopiperidin-3-yl)-4-((18-(4-(4-(5-(2-fluoro-6-methoxyphenyl)-1H-pyrazolo[4,3-d]pyrimidin-3-yl)phenyl)piperazin-1-yl)-18-oxo-3,6,9,12,15-pentaoxaoctadecyl)amino)isoindoline-1,3-dione |
| 198 | HC90-61 | 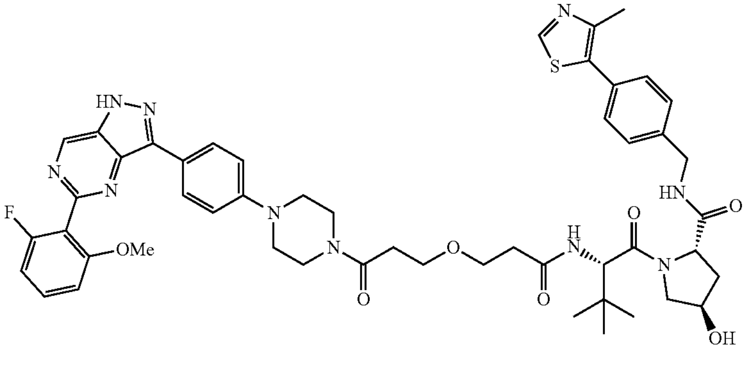 [SMILES: COc1cccc(F)c1-c1ncc2[nH]nc(-c3ccc(N4CCN(C(=O)CCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(3-(3-(4-(4-(5-(2-fluoro-6-methoxyphenyl)-1H-pyrazolo[4,3-d]pyrimidin-3-yl)phenyl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide |
| 199 | HC90-66 | 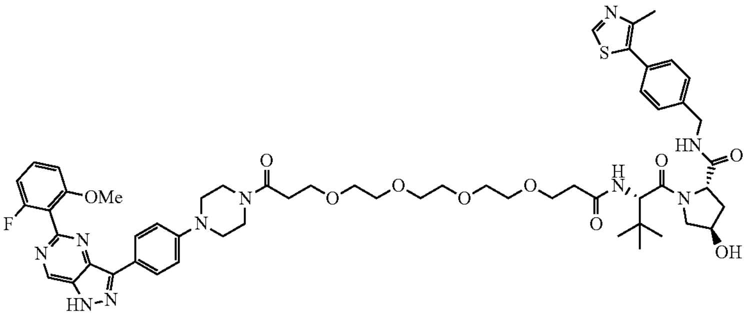 [SMILES: COc1cccc(F)c1-c1ncc2[nH]nc(-c3ccc(N4CCN(C(=O)CCOCCOCCOCCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(tert-buty)-19-(4-(4-(5-(2-fluoro-6-methoxyphenyl)-1H-pyrazolo[4,3-d]pyrimidin-3-yl)phenyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued

| Ex am- ples | Com- pound code | Structure | Chemical Name |
|---|---|---|---|
| 200 | HC90-69 | 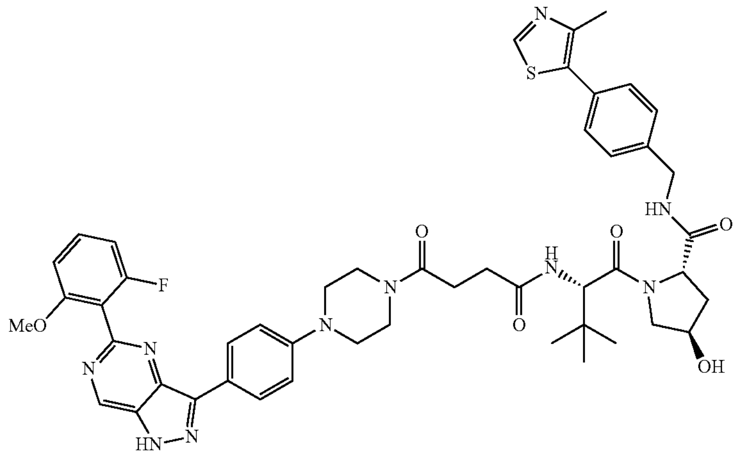 [SMILES: COc1cccc(F)c1-c1ncc2[nH]nc(-c3ccc(N4CCN(C(=O)CCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(4-(4-(4-(5-(2-fluoro-6-methoxyphenyl)-1H-pyrazolo[4,3-d]pyrimidin-3-yl)phenyl)piperazin-1-yl)-4-oxobutanamido)-3,3-dimethylbutanoyl)-4-hydroxy-N-(4-(4-methylthiazol-5-yl)benzyl)pyrrolidine-2-carboxamide |
| 201 | HC90-70 | 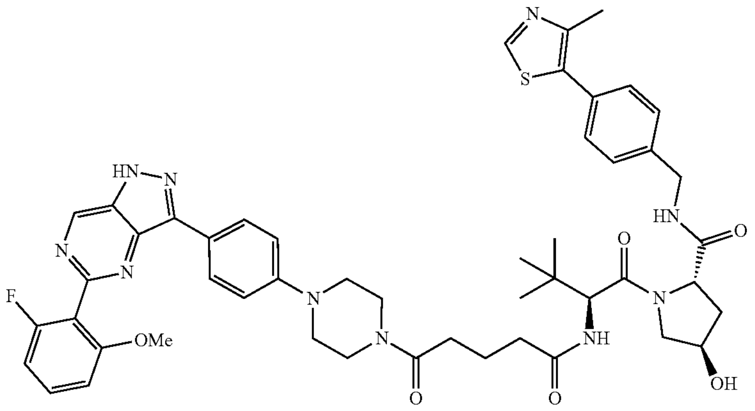 [SMILES: COc1cccc(F)c1-c1ncc2[nH]nc(-c3ccc(N4CCN(C(=O)CCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(5-(4-(4-(5-(2-fluoro-6-methoxyphenyl)-1H-pyrazolo[4,3-d]pyrimidin-3-yl)phenyl)piperazin-1-yl)-5-oxopentanamido)-3,3-dimethylbutanoyl)-4-hydroxy-N-(4-(4-methylthiazol-5-yl)benzyl)pyrrolidine-2-carboxamide |
| 202 | HC90-71 | 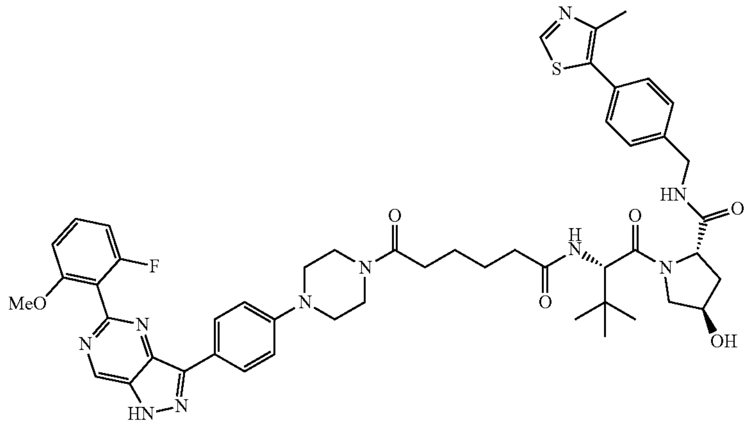 [SMILES: COc1cccc(F)c1-c1ncc2[nH]nc(-c3ccc(N4CCN(C(=O)CCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(6-(4-(4-(5-(2-fluoro-6-methoxyphenyl)-1H-pyrazolo[4,3-d]pyrimidin-3-yl)phenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide |

TABLE 1-continued

| Examples | Compound code | Structure | Chemical Name |
|---|---|---|---|
| 203 | HC90-72 | 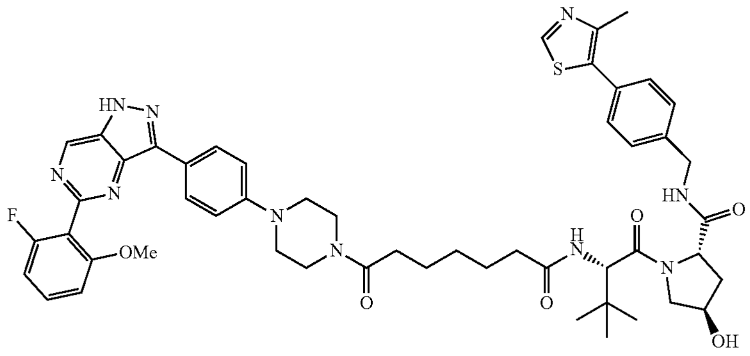 [SMILES: COc1cccc(F)c1-c1ncc2[nH]nc(-c3ccc(N4CCN(C(=O)CCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(7-(4-(4-(5-(2-fluoro-6-methoxyphenyl)-1H-pyrazolo[4,3-d]pyrimidin-3-yl)phenyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| 204 | HC90-73 | 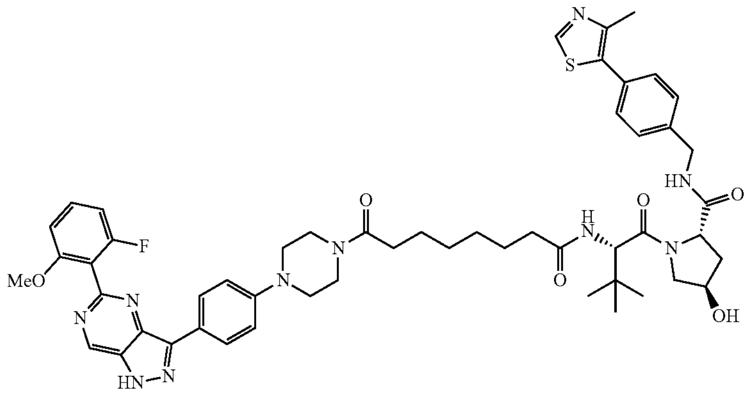 [SMILES: COc1cccc(F)c1-c1ncc2[nH]nc(-c3ccc(N4CCN(C(=O)CCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(8-(4-(4-(5-(2-fluoro-6-methoxyphenyl)-1H-pyrazolo[4,3-d]pyrimidin-3-yl)phenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| 205 | HC90-74 | 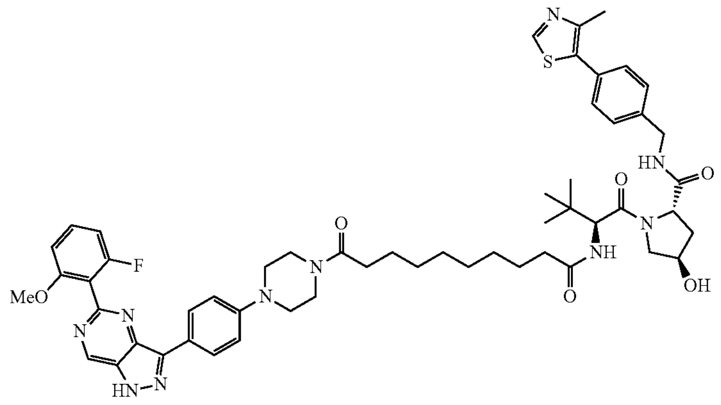 [SMILES: COc1cccc(F)c1-c1ncc2[nH]nc(-c3ccc(N4CCN(C(=O)CCCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(10-(4-(4-(5-(2-fluoro-6-methoxyphenyl)-1H-pyrazolo[4,3-d]pyrimidin-3-yl)phenyl)piperazin-1-yl)-10-oxodecanamido)-3,3-dimethylbutanoyl)-4-hydroxy-N-(4-(4-methylthiazol-5-yl)benzyl)pyrrolidine-2-carboxamide |
| 206 | HC90-84 | 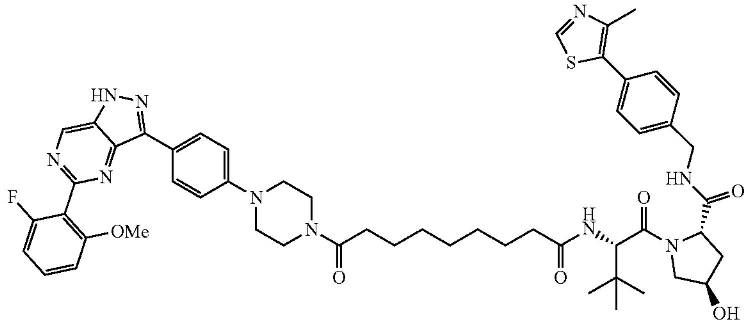 [SMILES: COc1cccc(F)c1-c1ncc2[nH]nc(-c3ccc(N4CCN(C(=O)CCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(9-(4-(4-(5-(2-fluoro-6-methoxyphenyl)-1H-pyrazolo[4,3-d]pyrimidin-3-yl)phenyl)piperazin-1-yl)-9-oxononanamido)-3,3-dimethylbutanoyl)-4-hydroxy-N-(4-(4-methylthiazol-5-yl)benzyl)pyrrolidine-2-carboxamide |

TABLE 1-continued

| Ex am-ples | Com-pound code | Structure | Chemical Name |
|---|---|---|---|
| 207 | HC90-85 | 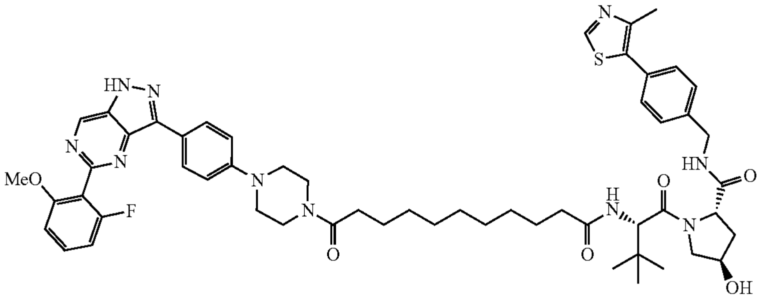 [SMILES: COc1cccc(F)c1-c1ncc2[nH]nc(-c3ccc(N4CCN(C(=O)CCCCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(11-(4-(4-(5-(2-fluoro-6-methoxyphenyl)-1H-pyrazolo[4,3-d]pyrimidin-3-yl)phenyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |
| 209 | HC90-86 | 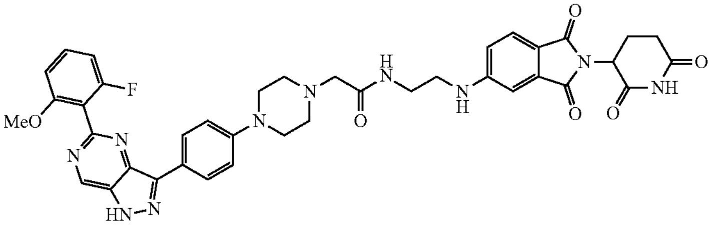 [SMILES: COc1cccc(F)c1-c1ncc2[nH]nc(-c3ccc(N4CCN(CC(=O)NCCNc5ccc6c(c5)C(=O)N(C5CCC(=O)NC5=O)C6=O)CC4)cc3)c2n1] | N-(2-((2-(2,6-dioxopiperidin-3-yl)-1,3-dioxoisoindolin-5-yl)amino)ethyl)-2-(4-(4-(5-(2-fluoro-6-methoxyphenyl)-1H-pyrazolo[4,3-d]pyrimidin-3-yl)phenyl)piperazin-1-yl)acetamide |
| 210 | HC90-87 | 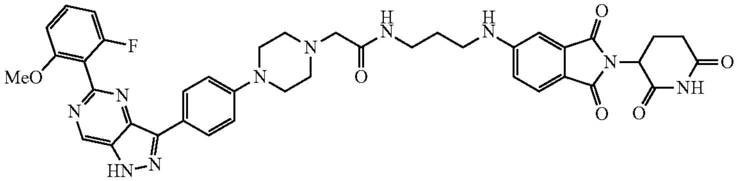 [SMILES: COc1cccc(F)c1-c1ncc2[nH]nc(-c3ccc(N4CCN(CC(=O)NCCCNc5ccc6c(c5)C(=O)N(C5CCC(=O)NC5=O)C6=O)CC4)cc3)c2n1] | N-(3-((2-(2,6-dioxopiperidin-3-yl)-1,3-dioxoisoindolin-5-yl)amino)propyl)-2-(4-(4-(5-(2-fluoro-6-methoxyphenyl)-1H-pyrazolo[4,3-d]pyrimidin-3-yl)phenyl)piperazin-1-yl)acetamide |
| 211 | HC90-88 | 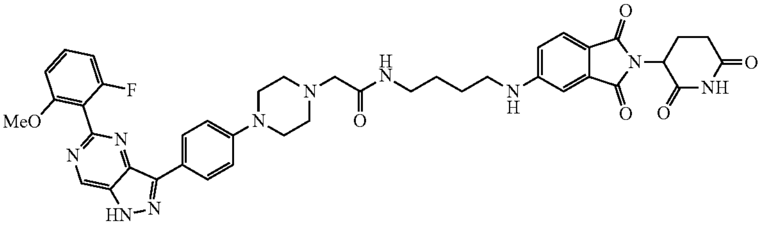 [SMILES: COc1cccc(F)c1-c1ncc2[nH]nc(-c3ccc(N4CCN(CC(=O)NCCCCNc5ccc6c(c5)C(=O)N(C5CCC(=O)NC5=O)C6=O)CC4)cc3)c2n1] | N-(4-((2-(2,6-dioxopiperidin-3-yl)-1,3-dioxoisoindolin-5-yl)amino)butyl)-2-(4-(4-(5-(2-fluoro-6-methoxyphenyl)-1H-pyrazolo[4,3-d]pyrimidin-3-yl)phenyl)piperazin-1-yl)acetamide |
| 212 | HC90-89 | 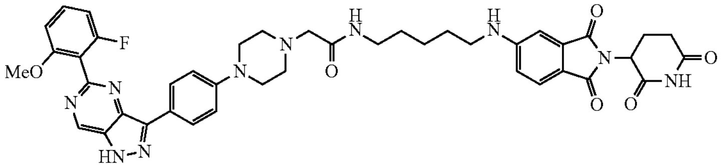 [SMILES: COc1cccc(F)c1-c1ncc2[nH]nc(-c3ccc(N4CCN(CC(=O)NCCCCCNc5ccc6c(c5)C(=O)N(C5CCC(=O)NC5=O)C6=O)CC4)cc3)c2n1] | N-(5-((2-(2,6-dioxopiperidin-3-yl)-1,3-dioxoisoindolin-5-yl)amino)pentyl)-2-(4-(4-(5-(2-fluoro-6-methoxyphenyl)-1H-pyrazolo[4,3-d]pyrimidin-3-yl)phenyl)piperazin-1-yl)acetamide |
| 213 | HC90-90 | 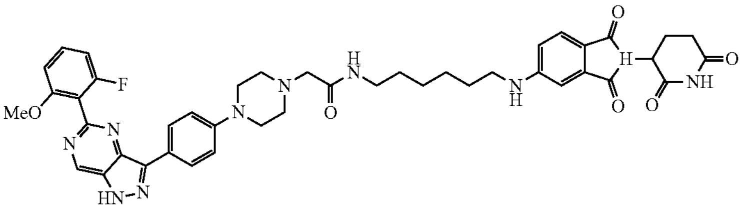 | N-(6-((2-(2,6-dioxopiperidin-3-yl)-1,3-dioxoisoindolin-5-yl)amino)hexyl)-2-(4-(4-(5-(2-fluoro-6-methoxyphenyl)-1H-pyrazolo[4,3-d]pyrimidin-3-yl)phenyl)piperazin-1-yl)acetamide |
| 214 | HC90-91 | 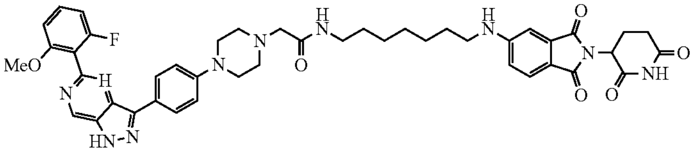 | N-(7-((2-(2,6-dioxopiperidin-3-yl)-1,3-dioxoisoindolin-5-yl)amino)heptyl)-2-(4-(4-(5-(2-fluoro-6-methoxyphenyl)-1H-pyrazolo[4,3-d]pyrimidin-3-yl)phenyl)piperazin-1-yl)acetamide |

TABLE 1-continued

| Examples | Compound code | Structure | Chemical Name |
|---|---|---|---|
| 215 | HC90-92 | 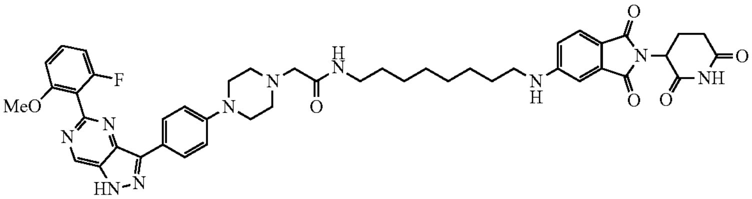 [SMILES: COc1cccc(F)c1-c1ncc2[nH]nc(-c3ccc(N4CCN(CC(=O)NCCCCCCCCNc5ccc6c(c5)C(=O)N(C5CCC(=O)NC5=O)C6=O)CC4)cc3)c2n1] | N-(8-((2-(2,6-dioxopiperidin-3-yl)-1,3-dioxoisoindolin-5-yl)amino)octyl)-2-(4-(4-(5-(2-fluoro-6-methoxyphenyl)-1H-pyrazolo[4,3-d]pyrimidin-3-yl)phenyl)piperazin-1-yl)acetamide |
| 216 | HC90-93 | 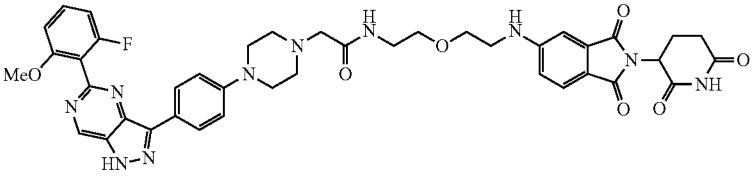 [SMILES: COc1cccc(F)c1-c1ncc2[nH]nc(-c3ccc(N4CCN(CC(=O)NCCOCCNc5ccc6c(c5)C(=O)N(C5CCC(=O)NC5=O)C6=O)CC4)cc3)c2n1] | N-(2-(2-((2-(2,6-dioxopiperidin-3-yl)-1,3-dioxoisoindolin-5-yl)amino)ethoxy)ethyl)-2-(4-(4-(5-(2-fluoro-6-methoxyphenyl)-1H-pyrazolo[4,3-d]pyrimidin-3-yl)phenyl)piperazin-1-yl)acetamide |
| 217 | HC90-94 | 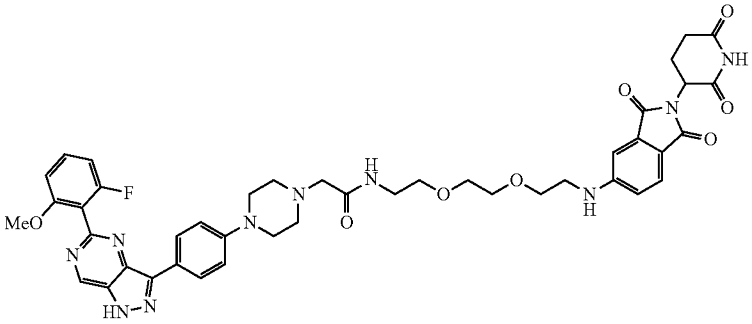 [SMILES: COc1cccc(F)c1-c1ncc2[nH]nc(-c3ccc(N4CCN(CC(=O)NCCOCCOCCNc5ccc6c(c5)C(=O)N(C5CCC(=O)NC5=O)C6=O)CC4)cc3)c2n1] | N-(2-(2-(2-((2-(2,6-dioxopiperidin-3-yl)-1,3-dioxoisoindolin-5-yl)amino)ethoxy)ethoxy)ethyl)-2-(4-(4-(5-(2-fluoro-6-methoxyphenyl)-1H-pyrazolo[4,3-d]pyrimidin-3-yl)phenyl)piperazin-1-yl)acetamide |
| 218 | HC90-95 | 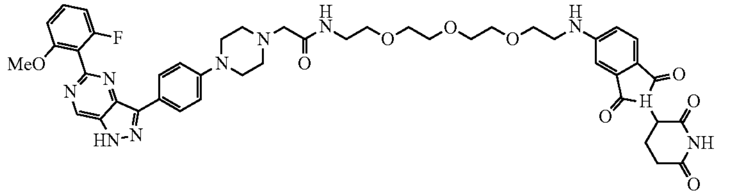 | N-(2-(2-(2-(2-((2-(2,6-dioxopiperidin-3-yl)-1,3-dioxoisoindolin-5-yl)amino)ethoxy)ethoxy)ethoxy)ethyl)-2-(4-(4-(5-(2-fluoro-6-methoxyphenyl)-1H-pyrazolo[4,3-d]pyrimidin-3-yl)phenyl)piperazin-1-yl)acetamide |
| 219 | HC90-96 | 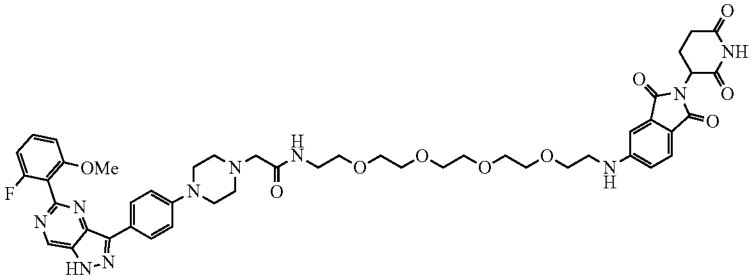 [SMILES: COc1cccc(F)c1-c1ncc2[nH]nc(-c3ccc(N4CCN(CC(=O)NCCOCCOCCOCCOCCNc5ccc6c(c5)C(=O)N(C5CCC(=O)NC5=O)C6=O)CC4)cc3)c2n1] | N-(14-((2-(2,6-dioxopiperidin-3-yl)-1,3-dioxoisoindolin-5-yl)amino)-3,6,9,12-tetraoxatetradecyl)-2-(4-(4-(5-(2-fluoro-6-methoxyphenyl)-1H-pyrazolo[4,3-d]pyrimidin-3-yl)phenyl)piperazin-1-yl)acetamide |
| 220 | HC90-97 | 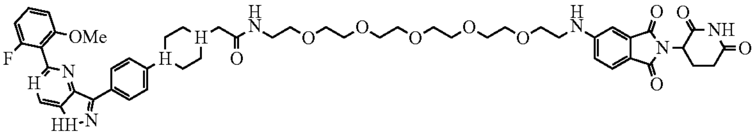 | N-(17-((2-(2,6-dioxopiperidin-3-yl)-1,3-dioxoisoindolin-5-yl)amino)-3,6,9,12,15-pentaoxaheptadecyl)-2-(4-(4-(5-(2-fluoro-6-methoxyphenyl)-1H-pyrazolo[4,3-d]pyrimidin-3-yl)phenyl)piperazin-1-yl)acetamide |

TABLE 1-continued

| Examples | Compound code | Structure | Chemical Name |
|---|---|---|---|
| 221 | HC90-102 | 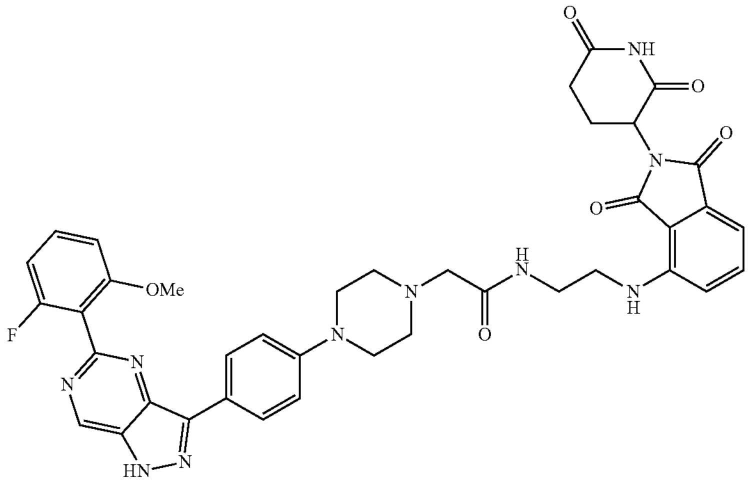 [SMILES: COc1cccc(F)c1-c1ncc2[nH]nc(-c3ccc(N4CCN(CC(=O)NCCNc5cccc6c5C(=O)N(C5CCC(=O)NC5=O)C6=O)CC4)cc3)c2n1] | N-(2-((2-(2,6-dioxopiperidin-3-yl)-1,3-dioxoisoindolin-4-yl)amino)ethyl)-2-(4-(4-(5-(2-fluoro-6-methoxyphenyl)-1H-pyrazolo[4,3-d]pyrimidin-3-yl)phenyl)piperazin-1-yl)acetamide |
| 222 | HC90-103 | 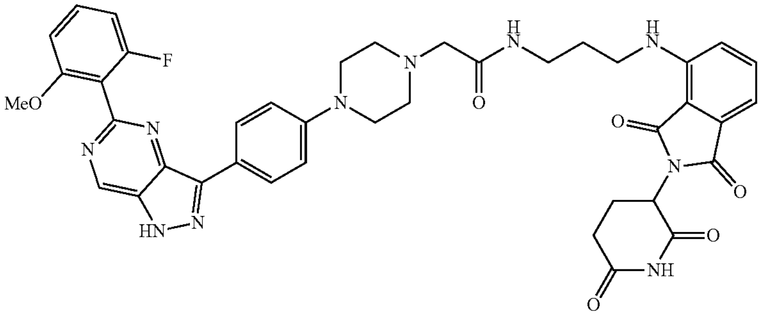 [SMILES: COc1cccc(F)c1-c1ncc2[nH]nc(-c3ccc(N4CCN(CC(=O)NCCCNc5cccc6c5C(=O)N(C5CCC(=O)NC5=O)C6=O)CC4)cc3)c2n1] | N-(3-((2-(2,6-dioxopiperidin-3-yl)-1,3-dioxoisoindolin-4-yl)amino)propyl)-2-(4-(4-(5-(2-fluoro-6-methoxyphenyl)-1H-pyrazolo[4,3-d]pyrimidin-3-yl)phenyl)piperazin-1-yl)acetamide |
| 223 | HC90-104 | 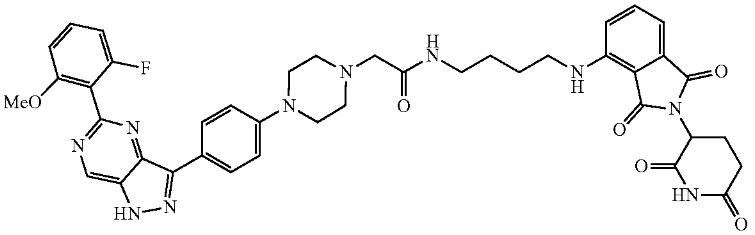 [SMILES: COc1cccc(F)c1-c1ncc2[nH]nc(-c3ccc(N4CCN(CC(=O)NCCCCNc5cccc6c5C(=O)N(C5CCC(=O)NC5=O)C6=O)CC4)cc3)c2n1] | N-(4-((2-(2,6-dioxopiperidin-3-yl)-1,3-dioxoisoindolin-4-yl)amino)butyl)-2-(4-(4-(5-(2-fluoro-6-methoxyphenyl)-1H-pyrazolo[4,3-d]pyrimidin-3-yl)phenyl)piperazin-1-yl)acetamide |
| 224 | HC90-105 | 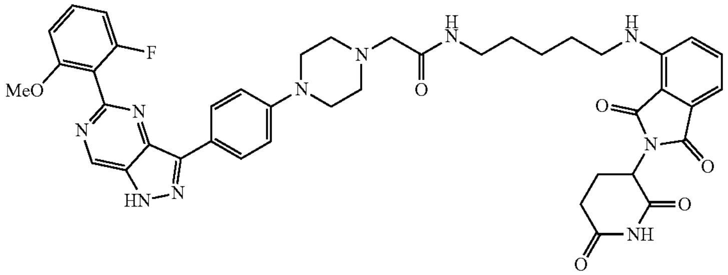 [SMILES: COc1cccc(F)c1-c1ncc2[nH]nc(-c3ccc(N4CCN(CC(=O)NCCCCCNc5cccc6c5C(=O)N(C5CCC(=O)NC5=O)C6=O)CC4)cc3)c2n1] | N-(5-((2-(2,6-dioxopiperidin-3-yl)-1,3-dioxoisoindolin-4-yl)amino)pentyl)-2-(4-(4-(5-(2-fluoro-6-methoxyphenyl)-1H-pyrazolo[4,3-d]pyrimidin-3-yl)phenyl)piperazin-1-yl)acetamide |
| 225 | HC90-106 | 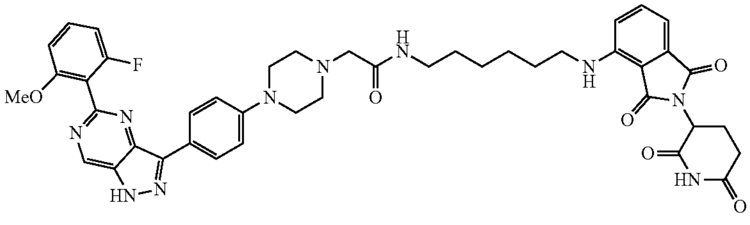 [SMILES: COc1cccc(F)c1-c1ncc2[nH]nc(-c3ccc(N4CCN(CC(=O)NCCCCCCNc5cccc6c5C(=O)N(C5CCC(=O)NC5=O)C6=O)CC4)cc3)c2n1] | N-(6-((2-(2,6-dioxopiperidin-3-yl)-1,3-dioxoisoindolin-4-yl)amino)hexyl)-2-(4-(4-(5-(2-fluoro-6-methoxyphenyl)-1H-pyrazolo[4,3-d]pyrimidin-3-yl)phenyl)piperazin-1-yl)acetamide |

TABLE 1-continued

| Ex am- ples | Com- pound code | Structure | Chemical Name |
|---|---|---|---|
| 226 | HC90-107 | 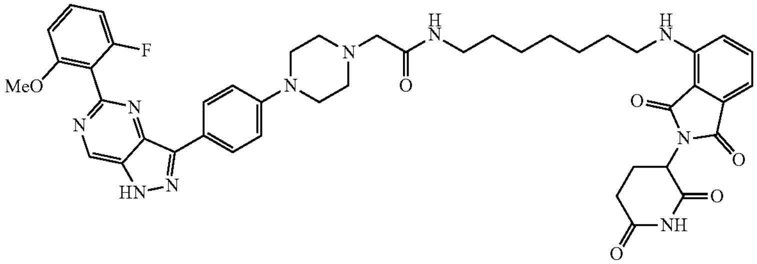 [SMILES: COc1cccc(F)c1-c1ncc2[nH]nc(-c3ccc(N4CCN(CC(=O)NCCCCCCCNc5cccc6c5C(=O)N(C5CCC(=O)NC5=O)C6=O)CC4)cc3)c2n1] | N-(7-((2-(2,6-dioxopiperidin-3-yl)-1,3-dioxoisoindolin-4-yl)amino)heptyl)-2-(4-(4-(5-(2-fluoro-6-methoxyphenyl)-1H-pyrazolo[4,3-d]pyrimidin-3-yl)phenyl)piperazin-1-yl)acetamide |
| 227 | HC90-108 | 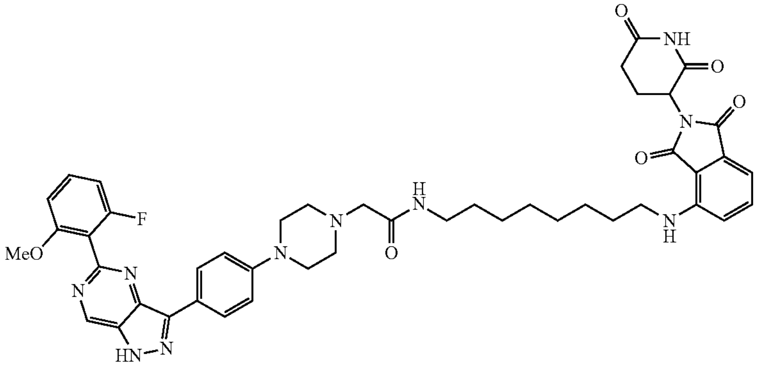 [SMILES: COc1cccc(F)c1-c1ncc2[nH]nc(-c3ccc(N4CCN(CC(=O)NCCCCCCCCNc5cccc6c5C(=O)N(C5CCC(=O)NC5=O)C6=O)CC4)cc3)c2n1] | N-(8-((2-(2,6-dioxopiperidin-3-yl)-1,3-dioxoisoindolin-4-yl)amino)octyl)-2-(4-(4-(5-(2-fluoro-6-methoxyphenyl)-1H-pyrazolo[4,3-d]pyrimidin-3-yl)phenyl)piperazin-1-yl)acetamide |
| 228 | HC90-109 | 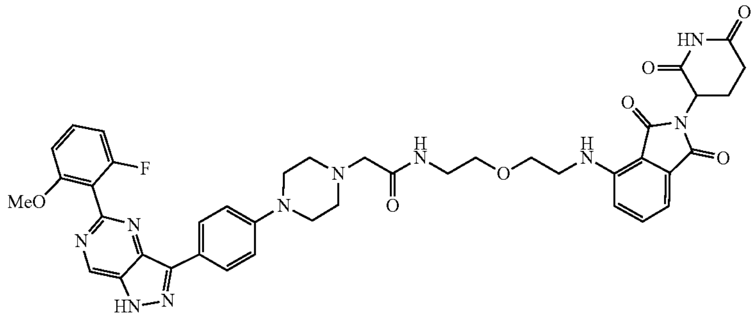 [SMILES: COc1cccc(F)c1-c1ncc2[nH]nc(-c3ccc(N4CCN(CC(=O)NCCOCCNc5cccc6c5C(=O)N(C5CCC(=O)NC5=O)C6=O)CC4)cc3)c2n1] | N-(2-(2-((2-(2,6-dioxopiperidin-3-yl)-1,3-dioxoisoindolin-4-yl)amino)ethoxy)ethyl)-2-(4-(4-(5-(2-fluoro-6-methoxyphenyl)-1H-pyrazolo[4,3-d]pyrimidin-3-yl)phenyl)piperazin-1-yl)acetamide |
| 229 | HC90-110 | 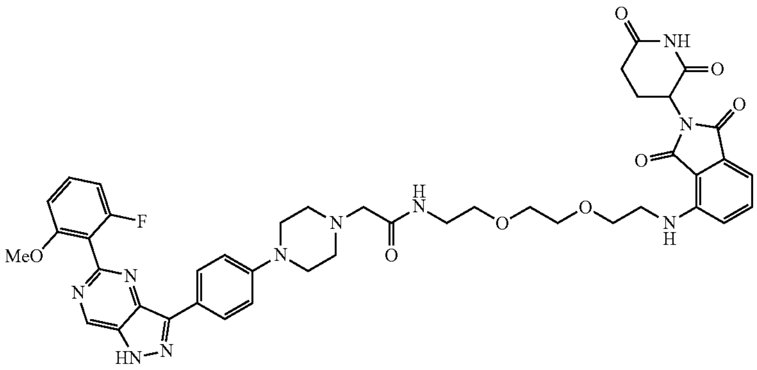 [SMILES: COc1cccc(F)c1-c1ncc2[nH]nc(-c3ccc(N4CCN(CC(=O)NCCOCCOCCNc5cccc6c5C(=O)N(C5CCC(=O)NC5=O)C6=O)CC4)cc3)c2n1] | N-(2-(2-(2-((2-(2,6-dioxopiperidin-3-yl)-1,3-dioxoisoindolin-4-yl)amino)ethoxy)ethoxy)ethyl)-2-(4-(4-(5-(2-fluoro-6-methoxyphenyl)-1H-pyrazolo[4,3-d]pyrimidin-3-yl)phenyl)piperazin-1-yl)acetamide |
| 230 | HC90-111 | 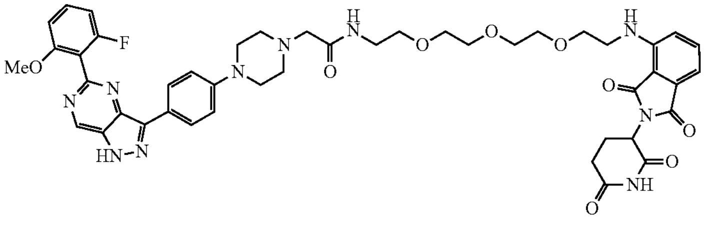 [SMILES: COc1cccc(F)c1-c1ncc2[nH]nc(-c3ccc(N4CCN(CC(=O)NCCOCCOCCOCCNc5cccc6c5C(=O)N(C5CCC(=O)NC5=O)C6=O)CC4)cc3)c2n1] | N-(2-(2-(2-(2-((2-(2,6-dioxopiperidin-3-yl)-1,3-dioxoisoindolin-4-yl)amino)ethoxy)ethoxy)ethoxy)ethyl)-2-(4-(4-(5-(2-fluoro-6-methoxyphenyl)-1H-pyrazolo[4,3-d]pyrimidin-3-yl)phenyl)piperazin-1-yl)acetamide |

TABLE 1-continued

| Examples | Compound code | Structure | Chemical Name |
| --- | --- | --- | --- |
| 231 | HC90-112 | 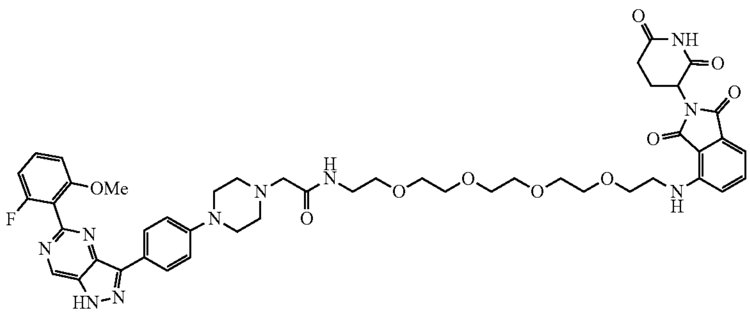 [SMILES: COc1cccc(F)c1-c1ncc2[nH]nc(-c3ccc(N4CCN(CC(=O)NCCOCCOCCOCCOCCNc5cccc6c5C(=O)N(C5CCC(=O)NC5=O)C6=O)CC4)cc3)c2n1] | N-(14-((2-(2,6-dioxopiperidin-3-yl)-1,3-dioxoisoindolin-4-yl)amino)-3,6,9,12-tetraoxatetradecyl)-2-(4-(4-(5-(2-fluoro-6-methoxyphenyl)-1H-pyrazolo[4,3-d]pyrimidin-3-yl)phenyl)piperazin-1-yl)acetamide |
| 232 | HC90-113 | 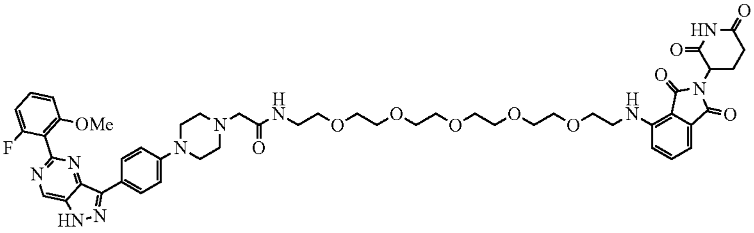 [SMILES: COc1cccc(F)c1-c1ncc2[nH]nc(-c3ccc(N4CCN(CC(=O)NCCOCCOCCOCCOCCOCCNc5cccc6c5C(=O)N(C5CCC(=O)NC5=O)C6=O)CC4)cc3)c2n1] | N-(17-((2-(2,6-dioxopiperidin-3-yl)-1,3-dioxoisoindolin-4-yl)amino)-3,6,9,12,15-pentaoxaheptadecyl)-2-(4-(4-(5-(2-fluoro-6-methoxyphenyl)-1H-pyrazolo[4,3-d]pyrimidin-3-yl)phenyl)piperazin-1-yl)acetamide |
| 233 | HC90-117 | 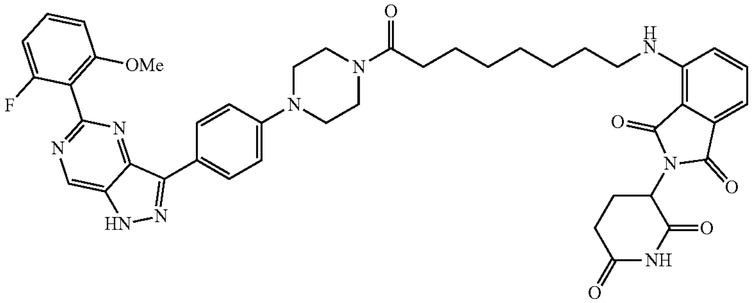 [SMILES: COc1cccc(F)c1-c1ncc2[nH]nc(-c3ccc(N4CCN(C(=O)CCCCCCCNc5cccc6c5C(=O)N(C5CCC(=O)NC5=O)C6=O)CC4)cc3)c2n1] | 2-(2,6-dioxopiperidin-3-yl)-4-((8-(4-(4-(5-(2-fluoro-6-methoxyphenyl)-1H-pyrazolo[4,3-d]pyrimidin-3-yl)phenyl)piperazin-1-yl)-8-oxooctyl)amino)isoindoline-1,3-dione |
| 234 | HC90-119 | 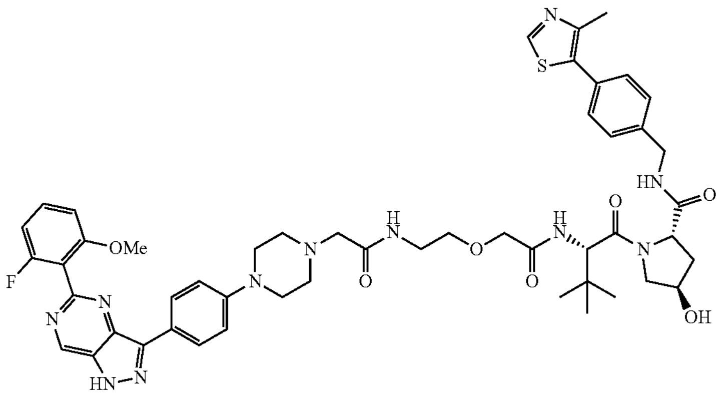 | (2S,4R)-1-((S)-2-(2-(2-(2-(4-(4-(5-(2-fluoro-6-methoxyphenyl)-1H-pyrazolo[4,3-d]pyrimidin-3-yl)phenyl)piperazin-1-yl)acetamido)ethoxy)acetamido)-3,3-dimethylbutanoyl)-4-hydroxy-N-(4-(4-methylthiazol-5-yl)benzyl)pyrrolidine-2-carboxamide |

TABLE 1-continued

| Ex am- ples | Com- pound code | Structure | Chemical Name |
|---|---|---|---|
| 235 | HC90-120 | 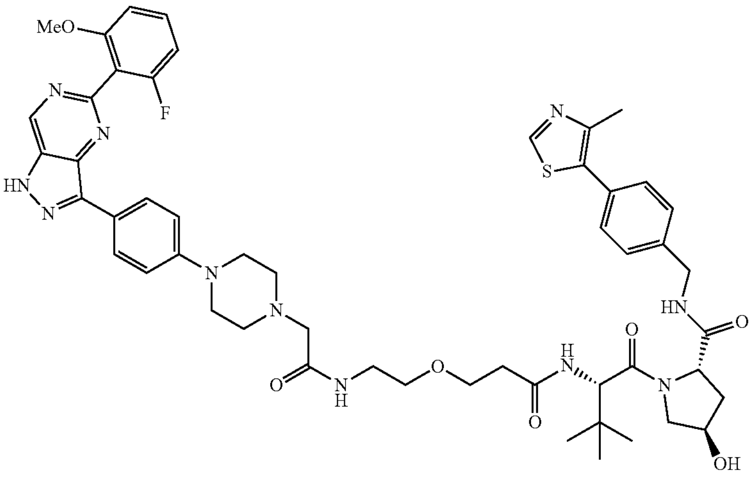 [SMILES: COc1cccc(F)c1-c1ncc2[nH]nc(-c3ccc(N4CCN(CC(=O)NCCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(3-(2-(2-(4-(4-(5-(2-fluoro-6-methoxyphenyl)-1H-pyrazolo[4,3-d]pyrimidin-3-yl)phenyl)piperazin-1-yl)acetamido)ethoxy)propanamido)-3,3-dimethylbutanoyl)-4-hydroxy-N-(4-(4-methylthiazol-5-yl)benzyl)pyrrolidine-2-carboxamide |
| 236 | HC90-121 | 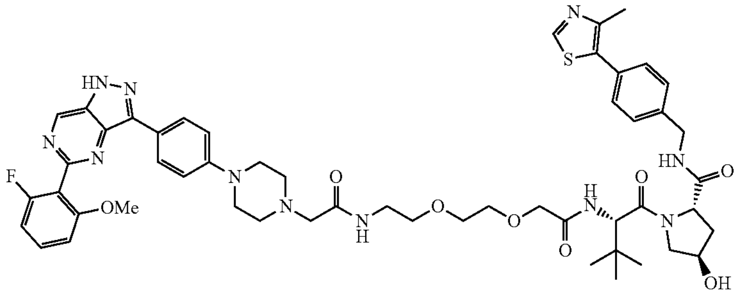 [SMILES: COc1cccc(F)c1-c1ncc2[nH]nc(-c3ccc(N4CCN(CC(=O)NCCOCCOCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(tert-butyl)-14-(4-(4-(5-(2-fluoro-6-methoxyphenyl)-1H-pyrazolo[4,3-d]pyrimidin-3-yl)phenyl)piperazin-1-yl)-4,13-dioxo-6,9-dioxa-3,12-diazatetradecanoyl)-4-hydroxy-N-(4-(4-methylthiazol-5-yl)benzyl)pyrrolidine-2-carboxamide |
| 237 | HC90-122 | 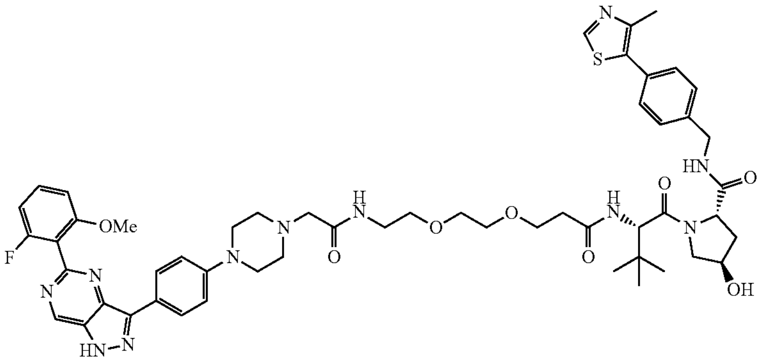 [SMILES: COc1cccc(F)c1-c1ncc2[nH]nc(-c3ccc(N4CCN(CC(=O)NCCOCCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-14-(tert-butyl)-1-(4-(4-(5-(2-fluoro-6-methoxyphenyl)-1H-pyrazolo[4,3-d]pyrimidin-3-yl)phenyl)piperazin-1-yl)-2,12-dioxo-6,9-dioxa-3,13-diazapentadecan-15-oyl)-4-hydroxy-N-(4-(4-methylthiazol-5-yl)benzyl)pyrrolidine-2-carboxamide |
| 238 | HC90-123 | 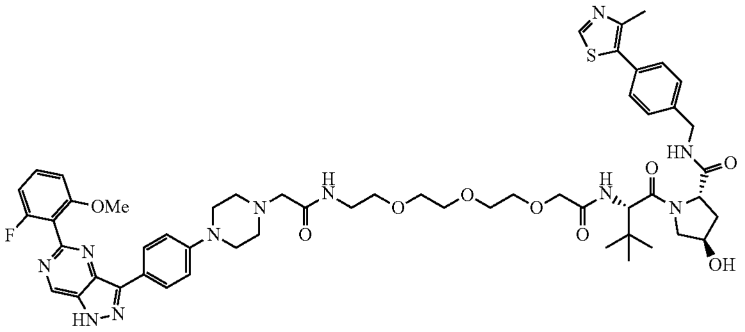 [SMILES: COc1cccc(F)c1-c1ncc2[nH]nc(-c3ccc(N4CCN(CC(=O)NCCOCCOCCOCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(tert-butyl)-17-(4-(4-(5-(2-fluoro-6-methoxyphenyl)-1H-pyrazolo[4,3-d]pyrimidin-3-yl)phenyl)piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide |

TABLE 1-continued

| Ex am- ples | Com- pound code | Structure | Chemical Name |
|---|---|---|---|
| 239 | HC90-124 | 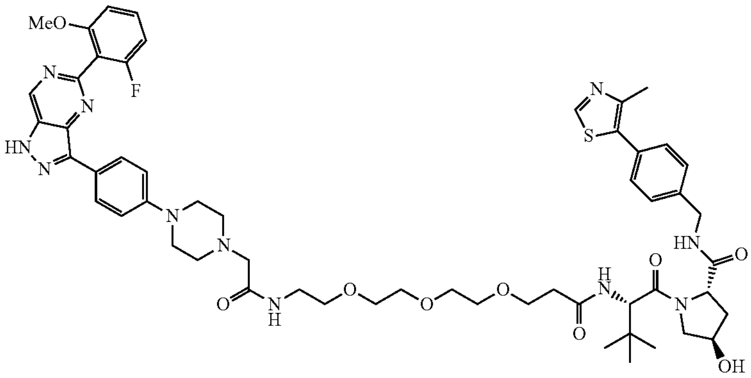 [SMILES: COc1cccc(F)c1-c1ncc2[nH]nc(-c3ccc(N4CCN(CC(=O)NCCOCCOCCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-17-(tert-butyl)-1-(4-(4-(5-(2-fluoro-6-methoxyphenyl)-1H-pyrazolo[4,3-d]pyrimidin-3-yl)phenyl)piperazin-1-yl)-2,15-dioxo-6,9,12-trioxa-3,16-diazaoctadecan-18-oyl)-4-hydroxy-N-(4-(4-methylthiazol-5-yl)benzyl)pyrrolidine-2-carboxamide |
| 240 | HC90-125 | 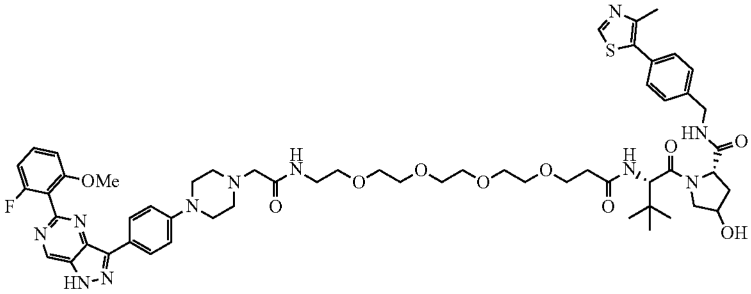 [SMILES: COc1cccc(F)c1-c1ncc2[nH]nc(-c3ccc(N4CCN(CC(=O)NCCOCCOCCOCCOCCC(=O)N[C@H](C(=O)N5CC(O)C[C@H]5C(=O)NCc5ccc(-c6scnc6C)cc5)C(C)(C)C)CC4)cc3)c2n1] | (2S,4R)-1-((S)-20-(tert-butyl)-1-(4-(4-(5-(2-fluoro-6-methoxyphenyl)-1H-pyrazolo[4,3-d]pyrimidin-3-yl)phenyl)piperazin-1-yl)-2,18-dioxo-6,9,12,15-tetraoxa-3,19-diazahenicosan-21-oyl)-4-hydroxy-N-(4-(4-methylthiazol-5-yl)benzyl)pyrrolidine-2-carboxamide |
| 241 | HC90-126 | 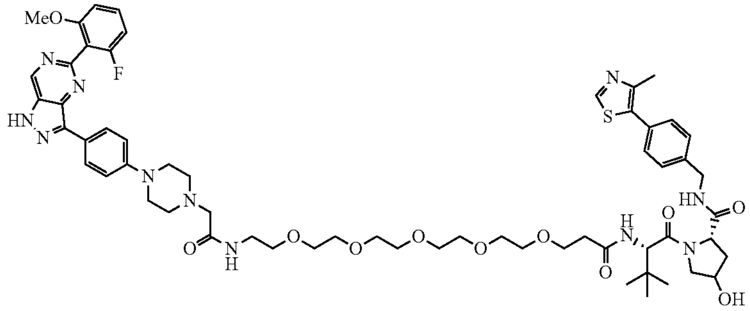 [SMILES: COc1cccc(F)c1-c1ncc2[nH]nc(-c3ccc(N4CCN(CC(=O)NCCOCCOCCOCCOCCOCCC(=O)N[C@H](C(=O)N5CC(O)C[C@H]5C(=O)NCc5ccc(-c6scnc6C)cc5)C(C)(C)C)CC4)cc3)c2n1] | (2S,4R)-1-((S)-23-(tert-butyl)-1-(4-(4-(5-(2-fluoro-6-methoxyphenyl)-1H-pyrazolo[4,3-d]pyrimidin-3-yl)phenyl)piperazin-1-yl)-2,21-dioxo-6,9,12,15,18-pentaoxa-3,22-diazatetracosan-24-oyl)-4-hydroxy-N-(4-(4-methylthiazol-5-yl)benzyl)pyrrolidine-2-carboxamide |
| 242 | HC90-127 | 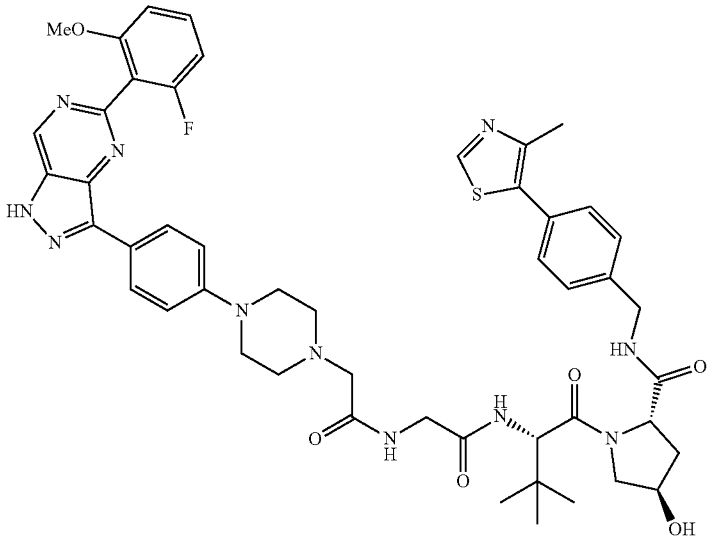 [SMILES: COc1cccc(F)c1-c1ncc2[nH]nc(-c3ccc(N4CCN(CC(=O)NCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(2-(2-(4-(4-(5-(2-fluoro-6-methoxyphenyl)-1H-pyrazolo[4,3-d]pyrimidin-3-yl)phenyl)piperazin-1-yl)acetamido)acetamido)-3,3-dimethylbutanoyl)-4-hydroxy-N-(4-(4-methylthiazol-5-yl)benzyl)pyrrolidine-2-carboxamide |

TABLE 1-continued

| Ex am- ples | Com- pound code | Structure | Chemical Name |
| --- | --- | --- | --- |
| 243 | HC90-128 | 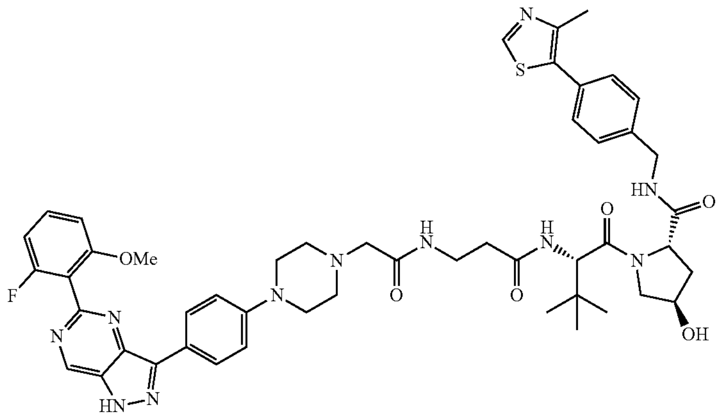 [SMILES: COc1cccc(F)c1-c1ncc2[nH]nc(-c3ccc(N4CCN(CC(=O)NCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(3-(2-(4-(4-(5-(2-fluoro-6-methoxyphenyl)-1H-pyrazolo[4,3-d]pyrimidin-3-yl)phenyl)piperazin-1-yl)acetamido)propanamido)-3,3-dimethylbutanoyl)-4-hydroxy-N-(4-(4-methylthiazol-5-yl)benzyl)pyrrolidine-2-carboxamide |
| 244 | HC90-129 | 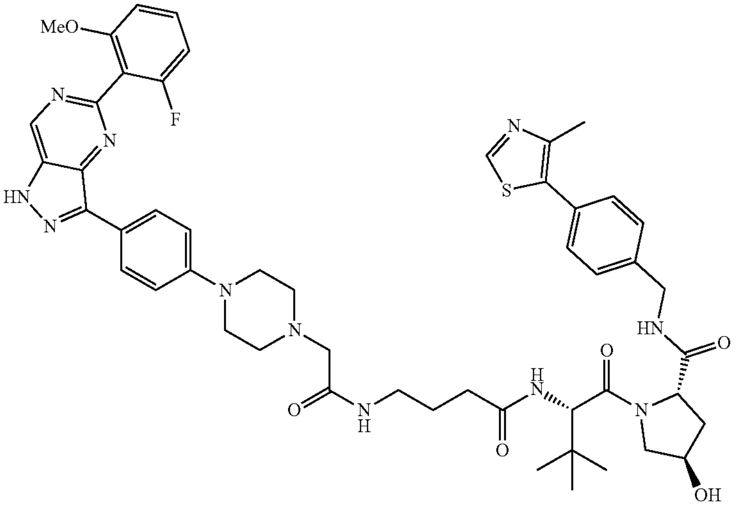 [SMILES: COc1cccc(F)c1-c1ncc2[nH]nc(-c3ccc(N4CCN(CC(=O)NCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(4-(2-(4-(4-(5-(2-fluoro-6-methoxyphenyl)-1H-pyrazolo[4,3-d]pyrimidin-3-yl)phenyl)piperazin-1-yl)acetamido)butanamido)-3,3-dimethylbutanoyl)-4-hydroxy-N-(4-(4-methylthiazol-5-yl)benzyl)pyrrolidine-2-carboxamide |
| 245 | HC90-130 | 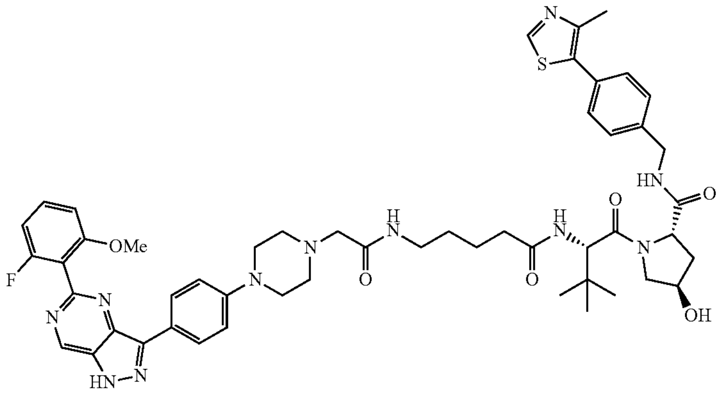 [SMILES: COc1cccc(F)c1-c1ncc2[nH]nc(-c3ccc(N4CCN(CC(=O)NCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(5-(2-(4-(4-(5-(2-fluoro-6-methoxyphenyl)-1H-pyrazolo[4,3-d]pyrimidin-3-yl)phenyl)piperazin-1-yl)acetamido)pentanamido)-3,3-dimethylbutanoyl)-4-hydroxy-N-(4-(4-methylthiazol-5-yl)benzyl)pyrrolidine-2-carboxamide |

TABLE 1-continued

| Examples | Compound code | Structure | Chemical Name |
|---|---|---|---|
| 246 | HC90-131 | 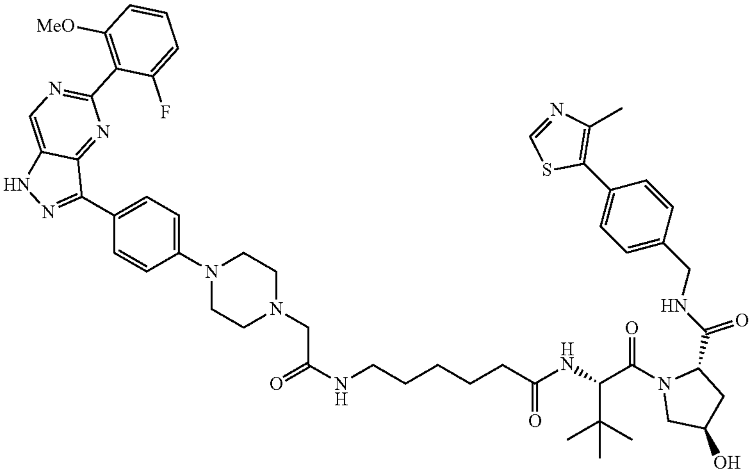 | (2S,4R)-1-((S)-2-(6-(2-(4-(4-(5-(2-fluoro-6-methoxyphenyl)-1H-pyrazolo[4,3-d]pyrimidin-3-yl)phenyl)piperazin-1-yl)acetamido)hexanamido)-3,3-dimethylbutanoyl)-4-hydroxy-N-(4-(4-methylthiazol-5-yl)benzyl)pyrrolidine-2-carboxamide |
| 247 | HC90-132 | 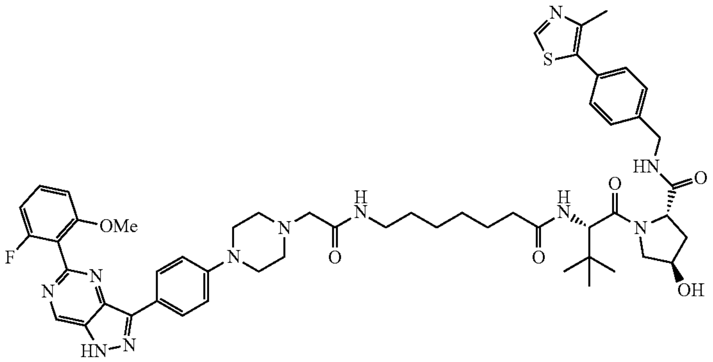 [SMILES: COc1cccc(F)c1-c1ncc2[nH]nc(-c3ccc(N4CCN(CC(=O)NCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(7-(2-(4-(4-(5-(2-fluoro-6-methoxyphenyl)-1H-pyrazolo[4,3-d]pyrimidin-3-yl)phenyl)piperazin-1-yl)acetamido)heptanamido)-3,3-dimethylbutanoyl)-4-hydroxy-N-(4-(4-methylthiazol-5-yl)benzyl)pyrrolidine-2-carboxamide |
| 248 | HC90-133 | 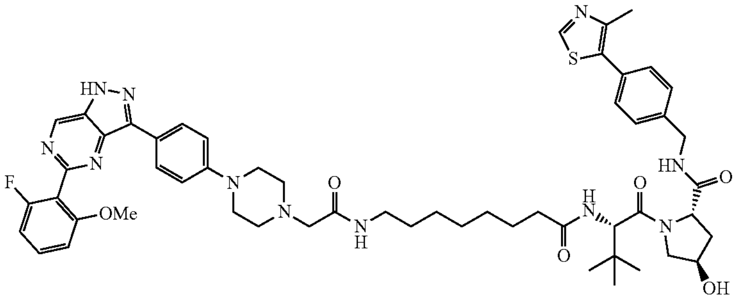 [SMILES: COc1cccc(F)c1-c1ncc2[nH]nc(-c3ccc(N4CCN(CC(=O)NCCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(8-(2-(4-(4-(5-(2-fluoro-6-methoxyphenyl)-1H-pyrazolo[4,3-d]pyrimidin-3-yl)phenyl)piperazin-1-yl)acetamido)octanamido)-3,3-dimethylbutanoyl)-4-hydroxy-N-(4-(4-methylthiazol-5-yl)benzyl)pyrrolidine-2-carboxamide |
| 249 | HC90-134 | 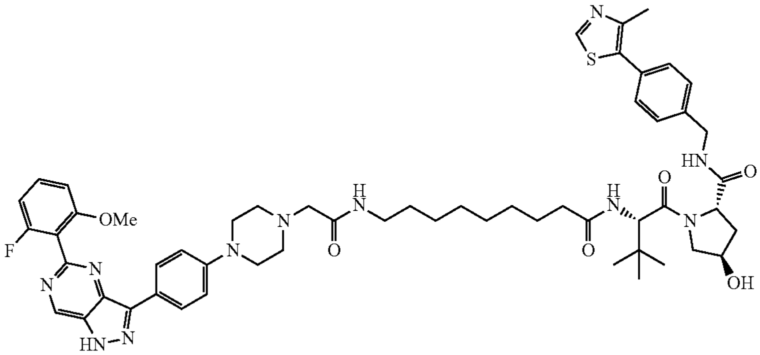 [SMILES: COc1cccc(F)c1-c1ncc2[nH]nc(-c3ccc(N4CCN(CC(=O)NCCCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(9-(2-(4-(4-(5-(2-fluoro-6-methoxyphenyl)-1H-pyrazolo[4,3-d]pyrimidin-3-yl)phenyl)piperazin-1-yl)acetamido)nonanamido)-3,3-dimethylbutanoyl)-4-hydroxy-N-(4-(4-methylthiazol-5-yl)benzyl)pyrrolidine-2-carboxamide |

TABLE 1-continued

| Ex am- ples | Com- pound code | Structure | Chemical Name |
|---|---|---|---|
| 250 | HC90-135 | 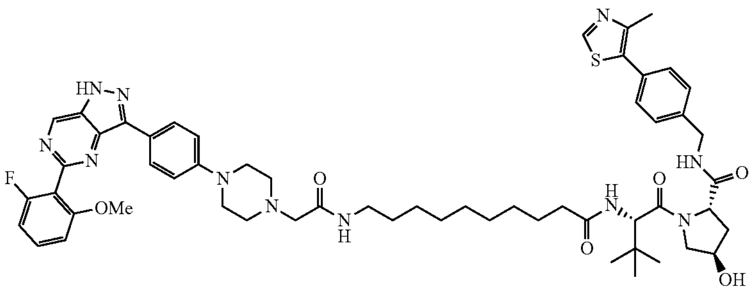 [SMILES: COc1cccc(F)c1-c1ncc2[nH]nc(-c3ccc(N4CCN(CC(=O)NCCCCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(10-(2-(4-(4-(5-(2-fluoro-6-methoxyphenyl)-1H-pyrazolo[4,3-d]pyrimidin-3-yl)phenyl)piperazin-1-yl)acetamido)decanamido)-3,3-dimethylbutanoyl)-4-hydroxy-N-(4-(4-methylthiazol-5-yl)benzyl)pyrrolidine-2-carboxamide |
| 251 | HC90-136 | 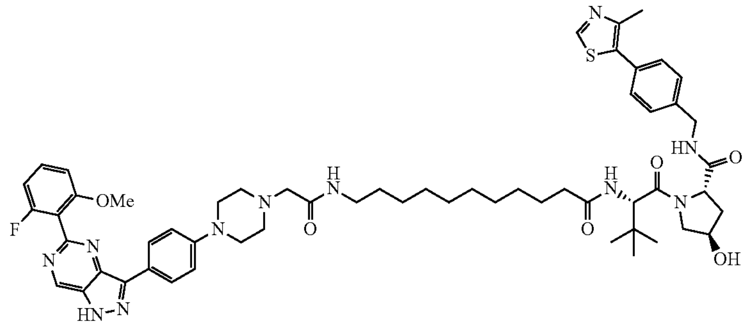 [SMILES: COc1cccc(F)c1-c1ncc2[nH]nc(-c3ccc(N4CCN(CC(=O)NCCCCCCCCCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(11-(2-(4-(4-(5-(2-fluoro-6-methoxyphenyl)-1H-pyrazolo[4,3-d]pyrimidin-3-yl)phenyl)piperazin-1-yl)acetamido)undecanamido)-3,3-dimethylbutanoyl)-4-hydroxy-N-(4-(4-methylthiazol-5-yl)benzyl)pyrrolidine-2-carboxamide |
| 252 | HC90-60 | 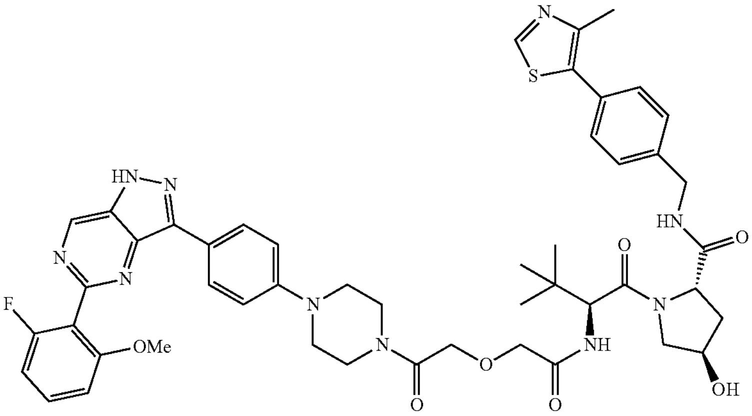 [SMILES: COc1cccc(F)c1-c1ncc2[nH]nc(-c3ccc(N4CCN(C(=O)COCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(2-(2-(4-(4-(5-(2-fluoro-6-methoxyphenyl)-1H-pyrazolo[4,3-d]pyrimidin-3-yl)phenyl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |
| 253 | HC90-62 | 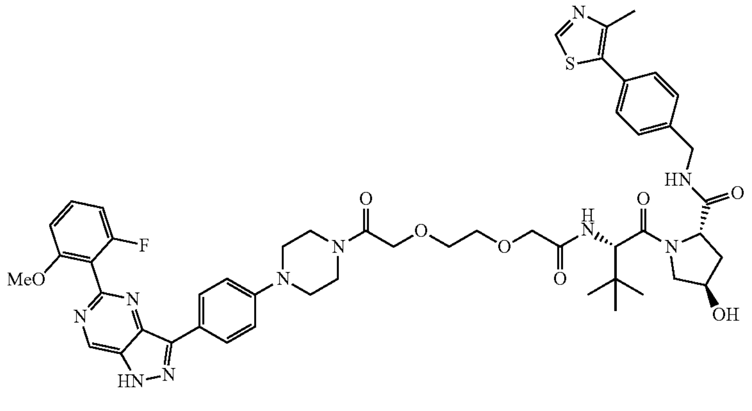 [SMILES: COc1cccc(F)c1-c1ncc2[nH]nc(-c3ccc(N4CCN(C(=O)COCCOCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(2-(2-(2-(4-(4-(5-(2-fluoro-6-methoxyphenyl)-1H-pyrazolo[4,3-d]pyrimidin-3-yl)phenyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

| Examples | Compound code | Structure | Chemical Name |
|---|---|---|---|
| 254 | HC90-63 | 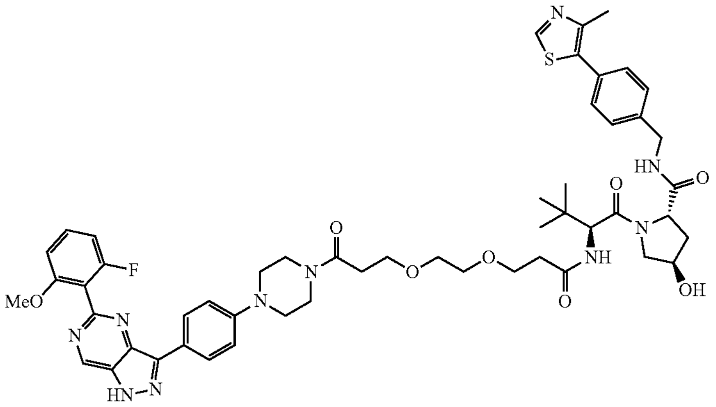 [SMILES: COc1cccc(F)c1-c1ncc2[nH]nc(-c3ccc(N4CCN(C(=O)CCOCCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(3-(2-(3-(4-(4-(5-(2-fluoro-6-methoxyphenyl)-1H-pyrazolo[4,3-d]pyrimidin-3-yl)phenyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |
| 255 | HC90-64 | 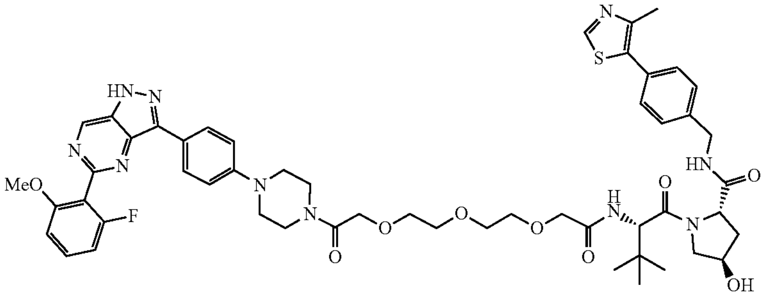 [SMILES: COc1cccc(F)c1-c1ncc2[nH]nc(-c3ccc(N4CCN(C(=O)COCCOCCOCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(tert-butyl)-14-(4-(4-(5-(2-fluoro-6-methoxyphenyl)-1H-pyrazolo[4,3-d]pyrimidin-3-yl)phenyl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide |
| 256 | HC90-65 | 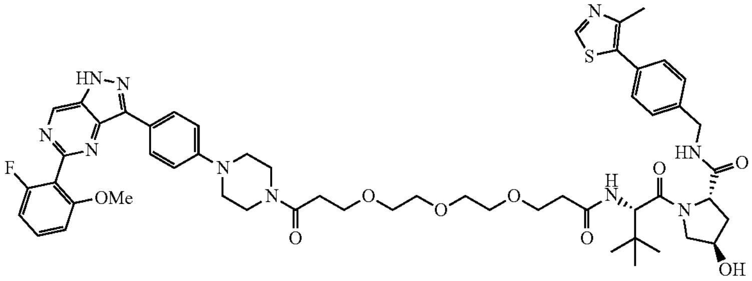 [SMILES: COc1cccc(F)c1-c1ncc2[nH]nc(-c3ccc(N4CCN(C(=O)CCOCCOCCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(tert-butyl)-16-(4-(4-(5-(2-fluoro-6-methoxyphenyl)-1H-pyrazolo[4,3-d]pyrimidin-3-yl)phenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| 257 | HC90-67 | 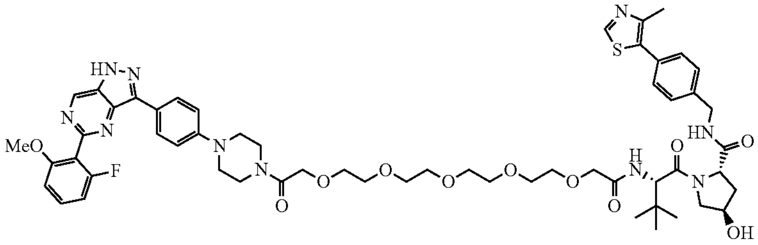 [SMILES: COc1cccc(F)c1-c1ncc2[nH]nc(-c3ccc(N4CCN(C(=O)COCCOCCOCCOCCOCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(tert-butyl)-20-(4-(4-(5-(2-fluoro-6-methoxyphenyl)-1H-pyrazolo[4,3-d]pyrimidin-3-yl)phenyl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |
| 258 | HC90-68 | 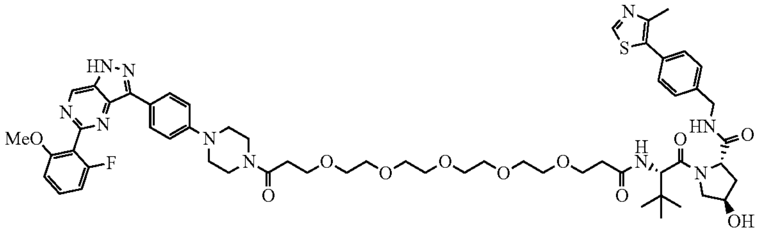 [SMILES: COc1cccc(F)c1-c1ncc2[nH]nc(-c3ccc(N4CCN(C(=O)CCOCCOCCOCCOCCOCCC(=O)N[C@H](C(=O)N5C[C@H](O)C[C@H]5C(=O)NCc5ccc(-c6scnc6C)cc5)C(C)(C)C)CC4)cc3)c2n1] | (2S,4R)-1-((S)-2-(tert-butyl)-22-(4-(4-(5-(2-fluoro-6-methoxyphenyl)-1H-pyrazolo[4,3-d]pyrimidin-3-yl)phenyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |

TABLE 1-continued

| Ex am- ples | Com- pound code | Structure | Chemical Name |
|---|---|---|---|
| 260 | HC90-114 | 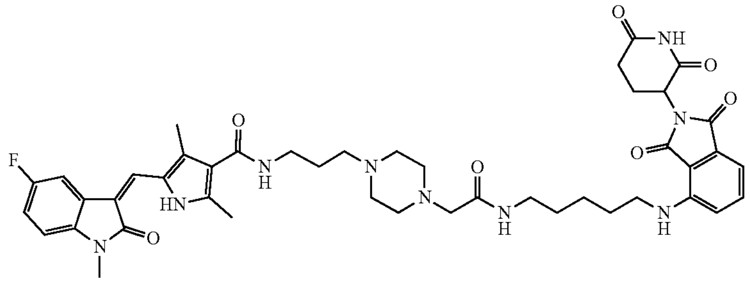 [SMILES: Cc1[nH]c(/C=C2\C(=O)N(C)c3ccc(F)cc32)c(C)c1C(=O)NCCCN1CCN(CC(=O)NCCCCCNc2cccc3c2C(=O)N(C2CCC(=O)NC2=O)C3=O)CC1] | (Z)-N-(3-(4-(2-((5-((2-(2,6-dioxopiperidin-3-yl)-1,3-dioxoisoindolin-4-yl)amino)pentyl)amino)-2-oxoethyl)piperazin-1-yl)propyl)-5-((5-fluoro-1-methyl-2-oxoindolin-3-ylidene)methyl)-2,4-dimethyl-1H-pyrrole-3-carboxamide |
| 261 | HC90-115 | 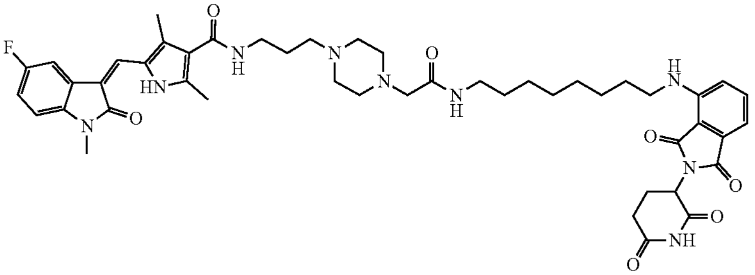 [SMILES: Cc1[nH]c(/C=C2\C(=O)N(C)c3ccc(F)cc32)c(C)c1C(=O)NCCCN1CCN(CC(=O)NCCCCCCCCNc2cccc3c2C(=O)N(C2CCC(=O)NC2=O)C3=O)CC1] | (Z)-N-(3-(4-(2-((8-((2-(2,6-dioxopiperidin-3-yl)-1,3-dioxoisoindolin-4-yl)amino)octyl)amino)-2-oxoethyl)piperazin-1-yl)propyl)-5-((5-fluoro-1-methyl-2-oxoindolin-3-ylidene)methyl)-2,4-dimethyl-1H-pyrrole-3-carboxamide |
| 263 | HC90-168 | 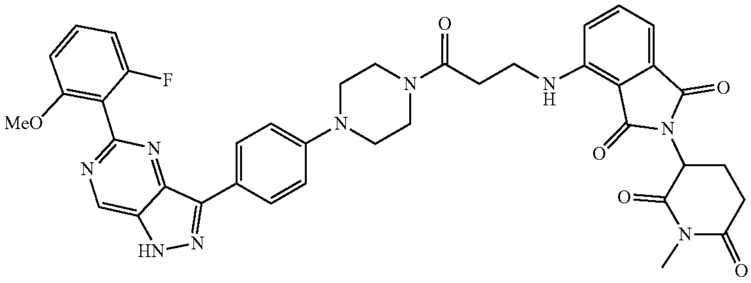 [SMILES: COc1cccc(F)c1-c1ncc2[nH]nc(-c3ccc(N4CCN(C(=O)CCNc5cccc6c5C(=O)N(C5CCC(=O)N(C)C5=O)C6=O)CC4)cc3)c2n1] | 4-((3-(4-(4-(5-(2-fluoro-6-methoxyphenyl)-1H-pyrazolo[4,3-d]pyrimidin-3-yl)phenyl)piperazin-1-yl)-3-oxopropyl)amino)-2-(1-methyl-2,6-dioxopiperidin-3-yl)isoindoline-1,3-dione |
| 264 | HC90-169 | 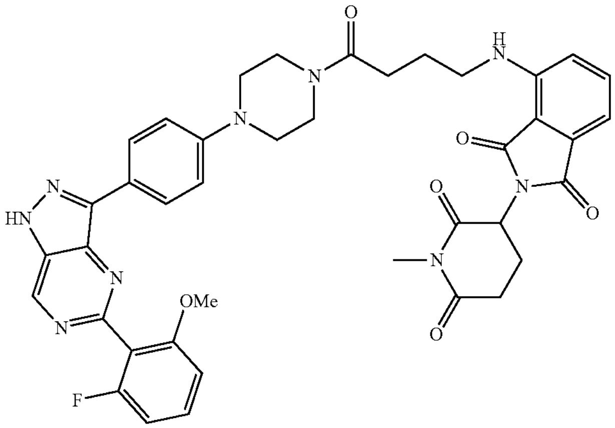 [SMILES: COc1cccc(F)c1-c1ncc2[nH]nc(-c3ccc(N4CCN(C(=O)CCCNc5cccc6c5C(=O)N(C5CCC(=O)N(C)C5=O)C6=O)CC4)cc3)c2n1] | 4-((4-(4-(4-(5-(2-fluoro-6-methoxyphenyl)-1H-pyrazolo[4,3-d]pyrimidin-3-yl)phenyl)piperazin-1-yl)-4-oxobutyl)amino)-2-(1-methyl-2,6-dioxopiperidin-3-yl)isoindoline-1,3-dione |

TABLE 2
| Examples | Structure | Chemical Name |
| --- | --- | --- |
| 265 | 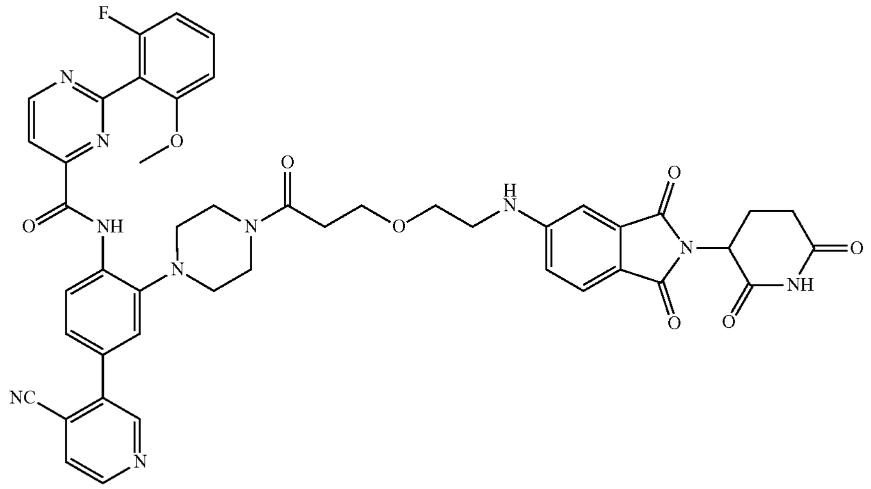 [SMILES: COc1cccc(F)c1-c1nccc(C(=O)Nc2ccc(-c3cnccc3C#N)cc2N2CCN(C(=O)CCOCCNc3ccc4c(c3)C(=O)N(C3CCC(=O)NC3=O)C4=O)CC2)n1] | N-(4-(4-cyanopyridin-3-yl)-2-(4-(3-(2-((2-(2,6-dioxopiperidin-3-yl)-1,3-dioxoisoindolin-5-yl)amino)ethoxy)propanoyl) piperazin-1-yl)phenyl)-2-(2-fluoro-6-methoxyphenyl)pyrimidine-4-carboxamide |
| 266 | 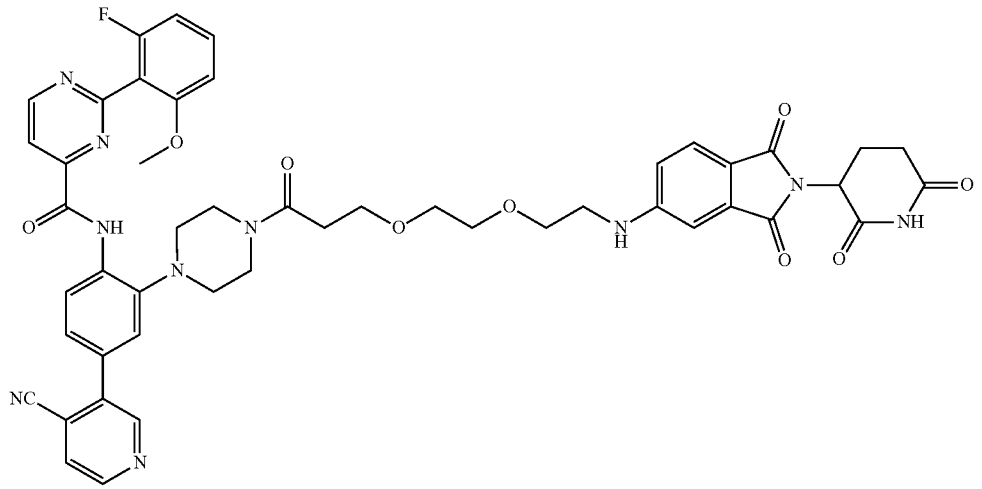 [SMILES: COc1cccc(F)c1-c1nccc(C(=O)Nc2ccc(-c3cnccc3C#N)cc2N2CCN(C(=O)CCOCCOCCNc3ccc4c(c3)C(=O)N(C3CCC(=O)NC3=O)C4=O)CC2)n1] | N-(4-(4-cyanopyridin-3-yl)-2-(4-(3-(2-(2-((2-(2,6-dioxopiperidin-3-yl)-1,3-dioxoisoindolin-5-yl)amino)ethoxy)ethoxy)propanoyl) piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 267 | 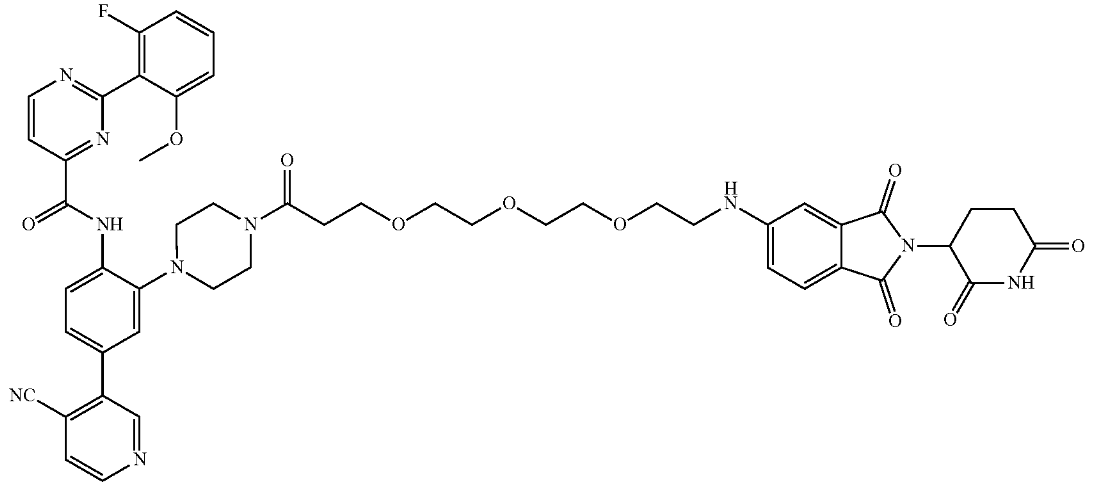 [SMILES: COc1cccc(F)c1-c1nccc(C(=O)Nc2ccc(-c3cnccc3C#N)cc2N2CCN(C(=O)CCOCCOCCOCCNc3ccc4c(c3)C(=O)N(C3CCC(=O)NC3=O)C4=O)CC2)n1] | N-(4-(4-cyanopyridin-3-yl)-2-(4-(3-(2-(2-(2-((2-(2,6-dioxopiperidin-3-yl)-1,3-dioxoisoindolin-5-yl)amino)ethoxy)ethoxy)ethoxy)propanoyl)piperazin-1-yl)phenyl)-2-(2-fluoro-6-methoxyphenyl)pyrimidine-4-carboxamide |
| 268 | 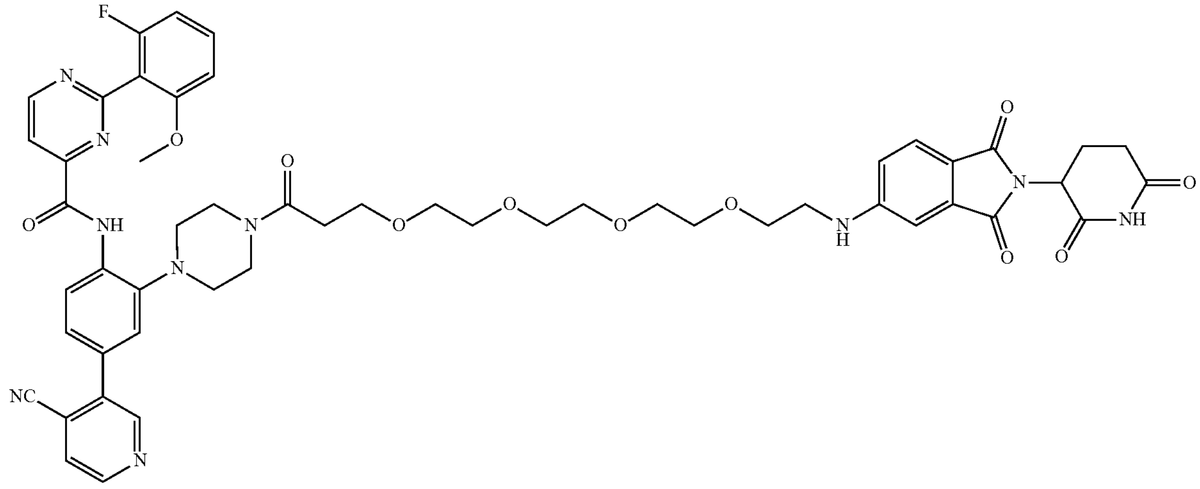 [SMILES: COc1cccc(F)c1-c1nccc(C(=O)Nc2ccc(-c3cnccc3C#N)cc2N2CCN(C(=O)CCOCCOCCOCCOCCNc3ccc4c(c3)C(=O)N(C3CCC(=O)NC3=O)C4=O)CC2)n1] | N-(4-(4-cyanopyridin-3-yl)-2-(4-(1-((2-(2,6-dioxopiperidin-3-yl)-1,3-dioxoisoindolin-5-yl)amino)-3,6,9,12-tetraoxapentadecan-15-oyl)piperazin-1-yl)phenyl)-2-(2-fluoro-6-methoxyphenyl)pyrimidine-4-carboxamide |

TABLE 2-continued
| Examples | Structure | Chemical Name |
|---|---|---|
| 269 | 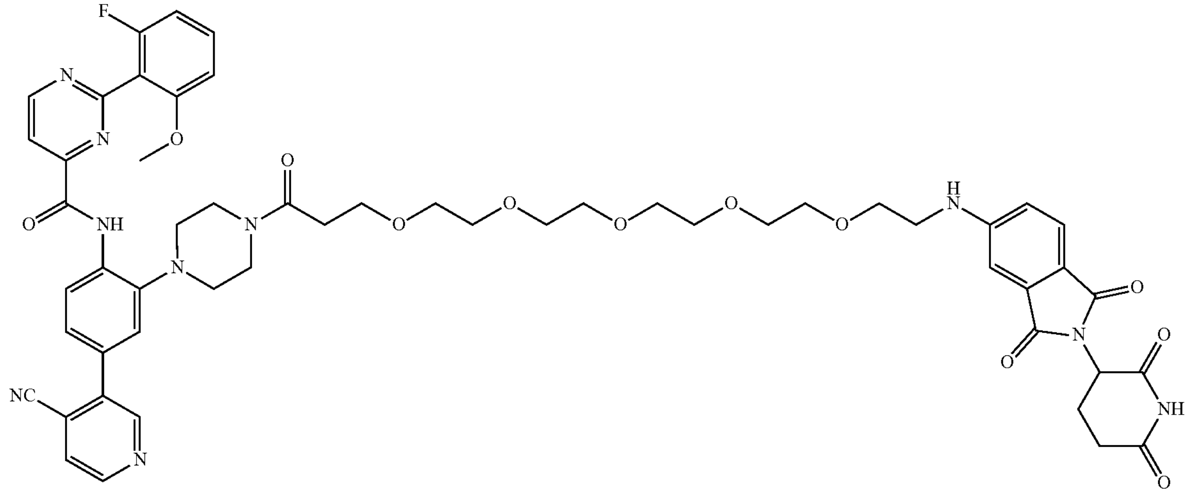 [SMILES: COc1cccc(F)c1-c1nccc(C(=O)Nc2ccc(-c3cnccc3C#N)cc2N2CCN(C(=O)CCOCCOCCOCCOCCOCCNc3ccc4c(c3)C(=O)N(C3CCC(=O)NC3=O)C4=O)CC2)n1] | N-(4-(4-cyanopyridin-3-yl)-2-(4-(1-((2-(2,6-dioxopiperidin-3-yl)-1,3-dioxoisoindolin-5-yl)amino)-3,6,9,12,15-pentaoxaoctadecan-18-oyl)piperazin-1-yl)phenyl)-2-(2-fluoro-6-methoxyphenyl)pyrimidine-4-carboxamide |
| 270 | 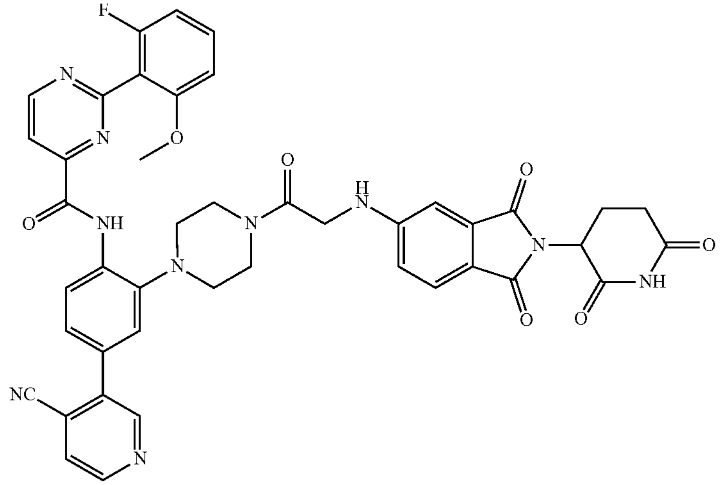 [SMILES: COc1cccc(F)c1-c1nccc(C(=O)Nc2ccc(-c3cnccc3C#N)cc2N2CCN(C(=O)CNc3ccc4c(c3)C(=O)N(C3CCC(=O)NC3=O)C4=O)CC2)n1] | N-(4-(4-cyanopyridin-3-yl)-2-(4-((2-(2,6-dioxopiperidin-3-yl)-1,3-dioxoisoindolin-5-yl)glycyl)piperazin-1-yl)phenyl)-2-(2-fluoro-6-methoxyphenyl)pyrimidine-4-carboxamide |

TABLE 2-continued
| Examples | Structure | Chemical Name |
| --- | --- | --- |
| 271 | 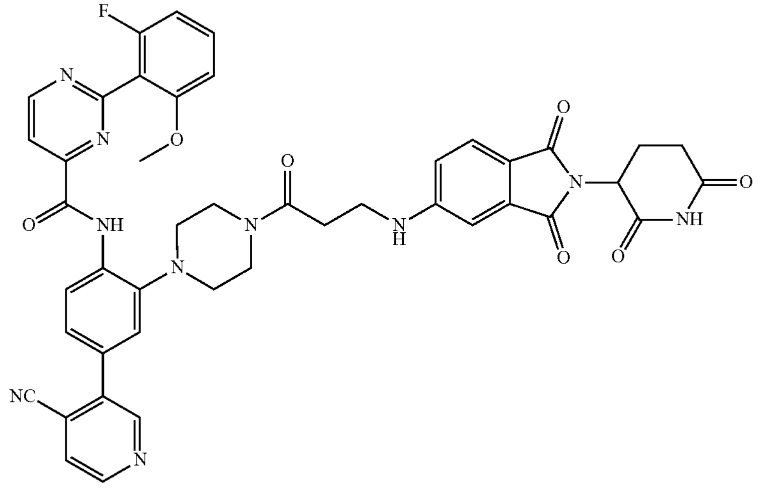 [SMILES: COc1cccc(F)c1-c1nccc(C(=O)Nc2ccc(-c3cnccc3C#N)cc2N2CCN(C(=O)CCNc3ccc4c(c3)C(=O)N(C3CCC(=O)NC3=O)C4=O)CC2)n1] | N-(4-(4-cyanopyridin-3-yl)-2-(4-(3-((2-(2,6-dioxopiperidin-3-yl)-1,3-dioxoisoindolin-5-yl)amino)propanoyl)piperazin-1-yl)phenyl)-2-(2-fluoro-6-methoxyphenyl)pyrimidine-4-carboxamide |
| 272 | 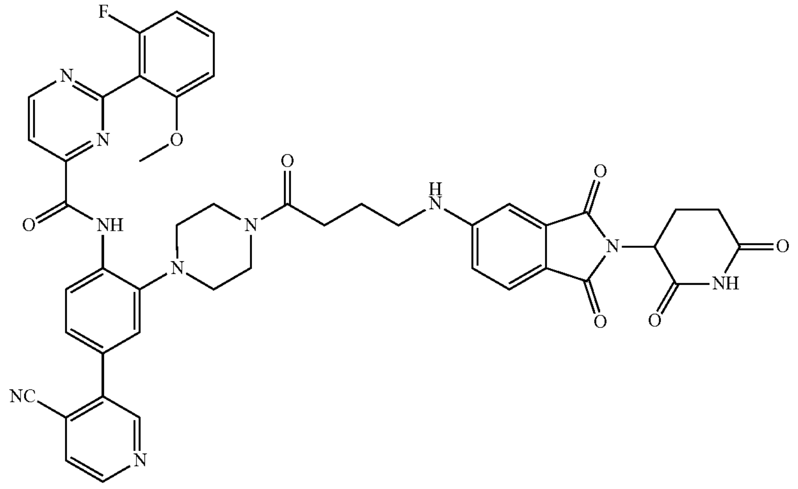 [SMILES: COc1cccc(F)c1-c1nccc(C(=O)Nc2ccc(-c3cnccc3C#N)cc2N2CCN(C(=O)CCCNc3ccc4c(c3)C(=O)N(C3CCC(=O)NC3=O)C4=O)CC2)n1] | N-(4-(4-cyanopyridin-3-yl)-2-(4-(4-((2-(2,6-dioxopiperidin-3-yl)-1,3-dioxoisoindolin-5-yl)amino)butanoyl)piperazin-1-yl)phenyl)-2-(2-fluoro-6-methoxyphenyl)pyrimidine-4-carboxamide |

TABLE 2-continued
| Examples | Structure | Chemical Name |
| --- | --- | --- |
| 273 | 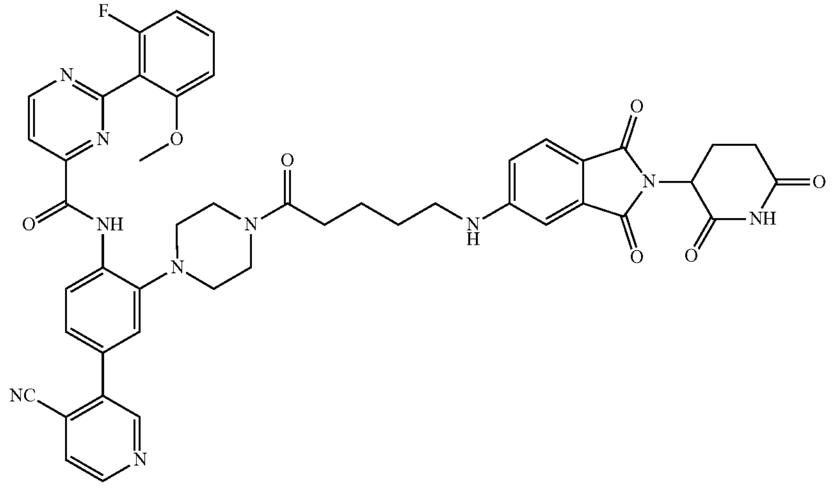 [SMILES: COc1cccc(F)c1-c1nccc(C(=O)Nc2ccc(-c3cnccc3C#N)cc2N2CCN(C(=O)CCCCNc3ccc4c(c3)C(=O)N(C3CCC(=O)NC3=O)C4=O)CC2)n1] | N-(4-(4-cyanopyridin-3-yl)-2-(4-(5-((2-(2,6-dioxopiperidin-3-yl)-1,3-dioxoisoindolin-5-yl)amino)pentanoyl)piperazin-1-yl)phenyl)-2-(2-fluoro-6-methoxyphenyl)pyrimidine-4-carboxamide |
| 274 | 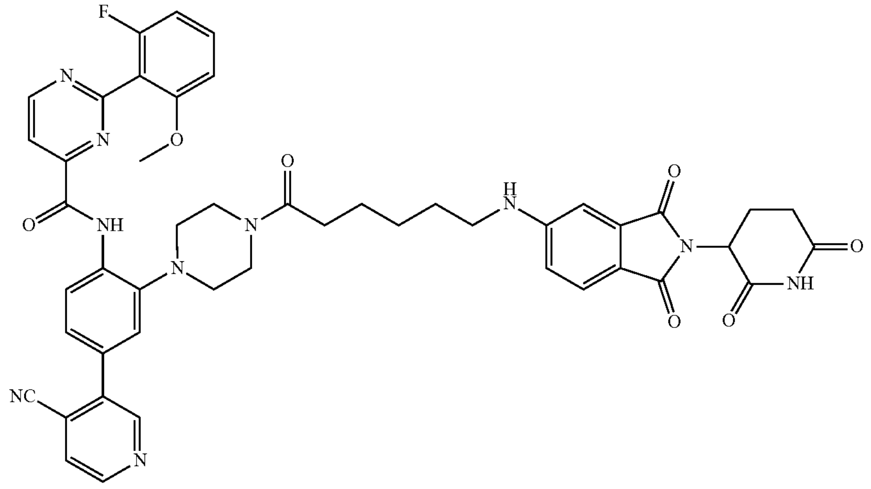 [SMILES: COc1cccc(F)c1-c1nccc(C(=O)Nc2ccc(-c3cnccc3C#N)cc2N2CCN(C(=O)CCCCCNc3ccc4c(c3)C(=O)N(C3CCC(=O)NC3=O)C4=O)CC2)n1] | N-(4-(4-cyanopyridin-3-yl)-2-(4-(6-((2-(2,6-dioxopiperidin-3-yl)-1,3-dioxoisoindolin-5-yl)amino)hexanoyl)piperazin-1-yl)phenyl)-2-(2-fluoro-6-methoxyphenyl)pyrimidine-4-carboxamide |

TABLE 2-continued
| Examples | Structure | Chemical Name |
| --- | --- | --- |
| 275 | 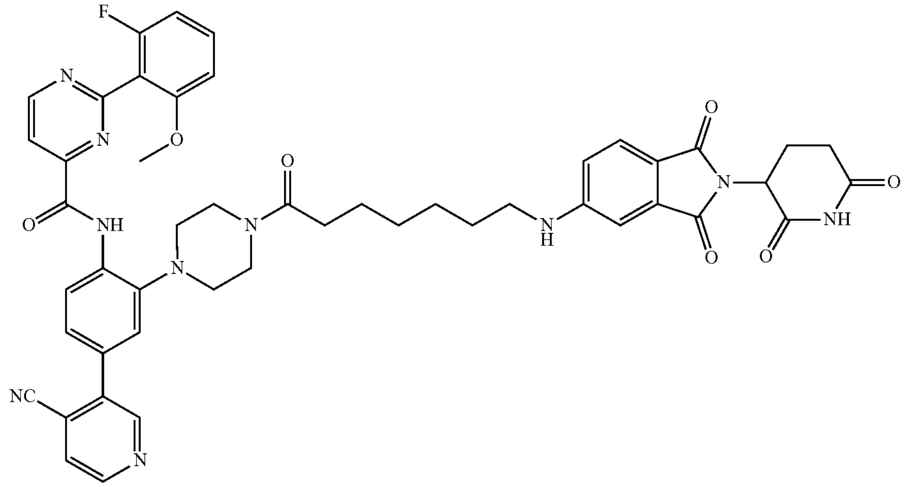 [SMILES: COc1cccc(F)c1-c1nccc(C(=O)Nc2ccc(-c3cnccc3C#N)cc2N2CCN(C(=O)CCCCCCNc3ccc4c(c3)C(=O)N(C3CCC(=O)NC3=O)C4=O)CC2)n1] | N-(4-(4-cyanopyridin-3-yl)-2-(4-(7-((2-(2,6-dioxopiperidin-3-yl)-1,3-dioxoisoindolin-5-yl)amino)heptanoyl)piperazin-1-yl)phenyl)-2-(2-fluoro-6-methoxyphenyl)pyrimidine-4-carboxamide |
| 276 | 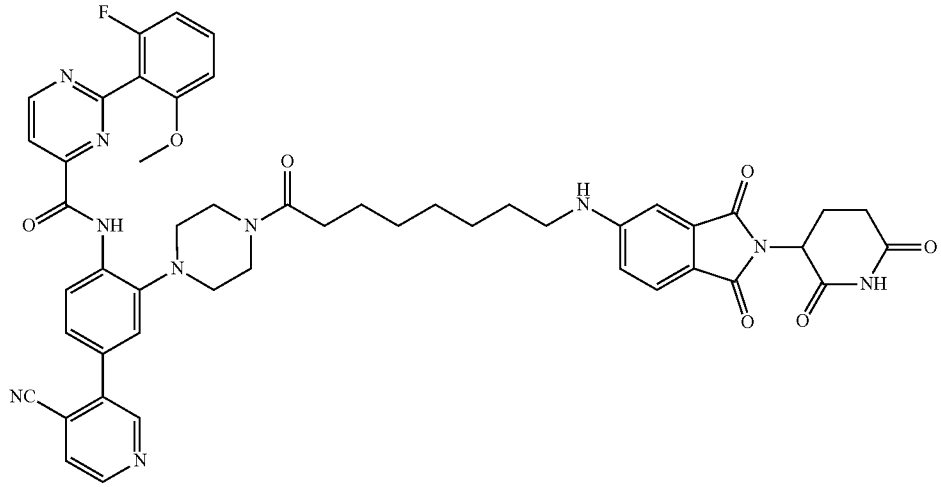 [SMILES: COc1cccc(F)c1-c1nccc(C(=O)Nc2ccc(-c3cnccc3C#N)cc2N2CCN(C(=O)CCCCCCCNc3ccc4c(c3)C(=O)N(C3CCC(=O)NC3=O)C4=O)CC2)n1] | N-(4-(4-cyanopyridin-3-yl)-2-(4-(8-((2-(2,6-dioxopiperidin-3-yl)-1,3-dioxoisoindolin-5-yl)amino)octanoyl)piperazin-1-yl)phenyl)-2-(2-fluoro-6-methoxyphenyl)pyrimidine-4-carboxamide |

TABLE 2-continued
| Examples | Structure | Chemical Name |
| --- | --- | --- |
| 277 | 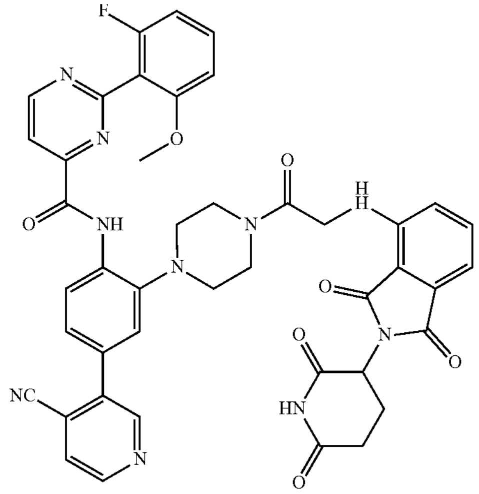 | N-(4-(4-cyanopyridin-3-yl)-2-(4-((2-(2,6-dioxopiperidin-3-yl)-1,3-dioxoisoindolin-4-yl)glycyl)piperazin-1-yl)phenyl)-2-(2-fluoro-6-methoxyphenyl)pyrimidine-4-carboxamide |
| 278 | 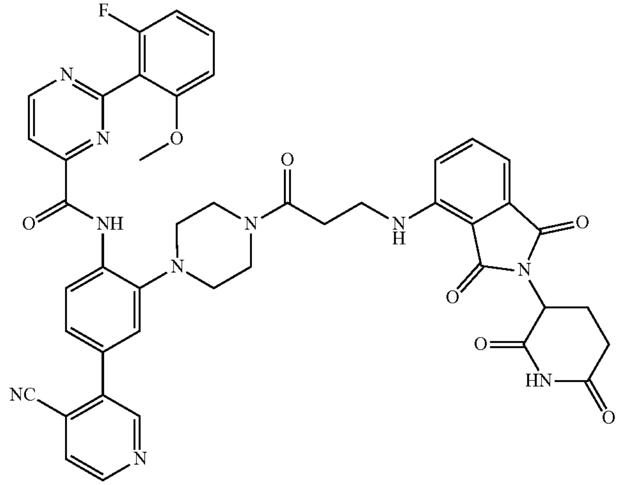 [SMILES: COc1cccc(F)c1-c1nccc(C(=O)Nc2ccc(-c3cnccc3C#N)cc2N2CCN(C(=O)CCNc3cccc4c3C(=O)N(C3CCC(=O)NC3=O)C4=O)CC2)n1] | N-(4-(4-cyanopyridin-3-yl)-2-(4-(3-((2-(2,6-dioxopiperidin-3-yl)-1,3-dioxoisoindolin-4-yl)amino)propanoyl)piperazin-1-yl)phenyl)-2-(2-fluoro-6-methoxyphenyl)pyrimidine-4-carboxamide |

TABLE 2-continued
| Examples | Structure | Chemical Name |
|---|---|---|
| 279 | 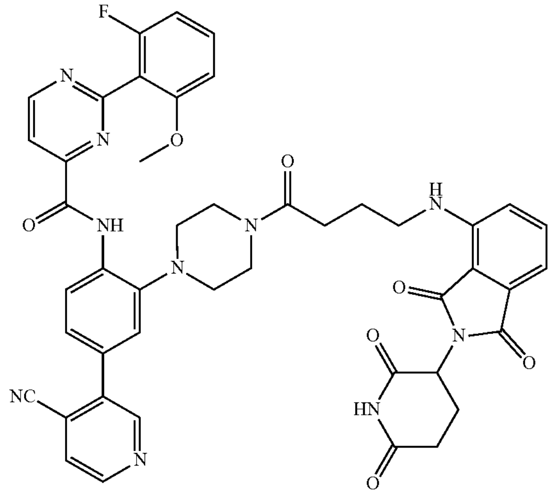 [SMILES: COc1cccc(F)c1-c1nccc(C(=O)Nc2ccc(-c3cnccc3C#N)cc2N2CCN(C(=O)CCCNc3cccc4c3C(=O)N(C3CCC(=O)NC3=O)C4=O)CC2)n1] | N-(4-(4-cyanopyridin-3-yl)-2-(4-(4-((2-(2,6-dioxopiperidin-3-yl)-1,3-dioxoisoindolin-4-yl)amino)butanoyl)piperazin-1-yl)phenyl)-2-(2-fluoro-6-methoxyphenyl)pyrimidine-4-carboxamide |
| 280 | 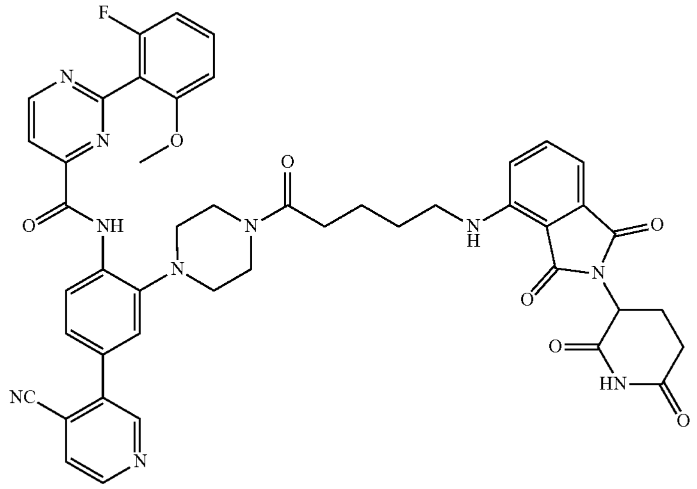 [SMILES: COc1cccc(F)c1-c1nccc(C(=O)Nc2ccc(-c3cnccc3C#N)cc2N2CCN(C(=O)CCCCNc3cccc4c3C(=O)N(C3CCC(=O)NC3=O)C4=O)CC2)n1] | N-(4-(4-cyanopyridin-3-yl)-2-(4-(5-((2-(2,6-dioxopiperidin-3-yl)-1,3-dioxoisoindolin-4-yl)amino)pentanoyl)piperazin-1-yl)phenyl)-2-(2-fluoro-6-methoxyphenyl)pyrimidine-4-carboxamide |

TABLE 2-continued
| Examples | Structure | Chemical Name |
| --- | --- | --- |
| 281 | 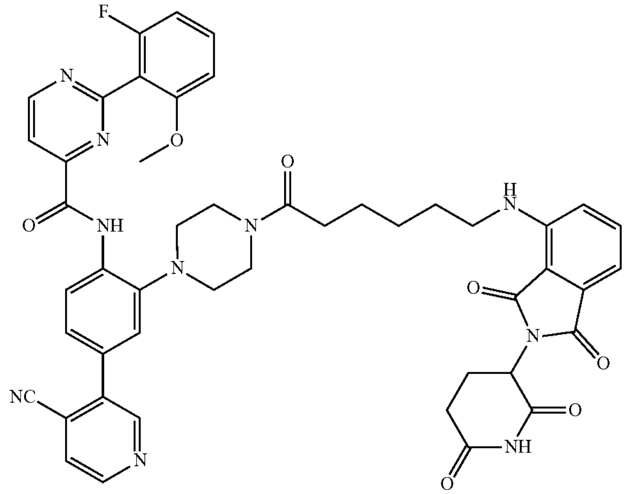 [SMILES: COc1cccc(F)c1-c1nccc(C(=O)Nc2ccc(-c3cnccc3C#N)cc2N2CCN(C(=O)CCCCCNc3cccc4c3C(=O)N(C3CCC(=O)NC3=O)C4=O)CC2)n1] | N-(4-(4-cyanopyridin-3-yl)-2-(4-(6-((2-(2,6-dioxopiperidin-3-yl)-1,3-dioxoisoindolin-4-yl)amino)hexanoyl)piperazin-1-yl)phenyl)-2-(2-fluoro-6-methoxyphenyl)pyrimidine-4-carboxamide |
| 282 | 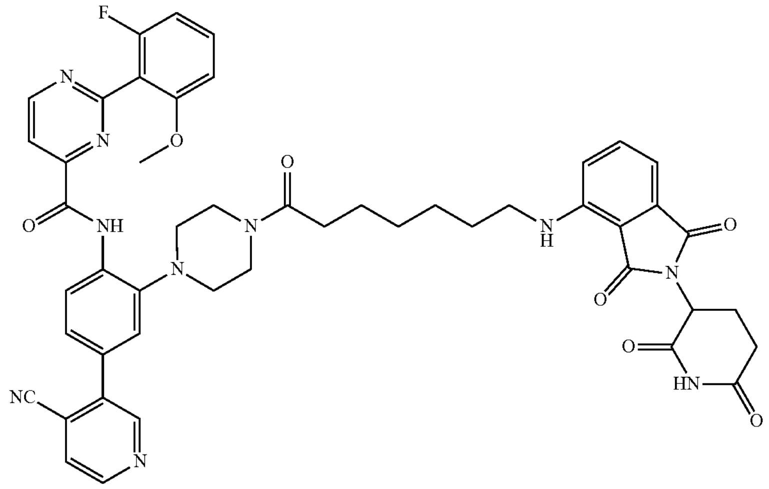 [SMILES: COc1cccc(F)c1-c1nccc(C(=O)Nc2ccc(-c3cnccc3C#N)cc2N2CCN(C(=O)CCCCCCNc3cccc4c3C(=O)N(C3CCC(=O)NC3=O)C4=O)CC2)n1] | N-(4-(4-cyanopyridin-3-yl)-2-(4-(7-((2-(2,6-dioxopiperidin-3-yl)-1,3-dioxoisoindolin-4-yl)amino)heptanoyl)piperazin-1-yl)phenyl)-2-(2-fluoro-6-methoxyphenyl)pyrimidine-4-carboxamide |

TABLE 2-continued
| Examples | Structure | Chemical Name |
|---|---|---|
| 283 | 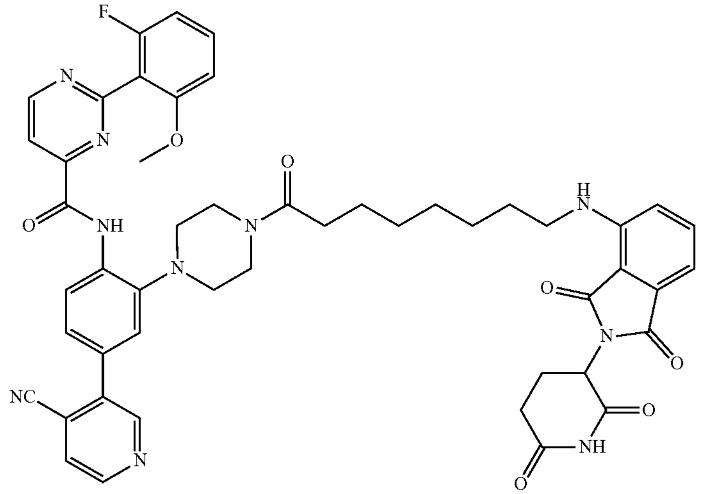 [SMILES: COc1cccc(F)c1-c1nccc(C(=O)Nc2ccc(-c3cnccc3C#N)cc2N2CCN(C(=O)CCCCCCCNc3cccc4c3C(=O)N(C3CCC(=O)NC3=O)C4=O)CC2)n1] | N-(4-(4-cyanopyridin-3-yl)-2-(4-(8-((2-(2,6-dioxopiperidin-3-yl)-1,3-dioxoisoindolin-4-yl)amino)octanoyl)piperazin-1-yl)phenyl)-2-(2-fluoro-6-methoxyphenyl)pyrimidine-4-carboxamide |
| 284 | 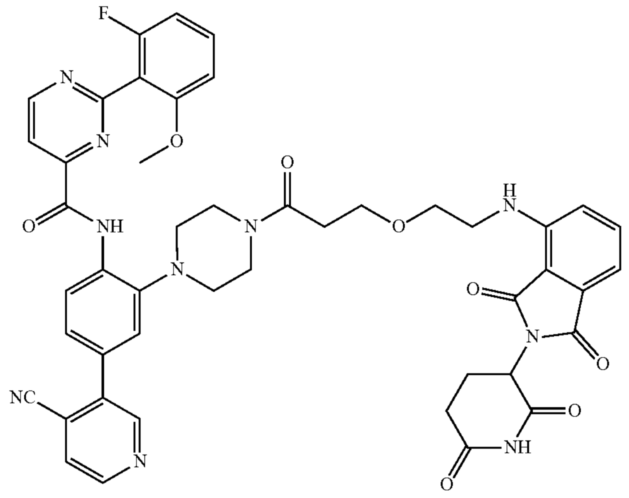 [SMILES: COc1cccc(F)c1-c1nccc(C(=O)Nc2ccc(-c3cnccc3C#N)cc2N2CCN(C(=O)CCOCCNc3cccc4c3C(=O)N(C3CCC(=O)NC3=O)C4=O)CC2)n1] | N-(4-(4-cyanopyridin-3-yl)-2-(4-(3-(2-((2-(2,6-dioxopiperidin-3-yl)-1,3-dioxoisoindolin-4-yl)amino)ethoxy)propanoyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 285 | 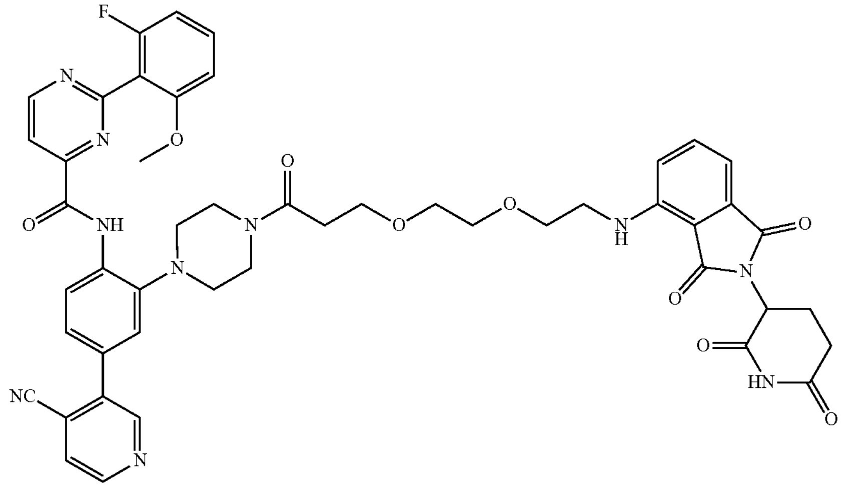 [SMILES: COc1cccc(F)c1-c1nccc(C(=O)Nc2ccc(-c3cnccc3C#N)cc2N2CCN(C(=O)CCOCCOCCNc3cccc4c3C(=O)N(C3CCC(=O)NC3=O)C4=O)CC2)n1] | N-(4-(4-cyanopyridin-3-yl)-2-(4-(3-(2-(2-((2-(2,6-dioxopiperidin-3-yl)-1,3-dioxoisoindolin-4-yl)amino)ethoxy)ethoxy)propanoyl)piperazin-1-yl)phenyl)-2-(2-fluoro-6-methoxyphenyl)pyrimidine-4-carboxamide |
| 286 | 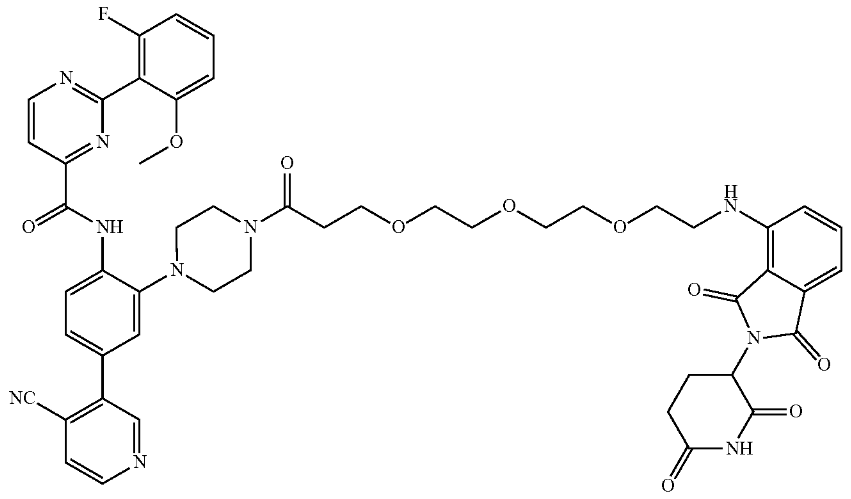 [SMILES: COc1cccc(F)c1-c1nccc(C(=O)Nc2ccc(-c3cnccc3C#N)cc2N2CCN(C(=O)CCOCCOCCOCCNc3cccc4c3C(=O)N(C3CCC(=O)NC3=O)C4=O)CC2)n1] | N-(4-(4-cyanopyridin-3-yl)-2-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 287 | 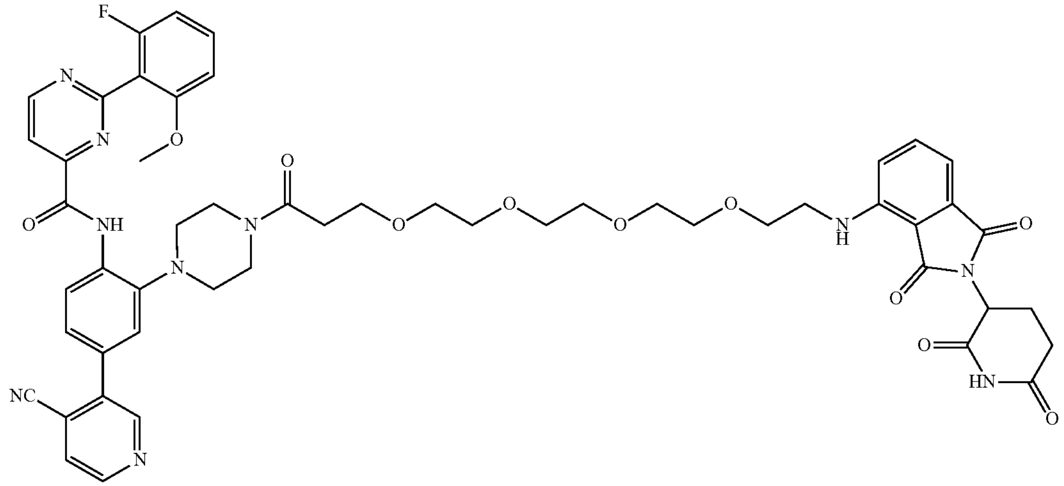 [SMILES: COc1cccc(F)c1-c1nccc(C(=O)Nc2ccc(-c3cnccc3C#N)cc2N2CCN(C(=O)CCOCCOCCOCCOCCNc3cccc4c3C(=O)N(C3CCC(=O)NC3=O)C4=O)CC2)n1] | N-(4-(4-cyanopyridin-3-yl)-2-(4-(1-((2-(2,6-dioxopiperidin-3-yl)-1,3-dioxoisoindolin-4-yl)amino)-3,6,9,12-tetraoxapentadecan-15-oyl)piperazin-1-yl)phenyl)-2-(2-fluoro-6-methoxyphenyl)pyrimidine-4-carboxamide |
| 288 | 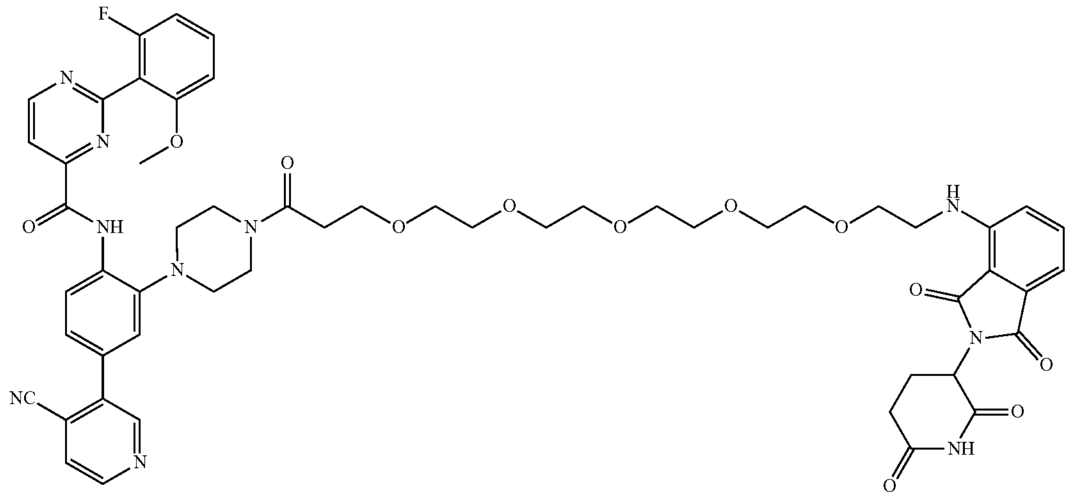 [SMILES: COc1cccc(F)c1-c1nccc(C(=O)Nc2ccc(-c3cnccc3C#N)cc2N2CCN(C(=O)CCOCCOCCOCCOCCOCCNc3cccc4c3C(=O)N(C3CCC(=O)NC3=O)C4=O)CC2)n1] | N-(4-(4-cyanopyridin-3-yl)-2-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 289 | 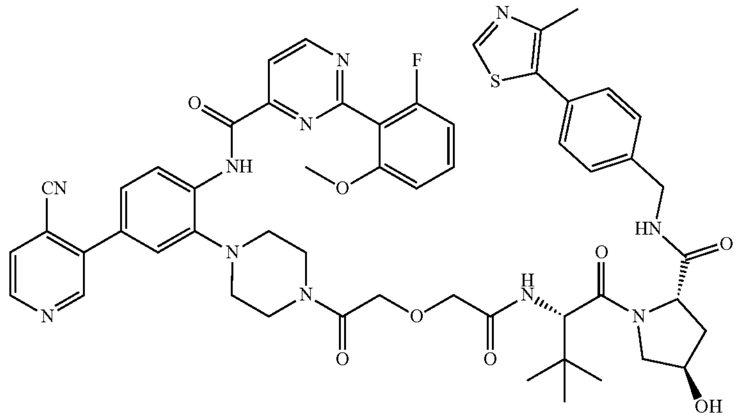 [SMILES: COc1cccc(F)c1-c1nccc(C(=O)Nc2ccc(-c3cnccc3C#N)cc2N2CCN(C(=O)COCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)piperazin-1-yl)phenyl)-2-(2-fluoro-6-methoxyphenyl)pyrimidine-4-carboxamide |
| 290 | 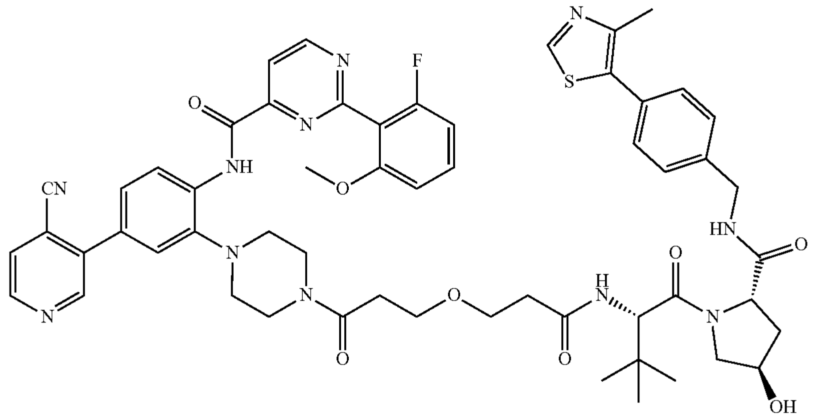 [SMILES: COc1cccc(F)c1-c1nccc(C(=O)Nc2ccc(-c3cnccc3C#N)cc2N2CCN(C(=O)CCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)piperazin-1-yl)phenyl)-2-(2-fluoro-6-methoxyphenyl)pyrimidine-4-carboxamide |

TABLE 2-continued
| Examples | Structure | Chemical Name |
|---|---|---|
| 291 | 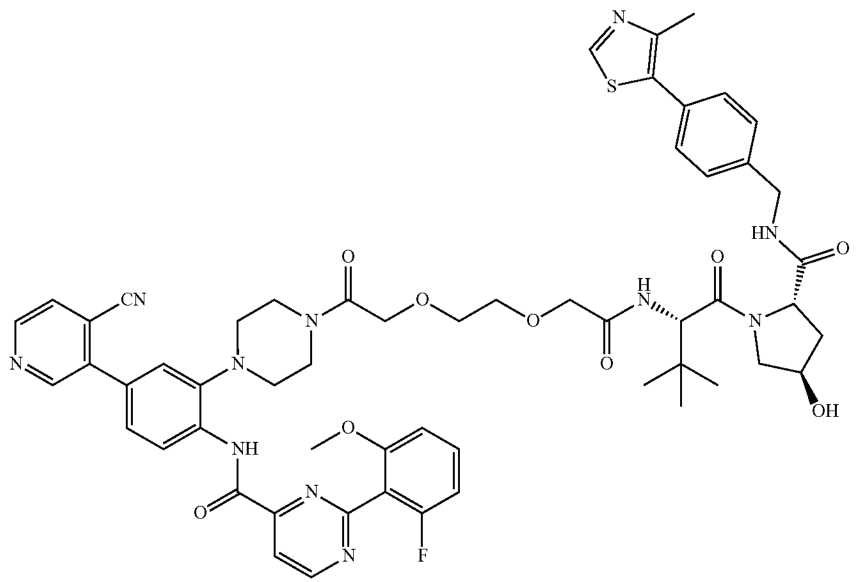 [SMILES: COc1cccc(F)c1-c1nccc(C(=O)Nc2ccc(-c3cnccc3C#N)cc2N2CCN(C(=O)COCCOCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 292 | 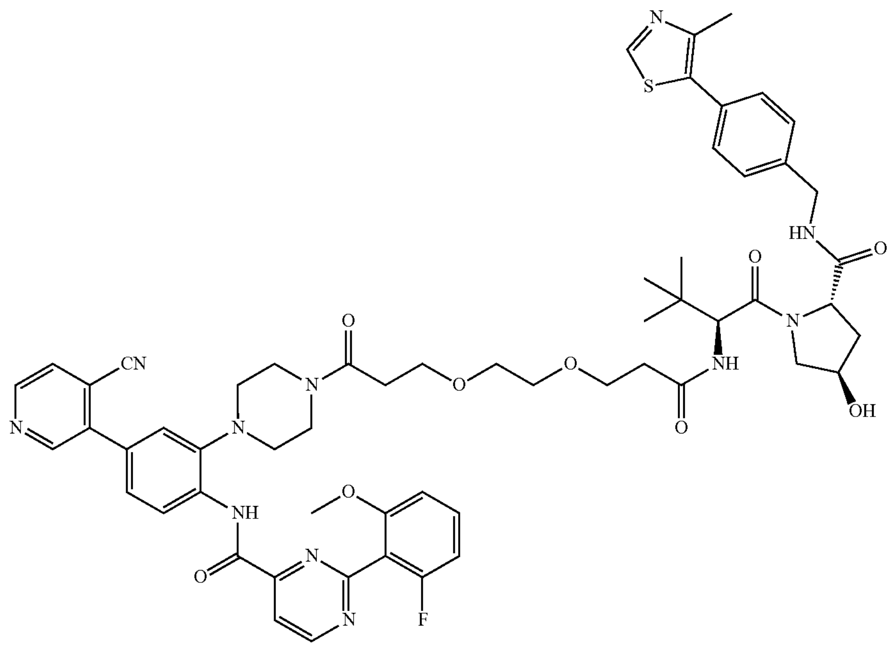 [SMILES: COc1cccc(F)c1-c1nccc(C(=O)Nc2ccc(-c3cnccc3C#N)cc2N2CCN(C(=O)CCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoyl)piperazin-1-yl)phenyl)-2-(2-fluoro-6-methoxyphenyl)pyrimidine-4-carboxamide |
| 293 | 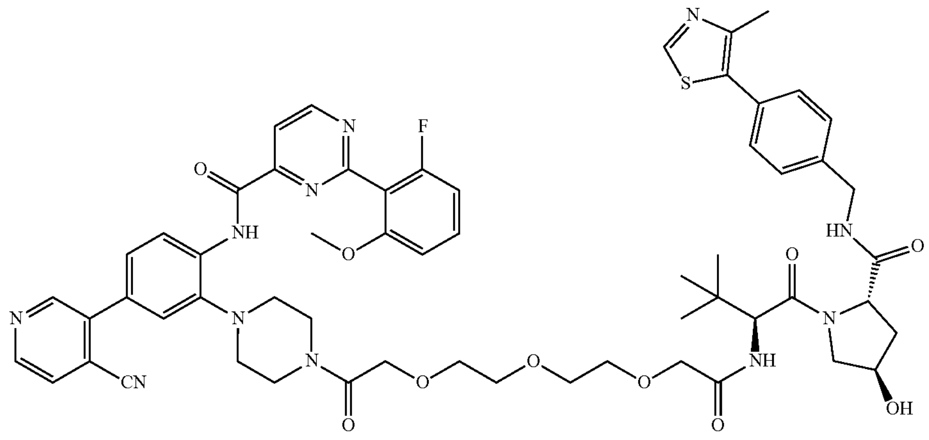 [SMILES: COc1cccc(F)c1-c1nccc(C(=O)Nc2ccc(-c3cnccc3C#N)cc2N2CCN(C(=O)COCCOCCOCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 294 | 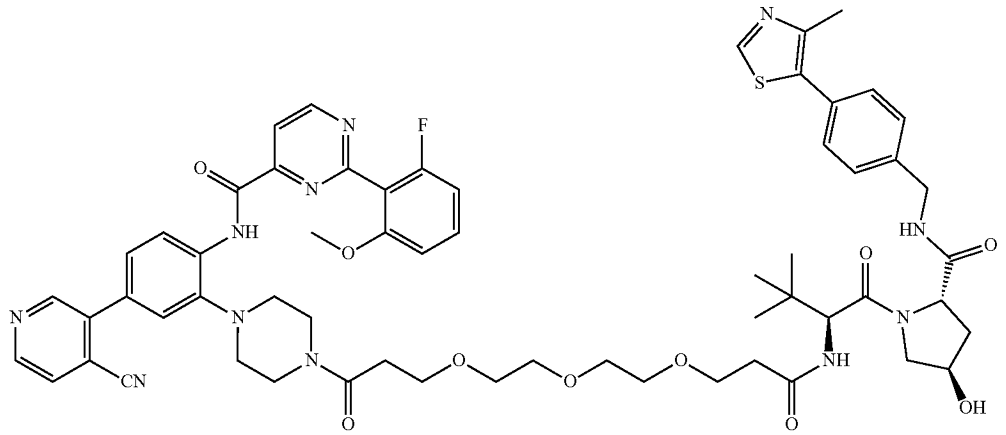 [SMILES: COc1cccc(F)c1-c1nccc(C(=O)Nc2ccc(-c3cnccc3C#N)cc2N2CCN(C(=O)CCOCCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)phenyl)-2-(2-fluoro-6-methoxyphenyl)pyrimidine-4-carboxamide |
| 295 | 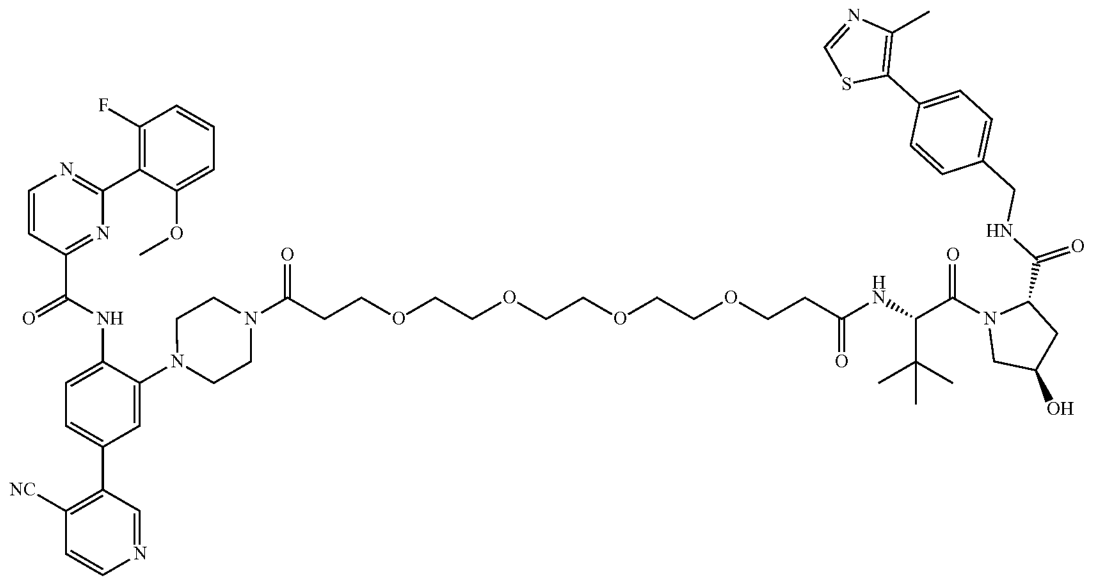 [SMILES: COc1cccc(F)c1-c1nccc(C(=O)Nc2ccc(-c3cnccc3C#N)cc2N2CCN(C(=O)CCOCCOCCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 296 | 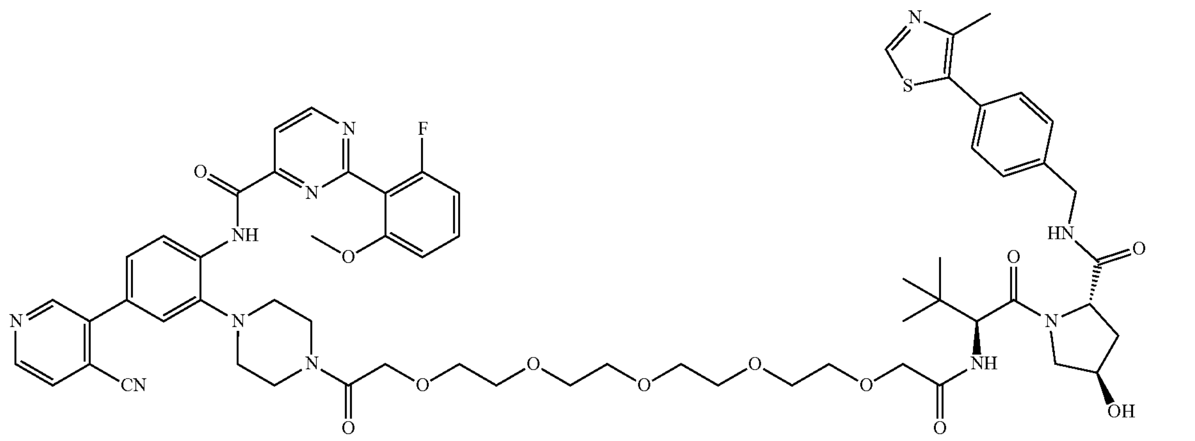 [SMILES: COc1cccc(F)c1-c1nccc(C(=O)Nc2ccc(-c3cnccc3C#N)cc2N2CCN(C(=O)COCCOCCOCCOCCOCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoyl)piperazin-1-yl)phenyl)-2-(2-fluoro-6-methoxyphenyl)pyrimidine-4-carboxamide |
| 297 | 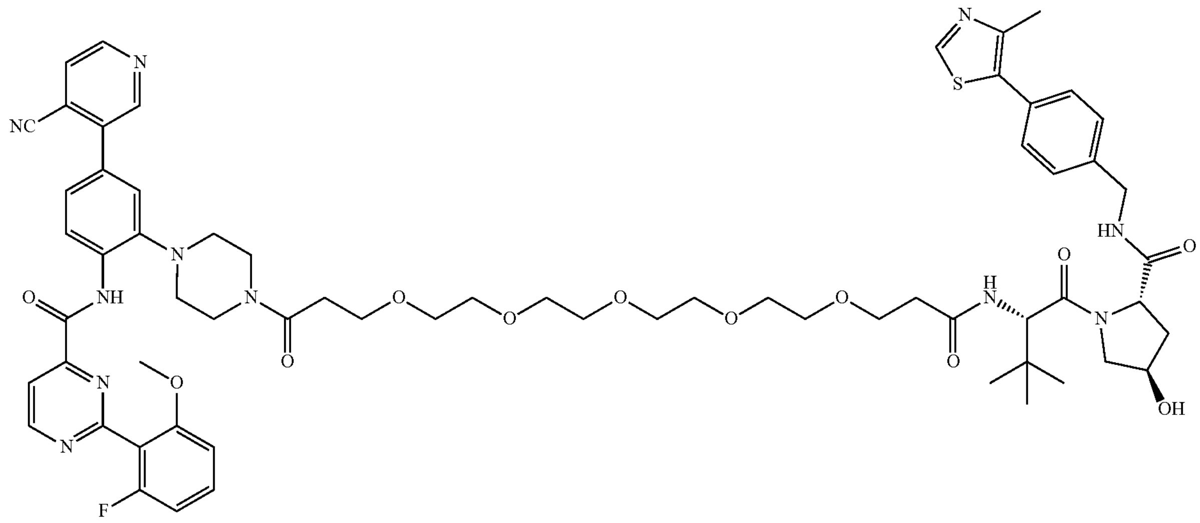 [SMILES: COc1cccc(F)c1-c1nccc(C(=O)Nc2ccc(-c3cnccc3C#N)cc2N2CCN(C(=O)CCOCCOCCOCCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 298 | 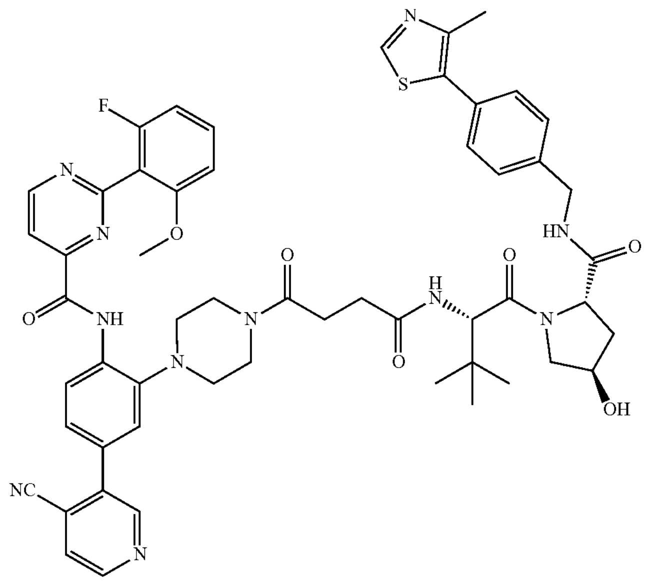 [SMILES: COc1cccc(F)c1-c1nccc(C(=O)Nc2ccc(-c3cnccc3C#N)cc2N2CCN(C(=O)CCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)phenyl)-2-(2-fluoro-6-methoxyphenyl)pyrimidine-4-carboxamide |
| 299 | 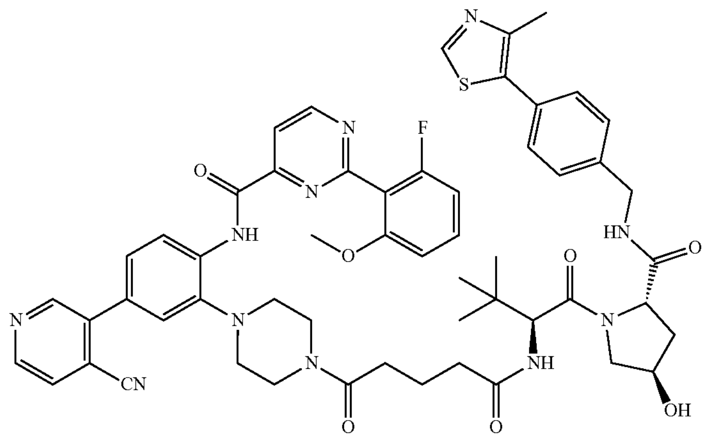 [SMILES: COc1cccc(F)c1-c1nccc(C(=O)Nc2ccc(-c3cnccc3C#N)cc2N2CCN(C(=O)CCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 300 | 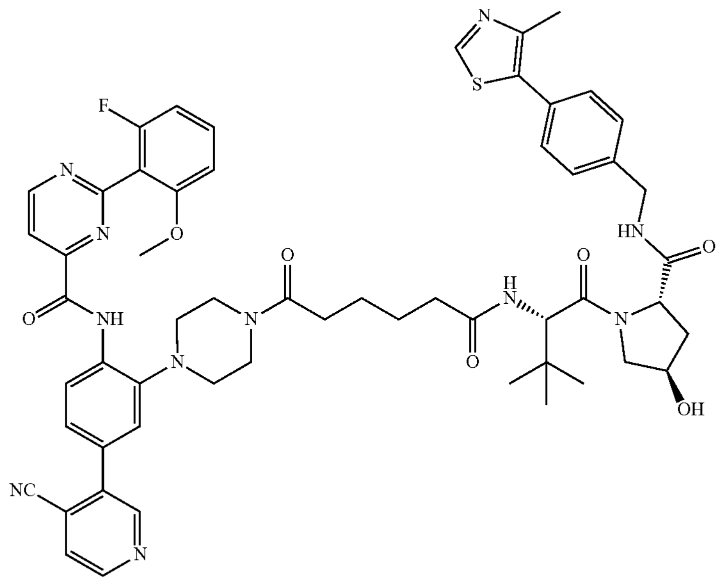 [SMILES: COc1cccc(F)c1-c1nccc(C(=O)Nc2ccc(-c3cnccc3C#N)cc2N2CCN(C(=O)CCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)phenyl)-2-(2-fluoro-6-methoxyphenyl)pyrimidine-4-carboxamide |
| 301 | 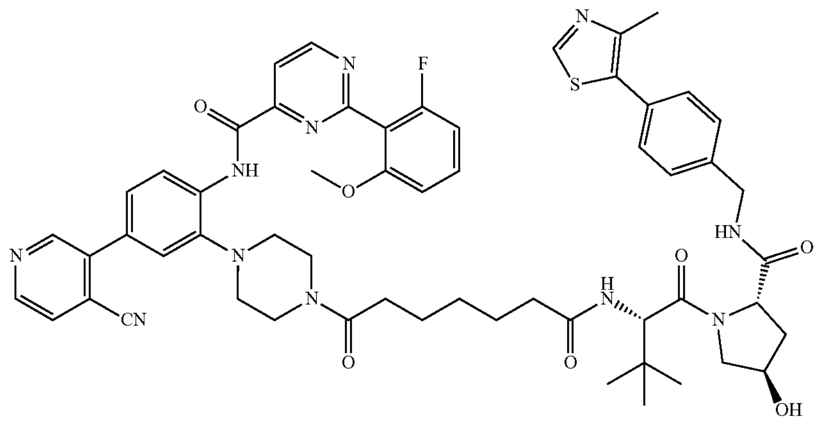 [SMILES: COc1cccc(F)c1-c1nccc(C(=O)Nc2ccc(-c3cnccc3C#N)cc2N2CCN(C(=O)CCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 302 | 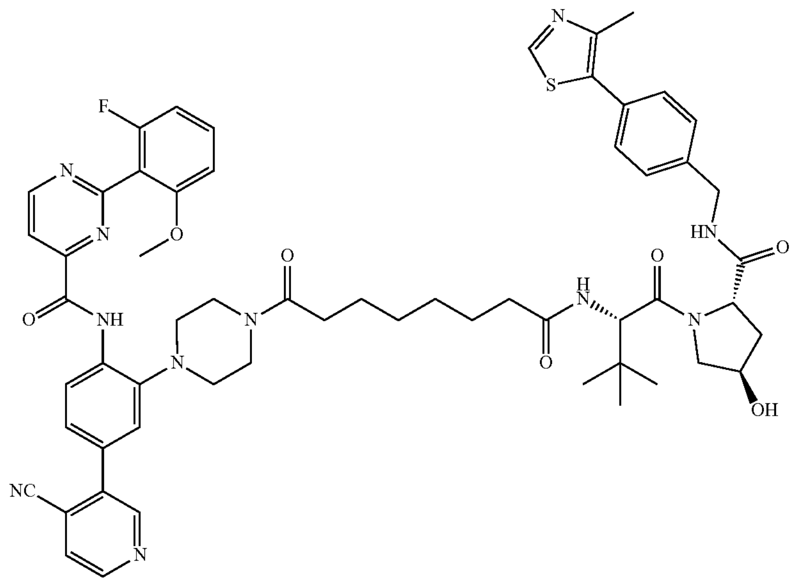 [SMILES: COc1cccc(F)c1-c1nccc(C(=O)Nc2ccc(-c3cnccc3C#N)cc2N2CCN(C(=O)CCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)phenyl)-2-(2-fluoro-6-methoxyphenyl)pyrimidine-4-carboxamide |
| 303 | 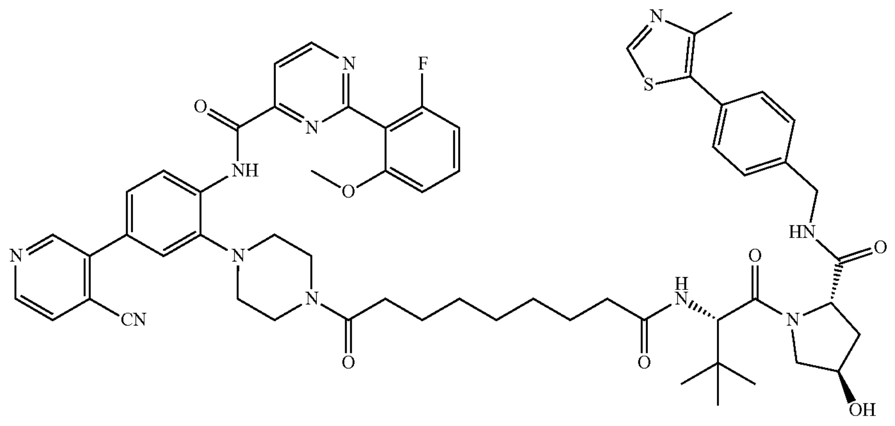 [SMILES: COc1cccc(F)c1-c1nccc(C(=O)Nc2ccc(-c3cnccc3C#N)cc2N2CCN(C(=O)CCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 304 | 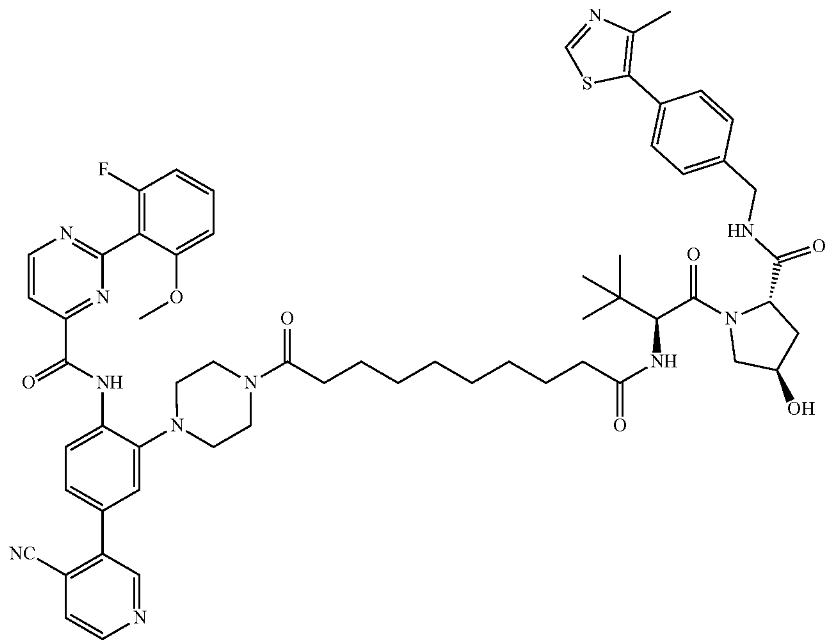 [SMILES: COc1cccc(F)c1-c1nccc(C(=O)Nc2ccc(-c3cnccc3C#N)cc2N2CCN(C(=O)CCCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)phenyl)-2-(2-fluoro-6-methoxyphenyl)pyrimidine-4-carboxamide |
| 305 | 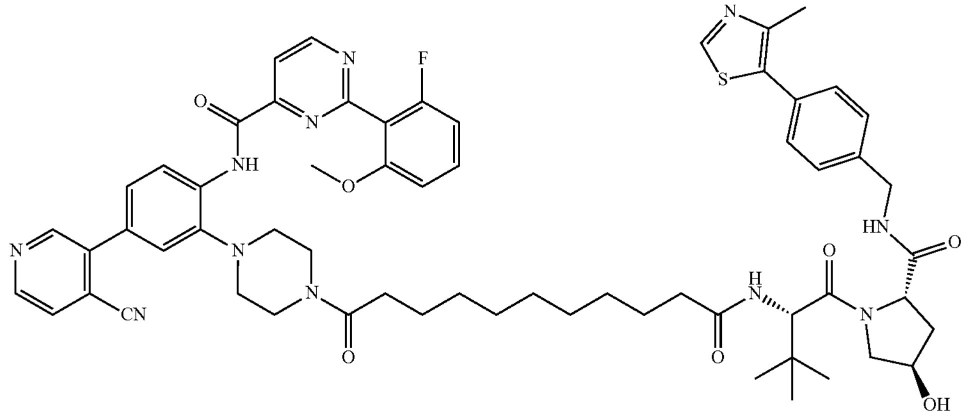 [SMILES: COc1cccc(F)c1-c1nccc(C(=O)Nc2ccc(-c3cnccc3C#N)cc2N2CCN(C(=O)CCCCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 306 | 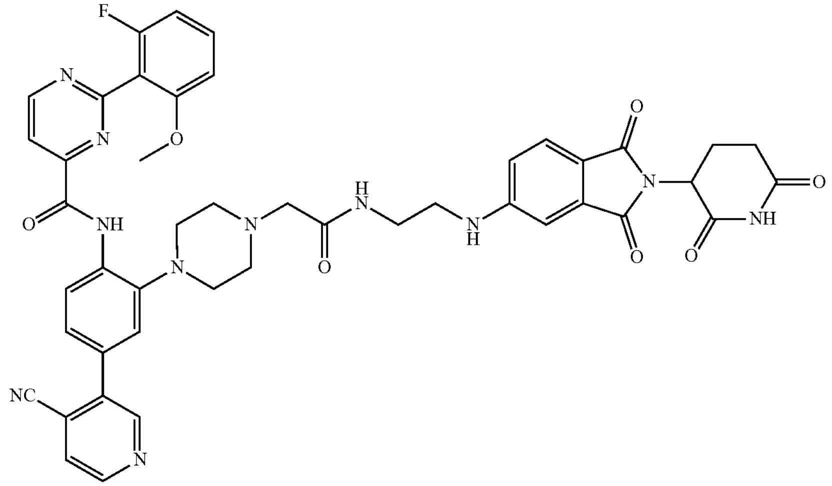 [SMILES: COc1cccc(F)c1-c1nccc(C(=O)Nc2ccc(-c3cnccc3C#N)cc2N2CCN(CC(=O)NCCNc3ccc4c(c3)C(=O)N(C3CCC(=O)NC3=O)C4=O)CC2)n1] | N-(4-(4-cyanopyridin-3-yl)-2-(4-(2-((2-((2-(2,6-dioxopiperidin-3-yl)-1,3-dioxoisoindolin-5-yl)amino)ethyl)amino)-2-oxoethyl)piperazin-1-yl)phenyl)-2-(2-fluoro-6-methoxyphenyl)pyrimidine-4-carboxamide |
| 307 | 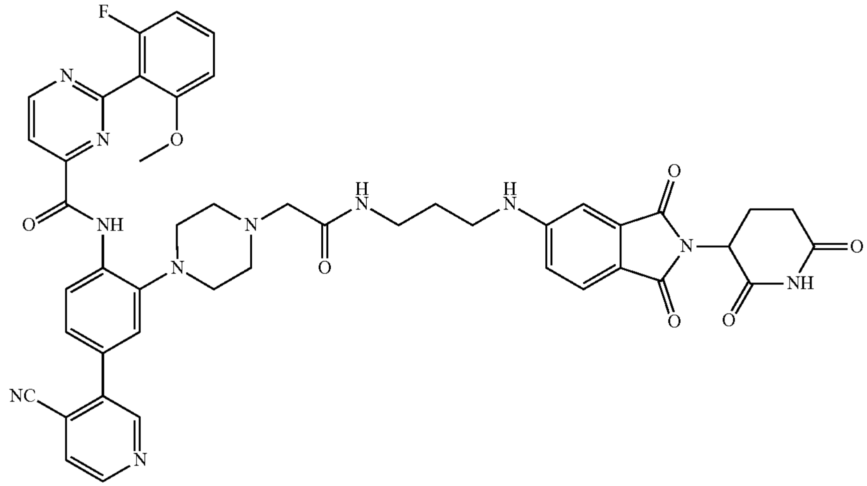 [SMILES: COc1cccc(F)c1-c1nccc(C(=O)Nc2ccc(-c3cnccc3C#N)cc2N2CCN(CC(=O)NCCCNc3ccc4c(c3)C(=O)N(C3CCC(=O)NC3=O)C4=O)CC2)n1] | N-(4-(4-cyanopyridin-3-yl)-2-(4-(2-((3-((2-(2,6-dioxopiperidin-3-yl)-1,3-dioxoisoindolin-5-yl)amino)propyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 308 | 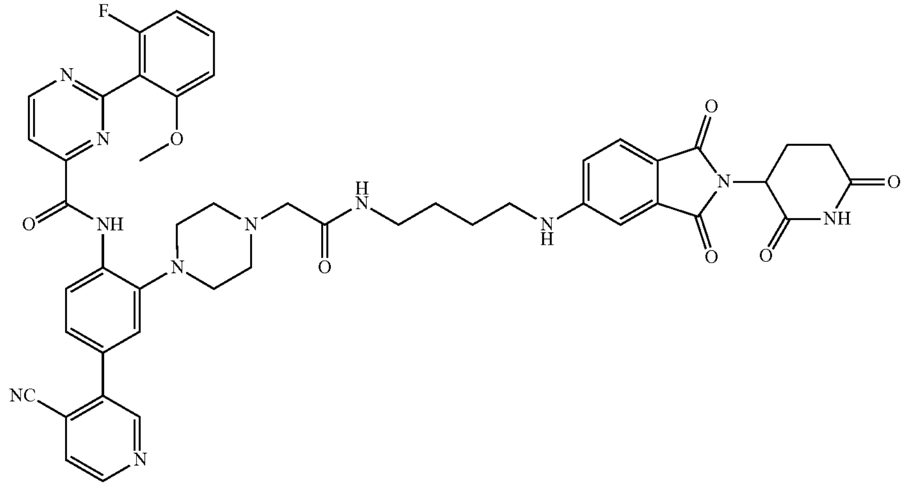 [SMILES: COc1cccc(F)c1-c1nccc(C(=O)Nc2ccc(-c3cnccc3C#N)cc2N2CCN(CC(=O)NCCCCNc3ccc4c(c3)C(=O)N(C3CCC(=O)NC3=O)C4=O)CC2)n1] | N-(4-(4-cyanopyridin-3-yl)-2-(4-(2-((4-((2-(2,6-dioxopiperidin-3-yl)-1,3-dioxoisoindolin-5-yl)amino)butyl)amino)-2-oxoethyl)piperazin-1-yl)phenyl)-2-(2-fluoro-6-methoxyphenyl)pyrimidine-4-carboxamide |
| 309 | 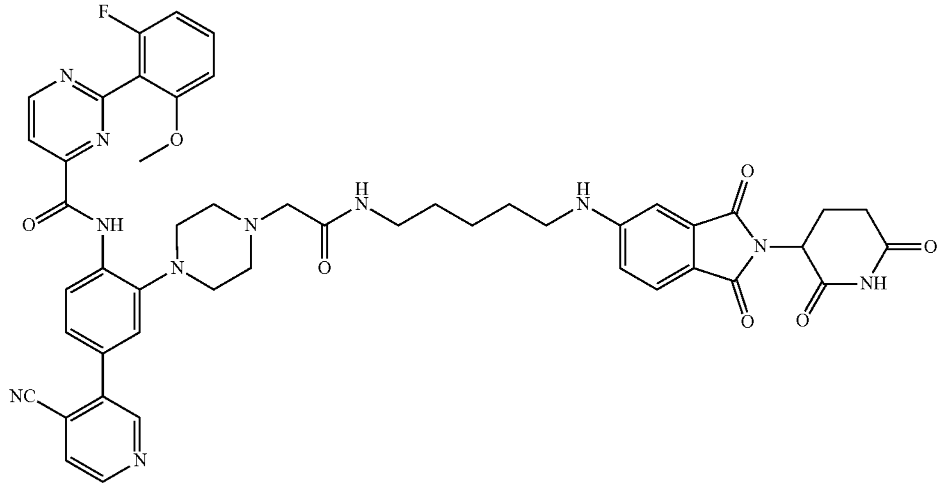 [SMILES: COc1cccc(F)c1-c1nccc(C(=O)Nc2ccc(-c3cnccc3C#N)cc2N2CCN(CC(=O)NCCCCCNc3ccc4c(c3)C(=O)N(C3CCC(=O)NC3=O)C4=O)CC2)n1] | N-(4-(4-cyanopyridin-3-yl)-2-(4-(2-((5-((2-(2,6-dioxopiperidin-3-yl)-1,3-dioxoisoindolin-5-yl)amino)pentyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 310 | 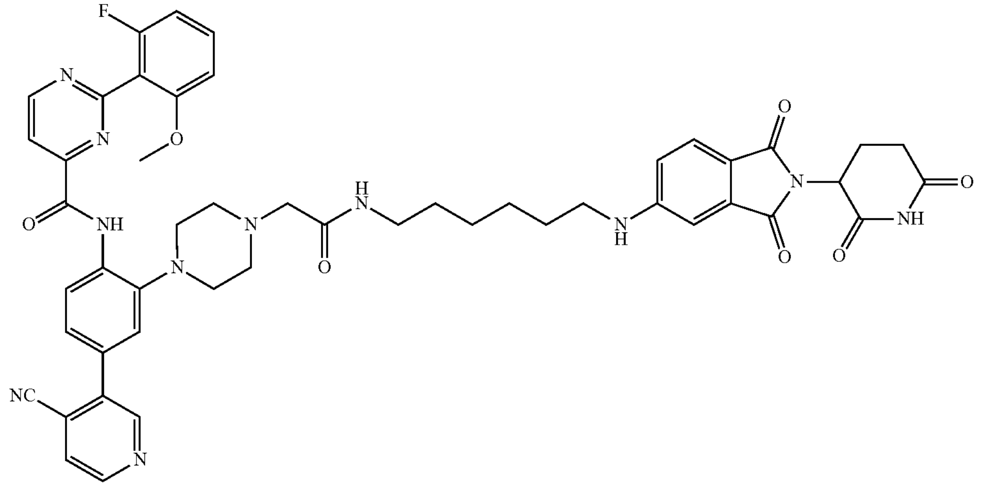 [SMILES: COc1cccc(F)c1-c1nccc(C(=O)Nc2ccc(-c3cnccc3C#N)cc2N2CCN(CC(=O)NCCCCCCNc3ccc4c(c3)C(=O)N(C3CCC(=O)NC3=O)C4=O)CC2)n1] | N-(4-(4-cyanopyridin-3-yl)-2-(4-(2-((6-((2-(2,6-dioxopiperidin-3-yl)-1,3-dioxoisoindolin-5-yl)amino)hexyl)amino)-2-oxoethyl)piperazin-1-yl)phenyl)-2-(2-fluoro-6-methoxyphenyl)pyrimidine-4-carboxamide |
| 311 | 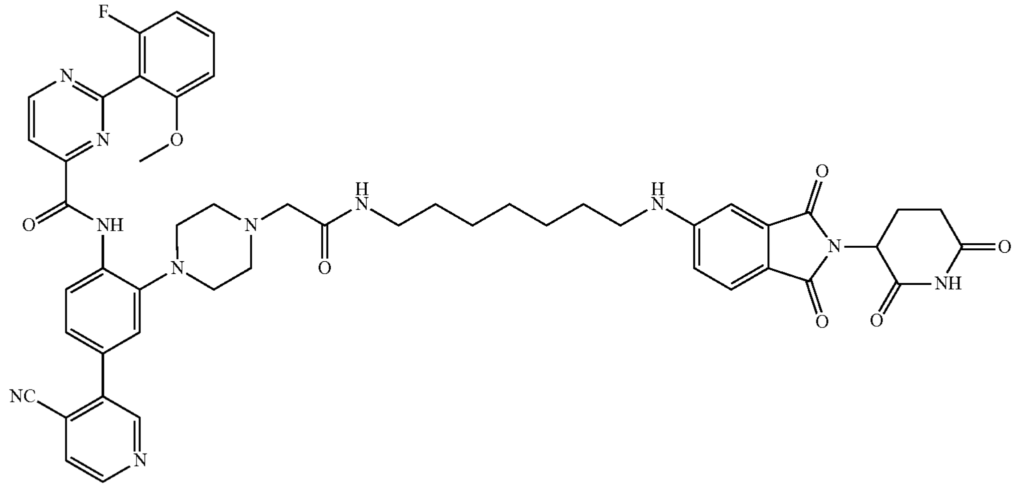 [SMILES: COc1cccc(F)c1-c1nccc(C(=O)Nc2ccc(-c3cnccc3C#N)cc2N2CCN(CC(=O)NCCCCCCCNc3ccc4c(c3)C(=O)N(C3CCC(=O)NC3=O)C4=O)CC2)n1] | N-(4-(4-cyanopyridin-3-yl)-2-(4-(2-((7-((2-(2,6-dioxopiperidin-3-yl)-1,3-dioxoisoindolin-5-yl)amino)heptyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 312 | 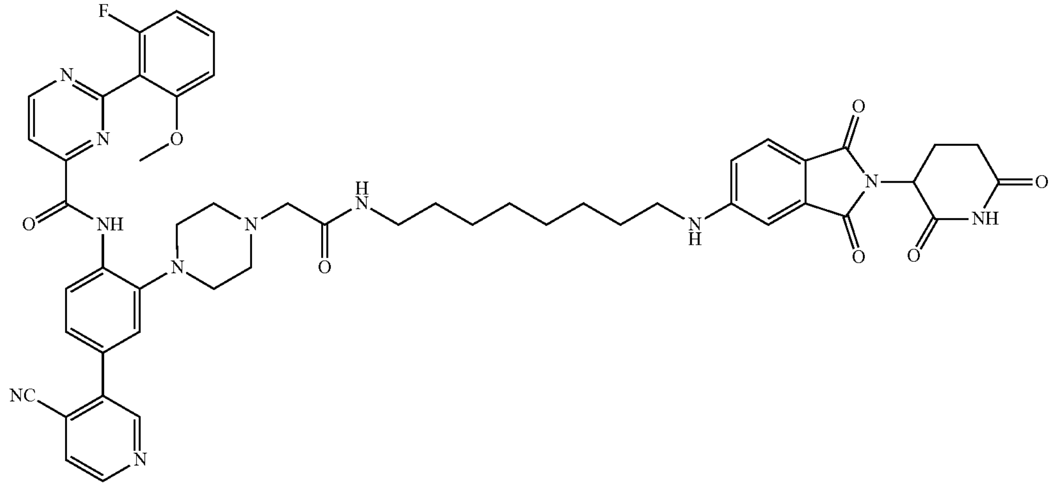 [SMILES: COc1cccc(F)c1-c1nccc(C(=O)Nc2ccc(-c3cnccc3C#N)cc2N2CCN(CC(=O)NCCCCCCCCNc3ccc4c(c3)C(=O)N(C3CCC(=O)NC3=O)C4=O)CC2)n1] | N-(4-(4-cyanopyridin-3-yl)-2-(4-(2-((8-((2-(2,6-dioxopiperidin-3-yl)-1,3-dioxoisoindolin-5-yl)amino)octyl)amino)-2-oxoethyl)piperazin-1-yl)phenyl)-2-(2-fluoro-6-methoxyphenyl)pyrimidine-4-carboxamide |
| 313 | 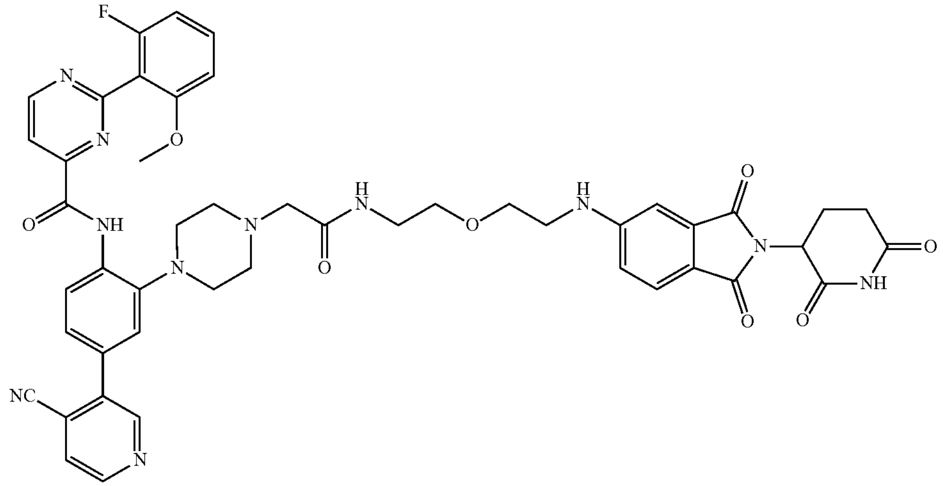 [SMILES: COc1cccc(F)c1-c1nccc(C(=O)Nc2ccc(-c3cnccc3C#N)cc2N2CCN(CC(=O)NCCOCCNc3ccc4c(c3)C(=O)N(C3CCC(=O)NC3=O)C4=O)CC2)n1] | N-(4-(4-cyanopyridin-3-yl)-2-(4-(2-((2-(2-((2-(2,6-dioxopiperidin-3-yl)-1,3-dioxoisoindolin-5-yl)amino)ethoxy)ethyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 314 | 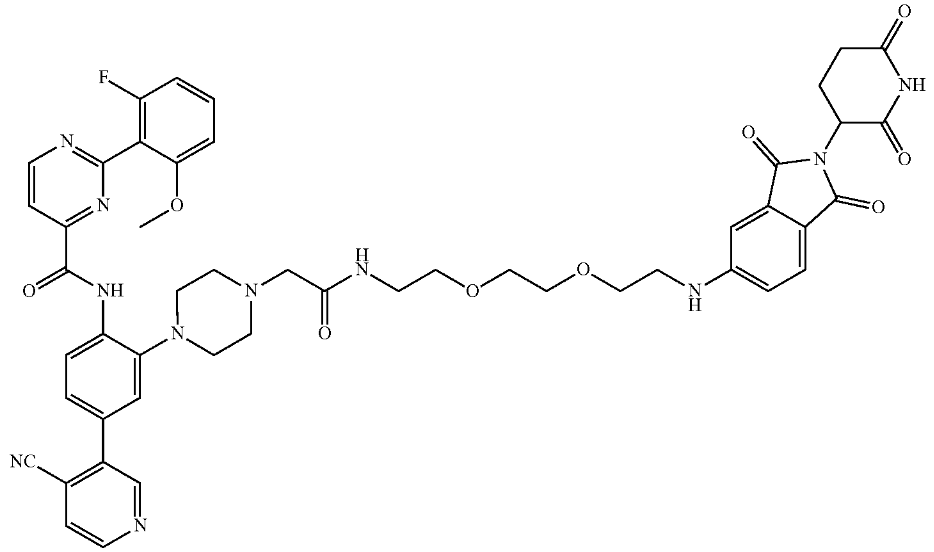 [SMILES: COc1cccc(F)c1-c1nccc(C(=O)Nc2ccc(-c3cnccc3C#N)cc2N2CCN(CC(=O)NCCOCCOCCNc3ccc4c(c3)C(=O)N(C3CCC(=O)NC3=O)C4=O)CC2)n1] | N-(4-(4-cyanopyridin-3-yl)-2-(4-(2-((2-(2-(2-((2-(2,6-dioxopiperidin-3-yl)-1,3-dioxoisoindolin-5-yl)amino)ethoxy)ethoxy)ethyl)amino)-2-oxoethyl)piperazin-1-yl)phenyl)-2-(2-fluoro-6-methoxyphenyl)pyrimidine-4-carboxamide |
| 315 | 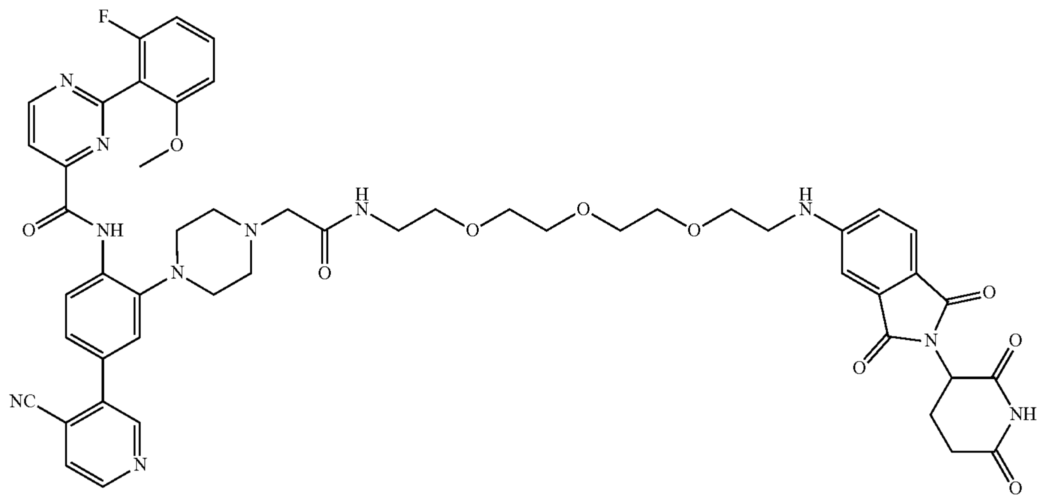 [SMILES: COc1cccc(F)c1-c1nccc(C(=O)Nc2ccc(-c3cnccc3C#N)cc2N2CCN(CC(=O)NCCOCCOCCOCCNc3ccc4c(c3)C(=O)N(C3CCC(=O)NC3=O)C4=O)CC2)n1] | N-(4-(4-cyanopyridin-3-yl)-2-(4-(14-((2-(2,6-dioxopiperidin-3-yl)-1,3-dioxoisoindolin-5-yl)amino)-2-oxo-6,9,12-trioxa-3-azatetradecyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 316 | 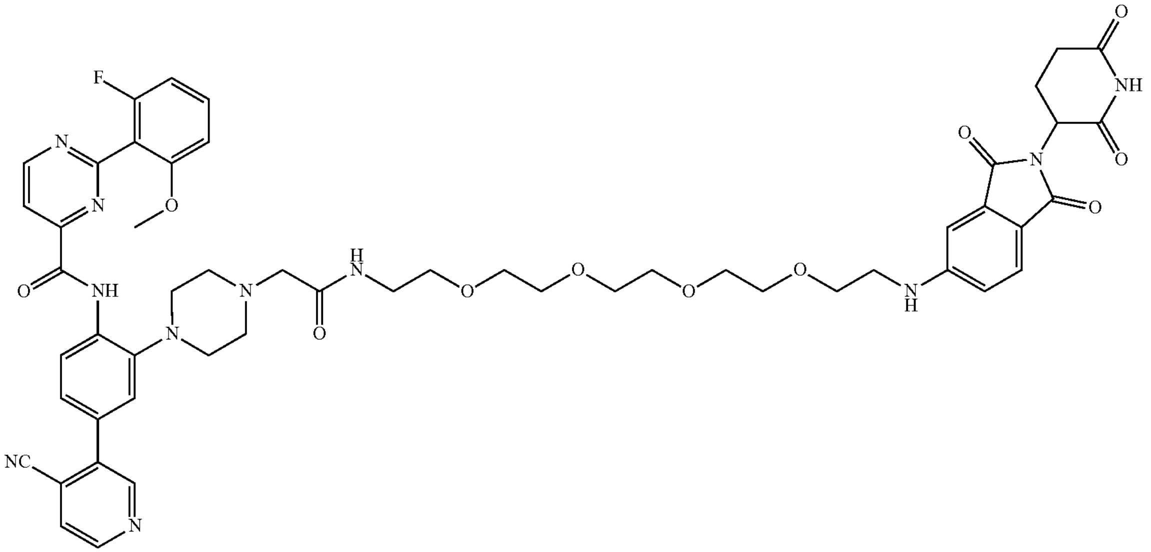 [SMILES: COc1cccc(F)c1-c1nccc(C(=O)Nc2ccc(-c3cnccc3C#N)cc2N2CCN(CC(=O)NCCOCCOCCOCCOCCNc3ccc4c(c3)C(=O)N(C3CCC(=O)NC3=O)C4=O)CC2)n1] | N-(4-(4-cyanopyridin-3-yl)-2-(4-(17-((2-(2,6-dioxopiperidin-3-yl)-1,3-dioxoisoindolin-5-yl)amino)-2-oxo-6,9,12,15-tetraoxa-3-azaheptadecyl)piperazin-1-yl)phenyl)-2-(2-fluoro-6-methoxyphenyl)pyrimidine-4-carboxamide |
| 317 | 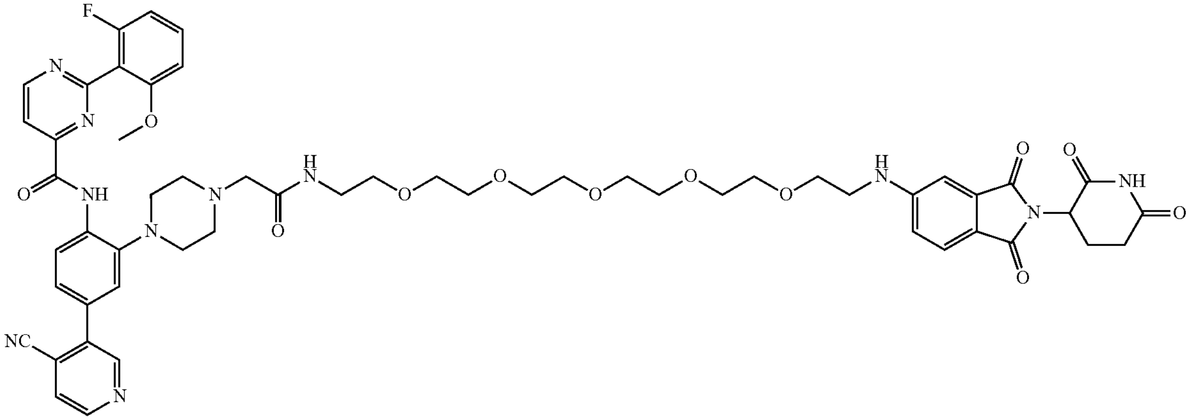 [SMILES: COc1cccc(F)c1-c1nccc(C(=O)Nc2ccc(-c3cnccc3C#N)cc2N2CCN(CC(=O)NCCOCCOCCOCCOCCOCCNc3ccc4c(c3)C(=O)N(C3CCC(=O)NC3=O)C4=O)CC2)n1] | N-(4-(4-cyanopyridin-3-yl)-2-(4-(20-((2-(2,6-dioxopiperidin-3-yl)-1,3-dioxoisoindolin-5-yl)amino)-2-oxo-6,9,12,15,18-pentaoxa-3-azaicosyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 318 | 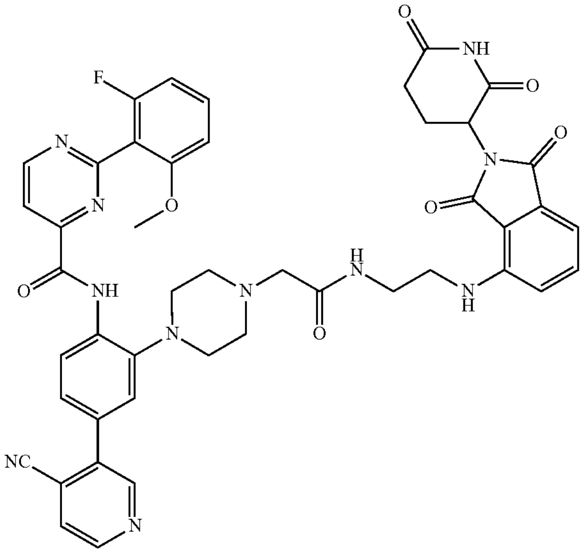 [SMILES: COc1cccc(F)c1-c1nccc(C(=O)Nc2ccc(-c3cnccc3C#N)cc2N2CCN(CC(=O)NCCNc3cccc4c3C(=O)N(C3CCC(=O)NC3=O)C4=O)CC2)n1] | N-(4-(4-cyanopyridin-3-yl)-2-(4-(2-((2-((2-(2,6-dioxopiperidin-3-yl)-1,3-dioxoisoindolin-4-yl)amino)ethyl)amino)-2-oxoethyl)piperazin-1-yl)phenyl)-2-(2-fluoro-6-methoxyphenyl)pyrimidine-4-carboxamide |
| 319 | 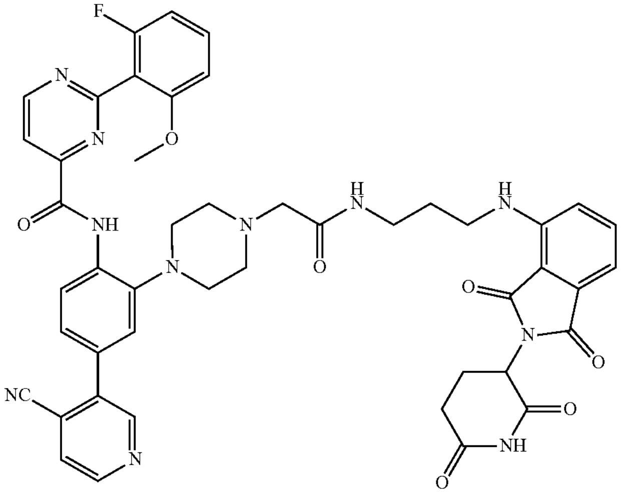 [SMILES: COc1cccc(F)c1-c1nccc(C(=O)Nc2ccc(-c3cnccc3C#N)cc2N2CCN(CC(=O)NCCCNc3cccc4c3C(=O)N(C3CCC(=O)NC3=O)C4=O)CC2)n1] | N-(4-(4-cyanopyridin-3-yl)-2-(4-(2-((3-((2-(2,6-dioxopiperidin-3-yl)-1,3-dioxoisoindolin-4-yl)amino)propyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 320 | 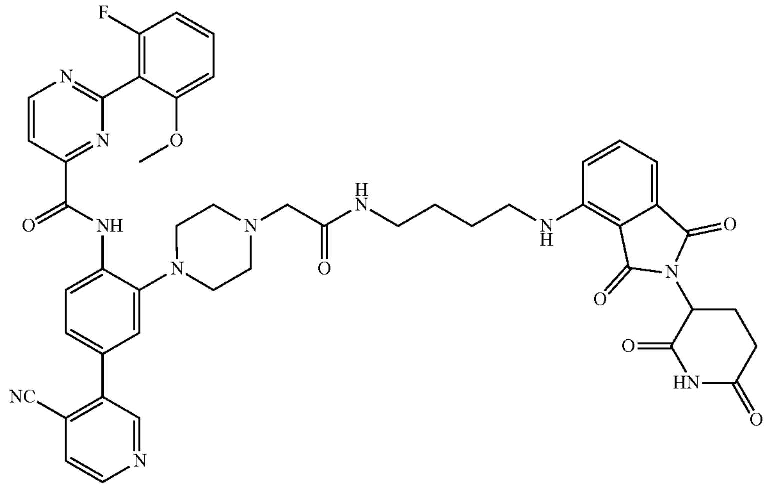 [SMILES: COc1cccc(F)c1-c1nccc(C(=O)Nc2ccc(-c3cnccc3C#N)cc2N2CCN(CC(=O)NCCCCNc3cccc4c3C(=O)N(C3CCC(=O)NC3=O)C4=O)CC2)n1] | N-(4-(4-cyanopyridin-3-yl)-2-(4-(2-((4-((2-(2,6-dioxopiperidin-3-yl)-1,3-dioxoisoindolin-4-yl)amino)butyl)amino)-2-oxoethyl)piperazin-1-yl)phenyl)-2-(2-fluoro-6-methoxyphenyl)pyrimidine-4-carboxamide |
| 321 | 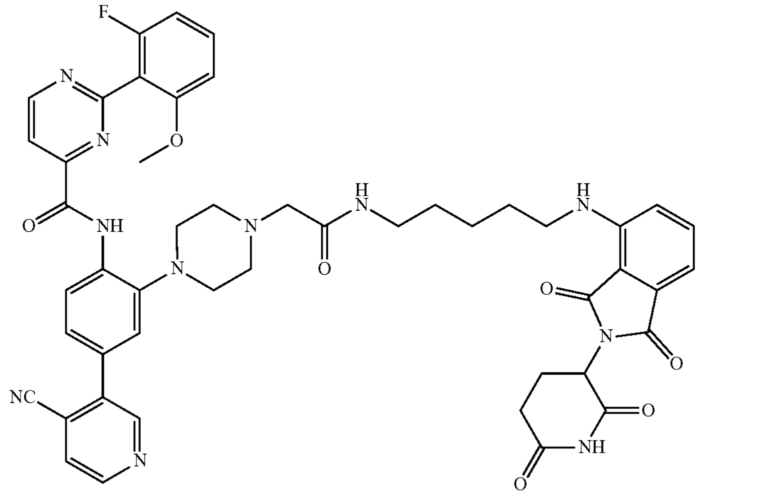 [SMILES: COc1cccc(F)c1-c1nccc(C(=O)Nc2ccc(-c3cnccc3C#N)cc2N2CCN(CC(=O)NCCCCCNc3cccc4c3C(=O)N(C3CCC(=O)NC3=O)C4=O)CC2)n1] | N-(4-(4-cyanopyridin-3-yl)-2-(4-(2-((5-((2-(2,6-dioxopiperidin-3-yl)-1,3-dioxoisoindolin-4-yl)amino)pentyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 322 | 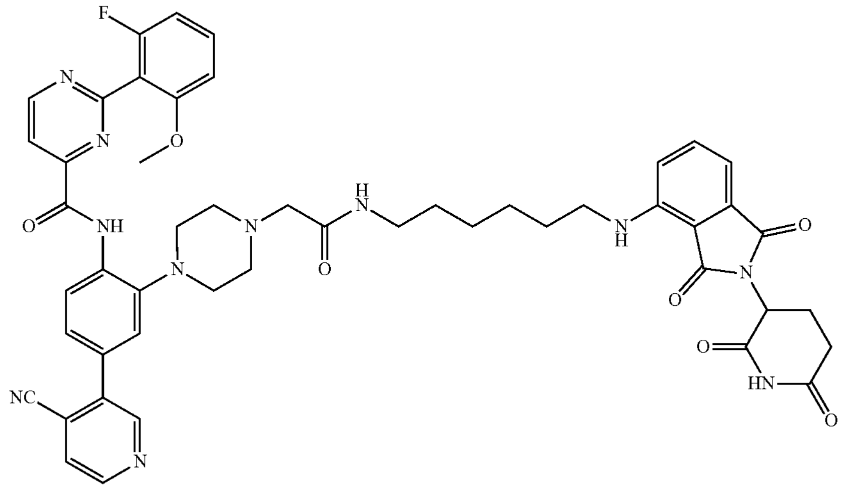 [SMILES: COc1cccc(F)c1-c1nccc(C(=O)Nc2ccc(-c3cnccc3C#N)cc2N2CCN(CC(=O)NCCCCCCNc3cccc4c3C(=O)N(C3CCC(=O)NC3=O)C4=O)CC2)n1] | N-(4-(4-cyanopyridin-3-yl)-2-(4-(2-((6-((2-(2,6-dioxopiperidin-3-yl)-1,3-dioxoisoindolin-4-yl)amino)hexyl)amino)-2-oxoethyl)piperazin-1-yl)phenyl)-2-(2-fluoro-6-methoxyphenyl)pyrimidine-4-carboxamide |
| 323 | 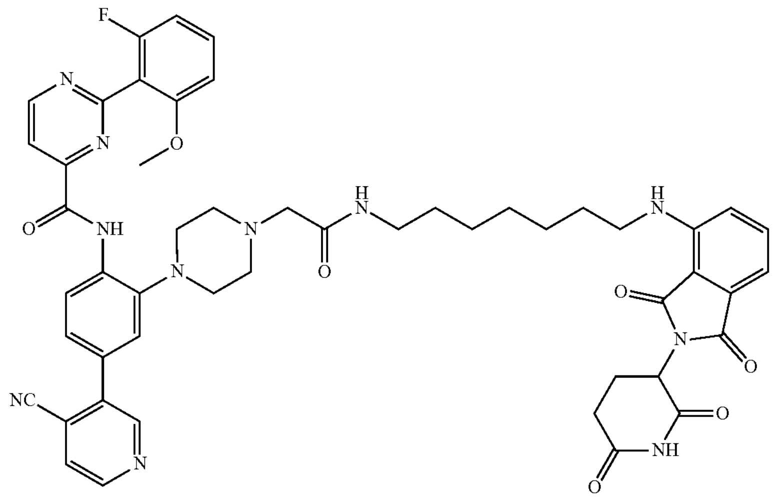 [SMILES: COc1cccc(F)c1-c1nccc(C(=O)Nc2ccc(-c3cnccc3C#N)cc2N2CCN(CC(=O)NCCCCCCCNc3cccc4c3C(=O)N(C3CCC(=O)NC3=O)C4=O)CC2)n1] | N-(4-(4-cyanopyridin-3-yl)-2-(4-(2-((7-((2-(2,6-dioxopiperidin-3-yl)-1,3-dioxoisoindolin-4-yl)amino)heptyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 324 | 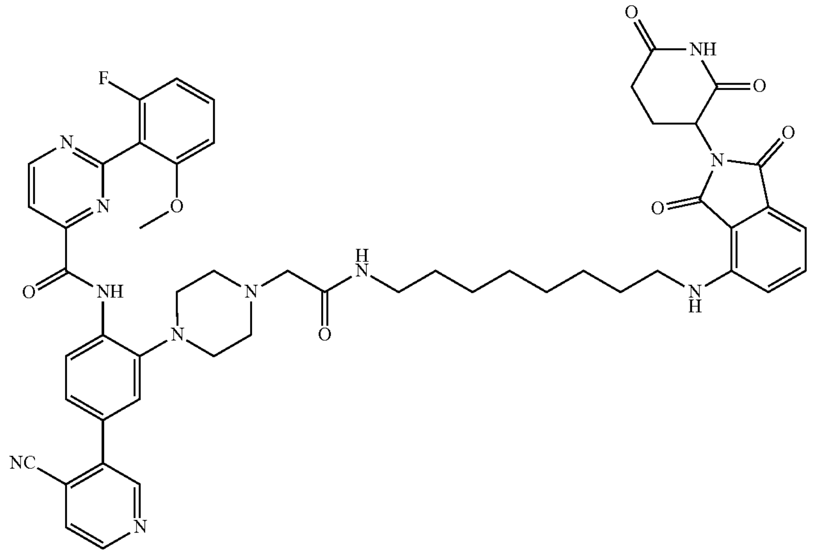 [SMILES: COc1cccc(F)c1-c1nccc(C(=O)Nc2ccc(-c3cnccc3C#N)cc2N2CCN(CC(=O)NCCCCCCCCNc3cccc4c3C(=O)N(C3CCC(=O)NC3=O)C4=O)CC2)n1] | N-(4-(4-cyanopyridin-3-yl)-2-(4-(2-((8-((2-(2,6-dioxopiperidin-3-yl)-1,3-dioxoisoindolin-4-yl)amino)octyl)amino)-2-oxoethyl)piperazin-1-yl)phenyl)-2-(2-fluoro-6-methoxyphenyl)pyrimidine-4-carboxamide |
| 325 | 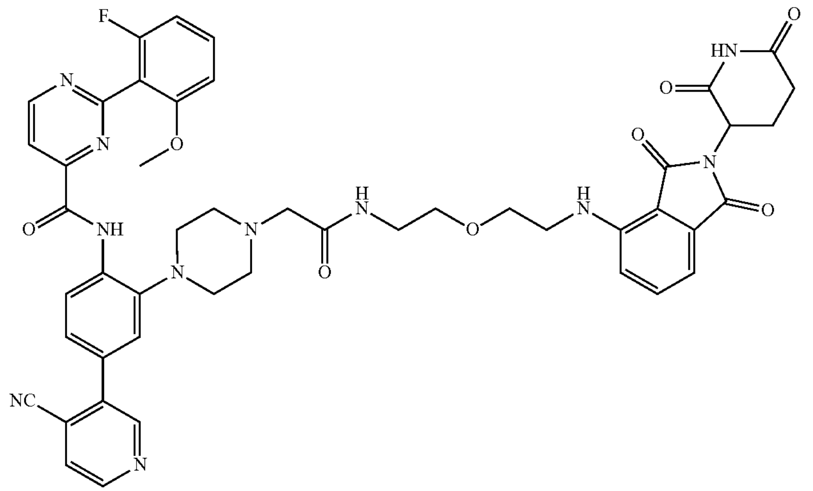 [SMILES: COc1cccc(F)c1-c1nccc(C(=O)Nc2ccc(-c3cnccc3C#N)cc2N2CCN(CC(=O)NCCOCCNc3cccc4c3C(=O)N(C3CCC(=O)NC3=O)C4=O)CC2)n1] | N-(4-(4-cyanopyridin-3-yl)-2-(4-(2-((2-(2-((2-(2,6-dioxopiperidin-3-yl)-1,3-dioxoisoindolin-4-yl)amino)ethoxy)ethyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 326 | 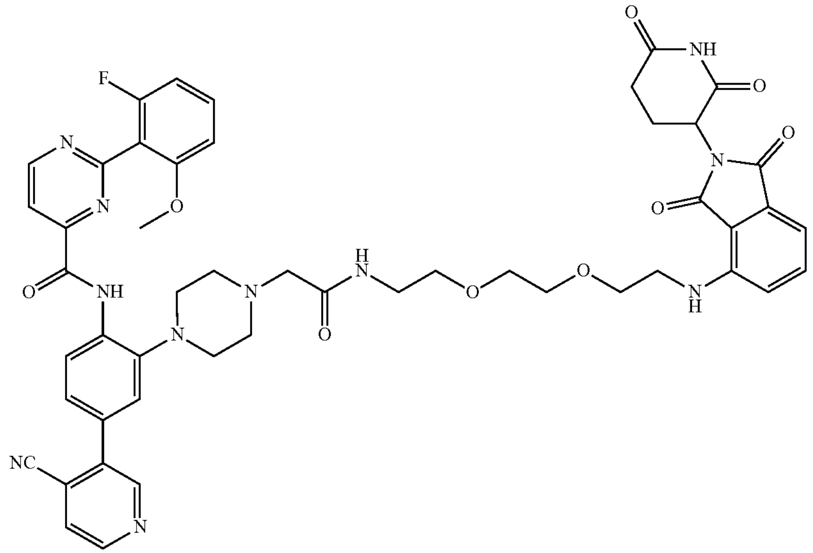 [SMILES: COc1cccc(F)c1-c1nccc(C(=O)Nc2ccc(-c3cnccc3C#N)cc2N2CCN(CC(=O)NCCOCCOCCNc3cccc4c3C(=O)N(C3CCC(=O)NC3=O)C4=O)CC2)n1] | N-(4-(4-cyanopyridin-3-yl)-2-(4-(2-((2-(2-(2-((2-(2,6-dioxopiperidin-3-yl)-1,3-dioxoisoindolin-4-yl)amino)ethoxy)ethoxy)ethyl)amino)-2-oxoethyl)piperazin-1-yl)phenyl)-2-(2-fluoro-6-methoxyphenyl)pyrimidine-4-carboxamide |
| 327 | 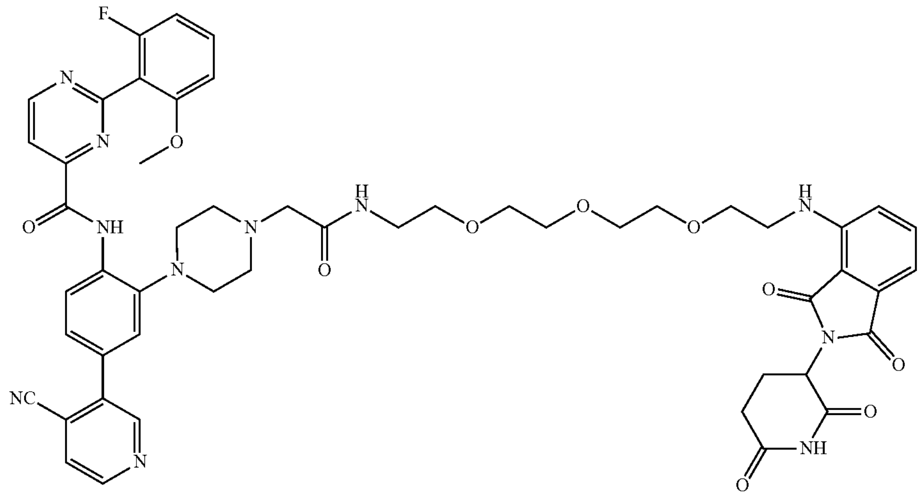 [SMILES: COc1cccc(F)c1-c1nccc(C(=O)Nc2ccc(-c3cnccc3C#N)cc2N2CCN(CC(=O)NCCOCCOCCOCCNc3cccc4c3C(=O)N(C3CCC(=O)NC3=O)C4=O)CC2)n1] | N-(4-(4-cyanopyridin-3-yl)-2-(4-(14-((2-(2,6-dioxopiperidin-3-yl)-1,3-dioxoisoindolin-4-yl)amino)-2-oxo-6,9,12-trioxa-3-azatetradecyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 328 | 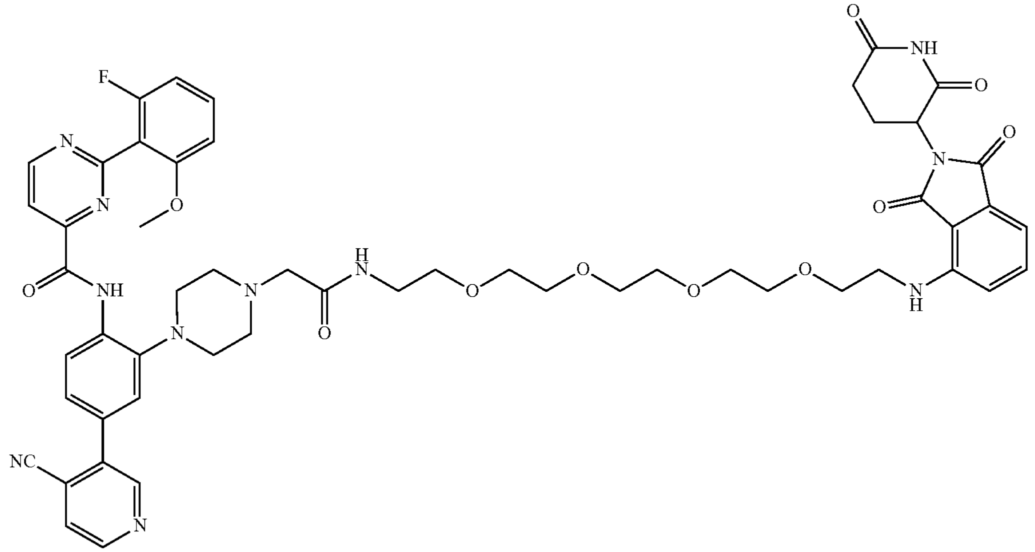 [SMILES: COc1cccc(F)c1-c1nccc(C(=O)Nc2ccc(-c3cnccc3C#N)cc2N2CCN(CC(=O)NCCOCCOCCOCCOCCNc3cccc4c3C(=O)N(C3CCC(=O)NC3=O)C4=O)CC2)n1] | N-(4-(4-cyanopyridin-3-yl)-2-(4-(17-((2-(2,6-dioxopiperidin-3-yl)-1,3-dioxoisoindolin-4-yl)amino)-2-oxo-6,9,12,15-tetraoxa-3-azaheptadecyl)piperazin-1-yl)phenyl)-2-(2-fluoro-6-methoxyphenyl)pyrimidine-4-carboxamide |
| 329 | 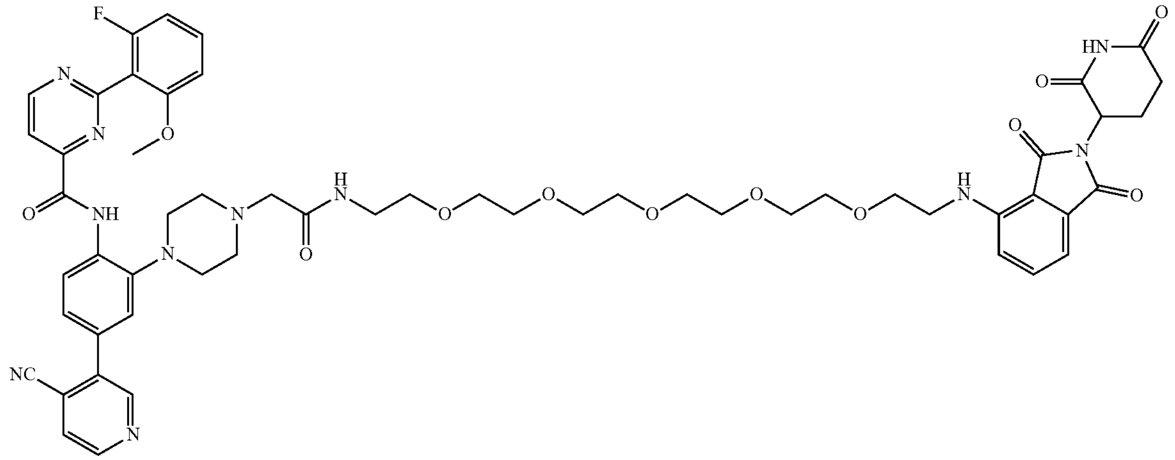 [SMILES: COc1cccc(F)c1-c1nccc(C(=O)Nc2ccc(-c3cnccc3C#N)cc2N2CCN(CC(=O)NCCOCCOCCOCCOCCOCCNc3cccc4c3C(=O)N(C3CCC(=O)NC3=O)C4=O)CC2)n1] | N-(4-(4-cyanopyridin-3-yl)-2-(4-(20-((2-(2,6-dioxopiperidin-3-yl)-1,3-dioxoisoindolin-4-yl)amino)-2-oxo-6,9,12,15,18-pentaoxa-3-azaicosyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 330 | 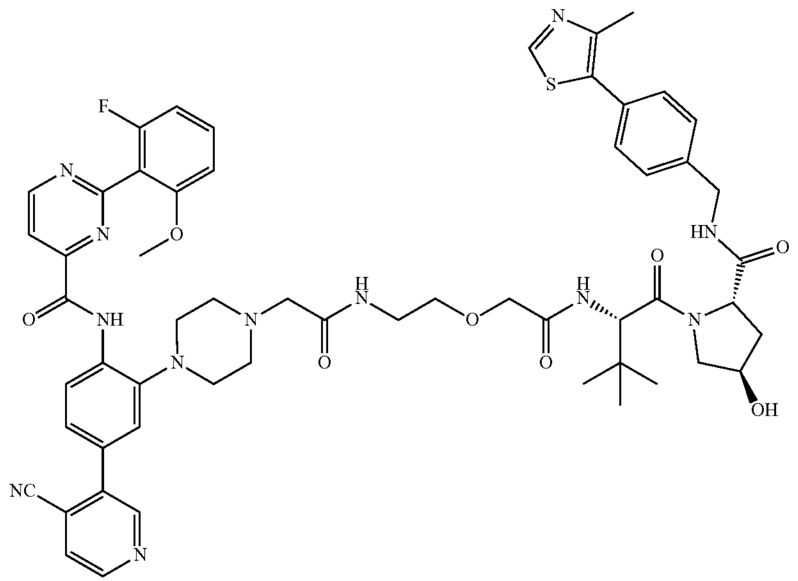 [SMILES: COc1cccc(F)c1-c1nccc(C(=O)Nc2ccc(-c3cnccc3C#N)cc2N2CCN(CC(=O)NCCOCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethyl)amino)-2-oxoethyl)piperazin-1-yl)phenyl)-2-(2-fluoro-6-methoxyphenyl)pyrimidine-4-carboxamide |
| 331 | 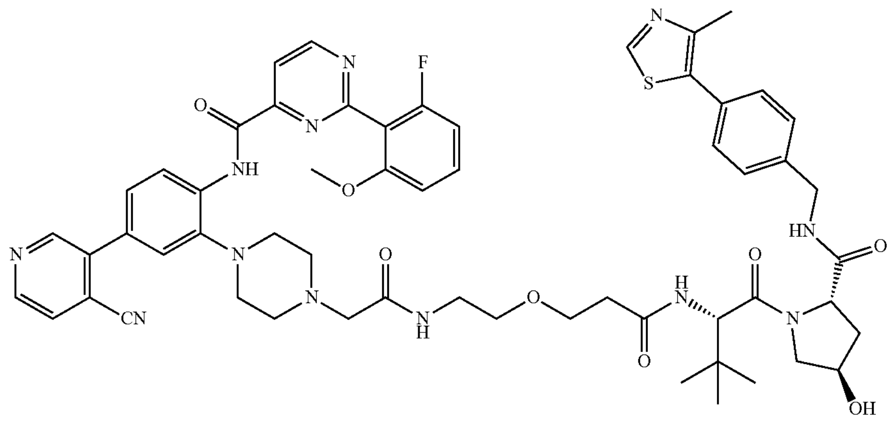 | N-(4-(4-cyanopyridin-3-yl)-2-(4-(2-((2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 332 | 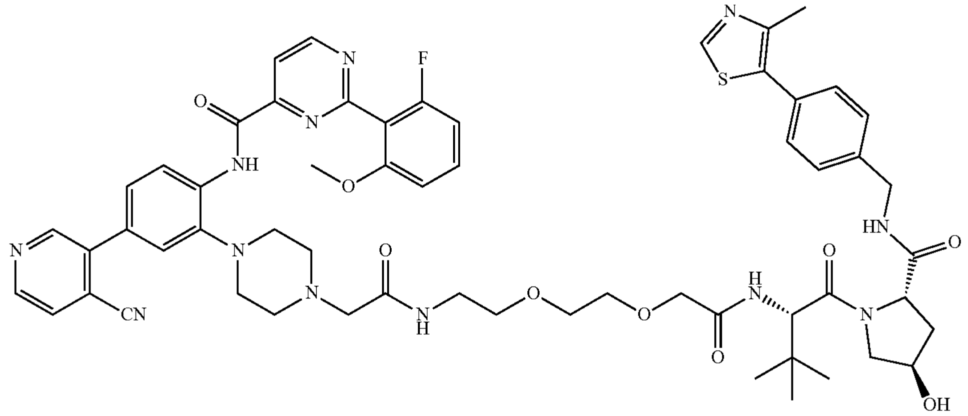 [SMILES: COc1cccc(F)c1-c1nccc(C(=O)Nc2ccc(-c3cnccc3C#N)cc2N2CCN(CC(=O)NCCOCCOCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-13-((2S,4R)-4-hydroxy-2-((4-(4-methylthiazol-5-yl)benzyl)carbamoyl)pyrrolidine-1-carbonyl)-14,14-dimethyl-2,11-dioxo-6,9-dioxa-3,12-diazapentadecyl)piperazin-1-yl)phenyl)-2-(2-fluoro-6-methoxyphenyl)pyrimidine-4-carboxamide |
| 333 | 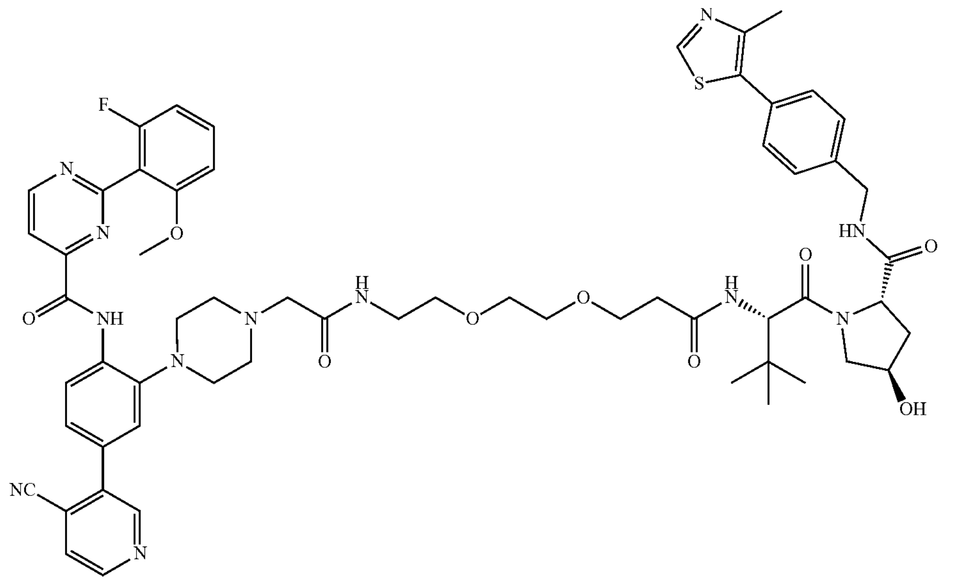 [SMILES: COc1cccc(F)c1-c1nccc(C(=O)Nc2ccc(-c3cnccc3C#N)cc2N2CCN(CC(=O)NCCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-14-((2S,4R)-4-hydroxy-2-((4-(4-methylthiazol-5-yl)benzyl)carbamoyl)pyrrolidine-1-carbonyl)-15,15-dimethyl-2,12-dioxo-6,9-dioxa-3,13-diazahexadecyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 334 | 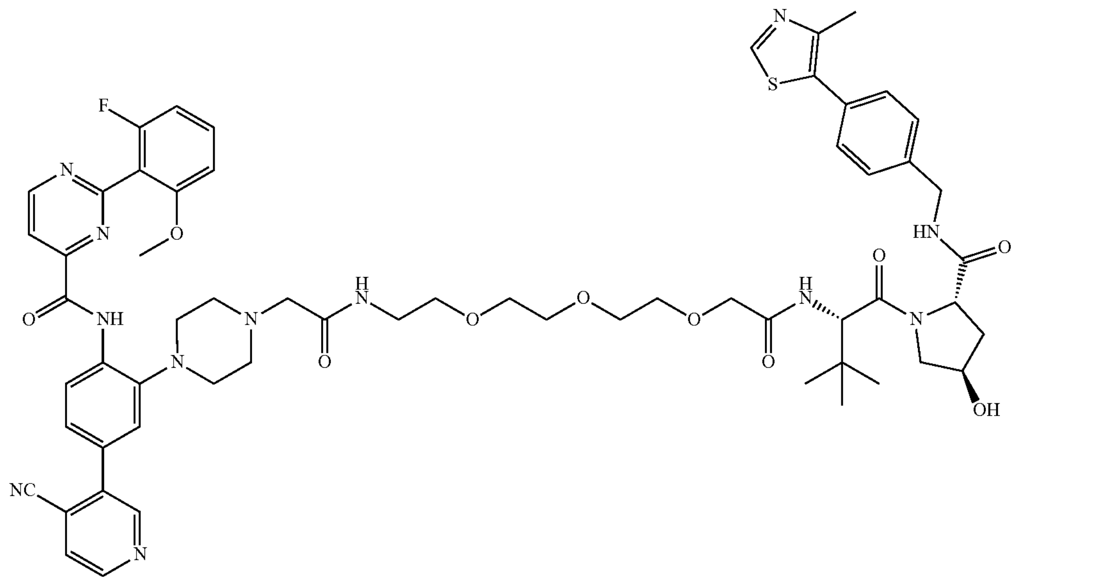 | N-(4-(4-cyanopyridin-3-yl)-2-(4-((S)-16-((2S,4R)-4-hydroxy-2-((4-(4-methylthiazol-5-yl)benzyl)carbamoyl)pyrrolidine-1-carbonyl)-17,17-dimethyl-2,14-dioxo-6,9,12-trioxa-3,15-diazaoctadecyl)piperazin-1-yl)phenyl)-2-(2-fluoro-6-methoxyphenyl)pyrimidine-4-carboxamide |
| 335 | 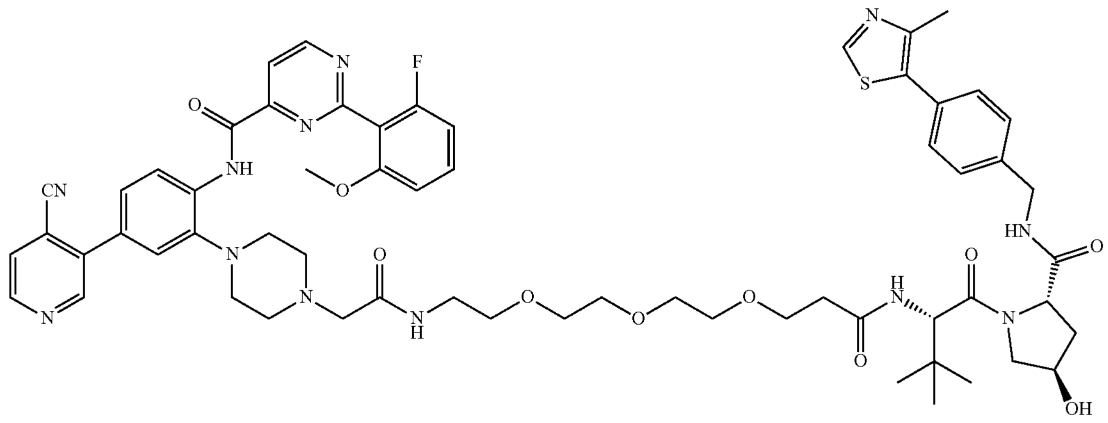 [SMILES: COc1cccc(F)c1-c1nccc(C(=O)Nc2ccc(-c3cnccc3C#N)cc2N2CCN(CC(=O)NCCOCCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-17-((2S,4R)-4-hydroxy-2-((4-(4-methylthiazol-5-yl)benzyl)carbamoyl)pyrrolidine-1-carbonyl)-18,18-dimethyl-2,15-dioxo-6,9,12-trioxa-3,16-diazanonadecyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 336 | 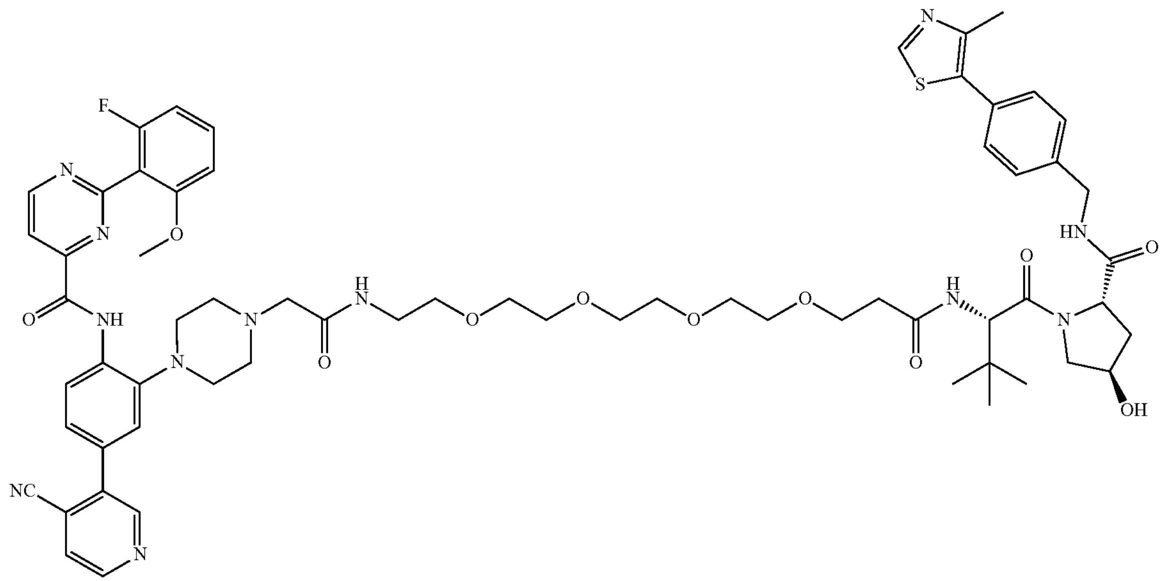 [SMILES: COc1cccc(F)c1-c1nccc(C(=O)Nc2ccc(-c3cnccc3C#N)cc2N2CCN(CC(=O)NCCOCCOCCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-20-((2S,4R)-4-hydroxy-2-((4-(4-methylthiazol-5-yl)benzyl)carbamoyl)pyrrolidine-1-carbonyl)-21,21-dimethyl-2,18-dioxo-6,9,12,15-tetraoxa-3,19-diazadocosyl)piperazin-1-yl)phenyl)-2-(2-fluoro-6-methoxyphenyl)pyrimidine-4-carboxamide |
| 337 | 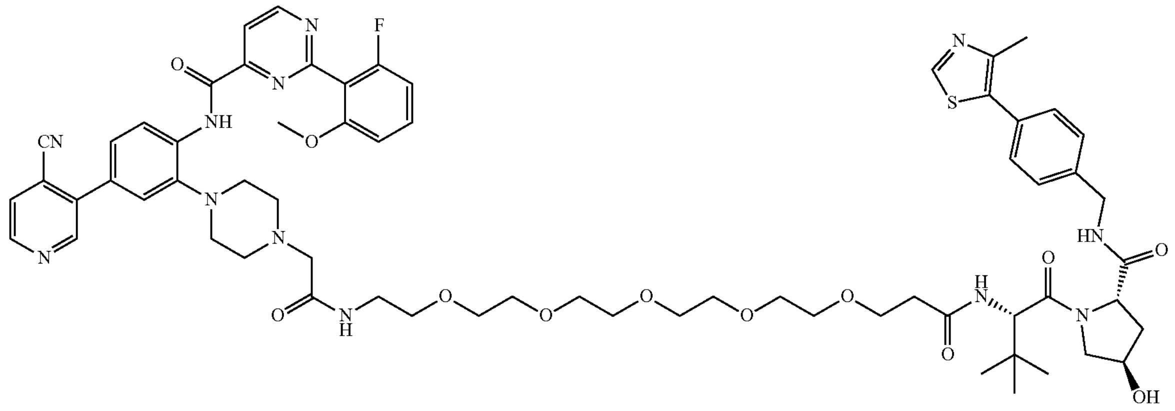 [SMILES: COc1cccc(F)c1-c1nccc(C(=O)Nc2ccc(-c3cnccc3C#N)cc2N2CCN(CC(=O)NCCOCCOCCOCCOCCOCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-((S)-23-((2S,4R)-4-hydroxy-2-((4-(4-methylthiazol-5-yl)benzyl)carbamoyl)pyrrolidine-1-carbonyl)-24,24-dimethyl-2,21-dioxo-6,9,12,15,18-pentaoxa-3,22-diazapentacosyl)piperazin-1-yl)phenyl)-2-(2-fluoro-6-methoxyphenyl)pyrimidine-4-carboxamide |

TABLE 2-continued
| Examples | Structure | Chemical Name |
|---|---|---|
| 338 | 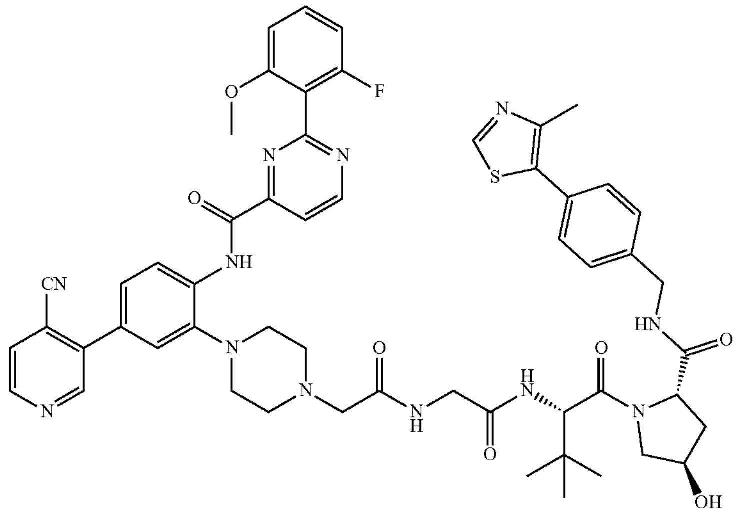 [SMILES: COc1cccc(F)c1-c1nccc(C(=O)Nc2ccc(-c3cnccc3C#N)cc2N2CCN(CC(=O)NCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 339 | 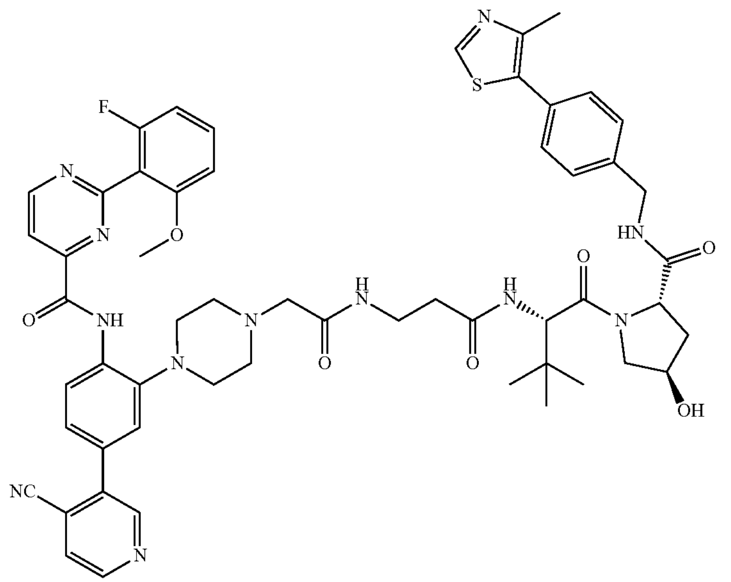 [SMILES: COc1cccc(F)c1-c1nccc(C(=O)Nc2ccc(-c3cnccc3C#N)cc2N2CCN(CC(=O)NCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropyl)amino)-2-oxoethyl)piperazin-1-yl)phenyl)-2-(2-fluoro-6-methoxyphenyl)pyrimidine-4-carboxamide |
| 340 | 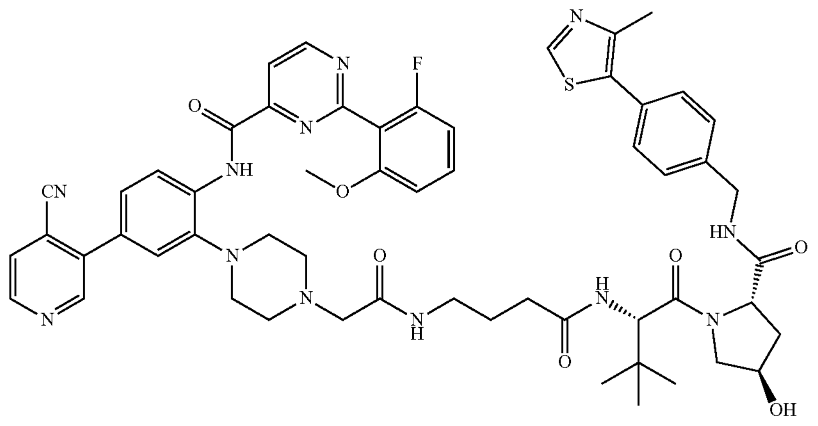 [SMILES: COc1cccc(F)c1-c1nccc(C(=O)Nc2ccc(-c3cnccc3C#N)cc2N2CCN(CC(=O)NCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
|---|---|---|
| 341 | 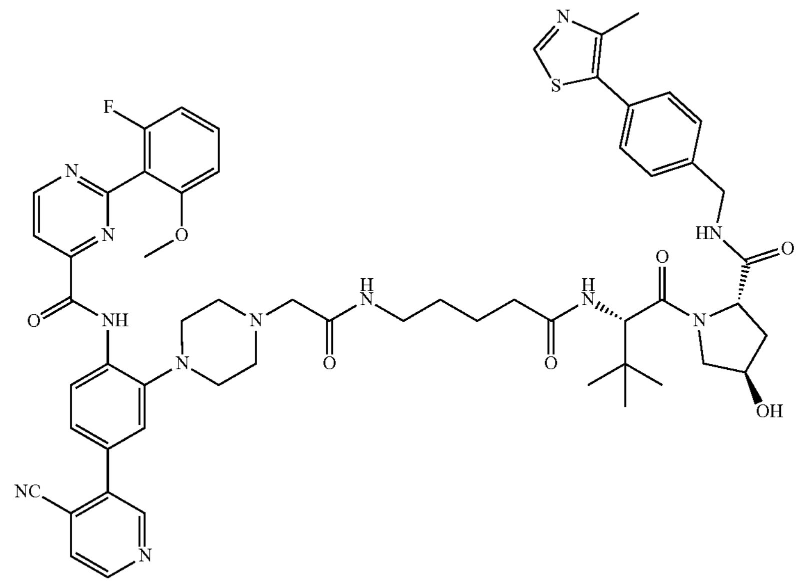 | N-(4-(4-cyanopyridin-3-yl)-2-(4-(2-((5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentyl)amino)-2-oxoethyl)piperazin-1-yl)phenyl)-2-(2-fluoro-6-methoxyphenyl)pyrimidine-4-carboxamide |
| 342 | 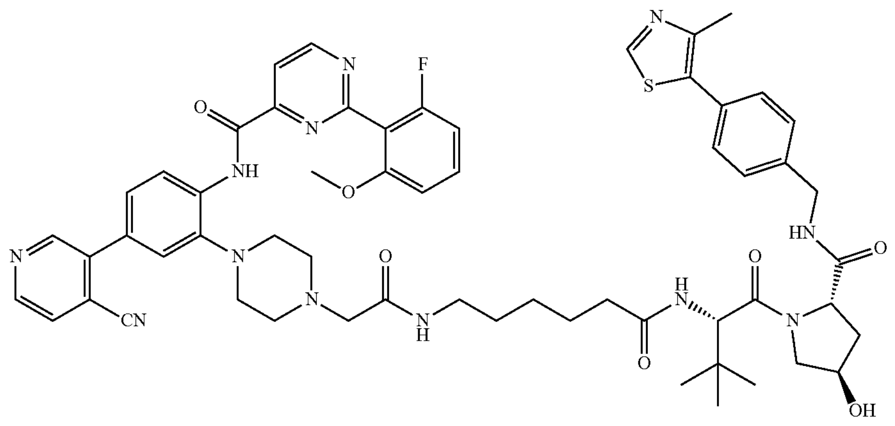 [SMILES: COc1cccc(F)c1-c1nccc(C(=O)Nc2ccc(-c3cnccc3C#N)cc2N2CCN(CC(=O)NCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 343 | 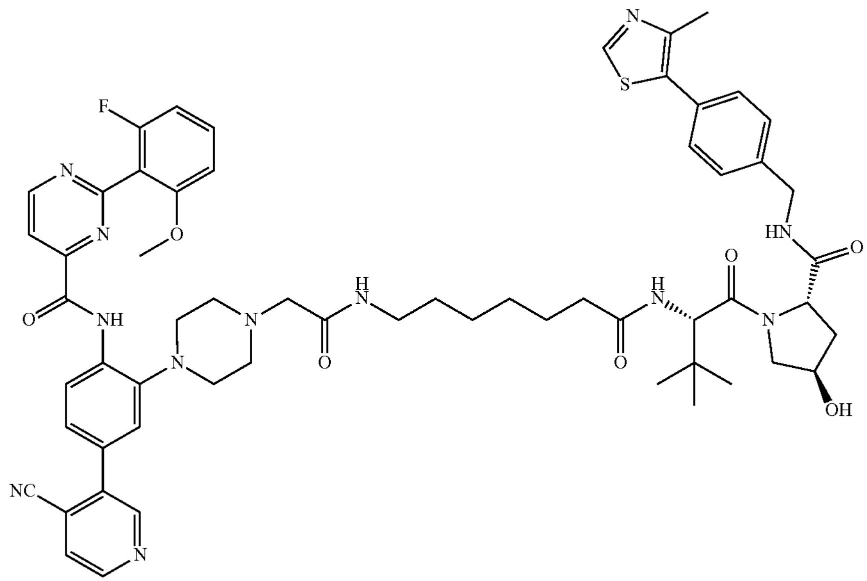 [SMILES: COc1cccc(F)c1-c1nccc(C(=O)Nc2ccc(-c3cnccc3C#N)cc2N2CCN(CC(=O)NCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptyl)amino)-2-oxoethyl)piperazin-1-yl)phenyl)-2-(2-fluoro-6-methoxyphenyl)pyrimidine-4-carboxamide |
| 344 | 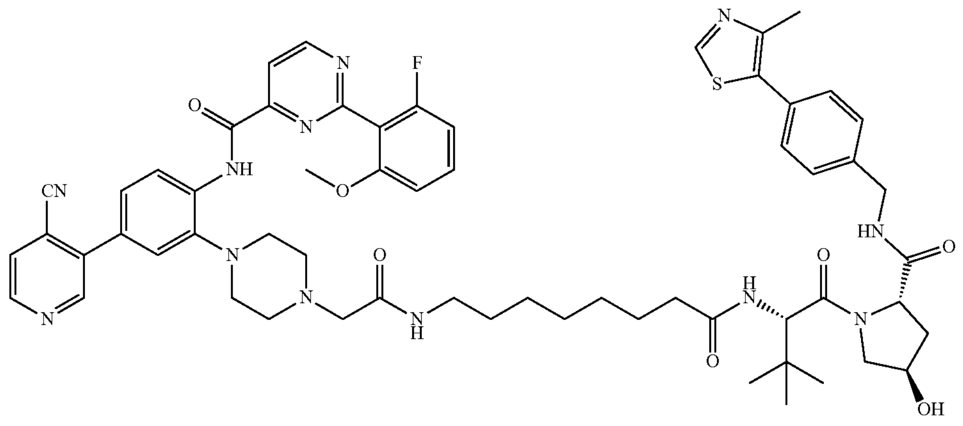 [SMILES: COc1cccc(F)c1-c1nccc(C(=O)Nc2ccc(-c3cnccc3C#N)cc2N2CCN(CC(=O)NCCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)amino)-2-oxoethyl)piperazin-1-yl)phenyl)-2-(2-fluoro-6-methoxyphenyl)pyrimidine-4-carboxamide |

TABLE 2-continued

| Examples | Structure | Chemical Name |
| --- | --- | --- |
| 345 | 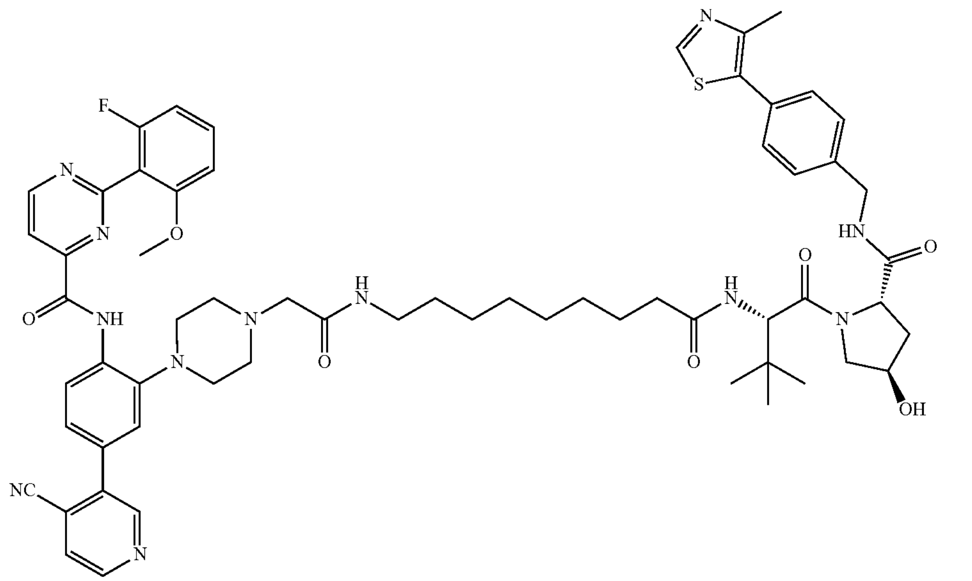 [SMILES: COc1cccc(F)c1-c1nccc(C(=O)Nc2ccc(-c3cnccc3C#N)cc2N2CCN(CC(=O)NCCCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononyl)amino)-2-oxoethyl)piperazin-1-yl)phenyl)-2-(2-fluoro-6-methoxyphenyl)pyrimidine-4-carboxamide |
| 346 | 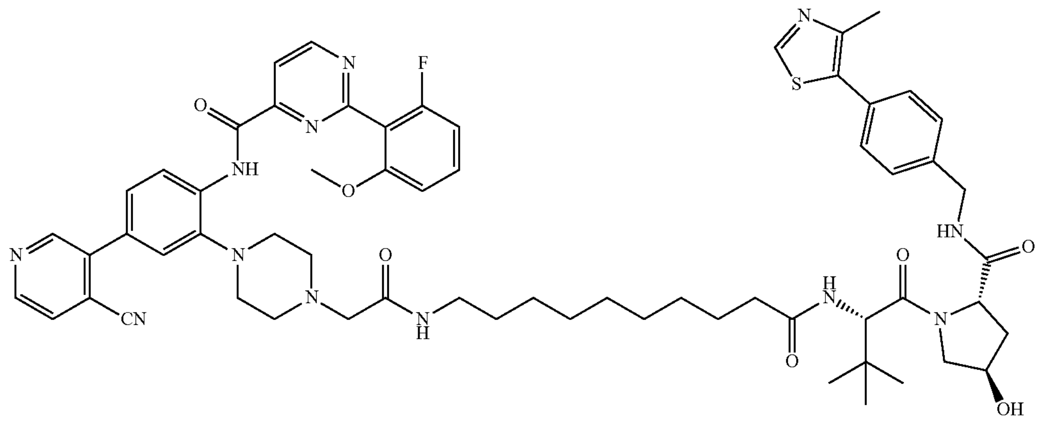 [SMILES: COc1cccc(F)c1-c1nccc(C(=O)Nc2ccc(-c3cnccc3C#N)cc2N2CCN(CC(=O)NCCCCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)amino)-2-oxoethyl)piperazin-1-yl)phenyl)-2-(2-fluoro-6-methoxyphenyl)pyrimidine-4-carboxamide |

TABLE 2-continued
| Examples | Structure | Chemical Name |
|---|---|---|
| 347 | 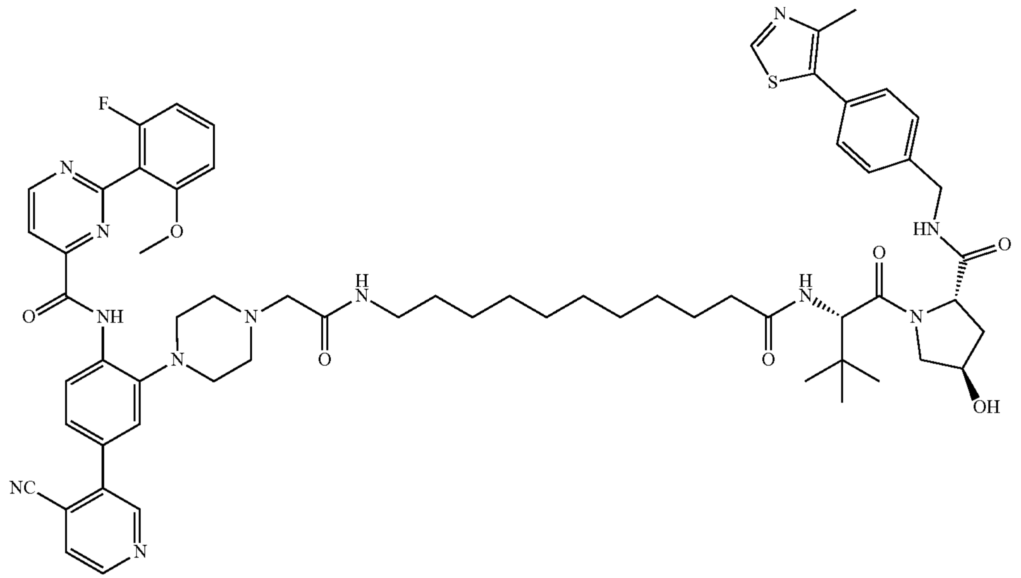 [SMILES: COc1cccc(F)c1-c1nccc(C(=O)Nc2ccc(-c3cnccc3C#N)cc2N2CCN(CC(=O)NCCCCCCCCCCC(=O)N[C@H](C(=O)N3C[C@H](O)C[C@H]3C(=O)NCc3ccc(-c4scnc4C)cc3)C(C)(C)C)CC2)n1] | N-(4-(4-cyanopyridin-3-yl)-2-(4-(2-((11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecyl)amino)-2-oxoethyl)piperazin-1-yl)phenyl)-2-(2-fluoro-6-methoxyphenyl)pyrimidine-4-carboxamide |

In Table 1 and Table 2, the left portion of the structure of the HPK1 disruptors/degraders binds to HPK1 and the right portion of the structure recruits the ubiquitination machinery to HPK1, which induces poly-ubiquitination and degradation of HPK1 at the proteasome.

Compounds corresponding to Examples 1-264 have been synthesized and final compounds are provided with a Compound Code in Table 1. Compounds in Table 2 corresponding to Examples 265-347 have not been synthesized and are not provided with a Compound Code. These compounds may be synthesized according to the schemes set forth above.

As used herein, in case of discrepancy between the structure and chemical name provided for a particular compound, the given structure shall control.

Figure 2:
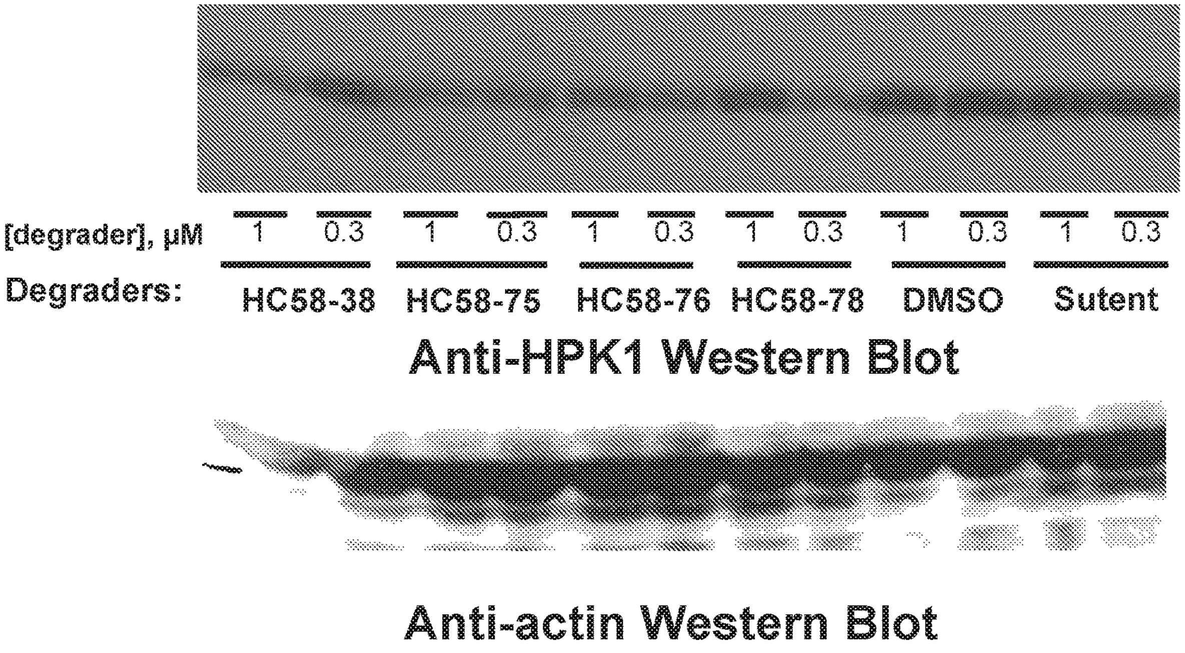
FIG. 2 is a Western blot analysis showing that HC58 series degraders could reduce the endogenous level of HPK1 in Jurkat T cells.
Figure 3:
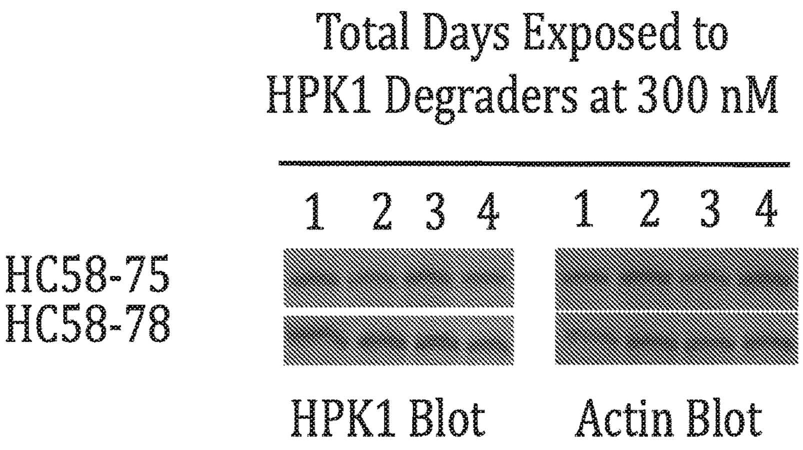
FIG. 3 is a Western blot analysis showing that the HC58 series degraders, HC58-75 and HC58-78 could reduce the endogenous level of HPK1 in Jurkat T cells on multiple day post exposure to HC58 series.
Figure 4A:
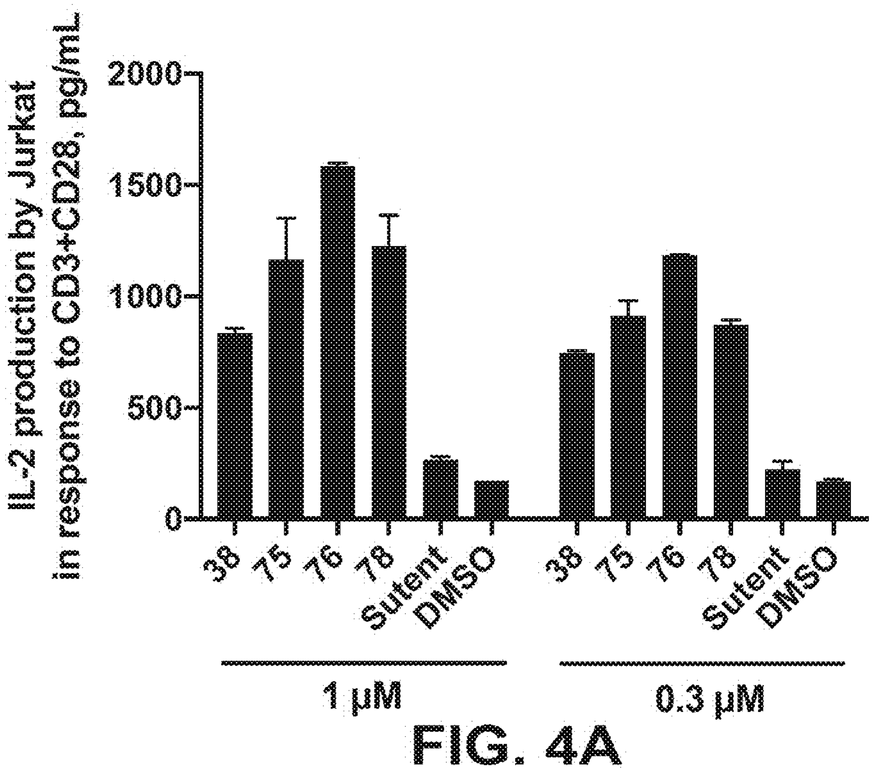
FIG. 4 is a Western blot analysis revealed that the HC58 series degraders could reduce the endogenous level of HPK1 in Jurkat T cells, relative to DMSO and other controls. (A) Amounts of IL-2 produced in response to TCR engagement. (B) Fold IL-2 increase after Degrader treatment.
Figure 4B:
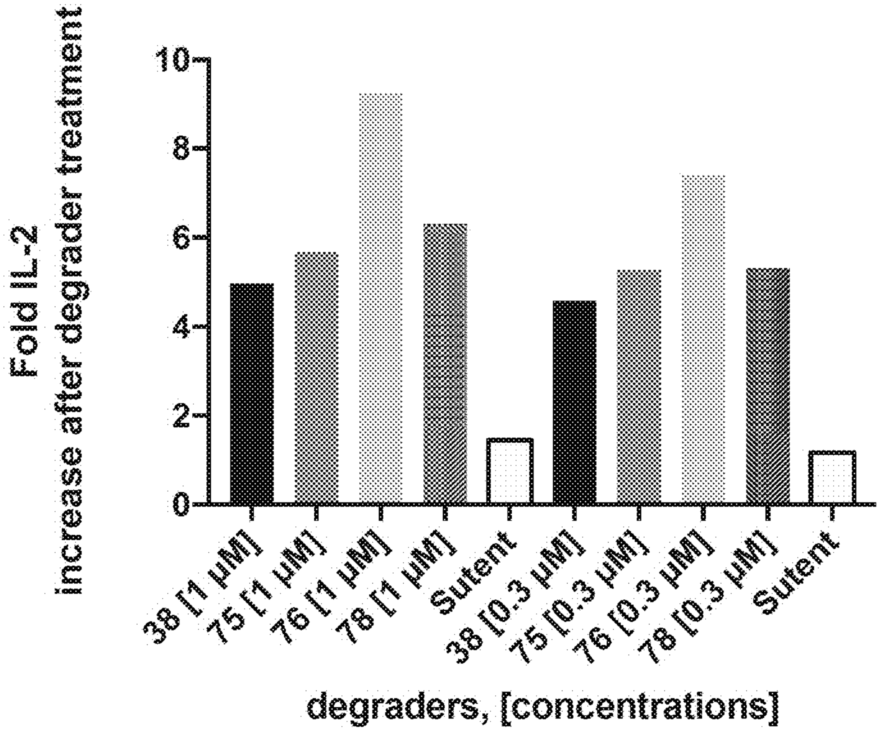
Figure 5A:
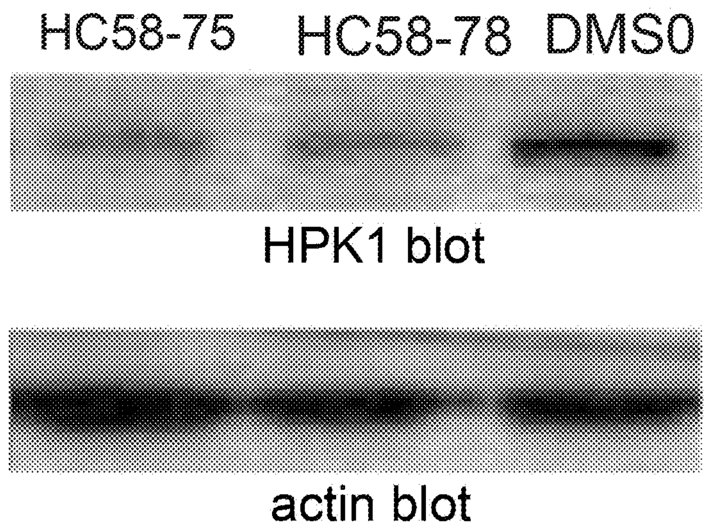
FIG. 5 is a set of graphs showing that treating primary T cells with the lead HPK1 degraders from the HC58 series conferred murine primary T cells with elevated IL-2 response, as well as an enhanced proliferative response to the anti-CD28 X anti-CD28 mAb-mediated receptor cross-linking.
Figure 5B:
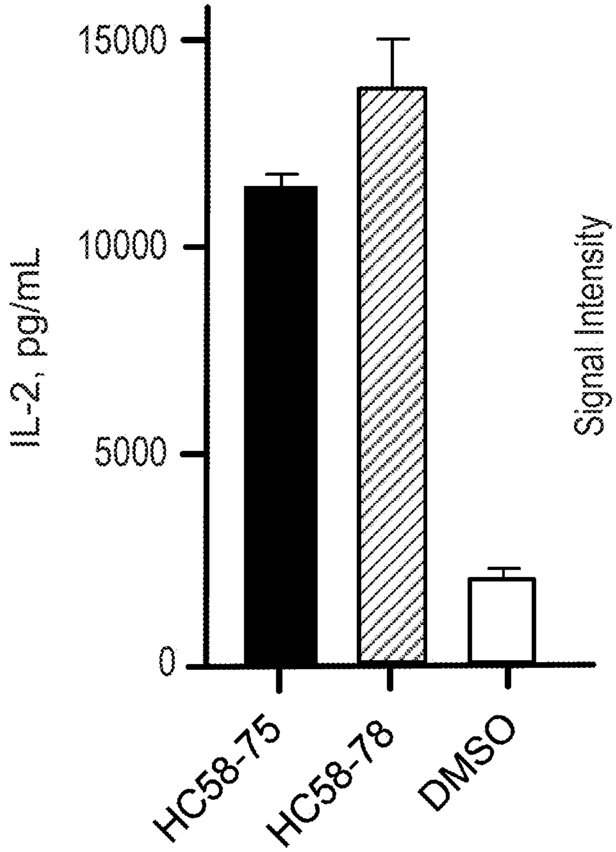
Figure 5C:
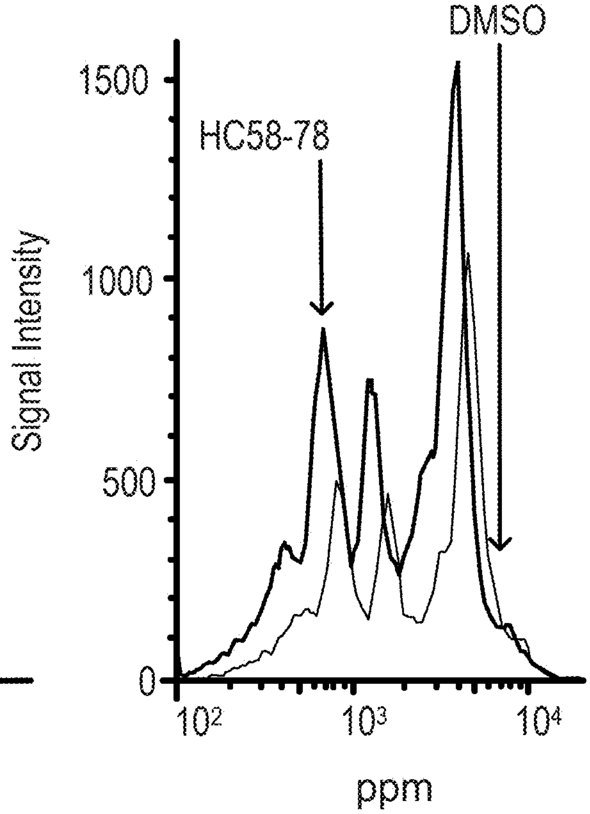

EXAMPLE 348. Several compounds according to the present invention employing the indolin-2-one HPK1 binding base, (which henceforth shall be referred to as the HC58 series, the HC65 series and the HC75 series) were assessed on their abilities to degrade HPK1 and produce an elevated IL-2 response profile upon stimulation by anti-CD3- and anti-CD28-mAb-mediated (CD3XCD28) stimulation (FIGS. 1-4). The elevated IL-2 response profile induced by TCR engagement after exposure to HC58 series of HPK1 degraders is shown in FIG. 1. Western blot analysis revealed that some degraders were able to reduce the expression level of HPK1 protein in Jurkat T cell line by approximately 75% (FIGS. 2 and 3). Furthermore, Jurkat cells treated with these HPK1 degraders also exhibited elevated TCR-induced IL-2 response profile—nearly 10 fold higher than the DMSO treated control—that is similar to the profile observed in $HPK1^{-/-}$ T cells (FIG. 4). A select sub-set of the lead HPK1 degraders from the HC58 series were further characterized to determine whether they could degrade primary mouse T cells. Evidence was found which suggests that either 300 nM HC58-76 or 300 nM HC58-78 HPK1 degraders could degrade more HPK1 protein in primary T cells than in Jurkat T cells (FIG. 5A). Both the HC58-75- and HC58-78-treated T cells produced more IL-2 than the DMSO-treated counterpart (FIG. 5B). Lastly, HC58-78 could induce primary murine T cells to proliferate much more quickly than the DMSO-treated counterpart (FIG. 5C). Similar results were found in HC58-75-treated T cells (data not shown).

Figure 6:
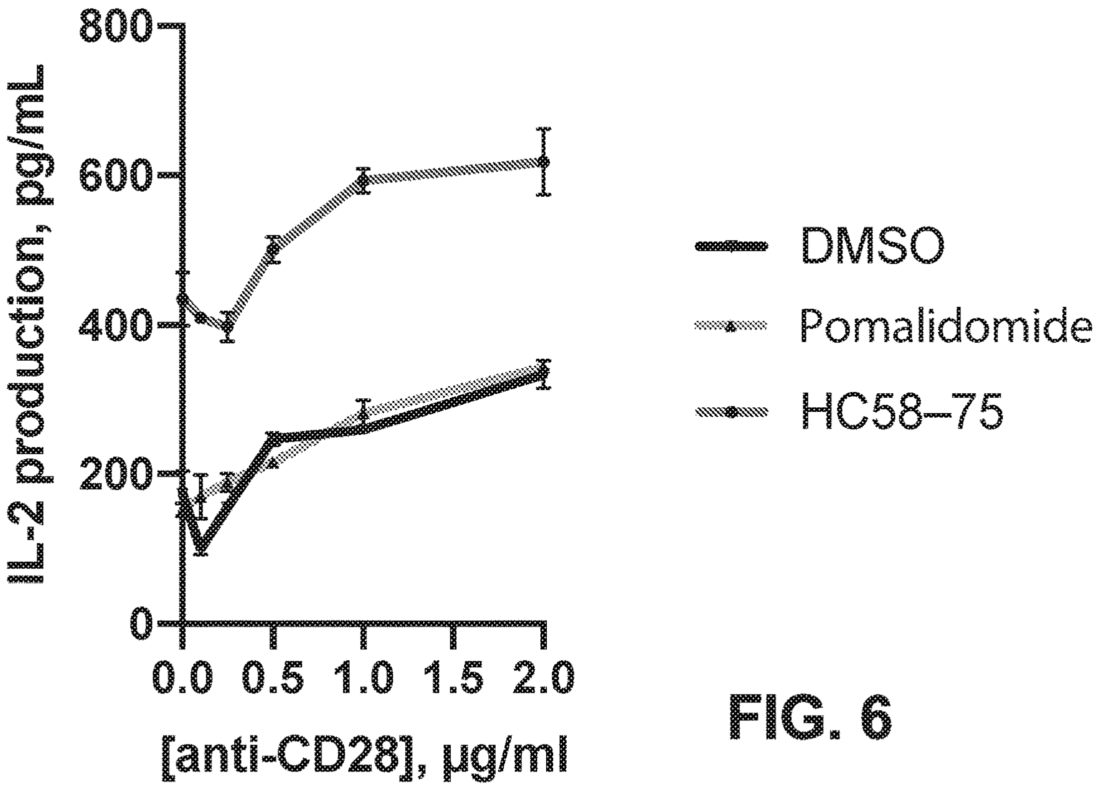
FIG. 6 is a graph showing CD28-independent IL-2 production by HC58-75-treated $CD4^+$ T cells upon being stimulated by a fixed concentration of plate-bound anti-CD38 and varying concentrations of soluble anti-CD28 mAb.

EXAMPLE 34. I was observed that $HPK1^{-/-}$ T cells, unlike their wild type counterparts, could readily produce IL-2 in response to CD3 □ crosslinking alone (data not shown). To assess whether HPK1 degraders could confer the same ability to produce IL-2 in a CD28-independent manner, $CD4^+$ primary murine T cells prepared as described in FIG. 5 were treated with 500 nM of HC58-75 HPK1 degrader or DMSO or Pomalidomide as controls. Their abilities to produce IL-2 in response a fixed concentration of plate-bound anti-CD3□ mAb (5 μg/mL) in conjunction with varying soluble concentration of anti-CD28 mAb was then assessed. Quantitative IL-2 ELISA analysis revealed that the HC58-75-treated T cells could produce IL-2 without the help of CD28 co-receptor engagement, which is similar to the IL-2 response produced by $HPK1^{-/-}$ T cells (FIG. 6 and data not shown).

Figure 7:
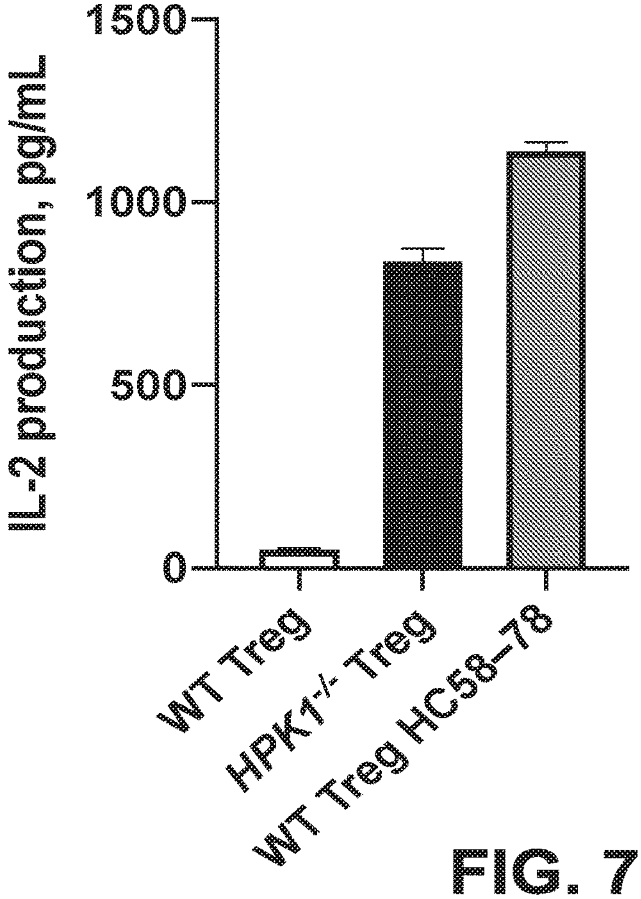
FIG. 7 is a graph showing treating primary $GFP^+$ Tregs with the HC58-78 HPK1 degrader conferred Tregs with an elevated IL-2 production in response to the stimulation by TCR engagement.

EXAMPLE 350. It was observed that $HPK1^{-/-}$ regulatory T cells (Treg), unlike their wild type counterparts, could readily produce IL-2 in response to CD3XCD28 stimulation. Taking advantage of the FoxP3-driven eGFP reporter mice that express eGFP only in the $FoxP3^+$ regulatory T cells (Tregs), bonafide Tregs were purified from spleens and lymph nodes by FACS-assisted sorting of $CD4^+eGFP^+$ Tregs and used as the source of ex vivo functional studies. The ability of the wild type Treg, the $HPK1^{-/-}$ Tregs and the HC58-78-treated wild type Tregs to produce IL-2 in response to CD3XCD28 stimulation was compared. Analysis of quantitative IL-2 ELISA revealed that the HC58-78-treated Tregs produced IL-2 at level comparable to that produced by $HPK1^{-/-}$ Tregs (FIG. 7, the black and grey histogram bars and data not shown). Wild type regulatory T cells could not produce the IL-2 in response to the same stimulation due to the transcriptional repression of the IL-2 locus by the FoxP3 transcription factor (FIG. 7, the white histogram bar).

Figure 8:
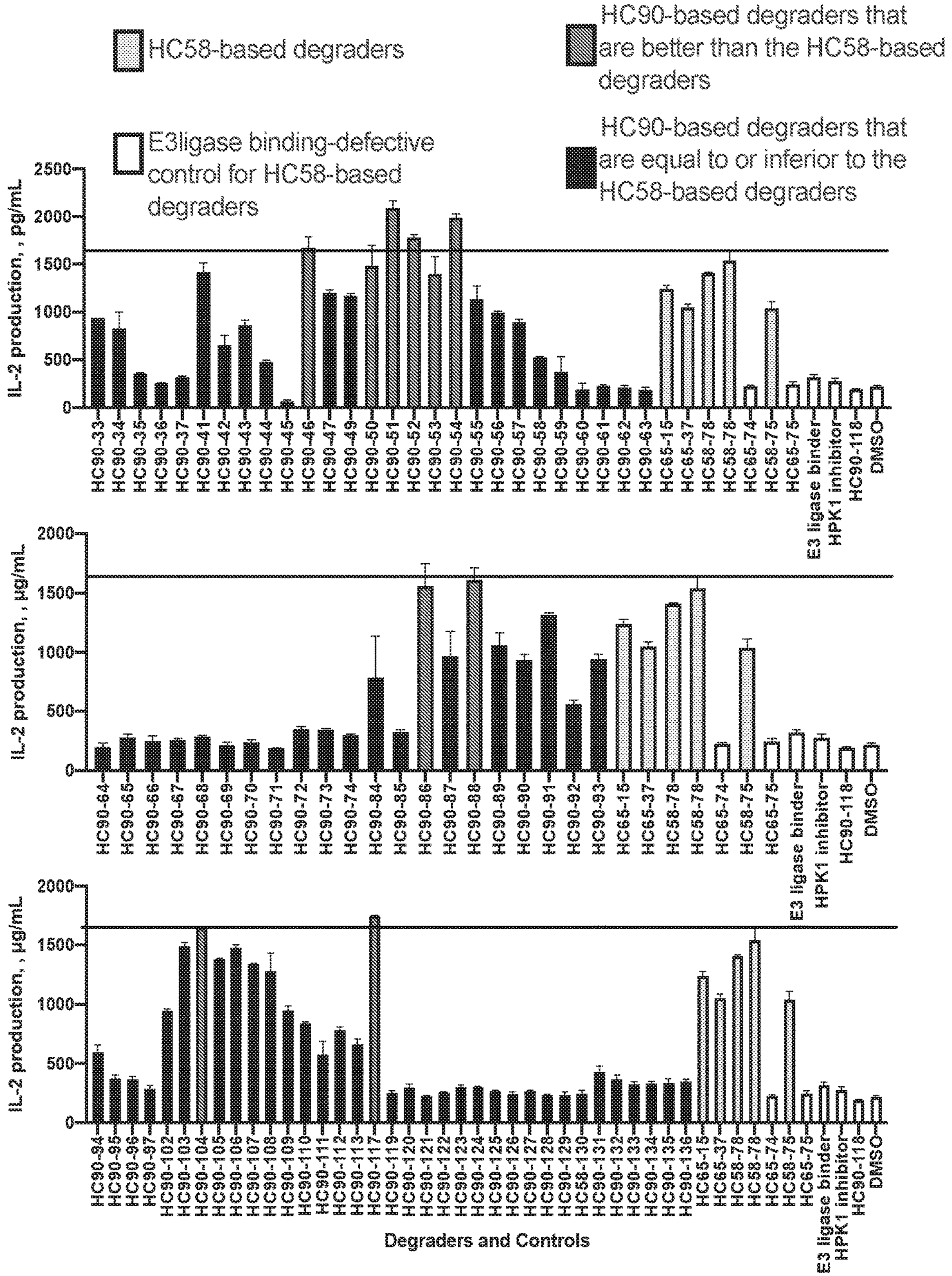
FIG. 8 is a set of graphs showing screening the HC90 HPK1 degrader series for compounds that could elicit superior IL-2 production when compared to the level elicited by the lead HC58 series compounds.
Figure 9:
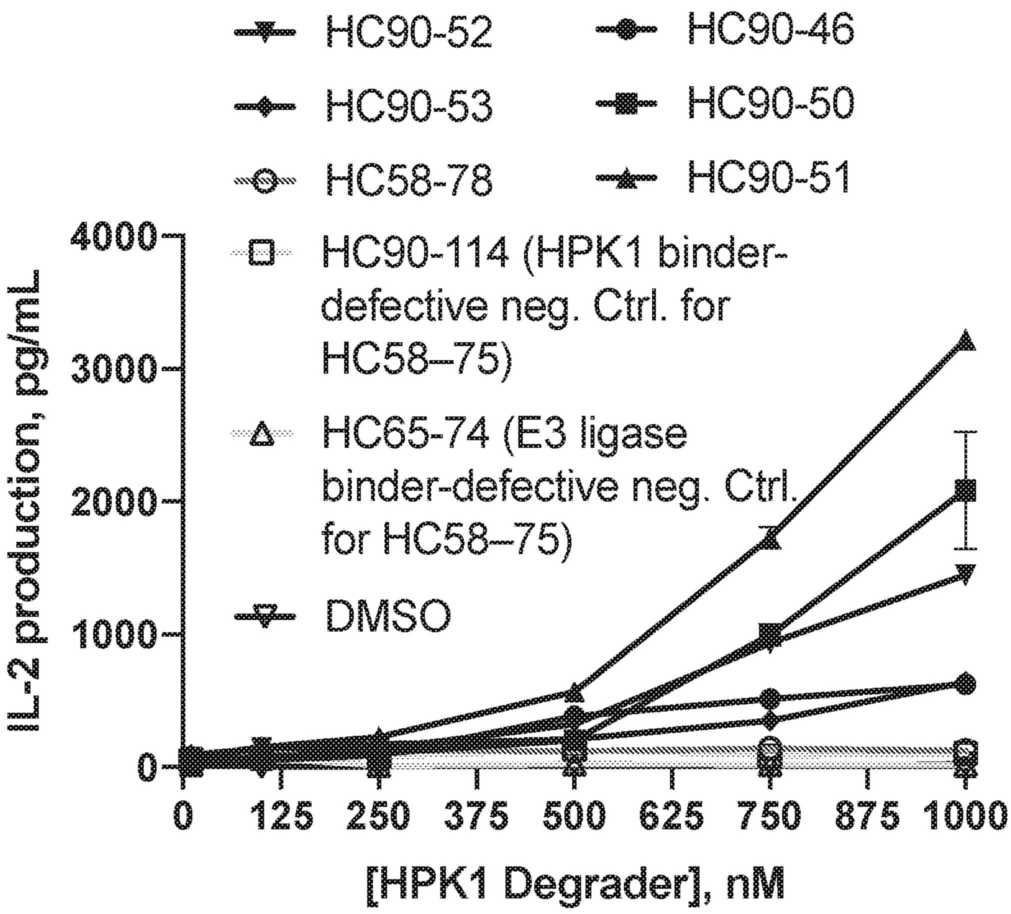
FIG. 9 is a graph showing IL-2 response profiles elicited by varying concentrations of the lead HC90 compounds in Jurkat T cells.
Figure 10:
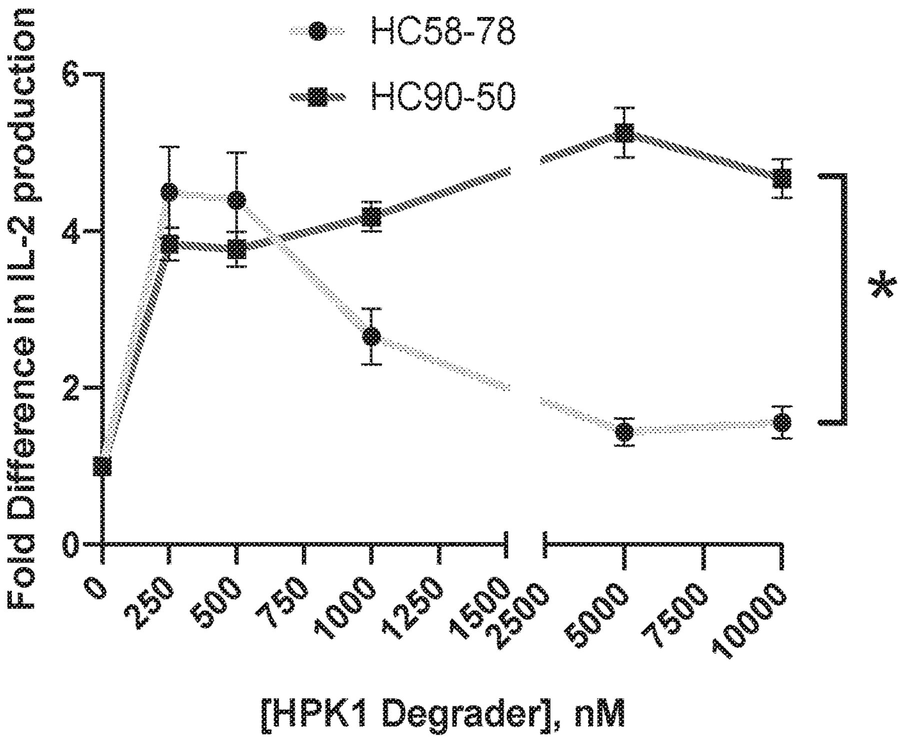
FIG. 10 is a graph showing IL-2 produced by HC58-78-treated or HC90-50-treated human PBMC, shown as fold differences in IL-2 produced by the degrader-treated cells relative to IL-2 produced by the DMSO-treated cells.

EXAMPLE 351. In an effort to improve the potency of HPK1 degraders, additional HPK1 degraders that utilize a different HPK1 binding scaffold (pyrazolo-pyrimidine) were designed and synthesized (referred to as the HC90 series). Jurkat cells that were pre-treated with each member of the HC90 HPK1 degrader series (500 nM) were screened for the amount of IL-2 produced in response CD3XCD28 stimulation. The levels of IL-2 produced were compared to the level produced by T cells that were treated by selected compounds from the HC58 series (FIG. 8). Compounds that endowed Jurkat cells with either comparable or superior IL-2 response profiles when compared to the lead HC58 compounds (FIG. 8, red histogram bars) were selected for confirmatory assessment in the presence of a wider ranges of compound concentrations (FIG. 9). The top two compounds from the HC90 series, the HC90-50 and HC90-51 (FIG. 9, black triangle and black square) were selected as lead compounds for the HC90 series and were subjected to additional analysis. Furthermore, compound HC58-78 and HC90-50 were also assessed for their abilities to enhance the CD3XCD28-induced IL-2 response by primary human PBMC (FIG. 10).

Figure 11:
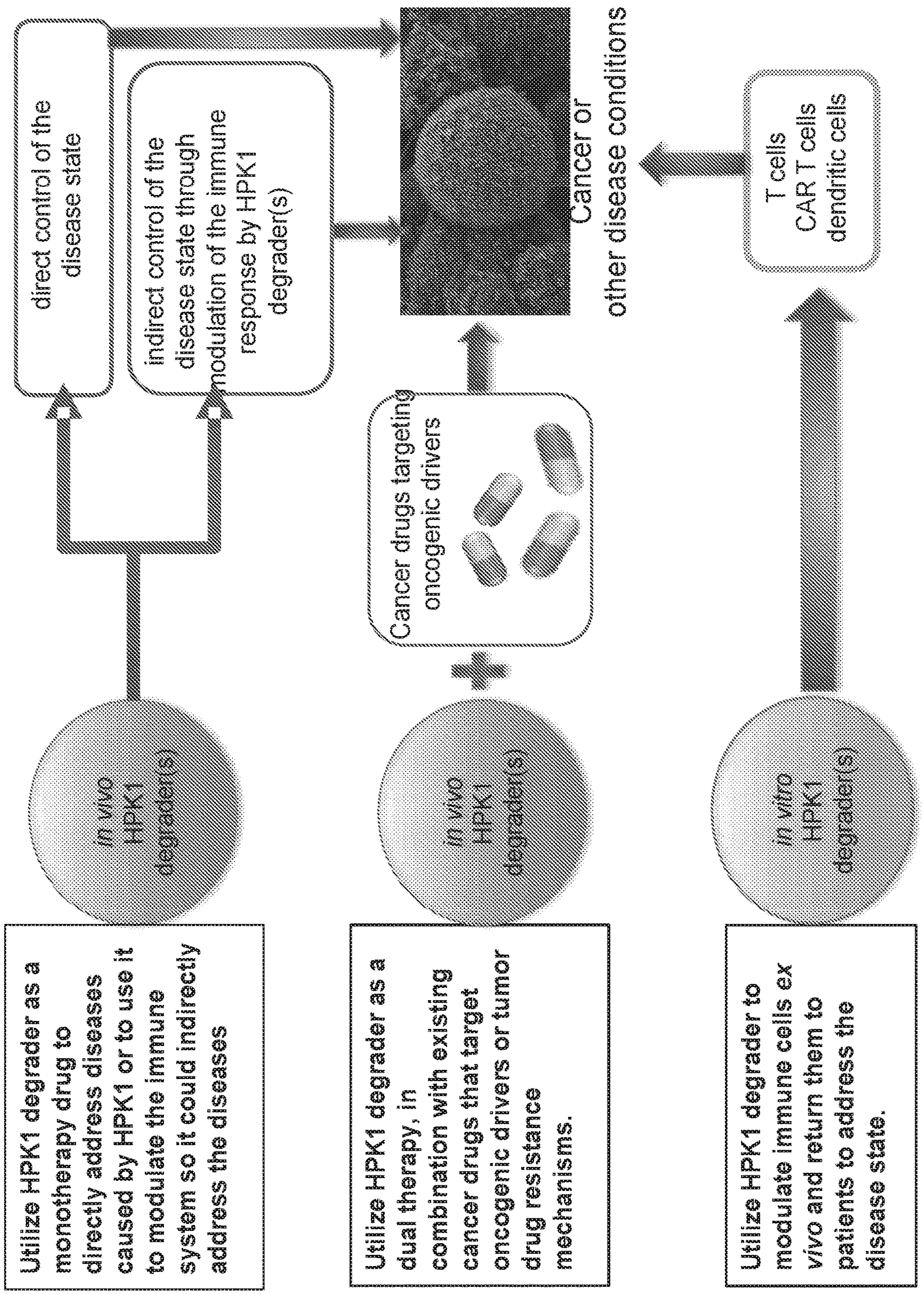
FIG. 11 is a schematic depiction of how HPK1 degraders might be used as therapeutic agents to directly or indirectly treat various disease states.

EXAMPLE 352. In an aspect, this disclosure provides several methods of treating HPK1-mediated diseases or diseases that could be controlled by the reduction of HPK1 expression level through administration of the compounds (HPK1 degraders) described herein. Compounds that could alter the expression level of HPK1 could be administered in vivo systematically alone, or in conjunction with other drugs, to directly or indirectly address the disease state. Alternatively, the HPK1 degraders could be administered externally to the ex vivo cells that had been prepared for therapeutic use, and then returned to the patients to address the disease state in vivo. These therapeutic concepts are schematically depicted in FIG. 11.

Figure 12:
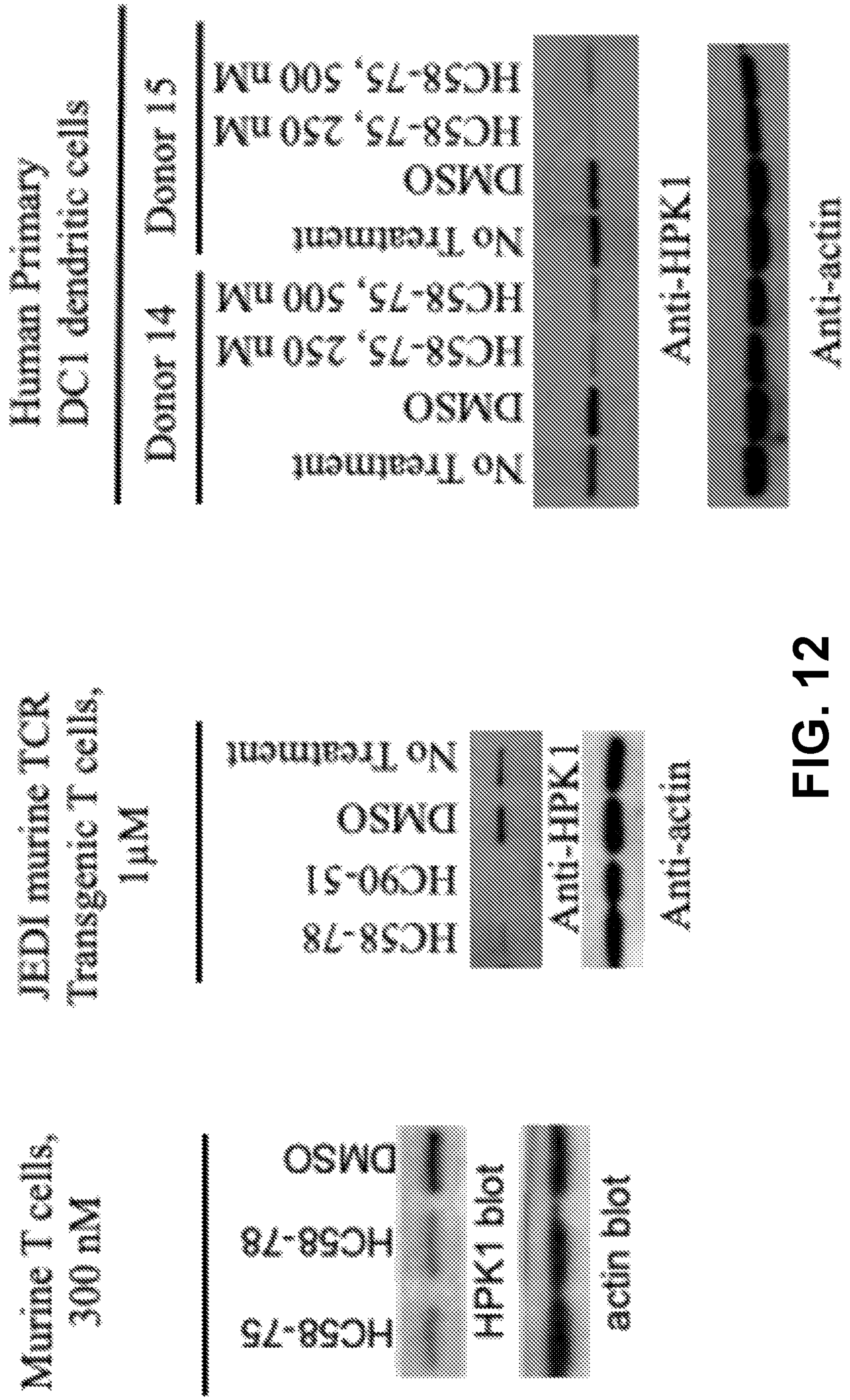
FIG. 12 is a series of blots showing HPK1 degraders could effectively degrade endogenous HPK1 in murine T cells, murin TCR transgenic T cells and in human DC1 dendritic cells.

EXAMPLE 353. HPK1 is expressed in all hematopoietic cells examined to date, including T cells, B cells, dendritic cells and neutrophils. Because the breath of therapeutic approaches might involve the use of Chimeric Antigen Receptor (CAR) T cells, dendritic cells, TCR transgenic T cells and Tumor Infiltrating Lymphocytes (TILs), selected HPK1 degraders were evaluated to determine whether they could degrade HPK1 effectively in some of these cell types. FIG. 12 revealed that HPK1 degraders could degrade HPK1 in murine primary T cells and in the JEDI TCR transgenic T cells as well. Potent degradation of HPK1 by HPK1 degraders was also observed in the human DC1 dendritic cells.

Figure 13:
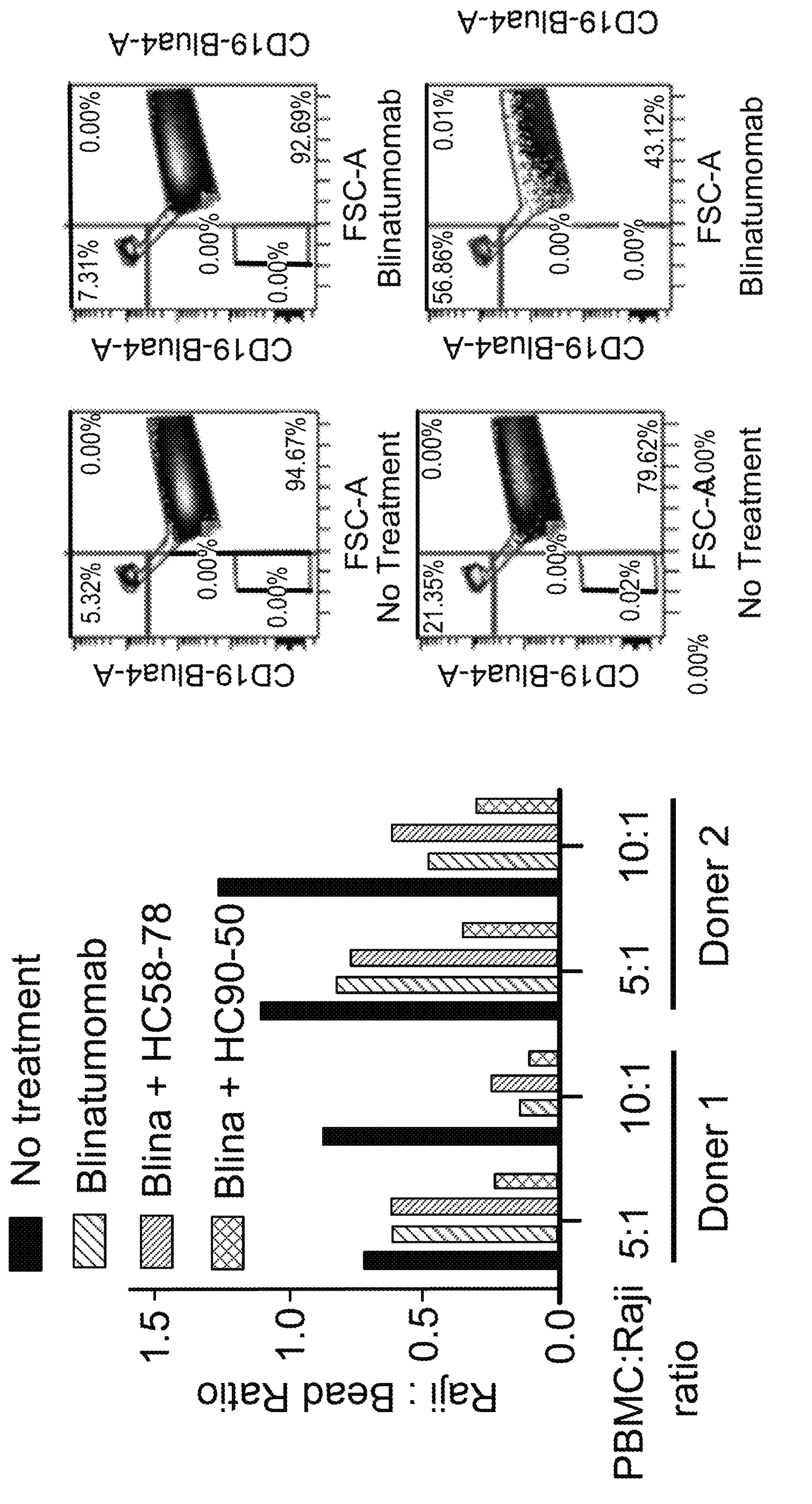
FIG. 13 is a set of graphs showing HPK1 degraders could effectively enhance Blinatumomab-mediated killing of the human $CD19^+$ B Cell Acute Lymphoblastic Leukemia cells, Raji.

EXAMPLE 354. One of the approaches schematically depicted in FIG. 11 is the use of HPK1 degraders in conjunction with other drugs. The ability of HPK1 degraders to enhance the T cell-mediated killing of $CD19^+$ B-Cell Acute Lymphoblastic Leukemia treated with blinatumomab was assessed. It was demonstrated that human PBMC that were treated with HPK1 degraders could aid blinatumomab in killing more human $CD19^+$ B Cell Acute Lymphoblastic Leukemia cells, Raji (FIG. 13).

Figure 14B:
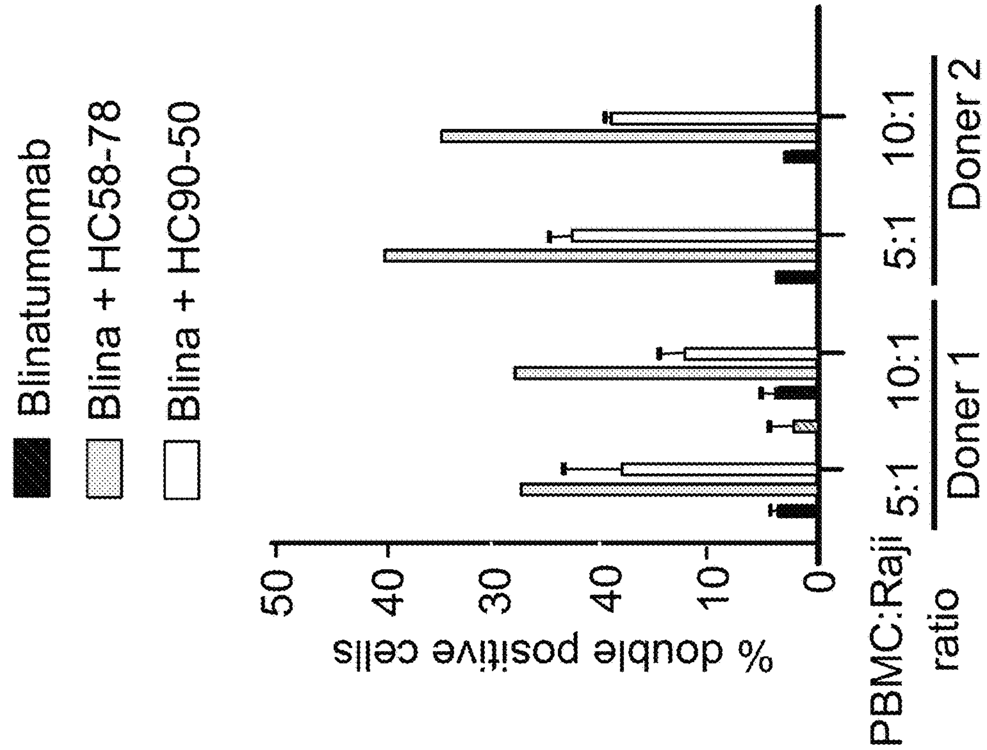
FIG. 14 is a set of graphs showing HPK1 degraders could effectively degrade pro-inflammatory cytokine produced by the Blinatumomab-treated PBMC cells. (A) A representative intracellular cytokine staining pattern for the expression of IFNγ and TNFα by HPK1 degrader/Blinatumomab-treated PBMC cells. (B) Averaged percentage of cells that are stained positive for both IFNγ and TNFα in HPK1 degrader/Blinatumomab-treated PBMC cells.
Figure 14A:
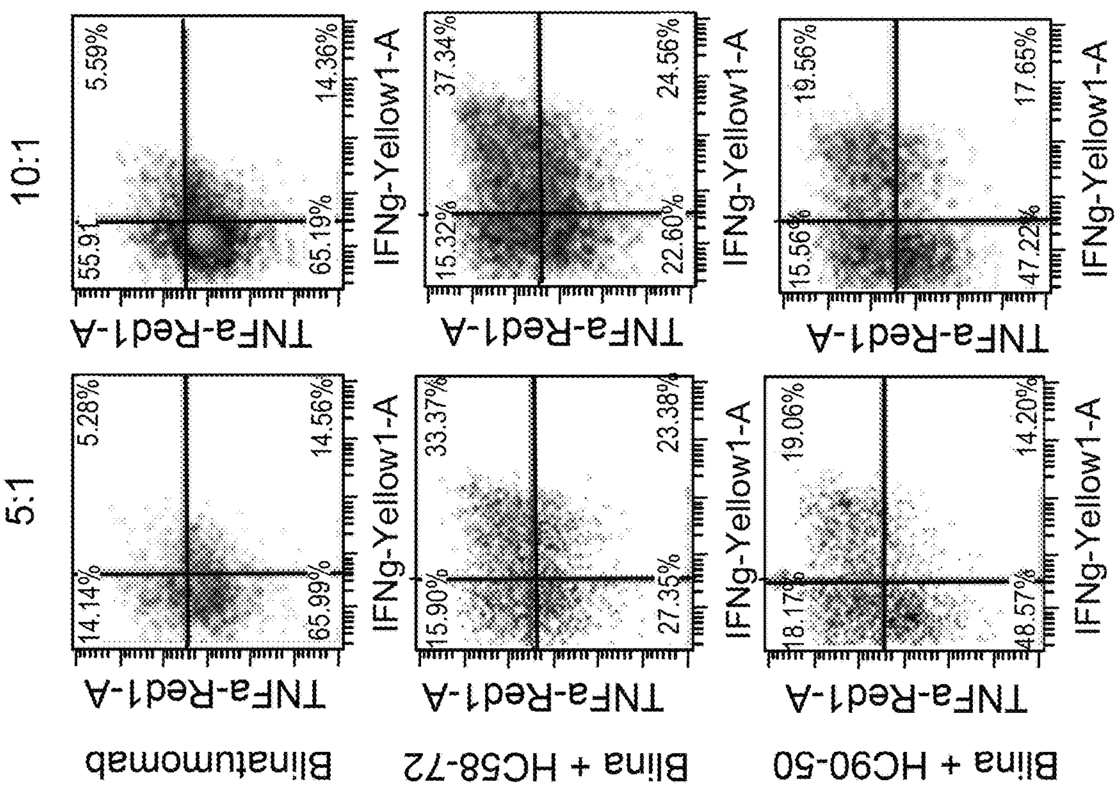

EXAMPLE 355. One of the mechanisms employed by PBMC to kill their target cells is by releasing IFNγ and TNFα production. These inflammatory cytokines are known have potent cytolytic effects on cancer cells. FACS analysis of anti-IFNγ and TNFα intracellular staining revealed that combining either HC58-78 or HC90-50 with blinatumomab significantly increased the percentage of human PBMCs that express high level of IFNγ and TNFα (FIGS. 14A and 14B). These data suggest that the elevated level of IFNγ and TNFα produced by blinatumomab-treated PBMC might be responsible for the more effective killing of the $CD19^+$ B Cell Acute Lymphoblastic Leukemia cells. Mediated PBMC killing of the Raji cells is most evident at PBMC:Raji ratio of 5:1 (FIG. 13).

Materials And Methods:

General Chemistry Methods

For the synthesis of intermediates and examples (1-89) below, HPLC spectra for all compounds were acquired using an Agilent 1200 Series system with DAD detector. Chromatography was performed on a 2.1×150 mm Zorbax 300SB-C18 5 μm column with water containing 0.1% formic acid as solvent A and acetonitrile containing 0.1% formic acid as solvent B at a flow rate of 0.4 ml/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Nuclear Magnetic Resonance (NMR) spectra were acquired on a Bruker DRX-600 spectrometer with 600 MHz for proton ($^1H$ NMR) and 150 MHz for carbon ($^{13}C$ NMR); chemical shifts are reported in (δ). Preparative HPLC was performed on Agilent Prep 1200 series with UV detector set to 254 nm. Samples were injected onto a Phenomenex Luna 250×30 mm, 5 μm, $C_{18}$ column at room temperature. The flow rate was 40 ml/min. A linear gradient was used with 10% (or 50%) of MeOH (A) in $H_2O$ (with 0.1% TFA) (B) to 100% of MeOH (A). HPLC was used to establish the purity of target compounds. All final compounds had >95% purity using the HPLC methods described above.

Cell Lines and Tissue Culture

The Jurkat (sub-clone E6-1 [ATCC® TIB-152™]) is a human acute T cell leukemia cell line that was established from the peripheral blood of a 14 year old boy. (Weiss 1984) (Gillis 1980). Schneider U, et al. Characterization of EBV-genome negative “null” and “T” cell lines derived from children with acute lymphoblastic leukemia and leukemic transformed non-Hodgkin lymphoma. Int. J. Cancer 19: 621-626, 1977. PubMed: 68013. Clone E6-1 cells is a preferred cellular platform for studying T cell activation in response to T cell receptor engagement because it produces the cytokine IL-2, which could be used as proxy readout for the level of T cell activation. While the Jurkat cell would produce IL-2 when stimulated with phorbol esters and either lectins or monoclonal antibodies CD3ε itself, the stimulation that most mimic T cell activation in vivo is to use anti-CD3ε monoclonal antibody in conjunction with anti-CD28 monoclonal antibody. It is this activation method that was used to stimulate Jurkat T cells to that had been treated with degraders of interest. Specifically, the anti-CD3ε monoclonal antibody (OKT3 clone, 5 μg per mL) is absorbed onto 96-well polystyrene tissue culture plate to form a planar surface that mimics the surface of antigen presentating cells. Excess non-absorbed antibody is washed off with phosphate buffer saline 3 times and would be used to intiate stimulation of Jurkat T cells that had been pre-treated with indicated concentration of the degraders. Jurkat cells were resuspended in culture medium (RPMI-1640, 10% FCS, 1× L-glutamine and 1× penicillin and streptomycin). Fifty thousands Jurkat cells were added to each well in duplicate, in the presence of (5 μg per mL of anti-CD28 monoclonal antibody). The plate is then placed into a humidity controlled, 5% $CO_2$ incubator for 24 hours. The indicated concentration of degrader is maintained through out the stimulation period of 24 hours. Supernatant from Jukat cells were collected and the amount of IL-2 present in the supernatant was assessed by standard anti-human IL-2 ELISA.

The ability of degraders to degrade HPK protein level in treated Jukat cels was determined by Western blot, using anti-human HPK1 polyclonal antibody as probe (CSL). Degrader-treated Jurkat cells were lysed in standard NP-40 lysis buffer and lysate equalvalent to $1\times10^6$ Jurkat cells were loaded into each well of the 10% poly-acrylamide gel and subjected to electrophoretic separation by SDS-PAGE. Proteins in lysates that had been resolved by SDS-PAGE were transferred to PVDF support matrix, blocked by 4% BSA containing solution and probed with anti-human HPK1 antibody, using standard Western blotting procedure.

To determine the number of $CD19^+$ Raji cells killed by human PBMC that were activated by the Blinatumomab-mediated activation, we used CountBright cell counting beads to estimate the number of cells remained after 72 hours of co-culturing of PBMC and Raji. As for the intracellular staining of the TNFα and the IFNγ, the standard para-formaldehyde-based “fix and perm” procedure was used in order to quantitate the amount of intracellular cytokine trapped inside the cells by brefeldin A. FACS analysis of stained cells is performed by BD’s LSR II FACS.

Other Aspects

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Alzabin, S., Bhardwaj, N., Kiefer, F., Sawasdikosol, S., and Burakoff, S. (2009). Hematopoietic progenitor kinase 1 is a negative regulator of dendritic cell activation. J Immunol 182, 6187-6194.

Alzabin, S., Pyarajan, S., Yee, H., Kiefer, F., Suzuki, A., Burakoff, S., and Sawasdikosol, S. (2010). Hematopoietic progenitor kinase 1 is a critical component of prostaglandin E2-mediated suppression of the anti-tumor immune response. Cancer Immunol Immunother 59, 419-429.

Bondeson, D. P., Mares, A., Smith, I. E., Ko, E., Campos, S., Miah, A. H., Mulholland, K. E., Routly, N., Buckley, D. L., Gustafson, J. L., et al. (2015). Catalytic in vivo protein knockdown by small-molecule PROTACs. Nat Chem Biol 11, 611-617.

Buckley, D. L., and Crews, C. M. (2014). Small-molecule control of intracellular protein levels through modulation of the ubiquitin proteasome system. Angew Chem Int Ed Engl 53, 2312-2330.

Buckley, D. L., Gustafson, J. L., Van Molle, I., Roth, A. G., Tae, H. S., Gareiss, P. C., Jorgensen, W. L., Ciulli, A., and Crews, C. M. (2012a). Small-molecule inhibitors of the interaction between the E3 ligase VHL and HIF1alpha. Angew Chem Int Ed Engl 51, 11463-11467.

Buckley, D. L., Raina, K., Darricarrere, N., Hines, J., Gustafson, J. L., Smith, I. E., Miah, A. H., Harling, J. D., and Crews, C. M. (2015). HaloPROTACS: Use of Small Molecule PROTACs to Induce Degradation of HaloTag Fusion Proteins. ACS Chem Biol 10, 1831-1837.

Buckley, D. L., Van Molle, I., Gareiss, P. C., Tae, H. S., Michel, J., Noblin, D. J., Jorgensen, W. L., Ciulli, A., and Crews, C. M. (2012b). Targeting the von Hippel-Lindau E3 ubiquitin ligase using small molecules to disrupt the VHL/HIF-1alpha interaction. J Am Chem Soc 134, 4465-4468.

Burnet, F. M. (1970). The concept of immunological surveillance. Progress in experimental tumor research 13, 1-27.

Chamberlain, P. P., Lopez-Girona, A., Miller, K., Carmel, G., Pagarigan, B., Chie-Leon, B., Rychak, E., Corral, L. G., Ren, Y. J., Wang, M., et al. (2014). Structure of the human Cereblon-DDB1-lenalidomide complex reveals basis for responsiveness to thalidomide analogs. Nat Struct Mol Biol 21, 803-809.

Corthay, A. (2014). Does the immune system naturally protect against cancer? Frontiers in immunology 5, 197.

Davies, T. G., Wixted, W. E., Coyle, I E., Griffiths-Jones, C., Heam, K., Mcl†fonamin, R., Norton, D., Rich, S. J., Richardson, C., Saxty, G., et al. (2016). Monoacidic Inhibitors of the Kelch-like ECH-Associated Protein 1: Nuclear Factor Erythroid 2-Related Factor 2 (KEAP1: NRF2) Protein-Protein Interaction with High Cell Potency Identified by Fragment-Based Discovery. J Med Chem 59, 3991-4006.

Fischer, E. S., Bohm, K., Lydeard, J. R., Yang, H., Stadler, M. B., Cavadini, S., Nagel, J., Serluca, F., Acker, V., Lingaraju, G. M., et al. (2014). Structure of the DDB1-CRBN E3 ubiquitin ligase in complex with thalidomide. Nature 512, 49-53.

Galdeano, C., Gadd, M. S., Soares, P., Scaffidi, S., Van Molle, I., Birced, I., Hewitt, S., Dias, D. M., and Ciulli, A. (2014). Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem 57, 8657-8663.

Gillis, S., and J. Watson. 1980. Biochemical and biological characterization of lymphocyte regulatory molecules. V. Identification of an interleukin 2-producing human leukemia T cell line. The Journal of experimental medicine 152: 1709-1719.

Hernandez, S., Qing, J., Thibodeau, R. H., Du, X., Park, S., Lee, H. M., Xu, M., Oh, S., Navarro, A., Roose-Girma, M., et al. (2018). The Kinase Activity of Hematopoietic Progenitor Kinase 1 Is Essential for the Regulation of T Cell Function. Cell reports 25, 80-94.

Hu, M. C., Qiu, W. R., Wang, X., Meyer, C. F., and Tan, T. H. (1996). Human HPK1, a novel human hematopoietic progenitor kinase that activates the JNK/SAPK kinase cascade. Genes Dev 10, 2251-2264.

Ito, T., Ando, H., Suzuki, T., Ogura, T., Hotta, K., Imamura, Y., Yamaguchi, Y., and Handa, H. (2010). Identification of a primary target of thalidomide teratogenicity. Science 327, 1345-1350.

Kiefer, F., Tibbles, L. A., Anafi, M., Janssen, A., Zanke, B. W., Lassam, N., Pawson, T., Woodgett, J. R., and Iscove, N. N. (1996). HPK1, a hematopoietic protein kinase activating the SAPK/JNK pathway. EMBO J 15, 7013-7025.

Lai, A. C., Toure, M., Hellerschmied, D., Salami, J., Jaime-Figueroa, S., Ko, E., Hines, J., and Crews, C. M. (2016). Modular PROTAC Design for the Degradation of Oncogenic BCR-ABL. Angew Chem Int Ed Engl 55, 807-810.

Ling, P., Meyer, C. F., Redmond, L. P., Shui, J. W., Davis, B., Rich, R. R., Hu, M. C., Wange, R. L., and Tan, T. H. (2001). Involvement of hematopoietic progenitor kinase 1 in T cell receptor signaling. The Journal of biological chemistry 276, 18908-18914.

Liou, J., Kiefer, F., Dang, A., Hashimoto, A., Cobb, M. H., Kurosaki, T., and Weiss, A. (2000). HPK1 is activated by lymphocyte antigen receptors and negatively regulates AP-1. Immunity 12, 399-408.

Liu, J., Curtin, J., You, D., Hillerman, S., Li-Wang, B., Eraslan, R., Xie, J., Swanson, J., Ho, C. P., Oppenheimer, S., et al. (2019). Critical role of kinase activity of hematopoietic progenitor kinase 1 in anti-tumor immune surveillance. PloS one 14, e0212670.

Lu, J., Qian, Y., Altieri, M., Dong, H., Wang, J., Raina, K., Hines, J., Winkler, J. D., Crew, A. P., Coleman, K., et al. (2015). Hijacking the E3 Ubiquitin Ligase Cereblon to Efficiently Target BRD4. Chemistry & biology 22, 755-763.

Ohoka, N, Okuhira, K., Ito, M, Nagai, K, Shibata, N., Hattori, T., Ujikawa, O, Shimokawa, K., Sano, O., Koyama, R., et al (2017). In Vivo Knockdown of Pathogenic Proteins via Specific and Nongenetic Inhibitor of Apoptosis Protein (IAP)-dependent Protein Erasers (SNIPERs). J Biol Chem 292, 4556-4570.

Okuhira, K., Ohoka, N., Sai, K., Nishimaki-Mogami, T., Itoh, Y., Ishikawa, M., Hashimoto, Y., and Naito, M. (2011). Specific degradation of CRABP-II via cIAPl-mediated ubiquitylationinduced by hybrid molecules that crosslink cIAPl and the target protein. FEBS Lett 585, 1147-1152.

Ribas, A., and Wolchok, J. D. (2018). Cancer immunotherapy using checkpoint blockade. Science (New York, NY 359, 1350-1355.

Sawasdikosol, S., Pyarajan, S., Alzabin, S., Matejovic, G., and Burakoff, S. J. (2007). Prostaglandin E2 activates HPK1 kinase activity via a PKA-dependent pathway. The Journal of biological chemistry 282, 34693-34699.

Sawasdikosol, S., Russo, K. M., and Burakoff, S. J. (2003). Hematopoietic progenitor kinase 1 (HPK1) regulates prostaglandin E2-induced fos gene transcription. Blood 101, 3687-3689.

Sawasdikosol, S., Zha, R., Yang, B., and Burakoff, S. (2012). HPK1 as a novel target for cancer immunotherapy. Immunologic research 54, 262-265.

Shibata, N., Miyamoto, N., Nagai, K., Shimokawa, K., Sameshima, T., Ohoka, N., Hattori, T., Imaeda, Y, Nara, H., Cho, N., et al. (2017). Development of protein degradation inducers of oncogenic BCR-ABL protein by conjugation of ABL kinase inhibitors and IAP ligands. Cancer Sci 108, 1657-1666.

Shui, J. W., Boomer, J. S., Han, J., Xu, J., Dement, G. A., Zhou, G., and Tan, T. H. (2007). Hematopoietic progenitor kinase 1 negatively regulates T cell receptor signaling and T cell-mediated immune responses. Nat Immunol 8, 84-91.

Sun, D., Li, Z, Rew, Y., Gribble, M, Bartberger, M. D., Beck, H. P., Canon, J., Chen, A., Chen, X, Chow, D., et al. (2014). Discovery of AMG 232, a potent, selective, and orally bioavailable MDM2-p53 inhibitor in clinical development. J Med Chem 57, 1454-1472.

Weiss, A., R. L. Wiskocil, and J. D. Stobo. 1984. The role of T3 surface molecules in the activation of human T cells:

a two-stimulus requirement for IL 2 production reflects events occurring at a pre-translational level. J Immunol 133: 123-128.

Winter, G. E., Buckley, D. L., Paulk, J., Roberts, J. M., Souza, A., Dhe-Paganon, S., and Bradner, J. E. (2015). Phthalimide conjugation as a strategy for in vivo target protein degradation. Science 348, 1376-1381.

Xie, T., Lim, S. M., Westover, K. D., Dodge, M. E., Ercan, D., Ficarro, S. B., Udayakumar, D., Gurbani, D., Tae, H. S., Riddle, S. M., et al. (2014). Pharmacological targeting of the pseudokinase Her3. Nat Chem Biol 10, 1006-1012.

Zengerle, M., Chan, K. H., and Ciulli, A. (2015). Selective Small Molecule Induced Degradation of the BET Bromodomain Protein BRD4. ACS Chem Biol 10, 1770-1777.

What is claimed is:

1. A bivalent compound comprising a hematopoietic progenitor kinase 1 (HPK1) ligand conjugated to a degradation/disruption tag, selected from the group consisting of:

2-(2,6-dioxopiperidin-3-yl)-5-((7-(4-(4-(5-(2-fluoro-6-methoxyphenyl)-1H-pyrazolo[4,3-d]pyrimidin-3-yl)phenyl)piperazin-1-yl)-7-oxoheptyl)amino)isoindoline-1,3-dione (HC90-46);

2-(2,6-dioxopiperidin-3-yl)-4-((3-(4-(4-(5-(2-fluoro-6-methoxyphenyl)-1H-pyrazolo[4,3-d]pyrimidin-3-yl)phenyl)piperazin-1-yl)-3-oxopropyl)amino)isoindoline-1,3-dione (HC90-50);

2-(2,6-dioxopiperidin-3-yl)-4-((4-(4-(4-(5-(2-fluoro-6-methoxyphenyl)-1H-pyrazolo[4,3-d]pyrimidin-3-yl)phenyl)piperazin-1-yl)-4-oxobutyl)amino)isoindoline-1,3-dione (HC90-51);

2-(2,6-dioxopiperidin-3-yl)-4-((5-(4-(4-(5-(2-fluoro-6-methoxyphenyl)-1H-pyrazolo[4,3-d]pyrimidin-3-yl)phenyl)piperazin-1-yl)-5-oxopentyl)amino)isoindoline-1,3-dione (HC90-52);

2-(2,6-dioxopiperidin-3-yl)-4-((6-(4-(4-(5-(2-fluoro-6-methoxyphenyl)-1H-pyrazolo[4,3-d]pyrimidin-3-yl)phenyl)piperazin-1-yl)-6-oxohexyl)amino)isoindoline-1,3-dione (HC90-53);

2-(2,6-dioxopiperidin-3-yl)-4-((7-(4-(4-(5-(2-fluoro-6-methoxyphenyl)-1H-pyrazolo[4,3-d]pyrimidin-3-yl)phenyl)piperazin-1-yl)-7-oxoheptyl)amino)isoindoline-1,3-dione (HC90-54);

N-(2-((2-(2,6-dioxopiperidin-3-yl)-1,3-dioxoisoindolin-5-yl)amino)ethyl)-2-(4-(4-(5-(2-fluoro-6-methoxyphenyl)-1H-pyrazolo[4,3-d]pyrimidin-3-yl)phenyl)piperazin-1-yl)acetamide (HC90-86);

N-(4-((2-(2,6-dioxopiperidin-3-yl)-1,3-dioxoisoindolin-5-yl)amino)butyl)-2-(4-(4-(5-(2-fluoro-6-methoxyphenyl)-1H-pyrazolo[4,3-d]pyrimidin-3-yl)phenyl)piperazin-1-yl)acetamide (HC90-88);

N-(4-((2-(2,6-dioxopiperidin-3-yl)-1,3-dioxoisoindolin-4-yl)amino)butyl)-2-(4-(4-(5-(2-fluoro-6-methoxyphenyl)-1H-pyrazolo[4,3-d]pyrimidin-3-yl)phenyl)piperazin-1-yl)acetamide (HC90-104);

2-(2,6-dioxopiperidin-3-yl)-4-((8-(4-(4-(5-(2-fluoro-6-methoxyphenyl)-1H-pyrazolo[4,3-d]pyrimidin-3-yl)phenyl)piperazin-1-yl)-8-oxooctyl)amino)isoindoline-1,3-dione (HC90-117);

and pharmaceutically acceptable salts thereof.

2. A method of treating an HPK1-mediated disease in a subject in need thereof, comprising:

administering to a subject having an HPKI-mediated disease, a bivalent compound according to claim 1.

3. A method of treating cancer in a subject in need thereof, comprising:

administering to a subject having cancer, a pharmaceutical composition including a bivalent compound according to claim 1, and a pharmaceutically acceptable carrier, and a pharmaceutical composition including a checkpoint inhibitor and a pharmaceutically acceptable carrier.

* * * * *